US012269831B2

(12) United States Patent
Clemens et al.

(10) Patent No.: US 12,269,831 B2
(45) Date of Patent: Apr. 8, 2025

(54) MODULATORS OF CYSTIC FIBROSIS TRANSMEMBRANE CONDUCTANCE REGULATOR

(71) Applicant: Vertex Pharmaceuticals Incorporated, Boston, MA (US)

(72) Inventors: Jeremy J. Clemens, San Diego, CA (US); Brett C. Bookser, San Diego, CA (US); Thomas Cleveland, San Marcos, CA (US); Timothy R. Coon, Carlsbad, CA (US); Michel Gallant, Pierrefonds (CA); Peter Diederik Jan Grootenhuis, Del Mar, CA (US); Sara Sabina Hadida Ruah, La Jolla, CA (US); Julie Laterreur, San Diego, CA (US); Vito Melillo, Escondido, CA (US); Mark Thomas Miller, Rancho Santa Fe, CA (US); Prasuna Paraselli, San Diego, CA (US); Yeeman K. Ramtohul, Pierrefonds (CA); Thumkunta Jagadeeswar Reddy, Pierrefonds (CA); Claudio Sturino, Ile Bizard (CA); Lino Valdez, San Diego, CA (US); Jinglan Zhou, San Diego, CA (US); Minson Baek, San Diego, CA (US); William Schulz Bechara, Laval (CA)

(73) Assignee: Vertex Pharmaceuticals Incorporated, Boston, MA (US)

( * ) Notice: Subject to any disclaimer, the term of this patent is extended or adjusted under 35 U.S.C. 154(b) by 346 days.

(21) Appl. No.: 17/395,838

(22) Filed: Aug. 6, 2021

(65) Prior Publication Data
US 2022/0041621 A1 Feb. 10, 2022

Related U.S. Application Data

(60) Provisional application No. 63/063,194, filed on Aug. 7, 2020.

(51) Int. Cl.
*C07D 498/18* (2006.01)
*A61K 45/06* (2006.01)
*C07D 213/26* (2006.01)
*C07D 271/10* (2006.01)

(52) U.S. Cl.
CPC ............ *C07D 498/18* (2013.01); *A61K 45/06* (2013.01)

(58) Field of Classification Search
None
See application file for complete search history.

(56) References Cited

U.S. PATENT DOCUMENTS

| | | |
|---|---|---|
| 7,407,976 B2 | 8/2008 | Miller et al. |
| 7,495,103 B2 | 2/2009 | Hadida-Ruah et al. |
| 7,553,855 B2 | 6/2009 | Young et al. |
| 7,598,412 B2 | 10/2009 | Hadida Ruah et al. |
| 7,645,789 B2 | 1/2010 | Hadida Ruah et al. |
| 7,659,268 B2 | 2/2010 | Hadida-Ruah et al. |
| 7,671,221 B2 | 3/2010 | Hadida Ruah et al. |
| 7,691,902 B2 | 4/2010 | Hadida Ruah et al. |
| 7,741,321 B2 | 6/2010 | Hadida Ruah et al. |
| 7,754,739 B2 | 7/2010 | Hadida Ruah et al. |
| 7,776,905 B2 | 8/2010 | Hadida Ruah et al. |
| 7,846,951 B2 | 12/2010 | Miller et al. |
| 7,956,052 B2 | 6/2011 | Hadida Ruah et al. |
| 7,973,038 B2 | 7/2011 | Hadida Ruah et al. |
| 7,973,169 B2 | 7/2011 | Hadida Ruah et al. |
| 7,977,322 B2 | 7/2011 | Ruah et al. |
| 7,999,113 B2 | 8/2011 | Hadida-Ruah et al. |
| 8,012,999 B2 | 9/2011 | Hadida Ruah et al. |
| 8,039,491 B2 | 10/2011 | Hadida Ruah et al. |
| 8,076,357 B2 | 12/2011 | Young et al. |
| 8,101,767 B2 | 1/2012 | Ruah et al. |
| 8,124,781 B2 | 2/2012 | Siesel |
| 8,163,772 B2 | 4/2012 | DeMattei et al. |
| 8,188,283 B2 | 5/2012 | Binch et al. |
| 8,227,615 B2 | 7/2012 | Hadida-Ruah et al. |
| 8,232,302 B2 | 7/2012 | Miller et al. |
| 8,242,149 B2 | 8/2012 | Ruah et al. |
| 8,299,099 B2 | 10/2012 | Ruah et al. |
| 8,314,239 B2 | 11/2012 | Binch et al. |
| 8,314,256 B2 | 11/2012 | Ruah et al. |
| 8,318,733 B2 | 11/2012 | Hadida-Ruah et al. |
| 8,324,207 B2 | 12/2012 | Hadida Ruah et al. |
| 8,324,242 B2 | 12/2012 | Ruah et al. |
| 8,344,147 B2 | 1/2013 | Ambhaikar et al. |
| 8,354,427 B2 | 1/2013 | Van Goor |

(Continued)

FOREIGN PATENT DOCUMENTS

| | | |
|---|---|---|
| WO | WO 2004/058717 A1 | 7/2004 |
| WO | WO 2004/080972 A1 | 9/2004 |

(Continued)

OTHER PUBLICATIONS

Bose, S et al. *J. Cyst. Fibros*. 2020, 19 Suppl 1, S25-S32.
Brasell, E.J. et al. *PLoS One* 2019, 14 (12), e0223954.
Crawford, D.K. *J. Pharmacol. Exp. Ther*. 2020, 374 (2), 264-272.
Phuan, P.-W. et al. *J. Cyst. Fibros*. 2018, 17(5), 595-606.
Kunzelmann, K. et al., *Front. Pharmacol*. 2019, 10, 3.
Pedemonte, N. et al. *Sci. Adv*. 2020, 6 (8), eaay9669.
Phuan, P.-W. et al. *Sci. Rep*. 2019, 9 (1), 17640.
Smith, N.J, Solovay, C.F., *Pharm. Pat. Anal*. 2017, 6 (4), 179-188.

(Continued)

*Primary Examiner* — Brian J Davis
(74) *Attorney, Agent, or Firm* — Finnegan, Henderson, Farabow, Garrett & Dunner, LLP

(57) ABSTRACT

This disclosure provides modulators of Cystic Fibrosis Transmembrane Conductance Regulator (CFTR), pharmaceutical compositions containing at least one such modulator, methods of treatment of cystic fibrosis using such modulators and pharmaceutical compositions, and processes for making such modulators.

41 Claims, 8 Drawing Sheets

(56) References Cited

U.S. PATENT DOCUMENTS

| | | |
|---|---|---|
| 8,362,253 B2 | 1/2013 | DeMattei et al. |
| 8,367,660 B2 | 2/2013 | Binch et al. |
| 8,389,727 B2 | 3/2013 | Zhang et al. |
| 8,399,479 B2 | 3/2013 | Binch et al. |
| 8,404,849 B2 | 3/2013 | Sun et al. |
| 8,404,865 B2 | 3/2013 | Ambhaikar et al. |
| 8,410,132 B2 | 4/2013 | Binch et al. |
| 8,410,274 B2 | 4/2013 | Hurter et al. |
| 8,415,387 B2 | 4/2013 | Ruah et al. |
| 8,431,605 B2 | 4/2013 | Hadida Ruah et al. |
| 8,436,014 B2 | 5/2013 | Zhang et al. |
| 8,461,156 B2 | 6/2013 | Hadida Ruah et al. |
| 8,461,342 B2 | 6/2013 | Siesel |
| 8,461,352 B2 | 6/2013 | Ambhaikar et al. |
| 8,471,029 B2 | 6/2013 | Arekar et al. |
| 8,476,442 B2 | 7/2013 | DeMattei et al. |
| 8,507,524 B2 | 8/2013 | Ruah et al. |
| 8,507,534 B2 | 8/2013 | Keshavarz-Shokri et al. |
| 8,507,687 B2 | 8/2013 | Keshavarz-Shokri et al. |
| 8,513,282 B2 | 8/2013 | Binch et al. |
| 8,524,767 B2 | 9/2013 | Miller et al. |
| 8,524,910 B2 | 9/2013 | Hadida Ruah et al. |
| 8,541,453 B2 | 9/2013 | Hadida-Ruah et al. |
| 8,552,006 B2 | 10/2013 | Binch et al. |
| 8,552,034 B2 | 10/2013 | Verwijs et al. |
| 8,563,573 B2 | 10/2013 | Ruah et al. |
| 8,563,593 B2 | 10/2013 | Alargova et al. |
| 8,575,209 B2 | 11/2013 | Ruah et al. |
| 8,586,615 B2 | 11/2013 | Hadida-Ruah et al. |
| 8,592,602 B2 | 11/2013 | Siesel |
| 8,598,181 B2 | 12/2013 | Hadida Ruah et al. |
| 8,598,205 B2 | 12/2013 | Binch et al. |
| 8,604,203 B2 | 12/2013 | Binch et al. |
| 8,609,703 B2 | 12/2013 | Ruah et al. |
| 8,614,325 B2 | 12/2013 | Yang et al. |
| 8,614,327 B2 | 12/2013 | Sheth et al. |
| 8,623,894 B2 | 1/2014 | DeMattei et al. |
| 8,623,905 B2 | 1/2014 | Ruah et al. |
| 8,629,162 B2 | 1/2014 | Hadida-Ruah et al. |
| 8,633,189 B2 | 1/2014 | Binch et al. |
| 8,642,609 B2 | 2/2014 | Makings et al. |
| 8,653,103 B2 | 2/2014 | Keshavarz-Shokri et al. |
| 8,674,108 B2 | 3/2014 | Luisi et al. |
| 8,710,075 B2 | 4/2014 | Binch et al. |
| 8,716,338 B2 | 5/2014 | Young |
| 8,722,704 B2 | 5/2014 | Hadida Ruah et al. |
| 8,741,922 B2 | 6/2014 | Zhang et al. |
| 8,741,925 B2 | 6/2014 | Hadida-Ruah et al. |
| 8,741,933 B2 | 6/2014 | Hadida Ruah et al. |
| 8,741,939 B2 | 6/2014 | Hadida Ruah et al. |
| 8,742,122 B2 | 6/2014 | Keshavarz-Shokri et al. |
| 8,748,612 B2 | 6/2014 | Binch et al. |
| 8,754,222 B2 | 6/2014 | Ambhaikar et al. |
| 8,754,224 B2 | 6/2014 | Hurter et al. |
| 8,759,335 B2 | 6/2014 | Hadida Ruah et al. |
| 8,765,957 B2 | 7/2014 | DeMattei et al. |
| 8,785,476 B2 | 7/2014 | Arekar et al. |
| 8,785,640 B2 | 7/2014 | Binch et al. |
| 8,796,308 B2 | 8/2014 | Yang et al. |
| 8,796,312 B2 | 8/2014 | Hadida Ruah et al. |
| 8,802,700 B2 | 8/2014 | Sheth et al. |
| 8,802,844 B2 | 8/2014 | Gallardo-Godoy |
| 8,802,868 B2 | 8/2014 | Keshavarz-Shokri et al. |
| 8,816,093 B2 | 8/2014 | Siesel |
| 8,822,451 B2 | 9/2014 | Ruah et al. |
| 8,829,204 B2 | 9/2014 | Hadida-Ruah et al. |
| 8,835,639 B2 | 9/2014 | DeMattei et al. |
| 8,846,718 B2 | 9/2014 | Keshavarz-Shokri et al. |
| 8,846,753 B2 | 9/2014 | Hadida Ruah et al. |
| 8,853,254 B2 | 10/2014 | Hadida Ruah et al. |
| 8,853,415 B2 | 10/2014 | Hadida Ruah et al. |
| 8,865,902 B2 | 10/2014 | Morgan |
| 8,883,206 B2 | 11/2014 | Doukou et al. |
| 8,884,018 B2 | 11/2014 | Ambhaikar et al. |
| 8,889,875 B2 | 11/2014 | Ruah et al. |
| 8,912,199 B2 | 12/2014 | Hadida Ruah et al. |
| 8,952,049 B2 | 2/2015 | Ruah et al. |
| 8,952,050 B2 | 2/2015 | Ruah et al. |
| 8,962,856 B2 | 2/2015 | Hadida-Ruah et al. |
| 8,969,382 B2 | 3/2015 | Binch et al. |
| 8,969,386 B2 | 3/2015 | Hadida-Ruah et al. |
| 8,969,574 B2 | 3/2015 | Keshavarz-Shokri et al. |
| 8,993,600 B2 | 3/2015 | Hadida Ruah et al. |
| 8,999,976 B2 | 4/2015 | Binch et al. |
| 9,012,473 B2 | 4/2015 | Hadida Ruah et al. |
| 9,012,496 B2 | 4/2015 | Alargova et al. |
| 9,012,652 B2 | 4/2015 | Siesel |
| 9,035,072 B2 | 5/2015 | Belmont et al. |
| 9,045,425 B2 | 6/2015 | Luisi et al. |
| 9,051,303 B2 | 6/2015 | Keshavarz-Shokri et al. |
| 9,051,324 B2 | 6/2015 | Binch et al. |
| 9,079,916 B2 | 7/2015 | Hadida Ruah et al. |
| 9,090,619 B2 | 7/2015 | Hadida-Ruah et al. |
| 9,102,672 B2 | 8/2015 | Hadida-Ruah et al. |
| 9,139,530 B2 | 9/2015 | Hurter et al. |
| 9,150,552 B2 | 10/2015 | Keshavarz-Shokri et al. |
| 9,181,192 B2 | 11/2015 | Morgan |
| 9,192,606 B2 | 11/2015 | Young |
| 9,216,969 B2 | 12/2015 | Ruah et al. |
| 9,241,934 B2 | 1/2016 | Verwijs et al. |
| 9,249,131 B2 | 2/2016 | Hadida Ruah et al. |
| 9,254,291 B2 | 2/2016 | Looker et al. |
| 9,314,455 B2 | 4/2016 | Keshavarz-Shokri et al. |
| 9,321,725 B2 | 4/2016 | Miller et al. |
| 9,351,962 B2 | 5/2016 | Ruah et al. |
| 9,371,287 B2 | 6/2016 | DeMattei et al. |
| 9,399,648 B2 | 7/2016 | Gallardo-Godoy |
| 9,434,717 B2 | 9/2016 | Keshavarz-Shokri et al. |
| 9,504,683 B2 | 11/2016 | Hadida Ruah et al. |
| 9,512,079 B2 | 12/2016 | Morgan |
| 9,522,145 B2 | 12/2016 | Hadida Ruah et al. |
| 9,550,761 B2 | 1/2017 | Hadida-Ruah et al. |
| 9,670,163 B2 | 6/2017 | Hurter et al. |
| 9,701,639 B2 | 7/2017 | Strohmeier et al. |
| 9,725,440 B2 | 8/2017 | Hadida-Ruah et al. |
| 9,732,080 B2 | 8/2017 | Hadida-Ruah et al. |
| 9,751,839 B2 | 9/2017 | DeMattei et al. |
| 9,751,890 B2 | 9/2017 | Hadida Ruah et al. |
| 9,758,510 B2 | 9/2017 | Hadida Ruah et al. |
| 9,776,968 B2 | 10/2017 | Siesel |
| 9,782,408 B2 | 10/2017 | Miller et al. |
| 9,840,499 B2 | 12/2017 | Keshavarz-Shokri et al. |
| 9,931,334 B2 | 4/2018 | Hurter et al. |
| 9,974,781 B2 | 5/2018 | Hadida Ruah et al. |
| 10,022,352 B2 | 7/2018 | Hadida Ruah et al. |
| 10,047,053 B2 | 8/2018 | Morgan |
| 10,058,546 B2 | 8/2018 | Alargova et al. |
| 10,071,979 B2 | 9/2018 | Tanoury et al. |
| 10,076,513 B2 | 9/2018 | Verwijs et al. |
| 10,081,621 B2 | 9/2018 | Keshavarz-Shokri et al. |
| 10,206,877 B2 | 2/2019 | Phenix et al. |
| 10,231,932 B2 | 3/2019 | Swinney et al. |
| 10,239,867 B2 | 3/2019 | Hadida Ruah et al. |
| 10,258,624 B2 | 4/2019 | Miller et al. |
| 10,272,046 B2 | 4/2019 | Dokou et al. |
| 10,302,602 B2 | 5/2019 | Borsje et al. |
| 10,479,766 B2 | 11/2019 | Morgan et al. |
| 10,537,565 B2 | 1/2020 | Hurter et al. |
| 10,570,115 B2 | 2/2020 | Alcacio et al. |
| 10,597,384 B2 | 3/2020 | Keshavarz-Shokri et al. |
| 10,626,111 B2 | 4/2020 | Hadida Ruah et al. |
| 10,646,481 B2 | 5/2020 | William et al. |
| 10,654,829 B2 | 5/2020 | Dhamankar et al. |
| 10,662,192 B2 | 5/2020 | Hadida-Ruah et al. |
| 10,758,534 B2 | 9/2020 | Miller et al. |
| 10,759,721 B2 | 9/2020 | Morgan et al. |
| 10,793,547 B2 | 10/2020 | Abela et al. |
| 10,894,773 B2 | 1/2021 | Morgan et al. |
| 10,906,891 B2 | 2/2021 | Keshavarz-Shokri et al. |
| 10,975,061 B2 | 4/2021 | Hadida Ruah et al. |
| 10,980,746 B2 | 4/2021 | Phenix et al. |
| 10,987,348 B2 | 4/2021 | Hadida Ruah et al. |
| 11,052,075 B2 | 7/2021 | Verwijs et al. |
| 11,084,804 B2 | 8/2021 | Hadida Ruah et al. |

(56) References Cited

U.S. PATENT DOCUMENTS

| | | |
|---|---|---|
| 11,155,533 B2 | 10/2021 | Dhamankar et al. |
| 11,179,367 B2 | 11/2021 | Chu et al. |
| 11,186,566 B2 | 11/2021 | Alcacio et al. |
| 11,253,509 B2 | 2/2022 | Chen et al. |
| 11,291,662 B2 | 4/2022 | Hurter et al. |
| 11,414,439 B2 | 8/2022 | Abela et al. |
| 11,426,407 B2 | 8/2022 | Miller et al. |
| 11,434,201 B2 | 9/2022 | Angell et al. |
| 11,453,655 B2 | 9/2022 | Abela et al. |
| 11,465,985 B2 | 10/2022 | Angell et al. |
| 11,517,564 B2 | 12/2022 | Chen et al. |
| 11,564,916 B2 | 1/2023 | Rowe et al. |
| 11,578,062 B2 | 2/2023 | Keshavarz-Shokri et al. |
| 11,584,761 B2 | 2/2023 | Angell et al. |
| 11,639,347 B2 | 5/2023 | Hadida Ruah et al. |
| 11,708,331 B2 | 7/2023 | Lewandowski et al. |
| 2005/0113423 A1 | 5/2005 | Van Goor et al. |
| 2007/0105833 A1 | 5/2007 | Ruah et al. |
| 2007/0218138 A1 | 9/2007 | Bittorf et al. |
| 2009/0105272 A1 | 4/2009 | Grootenhuis et al. |
| 2009/0176839 A1 | 7/2009 | Keshavarz-Shokri et al. |
| 2009/0246820 A1 | 10/2009 | Singh et al. |
| 2010/0036130 A1 | 2/2010 | Siesel |
| 2010/0074949 A1 | 3/2010 | Rowe et al. |
| 2010/0125090 A1 | 5/2010 | Hadida Ruah et al. |
| 2010/0144798 A1 | 6/2010 | Van Goor et al. |
| 2010/0227888 A1 | 9/2010 | Ruah et al. |
| 2010/0256184 A1 | 10/2010 | Rowe et al. |
| 2011/0064811 A1 | 3/2011 | Hurter et al. |
| 2011/0098311 A1 | 4/2011 | Van Goor et al. |
| 2011/0177999 A1 | 7/2011 | Singh et al. |
| 2011/0251253 A1 | 10/2011 | Keshavarz-Shokri et al. |
| 2011/0257223 A1 | 10/2011 | Van Goor et al. |
| 2011/0288122 A1 | 11/2011 | Van Goor et al. |
| 2012/0035179 A1 | 2/2012 | Hadida-Ruah et al. |
| 2012/0046330 A1 | 2/2012 | Alargova et al. |
| 2012/0064157 A1 | 3/2012 | Dokou et al. |
| 2012/0122921 A1 | 5/2012 | DeMattei et al. |
| 2012/0122922 A1 | 5/2012 | Young et al. |
| 2012/0184583 A1 | 7/2012 | Van Goor et al. |
| 2012/0220625 A1 | 8/2012 | Rowe et al. |
| 2012/0232059 A1 | 9/2012 | Hadida-Ruah et al. |
| 2012/0258983 A1 | 10/2012 | Rowe et al. |
| 2013/0012536 A1 | 1/2013 | Hadida Ruah et al. |
| 2013/0018071 A1 | 1/2013 | Arekar et al. |
| 2013/0085158 A1 | 4/2013 | Keshavarz-Shokri et al. |
| 2013/0090354 A1 | 4/2013 | Van Goor et al. |
| 2013/0095181 A1 | 4/2013 | Verwijs et al. |
| 2013/0131107 A1 | 5/2013 | Van Goor et al. |
| 2013/0143919 A1 | 6/2013 | Van Goor et al. |
| 2013/0158071 A1 | 6/2013 | Van Goor et al. |
| 2013/0186801 A1 | 7/2013 | Verwijs |
| 2013/0224293 A1 | 8/2013 | Dokou et al. |
| 2013/0231368 A1 | 9/2013 | Zhang et al. |
| 2013/0245010 A1 | 9/2013 | Hadida Ruah et al. |
| 2013/0245011 A1 | 9/2013 | Hadida Ruah et al. |
| 2013/0303484 A1 | 11/2013 | Grootenhuis et al. |
| 2013/0331567 A1 | 12/2013 | Hadida-Ruah et al. |
| 2014/0023706 A1 | 1/2014 | Verwijs et al. |
| 2014/0094499 A1 | 4/2014 | Alargova et al. |
| 2014/0112988 A1 | 4/2014 | Rowe et al. |
| 2014/0142138 A1 | 5/2014 | Van Goor et al. |
| 2014/0155431 A1 | 6/2014 | Hadida-Ruah et al. |
| 2014/0155626 A1 | 6/2014 | Hadida Ruah et al. |
| 2014/0163011 A1 | 6/2014 | Hadida-Ruah et al. |
| 2014/0163068 A1 | 6/2014 | Verwijs et al. |
| 2014/0221424 A1 | 8/2014 | Zha |
| 2014/0235668 A1 | 8/2014 | Binch et al. |
| 2014/0243289 A1 | 8/2014 | Grootenhuis et al. |
| 2014/0303204 A1 | 10/2014 | Binch et al. |
| 2014/0303205 A1 | 10/2014 | Yang et al. |
| 2014/0315948 A1 | 10/2014 | Rowe et al. |
| 2014/0323521 A1 | 10/2014 | Van Goor et al. |
| 2014/0329855 A1 | 11/2014 | Arekar et al. |
| 2014/0336393 A1 | 11/2014 | Ambhaikar et al. |
| 2014/0343098 A1 | 11/2014 | Sheth et al. |
| 2014/0350281 A1 | 11/2014 | DeMattei et al. |
| 2015/0010628 A1 | 1/2015 | Dokou et al. |
| 2015/0024047 A1 | 1/2015 | Dokou et al. |
| 2015/0031722 A1 | 1/2015 | Hadida-Ruah et al. |
| 2015/0065487 A1 | 3/2015 | Hadida-Ruah et al. |
| 2015/0065497 A1 | 3/2015 | Hadida Ruah et al. |
| 2015/0065500 A1 | 3/2015 | Hadida-Ruah et al. |
| 2015/0080431 A1 | 3/2015 | Van Goor et al. |
| 2015/0094304 A1 | 4/2015 | Ruah et al. |
| 2015/0119441 A1 | 4/2015 | Hadida Ruah et al. |
| 2015/0150879 A2 | 6/2015 | Van Goor et al. |
| 2015/0174098 A1 | 6/2015 | Ruah et al. |
| 2015/0182517 A1 | 7/2015 | Alargova et al. |
| 2015/0231142 A1 | 8/2015 | Van Goor et al. |
| 2015/0246031 A1 | 9/2015 | Dokou et al. |
| 2015/0293078 A1 | 10/2015 | Singh et al. |
| 2015/0315186 A2 | 11/2015 | Hadida-Ruah et al. |
| 2015/0336898 A1 | 11/2015 | Grootenhuis et al. |
| 2016/0022664 A2 | 1/2016 | Van Goor et al. |
| 2016/0022665 A2 | 1/2016 | Van Goor et al. |
| 2016/0039800 A1 | 2/2016 | Young |
| 2016/0067239 A9 | 3/2016 | Van Goor et al. |
| 2016/0120841 A1 | 5/2016 | Kym et al. |
| 2016/0143898 A1 | 5/2016 | Hadida Ruah et al. |
| 2016/0166540 A1 | 6/2016 | Looker et al. |
| 2016/0221952 A1 | 8/2016 | Yang et al. |
| 2016/0228414 A1 | 8/2016 | Hadida Ruah et al. |
| 2016/0318931 A1 | 11/2016 | Hadida-Ruah et al. |
| 2016/0324788 A1 | 11/2016 | Verwijs |
| 2016/0324846 A1 | 11/2016 | Verwijs et al. |
| 2016/0354316 A1 | 12/2016 | Swinney et al. |
| 2017/0100340 A1 | 4/2017 | Dokou et al. |
| 2017/0101405 A1 | 4/2017 | Akkari et al. |
| 2017/0107205 A1 | 4/2017 | Hadida Ruah et al. |
| 2017/0107206 A1 | 4/2017 | Hadida Ruah et al. |
| 2017/0137383 A1 | 5/2017 | Morgan |
| 2018/0008546 A1 | 1/2018 | Verwijs et al. |
| 2018/0125838 A1 | 5/2018 | Uttamsingh |
| 2018/0127398 A1 | 5/2018 | Keshavarz-Shokri et al. |
| 2018/0153874 A1 | 6/2018 | Van Goor et al. |
| 2018/0280349 A1 | 10/2018 | Van Goor et al. |
| 2018/0353500 A1 | 12/2018 | Braman |
| 2019/0038615 A1 | 2/2019 | Van Goor et al. |
| 2019/0055220 A1 | 2/2019 | Bear et al. |
| 2019/0070155 A1 | 3/2019 | Verwijs et al. |
| 2019/0076419 A1 | 3/2019 | Hadida Ruah et al. |
| 2019/0210991 A1 | 7/2019 | Tanoury et al. |
| 2019/0274959 A1 | 9/2019 | Dokou et al. |
| 2020/0031776 A1 | 1/2020 | Morgan et al. |
| 2020/0085750 A1 | 3/2020 | Verwijs |
| 2020/0115366 A1 | 4/2020 | Hadida Ruah et al. |
| 2020/0171015 A1 | 6/2020 | Haseltine et al. |
| 2020/0338063 A1 | 10/2020 | Verwijs et al. |
| 2020/0352930 A1 | 11/2020 | Hurter et al. |
| 2020/0377484 A1 | 12/2020 | Keshavarz-Shokri et al. |
| 2021/0023070 A1 | 1/2021 | Rowe et al. |
| 2021/0024505 A1 | 1/2021 | Hadida Ruah et al. |
| 2021/0052570 A1 | 2/2021 | Uttamsingh |
| 2021/0069174 A1 | 3/2021 | Chu et al. |
| 2021/0139514 A1 | 5/2021 | Abela et al. |
| 2021/0228489 A1 | 7/2021 | Dokou et al. |
| 2021/0238158 A1 | 8/2021 | Tanoury et al. |
| 2021/0308053 A1 | 10/2021 | Phenix et al. |
| 2021/0340128 A1 | 11/2021 | Keshavarz-Shokri et al. |
| 2022/0031679 A1 | 2/2022 | Verwijs et al. |
| 2022/0041621 A1 | 2/2022 | Clemens et al. |
| 2022/0153729 A1 | 5/2022 | Hadida Ruah et al. |
| 2022/0257564 A1 | 8/2022 | Chu et al. |
| 2022/0306606 A1 | 9/2022 | Alcacio et al. |
| 2022/0354797 A1 | 11/2022 | Verwijs et al. |
| 2023/0127655 A1 | 4/2023 | Hadida Ruah et al. |
| 2023/0233560 A1 | 7/2023 | Miller et al. |
| 2023/0241045 A1 | 8/2023 | Chen et al. |

(56) References Cited

U.S. PATENT DOCUMENTS

| | | |
|---|---|---|
| 2023/0357191 A1 | 11/2023 | Abela et al. |
| 2024/0025877 A1 | 1/2024 | Angell et al. |

FOREIGN PATENT DOCUMENTS

| | | | |
|---|---|---|---|
| WO | WO 2004/111014 A1 | 12/2004 | |
| WO | WO 2005/026137 A2 | 3/2005 | |
| WO | WO 2005/049018 A1 | 6/2005 | |
| WO | WO 2005/075435 A1 | 8/2005 | |
| WO | WO 2006/002421 A2 | 1/2006 | |
| WO | WO 2006/099256 A2 | 9/2006 | |
| WO | WO 2006/127588 A2 | 11/2006 | |
| WO | WO 2007/021982 A2 | 2/2007 | |
| WO | WO 2007/044560 A2 | 4/2007 | |
| WO | WO 2007/056341 A1 | 5/2007 | |
| WO | WO 2007/075901 A2 | 7/2007 | |
| WO | WO 2007/075946 A1 | 7/2007 | |
| WO | WO 2007/079139 A2 | 7/2007 | |
| WO | WO 2007/087066 A2 | 8/2007 | |
| WO | WO 2007/109605 A2 | 9/2007 | |
| WO | WO 2007/117715 A2 | 10/2007 | |
| WO | WO 2007/134279 A2 | 11/2007 | |
| WO | WO 2008/092231 A1 | 8/2008 | |
| WO | WO 2008/127399 A2 | 10/2008 | |
| WO | WO 2008/147952 A1 | 12/2008 | |
| WO | WO 2009/006315 A1 | 1/2009 | |
| WO | WO 2009/023509 A2 | 2/2009 | |
| WO | WO 2009/036412 A1 | 3/2009 | |
| WO | WO 2009/038683 A2 | 3/2009 | |
| WO | WO 2009/038913 A2 | 3/2009 | |
| WO | WO 2009/073757 A1 | 6/2009 | |
| WO | WO 2009/076141 A2 | 6/2009 | |
| WO | WO 2009/076142 A2 | 6/2009 | |
| WO | WO 2009/076593 A1 | 6/2009 | |
| WO | WO 2009/108657 A2 | 9/2009 | |
| WO | WO 2010/019239 A2 | 2/2010 | |
| WO | WO 2010/037066 A2 | 4/2010 | |
| WO | WO 2010/048526 A2 | 4/2010 | |
| WO | WO 2010/053471 A1 | 5/2010 | |
| WO | WO 2010/054138 A2 | 5/2010 | |
| WO | WO 2010/078103 A1 | 7/2010 | |
| WO | WO 2010/108155 A1 | 9/2010 | |
| WO | WO 2010/108162 A1 | 9/2010 | |
| WO | WO 2010/151747 A1 | 12/2010 | |
| WO | WO 2011/019413 A1 | 2/2011 | |
| WO | WO 2011/050325 A1 | 4/2011 | |
| WO | WO 2011/072241 A1 | 6/2011 | |
| WO | WO 2011/116397 A1 | 9/2011 | |
| WO | WO 2011/119984 A1 | 9/2011 | |
| WO | WO 2011/127241 A2 | 10/2011 | |
| WO | WO 2011/127290 A2 | 10/2011 | |
| WO | WO 2011/133751 A2 | 10/2011 | |
| WO | WO 2011/133951 A1 | 10/2011 | |
| WO | WO 2011/133953 A1 | 10/2011 | |
| WO | WO 2012/027247 A2 | 3/2012 | |
| WO | WO 2012/027731 A2 | 3/2012 | |
| WO | WO 2012/158885 A1 | 11/2012 | |
| WO | WO 2012/170061 A1 | 12/2012 | |
| WO | WO 2013/038386 A1 * | 3/2013 | ........... C07D 413/04 |
| WO | WO 2013/070961 A1 | 5/2013 | |
| WO | WO 2013/112804 A1 | 8/2013 | |
| WO | WO 2013/130669 A1 | 9/2013 | |
| WO | WO 2013/158121 A1 | 10/2013 | |
| WO | WO 2013/185112 A1 | 12/2013 | |
| WO | WO 2014/014841 A1 | 1/2014 | |
| WO | WO 2014/071122 A1 | 5/2014 | |
| WO | WO 2014/078842 A1 | 5/2014 | |
| WO | WO 2015/048301 A1 | 4/2015 | |
| WO | WO 2015/073231 A1 | 7/2015 | |
| WO | WO 2015/160787 A1 | 10/2015 | |
| WO | WO 2016/057572 A1 | 4/2016 | |
| WO | WO 2016/057730 A1 | 4/2016 | |
| WO | WO 2016/081556 A1 | 5/2016 | |
| WO | WO 2016/105485 A2 | 6/2016 | |
| WO | WO 2016/160945 A1 | 10/2016 | |
| WO | WO 2017/009804 A1 | 1/2017 | |
| WO | WO 2017/053455 A1 | 3/2017 | |
| WO | WO 2017/053711 A2 | 3/2017 | |
| WO | WO 2017/062581 A1 | 4/2017 | |
| WO | WO 2017/173274 A1 | 10/2017 | |
| WO | WO 2018/064632 A1 | 4/2018 | |
| WO | WO 2018/065921 A1 | 4/2018 | |
| WO | WO 2018/080591 A1 | 5/2018 | |
| WO | WO 2018/107100 A1 | 6/2018 | |
| WO | WO 2018/183367 A1 | 10/2018 | |
| WO | WO 2018/227049 A1 | 12/2018 | |
| WO | WO 2019/010092 A1 | 1/2019 | |
| WO | WO 2019/014352 A1 | 1/2019 | |
| WO | WO 2019/018353 A1 | 1/2019 | |
| WO | WO 2019/018395 A1 | 1/2019 | |
| WO | WO 2019/028228 A1 | 2/2019 | |
| WO | WO 2019/079760 A1 | 4/2019 | |
| WO | WO 2019/109021 A1 | 6/2019 | |
| WO | WO 2019/113089 A1 | 6/2019 | |
| WO | WO 2019/113476 A2 | 6/2019 | |
| WO | WO 2019/152940 A1 | 8/2019 | |
| WO | WO 2019/161078 A1 | 8/2019 | |
| WO | WO 2019/026075 A1 | 10/2019 | |
| WO | WO 2019/191620 A1 | 10/2019 | |
| WO | WO 2019/195739 A1 | 10/2019 | |
| WO | WO 2019/200246 A1 | 10/2019 | |
| WO | WO 2020/102346 A1 | 5/2020 | |
| WO | WO 2020/206080 A1 | 10/2020 | |
| WO | WO 2020/214921 A1 | 10/2020 | |
| WO | WO 2020/242935 A1 | 12/2020 | |
| WO | WO 2021/030552 A1 | 2/2021 | |
| WO | WO 2021/030554 A1 | 2/2021 | |
| WO | WO 2021/030555 A1 | 2/2021 | |
| WO | WO 2021/030556 A1 | 2/2021 | |
| WO | WO 2022/032068 A1 | 2/2022 | |
| WO | WO 2022/036060 A1 | 2/2022 | |
| WO | WO 2022/076618 A1 | 4/2022 | |
| WO | WO 2022/076624 A1 | 4/2022 | |
| WO | WO 2022/109573 A1 | 5/2022 | |

OTHER PUBLICATIONS

Son, J.-H. et al., *Eur. J. of Med. Chem.* 2020, 112888.
Bastin, Richard J., et al., *Org. Pro. Res. Dev.* 2000, 4(5), 427-435.
Caira, Mino. R., et al. *Top. Curr. Chem.* 1998, 163-208.
Donaldson, Scott H. et al. "Tezacaftor/Ivacaftor in Subjects with Cystic Fibrosis and F508del/F508del-CFTR or F508del/G551D-CFTR", Am. J. Respir. Crit. Care Med. 2017, 197(2): 214-224.
International Patent Application No. PCT/US2021/044895: International Search Report and Written Opinion, mailed Oct. 29, 2021 (10 pages).
Lopes-Pacheco, M., *Front. Pharmacol.* 2020, 10, 1662.
Sabnis, Ram W. *ACS Med. Chem. Lett.* 2022, 13, 7, 1014-1015.

* cited by examiner

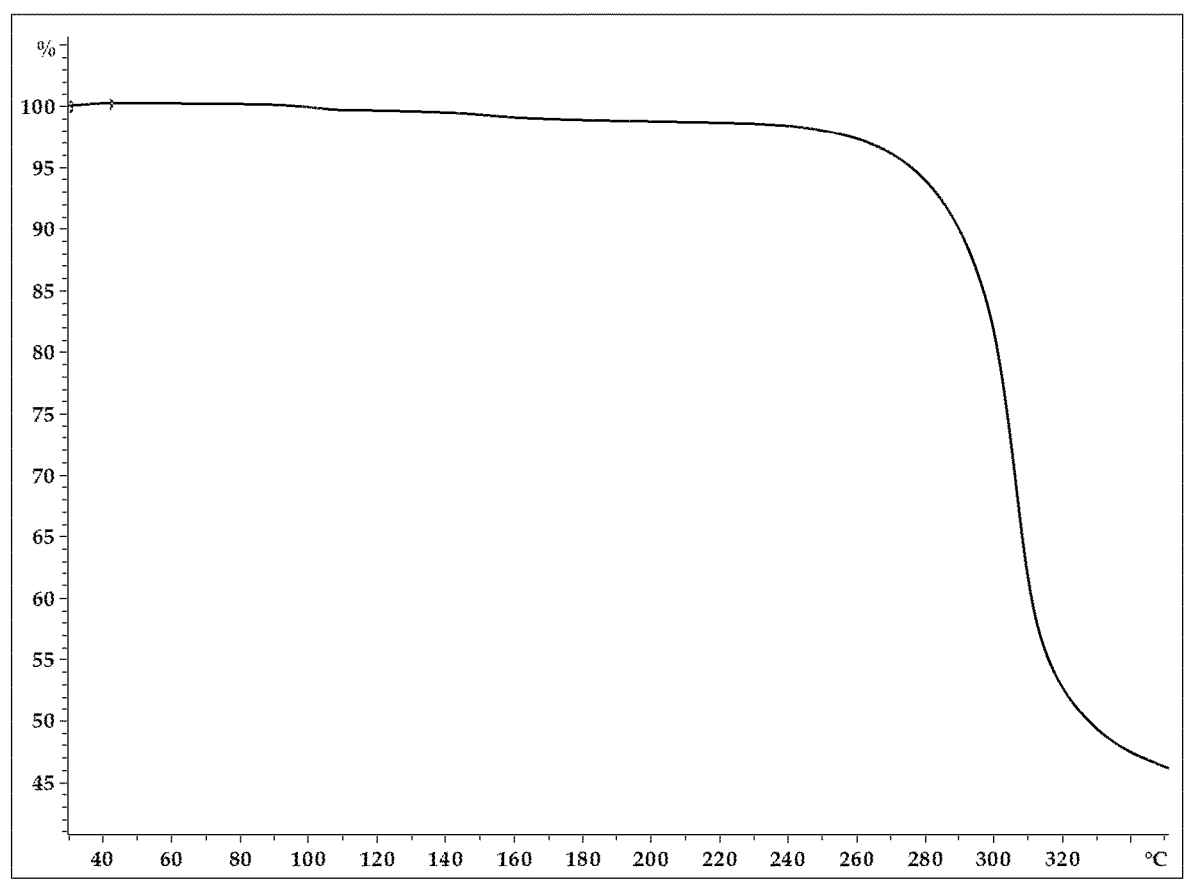

MODULATORS OF CYSTIC FIBROSIS TRANSMEMBRANE CONDUCTANCE REGULATOR

This application claims the benefit of U.S. Provisional Application No. 63/063,194, filed on Aug. 7, 2020, the contents of which are incorporated by reference in its entirety.

The invention relates to modulators of Cystic Fibrosis Transmembrane Conductance Regulator (CFTR), pharmaceutical compositions containing the modulators, methods of treating cystic fibrosis and CFTR-mediated disorders using such modulators and pharmaceutical compositions, and processes for making such modulators.

Cystic fibrosis (CF) is a recessive genetic disease that affects approximately 83,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to increased mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease-causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease-causing. The most prevalent disease-causing mutation is a deletion of phenylalanine at position 508 of the CFTR amino acid sequence and is commonly referred to as the F508del mutation. This mutation occurs in many of the cases of cystic fibrosis and is associated with severe disease.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC (epithelial sodium channel) and CFTR present on the apical membrane and the $Na^+$-$K^+$-ATPase pump and $Cl^-$ channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+$/2$Cl^-$/$K^+$ co-transporter, $Na^+$-$K^+$-ATPase pump and the basolateral membrane $K^+$ channels on the basolateral surface and CFTR on the luminal side coordinate the secretion of chloride. Because water is probably never actively transported itself, its flow across epithelia depends on tiny transepithelial osmotic gradients generated by the bulk flow of sodium and chloride.

A number of CFTR modulators have recently been identified. These modulators can be characterized as, for example, potentiators, correctors, potentiator enhancers/co-potentiators, amplifiers, readthrough agents, and nucleic acid therapies. CFTR modulators that increase the channel gating activity of mutant and wild-type CFTR at the epithelial cell surface are known as potentiators. Correctors improve faulty protein processing and resulting trafficking to the epithelial surface. Ghelani and Schneider-Futschik (2020) ACS Pharmacol. Transl. Sci. 3:4-10. There are three CFTR correctors approved by the U.S. FDA for treatment of cystic fibrosis. However, monotherapy with some CFTR correctors has not been found to be effective enough and as a result combination therapy with a potentiator is needed to enhance CFTR activity. There is currently only one CFTR potentiator that is approved for the treatment of cystic fibrosis. Thus, although the treatment of cystic fibrosis has been transformed by these new small molecule CFTR modulators, new and better modulators are needed to prevent disease progression, reduce the severity of the cystic fibrosis and other CFTR-mediated diseases, and to treat the more severe forms of these diseases.

One aspect of the invention provides novel compounds, including compounds of Formulae I, I', I'', I''', Ia, IIa, IIa', IIb, IIe, IId, IIe, IIf, IIIa, IIIa', IIIb, IIIc, IIId, IIIe, and IIIf, Compounds 1 to 53, Compounds 54 to 77, pharmaceutically acceptable salts thereof, and deuterated derivatives of any of the foregoing.

For example, compounds of Formula I can be depicted as:

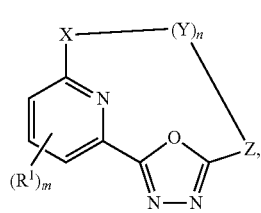

and deuterated derivatives and pharmaceutically acceptable salts thereof, wherein:

X is selected from —O—, —S—, —SO—, and —SO$_2$—;
each Y is independently selected from —C(R$^Y$)$_2$—, —O—, —CO—, and

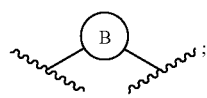

each R$^Y$ is independently selected from hydrogen, halogen, C$_1$-C$_6$ alkyl (optionally substituted with 1-3 groups independently selected from hydroxy and Q), C$_3$-C$_8$ cycloalkyl, C$_6$-C$_{10}$ aryl, 5- to 10-membered heteroaryl, —OR$^{r1}$, —CO$_2$R$^{r1}$, —COR$^{r1}$, —CON(R$^{r1}$)$_2$, and —NR$^{r1}$—; or two instances of R$^Y$ on the same atom are taken together to form a ring selected from C$_3$-C$_8$ cycloalkyl and 3- to 6-membered heterocyclyl;

or two instances of $R^Y$, one of which is on one atom and the second of which is on an adjacent atom, are taken together to form a pi bond;

each $R^{Y1}$ is independently selected from hydrogen and $C_1$-$C_6$ alkyl, or two instances of $R^{Y1}$ bonded to the same nitrogen taken together form a 3- to 6-membered heterocyclyl;

Ring B is selected from:
$C_6$-$C_{10}$ aryl (optionally substituted with 1-3 groups independently selected from halogen, $C_1$-$C_6$ alkyl, and $C_1$-$C_6$ alkoxy),
$C_3$-$C_8$ cycloalkyl,
5- to 10-membered heteroaryl, and
3- to 6-membered heterocyclyl (optionally substituted with 1-3 groups independently selected from $C_1$-$C_6$ alkyl);

each Q is independently selected from:
$C_1$-$C_6$ alkyl optionally substituted with 1-3 groups independently selected from:
halogen,
oxo,
$C_6$-$C_{10}$ aryl (optionally substituted with 1-3 groups independently selected from halogen and —$OCF_3$), and
$C_3$-$C_8$ cycloalkyl,
$C_3$-$C_8$ cycloalkyl optionally substituted with 1-3 groups independently selected from:
halogen,
CN,
$C_1$-$C_6$ alkyl (optionally substituted with 1-3 groups independently selected from halogen, —$NH_2$, and —NHCOMe),
$C_1$-$C_6$ alkoxy,
$C_6$-$C_{10}$ aryl (optionally substituted with 1-3 groups independently selected from $C_1$-$C_6$ alkyl), and
$C_3$-$C_8$ cycloalkyl,
$C_6$-$C_{10}$ aryl optionally substituted with 1-3 groups independently selected from:
halogen,
CN,
$C_1$-$C_6$ alkyl (optionally substituted with 1-3 groups independently selected from halogen and hydroxy),
$C_1$-$C_6$ alkoxy optionally substituted with 1-4 groups independently selected from:
halogen,
$C_3$-$C_8$ cycloalkyl (optionally substituted with $CF_3$),
$C_3$-$C_8$ cycloalkyl (optionally substituted with 1-3 groups independently selected from halogen, $CF_3$, $OCF_3$, and $C_1$-$C_6$ alkyl), and
$C_6$-$C_{10}$ aryl,
5- to 10-membered heteroaryl optionally substituted with 1-3 groups independently selected from:
halogen,
$C_1$-$C_6$ alkyl (optionally substituted with 1-3 groups independently selected from halogen),
$C_3$-$C_8$ cycloalkyl (optionally substituted with 1-3 $CF_3$ groups), and
3- to 10-membered heterocyclyl,
3- to 10-membered heterocyclyl optionally substituted with 1-3 groups independently selected from:
$C_1$-$C_6$ alkyl (optionally substituted with 1-3 groups independently selected from oxo and $C_3$-$C_8$ cycloalkyl), and
oxo;

each $R^1$ is independently selected from halogen, $C_1$-$C_6$ alkyl (optionally substituted with 1-6 groups independently selected from halogen and hydroxy), —$OR^2$, —$N(R^2)_2$, —$CO_2R^2$, —CO—$N(R^2)_2$, —CN, phenyl, benzyl, $C_1$-$C_6$ alkoxy, $C_3$-$C_8$ cycloalkyl, 5- to 6-membered heteroaryl, 3- to 6-membered heterocyclyl, —$SO_2R^2$, —$SR^2$, —$SOR^2$, —PO$(OR^2)_2$, and —PO$(R^2)_2$;

each $R^2$ is independently selected from hydrogen, $C_1$-$C_6$ alkyl (optionally substituted with 1-6 groups independently selected from halogen), and $C_6$-$C_{10}$ aryl (optionally substituted with $C_1$-$C_6$ alkoxy, which is optionally substituted with 1-6 groups independently selected from halogen);

Z is selected from

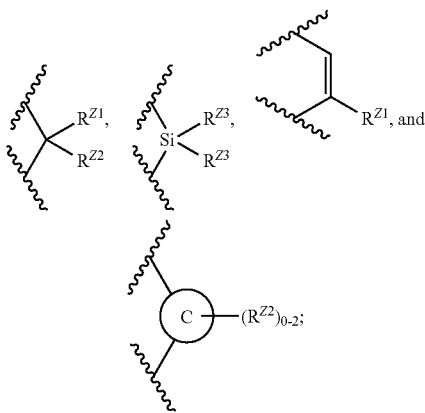

wherein Ring C is selected from $C_6$-$C_{10}$ aryl and 5- to 10-membered heteroaryl;

$R^{Z1}$ is selected from hydrogen, —CN, $C_1$-$C_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

$R^{Z2}$ is selected from hydrogen, halogen, and hydroxy, or $R^{Z1}$ and $R^{Z2}$ taken together form a group selected from oxo and =N—OH;

each $R^{Z3}$ is independently selected from hydroxy, $C_1$-$C_6$ alkoxy, $C_1$-$C_6$ alkyl, $C_1$-$C_6$ haloalkyl, and $C_6$-$C_{10}$ aryl; or two instances of $R^{Z3}$ are taken together to form a 3- to 6-membered heterocyclyl;

n is selected from 4, 5, 6, 7, and 8; and
m is selected from 0, 1, 2, and 3.

In some embodiments, X is —O—.

In some embodiments, each $R^Y$ is independently selected from hydrogen, halogen, $C_1$-$C_6$ alkyl (optionally substituted with 1-3 groups independently selected from hydroxy and Q), $C_3$-$C_8$ cycloalkyl, and —$OR^{Y1}$, wherein Q and $R^{Y1}$ are as defined above. In some embodiments, —$OR^{Y1}$ is —OH.

In some embodiments, each Q is independently selected from $C_3$-$C_8$ cycloalkyl and $C_6$-$C_{10}$ aryl optionally substituted with 1-3 groups independently selected from halogen and $C_1$-$C_6$ alkyl. In some embodiments, each Q is independently selected from:

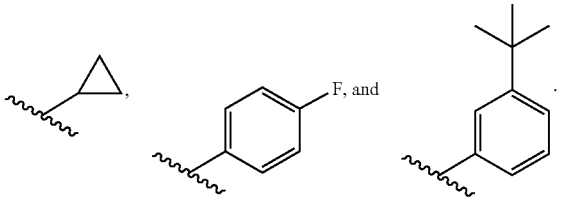

In some embodiments, each $R^Y$ is independently selected from: hydrogen, fluorine,

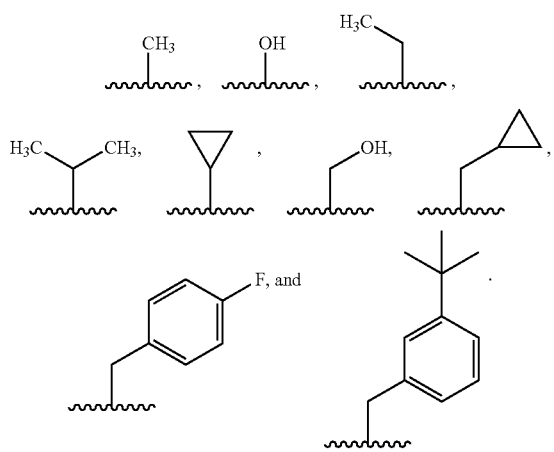

In some embodiments, Ring B is selected from $C_3$-$C_8$ cycloalkyl and phenyl optionally substituted with 1-3 groups independently selected from halogen. In some embodiments, Ring B is selected from:

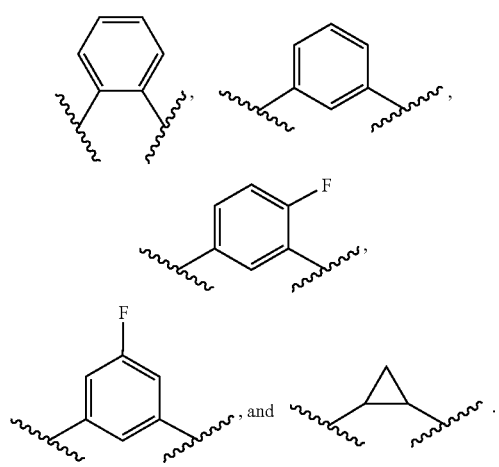

In some embodiments, n is selected from 4, 5, and 6.

In some embodiments, —$(Y)_n$— is a group selected from:

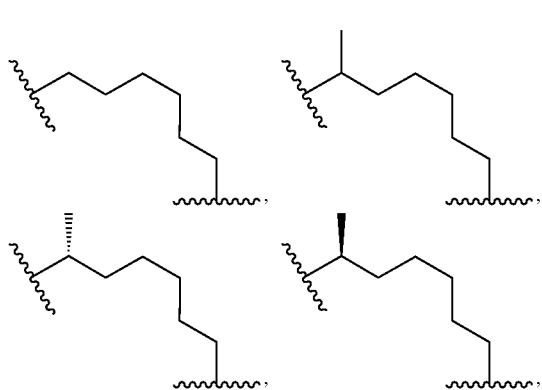

-continued

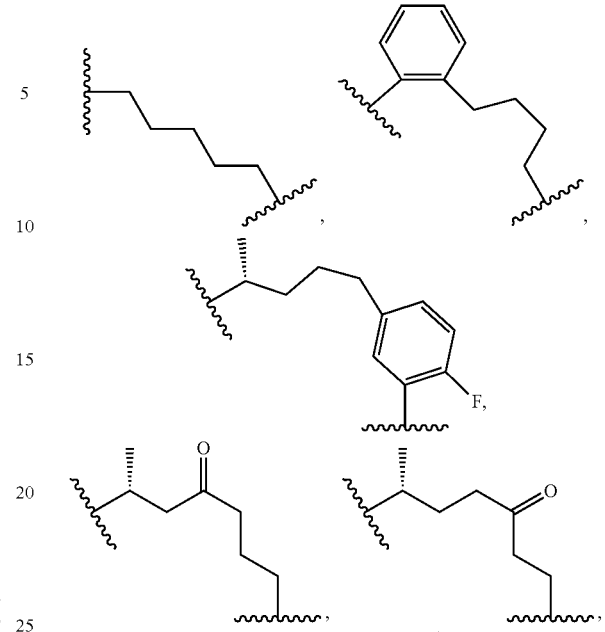

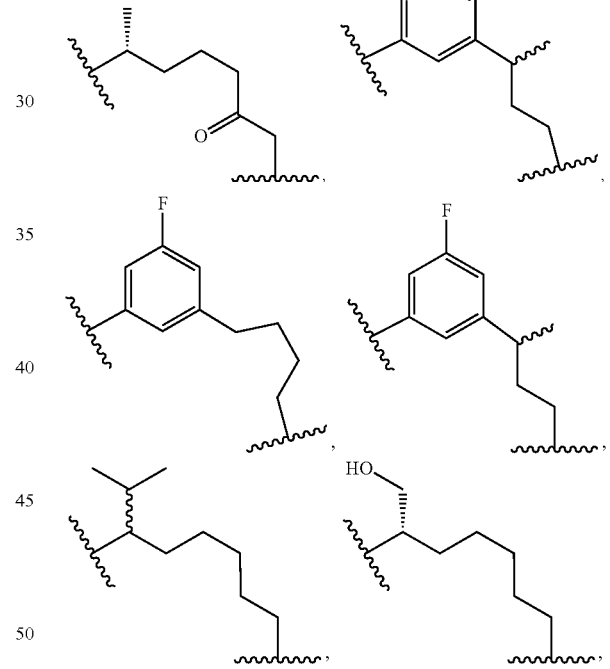

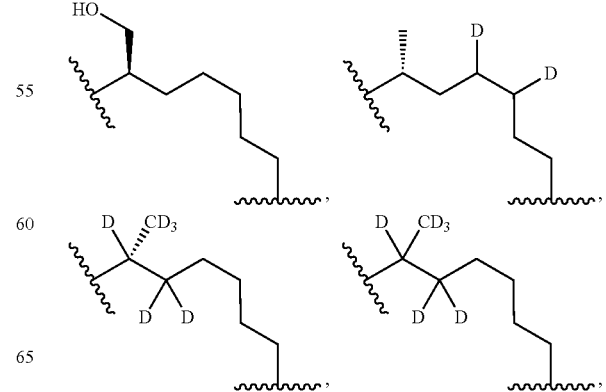

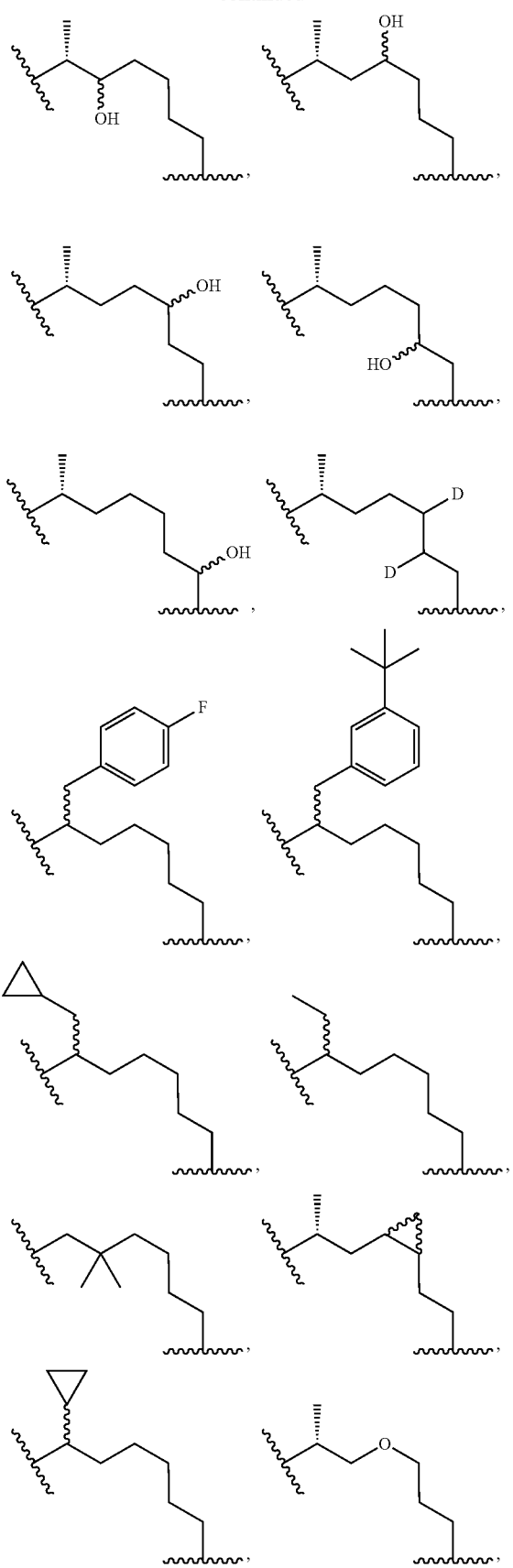

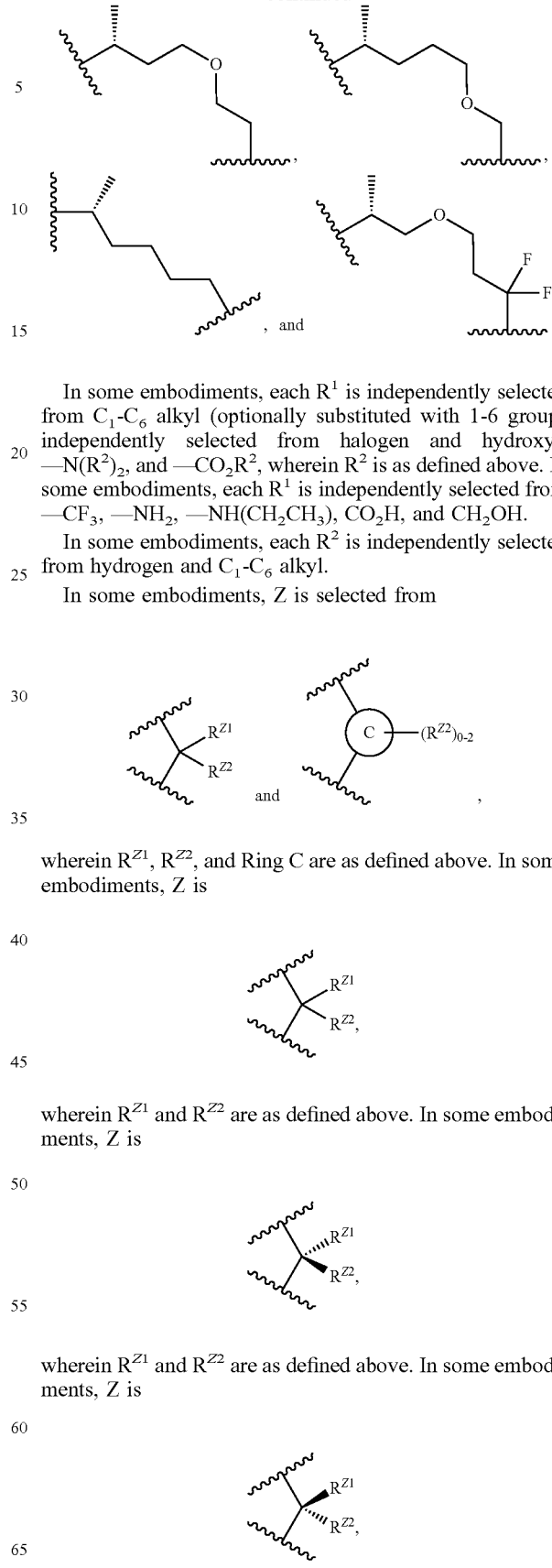

In some embodiments, each $R^1$ is independently selected from $C_1$-$C_6$ alkyl (optionally substituted with 1-6 groups independently selected from halogen and hydroxy), —N($R^2$)$_2$, and —CO$_2$$R^2$, wherein $R^2$ is as defined above. In some embodiments, each $R^1$ is independently selected from —CF$_3$, —NH$_2$, —NH(CH$_2$CH$_3$), CO$_2$H, and CH$_2$OH.

In some embodiments, each $R^2$ is independently selected from hydrogen and $C_1$-$C_6$ alkyl.

In some embodiments, Z is selected from

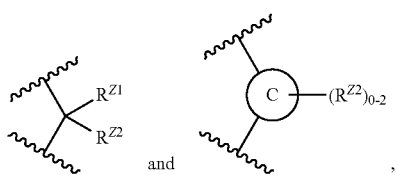

and wherein $R^{Z1}$, $R^{Z2}$, and Ring C are as defined above. In some embodiments, Z is

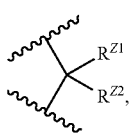

wherein $R^{Z1}$ and $R^{Z2}$ are as defined above. In some embodiments, Z is

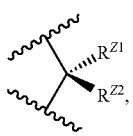

wherein $R^{Z1}$ and $R^{Z2}$ are as defined above. In some embodiments, Z is


wherein $R^{Z1}$ and $R^{Z2}$ are as defined above. In some embodiments, Z is

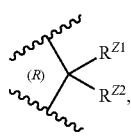

wherein $R^{Z1}$ and $R^{Z2}$ are as defined above, and wherein (R) refers to the stereochemical designation of the central carbon atom under the Cahn-Ingold-Prelog convention. In some embodiments, Z is

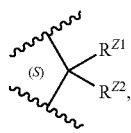

wherein $R^{Z1}$ and $R^{Z2}$ are as defined above, and wherein (S) refers to the stereochemical designation of the central carbon atom under the Cahn-Ingold-Prelog convention.

In some embodiments, the group:

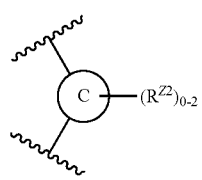

is selected from:

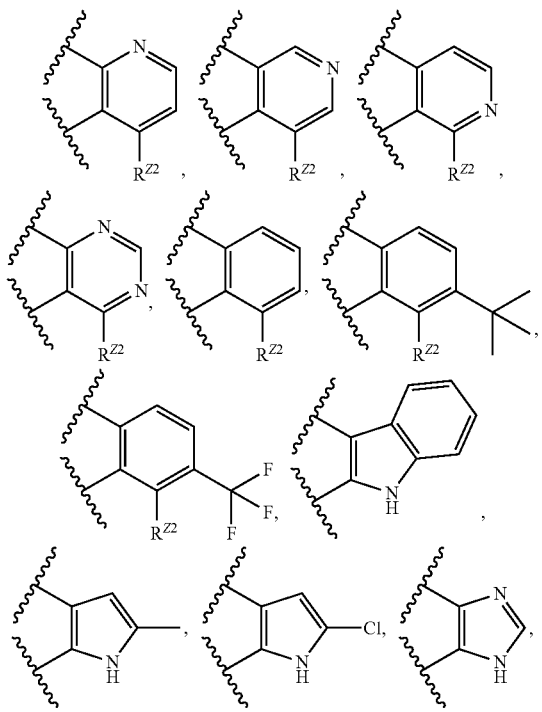

-continued

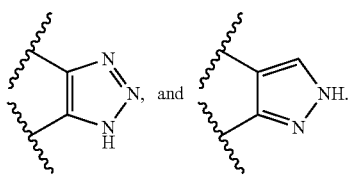

In some embodiments, the group:

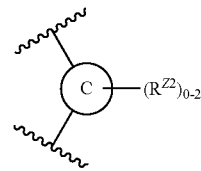

is selected from:

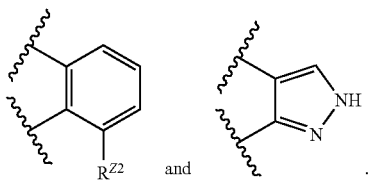

In some embodiments, $R^{Z1}$ is selected from hydrogen and $C_1$-$C_6$ alkyl (optionally substituted with 1-3 groups selected from halogen). In some embodiments, $R^{Z1}$ is selected from hydrogen and —$CF_3$. In some embodiments, $R^{Z1}$ is —$CF_3$.

In some embodiments, $R^{Z2}$ is hydroxy.

In some embodiments, Z is selected from:

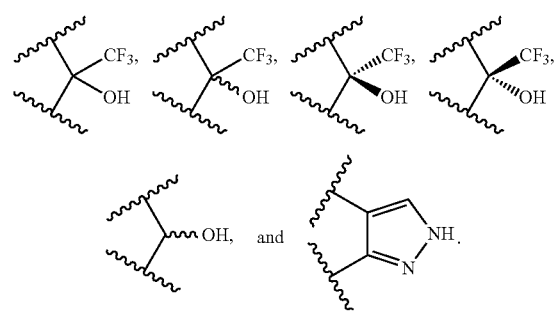

In some embodiments, Z is

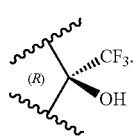

In some embodiments, Z is

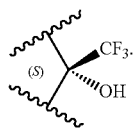

In some embodiments, Z is

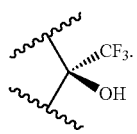

In some embodiments, Z is

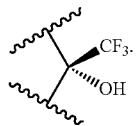

In some embodiments, m is selected from 1 and 2.

In some embodiments, compounds of the invention are encompassed by Formula I'

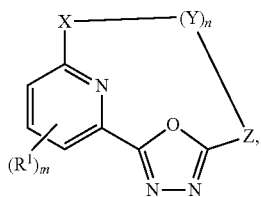

and deuterated derivatives and pharmaceutically acceptable salts thereof, wherein:

X is —O—;

each Y is independently selected from —C($R^Y$)$_2$—, —O—, and

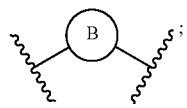

each $R^Y$ is independently selected from hydrogen and $C_1$-$C_6$ alkyl (optionally substituted with 1-3 groups independently selected from hydroxy and Q);

Ring B is selected from $C_3$-$C_8$ cycloalkyl groups:

each Q is independently selected from $C_3$-$C_8$ cycloalkyl and $C_6$-$C_{10}$ aryl optionally substituted with 1-3 groups independently selected from halogen and $C_1$-$C_6$ alkyl, each $R^1$ is independently selected from $C_1$-$C_6$ alkyl (optionally substituted with 1-6 groups independently selected from halogen) and —NH$_2$;

Z is

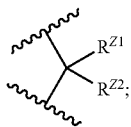

$R^{Z1}$ is selected from $C_1$-$C_6$ alkyl (optionally substituted with 1-6 groups independently selected from halogen);

$R^{Z2}$ is hydroxy;

n is selected from 5 and 6; and m is 2.

In some embodiments, each Q of Formula I' is independently selected from:

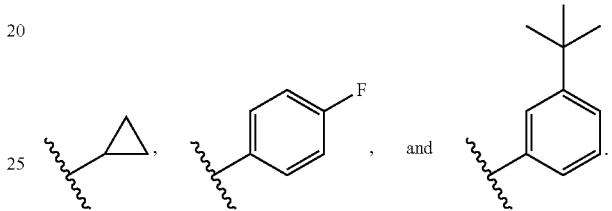

In some embodiments, each $R^Y$ of Formula I' is independently selected from: hydrogen,

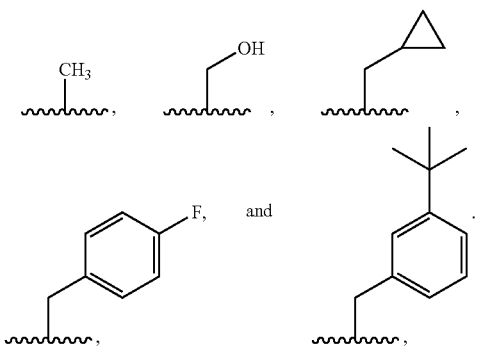

In some embodiments, Ring B of Formula I' is

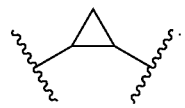

In some embodiments, —(Y)$_n$— of Formula I' is a group selected from:

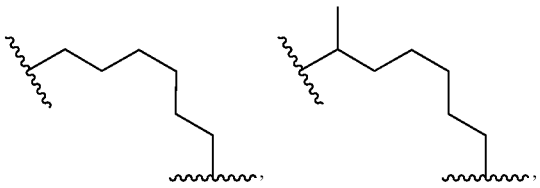

-continued

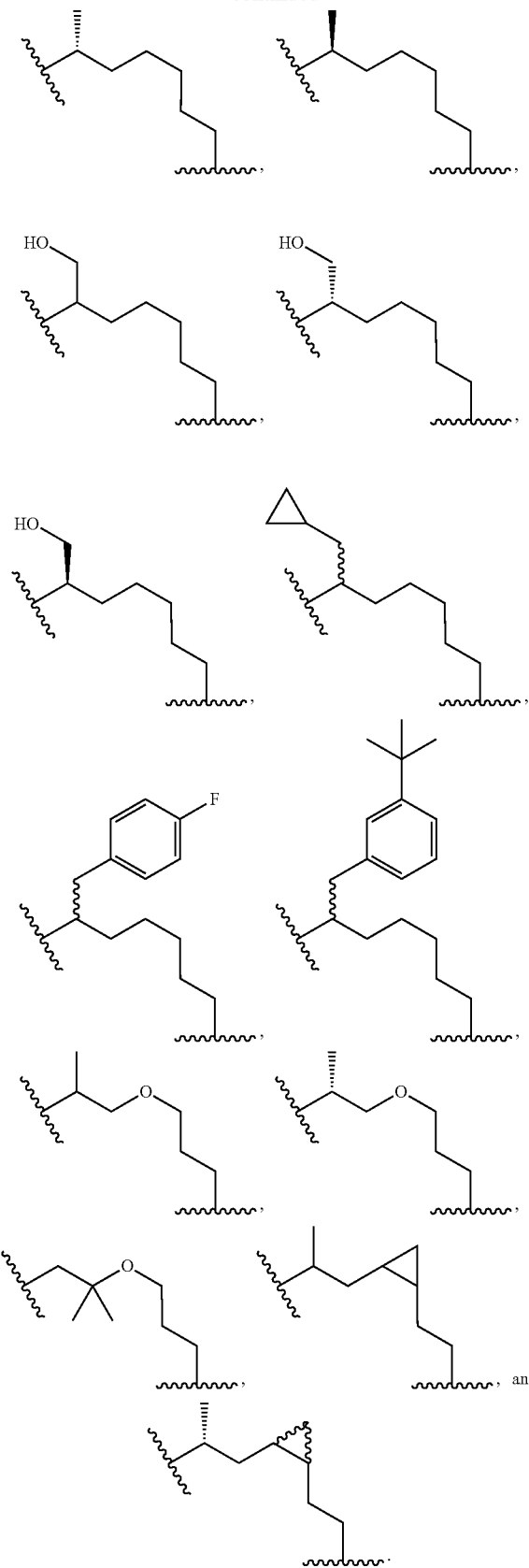

In some embodiments, $R^{Z1}$ in Formula I' is —$CF_3$.

In some embodiments, Z in Formula I' is

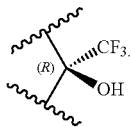

In some embodiments, Z in Formula I' is

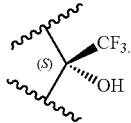

In some embodiments, n in Formula I' is 5. In some embodiments, n in Formula I' is 6.

In some embodiments, compounds of the invention are encompassed by Formula I":

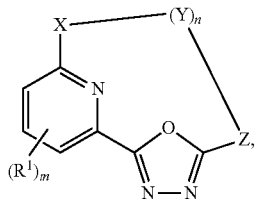

I"

and deuterated derivatives and pharmaceutically acceptable salts thereof, wherein:

X is selected from —O—, —S—, —SO—, and —$SO_2$—;
each Y is independently selected from —$C(R^Y)_2$—, —O—, —CO—, and

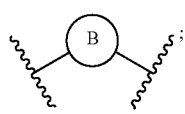

each $R^Y$ is independently selected from hydrogen, halogen, $C_1$-$C_6$ alkyl (optionally substituted with 1-3 groups independently selected from hydroxy and Q), $C_6$-$C_{10}$ aryl, 5- to 10-membered heteroaryl, —$OR^{Y1}$, —$CO_2R^{Y1}$, —$COR^{Y1}$, —$CON(R^{Y1})_2$, and —$NR^{Y1}$—; or two instances of $R^Y$ on the same atom are taken together to form a ring selected from $C_3$-$C_8$ cycloalkyl and 3- to 6-membered heterocyclyl; or two instances of $R^Y$, one of which is on one atom and the second of which is on an adjacent atom, are taken together to form a pi bond;

each $R^Y$ is independently selected from hydrogen, halogen, $C_1$-$C_6$ alkyl (optionally substituted with 1-3 groups independently selected from hydroxy and Q), $C_6$-$C_{10}$ aryl, 5- to 10-membered heteroaryl, —$OR^{Y1}$, —$CO_2R^{Y1}$, —$COR^{Y1}$, —$CON(R^{Y1})_2$, and —$NR^{Y1}$—; or two instances of $R^Y$, one of which is on one atom and the second of which is on an adjacent atom, are taken together to form a pi bond;

each $R^{Y1}$ is independently selected from hydrogen and $C_1$-$C_6$ alkyl, or two instances of $R^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);
each Q is independently selected from:
C$_1$-C$_6$ alkyl optionally substituted with 1-3 groups independently selected from:
  halogen,
  oxo,
  C$_6$-C$_{10}$ aryl (optionally substituted with 1-3 groups independently selected from halogen and —OCF$_3$), and
  C$_3$-C$_8$ cycloalkyl,
C$_3$-C$_8$ cycloalkyl optionally substituted with 1-3 groups independently selected from:
  halogen,
  CN,
  C$_1$-C$_6$ alkyl (optionally substituted with 1-3 groups independently selected from halogen, —NH$_2$, and —NHCOMe),
  C$_1$-C$_6$ alkoxy,
  C$_6$-C$_{10}$ aryl (optionally substituted with 1-3 groups independently selected from C$_1$-C$_6$ alkyl), and
  C$_3$-C$_8$ cycloalkyl,
C$_6$-C$_{10}$ aryl optionally substituted with 1-3 groups independently selected from:
  halogen,
  CN,
  C$_1$-C$_6$ alkyl (optionally substituted with 1-3 groups independently selected from halogen and hydroxy),
  C$_1$-C$_6$ alkoxy optionally substituted with 1-4 groups independently selected from:
    halogen,
    C$_3$-C$_8$ cycloalkyl (optionally substituted with CF$_3$),
    C$_3$-C$_8$ cycloalkyl (optionally substituted with 1-3 groups independently selected from halogen, CF$_3$, OCF$_3$, and C$_1$-C$_6$ alkyl), and
  C$_6$-C$_{10}$ aryl,
5- to 10-membered heteroaryl optionally substituted with 1-3 groups independently selected from:
  halogen,
  C$_1$-C$_6$ alkyl (optionally substituted with 1-3 groups independently selected from halogen),
  C$_3$-C$_8$ cycloalkyl (optionally substituted with 1-3 CF$_3$ groups), and
  3- to 10-membered heterocyclyl,
3- to 10-membered heterocyclyl optionally substituted with 1-3 groups independently selected from:
  C$_1$-C$_6$ alkyl (optionally substituted with 1-3 groups independently selected from oxo and C$_3$-C$_8$ cycloalkyl), and
  oxo;
each is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;
each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);

Z is selected from

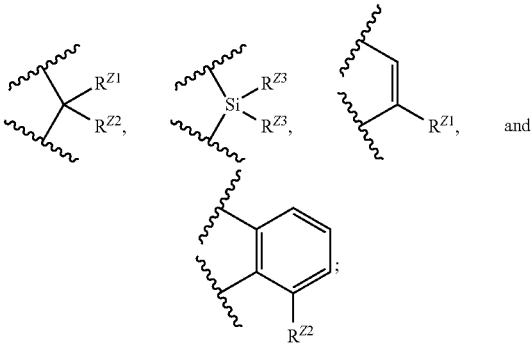

R$^{Z1}$ is selected from hydrogen, —CN, C$_1$-C$_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

R$^{Z2}$ is selected from hydrogen, halogen, and hydroxy, or R$^{Z1}$ and R$^{Z2}$ taken together form a group selected from oxo and =N—OH;

each R$^{Z3}$ is independently selected from hydroxy, C$_1$-C$_6$ alkoxy, C$_1$-C$_6$ alkyl, and C$_6$-C$_{10}$ aryl; or two instances of R$^{Z3}$ are taken together to form a 3- to 6-membered heterocyclyl;

n is selected from 4, 5, 6, and 7; and m is selected from 0, 1, 2, and 3.

In some embodiments, X in Formula I" is —O—.

In some embodiments, each Y in Formula I" is independently selected from —C(R$^Y$)$_2$—, —CO—, and

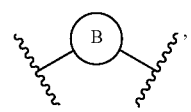

wherein R$^Y$ and Ring B are as defined for Formula I".

In some embodiments, each Y in Formula I" is —C(R$^Y$)$_2$—, wherein R$^Y$ is as defined for Formula I".

In some embodiments, each R$^Y$ in Formula I" is independently selected from hydrogen, C$_1$-C$_6$ alkyl (optionally substituted with 1-3 groups independently selected from hydroxy and Q), and —OR$^{Y1}$, wherein R$^{Y1}$ and Q are as defined for Formula I".

In some embodiments, each R$^Y$ in Formula I" is independently selected from: hydrogen,

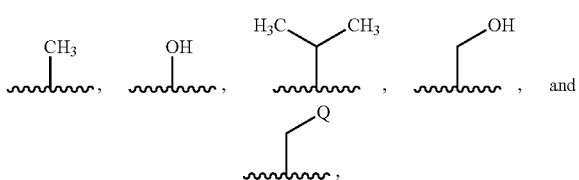

wherein Q is as defined for Formula I".-

In some embodiments, each Q in Formula I'' is independently selected from:
C$_3$-C$_8$ cycloalkyl,
C$_6$-C$_{10}$ aryl optionally substituted with 1-3 groups independently selected from halogen and C$_1$-C$_6$ alkyl.
In some embodiments, each Q in Formula I'' is independently selected from:

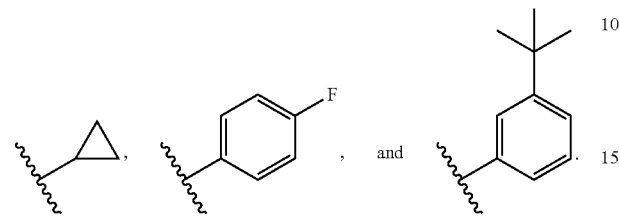

In some embodiments, Ring B in Formula I'' is selected from C$_6$-C$_{10}$ aryl optionally substituted with 1-3 groups independently selected from halogen.
In some embodiments, Ring B in Formula I'' is selected from:

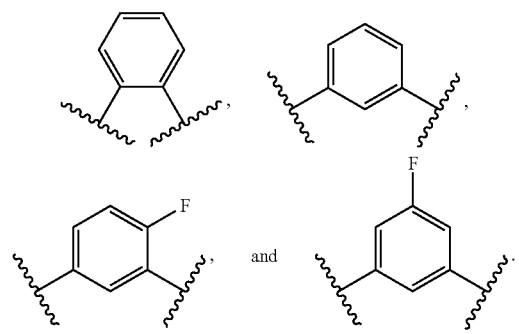

In some embodiments, —(Y)$_n$— in Formula I'' is a group selected from:

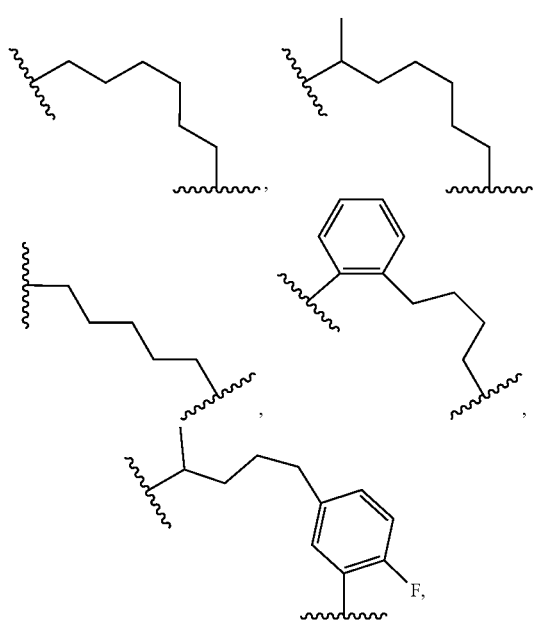

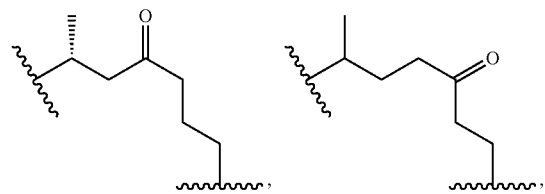

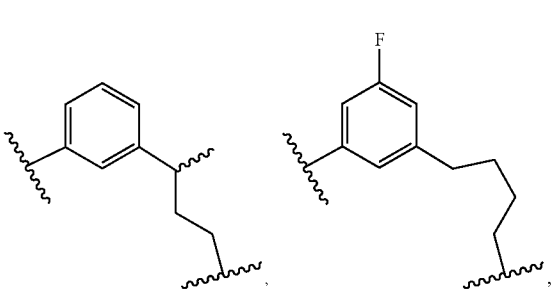

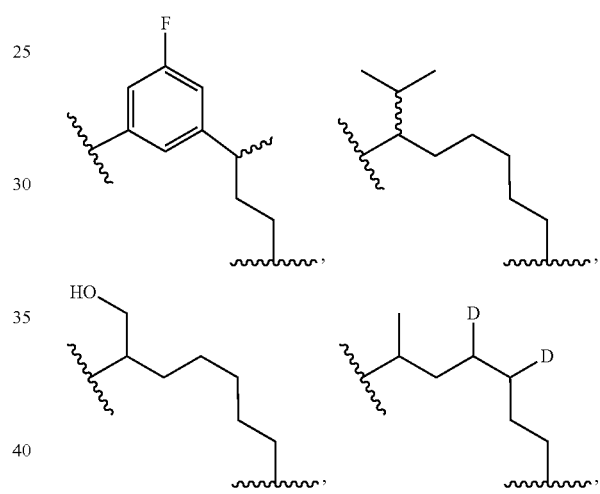

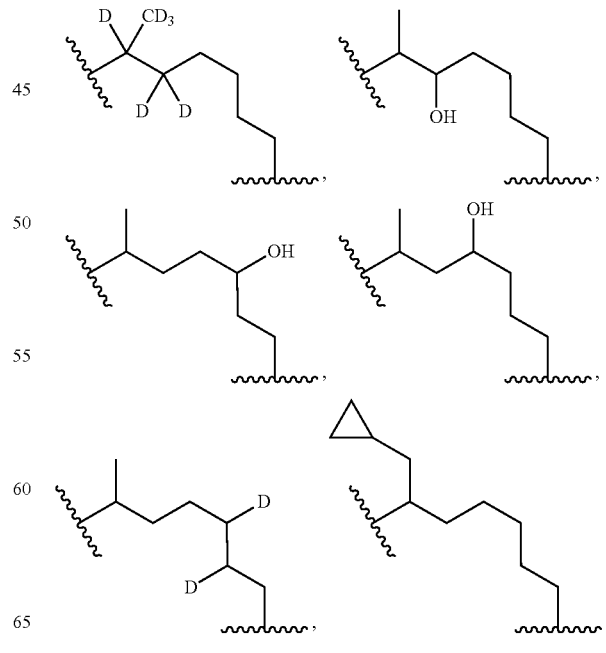

-continued

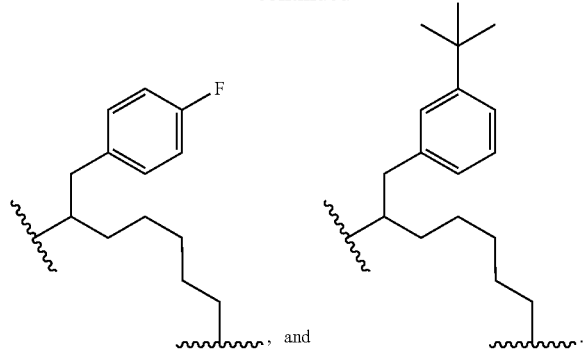

In some embodiments, each in Formula I" is independently selected from $C_1$-$C_6$ alkyl (optionally substituted with 1-3 groups independently selected from halogen) and —N($R^2$)$_2$, wherein $R^2$ is as defined for Formula I". In some embodiments, each $R^1$ in Formula I" is independently selected from —CF$_3$ and —N($R^2$)$_2$, wherein $R^2$ is as defined for Formula I".

In some embodiments, each $R^2$ in Formula I" is independently selected from hydrogen, $C_1$-$C_6$ alkyl (optionally substituted with 1-3 groups independently selected from halogen), and $C_6$-$C_{10}$ aryl (optionally substituted with $C_1$-$C_6$ alkoxy optionally substituted with 1-3 groups independently selected from halogen). In some embodiments, each $R^2$ in Formula I" is independently selected from hydrogen and $C_1$-$C_6$ alkyl. In some embodiments, each $R^2$ in Formula I" is hydrogen.

In some embodiments, Z in Formula I" is

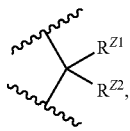

wherein $R^{Z1}$ and $R^{Z2}$ are as defined for Formula I". In some embodiments, Z in Formula I" is

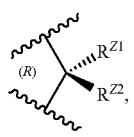

wherein $R^{Z1}$ and $R^{Z2}$ are as defined for Formula I". In some embodiments, Z in Formula I" is

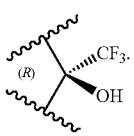

In some embodiments, $R^{Z1}$ in Formula I" is selected from $C_1$-$C_6$ alkyl (optionally substituted with 1-3 groups selected from halogen). In some embodiments, $R^{Z1}$ in Formula I" is —CF$_3$.

In some embodiments, $R^{Z2}$ in Formula I" is hydroxy.

In some embodiments, n in Formula I, I', and/or I" is selected from 4, 5, and 6. In some embodiments, n in Formula I, I', and/or I" is 5. In some embodiments, n in Formula I, I', and/or I" is 6.

In some embodiments, m in Formula I, I', and/or I" is selected from 1 and 2. In some embodiments, m in Formula I, I', and/or I" is 1. In some embodiments, m in Formula I, I', and/or I" is 2.

Another aspect of the invention provides pharmaceutical compositions comprising at least one compound chosen from the novel compounds disclosed herein, pharmaceutically acceptable salts thereof, and deuterated derivatives of any of the foregoing, and at least one pharmaceutically acceptable carrier, which compositions may further include at least one additional active pharmaceutical ingredient. Thus, another aspect of the invention provides methods of treating the CFTR-mediated disease cystic fibrosis comprising administering at least one of compound chosen from the novel compounds disclosed herein, pharmaceutically acceptable salts thereof, and deuterated derivatives of any of the foregoing, and at least one pharmaceutically acceptable carrier, optionally as part of a pharmaceutical composition comprising at least one additional component, to a subject in need thereof.

In certain embodiments, the pharmaceutical compositions of the invention comprise at least one compound chosen from compounds of Formulae I, I', I", I''', Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof. In some embodiments, compositions comprising at least one compound chosen from compounds of Formulae I, I', I", I''', Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof may optionally further comprise at least one compound chosen from Compound II, Compound IV, Compound V, Compound VI, Compound VII, Compound VIII, Compound IX, Compound X, and pharmaceutically acceptable salts and deuterated derivatives thereof.

Another aspect of the invention provides methods of treating the CFTR-mediated disease cystic fibrosis comprising administering to a patient in need thereof at least one compound chosen from the novel compounds disclosed herein, pharmaceutically acceptable salts thereof, and deuterated derivatives of any of the foregoing, and optionally further administering one or more additional CFTR modulating agents selected from (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide (Compound II), N-[2,4-bis(1,1-dimethylethyl)-5-hydroxyphenyl]-1,4-dihydro-4-oxoquinoline-3-carboxamide (Compound III) or N-(2-(tert-butyl)-5-hy droxy-4-(2-(methyl-d3)propan-2-yl-1,1,1,3,3,3-d6)phenyl)-4-oxo-1,4-dihydroquinoline-3-carboxamide (Compound III-d), 3-(6-(1-(2,2-difluorobenzo[d][1,3]dioxol-5-yl)cyclopropane carboxamido)-3-methylpyridin-2-yl)benzoic acid (Compound IV), N-(1,3-dimethylpyrazol-4-yl)sulfonyl-6-[3-(3,3,3-trifluoro-2,2-dimethyl-propoxy) pyrazol-1-yl]-2-[(4S)-2,2,4-trimethylpyrrolidin-1-yl] pyridine-3-carboxamide (Compound V), N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide (Compound VI), (14S)-8-[3-(2-{dispiro[2.0.2.1]heptan-7-yl}ethoxy)-1H-pyrazol-1-yl]-12,12-dimethyl-2$\lambda^6$-thia-3,9,11,18,23-pentaazatetracyclo [17.3.1.1$^{11,14}$.0$^{5,10}$]tetracosa-1(22),5,7,9,19(23),20- hexaene-2,2,4-trione (Compound VII), (11R)-6-(2,6-dimethylphenyl)-11-(2-methylpropyl)-12-{spiro[2.3]hexan-5-yl}-9-oxa-2λ⁶-thia-3,5,12,19-tetraazatricyclo[12.3.1.1⁴,⁸]nonadeca-1(17),4(19),5,7,14(18),15-hexaene-2,2,13-trione (Compound VIII); N-(benzenesulfonyl)-6-(3-fluoro-5-isobutoxy-phenyl)-2-[(4S)-2,2,4-trimethylpyrrolidin-1-yl]pyridine-3-carboxamide (Compound IX), and N-[(6-amino-2-pyridyl)sulfonyl]-6-(3-fluoro-5-isobutoxy-phenyl)-2-[(4S)-2,2,4-trimethylpyrrolidin-1-yl]pyridine-3-carboxamide (Compound X).

Another aspect of the invention provides methods of treating the CFTR-mediated disease cystic fibrosis comprising administering to a patient in need thereof at least one compound chosen from the novel compounds disclosed herein, pharmaceutically acceptable salts thereof, and deuterated derivatives of any of the foregoing, and optionally further administering one or more additional CFTR modulating agents selected from:

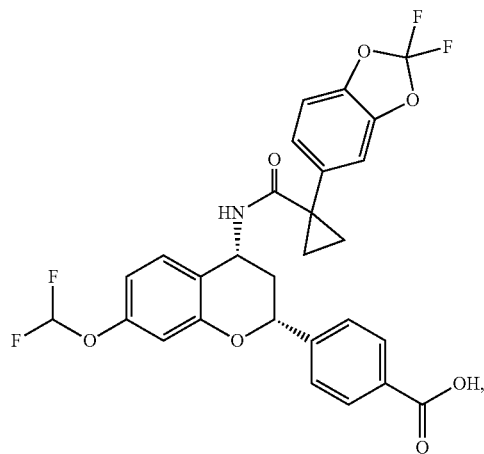

(galicaftor or ABBV-2222)

disclosed in United States Patent Application Publication No. 2016-0120841;

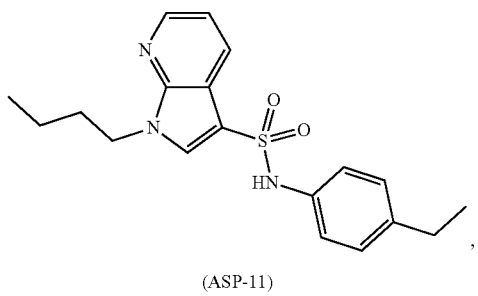 [SMILES: CCCCn1cc(S(=O)(=O)Nc2ccc(CC)cc2)c2cccnc21]

(ASP-11)

disclosed in *Journal of Cystic Fibrosis* (2018), 17(5), 595-606, and:

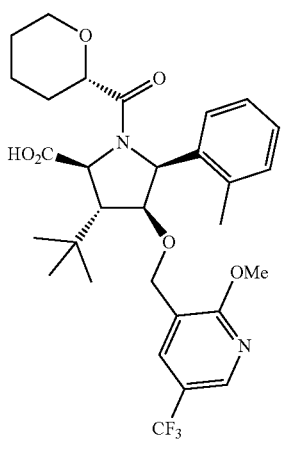

(ABBV-3221)

disclosed in WO 2018/065921;

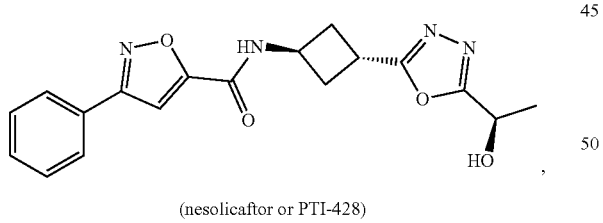

(nesolicaftor or PTI-428)

disclosed in WO 2016/105485. In one embodiment, the additional CFTR modulating agent is ASP-11. In one embodiment, the additional CFTR modulating agent is PTI-428.

Another aspect of the invention provides methods of treating the CFTR-mediated disease cystic fibrosis comprising administering to a patient in need thereof at least one compound chosen from the novel compounds disclosed herein, pharmaceutically acceptable salts thereof, and deuterated derivatives of any of the foregoing, and optionally further administering one or more additional CFTR modulating agents selected from:

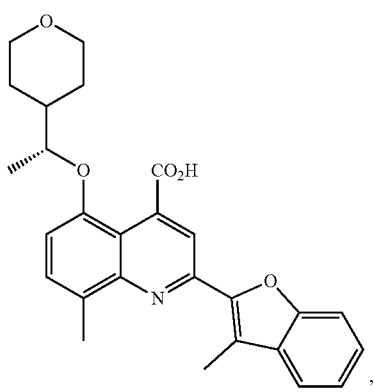

(posenacaftor or PTI-801)

disclosed in WO 2017/062581; ABBV-2851, disclosed in WO 2017/009804; GLPG2737, disclosed in United States Patent Application Publication No. 2017-0101405; ABBV-3748; ABBV-3903; and ABBV-119.

Another aspect of the invention provides compounds of Formulae I, I', I", I"', Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof, for use in any of the methods described herein.

BRIEF DESCRIPTION OF THE FIGURES

FIG. 6A provides a thermogravimetric analysis (TGA) curve for Compound 11 heptane solvate (Drying Condition 1).

DEFINITIONS

Figure 1:
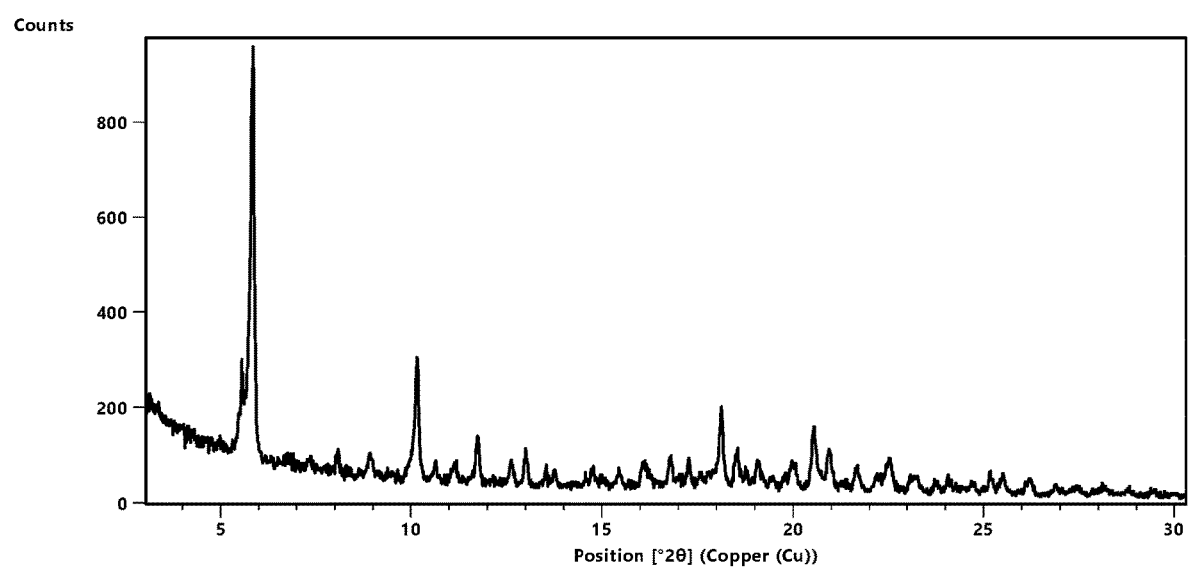
FIG. 1 provides an X-ray power diffraction (XRPD) pattern of Compound 11 heptane solvate.

"Compound II" as used herein, refers to (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide, which can be depicted with the following structure:

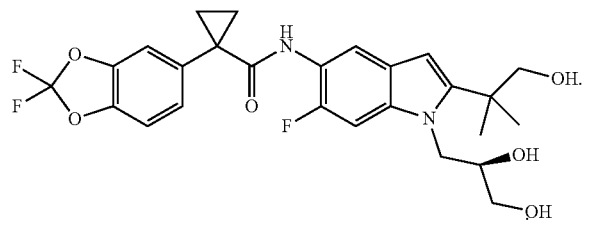

II

Compound II may be in the form of a pharmaceutically acceptable salt. Compound II and methods of making and using Compound II are disclosed in WO 2010/053471, WO 2011/119984, WO 2011/133751, WO 2011/133951, and WO 2015/160787, each incorporated herein by reference.

"Compound III" as used throughout this disclosure refers to N-(5-hydroxy-2,4-di-tert-butyl-phenyl)-4-oxo-1H-quinoline-3-carboxamide which is depicted by the structure:

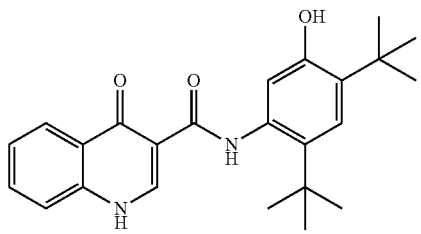

III

Compound III may also be in the form of a pharmaceutically acceptable salt. Compound III and methods of making and using Compound III are disclosed in WO 2006/002421, WO 2007/079139, WO 2010/108162, and WO 2010/019239, each incorporated herein by reference.

In some embodiments, a deuterated derivative of Compound III (Compound III-d) is employed in the compositions and methods disclosed herein. A chemical name for Compound III-d is N-(2-(tert-butyl)-5-hydroxy-4-(2-(methyl-d3) propan-2-yl-1,1,1,3,3,3-d6)phenyl)-4-oxo-1,4-dihydroquinoline-3-carboxamide, as depicted by the structure:

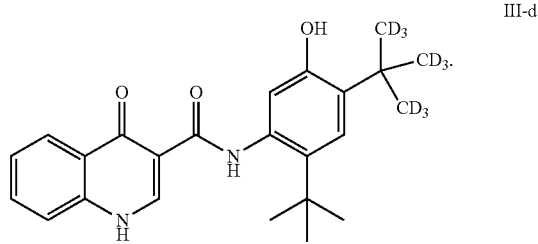 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]

III-d

Compound III-d may be in the form of a pharmaceutically acceptable salt. Compound III-d and methods of making and using Compound III-d are disclosed in WO 2012/158885, WO 2014/078842, and U.S. Pat. No. 8,865,902, incorporated herein by reference.

"Compound IV" as used herein, refers to 3-(6-(1-(2,2-difluorobenzo[d][1,3]dioxol-5-yl)cyclopropanecarboxamido)-3-methylpyridin-2-yl)benzoic acid, which is depicted by the chemical structure:

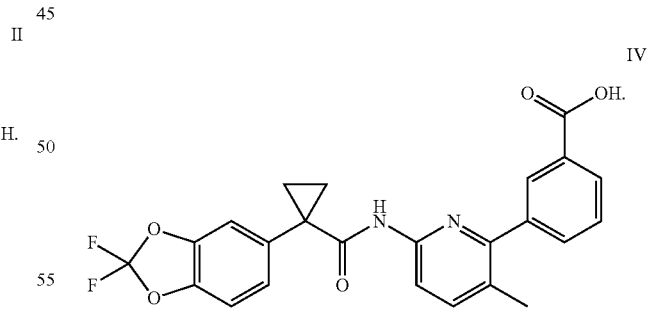

IV

Compound IV may be in the form of a pharmaceutically acceptable salt. Compound IV and methods of making and using Compound IV are disclosed in WO 2007/056341, WO 2009/073757, and WO 2009/076142, incorporated herein by reference.

"Compound V" as used herein, refers to N-(1,3-dimethylpyrazol-4-yl)sulfonyl-6-[3-(3,3,3-trifluoro-2,2-dimethylpropoxy)pyrazol-1-yl]-2-[(4S)-2,2,4-tri methylpyrroli din-1-yl]pyridine-3-carboxamide, which is depicted by the chemical structure:

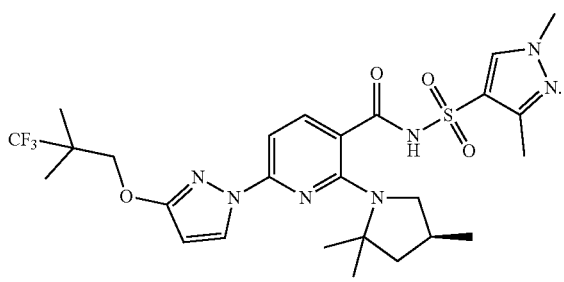

V

Compound V may be in the form of a pharmaceutically acceptable salt. Compound V and methods of making and using Compound V are disclosed in WO 2018/107100 and WO 2019/113476, incorporated herein by reference.

"Compound VI" as used herein, refers to N-(benzenesulfonyl)-6-[3-[2-[1-(trifluoromethyl) cyclopropyl]ethoxy] pyrazol-1-yl]-2-[(4S)-2,2,4-trimethylpyrrolidin-1-yl]pyridine-3-carboxamide, which is depicted by the chemical structure:

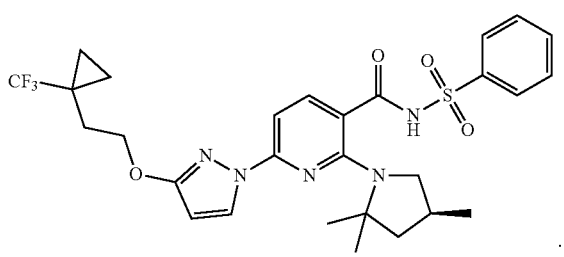

VI

Compound VI may be in the form of a pharmaceutically acceptable salt. Compound VI and methods of making and using Compound VI are disclosed in WO 2018/064632, incorporated herein by reference.

"Compound VII" as used herein, refers to (14S)-8-[3-(2-{dispiro[2.0.2.1]heptan-7-yl}ethoxy)-1H-pyrazol-1-yl]-12,12-dimethyl-2$\lambda^6$-thia-3,9,11,18,23-p entaazatetracyclo [17.3.1.111,14.05,10]tetracosa-1(22),5,7,9,19(23),20-hexaene-2,2,4-trione, which is depicted by the chemical structure:

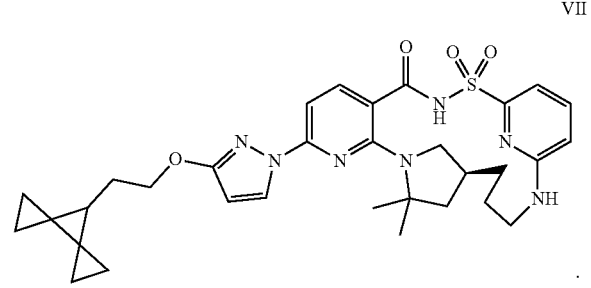 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

VII

Compound VII may be in the form of a pharmaceutically acceptable salt. Compound VII and methods of making and using Compound VII are disclosed in WO 2019/152940 and United States Provisional Patent Application No. 62/886,660, incorporated herein by reference.

"Compound VIII" as used herein, refers to (11R)-6-(2,6-dimethylphenyl)-11-(2-methylpropyl)-12-{spiro[2.3]hexan-5-yl}-9-oxa-2$\lambda^6$-thia-3,5,12,19-tetraazatricyclo[12.3.1.14,8]nonadeca-1(17),4(19),5,7,14(18),15-hexaene-2,2,13-trione, which is depicted by the chemical structure:

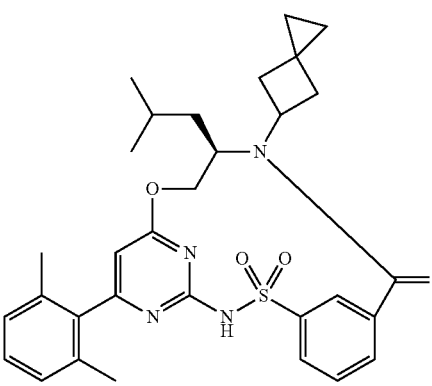

VIII

Compound VIII may be in the form of a pharmaceutically acceptable salt. Compound VIII and methods of making and using Compound VIII are disclosed in PCT/US2020/026331, incorporated herein by reference.

"Compound IX" as used herein, refers to N-(benzenesulfonyl)-6-(3-fluoro-5-isobutoxy-phenyl)-2-[(4S)-2,2,4-trimethylpyrrolidin-1-yl]pyridine-3-carboxamide, which is depicted by the chemical structure:

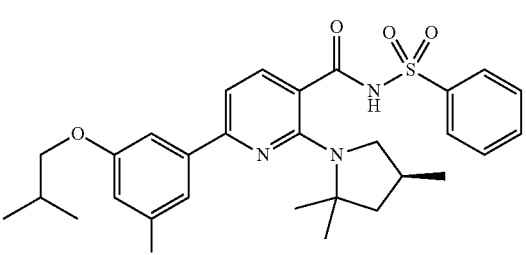

IX

Compound IX may be in the form of a pharmaceutically acceptable salt. Compound IX and methods of making and using Compound IX are disclosed in WO 2016/057572, incorporated herein by reference.

"Compound X" as used herein, refers to N-[(6-amino-2-pyridyl)sulfonyl]-6-(3-fluoro-5 s obutoxy-phenyl)-2-[(4S)-2,2,4-trimethylpyrrolidin-1-yl]pyridine-3-carboxamide, which is depicted by the chemical structure:

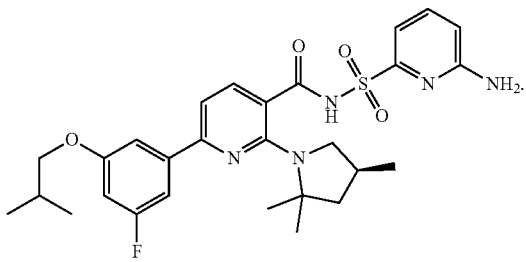

Compound X may be in the form of a pharmaceutically acceptable salt. Compound X and methods of making and using Compound X are disclosed in WO 2016/057572, incorporated herein by reference.

As used herein, the term "alkyl" refers to a saturated, branched or unbranched aliphatic hydrocarbon containing carbon atoms (such as, for example, 1, 2, 3, 4, 5, 6, 7, 8, 9, 10, 11, 12, 13, 14, 15, 16, 17, 18, 19, or 20 carbon atoms). Alkyl groups may be substituted or unsubstituted.

As used herein, the term "pi bond" refers to a covalent bond formed by the p orbitals of adjacent atoms. Pi bonds exist where there is a multiple bond, i.e., a double or triple bond, between two atoms. For example, a carbon-carbon double bond consists of one pi bond, and a carbon-carbon triple bond consists of two pi bonds.

As used herein, the term "haloalkyl group" refers to an alkyl group substituted with one or more halogen atoms.

The term "alkoxy" as used herein refers to an alkyl or cycloalkyl covalently bonded to an oxygen atom. Alkoxy groups may be substituted or unsubstituted.

As used herein, the term "haloalkoxyl group" refers to an alkoxy group substituted with one or more halogen atoms.

As used herein, "cycloalkyl" refers to a cyclic, bicyclic, tricyclic, or polycyclic non-aromatic hydrocarbon groups having 3 to 12 carbons (such as, for example 3-10 carbons). "Cycloalkyl" groups encompass monocyclic, bicyclic, tricyclic, bridged, fused, and spiro rings, including mono spiro and dispiro rings. Non-limiting examples of cycloalkyl groups are cyclopropyl, cyclobutyl, cyclopentyl, cyclohexyl, adamantyl, norbornyl, and dispiro[2.0.2.1]heptane. Cycloalkyl groups may be substituted or unsubstituted.

The term "heteroaryl ring" as used herein refers to an aromatic ring comprising at least one ring atom that is a heteroatom, such as O, N, or S.

As used herein, the terms "heterocyclyl ring" and "heterocyclyl" refer to a non-aromatic hydrocarbon containing 3 to 12 atoms in a ring (such as, for example 3-10 atoms) comprising at least one ring atom that is a heteroatom, such as O, N, S, or Si. "Heterocyclyl" rings encompass monocyclic, bicyclic, tricyclic, polycyclic, bridged, fused, and spiro rings, including mono spiro and dispiro rings.

"Substituted" indicates that at least one hydrogen of the "substituted" group is replaced by a substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position.

Examples of protecting groups for nitrogen include, for example, t-butyl carbamate (Boc), benzyl (Bn), para-methoxybenzyl (PMB), tetrahydropyranyl (THP), 9-fluorenylmethyl carbamate (Fmoc), benzyl carbamate (Cbz), methyl carbamate, ethyl carbamate, 2,2,2-trichloroethyl carbamate (Troc), 2-trimethylsilylethyl carbamate (Teoc), allyl carbamate (Aloc or Alloc), formamide, acetamide, benzamide, allylamine, trifluoroacetamide, triphenylmethylamine, benzylideneamine, and p-toluenesulfonamide. A comprehensive list of nitrogen protecting groups can be found in Wuts, P. G. M. "Greene's Protective Groups in Organic Synthesis: Fifth Edition," 2014, John Wiley and Sons.

As used herein, "deuterated derivative(s)" means the same chemical structure, with one or more hydrogen atoms replaced by a deuterium atom. In some embodiments, the deuterated derivatives are compounds where one or more hydrogen atoms of an alkyl group are replaced by a deuterium atom.

As used herein, "CFTR" means cystic fibrosis transmembrane conductance regulator.

As used herein, the term "CFTR modulator" refers to a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface.

As used herein, the term "CFTR potentiator" refers to a compound that increases the channel activity of CFTR protein located at the cell surface, resulting in enhanced ion transport. The novel compounds disclosed herein are CFTR potentiators.

As used herein, the term "CFTR potentiator enhancer", "CFTR potentiation enhancer", and "CFTR co-potentiator" are used interchangeably and refer to a compound that enhances CFTR potentiation.

As used herein, the term "active pharmaceutical ingredient" ("API") or "therapeutic agent" refers to a biologically active compound.

As used herein, the term "one or more additional therapeutic agent(s) comprise(s)," includes the possibility that there is only one therapeutic agent.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment and will be ascertainable by one skilled in the art using known techniques (see, e.g., Lloyd (1999) The Art, Science and Technology of Pharmaceutical Compounding).

As used herein, the terms "treatment," "treating," and the like generally mean the improvement in one or more symptoms of CF or lessening the severity of CF or one or more symptoms of CF in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The terms "about" and "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent. The terms "about" and "approximately" may refer to an acceptable error for a particular value as determined by one of skill in the art, which depends in part on how the values is measured or determined. In some embodiments, the terms "about" and "approximately" mean within 20%, 15%, 10%, 5%, 4%, 3%, 2%, 1%, or 0.5% of a given value or range. As used herein, the symbol "~" appearing immediately before a numerical value has the same meaning as the terms "about" and "approximately."

As used herein, the term "solvent" refers to any liquid in which the product is at least partially soluble (solubility of product>1 g/L).

As used herein, the term "room temperature" or "ambient temperature" means 15° C. to 30° C.

It will be appreciated that certain compounds of this invention may exist as separate stereoisomers or enantiomers and/or mixtures of those stereoisomers or enantiomers. As used in the chemical structures disclosed herein, a "wedge" (◢) or "hash" (...) bond to a stereogenic atom indicates a chiral center of known absolute stereochemistry (i.e., one stereoisomer). As used in the chemical structures disclosed herein, a "wavy" bond (∿) to a stereogenic atom indicates a chiral center of unknown absolute stereochemistry (i.e., one stereoisomer). As used in the chemical structures disclosed herein, a "wavy" bond (∿) to a double-bonded carbon indicates a mixture of E/Z isomers. As used in the chemical structures disclosed herein, a ∕ ("straight") bond to a stereogenic atom indicates where there is a mixture (e.g., a racemate or enrichment). As used herein, two ∕ ("straight") bonds to a double-bonded carbon indicates that the double bond possesses the E/Z stereochemistry as drawn. As used in the chemical structures disclosed herein, a ⊥ (a "wavy" line perpendicular to a "straight" bond to group "A") indicates that group "A" is a substituent whose point of attachment is at the end of the bond that terminates at the "wavy" line. As used herein, a stereogenic atom that is notated with an (R) or (S) indicates the stereochemical designation of the stereogenic atom under the Cahn-Ingold-Prelog convention.

Certain compounds disclosed herein may exist as tautomers and both tautomeric forms are intended, even though only a single tautomeric structure is depicted. For example, a description of Compound A is understood to include its tautomer Compound B and vice versa, as well as mixtures thereof:

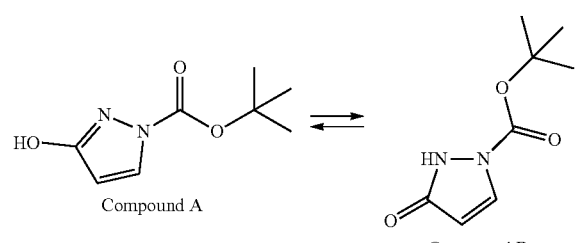

Compound A    Compound B

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. A "free base" form of a compound, for example, does not contain an ionically bonded salt.

The phrase "and pharmaceutically acceptable salts and deuterated derivatives thereof" is used interchangeably with "and pharmaceutically acceptable salts thereof and deuterated derivatives of any of the forgoing" in reference to one or more compounds or formulae of the invention. These phrases are intended to encompass pharmaceutically acceptable salts of any one of the referenced compounds, deuterated derivatives of any one of the referenced compounds, and pharmaceutically acceptable salts of those deuterated derivatives.

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form.

Suitable pharmaceutically acceptable salts are, for example, those disclosed in S. M. Berge, et al. *J. Pharmaceutical Sciences*, 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teoclate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^+(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

As used herein, the term "amorphous" refers to a solid material having no long-range order in the position of its molecules. Amorphous solids are generally supercooled liquids in which the molecules are arranged in a random manner so that there is no well-defined arrangement, e.g., molecular packing, and no long-range order. Amorphous solids are generally isotropic, i.e., exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material. In some embodiments, a solid material may comprise an amorphous compound, and the material may, for example, be characterized by a lack of sharp characteristic crystalline peak(s) in its XRPD spectrum (i.e., the material is not crystalline, but is amorphous, as determined by XRPD). Instead, one or several broad peaks (e.g., halos) may appear in the XRPD pattern of the material. See US 2004/0006237 for a comparison of XRPDs of an amorphous material and crystalline material. A solid material, comprising an amorphous compound, may be characterized by, for example, a glass transition temperature which is lower than the melting point of a pure crystalline solid. Other techniques, such as, for example, solid state NMR may also be used to characterize crystalline or amorphous forms.

As used herein, the terms "crystal form," "crystalline form," and "Form" interchangeably refer to a crystal structure (or polymorph) having a particular molecular packing arrangement in the crystal lattice. Crystalline forms can be identified and distinguished from each other by one or more characterization techniques including, for example, X-ray powder diffraction (XRPD), single crystal X-ray diffraction, and $^{13}C$ solid state nuclear magnetic resonance ($^{13}C$ SSNMR). Accordingly, as used herein, the terms "crystalline Form [X] of Compound I" refer to unique crystalline forms that can be identified and distinguished from other crystalline forms by one or more characterization techniques including, for example, XRPD, single crystal X-ray diffraction, and $^{13}C$ SSNMR. In some embodiments, the novel crystalline forms are characterized by an X-ray powder diffractogram having one or more signals at one or more specified two-theta values (°2θ).

As used herein, the term "free form" refers to a non-ionized version of the compound in the solid state. Examples of free forms include free bases and free acids.

As used herein, the term "solvate" refers to a crystal form comprising one or more molecules of a compound of the present disclosure and, incorporated into the crystal lattice, one or more molecules of a solvent or solvents in stoichiometric or nonstoichiometric amounts. When the solvent is water, the solvate is referred to as a "hydrate."

In some embodiments, a solid material may comprise a mixture of crystalline solids and amorphous solids. A solid material comprising an amorphous compound may also, for example, contain up to 30% of a crystalline solid. In some embodiments, a solid material prepared to comprise an amorphous compound may also, for example, contain up to 25%, 20%, 15%, 10%, 5%, or 2% of a crystalline solid. In embodiments wherein the solid material contains a mixture of crystalline solids and amorphous solids, the characterizing data, such as XRPD, may contain indicators of both crystalline and amorphous solids. In some embodiments, a crystalline form of this disclosure may contain up to 30% amorphous compound. In some embodiments, a crystalline preparation of a compound of Formula I may contain up to 25%, 20%, 15%, 10%, 5%, or 2% of an amorphous solid.

As used herein, the term "substantially amorphous" refers to a solid material having little or no long-range order in the position of its molecules. For example, substantially amorphous materials have less than 15% crystallinity (e.g., less than 10% crystallinity, less than 5% crystallinity, or less than 2% crystallinity). It is also noted that the term "substantially amorphous" includes the descriptor, "amorphous," which refers to materials having no (0%) crystallinity.

As used herein, the term "substantially crystalline" refers to a solid material having little or no amorphous molecules. For example, substantially crystalline materials have less than 15% amorphous molecules (e.g., less than 10% amorphous molecules, less than 5% amorphous molecules, or less than 2% amorphous molecules). It is also noted that the term "substantially crystalline" includes the descriptor "crystalline," which refers to materials that are 100% crystalline form.

As used herein, a crystalline form is "substantially pure" when it accounts for an amount by weight equal to or greater than 90% of the sum of all solid form(s) in a sample as determined by a method in accordance with the art, such as quantitative XRPD. In some embodiments, the solid form is "substantially pure" when it accounts for an amount by weight equal to or greater than 95% of the sum of all solid form(s) in a sample. In some embodiments, the solid form is "substantially pure" when it accounts for an amount by weight equal to or greater than 99% of the sum of all solid form(s) in a sample. It is also noted that the term "substantially pure" includes the descriptor "pure," which refers to materials that are 100% pure.

As used herein, the term "XRPD" refers to the analytical characterization method of X-ray powder diffraction. XRPD patterns disclosed herein were recorded at ambient conditions in transmission or reflection geometry using a diffractometer.

As used herein, the term "ambient conditions" means room temperature, open air condition and uncontrolled humidity condition. The terms "room temperature" and "ambient temperature" mean 15° C. to 30° C.

As used herein, the terms "X-ray powder diffractogram," "X-ray powder diffraction pattern," "XRPD pattern," "XRPD spectrum" interchangeably refer to an experimentally obtained pattern plotting signal positions (on the abscissa) versus signal intensities (on the ordinate). For an amorphous material, an X-ray powder diffractogram may include one or more broad signals; and for a crystalline material, an X-ray powder diffractogram may include one or more signals, each identified by its angular value as measured in degrees 2θ (°2θ), depicted on the abscissa of an X-ray powder diffractogram, which may be expressed as "a signal at . . . degrees two-theta," "a signal at [a] two-theta value(s)of . . . " and/or "a signal at at least . . . two-theta value(s) selected from . . . ."

A "signal" or "peak" as used herein refers to a point in the XRPD pattern where the intensity as measured in counts is at a local maximum. One of ordinary skill in the art would recognize that one or more signals (or peaks) in an XRPD pattern may overlap and may, for example, not be apparent to the naked eye. Indeed, one of ordinary skill in the art would recognize that some art-recognized methods are capable of and suitable for determining whether a signal exists in a pattern, such as Rietveld refinement.

As used herein, "a signal at . . . degrees two-theta" refer to X-ray reflection positions as measured and observed in X-ray powder diffraction experiments (°2θ).

The repeatability of the measured angular values is in the range of ±0.2° 2θ, i.e., the angular value can be at the recited angular value +0.2 degrees two-theta, the angular value −0.2 degrees two-theta, or any value between those two end points (angular value +0.2 degrees two-theta and angular value −0.2 degrees two-theta).

The terms "signal intensities" and "peak intensities" interchangeably refer to relative signal intensities within a given X-ray powder diffractogram. Factors that can affect the relative signal or peak intensities include sample thickness and preferred orientation (e.g., the crystalline particles are not distributed randomly).

As used herein, an X-ray powder diffractogram is "substantially similar to that in [a particular] Figure" when at least 90%, such as at least 95%, at least 98%, or at least 99%, of the signals in the two diffractograms overlap. In determining "substantial similarity," one of ordinary skill in the art will understand that there may be variation in the intensities and/or signal positions in XRPD diffractograms even for the same crystalline form. Thus, those of ordinary skill in the art will understand that the signal maximum values in XRPD diffractograms (in degrees two-theta) generally mean that value is identified as ±0.2 degrees two-theta of the reported value, an art-recognized variance.

As used herein, a solid state nuclear magnetic resonance (SSNMR) spectrum is "substantially similar to that in [a particular] Figure" when at least 90%, such as at least 95%, at least 98%, or at least 99%, of the signals in the two spectra overlap. In determining "substantial similarity," one of ordinary skill in the art will understand that there may be variation in the intensities and/or signal positions in SSNMR spectra even for the same crystalline form. Thus, those of ordinary skill in the art will understand that the chemical shifts in SSNMR spectra (in parts per million (ppm) referred to herein) generally mean that value is identified as ±0.2 ppm of the reported value, an art-recognized variance.

The term "X-ray powder diffractogram having a signal at . . . two-theta values" as used herein refers to an XRPD pattern that contains X-ray reflection positions as measured and observed in X-ray powder diffraction experiments (° two-theta).

As used herein, the term "DSC" refers to the analytical method of Differential Scanning calorimetry.

As used herein, the term "onset of decomposition" refers to the intersection point of the baseline before transition and the interflection tangent.

As used herein, the term "glass transition temperature" or "Tg" refers to the temperature above which a hard and brittle "glassy" amorphous solid becomes viscous or rubbery.

As used herein, the term "TGA" refers to the analytical method of Thermo Gravimetric (or thermogravimetric) Analysis.

DETAILED DESCRIPTION OF EMBODIMENTS

In addition to compounds of Formula I, I', and I", pharmaceutically acceptable salts thereof, and deuterated derivatives of those compounds and salts, the invention provides compounds of Formulae I''', Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof.

For example, in some embodiments, the compound of Formula I is selected from compounds of Formula Ia:

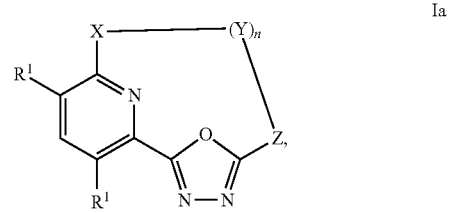

and deuterated derivatives and pharmaceutically acceptable salts thereof, wherein:

X is selected from —O—, —S—, —SO—, and —SO$_2$—;

each Y is independently selected from —C(R$^Y$)$_2$—, —O—, —CO—, and

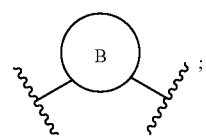

each R$^Y$ is independently selected from hydrogen, halogen, C$_1$-C$_6$ alkyl (optionally substituted with 1-3 groups independently selected from hydroxy and Q), C$_6$-C$_{10}$ aryl, 5- to 10-membered heteroaryl, —OR$^{Y1}$, —CO$_2$R$^{Y1}$, —COR$^{Y1}$, —CON($R^{Y1}$)$_2$, and —$NR^{Y1}$—; or two instances of $R^Y$ on the same atom are taken together to form a ring selected from $C_3$-$C_8$ cycloalkyl and 3- to 6-membered heterocyclyl; or two instances of $R^Y$, one of which is on one atom and the second of which is on an adjacent atom, are taken together to form a pi bond;

each $R^{Y1}$ is independently selected from hydrogen and $C_1$-$C_6$ alkyl, or two instances of $R^{Y1}$ bonded to the same nitrogen taken together form a 3- to 6-membered heterocyclyl;

Ring B is selected from:
$C_6$-$C_{10}$ aryl (optionally substituted with 1-3 groups independently selected from halogen, $C_1$-$C_6$ alkyl, and $C_1$-$C_6$ alkoxy),
$C_3$-$C_8$ cycloalkyl,
5- to 10-membered heteroaryl, and
3- to 6-membered heterocyclyl (optionally substituted with 1-3 groups independently selected from $C_1$-$C_6$ alkyl);

each Q is independently selected from:
$C_1$-$C_6$ alkyl optionally substituted with 1-3 groups independently selected from:
halogen,
oxo,
$C_6$-$C_{10}$ aryl (optionally substituted with 1-3 groups independently selected from halogen and —$OCF_3$), and
$C_3$-$C_8$ cycloalkyl,
$C_3$-$C_8$ cycloalkyl optionally substituted with 1-3 groups independently selected from:
halogen,
CN,
$C_1$-$C_6$ alkyl (optionally substituted with 1-3 groups independently selected from halogen, —$NH_2$, and —NHCOMe),
$C_1$-$C_6$ alkoxy,
$C_6$-$C_{10}$ aryl (optionally substituted with 1-3 groups independently selected from $C_1$-$C_6$ alkyl), and
$C_3$-$C_8$ cycloalkyl,
$C_6$-$C_{10}$ aryl optionally substituted with 1-3 groups independently selected from:
halogen,
CN,
$C_1$-$C_6$ alkyl (optionally substituted with 1-3 groups independently selected from halogen and hydroxy),
$C_1$-$C_6$ alkoxy optionally substituted with 1-4 groups independently selected from:
halogen,
$C_3$-$C_8$ cycloalkyl (optionally substituted with $CF_3$),
$C_3$-$C_8$ cycloalkyl (optionally substituted with 1-3 groups independently selected from halogen, $CF_3$, $OCF_3$, and $C_1$-$C_6$ alkyl), and
$C_6$-$C_{10}$ aryl,
5- to 10-membered heteroaryl optionally substituted with 1-3 groups independently selected from:
halogen,
$C_1$-$C_6$ alkyl (optionally substituted with 1-3 groups independently selected from halogen),
$C_3$-$C_8$ cycloalkyl (optionally substituted with 1-3 $CF_3$ groups), and
3- to 10-membered heterocyclyl,
3- to 10-membered heterocyclyl optionally substituted with 1-3 groups independently selected from:
$C_1$-$C_6$ alkyl (optionally substituted with 1-3 groups independently selected from oxo and $C_3$-$C_8$ cycloalkyl), and
oxo;

each $R^1$ is independently selected from halogen, $C_1$-$C_6$ alkyl (optionally substituted with 1-6 groups independently selected from halogen), —$OR^2$, —$N(R^2)_2$, —$CO_2R^2$, —CO—$N(R^2)_2$, —CN, phenyl, benzyl, $C_1$-$C_6$ alkoxy, $C_1$-$C_6$ alkyl, $C_3$-$C_8$ cycloalkyl, 5- to 6-membered heteroaryl, 3- to 6-membered heterocyclyl, —$SO_2R^2$, —$SR^2$, —$SOR^2$, —PO($OR^2$)$_2$, and —PO($R^2$)$_2$;

each $R^2$ is independently selected from hydrogen, $C_1$-$C_6$ alkyl (optionally substituted with 1-3 groups independently selected from halogen), and $C_6$-$C_{10}$ aryl (optionally substituted with $C_1$-$C_6$ alkoxy, which is optionally substituted with 1-6 groups independently selected from halogen);

Z is selected from

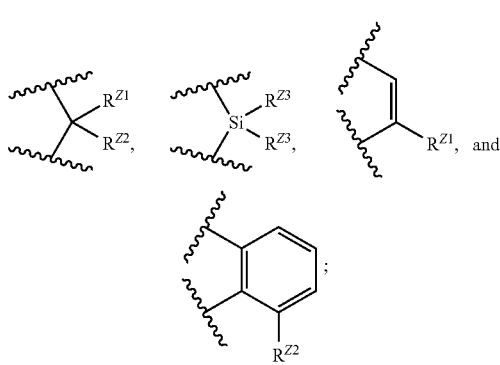

$R^{Z1}$ is selected from hydrogen, —CN, $C_1$-$C_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

$R^{Z2}$ is selected from hydrogen, halogen, and hydroxy, or $R^{Z1}$ and $R^{Z2}$ taken together form a group selected from oxo and =N—OH;

each $R^{Z3}$ is independently selected from hydroxy, $C_1$-$C_6$ alkoxy, $C_1$-$C_6$ alkyl, and $C_6$-$C_{10}$ aryl; or two instances of $R^{Z3}$ are taken together to form a 3- to 6-membered heterocyclyl; and n is selected from 4, 5, 6, and 7.

In some embodiments, X in Formula Ia is —O—.

In some embodiments, each Y in Formula Ia is independently selected from —C($R^Y$)$_2$—, —CO—, and

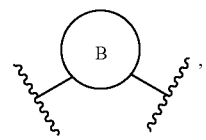

wherein $R^Y$ and Ring B are as defined for Formula Ia.

In some embodiments, each Y in Formula Ia is —C($R^Y$)$_2$—, wherein $R^Y$ is as defined for Formula Ia.

In some embodiments, each $R^Y$ in Formula Ia is independently selected from hydrogen, $C_1$-$C_6$ alkyl (optionally substituted with 1-3 groups independently selected from hydroxy and Q), and —$OR^{Y1}$, wherein Q and $R^{Y1}$ are as defined for Formula Ia.-

In some embodiments, each $R^Y$ in Formula Ia is independently selected from: hydrogen,

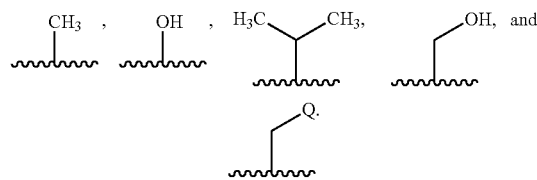

In some embodiments, each Q in Formula Ia is independently selected from:

$C_3$-$C_8$ cycloalkyl, $C_6$-$C_{10}$ aryl optionally substituted with 1-3 groups independently selected from halogen and $C_1$-$C_6$ alkyl.

In some embodiments, each Q in Formula Ia is independently selected from:

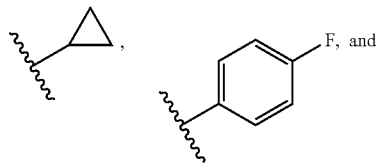

In some embodiments, Ring B in Formula Ia is selected from $C_6$-$C_{10}$ aryl optionally substituted with 1-3 groups independently selected from halogen.

In some embodiments, Ring B in Formula Ia is selected from:

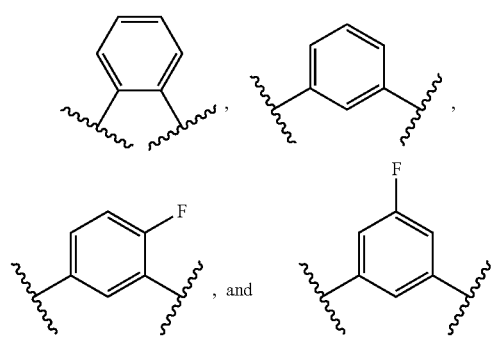

In some embodiments, —(Y)$_n$— in Formula Ia is a group selected from:

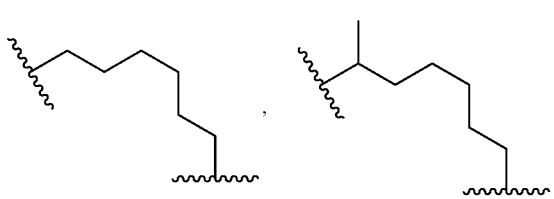

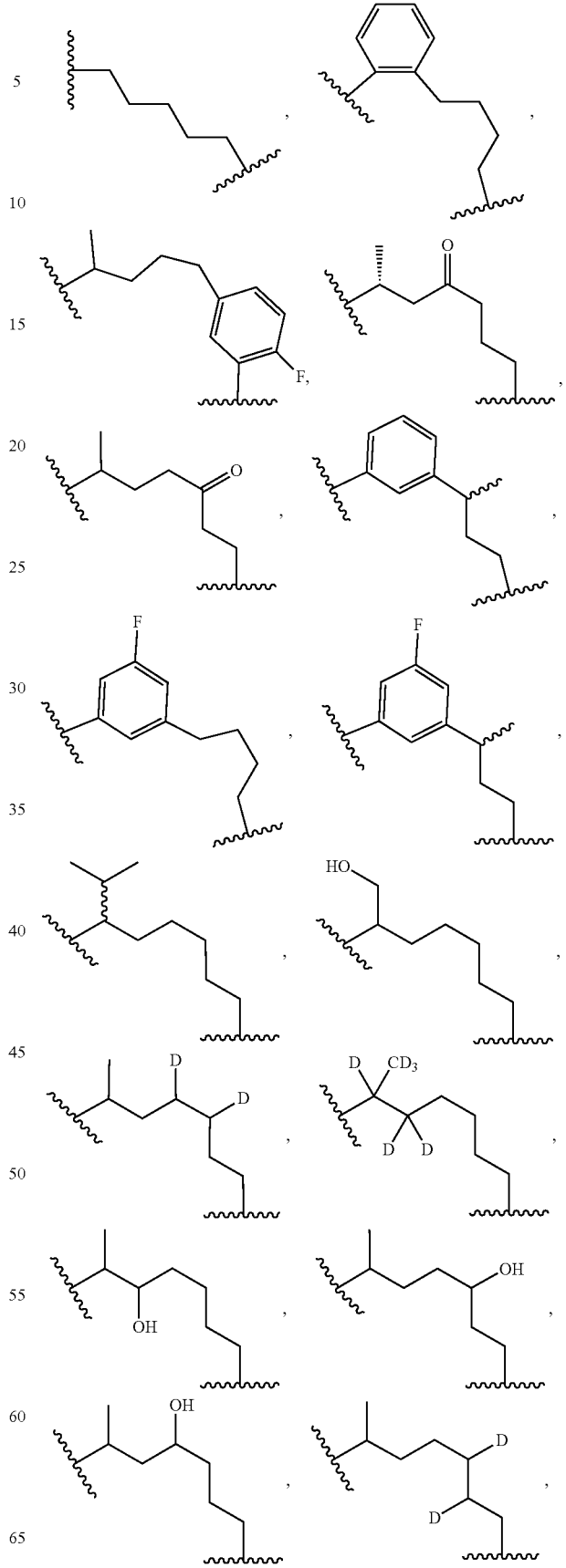

-continued

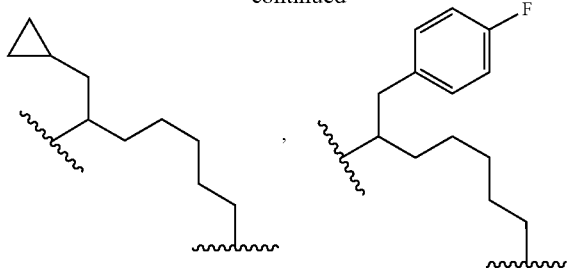

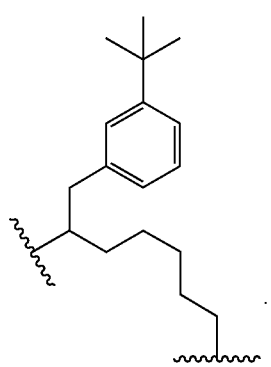

In some embodiments, each in Formula Ia is independently $C_1$-$C_6$ alkyl (optionally substituted with 1-3 groups independently selected from halogen) and —N($R^2$)$_2$, wherein $R^2$ is as defined for Formula Ia. In some embodiments, each $R^1$ in Formula Ia is independently selected from —$CF_3$ and —N($R^2$)$_2$, wherein $R^2$ is as defined for Formula Ia.

In some embodiments, each $R^2$ in Formula Ia is independently selected from hydrogen, $C_1$-$C_6$ alkyl (optionally substituted with 1-3 groups independently selected from halogen), and $C_6$-$C_{10}$ aryl (optionally substituted with $C_1$-$C_6$ alkoxy, which is optionally substituted with 1-3 groups independently selected from halogen). In some embodiments, each $R^2$ in Formula Ia is independently selected from hydrogen and $C_1$-$C_6$ alkyl. In some embodiments, each $R^2$ in Formula Ia is hydrogen.

In some embodiments, Z in Formula Ia is

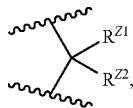

wherein $R^{Z1}$ and $R^{Z2}$ are as defined for Formula Ia.

In some embodiments, $R^{Z1}$ in Formula Ia is selected from $C_1$-$C_6$ alkyl (optionally substituted with 1-3 groups selected from halogen). In some embodiments, $R^{Z1}$ in Formula Ia is —$CF_3$.

In some embodiments, $R^{Z2}$ in Formula Ia is hydroxy.

In some embodiments, n in Formula Ia is selected from 4, 5, and 6. In some embodiments, n in Formula Ia is 6.

In some embodiments, the compound of Formula I is selected from compounds of Formulae IIa, IIb, and IIc:

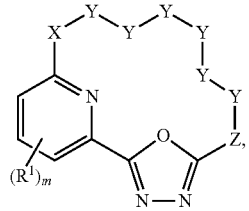

IIa

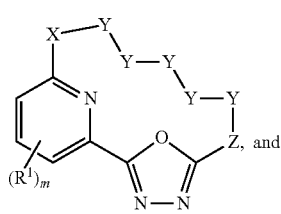

IIb

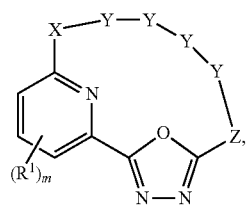

IIc and deuterated derivatives and pharmaceutically acceptable salts thereof, wherein:

X is selected from —O—, —S—, —SO—, and —SO$_2$—;
each Y is independently selected from —C($R^Y$)$_2$—, —O—, —CO—, and

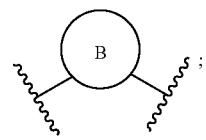

each $R^Y$ is independently selected from hydrogen, halogen, $C_1$-$C_6$ alkyl (optionally substituted with 1-3 groups independently selected from hydroxy and Q), $C_6$-$C_{10}$ aryl, 5- to 10-membered heteroaryl, —$OR^{Y1}$, —$CO_2R^{Y1}$, —$COR^{Y1}$, —$CON(R^{Y1})_2$, and —$NR^{Y1}$—; or two instances of $R^Y$ on the same atom are taken together to form a ring selected from $C_3$-$C_8$ cycloalkyl and 3- to 6-membered heterocyclyl; or two instances of $R^Y$, one of which is on one atom and the second of which is on an adjacent atom, are taken together to form a pi bond;

each $R^{Y1}$ is independently selected from hydrogen and $C_1$-$C_6$ alkyl, or two instances of $R^{Y1}$ bonded to the same nitrogen taken together form a 3- to 6-membered heterocyclyl;

Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);

each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;
each R$^1$ is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;
each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);
Z is selected from

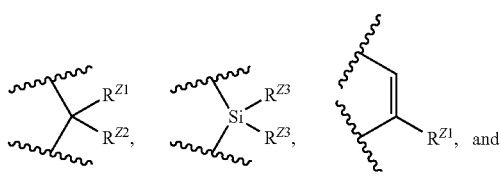

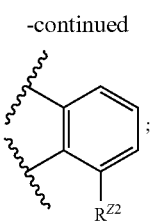

R$^{Z1}$ is selected from hydrogen, —CN, C$_1$-C$_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

R$^{Z2}$ is selected from hydrogen, halogen, and hydroxy, or R$^{Z1}$ and R$^{Z2}$ taken together form a group selected from oxo and =N—OH;

each R$^{Z3}$ is independently selected from hydroxy, C$_1$-C$_6$ alkoxy, C$_1$-C$_6$ alkyl, and C$_6$-C$_{10}$ aryl; or two instances of R$^{Z3}$ are taken together to form a 3- to 6-membered heterocyclyl; and m is selected from 0, 1, 2, and 3.

In some embodiments, m in Formulae IIa, IIb, or IIc is selected from 1 and 2. In some embodiments, m in Formulae IIa, IIb, or IIc is 2.

In some embodiments, the compound of Formula I is selected from compounds of Formulae IId, IIe, and IIf:

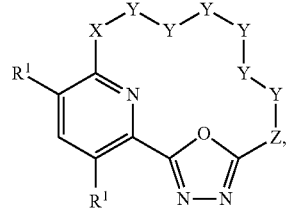

IId

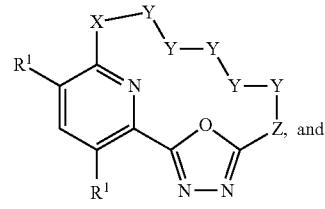

IIe

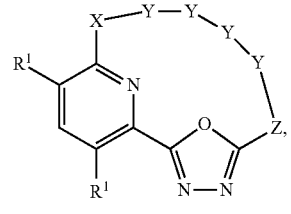

IIf and deuterated derivatives and pharmaceutically acceptable salts thereof, wherein:

X is selected from —O—, —S—, —SO—, and —SO$_2$—;

each Y is independently selected from —C(R$^Y$)$_2$—, —O—, —CO—, and

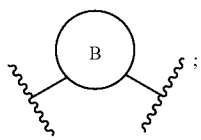

each $R^Y$ is independently selected from hydrogen, halogen, $C_1$-$C_6$ alkyl (optionally substituted with 1-3 groups independently selected from hydroxy and Q), $C_6$-$C_{10}$ aryl, 5- to 10-membered heteroaryl, —$OR^{Y1}$, —$CO_2R^{Y1}$, —$COR^{Y1}$, —$CON(R^{Y1})_2$, and —$NR^{Y1}$—; or two instances of $R^Y$ on the same atom are taken together to form a ring selected from $C_3$-$C_8$ cycloalkyl and 3- to 6-membered heterocyclyl; or two instances of $R^Y$, one of which is on one atom and the second of which is on an adjacent atom, are taken together to form a pi bond;

each $R^{Y1}$ is independently selected from hydrogen and $C_1$-$C_6$ alkyl, or two instances of $R^{Y1}$ bonded to the same nitrogen taken together form a 3- to 6-membered heterocyclyl;

Ring B is selected from:
$C_6$-$C_{10}$ aryl (optionally substituted with 1-3 groups independently selected from halogen, $C_1$-$C_6$ alkyl, and $C_1$-$C_6$ alkoxy),
$C_3$-$C_8$ cycloalkyl,
5- to 10-membered heteroaryl, and
3- to 6-membered heterocyclyl (optionally substituted with 1-3 groups independently selected from $C_1$-$C_6$ alkyl);

each Q is independently selected from:
$C_1$-$C_6$ alkyl optionally substituted with 1-3 groups independently selected from:
halogen,
oxo,
$C_6$-$C_{10}$ aryl (optionally substituted with 1-3 groups independently selected from halogen and —$OCF_3$), and
$C_3$-$C_8$ cycloalkyl,
$C_3$-$C_8$ cycloalkyl optionally substituted with 1-3 groups independently selected from:
halogen,
CN,
$C_1$-$C_6$ alkyl (optionally substituted with 1-3 groups independently selected from halogen, —$NH_2$, and —NHCOMe),
$C_1$-$C_6$ alkoxy,
$C_6$-$C_{10}$ aryl (optionally substituted with 1-3 groups independently selected from $C_1$-$C_6$ alkyl), and
$C_3$-$C_8$ cycloalkyl,
$C_6$-$C_{10}$ aryl optionally substituted with 1-3 groups independently selected from:
halogen,
CN,
$C_1$-$C_6$ alkyl (optionally substituted with 1-3 groups independently selected from halogen and hydroxy),
$C_1$-$C_6$ alkoxy optionally substituted with 1-4 groups independently selected from:
halogen,
$C_3$-$C_8$ cycloalkyl (optionally substituted with $CF_3$),
$C_3$-$C_8$ cycloalkyl (optionally substituted with 1-3 groups independently selected from halogen, $CF_3$, $OCF_3$, and $C_1$-$C_6$ alkyl), and
$C_6$-$C_{10}$ aryl,
5- to 10-membered heteroaryl optionally substituted with 1-3 groups independently selected from:
halogen,
$C_1$-$C_6$ alkyl (optionally substituted with 1-3 groups independently selected from halogen),
$C_3$-$C_8$ cycloalkyl (optionally substituted with 1-3 $CF_3$ groups), and
3- to 10-membered heterocyclyl,
3- to 10-membered heterocyclyl optionally substituted with 1-3 groups independently selected from:
$C_1$-$C_6$ alkyl (optionally substituted with 1-3 groups independently selected from oxo and $C_3$-$C_8$ cycloalkyl), and
oxo;

each is independently selected from halogen, $C_1$-$C_6$ alkyl (optionally substituted with 1-6 groups independently selected from halogen), —$OR^2$, —$N(R^2)_2$, —$CO_2R^2$, —CO—$N(R^2)_2$, —CN, phenyl, benzyl, $C_1$-$C_6$ alkoxy, $C_1$-$C_6$ alkyl, $C_3$-$C_8$ cycloalkyl, 5- to 6-membered heteroaryl, 3- to 6-membered heterocyclyl, —$SO_2R^2$, —$SR^2$, —$SOR^2$, —$PO(OR^2)_2$, and —$PO(R^2)_2$;

each $R^2$ is independently selected from hydrogen, $C_1$-$C_6$ alkyl (optionally substituted with 1-6 groups independently selected from halogen), and $C_6$-$C_{10}$ aryl (optionally substituted with $C_1$-$C_6$ alkoxy, which is optionally substituted with 1-6 groups independently selected from halogen);

Z is selected from

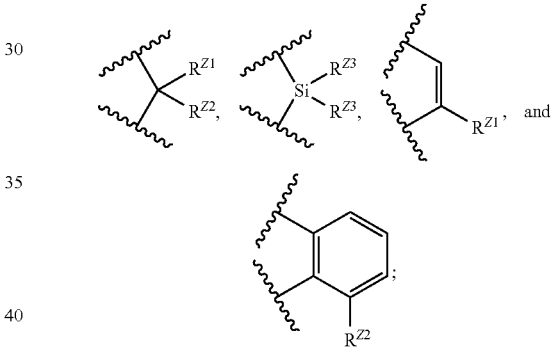

$R^{Z1}$ is selected from hydrogen, —CN, $C_1$-$C_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

$R^{Z2}$ is selected from hydrogen, halogen, and hydroxy, or $R^{Z1}$ and $R^{Z2}$ taken together form a group selected from oxo and =N—OH; and each $R^{Z3}$ is independently selected from hydroxy, $C_1$-$C_6$ alkoxy, $C_1$-$C_6$ alkyl, and $C_6$-$C_{10}$ aryl; or two instances of $R^{Z3}$ are taken together to form a 3- to 6-membered heterocyclyl.

In some embodiments, X in Formulae IIa, IIb, IIc, IId, IIe, or IIf is —O—.

In some embodiments, each Y in Formulae IIa, IIb, IIc, IId, IIe, or IIf is independently selected from —$C(R^Y)_2$—, —CO—, and

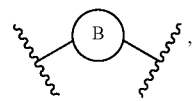

wherein $R^Y$ and Ring B are as defined for Formulae IIa, IIb, IIc, IId, IIe, or IIf.

In some embodiments, each Y in Formulae IIa, IIb, IIc, IId, IIe, or IIf is —C(R$^Y$)$_2$—, wherein R$^Y$ is as defined for Formulae IIa, IIb, IIc, IId, IIe, or IIf.

In some embodiments, each R$^Y$ in Formulae IIa, IIb, IIc, IId, IIe, or IIf is independently selected from hydrogen, C$_1$-C$_6$ alkyl (optionally substituted with 1-3 groups independently selected from hydroxy and Q), and —OR$^{Y1}$, wherein Q and R$^{Y1}$ are as defined for Formulae IIa, IIb, IIc, IId, IIe, or IIf.

In some embodiments, each R$^Y$ in Formulae IIa, IIb, IIc, IId, IIe, or IIf is independently selected from: hydrogen,

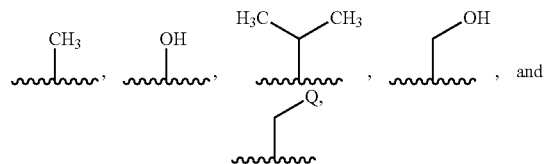

wherein Q is as defined for Formulae IIa, IIb, IIc, IId, IIe, or IIf.

In some embodiments, each Q in Formulae IIa, IIb, IIc, IId, IIe, or IIf is independently selected from:
C$_3$-C$_8$ cycloalkyl,
C$_6$-C$_{10}$ aryl optionally substituted with 1-3 groups independently selected from halogen and C$_1$-C$_6$ alkyl.

In some embodiments, each Q in Formulae IIa, IIb, IIc, IId, IIe, or IIf is independently selected from:

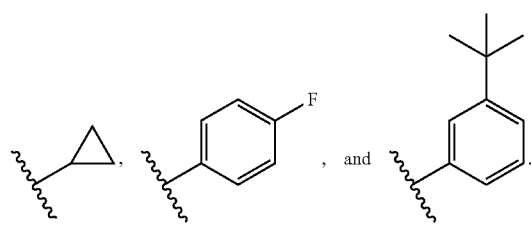

In some embodiments, Ring B in Formulae IIa, IIb, IIc, IId, IIe, or IIf is selected from C$_6$-C$_{10}$ aryl optionally substituted with 1-3 groups independently selected from halogen.

In some embodiments, Ring B in Formulae IIa, IIb, IIc, IId, IIe, or IIf is selected from:

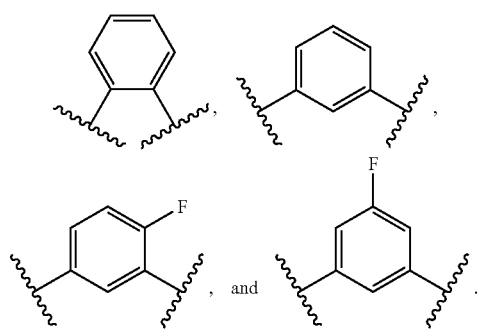

In some embodiments, each R$^1$ in Formulae IIa, IIb, IIc, IId, IIe, or IIf is independently C$_1$-C$_6$ alkyl (optionally substituted with 1-3 groups independently selected from halogen) and —N(R$^2$)$_2$ wherein R$^2$ is as defined for Formulae IIa, IIb, IIc, IId, IIe, or IIf. In some embodiments, each R$^1$ in Formulae IIa, IIb, IIc, IId, IIe, or IIf is independently selected from —CF$_3$ and —N(R$^2$)$_2$ wherein R$^2$ is as defined for Formulae IIa, IIb, IIc, IId, IIe, or IIf.

In some embodiments, each R$^2$ in Formulae IIa, IIb, IIc, IId, IIe, or IIf is independently selected from hydrogen, C$_1$-C$_6$ alkyl (optionally substituted with 1-3 groups independently selected from halogen), and C$_6$-C$_{10}$ aryl (optionally substituted with C$_1$-C$_6$ alkoxy, which is optionally substituted with 1-3 groups independently selected from halogen). In some embodiments, each R$^2$ in Formulae IIa, IIb, IIc, IId, IIe, or IIf is independently selected from hydrogen and C$_1$-C$_6$ alkyl. In some embodiments, each R$^2$ in Formulae IIa, IIb, IIc, IId, IIe, or IIf is hydrogen.

In some embodiments, Z in Formulae IIa, IIb, IIc, IId, IIe, or IIf is

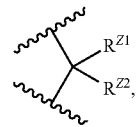

wherein R$^{Z1}$ and R$^{Z2}$ are as defined for Formulae IIa, IIb, IIc, IId, IIe, or IIf.

In some embodiments, R$^{Z1}$ in Formulae IIa, IIb, IIc, IId, IIe, or IIf is selected from C$_1$-C$_6$ alkyl (optionally substituted with 1-3 groups selected from halogen). In some embodiments, R$^{Z1}$ in Formulae IIa, IIb, IIc, IId, IIe, or IIf is —CF$_3$.

In some embodiments, R$^{Z2}$ in Formulae IIa, IIb, IIc, IId, IIe, or IIf is hydroxy.

In some embodiments, the compound of Formula I is selected from compounds of Formulae IIIa, IIIb, and IIIc:

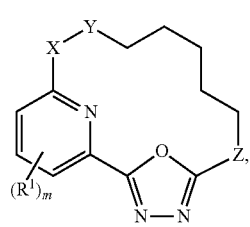

IIIa

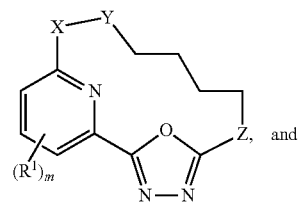

IIIb

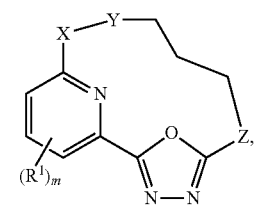

IIIc and deuterated derivatives and pharmaceutically acceptable salts thereof, wherein:

X is selected from —O—, —S—, —SO—, and —SO$_2$—;

each Y is independently selected from —C(R$^Y$)$_2$—, —O—, —CO—, and

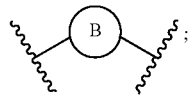

each R$^Y$ is independently selected from hydrogen, halogen, C$_1$-C$_6$ alkyl (optionally substituted with 1-3 groups independently selected from hydroxy and Q), C$_6$-C$_{10}$ aryl, 5- to 10-membered heteroaryl, —OR$^{Y1}$, —CO$_2$R$^{Y1}$, —COR$^{Y1}$, —CON(R$^{Y1}$)$_2$, and —NR$^{Y1}$—; or two instances of R$^Y$ on the same atom are taken together to form a ring selected from C$_3$-C$_8$ cycloalkyl and 3- to 6-membered heterocyclyl; or two instances of R$^Y$, one of which is on one atom and the second of which is on an adjacent atom, are taken together to form a pi bond;

each R$^{Y1}$ is independently selected from hydrogen and C$_1$-C$_6$ alkyl, or two instances of R$^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);

each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl, 5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;

each R$^1$ is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;

each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);

Z is selected from

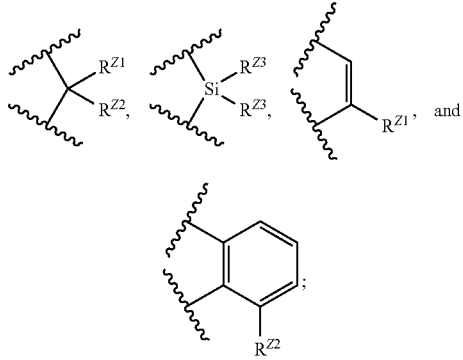

R$^{Z1}$ is selected from hydrogen, —CN, C$_1$-C$_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

R$^{Z2}$ is selected from hydrogen, halogen, and hydroxy, or R$^{Z1}$ and R$^{Z2}$ taken together form a group selected from oxo and =N—OH;

each R$^{Z3}$ is independently selected from hydroxy, C$_1$-C$_6$ alkoxy, C$_1$-C$_6$ alkyl, and C$_6$-C$_{10}$ aryl; or two instances of R$^{Z3}$ are taken together to form a 3- to 6-membered heterocyclyl; and m is selected from 0, 1, 2, and 3.

In some embodiments, m in Formulae IIIa, IIIb, or IIIc is selected from 1 and 2. In some embodiments, m in Formulae IIIa, IIIb, and IIIc is 2.

In some embodiments, the compound of Formula I is selected from compounds of Formulae IIId, IIIe, and IIIr

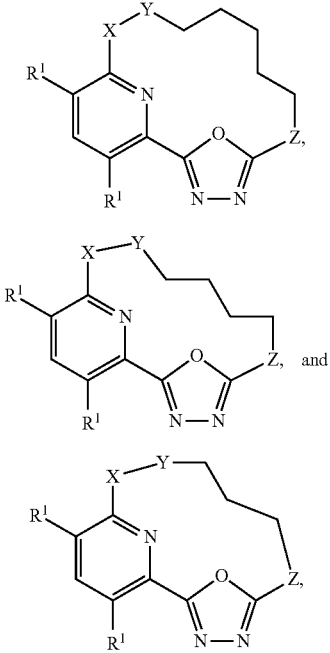

and deuterated derivatives and pharmaceutically acceptable salts thereof, wherein:

X is selected from —O—, —S—, —SO—, and —SO$_2$—;
each Y is independently selected from —C(R$^Y$)$_2$—, —O—, —CO—, and

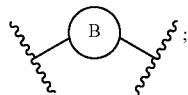

each R$^Y$ is independently selected from hydrogen, halogen, C$_1$-C$_6$ alkyl (optionally substituted with 1-3 groups independently selected from hydroxy and Q), C$_6$-C$_{10}$ aryl, 5- to 10-membered heteroaryl, —OR$^{Y1}$, —CO$_2$R$^{Y1}$, —COR$^{Y1}$, —CON(R$^{Y1}$)$_2$, and —NR$^{Y1}$—; or two instances of R$^Y$ on the same atom are taken together to form a ring selected from C$_3$-C$_8$ cycloalkyl and 3- to 6-membered heterocyclyl; or two instances of R$^Y$, one of which is on one atom and the second of which is on an adjacent atom, are taken together to form a pi bond;

each R$^{Y1}$ is independently selected from hydrogen and C$_1$-C$_6$ alkyl, or two instances of R$^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);

each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;

each R$^1$ is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;

each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);

Z is selected from

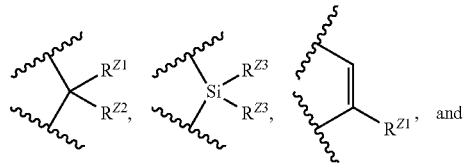

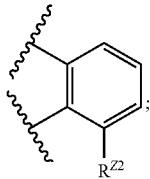

$R^{Z1}$ is selected from hydrogen, —CN, $C_1$-$C_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

$R^{Z2}$ is selected from hydrogen, halogen, and hydroxy, or $R^{Z1}$ and $R^{Z2}$ taken together form a group selected from oxo and =N—OH;

each $R^{Z3}$ is independently selected from hydroxy, $C_1$-$C_6$ alkoxy, $C_1$-$C_6$ alkyl, and $C_6$-$C_{10}$ aryl; or two instances of $R^{Z3}$ are taken together to form a 3- to 6-membered heterocyclyl.

In some embodiments, X in Formulae IIIa, IIIb, IIIc, IIId, IIIe, or IIIf is —O—.

In some embodiments, each Y in Formulae IIIa, IIIb, IIIc, IIId, IIIe, or IIIf is independently selected from —C($R^Y$)$_2$—, —CO—, and

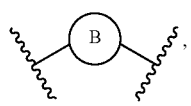

wherein $R^Y$ and Ring B as defined for Formulae IIIa, IIIb, IIIc, IIId, IIIe, or IIIf.

In some embodiments, each Y in Formulae IIIa, IIIb, IIIc, IIId, IIIe, or IIIf is —C($R^Y$)$_2$—, wherein $R^Y$ is as defined for Formulae IIIa, IIIb, IIIc, IIId, IIIe, or IIIf.

In some embodiments, each $R^Y$ in Formulae IIIa, IIIb, IIIc, IIId, IIIe, or IIIf is independently selected from hydrogen, $C_1$-$C_6$ alkyl (optionally substituted with 1-3 groups independently selected from hydroxy and Q), and —$OR^{Y1}$, wherein Q and $R^{Y1}$ are as defined for Formulae IIIa, IIIb, IIIc, IIId, IIIe, or IIIf.

In some embodiments, each $R^Y$ in Formulae IIIa, IIIb, IIIc, IIId, IIIe, or IIIf is selected from: hydrogen,

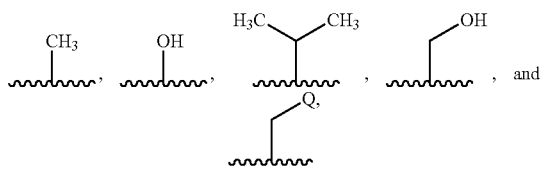

wherein Q is as defined for Formulae IIIa, IIIb, IIIc, IIId, IIIe, or IIIf.

In some embodiments, each Q in Formulae IIIa, IIIb, IIIc, IIId, IIIe, or IIIf is independently selected from:

$C_3$-$C_8$ cycloalkyl, $C_6$-$C_{10}$ aryl optionally substituted with 1-3 groups independently selected from halogen and $C_1$-$C_6$ alkyl.

In some embodiments, each Q in Formulae IIIa, IIIb, IIIc, IIId, IIIe, or IIIf is independently selected from:

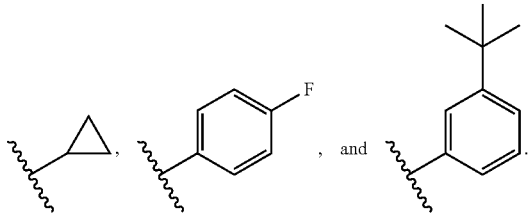

In some embodiments, Ring B in Formulae IIIa, IIIb, IIIc, IIId, IIIe, or IIIf is selected from $C_6$-$C_{10}$ aryl optionally substituted with 1-3 groups independently selected from halogen.

In some embodiments, Ring B in Formulae IIIa, IIIb, IIIc, IIId, IIIe, or IIIf is selected from:

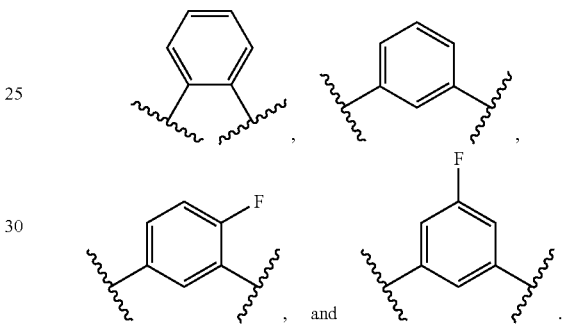

In some embodiments, each $R^1$ in Formulae IIIa, IIIb, IIIc, IIId, IIIe, or IIIf is independently $C_1$-$C_6$ alkyl (optionally substituted with 1-3 groups independently selected from halogen) and —N($R^2$)$_2$, wherein $R^2$ is as defined for Formulae IIIa, IIIb, IIIc, IIId, IIIe, or IIIf. In some embodiments, each $R^1$ in Formulae IIIa, IIIb, IIIc, IIId, IIIe, or IIIf is independently selected from —CF$_3$ and —N($R^2$)$_2$, wherein $R^2$ is as defined for Formulae IIIa, IIIb, IIIc, IIId, IIIe, or IIIf.

In some embodiments, each $R^2$ in Formulae IIIa, IIIb, IIIc, IIId, IIIe, or IIIf is independently selected from hydrogen, $C_1$-$C_6$ alkyl (optionally substituted with 1-3 groups independently selected from halogen), and $C_6$-$C_{10}$ aryl (optionally substituted with $C_1$-$C_6$ alkoxy, which is optionally substituted with 1-3 groups independently selected from halogen). In some embodiments, each $R^2$ in Formulae IIIa, IIIb, IIIc, IIId, IIIe, or IIIf is independently selected from hydrogen and $C_1$-$C_6$ alkyl.

In some embodiments, each $R^2$ in Formulae IIIa, IIIb, IIIc, IIId, IIIe, or IIIf is hydrogen.

In some embodiments, Z in Formulae IIIa, IIIb, IIIc, IIId, IIIe, or IIIf is

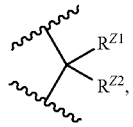

wherein Z is as defined for Formulae IIIa, IIIb, IIIc, IIId, IIIe, or IIIf.

In some embodiments, $R^{Z1}$ in Formulae IIIa, IIIb, IIIc, IIId, IIIe, or IIIf is selected from $C_1$-$C_6$ alkyl (optionally substituted with 1-3 groups selected from halogen). In some embodiments, $R^{Z1}$ in Formulae IIIa, IIIb, IIIc, IIId, IIIe, or IIIf is —$CF_3$.

In some embodiments, $R^{Z2}$ in Formulae IIIa, IIIb, IIIc, IIId, IIIe, or IIIf is hydroxy.

In some embodiments, the compound of Formula I is selected from compounds of Formula I''':

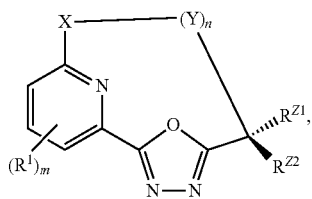

I''' and deuterated derivatives and pharmaceutically acceptable salts thereof, wherein:

X is selected from —O—, —S—, —SO—, and —SO$_2$—;

each Y is independently selected from —C($R^Y$)$_2$—, —O—, —CO—, and

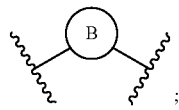

each $R^Y$ is independently selected from hydrogen, halogen, $C_1$-$C_6$ alkyl (optionally substituted with 1-3 groups independently selected from hydroxy and Q), $C_3$-$C_8$ cycloalkyl, $C_6$-$C_{10}$ aryl, 5- to 10-membered heteroaryl, —$CO_2R^{Y1}$, —CON($R^{Y1}$)$_2$, and —$NR^{Y1}$—; or two instances of $R^Y$ on the same atom are taken together to form a ring selected from $C_3$-$C_8$ cycloalkyl and 3- to 6-membered heterocyclyl; or two instances of $R^Y$, one of which is on one atom and the second of which is on an adjacent atom, are taken together to form a pi bond;

each $R^{Y1}$ is independently selected from hydrogen and $C_1$-$C_6$ alkyl, or two instances of $R^{Y1}$ bonded to the same nitrogen taken together form a 3- to 6-membered heterocyclyl;

Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);

each Q is independently selected from:
  $C_1$-$C_6$ alkyl optionally substituted with 1-3 groups independently selected from:
    halogen,
    oxo,
    $C_6$-$C_{10}$ aryl (optionally substituted with 1-3 groups independently selected from halogen and —$OCF_3$), and
    $C_3$-$C_8$ cycloalkyl,
  $C_3$-$C_8$ cycloalkyl optionally substituted with 1-3 groups independently selected from:
    halogen,
    CN,
    $C_1$-$C_6$ alkyl (optionally substituted with 1-3 groups independently selected from halogen, —$NH_2$, and —NHCOMe),
    $C_1$-$C_6$ alkoxy,
    $C_6$-$C_{10}$ aryl (optionally substituted with 1-3 groups independently selected from $C_1$-$C_6$ alkyl), and
    $C_3$-$C_8$ cycloalkyl,
  $C_6$-$C_{10}$ aryl optionally substituted with 1-3 groups independently selected from:
    halogen,
    CN,
    $C_1$-$C_6$ alkyl (optionally substituted with 1-3 groups independently selected from halogen and hydroxy),
    $C_1$-$C_6$ alkoxy optionally substituted with 1-4 groups independently selected from:
      halogen,
      $C_3$-$C_8$ cycloalkyl (optionally substituted with $CF_3$),
      $C_3$-$C_8$ cycloalkyl (optionally substituted with 1-3 groups independently selected from halogen, $CF_3$, $OCF_3$, and $C_1$-$C_6$ alkyl), and
    $C_6$-$C_{10}$ aryl,
  5- to 10-membered heteroaryl optionally substituted with 1-3 groups independently selected from:
    halogen,
    $C_1$-$C_6$ alkyl (optionally substituted with 1-3 groups independently selected from halogen),
    $C_3$-$C_8$ cycloalkyl (optionally substituted with 1-3 $CF_3$ groups), and
    3- to 10-membered heterocyclyl,
  3- to 10-membered heterocyclyl optionally substituted with 1-3 groups independently selected from:
    $C_1$-$C_6$ alkyl (optionally substituted with 1-3 groups independently selected from oxo and $C_3$-$C_8$ cycloalkyl), and
    oxo;

each is independently selected from halogen, $C_1$-$C_6$ alkyl (optionally substituted with 1-6 groups independently selected from halogen and hydroxy), —$OR^2$, —N($R^2$)$_2$, —$CO_2R^2$, —CO—N($R^2$)$_2$, —CN, phenyl, benzyl, $C_1$-$C_6$ alkoxy, $C_3$-$C_8$ cycloalkyl, 5- to 6-membered heteroaryl, 3- to 6-membered heterocyclyl, —$SO_2R^2$, —$SR^2$, —$SOR^2$, —PO(OR$^2$)$_2$, and —PO($R^2$)$_2$;

each $R^2$ is independently selected from hydrogen, $C_1$-$C_6$ alkyl (optionally substituted with 1-6 groups independently selected from halogen), and $C_6$-$C_{10}$ aryl (optionally substituted with $C_1$-$C_6$ alkoxy, which is optionally substituted with 1-6 groups independently selected from halogen);

$R^{Z1}$ is selected from hydrogen, —CN, $C_1$-$C_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

$R^{Z2}$ is selected from hydrogen, halogen, and hydroxy, or $R^{Z1}$ and $R^{Z2}$ taken together form a group selected from oxo and =N—OH;

n is selected from 4, 5, 6, 7, and 8; and m is selected from 0, 1, 2, and 3.

In some embodiments, X in Formula I''' is —O—.

In some embodiments, each $R^Y$ in Formula I''' is independently selected from hydrogen, halogen, $C_1$-$C_6$ alkyl (optionally substituted with 1-3 groups independently selected from hydroxy and Q), $C_3$-$C_8$ cycloalkyl, and —$OR^{Y1}$, wherein Q and $R^{Y1}$ are as defined for Formula I'''. In some embodiments, —$OR^{Y1}$ in Formula I''' is —OH.-

In some embodiments, each Q in Formula I'" is independently selected from $C_3$-$C_8$ cycloalkyl and $C_6$-$C_{10}$ aryl optionally substituted with 1-3 groups independently selected from halogen and $C_1$-$C_6$ alkyl. In some embodiments, each Q in Formula I'" is independently selected from:

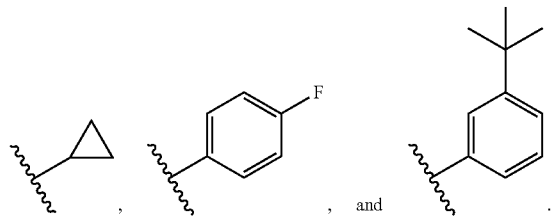

In some embodiments, each $R^Y$ in Formula I'" is independently selected from: hydrogen, fluorine,

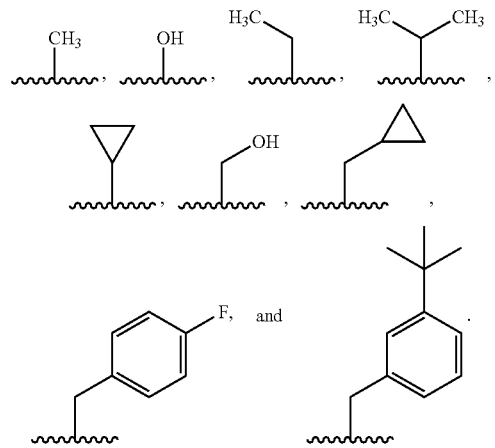

In some embodiments, Ring B in Formula I'" is selected from $C_3$-$C_8$ cycloalkyl and phenyl optionally substituted with 1-3 groups independently selected from halogen. In some embodiments, Ring B in Formula I'" is selected from:

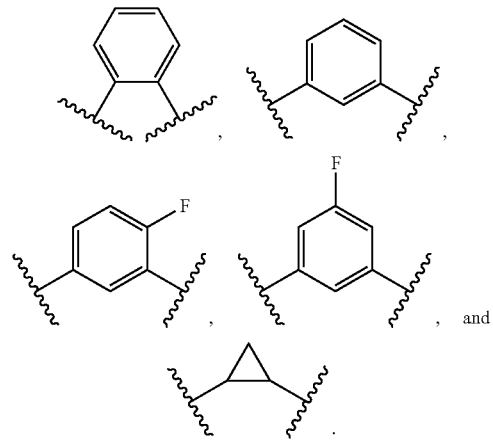

In some embodiments, n in Formula I'" is selected from 4, 5, and 6.

In some embodiments, —$(Y)_n$— in Formula I'" is a group selected from:

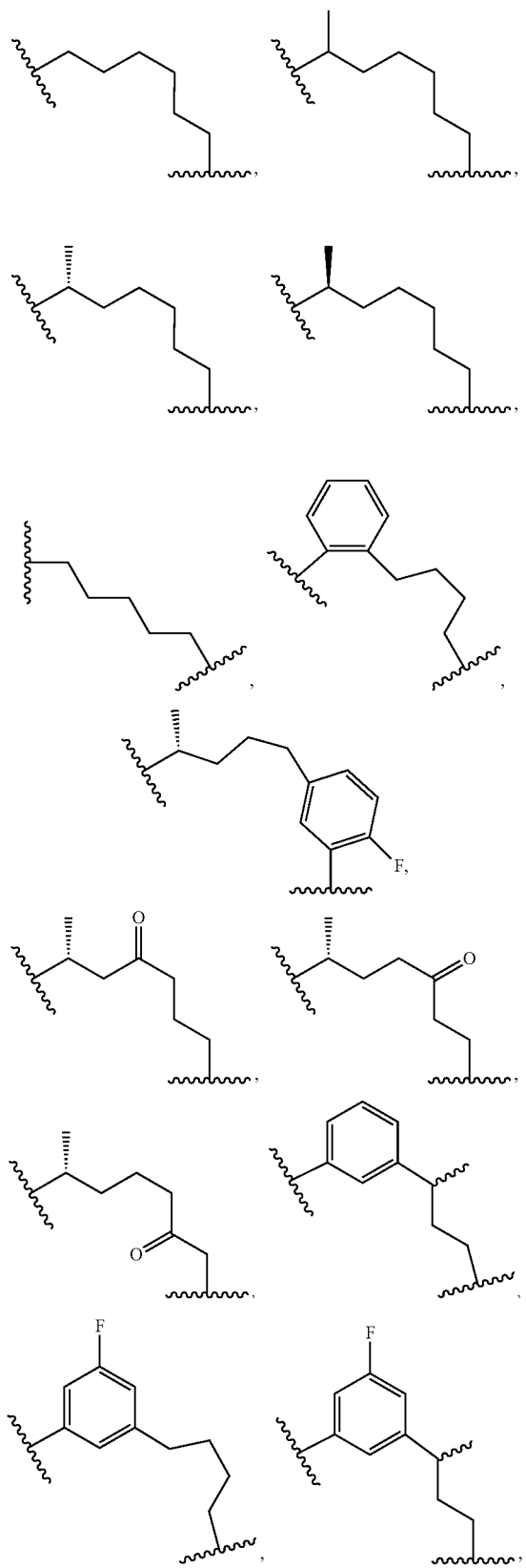

-continued

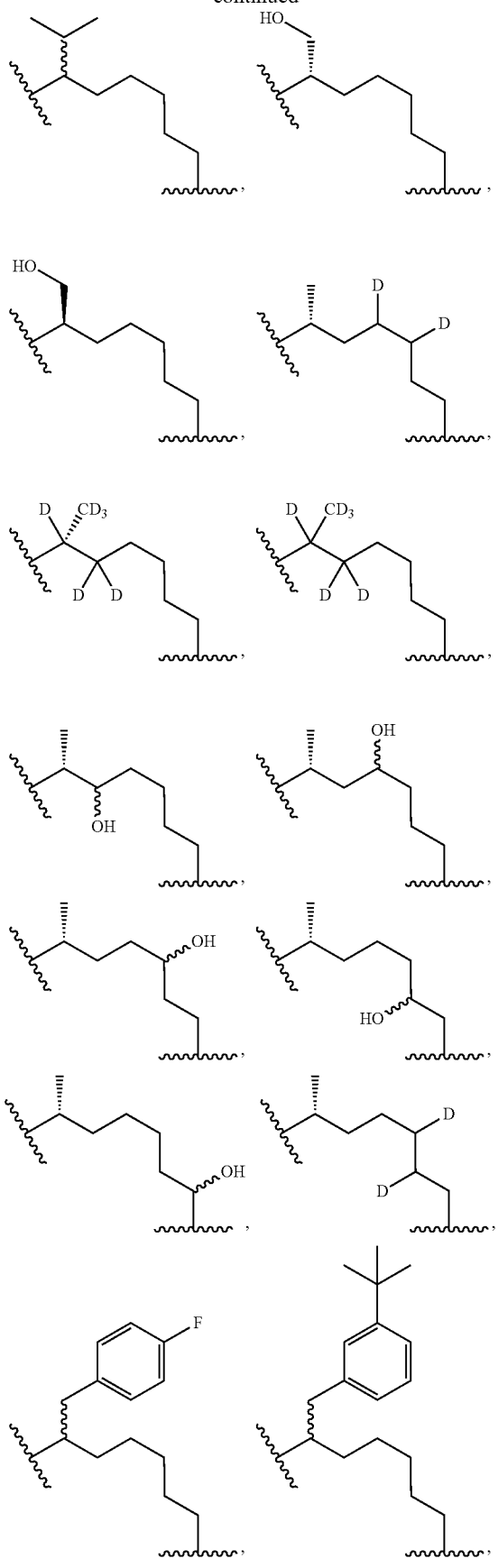

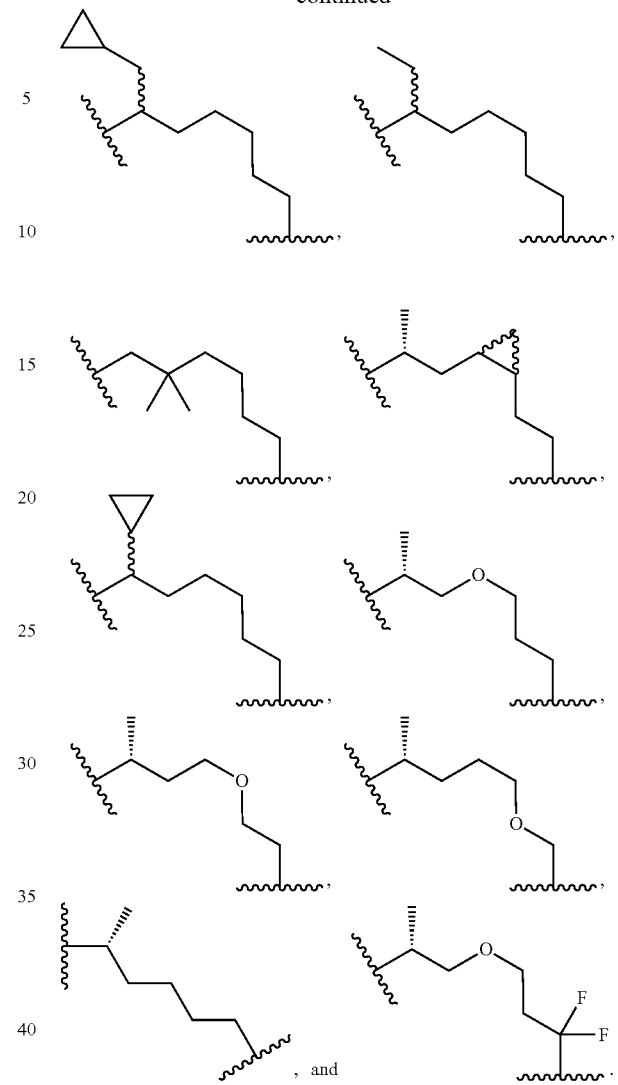

, and

In some embodiments, each in Formula I''' is independently selected from $C_1$-$C_6$ alkyl (optionally substituted with 1-6 groups independently selected from halogen and hydroxy), —$N(R^2)_2$, and —$CO_2R^2$, wherein $R^2$ is as defined for Formula I'''. In some embodiments, each $R^1$ in Formula I''' is independently selected from —$CF_3$, —$NH_2$, —NH($CH_2CH_3$), $CO_2H$, and $CH_2OH$.

In some embodiments, each $R^2$ in Formula I''' is independently selected from hydrogen and $C_1$-$C_6$ alkyl.

In some embodiments, $R^{Z1}$ in Formula I''' is selected from hydrogen and $C_1$-$C_6$ alkyl (optionally substituted with 1-6 groups selected from halogen). In some embodiments, $R^{Z1}$ in Formula I''' is —$CF_3$.

In some embodiments, $R^{Z2}$ in Formula I''' is hydroxy.

In some embodiments, $R^{Z1}$ in Formula I''' is $C_1$-$C_6$ alkyl (optionally substituted with 1-6 groups selected from halogen) and $R^{Z2}$ in Formula I''' is hydroxy. In some embodiments, $R^{Z1}$ in Formula I''' is —$CF_3$ and $R^{Z2}$ in Formula I''' is hydroxy.

In some embodiments, m in Formula I''' is selected from 1 and 2.

In some embodiments, the compound of Formula I is selected from compounds of Formula IIa':

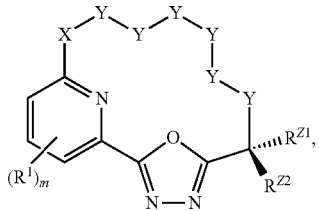

IIa' and deuterated derivatives and pharmaceutically acceptable salts thereof, wherein:

X is selected from —O—, —S—, —SO—, and —SO$_2$—;

each Y is independently selected from —C(R$^Y$)$_2$—, —O—, —CO—, and

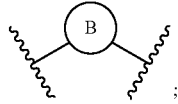

;

each R$^Y$ is independently selected from hydrogen, halogen, C$_1$-C$_6$ alkyl (optionally substituted with 1-3 groups independently selected from hydroxy and Q), C$_6$-C$_{10}$ aryl, 5- to 10-membered heteroaryl, —OR$^{Y1}$, —CO$_2$R$^{Y1}$, —COR$^{Y1}$, —CON(R$^{Y1}$)$_2$, and —NR$^{Y1}$—; or two instances of R$^Y$ on the same atom are taken together to form a ring selected from C$_3$-C$_8$ cycloalkyl and 3- to 6-membered heterocyclyl; or two instances of R$^Y$, one of which is on one atom and the second of which is on an adjacent atom, are taken together to form a pi bond;

each R$^{Y1}$ is independently selected from hydrogen and C$_1$-C$_6$ alkyl, or two instances of R$^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);

each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;

each is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;

each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);

R$^{Z1}$ is selected from hydrogen, —CN, C$_1$-C$_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

R$^{Z2}$ is selected from hydrogen, halogen, and hydroxy, or R$^{Z1}$ and R$^{Z2}$ taken together form a group selected from oxo and =N—OH; and m is selected from 0, 1, 2, and 3.

In some embodiments, m in Formula IIa' is selected from 1 and 2. In some embodiments, m in Formula IIa' is 2.

In some embodiments, X in Formula IIa' is —O—.

In some embodiments, each Y in Formula IIa' is independently selected from —C(R$^Y$)$_2$—, —CO—, and

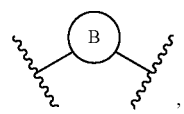

, wherein R$^Y$ and Ring B are as defined for Formula IIa'.

In some embodiments, each Y in Formula IIa' is —C(R$^Y$)$_2$—, wherein R$^Y$ is as defined for Formula IIa'.

In some embodiments, each R$^Y$ in Formula IIa' is independently selected from hydrogen, C$_1$-C$_6$ alkyl (optionally substituted with 1-3 groups independently selected from hydroxy and Q), and —OR$^{Y1}$, wherein Q and R$^{Y1}$ are as defined for Formula IIa'.

In some embodiments, each R$^Y$ in Formula IIa' is independently selected from: hydrogen,

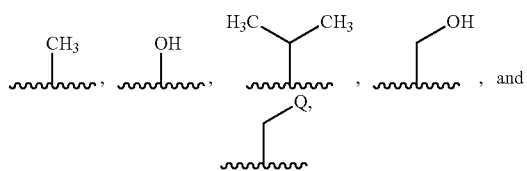

wherein Q is as defined for Formula IIa'.

In some embodiments, each Q in Formula IIa' is independently selected from:
$C_3$-$C_8$ cycloalkyl,
$C_6$-$C_{10}$ aryl optionally substituted with 1-3 groups independently selected from halogen and $C_1$-$C_6$ alkyl.

In some embodiments, each Q in Formula IIa' is independently selected from:

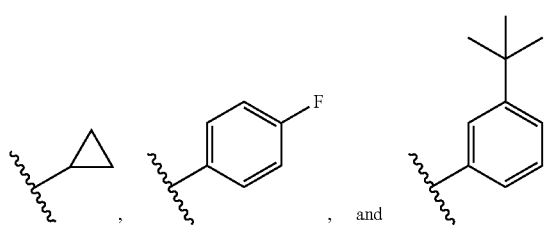

In some embodiments, Ring B in Formula IIa' is selected from $C_6$-$C_{10}$ aryl optionally substituted with 1-3 groups independently selected from halogen.

In some embodiments, Ring B in Formula IIa' is selected from:

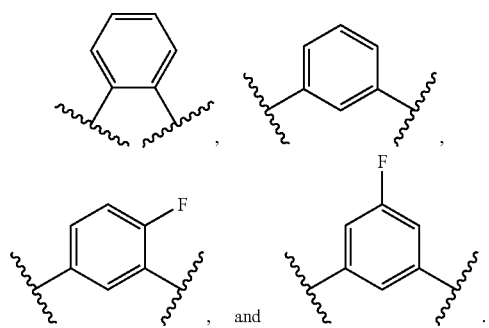

In some embodiments, each in Formula IIa' is independently $C_1$-$C_6$ alkyl (optionally substituted with 1-3 groups independently selected from halogen) and —N(R$^2$)$_2$ wherein R$^2$ is as defined for Formula IIa'. In some embodiments, each R$^1$ in Formula IIa' is independently selected from —CF$_3$ and —N(R$^2$)$_2$ wherein R$^2$ is as defined for Formula IIa'.

In some embodiments, each R$^2$ in Formula IIa' is independently selected from hydrogen, $C_1$-$C_6$ alkyl (optionally substituted with 1-3 groups independently selected from halogen), and $C_6$-$C_{10}$ aryl (optionally substituted with $C_1$-$C_6$ alkoxy, which is optionally substituted with 1-3 groups independently selected from halogen). In some embodiments, each R$^2$ in Formula IIa' is independently selected from hydrogen and $C_1$-$C_6$ alkyl. In some embodiments, each R$^2$ in Formula IIa' is hydrogen.

In some embodiments, R$^{Z1}$ in Formula IIa' is selected from $C_1$-$C_6$ alkyl (optionally substituted with 1-6 groups selected from halogen). In some embodiments, R$^{Z1}$ in Formula IIa' is —CF$_3$.

In some embodiments, R$^{Z2}$ in Formula IIa' is hydroxy.

In some embodiments, R$^{Z1}$ in Formula IIa' is $C_1$-$C_6$ alkyl (optionally substituted with 1-6 groups selected from halogen) and R$^{Z2}$ in Formula IIa' is hydroxy. In some embodiments, R$^{Z1}$ in Formula IIa' is —CF$_3$ and R$^{Z2}$ in Formula IIa' is hydroxy.

In some embodiments, the compound of Formula I is selected from compounds of Formula IIIa':

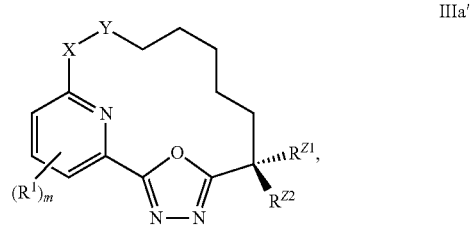

and deuterated derivatives and pharmaceutically acceptable salts thereof, wherein:
X is selected from —O—, —S—, —SO—, and —SO$_2$—;
each Y is independently selected from —C(R$^Y$)$_2$—, —O—, —CO—, and

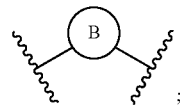

each R$^Y$ is independently selected from hydrogen, halogen, $C_1$-$C_6$ alkyl (optionally substituted with 1-3 groups independently selected from hydroxy and Q), $C_6$-$C_{10}$ aryl, 5- to 10-membered heteroaryl, —OR$^{Y1}$, —CO$_2$R$^{Y1}$, —COR$^{Y1}$, —CON(R$^{Y1}$)$_2$, and —NR$^{Y1}$—; or two instances of R$^Y$ on the same atom are taken together to form a ring selected from $C_3$-$C_8$ cycloalkyl and 3- to 6-membered heterocyclyl; or two instances of R$^Y$, one of which is on one atom and the second of which is on an adjacent atom, are taken together to form a pi bond;
each R$^{Y1}$ is independently selected from hydrogen and $C_1$-$C_6$ alkyl, or two instances of R$^{Y1}$ bonded to the same nitrogen taken together form a 3- to 6-membered heterocyclyl;
Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);
each Q is independently selected from:
  $C_1$-$C_6$ alkyl optionally substituted with 1-3 groups independently selected from:
    halogen, oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;
each R$^1$ is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;
each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);
R$^{Z1}$ is selected from hydrogen, —CN, C$_1$-C$_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;
R$^{Z2}$ is selected from hydrogen, halogen, and hydroxy, or R$^{Z1}$ and R$^{Z2}$ taken together form a group selected from oxo and =N—OH; and
m is selected from 0, 1, 2, and 3.

In some embodiments, X in Formula IIIa' is —O—.

In some embodiments, each Y in Formula IIIa' is independently selected
from —C(R$^Y$)$_2$—, —CO—, and

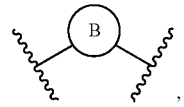

wherein R$^Y$ and Ring B as defined for Formula IIIa'.

In some embodiments, each Y in Formula IIIa' is —C(R$^Y$)$_2$—, wherein R$^Y$ is as defined for Formula IIIa'.

In some embodiments, each R$^Y$ in Formula IIIa' is independently selected from hydrogen, C$_1$-C$_6$ alkyl (optionally substituted with 1-3 groups independently selected from hydroxy and Q), and —OR$^{Y1}$, wherein Q and R$^{Y1}$ are as defined for Formula IIIa'.

In some embodiments, each R$^Y$ in Formula IIIa' is independently selected from: hydrogen,

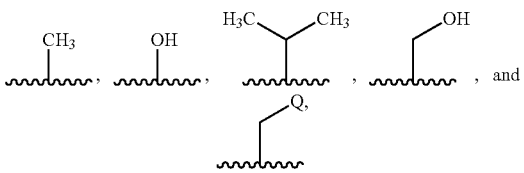

wherein Q is as defined for Formula IIIa'.

In some embodiments, each Q in Formula IIIa' is independently selected from:
C$_3$-C$_8$ cycloalkyl,
C$_6$-C$_{10}$ aryl optionally substituted with 1-3 groups independently selected from halogen and C$_1$-C$_6$ alkyl.

In some embodiments, each Q in Formula IIIa' is independently selected from:

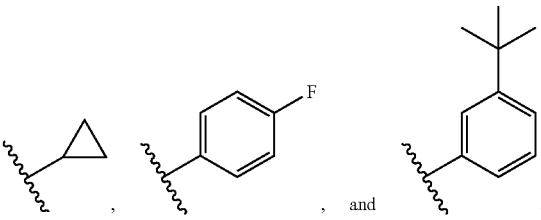

In some embodiments, Ring B in Formula IIIa' is selected from C$_6$-C$_{10}$ aryl optionally substituted with 1-3 groups independently selected from halogen.

In some embodiments, Ring B in Formula IIIa' is selected from:

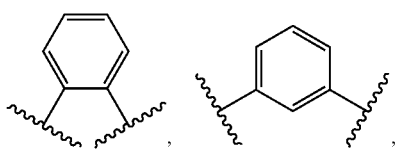

-continued

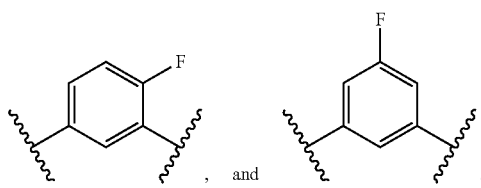, and

In some embodiments, each in Formula IIIa' is independently $C_1$-$C_6$ alkyl (optionally substituted with 1-3 groups independently selected from halogen) and —N(R²)₂, wherein R² is as defined for Formula IIIa'. In some embodiments, each in Formula IIIa' is independently selected from —CF₃ and —N(R²)₂, wherein R² is as defined for Formula IIIa'.

In some embodiments, each R² in Formula IIIa' is independently selected from hydrogen, $C_1$-$C_6$ alkyl (optionally substituted with 1-3 groups independently selected from halogen), and $C_6$-$C_{10}$ aryl (optionally substituted with $C_1$-$C_6$ alkoxy, which is optionally substituted with 1-3 groups independently selected from halogen). In some embodiments, each R² in Formula IIIa' is independently selected from hydrogen and $C_1$-$C_6$ alkyl.

In some embodiments, each R² in Formula IIIa' is hydrogen.

In some embodiments, $R^{Z1}$ in Formula IIIa' is selected from $C_1$-$C_6$ alkyl (optionally substituted with 1-6 groups selected from halogen). In some embodiments, $R^{Z1}$ in Formula IIIa' is —CF₃.

In some embodiments, $R^{Z2}$ in Formula IIIa' is hydroxy.

In some embodiments, $R^{Z1}$ in Formula IIIa' is $C_1$-$C_6$ alkyl (optionally substituted with 1-6 groups selected from halogen) and $R^{Z2}$ in Formula IIIa' is hydroxy. In some embodiments, $R^{Z1}$ in Formula IIIa' is —CF₃ and $R^{Z2}$ in Formula IIIa' is hydroxy.

Compounds of the invention include Compounds 1-53 and 54-77, and deuterated derivatives and pharmaceutically acceptable salts thereof.

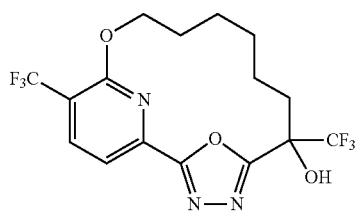 [SMILES: OC1(C(F)(F)F)CCCCCCOc2nc(ccc2C(F)(F)F)C2=NN=C1O2]

1

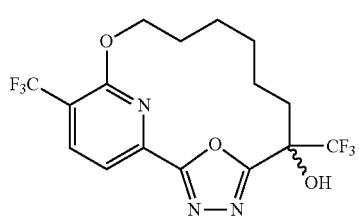

2 enantiomer 1

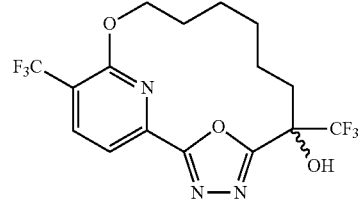

3 enantiomer 2

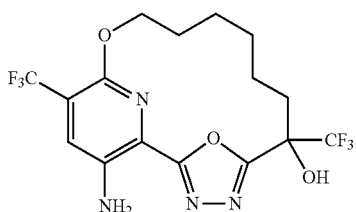

4

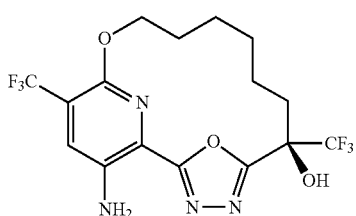

5

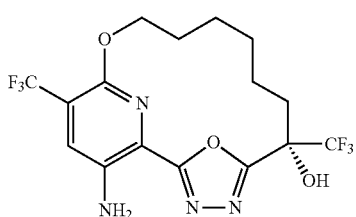

6

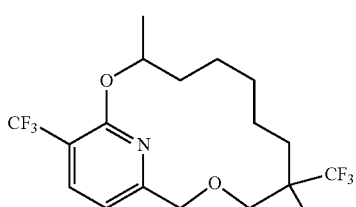

7 diastereomer pair 1

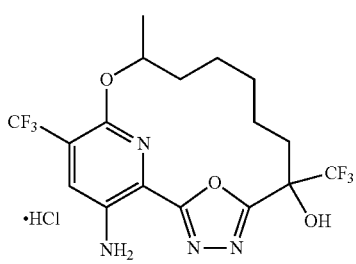

8 diastereomer pair 2

9
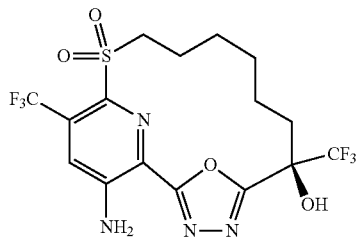
Enantiomer 1
10
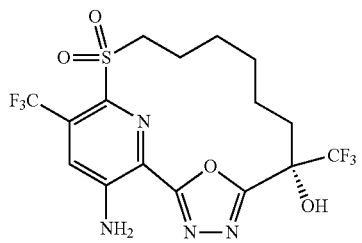
Enantiomer 2
11
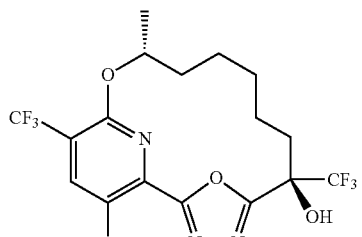
12
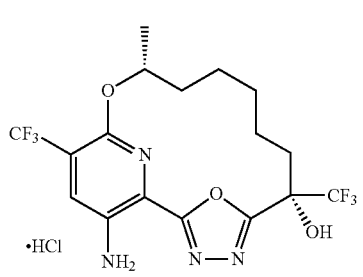 [SMILES: Cl ; C[C@@H]1CCCCC[C@@](O)(C(F)(F)F)C2=NN=C(O2)c2nc(c(C(F)(F)F)cc2N)O1]
13
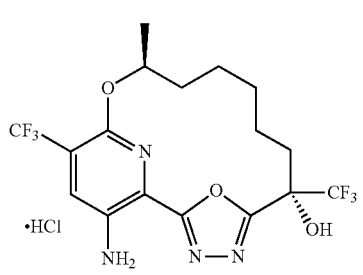 [SMILES: Cl ; C[C@H]1CCCCC[C@@](O)(C(F)(F)F)C2=NN=C(O2)c2nc(c(C(F)(F)F)cc2N)O1]
14
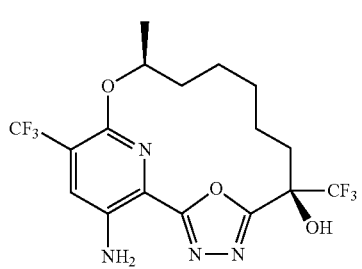
15
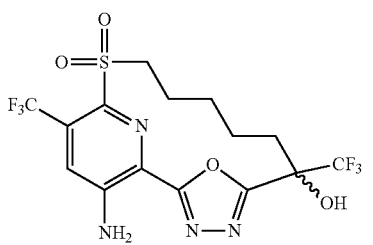
enantiomer 1
16
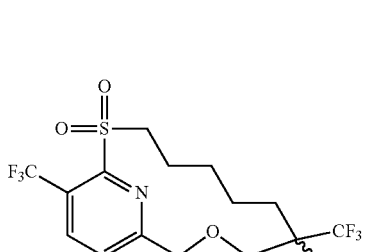
enantiomer 2
17
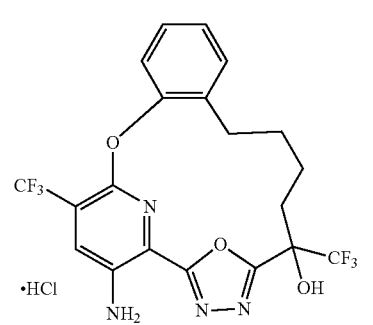 [SMILES: Cl ; Nc1cc(C(F)(F)F)c2nc1C1=NN=C(O1)C(O)(C(F)(F)F)CCCCc1ccccc1O2]
18
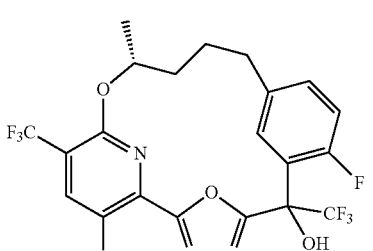
diastereomer pair
19
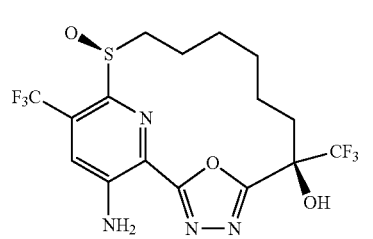

| 69 -continued | | 70 -continued | |
|---|---|---|---|
| 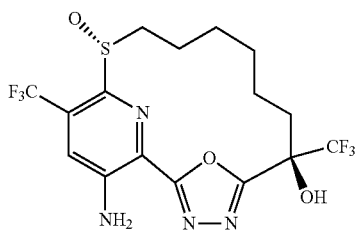 | 20 | 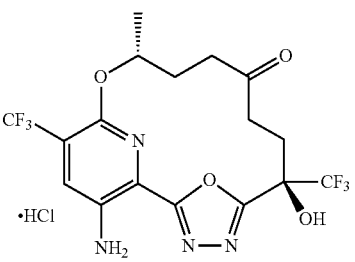 | 26 |
| 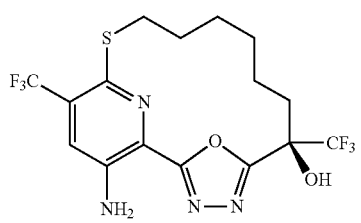 | 21 | 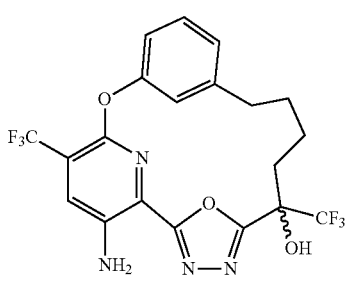
enantiomer 1 | 27 |
| 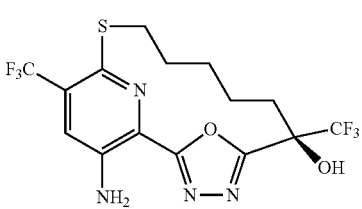 [SMILES: Nc1cc(C(F)(F)F)c2nc1C1=NN=C(O1)[C@@](O)(C(F)(F)F)CCCCCS2] | 22 | 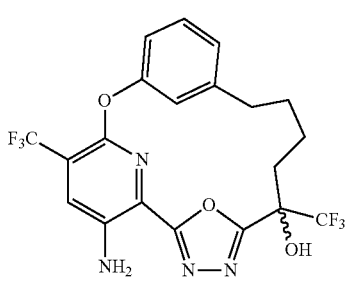
enantiomer 2 | 28 |
| 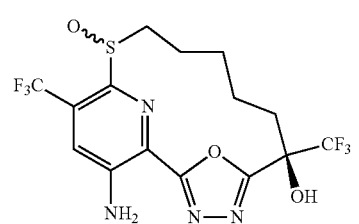
enantiomer 1 | 23 | 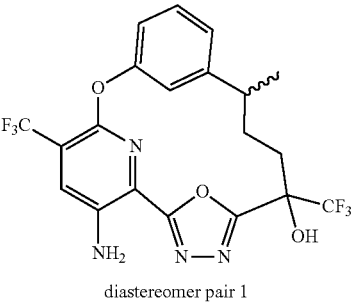 [SMILES: CC1CCC(O)(C(F)(F)F)c2nnc(o2)-c2nc(c(C(F)(F)F)cc2N)Oc2cccc1c2]
diastereomer pair 1 | 29 |
| 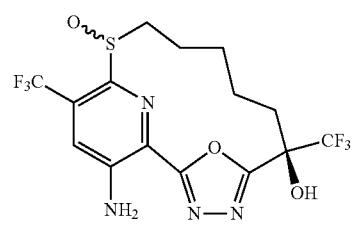
enantiomer 2 | 24 | 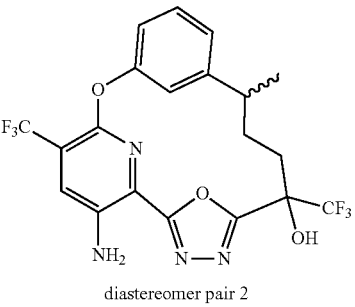 [SMILES: CC1CCC(O)(C(F)(F)F)c2nnc(o2)-c2nc(c(C(F)(F)F)cc2N)Oc2cccc1c2]
diastereomer pair 2 | 30 |
| 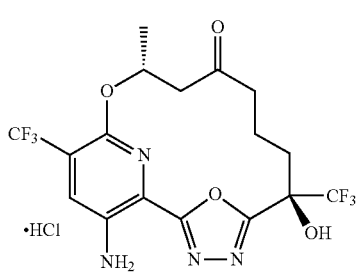 | 25 | | |

| | |
|---|---|
| 31 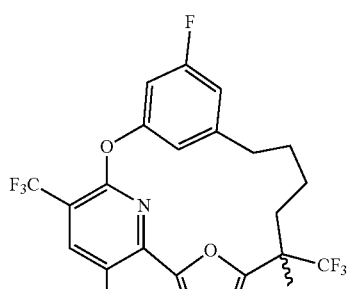<br>enantiomer 1 | 35 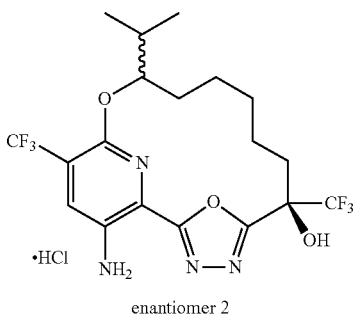<br>enantiomer 2 |
| 32 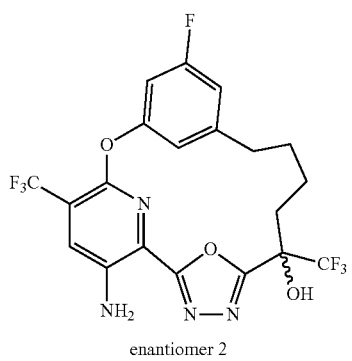 [SMILES: Nc1cc(C(F)(F)F)c2nc1-c1nnc(o1)C(O)(C(F)(F)F)CCCCc1cc(F)cc(c1)O2]<br>enantiomer 2 | 36 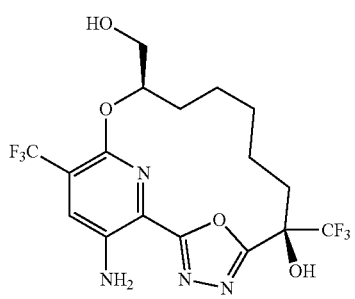 |
| 33 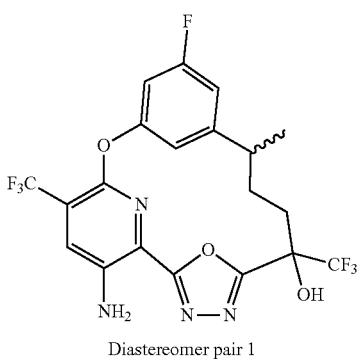 [SMILES: CC1CCC(O)(C(F)(F)F)c2nnc(o2)-c2nc(c(C(F)(F)F)cc2N)Oc2cc(F)cc1c2]<br>Diastereomer pair 1 | 37 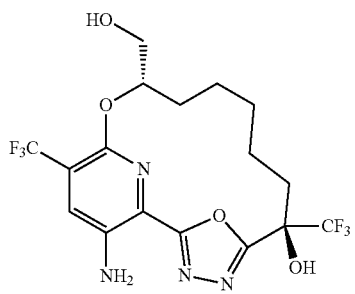 |
| 34 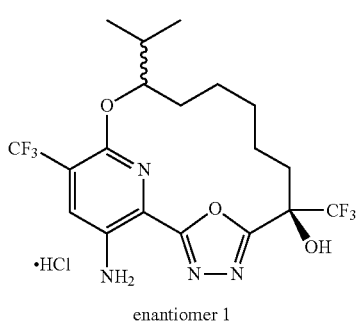 [SMILES: CC(C)C1CCCCC[C@](O)(C(F)(F)F)C2=NN=C(O2)c2nc(c(C(F)(F)F)cc2N)O1 ; Cl]<br>enantiomer 1 | 38 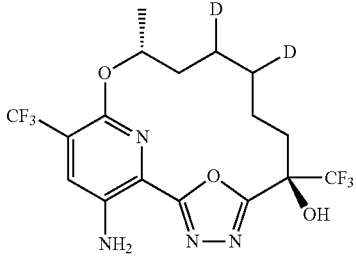 |
| | 39 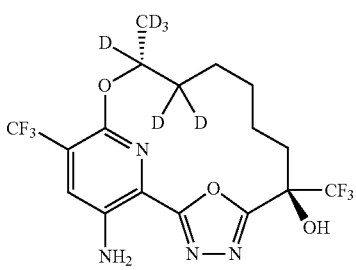 [SMILES: [2H]C([2H])([2H])[C@@]1([2H])Oc2nc(c(N)cc2C(F)(F)F)C2=NN=C(O2)[C@@](O)(C(F)(F)F)CCCCC1([2H])[2H]] |

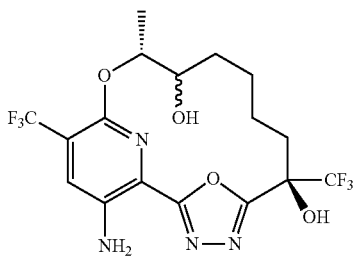
diastereomer 1
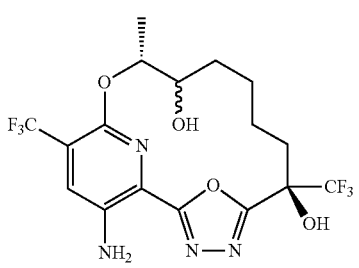
diastereomer 2
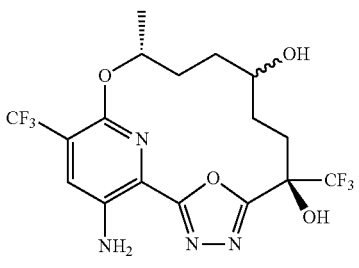
diastereomer 1
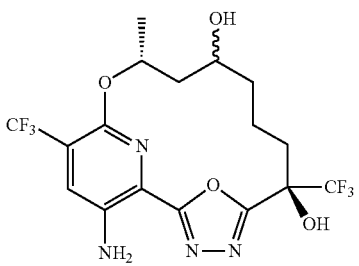
regioisomeric diastereomer 1
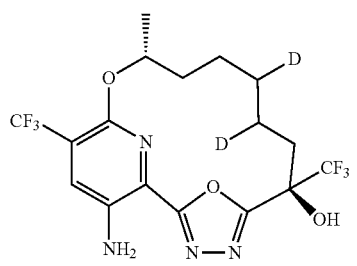 [SMILES: [2H]C1CC[C@@H](C)Oc2nc(c(N)cc2C(F)(F)F)C2=NN=C(O2)[C@@](O)(C(F)(F)F)CC1[2H]]
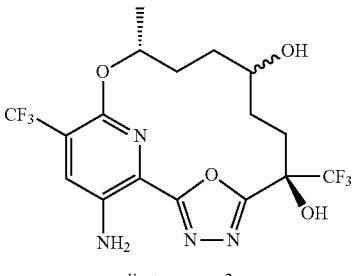
diastereomer 2
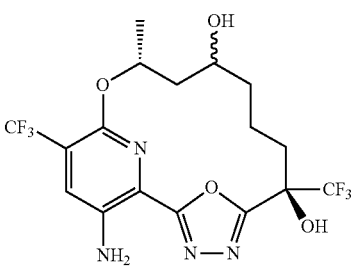
diastereomer 2
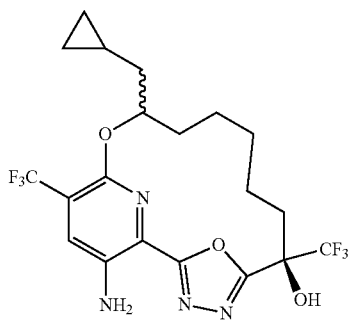
enantiomer 1
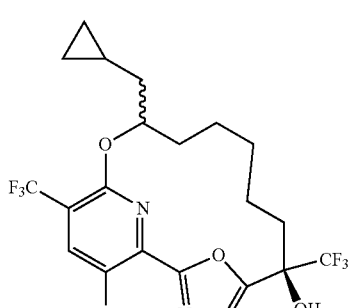
enantiomer 2

75
-continued
49
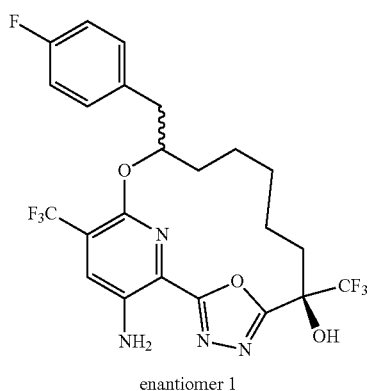 [SMILES: Nc1cc(C(F)(F)F)c2nc1C1=NN=C(O1)[C@@](O)(C(F)(F)F)CCCCCC(Cc1ccc(F)cc1)O2]
enantiomer 1
50
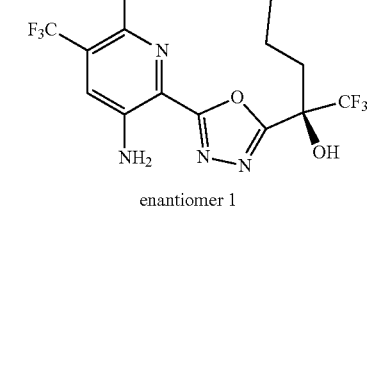
enantiomer 2
51
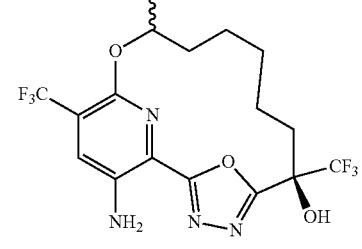
enantiomer 1
76
-continued
52
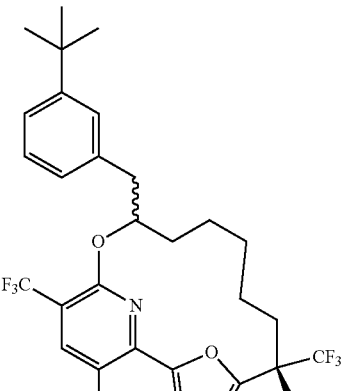
enantiomer 2
53
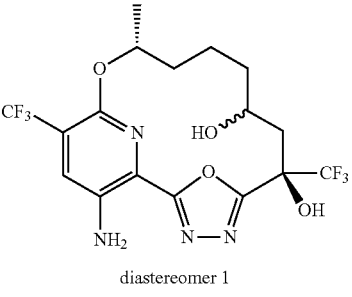 [SMILES: C[C@@H]1CCCC(O)C[C@](O)(C(F)(F)F)C2=NN=C(O2)c2nc(c(C(F)(F)F)cc2N)O1]
diastereomer 1
54
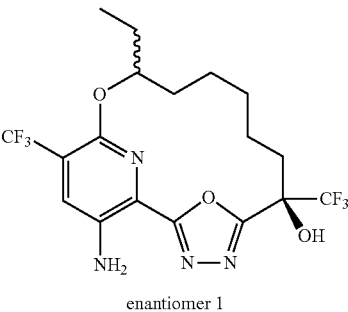 [SMILES: CCC1CCCCC[C@](O)(C(F)(F)F)C2=NN=C(O2)c2nc(c(C(F)(F)F)cc2N)O1]
enantiomer 1
55
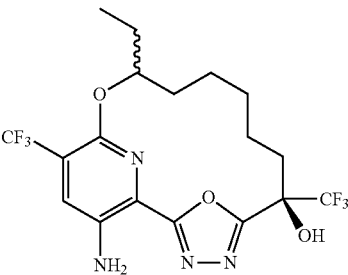
enantiomer 2

| 77 -continued | | 78 -continued | |
|---|---|---|---|
| 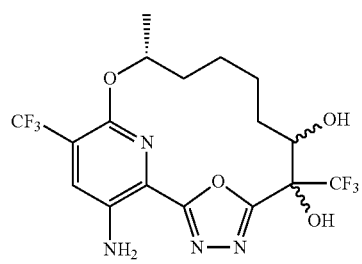 enantiomer 1 | 56 | 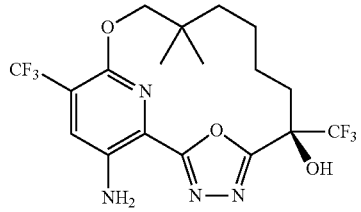 | 61 |
| 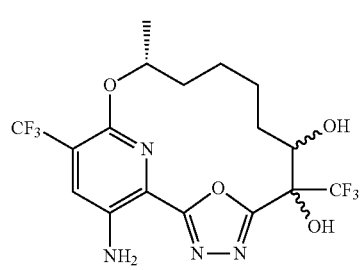 enantiomer 2 | 57 | 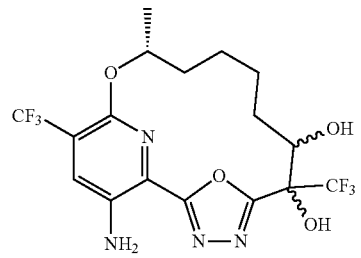 enantiomer 3 | 62 |
| 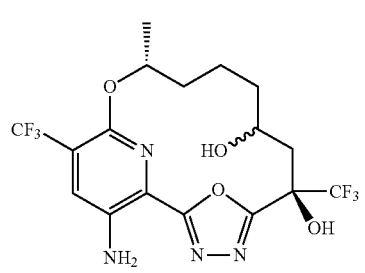 diastereomer 2 | 58 | 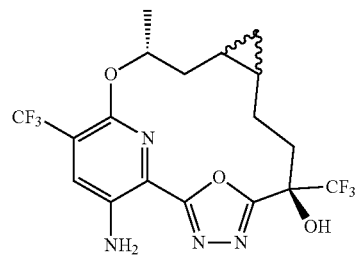 enantiomer 1 | 63 |
| 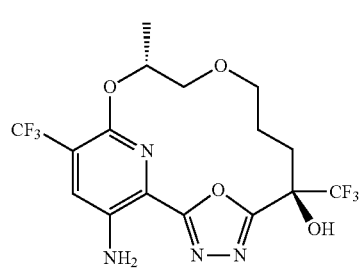 | 59 | 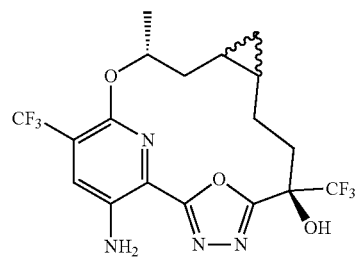 enantiomer 2 | 64 |
| 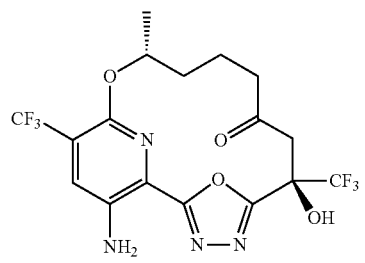 [SMILES: C[C@@H]1CCCC(=O)C[C@](O)(C(F)(F)F)C2=NN=C(O2)c2nc(c(C(F)(F)F)cc2N)O1] | 60 | 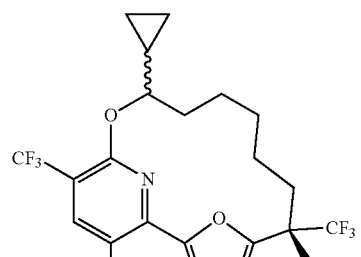 enantiomer 1 | 65 |

-continued
| | |
|---|---|
| 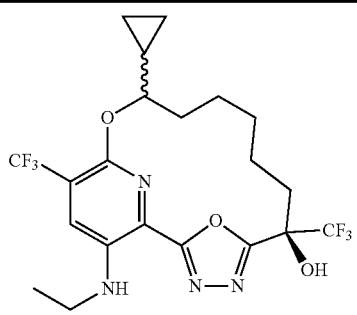<br>enantiomer 2 | 66 |
| 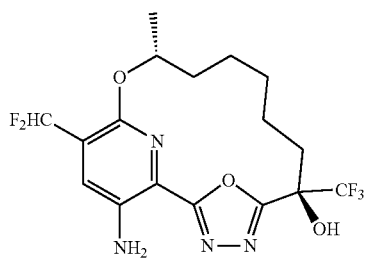 [SMILES: C[C@@H]1CCCCC[C@](O)(C(F)(F)F)C2=NN=C(O2)c2nc(c(C(F)F)cc2N)O1] | 67 |
| 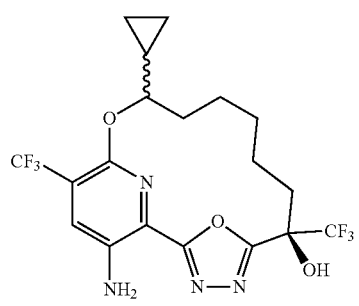<br>enantiomer 1 | 68 |
| 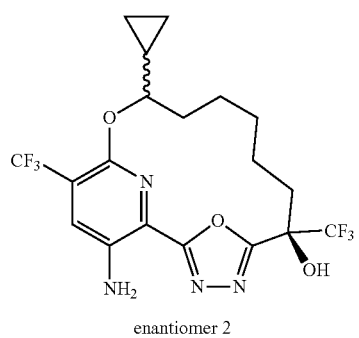 [SMILES: Nc1cc(C(F)(F)F)c2nc1C1=NN=C(O1)[C@@](O)(C(F)(F)F)CCCCCC(C1CC1)O2]<br>enantiomer 2 | 69 |
| 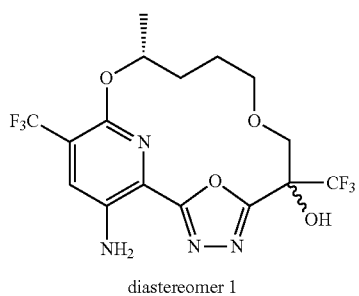 [SMILES: C[C@@H]1CCCOCC(O)(C(F)(F)F)C2=NN=C(O2)c2nc(c(C(F)(F)F)cc2N)O1]<br>diastereomer 1 | 70 |
-continued
| | |
|---|---|
| 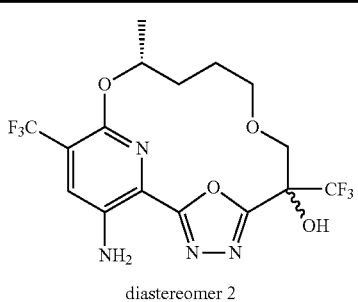<br>diastereomer 2 | 71 |
| 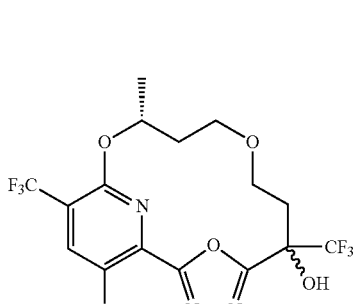<br>diastereomer 1 | 72 |
| 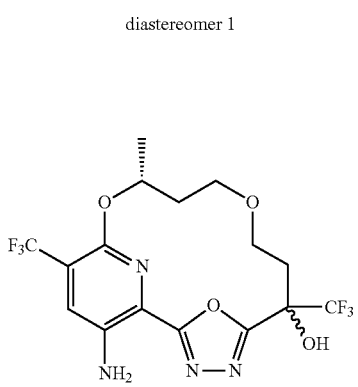<br>diastereomer 2 | 73 |
| 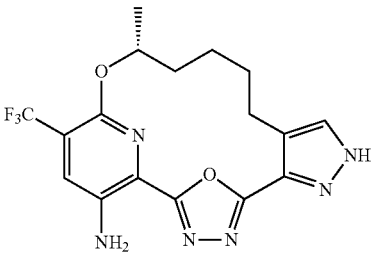 [SMILES: C[C@@H]1CCCCc2c[nH]nc2C2=NN=C(O2)c2nc(c(C(F)(F)F)cc2N)O1] | 74 |
| 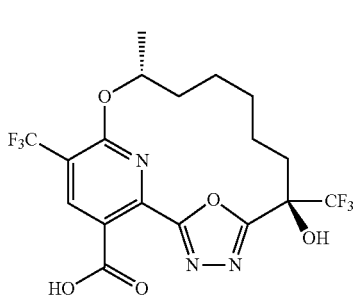 [SMILES: C[C@@H]1CCCCC[C@](O)(C(F)(F)F)C2=NN=C(O2)c2nc(c(C(F)(F)F)cc2C(=O)O)O1] | 75 |

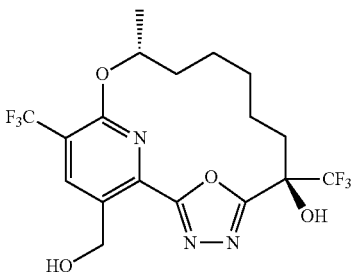 [SMILES: C[C@@H]1CCCCC[C@](O)(C(F)(F)F)C2=NN=C(O2)c2nc(c(C(F)(F)F)cc2CO)O1]

76

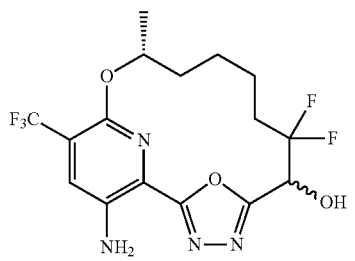

77 diastereomer 1

Methods of Treatment

Any of the novel compounds disclosed herein, such as for example, compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, pharmaceutically acceptable salts thereof, and deuterated derivatives of such compounds and salts can act as a CFTR modulator, i.e., it modulates CFTR activity in the body. Individuals suffering from a mutation in the gene encoding CFTR may benefit from receiving a CFTR modulator. A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect). Some CFTR mutations exhibit characteristics of multiple classes. Certain mutations in the CFTR gene result in cystic fibrosis.

Thus, in some embodiments, the invention provides methods of treating, lessening the severity of, or symptomatically treating cystic fibrosis in a patient comprising administering to the patient an effective amount of any of the novel compounds disclosed herein, such as for example, compounds of Formulae I, I', I'', I''', Ia, IIa, IIa', IIb, IIc, IId, IIe, IIf, IIIa, IIIa', IIIb, IIIc, IIId, IIIe, and IIIf, Compounds 1 to 53, Compounds 54 to 77, pharmaceutically acceptable salts thereof, and/or deuterated derivatives of such compounds and salts, alone or in combination with another active ingredient, such as another CFTR modulating agent. In some embodiments, the patient has an F508del/minimal function (MF) genotype, F508del/F508del genotype (homozygous for the F508del mutation), F508del/gating genotype, or F508del/residual function (RF) genotype. In some embodiments the patient is heterozygous and has one F508del mutation. In some embodiments the patient is homozygous for the N1303K mutation.

In some embodiments, 1 mg to 1000 mg of a compound disclosed herein, a pharmaceutically acceptable salt thereof, or a deuterated derivative of such compound or salt are administered daily.

In some embodiments, the patient is heterozygous and has an F508del mutation on one allele and a mutation on the other allele selected from Table 2:

TABLE 2

CFTR Mutations

| Mutation | | | | |
|---|---|---|---|---|
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185+1G→T | 711+5G→A | 1717-8G→A | 2622+1G→A | 3121-1G→A |
| 296+1G→A | 712-1G→T | 1717-1G→A | 2790-1G→C | 3500-2A→G |
| 296+1G→T | 1248+1G→A | 1811+1G→C | 3040G→C | 3600+2insT |
| 405+1G→A | 1249-1G→A | 1811+1.6kbA→2G | (G970R) | 3850-1G→A |
| 405+3A→C | 1341+1G→A | 1811+1643G→T | 3120G→A | 4005+1G→A |
| 406-1G→A | 1525-2A→G | 1812-1G→A | 3120+1G→A | 4374+1G→T |
| 621+1G→T | 1525-1G→A | 1898+1G→A | 3121-2A→G | |
| 711+1G→T | | 1898+1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |
| 365-366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G | 3007delG | 4016insT |

TABLE 2-continued

| CFTR Mutations | | | | |
|---|---|---|---|---|
| 457TAT→G Mutation | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609del CA | 2594delGT | 3659delC | |
| CFTRdele1 | CFTRdele16-17b | 1461ins4 | | |
| CFTRdele2 | CFTRdele17a,17b | 1924del7 | | |
| CFTRdele2,3 | CFTRdele17a-18 | 2055del9→A | | |
| CFTRdele2-4 | CFTRdele19 | 2105-2117del13insAGAAA | | |
| CFTRdele3-10,14b-16 | CFTRdele19-21 | 2372del8 | | |
| CFTRdele4-7 | CFTRdele21 | 2721del11 | | |
| CFTRdele4-11 | CFTRdele22-24 | 2991del32 | | |
| CFTR50kbdel | CFTRdele22,23 | 3667ins4 | | |
| CFTRdup6b-10 | 124del23bp | 4010del4 | | |
| CFTRdele11 | 602del14 | 4209TGTT→AA | | |
| CFTRdele13,14a | 852del22 | | | |
| CFTRdele14b-17b | 991del5 | | | |
| A46D | V520F | Y569D | N1303K | |
| G85E | A559T | L1065P | | |
| R347P | R560T | R1066C | | |
| L467P | R560S | L1077P | | |
| I507del | A561E | M1101K | | |

In some embodiments, the disclosure also is directed to methods of treatment using isotope-labelled compounds of the afore-mentioned compounds, or pharmaceutically acceptable salts thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively.

The isotope-labelled compounds and salts can be used in a number of beneficial ways. They can be suitable for medicaments and/or various types of assays, such as substrate tissue distribution assays. For example, tritium ($^{3}H$)- and/or carbon-14 ($^{14}C$)-labelled compounds are particularly useful for various types of assays, such as substrate tissue distribution assays, due to relatively simple preparation and excellent detectability. For example, deuterium ($^{2}H$)-labelled ones are therapeutically useful with potential therapeutic advantages over the non-$^{2}H$-labelled compounds. In general, deuterium ($^{2}H$)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^{2}H$)-labelled ones. In some specific embodiments, the isotope-labelled compounds and salts are deuterium ($^{2}H$)-labelled, wherein one or more hydrogen atoms therein have been replaced by deuterium. In chemical structures, deuterium is represented as "$^{2}H$" or "D."

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

The deuterium ($^{2}H$)-labelled compounds and salts can modulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. For a further discussion, see S. L. Harbeson and R. D. Tung, *Deuterium In Drug Discovery and Development*, Ann. Rep. Med. Chem. 2011, 46, 403-417, which is incorporated herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Combination Therapies

One aspect disclosed herein provides methods of treating cystic fibrosis and other CFTR-mediated diseases using any of the novel compounds disclosed herein, such as for example, compounds of Formulae I, I', I", I'", Ia, IIa, IIa', IIb, IIc, IId, IIe, IIf, IIIa, IIIa', IIIb, IIIc, IIId, IIIe, and IIIf, Compounds 1 to 53, Compounds 54 to 77, pharmaceutically acceptable salts thereof, and deuterated derivatives of such compounds and salts in combination with at least one additional active pharmaceutical ingredient.

Thus, in some embodiments, the invention provides methods of treating, lessening the severity of, or symptomatically treating cystic fibrosis in a patient comprising administering to the patient an effective amount of any of the novel compounds disclosed herein, such as for example, compounds of Formulae I, I', I", I'", Ia, IIa, IIa', IIb, IIc, IId, IIe, IIf, IIIa, IIIa', IIIb, IIIc, IIId, IIIe, and IIIf, Compounds 1 to 53, Compounds 54 to 77, pharmaceutically acceptable salts thereof, and/or deuterated derivatives of such compounds and salts, alone or in combination with at least one additional active pharmaceutical ingredient, such as, e.g., a CFTR modulating agent.

In some embodiments, at least one additional active pharmaceutical ingredient is selected from mucolytic agents, bronchodilators, antibiotics, anti-infective agents, and anti-inflammatory agents.

In some embodiments, the additional therapeutic agent is an antibiotic. Exemplary antibiotics useful herein include tobramycin, including tobramycin inhaled powder (TIP), azithromycin, aztreonam, including the aerosolized form of aztreonam, amikacin, including liposomal formulations thereof, ciprofloxacin, including formulations thereof suitable for administration by inhalation, levoflaxacin, including aerosolized formulations thereof, and combinations of two antibiotics, e.g., fosfomycin and tobramycin.

In some embodiments, the additional agent is a mucolyte. Exemplary mucolytes useful herein includes Pulmozyme®.

In some embodiments, the additional agent is a bronchodilator. Exemplary bronchodilators include albuterol, metaprotenerol sulfate, pirbuterol acetate, salmeterol, or tetrabuline sulfate.

In some embodiments, the additional agent is an anti-inflammatory agent, i.e., an agent that can reduce the inflammation in the lungs. Exemplary such agents useful herein include ibuprofen, docosahexanoic acid (DHA), sildenafil, inhaled glutathione, pioglitazone, hydroxychloroquine, or simavastatin.

In some embodiments, the additional agent is a nutritional agent. Exemplary nutritional agents include pancrelipase (pancreating enzyme replacement), including Pancrease®, Pancreacarb®, Ultrase®, or Creon®, Liprotomase® (formerly Trizytek®), Aquadeks®, or glutathione inhalation. In one embodiment, the additional nutritional agent is pancrelipase.

In some embodiments, at least one additional active pharmaceutical ingredient is selected from CFTR modulating agents. In some embodiments, the CFTR modulating agent is a CFTR corrector. In some embodiments, the CFTR modulating agent is a CFTR potentiator enhancer/co-potentiator (for example, ASP-11). In some embodiments, the at least one additional active pharmaceutical ingredient is a CFTR amplifier. In some embodiments, the at least one additional active pharmaceutical ingredient is a CFTR read-through agent. In some embodiments, the at least one additional active pharmaceutical ingredient is a CFTR nucleic acid therapy.

In some embodiments, the at least one additional active pharmaceutical ingredient is a ENaC inhibitor. In some embodiments, the at least one additional active pharmaceutical ingredient is a TMEM16A modulator. In some embodiments, the at least one additional active pharmaceutical ingredient is a GPR39 agonist.

In some embodiments, the at least one additional active pharmaceutical ingredient is chosen from (a) Compound II and pharmaceutically acceptable salts and deuterated derivatives thereof; (b) Compound IV and pharmaceutically acceptable salts and deuterated derivatives thereof, (c) Compound V and pharmaceutically acceptable salts and deuterated derivatives thereof, (d) Compound VI and pharmaceutically acceptable salts and deuterated derivatives thereof, (e) Compound VII and pharmaceutically acceptable salts and deuterated derivatives thereof, and (f) Compound VIII and pharmaceutically acceptable salts and deuterated derivatives thereof. Thus, in some embodiments, the combination therapies provided herein comprise a compound selected from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof, and at least one compound chosen from Compound II, Compound IV, Compound V, Compound VI, Compound VII, Compound VIII, Compound IX, Compound X, and pharmaceutically acceptable salts and deuterated derivatives thereof. In some embodiments, the combination therapies provided herein comprise (a) at least one compound chosen from compounds of Formulae I, I', I", I'", Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof; (b) at least one compound chosen from Compound II, Compound IV, and pharmaceutically acceptable salts and deuterated derivatives thereof, and (c) at least one compound chosen from Compound V, Compound VI, Compound VII, Compound VIII, Compound IX, Compound X, and pharmaceutically acceptable salts and deuterated derivatives thereof. In some embodiments, the combination therapies provided herein comprise (a) at least one compound chosen from compounds of Formulae I, I', I", I'", Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof; (b) at least one compound selected from Compound II and pharmaceutically acceptable salts and deuterated derivatives thereof; and (c) at least one compound chosen from Compound VII and pharmaceutically acceptable salts and deuterated derivatives thereof.

In some embodiments, the combination therapies provided herein comprise (a) a compound selected from compounds of Formulae I, I', I", I'", Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof; (b) at least one compound chosen from Compound II, Compound IV, Compound V, Compound VI, Compound VII, Compound VIII, Compound IX, Compound X, and pharmaceutically acceptable salts and deuterated derivatives thereof; and (c) at least one compound chosen from compounds disclosed in WO 2016/105485, United States Patent Application Publication No. 2016-0120841, United States Patent Application Publication No. 2017-0101405, WO 2017/009804, WO 2018/065921, WO 2017/062581, or *Journal of Cystic Fibrosis* (2018), 17(5), 595-606.

In some embodiments, the combination therapies provided herein comprise (a) a compound selected from compounds of Formulae I, I', I", I''', Ia, IIa, IIa', IIb, IIc, IId, IIe, IIf, IIIa, IIIa', IIIb, IIIc, IIId, IIIe, and IIIf; Compounds 1 to 53, Compounds 54 to 77, and pharmaceutically acceptable salts and deuterated derivatives thereof; (b) at least one compound chosen from Compound II, Compound IV, Compound V, Compound VI, Compound VII, Compound VIII, Compound IX, Compound X, and pharmaceutically acceptable salts and deuterated derivatives thereof; and (c) at least one compound chosen from PTI-428, ASP-11, ABBV-2222, ABBV-2851, GLPG2737, ABBV-3221, ABBV-3748, ABBV-3903, ABBV-119, and PTI-801.

In some embodiments, the combination therapies provided herein comprise (a) a compound selected from compounds of Formulae I, I', I", I''', Ia, IIa, IIa', IIb, IIc, IId, IIe, IIf, IIIa, IIIa', IIIb, IIIc, IIId, IIIe, and IIIf; Compounds 1 to 53, Compounds 54 to 77, and pharmaceutically acceptable salts and deuterated derivatives thereof; and (b) at least two compounds chosen from compounds disclosed in WO 2019/195739, WO 2019/200246, WO 2021/030555, WO 2021/030556, WO 2017/173274, WO 2019/010092, WO 2019/018353, WO 2010/053471, WO 2011/119984, WO 2011/133751, WO 2011/133951, WO 2015/160787, WO 2007/056341, WO 2009/073757, WO 2009/076142, WO 2018/107100, WO 2019/113476, WO 2018/064632, WO 2019/152940, WO 2016/057572, WO 2021/030554, WO 2020/206080, WO 2016/105485, United States Patent Application Publication No. 2016-0120841, United States Patent Application Publication No. 2017-0101405, WO 2017/009804, WO 2018/065921, WO 2017/062581, *Journal of Cystic Fibrosis* (2018), 17(5), 595-606, Pedemonte, N. et al. *Sci. Adv.* 2020, 6 (8), eaay9669, Phuan, P.-W. et al. *Sci. Rep.* 2019, 9 (1), 17640, Bose, S. et al. *J. Cyst. Fibros.* 2020, 19 Suppl 1, S25-S32, Crawford, D. K. *J. Pharmacol. Exp. Ther.* 2020, 374 (2), 264-272, Brasell, E. J. et al. *PLoS One* 2019, 14 (12), e0223954, Smith, N. J, Solovay, C. F., *Pharm. Pat. Anal.* 2017, 6 (4), 179-188, Kunzelmann, K. et al., *Front. Pharmacol.* 2019, 10, 3, or Son, J.-H. et al., *Eur. J. of Med. Chem.* 2020, 112888.

In some embodiments, the combination therapies provided herein comprise (a) a compound selected from compounds of Formulae I, I', I", I''', Ia, IIa, IIa', IIb, IIc, IId, IIe, IIf, IIIa, IIIa', IIIb, IIIc, IIId, IIIe, and IIIf; Compounds 1 to 53, Compounds 54 to 77, and pharmaceutically acceptable salts and deuterated derivatives thereof, and (b) at least two compounds chosen from Compound II, Compound IV, Compound V, Compound VI, Compound VII, Compound VIII, Compound IX, Compound X, PTI-428, ASP-11, ABBV-2222, ABBV-2851, GLPG2737, ABBV-3221, ABBV-3748, ABBV-3903, ABBV-119, and PTI-801, and pharmaceutically acceptable salts and deuterated derivatives thereof.

In some embodiments, the combination therapies provided herein comprise (a) a compound selected from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; (b) at least one compound chosen from Compound II, Compound III, Compound III-d, Compound IV, Compound V, Compound VI, Compound VII, Compound VIII, Compound IX, Compound X, PTI-428, ASP-11, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, PTI-801, FDL-176, PTI-808 (dirocaftor), GLPG1837, GLPG2451/ABBV-2451, QBW251 (icenticaftor), GLPG3067/ABBV-3067 (Navocaftor), ABBV-191, ELX-02, MRT5005, Lunar-CF, RCT223, amiloride, ETD001, $CF_{552}$, GS-9411, GS-5737, P-1037 (VX-371), P-1055 (VX-551), AZD5634, SPX-101, Ionis-ENaC-2.5 Rx, BI 1265162, AZ5634, ARO-ENaC1001, ETD002, and DS-1039, and pharmaceutically acceptable salts and deuterated derivatives thereof; and (c) at least one pharmaceutically acceptable carrier.

In some embodiments, at least one compound chosen from compounds of Formulae I, I', I", I''', Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof is administered in combination with at least one compound chosen from Compound II and pharmaceutically acceptable salts and deuterated derivatives thereof. In some embodiments, at least one compound chosen from compounds of Formulae I, I', I", I''', Ia, IIa, IIa', IIb, IIc, IId, IIe, IIf, IIIa, IIIb, IIIc, IIId, IIIe, and IIIf; Compounds 1 to 53, Compounds 54 to 77, and pharmaceutically acceptable salts and deuterated derivatives thereof is administered in combination with at least one compound chosen from Compound IV and pharmaceutically acceptable salts and deuterated derivatives thereof. In some embodiments, at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof is administered in combination with at least one compound chosen from Compound V and pharmaceutically acceptable salts and deuterated derivatives thereof. In some embodiments, at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof is administered in combination with at least one compound chosen from Compound VI and pharmaceutically acceptable salts and deuterated derivatives thereof. In some embodiments, at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof is administered in combination with at least one compound chosen from Compound VII and pharmaceutically acceptable salts and deuterated derivatives thereof. In some embodiments, at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof is administered in combination with at least one compound chosen from Compound VIII and pharmaceutically acceptable salts and deuterated derivatives thereof.

Each of the compounds of Formulae I, I', I", I''', Ia, IIa, IIa', IIb, IIc, IId, IIe, IIf, IIIa, IIIb, IIIc, IIId, IIIe, and IIIf; Compounds 1 to 53, Compounds 54 to 77, Compound II, Compound IV, Compound V, Compound VI, Compound VII, Compound VIII, Compound IX, Compound X, and their pharmaceutically acceptable salts and deuterated derivatives thereof, independently can be administered once daily, twice daily, or three times daily. In some embodiments, at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof is administered once daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf; Compounds 1 to 53, Compounds 54 to 77, and pharmaceutically acceptable salts and deuterated derivatives thereof is administered twice daily. In some embodiments, at least one compound chosen from compounds of Formulae I, I', I", I'", Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof and at least one compound chosen from Compound II and pharmaceutically acceptable salts thereof are administered once daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIf, Compounds 1 to 53, Compounds 54 to 77, and pharmaceutically acceptable salts and deuterated derivatives thereof and at least one compound chosen from Compound II and pharmaceutically acceptable salts thereof are administered twice daily. In some embodiments, at least one compound chosen from compounds of Formulae I, I', I", I', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound IV and pharmaceutically acceptable salts thereof are administered once daily. In some embodiments, at least one compound chosen from compounds of Formulae I, I', I", I'", IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound IV and pharmaceutically acceptable salts thereof are administered twice daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound V and pharmaceutically acceptable salts thereof are administered once daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound V and pharmaceutically acceptable salts thereof are administered twice daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound VI and pharmaceutically acceptable salts thereof are administered once daily. In some embodiments, at least one compound chosen from compounds of Formulae I, I', I", I'", IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound VI and pharmaceutically acceptable salts thereof are administered twice daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound VII and pharmaceutically acceptable salts thereof are administered once daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound VII and pharmaceutically acceptable salts thereof are administered twice daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound VIII and pharmaceutically acceptable salts thereof are administered once daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least one compound chosen from Compound VIII and pharmaceutically acceptable salts thereof are administered twice daily.

In some embodiments, at least one compound chosen from compounds of Formulae I, I', I", I'", Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof; at least one compound chosen from Compound II, Compound IV, and pharmaceutically acceptable salts thereof; and at least one compound chosen from Compound V, Compound VI, Compound VII, Compound VIII, Compound IX, Compound X, and pharmaceutically acceptable salts thereof are administered once daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; at least one compound chosen from Compound II, Compound IV, and pharmaceutically acceptable salts thereof; and at least one compound chosen from Compound V, Compound VI, Compound VII, Compound VIII, Compound IX, Compound X, and pharmaceutically acceptable salts thereof are administered twice daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; at least one compound chosen from Compound II and pharmaceutically acceptable salts thereof; and at least one compound chosen from Compound VII and pharmaceutically acceptable salts thereof are administered once daily. In some embodiments, at least one compound chosen from compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; at least one compound chosen from Compound II and pharmaceutically acceptable salts thereof; and at least one compound chosen from Compound VII and pharmaceutically acceptable salts thereof are administered twice daily.

Compounds of Formulae I, I', I", I'", Ia, IIa, IIa', IIb, IIc, IId, IIe, IIf, IIIa, IIIb, IIIc, IIId, IIIe, and IIIf, Compounds 1 to 53, Compounds 54 to 77, Compound II, Compound IV, Compound V, Compound VI, Compound VII, Compound VIII, Compound IX, Compound X, and their pharmaceutically acceptable salts and deuterated derivatives thereof can be administered in a single pharmaceutical composition or separate pharmaceutical compositions. Such pharmaceutical compositions can be administered once daily or multiple times daily, such as twice daily. As used herein, the phrase that a given amount of API (e.g., Compound II, Compound VII, or pharmaceutically acceptable salts thereof) is administered once or twice daily or per day means that said given amount is administered per dosing, which may occur once or twice daily.

In some embodiments, at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof is administered in a first pharmaceutical composition; and at least one compound chosen from Compound VII and pharmaceutically acceptable salts thereof is administered in a second pharmaceutical composition.

In some embodiments, at least one compound chosen from compounds of Formulae I, I', I", I''', Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof is administered in a first pharmaceutical composition; at least one compound chosen from Compound II and pharmaceutically acceptable salts thereof is administered in a second pharmaceutical composition; and at least one compound chosen from Compound VII and pharmaceutically acceptable salts thereof is administered in a third pharmaceutical composition.

Any suitable pharmaceutical compositions known in the art can be used for compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, Compound II, Compound IV, Compound V, Compound VI, Compound VII, Compound VIII, Compound IX, Compound X, and pharmaceutically acceptable salts and deuterated derivatives thereof. Some exemplary pharmaceutical compositions for Compound II and its pharmaceutically acceptable salts can be found in WO 2011/119984 and WO 2014/014841, incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, and some exemplary pharmaceutical compositions for Compound III-d and its pharmaceutically acceptable salts can be found in U.S. Pat. Nos. 8,865,902, 9,181,192, 9,512,079, WO 2017/053455, and WO 2018/080591, all of which are incorporated herein by reference. Some exemplary pharmaceutical compositions for Compound IV and its pharmaceutically acceptable salts can be found in WO 2010/037066, WO 2011/127421, and WO 2014/071122, incorporated herein by reference. Some exemplary pharmaceutical compositions for Compound V and its pharmaceutically acceptable salts can be found in WO 2019/152940, incorporated herein by reference. Some exemplary pharmaceutical compositions for Compound VI and its pharmaceutically acceptable salts can be found in WO 2019/079760, incorporated herein by reference.

Pharmaceutical Compositions

Another aspect of the invention provides a pharmaceutical composition comprising at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof, and at least one pharmaceutically acceptable carrier.

In some embodiments, the invention provides pharmaceutical compositions comprising at least one compound chosen from compounds of Formulae I, I', I", I''', Ia, IIa, IIa', IIb, IIc, IId, IIe, IIf, IIIa, IIIa', IIIb, IIIc, IIId, IIIe, and IIIf, Compounds 1 to 53, Compounds 54 to 77, and pharmaceutically acceptable salts and deuterated derivatives thereof in combination with at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the at least one additional active pharmaceutical ingredient is a compound that enhances CFTR potentiation, i.e., a CFTR potentiator enhancer/co-potentiator. In some embodiments, the at least one additional active pharmaceutical ingredient is a CFTR amplifier. In some embodiments, the at least one additional active pharmaceutical ingredient is a CFTR readthrough agent. In some embodiments, the at least one additional active pharmaceutical ingredient is a CFTR nucleic acid therapy. In some embodiments, the at least one additional active pharmaceutical ingredient is a ENaC inhibitor. In some embodiments, the at least one additional active pharmaceutical ingredient is a TMEM16A modulator. In some embodiments, the at least one additional active pharmaceutical ingredient is a GPR39 agonist. In some embodiments, the pharmaceutical composition comprises at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least two additional active pharmaceutical ingredients, each of which is a CFTR corrector. In some embodiments, the pharmaceutical composition comprises at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof and at least two additional active pharmaceutical ingredients, one of which is a CFTR corrector and one of which is a CFTR potentiator enhancer.

In some embodiments, the invention provides a pharmaceutical composition comprising (a) at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof, (b) at least one compound chosen from Compound II, Compound IV, Compound V, Compound VI, Compound VII, Compound VIII, Compound IX, Compound X, and pharmaceutically acceptable salts thereof, and (c) at least one pharmaceutically acceptable carrier.

In some embodiments, the invention provides a pharmaceutical composition comprising (a) at least one compound chosen from compounds of Formulae I, I', I", I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof, (b) at least one compound chosen from Compound II and pharmaceutically acceptable salts thereof, and (c) at least one pharmaceutically acceptable carrier.

In some embodiments, the invention provides a pharmaceutical composition comprising (a) at least one compound chosen from compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof, (b) at least one compound chosen from Compound VII and pharmaceutically acceptable salts thereof, and (c) at least one pharmaceutically acceptable carrier.

In some embodiments, the disclosure provides a pharmaceutical composition comprising (a) at least one compound chosen from compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof, (b) at least one compound chosen from Compound II, Compound IV, and pharmaceutically acceptable salts thereof, (c) at least one compound chosen from Compound V, Compound VI, Compound VII, Compound VIII, Compound IX, Compound X, and pharmaceutically acceptable salts thereof, and (d) at least one pharmaceutically acceptable carrier.

In some embodiments, the disclosure provides a pharmaceutical composition comprising (a) at least one compound chosen from compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof, (b) at least one compound chosen from Compound II and pharmaceutically acceptable salts thereof, (c) at least one compound chosen from Compound VII and pharmaceutically acceptable salts thereof, and (d) at least one pharmaceutically acceptable carrier.

In some embodiments, the pharmaceutical compositions provided herein comprise (a) a compound selected from compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; (b) at least one compound chosen from Compound II, Compound IV, Compound V, Compound VI, Compound VII, Compound VIII, Compound IX, Compound X, and pharmaceutically acceptable salts and deuterated derivatives thereof; (c) at least one compound chosen from compounds disclosed in WO 2016/105485, United States Patent Application Publication No. 2016-0120841, United States Patent Application Publication No. 2017-0101405, WO 2017/009804, WO 2018/065921, WO 2017/062581, *Journal of Cystic Fibrosis* (2018), 17(5), 595-606, Pedemonte, N. et al. *Sci. Adv.* 2020, 6 (8), eaay9669, Phuan, P.-W. et al. *Sci. Rep.* 2019, 9 (1), 17640, Bose, S. et al. *J. Cyst. Fibros.* 2020, 19 Suppl 1, S25-S32, Crawford, D. K. *J Pharmacol. Exp. Ther.* 2020, 374 (2), 264-272, Brasell, E. J. et al. *PLoS One* 2019, 14 (12), e0223954, Smith, N. J, Solovay, C. F., *Pharm. Pat. Anal.* 2017, 6 (4), 179-188, Kunzelmann, K. et al., *Front. Pharmacol.* 2019, 10, 3, or Son, J.-H. et al., *Eur. J. of Med. Chem.* 2020, 112888; and (d) at least one pharmaceutically acceptable carrier.

In some embodiments, the pharmaceutical compositions provided herein comprise (a) a compound selected from compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; (b) at least one compound chosen from Compound II, Compound IV, Compound V, Compound VI, Compound VII, Compound VIII, Compound IX, Compound X, and pharmaceutically acceptable salts and deuterated derivatives thereof; (c) at least one compound chosen from PTI-428, ASP-11, ABBV-2222, ABBV-2851, GLPG2737, ABBV-3221, ABBV-3748, ABBV-3903, ABBV-119, and PTI-801; and (d) at least one pharmaceutically acceptable carrier.

In some embodiments, the pharmaceutical compositions provided herein comprise (a) a compound selected from compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; (b) at least two compounds chosen from compounds disclosed in WO 2019/195739, WO 2019/200246, WO 2021/030555, WO 2021/030556, WO 2017/173274, WO 2019/010092, WO 2019/018353, WO 2010/053471, WO 2011/119984, WO 2011/133751, WO 2011/133951, WO 2015/160787, WO 2007/056341, WO 2009/073757, WO 2009/076142, WO 2018/107100, WO 2019/113476, WO 2018/064632, WO 2019/152940, WO 2016/057572, WO 2021/030554, WO 2020/206080, WO 2016/105485, United States Patent Application Publication No. 2016-0120841, United States Patent Application Publication No. 2017-0101405, WO 2017/009804, WO 2018/065921, WO 2017/062581, *Journal of Cystic Fibrosis* (2018), 17(5), 595-606, Pedemonte, N. et al. *Sci. Adv.* 2020, 6 (8), eaay9669, Phuan, P.-W. et al. *Sci. Rep.* 2019, 9 (1), 17640, Bose, S. et al. *J. Cyst. Fibros.* 2020, 19 Suppl 1, S25-S32, Crawford, D. K. *J Pharmacol. Exp. Ther.* 2020, 374 (2), 264-272, Brasell, E. J. et al. *PLoS One* 2019, 14 (12), e0223954, Smith, N. J, Solovay, C. F., *Pharm. Pat. Anal.* 2017, 6 (4), 179-188, Kunzelmann, K. et al., *Front. Pharmacol.* 2019, 10, 3, or Son, J.-H. et al., *Eur. J. of Med. Chem.* 2020, 112888; and (c) at least one pharmaceutically acceptable carrier.

In some embodiments, the pharmaceutical compositions provided herein comprise (a) a compound selected from compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; (b) at least two compounds chosen from Compound II, Compound IV, Compound V, Compound VI, Compound VII, Compound VIII, Compound IX, Compound X, PTI-428, ASP-11, ABBV-2222, ABBV-2851, GLPG2737, ABBV-3221, ABBV-3748, ABBV-3903, ABBV-119, and PTI-801, and pharmaceutically acceptable salts and deuterated derivatives thereof; and (c) at least one pharmaceutically acceptable carrier.

In some embodiments, the pharmaceutical compositions provided herein comprise (a) a compound selected from compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts and deuterated derivatives thereof; (b) at least one compound chosen from Compound II, Compound III, Compound III-d, Compound IV, Compound V, Compound VI, Compound VII, Compound VIII, Compound IX, Compound X, PTI-428, ASP-11, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, PTI-801, FDL-176, PTI-808 (dirocaftor), GLPG1837, GLPG2451/ABBV-2451, QBW251 (icenticaftor), GLPG3067/ABBV-3067 (Navocaftor), ABBV-191, ELX-02, MRT5005, Lunar-CF, RCT223, amiloride, ETD001, $CF_{552}$, GS-9411, GS-5737, P-1037 (VX-371), P-1055 (VX-551), AZD5634, SPX-101, Ionis-ENaC-2.5 Rx, BI 1265162, AZ5634, ARO-ENaC1001, ETD002, and DS-1039, and pharmaceutically acceptable salts and deuterated derivatives thereof; and (c) at least one pharmaceutically acceptable carrier.

Any pharmaceutical composition disclosed herein may comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

The pharmaceutical compositions described herein are useful for treating cystic fibrosis and other CFTR-mediated diseases.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

Compound 11 Heptane Solvate

In some embodiments, the invention provides solvated crystalline forms of Compound 11. In some embodiments, the solvated crystalline form is a heptane solvate. In some embodiments, the invention provides Compound 11 heptane solvate. FIG. 1 provides an X-ray powder diffractogram of Compound 11 heptane solvate at room temperature.

In some embodiments, Compound 11 heptane solvate is substantially pure. In some embodiments, Compound 11 heptane solvate is substantially crystalline. In some embodiments, Compound 11 heptane solvate is characterized by an X-ray powder diffractogram generated by an X-ray powder diffraction analysis with an incident beam of Cu Kα radiation. In some embodiments, Compound 11 heptane solvate has many molecules in an asymmetric unit. In some embodiments, Compound 11 heptane solvate is a physical mixture of crystal lattices. In some embodiments, Compound 11 heptane solvate has a variable amount of heptane in the crystal lattice. In some embodiments, Compound 11 heptane solvate has a stoichiometric amount of heptane in the crystal lattice. In some embodiments, Compound 11 heptane solvate has a nonstoichiometric amount of heptane in the crystal lattice.

In some embodiments, Compound 11 heptane solvate is characterized by an X-ray powder diffractogram having a signal at 5.8±0.2 degrees two-theta. In some embodiments, Compound 11 heptane solvate is characterized by an X-ray powder diffractogram having a signal at 10.1±0.2 degrees two-theta. In some embodiments, Compound 11 heptane solvate is characterized by an X-ray powder diffractogram having a signal at 11.7±0.2 degrees two-theta. In some embodiments, Compound 11 heptane solvate is characterized by an X-ray powder diffractogram having one, two, or three signals selected from 5.8±0.2 degrees two-theta, 10.1±0.2 degrees two-theta, and 11.7±0.2 degrees two-theta.

In some embodiments, Compound 11 heptane solvate is characterized by an X-ray powder diffractogram having (a) one, two, or three signals selected from 5.8±0.2 degrees two-theta, 10.1±0.2 degrees two-theta, and 11.7±0.2 degrees two-theta, and (b) one, two, three, or four signals selected from 5.6±0.2 degrees two-theta, 18.1±0.2 degrees two-theta, 20.5±0.2 degrees two-theta, and 20.9±0.2 degrees two-theta. In some embodiments, Compound 11 heptane solvate is characterized by an X-ray powder diffractogram having signals at 5.6±0.2 degrees two-theta, 5.8±0.2 degrees two-theta, 10.1±0.2 degrees two-theta, 11.7±0.2 degrees two-theta, 18.1±0.2 degrees two-theta, 20.5±0.2 degrees two-theta, and 20.9±0.2 degrees two-theta.

In some embodiments, Compound 11 heptane solvate is characterized by an X-ray powder diffractogram substantially similar to FIG. 1.

In some embodiments, Compound 11 heptane solvate is characterized as having a $^{13}$C SSNMR spectrum with a peak at 166.3±0.2 ppm. In some embodiments, Compound 11 heptane solvate is characterized as having a $^{13}$C SSNMR spectrum with a peak at 165.8±0.2 ppm. In some embodiments, Compound 11 heptane solvate is characterized as having a $^{13}$C SSNMR spectrum with a peak at 164.6±0.2 ppm. In some embodiments, Compound 11 heptane solvate is characterized as having a $^{13}$C SSNMR spectrum with a peak at 163.4±0.2 ppm. In some embodiments, Compound 11 heptane solvate is characterized as having a $^{13}$C SSNMR spectrum with a peak at 154.8±0.2 ppm. In some embodiments, Compound 11 heptane solvate is characterized as having a $^{13}$C SSNMR spectrum with a peak at 154.0±0.2 ppm. In some embodiments, Compound 11 heptane solvate is characterized as having a $^{13}$C SSNMR spectrum with a peak at 152.1±0.2 ppm. In some embodiments, Compound 11 heptane solvate is characterized as having a $^{13}$C SSNMR spectrum with a peak at 151.6±0.2 ppm. In some embodiments, Compound 11 heptane solvate is characterized as having a $^{13}$C SSNMR spectrum with a peak at 140.2±0.2 ppm. In some embodiments, Compound 11 heptane solvate is characterized as having a $^{13}$C SSNMR spectrum with a peak at 139.4±0.2 ppm. In some embodiments, Compound 11 heptane solvate is characterized as having a $^{13}$C SSNMR spectrum with a peak at 138.5±0.2 ppm. In some embodiments, Compound 11 heptane solvate is characterized as having a $^{13}$C SSNMR spectrum with a peak at 138.0±0.2 ppm. In some embodiments, Compound 11 heptane solvate is characterized as having a $^{13}$C SSNMR spectrum with a peak at 135.1±0.2 ppm. In some embodiments, Compound 11 heptane solvate is characterized as having a $^{13}$C SSNMR spectrum with a peak at 134.6±0.2 ppm. In some embodiments, Compound 11 heptane solvate is characterized as having a $^{13}$C SSNMR spectrum with a peak at 131.3±0.2 ppm. In some embodiments, Compound 11 heptane solvate is characterized as having a $^{13}$C SSNMR spectrum with a peak at 130.2±0.2 ppm. In some embodiments, Compound 11 heptane solvate is characterized as having a $^{13}$C SSNMR spectrum with a peak at 129.6±0.2 ppm. In some embodiments, Compound 11 heptane solvate is characterized as having a $^{13}$C SSNMR spectrum with a peak at 128.5±0.2 ppm. In some embodiments, Compound 11 heptane solvate is characterized as having a $^{13}$C SSNMR spectrum with a peak at 125.7±0.2 ppm. In some embodiments, Compound 11 heptane solvate is characterized as having a $^{13}$C SSNMR spectrum with a peak at 123.7±0.2 ppm. In some embodiments, Compound 11 heptane solvate is characterized as having a $^{13}$C SSNMR spectrum with a peak at 123.2±0.2 ppm. In some embodiments, Compound 11 heptane solvate is characterized as having a $^{13}$C SSNMR spectrum with a peak at 122.9±0.2 ppm. In some embodiments, Compound 11 heptane solvate is characterized as having a $^{13}$C SSNMR spectrum with a peak at 121.1±0.2 ppm. In some embodiments, Compound 11 heptane solvate is characterized as having a $^{13}$C SSNMR spectrum with a peak at 120.2±0.2 ppm. In some embodiments, Compound 11 heptane solvate is characterized as having a $^{13}$C SSNMR spectrum with a peak at 119.2±0.2 ppm. In some embodiments, Compound 11 heptane solvate is characterized as having a $^{13}$C SSNMR spectrum with a peak at 117.8±0.2 ppm. In some embodiments, Compound 11 heptane solvate is characterized as having a $^{13}$C SSNMR spectrum with a peak at 76.2±0.2 ppm. In some embodiments, Compound 11 heptane solvate is characterized as having a $^{13}$C SSNMR spectrum with a peak at 74.4±0.2 ppm. In some embodiments, Compound 11 heptane solvate is characterized as having a $^{13}$C SSNMR spectrum with a peak at 73.7±0.2 ppm. In some embodiments, Compound 11 heptane solvate is characterized as having a $^{13}$C SSNMR spectrum with a peak at 73.3±0.2 ppm. In some embodiments, Compound 11 heptane solvate is characterized as having a $^{13}$C SSNMR spectrum with a peak at 40.0±0.2 ppm. In some embodiments, Compound 11 heptane solvate is characterized as having a $^{13}$C SSNMR spectrum with a peak at 38.6±0.2 ppm. In some embodiments, Compound 11 heptane solvate is characterized as having a $^{13}$C SSNMR spectrum with a peak at 37.6±0.2 ppm. In some embodiments, Compound 11 heptane solvate is characterized as having a $^{13}$C SSNMR spectrum with a peak at 36.9±0.2 ppm. In some embodiments, Compound 11 heptane solvate is characterized as having a $^{13}$C SSNMR spectrum with a peak at 35.7±0.2 ppm. In some embodiments, Compound 11 heptane solvate is characterized as having a $^{13}$C SSNMR spectrum with a peak at 33.6±0.2 ppm. In some embodiments, Compound 11 heptane solvate is characterized as having a $^{13}$C SSNMR spectrum with a peak at 32.5±0.2 ppm. In some embodiments, Compound 11 heptane solvate is characterized as having a $^{13}$C SSNMR spectrum with a peak at 32.0±0.2 ppm. In some embodiments, Compound 11 heptane solvate is characterized as having a $^{13}$C SSNMR spectrum with a peak at 30.4±0.2 ppm. In some embodiments, Compound 11 heptane solvate is characterized as having a $^{13}$C SSNMR spectrum with a peak at 30.1±0.2 ppm. In some embodiments, Compound 11 heptane solvate is characterized as having a $^{13}$C SSNMR spectrum with a peak at 29.5±0.2 ppm. In some embodiments, Compound 11 heptane solvate is characterized as having a $^{13}$C SSNMR spectrum with a peak at 28.8±0.2 ppm. In some embodiments, Compound 11 heptane solvate is characterized as having a $^{13}$C SSNMR spectrum with a peak at 28.1±0.2 ppm. In some embodiments, Compound 11 heptane solvate is characterized as having a $^{13}$C SSNMR spectrum with a peak at 27.1±0.2 ppm. In some embodiments, Compound 11 heptane solvate is characterized as having a $^{13}$C SSNMR spectrum with a peak at 25.3±0.2 ppm. In some embodiments, Compound 11 heptane solvate is characterized as having a $^{13}$C SSNMR spectrum with a peak at 23.1±0.2 ppm. In some embodiments, Compound 11 heptane solvate is characterized as having a $^{13}$C SSNMR spectrum with a peak at 22.7±0.2 ppm. In some embodiments, Compound 11 heptane solvate is characterized as having a $^{13}$C SSNMR spectrum with a peak at 22.0±0.2 ppm. In some embodiments, Compound 11 heptane solvate is characterized as having a $^{13}$C SSNMR spectrum with a peak at 21.6±0.2 ppm. In some embodiments, Compound 11 heptane solvate is characterized as having a $^{13}$C SSNMR spectrum with a peak at 20.3±0.2 ppm. In some embodiments, Compound 11 heptane solvate is characterized as having a $^{13}$C SSNMR spectrum with a peak at 19.6±0.2 ppm. In some embodiments, Compound 11 heptane solvate is characterized as having a $^{13}$C SSNMR spectrum with a peak at 18.3±0.2 ppm. In some embodiments, Compound 11 heptane solvate is characterized as having a $^{13}$C SSNMR spectrum with a peak at 17.6±0.2 ppm. In some embodiments, Compound 11 heptane solvate is characterized as having a $^{13}$C SSNMR spectrum with a peak at 13.8±0.2 ppm. In some embodiments, Compound 11 heptane solvate is characterized as having a $^{13}$C SSNMR spectrum with a peak at 13.1±0.2 ppm. In some embodiments, Compound 11 heptane solvate is characterized as having a $^{13}$C SSNMR spectrum with a peak at 12.5±0.2 ppm.

In some embodiments, Compound 11 heptane solvate is characterized as having a $^{13}$C SSNMR spectrum with one, two, three, four, five, six, seven, eight, nine, ten, or more peaks selected from 166.3±0.2 ppm, 165.8±0.2 ppm, 164.6±0.2 ppm, 163.4±0.2 ppm, 154.8±0.2 ppm, 154.0±0.2 ppm, 152.1±0.2 degppm, 151.6±0.2 ppm, 140.2±0.2 ppm, 139.4±0.2 ppm, 138.5±0.2 ppm, 138.0±0.2 ppm, 135.1±0.2 ppm, 134.6±0.2 ppm, 131.3±0.2 ppm, 130.2±0.2 ppm, 129.6±0.2 ppm, 128.5±0.2 ppm, 125.7±0.2 ppm, 123.7±0.2 ppm, 123.2±0.2 ppm, 122.9±0.2 ppm, 121.1±0.2 ppm, 120.2±0.2 ppm, 119.2±0.2 ppm, 117.8±0.2 ppm, 76.2±0.2 ppm, 74.4±0.2 ppm, 73.7±0.2 ppm, 73.3±0.2 ppm, 40.0±0.2 ppm, 38.6±0.2 ppm, 37.6±0.2 ppm, 36.9±0.2 ppm, 35.7±0.2 ppm, 33.6±0.2 ppm, 32.5±0.2 ppm, 32.0±0.2 ppm, 30.4±0.2 ppm, 30.1±0.2 ppm, 29.5±0.2 ppm, 28.8±0.2 ppm, 28.1±0.2 ppm, 27.1±0.2 ppm, 25.3±0.2 ppm, 23.1±0.2 ppm, 22.7±0.2 ppm, 22.0±0.2 ppm, 21.6±0.2 ppm, 20.3±0.2 ppm, 19.6±0.2 ppm, 18.3±0.2 ppm, 17.6±0.2 ppm, 13.8±0.2 ppm, 13.1±0.2 ppm, and 12.5±0.2 ppm.

Figure 3:
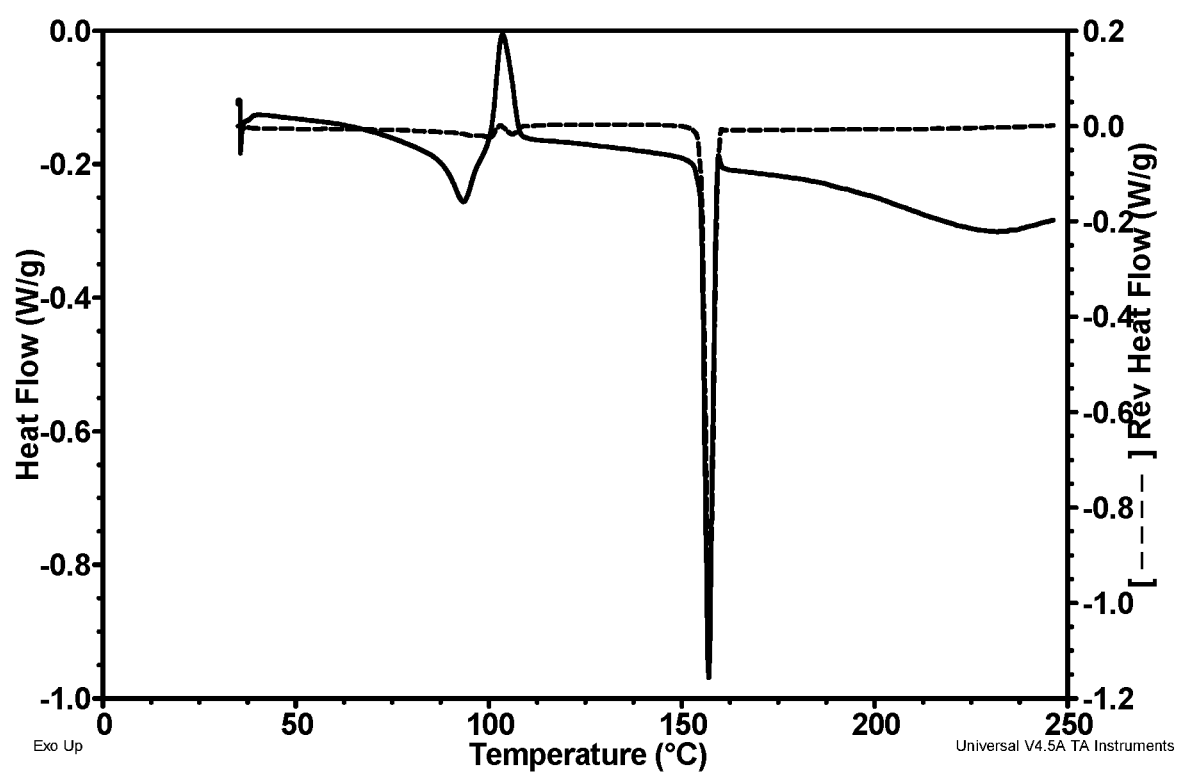
FIG. 3 provides a DSC analysis of Compound 11 heptane solvate.

In some embodiments, Compound 11 heptane solvate is characterized by a $^{13}$C SSNMR spectrum substantially similar to FIG. 3.

In some embodiments, Compound 11 heptane solvate is characterized as having a $^{19}$F SSNMR spectrum with a peak at −63.5±0.2 ppm. In some embodiments, Compound 11 heptane solvate is characterized as having a $^{19}$F SSNMR spectrum with a peak at −63.8±0.2 ppm. In some embodiments, Compound 11 heptane solvate is characterized as having a $^{19}$F SSNMR spectrum with a peak at −65.1±0.2 ppm. In some embodiments, Compound 11 heptane solvate is characterized as having a $^{19}$F SSNMR spectrum with a peak at −65.8±0.2 ppm. In some embodiments, Compound 11 heptane solvate is characterized as having a $^{19}$F SSNMR spectrum with a peak at −66.3±0.2 ppm. In some embodiments, Compound 11 heptane solvate is characterized as having a $^{19}$F SSNMR spectrum with a peak at −67.0±0.2 ppm. In some embodiments, Compound 11 heptane solvate is characterized as having a $^{19}$F SSNMR spectrum with a peak at −74.0±0.2 ppm. In some embodiments, Compound 11 heptane solvate is characterized as having a $^{19}$F SSNMR spectrum with a peak at −74.9±0.2 ppm. In some embodiments, Compound 11 heptane solvate is characterized as having a $^{19}$F SSNMR spectrum with a peak at −76.6±0.2 ppm.

In some embodiments, Compound 11 heptane solvate is characterized as having a $^{19}$F SSNMR spectrum with one, two, or three peaks selected from −65.1±0.2 ppm, −67.0±0.2 ppm, and −76.6±0.2 ppm. In some embodiments, Compound 11 heptane solvate is characterized as having a $^{19}$F SSNMR spectrum with one, two, three, four, or five peaks selected from −63.5±0.2 ppm, −65.1±0.2 ppm, −67.0±0.2 ppm, −74.9±0.2 ppm, and −76.6±0.2 ppm. In some embodiments, Compound 11 heptane solvate is characterized as having a $^{19}$F SSNMR spectrum with one, two, three, four, five, or more peaks selected from −63.5±0.2 ppm, −63.8±0.2 ppm, −65.1±0.2 ppm, −65.8±0.2 ppm, −66.3±0.2 ppm, −67.0±0.2 ppm, −74.0±0.2 ppm, −74.9±0.2 ppm, and −76.6±0.2 ppm. In some embodiments, Compound 11 heptane solvate is characterized as having a $^{19}$F SSNMR spectrum with one, two, three, four, five, or more peaks selected from −63.5±0.2 ppm, −63.8±0.2 ppm, −65.1±0.2 ppm, −65.8±0.2 ppm, −66.3±0.2 ppm, −67.0±0.2 ppm, −74.0±0.2 ppm, −74.9±0.2 ppm, −76.6±0.2 ppm, and −77.6±0.2 ppm.

Figure 4:
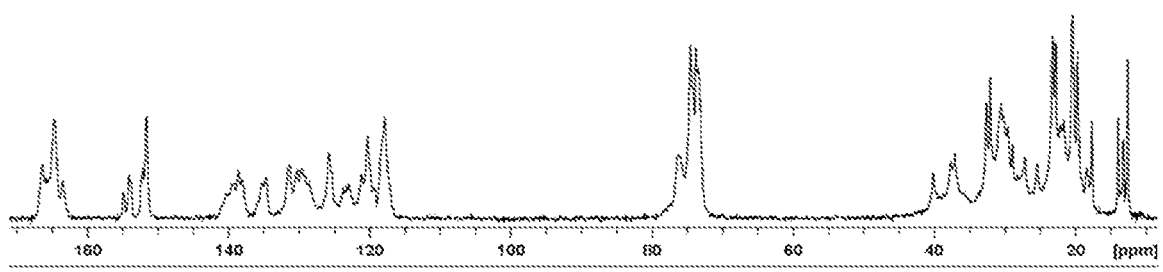
FIG. 4 provides a $^{13}C$ solid-state NMR spectrum of Compound 11 heptane solvate.
Figure 5:
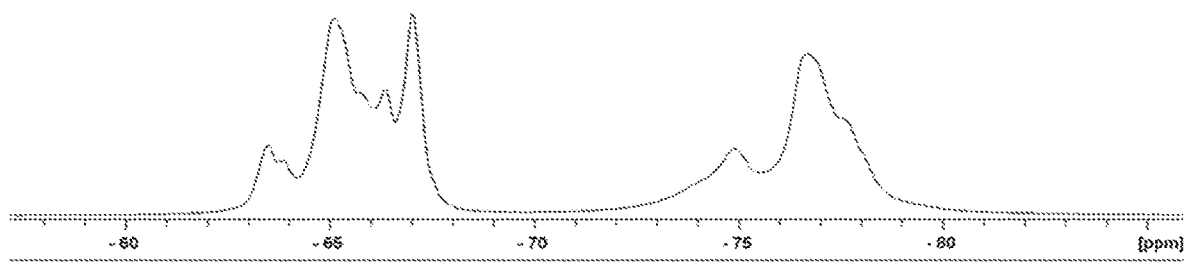
FIG. 5 provides a $^{19}F$ solid-state NMR spectrum of Compound 11 heptane solvate.

In some embodiments, Compound 11 heptane solvate is characterized by a $^{19}$F SSNMR spectrum substantially similar to FIG. 4.

Another aspect of the invention provides a process for preparing a solvated crystalline solid form of Compound 11 comprising dissolving Compound 11 in one or more solvents to form a mixture and crystallising the compound from the mixture. In some embodiment the one or more solvents comprises heptane. In some embodiment the one or more solvents comprises heptane and dichloromethane.

Another aspect of the invention provides a method of making Compound 11 heptane solvate. In some embodiments, the method of making Compound 11 heptane solvate comprises: (i) dissolving Compound 11 in heptane and dichloromethane to form a mixture; (ii) concentrating the mixture; (iii) collecting solids from the mixture; and (iv) drying the collected solids. In some embodiments, (ii) optionally comprises swirling the mixture at room temperature. In some embodiments, (iii) optionally comprises rinsing the collected solids with cold heptane. In some embodiments, the method of making Compound 11 heptane solvate comprises dissolving Compound 11 in heptane and dichloromethane, concentrating under rotary evaporation, swirling at room temperature, filtering the solids, washing the solids with cold heptane, and drying under vacuum to provide Compound 11 heptane solvate.

Non-Limiting Exemplary Embodiments

1. A compound selected from compounds of Formula I:

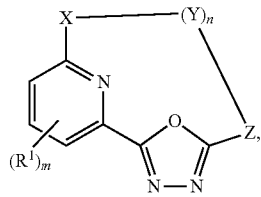

and deuterated derivatives and pharmaceutically acceptable salts thereof, wherein:

X is selected from —O—, —S—, —SO—, and —SO$_2$—;

each Y is independently selected from —C(R$^Y$)$_2$—, —O—, —CO—, and

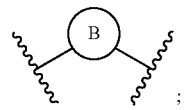

each R$^Y$ is independently selected from hydrogen, halogen, C$_1$-C$_6$ alkyl (optionally substituted with 1-3 groups independently selected from hydroxy and Q), C$_3$-C$_8$ cycloalkyl, C$_6$-C$_{10}$ aryl, 5- to 10-membered heteroaryl, —OR$^{Y1}$, —CO$_2$R$^{Y1}$, —COR$^{Y1}$, —CON(R$^{Y1}$)$_2$, and —NR$^{Y1}$—; or two instances of R$^Y$ on the same atom are taken together to form a ring selected from C$_3$-C$_8$ cycloalkyl and 3- to 6-membered heterocyclyl; or two instances of R$^Y$, one of which is on one atom and the second of which is on an adjacent atom, are taken together to form a pi bond;

each R$^{Y1}$ is independently selected from hydrogen and C$_1$-C$_6$ alkyl, or two instances of R$^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);

each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN, C₁-C₆ alkyl (optionally substituted with 1-3 groups independently selected from halogen, —NH₂, and —NHCOMe),
C₁-C₆ alkoxy,
C₆-C₁₀ aryl (optionally substituted with 1-3 groups independently selected from C₁-C₆ alkyl), and
C₃-C₈ cycloalkyl,
C₆-C₁₀ aryl optionally substituted with 1-3 groups independently selected from:
halogen,
CN,
C₁-C₆ alkyl (optionally substituted with 1-3 groups independently selected from halogen and hydroxy),
C₁-C₆ alkoxy optionally substituted with 1-4 groups independently selected from:
halogen,
C₃-C₈ cycloalkyl (optionally substituted with CF₃),
C₃-C₈ cycloalkyl (optionally substituted with 1-3 groups independently selected from halogen, CF₃, OCF₃, and C₁-C₆ alkyl), and
C₆-C₁₀ aryl,
5- to 10-membered heteroaryl optionally substituted with 1-3 groups independently selected from:
halogen,
C₁-C₆ alkyl (optionally substituted with 1-3 groups independently selected from halogen),
C₃-C₈ cycloalkyl (optionally substituted with 1-3 CF₃ groups), and
3- to 10-membered heterocyclyl,
3- to 10-membered heterocyclyl optionally substituted with 1-3 groups independently selected from:
C₁-C₆ alkyl (optionally substituted with 1-3 groups independently selected from oxo and C₃-C₈ cycloalkyl), and
oxo; each is independently selected from halogen, C₁-C₆ alkyl (optionally substituted with 1-6 groups independently selected from halogen and hydroxy), —OR², —N(R²)₂, —CO₂R², —CO—N(R²)₂, —CN, phenyl, benzyl, C₁-C₆ alkoxy, C₃-C₈ cycloalkyl, 5- to 6-membered heteroaryl, 3- to 6-membered heterocyclyl, —SO₂R², —SR², —SOR², —PO(OR²)₂, and —PO(R²)₂;
each R² is independently selected from hydrogen, C₁-C₆ alkyl (optionally substituted with 1-6 groups independently selected from halogen), and C₆-C₁₀ aryl (optionally substituted with C₁-C₆ alkoxy, which is optionally substituted with 1-6 groups independently selected from halogen);
Z is selected from

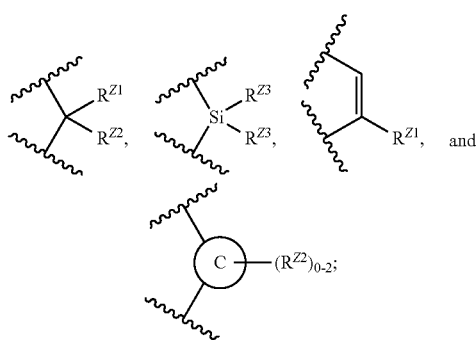

wherein Ring C is selected from C₆-C₁₀ aryl and 5- to 10-membered heteroaryl;

R^{Z1} is selected from hydrogen, —CN, C₁-C₆ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;
R^{Z2} is selected from hydrogen, halogen, and hydroxy, or R^{Z1} and R^{Z2} taken together form a group selected from oxo and =N—OH;
each R^{Z3} is independently selected from hydroxy, C₁-C₆ alkoxy, C₁-C₆ alkyl, C₁-C₆ haloalkyl, and C₆-C₁₀ aryl; or two instances of R^{Z3} are taken together to form a 3- to 6-membered heterocyclyl;
n is selected from 4, 5, 6, 7, and 8; and
m is selected from 0, 1, 2, and 3.
2. The compound, deuterated derivative, or pharmaceutically acceptable salt according to Embodiment 1, wherein:
X is selected from —O—, —S—, —SO—, and —SO₂—;
each Y is independently selected from —C(R^Y)₂—, —O—, —CO—, and

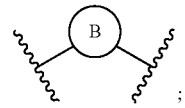

each R^Y is independently selected from hydrogen, halogen, C₁-C₆ alkyl (optionally substituted with 1-3 groups independently selected from hydroxy and Q), C₆-C₁₀ aryl, 5- to 10-membered heteroaryl, —OR^{Y1}, —CO₂R^{Y1}, —COR^{Y1}, —CON(R^{Y1})₂, and —NR^{Y1}; or two instances of R^Y on the same atom are taken together to form a ring selected from C₃-C₈ cycloalkyl and 3- to 6-membered heterocyclyl; or two instances of R^Y, one of which is on one atom and the second of which is on an adjacent atom, are taken together to form a pi bond;
each R^{Y1} is independently selected from hydrogen and C₁-C₆ alkyl, or two instances of R^{Y1} bonded to the same nitrogen taken together form a 3- to 6-membered heterocyclyl;
Ring B is selected from:
C₆-C₁₀ aryl (optionally substituted with 1-3 groups independently selected from halogen, C₁-C₆ alkyl, and C₁-C₆ alkoxy),
C₃-C₈ cycloalkyl,
5- to 10-membered heteroaryl, and
3- to 6-membered heterocyclyl (optionally substituted with 1-3 groups independently selected from C₁-C₆ alkyl);
each Q is independently selected from:
C₁-C₆ alkyl optionally substituted with 1-3 groups independently selected from:
halogen,
oxo,
C₆-C₁₀ aryl (optionally substituted with 1-3 groups independently selected from halogen and —OCF₃), and
C₃-C₈ cycloalkyl,
C₃-C₈ cycloalkyl optionally substituted with 1-3 groups independently selected from:
halogen,
CN,
C₁-C₆ alkyl (optionally substituted with 1-3 groups independently selected from halogen, —NH₂, and —NHCOMe),
C₁-C₆ alkoxy, C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
  halogen,
  CN,
  C$_1$-C$_6$ alkyl (optionally substituted with 1-3 groups independently selected from halogen and hydroxy),
  C$_1$-C$_6$ alkoxy optionally substituted with 1-4 groups independently selected from:
    halogen,
    C$_3$-C$_8$ cycloalkyl (optionally substituted with CF$_3$),
    C$_3$-C$_8$ cycloalkyl (optionally substituted with 1-3 groups independently selected from halogen, CF$_3$, OCF$_3$, and C$_1$-C$_6$ alkyl), and
  C$_6$-C$_{10}$ aryl,
5- to 10-membered heteroaryl optionally substituted with 1-3 groups independently selected from:
  halogen,
  C$_1$-C$_6$ alkyl (optionally substituted with 1-3 groups independently selected from halogen),
  C$_3$-C$_8$ cycloalkyl (optionally substituted with 1-3 CF$_3$ groups), and
  3- to 10-membered heterocyclyl,
3- to 10-membered heterocyclyl optionally substituted with 1-3 groups independently selected from:
  C$_1$-C$_6$ alkyl (optionally substituted with 1-3 groups independently selected from oxo and C$_3$-C$_8$ cycloalkyl), and
  oxo;
each R$^1$ is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;
each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);
Z is selected from

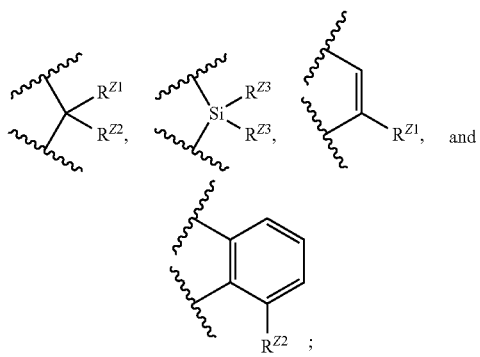

R$^{Z1}$ is selected from hydrogen, —CN, C$_1$-C$_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

R$^{Z2}$ is selected from hydrogen, halogen, and hydroxy, or R$^{Z1}$ and R$^{Z2}$ taken together form a group selected from oxo and =N—OH;

each R$^{Z3}$ is independently selected from hydroxy, C$_1$-C$_6$ alkoxy, C$_1$-C$_6$ alkyl, and C$_6$-C$_{10}$ aryl; or two instances of R$^{Z3}$ are taken together to form a 3- to 6-membered heterocyclyl;

n is selected from 4, 5, 6, and 7; and m is selected from 0, 1, 2, and 3.

3. The compound, deuterated derivative, or pharmaceutically acceptable salt according to Embodiment 1 or 2, wherein X is —O—.

4. The compound, deuterated derivative, or pharmaceutically acceptable salt according to any one of Embodiments 1-3, wherein each Y is independently selected from —C(R$^Y$)$_2$—, —CO—, and

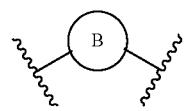

5. The compound, deuterated derivative, or pharmaceutically acceptable salt according to any one of Embodiments 1-4, wherein each R$^Y$ is independently selected from hydrogen, C$_1$-C$_6$ alkyl (optionally substituted with 1-3 groups independently selected from hydroxy and Q), and —OR$^{Y1}$.

6. The compound, deuterated derivative, or pharmaceutically acceptable salt according to any one of Embodiments 1-5, wherein each R$^Y$ is independently selected from: hydrogen,

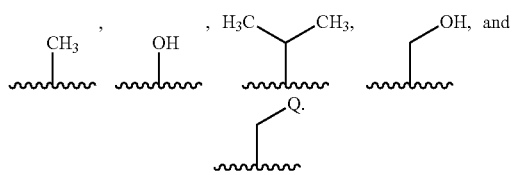

7. The compound, deuterated derivative, or pharmaceutically acceptable salt according to any one of Embodiments 1-6, wherein each Q is independently selected from:
  C$_3$-C$_8$ cycloalkyl,
  C$_6$-C$_{10}$ aryl optionally substituted with 1-3 groups independently selected from halogen and C$_1$-C$_6$ alkyl.

8. The compound, deuterated derivative, or pharmaceutically acceptable salt according to any one of Embodiments 1-7, wherein each Q is independently selected from:

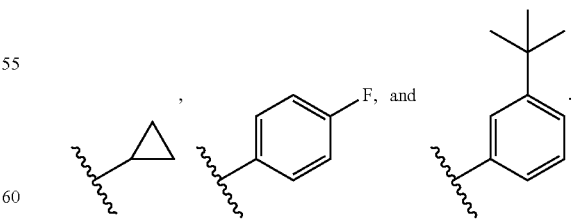

9. The compound, deuterated derivative, or pharmaceutically acceptable salt according to any one of Embodiments 1-8, wherein Ring B is selected from C$_6$-C$_{10}$ aryl optionally substituted with 1-3 groups independently selected from halogen.

10. The compound, deuterated derivative, or pharmaceutically acceptable salt according to any one of Embodiments 1-9, wherein Ring B is selected from:
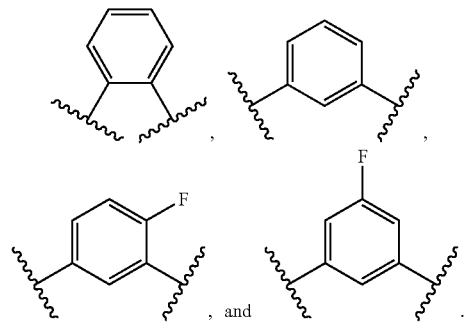
and
11. The compound, deuterated derivative, or pharmaceutically acceptable salt according to any one of Embodiments 1-10, wherein —(Y)$_n$— is a group selected from:
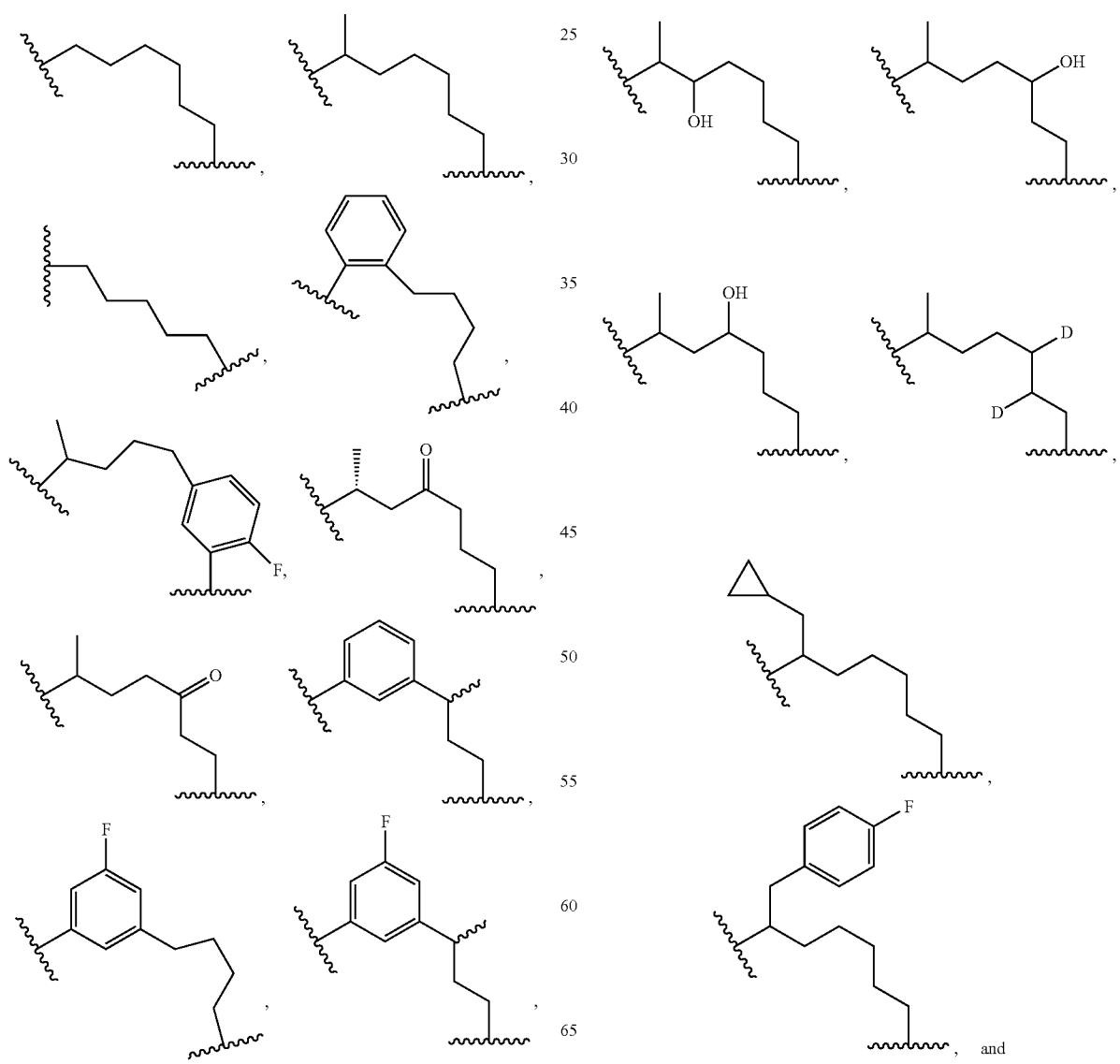
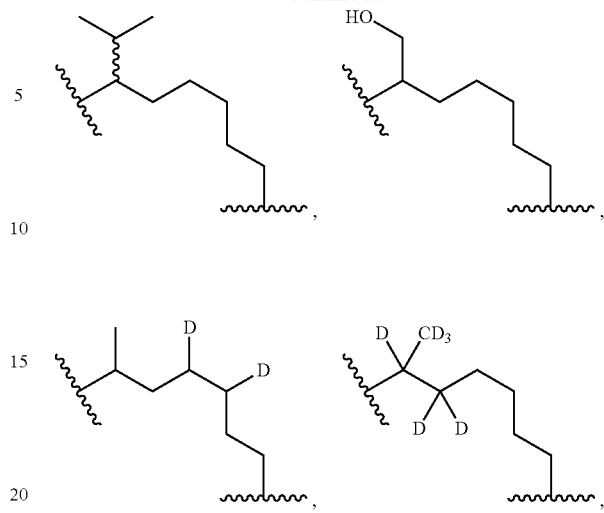

-continued

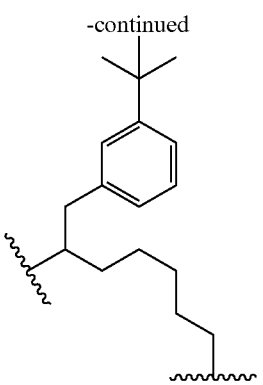

12. The compound, deuterated derivative, or pharmaceutically acceptable salt according to any one of Embodiments 1-11, wherein each Y is —C(R$^Y$)$_2$—.

13. The compound, deuterated derivative, or pharmaceutically acceptable salt according to any one of Embodiments 1-12, wherein each R$^1$ is independently selected from —CF$_3$ and —N(R$^2$)$_2$.

14. The compound, deuterated derivative, or pharmaceutically acceptable salt according to any one of Embodiments 1-13, wherein each R$^2$ is independently selected from hydrogen and C$_1$-C$_6$ alkyl.

15. The compound, deuterated derivative, or pharmaceutically acceptable salt according to any one of Embodiments 1-14, wherein each R$^2$ is hydrogen.

16. The compound, deuterated derivative, or pharmaceutically acceptable salt according to any one of Embodiments 1-15, wherein Z is

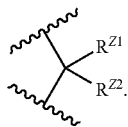

17. The compound, deuterated derivative, or pharmaceutically acceptable salt according to any one of Embodiments 1-16, wherein R$^{Z1}$ is selected from C$_1$-C$_6$ alkyl (optionally substituted with 1-3 groups selected from halogen).

18. The compound, deuterated derivative, or pharmaceutically acceptable salt according to any one of Embodiments 1-17, wherein R$^{Z1}$ is —CF$_3$.

19. The compound, deuterated derivative, or pharmaceutically acceptable salt according to any one of Embodiments 1-18, wherein R$^{Z2}$ is hydroxy.

20. The compound, deuterated derivative, or pharmaceutically acceptable salt according to any one of Embodiments 1-19, wherein n is selected from 4, 5, and 6.

21. The compound, deuterated derivative, or pharmaceutically acceptable salt according to any one of Embodiments 1-20, wherein n is 6.

22. The compound, deuterated derivative, or pharmaceutically acceptable salt according to any one of Embodiments 1-21, wherein m is selected from 1 and 2.

23. The compound, deuterated derivative, or pharmaceutically acceptable salt according to any one of Embodiments 1-22, wherein m is 2.

24. A compound selected from compounds of Formula Ia:

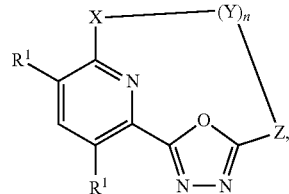

Ia and deuterated derivatives and pharmaceutically acceptable salts thereof, wherein:
X is selected from —O—, —S—, —SO—, and —SO$_2$—;
each Y is independently selected from —C(R$^Y$)$_2$—, —O—, —CO—, and

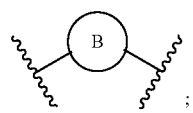

each R$^Y$ is independently selected from hydrogen, halogen, C$_1$-C$_6$ alkyl (optionally substituted with 1-3 groups independently selected from hydroxy and Q), C$_6$-C$_{10}$ aryl, 5- to 10-membered heteroaryl, —OR$^{Y1}$, —CO$_2$R$^{Y1}$, —COR$^{Y1}$, —CON(R$^{Y1}$)$_2$, and —NR$^{Y1}$—; or two instances of R$^Y$ on the same atom are taken together to form a ring selected from C$_3$-C$_8$ cycloalkyl and 3- to 6-membered heterocyclyl; or two instances of R$^Y$, one of which is on one atom and the second of which is on an adjacent atom, are taken together to form a pi bond;
each R$^{Y1}$ is independently selected from hydrogen and C$_1$-C$_6$ alkyl, or two instances of R$^{Y1}$ bonded to the same nitrogen taken together form a 3- to 6-membered heterocyclyl;
Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);
each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl, C$_6$-C$_{10}$ aryl optionally substituted with 1-3 groups independently selected from:
  halogen,
  CN,
  C$_1$-C$_6$ alkyl (optionally substituted with 1-3 groups independently selected from halogen and hydroxy),
  C$_1$-C$_6$ alkoxy optionally substituted with 1-4 groups independently selected from:
    halogen,
    C$_3$-C$_8$ cycloalkyl (optionally substituted with CF$_3$),
    C$_3$-C$_8$ cycloalkyl (optionally substituted with 1-3 groups independently selected from halogen, CF$_3$, OCF$_3$, and C$_1$-C$_6$ alkyl), and
  C$_6$-C$_{10}$ aryl,
5- to 10-membered heteroaryl optionally substituted with 1-3 groups independently selected from:
  halogen,
  C$_1$-C$_6$ alkyl (optionally substituted with 1-3 groups independently selected from halogen),
  C$_3$-C$_8$ cycloalkyl (optionally substituted with 1-3 CF$_3$ groups), and
  3- to 10-membered heterocyclyl,
3- to 10-membered heterocyclyl optionally substituted with 1-3 groups independently selected from:
  C$_1$-C$_6$ alkyl (optionally substituted with 1-3 groups independently selected from oxo and C$_3$-C$_8$ cycloalkyl), and
  oxo;
each is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;
each R$^2$ is independently selected from hydrogen, C$_1$-C$_6$ alkyl (optionally substituted with 1-3 groups independently selected from halogen), and C$_6$-C$_{10}$ aryl (optionally substituted with C$_1$-C$_6$ alkoxy, which is optionally substituted with 1-6 groups independently selected from halogen);
Z is selected from

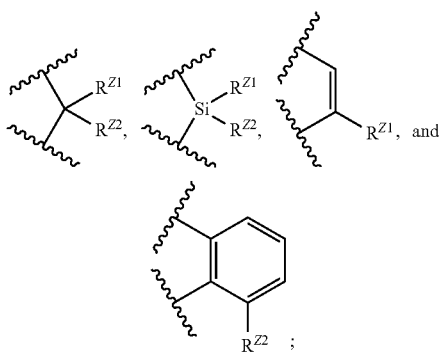

R$^{Z1}$ is selected from hydrogen, —CN, C$_1$-C$_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;
R$^{Z2}$ is selected from hydrogen, halogen, and hydroxy, or R$^{Z1}$ and R$^{Z2}$ taken together form a group selected from oxo and =N—OH;

each R$^{Z3}$ is independently selected from hydroxy, C$_1$-C$_6$ alkoxy, C$_1$-C$_6$ alkyl, and C$_6$-C$_{10}$ aryl; or two instances of R$^{Z3}$ are taken together to form a 3- to 6-membered heterocyclyl; and
n is selected from 4, 5, 6, and 7.

25. The compound, deuterated derivative, or pharmaceutically acceptable salt according to Embodiment 24, wherein X is —O—.

26. The compound, deuterated derivative, or pharmaceutically acceptable salt according to Embodiment 24 or 25, wherein each Y is independently selected from —C(R$^Y$)$_2$—, —CO—, and

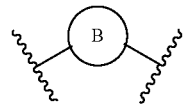

27. The compound, deuterated derivative, or pharmaceutically acceptable salt according to any one of Embodiments 24-26, wherein each R$^Y$ is independently selected from hydrogen, C$_1$-C$_6$ alkyl (optionally substituted with 1-3 groups independently selected from hydroxy and Q), and —OR$^{Y1}$.

28. The compound, deuterated derivative, or pharmaceutically acceptable salt according to any one of Embodiments 24-27, wherein each R$^Y$ is independently selected from:
hydrogen,

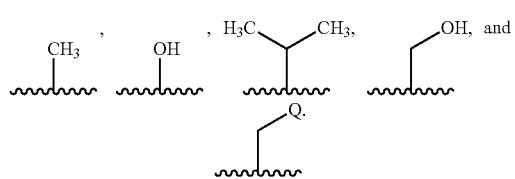

29. The compound, deuterated derivative, or pharmaceutically acceptable salt according to any one of Embodiments 24-28, wherein each Q is independently selected from:
  C$_3$-C$_8$ cycloalkyl,
  C$_6$-C$_{10}$ aryl optionally substituted with 1-3 groups independently selected from halogen and C$_1$-C$_6$ alkyl.

30. The compound, deuterated derivative, or pharmaceutically acceptable salt according to any one of Embodiments 24-29, wherein each Q is independently selected from:

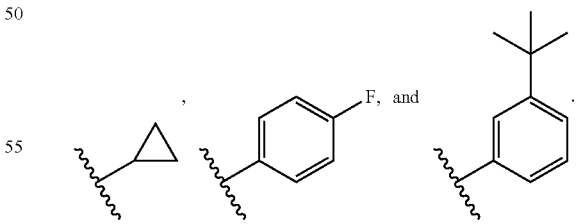

31. The compound, deuterated derivative, or pharmaceutically acceptable salt according to any one of Embodiments 24-30, wherein Ring B is selected from C$_6$-C$_{10}$ aryl optionally substituted with 1-3 groups independently selected from halogen.

32. The compound, deuterated derivative, or pharmaceutically acceptable salt according to any one of Embodiments 24-31, wherein Ring B is selected from:

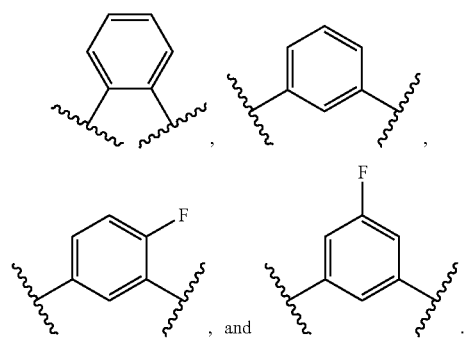
33. The compound, deuterated derivative, or pharmaceutically acceptable salt according to any one of Embodiments 24-32, wherein —(Y)$_n$— is a group selected from:
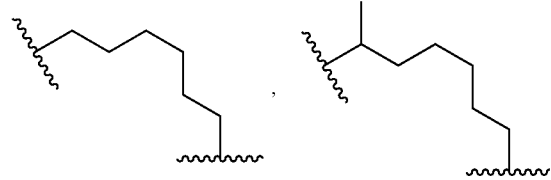
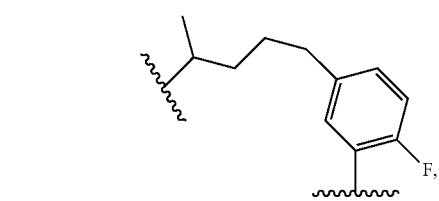
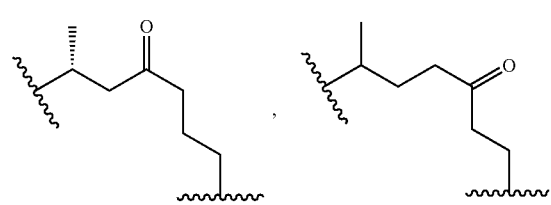
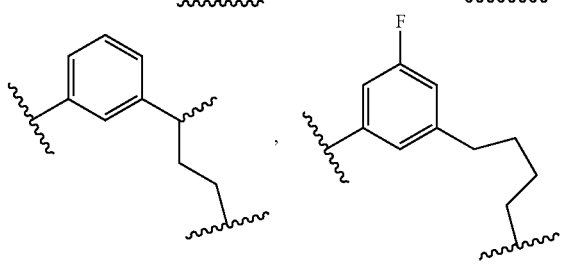
-continued
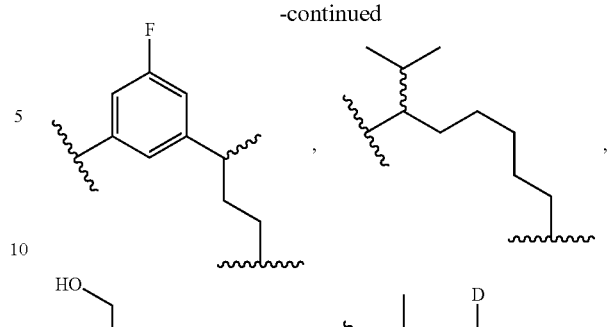
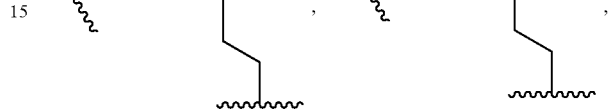
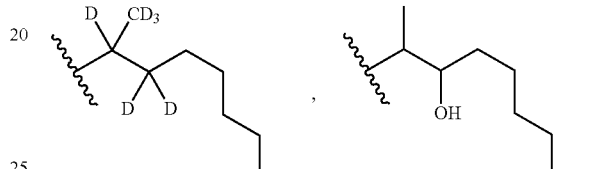
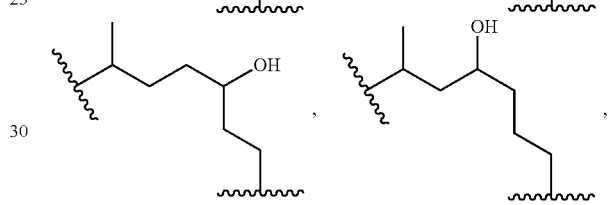
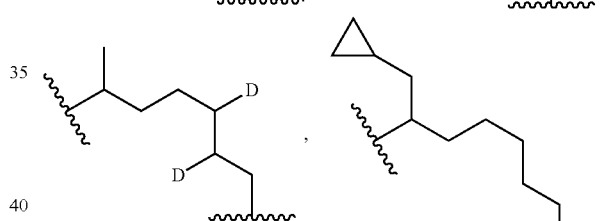
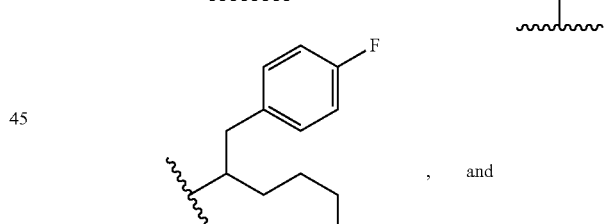
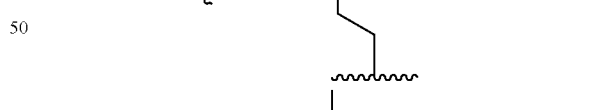, and
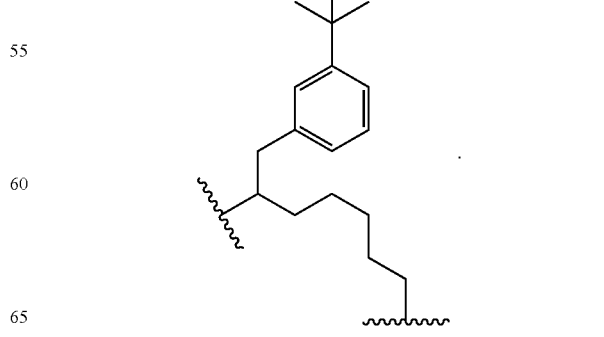

34. The compound, deuterated derivative, or pharmaceutically acceptable salt according to any one of Embodiments 24-33, wherein each Y is —C(R$^Y$)$_2$—.

35. The compound, deuterated derivative, or pharmaceutically acceptable salt according to any one of Embodiments 24-34, wherein each R$^1$ is independently selected from —CF$_3$ and —N(R$^2$)$_2$.

36. The compound, deuterated derivative, or pharmaceutically acceptable salt according to any one of Embodiments 24-35, wherein each R$^2$ is independently selected from hydrogen and C$_1$-C$_6$ alkyl.

37. The compound, deuterated derivative, or pharmaceutically acceptable salt according to any one of Embodiments 24-36, wherein each R$^2$ is hydrogen.

38. The compound, deuterated derivative, or pharmaceutically acceptable salt according to any one of Embodiments 24-37, wherein Z is

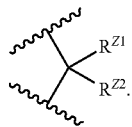

39. The compound, deuterated derivative, or pharmaceutically acceptable salt according to any one of Embodiments 24-38, wherein R$^{Z1}$ is selected from C$_1$-C$_6$ alkyl (optionally substituted with 1-3 groups selected from halogen).

40. The compound, deuterated derivative, or pharmaceutically acceptable salt according to any one of Embodiments 24-39, wherein R$^{Z1}$ is —CF$_3$.

41. The compound, deuterated derivative, or pharmaceutically acceptable salt according to any one of Embodiments 24-40, wherein R$^{Z2}$ is hydroxy.

42. The compound, deuterated derivative, or pharmaceutically acceptable salt according to any one of Embodiments 24-41, wherein n is selected from 4, 5, and 6.

43. The compound, deuterated derivative, or pharmaceutically acceptable salt according to any one of Embodiments 24-42, wherein n is 6.

44. A compound selected from compounds of Formulae IIa, IIb, and IIc:

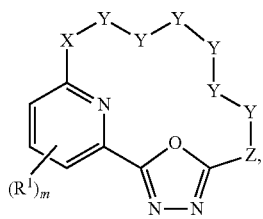

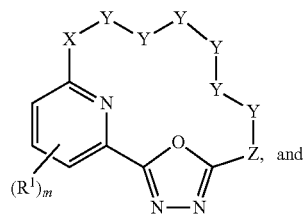

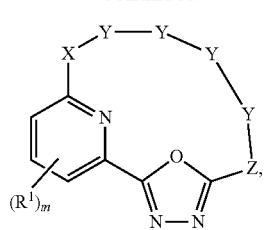

and deuterated derivatives and pharmaceutically acceptable salts thereof, wherein:

X is selected from —O—, —S—, —SO—, and —SO$_2$—;
each Y is independently selected from —C(R$^Y$)$_2$—, —O—, —CO—, and

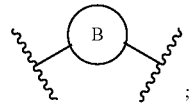

each R$^Y$ is independently selected from hydrogen, halogen, C$_1$-C$_6$ alkyl (optionally substituted with 1-3 groups independently selected from hydroxy and Q), C$_6$-C$_{10}$ aryl, 5- to 10-membered heteroaryl, —OR$^{Y1}$, —CO$_2$R$^{Y1}$, —COR$^{Y1}$, —CON(R$^{Y1}$)$_2$, and —NR$^{Y1}$—; or two instances of R$^Y$ on the same atom are taken together to form a ring selected from C$_3$-C$_8$ cycloalkyl and 3- to 6-membered heterocyclyl; or two instances of R$^Y$, one of which is on one atom and the second of which is on an adjacent atom, are taken together to form a pi bond;

each R$^{Y1}$ is independently selected from hydrogen and C$_1$-C$_6$ alkyl, or two instances of R$^{Y1}$ bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);

each Q is independently selected from:
C$_1$-C$_6$ alkyl optionally substituted with 1-3 groups independently selected from:
  halogen,
  oxo,
  C$_6$-C$_{10}$ aryl (optionally substituted with 1-3 groups independently selected from halogen and —OCF$_3$), and
  C$_3$-C$_8$ cycloalkyl,
C$_3$-C$_8$ cycloalkyl optionally substituted with 1-3 groups independently selected from:
  halogen,
  CN,
  C$_1$-C$_6$ alkyl (optionally substituted with 1-3 groups independently selected from halogen, —NH$_2$, and —NHCOMe),
  C$_1$-C$_6$ alkoxy,
  C$_6$-C$_{10}$ aryl (optionally substituted with 1-3 groups independently selected from C$_1$-C$_6$ alkyl), and
  C$_3$-C$_8$ cycloalkyl, C₆-C₁₀ aryl optionally substituted with 1-3 groups independently selected from:
halogen,
CN,
C₁-C₆ alkyl (optionally substituted with 1-3 groups independently selected from halogen and hydroxy),
C₁-C₆ alkoxy optionally substituted with 1-4 groups independently selected from:
halogen,
C₃-C₈ cycloalkyl (optionally substituted with CF₃),
C₃-C₈ cycloalkyl (optionally substituted with 1-3 groups independently selected from halogen, CF₃, OCF₃, and C₁-C₆ alkyl), and
C₆-C₁₀ aryl,
5- to 10-membered heteroaryl optionally substituted with 1-3 groups independently selected from:
halogen,
C₁-C₆ alkyl (optionally substituted with 1-3 groups independently selected from halogen),
C₃-C₈ cycloalkyl (optionally substituted with 1-3 CF₃ groups), and
3- to 10-membered heterocyclyl,
3- to 10-membered heterocyclyl optionally substituted with 1-3 groups independently selected from:
C₁-C₆ alkyl (optionally substituted with 1-3 groups independently selected from oxo and C₃-C₈ cycloalkyl), and
oxo;
each R¹ is independently selected from halogen, —CF₃, —OR², —N(R²)₂, —CO₂R², —CO—N(R²)₂, —CN, phenyl, benzyl, C₁-C₆ alkoxy, C₁-C₆ alkyl, C₃-C₈ cycloalkyl, 5- to 6-membered heteroaryl, 3- to 6-membered heterocyclyl, —SO₂R², —SR², —SOR², —PO(OR²)₂, and —PO(R²)₂;
each R² is independently selected from hydrogen, C₁-C₆ alkyl (optionally substituted with 1-3 groups independently selected from halogen), and C₆-C₁₀ aryl (optionally substituted with C₁-C₆ alkoxy, which is optionally substituted with 1-6 groups independently selected from halogen);
Z is selected from

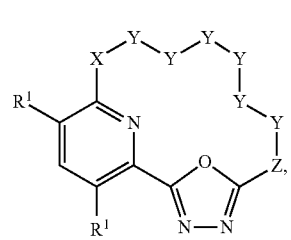

;

R^Z1 is selected from hydrogen, —CN, C₁-C₆ alkyl (optionally substituted with 1-3 groups selected from halogen and hydroxy), 3- to 6-membered heterocyclyl, 3- to 6-membered cycloalkyl, 5- to 6-membered aryl, and 5- to 6-membered heteroaryl;

R^Z2 is selected from hydrogen, halogen, and hydroxy, or R^Z1 and R^Z2 taken together form a group selected from oxo and =N—OH;

each R^Z3 is independently selected from hydroxy, C₁-C₆ alkoxy, C₁-C₆ alkyl, and C₆-C₁₀ aryl; or two instances of R^Z3 are taken together to form a 3- to 6-membered heterocyclyl; and m is selected from 0, 1, 2, and 3.

45. The compound, deuterated derivative, or pharmaceutically acceptable salt according to Embodiment 44, wherein m is selected from 1 and 2.

46. The compound, deuterated derivative, or pharmaceutically acceptable salt according to Embodiment 44 or 45, wherein m is 2.

47. A compound selected from compounds of Formulae IId, IIe, and IIf:

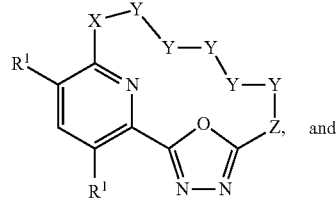

IId

IIe

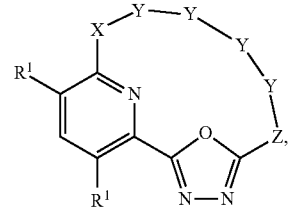

IIf and deuterated derivatives and pharmaceutically acceptable salts thereof, wherein:

X is selected from —O—, —S—, —SO—, and —SO₂—;

each Y is independently selected from —C(R^Y)₂—, —O—, —CO—, and

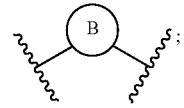

;

each R^Y is independently selected from hydrogen, halogen, C₁-C₆ alkyl (optionally substituted with 1-3 groups independently selected from hydroxy and Q), C₆-C₁₀ aryl, 5- to 10-membered heteroaryl, —OR^Y1, —CO₂R^Y1, —COR^Y1, —CON(R^Y1)₂, and —NR^Y1—; or two instances of R^Y on the same atom are taken together to form a ring selected from C₃-C₈ cycloalkyl and 3- to 6-membered heterocyclyl; or two instances of R^Y, one of which is on one atom and the second of which is on an adjacent atom, are taken together to form a pi bond;

each R^Y1 is independently selected from hydrogen and C₁-C₆ alkyl, or two instances of R^Y1 bonded to the same nitrogen taken together form a 3- to 6-membered heterocyclyl;

Ring B is selected from:
C$_6$-C$_{10}$ aryl (optionally substituted with 1-3 groups independently selected from halogen, C$_1$-C$_6$ alkyl, and C$_1$-C$_6$ alkoxy),
C$_3$-C$_8$ cycloalkyl,
5- to 10-membered heteroaryl, and
3- to 6-membered heterocyclyl (optionally substituted with 1-3 groups independently selected from C$_1$-C$_6$ alkyl);
each Q is independently selected from:
C$_1$-C$_6$ alkyl optionally substituted with 1-3 groups independently selected from:
halogen,
oxo,
C$_6$-C$_{10}$ aryl (optionally substituted with 1-3 groups independently selected from halogen and —OCF$_3$), and
C$_3$-C$_8$ cycloalkyl,
C$_3$-C$_8$ cycloalkyl optionally substituted with 1-3 groups independently selected from:
halogen,
CN,
C$_1$-C$_6$ alkyl (optionally substituted with 1-3 groups independently selected from halogen, —NH$_2$, and —NHCOMe),
C$_1$-C$_6$ alkoxy,
C$_6$-C$_{10}$ aryl (optionally substituted with 1-3 groups independently selected from C$_1$-C$_6$ alkyl), and
C$_3$-C$_8$ cycloalkyl,
C$_6$-C$_{10}$ aryl optionally substituted with 1-3 groups independently selected from:
halogen,
CN,
C$_1$-C$_6$ alkyl (optionally substituted with 1-3 groups independently selected from halogen and hydroxy),
C$_1$-C$_6$ alkoxy optionally substituted with 1-4 groups independently selected from:
halogen,
C$_3$-C$_8$ cycloalkyl (optionally substituted with CF$_3$),
C$_3$-C$_8$ cycloalkyl (optionally substituted with 1-3 groups independently selected from halogen, CF$_3$, OCF$_3$, and C$_1$-C$_6$ alkyl), and
C$_6$-C$_{10}$ aryl,
5- to 10-membered heteroaryl optionally substituted with 1-3 groups independently selected from:
halogen,
C$_1$-C$_6$ alkyl (optionally substituted with 1-3 groups independently selected from halogen),
C$_3$-C$_8$ cycloalkyl (optionally substituted with 1-3 CF$_3$ groups), and
3- to 10-membered heterocyclyl,
3- to 10-membered heterocyclyl optionally substituted with 1-3 groups independently selected from:
C$_1$-C$_6$ alkyl (optionally substituted with 1-3 groups independently selected from oxo and C$_3$-C$_8$ cycloalkyl), and
oxo;
each R$^1$ is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;
each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);
Z is selected from

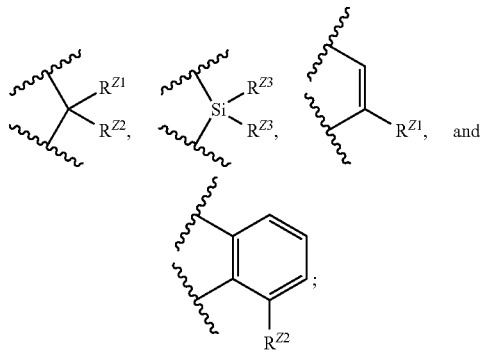

R$^{Z1}$ is selected from hydrogen, —CN, C$_1$-C$_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;
R$^{Z2}$ is selected from hydrogen, halogen, and hydroxy, or R$^{Z1}$ and R$^{Z2}$ taken together form a group selected from oxo and =N—OH; and
each R$^{Z3}$ is independently selected from hydroxy, C$_1$-C$_6$ alkoxy, C$_1$-C$_6$ alkyl, and C$_6$-C$_{10}$ aryl; or two instances of R$^{Z3}$ are taken together to form a 3- to 6-membered heterocyclyl.
48. The compound, deuterated derivative, or pharmaceutically acceptable salt according to any one of Embodiments 44-47, wherein X is —O—.
49. The compound, deuterated derivative, or pharmaceutically acceptable salt according to any one of Embodiments 44-48, wherein each Y is independently selected from —C(R$^Y$)$_2$—, —CO—, and

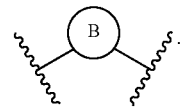

50. The compound, deuterated derivative, or pharmaceutically acceptable salt according to any one of Embodiments 44-49, wherein each R$^Y$ is independently selected from hydrogen, C$_1$-C$_6$ alkyl (optionally substituted with 1-3 groups independently selected from hydroxy and Q), and —OR$^{Y1}$.
51. The compound, deuterated derivative, or pharmaceutically acceptable salt according to any one of Embodiments 44-50, wherein each R$^Y$ is independently selected from:
hydrogen,

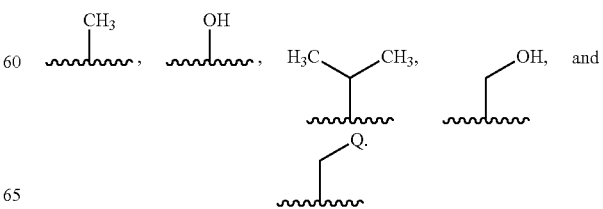

52. The compound, deuterated derivative, or pharmaceutically acceptable salt according to any one of Embodiments 44-51, wherein each Q is independently selected from:

$C_3$-$C_8$ cycloalkyl, $C_6$-$C_{10}$ aryl optionally substituted with 1-3 groups independently selected from halogen and $C_1$-$C_6$ alkyl.

53. The compound, deuterated derivative, or pharmaceutically acceptable salt according to any one of Embodiments 44-52, wherein each Q is independently selected from:

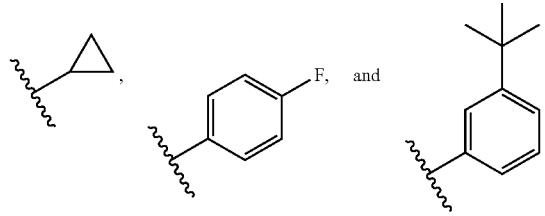

54. The compound, deuterated derivative, or pharmaceutically acceptable salt according to any one of Embodiments 44-53, wherein Ring B is selected from $C_6$-$C_{10}$ aryl optionally substituted with 1-3 groups independently selected from halogen.

55. The compound, deuterated derivative, or pharmaceutically acceptable salt according to any one of Embodiments 44-54, wherein Ring B is selected from:

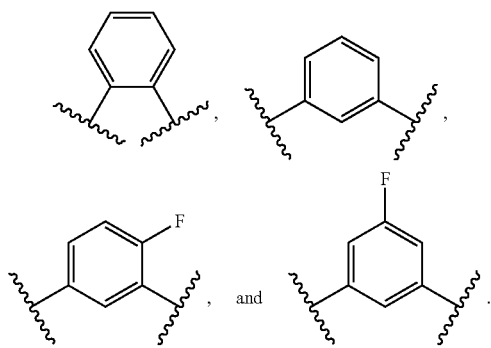

56. The compound, deuterated derivative, or pharmaceutically acceptable salt according to any one of Embodiments 44-55, wherein each Y is —C($R^Y$)$_2$—.

57. The compound, deuterated derivative, or pharmaceutically acceptable salt according to any one of Embodiments 44-56, wherein each $R^1$ is independently selected from —$CF_3$ and —N($R^2$)$_2$.

58. The compound, deuterated derivative, or pharmaceutically acceptable salt according to any one of Embodiments 44-57, wherein each $R^2$ is independently selected from hydrogen and $C_1$-$C_6$ alkyl.

59. The compound, deuterated derivative, or pharmaceutically acceptable salt according to any one of Embodiments 44-58, wherein each $R^2$ is hydrogen.

60. The compound, deuterated derivative, or pharmaceutically acceptable salt according to any one of Embodiments 44-59, wherein Z is

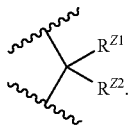

61. The compound, deuterated derivative, or pharmaceutically acceptable salt according to any one of Embodiments 44-60, wherein $R^{Z1}$ is selected from $C_1$-$C_6$ alkyl (optionally substituted with 1-3 groups selected from halogen).

62. The compound, deuterated derivative, or pharmaceutically acceptable salt according to any one of Embodiments 44-61, wherein $R^{Z1}$ is —$CF_3$.

63. The compound, deuterated derivative, or pharmaceutically acceptable salt according to any one of Embodiments 44-62, wherein $R^{Z2}$ is hydroxy.

64. A compound selected from compounds of Formulae IIIa, IIIb, and IIIc:

IIIa
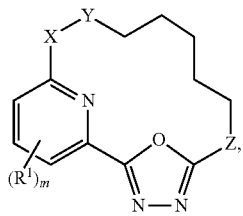

IIIb
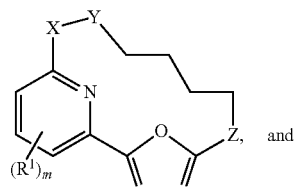

IIIc
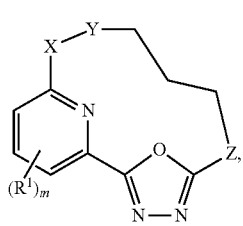

and deuterated derivatives and pharmaceutically acceptable salts thereof, wherein:

X is selected from —O—, —S—, —SO—, and —SO$_2$—;
each Y is independently selected from —C($R^Y$)$_2$—, —O—, —CO—, and

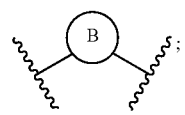

each $R^Y$ is independently selected from hydrogen, halogen, $C_1$-$C_6$ alkyl (optionally substituted with 1-3 groups independently selected from hydroxy and Q), $C_6$-$C_{10}$ aryl, 5- to 10-membered heteroaryl, —O$R^{Y1}$, —CO$_2R^{Y1}$, —CO$R^{Y1}$, —CON($R^{Y1}$)$_2$, and —N$R^{Y1}$—; or two instances of $R^Y$ on the same atom are taken together to form a ring selected from $C_3$-$C_8$ cycloalkyl and 3- to 6-membered heterocyclyl; or two instances of $R^Y$, one of which is on one atom and the second of which is on an adjacent atom, are taken together to form a pi bond;

each $R^{Y1}$ is independently selected from hydrogen and $C_1$-$C_6$ alkyl, or two instances of $R^{Y1}$ bonded to the same nitrogen taken together form a 3- to 6-membered heterocyclyl;

Ring B is selected from:
$C_6$-$C_{10}$ aryl (optionally substituted with 1-3 groups independently selected from halogen, $C_1$-$C_6$ alkyl, and $C_1$-$C_6$ alkoxy),
$C_3$-$C_8$ cycloalkyl,
5- to 10-membered heteroaryl, and
3- to 6-membered heterocyclyl (optionally substituted with 1-3 groups independently selected from $C_1$-$C_6$ alkyl);

each Q is independently selected from:
$C_1$-$C_6$ alkyl optionally substituted with 1-3 groups independently selected from:
halogen,
oxo,
$C_6$-$C_{10}$ aryl (optionally substituted with 1-3 groups independently selected from halogen and —$OCF_3$), and
$C_3$-$C_8$ cycloalkyl,
$C_3$-$C_8$ cycloalkyl optionally substituted with 1-3 groups independently selected from:
halogen,
CN,
$C_1$-$C_6$ alkyl (optionally substituted with 1-3 groups independently selected from halogen, —$NH_2$, and —NHCOMe),
$C_1$-$C_6$ alkoxy,
$C_6$-$C_{10}$ aryl (optionally substituted with 1-3 groups independently selected from $C_1$-$C_6$ alkyl), and
$C_3$-$C_8$ cycloalkyl,
$C_6$-$C_{10}$ aryl optionally substituted with 1-3 groups independently selected from:
halogen,
CN,
$C_1$-$C_6$ alkyl (optionally substituted with 1-3 groups independently selected from halogen and hydroxy),
$C_1$-$C_6$ alkoxy optionally substituted with 1-4 groups independently selected from:
halogen,
$C_3$-$C_8$ cycloalkyl (optionally substituted with $CF_3$),
$C_3$-$C_8$ cycloalkyl (optionally substituted with 1-3 groups independently selected from halogen, $CF_3$, $OCF_3$, and $C_1$-$C_6$ alkyl), and
$C_6$-$C_{10}$ aryl,
5- to 10-membered heteroaryl optionally substituted with 1-3 groups independently selected from:
halogen,
$C_1$-$C_6$ alkyl (optionally substituted with 1-3 groups independently selected from halogen),
$C_3$-$C_8$ cycloalkyl (optionally substituted with 1-3 $CF_3$ groups), and
3- to 10-membered heterocyclyl,
3- to 10-membered heterocyclyl optionally substituted with 1-3 groups independently selected from:
$C_1$-$C_6$ alkyl (optionally substituted with 1-3 groups independently selected from oxo and $C_3$-$C_8$ cycloalkyl), and
oxo;

each $R^1$ is independently selected from halogen, $C_1$-$C_6$ alkyl (optionally substituted with 1-6 groups independently selected from halogen), —$OR^2$, —$N(R^2)_2$, —$CO_2R^2$, —CO—$N(R^2)_2$, —CN, phenyl, benzyl, $C_1$-$C_6$ alkoxy, $C_1$-$C_6$ alkyl, $C_3$-$C_8$ cycloalkyl, 5- to 6-membered heteroaryl, 3- to 6-membered heterocyclyl, —$SO_2R^2$, —$SR^2$, —$SOR^2$, —PO$(OR^2)_2$, and —$PO(R^2)_2$;

each $R^2$ is independently selected from hydrogen, $C_1$-$C_6$ alkyl (optionally substituted with 1-6 groups independently selected from halogen), and $C_6$-$C_{10}$ aryl (optionally substituted with $C_1$-$C_6$ alkoxy, which is optionally substituted with 1-6 groups independently selected from halogen);

Z is selected from

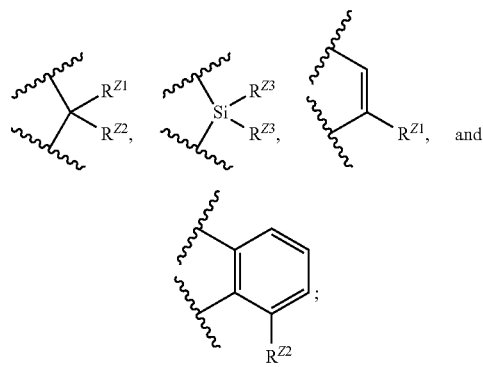

$R^{Z1}$ is selected from hydrogen, —CN, $C_1$-$C_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

$R^{Z2}$ is selected from hydrogen, halogen, and hydroxy, or $R^{Z1}$ and $R^{Z2}$ taken together form a group selected from oxo and =N—OH;

each $R^{Z3}$ is independently selected from hydroxy, $C_1$-$C_6$ alkoxy, $C_1$-$C_6$ alkyl, and $C_6$-$C_{10}$ aryl; or two instances of $R^{Z3}$ are taken together to form a 3- to 6-membered heterocyclyl; and m is selected from 0, 1, 2, and 3.

65. The compound, deuterated derivative, or pharmaceutically acceptable salt according to Embodiment 64, wherein m is selected from 1 and 2.

66. The compound, deuterated derivative, or pharmaceutically acceptable salt according to Embodiment 64 or 65, wherein m is 2.

67. A compound selected from compounds of Formulae IIId, IIIe, and IIIf:

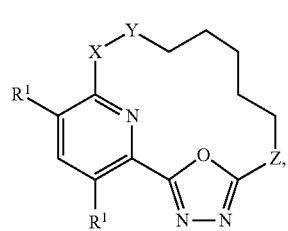

IIId

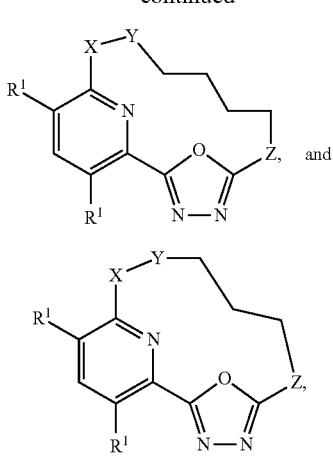

IIIe

IIIf and deuterated derivatives and pharmaceutically acceptable salts thereof, wherein:

X is selected from —O—, —S—, —SO—, and —SO$_2$—;

each Y is independently selected from —C(R$^Y$)$_2$—, —O—, —CO—, and

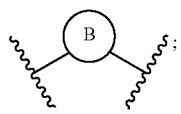

each R$^Y$ is independently selected from hydrogen, halogen, C$_1$-C$_6$ alkyl (optionally substituted with 1-3 groups independently selected from hydroxy and Q), C$_6$-C$_{10}$ aryl, 5- to 10-membered heteroaryl, —OR$^{Y1}$, —CO$_2$R$^{Y1}$, —COR$^{Y1}$, —CON(R$^{Y1}$)$_2$, and —NR$^{Y1}$—; or two instances of R$^Y$ on the same atom are taken together to form a ring selected from C$_3$-C$_8$ cycloalkyl and 3- to 6-membered heterocyclyl; or two instances of R$^Y$, one of which is on one atom and the second of which is on an adjacent atom, are taken together to form a pi bond;

each R$^{Y1}$ is independently selected from hydrogen and C$_1$-C$_6$ alkyl, or two instances of R$^{Y1}$ bonded to the same nitrogen taken together form a 3- to 6-membered heterocyclyl;

Ring B is selected from:
  C$_6$-C$_{10}$ aryl (optionally substituted with 1-3 groups independently selected from halogen, C$_1$-C$_6$ alkyl, and C$_1$-C$_6$ alkoxy),
  C$_3$-C$_8$ cycloalkyl,
  5- to 10-membered heteroaryl, and
  3- to 6-membered heterocyclyl (optionally substituted with 1-3 groups independently selected from C$_1$-C$_6$ alkyl);

each Q is independently selected from:
  C$_1$-C$_6$ alkyl optionally substituted with 1-3 groups independently selected from:
    halogen,
    oxo,
    C$_6$-C$_{10}$ aryl (optionally substituted with 1-3 groups independently selected from halogen and —OCF$_3$), and
    C$_3$-C$_8$ cycloalkyl,
  C$_3$-C$_8$ cycloalkyl optionally substituted with 1-3 groups independently selected from:
    halogen,
    CN,
    C$_1$-C$_6$ alkyl (optionally substituted with 1-3 groups independently selected from halogen, —NH$_2$, and —NHCOMe),
    C$_1$-C$_6$ alkoxy,
    C$_6$-C$_{10}$ aryl (optionally substituted with 1-3 groups independently selected from C$_1$-C$_6$ alkyl), and
    C$_3$-C$_8$ cycloalkyl,
  C$_6$-C$_{10}$ aryl optionally substituted with 1-3 groups independently selected from:
    halogen,
    CN,
    C$_1$-C$_6$ alkyl (optionally substituted with 1-3 groups independently selected from halogen and hydroxy),
    C$_1$-C$_6$ alkoxy optionally substituted with 1-4 groups independently selected from:
      halogen,
      C$_3$-C$_8$ cycloalkyl (optionally substituted with CF$_3$),
    C$_3$-C$_8$ cycloalkyl (optionally substituted with 1-3 groups independently selected from halogen, CF$_3$, OCF$_3$, and C$_1$-C$_6$ alkyl), and
    C$_6$-C$_{10}$ aryl,
  5- to 10-membered heteroaryl optionally substituted with 1-3 groups independently selected from:
    halogen,
    C$_1$-C$_6$ alkyl (optionally substituted with 1-3 groups independently selected from halogen),
    C$_3$-C$_8$ cycloalkyl (optionally substituted with 1-3 CF$_3$ groups), and
    3- to 10-membered heterocyclyl,
  3- to 10-membered heterocyclyl optionally substituted with 1-3 groups independently selected from:
    C$_1$-C$_6$ alkyl (optionally substituted with 1-3 groups independently selected from oxo and C$_3$-C$_8$ cycloalkyl), and
    oxo;

each is independently selected from halogen, C$_1$-C$_6$ alkyl (optionally substituted with 1-6 groups independently selected from halogen), —OR$^2$, —N(R$^2$)$_2$, —CO$_2$R$^2$, —CO—N(R$^2$)$_2$, —CN, phenyl, benzyl, C$_1$-C$_6$ alkoxy, C$_1$-C$_6$ alkyl, C$_3$-C$_8$ cycloalkyl, 5- to 6-membered heteroaryl, 3- to 6-membered heterocyclyl, —SO$_2$R$^2$, —SR$^2$, —SOR$^2$, —PO(OR$^2$)$_2$, and —PO(R$^2$)$_2$;

each R$^2$ is independently selected from hydrogen, C$_1$-C$_6$ alkyl (optionally substituted with 1-6 groups independently selected from halogen), and C$_6$-C$_{10}$ aryl (optionally substituted with C$_1$-C$_6$ alkoxy, which is optionally substituted with 1-6 groups independently selected from halogen);

Z is selected from

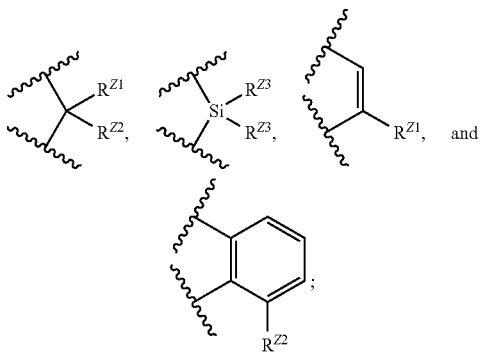

$R^{Z1}$ is selected from hydrogen, —CN, $C_1$-$C_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

$R^{Z2}$ is selected from hydrogen, halogen, and hydroxy, or $R^{Z1}$ and $R^{Z2}$ taken together form a group selected from oxo and =N—OH;

each $R^{Z3}$ is independently selected from hydroxy, $C_1$-$C_6$ alkoxy, $C_1$-$C_6$ alkyl, and $C_6$-$C_{10}$ aryl; or two instances of $R^{Z3}$ are taken together to form a 3- to 6-membered heterocyclyl.

68. The compound, deuterated derivative, or pharmaceutically acceptable salt according to any one of Embodiments 64-67, wherein X is —O—.

69. The compound, deuterated derivative, or pharmaceutically acceptable salt according to any one of Embodiments 64-68, wherein each Y is independently selected from —C($R^Y$)$_2$—, —CO—, and

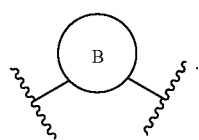

70. The compound, deuterated derivative, or pharmaceutically acceptable salt according to any one of Embodiments 64-69, wherein each $R^Y$ is independently selected from hydrogen, $C_1$-$C_6$ alkyl (optionally substituted with 1-3 groups independently selected from hydroxy and Q), and —$OR^{Y1}$.

71. The compound, deuterated derivative, or pharmaceutically acceptable salt according to any one of Embodiments 64-70, wherein each $R^Y$ is independently selected from: hydrogen,

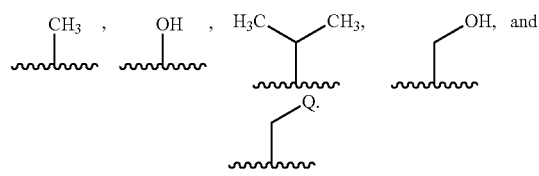

72. The compound, deuterated derivative, or pharmaceutically acceptable salt according to any one of Embodiments 64-71, wherein each Q is independently selected from:
$C_3$-$C_8$ cycloalkyl,
$C_6$-$C_{10}$ aryl optionally substituted with 1-3 groups independently selected from halogen and $C_1$-$C_6$ alkyl.

73. The compound, deuterated derivative, or pharmaceutically acceptable salt according to any one of Embodiments 64-72, wherein each Q is independently selected from:

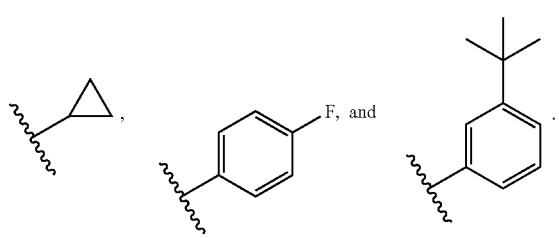

74. The compound, deuterated derivative, or pharmaceutically acceptable salt according to any one of Embodiments 64-73, wherein Ring B is selected from $C_6$-$C_{10}$ aryl optionally substituted with 1-3 groups independently selected from halogen.

75. The compound, deuterated derivative, or pharmaceutically acceptable salt according to any one of Embodiments 64-74, wherein Ring B is selected from:

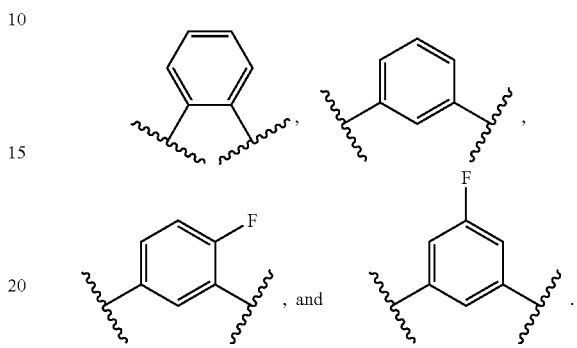

76. The compound, deuterated derivative, or pharmaceutically acceptable salt according to any one of Embodiments 64-75, wherein each Y is —C($R^Y$)$_2$—.

77. The compound, deuterated derivative, or pharmaceutically acceptable salt according to any one of Embodiments 64-76, wherein each $R^1$ is independently selected from —$CF_3$ and —N($R^2$)$_2$.

78. The compound, deuterated derivative, or pharmaceutically acceptable salt according to any one of Embodiments 64-77, wherein each $R^2$ is independently selected from hydrogen and $C_1$-$C_6$ alkyl.

79. The compound, deuterated derivative, or pharmaceutically acceptable salt according to any one of Embodiments 64-78, wherein each $R^2$ is hydrogen.

80. The compound, deuterated derivative, or pharmaceutically acceptable salt according to any one of Embodiments 64-79, wherein Z is

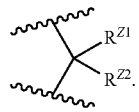

81. The compound, deuterated derivative, or pharmaceutically acceptable salt according to any one of Embodiments 64-80, wherein $R^{Z1}$ is selected from $C_1$-$C_6$ alkyl (optionally substituted with 1-3 groups selected from halogen).

82. The compound, deuterated derivative, or pharmaceutically acceptable salt according to any one of Embodiments 64-81, wherein $R^{Z1}$ is —$CF_3$.

83. The compound, deuterated derivative, or pharmaceutically acceptable salt according to any one of Embodiments 64-82, wherein $R^{Z2}$ is hydroxy.

84. The compound, deuterated derivative, or pharmaceutically acceptable salt according to Embodiment 1, wherein X is —O—.

85. The compound, deuterated derivative, or pharmaceutically acceptable salt according to Embodiment 1 or 84, wherein each $R^Y$ is independently selected from hydrogen, halogen, $C_1$-$C_6$ alkyl (optionally substituted with 1-3 groups independently selected from hydroxy and Q), $C_3$-$C_8$ cycloalkyl, and —$OR^{Y1}$.

86. The compound, deuterated derivative, or pharmaceutically acceptable salt according to any one of Embodiments 1, 84, and 85, wherein —OR$^{Y1}$ is —OH.

87. The compound, deuterated derivative, or pharmaceutically acceptable salt according to any one of Embodiments 1 and 84-86, wherein each Q is independently selected from:

C$_3$-C$_8$ cycloalkyl,

C$_6$-C$_{10}$ aryl optionally substituted with 1-3 groups independently selected from halogen and C$_1$-C$_6$ alkyl.

88. The compound, deuterated derivative, or pharmaceutically acceptable salt according to any one of Embodiments 1 and 84-87, wherein each Q is independently selected from:

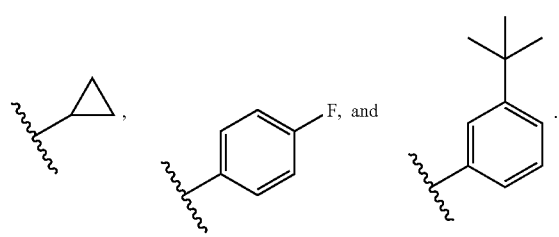

89. The compound, deuterated derivative, or pharmaceutically acceptable salt according to any one of Embodiments 1 and 84-88, wherein each R$^Y$ is independently selected from: hydrogen, fluorine,

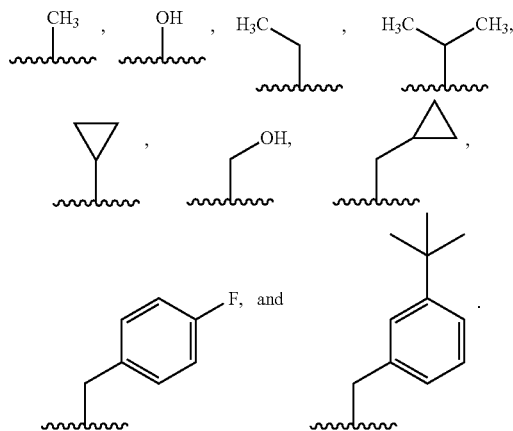

90. The compound, deuterated derivative, or pharmaceutically acceptable salt according to any one of Embodiments 1 and 84-89, wherein Ring B is selected from C$_3$-C$_8$ cycloalkyl and phenyl optionally substituted with 1-3 groups independently selected from halogen.

91. The compound, deuterated derivative, or pharmaceutically acceptable salt according to any one of Embodiments 1 and 84-90, wherein Ring B is selected from:

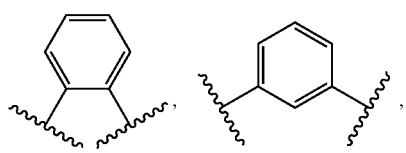

-continued

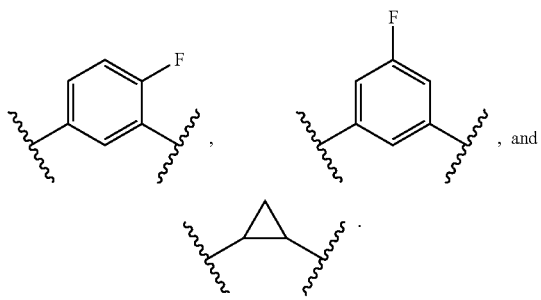

92. The compound, deuterated derivative, or pharmaceutically acceptable salt according to any one of Embodiments 1 and 84-91, wherein n is selected from 4, 5, and 6.

93. The compound, deuterated derivative, or pharmaceutically acceptable salt according to any one of Embodiments 1 and 84-92, wherein —(Y)$_n$— is a group selected from:

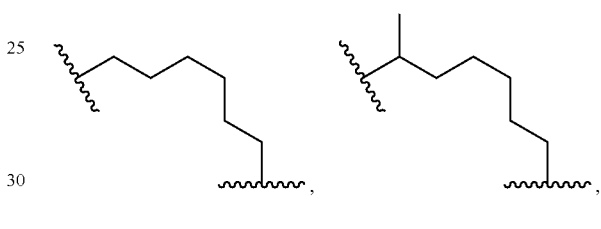

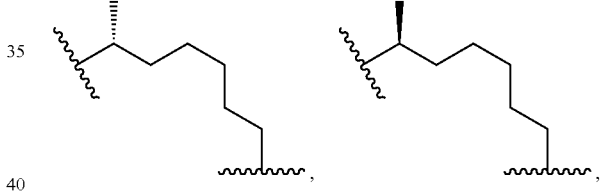

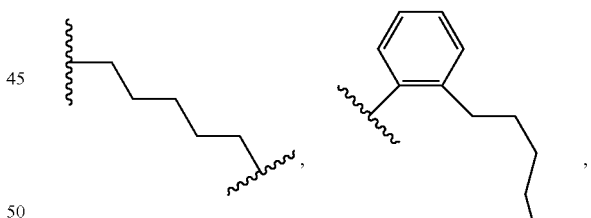

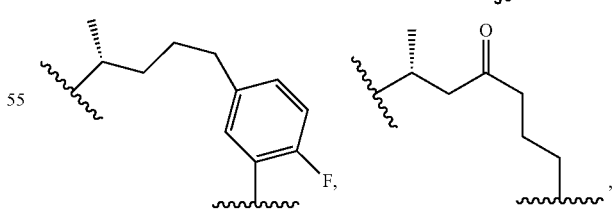

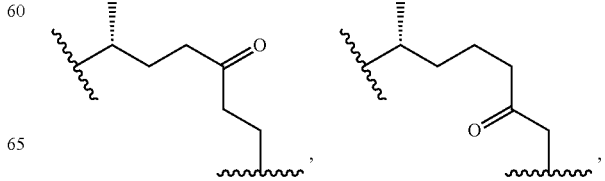

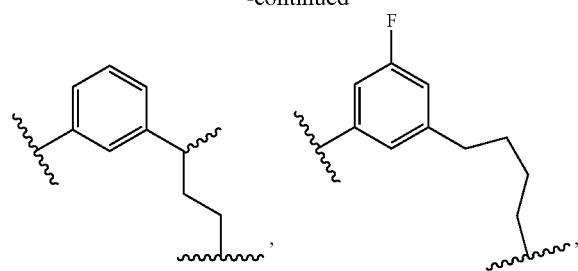
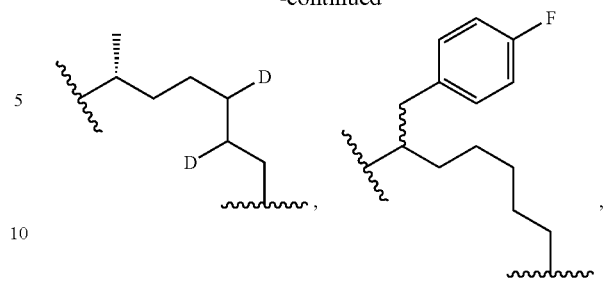
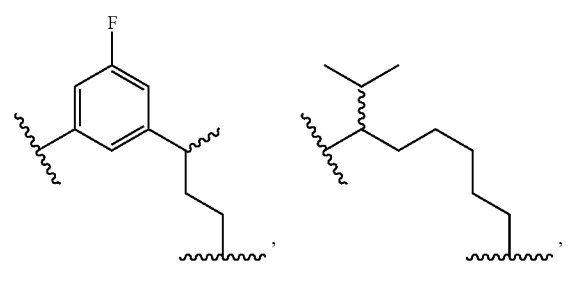
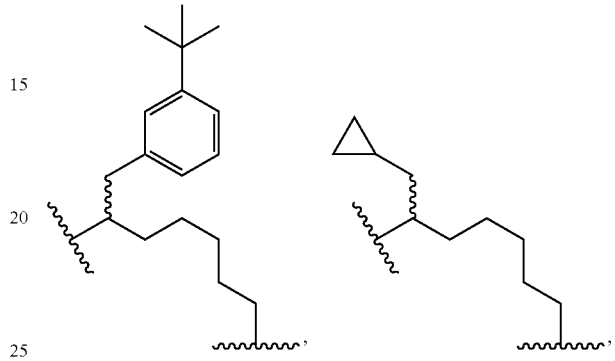
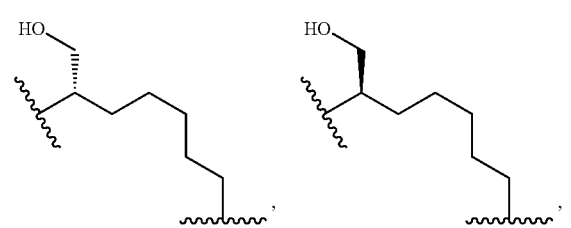
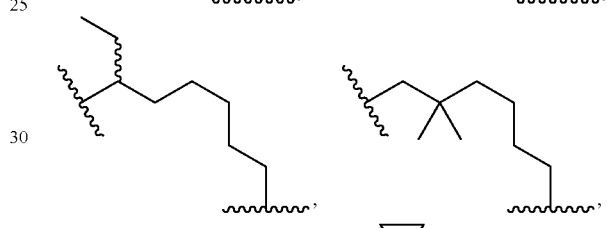
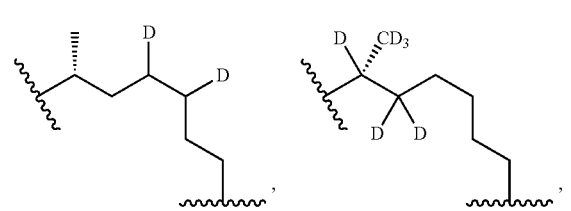
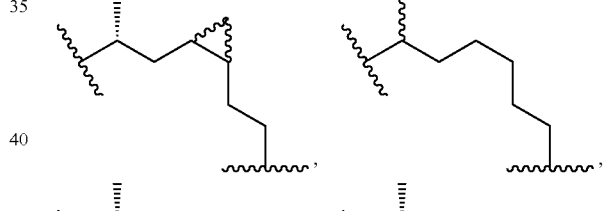
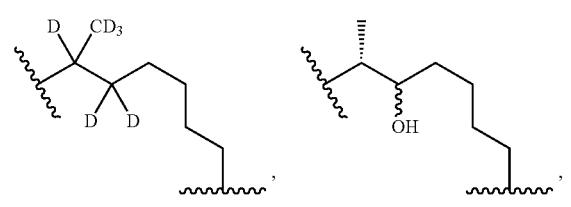
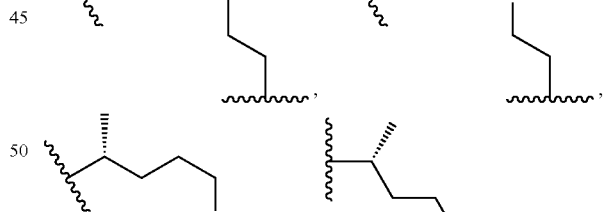
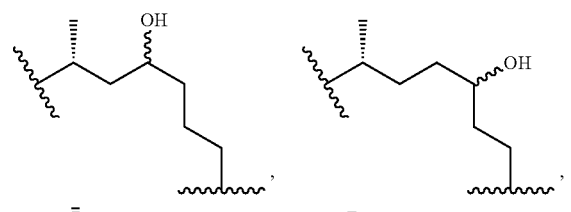
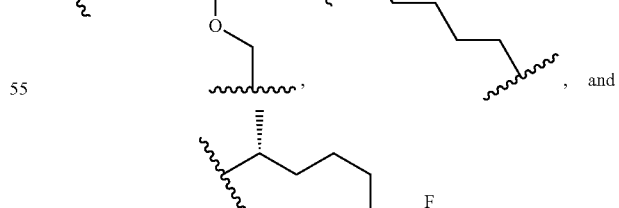
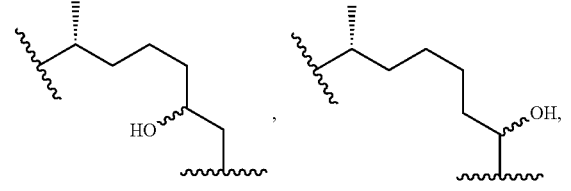
94. The compound, deuterated derivative, or pharmaceutically acceptable salt according to any one of Embodiments 1 and 84-93, wherein each $R^1$ is independently selected from $C_1$-$C_6$ alkyl (optionally substituted with 1-6 groups independently selected from halogen and hydroxy), —N($R^2$)$_2$, and —CO$_2$$R^2$.

95. The compound, deuterated derivative, or pharmaceutically acceptable salt according to any one of Embodiments 1 and 85-94, wherein each $R^2$ is independently selected from hydrogen and $C_1$-$C_6$ alkyl.

96. The compound, deuterated derivative, or pharmaceutically acceptable salt according to any one of Embodiments 1 and 84-95, wherein each $R^1$ is independently selected from —CF$_3$, —NH$_2$, —NH(CH$_2$CH$_3$), CO$_2$H, and CH$_2$OH.

97. The compound, deuterated derivative, or pharmaceutically acceptable salt according to any one of Embodiments 1 and 84-96, wherein Z is selected from

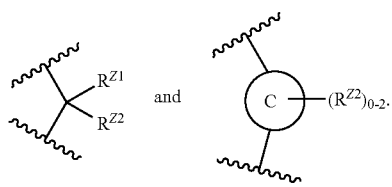

98. The compound, deuterated derivative, or pharmaceutically acceptable salt according to any one of Embodiments 1 and 84-97, wherein the group:

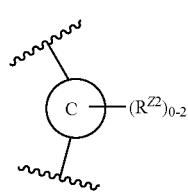

is selected from:

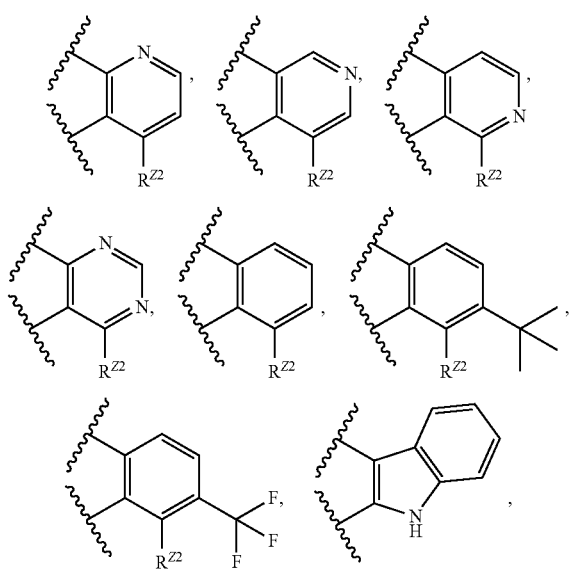

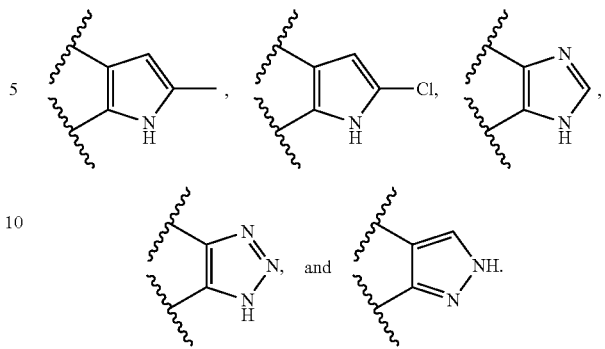

99. The compound, deuterated derivative, or pharmaceutically acceptable salt according to any one of Embodiments 1 and 84-98, wherein the group:

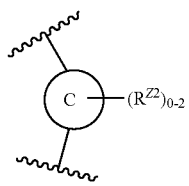

is selected from:

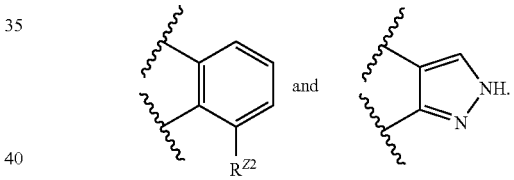

100. The compound, deuterated derivative, or pharmaceutically acceptable salt according to any one of Embodiments 1 and 84-99, wherein $R^{Z1}$ is selected from hydrogen and $C_1$-$C_6$ alkyl (optionally substituted with 1-3 groups selected from halogen).

101. The compound, deuterated derivative, or pharmaceutically acceptable salt according to any one of Embodiments 1 and 84-100, wherein $R^{Z1}$ is selected from hydrogen and —CF$_3$.

102. The compound, deuterated derivative, or pharmaceutically acceptable salt according to any one of Embodiments 1 and 84-101, wherein $R^{Z2}$ is hydroxy.

103. The compound, deuterated derivative, or pharmaceutically acceptable salt according to any one of Embodiments 1 and 84-102, wherein Z is selected from:

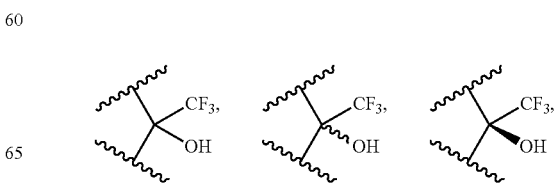

-continued

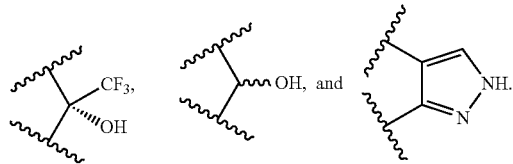

104. The compound, deuterated derivative, or pharmaceutically acceptable salt according to any one of Embodiments 1 and 84-103, wherein m is selected from 1 and 2.

105. The compound, deuterated derivative, or pharmaceutically acceptable salt according to any one of Embodiments 1, 2, and 84-104, wherein:

X is —O—;

each Y is independently selected from —C(R$^Y$)$_2$—, —O—, and

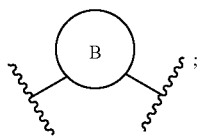

each R$^Y$ is independently selected from hydrogen and C$_1$-C$_6$ alkyl (optionally substituted with 1-3 groups independently selected from hydroxy and Q);

Ring B is selected from C$_3$-C$_8$ cycloalkyl groups:

each Q is independently selected from: C$_3$-C$_8$ cycloalkyl and C$_6$-C$_{10}$ aryl optionally substituted with 1-3 groups independently selected from halogen and C$_1$-C$_6$ alkyl, each R$^1$ is independently selected from C$_1$-C$_6$ alkyl (optionally substituted with 1-6 groups independently selected from halogen) and —NH$_2$;

Z is

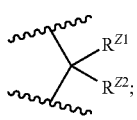

R$^{Z1}$ is selected from C$_1$-C$_6$ alkyl (optionally substituted with 1-6 groups independently selected from halogen);

R$^{Z2}$ is hydroxy;

n is selected from 5 and 6; and m is 2.

106. The compound, deuterated derivative, or pharmaceutically acceptable salt according to any one of Embodiments 1, 2, and 84-105, wherein each Q is independently selected from:

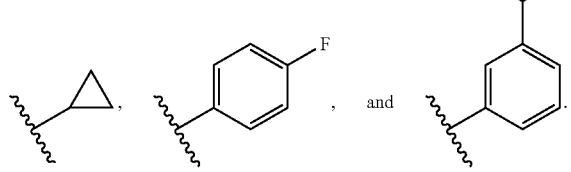

107. The compound, deuterated derivative, or pharmaceutically salt according to any one of Embodiments 1, 2, and 84-106, wherein each R$^Y$ is independently selected from: hydrogen,

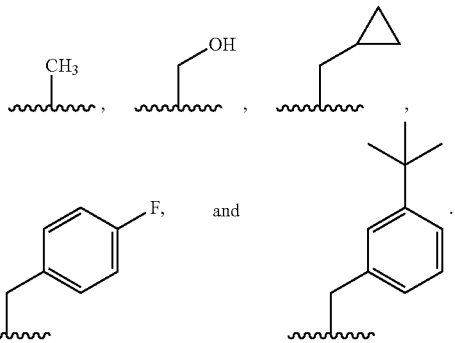

108. The compound, deuterated derivative, or pharmaceutically acceptable salt according to any one of Embodiments 1, 2, and 84-107, wherein Ring B is

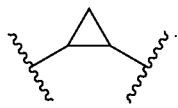

109. The compound, deuterated derivative, or pharmaceutically acceptable salt according to any one of Embodiments 1, 2, and 84-108, wherein —(Y)$_n$— is a group selected from:

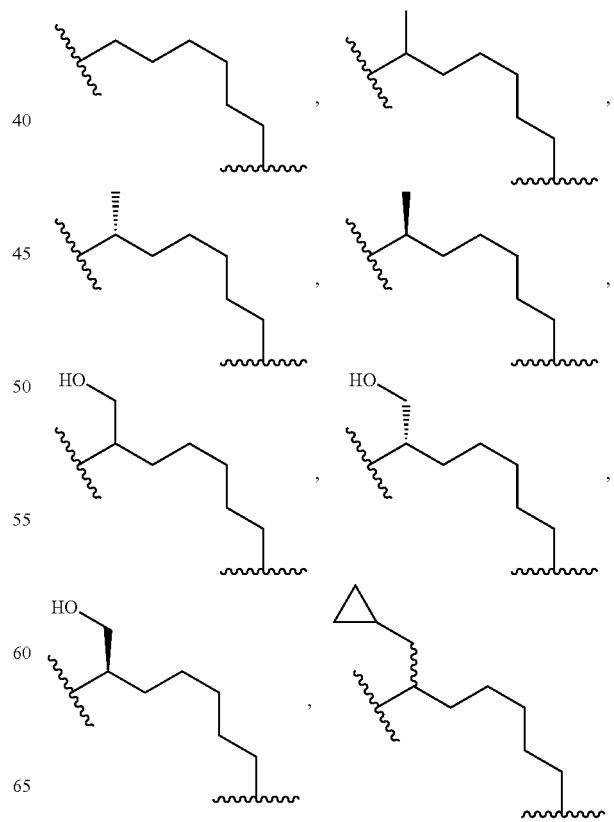

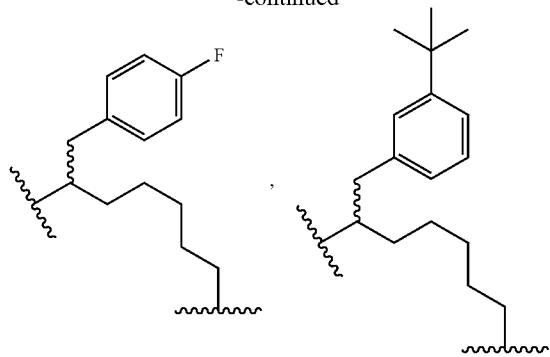

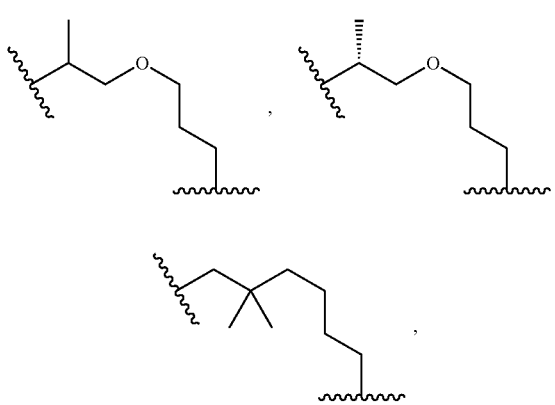

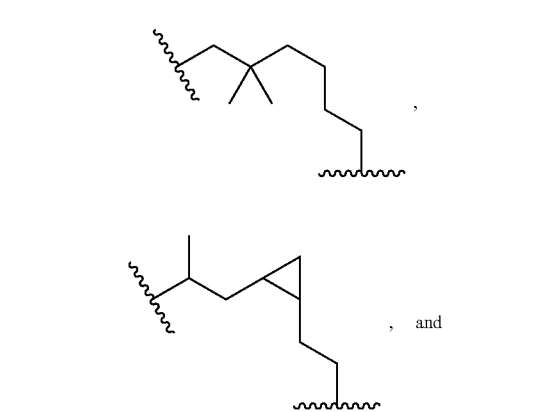

110. The compound, deuterated derivative, or pharmaceutically acceptable salt according to any one of Embodiments 1, 2, and 84-109, wherein $R^{Z1}$ is —$CF_3$.

111. The compound, deuterated derivative, or pharmaceutically acceptable salt according to any one of Embodiments 1, 2, and 84-110, wherein n is 5.

112. The compound, deuterated derivative, or pharmaceutically acceptable salt according to any one of Embodiments 1, 2, and 84-110, wherein n is 6.

113. A compound selected from compounds of Table 12, pharmaceutically acceptable salts thereof, and deuterated derivatives of any of the foregoing.

114. A compound selected from compounds of Table 13, pharmaceutically acceptable salts thereof, and deuterated derivatives of any of the foregoing.

115. A compound according to Embodiment 113, wherein the compound is selected from:

| Comp. No. | Structure |
|---|---|
| 5 | 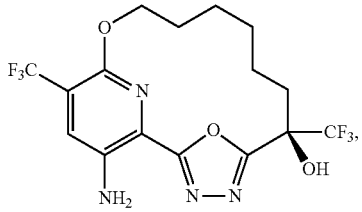 |
| 11 | 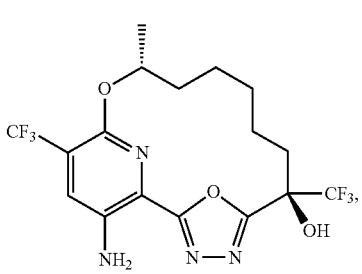 [SMILES: C[C@@H]1CCCCC[C@](O)(C(F)(F)F)C2=NN=C(O2)c2nc(c(C(F)(F)F)cc2N)O1] |
| 14 | 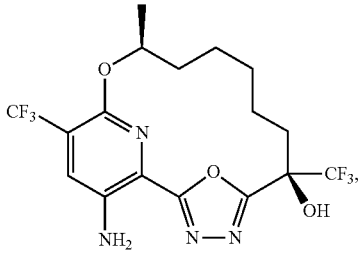 |
| 36 | 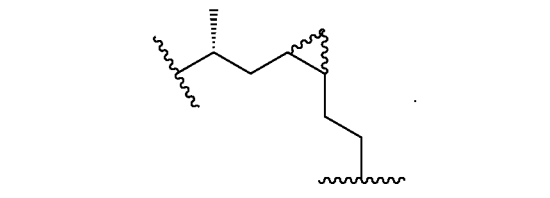 |
| 37 | 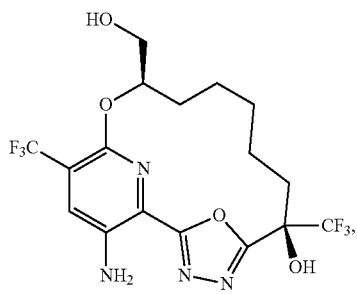 [SMILES: Nc1cc(C(F)(F)F)c2nc1C1=NN=C(O1)[C@@](O)(C(F)(F)F)CCCCC[C@H](CO)O2] |

deuterated derivatives thereof, and pharmaceutically acceptable salts of any of the foregoing.
116. A compound according to Embodiment 114, wherein the compound is selected from:

| Comp. No. | Structure |
|---|---|
| 64 | 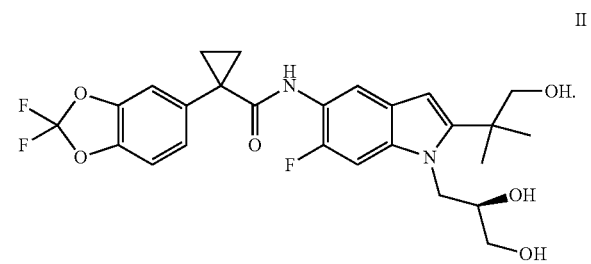 [SMILES: CC(C)(CO)c1cc2cc(NC(=O)C3(c4ccc5c(c4)OC(F)(F)O5)CC3)c(F)cc2n1C[C@@H](O)CO] enantiomer 2 | deuterated derivatives thereof, and pharmaceutically acceptable salts of any of the foregoing.

117. A pharmaceutical composition comprising a compound, deuterated derivative, or pharmaceutically acceptable salt of any one of Embodiments 1-116 and a pharmaceutically acceptable carrier.

118. The pharmaceutical composition according to Embodiment 117, further comprising one or more additional therapeutic agent(s).

119. The pharmaceutical composition according to Embodiment 118, wherein the one or more additional therapeutic agent(s) comprise(s) a compound with CFTR modulating activity or a salt or deuterated derivative thereof.

120. The pharmaceutical composition according to Embodiment 118 or 119, wherein the one or more additional therapeutic agent(s) comprise(s) a CFTR corrector.

121. The pharmaceutical composition according to any one of Embodiments 118-120, wherein the one or more additional therapeutic agent(s) comprise(s) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl) cyclopropanecarboxamide (Compound II):

II

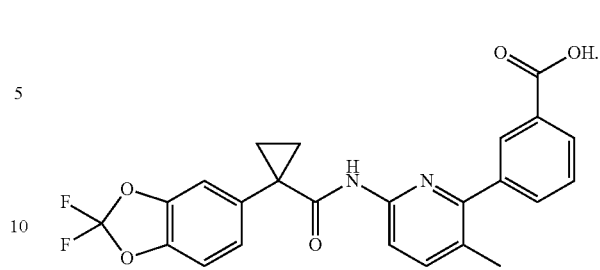

122. The pharmaceutical composition according to any one of Embodiments 118-121, wherein the one or more additional therapeutic agent(s) comprise(s) 3-(6-(1-(2,2-difluorobenzo[d][1,3]dioxol-5-yl)cyclopropanecarboxamido)-3-methylpyridin-2-yl)benzoic acid (Compound IV):

IV

123. The pharmaceutical composition according to any one of Embodiments 118-122, wherein the one or more additional therapeutic agent(s) comprise(s) N-(1,3-dimethylpyrazol-4-yl)sulfonyl-6-[3-(3,3,3-trifluoro-2,2-dimethylpropoxy)pyrazol-1-yl]-2-[(4S)-2,2,4-trimethylpyrrolidin-1-yl]pyridine-3-carboxamide (Compound V):

V

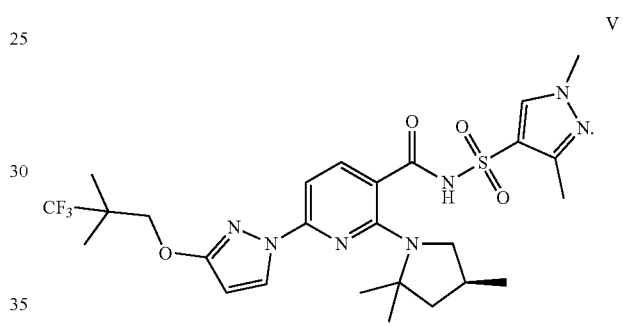

124. The pharmaceutical composition according to any one of Embodiments 118-123, wherein the one or more additional therapeutic agent(s) comprise(s) N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide (Compound VI):

VI

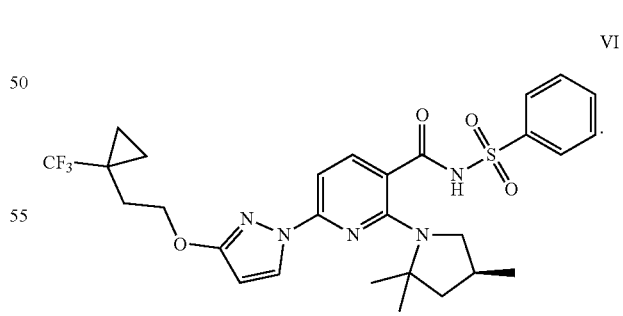

125. The pharmaceutical composition according to any one of Embodiments 118-124, wherein the one or more additional therapeutic agent(s) comprise(s) (14S)-8-[3-(2-{dispiro[2.0.2.1]heptan-7-yl}ethoxy)-1H-pyrazol-1-yl]-12,12-dimethyl-2$\lambda^6$-thia-3,9,11,18,23-pentaazatetracyclo[17.3.1.1¹¹,¹⁴.0⁵,¹⁰]tetracosa-1(22),5,7,9,19(23),20-hexaene-2,2,4-trione (Compound VII):

VII

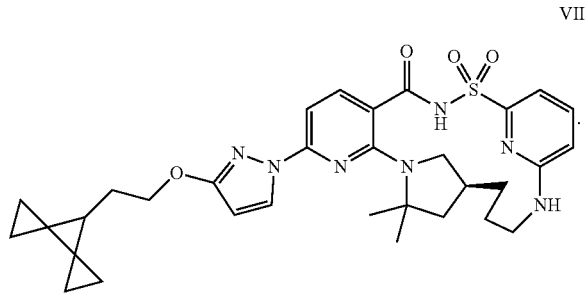 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

126. The pharmaceutical composition according to any one of Embodiments 118-125, wherein the one or more additional therapeutic agent(s) comprise(s) (11R)-6-(2,6-dimethylphenyl)-11-(2-methylpropyl)-12-{spiro[2.3]hexan-5-yl}-9-oxa-2λ⁶-thia-3,5,12,19-tetraazatricyclo[12.3.1.1⁴,⁸]nonadeca-1(17),4(19),5,7,14(18),15-hexaene-2,2,13-trione (Compound VIII):

VIII

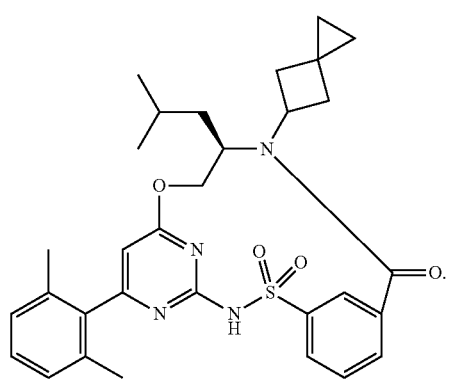

127. The pharmaceutical composition according to any one of Embodiments 118-126, wherein the one or more additional therapeutic agent(s) comprise(s) at least one compound selected from PTI-428, ABBV-2222, ABBV-2851, GLPG2737, ABBV-3221, ABBV-3748, ABBV-3903, ABBV-119, and PTI-801.

128. The pharmaceutical composition according to any one of Embodiments 118-127, wherein the one or more additional therapeutic agent(s) comprise(s) a CFTR potentiator enhancer.

129. The pharmaceutical composition according to any one of Embodiments 118-128, wherein the one or more additional therapeutic agent(s) comprise(s) ASP-11.

130. A method of treating cystic fibrosis, comprising administering an effective amount of the compound, salt, or deuterated derivative according to any one of Embodiments 1-116 or the pharmaceutical composition according to any one of Embodiments 117-129 to a patient in need thereof.

131. The method according to Embodiment 130, further comprising administering one or more additional therapeutic agent(s).

132. The method according to Embodiment 131, wherein the one or more additional therapeutic agent(s) comprise(s) a compound with CFTR modulating activity or a salt or deuterated derivative thereof.

133. The method according to Embodiment 131 or 132, wherein the one or more additional therapeutic agent(s) comprise(s) a CFTR corrector.

134. The method according to any one of Embodiments 131-133, wherein the one or more additional therapeutic agent(s) comprise(s) (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (Compound II):

II

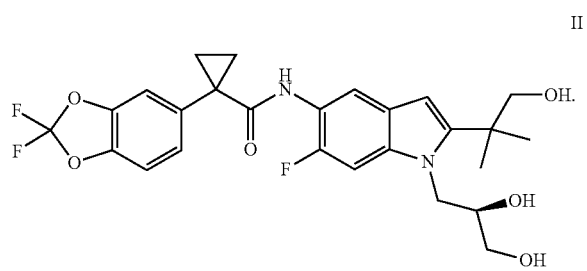 [SMILES: CC(C)(CO)c1cc2cc(NC(=O)C3(c4ccc5c(c4)OC(F)(F)O5)CC3)c(F)cc2n1C[C@@H](O)CO]

135. The method according to any one of Embodiments 131-134, wherein the one or more additional therapeutic agent(s) comprise(s) 3-(6-(1-(2,2-difluorobenzo[d][1,3]dioxol-5-yl)cyclopropanecarboxamido)-3-methylpyridin-2-yl)benzoic acid (Compound IV):

IV

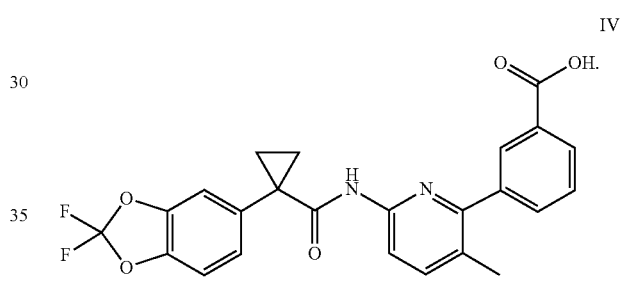

136. The method according to any one of Embodiments 131-135, wherein the one or more additional therapeutic agent(s) comprise(s) N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound V):

V

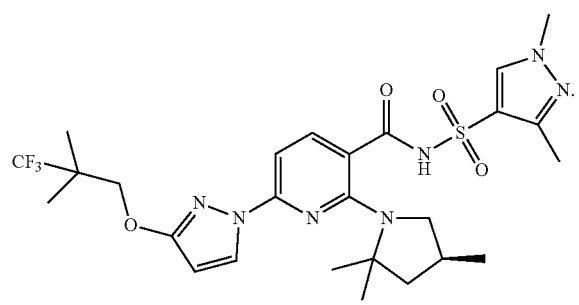

137. The method according to any one of Embodiments 131-136, wherein the one or more additional therapeutic agent(s) comprise(s)N-(benzenesulfonyl)-6-[3-[2-[1-(trifluoromethyl) cyclopropyl]ethoxy]pyrazol-1-yl]-2-[(4S)-2,2,4-trimethylpyrrolidin-1-yl]pyridine-3-carboxamide (Compound VI):

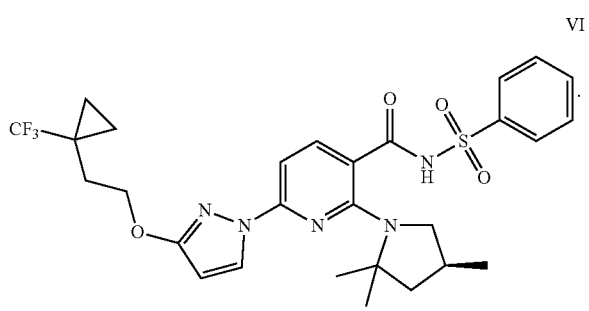 [SMILES: C[C@@H]1CN(c2nc(-n3ccc(OCCC4(C(F)(F)F)CC4)n3)ccc2C(=O)NS(=O)(=O)c2ccccc2)C(C)(C)C1]

138. The method according to any one of Embodiments 131-137, wherein the one or more additional therapeutic agent(s) comprise(s) (14S)-8-[3-(2-{dispiro[2.0.2.1]heptan-7-yl}ethoxy)-1H-pyrazol-1-yl]-12,12-dimethyl-2λ⁶-thia-3,9,11,18,23-pentaazatetracyclo [17.3.1.1¹¹,¹⁴.0⁵,¹⁰]tetracosa-1(22),5,7,9,19(23),20-hexaene-2,2,4-trione (Compound VII):

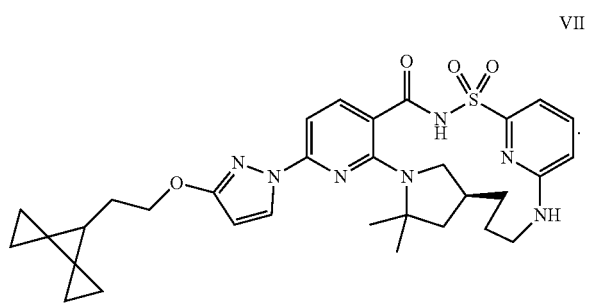 [SMILES: CC1(C)C[C@@H]2CCCNc3cccc(n3)S(=O)(=O)NC(=O)c3ccc(-n4ccc(OCCC5C6(CC6)C56CC6)n4)nc3N1C2]

139. The method according to any one of Embodiments 131-138, wherein the one or more additional therapeutic agent(s) comprise(s) (11R)-6-(2,6-dimethylphenyl)-11-(2-methylpropyl)-12-{spiro[2.3]hexan-5-yl}-9-oxa-2λ⁶thia-3,5,12,19-tetraazatricyclo[12.3.1.1⁴,⁸]nonadeca-1(17),4(19),5,7,14(18),15-hexaene-2,2,13-trione (Compound VIII):

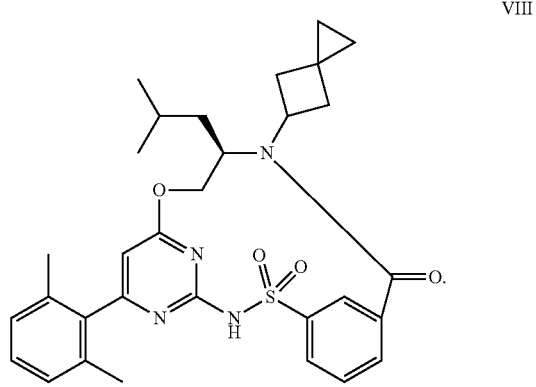 [SMILES: Cc1cccc(C)c1-c1cc2nc(n1)NS(=O)(=O)c1cccc(c1)C(=O)N(C1CC3(CC3)C1)[C@H](CC(C)C)CO2]

140. The method according to any one of Embodiments 131-139, wherein the one or more additional thereapeutic agent(s) comprise(s) at least one compound selected from PTI-428, ABBV-2222, ABBV-2851, GLPG2737, ABBV-3221, ABBV-3748, ABBV-3903, ABBV-119, and PTI-801.

141. The method according to any one of Embodiments 131-140, wherein the one or more additional thereapeutic agent(s) comprise(s) a CFTR potentiator enhancer.

142. The method according to any one of Embodiments 131-141, wherein the one or more additional thereapeutic agent(s) comprise(s) ASP-11.

143. The compound, deuterated derivative, or pharmaceutically acceptable salt of any one of Embodiments 1-116 or the pharmaceutical composition according to any one of Embodiments 117-129 for use in the treatment of cystic fibrosis.

144. Use of the compound, deuterated derivative, or pharmaceutically acceptable salt of any one of Embodiments 1-117 in the manufacture of a medicament for the treatment of cystic fibrosis.

145. Use of the pharmaceutical composition according to any one of Embodiments 117-129 in the manufacture of a medicament for the treatment of cystic fibrosis.

146. Substantially crystalline Compound 11 heptane solvate (i.e., wherein less than 15% of Compound 11 is in amorphous form, wherein less than 10% of Compound 11 is in amorphous form, wherein less than 5% of Compound 11 is in amorphous form).

147. The Compound 11 according to Embodiment 146, wherein Compound 11 is 100% crystalline heptane solvate.

148. The crystalline Compound 11 heptane solvate according to Embodiment 146 or 147, characterized by an X-ray powder diffractogram having one, two, or three signals selected from 5.8±0.2 degrees two-theta, 10.1±0.2 degrees two-theta, and 11.7±0.2 degrees two-theta.

149. The crystalline Compound 11 heptane solvate according to any one of Embodiments 146-148, characterized by an X-ray powder diffractogram having (a) one, two, or three signals selected selected from 5.8±0.2 degrees two-theta, 10.1±0.2 degrees two-theta, and 11.7±0.2 degrees two-theta, and (b) one, two, three, or four signals selected from 5.6±0.2 degrees two-theta, 18.1±0.2 degrees two-theta, 20.5±0.2 degrees two-theta, and 20.9±0.2 degrees two-theta.

150. The crystalline Compound 11 heptane solvate according to any one of Embodiments 146-149, characterized by an X-ray powder diffractogram having signals at 5.6±0.2 degrees two-theta, 5.8±0.2 degrees two-theta, 10.1±0.2 degrees two-theta, 11.7±0.2 degrees two-theta, 18.1±0.2 degrees.

151. The crystalline Compound 11 heptane solvate according to any one of Embodiments 146-150, characterized by an X-ray powder diffractogram substantially similar to FIG. 1.

152. The crystalline Compound 11 heptane solvate according to any one of Embodiments 146-151, characterized by a ¹³C ssNMR spectrum having one, two, three, four, five, six, seven, eight, nine, ten, or more peaks selected from 166.3±0.2 ppm, 165.8±0.2 ppm, 164.6±0.2 ppm, 163.4±0.2 ppm, 154.8±0.2 ppm, 154.0±0.2 ppm, 152.1±0.2 ppm, 151.6±0.2 ppm, 140.2±0.2 ppm, 139.4±0.2 ppm, 138.5±0.2 ppm, 138.0±0.2 ppm, 135.1±0.2 ppm, 134.6±0.2 ppm, 131.3±0.2 ppm, 130.2±0.2 ppm, 129.6±0.2 ppm, 128.5±0.2 ppm, 125.7±0.2 ppm, 123.7±0.2 ppm, 123.2±0.2 ppm, 122.9±0.2 ppm, 121.1±0.2 ppm, 120.2±0.2 ppm, 119.2±0.2 ppm, 117.8±0.2 ppm, 76.2±0.2 ppm, 74.4±0.2 ppm, 73.7±0.2 ppm, 73.3±0.2 ppm, 40.0±0.2 ppm, 38.6±0.2 ppm, 37.6±0.2 ppm, 36.9±0.2 ppm, 35.7±0.2 ppm, 33.6±0.2 ppm, 32.5±0.2 ppm, 32.0±0.2 ppm, 30.4±0.2 ppm, 30.1±0.2 ppm, 29.5±0.2 ppm, 28.8±0.2 ppm, 28.1±0.2 ppm, 27.1±0.2 ppm, 25.3±0.2 ppm, 23.1±0.2 ppm, 22.7±0.2 ppm, 22.0±0.2 ppm, 21.6±0.2 ppm, 20.3±0.2 ppm, 19.6±0.2 ppm, 18.3±0.2 ppm, 17.6±0.2 ppm, 13.8±0.2 ppm, 13.1±0.2 ppm, and 12.5±0.2 ppm.

153. The crystalline Compound 11 heptane solvate according to any one of Embodiments 146-152, characterized by a ¹³C SSNMR spectrum substantially similar to FIG. 3.

154. The crystalline Compound 11 heptane solvate according to any one of Embodiments 146-153, characterized as having a $^{19}$F SSNMR spectrum with one, two, three, four, five, or more peaks selected from −63.5±0.2 ppm, −63.8±0.2 ppm, −65.1±0.2 ppm, −65.8±0.2 ppm, −66.3±0.2 ppm, −67.0±0.2 ppm, −74.0±0.2 ppm, −74.9±0.2 ppm, and −76.6±0.2 ppm.

155. The crystalline Compound 11 heptane solvate according to any one of Embodiments 146-154, characterized as having a $^{19}$F SSNMR spectrum with one, two, three, four, five, or more peaks selected from −63.5±0.2 ppm, −63.8±0.2 ppm, −65.1±0.2 ppm, −65.8±0.2 ppm, −66.3±0.2 ppm, −67.0±0.2 ppm, −74.0±0.2 ppm, −74.9±0.2 ppm, −76.6±0.2 ppm, and −77.6±0.2 ppm.

156. The crystalline Compound 11 heptane solvate according to any one of Embodiments 146-155, characterized as having a $^{19}$F SSNMR spectrum with a peak at −67.0±0.2 ppm.

157. The crystalline Compound 11 heptane solvate according to any one of Embodiments 146-156, characterized as having a $^{19}$F SSNMR spectrum with a peak at −65.1±0.2 ppm.

158. The crystalline Compound 11 heptane solvate according to any one of Embodiments 146-157, characterized as having a $^{19}$F SSNMR spectrum with a peak at −76.6±0.2 ppm.

159. The crystalline Compound 11 heptane solvate according to any one of Embodiments 146-158, characterized as having a $^{19}$F SSNMR spectrum with a peak at −63.5±0.2 ppm.

160. The crystalline Compound 11 heptane solvate according to any one of Embodiments 146-159, characterized as having a $^{19}$F SSNMR spectrum with a peak at −74.9±0.2 ppm.

161. The crystalline Compound 11 heptane solvate according to any one of Embodiments 146-160, characterized as having a $^{19}$F SSNMR spectrum with at least one peak selected from −65.1±0.2 ppm, −67.0±0.2 ppm, and −76.6±0.2 ppm.

162. The crystalline Compound 11 heptane solvate according to any one of Embodiments 146-161, characterized as having a $^{19}$F SSNMR spectrum with peaks at −65.1±0.2 ppm, −67.0±0.2 ppm, and −76.6±0.2 ppm.

163. The crystalline Compound 11 heptane solvate according to any one of Embodiments 146-162, characterized as having a $^{19}$F SSNMR spectrum with at least one peak selected from −63.5±0.2 ppm, −65.1±0.2 ppm, −67.0±0.2 ppm, −74.9±0.2 ppm, and −76.6±0.2 ppm.

164. The crystalline Compound 11 heptane solvate according to any one of Embodiments 146-163, characterized as having a $^{19}$F SSNMR spectrum with peaks at −63.5±0.2 ppm, −65.1±0.2 ppm, −67.0±0.2 ppm, −74.9±0.2 ppm, and −76.6±0.2 ppm.

165. The crystalline Compound 11 heptane solvate according to any one of Embodiments 146-164, characterized by a $^{19}$F SSNMR spectrum substantially similar to FIG. 4.

166. The crystalline Compound 11 heptane solvate according to any one of Embodiments 146-165, prepared by a process comprising dissolving Compound 11 in heptane and dichloromethane, concentrating under rotary evaporation, swirling at room temperature, filtering the solids, washing the solids with cold heptane, and drying under vacuum to provide Compound 11 heptane solvate.

167. A method of preparing the crystalline Compound 11 heptane solvate according to any one of Embodiments 146-166, prepared by a process comprising dissolving Compound 11 in heptane and dichloromethane, concentrating under rotary evaporation, swirling at room temperature, filtering the solids, washing the solids with cold heptane, and drying under vacuum to provide Compound 11 heptane solvate.

168. The pharmaceutical composition according to any one of Embodiments 118-126, wherein the one or more additional therapeutic agent(s) comprise(s) at least one compound selected from Compound II, Compound III, Compound III-d, Compound IV, Compound V, Compound VI, Compound VII, Compound VIII, Compound IX, Compound X, PTI-428, ASP-11, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, PTI-801, FDL-176, PTI-808 (dirocaftor), GLPG1837, GLPG2451/ABBV-2451, QBW251 (icenticaftor), GLPG3067/ABBV-3067 (Navocaftor), ABBV-191, ELX-02, MRT5005, Lunar-CF, RCT223, amiloride, ETD001, $CF_{552}$, GS-9411, GS-5737, P-1037 (VX-371), P-1055 (VX-551), AZD5634, SPX-101, Ionis-ENaC-2.5 Rx, BI 1265162, AZ5634, ARO-ENaC1001, ETD002, and DS-1039.

169. The method according to any one of Embodiments 131-139, wherein the one or more additional thereapeutic agent(s) comprise(s) at least one compound selected from Compound II, Compound III, Compound III-d, Compound IV, Compound V, Compound VI, Compound VII, Compound VIII, Compound IX, Compound X, PTI-428, ASP-11, ABBV-2222, ABBV-2851, GLPG2737, ABBV-3221, ABBV-3748, ABBV-3903, ABBV-119, FDL-169, ARN5562, ARN21586, ARN22081, ARN22652, ARN23765, ARN23766, PTI-801, FDL-176, PTI-808 (dirocaftor), GLPG1837, GLPG2451/ABBV-2451, QBW251 (icenticaftor), GLPG3067/ABBV-3067 (Navocaftor), ABBV-191, ELX-02, MRT5005, Lunar-CF, RCT223, amiloride, ETD001, $CF_{552}$, GS-9411, GS-5737, P-1037 (VX-371), P-1055 (VX-551), AZD5634, SPX-101, Ionis-ENaC-2.5 Rx, BI 1265162, AZ5634, ARO-ENaC1001, ETD002, and DS-1039.

170. Substantially crystalline Compound 6 (free form) (i.e., wherein less than 15% of
Compound 6 is in amorphous form, wherein less than 10% of Compound 6 is in amorphous form, wherein less than 5% of Compound 6 is in amorphous form).

171. The Compound 6 (free form) according to Embodiment 170, wherein Compound 6 is 100% crystalline Compound 6 (free form).

172. The crystalline Compound 6 (free form) according to Embodiment 170 or 171, characterized by a monoclinic crystal system, a P21 space group, and unit cell dimensions measured at 100 K on a Bruker diffractometer equipped with Cu K$_\alpha$ radiation (λ=1.5478 Å) of:

| a | 9.6 ± 0.1 Å | α | 90° |
|---|---|---|---|
| b | 13.6 ± 0.1 Å | β | 105.3° ± 0.1° |
| c | 13.8 ± 0.1 Å | γ | 90° |

173. Substantially crystalline Compound 19 (free form) (i.e., wherein less than 15% of Compound 19 is in amorphous form, wherein less than 10% of Compound 19 is in amorphous form, wherein less than 5% of Compound 19 is in amorphous form).

174. The Compound 19 (free form) according to Embodiment 173, wherein Compound 19 is 100% crystalline Compound 19 (free form).

175. The crystalline Compound 19 (free form) according to Embodiment 173 or 174, characterized by a tetragonal crystal system, a P4₁2₁2 space group, and unit cell dimensions measured at 100 K on a Bruker diffractometer equipped with Mo K$_\alpha$ radiation ($\lambda$=0.71073 Å) of:

| a | 9.8 ± 0.1 Å | α | 90° |
|---|---|---|---|
| b | 9.8 ± 0.1 Å | β | 90° |
| c | 37.1 ± 0.1 Å | γ | 90° |

176. Substantially crystalline Compound 20 (free form) (i.e., wherein less than 15% of Compound 20 is in amorphous form, wherein less than 10% of Compound 20 is in amorphous form, wherein less than 5% of Compound 20 is in amorphous form).

177. The Compound 20 (free form) according to Embodiment 176, wherein Compound 20 is 100% crystalline Compound 20 (free form).

178. The crystalline Compound 20 (free form) according to Embodiment 176 or 177, characterized by an orthorhombic crystal system, a P2₁2₁2₁ space group, and unit cell dimensions measured at 100 K on a Bruker diffractometer equipped with Mo K$_\alpha$ radiation ($\lambda$=0.71073 Å) of:

| a | 10.7 ± 0.1 Å | α | 90° |
|---|---|---|---|
| b | 13.7 ± 0.1 Å | β | 90° |
| c | 25.5 ± 0.1 Å | γ | 90° |

EXAMPLES

General Experimental Procedures
Abbreviations
ACN: Acetonitrile
AcOH: Acetic acid
BCl₃: Boron trichloride
Boc anhydride ((Boc)₂O): Di-tert-butyl dicarbonate
CDCl₃: Chloroform-d
CDI: 1,1'-Carbonyldiimidazole
CD₃OD: Methyl-d₃ alcohol-d
CH₂Cl₂: Dichloromethane
CH₃CN: Acetonitrile
CO₂: Carbon dioxide
Cs₂CO₃: Cesium carbonate
CuBr₂: Copper(II) bromide
CuI: Copper(I)iodide
DCE: 1,2-Dichloroethane
DCM: Dichloromethane
DDQ: 2,3-Dichloro-5,6-dicyano-1,4-benzoquinone
DI: Deionized
DIAD: Diisopropyl azodicarboxylate
DIEA: DIPEA; N,N-Diisopropylethylamine
DMAP: 4-Dimethylaminopyridine
DMF: N,N-Dimethylformamide
DMSO: Dimethyl sulfoxide
DMSO-d₆: Dimethyl sulfoxide-d₆
EA: Ethyl acetate
ELSD: Evaporative light scattering detector
Et₂O: Diethyl ether
EtOAc: Ethyl acetate
EtOH: Ethanol
ESI-MS: Electrospray ionization mass spectrometry
Grubbs 1ˢᵗ Generation catalyst: Dichloro(benzylidene)bis(tricyclohexylphosphine)ruthenium(II)
Grubbs 2ⁿᵈ Generation catalyst: [1,3-Bis(2,4,6-trimethylphenypimidazolidin-2-ylidene]-dichloro-[(2-isopropoxyphenyl)methylene]ruthenium
H₂: Hydrogen
HATU: N-[(Dimethylamino)-1H-1,2,3-triazolo-[4,5-b]pyridin-1-ylmethylene]-N-methylmethanaminium hexafluorophosphate N-oxide
HCl: Hydrochloric acid
HFIP: Hexafluoroisopropanol
Hoveyda-Grubbs 2ⁿᵈ Generation catalyst: Dichloro[1,3-bis(2,4,6-trimethylphenyl)-2-imidazolidinylidene](2-isopropoxyphenylmethylene)ruthenium(II)
HPLC: High performance liquid chromatography
IPA: Isopropanol
IPAC: Isopropyl acetate
iPrOH: Isopropanol
KHSO₄: Potassium bisulfate
LC: Liquid chromatography
LCMS: Liquid chromatography mass spectrometry
LDA: Lithium diisopropylamide
LiOH: Lithium hydroxide
MeCN: Acetonitrile
MeTHF or 2-MeTHF: 2-Methyltetrahydrofuran
MeOH: Methanol
MTBE: Methyl tert-butyl ether
MgSO₄: Magnesium sulfate
n-BuLi: n-Butyllithium
NaBH₄: Sodium borohydride
NaHCO₃: Sodium bicarbonate
NaHMDS: Sodium bis(trimethylsilyl)amide
NaOH: Sodium hydroxide
Na₂S₂O₃: Sodium thiosulfate
Na₂SO₄: Sodium sulfate
NBS: N-Bromosuccinimide
NMP: N-Methyl-2-pyrrolidone
NMR: Nuclear magnetic resonance
Pd/C: Palladium on carbon
Pd(OAc)₂: Palladium(II) acetate
rt: Room temperature
SFC: Supercritical fluid chromatography
Silica Cat Pd: Palladium on Silica
SilicaMetS: Silica Supported Metal Scavenger
SiO₂: Silica gel
T₃P: 1-Propanephosphonic anhydride
TBAI: Tetrabutylammonium iodide
TEA: Triethylamine
TFA: Trifluoroacetic acid
THF: Tetrahydrofuran
UPLC: Ultra Performance Liquid Chromatography
Xantphos: 4,5-Bis(diphenylphosphino)-9,9-dimethylxanthene
XPhos Pd G3: (2-Dicyclohexylphosphino-2',4',6'-triisopropyl-1,1'-biphenyl)[2-(2'-amino-1,1¹-biphenyl)]palladium(II) methanesulfonate
Zhan catalyst-1B: Dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II)

General Methods

Reagents and starting materials were obtained by commercial sources unless otherwise stated and were used without purification.

Proton and carbon NMR spectra were acquired on either a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. All proton and carbon spectra were acquired with temperature control at 30° C. using standard, previously published pulse sequences and routine processing parameters.

NMR (1D & 2D) spectra were also recorded on a Bruker AVNEO 400 MHz spectrometer operating at 400 MHz and 100 MHz respectively equipped with a 5 mm multinuclear Iprobe.

NMR spectra were also recorded on a Varian Mercury NMR instrument at 300 MHz for $^1$H using a 45 degree pulse angle, a spectral width of 4800 Hz and 28860 points of acquisition. FID were zero-filled to 32 k points and a line broadening of 0.3 Hz was applied before Fourier transform. $^{19}$F NMR spectra were recorded at 282 MHz using a 30 degree pulse angle, a spectral width of 100 kHz and 59202 points were acquired. FID were zero-filled to 64 k points and a line broadening of 0.5 Hz was applied before Fourier transform.

NMR spectra were also recorded on a Bruker Avance III HD NMR instrument at 400 MHz for $^1$H using a 30 degree pulse angle, a spectral width of 8000 Hz and 128 k points of acquisition. FID were zero-filled to 256 k points and a line broadening of 0.3 Hz was applied before fourrier transform. $^{19}$F NMR spectra were recorded at 377 MHz using a 30 deg pulse angle, a spectral width of 89286 Hz and 128 k points were acquired. FID were zero-filled to 256 k points and a line broadening of 0.3 Hz was applied before Fourier transform.

NMR spectra were also recorded on a Bruker AC 250 MHz instrument equipped with a: 5 mm QNP(H1/C13/F19/P31) probe (type: 250-SB, s #23055/0020) or on a Varian 500 MHz instrument equipped with a ID PFG, 5 mm, 50-202/500 MHz probe (model/part #99337300).

Unless stated to the contrary in the following examples, final purity of compounds was determined by reversed phase UPLC using an Acquity UPLC BEH Cls column (50×2.1 mm, 1.7 µm particle) made by Waters (pn: 186002350), and a dual gradient run from 1-99% mobile phase B over 3.0 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 µL, and column temperature=60° C. Final purity was calculated by averaging the area under the curve (AUC) of two UV traces (220 nm, 254 nm). Low-resolution mass spectra were reported as $[M+1]^+$ species obtained using a single quadrupole mass spectrometer equipped with an electrospray ionization (ESI) source capable of achieving a mass accuracy of 0.1 Da and a minimum resolution of 1000 (no units on resolution) across the detection range.

Solid-state NMR (SSNMR) spectra were recorded on a Bruker-Biospin 400 MHz wide-bore spectrometer equipped with Bruker-Biospin 4 mm HFX probe. Samples were packed into 4 mm ZrO2 rotors and spun under Magic Angle Spinning (MAS) condition with spinning speed typically set to 12.5 kHz. The proton relaxation time was measured using $^1$H MAS $T_1$ saturation recovery relaxation experiment in order to set up proper recycle delay of the $^{13}$C cross-polarization (CP) MAS experiment. The fluorine relaxation time was measured using $^{19}$F MAS $T_1$ saturation recovery relaxation experiment in order to set up proper recycle delay of the $^{19}$F MAS experiment. The CP contact time of carbon CPMAS experiment was set to 2 ms. A CP proton pulse with linear ramp (from 50% to 100%) was employed. The carbon Hartmann-Hahn match was optimized on external reference sample (glycine). Both carbon and fluorine spectra were recorded with proton decoupling using TPPM15 decoupling sequence with the field strength of approximately 100 kHz.

General Synthetic Schemes

Another aspect of the disclosure provides methods for making compounds of Formulae I, I', I'', I''', Ia, IIa, IIa', IIb, IIc, IId, IIe, IIf, IIIa, IIIb, IIIc, IIId, IIIe, and IIIf, Compounds 1 to 53, Compounds 54 to 77, and pharmaceutically acceptable salts of any of those compounds, deuterated derivatives of any of the foregoing, and intermediates for making any of the foregoing. In some embodiments of the following Schemes and Examples, each nitrogen and oxygen atom may optionally have, in addition to or in place of a specified variable substituent, one or more protecting groups selected from the range of protecting groups disclosed herein. In some embodiments of the following Schemes and Examples, each compound may be replaced with its deuterated derivative.

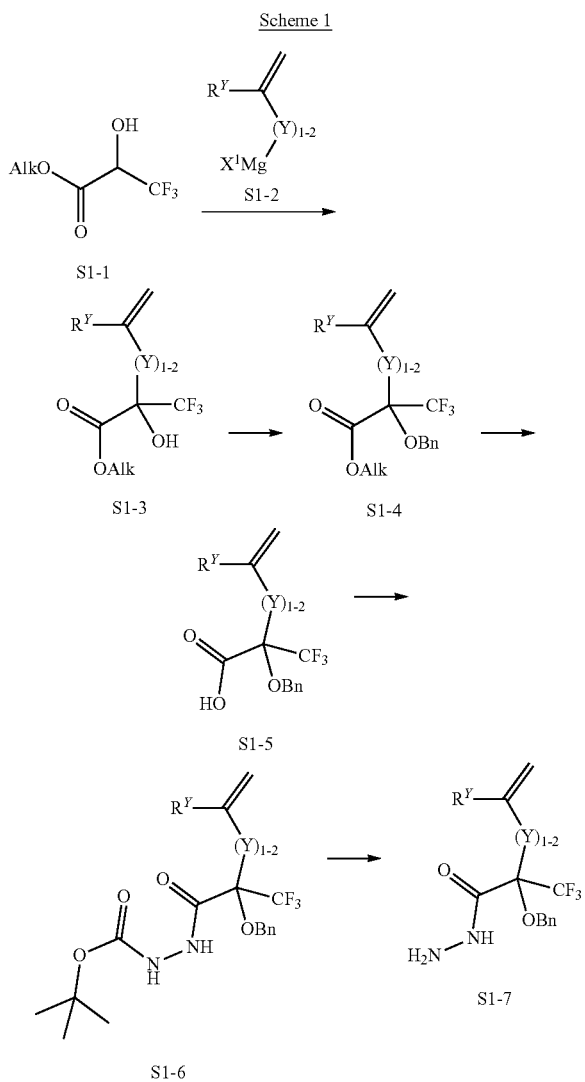

Scheme 1

Scheme 1 refers to processes for preparing an intermediate compound of Formula S1-7 from a compound of Formula S1-1. Alk is selected from $C_1$-$C_6$ linear or branched alkyl groups. $X^1$ is selected from halogens such as Cl, I, or Br. Y and $R^Y$ are as defined for Formula I above.

Any suitable conditions for a Grignard addition can be used to react a compound of Formula S1-1 with a compound of Formula S1-2 to form a compound of Formula S1-3. For example, the Grignard addition of a compound of Formula S1-1 with a compound of Formula S1-2 may be performed in Et₂O at −78° C., followed by addition of 1 N aqueous HCl to yield a compound of Formula S1-3. Conversion of a compound of Formula S1-3 to a compound of Formula S1-4 may be accomplished by any suitable benzylation procedure. Conversion of an ester of Formula S1-4 to a carboxylic acid of Formula S1-5 may be accomplished by any suitable hydrolysis conditions. For example, conversion of a carboxylic acid of Formula S1-5 to a compound of Formula S1-6 may be accomplished by reacting a compound of Formula S1-5 with HATU and Et₃N in DMF, followed by addition of tert-butyl N-aminocarbamate. Any suitable hydrolysis conditions may be used to convert a carbamate of Formula S1-6 to a hydrazide of Formula S1-7. For example, a compound of Formula S1-7 may be obtained by reacting a compound of Formula S1-6 with HCl in CH₂Cl₂ at ambient temperature.

compound of Formula S2-2 can be reacted with DIPEA in acetonitrile, followed by addition of p-toluenesulfonyl chloride, to yield an oxadiazole of Formula S2-3.

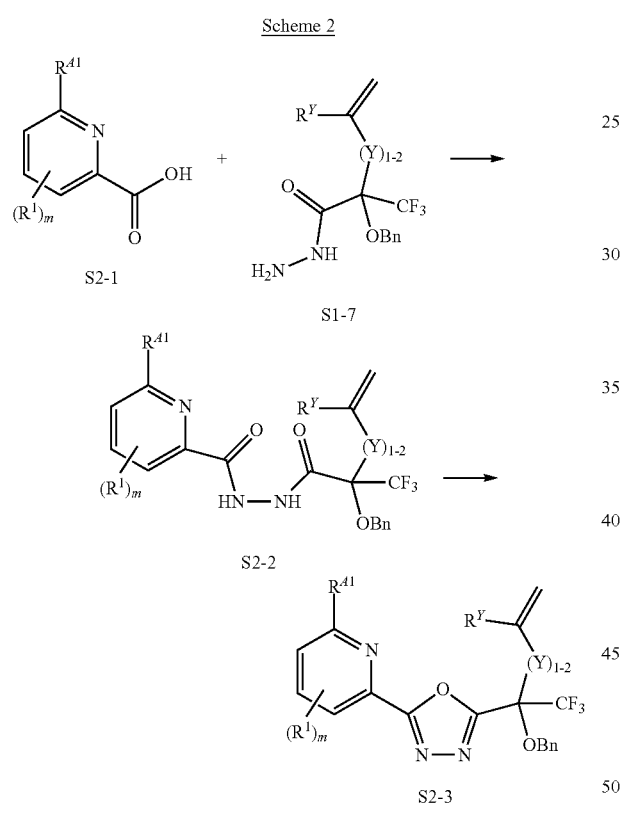

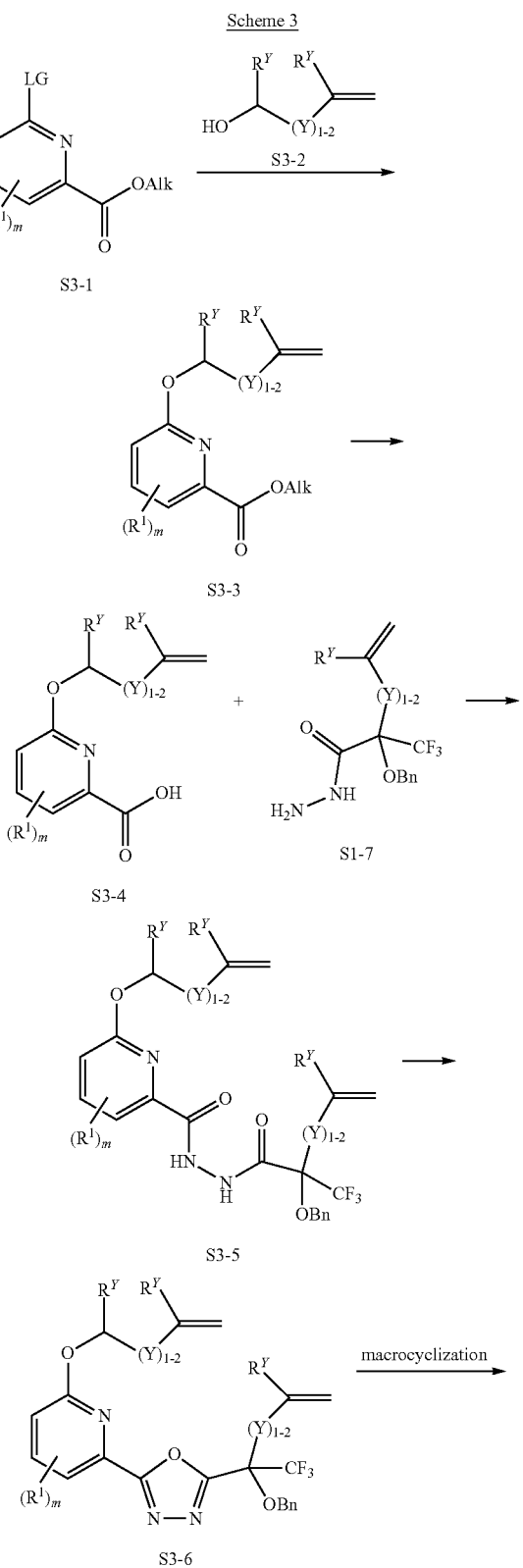

Scheme 2 refers to processes for preparing an intermediate compound of Formula S2-3 from a compound of Formula S2-1. $R^{A1}$ is selected from —X—(Y)$_{2-4}$-C(R$^Y$)=C(R$^Y$)$_2$, —OH, —OPG (wherein PG is a suitable protecting group), and halogen. $R^1$, m, X, Y, and $R^Y$ are as defined for Formula I above.

Any suitable conditions to form an amide bond can be used to produce a compound of Formula S2-2 from a compound of Formula S2-1 and a compound of Formula S1-7. For example, a compound of Formula S2-1 can be reacted with CDI in acetonitrile and DMF, followed by addition of a compound of Formula S1-7, to yield a compound of Formula S2-2. A compound of Formula S2-2 can be converted to a compound of Formula S2-3 using any conditions suitable for oxadiazole formation. For example, a

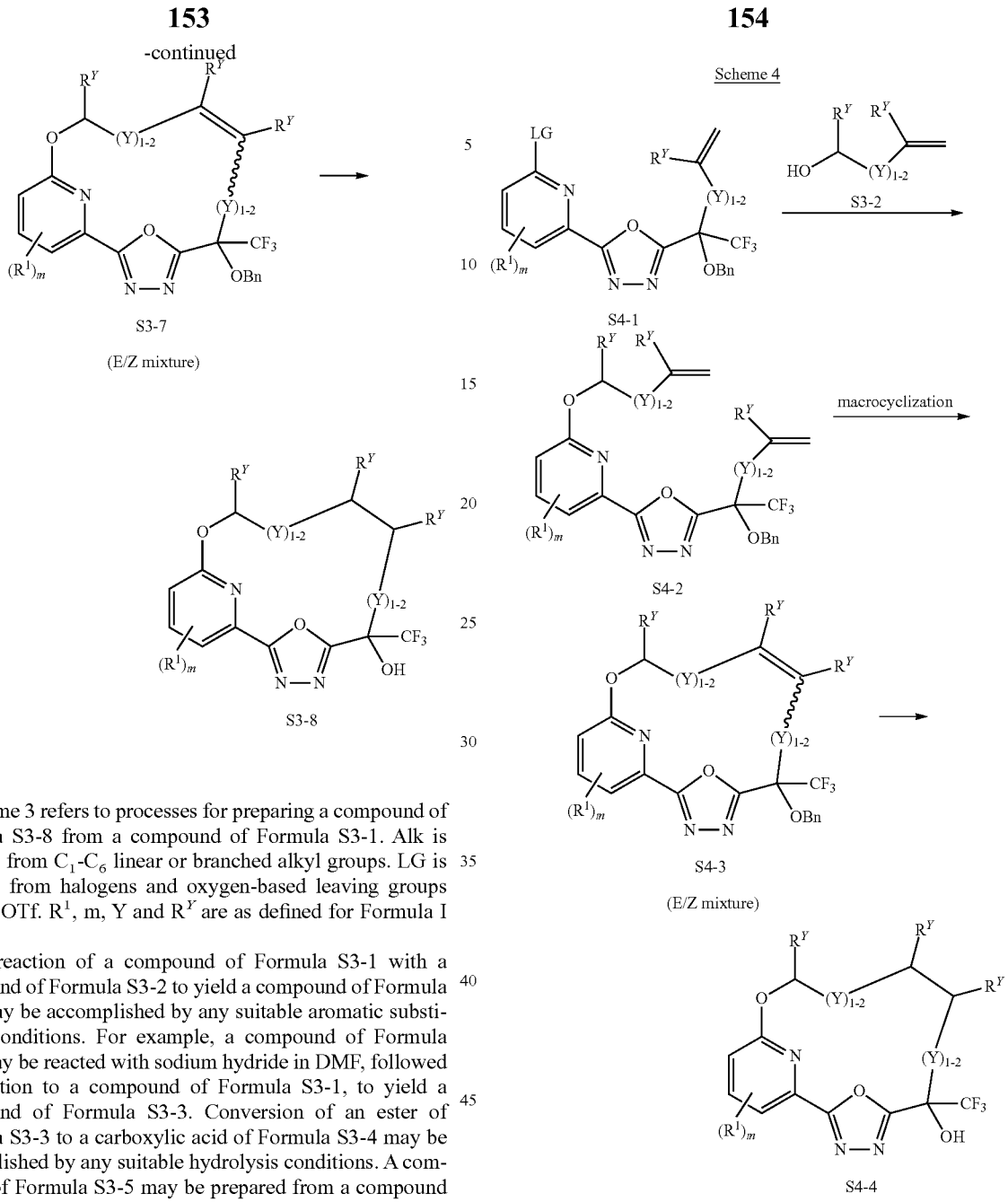

Scheme 3 refers to processes for preparing a compound of Formula S3-8 from a compound of Formula S3-1. Alk is selected from $C_1$-$C_6$ linear or branched alkyl groups. LG is selected from halogens and oxygen-based leaving groups such as OTf. $R^1$, m, Y and $R^Y$ are as defined for Formula I above.

The reaction of a compound of Formula S3-1 with a compound of Formula S3-2 to yield a compound of Formula S3-3 may be accomplished by any suitable aromatic substitution conditions. For example, a compound of Formula S3-2 may be reacted with sodium hydride in DMF, followed by addition to a compound of Formula S3-1, to yield a compound of Formula S3-3. Conversion of an ester of Formula S3-3 to a carboxylic acid of Formula S3-4 may be accomplished by any suitable hydrolysis conditions. A compound of Formula S3-5 may be prepared from a compound of Formula S3-4 and a compound of Formula S1-7 using any suitable amide bond formation conditions. A compound of Formula S3-5 can be converted to a compound of Formula S3-6 using any conditions suitable for oxadiazole formation. For example, a compound of Formula S3-5 can be reacted with methoxycarbonyl-(triethylammonio)sulfonyl-azanide in THF to yield an oxadiazole of Formula S3-6. Macrocyclization of a compound of Formula S3-6 may be accomplished by any suitable ring-closing metathesis conditions. For example, a compound of Formula S3-6 may be reacted in the presence of [1,3-bis(2,4,6-trimethylphenyl)imidazolidin-2-ylidene]-dichloro-[(2-isopropoxy-5-nitro-phenyl)methylene]ruthenium in DCE to yield a macrocycle of Formula S3-7 as a mixture of E/Z isomers (as denoted by the ⁓ bond). Conversion of an unsaturated compound of Formula S3-7 to a macrocycle of Formula S3-8 can be accomplished using any suitable procedure for olefin reduction and benzyl deprotection.

Scheme 4 refers to processes for preparing a compound of Formula S4-4 from a compound of Formula S4-1. LG is selected from halogens, hydroxy, and oxygen-based leaving groups such as OTf. $R^1$, m, Y and $R^Y$ are as defined for Formula I above.

The reaction of a compound of Formula S4-1 with a compound of Formula S3-2 to yield a compound of Formula S4-2 may be accomplished by any suitable aromatic substitution conditions or Mitsunobu conditions. For example, a compound of Formula S4-1 may be reacted an alcohol of Formula S3-2 with cesium carbonate and iodocopper in DMSO. Macrocyclization of a compound of Formula S4-2 may be accomplished by any suitable ring-closing metathesis conditions. For example, a compound of Formula S4-2 may be reacted in the presence of Grubbs $2^{nd}$ generation catalyst in DCE to yield a macrocycle of Formula S4-3 as a mixture of E/Z isomers (as denoted by the ⁓ bond).

Conversion of an unsaturated compound of Formula S4-3 to a macrocycle of Formula S4-4 can be accomplished using any suitable procedure for olefin reduction and benzyl deprotection.

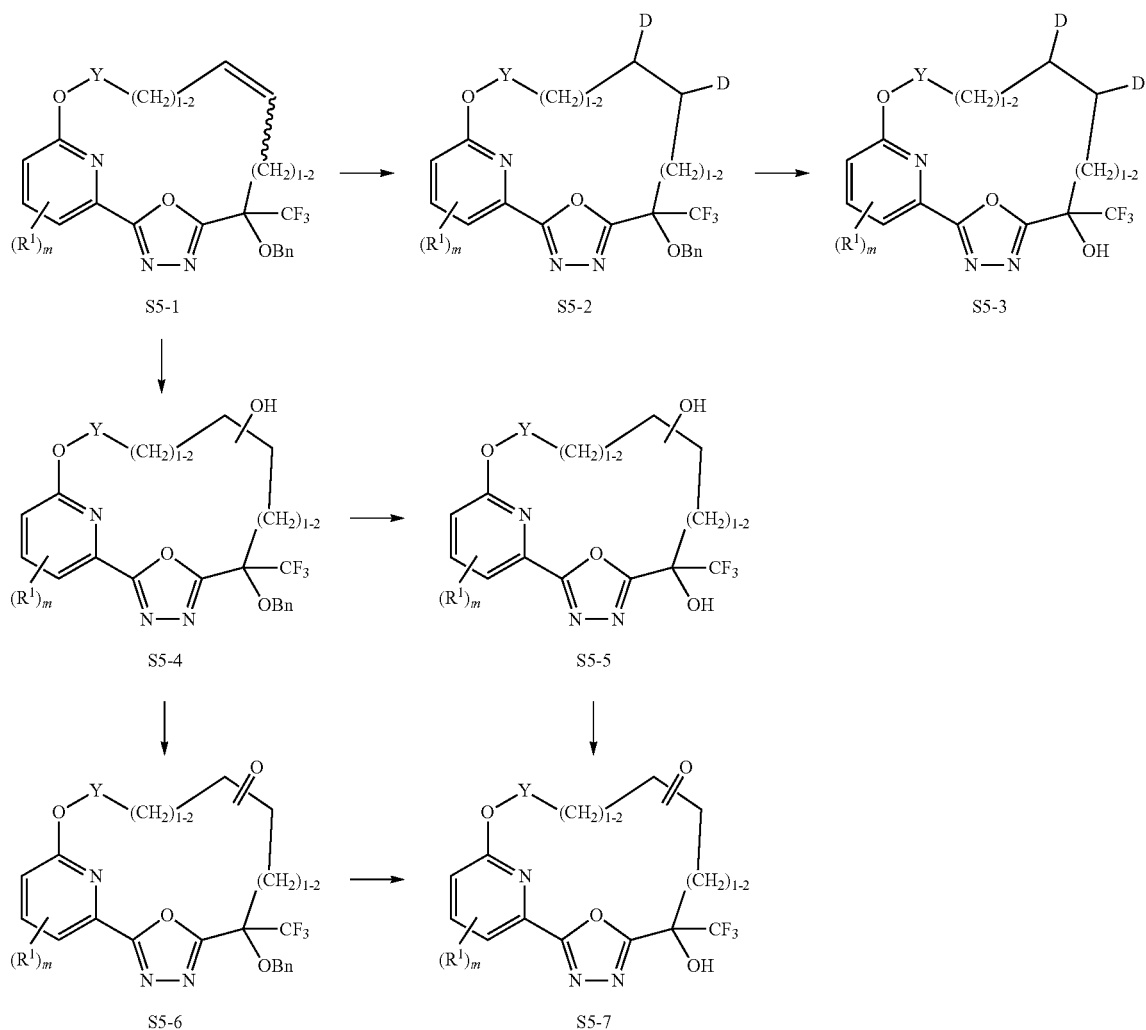

Scheme 5

Scheme 5 refers to processes for preparing a compound of Formula S5-3, a compound of Formula S5-6, and a compound of Formula S5-7 from a compound of Formula S5-1. $R^1$, m, and Y are as defined for Formula I above.

The conversion of a compound of Formula S5-1 to a deuterated compound of Formula S5-2 may be accomplished by any suitable catalytic deuteration conditions. For example, a compound of Formula S5-1 may be reacted with 10% palladium on carbon in $CD_3OD$ under a deuterium gas atmosphere to yield a compound of Formula S5-2. Conversion of a benzyl-protected compound of Formula S5-2 to a free alcohol of Formula S5-3 may be accomplished by any suitable deprotection conditions.

Conversion of an unsaturated compound of Formula S5-1 to an alcohol of Formula S5-4 may be accomplished by any suitable hydroboration/oxidation conditions. For example, a compound of Formula S5-1 may be reacted with borane dimethylsulfide complex in THF, followed by quenching with aqueous NaOH and a subsequent addition of hydrogen peroxide to yield an alcohol of Formula S5-4 as a mixture of regioisomers. Debenzylation of a compound of Formula S5-4 to yield a compound of Formula S5-5 may be accomplished using any suitable benzyl deprotection conditions. Conversion of a compound of Formula S5-5 to a compound Formula S5-7 may be accomplished by any suitable oxidation conditions. For example, a compound of Formula S5-5 may be reacted with $NaHCO_3$ and Dess-Martin periodinane in $CH_2Cl_2$ to yield a compound of Formula S5-7.

In an alternative route, conversion of a compound of Formula S5-4 to a compound of Formula S5-6 may be accomplished by any suitable oxidation conditions. For example, a compound of Formula S5-4 may be reacted with Dess-Martin periodinane in $CH_2Cl_2$ to yield a compound of Formula S5-6. Debenzylation of a compound of Formula S5-6 to yield a compound of Formula S5-7 may be accomplished using any suitable benzyl deprotection conditions.

Scheme 6

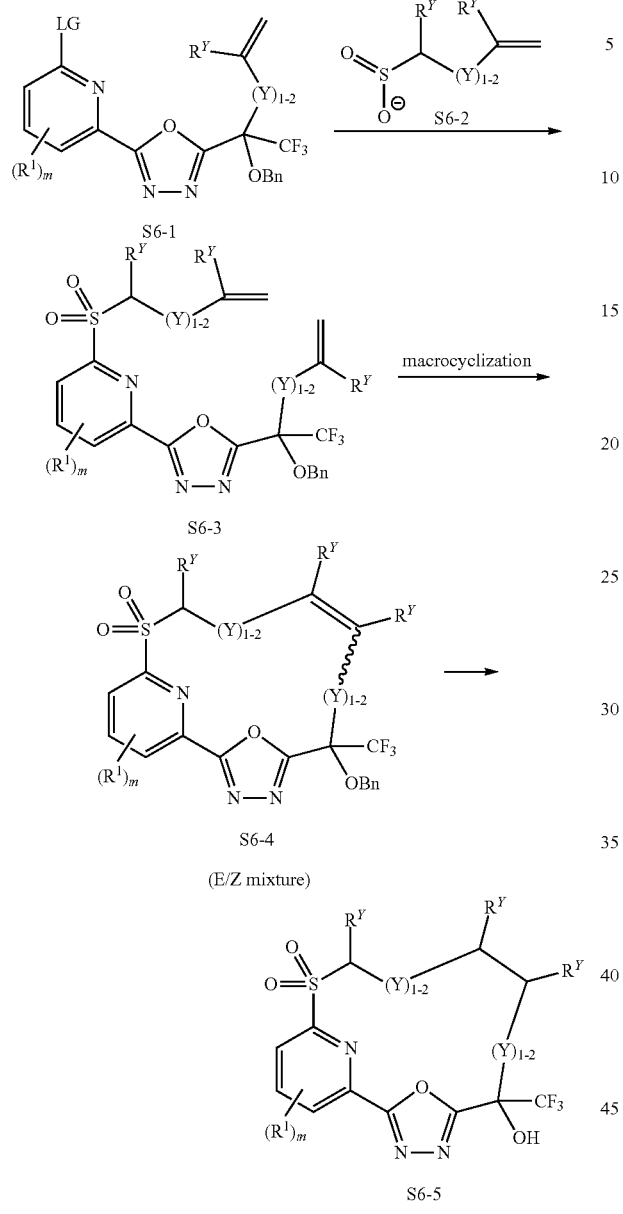

Scheme 6 refers to processes for preparing a compound of Formula S6-5 from a compound of Formula S6-1. LG is selected from halogens and oxygen-based leaving groups such as OTf. $R^1$, m, Y, and $R^Y$ are as defined for Formula I above.

The conversion of a compound of Formula S6-1 and a compound of Formula S6-2 to a compound of Formula S6-3 may be accomplished by any suitable aromatic substitution conditions. For example, a compound of Formula S6-1 may be reacted with a compound of Formula S6-2 and DMSO. Macrocyclization of a compound of Formula S6-3 may be accomplished by any suitable ring-closing metathesis conditions. For example, a compound of Formula S6-3 may be reacted in the presence of benzylidene-[1,3-bis(2,4,6-trimethylphenyl)imidazolidin-2-ylidene]-dichloro-ruthenium; tricyclohexylphosphane in DCE to yield a macrocycle of Formula S6-4 as a mixture of E/Z isomers (as denoted by the bond). Conversion of an unsaturated compound of Formula S6-4 to a macrocycle of Formula S6-5 can be accomplished using any suitable procedure for olefin reduction and benzyl deprotection.

Scheme 7

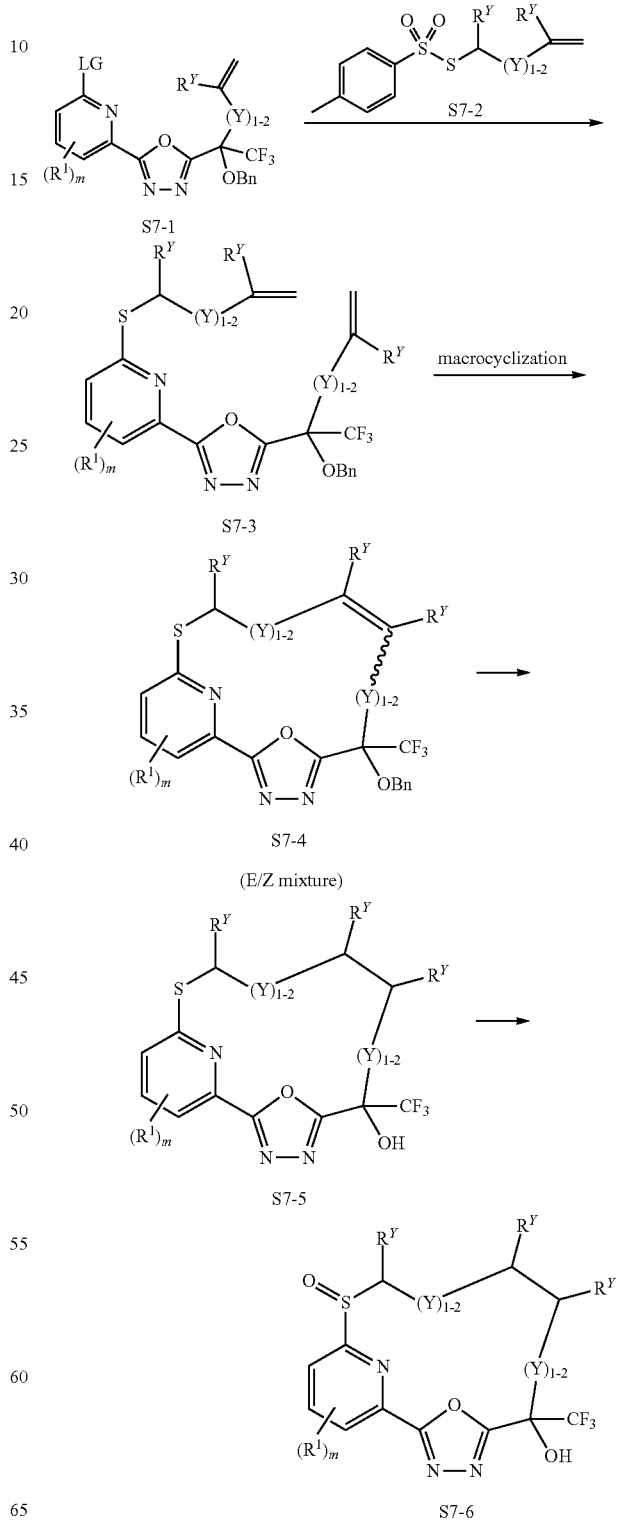

Scheme 7 refers to processes for preparation of a compound of Formula S7-6 from a compound of Formula S7-1. $R^1$, m, Y, and $R^Y$ are as defined for Formula I above. LG is selected from halogens and oxygen-based leaving groups such as OTf.

Reaction of a compound of Formula S7-1 with a compound of Formula S7-2 to form a compound of Formula S7-3 can be accomplished by any suitable lithiation procedure. For example, the reaction of a compound of Formula S7-1 with a compound of Formula S7-2 may be performed in ether at −78° C. with n-BuLi to form a compound of Formula S7-3. Conversion of a compound of Formula S7-3 to a compound of Formula S7-4 may be accomplished by any suitable ring-closing metathesis procedure. For example, the ring-closing metathesis reaction of the compound of Formula S7-3 may be accomplished in the presence of benzylidene-[1,3-bis(2,4,6-trimethylphenyl)imidazolidin-2-ylidene]-dichloro-ruthenium; tricyclohexylphosphane in DCE to yield a compound of Formula S7-4 as a mixture of E/Z isomers (as denoted by the $\sim$ bond). Conversion of a compound of Formula S7-4 to a compound of Formula S7-5 may be accomplished by any suitable procedure for olefin reduction and benzyl deprotection. Conversion of a compound of Formula S7-5 to a compound of Formula S7-6 may be accomplished by any suitable procedure for oxidizing a thioether to a sulfoxide.

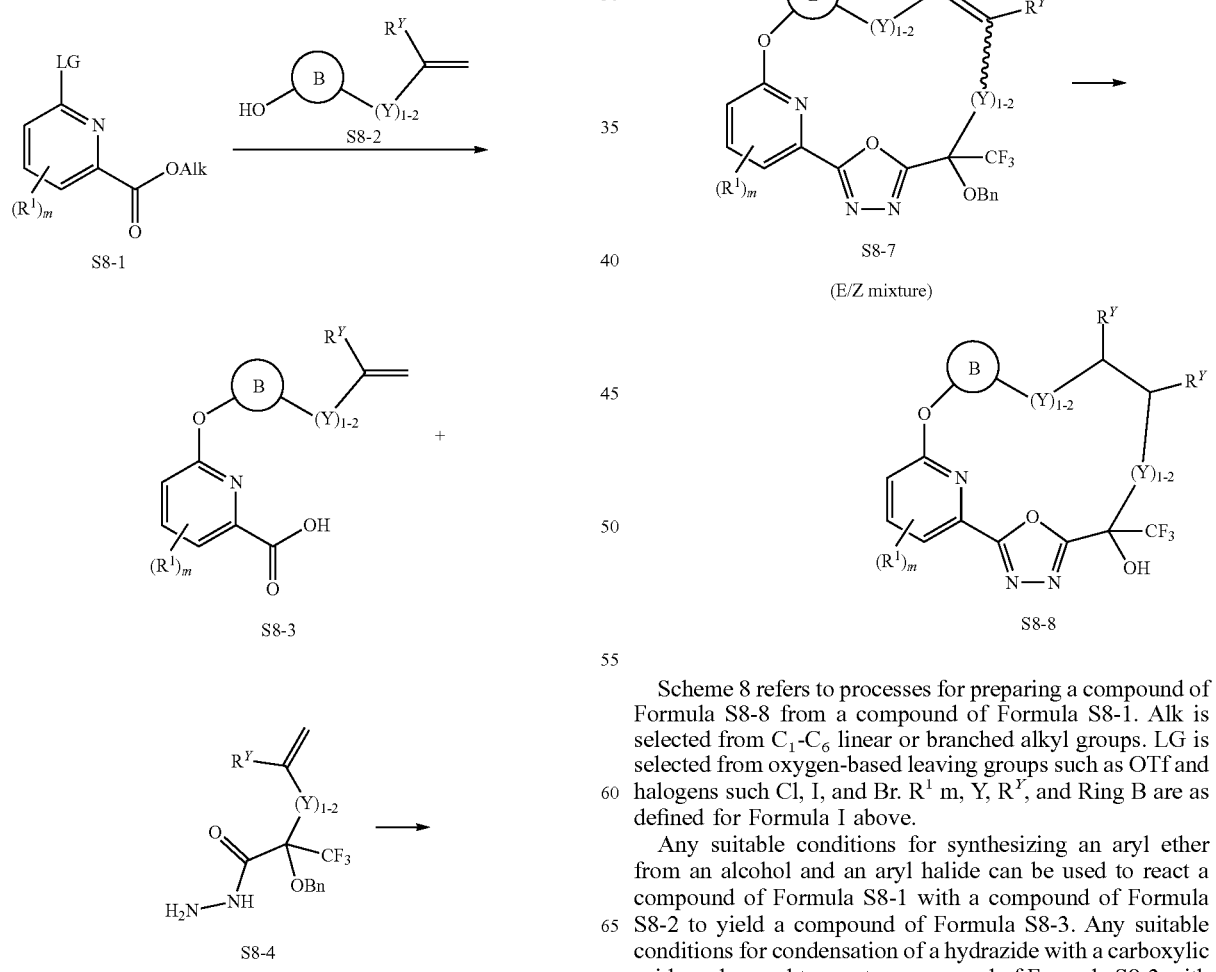

Scheme 8 refers to processes for preparing a compound of Formula S8-8 from a compound of Formula S8-1. Alk is selected from $C_1$-$C_6$ linear or branched alkyl groups. LG is selected from oxygen-based leaving groups such as OTf and halogens such Cl, I, and Br. $R^1$ m, Y, $R^Y$, and Ring B are as defined for Formula I above.

Any suitable conditions for synthesizing an aryl ether from an alcohol and an aryl halide can be used to react a compound of Formula S8-1 with a compound of Formula S8-2 to yield a compound of Formula S8-3. Any suitable conditions for condensation of a hydrazide with a carboxylic acid can be used to react a compound of Formula S8-3 with a compound of Formula S8-4 to form a compound of Formula S8-5. Any suitable conditions for oxadiazole formation from a hydrazide can be used to convert a compound of Formula S8-5 to a compound of Formula S8-6. Conversion of a compound of Formula S8-6 to a compound of Formula S8-7 may be accomplished by any suitable ring-closing metathesis procedure. For example, the ring-closing metathesis reaction of the compound of Formula S8-6 may be accomplished in the presence of benzylidene-[1,3-bis(2,4,6-trimethylphenyl)imidazolidin-2-ylidene]-dichloro-ruthenium;tricyclohexylphosphane in DCE to yield a compound of Formula S8-7 as a mixture of E/Z isomers (as denoted by the ⌇ bond). Conversion of a compound of Formula S8-7 to a compound of Formula S8-8 may be accomplished by any suitable procedure for olefin reduction and benzyl deprotection.

based leaving groups such as OTf and halogens such Cl, I, and Br. $L^x$ is selected from halogens such as Cl, I, or Br.

Any suitable conditions for synthesizing an aryl ether from an alcohol and an aryl halide can be used to react a compound of Formula S9-1 with a compound of Formula S9-2 to form a compound of Formula S9-3. Conversion of a compound of Formula S9-3 to a compound of Formula S9-4 and/or a compound of Formula S9-5 may be accomplished by any suitable cross-coupling procedure. For example, the macrocyclization reaction of the compound of Formula S9-3 may be accomplished in the presence of palladium (II) acetate, tris-o-tolylphosphane, and triethylamine in acetonitrile to yield the compound of Formula S9-4 and/or the compound of Formula S9-5. Conversion of a compound of Formula S9-4 to a compound of Formula S9-6 and conversion of a compound of Formula S9-5 to a compound of Formula S9-7 may be accomplished by any suitable procedure olefin reduction and benzyl deprotection.

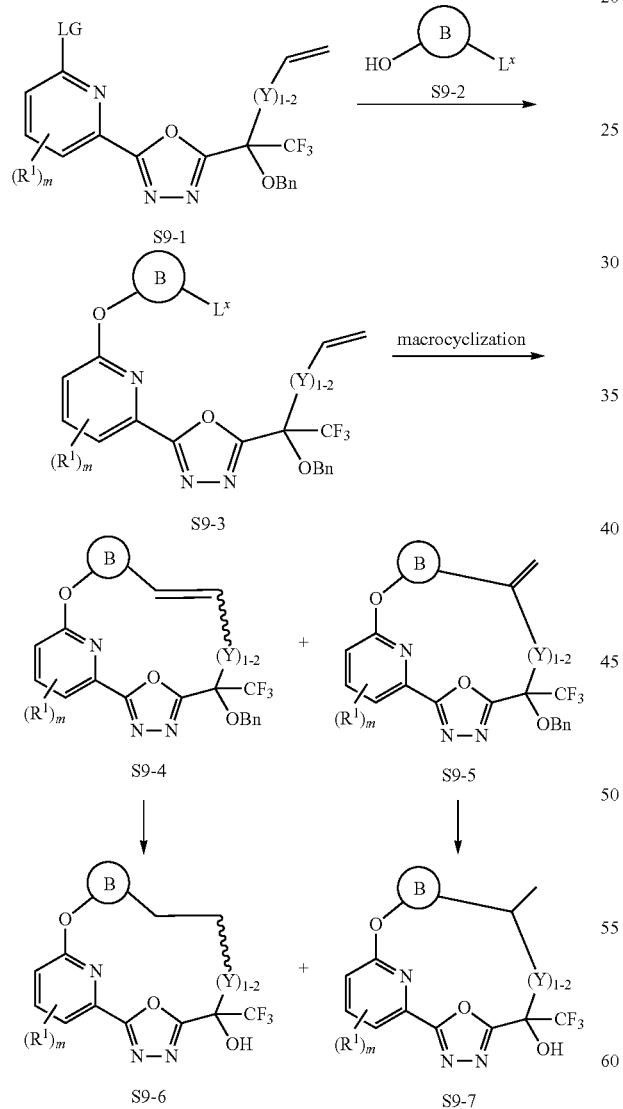

Scheme 9

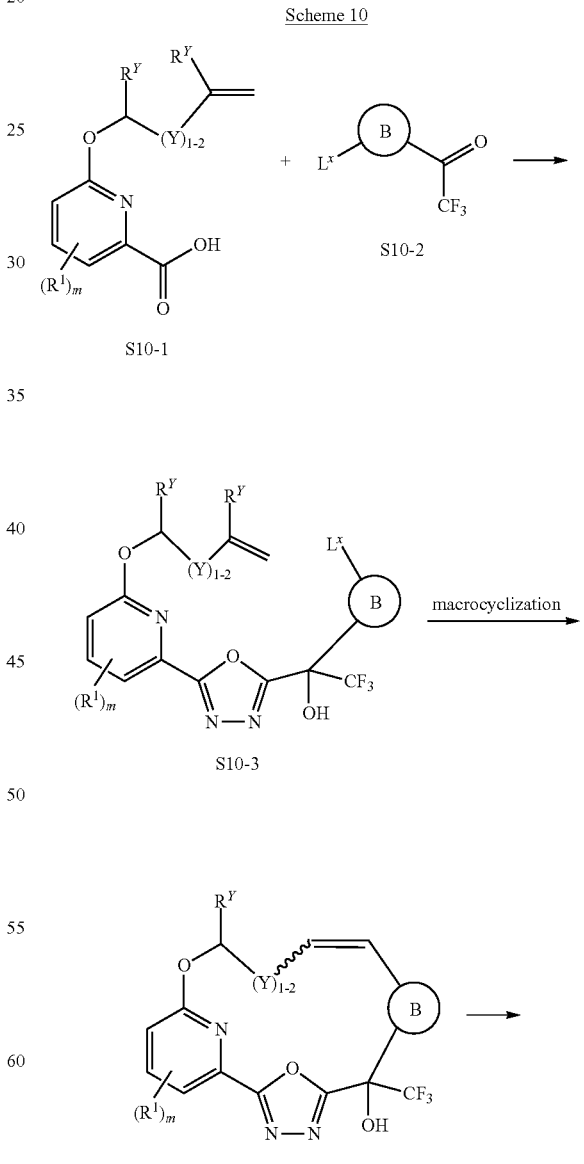

Scheme 10

Scheme 9 refers to processes for preparing a compound of Formula S9-6 and a compound of Formula S9-7 from a compound of Formula S9-1. $R^1$, m, Y, $R^Y$, and Ring B are as defined for Formula I above. LG is selected from oxygen-

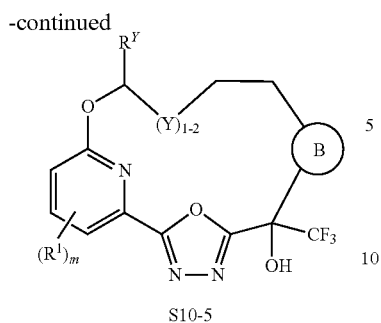

S10-5

Scheme 10 refers to processes for preparing a compound of Formula S10-6 from a compound of Formula S10-1. $R^1$, m, Y, $R^Y$, and Ring B are as defined for Formula I above. $L^x$ is selected from halogens such as Cl, I, or Br.

Reaction of a compound of Formula S10-1 with a compound of Formula S10-2 to yield a compound of Formula S10-3 may be accomplished using any suitable oxadiazole formation procedure. For example, a compound of Formula S10-1 may be reacted with a compound of Formula S10-2 and (isocyanoimino)triphenylphosphorane to yield a compound of Formula S10-3. Conversion of a compound of Formula S10-3 to a compound of Formula S10-4 may be accomplished by any suitable cross-coupling procedure. For example, the macrocyclization reaction of the compound of Formula S10-3 may be accomplished in the presence of palladium (II) acetate, tris-o-tolylphosphane, and triethylamine in acetonitrile to yield a compound of Formula S10-4 as a mixture of E/Z isomers (as denoted by the ∼ bond). Conversion of a compound of Formula S10-4 to a compound of Formula S10-5 may be accomplished by any suitable procedure for reducing olefins.

Procedures for the Synthesis of Common Intermediates

Intermediate 1: Preparation of Methyl 6-chloro-3-nitro-5-(trifluoromethyl)pyridine-2-carboxylate

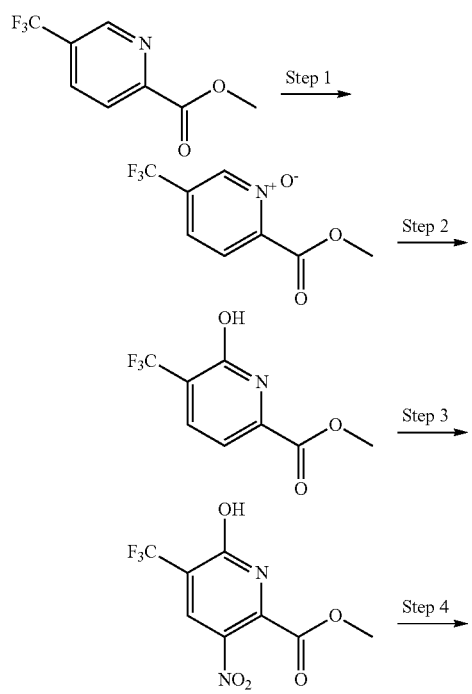

Step 1: Methyl 1-oxido-5-(trifluoromethyl)pyridin-1-ium-2-carboxylate

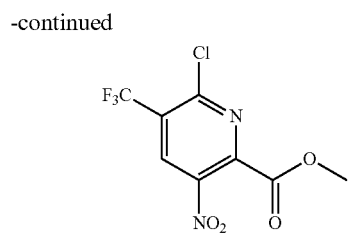

Urea hydrogen peroxide (62.7 g, 646.53 mmol) was added portion-wise to a stirred solution of methyl 5-(trifluoromethyl)pyridine-2-carboxylate (40 g, 191.09 mmol) in 1,2-dichloroethane (300 mL) at 0° C. Trifluoroacetic anhydride (107.70 g, 72 mL, 507.65 mmol) was then added over 30 minutes at a temperature of −10° C., with cooling bath ($CO_2$/acetone bath). The reaction mixture was then stirred for a further 30 minutes at a temperature of 0° C. and then for 1 hour at ambient temperature. The reaction mixture was then poured into cooled ice-water (600 mL). The mixture was diluted with dichloromethane (300 mL) and then layers were separated. The aqueous phase was extracted with dichloromethane (2×200 mL). The combined organic phase was washed with water (2×300 mL) and brine (1×200 mL), dried over anhydrous sodium sulfate, filtered and concentrated under reduced pressure to give methyl 1-oxido-5-(trifluoromethyl)pyridin-1-ium-2-carboxylate (47.6 g, 90%) as light yellow solid. $^1$H NMR (300 MHz, DMSO-$d_6$) δ 8.89 (s, 1H), 8.02-7.90 (m, 1H), 7.86-7.72 (m, 1H), 3.89 (s, 3H) ppm. $^{19}$F NMR (282 MHz, DMSO-$d_6$) δ −62.00 (s, 3F) ppm. ESI-MS m/z calc. 221.02998, found 222.1 (M+1)⁺; Retention time: 1.24 minutes. LCMS Method: Kinetex Polar $C_{18}$ 3.0×50 mm 2.6 μm, 3 min, 5-95% acetonitrile in $H_2O$ (0.1% formic acid) 1.2 mL/min.

Step 2: Methyl 6-hydroxy-5-(trifluoromethyl)pyridine-2-carboxylate

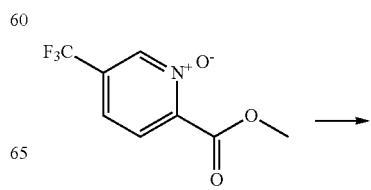

-continued

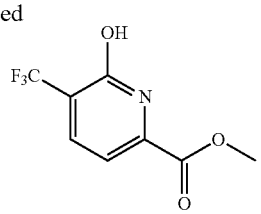

Trifluoroacetic anhydride (291.62 g, 193 mL, 1.3885 mol) was added drop-wise to a mixture of methyl 1-oxido-5-(trifluoromethyl)pyridin-1-ium-2-carboxylate (51.058 g, 230.66 mmol) in DMF (305 mL) at 0° C. The mixture was then stirred at room temperature overnight. The mixture was concentrated under reduced pressure to remove excess of trifluoroacetic acid. The residual DMF solution was poured dropwise to a 0° C. cooled and stirring water volume (1000 mL). The precipitated solid was collected by filtration and then washed with water (300 mL). The solid was dried over high vacuum to afford methyl 6-hydroxy-5-(trifluoromethyl)pyridine-2-carboxylate (45.24 g, 86%) as white solid. $^1$H NMR (300 MHz, DMSO-$d_6$) δ 7.90 (d, J=7.2 Hz, 1H), 7.03 (d, J=7.2 Hz, 1H), 4.02 (s, 3H) ppm. $^{19}$F NMR (282 MHz, DMSO-$d_6$) δ −66.39 (s, 3F) ppm. ESI-MS m/z calc. 221.03, found 222.1 (M+1)$^+$; Retention time: 1.43 minutes. LCMS Method: Kinetex Polar $C_{18}$ 3.0×50 mm 2.6 µm, 3 min, 5-95% acetonitrile in $H_2O$ (0.1% formic acid) 1.2 mL/min.

Step 3: Methyl 6-hydroxy-3-nitro-5-(trifluoromethyl)pyridine-2-carboxylate

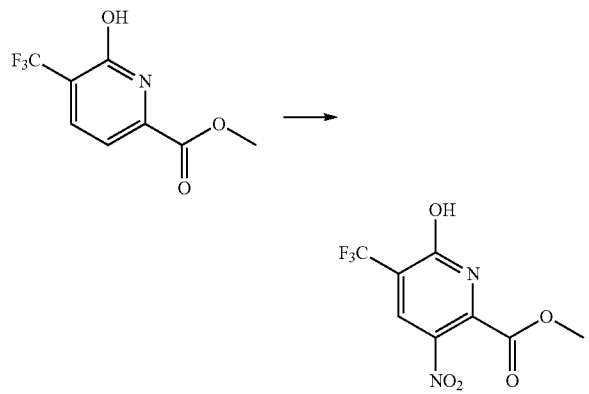

To an ice-cooled solution of methyl 6-hydroxy-5-(trifluoromethyl)pyridine-2-carboxylate (33.04 g, 149.41 mmol) in sulfuric acid (200 mL of 18.4 M, 3.6800 mol) was added nitric acid (13 mL of 15.8 M, 205.40 mmol) dropwise. After 5 min, the ice bath was removed, and the reaction mixture was stirred at 38° C. overnight. The reaction was not completed, nitric acid (3 mL of 15.8 M, 47.400 mmol) was added dropwise at room temperature and the reaction was heated at 38° C. for 4.5 hours. The reaction was poured slowly into ice-cold water (900 mL) and the mixture was cooled at 0° C. for 15 minutes. Then the resultant solid was isolated by filtration and washed with water (600 mL). The solid was dried overnight under high vacuum to give methyl 6-hydroxy-3-nitro-5-(trifluoromethyl)pyridine-2-carboxylate (39.49 g, 99%) as white solid. $^1$H NMR (300 MHz, DMSO-$d_6$) δ 8.54 (s, 1H), 3.95 (s, 3H) ppm. $^{19}$F NMR (282 MHz, DMSO-$d_6$) δ −64.56 (s, 3F) ppm. ESI-MS m/z calc. 266.0151, found 267.1 (M+1)$^+$; Retention time: 1.64 minutes. LCMS Method: Kinetex Polar $C_{18}$ 3.0×50 mm 2.6 µm, 3 min, 5-95% acetonitrile in $H_2O$ (0.1% formic acid) 1.2 mL/min.

Step 4: Methyl 6-chloro-3-nitro-5-(trifluoromethyl)pyridine-2-carboxylate

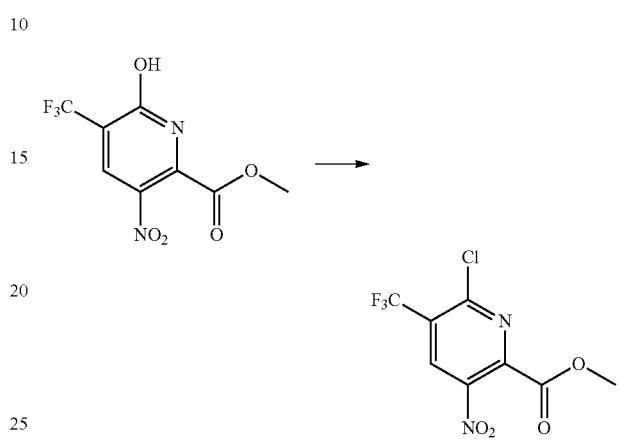

A mixture of methyl 6-hydroxy-3-nitro-5-(trifluoromethyl)pyridine-2-carboxylate (10 g, 37.575 mmol) and phenyl dichlorophosphate (48.008 g, 34 mL, 227.55 mmol) was heated at 170° C. for 90 minutes. After cooling to room temperature, the mixture was diluted with ethyl acetate (400 mL) and washed with brine (2×200 mL). The organic phase was dried on anhydrous sodium sulfate, filtered and concentrated under reduced pressure. Purification by silica gel chromatography (0% to 15% of ethyl acetate in heptanes) provided methyl 6-chloro-3-nitro-5-(trifluoromethyl)pyridine-2-carboxylate (5.45 g, 50%) as a yellow solid. $^1$H NMR (300 MHz, CDCl$_3$) δ 8.75 (s, 1H), 4.07 (s, 3H) ppm. $^{19}$F NMR (282 MHz, CDCl$_3$) δ −64.12 (s, 3F) ppm. ESI-MS m/z calc. 283.9812, found 285.0 (M+1)$^+$; Retention time: 1.95 minutes. LCMS Method: Kinetex Polar $C_{18}$ 3.0×50 mm 2.6 µm, 3 min, 5-95% acetonitrile in $H_2O$ (0.1% formic acid) 1.2 mL/min.

Intermediate 2: Preparation of 6-hydroxy-3-nitro-5-(trifluoromethyl)pyridine-2-carboxylic acid

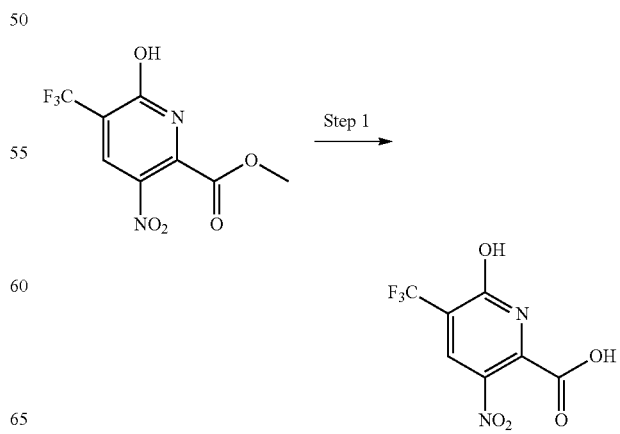

Step 1: 6-Hydroxy-3-nitro-5-(trifluoromethyl)pyridine-2-carboxylic acid

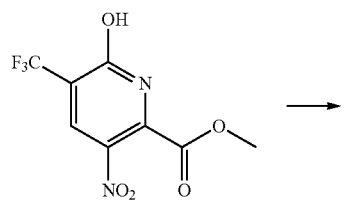

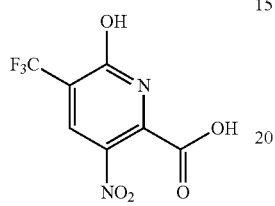

A mixture of methyl 6-hydroxy-3-nitro-5-(trifluoromethyl)pyridine-2-carboxylate (32 g, 120.24 mmol) in THF (180 mL) and water (180 mL) was treated with lithium hydroxide monohydrate (15.14 g, 360.79 mmol) and stirred at 27° C. overnight. The crude reaction mixture was cooled at room temperature and the pH adjusted to 2 with a 0.5 M aqueous solution of hydrochloric acid (380 mL), then transferred to a 1-L separatory funnel with 2-methyl THF and extracted. The layers were separated and the organic layer was then washed with water (150 mL), brine (150 mL), dried over sodium sulfate, filtered and concentrated under reduced pressure to afford 6-hydroxy-3-nitro-5-(trifluoromethyl)pyridine-2-carboxylic acid (29.61 g, 96%) as off-white solid. $^1$H NMR (300 MHz, DMSO-$d_6$) δ 8.45 (s, 1H) ppm. $^{19}$F NMR (282 MHz, DMSO-$d_6$) δ −64.53 (s, 3F) ppm. ESI-MS m/z calc. 251.9994, found 253.0 (M+1)$^+$; Retention time: 0.79 minutes. LCMS Method: Kinetex Polar $C_{18}$ 3.0×50 mm 2.6 μm, 3 min, 5-95% acetonitrile in $H_2O$ (0.1% formic acid) 1.2 mL/min.

Intermediate 3: Preparation of 6-chloro-3-nitro-5-(trifluoromethyl)pyridine-2-carboxylic acid

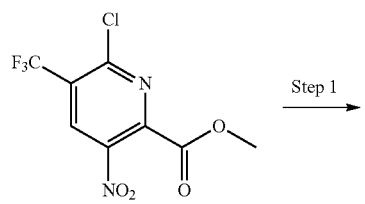

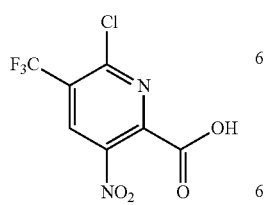

Step 1: 6-Chloro-3-nitro-5-(trifluoromethyl)pyridine-2-carboxylic acid

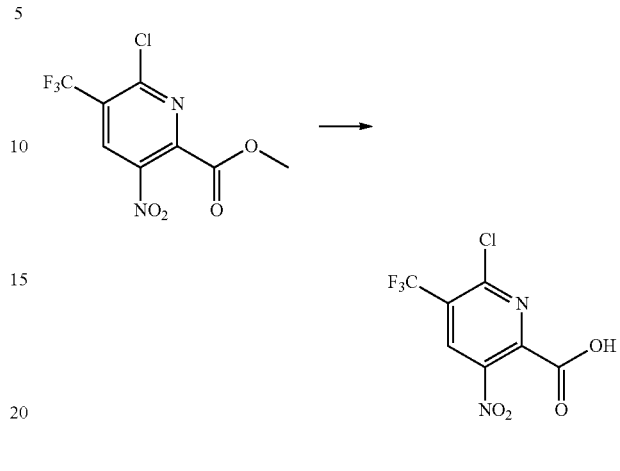

To a solution of methyl 6-chloro-3-nitro-5-(trifluoromethyl)pyridine-2-carboxylate (1.14 g, 4.006 mmol) in THF (48.51 mL) and water (24.26 mL) at 0° C. was added lithium hydroxide monohydrate (201.7 mg, 4.807 mmol). The reaction was allowed to warm to room temperature then stirred for 2 hours. The solution was acidified to pH ~2-3 by the addition of 1 N HCl, then extracted with EtOAc. The organic phase was washed with water and brine, then dried over sodium sulfate, filtered and concentrated to afford, as a clear syrup, 6-chloro-3-nitro-5-(trifluoromethyl)pyridine-2-carboxylic acid (1.05 g, 97%). ESI-MS m/z calc. 269.9655, found 271.0 (M+1)$^+$; Retention time: 0.37 minutes determined by reversed phase UPLC using an Acquity UPLC BEH $C_{18}$ column (30×2.1 mm, 1.7 μm particle) made by Waters (pn: 186002349), and a dual gradient run from 1-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

Intermediate 4: Preparation of methyl 3-[bis(tert-butoxycarbonyl)amino]-6-bromo-5-(trifluoromethyppyridine-2-carboxylate

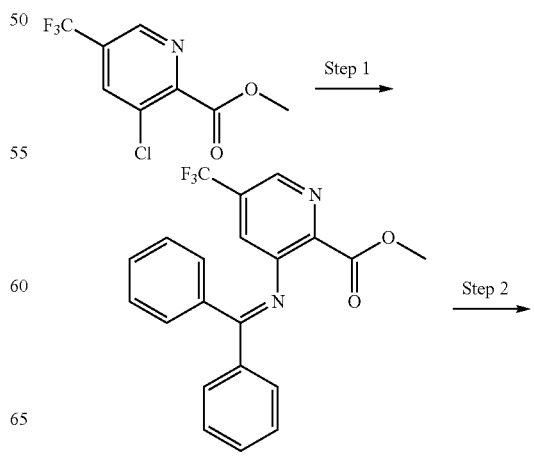

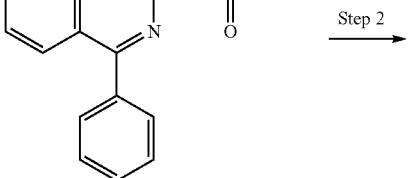

-continued

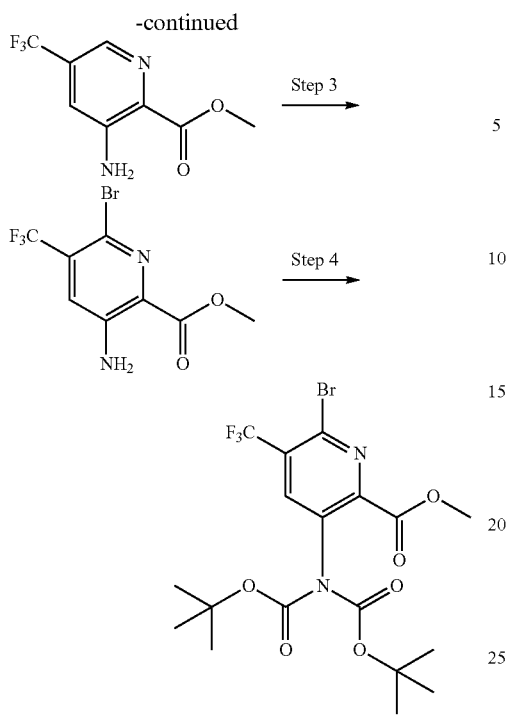

Step 1: Methyl 3-(benzhydrylideneamino)-5-(trifluoromethyl)pyridine-2-carboxylate

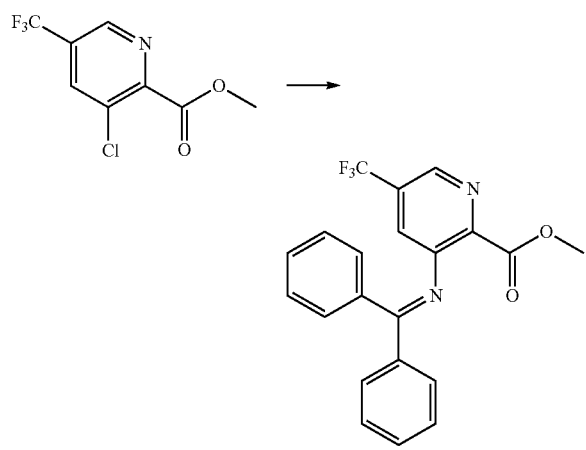

A mixture of methyl 3-chloro-5-(trifluoromethyl)pyridine-2-carboxylate (47.3 g, 197.43 mmol), diphenylmethanimine (47 g, 259.33 mmol), Xantphos (9.07 g, 15.675 mmol), and cesium carbonate (131 g, 402.06 mmol) in dioxane (800 mL) was degassed with bubbling nitrogen for 30 minutes. Pd(OAc)₂ (3.52 g, 15.679 mmol) was added and the system was purged with nitrogen three times. The reaction mixture was heated at 100° C. for 18 h. The reaction was cooled to room temperature and filtered on a pad of Celite. The cake was washed with EtOAc and solvents were evaporated under reduced pressure to give methyl 3-(benzhydrylideneamino)-5-(trifluoromethyl)pyridine-2-carboxylate (90 g, 84%) as yellow solid. ESI-MS m/z calc. 384.10855, found 385.1 (M+1)⁺; Retention time: 2.24 minutes. LCMS Method: Kinetex C₁₈ 4.6×50 mm 2.6 µM, 2.0 mL/min, 95% H₂O (0.1% formic acid)+5% acetonitrile (0.1% formic acid) to 95% acetonitrile (0.1% formic acid) gradient (2.0 min) then held at 95% acetonitrile (0.1% formic acid) for 1.0 min.

Step 2: Methyl 3-amino-5-(trifluoromethyl)pyridine-2-carboxylate

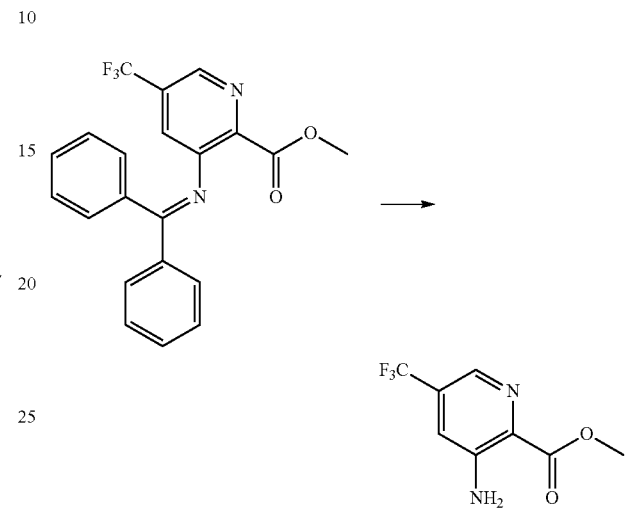

To a suspension of methyl 3-(benzhydrylideneamino)-5-(trifluoromethyl)pyridine-2-carboxylate (65 g, 124.30 mmol) in methanol (200 mL) was added HCl (3 M in methanol) (146 mL of 3 M, 438.00 mmol). The mixture was stirred at room temperature for 1.5 hour then the solvent was removed under reduced pressure. The residue was taken up in ethyl acetate (2 L) and dichloromethane (500 mL). The organic phase was washed with 5% aqueous sodium bicarbonate solution (3×500 mL) and brine (2×500 mL), dried over anhydrous sodium sulfate, filtered and the solvent was removed under reduced pressure. The residue was triturated with heptanes (2×50 mL) and the mother liquors were discarded. The solid obtained was triturated with a mixture of dichloromethane and heptanes (1:1, 40 mL) and filtered to afford methyl 3-amino-5-(trifluoromethyl)pyridine-2-carboxylate (25.25 g, 91%) as yellow solid. ¹H NMR (300 MHz, CDCl₃) δ 8.24 (s, 1H), 7.28 (s, 1H), 5.98 (br. s, 2H), 4.00 (s, 3H) ppm. ¹⁹F NMR (282 MHz, CDCl₃) δ −63.23 (s, 3F) ppm. ESI-MS m/z calc. 220.046, found 221.1 (M+1)⁺; Retention time: 1.62 minutes. LCMS Method: Kinetex Polar C₁₈ 3.0×50 mm 2.6 µm, 3 min, 5-95% acetonitrile in H₂O (0.1% formic acid) 1.2 mL/min.

Step 3: Methyl 3-amino-6-bromo-5-(trifluoromethyl)pyridine-2-carboxylate

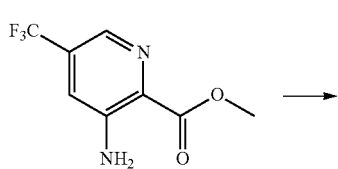

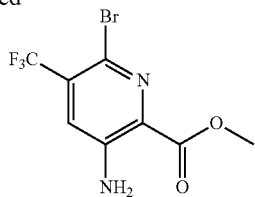

To a solution of methyl 3-amino-5-(trifluoromethyl)pyridine-2-carboxylate (18.75 g, 80.91 mmol) in acetonitrile (300 mL) at 0° C. was added portion wise N-bromosuccinimide (18.7 g, 105.3 mmol). The mixture was stirred overnight at 25° C. Ethyl acetate (1000 mL) was added. The organic layer was washed with 10% sodium thiosulfate solution (3×200 mL) which were back extracted with ethyl acetate (2×200 mL). The combined organic extracts were washed with saturated sodium bicarbonate solution (3×200 mL), brine (200 mL), dried over sodium sulfate and concentrated in vacuo to provide methyl 3-amino-6-bromo-5-(trifluoromethyl)pyridine-2-carboxylate (25.46 g, 98%). $^1$1-INMR (300 MHz, CDCl$_3$) δ 3.93-4.03 (m, 3H), 6.01 (br. s., 2H), 7.37 (s, 1H) ppm. $^{19}$F NMR (282 MHz, CDCl$_3$) ppm −64.2 (s, 3F). ESI-MS m/z calc. 297.9565, found 299.0 (M+1)$^+$; Retention time: 2.55 minutes. LCMS Method: Kinetex C$_{18}$ 4.6×50 mm 2.6 μM. Temp: 45° C., Flow: 2.0 mL/min, Run Time: 6 min. Mobile Phase: Initial 95% H$_2$O (0.1% formic acid) and 5% acetonitrile (0.1% formic acid) linear gradient to 95% acetonitrile (0.1% formic acid) for 4.0 min then held at 95% acetonitrile (0.1% formic acid) for 2.0 min.

Step 4: Methyl 3-[bis(tert-butoxycarbonyl)amino]-6-bromo-5-(trifluoromethyppyridine-2-carboxylate

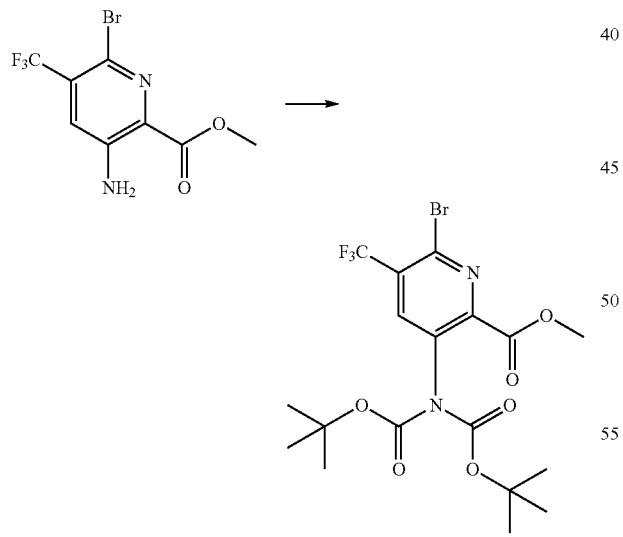

A mixture of methyl 3-amino-6-bromo-5-(trifluoromethyl)pyridine-2-carboxylate (5 g, 15.549 mmol), (Boc)$_2$O (11 g, 11.579 mL, 50.402 mmol), DMAP (310 mg, 2.5375 mmol) and CH$_2$Cl$_2$ (150 mL) was stirred at room temperature overnight. The reaction mixture was concentrated under reduced pressure and purification by silica gel chromatography (0-15% ethyl acetate in heptane) provided methyl 3-[bis(tert-butoxycarbonyl)amino]-6-bromo-5-(trifluoromethyl)pyridine-2-carboxylate (6.73 g, 87%) as light yellow solid. $^1$H NMR (300 MHz, CDCl$_3$) δ 1.42 (s, 18H), 3.96 (s, 3H), 7.85 (s, 1H) ppm. $^{19}$F NMR (282 MHz, CDCl$_3$) δ −63.9 (s, 3F) ppm. ESI-MS m/z calc. 498.06134, Retention time: 2.34 minutes. LCMS Method: Kinetex C$_{18}$ 4.6×50 mm 2.6 μM. Temp: 45° C., Flow: 2.0 mL/min, Run Time: 3 min. Mobile Phase: Initial 95% H$_2$O (0.1% formic acid) and 5% acetonitrile (0.1% formic acid) linear gradient to 95% acetonitrile (0.1% formic acid) for 2.0 min then held at 95% acetonitrile (0.1% formic acid) for 1.0 min.

Intermediate 5: Preparation of 6-bromo-3-(tert-butoxycarbonylamino)-5-(trifluoromethyl)pyridine-2-carboxylic acid

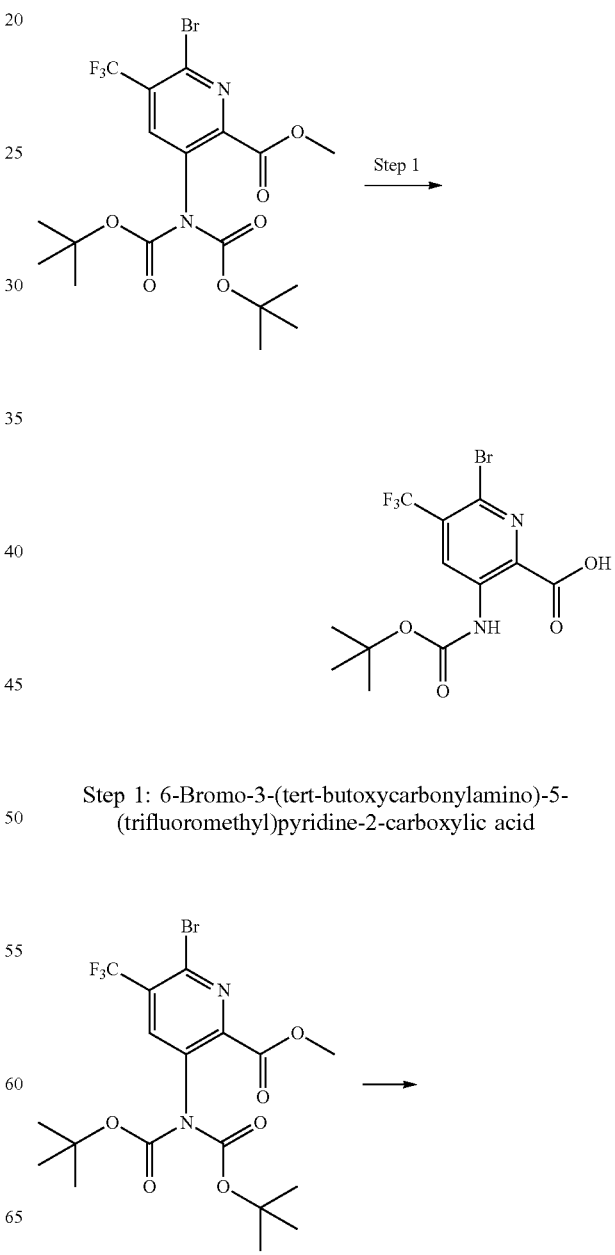

Step 1: 6-Bromo-3-(tert-butoxycarbonylamino)-5-(trifluoromethyl)pyridine-2-carboxylic acid -continued

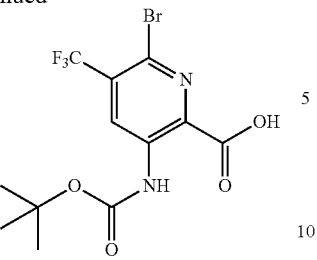

Step 1: Methyl 3-amino-5-fluoro-pyridine-2-carboxylate

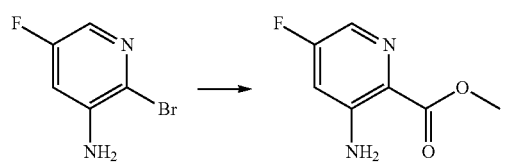

To a mixture of methyl 3-[bis(tert-butoxycarbonyl)amino]-6-bromo-5-(trifluoromethyl)pyridine-2-carboxylate (247 g, 494.7 mmol) in THF (1.0 L) was added a solution of LiOH (47.2 g, 1.971 mol) in water (500 mL). The mixture was stirred at ambient temperature for 18 h affording a yellow slurry. The mixture was cooled with an ice-bath and slowly acidified with HCl (1000 mL of 2 M, 2.000 mol) keeping the reaction temperature <15° C. The mixture was diluted with heptane (1.5 L), mixed and the organic phase separated. The aqueous phase was extracted with heptane (500 mL). The combined organic phases were washed with brine, dried over MgSO$_4$, filtered and concentrated in vacuo. The crude oil was dissolved in heptane (600 mL), seeded and stirred at ambient temperature for 18 h affording a thick slurry. The slurry was diluted with cold heptane (500 mL) and the precipitate collected using a medium frit. The filter cake was washed with cold heptane and air dried for 1 h, then in vacuo at 45° C. for 48 h to afford 6-bromo-3-(tert-butoxycarbonylamino)-5-(trifluoromethyl)pyridine-2-carboxylic acid (158.3 g, 83%). $^1$H NMR (400 MHz, DMSO-d$_6$) δ 10.38 (s, 1H), 9.01 (s, 1H), 1.50 (s, 9H) ppm. ESI-MS m/z calc. 383.99326, found 384.9 (M+1)$^+$; Retention time: 2.55 minutes. LCMS Method Detail: Final purity was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 4.5 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Intermediate 6: Preparation of methyl 3-amino-6-bromo-5-fluoro-pyridine-2-carboxylate

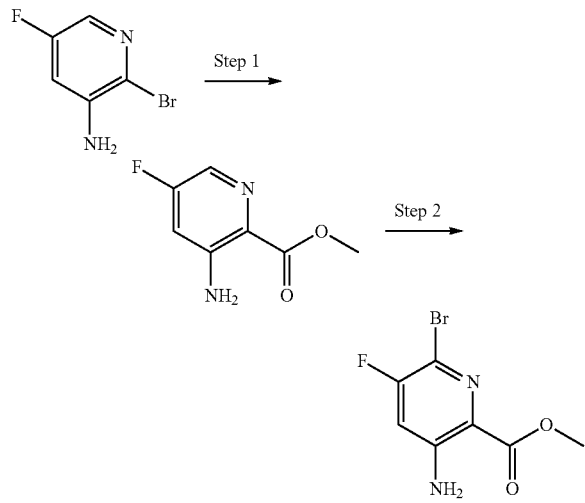

In an autoclave (600 mL) was added 2-bromo-5-fluoropyridin-3-amine (22 g, 115.18 mmol), methanol (250 mL), triethylamine (23.232 g, 32 mL, 229.59 mmol) and [1,1'-bis(diphenylphosphino)ferrocene]dichloropalladium(II) (2.1 g, 2.8700 mmol). The autoclave was purged with nitrogen, then with carbon monoxide. The mixture was heated to 130° C. and the carbon monoxide pressure was adjusted to 120 psi. The mixture was stirred for 3 h at 130° C., then cooled to 25° C. The mixture was purged with nitrogen and concentrated under vacuum. The resulting solid was diluted with ethyl acetate (500 mL). Water (200 mL) and sodium carbonate (15 g) were added and the mixture was vigorously stirred for 20 minutes. The layers were separated. The organic layer was washed with water (100 mL) and brine (100 mL), dried over sodium sulfate, filtered and evaporated under reduced pressure to provide methyl 3-amino-5-fluoro-pyridine-2-carboxylate (14.4 g, 53%) as brown solid. $^1$H NMR (400 MHz, CDCl$_3$) δ 7.90 (s, 1H), 6.72 (d, J=9.8 Hz, 1H), 5.94 (br. s, 2H), 3.96 (s, 3H) ppm. ESI-MS m/z calc. 170.04915, found 171.1 (M+1)$^+$; Retention time: 1.35 minutes. LCMS Method: Kinetex Polar C$_{18}$ 3.0×50 mm 2.6 μm, 3 min, 5-95% acetonitrile in H$_2$O (0.1% formic acid) 1.2 mL/min.

Step 2: Methyl 3-amino-6-bromo-5-fluoro-pyridine-2-carboxylate

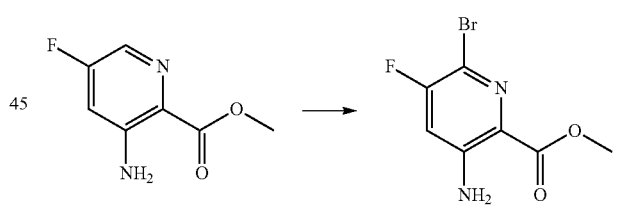

To a solution of methyl 3-amino-5-fluoro-pyridine-2-carboxylate (2.03 g, 11.931 mmol) in acetonitrile (40 mL), Ar-bromosucciMmicle (2.34 g, 13.147 mmol) was added portion-wise. After stirring at room temperature for 2 h, the reaction mixture was diluted with EtOAc (150 mL), washed with a saturated aqueous NaHCO$_3$ (150 mL) and brine (150 mL), then dried over sodium sulfate and concentrated under reduced pressure. Purification by silica gel chromatography (20% to 60% ethyl acetate in heptanes) provided methyl 3-amino-6-bromo-5-fluoro-pyridine-2-carboxylate (2.9 g, 98%) as white solid. $^1$H NMR (300 MHz, CDCl$_3$) δ 6.80 (d, J=8.5 Hz, 1H), 5.98 (br. s., 2H), 4.22-3.72 (m, 3H) ppm. $^{19}$F NMR (282 MHz, CDCl$_3$) δ −105.70 (d, J=9.2 Hz, 1F) ppm. ESI-MS m/z calc. 247.9597, found 248.9 (M+1)$^+$; Retention time: 1.73 minutes. LCMS Method: Kinetex Polar C$_{18}$ 3.0×50 mm 2.6 μm, 3 min, 5-95% acetonitrile in H$_2$O (0.1% formic acid) 1.2 mL/min.

Intermediate 7: Preparation of 2-benzyloxy-2-(trifluoromethyl)hex-5-enehydrazide (hydrochloride salt)

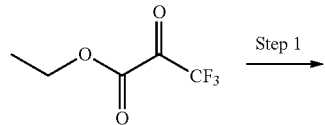

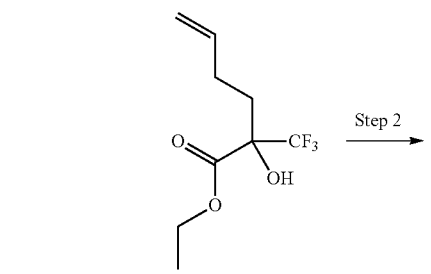

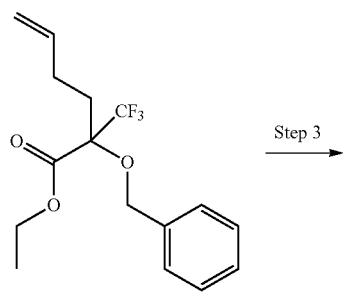

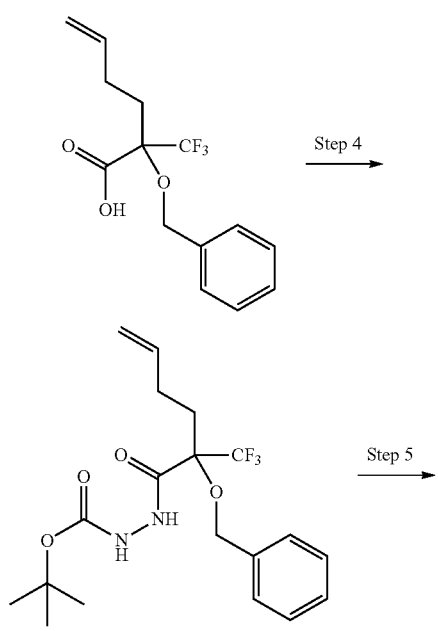

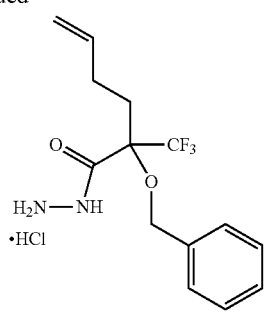

Step 1: Ethyl 2-hydroxy-2-(trifluoromethyl)hex-5-enoate

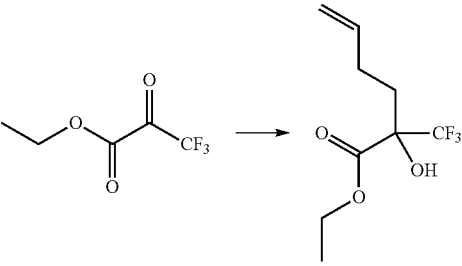

To a solution of ethyl 3,3,3-trifluoro-2-oxo-propanoate (25.15 g, 147.87 mmol) in Et$_2$O (270 mL) at −78° C. was added bromo(but-3-enyl)magnesium in THF (190 mL of 0.817 M, 155.23 mmol) dropwise over a period of 1.5 h (inner temperature −72° C. to −76° C.). The mixture was stirred at −78° C. for 20 min. The dry ice-acetone bath was removed. The mixture was slowly warm to 5° C. during 1 h, added to a mixture of 1 N aqueous HCl (170 mL) and crushed ice (150 g) (pH=4). The two layers were separated. The organic layer was concentrated, and the residue was combined with aqueous phase and extracted with EtOAc (2×150 mL). The combined organic phase was washed with 5% aqueous NaHCO$_3$ (50 mL) and brine (20 mL), dried with Na$_2$SO$_4$. The mixture was filtered and concentrated, and co-evaporated with THF (2×40 mL) to give ethyl 2-hydroxy-2-(trifluoromethyl)hex-5-enoate (37.44 g, 96%) as colorless oil. $^1$H NMR (300 MHz, CDCl$_3$) δ 5.77 (ddt, J=17.0, 10.4, 6.4 Hz, 1H), 5.15-4.93 (m, 2H), 4.49-4.28 (m, 2H), 3.88 (s, 1H), 2.35-2.19 (m, 1H), 2.17-1.89 (m, 3H), 1.34 (t, J=7.0 Hz, 3H) ppm. $^{19}$F NMR (282 MHz, CDCl$_3$) δ −78.74 (s, 3F) ppm.

Step 2: Ethyl 2-benzyloxy-2-(trifluoromethyl)hex-5-enoate

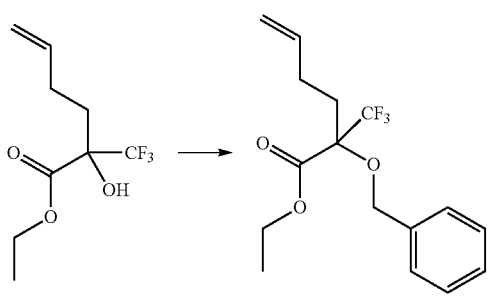 [SMILES: C=CCCC(O)(C(=O)OCC)C(F)(F)F ; C=CCCC(OCc1ccccc1)(C(=O)OCC)C(F)(F)F]

To a solution of ethyl 2-hydroxy-2-(trifluoromethyl)hex-5-enoate (24.29 g, 87.6% purity, 94.070 mmol) in DMF (120 mL) at 0° C. was added NaH (60% in mineral oil, 5.64 g, 141.01 mmol) portion-wise. The mixture was stirred at 0° C. for 10 min. Benzyl bromide (24.13 g, 141.08 mmol) and TBAI (8.68 g, 23.500 mmol) were added. The mixture was stirred at room temperature overnight. NH$_4$Cl (3 g, 0.6 eq) was added. The mixture was stirred for 10 min. 30 mL of EtOAc was added, then ice-water was added (400 g). The mixture was extracted with CH$_2$Cl$_2$ and the combined organic layers were concentrated. Purification by silica gel chromatography (0-20% CH$_2$Cl$_2$ in heptanes) provided ethyl 2-benzyloxy-2-(trifluoromethyl)hex-5-enoate (26.05 g, 88%) as pink oil. $^1$H NMR (300 MHz, CDCl$_3$) δ 1.34 (t, J=7.2 Hz, 3H), 2.00-2.19 (m, 3H), 2.22-2.38 (m, 1H), 4.33 (q, J=7.2 Hz, 2H), 4.64 (d, J=10.6 Hz, 1H), 4.84 (d, J=10.9 Hz, 1H), 4.91-5.11 (m, 2H), 5.62-5.90 (m, 1H), 7.36 (s, 5H) ppm. $^{19}$F NMR (282 MHz, CDCl$_3$) δ −70.5 (s, 3F) ppm. ESI-MS m/z calc. 316.12863, found 317.1 (M+1)$^+$; Retention time: 2.47 minutes. LCMS Method: Kinetex C$_{18}$ 4.6×50 mm 2.6 μM. Temp: 45° C., Flow: 2.0 mL/min, Run Time: 3 min. Mobile Phase: Initial 95% H$_2$O (0.1% formic acid) and 5% acetonitrile (0.1% formic acid) linear gradient to 95% acetonitrile (0.1% formic acid) for 2.0 min then held at 95% acetonitrile (0.1% formic acid) for 1.0 min.

Step 3: 2-Benzyloxy-2-(trifluoromethyl)hex-5-enoic acid

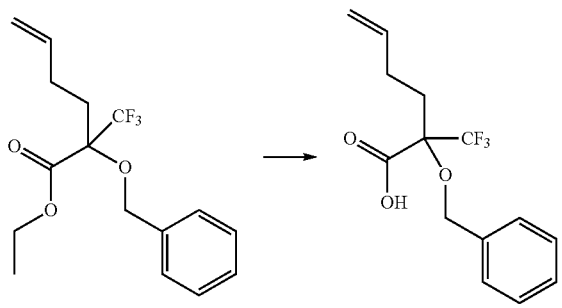 [SMILES: C=CCCC(OCc1ccccc1)(C(=O)OCC)C(F)(F)F ; C=CCCC(OCc1ccccc1)(C(=O)O)C(F)(F)F]

A solution of sodium hydroxide (7.86 g, 196.51 mmol) in water (60 mL) was added to a solution of ethyl 2-benzyloxy-2-(trifluoromethyl)hex-5-enoate (24.86 g, 78.593 mmol) in methanol (210 mL). The reaction was heated at 50° C. overnight. The reaction was concentrated to remove methanol, diluted with water (150 mL) and the carboxylate sodium salt was washed with heptane (1×100 mL). The aqueous solution was acidified to pH=2 with aqueous 3N solution of HCl. The carboxylic acid was extracted with dichloromethane (3×100 mL) and dried over sodium sulfate. The solution was filtered and concentrated to give 2-benzyloxy-2-(trifluoromethyl)hex-5-enoic acid (22.57 g, 97%) as pale yellow oil. $^1$H NMR (300 MHz, DMSO-d$_6$) δ 14.31 (br. s., 1H), 7.55-7.20 (m, 5H), 5.93-5.70 (m, 1H), 5.17-4.91 (m, 2H), 4.85-4.68 (m, 1H), 4.67-4.55 (m, 1H), 2.32-1.94 (m, 4H) ppm. $^{19}$F NMR (282 MHz, DMSO-d$_6$) δ −70.29 (s, 3F) ppm. ESI-MS m/z calc. 288.09732, found 287.1 (M−1); Retention time: 3.1 minutes. LCMS Method: Kinetex Polar C$_{18}$ 3.0×50 mm 2.6 μm, 6 min, 5-95% acetonitrile in H$_2$O (0.1% formic acid) 1.2 mL/min.

Step 4: tert-Butyl N-[[2-benzyloxy-2-(trifluoromethyl)hex-5-enoyl]amino]carbamate

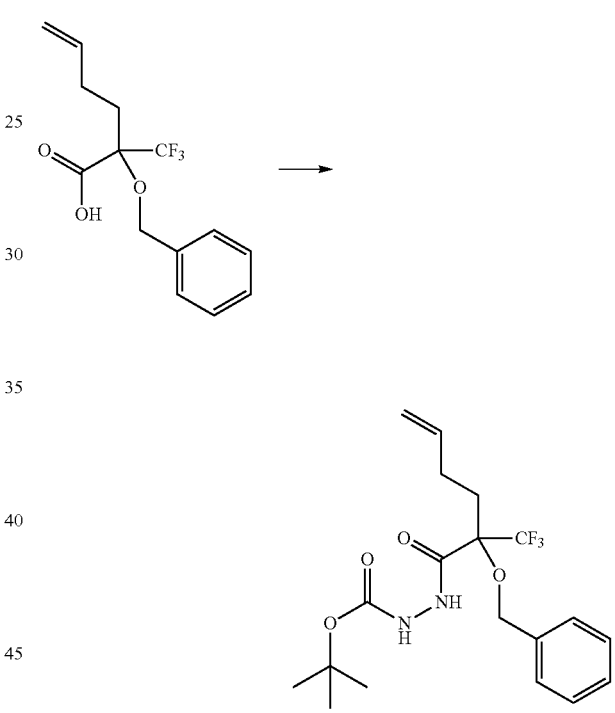

To a solution of 2-benzyloxy-2-(trifluoromethyl)hex-5-enoic acid (21.92 g, 92.4% purity, 70.263 mmol) in DMF (130 mL) was added HATU (37.2 g, 97.836 mmol) and Et$_3$N (15 g, 148.24 mmol). The mixture was stirred for 10 minutes then tert-butyl N-aminocarbamate (12.2 g, 92.312 mmol) was added. The mixture was stirred at 25° C. overnight and at 40° C. for 1 h. The mixture was diluted with ice-water (500 g) and extracted with CH$_2$Cl$_2$. The organic layer dried over anhydrous sodium sulfate and was concentrated. Purification by silica gel chromatography (0-30% EtOAc in heptanes) provided tert-butyl N-[[2-benzyloxy-2-(trifluoromethyl)hex-5-enoyl]amino]carbamate (26.08 g, 92%) as white solid. $^1$H NMR (300 MHz, CDCl$_3$) δ 1.46 (s, 9H), 2.10-2.31 (m, 3H), 2.34-2.51 (m, 1H), 4.60-4.72 (m, 1H), 4.73-4.86 (m, 1H), 4.95-5.19 (m, 2H), 5.83 (ddt, J=16.7, 10.4, 6.1 Hz, 1H), 6.28 (br. s., 1H), 7.30-7.51 (m, 5H), 8.34 (d, J=2.6 Hz, 1H) ppm. $^{19}$F NMR (282 MHz, CDCl$_3$) ppm −73.6 (s, 3F) ppm.

Step 5:
2-Benzyloxy-2-(trifluoromethyl)hex-5-enehydrazide

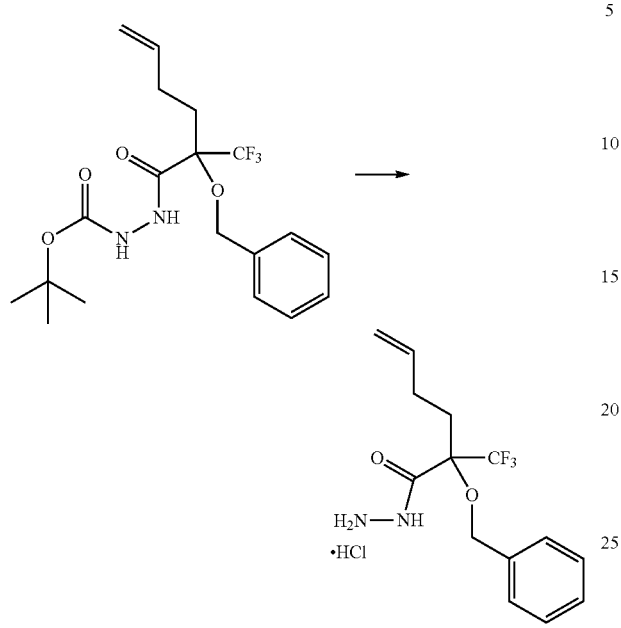

To a solution of tert-butyl N-[[2-benzyloxy-2-(trifluoromethyphex-5-enoyl]amino]carbamate (43.12 g, 107.2 mmol) in CH$_2$Cl$_2$ (200 mL) was added HCl (100 mL of 4 M, 400.0 mmol) and the mixture was stirred at ambient temperature for 7 h. The solvent was removed in vacuo, the residue stripped 2 times from heptane and the resultant solid was dried in vacuo using a high vac for 20 h giving 2-benzyloxy-2-(trifluoromethyl)hex-5-enehydrazide (Hydrochloride salt) (35 g, 96%). $^1$H NMR (400 MHz, Chloroform-d) δ 9.92 (s, 2H), 7.41-7.31 (m, 2H), 7.30-7.24 (m, 2H), 7.24-7.16 (m, 1H), 5.72-5.57 (m, 1H), 5.02-4.87 (m, 2H), 4.71 (d, J=10.9 Hz, 1H), 4.62 (d, J=11.0 Hz, 1H), 3.70 (s, 2H), 2.34-1.85 (m, 4H) ppm. ESI-MS m/z calc. 302.1242, found 303.2 (M+1)$^+$; Retention time: 1.5 minutes. Final purity was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Intermediate 8: Preparation of [6-[5-[1-benzyloxy-1-(trifluoromethyl)pent-4-enyl]-1,3,4-oxadiazol-2-yl]-5-nitro-3-(trifluoromethyl)-2-pyridyl]trifluoromethanesulfonate

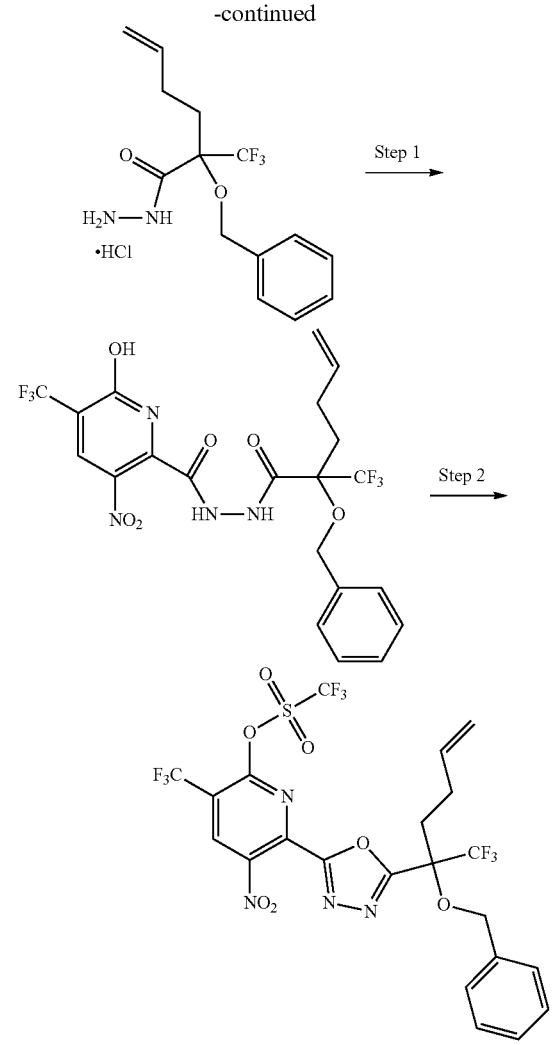

Step 1: N'-[2-Benzyloxy-2-(trifluoromethyl)hex-5-enoyl]-6-hydroxy-3-nitro-5-(trifluoromethyl)pyridine-2-carbohydrazide

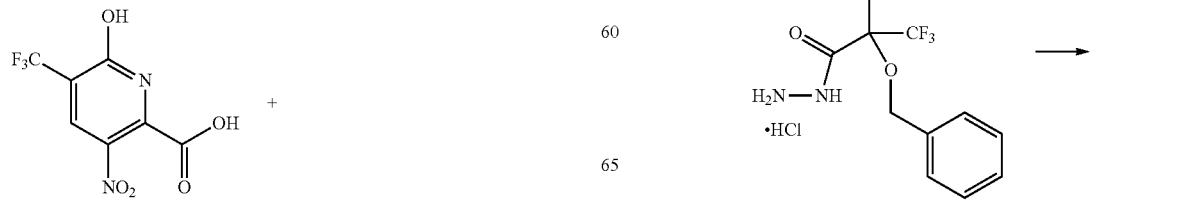

181

-continued

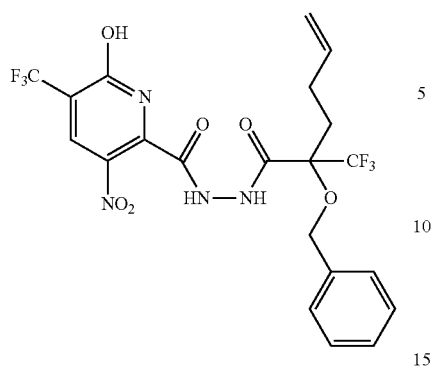

To a solution of 6-hydroxy-3-nitro-5-(trifluoromethyl)pyridine-2-carboxylic acid (29.92 g, 102.66 mmol) in acetonitrile (300 mL) and DMF (60 mL) was added CDI (17.48 g, 107.80 mmol). The mixture was stirred for 0.5 h at room temperature, then 2-benzyloxy-2-(trifluoromethyl)hex-5-enehydrazide (hydrochloride salt) (33.04 g, 97.534 mmol) was added in portions. The reaction mixture was stirred at 26° C. for 19 hours. The reaction mixture was transferred to an extraction funnel rinsing with water (300 mL) and 2-Me THF (400 mL). The mixture was extracted with 2-Me THF (3×400 mL). The combined organic layer was washed with 0.5 N aqueous solution of HCl (3×300 mL), brine (3×250 mL), dried over anhydrous Na₂SO₄, filtered and concentrated by evaporation under reduced pressure. It was then solubilized twice in dichloromethane (2×300 mL) and the volatiles were removed by evaporation under reduced pressure to provide N'-[2-benzyloxy-2-(trifluoromethyphex-5-enoyl]-6-hydroxy-3-nitro-5-(trifluoromethyl)pyridine-2-carbohydrazide (58.5 g, 94%) as brown foam residue. ESI-MS m/z calc. 536.11304, found 537.2 (M+1)⁺. Retention time: 2.03 minutes; LCMS Method: Kinetex Polar C₁₈ 3.0×50 mm 2.6 μm, 3 min, 5-95% acetonitrile in H₂O (0.1% formic acid) 1.2 mL/min.

Step 2: [6-[5-[1-Benzyloxy-1-(trifluoromethyl)pent-4-enyl]-1,3,4-oxadiazol-2-yl]-5-nitro-3-(trifluoromethyl)-2-pyridyl]trifluoromethanesulfonate

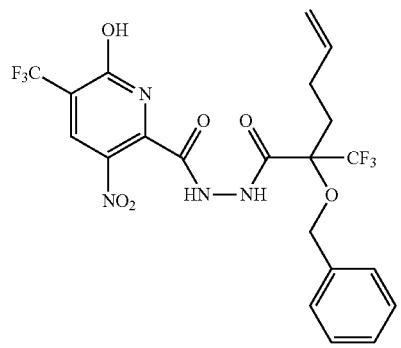

→

182

-continued

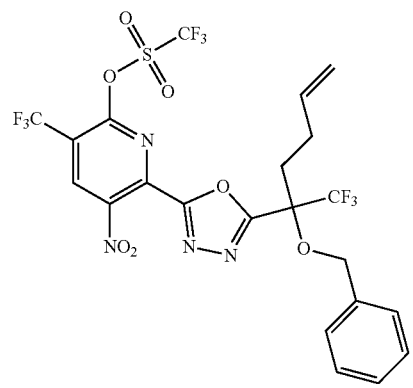

To a 0° C. solution of N'-[2-benzyloxy-2-(trifluoromethyphex-5-enoyl]-6-hydroxy-3-nitro-5-(trifluoromethyl)pyridine-2-carbohydrazide (9.76 g, 16.922 mmol) in dichloromethane (190 mL) was added DIPEA (8.0136 g, 10.8 mL, 62.004 mmol) followed by trifluoromethylsulfonyl trifluoromethanesulfonate (12.410 g, 7.4 mL, 43.985 mmol). The ice-cold bath was removed after 20 min and the reaction was stirred at room temperature for 2.5 hours. The mixture was transferred to a separatory funnel provided with ice-cold aqueous 1.0 N solution of HCl, and EtOAc (300 mL). The organic layer was separated, and the aqueous phase extracted with ethyl acetate (2×150 mL). The combined organic layer was washed again with ice-cold HCl 1.0 N aqueous solution (60 mL) and brine (3×40 mL), dried over anhydrous Na₂SO₄, filtered and concentrated under reduced pressure. Purification by silica gel chromatography (0-10% EtOAc in heptanes) provided [6-[5-[1-benzyloxy-1-(trifluoromethyl)pent-4-enyl]-1,3,4-oxadiazol-2-yl]-5-nitro-3-(trifluoromethyl)-2-pyridyl]trifluoromethanesulfonate (5.334 g, 40%) as an orange oil. ¹H NMR (300 MHz, CDCl₃) δ 8.74 (s, 1H), 7.50-7.27 (m, 5H), 5.87-5.68 (m, 1H), 5.12-4.96 (m, 2H), 4.88 (d, J=10.6 Hz, 1H), 4.67 (d, J=10.9 Hz, 1H), 2.60-2.16 (m, 4H) ppm. ¹⁹F NMR (282 MHz, CDCl₃) δ −62.68 (s, 3F), −71.80 (s, 3F), −73.04 (s, 3F) ppm. ESI-MS m/z calc. 650.0518, found 651.1 (M+1)⁺; Retention time: 3.94 minutes. LCMS Method: Kinetex Polar C₁₈ 3.0×50 mm 2.6 μm, 6 min, 5-95% acetonitrile in H₂O (0.1% formic acid) 1.2 mL/min.

Intermediate 9: Preparation of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate

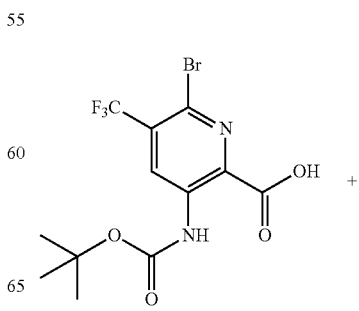 +

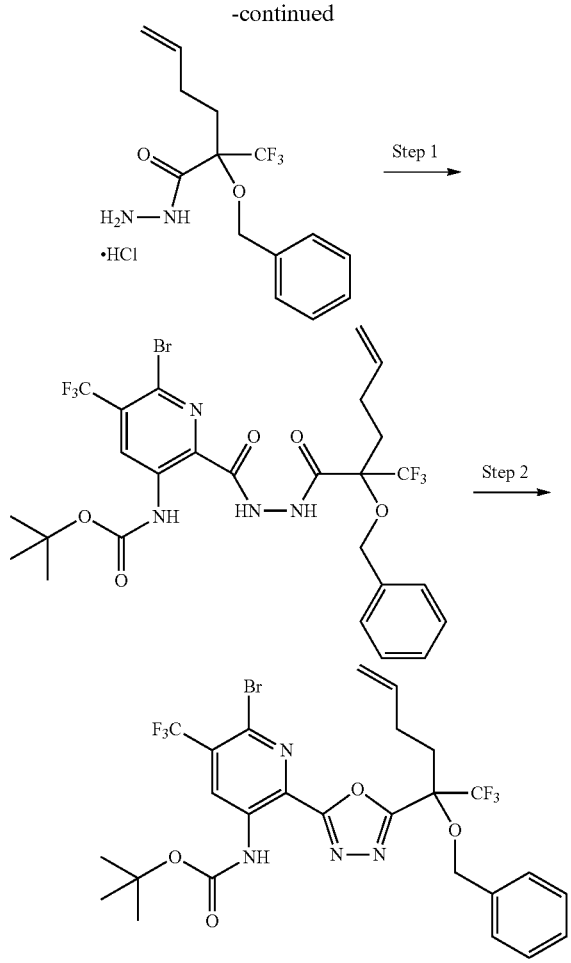

Step 1: tert-Butyl N-[2-[[[2-benzyloxy-2-(trifluoromethyl)hex-5-enoyl]amino]carbamoyl]-6-bromo-5-(trifluoromethyl)-3-pyridyl]carbamate

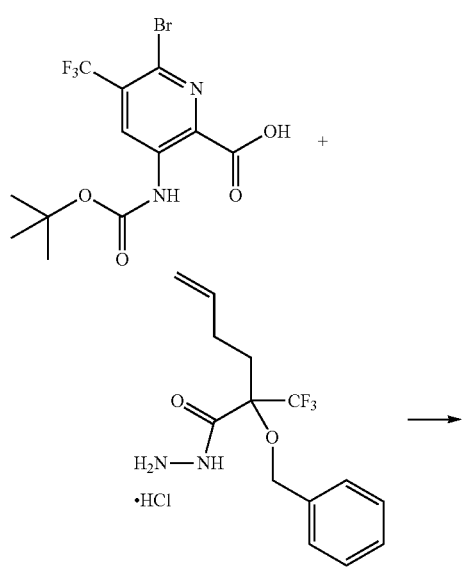

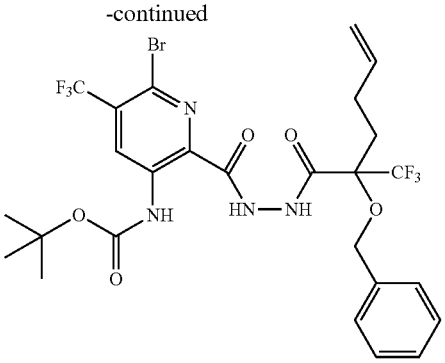

To a mixture of 6-bromo-3-(tert-butoxycarbonylamino)-5-(trifluoromethyl)pyridine-2-carboxylic acid (239.2 g, 621.1 mmol) and 2-benzyloxy-2-(trifluoromethyl)hex-5-enehydrazide (hydrochloride salt) (230.1 g, 761.2 mmol) in EtOAc (2.2 L) at ambient temperature was added pyridine (200 mL, 2.473 mol) which afforded a precipitate. To the mixture was added 1-propanephosphonic anhydride (500 g of 50% w/w, 785.7 mmol) and the reaction mixture was stirred at ambient temperature for 12 h. The reaction was quenched with the slow addition of NaOH (149 g of 50 w/w, 1.863 mol) in water (2 L) and the mixture was stirred for 15 min. The organic phase was separated, and the aqueous phase extracted with EtOAc (1 L). The combined organic phases washed with brine, dried over $MgSO_4$, filtered and concentrated in vacuo. After half of the solvent was removed, the organic phase was washed 2 times with aqueous HCl (1000 mL of 1 M, 1.000 mol). The organic phase was dried over $MgSO_4$, filtered and concentrated in vacuo. The crude product was slurried in warm heptane (2.5 L) and MTBE (0.25 L) and the mixture stirred at ambient temperature for 12 h affording a light yellow slurry. The slurry was filtered, and the resultant filter cake was washed 2 times with 1 L 10% MTBE/heptane. The off-white solid was air dried for 2 h, then in vacuo at 40° C. for 20 h giving tert-butyl N-[2-[[[2-benzyloxy-2-(trifluoromethyl)hex-5-enoyl]amino]carbamoyl]-6-bromo-5-(trifluoromethyl)-3-pyridyl]carbamate (379.9 g, 91%). $^1$H NMR (400 MHz, DMSO-$d_6$) δ 11.09 (s, 1H), 10.92 (s, 1H), 10.35 (s, 1H), 9.15 (s, 1H), 7.50 (d, J=7.4 Hz, 2H), 7.36 (dt, J=24.4, 7.2 Hz, 3H), 5.87 (ddt, J=16.0, 10.4, 5.2 Hz, 1H), 5.09 (d, J=16.9 Hz, 1H), 5.02 (d, J=10.1 Hz, 1H), 4.84 (q, J=11.4 Hz, 2H), 2.35-2.12 (m, 4H), 1.49 (s, 9H) ppm. ESI-MS m/z calc. 668.1069, found 670.9 (M+1)$^+$; Retention time: 3.5 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 5.0 minutes. Mobile phase A=$H_2O$ (0.05% $CF_3CO_2H$). Mobile phase B=acetonitrile (0.035% $CF_3CO_2H$). Flow rate=1.2 mL/min, injection volume=1.5 μL, and column temperature=60° C.

Step 2: tert-Butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate

Intermediate 10: Preparation of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

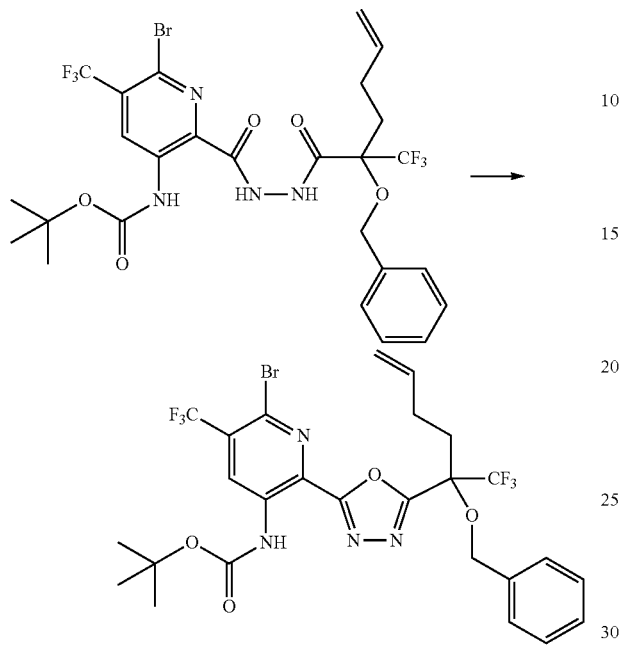

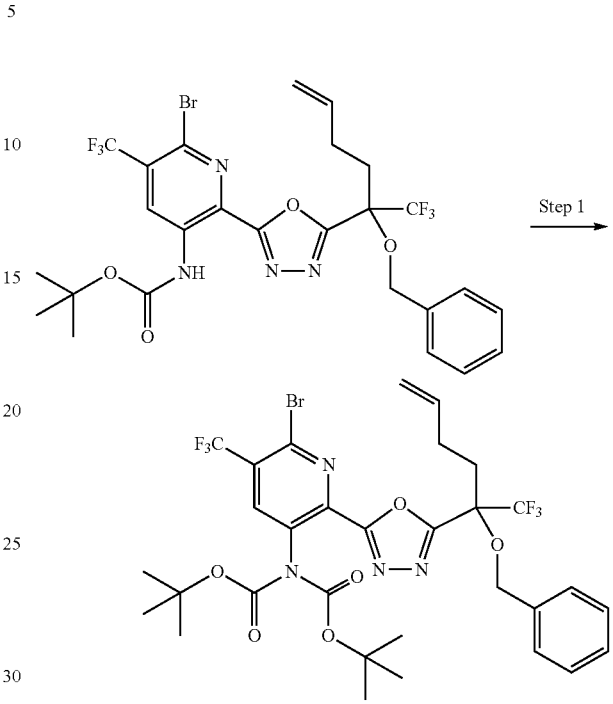

tert-Butyl N-[2-[[[2-benzyloxy-2-(trifluoromethyl)hex-5-enoyl]amino]carbamoyl]-6-bromo-5-(trifluoromethyl)-3-pyridyl]carbamate (102 g, 150.8 mmol) was dissolved in anhydrous acetonitrile (1000 mL) and DIPEA (92 mL, 528.2 mmol) was added. The resultant orange solution was heated to 70° C. (internal temp) making a clear yellow solution. Then p-toluenesulfonyl chloride (37.4 g, 196.2 mmol) was added in 3 equal portions of 12.47 g separated by 10 minutes and then the reaction was heated for another 30 min. The reaction was cooled to room temperature and the acetonitrile was concentrated under reduced pressure. To the mixture was added 1000 mL MTBE, then 800 mL water, and the mixture was stirred, and the layers were separated. The organic layer was washed with a solution of citric acid (36.3 g, 188.9 mmol) in 700 mL water, then 400 mL saturated NaHCO$_3$, then 300 mL brine. The organic layer was then dried over anhydrous MgSO$_4$ and concentrated under reduced pressure. The material was purified using silica gel chromatography using a gradient of 15% to 50% of 8% EtOAc in hexanes (B) and Hexanes (A) to provide tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate (91.7 g, 93%). $^1$H NMR (400 MHz, Chloroform-d) δ 10.18 (s, 1H), 9.35 (s, 1H), 7.55-7.47 (m, 2H), 7.45-7.37 (m, 2H), 7.36-7.28 (m, 1H), 5.83-5.68 (m, 1H), 5.10-4.93 (m, 2H), 4.82 (d, J=10.5 Hz, 1H), 4.69 (d, J=10.5 Hz, 1H), 2.59-2.13 (m, 4H), 1.56 (s, 9H) ppm. ESI-MS m/z calc. 650.0963, found 651.0 (M+1)$^+$; Retention time: 3.81 minutes. Final purity was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 4.5 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Step 1: tert-Butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

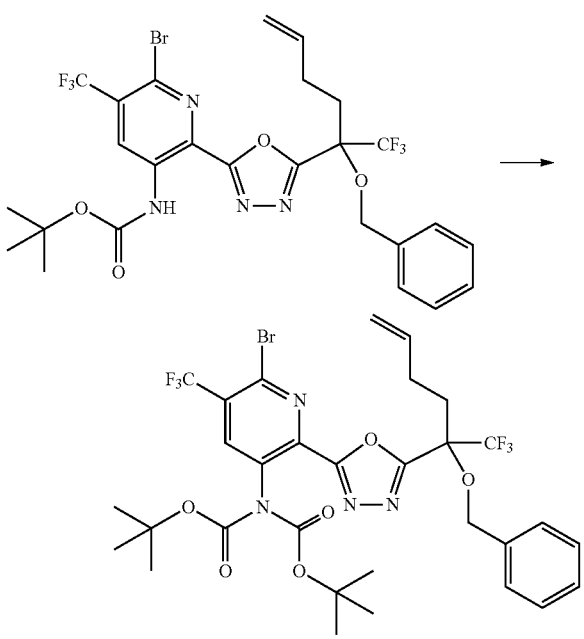

Into a solution of ter t-butyl N-[2-[5-[1-benzyloxy-1-(trifluoromethyl)pent-4-enyl]-1,3,4-oxadiazol-2-yl]-6- bromo-5-(trifluoromethyl)-3-pyridyl]carbamate (30 g, 41.910 mmol) in MTBE (300 mL) was added DIEA (6.6780 g, 9 mL, 51.670 mmol), DMAP (0.28 g, 2.2919 mmol) and Boc anhydride (20.1 g, 21.158 mL, 92.097 mmol). The resulting yellow cloudy solution was stirred at 35° C. overnight. After cooling to room temperature, the solvent was evaporated. The yellow oily residue was then dissolved in 300 mL DCM and was washed with water (300 mL), followed by brine (300 mL). The organic layer was separated, dried over anhydrous sodium sulfate, filtered, and concentrated. Purification by silica gel chromatography (0% to 20% EtOAc in hexanes) provided tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (28.68 g, 87%) as white solid. $^1$H NMR (500 MHz, DMSO-d$_6$) δ 8.89 (s, 1H), 7.51 (d, J=7.4 Hz, 2H), 7.43 (t, J=7.5 Hz, 2H), 7.35 (t, J=7.3 Hz, 1H), 5.96-5.76 (m, 1H), 5.11 (d, J=17.2 Hz, 1H), 5.01 (d, J=10.1 Hz, 1H), 4.73 (d, J=10.7 Hz, 1H), 4.66 (d, J=10.6 Hz, 1H), 2.65-2.51 (m, 2H), 2.36-2.17 (m, 2H), 1.27 (d, J=23.5 Hz, 18H) ppm.

Intermediate 11: Preparation of 2-benzyloxy-2-(trifluoromethyl)pent-4-enehydrazide (hydrochloride salt)

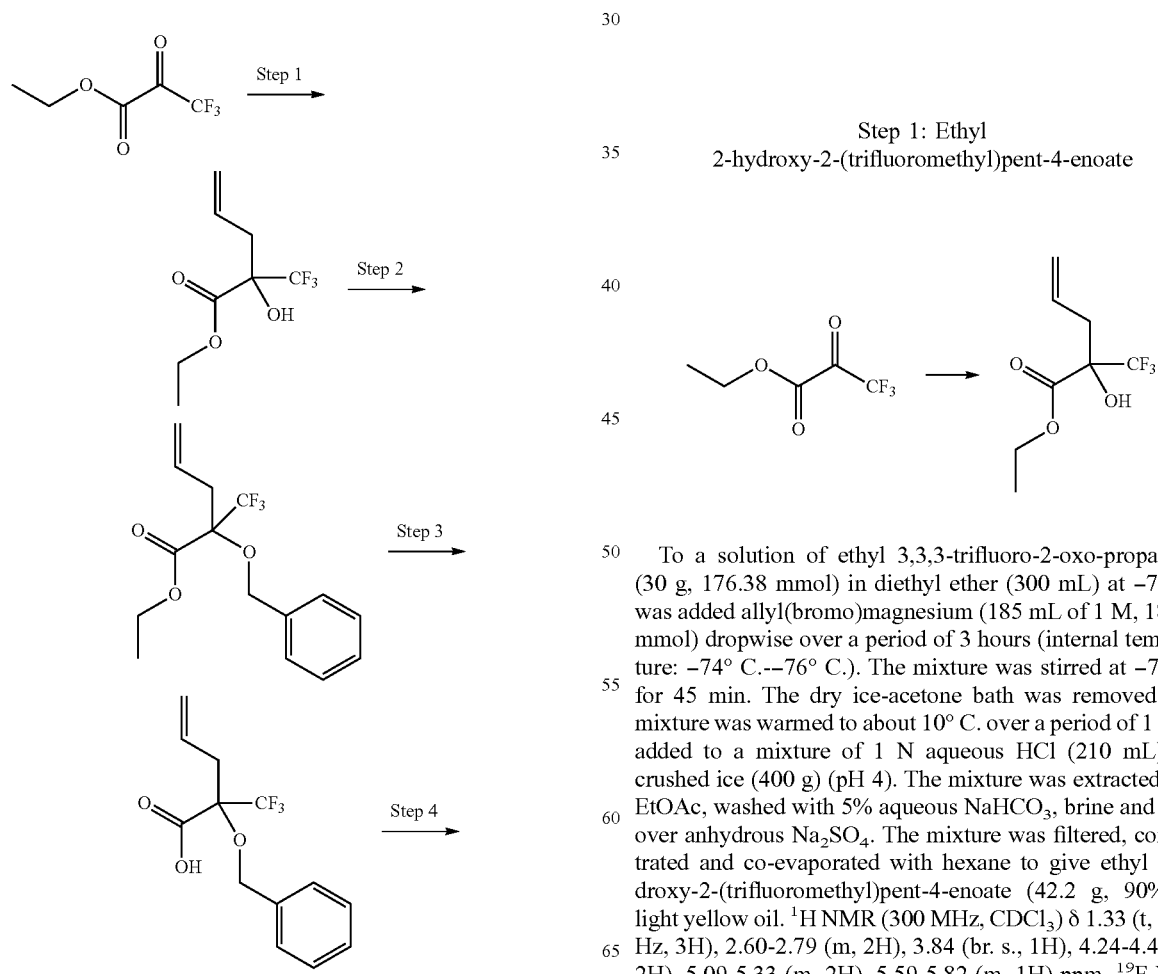

Step 1: Ethyl 2-hydroxy-2-(trifluoromethyl)pent-4-enoate

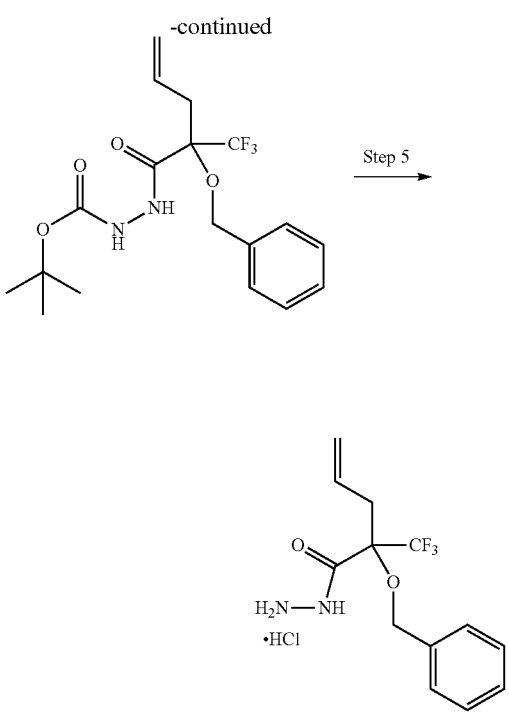

To a solution of ethyl 3,3,3-trifluoro-2-oxo-propanoate (30 g, 176.38 mmol) in diethyl ether (300 mL) at −78° C. was added allyl(bromo)magnesium (185 mL of 1 M, 185.00 mmol) dropwise over a period of 3 hours (internal temperature: −74° C.–−76° C.). The mixture was stirred at −78° C. for 45 min. The dry ice-acetone bath was removed. The mixture was warmed to about 10° C. over a period of 1 h and added to a mixture of 1 N aqueous HCl (210 mL) and crushed ice (400 g) (pH 4). The mixture was extracted with EtOAc, washed with 5% aqueous NaHCO$_3$, brine and dried over anhydrous Na$_2$SO$_4$. The mixture was filtered, concentrated and co-evaporated with hexane to give ethyl 2-hydroxy-2-(trifluoromethyl)pent-4-enoate (42.2 g, 90%) as light yellow oil. $^1$H NMR (300 MHz, CDCl$_3$) δ 1.33 (t, J=7.1 Hz, 3H), 2.60-2.79 (m, 2H), 3.84 (br. s., 1H), 4.24-4.48 (m, 2H), 5.09-5.33 (m, 2H), 5.59-5.82 (m, 1H) ppm. $^{19}$F NMR (282 MHz, CDCl$_3$) δ −78.5 (s, 3F) ppm.

Step 2: Ethyl 2-benzyloxy-2-(trifluoromethyl)pent-4-enoate

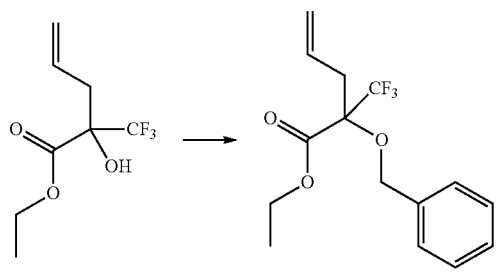 [SMILES: C=CCC(O)(C(=O)OCC)C(F)(F)F ; C=CCC(OCc1ccccc1)(C(=O)OCC)C(F)(F)F]

To a solution of ethyl 2-hydroxy-2-(trifluoromethyl)pent-4-enoate (18.56 g, 83.105 mmol) in DMF (100 mL) was added NaH (5.3 g, 60% w/w, 132.51 mmol) at 0° C. The reaction was stirred for 15 minutes and benzyl bromide (21.14 g, 15 mL, 121.12 mol) and tetrabutyl ammonium iodide (8.5 g, 23.012 mmol) were added. The mixture was stirred at room temperature overnight. The reaction was quenched with water (300 mL) and extracted with ethyl acetate (3×300 mL) before being washed with brine (500 mL) and dried over sodium sulfate. Purification by silica gel chromatography (20 to 60% DCM in hexanes) provided ethyl 2-benzyloxy-2-(trifluoromethyl)pent-4-enoate (22.01 g, 70%) as colorless oil. $^1$H NMR (250 MHz, CDCl$_3$) δ 7.55-7.25 (m, 5H), 6.00-5.80 (m, 1H), 5.30-5.10 (m, 2H), 4.86 (d, J=10.5 Hz, 1H), 4.68 (d, J=10.5 Hz, 1H), 4.33 (q, J=7.0 Hz, 2H), 2.81 (d, J=7.0 Hz, 2H), 1.34 (t, J=7.1 Hz, 3H) ppm. ESI-MS m/z calc. 302.113, found 303.5 (M+1)$^+$; Retention time: 4.14 minutes. LCMS Method: Merck Millipore Chromolith SpeedROD C$_{18}$ column (50×4.6 mm) and a dual gradient run from 5-100% mobile phase B over 6 minutes. Mobile phase A=water (0.1% CF$_3$CO$_2$H). Mobile phase B=acetonitrile (0.1% CF$_3$CO$_2$H).

Step 3: 2-Benzyloxy-2-(trifluoromethyl)pent-4-enoic acid

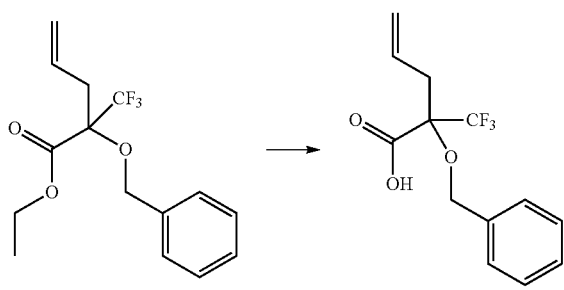 [SMILES: C=CCC(OCc1ccccc1)(C(=O)OCC)C(F)(F)F ; C=CCC(OCc1ccccc1)(C(=O)O)C(F)(F)F]

Into a solution of ethyl 2-benzyloxy-2-(trifluoromethyl)pent-4-enoate (28.99 g, 95.902 mmol) in methanol (150 mL) was added a solution of NaOH (7.6714 g, 191.80 mmol) in water (50 mL). The reaction mixture was stirred at 40° C. for 3 hours. The reaction mixture was concentrated under vacuum, the residue was diluted with water (200 mL) and washed with diethyl ether (200 mL). The aqueous layer was acidified with concentrated HCl to pH 1 and extracted with diethyl ether (3×200 mL). The combined organic layers were washed with brine, dried over anhydrous sodium sulfate, and concentrated under vacuum to furnish 2-benzyloxy-2-(trifluoromethyl)pent-4-enoic acid (28.04 g, 99%) as a light yellow liquid. $^1$H NMR (250 MHz, CDCl$_3$) δ 7.55-7.28 (m, 5H), 5.97-5.69 (m, 1H), 5.33-5.17 (m, 2H), 4.95-4.66 (m, 2H), 2.91 (d, J=7.1 Hz, 2H) ppm.

Step 4: tert-Butyl N-[[2-benzyloxy-2-(trifluoromethyl)pent-4-enoyl]amino]carbamate

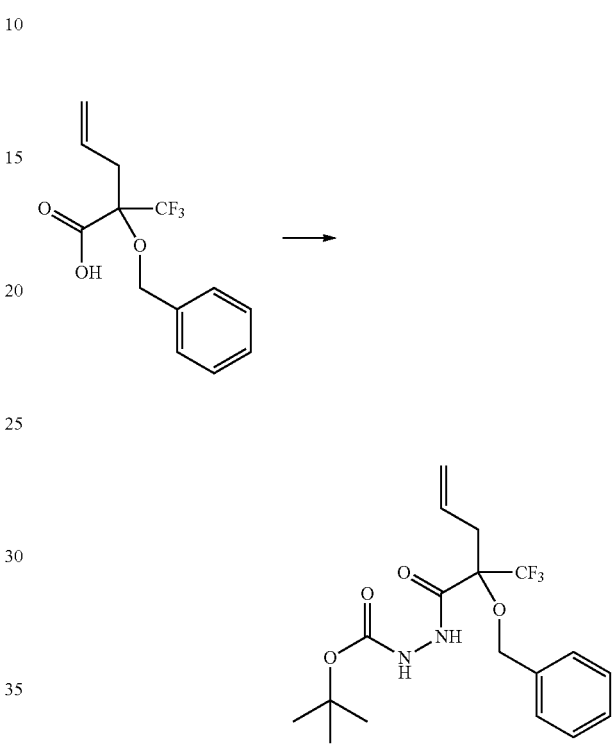

To a solution of 2-benzyloxy-2-(trifluoromethyl)pent-4-enoic acid (300 g, 1.094 mol) in DMF (2 L) was added HATU (530 g, 1.394 mol) and DIEA (400 mL, 2.296 mol) and the mixture was stirred at ambient temperature for 10 min. To the mixture was added tert-butyl N-aminocarbamate (152 g, 1.150 mol) and the mixture stirred at ambient temperature for 36 h. The reaction was quenched with cold water (4 L) and the mixture extracted 2× with EtOAc (2 L). The organic phase was washed brine, dried over MgSO$_4$, filtered and concentrated in vacuo. Purification by silica gel chromatography (0-40% EtOAc/hexanes) provided tert-butyl N-[[2-benzyloxy-2-(trifluoromethyl)pent-4-enoyl]amino]carbamate (386.49 g, 91%) as an oil which slowly crystallized to an off-white solid. $^1$H NMR (400 MHz, DMSO) δ 10.00 (d, J=37.9 Hz, 1H), 8.93 (s, 1H), 7.46-7.39 (m, 2H), 7.38-7.29 (m, 3H), 6.01-5.64 (m, 1H), 5.32 (d, J=17.1 Hz, 1H), 5.17 (d, J=10.1 Hz, 1H), 4.77 (s, 2H), 2.96 (qd, J=15.4, 6.8 Hz, 2H), 1.39 (d, J=17.3 Hz, 9H) ppm. ESI-MS m/z calc. 388.16098, found 389.0 (M+1)$^+$; Retention time: 2.51 minutes. Final purity was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 4.5 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Step 5:
2-Benzyloxy-2-(trifluoromethyl)pent-4-enehydrazide (hydrochloride salt)

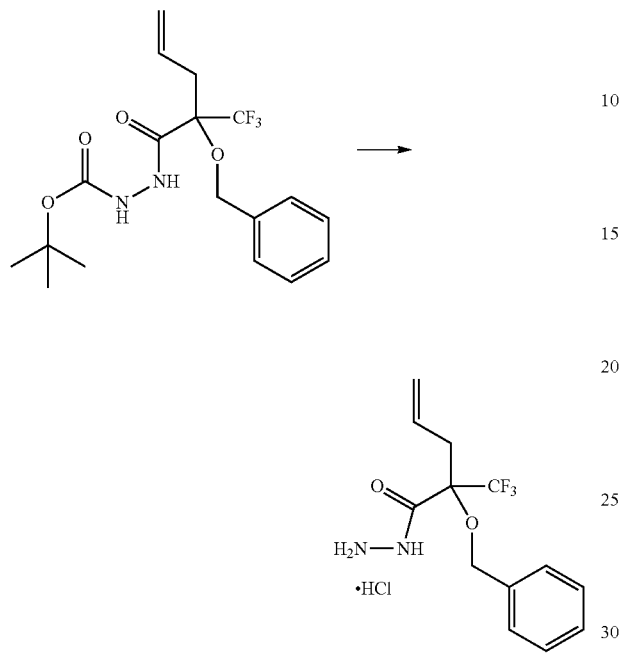

To a solution of tert-butyl N-[[2-benzyloxy-2-(trifluoromethyl)pent-4-enoyl]amino]carbamate (98.5 g, 240.94 mmol) in DCM (400 mL) was added HCl in dioxane (200 mL of 4 M, 800.00 mmol). The mixture was stirred at room temperature for 2 hours, concentrated and co-evaporated with DCM and hexanes to give 2-benzyloxy-2-(trifluoromethyl)pent-4-enehydrazide (hydrochloride salt) (81.15 g, 97%) as an off white solid. $^1$H NMR (500 MHz, DMSO-$d_6$) δ 11.07 (s, 1H), 7.70-7.16 (m, 5H), 5.87-5.61 (m, 1H), 5.45-5.09 (m, 2H), 4.79 (s, 2H), 3.6-3.4 (m, 2H), 3.23-3.07 (m, 1H), 3.04-2.87 (m, 1H) ppm. ESI-MS m/z calc. 288.10855, found 289.2 (M+1)$^+$; Retention time: 2.0 minutes. LCMS Method: Waters Cortex 2.7u $C_{18}$ (3.0 mm×50 mm), 55° C.; flow: 1.2 mL/min; mobile phase: 100% water with 0.1% trifluoroacetic acid then 100% acetonitrile with 0.1% trifluoroacetic acid, gradient of 5% to 100% B over 4 min, with equilibration at 100% B for 0.5 min, then 5% B over 1.5 min.

Intermediate 12: Preparation of [6-[5-[1-Benzyloxy-1-(trifluoromethyl)but-3-enyl]-1,3,4-oxadiazol-2-yl]-5-nitro-3-(trifluoromethyl)-2-pyridyl]trifluoromethanesulfonate

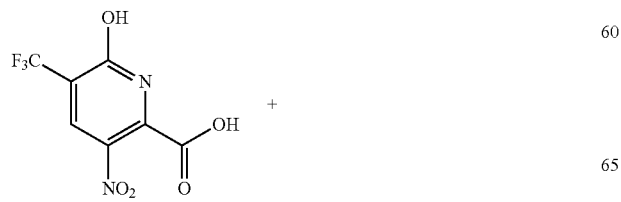

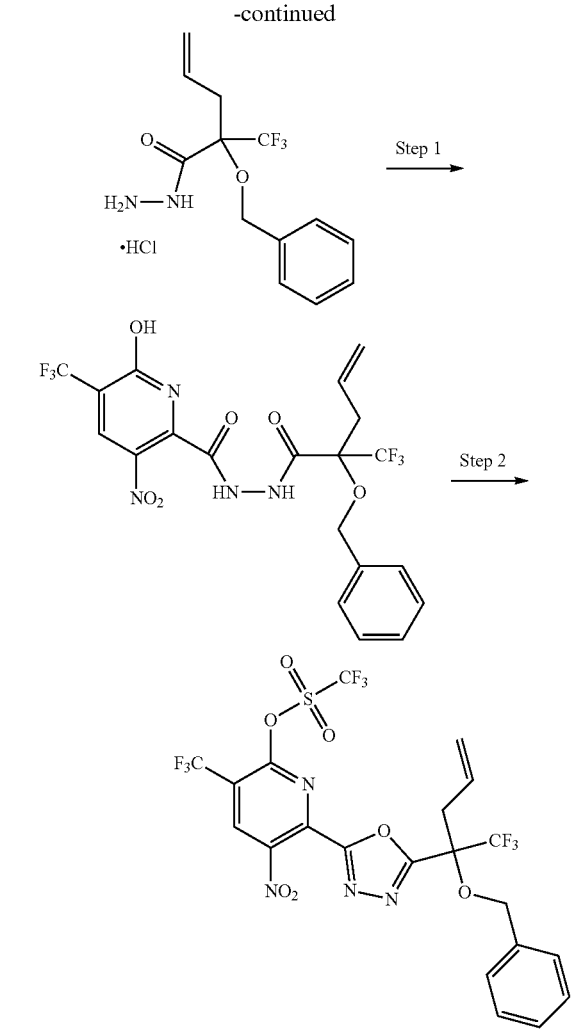

Step 1: N'-[2-benzyloxy-2-(trifluoromethyl)pent-4-enoyl]-6-hydroxy-3-nitro-5-(trifluoromethyl)pyridine-2-carbohydrazide

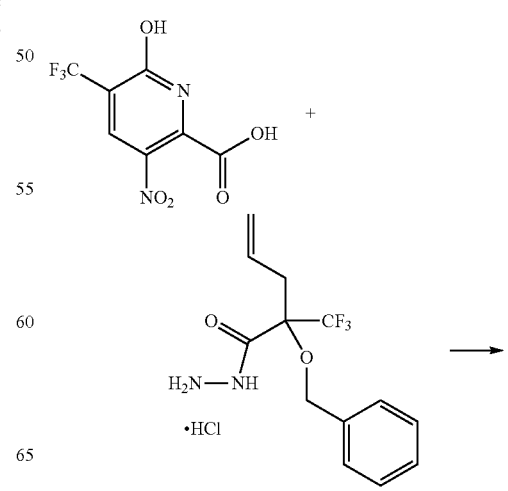

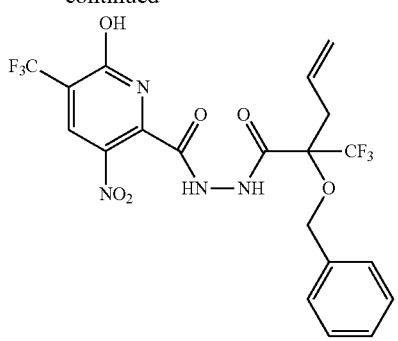

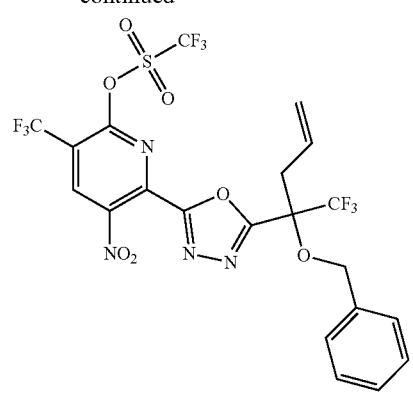

To a solution of 6-hydroxy-3-nitro-5-(trifluoromethyl)pyridine-2-carboxylic acid (8.5 g, 29.165 mmol) in acetonitrile (90 mL) and DMF (18 mL) was added CDI (5 g, 30.836 mmol). The mixture was stirred for 0.5 h at room temperature, then 2-benzyloxy-2-(trifluoromethyl)pent-4-enehydrazide (hydrochloride salt) (9 g, 27.716 mmol) was added. The reaction mixture was stirred at room temperature overnight. The reaction mixture was transferred to an extraction funnel rinsing with water (300 mL) and 2-Me THF (400 mL). The mixture was extracted with 2-methyl tetrahydrofuran (3×400 mL). The combined organic layer was washed with 0.5 N aqueous solution of HCl (3×300 mL), brine (3×250 mL), dried over anhydrous Na$_2$SO$_4$, filtered and concentrated under reduced pressure. It was then solubilized twice in dichloromethane (2×300 mL) and the volatiles were removed under reduced pressure giving N'-[2-benzyloxy-2-(trifluoromethyl)pent-4-enoyl]-6-hydroxy-3-nitro-5-(trifluoromethyl)pyridine-2-carbohydrazide (14.7 g, 75%) as yellow solid. ESI-MS m/z calc. 522.0974, found 523.1 (M+1)$^+$; Retention time: 2.08 minutes. LCMS Method: Kinetex Polar C$_{18}$ 3.0×50 mm 2.6 µm, 3 min, 5-95% acetonitrile in H$_2$O (0.1% formic acid) 1.2 mL/min.

Step 2: [6-[5-[1-Benzyloxy-1-(trifluoromethyl)but-3-enyl]-1,3,4-oxadiazol-2-yl]-5-nitro-3-(trifluoromethyl)-2-pyridyl] trifluoromethanesulfonate Trifluoromethylsulfonyl trifluoromethanesulfonate (14.758 g, 8.8 mL, 52.308 mmol) was added to N'-[2-benzyloxy-2-(trifluoromethyl)pent-4-enoyl]-6-hydroxy-3-nitro-5-(trifluoromethyl)pyridine-2-carbohydrazide (14.7 g, 20.712 mmol) and DIPEA (9.79 g, 13.2 mL, 75.783 mmol) in dichloromethane (175 mL) at 0° C. The ice-cold bath was removed after 20 min and the reaction was stirred at room temperature for 2.5 h. The mixture was transferred to a separatory funnel with ice-cold aqueous 1.0 N solution of HCl (180 mL), and EtOAc (500 mL). The organic layer was separated, and the aqueous phase extracted with ethyl acetate (2×120 mL). The combined organic layer was washed again with ice-cold HCl 1.0 N aqueous solution (120 mL) and brine (3×120 mL), dried over anhydrous Na$_2$SO$_4$, filtered and concentrated by evaporation under reduced pressure. Purification by silica gel chromatography (0% to 20% of ethyl acetate in heptanes) provided [6-[5-[1-benzyloxy-1-(trifluoromethyl)but-3-enyl]-1,3,4-oxadiazol-2-yl]-5-nitro-3-(trifluoromethyl)-2-pyridyl]trifluoromethanesulfonate (5.425 g, 40%) as an orange viscous oil. $^1$H NMR (300 MHz, CDCl$_3$) δ 8.65 (s, 1H), 7.36-7.21 (m, 5H), 5.93-5.74 (m, 1H), 5.28-5.10 (m, 2H), 4.78 (d, J=10.9 Hz, 1H), 4.60 (d, J=10.6 Hz, 1H), 3.21-3.05 (m, 2H) ppm. $^{19}$F NMR (282 MHz, CDCl$_3$) δ −62.69 (s, 3F), −71.82 (s, 3F), −73.32 (s, 3F) ppm. ESI-MS m/z calc. 636.03613, found 637.1 (M+1)$^+$; Retention time: 4.0 minutes. LCMS Method: Kinetex Polar C$_{18}$ 3.0×50 mm 2.6 µm, 6 min, 5-95% acetonitrile in H$_2$O (0.1% formic acid) 1.2 mL/min.

Intermediate 13: Preparation of tert-butyl N-[2-[5-[1-benzyloxy-1-(trifluoromethyl)but-3-enyl]-1,3,4-oxadiazol-2-yl]-6-bromo-5-(trifluoromethyl)-3-pyridyl]carbamate

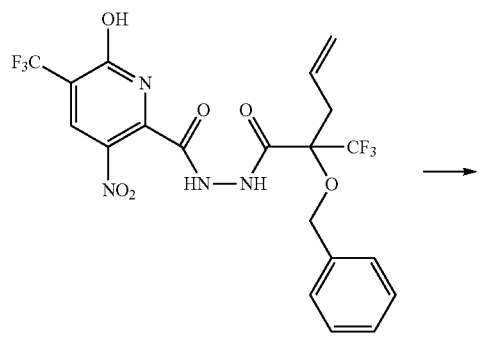

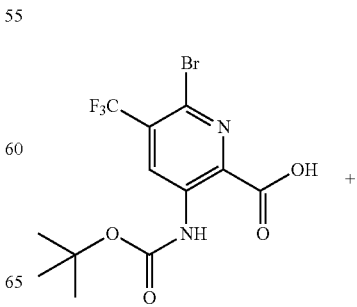

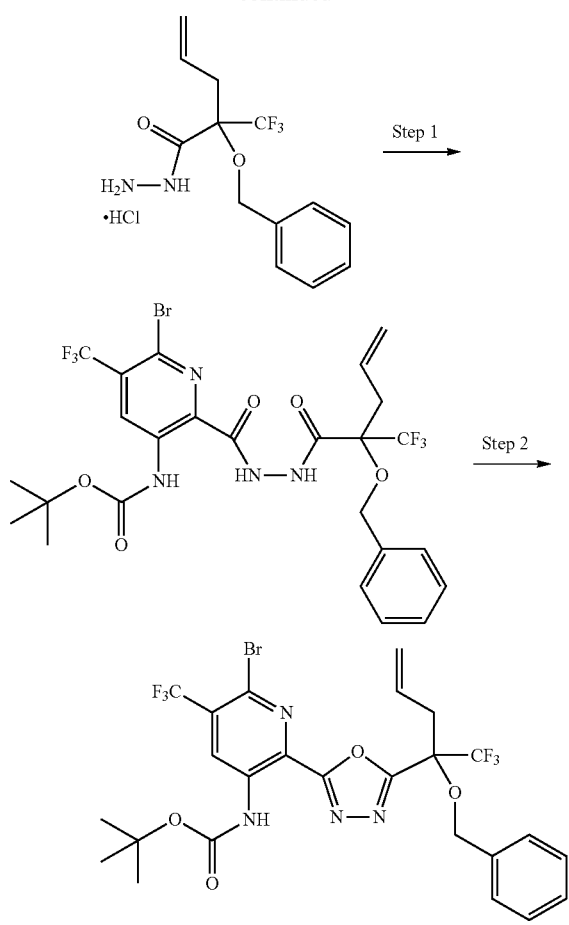

Step 1: tert-Butyl N-[2-[[[2-benzyloxy-2-(trifluoromethyl)pent-4-enoyl]amino]carbamoyl]-6-bromo-5-(trifluoromethyl)-3-pyridyl]carbamate

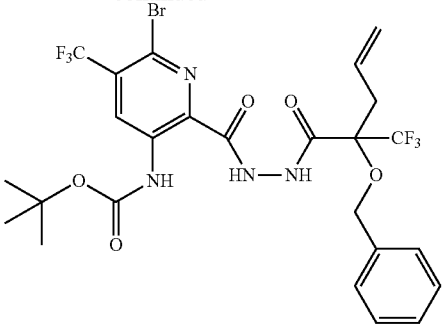

To a mixture of 6-bromo-3-(tert-butoxycarbonylamino)-5-(trifluoromethyl)pyridine-2-carboxylic acid (53 g, 137.6 mmol) and 2-benzyloxy-2-(trifluoromethyl)pent-4-enehydrazide (hydrochloride salt) (55 g, 169.4 mmol) in EtOAc (500 mL) at ambient temperature was added pyridine (44 mL, 544.0 mmol). To the mixture was added 1-propanephosphonic anhydride (111 g of 50% w/w, 174.4 mmol) and the reaction mixture stirred at ambient temperature for 12 h. The reaction was quenched with slow addition of NaOH (35 g of 50% w/w, 437.5 mmol) in water (500 mL) and the mixture stirred for 15 min. The organic phase was separated, and the aqueous phase extracted with EtOAc (500 mL). The combined organic phases washed with HCl (250 mL of 1 M, 250.0 mmol), brine, dried over MgSO$_4$, filtered and concentrated in vacuo. Purification by silica gel chromatography (0-20% EtOAc/hexanes) provided tert-butyl N-[2-[[[2-benzyloxy-2-(trifluoromethyl)pent-4-enoyl]amino]carbamoyl]-6-bromo-5-(trifluoromethyl)-3-pyridyl]carbamate (66 g, 73%) as pale pink solid. $^1$H NMR (400 MHz, DMSO) δ 11.11 (s, 1H), 10.91 (s, 1H), 10.40 (s, 1H), 9.16 (s, 1H), 7.47 (d, J=6.9 Hz, 2H), 7.42-7.29 (m, 3H), 5.91 (ddt, J=17.1, 10.6, 7.1 Hz, 1H), 5.37 (dd, J=17.2, 1.9 Hz, 1H), 5.22 (dd, J=10.4, 1.8 Hz, 1H), 4.85 (d, J=2.1 Hz, 2H), 3.20-2.91 (m, 2H), 1.50 (s, 9H) ppm. ESI-MS m/z calc. 654.09125, found 657.0 (M+1)$^+$; Retention time: 3.49 minutes. Final purity was determined by reversed phase UPLC using an Acquity UPLC BEH C$_{18}$ column (50×2.1 mm, 1.7 µm particle) made by Waters (pn: 186002350), and a dual gradient run from 1-99% mobile phase B over 4.5 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 µL, and column temperature=60° C.

Step 2: tert-Butyl N-[2-[5-[1-benzyloxy-1-(trifluoromethyl)but-3-enyl]-1,3,4-oxadiazol-2-yl]-6-bromo-5-(trifluoromethyl)-3-pyridyl]carbamate

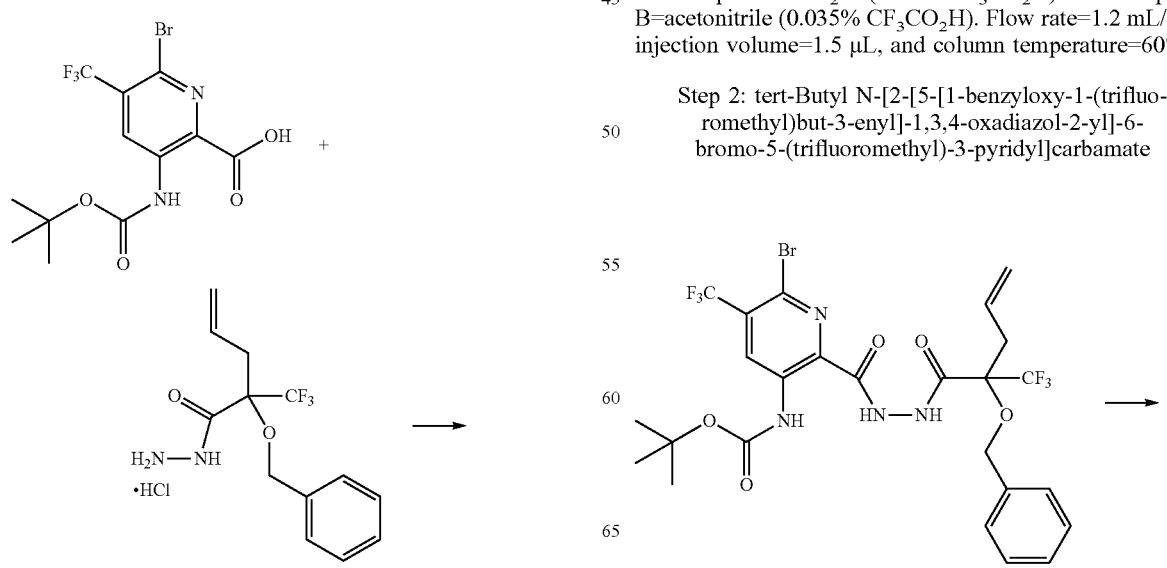

197

-continued

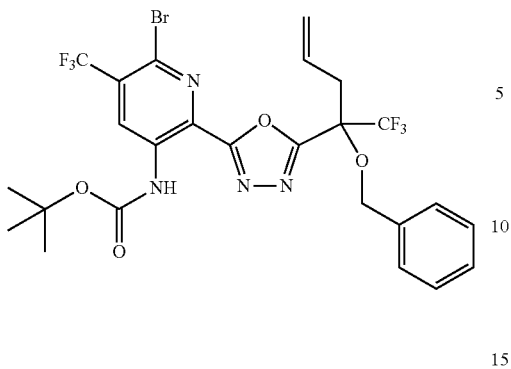

A solution of tert-butyl N-[2-[[[2-benzyloxy-2-(trifluoromethyl)pent-4-enoyl]amino]carbamoyl]-6-bromo-5-(trifluoromethyl)-3-pyridyl]carbamate (2.15 g, 3.2641 mmol) and DIPEA (1.12 g, 1.5 mL, 8.6117 mmol) in acetonitrile (43 mL) was heated at 50° C., then p-toluenesulfonyl chloride (765 mg, 4.0127 mmol) was added portion wise at 50° C. Resultant mixture was stirred at 70° C. for 2 hours. The reaction mixture was cooled, then basified with a saturated solution of sodium bicarbonate (100 mL) and extracted with ethyl acetate (3×50 mL). The combined organic layers were washed with brine (50 mL), dried over sodium sulfate, filtered and concentrated. Purification by silica gel chromatography (0% to 10% of ethyl acetate in heptanes) afforded tert-butyl N-[2-[5-[1-benzyloxy-1-(trifluoromethyl)but-3-enyl]-1,3,4-oxadiazol-2-yl]-6-bromo-5-(trifluoromethyl)-3-pyridyl]carbamate (1.7 g, 80%) as yellow viscous oil. $^1$H NMR (300 MHz, CDCl$_3$) δ 10.18 (br. s, 1H), 9.33 (br. s, 1H), 7.53-7.27 (m, 5H), 6.00-5.83 (m, 1H), 5.32-5.13 (m, 2H), 4.86-4.76 (m, 1H), 4.73-4.64 (m, 1H), 3.27-3.11 (m, 2H), 1.55 (s, 9H) ppm. $^{19}$F NMR (282 MHz, CDCl$_3$) δ −63.78 (s, 3F), −72.93 (s, 3F) ppm. No ionization by regular ESI method was observed, but ionization was observed using an APCI method: $(M-C_4H_8+1)^{++}=580.8$. ESI-MS m/z calc. 636.0807, Retention time: 2.7 minutes; LCMS Method: Kinetex Polar C$_{18}$ 3.0×50 mm 2.6 μm, 4 min, 5-95% acetonitrile in H$_2$O (0.1% formic acid) 1.2 mL/min.

Intermediate 14: Preparation of tert-butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]carbamate

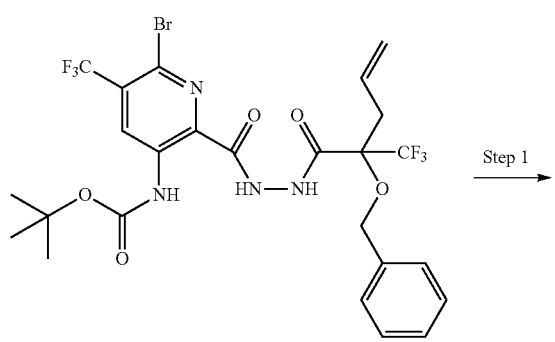

198

-continued

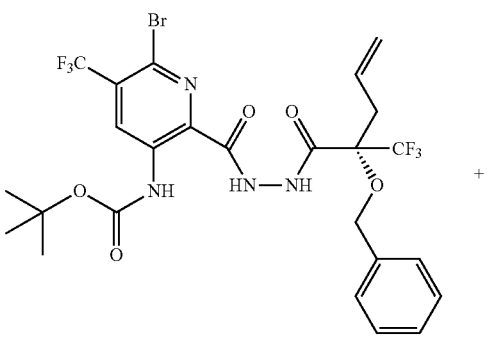

Enantiomer 1

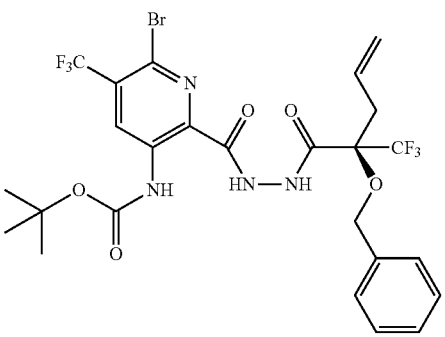

Enantiomer 2

↓ Step 2

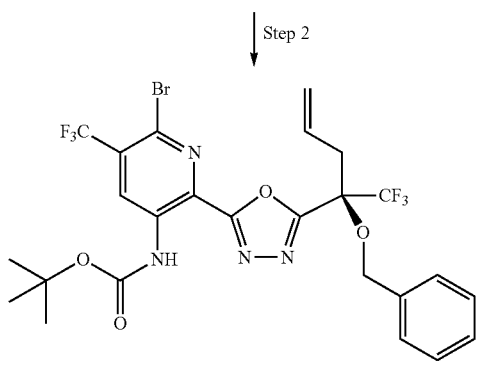

Step 1: tert-Butyl N-[2-[[[(2R)-2-benzyloxy-2-(trifluoromethyl)pent-4-enoyl]amino]carbamoyl]-6-bromo-5-(trifluoromethyl)-3-pyridyl]carbamate

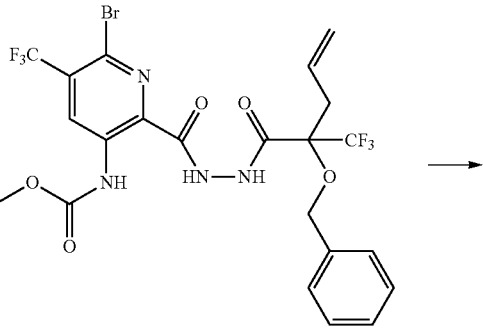

-continued

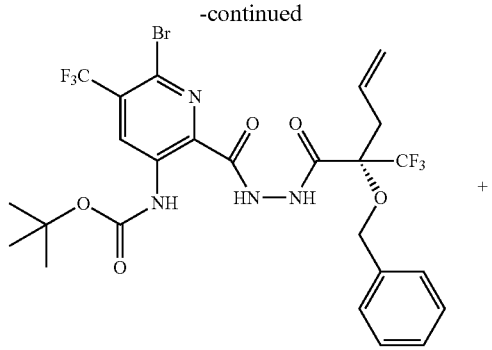

Enantiomer 1

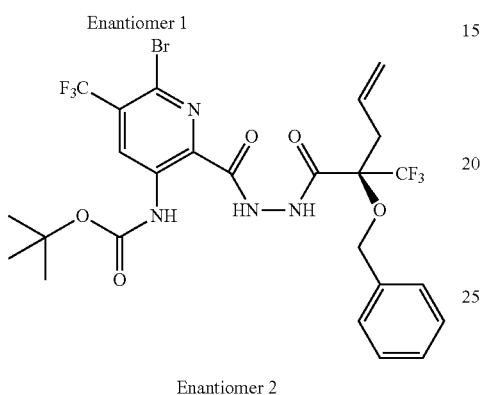

Enantiomer 2

The racemic tert-butyl N-[2-[[[2-benzyloxy-2-(trifluoromethyl)pent-4-enoyl]amino]carbamoyl]-6-bromo-5-(trifluoromethyl)-3-pyridyl]carbamate (24.5 g, 37.38 mmol) was purified by preparative chiral SFC by 500 μL injections of a 32 mg/mL solution onto a ChiralPak IC (250×21.2 mm), 5 μm column eluted at 40° C. at 70 mL/min with 8% MeOH (20 mM $NH_3$) and 92% $CO_2$. First eluting enantiomer-1 (Peak 1 at retention time=4.17 min) to provided tert-butyl N-[2-[[[(2S)-2-benzyloxy-2-(trifluoromethyl)pent-4-enoyl]amino]carbamoyl]-6-bromo-5-(trifluoromethyl)-3-pyridyl]carbamate (11.73 g, 96%). $^1$H NMR (400 MHz, Chloroform-d) δ 10.59 (s, 1H), 9.83 (s, 1H), 9.28 (s, 1H), 9.02 (d, J=29.6 Hz, 1H), 7.48-7.33 (m, 5H), 5.96-5.77 (m, 1H), 5.41 (d, J=1.6 Hz, 1H), 5.36-5.29 (m, 1H), 4.86 (s, 2H), 3.19 (dd, J=15.5, 5.9 Hz, 1H), 3.03 (dd, J=15.5, 7.8 Hz, 1H), 1.53 (s, 9H) ppm; $^{19}$F NMR (376 MHz, Chloroform-d) δ −63.89, −73.76 ppm. ESI-MS m/z calc. 654.09125, found 655.3 (M+1)$^+$; Retention time: 0.53 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

The later eluting enantiomer 2 (Peak 2 at retention time=6.63 min) provided tert-butyl N-[2-[[[(2R)-2-benzyloxy-2-(trifluoromethyl)pent-4-enoyl]amino]carbamoyl]-6-bromo-5-(trifluoromethyl)-3-pyridyl]carbamate (11.62 g, 95%). $^1$H NMR (400 MHz, Chloroform-d) δ 10.59 (s, 1H), 9.74 (s, 1H), 9.28 (s, 1H), 9.06 (s, 1H), 7.39 (d, J=4.4 Hz, 5H), 6.02-5.79 (m, 1H), 5.44-5.36 (m, 1H), 5.34 (dd, J=10.3, 1.3 Hz, 1H), 4.91-4.81 (m, 2H), 3.19 (dd, J=15.4, 5.8 Hz, 1H), 3.03 (dd, J=15.5, 7.8 Hz, 1H), 1.53 (s, 9H) ppm; $^{19}$F NMR (376 MHz, Chloroform-d) δ −63.89, −73.76 ppm. ESI-MS m/z calc. 654.09125, found 657.2 (M+1)$^+$; Retention time: 0.53 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

Step 2: tert-Butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]carbamate

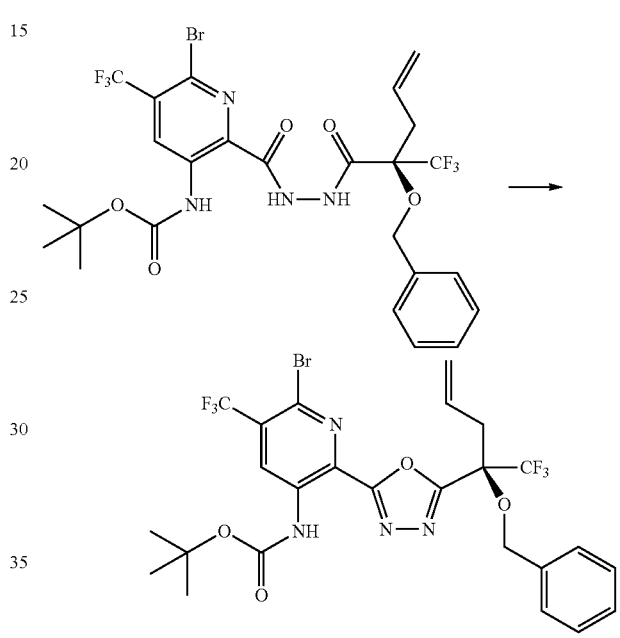

tert-Butyl N-[2-[[[(2R)-2-benzyloxy-2-(trifluoromethyl)pent-4-enoyl]amino]carbamoyl]-6-bromo-5-(trifluoromethyl)-3-pyridyl]carbamate (enantiomer 2) (24.97 g, 38.10 mmol) was dissolved in anhydrous acetonitrile (200 mL) under nitrogen, making a clear yellow solution. DIPEA (19.91 mL, 114.3 mmol) was added, and the solution turned orange. The solution was heated to 70° C., then p-toluenesulfonyl chloride (7.99 g, 41.91 mmol) was added in 3 portions at 30 min intervals and heated for about 3 h. The reaction mixture was cooled to room temperature and evaporated majority of the acetonitrile at 45° C. Added 145 mL MTBE, followed by a solution of citric acid (11.0 g, 57.25 mmol) in 250 mL water, stirred, then added 73 mL hexanes. Separated the layers and water layer extracted with MTBE. Combined the organic layers dried over $MgSO_4$, concentrated in vacuo at 45° C. Purification by silica gel chromatography (15% to 80% of hexanes (as solvent A) in 10% EtOAc/hexanes (as solvent B)) provided tert-butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]carbamate (20.47 g, 84%). $^1$H NMR (400 MHz, Chloroform-d) δ 10.18 (s, 1H), 9.34 (s, 1H), 7.48 (d, J=7.1 Hz, 2H), 7.39 (t, J=7.5 Hz, 2H), 7.31 (t, J=7.3 Hz, 1H), 6.00-5.81 (m, 1H), 5.25 (d, J=17.1, 1.6 Hz, 1H), 5.20 (d, J=10.1, 1.5 Hz, 1H), 4.82 (d, J=10.6 Hz, 1H), 4.70 (d, J=10.6 Hz, 1H), 3.30-3.09 (m, 2H), 1.56 (s, 9H) ppm. ESI-MS m/z calc. 636.0807, found 637.3 (M+1)$^+$; Retention time: 3.81 minutes. LCMS Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=acetonitrile (0.035% $CF_3CO_2H$). Flow rate=1.2 mL/min, injection volume=1.5 μL, and column temperature=60° C.

Intermediate 15: Preparation of tert-butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate

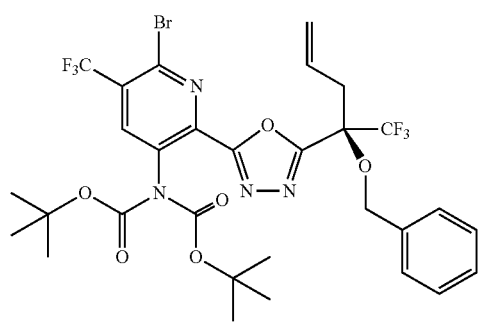

Step 1

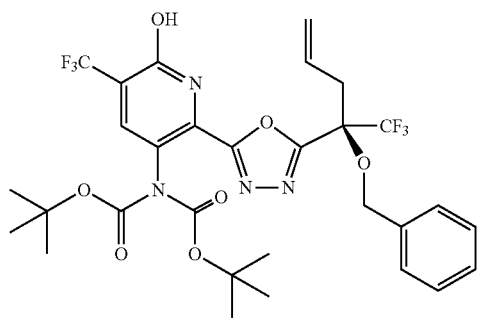

Step 1: tert-Butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate

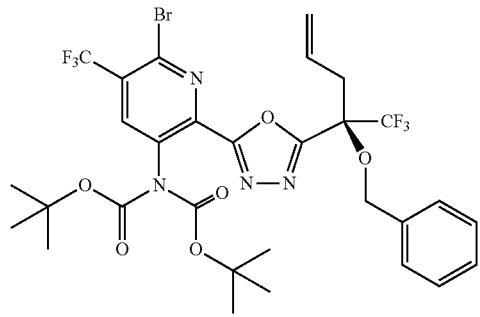

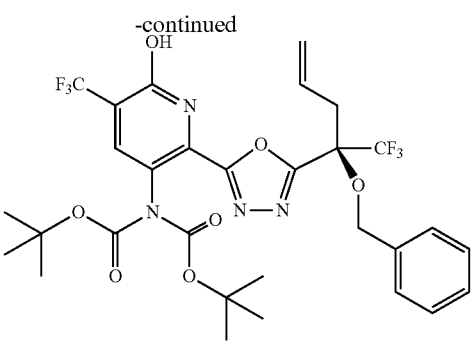

To a stirring solution of tert-butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]-N-tert-butoxycarbonyl-carbamate (5.52 g, 7.485 mmol) in DMSO (35.86 mL) at room temperature was added cesium acetate (1.437 g, 7.486 mmol) and the mixture was capped and heated under nitrogen atmosphere at 80° C. overnight. Cooled to room temperature and diluted with saturated aqueous $NH_4Cl$ then extracted with EtOAc (2×). Combined the organic fractions, dried over $MgSO_4$, filtered and concentrated to a yellow oil. Purification by silica gel chromatography (100% hexanes to 100% EtOAc) giving as a white solid, tert-butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate (1.8 g, 36%). ESI-MS m/z calc. 674.2175, found 575.2 (M-Boc)$^+$. Retention time: 0.45 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

Intermediate 16: Preparation of tert-butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]-N-tert-butoxycarbonyl-carbamate

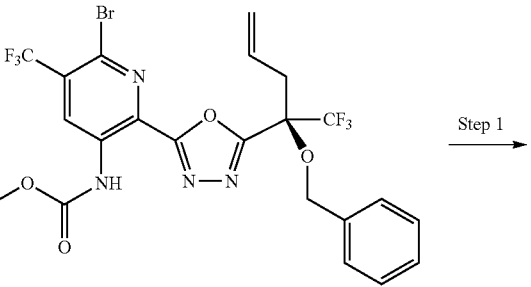

Step 1

Step 1: tert-Butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]-N-tert-butoxycarbonyl-carbamate

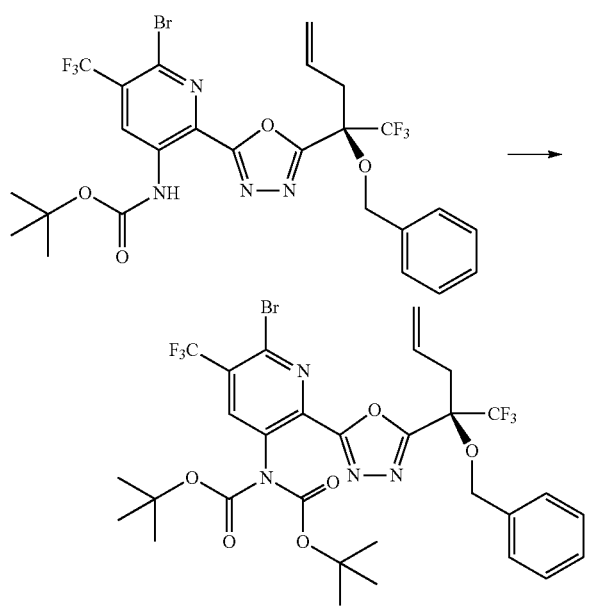

di-tert-Butyl dicarbonate (208 mg, 0.9530 mmol) and triethylamine (400 µL, 2.870 mmol) were added to a solution of tert-butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]carbamate (500 mg, 0.7531 mmol) dissolved in dioxane (5 mL) followed by DMAP (14 mg, 0.1146 mmol). The reaction mixture was stirred for 3 hours at room temperature. The mixture was concentrated to half of its volume and water was added. Extracted with ethyl acetate and combined organics washed with brine. The organics were separated, dried over sodium sulfate, and evaporated. Purification by silica gel chromatography (0 to 50% EtOAc in hexanes) provided tert-butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]-N-tert-butoxycarbonyl-carbamate (487 mg, 88%) as white solid. $^1$H NMR (400 MHz, DMSO-$d_6$) δ 8.90 (s, 1H), 7.49 (d, J=7.5 Hz, 2H), 7.42 (t, J=7.4 Hz, 2H), 7.35 (t, J=7.3 Hz, 1H), 5.93 (dq, J=17.1, 7.6 Hz, 1H), 5.38 (d, J=17.0 Hz, 1H), 5.25 (d, J=10.2 Hz, 1H), 4.78 (d, J=10.6 Hz, 1H), 4.65 (d, J=10.6 Hz, 1H), 2.50 (p, J=1.8 Hz, 2H), 1.27 (d, J=21.4 Hz, 18H) ppm. ESI-MS m/z calc. 736.1331, found 739.2 (M+1)$^+$; Retention time: 1.66 minutes. Final purity was determined by reversed phase UPLC using an Acquity UPLC BEH $C_{18}$ column (50×2.1 mm, 1.7 µm particle) made by Waters (pn: 186002350), and a dual gradient run from 50-99% mobile phase B over 2.9 minutes. Mobile phase A=$H_2O$ (0.05% $CF_3CO_2H$). Mobile phase B=acetonitrile (0.035% $CF_3CO_2H$). Flow rate=1.2 mL/min, injection volume=1.5 µL, and column temperature=60° C.

Intermediate 17: Preparation of (2R)-2-benzyloxy-2-(trifluoromethyl)hex-5-enoic acid

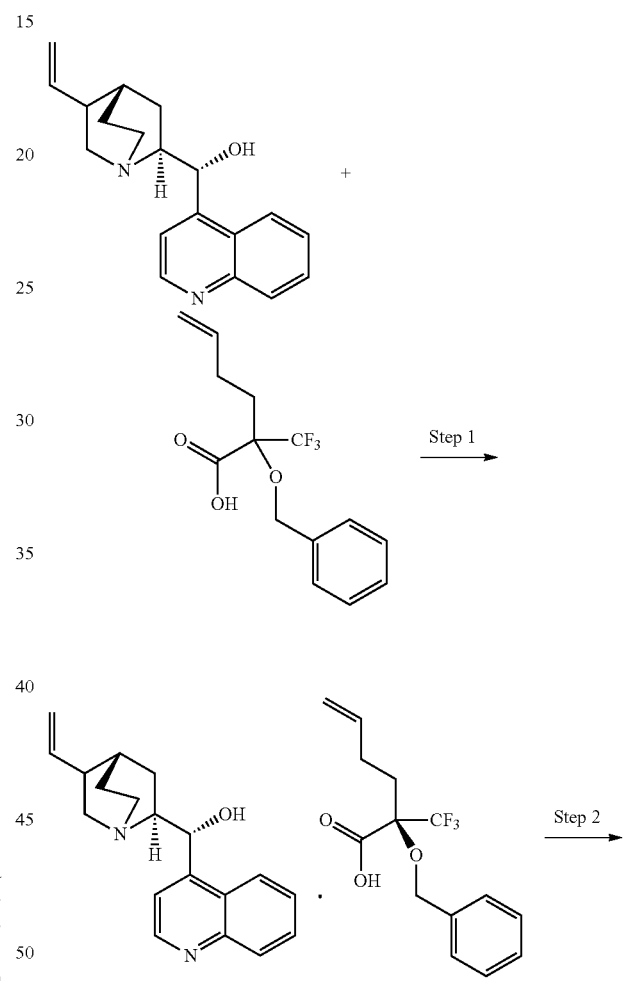

Step-1: (2R)-2-Benzyloxy-2-(trifluoromethyl)hex-5-enoic acid; (R)-4-quinolyl-[(2S,4S)-5-vinylquinuclidin-2-yl]methanol

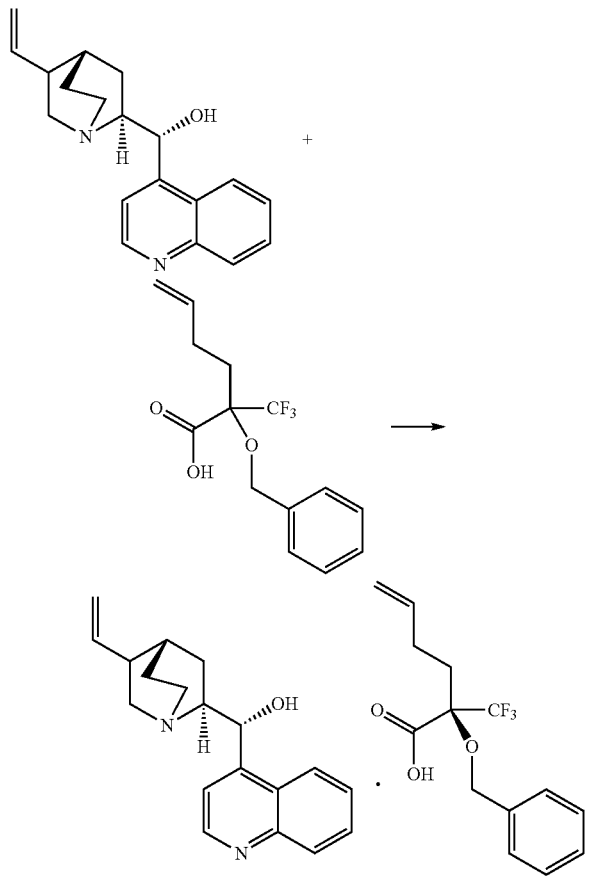

To a N₂ purged jacketed reactor set to 20° C. was added isopropyl acetate (IPAC, 100 L, 0.173 M, 20 Vols), followed by previously melted 2-benzyloxy-2-(trifluoromethyl)hex-5-enoic acid (5.00 kg, 17.345 mol) and cinchonidine (2.553 kg, 8.67 mol) made into a slurry with minor amount of the reaction solvent. The reactor was set to ramp internal temperature to 80° C. over 1 hour, with solids going in solution upon heating to set temperature, then the solution was held at temperature for at least 10 minutes, then cooled to 70° C. held and seeded with chiral salt (50 g, 1.0% by wt). The mixture was stirred for 10 minutes, then ramped to 20° C. internal temperature over 4 hours, then held overnight at 20° C. The mixture was filtered, cake washed with isopropyl acetate (10.0 L, 2.0 vols) and dried under vacuum. The cake was then dried in vacuo (50° C., vacuum) to afford 4.7 kg of salt. The resulting solid salt was returned to the reactor by making a slurry with a portion of isopropyl acetate (94 L, 20 vol based on current salt wt), and pumped into reactor and stirred. The mixture was then heated to 80° C. internal, stirred hot slurry for at least 10 minutes, then ramped to 20° C. over 4-6 h, then stirred overnight at 20° C. The material was then filtered and cake washed with isopropyl acetate (9.4 L, 2.0 vol), pulled dry, cake scooped out and dried in vacuo (50° C., vacuum) to afford 3.1 kg of solid. The solid (3.1 kg) and isopropyl acetate (62 L, 20 vol based on salt solid wt) was slurried and added to a reactor, stirred under N₂ purge and heated to 80° C. and held at temperature at least 10 minutes, then ramped to 20° C. over 4-6 hours, then stirred overnight. The mixture was filtered, cake washed with isopropyl acetate (6.2 L, 2 vol), pulled dry, scooped out and dried in vacuo (50° C., vac) to afford 2.25 kg of solid salt. The solid (2.25 kg) and isopropyl acetate (45 L, 20 vol based on salt solid wt) was slurried and added to a reactor, stirred under N₂ purge and heated to 80° C., held at temperature at least 10 minutes, then ramped to 20° C. over 4-6 hours, then stirred overnight. The mixture was filtered, cake washed with isopropyl acetate (4.5 L, 2 vol), pulled dry, scooped out and dried in vacuo (50° C. to afford (2R)-2-benzyloxy-2-(trifluoromethyl)hex-5-enoic acid;(R)-4-quinolyl-[(2S,4S)-5-vinylquinuclidin-2-yl]methanol (1.886 kg, >98.0% ee) as off-white to tan solid. Chiral purity was determined by Agilent 1200 HPLC instrument using Phenomenex Lux i-Amylose-3 column (3 μm, 150×4.6 mm) and a dual, isocratic gradient run 30% to 70% mobile phase B over 20.0 minutes. Mobile phase A=H₂O (0.1% CF₃CO₂H). Mobile phase B=MeOH (0.1% CF₃CO₂H). Flow rate=1.0 mL/min, injection volume=2 μL, and column temperature=30° C., sample concentration: 1 mg/mL in 60% acetonitrile/40% water.

Step 2: (2R)-2-Benzyloxy-2-(trifluoromethyl)hex-5-enoic acid

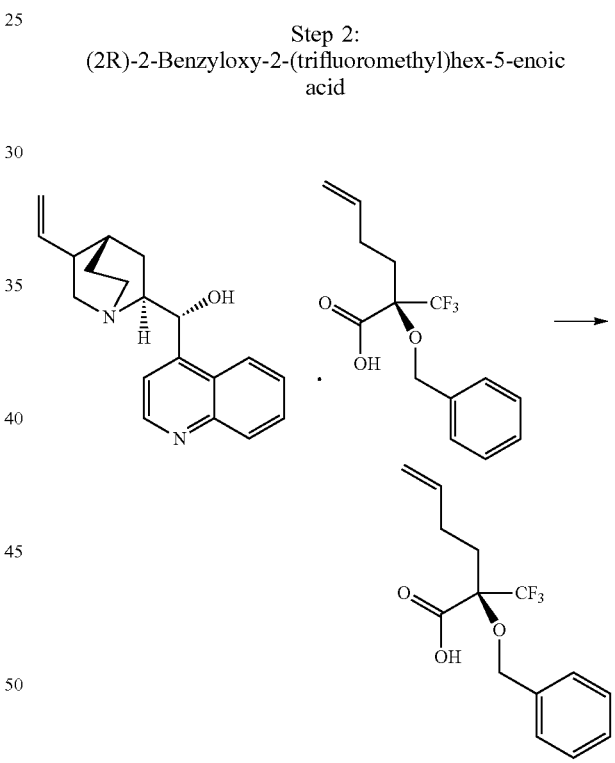

A suspension of (2R)-2-benzyloxy-2-(trifluoromethyl)hex-5-enoic acid; (R)-4-quinolyl-[(2S,4S)-5-vinylquinuclidin-2-yl]methanol (50 g, 87.931 mmol) in ethyl acetate (500.00 mL) was treated with an aqueous solution of hydrochloric acid (200 mL of 1 M, 200.00 mmol). After stirring 15 minutes at room temperature, the two phases were separated. The aqueous phase was extracted twice with ethyl acetate (200 mL). The combined organic layer was washed with 1 N HCl (100 mL). The organic layer was dried over sodium sulfate, filtered and concentrated. The material was dried over high vacuum overnight to give (2R)-2-benzyloxy-2-(trifluoromethyl)hex-5-enoic acid (26.18 g, 96%) as pale brown oil. ¹H NMR (400 MHz, CDCl₃) δ 7.46-7.31 (m, 5H), 5.88-5.73 (m, 1H), 5.15-4.99 (m, 2H), 4.88 (d, J=10.3 Hz, 1H), 4.70 (d, J=10.3 Hz, 1H), 2.37-2.12 (m, 4H) ppm. $^{19}$F NMR (377 MHz, CDCl$_3$) δ −71.63 (br s, 3F) ppm. ESI-MS m/z calc. 288.0973, found 287.0 (M−1)$^-$; Retention time: 2.15 minutes. LCMS Method: Kinetex Polar C$_{18}$ 3.0×50 mm 2.6 μm, 3 min, 5-95% acetonitrile in H$_2$O (0.1% formic acid) 1.2 mL/min.

Intermediate 18: Preparation of (2R)-2-benzyloxy-2-(trifluoromethyl)hex-5-enehydrazide

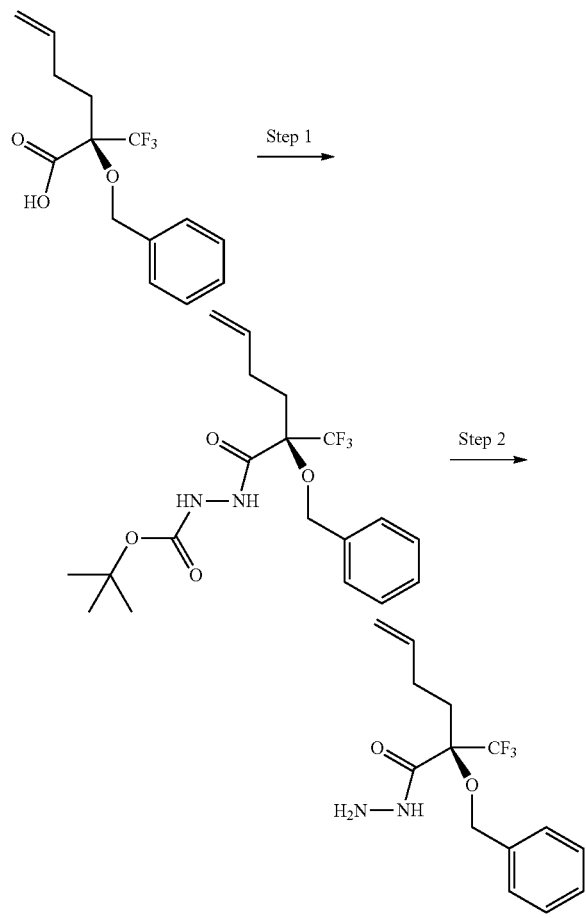

Step 1: tert-Butyl N-[[(2R)-2-benzyloxy-2-(trifluoromethyl)hex-5-enoyl]amino]carbamate

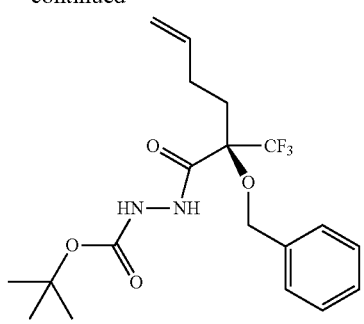

To a solution of (2R)-2-benzyloxy-2-(trifluoromethyl) hex-5-enoic acid (365 g, 1.266 mol) in DMF (2 L) was added HATU (612 g, 1.610 mol) and DIEA (450 mL, 2.584 mol) and the mixture was stirred at ambient temperature for 10 min. To the mixture was added tert-butyl N-aminocarbamate (200 g, 1.513 mol) (slight exotherm upon addition) and the mixture was stirred at ambient temperature for 16 h. The reaction was poured into ice water (5 L). The resultant precipitate was collected by filtration and washed with water. The solid was dissolved in EtOAc (2 L) and washed with brine. The organic phase was dried over MgSO$_4$, filtered and concentrated in vacuo. The oil was diluted with EtOAc (500 mL) followed by heptane (3 L) and stirred at ambient temperature for several hours affording a thick slurry. The slurry was diluted with additional heptane and filtered to collect fluffy white solid (343 g). The filtrate was concentrated and purification by silica gel chromatography (0-40% EtOAc/hexanes) provided tert-butyl N-[[(2R)-2-benzyloxy-2-(trifluoromethyphex-5-enoyl]amino]carbamate (464 g, 91%, combined with product from crystallization). ESI-MS m/z calc. 402.17664, found 303.0 (M+1-Boc)$^+$; Retention time: 2.68 minutes. Final purity was determined by reversed phase UPLC using an Acquity UPLC BEH C$_{18}$ column (50×2.1 mm, 1.7 μm particle) made by Waters (pn: 186002350) and a dual gradient run from 1-99% mobile phase B over 4.5 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C.

Step 2: (2R)-2-Benzyloxy-2-(trifluoromethyl)hex-5-enehydrazide

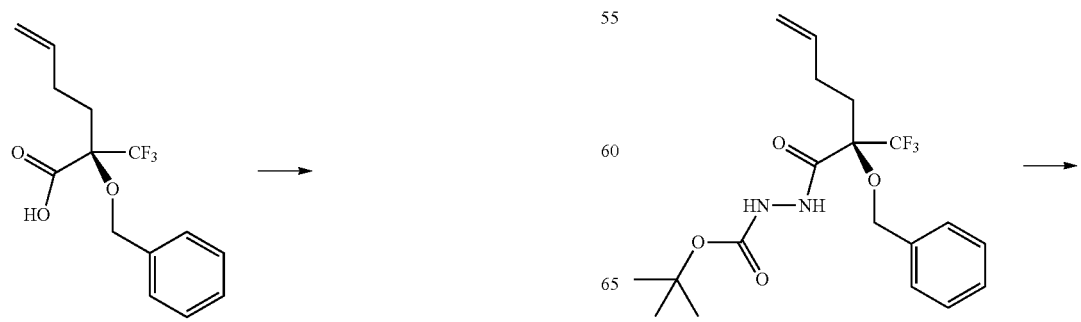

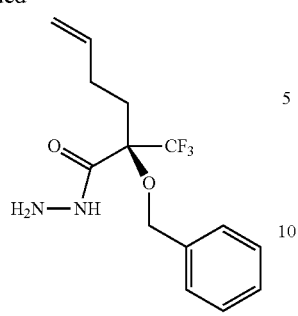

To a solution of tert-butyl N-[[(2R)-2-benzyloxy-2-(trifluoromethyl)hex-5-enoyl]amino]carbamate (464 g, 1.153 mol) in DCM (1.25 L) and was added HCl (925 mL of 4 M, 3.700 mol) and the mixture stirred at ambient temperature for 20 h. The mixture was concentrated in vacuo removing most of the DCM. The mixture was diluted with isopropyl acetate (1 L) and basified to pH=6 with NaOH (140 g of 50 w/w, 1.750 mol) in 1 L of ice water. The organic phase was separated and washed with 1 L of brine and the combined aqueous phases were extracted with isopropyl acetate (1 L). The combined organic phases were dried over MgSO$_4$, filtered and concentrated in vacuo affording a dark yellow oil of (2R)-2-benzyloxy-2-(trifluoromethyl)hex-5-enehydrazide (358 g, quant.). $^1$H NMR (400 MHz, CDCl$_3$) δ 8.02 (s, 1H), 7.44-7.29 (m, 5H), 5.81 (ddt, J=16.8, 10.1, 6.4 Hz, 1H), 5.13-4.93 (m, 2H), 4.75 (dd, J=10.5, 1.5 Hz, 1H), 4.61 (d, J=10.5 Hz, 1H), 3.78 (s, 2H), 2.43 (ddd, J=14.3, 11.0, 5.9 Hz, 1H), 2.26-1.95 (m, 3H) ppm. ESI-MS m/z calc. 302.1242, found 303.0 (M+1)$^+$; Retention time: 2.0 minutes. Final purity was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 4.5 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C.

Intermediate 19: Preparation of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate

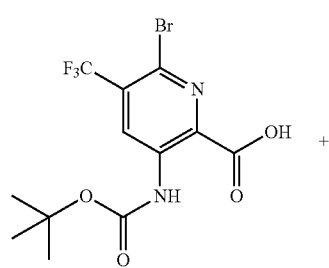

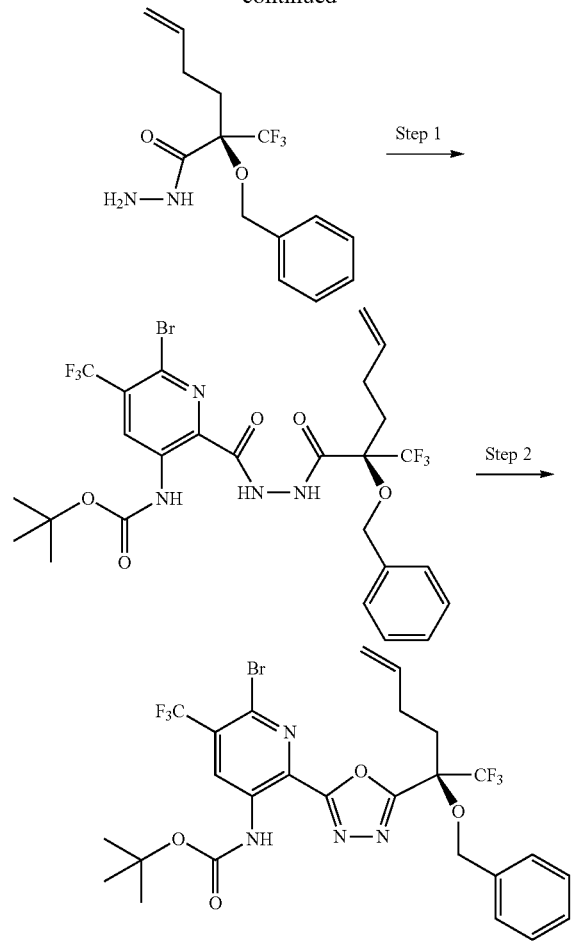

Step 1: tert-Butyl N-[2-[[[(2R)-2-benzyloxy-2-(trifluoromethyl)hex-5-enoyl]amino]carbamoyl]-6-bromo-5-(trifluoromethyl)-3-pyridyl]carbamate

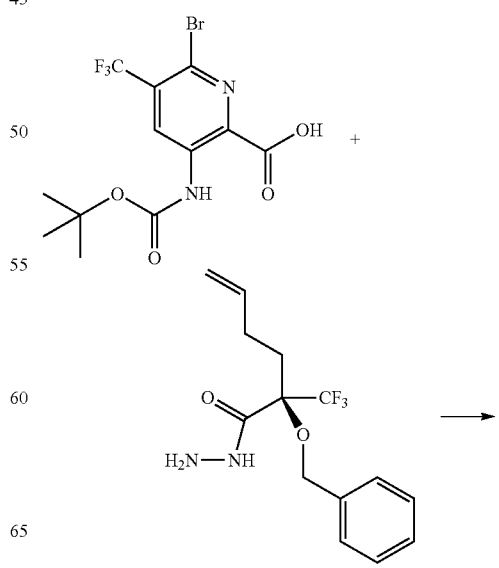

211

-continued

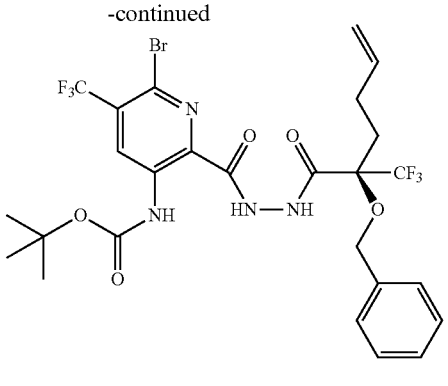

To a mixture of 6-bromo-3-(tert-butoxycarbonylamino)-5-(trifluoromethyl)pyridine-2-carboxylic acid (304 g, 789.3 mmol) and (2R)-2-benzyloxy-2-(trifluoromethyl)hex-5-en-ehydrazide (270 g, 893.2 mmol) in EtOAc (2.25 L) at ambient temperature was added DIEA (425 mL, 2.440 mol). To the mixture was slowly added $T_3P$ (622 g of 50% w/w, 977.4 mmol) using an ice-water bath to keep the temperature <35° C. (temperature rose to 34° C.) and the reaction mixture was stirred at ambient temperature for 18 h. Added additional DIEA (100 mL, 574.1 mmol) and $T_3P$ (95 g, 298.6 mmol) and stirred at ambient temperature for 2 days. Starting material was still observed and an additional $T_3P$ (252 g, 792 mmol) was added and stirred for 5 days. The reaction was quenched with the slow addition of water (2.5 L) and the mixture stirred for 30 min. The organic phase was separated, and the aqueous phase extracted with EtOAc (2 L). The combined organic phases were washed with brine, dried over $MgSO_4$, filtered and concentrated in vacuo. The crude product was dissolved in MTBE (300 mL) and diluted with heptane (3 L), the mixture stirred at ambient temperature for 12 h affording a light yellow slurry. The slurry was filtered, and the resultant solid was air dried for 2 h, then in vacuo at 40° C. for 48 h. The filtrate was concentrated in vacuo and purified by silica gel chromatography (0-20% EtOAc/hexanes) and combined with material obtained from crystallization providing tert-butyl N-[2-[[[(2R)-2-benzyloxy-2-(trifluoromethyphex-5-enoyl]amino]carbamoyl]-6-bromo-5-(trifluoromethyl)-3-pyridyl]carbamate (433 g, 82%). $^1$H NMR (400 MHz, DMSO) δ 11.07 (s, 1H), 10.91 (s, 1H), 10.32 (s, 1H), 9.15 (s, 1H), 7.53-7.45 (m, 2H), 7.45-7.28 (m, 3H), 5.87 (ddt, J=17.0, 10.2, 5.1 Hz, 1H), 5.09 (dq, J=17.1, 1.3 Hz, 1H), 5.02 (dd, J=10.3, 1.9 Hz, 1H), 4.84 (q, J=11.3 Hz, 2H), 2.37-2.13 (m, 4H), 1.49 (s, 9H) ppm. ESI-MS m/z calc. 668.1069, found 669.0 (M+1)$^+$; Retention time: 3.55 minutes. Final purity was determined by reversed phase UPLC using an Acquity UPLC BEH $C_{18}$ column (50×2.1 mm, 1.7 µm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 µL, and column temperature=60° C.

212

Step 2: tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate

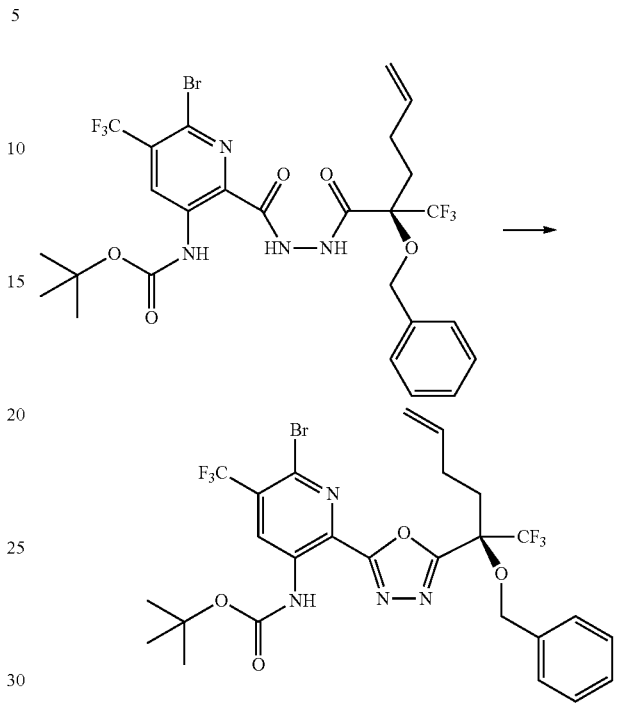

To a solution of tert-butyl N-[2-[[[(2R)-2-benzyloxy-2-(trifluoromethyphex-5-enoyl]amino]carbamoyl]-6-bromo-5-(trifluoromethyl)-3-pyridyl]carbamate (240 g, 358.5 mmol) in anhydrous acetonitrile (1.5 L) under nitrogen was added DIEA (230 mL, 1.320 mol) and the orange solution heated to 70° C. To the mixture was added p-toluenesulfonyl chloride (80.5 g, 422.2 mmol) in 3 equal portions over 1 h. The mixture was stirred at 70° C. for 9 h then additional p-toluenesulfonyl chloride (6.5 g, 34.09 mmol) was added. The mixture was stirred for a total of 24 h then allowed to cool to ambient temperature. Acetonitrile was removed in vacuo affording a dark orange oil which was diluted with EtOAc (1.5 L) and water (1.5 L). The organic phase was separated and washed with 500 mL of 1M HCl, 500 mL of brine, dried over $MgSO_4$, filtered and concentrated in vacuo. Purification by silica gel chromatography (0-20% EtOAc/hexanes) provided tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate (200 g, 86%). $^1$H NMR (400 MHz, DMSO) δ 10.11 (s, 1H), 9.10 (s, 1H), 7.55-7.48 (m, 2H), 7.47-7.28 (m, 3H), 5.87 (ddt, J=16.7, 10.2, 6.4 Hz, 1H), 5.11 (dt, J=17.2, 1.7 Hz, 1H), 5.01 (dt, J=10.2, 1.5 Hz, 1H), 4.74 (d, J=10.6 Hz, 1H), 4.65 (d, J=10.6 Hz, 1H), 2.55-2.42 (m, 2H), 2.30 (qd, J=11.3, 10.3, 6.9 Hz, 2H), 1.52 (s, 9H) ppm. ESI-MS m/z calc. 650.0963, found 650.0 (M+1)$^+$; Retention time: 3.78 minutes. Final purity was determined by reversed phase UPLC using an Acquity UPLC BEH $C_{18}$ column (50×2.1 mm, 1.7 µm particle) made by Waters (pn: 186002350), and a dual gradient run from 1-99% mobile phase B over 4.5 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 µL, and column temperature=60° C.

Intermediate 20: Preparation of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate

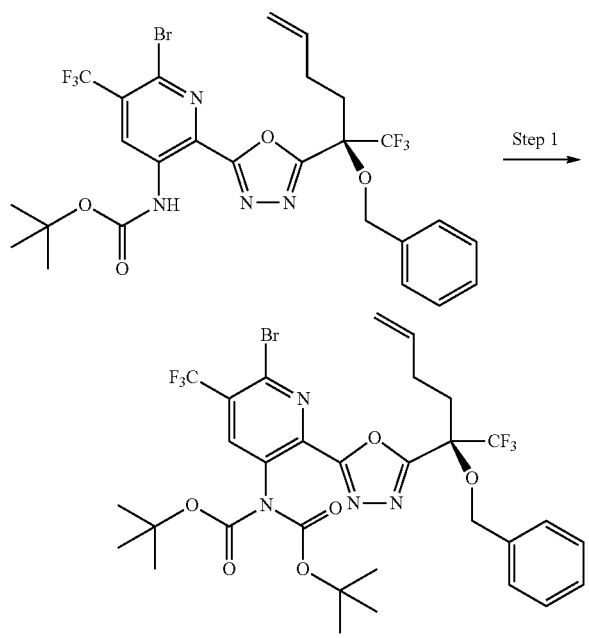

Step 1: tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate To a solution of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]carbamate (222 g, 340.8 mmol) in MTBE (1.333 L) was added DIPEA (65.3 mL, 374.9 mmol) followed DMAP (2.09 g, 17.11 mmol). Added a solution of di-tert-butyl dicarbonate (111.6 g, 511.3 mmol) in MTBE (250 mL) over approx. 8 minutes, and the resulting mixture was stirred for additional 30 min. Added 1 L of water and separated the layers. The organic layer was washed with KHSO$_4$ (886 mL of 0.5 M, 443.0 mmol), 300 mL brine, dried with MgSO$_4$ and most (>95%) of the MTBE was evaporated by rotary evaporation at 45° C., leaving a thick oil. Added 1.125 L of heptane, spun in the 45° C. rotovap bath until dissolved, then evaporated out 325 mL of solvent by rotary evaporation. The rotovap bath temp was allowed to drop to room temperature and product started crystallizing out during the evaporation. Then put the flask in a −20° C. freezer overnight. The resultant solid was filtered and washed with cold heptane and dried at room temperature for 3 days to give tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (240.8 g, 94%). $^1$H NMR (400 MHz, Chloroform-d) δ 7.95 (s, 1H), 7.52-7.45 (m, 2H), 7.44-7.36 (m, 2H), 7.36-7.29 (m, 1H), 5.83-5.67 (m, 1H), 5.08-5.00 (m, 1H), 5.00-4.94 (m, 1H), 4.79 (d, J=10.4 Hz, 1H), 4.64 (d, J=10.4 Hz, 1H), 2.57-2.26 (m, 3H), 2.26-2.12 (m, 1H), 1.41 (s, 18H) ppm. ESI-MS m/z calc. 750.14874, found 751.1 (M+1)$^+$; Retention time: 3.76 minutes. Final purity was determined by reversed phase UPLC using an Acquity UPLC BEH C$_{18}$ column (50×2.1 mm, 1.7 µm particle) made by Waters (pn: 186002350), and a dual gradient run from 1-99% mobile phase B over 4.5 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 and column temperature=60° C.

Intermediate 21: Preparation of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate

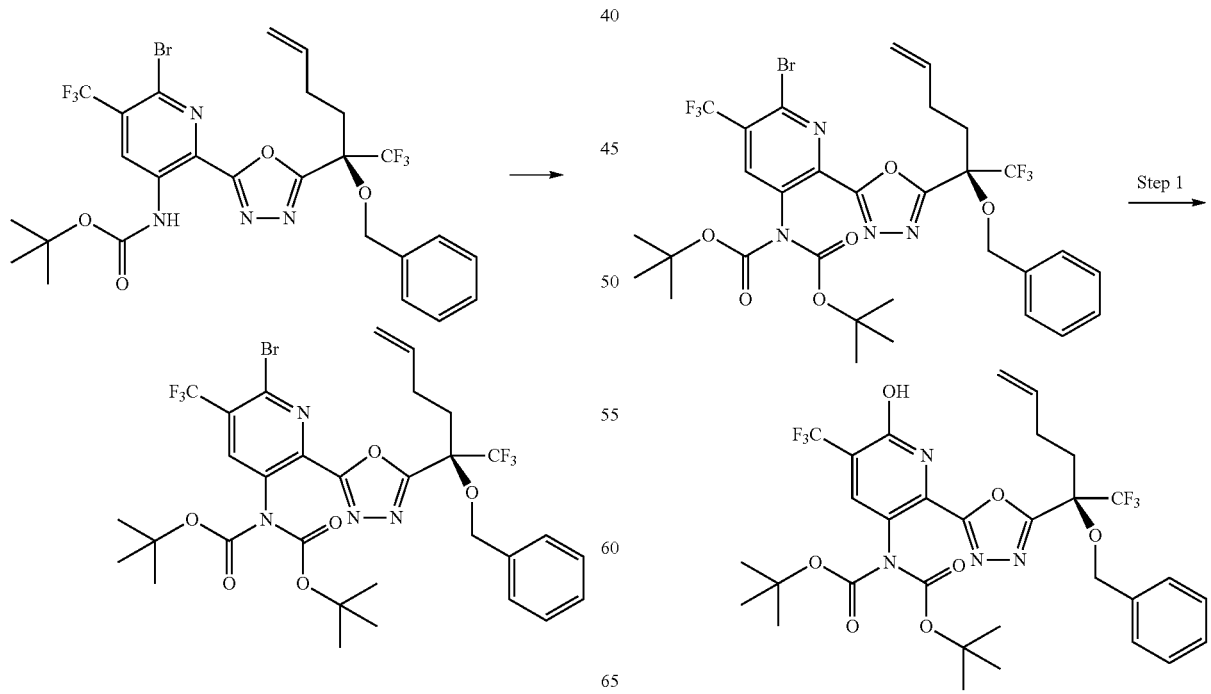

Step 1: tert-Butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate

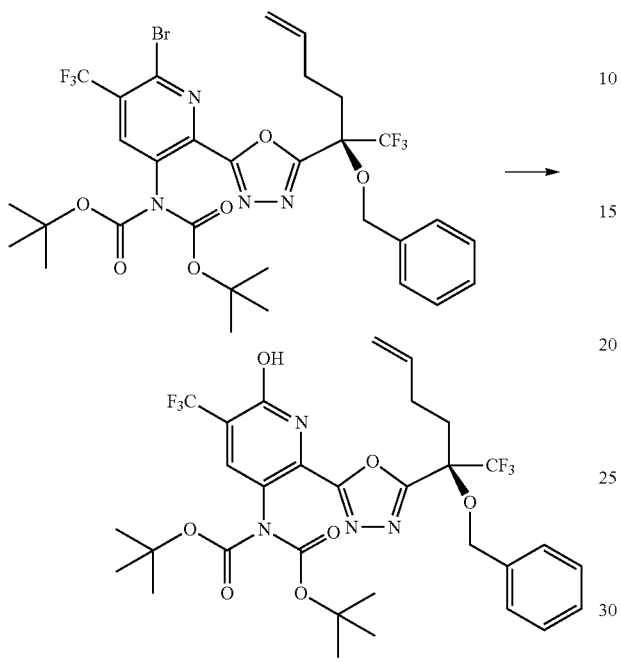

tert-Butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (280 g, 372.6 mmol) was dissolved in DMSO (1.82 L) (yellow solution) and treated with cesium acetate (215 g, 1.120 mol) under stirring at room temperature. The yellow suspension was heated at 80° C. for 5 h. The reaction mixture was cooled to room temperature and added to a stirred cold emulsion of water (5.5 L) with 1 kg ammonium chloride dissolved in it and a 1:1 mixture of MTBE and heptane (2 L) (in 20 L). The phases were separated and the organic phase washed water (3×3 L) and with brine (1×2.5 L). The organic phase was dried with MgSO$_4$, filtered and concentrated under reduced pressure. The resultant yellow solution was diluted with heptane (~1 L) and seeded with tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate and stirred on the rotavap at 100 mbar pressure at room temperature for 1.5 h. The solid mass was stirred mechanically for 2 h at room temperature, resultant thick fine suspension was filtered, washed with dry ice cold heptane and dried under vacuum at 45° C. with a nitrogen bleed for 16 h to give tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxy carbonyl-carbamate (220 g, 85%) as an off white solid. $^1$H NMR (400 MHz, DMSO-d$_6$) δ 13.28 (s, 1H), 8.43 (s, 1H), 7.58-7.26 (m, 5H), 5.85 (ddt, J=16.8, 10.3, 6.5 Hz, 1H), 5.10 (dq, J=17.2, 1.6 Hz, 1H), 5.01 (dq, J=10.2, 1.3 Hz, 1H), 4.76 (d, J=11.0 Hz, 1H), 4.65 (d, J=11.0 Hz, 1H), 2.55 (dd, J=9.6, 5.2 Hz, 2H), 2.23 (td, J=13.2, 10.0, 5.7 Hz, 2H), 1.27 (d, J=3.8 Hz, 18H) ppm. ESI-MS m/z calc. 688.23315, found 689.0 (M+1)$^+$; Retention time: 3.32 minutes. Final purity was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 4.5 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 μL, and column temperature=60° C.

Intermediate 22: Preparation of (2R)-2-benzyloxy-2-(trifluoromethyl)pent-4-enehydrazide

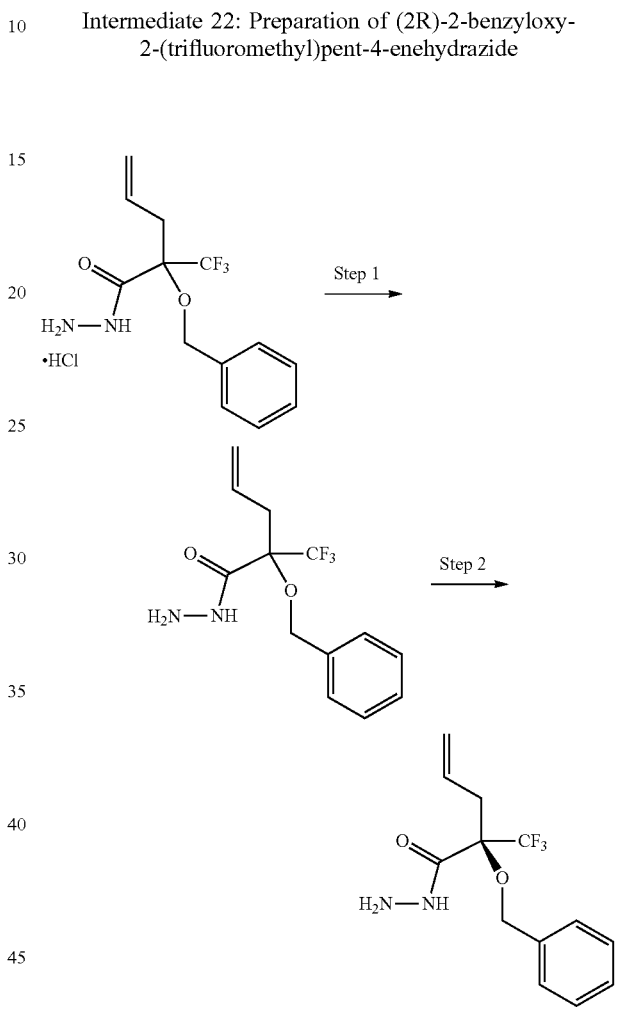

Step 1: 2-Benzyloxy-2-(trifluoromethyl)pent-4-enehydrazide

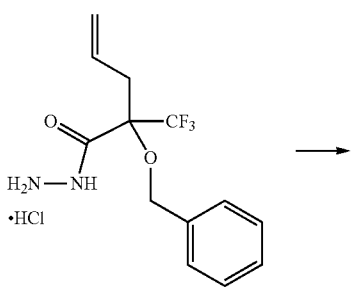

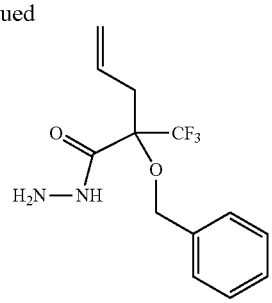

tert-Butyl N[[2-benzyloxy-2-(trifluoromethyl)pent-4-enoyl]amino]carbamate (386.49 g, 995.1 mmol) was dissolved in DCM (1.25 L) and toluene (250 mL) and treated with HCl (750 mL of 4 M, 3.000 mol) at room temperature and the yellow solution was stirred at room temperature for 18 h. The mixture was concentrated in vacuo and diluted with EtOAc (2 L). The mixture was treated with NaOH (600 mL of 2 M, 1.200 mol) and stirred at ambient temperature for 10 min. The organic phase was separated, washed with 1 L of brine, dried over MgSO$_4$, filtered and concentrated in vacuo and used directly in the ensuing step (trace toluene present), 2-benzyloxy-2-(trifluoromethyl)pent-4-enehydrazide (286 g, 100%). $^1$H NMR (400 MHz, DMSO) δ 9.34 (s, 1H), 7.40-7.22 (m, 5H), 5.69 (ddt, J=17.1, 10.3, 6.9 Hz, 1H), 5.33-5.23 (m, 1H), 5.15 (dd, J=10.3, 1.8 Hz, 1H), 4.73 (s, 2H), 4.51 (s, 2H), 3.05-2.87 (m, 2H) ppm. ESI-MS m/z calc. 288.10855, found 289.0 (M+1)$^+$; Retention time: 1.32 minutes. Final purity was determined by reversed phase UPLC using an Acquity UPLC BEH C$_{18}$ column (50×2.1 mm, 1.7 µm particle) made by Waters (pn: 186002350), and a dual gradient run from 1-99% mobile phase B over 2.9 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 µL, and column temperature=60° C.

Step 2: (2R)-2-Benzyloxy-2-(trifluoromethyl)pent-4-enehydrazide

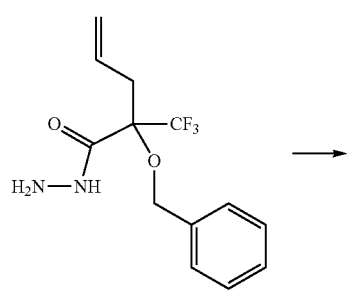

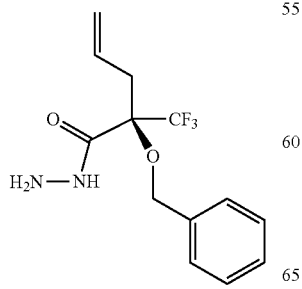

Racemic 2-benzyloxy-2-(trifluoromethyl)pent-4-enehydrazide (5.0 g, 17.35 mmol) was separated by chiral SFC using a ChiralPak IG column (250×21.2 mm; 5 µm) at 40° C. using a mobile phase 7% MeOH (plus 20 mM NH$_3$), 93% CO$_2$ at a 70 mL/min flow and concentration of the sample was 111 mg/mL in methanol (no modifier), injection volume=160 µL with an outlet pressure of 136 bar, detection wavelength of 210 nm providing as the second eluting enantiomer, (2R)-2-benzyloxy-2-(trifluoromethyl)pent-4-enehydrazide (1.7 g, 68%) as a white solid. $^1$H NMR (400 MHz, DMSO-d$_6$) δ 9.31 (s, 1H), 7.48-7.39 (m, 2H), 7.39-7.25 (m, 3H), 5.77-5.62 (m, 1H), 5.28 (dq, J=17.1, 1.6 Hz, 1H), 5.15 (dq, J=10.2, 1.5 Hz, 1H), 4.73 (s, 2H), 4.51 (s, 2H), 3.00 (dd, J=15.3, 7.5 Hz, 1H), 2.91 (dd, J=15.3, 6.4 Hz, 1H) ppm. ESI-MS m/z calc. 288.10855, found 289.2 (M+1)$^+$; Retention time: 1.28 minutes. Final purity was determined by reversed phase UPLC using an Acquity UPLC BEH C$_{18}$ column (50×2.1 mm, 1.7 µm particle) made by Waters (pn: 186002350), and a dual gradient run from 30-99% mobile phase B over 2.9 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 µL, and column temperature=60° C.

Intermediate 23: Preparation of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]carbamate

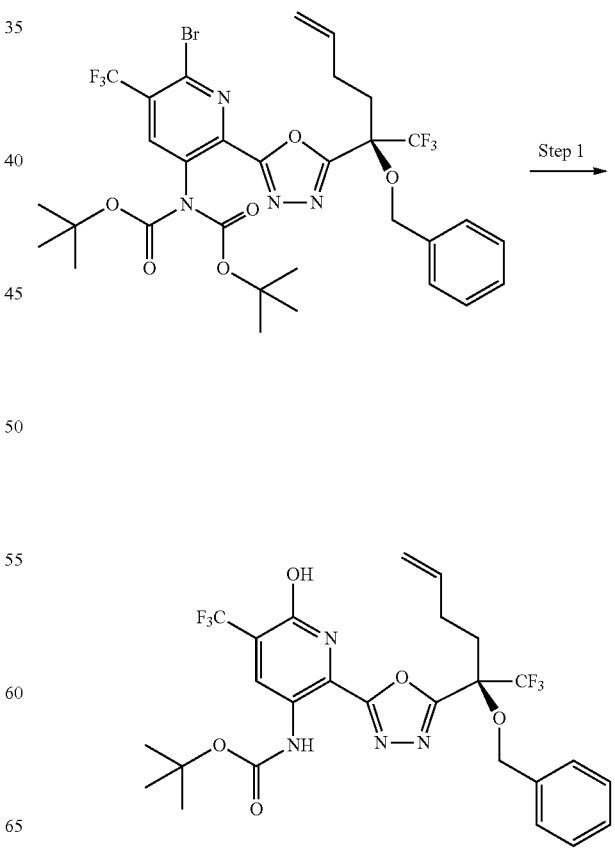

Step 1: tert-Butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]carbamate

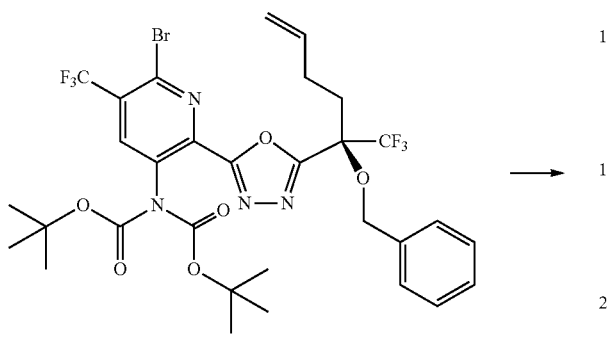

To a solution of tert-butyl N-[2-[5-[(1R)-1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (1.089 g, 1.449 mmol) in DMSO (13.61 mL) was added (2S)-pent-4-en-2-ol (745.5 µL, 7.244 mmol), cesium carbonate (1.496 g, 4.591 mmol) and iodocopper (63.93 mg, 0.3357 mmol) and the reaction mixture was heated at 80° C. for 1 h. The reaction mixture poured into saturated aqueous NH₄Cl and extracted with EtOAc. The organic layer was washed with brine, dried (MgSO₄), filtered and concentrated to an orange oil which was dissolved in THF (10.89 mL) and formic acid (10.89 mL, 288.7 mmol) was added, stirred 20 min then added formic acid (10.93 mL, 289.7 mmol) and stirred for 45 min. The reaction was quenched by slowly adding to saturated aqueous NaHCO₃ (vigorous gas evolution was observed) and EtOAc in a separatory funnel bringing the aqueous layer eventually to pH ~2-3. The aqueous layer was removed and the EtOAc layer was washed with saturated aqueous NaHCO₃ (still vigorous gas evolution) then dried over MgSO₄, filtered and concentrated to a yellow syrup which was purified by silica gel chromatography using a shallow gradient from 100% hexanes to 100% EtOAc giving several products including tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]carbamate in an impure form. This impure material was further purified by chromatography on a 275 g reverse phase $C_{18}$ column eluting with 50-100% acetonitrile/water giving as a clear syrup, tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]carbamate (126 mg, 15%). ESI-MS m/z calc. 588.1807, found 589.2 (M+1)⁺; Retention time: 0.51 minutes. Final purity was determined by reversed phase UPLC using an Acquity UPLC BEH $C_{18}$ column (30×2.1 mm, 1.7 µm particle) made by Waters (pn: 186002349), and a dual gradient run from 50-99% mobile phase B over 1.0 minutes. Mobile phase A=H₂O (0.05% CF₃CO₂H). Mobile phase B=CH₃CN (0.035% CF₃CO₂H). Flow rate=1.5 mL/min, injection volume=1.5 µL, and column temperature=60° C.

EXAMPLES

Example 1: Preparation of 6,15-bis(trifluoromethyl)-13,19-dioxa-3,4,18-triazatricyclo[12.3.1.1²,⁵]nonadeca-1(17),2,4,14(18),15-pentaen-6-ol, Compound 1

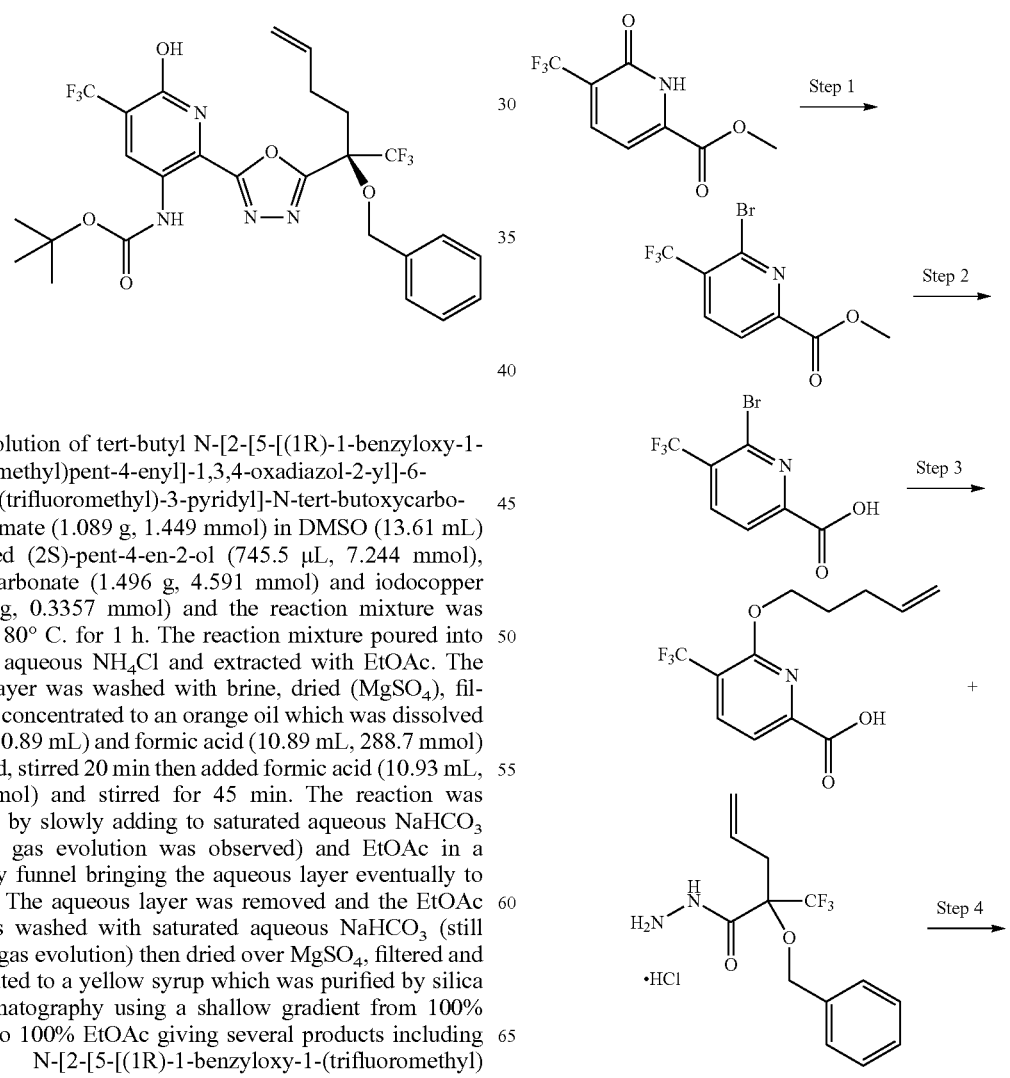

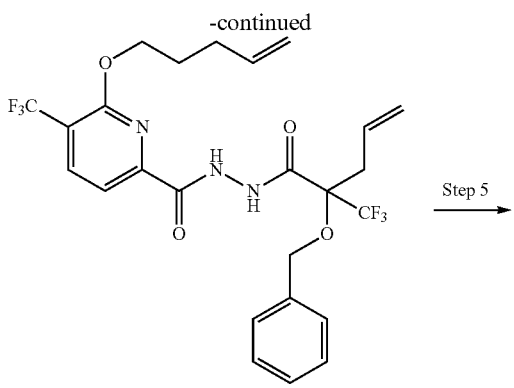

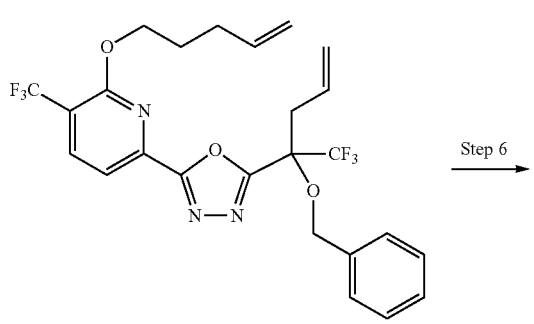

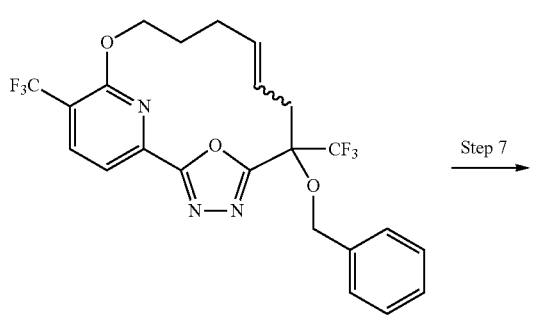

E/Z mixture

Step 1: Methyl 6-bromo-5-(trifluoromethyl)pyridine-2-carboxylate

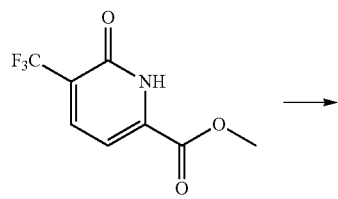

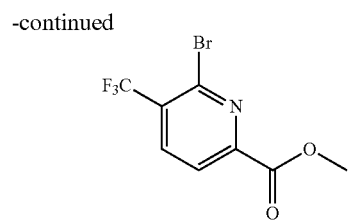

A mixture of methyl 6-oxo-5-(trifluoromethyl)-1H-pyridine-2-carboxylate (21.15 g, 95.64 mmol), POBr3 (41.14 g, 143.5 mmol) and DMF (350 mg, 4.788 mmol) in toluene (200 mL) was heated at 110° C. overnight. The mixture was cooled to 0° C. and poured on crushed ice (200 g). The mixture was neutralized to pH=7 with KHCO₃ (100 g, 10.5 eq) at <2° C. and extracted with EtOAc (2×200 mL). The combined organic layers were washed with 5% aqueous NaHCO₃ (100 mL) and brine (100 mL) and dried with Na₂SO₄. The mixture was filtered, and the solvent was removed by evaporation. The residue was triturated with heptanes/EtOAc (20:1) to give 22.92 g of pure product. The filtrate was concentrated to give 4.02 g, which was purified by flash chromatography (heptanes/EtOAc 0-30%) to give an additional 3.32 g of product. The two crops were combined to give methyl 6-bromo-5-(trifluoromethyl)pyridine-2-carboxylate (26.24 g, 96%) as a white solid. $^1$H NMR (300 MHz, CDCl₃) δ 4.04 (s, 3H), 8.05-8.30 (m, 2H) ppm. $^{19}$F NMR (282 MHz, CDCl₃) δ −63.8 (s, 3F) ppm. ESI-MS m/z calc. 282.9456, found 284.0 (M+1)⁺; Retention time: 4.04 minutes. LCMS Method: Symmetry, 4.6×75 mm 3.5 μm. Temp: 45° C., Flow: 2.0 mL/min, run time: 8 min. Mobile Phase: Initial 95% H₂O (0.1% formic acid) and 5% CH₃CN (0.1% formic acid) linear gradient to 95% CH₃CN (0.1% formic acid) for 6.0 min then held at 95% CH₃CN (0.1% formic acid) for 2.0 min.

Step 2: 6-Bromo-5-(trifluoromethyl)pyridine-2-carboxylic acid

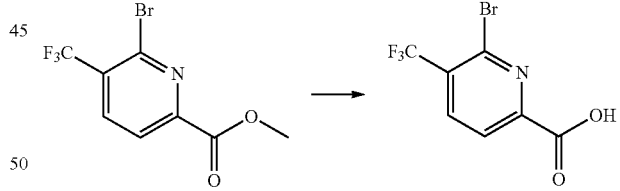

To a solution of methyl 6-bromo-5-(trifluoromethyl)pyridine-2-carboxylate (10.5 g, 36.968 mmol) in THF (100 mL) was added a solution of lithium hydroxide monohydrate (1.8 g, 42.894 mmol) in water (70 mL). This mixture was stirred 45 min at room temperature. The THF was evaporated in vacuo. Water (60 mL) was added to the remaining aqueous solution and the pH was adjusted to 3-4 by addition of 3 N hydrochloric acid (T<5° C.) leading to precipitation of the desired product. The solid was recovered by filtration and dried in-vacuo to give 6-bromo-5-(trifluoromethyl)pyridine-2-carboxylic acid (9.46 g, 95%) as a white solid. $^1$H NMR (300 MHz, CDCl₃) δ 8.18-8.28 (m, 1H), 8.28-8.39 (m, 1H) ppm. $^{19}$F NMR (282 MHz, CDCl₃) δ −63.8 (s, 3F) ppm. ESI-MS m/z calc. 268.92993, found 270.0 (M+1)⁺; Retention time: 2.08 minutes; LCMS Method: Kinetex C₁₈ 4.6×50 mm 2.6 µM. Temp: 45° C., Flow: 2.0 mL/min, Run Time: 6 min. Mobile Phase: Initial 95% H₂O (0.1% formic acid) and 5% CH₃CN (0.1% formic acid) linear gradient to 95% CH₃CN (0.1% formic acid) for 4.0 min then held at 95% CH₃CN (0.1% formic acid) for 2.0 min.

Step 3: 6-Pent-4-enoxy-5-(trifluoromethyl)pyridine-2-carboxylic acid

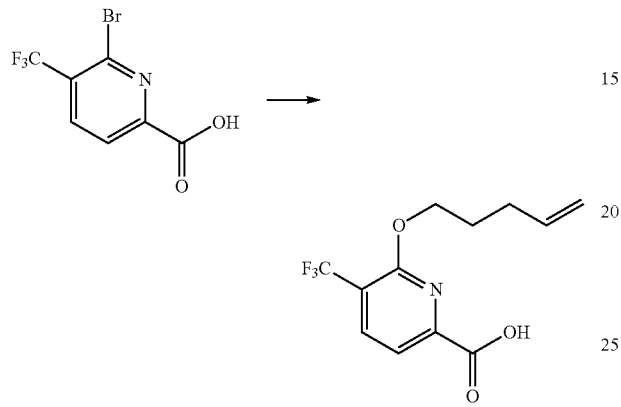

To a solution of pent-4-en-1-ol (1.5 mL, 14.79 mmol) in DMF (12 mL) was added sodium hydride (1.05 g of 60% w/w, 26.25 mmol) and the reaction mixture was stirred at room temperature for 0.5 h. The mixture was cooled to 0° C. and 6-bromo-5-(trifluoromethyl)pyridine-2-carboxylic acid (2 g, 7.407 mmol) in DMF (12 mL) was added. The reaction mixture was warmed to room temperature and stirred for another 2 h. The mixture was carefully quenched with water (2 mL). The solvent was removed in vacuo and the reaction mixture was diluted with MeOH and filtered. The filtrate was evaporated and purified by reverse phase chromatography on C₁₈ column using a gradient elution of 20%-70% water/acetonitrile and a flow rate of 80 mL/min over 20 min to afford 6-pent-4-enoxy-5-(trifluoromethyl)pyridine-2-carboxylic acid (1.73 g, 85%). ESI-MS m/z calc. 275.07693, found 274.0 (M−1)⁺; Retention time: 0.83 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 4: N'-[2-Benzyloxy-2-(trifluoromethyl)pent-4-enoyl]-6-pent-4-enoxy-5-(trifluoromethyl)pyridine-2-carbohydrazide

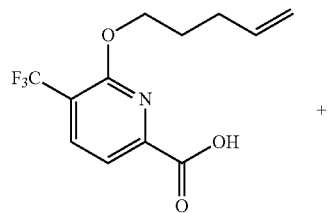

+

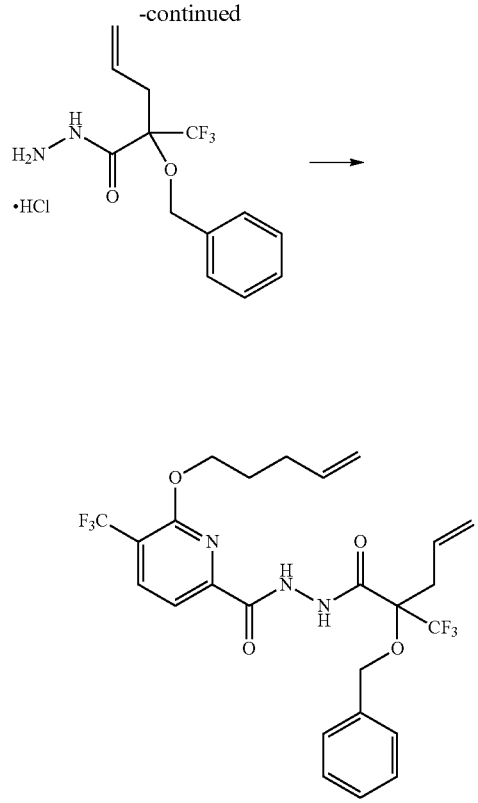

To a stirred solution of 6-pent-4-enoxy-5-(trifluoromethyl)pyridine-2-carboxylic acid (427.6 mg, 1.540 mmol) and HATU (761.2 mg, 2.002 mmol) in DMF (5 mL) was added DIPEA (697.4 µL, 4.004 mmol) (exotherm). After 5 min, 2-benzyloxy-2-(trifluoromethyl)pent-4-enehydrazide (hydrochloride salt) (500 mg, 1.540 mmol) was added in one portion and the mixture was stirred for 30 min. The reaction mixture was diluted with water (15 mL), extracted with ethyl acetate (3×15 mL) and the combined extracts were washed with brine then dried (MgSO₄). The residue was purified by silica gel chromatography eluting with a gradient of ethyl acetate in hexanes (10% to 33%) to afford N'-[2-benzyloxy-2-(trifluoromethyl)pent-4-enoyl]-6-pent-4-enoxy-5-(trifluoromethyl)pyridine-2-carbohydrazide (725 mg, 86%) as colorless gum. ¹H NMR (400 MHz, Chloroform-d) δ 9.71 (s, 1H), 9.16 (s, 1H), 7.96 (d, J=7.7 Hz, 1H), 7.77-7.70 (m, 1H), 7.38-7.26 (m, 5H), 5.88-5.72 (m, 2H), 5.36-5.22 (m, 2H), 5.05-4.90 (m, 2H), 4.85-4.73 (m, 2H), 4.40 (t, J=6.2 Hz, 2H), 3.11 (dd, J=15.5, 5.9 Hz, 1H), 2.96 (dd, J=15.5, 7.8 Hz, 1H), 2.25-2.13 (m, 2H), 1.87 (dt, J=7.9, 6.3 Hz, 2H) ppm. ESI-MS m/z calc. 545.1749, found 546.21 (M+1)⁺; Retention time: 1.12 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 5: 2-[1-Benzyloxy-1-(trifluoromethyl)but-3-enyl]-5-[6-pent-4-enoxy-5-(trifluoromethyl)-2-pyridyl]-1,3,4-oxadiazole

Step 6: 6-Benzyloxy-6,15-bis(trifluoromethyl)-13,19-dioxa-3,4,18-triazatricyclo[12.3.1.12,5]nonadeca-1(17),2,4,8,14(18),15-hexaene (E/Z Mixture)

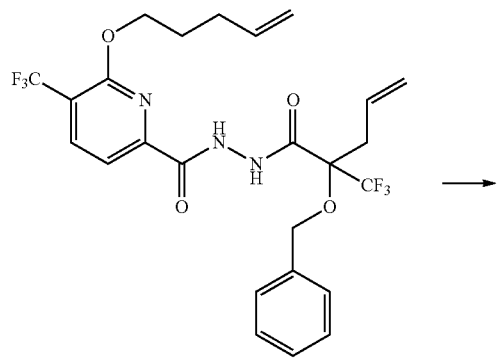

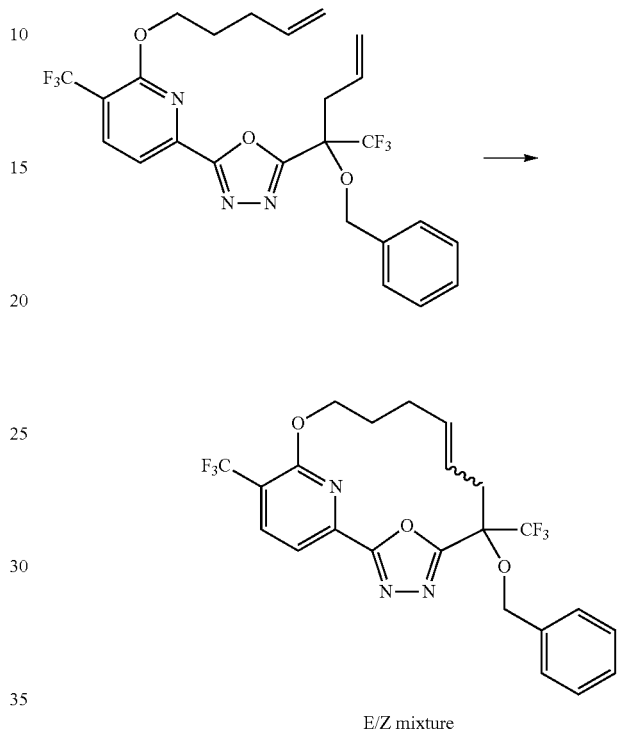

E/Z mixture

To a degassed solution of N'-[2-benzyloxy-2-(trifluoromethyl)pent-4-enoyl]-6-pent-4-enoxy-5-(trifluoromethyp-pyridine-2-carbohydrazide (100 mg, 0.1818 mmol) in THF (2 mL) was added methoxycarbonyl-(triethylammonio)sulfonyl-azanide (130 mg, 0.5455 mmol) in one portion. The resulting solution was heated in a sealed vial at 80° C. for 2 hours, solvent was evaporated then diluted the residue with ethyl acetate (10 mL), washed with 2N NaOH solution and 0.5 N HCl, brine, then dried (MgSO$_4$), filtered and concentrated. The residue was purified by silica gel chromatography eluting with a gradient of ethyl acetate in hexanes (5% to 26%, 8 column volumes) which afforded 2-[1-benzyloxy-1-(trifluoromethyl)but-3-enyl]-5-[6-pent-4-enoxy-5-(trifluoromethyl)-2-pyridyl]-1,3,4-oxadiazole (76 mg, 79%) as an oil. $^1$H NMR (400 MHz, Chloroform-d) δ 8.07-8.03 (m, 1H), 7.84 (dd, J=7.8, 0.8 Hz, 1H), 7.43-7.29 (m, 5H), 6.06-5.80 (m, 2H), 5.34-5.20 (m, 2H), 5.13-5.00 (m, 2H), 4.85 (d, J=10.8 Hz, 1H), 4.65 (d, J=10.9 Hz, 1H), 4.56 (t, J=6.3 Hz, 2H), 3.30-3.21 (m, 2H), 2.33-2.22 (m, 2H), 2.02-1.91 (m, 2H) ppm. ESI-MS m/z calc. 527.16437, found 528.21 (M+1)$^+$; Retention time: 1.23 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

To a degassed stirred solution of 2-[1-benzyloxy-1-(trifluoromethyl)but-3-enyl]-5-[6-pent-4-enoxy-5-(trifluoromethyl)-2-pyridyl]-1,3,4-oxadiazole (265 mg, 0.5024 mmol) in DCE (21 mL) was added [1,3-bis(2,4,6-trimethylphenyl)imidazolidin-2-ylidene]-dichloro-[(2-isopropoxy-5-nitrophenyl)methylene]ruthenium (68 mg, 0.1012 mmol), resultant mixture was purged with nitrogen and heated at 80° C. for 16 hours. The reaction mixture was concentrated and the residue was purified by silica gel chromatography eluting with a gradient of ethyl acetate in hexanes (5% to 40%, 12 column volumes) which afforded 6-benzyloxy-6,15-bis(trifluoromethyl)-13,19-dioxa-3,4,18-triazatricyclo[12.3.1.12,5]nonadeca-1(17),2,4,8,14(18),15-hexaene (E/Z mixture) (35 mg, 14%) as an oil and followed by dimeric side-product (85 mg) as white solid. $^1$H NMR (400 MHz, Chloroform-d) δ 8.06 (dd, J=7.7, 0.8 Hz, 1H), 7.86-7.79 (m, 1H), 7.28 (d, J=2.4 Hz, 4H), 7.23-7.16 (m, 1H), 6.13-5.99 (m, 1H), 5.90-5.77 (m, 1H), 4.91 (d, J=11.6 Hz, 1H), 4.79-4.46 (m, 3H), 3.18 (dd, J=14.6, 5.3 Hz, 1H), 2.81 (dd, J=14.5, 8.9 Hz, 1H), 2.24-1.90 (m, 4H) ppm. ESI-MS m/z calc. 499.13306, found 500.2 (M+1)$^+$; Retention time: 1.17 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 7: 6,15-bis(Trifluoromethyl)-13,19-dioxa-3,4,18-triazatricyclo[12.3.1.1²,⁵]nonadeca-1(17),2,4,14(18),15-pentaen-6-ol, Compound 1

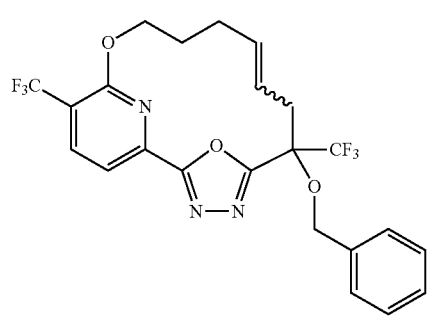

E/Z mixture

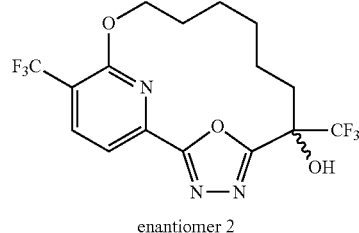

To a solution of 6-benzyloxy-6,15-bis(trifluoromethyl)-13,19-dioxa-3,4,18-triazatricyclo[12.3.1.1²,⁵]nonadeca-1(17),2,4,8,14(18),15-hexaene (E/Z mixture) (30 mg, 0.06007 mmol) in MeOH (3 mL) was added Silica Cat Pd (70 mg of 0.2 mmol/g, 0.01400 mmol) and stirred for 16 hours under hydrogen balloon. The mixture was diluted with ethyl acetate, filtered through a pad of Celite eluting with ethyl acetate and DCM then concentrated. The residue was purified by silica gel chromatography eluted with a gradient of ethyl acetate in hexanes (5% to 40%, 15 column volumes) followed by lyophilization using acetonitrile and water which afforded racemic 6,15-bis(trifluoromethyl)-13,19-dioxa-3,4,18-triazatricyclo[12.3.1.1²,⁵]nonadeca-1(17),2,4,14(18),15-pentaen-6-ol (17.5 mg, 70%) as a white solid. ¹H NMR (400 MHz, Chloroform-d) δ 8.08 (dd, J=7.7, 0.8 Hz, 1H), 7.85 (dd, J=7.7, 0.8 Hz, 1H), 4.69-4.60 (m, 1H), 4.54-4.42 (m, 1H), 3.94 (d, J=1.3 Hz, 1H), 2.52-1.34 (m, 10H) ppm. ESI-MS m/z calc. 411.10175, found 411.54 (M+1)⁺; Retention time: 3.7 minutes. Final purity was determined by reversed phase UPLC using an Acquity UPLC HSS T3 column made by Waters, and a dual gradient run from 5-85% mobile phase B over 6.0 minutes. Mobile phase A=water (with formic acid). Mobile phase B=acetonitrile (with formic acid).

Example 2: Preparation of 6,15-bis(trifluoromethyl)-13,19-dioxa-3,4,18-triazatricyclo[12.3.1.1²,⁵]nonadeca-1(17),2,4,14(18),15-pentaen-6-ol (enantiomer 1), Compound 2, and 6,15-bis(trifluoromethyl)-13,19-dioxa-3,4,18-triazatricyclo[12.3.1.1²,⁵]nonadeca-1(17),2,4,14(18),15-pentaen-6-ol (enantiomer 2), Compound 3

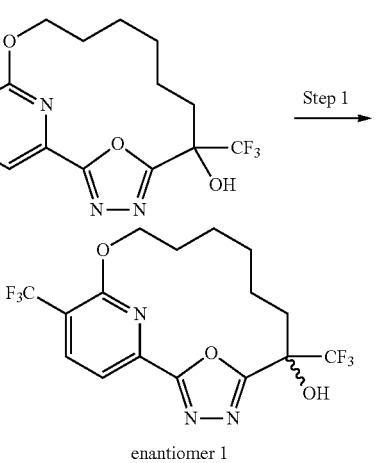

enantiomer 1 enantiomer 2

Step 1: 6,15-bis(Trifluoromethyl)-13,19-dioxa-3,4,18-triazatricyclo[12.3.1.1²,⁵]nonadeca-1(17),2,4,14(18),15-pentaen-6-ol (enantiomer 1), Compound 2, and 6,15-bis(Trifluoromethyl)-13,19-dioxa-3,4,18-triazatricyclo[12.3.1.1²,⁵]nonadeca-1(17),2,4,14(18),15-pentaen-6-ol (enantiomer 2), Compound 3

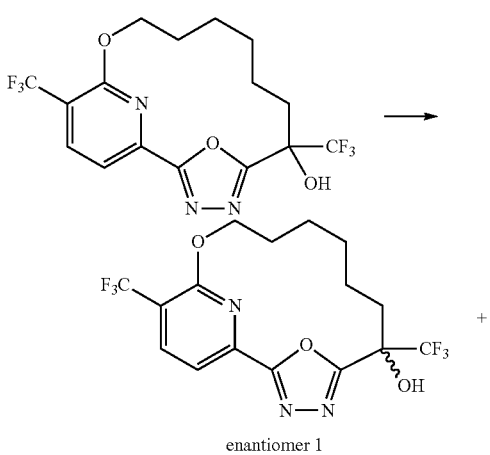

enantiomer 1

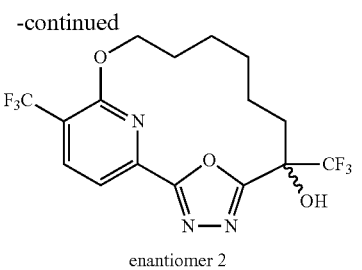

enantiomer 2

Racemic 6,15-bis(trifluoromethyl)-13,19-dioxa-3,4,18-triazatricyclo[12.3.1.1 2,5]nonadeca-1(17),2,4,14(18),15-pentaen-6-ol (9.5 mg, 0.02310 mmol) was separated by SFC using isocratic 3% methanol over 30 min on a Lux2 10×250 mm column to provide two single enantiomers. The first enantiomer to elute, 3.6 mg of 6,15-bis(trifluoromethyl)-13,19-dioxa-3,4,18-triazatricyclo[12.3.1.1 2,5]nonadeca-1(17),2,4,14(18),15-pentaen-6-ol (enantiomer 1), was enantiomerically pure however LCMS of this compound showed a polar impurity. This material was re-purified by silica gel chromatography eluting with a gradient of ethyl acetate in hexanes (5% to 40%, 15 column volumes) affording 6,15-bis(trifluoromethyl)-13,19-dioxa-3,4,18-triazatricyclo [12.3.1.1 2,5]nonadeca-1(17),2,4,14(18),15-pentaen-6-ol (enantiomer 1) (2.7 mg, 54%), chiral purity, >99.9%. ESI-MS m/z calc. 411.10175, found 412.21 (M+1)$^+$; Retention time: 3.76 minutes. Final purity was determined by reversed phase UPLC using an Acquity UPLC HSS T3 column made by Waters, and a dual gradient run from 5-85% mobile phase B over 6.0 minutes. Mobile phase A=water (with formic acid). Mobile phase B=acetonitrile (with formic acid). The second enantiomer to elute from the SFC separation was 6,15-bis(trifluoromethyl)-13,19-dioxa-3,4,18-triazatricyclo [12.3.1.1 2,5]nonadeca-1(17),2,4,14(18),15-pentaen-6-ol (3.3 mg, 69%), chiral purity, >99.9%, ESI-MS m/z calc. 411.10175, found 412.2 (M+1)$^+$; Retention time: 0.96 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Example 3: Preparation of 17-Amino-6,15-bis(trifluoromethyl)-13,19-dioxa-3,4,18-triazatricyclo [12.3.1.1 2,5]nonadeca-1(18),2,4,14,16-pentaen-6-ol (racemic), Compound 4

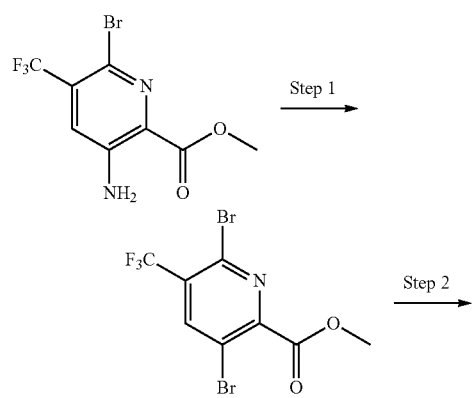

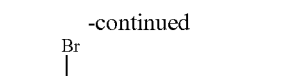

Step 3

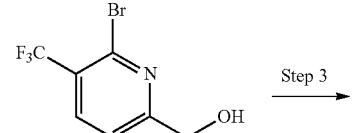

+

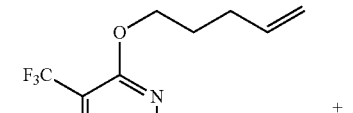

Step 4

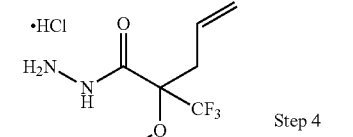

Step 5

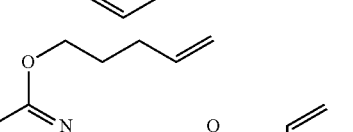

Step 6

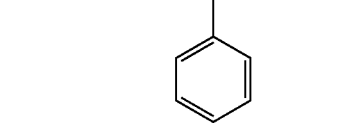

Step 7

E/Z mixture

-continued

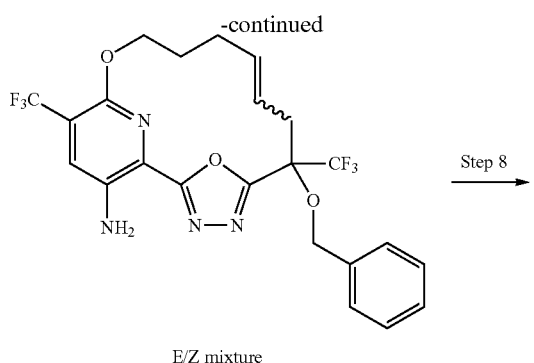

E/Z mixture

Step 8 →

Step 2: 3,6-Dibromo-5-(trifluoromethyl)pyridine-2-carboxylic acid

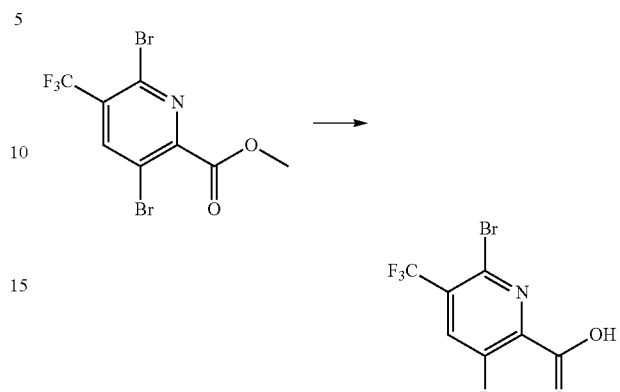

To a solution of methyl 3,6-dibromo-5-(trifluoromethyl)pyridine-2-carboxylate (1 g, 2.755 mmol) in THF (10 mL) was added a solution of lithium hydroxide monohydrate (2 mL of 1.7 M, 3.400 mmol) in water (2.8 mL). This mixture was stirred room temperature for 15 hours, concentrated by rotary evaporation, acidified with aqueous 2 N HCl and extracted with methylene chloride (3×15 mL). The combined extracts were passed through a phase separator and concentrated to afford 3,6-dibromo-5-(trifluoromethyl)pyridine-2-carboxylic acid (920 mg, 93%) as a brown solid. $^1$H NMR (400 MHz, Chloroform-d) δ 8.36 (s, 1H) ppm. ESI-MS m/z calc. 346.84042, found 347.91 (M+1)$^+$; Retention time: 0.51 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 3: 3-Bromo-6-pent-4-enoxy-5-(trifluoromethyl)pyridine-2-carboxylic acid

Step 1: Methyl 3,6-dibromo-5-(trifluoromethyl)pyridine-2-carboxylate

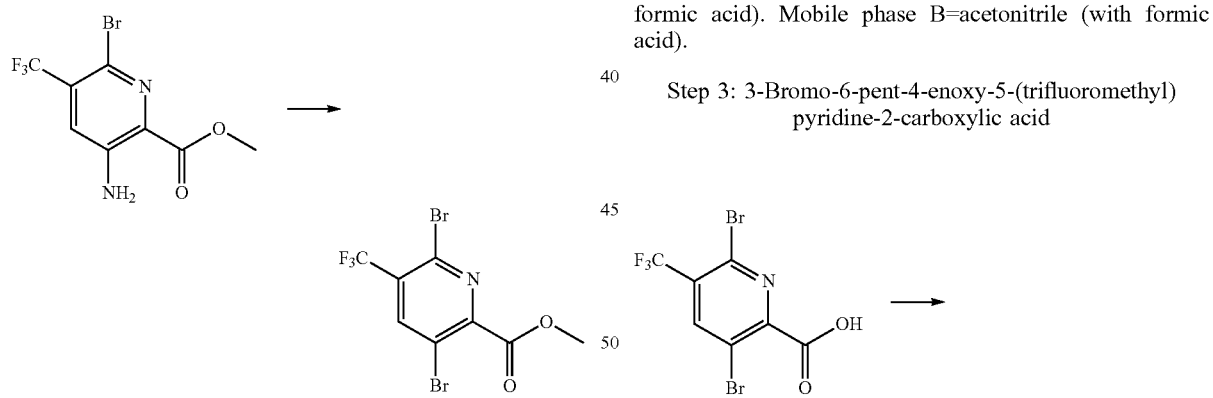

To methyl 3-amino-6-bromo-5-(trifluoromethyl)pyridine-2-carboxylate (approximately 2.5 g, 8.36 mmol) and CuBr$_2$ (approximately 2.801 g, 12.54 mmol) in acetonitrile (60.90 mL) at room temperature was added tert-butyl nitrite (approximately 1.293 g, 1.491 mL, 12.54 mmol) dropwise and the reaction was stirred at room temperature for 16 h in a closed atmosphere. Complete consumption of the SM was observed. The reaction was diluted with saturated aqueous NH$_4$Cl and the aqueous layer was extracted with CH$_2$Cl$_2$. The combined organic layers were dried over sodium sulfate and the solvent was removed under reduced pressure. The crude residue, methyl 3,6-dibromo-5-(trifluoromethyl)pyridine-2-carboxylate (1.6 g, 53%) was used in the next reaction without further purification.

To a stirred suspension of sodium hydride (310 mg of 60% w/w, 7.751 mmol) in DMF (6 mL) was added pent-4-en-1-ol (550 μL, 5.421 mmol) in DMF (2 mL) stirred at room temperature for 0.5 h. The mixture was cooled to 0° C., 3,6-dibromo-5-(trifluoromethyl)pyridine-2-carboxylic acid (920 mg, 2.566 mmol) in DMF (6 mL) was added, the reaction mixture was warmed to room temperature and stirred for a further 2 h. The mixture was carefully quenched with water (10 mL). Aqueous basic solution was washed with hexanes and ether (1:1), acidified with aqueous 2 N HCl, extracted with ether (3×20 mL) and combined extracts were washed with brine, dried (MgSO$_4$) and concentrated. Purification by column chromatography afforded still impure 3-bromo-6-pent-4-enoxy-5-(trifluoromethyl)pyridine-2-carboxylic acid (600 mg, 66%) as an oil which was used as such in the next step without further purification. ESI-MS m/z calc. 352.98743, found 354.01 (M+1)$^+$; Retention time: 0.86 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 4: N'-[2-Benzyloxy-2-(trifluoromethyl)pent-4-enoyl]-3-bromo-6-pent-4-enoxy-5-(trifluoromethyl)pyridine-2-carbohydrazide

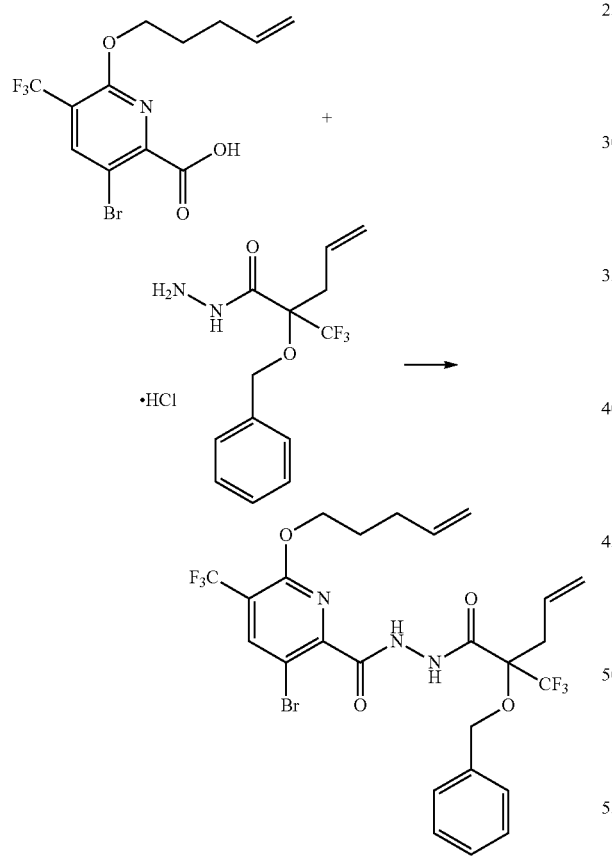

To a stirred solution of 3-bromo-6-pent-4-enoxy-5-(trifluoromethyl)pyridine-2-carboxylic acid (640 mg, 1.807 mmol) and HATU (885 mg, 2.328 mmol) in DMF (6 mL) was added DIPEA (1.1 mL, 6.315 mmol) (exotherm). After 5 min, 2-benzyloxy-2-(trifluoromethyl)pent-4-enehydrazide (hydrochloride salt) (600 mg, 1.791 mmol) was added in one portion and the mixture was stirred for 16 h. The reaction mixture was diluted with water (25 mL), extracted with ethyl acetate (3×25 mL) and combined extracts were washed with brine and dried (MgSO$_4$) then filtered and concentrated. The residue was purified by silica gel chromatography eluting with a gradient of ethyl acetate in hexanes (5% to 29%, 10 column volumes) to afford N'-[2-benzyloxy-2-(trifluoromethyl)pent-4-enoyl]-3-bromo-6-pent-4-enoxy-5-(trifluoromethyl)pyridine-2-carbohydrazide (340 mg, 26%) as colorless gum. $^1$H NMR (400 MHz, Chloroform-d) δ 9.81 (s, 1H), 9.31 (s, 1H), 8.14 (s, 1H), 7.40-7.35 (m, 5H), 5.88-5.75 (m, 2H), 5.38-5.26 (m, 2H), 5.07-4.95 (m, 2H), 4.83 (s, 2H), 4.43 (t, J=5.9 Hz, 2H), 3.20-2.97 (m, 2H), 2.28-2.19 (m, 2H), 1.96-1.87 (m, 2H) ppm. ESI-MS m/z calc. 623.08545, found 624.13 (M+1)$^+$; Retention time: 1.1 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 5: 2-[1-Benzyloxy-1-(trifluoromethyl)but-3-enyl]-5-[3-bromo-6-pent-4-enoxy-5-(trifluoromethyl)-2-pyridyl]-1,3,4-oxadiazole

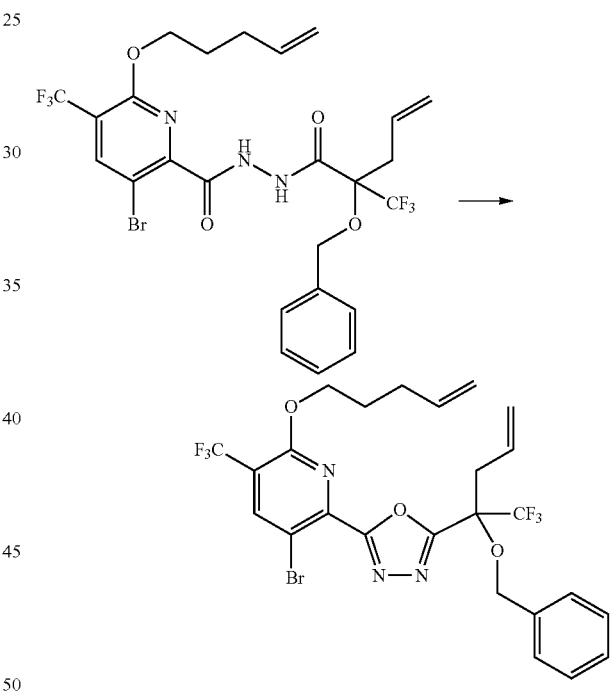

To a degassed solution of N'-[2-benzyloxy-2-(trifluoromethyl)pent-4-enoyl]-3-bromo-6-pent-4-enoxy-5-(trifluoromethyppyridine-2-carbohydrazide (340 mg, 0.4609 mmol) in THF (6 mL) was added methoxycarbonyl-(triethylammonio)sulfonyl-azanide (330 mg, 1.385 mmol) in one portion. Resultant solution was heated in a sealed vial at 80° C. for 2 hours. The mixture was quenched with 2 N NaOH (~1.5 mL) and water (5 mL), most of the solvent was evaporated then diluted with ethyl acetate (20 mL). The organic solution was washed with 0.5 N HCl, brine, dried (MgSO$_4$), filtered and concentrated. The residue was purified by silica gel chromatography eluting with a gradient of ethyl acetate in hexanes (0% to 12%, 12 column volumes) affording 2-[1-benzyloxy-1-(trifluoromethyl)but-3-enyl]-5-[3-bromo-6-pent-4-enoxy-5-(trifluoromethyl)-2-pyridyl]-1,3,4-oxadiazole (240 mg, 86%) as an oil. $^1$H NMR (400

MHz, Chloroform-d) δ 8.17 (s, 1H), 7.39-7.27 (m, 5H), 6.00-5.88 (m, 1H), 5.86-5.75 (m, 1H), 5.29-5.21 (m, 1H), 5.21-5.16 (m, 1H), 5.06-4.95 (m, 2H), 4.84 (d, J=10.8 Hz, 1H), 4.63 (d, J=10.8 Hz, 1H), 4.44 (t, J=6.3 Hz, 2H), 3.20 (t, J=6.0 Hz, 2H), 2.20 (q, J=7.2 Hz, 2H), 1.93-1.84 (m, 2H) ppm. ESI-MS m/z calc. 605.0749, found 607.12 (M+1)$^+$; Retention time: 1.22 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 6: 6-Benzyloxy-17-bromo-6,15-bis(trifluoromethyl)-13,19-dioxa-3,4,18-triazatricyclo[12.3.1.12,5]nonadeca-1(17),2,4,8,14(18),15-hexaene (E/Z Mixture)

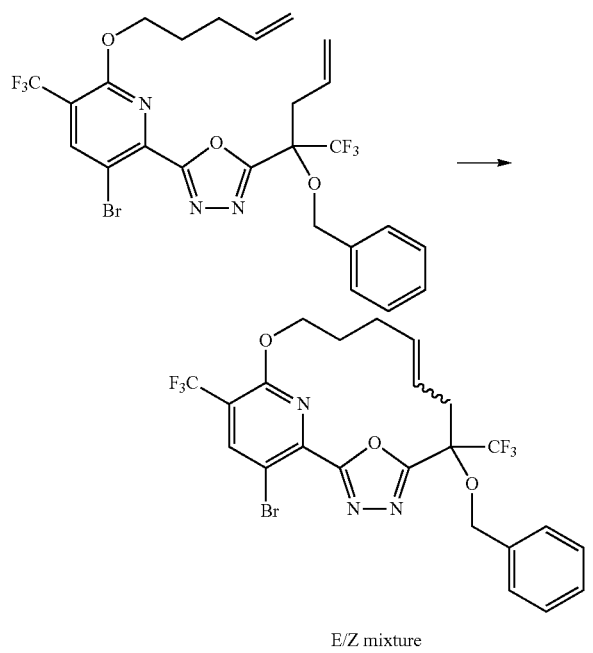

E/Z mixture

To a degassed stirred solution of 2-[1-benzyloxy-1-(trifluoromethyl)but-3-enyl]-5-[3-bromo-6-pent-4-enoxy-5-(trifluoromethyl)-2-pyridyl]-1,3,4-oxadiazole (247 mg, 0.4074 mmol) in DCE (20 mL) was added [1,3-bis(2,4,6-trimethylphenyl)imidazolidin-2-ylidene]-dichloro-[(2-isopropoxy-5-nitro-phenyl)methylene]ruthenium (50 mg, 0.07445 mmol) and the resulting mixture was purged with nitrogen and heated at 80° C. for 30 min. SiliaMetS (150 mg) was added, stirred for 30 min, filtered and rinsed with DCM then concentrated. The residue was purified by silica gel chromatography eluting with a gradient of ethyl acetate in hexanes (0% to 20%, 15 column volumes) to afford 6-benzyloxy-17-bromo-6,15-bis(trifluoromethyl)-13,19-dioxa-3,4,18-triazatricyclo[12.3.1.12,5]nonadeca-1(17),2,4,8,14 (18),15-hexaene (E/Z mixture) (100 mg, 42%) as a white solid. $^1$H NMR (400 MHz, Chloroform-d) δ 8.17 (brs, 1H), 7.25-7.24 (m, 2H), 7.24-7.23 (m, 2H), 7.18-7.12 (m, 1H), 5.88-5.80 (m, 2H), 4.88 (d, J=11.6 Hz, 1H), 4.69-4.57 (m, 1H), 4.53 (d, J=11.6 Hz, 1H), 4.50-4.41 (m, 1H), 3.12 (dd, J=14.4, 4.3 Hz, 1H), 2.72 (dd, J=14.6, 8.0 Hz, 1H), 2.19-1.83 (m, 4H) ppm. ESI-MS m/z calc. 577.0436, found 579.97 (M+1)$^+$; Retention time: 1.16 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 7: 6-Benzyloxy-6,15-bis(trifluoromethyl)-13,19-dioxa-3,4,18-triazatricyclo[12.3.1.12,5]nonadeca-1(17),2,4,8,14(18),15-hexaen-17-amine (E/Z Mixture)

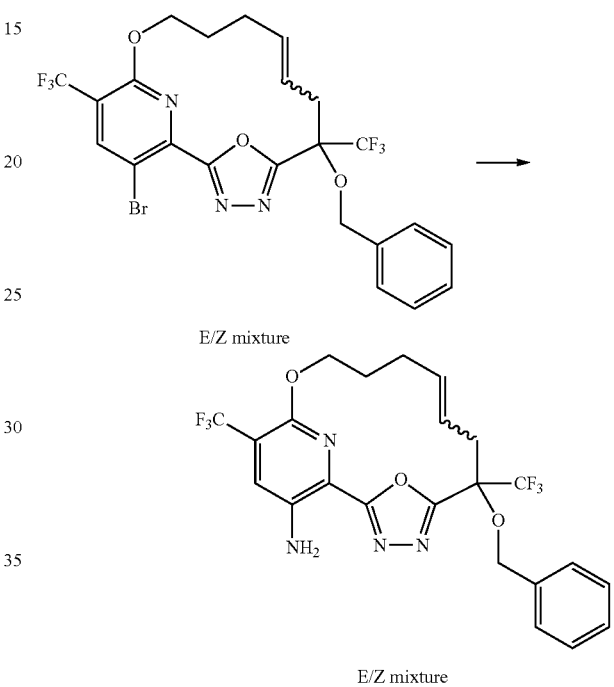

E/Z mixture

To a degassed mixture of 6-benzyloxy-17-bromo-6,15-bis(trifluoromethyl)-13,19-dioxa-3,4,18-triazatricyclo[12.3.1.12,5]nonadeca-1(17),2,4,8,14(18),15-hexaene (E/Z mixture) (35 mg, 0.06052 mmol), Xantphos (4 mg, 0.006913 mmol), diphenylmethanimine (14 μL) and cesium carbonate (40 mg, 0.1228 mmol) in dioxane (700 μL) was added Pd(OAc)$_2$ (1.8 mg, 0.008017 mmol). Degassed using vacuum/nitrogen and heated in a sealed vial at 100° C. for 2.5 hours, cooled to room temperature, diluted with water (2 mL), extracted with ethyl acetate (4×5 mL) and combined extracts were dried (MgSO$_4$), filtered and concentrated to afford the intermediate N-[6-benzyloxy-6,15-bis(trifluoromethyl)-13,19-dioxa-3,4,18-triazatricyclo[12.3.1.12,5]nonadeca-1(17),2,4,8,14(18),15-hexaen-17-yl]-1,1-diphenylmethanimine intermediate as a yellow liquid. ESI-MS m/z calc. 678.20654, found 678.38 (M+1)$^+$; Retention time: 2.16 minutes. Final purity was determined by reversed phase UPLC using an Acquity UPLC HSS T3 column made by Waters, and a dual gradient run from 50-100% mobile phase B over 3.0 minutes. Mobile phase A=water (with formic acid). Mobile phase B=acetonitrile (with formic acid). To a stirred solution of the crude N-[6-benzyloxy-6,15-bis(trifluoromethyl)-13,19-dioxa-3,4,18-triazatricyclo[12.3.1.12,5]nonadeca-1(17),2,4,8,14(18),15-hexaen-17-yl]-1,1-diphenyl-methanimine (E/Z mixture) (60 mg, 129%) in THF (2 mL) was added HCl (2 mL of 2 M, 4.000 mmol) at room temperature, stirred for 10 min, concentrated by rotary evaporation, diluted with water (1 mL), extracted with methylene chloride (3×5 mL) and the combined extracts were dried (MgSO$_4$), filtered and concentrated. The residue was purified by silica gel chromatography eluting with a gradient of ethyl acetate in hexanes (10% to 40%, 9 column volumes) which afforded 6-benzyloxy-6,15-bis(trifluoromethyl)-13,19-dioxa-3,4,18-triazatricyclo[12.3.1.1$^{2,5}$]nonadeca-1(17),2,4,8,14(18),15-hexaen-17-amine (E/Z mixture) (24 mg, 77%) as a brown solid. $^1$H NMR (400 MHz, Chloroform-d) δ 7.40 (brs, 1H), 7.27-7.22 (m, 4H), 7.20-7.14 (m, 1H), 6.09-5.98 (m, 1H), 5.78 (dt, J=14.9, 7.0 Hz, 1H), 5.32 (s, 2H), 4.86 (d, J=11.5 Hz, 1H), 4.56 (d, J=11.5 Hz, 1H), 4.53-4.32 (m, 2H), 3.14 (dd, J=14.6, 5.4 Hz, 1H), 2.78 (dd, J=14.5, 8.7 Hz, 1H), 2.18-1.84 (m, 4H) ppm. ESI-MS m/z calc. 514.144, found 515.15 (M+1)$^+$; Retention time: 1.14 minutes. Final purity was determined by reversed phase UPLC using an Acquity UPLC HSS T3 column made by Waters, and a dual gradient run from 15-98% mobile phase B over 1.5 minutes. Mobile phase A=water (with formic acid). Mobile phase B=acetonitrile (with formic acid).

Step 8: 17-Amino-6,15-bis(trifluoromethyl)-13,19-dioxa-3,4,18-triazatricyclo[12.3.1.1$^{2,5}$]nonadeca-1(18),2,4,14,16-pentaen-6-ol, Compound 4

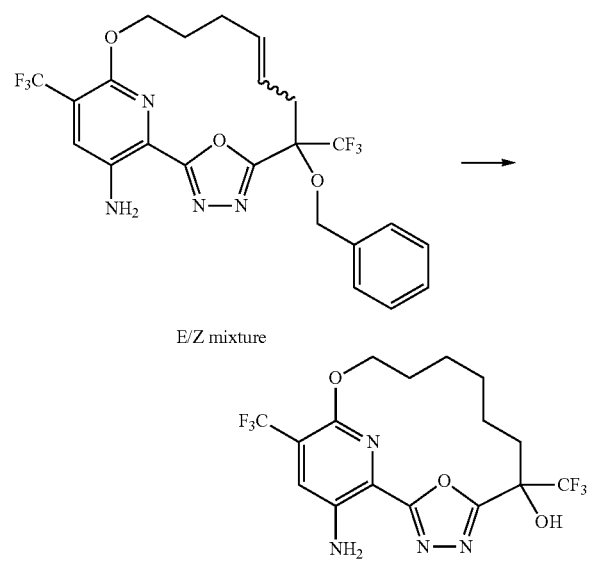

E/Z mixture

To a solution of 6-benzyloxy-6,15-bis(trifluoromethyl)-13,19-dioxa-3,4,18-triazatricyclo[12.3.1.1$^{2,5}$]nonadeca-1(17),2,4,8,14(18),15-hexaen-17-amine (E/Z mixture) (22 mg, 0.04277 mmol) in MeOH (3 mL) was added SiliaCat Pd (49 mg, 0.1944 mmol), stirred for 2 hours under hydrogen balloon then added an additional amount of SiliaCat Pd (20 mg of 0.2 mmol/g, 0.004000 mmol). Stirred for 2 hours and then the mixture was heated at 50° C. for 2 hours. The reaction was diluted with ethyl acetate, filtered through a pad of Celite eluting with ethyl acetate then concentrated. The residue was purified by silica gel chromatography eluting with a gradient of ethyl acetate in hexanes (10% to 50%, 15 column volumes) followed by lyophilization using acetonitrile and water which afforded 17-amino-6,15-bis(trifluoromethyl)-13,19-dioxa-3,4,18-triazatricyclo[12.3.1.1$^{2,5}$]nonadeca-1(18),2,4,14,16-pentaen-6-ol (14.5 mg, 77%) as a light yellow solid. $^1$H NMR (400 MHz, Chloroform-d) δ 7.36 (s, 1H), 5.18 (brs, 2H), 4.44-4.24 (m, 2H), 3.48 (brs, 1H), 2.35-2.11 (m, 2H), 2.09-1.94 (m, 1H), 1.92-1.69 (m, 1H), 1.67-1.33 (m, 6H) ppm. ESI-MS m/z calc. 426.11267, found 427.29 (M+1)$^+$; Retention time: 3.83 minutes. Final purity was determined by reversed phase UPLC using an Acquity UPLC HSS T3 column made by Waters, and a dual gradient run from 5-85% mobile phase B over 6.0 minutes. Mobile phase A=water (with formic acid). Mobile phase B=acetonitrile (with formic acid).

Example 4: Preparation of (6R)-17-amino-6,15-bis(trifluoromethyl)-13,19-dioxa-3,4,18-triazatricyclo[12.3.1.1$^{2,5}$]nonadeca-1(18),2,4,14,16-pentaen-6-ol, Compound 5

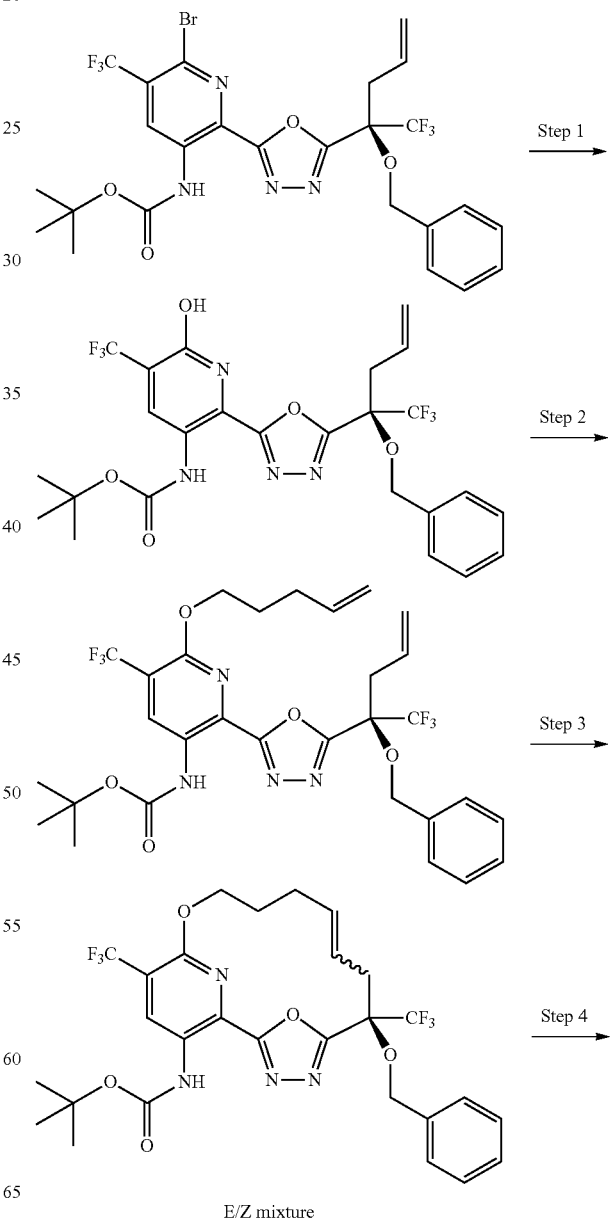

E/Z mixture

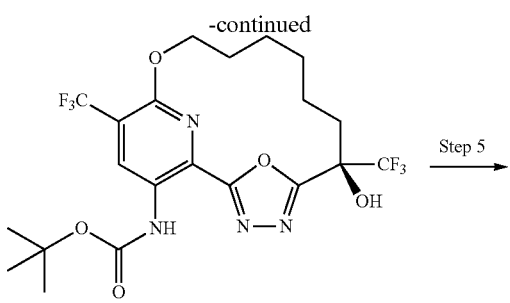

Step 1: tert-Butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]carbamate

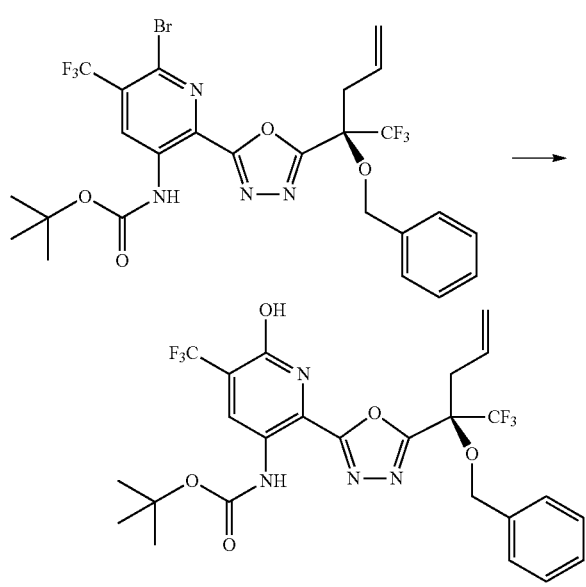

To a stirring solution of tert-butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]carbamate (10 g, 15.69 mmol) in DMSO (64.97 mL) at room temperature was added cesium acetate (3.012 g, 15.69 mmol) and the mixture was capped and heated under nitrogen atmosphere to 80° C. and stirred for 160 min. Reaction was stopped as it was progressing to the undesired N-acetyl product. Diluted the reaction mixture with water and extracted with EtOAc. Washed the organic layer with saturated aqueous NaHCO₃ (1×), saturated aqueous NH₄Cl (1×) and brine (1×), then dried (MgSO₄), filtered and concentrated to a residue which was purified by silica gel chromatography using a shallow gradient from 100% hexanes to 100% EtOAc. Mixed fractions were combined, concentrated and purified by $C_{18}$ reverse phase chromatography using a gradient run from 50%-99% mobile phase B over 15.0 minutes (mobile phase A=H₂O (5 mM HCl), mobile phase B=acetonitrile. Isolated tert-butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]carbamate (297.7 mg, 3%) as a minor product which was used directly in the ensuing step.

Step 2: tert-Butyl N-[2-[5-[(1R)-1-benzyloxy-1-(trifluoromethyl)but-3-enyl]-1,3,4-oxadiazol-2-yl]-6-pent-4-enoxy-5-(trifluoromethyl)-3-pyridyl]carbamate

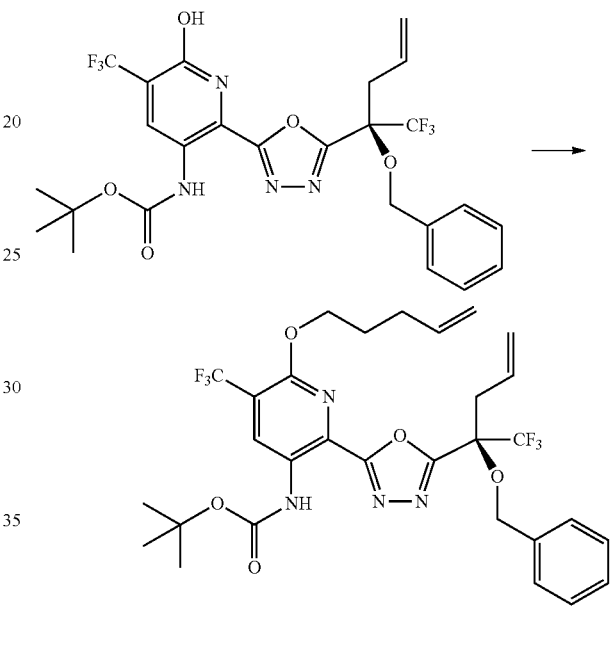

To a solution of tert-butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]carbamate (295 mg, 0.5135 mmol) and pent-4-en-1-ol (78.14 μL, 0.7702 mmol) in toluene (6.21 mL) was added triphenylphosphine (178.4 μL, 0.7700 mmol). After stirring at room temperature for 1 min, DIAD (161.8 μL, 0.8218 mmol) was added and the mixture was stirred at room temperature for 5 minutes. Diluted the reaction mixture with EtOAc then washed with saturated aqueous NaHCO₃ (1×), saturated aqueous NH₄Cl (1×) and brine (1×) then dried over MgSO₄, filtered and concentrated to a yellow oil which was purified by silica gel chromatography using a shallow gradient from 100% hexanes to 100% EtOAc giving as a clear, slightly yellow syrup, tert-butyl N-[2-[5-[(1R)-1-benzyloxy-1-(trifluoromethyl)but-3-enyl]-1,3,4-oxadiazol-2-yl]-6-pent-4-enoxy-5-(trifluoromethyl)-3-pyridyl]carbamate (271.9 mg, 82%). ESI-MS m/z calc. 642.22766, found 643.3 (M+1)⁺; Retention time: 0.83 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=H₂O (0.05% CF₃CO₂H). Mobile phase B=CH₃CN (0.035% CF₃CO₂H). Flow rate=1.5 mL/min, injection volume=1.5 μL, and column temperature=60° C.

Step 3: tert-Butyl N-[(6R)-6-benzyloxy-6,15-bis(trifluoromethyl)-13,19-dioxa-3,4,18-triazatricyclo[12.3.1.12,5]nonadeca-1(17),2,4,8,14(18),15-hexaen-17-yl]carbamate (E/Z Mixture)

Step 4: tert-Butyl N-[(6R)-6-hydroxy-6,15-bis(trifluoromethyl)-13,19-dioxa-3,4,18-triazatricyclo[12.3.1.12,5]nonadeca-1(17),2,4,14(18),15-pentaen-17-yl]carbamate

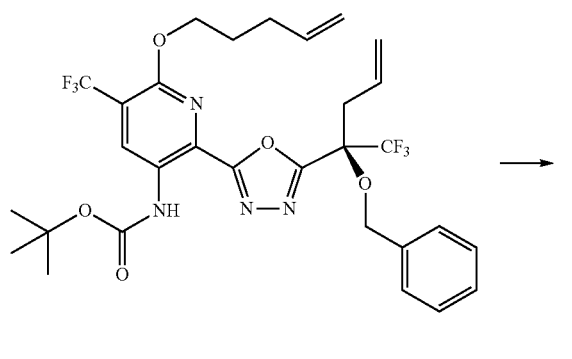

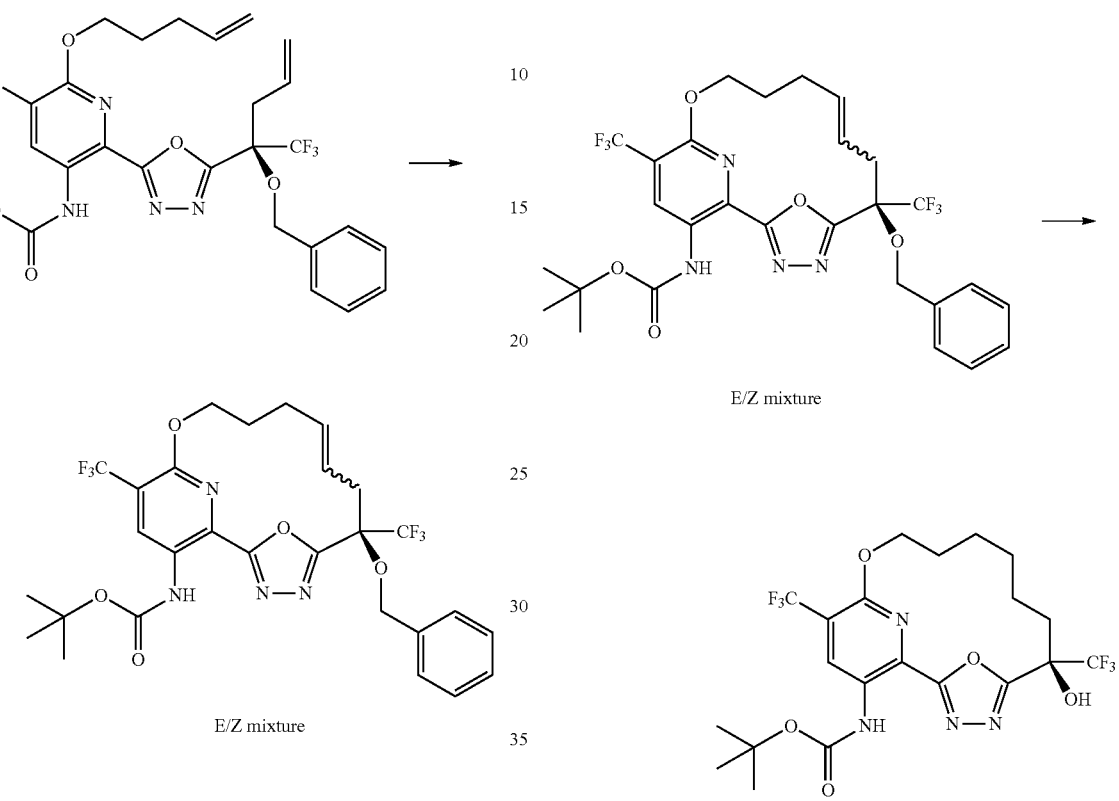

E/Z mixture

To a two neck flask bubbling in nitrogen added tert-butyl N-[2-[5-[(1R)-1-benzyloxy-1-(trifluoromethyl)but-3-enyl]-1,3,4-oxadiazol-2-yl]-6-pent-4-enoxy-5-(trifluoromethyl)-3-pyridyl]carbamate (271.9 mg, 0.4231 mmol) in DCE (62.54 mL) and heated to 60° C. Then added via syringe, Zhan catalyst-1B (77.63 mg, 0.1058 mmol) in dichloroethane (1 mL), heated reaction to 60° C. and stirred while bubbling nitrogen through the solution. Added dichloroethane intermittently as the reaction progressed to maintain volume. After 80 min, added Zhan catalyst-1B (46.56 mg, 0.06345 mmol) and continued stirring at 60° C. for 160 min. Allowed the reaction mixture to cool to room temperature then added 2-sulfanylpyridine-3-carboxylic acid (26.26 mg, 0.1692 mmol) and stirred for 5 min. Concentrated the reaction mixture by rotary evaporation then purified by silica gel chromatography using a shallow gradient from 100% hexanes to 100% EtOAc giving as a yellow solid, tert-butyl N-[(6R)-6-benzyloxy-6,15-bis(trifluoromethyl)-13,19-dioxa-3,4,18-triazatricyclo[12.3.1.12,5]nonadeca-1(17),2,4,8,14(18),15-hexaen-17-yl]carbamate (E/Z mixture) (169 mg, 65%). ESI-MS m/z calc. 614.1964, found 615.2 (M+1)+; Retention time: 0.75 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

To a solution of tert-butyl N-[(6R)-6-benzyloxy-6,15-bis(trifluoromethyl)-13,19-dioxa-3,4,18-triazatricyclo[12.3.1.12,5]nonadeca-1(17),2,4,8,14(18),15-hexaen-17-yl]carbamate (E/Z mixture) (167 mg, 0.2717 mmol) in AcOH (5.566 mL) was added Pd/C (88.83 mg of 10% w/w, 0.08347 mmol) and hydrogen gas was bubbled through the stirring mixture for 15 minutes then the reaction was sealed and capped with a hydrogen balloon and stirred for 2.5 h. Added palladium (28.91 mg of 10% w/w, 0.02717 mmol), stirred for 1 h then purged the flask with nitrogen and filtered over Celite eluting with EtOAc. The filtrate was concentrated then purified by silica gel chromatography using a shallow gradient from 100% hexanes to 100% EtOAc giving as a white foam, tert-butyl N-[(6R)-6-hydroxy-6,15-bis(trifluoromethyl)-13,19-dioxa-3,4,18-triazatricyclo[12.3.1.12,5]nonadeca-1(17),2,4,14(18),15-pentaen-17-yl]carbamate (143 mg, 100%). ESI-MS m/z calc. 526.1651, found 527.2 (M+1)+; Retention time: 0.52 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

Step 5: (6R)-17-Amino-6,15-bis(trifluoromethyl)-13,19-dioxa-3,4,18-triazatricyclo[12.3.1.1²,⁵]nonadeca-1(18),2,4,14,16-pentaen-6-ol, Compound 5

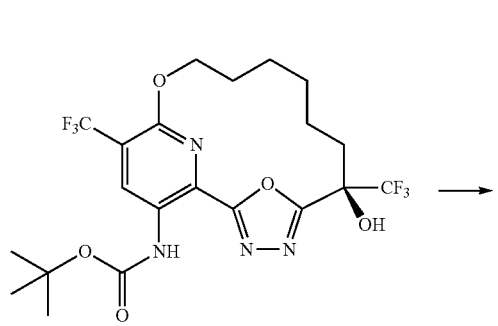

Example 5: Preparation of (6S)-17-amino-6,15-bis(trifluoromethyl)-13,19-dioxa-3,4,18-triazatricyclo[12.3.1.1²,⁵]nonadeca-1(18),2,4,14,16-pentaen-6-ol, Compound 6

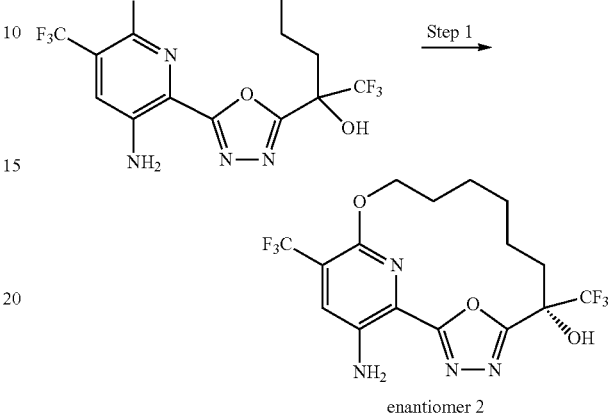

Step 1: (6S)-17-Amino-6,15-bis(trifluoromethyl)-13,19-dioxa-3,4,18-triazatricyclo[12.3.1.1²,⁵]nonadeca-1(18),2,4,14,16-pentaen-6-ol, Compound 6

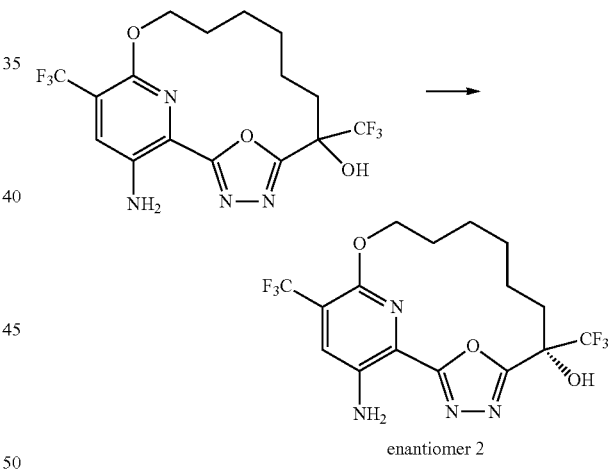

To a stirring solution of tert-butyl N-[(6R)-6-hydroxy-6,15-bis(trifluoromethyl)-13,19-dioxa-3,4,18-triazatricyclo[12.3.1.1²,⁵]nonadeca-1(17),2,4,14(18),15-pentaen-17-yl]carbamate (143 mg, 0.2716 mmol) in DCM (1.43 mL) was added TFA (522.9 μL, 6.787 mmol) and the resulting mixture was stirred at room temperature for 2 h then concentrated by rotary evaporation to a yellow residue which was dissolved in EtOAc and washed with saturated aqueous NaHCO₃ (1×), dried (MgSO₄), filtered and concentrated to a pale yellow residue. This material was purified by silica gel chromatography using a shallow gradient from 100% hexanes to 100% EtOAc giving as a pale yellow solid, (6R)-17-amino-6,15-bis(trifluoromethyl)-13,19-dioxa-3,4,18-triazatricyclo[12.3.1.1²,⁵]nonadeca-1(18),2,4,14,16-pentaen-6-ol (88.7 mg, 76%). ¹H NMR (400 MHz, DMSO) δ 7.80-7.76 (m, 1H), 7.55 (s, 1H), 6.37 (s, 2H), 4.44-4.27 (m, 2H), 2.20 (q, J=7.2 Hz, 1H), 2.10 (dd, J=14.7, 7.1 Hz, 1H), 2.06-1.96 (m, 1H), 1.80 (dd, J=11.3, 5.8 Hz, 1H), 1.69-1.53 (m, 4H), 1.42 (d, J=7.2 Hz, 2H) ppm. ESI-MS m/z calc. 426.11267, found 427.4 (M+1)⁺; Retention time: 1.86 minutes. Final purity was determined by reversed phase UPLC using an Acquity UPLC BEH C₁₈ column (50×2.1 mm, 1.7 μm particle) made by Waters (pn: 186002350), and a dual gradient run from 1-99% mobile phase B over 2.9 minutes. Mobile phase A=H₂O (0.05% CF₃CO₂H). Mobile phase B=CH₃CN (0.035% CF₃CO₂H). Flow rate=1.2 mL/min, injection volume=1.5 μL, and column temperature=60° C.

Racemic 17-amino-6,15-bis(trifluoromethyl)-13,19-dioxa-3,4,18-triazatricyclo[12.3.1.1²,⁵]nonadeca-1(18),2,4,14,16-pentaen-6-ol (32.6 mg, 0.07647 mmol) was separated by preparative SFC using a LUX-4 (25 cm×2.1 cm, 5 μM) column using methanol as solvent to give as the second enantiomer to elute, (6S)-17-amino-6,15-bis(trifluoromethyl)-13,19-dioxa-3,4,18-triazatricyclo[12.3.1.1²,⁵]nonadeca-1(18),2,4,14,16-pentaen-6-ol (11.8 mg, 72%). ¹H NMR (400 MHz, DMSO-d₆) δ 7.78 (s, 1H), 7.61 (s, 1H), 6.39 (s, 2H), 4.35 (s, 2H), 2.18 (s, 1H), 2.08 (d, J=39.0 Hz, 2H), 1.82 (s, 1H), 1.64 (s, 4H), 1.42 (s, 2H) ppm. ESI-MS m/z calc. 426.11267, found 427.0 (M+1)⁺; Retention time: 1.86 minutes. Final purity was determined by reversed phase UPLC using an Acquity UPLC BEH C₁₈ column (50×2.1 mm, 1.7 μm particle) made by Waters (pn: 186002350), and a dual gradient run from 1-99% mobile phase B over 2.9 minutes. Mobile phase A=H₂O (0.05% CF₃CO₂H). Mobile phase B=CH₃CN (0.035% CF₃CO₂H). Flow rate=1.2 mL/min, injection volume=1.5 μL, and column temperature=60° C.

Step 2: Solid Form Characterization of Crystalline Compound 6 (Neat Form)

Single crystals of crystalline Compound 6 (neat form) were grown by vapor diffusion of pentane into a solution of Compound 6 in 1,2-dicholorethane. X-ray diffraction data were acquired at 100 K on a Bruker diffractometer equipped with Cu K₊ radiation (λ=1.5478 Å) and a CCD detector. The structure was solved and refined using SHELX programs (Sheldrick, G. M., Acta Cryst., (2008) A64, 112-122). The results are summarized in Table 3 below.

TABLE 3

Single crystal elucidation of crystalline Compound 6 (neat form)

| Crystal System | Monoclinic |
|---|---|
| Space Group | P2₁ |
| a (Å) | 9.5564(4) |
| b (Å) | 13.5953(5) |
| c (Å) | 13.8474(5) |
| α (°) | 90 |
| β (°) | 105.3070(10) |
| γ (°) | 90 |
| V (Å³) | 1735.26(12) |
| Z/Z' | 4/1 |
| Temperature | 100 K |

Example 6: Preparation of 17-amino-12-methyl-6,15-bis(trifluoromethyl)-13,19-dioxa-3,4,18-triazatricyclo[12.3.1.1²,⁵]nonadeca-1(18),2,4,14,16-pentaen-6-ol (hydrochloride salt) (diastereomer pair 1), Compound 7, and 17-amino-12-methyl-6,15-bis(trifluoromethyl)-13,19-dioxa-3,4,18-triazatricyclo[12.3.1.1²,⁵]nonadeca-1(18),2,4,14,16-pentaen-6-ol (hydrochloride salt) (diastereomer pair 2), Compound 8

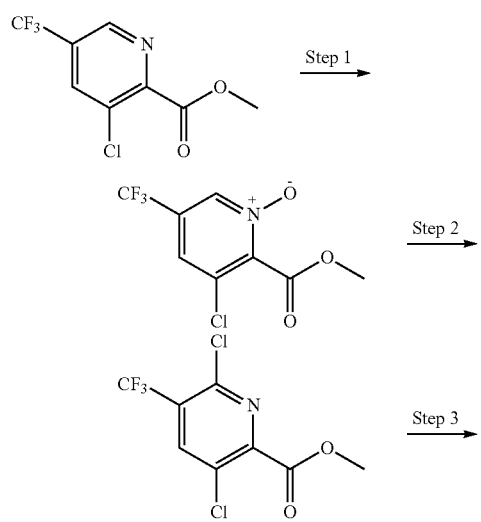

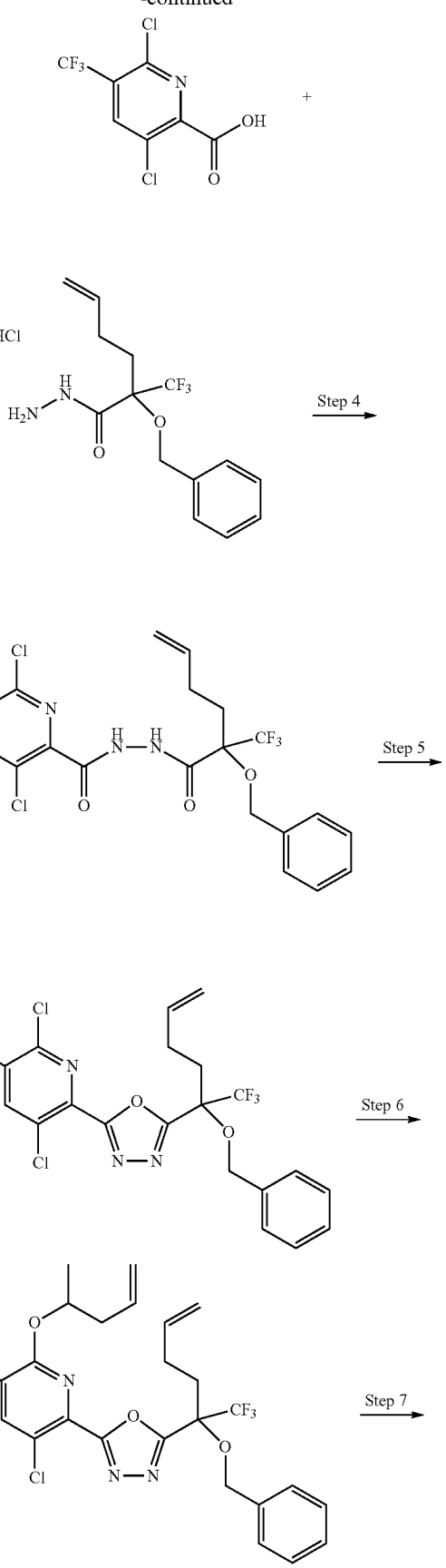

247

-continued

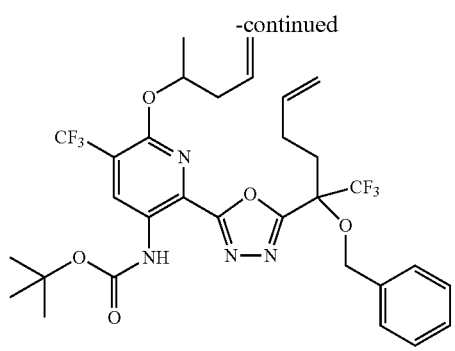

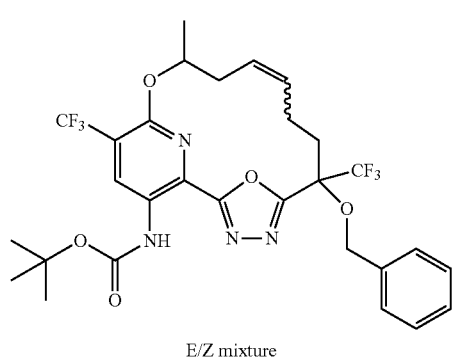

E/Z mixture

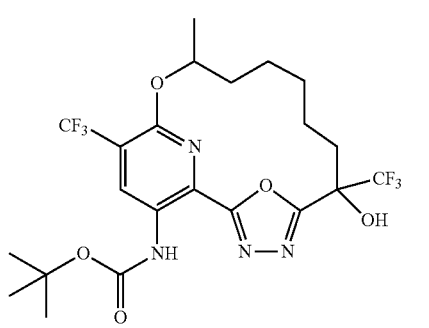

diastereomer pair 1 diastereomer pair 2

248

Step 1: Methyl 3-chloro-1-oxido-5-(trifluoromethyl)pyridin-1-ium-2-carboxylate

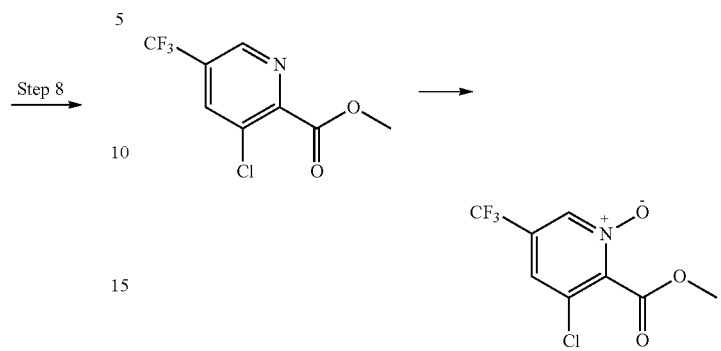

To a solution of methyl 3-chloro-5-(trifluoromethyl)pyridine-2-carboxylate (25 g, 102.26 mmol) in dichloromethane (250 mL) cooled to 0° C. was added urea hydrogen peroxide (34 g, 361.43 mmol) followed by the slow addition of trifluoroacetic anhydride (72.528 g, 48 mL, 345.32 mmol). The reaction mixture was stirred at room temperature for 3 h. The reaction mixture was then poured into ice-water (200 mL) and adjusted to pH=7-8 with 25% aqueous sodium hydroxide solution. The mixture was diluted with dichloromethane (100 mL) and then the layers were separated. The aqueous phase was extracted with dichloromethane (2×100 mL). The combined organic phases were washed with brine (250 mL), dried over anhydrous sodium sulfate, filtered and concentrated under reduced pressure to afford methyl 3-chloro-1-oxido-5-(trifluoromethyl)pyridin-1-ium-2-carboxylate (24.5 g, 94%) as a white solid which was used directly in the ensuing step. $^1$H NMR (300 MHz, DMSO-$d_6$) δ 9.00 (s, 1H), 8.25 (s, 1H), 3.97 (s, 3H) ppm. $^{19}$F NMR (282 MHz, DMSO-$d_6$) δ −61.75 (br. s., 3F) ppm. ESI-MS m/z calc. 254.99101, found 256.0 (M+1)$^+$; Retention time: 1.66 minutes; LCMS Method: Kinetex Polar $C_{18}$ 3.0×50 mm 2.6 µm, 3 min, 5-95% acetonitrile in water (0.1% formic acid) 1.2 mL/min.

Step 2: Methyl 3,6-dichloro-5-(trifluoromethyl)pyridine-2-carboxylate

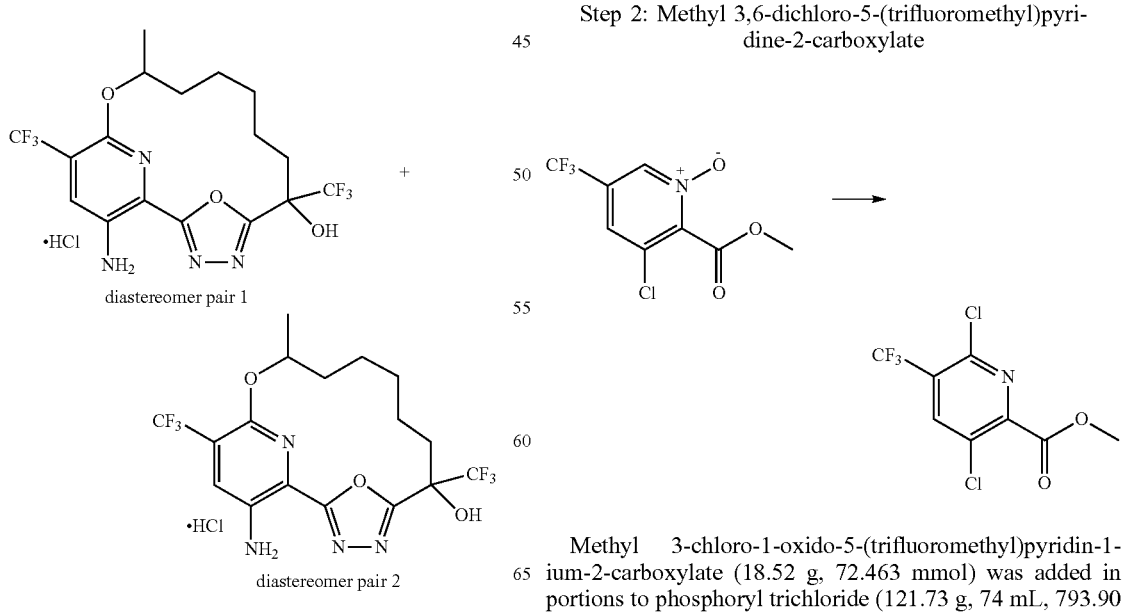

Methyl 3-chloro-1-oxido-5-(trifluoromethyl)pyridin-1-ium-2-carboxylate (18.52 g, 72.463 mmol) was added in portions to phosphoryl trichloride (121.73 g, 74 mL, 793.90 mmol) at 0° C. and the resulting mixture was stirred at 50°

C. overnight. Removal of the solvent in vacuo gave a black oil which was dissolved in ethyl acetate (200 mL) and carefully neutralized with a saturated aqueous solution of sodium carbonate until pH ~8. The mixture was extracted with ethyl acetate (2×500 mL) and the combined organic phases were washed with brine (250 mL), dried over anhydrous sodium sulfate, filtered and concentrated. The black oil was purified by flash chromatography on silica gel, eluting with a gradient from 0% to 20% ethyl acetate in heptanes to afford methyl 3,6-dichloro-5-(trifluoromethyl)pyridine-2-carboxylate (16.43 g, 83%) as a light yellow oil. $^1$H NMR (300 MHz, CDCl$_3$) δ 8.13 (s, 1H), 4.04 (d, J=1.8 Hz, 3H) ppm. $^{19}$F NMR (282 MHz, CDCl$_3$) ppm −64.2 (s, 3F) ppm. ESI-MS m/z calc. 272.95712, found 274.0 (M+1)$^+$; Retention time: 2.02 minutes; LCMS Method: Kinetex C$_{18}$ 4.6×50 mm 2.6 μM. Temp: 45° C., Flow: 2.0 mL/min, Run Time: 3 min. Mobile Phase: Initial 95% H$_2$O (0.1% formic acid) and 5% acetonitrile (0.1% formic acid) linear gradient to 95% acetonitrile (0.1% formic acid) for 2.0 min then held at 95% acetonitrile (0.1% formic acid) for 1.0 min.

Step 3: 3,6-Dichloro-5-(trifluoromethyl)pyridine-2-carboxylic acid

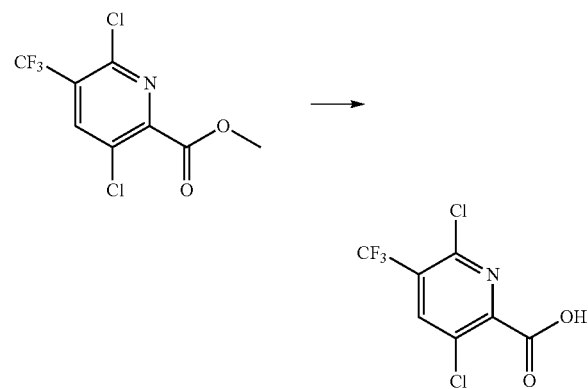

A mixture of methyl 3,6-dichloro-5-(trifluoromethyl)pyridine-2-carboxylate (14.63 g, 52.428 mmol) in THF (150 mL) and water (150 mL) was treated with lithium hydroxide monohydrate (4.5 g, 107.24 mmol) added portion-wise and the mixture was stirred vigorously at room temperature for 1.5 h. The crude reaction mixture was transferred to a 2 L separatory funnel with 5% citric acid (400 mL) and ethyl acetate (800 mL) and the layers were separated. The aqueous phase was extracted further with ethyl acetate (2×200 mL). The combined organic layers were then washed with water (120 mL), brine (2×120 mL), dried over sodium sulfate, filtered and concentrated under reduced pressure to afford 3,6-dichloro-5-(trifluoromethyl)pyridine-2-carboxylic acid (12.58 g, 92%) as a pale pink solid which was used directly in the ensuing step. $^1$H NMR (300 MHz, DMSO-d$_6$) δ 14.64 (br. s, 1H), 8.68 (s, 1H) ppm. $^{19}$F NMR (282 MHz, DMSO-d$_6$) δ −62.62 (s, 3F) ppm. ESI-MS m/z calc. 258.94147, found 257.9 (M+1)$^+$; Retention time: 1.51 minutes; LCMS Method: Kinetex Polar C$_{18}$ 3.0×50 mm 2.6 μm, 3 min, 5-95% acetonitrile in water (0.1% formic acid) 1.2 mL/min.

Step 4: N'-[2-Benzyloxy-2-(trifluoromethyl)hex-5-enoyl]-3,6-dichloro-5-(trifluoromethyl)pyridine-2-carbohydrazide

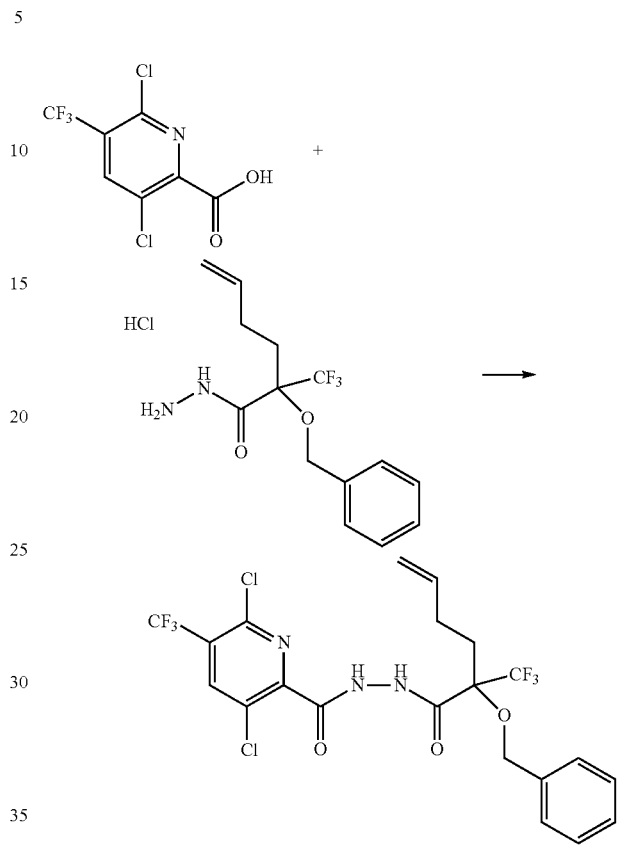

To a solution of 3,6-dichloro-5-(trifluoromethyl)pyridine-2-carboxylic acid (8.5 g, 32.693 mmol) in DMF (80 mL) was added triethylamine (10.890 g, 15 mL, 107.62 mmol) and HATU (15 g, 39.450 mmol). The mixture was stirred for 10 min, then 2-benzyloxy-2-(trifluoromethyl)hex-5-enehydrazide (hydrochloride salt) (11.51 g, 33.978 mmol) was added. The mixture was stirred at room temperature for 18 h, then poured into ice-cold water (200 g) and extracted with ethyl acetate (2×220 mL). The combined organic layers were washed with aqueous saturated sodium bicarbonate solution (2×80 mL), water (1×80 mL) and brine (2×80 mL). The organic layer was concentrated by evaporation under reduced pressure to give a dark yellow oil residue (19.2 g) that was combined with dichloromethane (100 mL) and pre-adsorbed on silica gel. Flash chromatography on silica gel (220 g column, crude dry loaded on 50 g of silica gel) using a gradient from 0% to 20% EtOAc in heptanes afforded N'-[2-benzyloxy-2-(trifluoromethyl)hex-5-enoyl]-3,6-dichloro-5-(trifluoromethyl)pyridine-2-carbohydrazide (11.37 g, 60%) as a white solid. $^1$H NMR (300 MHz, CDCl$_3$) δ 9.18 (br. s, 1H), 8.17 (s, 1H), 7.49-7.32 (m, 5H), 5.95-5.75 (m, 1H), 5.18-5.01 (m, 2H), 4.86 (d, J=10.3 Hz, 1H), 4.73 (d, J=10.6 Hz, 1H), 2.55-2.38 (m, 1H), 2.36-2.16 (m, 3H) ppm. $^{19}$F NMR (282 MHz, CDCl$_3$) δ −64.15 (s, 3F), −73.62 (s, 3F) ppm. ESI-MS m/z calc. 543.0551, found 544.1 (M+1)$^+$; Retention time: 2.25 minutes; LCMS Method: Kinetex Polar C$_{18}$ 3.0×50 mm 2.6 μm, 3 min, 5-95% acetonitrile in water (0.1% formic acid) 1.2 mL/min.

Step 5: 2-[1-Benzyloxy-1-(trifluoromethyl)pent-4-enyl]-5-[3,6-dichloro-5-(trifluoromethyl)-2-pyridyl]-1,3,4-oxadiazole

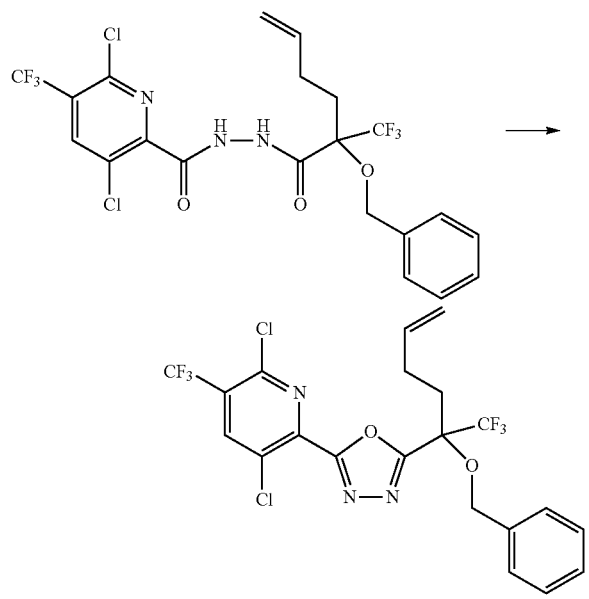

To a solution of N'-[2-benzyloxy-2-(trifluoromethyhex-5-enoyl]-3,6-dichloro-5-(trifluoromethyl)pyridine-2-carbohydrazide (10.37 g, 17.891 mmol) and N,N-diisopropylethylamine (6.5378 g, 8.9 mL, 50.079 mmol) in acetonitrile (240 mL) at 50° C. was added p-toluenesulfonyl chloride (4.15 g, 21.768 mmol) portion-wise. The mixture was stirred at 70° C. Upon completion (1 h), the reaction mixture was concentrated. The residue was dissolved in dichloromethane and washed with 5% aqueous sodium bicarbonate (20 mL), dried with anhydrous sodium sulfate. Flash chromatography on silica gel (40 g column, gradient from 0% to 15% EtOAc in heptanes) afforded 2-[1-benzyloxy-1-(trifluoromethyl)pent-4-enyl]-5-[3,6-dichloro-5-(trifluoromethyl)-2-pyridyl]-1,3,4-oxadiazole (8.1 g) as a white solid, containing residual p-toluenesulfonyl chloride. A 1.9 g fraction was dissolved in dichloromethane (40 mL) and added ammonium hydroxide (2.5 mL, 28-30% $NH_3$ basis) under stirring. The mixture was stirred at room temperature for 1 h, then transferred to a separatory funnel with ethyl acetate (160 mL) and separated. The organic layer was further washed with water (2×30 mL) and brine (30 mL), dried over anhydrous sodium sulfate and filtered. The volatiles of the filtrate were removed by evaporation under reduced pressure. The residue was dry loaded on silica gel (50 g) and purified by silica gel chromatography (80 g column) using a gradient from 0% to 10% EtOAc in heptanes giving 2-[1-benzyloxy-1-(trifluoromethyl)pent-4-enyl]-5-[3,6-dichloro-5-(trifluoromethyl)-2-pyridyl]-1,3,4-oxadiazole (1.7 g, 18%) as a white solid. The remaining 6.2 g fraction from the initial silica gel column was dissolved in dichloromethane (60 mL) and added ammonium hydroxide (5.0 mL, 28.0-30.0% $NH_3$ basis) under stirring. The mixture was stirred at room temperature for 1 h, then transferred to a separatory funnel with dichloromethane (100 mL) and separated. The organic layer was washed with water (2×30 mL) and brine (30 mL), dried over anhydrous sodium sulfate then filtered. The volatiles of the filtrate were removed by evaporation under reduced pressure. The residue was dry loaded on silica gel (50 g) and purified by silica gel chromatography on a 120 g column using a gradient from 0% to 10% ethyl acetate in heptanes giving 2-[1-benzyloxy-1-(trifluoromethyl)pent-4-enyl]-5-[3,6-dichloro-5-(trifluoromethyl)-2-pyridyl]-1,3,4-oxadiazole (5.87 g, 62%) as a white solid, calculated overall yield of product from both columns was 80%. $^1$H NMR (300 MHz, $CDCl_3$) δ 8.25 (s, 1H), 7.53-7.28 (m, 5H), 5.87-5.68 (m, 1H), 5.13-4.94 (m, 2H), 4.85 (d, J=10.6 Hz, 1H), 4.66 (d, J=10.9 Hz, 1H), 2.61-2.15 (m, 4H) ppm. $^{19}$F NMR (282 MHz, $CDCl_3$) δ −64.11 (s, 3F), −72.85 (s, 3F) ppm. ESI-MS m/z calc. 525.04456, found 526.1 $(M+1)^+$; Retention time: 2.42 minutes; LCMS Method: Kinetex Polar $C_{18}$ 3.0×50 mm 2.6 μm, 3 min, 5-95% acetonitrile in water (0.1% formic acid) 1.2 mL/min.

Step 6: 2-[1-Benzyloxy-1-(trifluoromethyl)pent-4-enyl]-5-[3-chloro-6-(1-methylbut-3-enoxy)-5-(trifluoromethyl)-2-pyridyl]-1,3,4-oxadiazole

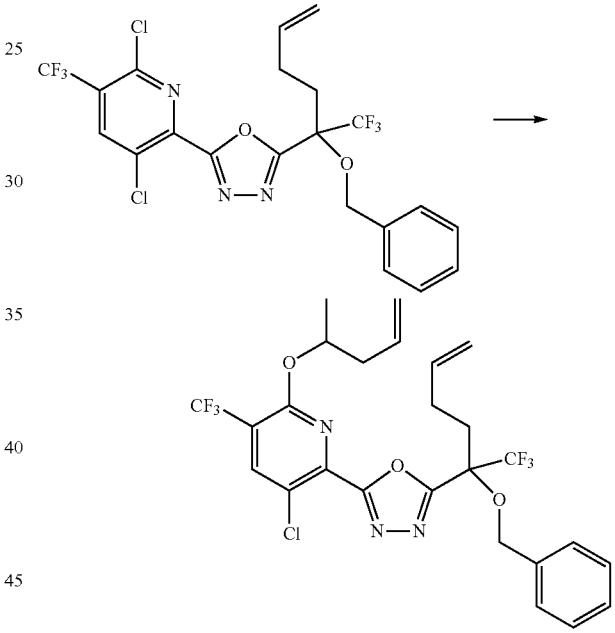

To a solution of 2-[1-benzyloxy-1-(trifluoromethyl)pent-4-enyl]-5-[3,6-dichloro-5-(trifluoromethyl)-2-pyridyl]-1,3,4-oxadiazole (1 g, 1.900 mmol) in DMSO (10 mL) was added pent-4-en-2-ol (502 mg, 5.828 mmol), $Cs_2CO_3$ (3.2 g, 9.821 mmol) and iodocopper (215 mg, 1.129 mmol) then the mixture was heated at 60° C. for 6 h. The reaction mixture was poured onto crushed ice and the resultant pasty material was dissolved in ethyl acetate, washed with brine, dried over anhydrous sodium sulphate, filtered and concentrated. The resultant brown residue was purified by silica gel chromatography using a shallow gradient from 100% hexanes to 50% EtOAc in hexanes to afford 2-[1-benzyloxy-1-(trifluoromethyl)pent-4-enyl]-5-[3-chloro-6-(1-methylbut-3-enoxy)-5-(trifluoromethyl)-2-pyridyl]-1,3,4-oxadiazole (427 mg, 39%). ESI-MS m/z calc. 575.14105, found 567.1 $(M+1)^+$; Retention time: 0.79 minutes. Final purity was determined by reversed phase UPLC using an Acquity UPLC BEH $C_{18}$ column (50×2.1 mm, 1.7 μm particle) made by Waters (pn: 186002350), and a dual gradient run from 30-99% mobile phase B over 2.9 minutes. Mobile phase A=water (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Step 7: tert-Butyl N-[2-[5-[1-benzyloxy-1-(trifluoromethyl)pent-4-enyl]-1,3,4-oxadiazol-2-yl]-6-(1-methylbut-3-enoxy)-5-(trifluoromethyl)-3-pyridyl]carbamate

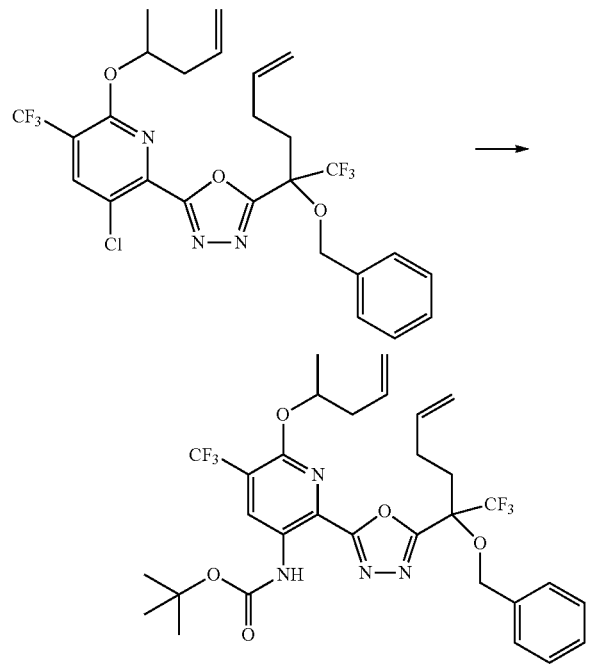

To a nitrogen degassed solution of 2-[1-benzyloxy-1-(trifluoromethyl)pent-4-enyl]-5-[3-chloro-6-(1-methylbut-3-enoxy)-5-(trifluoromethyl)-2-pyridyl]-1,3,4-oxadiazole (425 mg, 0.7379 mmol) in dioxane (5 mL), was added tert-butyl carbamate (262 mg, 2.237 mmol), XPhos Pd G3 (8.6 mg, 0.01016 mmol), palladium (II) acetate (4.2 mg, 0.01871 mmol) and Cs$_2$CO$_3$ (375 mg, 1.151 mmol) and heated the mixture in a sealed vial at 100° C. overnight. Cooled to room temperature, diluted with water (8 mL), extracted with ethyl acetate (3×70 mL) then combined extracts were washed with brine (15 mL), dried (sodium sulfate), filtered and concentrated. The resultant brown residue was purified by silica gel chromatography using a shallow gradient from 100% hexanes to 100% EtOAc to afford tert-butyl N-[2-[5-[1-benzyloxy-1-(trifluoromethyl)pent-4-enyl]-1,3,4-oxadiazol-2-yl]-6-(1-methylbut-3-enoxy)-5-(trifluoromethyl)-3-pyridyl]carbamate (152 mg, 31%) as a mixture of diastereomers. ESI-MS m/z calc. 656.24335, found 657.4 (M+1)$^+$; Retention time: 0.78 minutes. Final purity was determined by reversed phase UPLC using an Acquity UPLC BEH C$_{18}$ column (30×2.1 mm, 1.7 μm particle) made by Waters (pn: 186002349), and a dual gradient run from 50-99% mobile phase B over 1.0 minutes. Mobile phase A=water (0.05% CF$_3$CO$_2$H). Mobile phase B=acetonitrile (0.035% CF$_3$CO$_2$H). Flow rate=1.5 mL/min, injection volume=1.5 μL, and column temperature=60° C.

Step 8: tert-Butyl N-[6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaen-17-yl]carbamate (E/Z mixture)

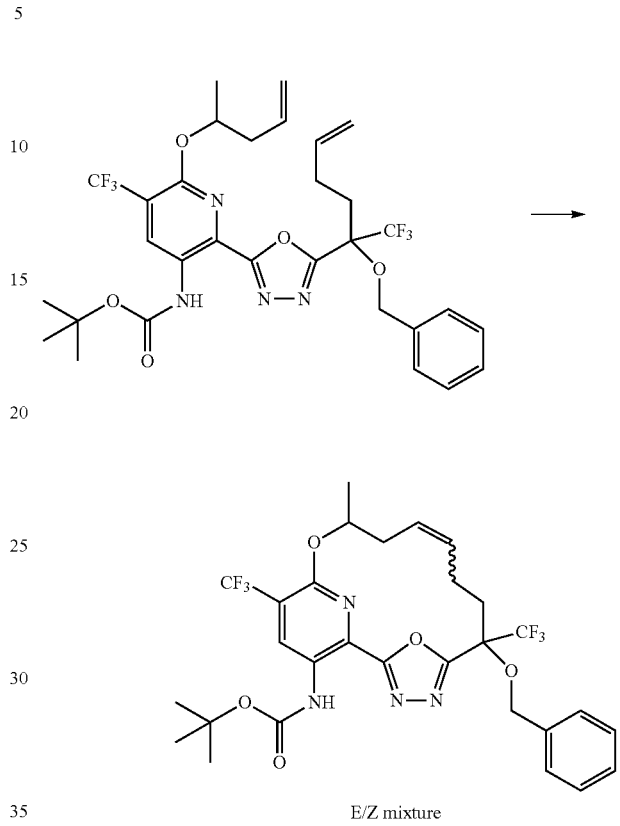

E/Z mixture

To a degassed solution of tert-butyl N-[2-[5-[1-benzyloxy-1-(trifluoromethyl)pent-4-enyl]-1,3,4-oxadiazol-2-yl]-6-(1-methylbut-3-enoxy)-5-(trifluoromethyl)-3-pyridyl]carbamate (150 mg, 0.2284 mmol) in DCE (50 mL) was added dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II) (Zhan catalyst-1B, 50 mg, 0.06221 mmol) and the reaction was heated at 70° C. overnight while continuously bubbling nitrogen into the solution with a gas outlet. The reaction mixture was then cooled to room temperature and concentrated under reduced pressure. Diluted with 1:4 EtOAc/hexanes and filtered through Celite. The filtrate was concentrated and the resultant brown residue was purified by silica gel chromatography using a shallow gradient from 100% hexanes to 30% EtOAc in hexanes to afford tert-butyl N-[6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaen-17-yl]carbamate (E/Z mixture) (52 mg, 36%) as a yellow oil. ESI-MS m/z calc. 628.21204, found 629.3 (M+1)$^+$; Retention time: 0.73 minutes. Final purity was determined by reversed phase UPLC using an Acquity UPLC BEH C$_{18}$ column (30×2.1 mm, 1.7 μm particle) made by Waters (pn: 186002349), and a dual gradient run from 50-99% mobile phase B over 1.0 minutes. Mobile phase A=water (0.05% CF$_3$CO$_2$H). Mobile phase B=acetonitrile (0.035% CF$_3$CO$_2$H). Flow rate=1.5 mL/min, injection volume=1.5 μL, and column temperature=60° C.

Step 9: tert-Butyl N-[6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate

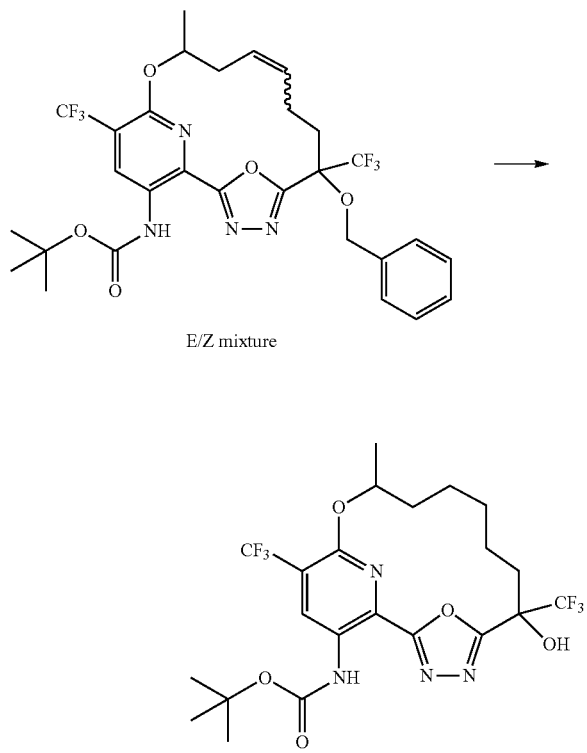 [SMILES: CC1CC=CCCC(OCc2ccccc2)(C(F)(F)F)C2=NN=C(O2)c2nc(c(C(F)(F)F)cc2NC(=O)OC(C)(C)C)O1 ; CC1CCCCCC(O)(C(F)(F)F)C2=NN=C(O2)c2nc(c(C(F)(F)F)cc2NC(=O)OC(C)(C)C)O1]

E/Z mixture

Combined tert-butyl N-[6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]carbamate (E/Z mixture) (52 mg, 0.08273 mmol), Pd/C (47 mg of 10% w/w, 0.04416 mmol), and AcOH (1 mL) in a Parr pressure vessel and sealed. Subjected to vacuum and backfilled with nitrogen gas three times then subjected to vacuum. Filled the vessel with hydrogen gas at 150 psi then stirred the mixture for 15 h. Subjected to vacuum and backfilled with nitrogen gas three times then diluted with ethyl acetate and filtered over Celite. The filtrate was concentrated and purified by reverse phase HPLC-MS using a gradient from 30% to 99% acetonitrile in water (+5 mM HCl) over 15.0 minutes to afford tert-butyl N-[6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (12.7 mg, 28%) as light brown solid. ESI-MS m/z calc. 540.1807, found 541.2 (M+1)$^+$; Retention time: 2.07 minutes. Final purity was determined by reversed phase UPLC using an Acquity UPLC BEH $C_{18}$ column (50×2.1 mm, 1.7 μm particle) made by Waters (pn: 186002350), and a dual gradient run from 50-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 10: 17-Amino-12-methyl-6,15-bis(trifluoromethyl)-13,19-dioxa-3,4,18-triazatricyclo[12.3.1.12,5]nonadeca-1(18),2,4,14,16-pentaen-6-ol (hydrochloride salt) (diastereomer pair 1), Compound 7, and 17-amino-12-methyl-6,15-bis(trifluoromethyl)-13,19-dioxa-3,4,18-triazatricyclo[12.3.1.12,5]nonadeca-1(18),2,4,14,16-pentaen-6-ol (hydrochloride salt) (diastereomer pair 2), Compound 8

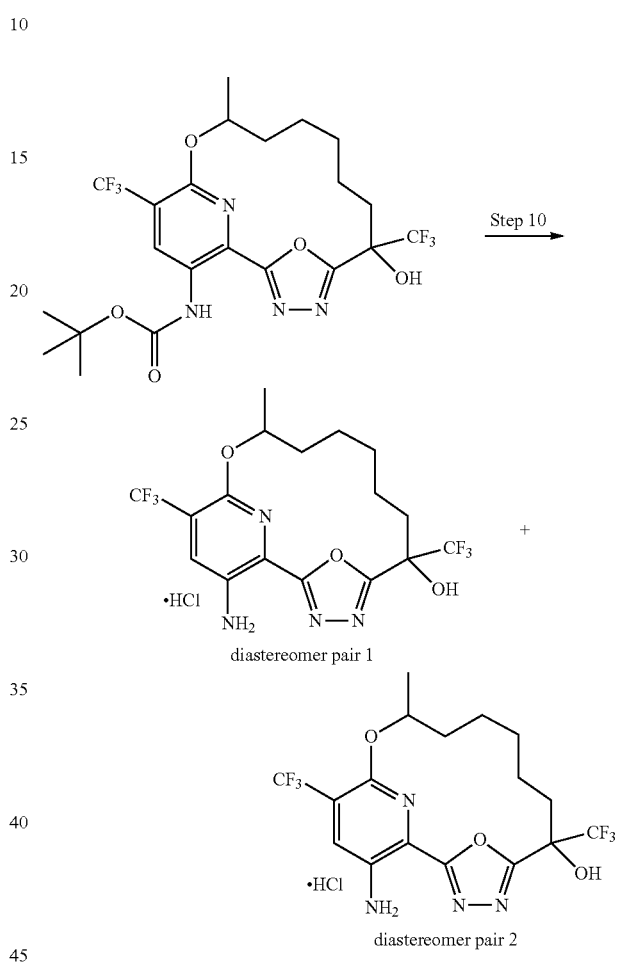

diastereomer pair 1 diastereomer pair 2

To a solution of tert-butyl N-[6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (12 mg, 0.02220 mmol) was added TFA (100 μL, 1.298 mmol) and dichloromethane (300 μL) (pre made solution of 1:4 TFA/dichloromethane) and the reaction was stirred at room temperature for about 1 h. Solvents were removed and dissolved in DMSO (1 mL) and the residue was purified by reverse phase HPLC-MS using a gradient from 1% to 99% acetonitrile in water (+5 mM HCl) over 15.0 minutes to afford as a light brown solid and the first eluting diastereomer pair, 17-amino-12-methyl-6,15-bis(trifluoromethyl)-13,19-dioxa-3,4,18-triazatricyclo[12.3.1.12,5]nonadeca-1(18),2,4,14,16-pentaen-6-ol (hydrochloride salt) (diastereomer pair 1) (2.1 mg, 38%). ESI-MS m/z calc. 440.1283, found 441.16 (M+1)$^+$; Retention time: 1.46 minutes. Final purity was determined by reversed phase UPLC using an Acquity UPLC BEH $C_{18}$ column (50×2.1 mm, 1.7 μm particle) made by Waters (pn: 186002350), and a dual gradient run from 30-99% mobile phase B over 2.9 minutes. Mobile phase A=water (0.05% $CF_3CO_2H$). Mobile phase B=acetonitrile (0.035% CF₃CO₂H). Flow rate=1.2 mL/min, injection volume=1.5 μL, and column temperature=60° C. The second eluting diastereomer pair, isolated as a light brown solid, was 17-amino-12-methyl-6,15-bis(trifluoromethyl)-13,19-dioxa-3,4,18-triazatricyclo[12.3.1.1²,⁵]nonadeca-1(18),2,4,14,16-pentaen-6-ol (hydrochloride salt) (diastereomer pair 2) (3.6 mg, 67%). ¹H NMR (500 MHz, DMSO-d₆) δ 7.76 (s, 1H), 7.63 (s, 1H), 6.36 (s, 2H), 4.77-4.65 (m, 1H), 2.55 (dd, J=8.8, 4.4 Hz, 1H), 2.17 (t, J=12.2 Hz, 1H), 2.09 (ddd, J=14.2, 10.5, 6.9 Hz, 1H), 1.68 (s, 1H), 1.59 (d, J=7.9 Hz, 2H), 1.48 (d, J=6.6 Hz, 3H), 1.33 (d, J=6.3 Hz, 3H), 1.14 (q, J=9.0, 8.0 Hz, 1H) ppm. ESI-MS m/z calc. 440.1283, found 441.2 (M+1)⁺; Retention time: 1.51 minutes. Final purity was determined by reversed phase UPLC using an Acquity UPLC BEH C₁₈ column (50×2.1 mm, 1.7 μm particle) made by Waters (pn: 186002350), and a dual gradient run from 30-99% mobile phase B over 2.9 minutes. Mobile phase A=water (0.05% CF₃CO₂H). Mobile phase B=acetonitrile (0.035% CF₃CO₂H). Flow rate=1.2 mL/min, injection volume=1.5 μL, and column temperature=60° C.

Example 7: Preparation of (6R)-17-amino-13,13-dioxo-6,15-bis(trifluoromethyl)-19-oxa-13λ⁶-thia-3,4,18-triazatricyclo[12.3.1.1²,⁵]nonadeca-1(18),2,4,14,16-pentaen-6-ol (enantiomer 1), Compound 9, and (6S)-17-amino-13,13-dioxo-6,15-bis(trifluoromethyl)-19-oxa-13λ⁶-thia-3,4,18-triazatricyclo[12.3.1.1²,⁵]nonadeca-1(18),2,4,14,16-pentaen-6-ol (enantiomer 2), Compound 10

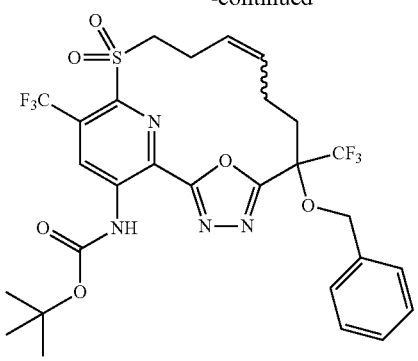

E/Z mixture

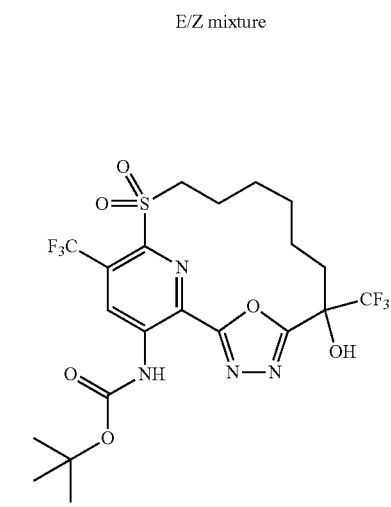

Step 3

Step 4

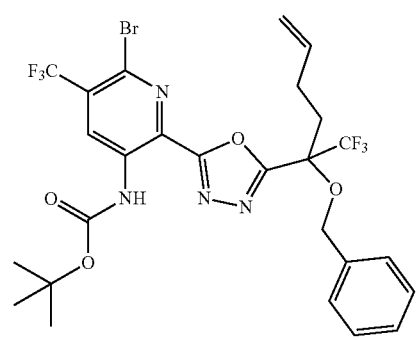

Step 1

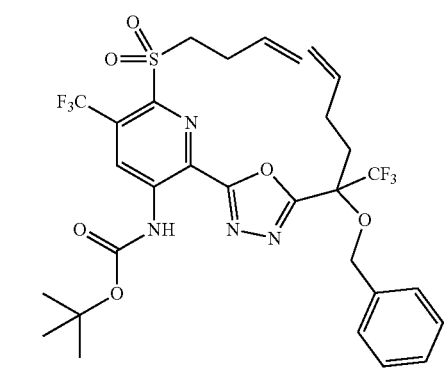

Step 2

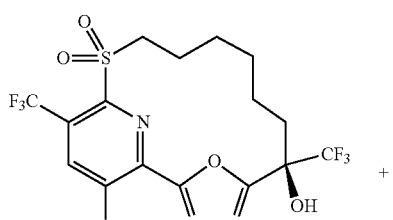

Enantiomer 1

+

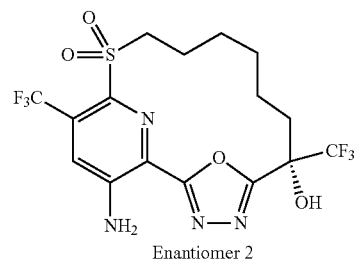

Enantiomer 2

Step 1: tert-Butyl N-[2-[5-[1-benzyloxy-t-(trifluoromethyl)pent-4-enyl]-1,3,4-oxadiazol-2-yl]-6-but-3-enylsulfonyl-5-(trifluoromethyl)-3-pyridyl]carbamate Step 2: tert-Butyl N-[6-(benzyloxy)-13,13-dioxo-6,15-bis(trifluoromethyl)-19-oxa-13λ⁶-thia-3,4,18-triazatricyclo[12.3.1.12,5]nonadeca-1(18),2,4,9,14,16-hexaen-17-yl]carbamate (E/Z Mixture)

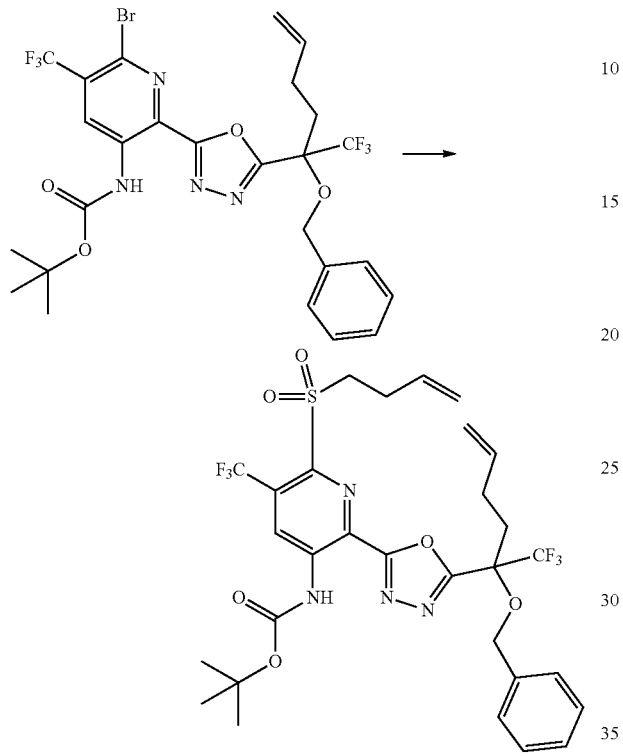

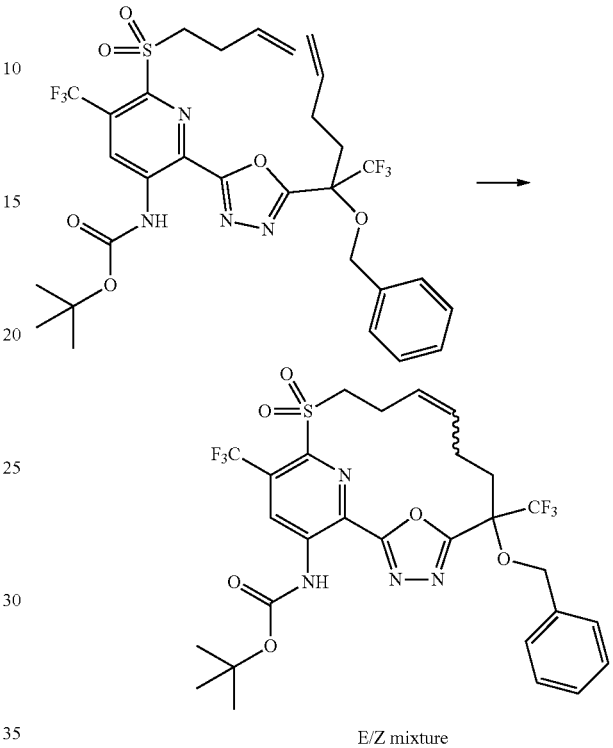

E/Z mixture

A mixture of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]carbamate (545 mg, 0.84 mmol), but-3-ene-1-sulfinate (sodium salt) (351 mg, 2.47 mmol), and CuI (472 mg, 2.48 mmol) in DMSO (5 mL) was heated at 100° C. for 3 h, then diluted with ether and water, the mixture filtered, the layers partitioned and the organic layer washed with water, brine, dried (MgSO₄) and evaporated. The residue was purified by silica gel chromatography (24 g SiO₂, 0-20% EtOAc in hexanes over 15 min) to provide tert-butyl N-[2-[5-[1-benzyloxy-1-(trifluoromethyl)pent-4-enyl]-1,3,4-oxadiazol-2-yl]-6-but-3-enylsulfonyl-5-(trifluoromethyl)-3-pyridyl]carbamate (327 mg, 57%). $^1$H NMR (400 MHz, Chloroform-d) δ 10.36 (s, 1H), 9.57 (s, 1H), 7.42-7.28 (m, 5H), 5.75 (tdt, J=17.0, 10.2, 6.5 Hz, 2H), 5.06 (dt, J=17.1, 1.4 Hz, 2H), 5.01 (d, J=10.2 Hz, 2H), 4.84 (d, J=10.9 Hz, 1H), 4.66 (d, J=10.8 Hz, 1H), 3.69 (hept, J=7.0 Hz, 2H), 2.65-2.58 (m, 2H), 2.56-2.31 (m, 2H), 2.30-2.18 (m, 1H), 1.59 (s, 9H), 1.55-1.51 (m, 1H)ppm. $^{19}$F NMR (376 MHz, Chloroform-d) δ -58.48, -72.86 ppm. ESI-MS m/z calc. 690.1947, found 691.2 (M+1)⁺; Retention time: 0.89 minutes. Final purity was determined by reversed phase UPLC using an Acquity UPLC BEH C$_{18}$ column (30×2.1 mm, 1.7 μm particle) made by Waters (pn: 186002349), and a dual gradient run from 1-99% mobile phase B over 1.0 minutes. Mobile phase A=H₂O (0.05% CF₃CO₂H). Mobile phase B=CH₃CN (0.035% CF₃CO₂H). Flow rate=1.5 mL/min, injection volume=1.5 μL, and column temperature=60° C.

A solution of tert-butyl N-[2-[5-[1-benzyloxy-1-(trifluoromethyl)pent-4-enyl]-1,3,4-oxadiazol-2-yl]-6-but-3-enylsulfonyl-5-(trifluoromethyl)-3-pyridyl]carbamate (300 mg, 0.4344 mmol) in 5 mL DCE was added dropwise over 5 min to a solution of benzylidene-[1,3-bis(2,4,6-trimethylphenypimidazolidin-2-ylidene]-dichloro-ruthenium;tricyclohexylphosphane (55 mg, 0.06478 mmol) in DCE (42 mL) heated at 70° C. with constant N₂ bubbling for 1 h. The solvent was evaporated and the residue purified by silica gel chromatography (24 g SiO₂, 0-20% EtOAc in hexane over 15 min) to provide tert-butyl N-[6-(benzyloxy)-13,13-dioxo-6,15-bi s (trifluoromethyl)-19-oxa-13λ⁶-thia-3,4,18-triazatricyclo[12.3.1.12,5]nonadeca-1 (18),2,4,9,14,16-hexaen-17-yl]carbamate (E/Z mixture) (157 mg, 55%). $^1$H NMR (400 MHz, Chloroform-d) δ 10.05 (s, 1H), 9.54 (s, 1H), 7.36-7.20 (m, 5H), 5.67 (q, J=8.3, 7.8 Hz, 1H), 5.48 (q, J=9.1, 8.7 Hz, 1H), 4.90 (s, 2H), 3.65 (ddd, J=14.6, 12.6, 4.4 Hz, 1H), 3.58-3.47 (m, 1H), 3.06-2.84 (m, 2H), 2.60-2.34 (m, 2H), 2.23 (t, J=10.5 Hz, 1H), 2.12-2.06 (m, 1H), 1.58 (d, J=2.9 Hz, 9H)ppm. $^{19}$F NMR (376 MHz, Chloroform-d) δ -58.72, -74.24 ppm. ESI-MS m/z calc. 662.1634, found 663.2 (M+1)⁺; Retention time: 0.85 minutes. Final purity was determined by reversed phase UPLC using an Acquity UPLC BEH C$_{18}$ column (30×2.1 mm, 1.7 μm particle) made by Waters (pn: 186002349), and a dual gradient run from 1-99% mobile phase B over 1.0 minutes. Mobile phase A=H₂O (0.05% CF₃CO₂H). Mobile phase B=CH₃CN (0.035% CF₃CO₂H). Flow rate=1.5 mL/min, injection volume=1.5 μL, and column temperature=60° C.

Step 3: tert-Butyl N-[6-hydroxy-13,13-dioxo-6,15-bis(trifluoromethyl)-19-oxa-13λ⁶-thia-3,4,18-triazatricyclo[12.3.1.1²,⁵]nonadeca-1(18),2,4,14,16-pentaen-17-yl]carbamate Step 4: (6R)-17-Amino-6-hydroxy-6,15-bis(trifluoromethyl)-19-oxa-13λ⁶-thia-3,4,18-triazatricyclo[12.3.1.1²,⁵]nonadeca-1(18),2,4,14,16-pentaene-13,13-dione (enantiomer 1), Compound 9, and (6S)-17-amino-6-hydroxy-6,15-bis(trifluoromethyl)-19-oxa-13λ⁶-thia-3,4,18-triazatricyclo[12.3.1.1²,⁵]nonadeca-1(18),2,4,14,16-pentaene-13,13-dione (enantiomer 2), Compound 10

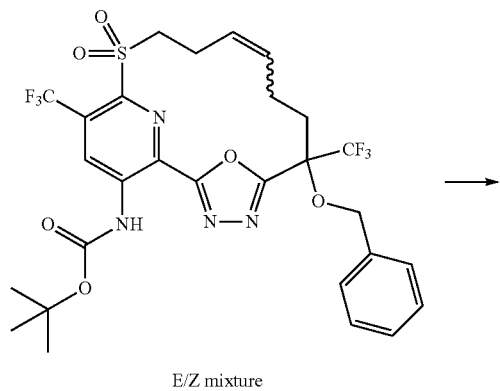

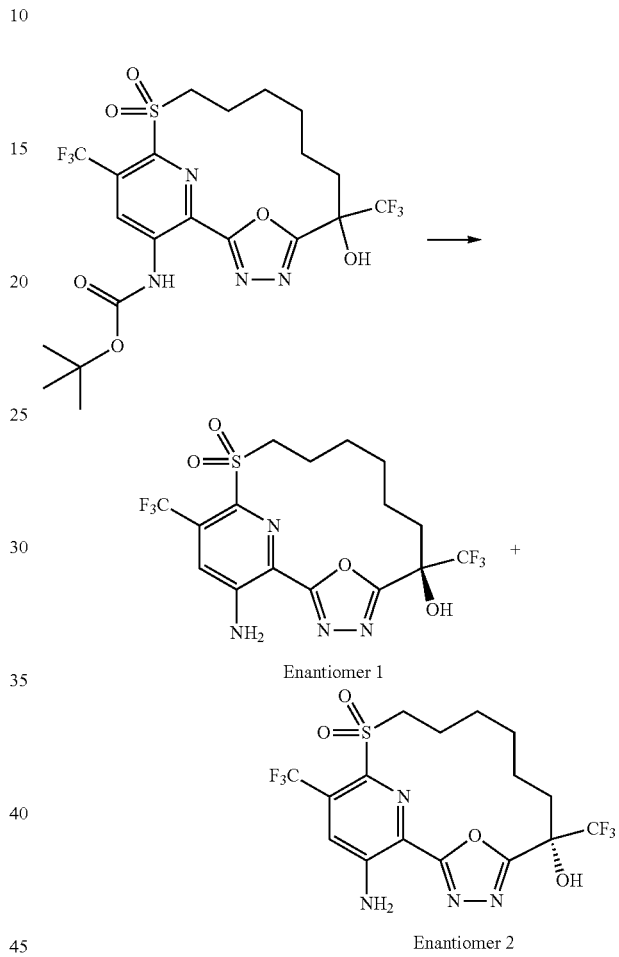

A mixture of tert-butyl N-[6-(benzyloxy)-13,13-dioxo-6,15-bis(trifluoromethyl)-19-oxa-13λ⁶-thia-3,4,18-triazatricyclo[12.3.1.1²,⁵]nonadeca-1(18),2,4,9,14,16-hexaen-17-yl]carbamate (E/Z mixture) (154 mg, 0.232 mmol), and Pd/C (74 mg of 10% w/w, 0.070 mmol) in AcOH (1.5 mL) was stirred at room temperature under 180 psi H₂ in a stainless steel pressure vessel for 15 h. Then the mixture was filtered and the filtrate evaporated to provide the target tert-butyl N-[6-hydroxy-13,13-dioxo-6,15-bis(trifluoromethyl)-19-oxa-13λ⁶-thia-3,4,18-triazatricyclo[12.3.1.1²,⁵]nonadeca-1(18),2,4,14,16-pentaen-17-yl]carbamate (136 mg, 96%), ESI-MS m/z calc. 574.1321, found 575.1 (M+1)⁺; Retention time: 0.72 minutes. Final purity was determined by reversed phase UPLC using an Acquity UPLC BEH C₁₈ column (30×2.1 mm, 1.7 μm particle) made by Waters (pn: 186002349), and a dual gradient run from 1-99% mobile phase B over 1.0 minutes. Mobile phase A=H₂O (0.05% CF₃CO₂H). Mobile phase B=CH₃CN (0.035% CF₃CO₂H). Flow rate=1.5 mL/min, injection volume=1.5 μL, and column temperature=60° C.

A mixture of tert-butyl N-[6-hydroxy-13,13-dioxo-6,15-bis(trifluoromethyl)-19-oxa-13λ⁶-thia-3,4,18-triazatricyclo[12.3.1.1²,⁵]nonadeca-1(18),2,4,14,16-pentaen-17-yl]carbamate (134 mg, 0.22 mmol), TFA (2 mL), triisopropylsilane (67 μL, 0.33 mmol) and water (100 μL) was stirred at room temperature for 30 min and then solvent evaporated. The residue was co-evaporated from acetonitrile (2×). The residue, dissolved into 2 mL acetonitrile, was subjected to preparative SFC with 330 μL injections through a preparative SFC eluting a gradient of 5 mM NH₃ in methanol to CO₂ (5-15% over 10 min) though a 21.2×250 mm AD column, 5 μm particle giving the first eluent (6R)-17-amino-6-hydroxy-6,15-bis(trifluoromethyl)-19-oxa-13λ⁶-thia-3,4,18-triazatricyclo[12.3.1.1²,⁵]nonadeca-1(18),2,4,14,16-pentaene-13,13-dione (enantiomer 1) (38 mg, 37%). ¹H NMR (400 MHz, DMSO-d₆) δ 7.93 (s, 1H), 7.66 (s, 3H, D₂O exchanged), 3.77-3.64 (m, 1H), 3.61-3.49 (m, 1H), 2.21 (t, J=12.1 Hz, 2H), 2.08 (d, J=15.0 Hz, 1H), 1.92 (dd, J=12.5, 7.2 Hz, 1H), 1.56 (m, 6H) ppm; ¹⁹F NMR (376 MHz, DMSO-d₆) δ −57.96, −78.11 ppm. ESI-MS m/z calc. 474.07965, found 475.0 (M+1)+; Retention time: 1.16 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=$CH_3CN$ (0.035% $CF_3CO_2H$). Flow rate=12 mL/min, injection volume=50 μL, and column temperature=25° C. UV/vis $\lambda_{max}$ 231, 277, 356 nm.

Further elution provided the second eluent (6S)-17-amino-6-hydroxy-6,15-bis(trifluoromethyl)-19-oxa-13$\lambda^6$-thia-3,4,18-tri azatricyclo[12.3.1.12,5]nonadeca-1(18),2,4,14,16-pentaene-13,13-dione (enantiomer 2) (36 mg, 35%). $^1$H NMR (400 MHz, DMSO-$d_6$) δ 7.93 (s, 1H), 7.66 (s, 3H, $D_2O$ exchanged), 3.77-3.63 (m, 1H), 3.56 (td, J=14.9, 13.7, 4.1 Hz, 1H), 2.21 (t, J=11.9 Hz, 2H), 2.08 (dd, J=14.1, 8.0 Hz, 1H), 1.97-1.84 (m, 1H), 1.56 (m, 6H) ppm; $^{19}$F NMR (376 MHz, DMSO-$d_6$) δ −57.96, −78.11. ESI-MS m/z calc. 474.07965, found 475.0 (M+1)+; Retention time: 1.16 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=$CH_3CN$ (0.035% $CF_3CO_2H$). Flow rate=12 mL/min, injection volume=50 ut, and column temperature=25° C.

Example 8: Preparation of (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol, Compound 11

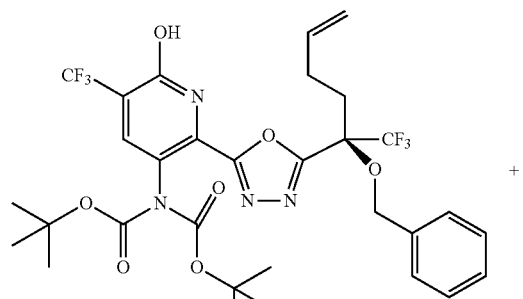

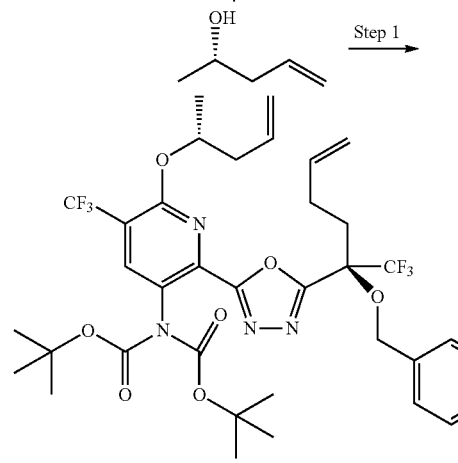

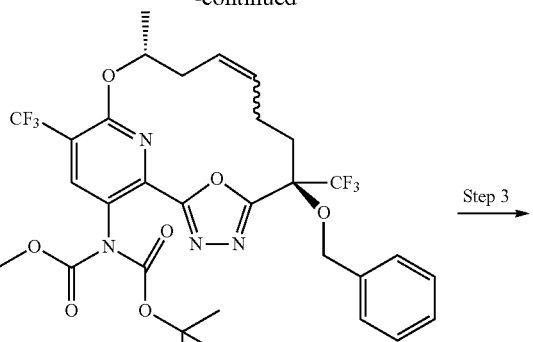

E/Z mixture

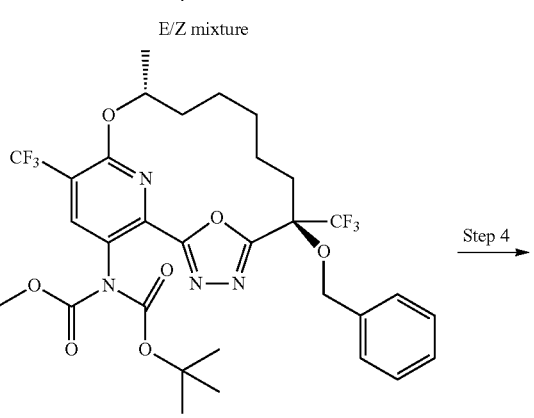

Step 1: tert-Butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate

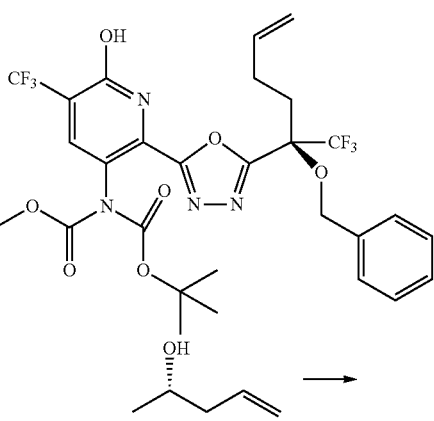

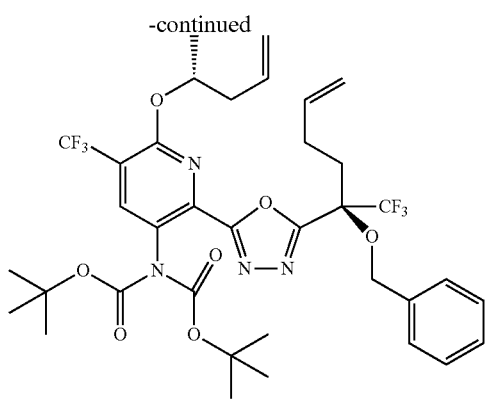

Dissolved tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (159.3 g, 231.3 mmol) and triphenylphosphine (72.9 g, 277.9 mmol) in toluene (1 L), then added (2S)-pent-4-en-2-ol (28.7 mL, 278.9 mmol). Heated this mixture to 45° C., then added DIAD (58.3 mL, 296.1 mmol) (exotherm) slowly over 40 min. For the next approximately 2 h, the mixture was cooled to room temperature. During this cooling period, after the first 10 minutes, triphenylphosphine (6.07 g, 23.14 mmol) was added. After a further 1 h, additional triphenylphosphine (3.04 g, 11.59 mmol) was added. After a further 23 min, DIAD (2.24 mL, 11.57 mmol) was added. After the ~2 h cooling to room temperature period, the mixture was cooled to 15° C., and seed crystals of DIAD-triphenylphosphine oxide complex were added which caused precipitation to occur, then added 1000 mL heptane. Stored the mixture at −20° C. for 3 days. Filtered out and discarded the precipitate and concentrated the filtrate to give a red residue/oil. Dissolved the residue in 613 mL heptane at 45° C., then cooled to 0° C., seeded with DIAD-triphenylphosphine oxide complex, stirred at 0° C. for 30 min, then filtered the solution. The filtrate was concentrated to a smaller volume, then loaded onto a 1.5 kg silica gel column (column volume=2400 mL, flow rate=600 mL/min). Ran a gradient of 1% to 6% EtOAc in hexanes over 32 minutes (8 column volumes), then held at 6% EtOAc in hexanes until the product finished eluting which gave tert-butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate (163.5 g, 93%). $^1$H NMR (400 MHz, Chloroform-d) δ 7.82 (s, 1H), 7.43-7.27 (m, 5H), 5.88-5.69 (m, 2H), 5.35 (h, J=6.2 Hz, 1H), 5.16-4.94 (m, 4H), 4.81 (d, J=10.7 Hz, 1H), 4.63 (d, J=10.7 Hz, 1H), 2.58-2.15 (m, 6H), 1.42 (s, 18H), 1.36 (d, J=6.2 Hz, 3H) ppm. ESI-MS m/z calc. 756.2958, found 757.3 (M+1)$^+$; Retention time: 4.0 minutes. Final purity was determined by reversed phase UPLC using an Acquity UPLC BEH $C_{18}$ column (50×2.1 mm, 1.7 µm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 µL, and column temperature=60° C.

Step 2: tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z Mixture)

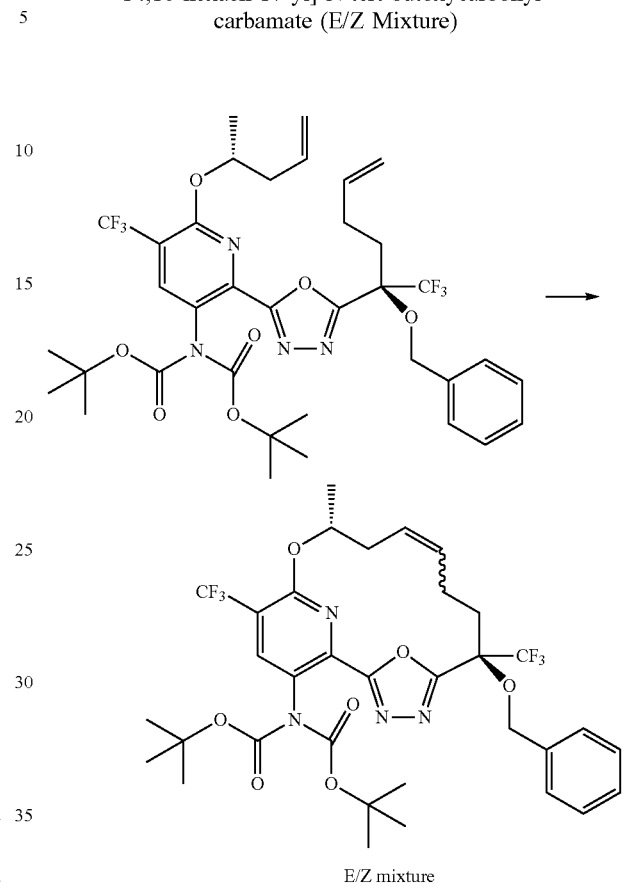

E/Z mixture

The following reaction was run, split equally between two, 12 L reaction flasks run in parallel. Mechanical stirring was employed, and reactions were subjected to a constant nitrogen gas purge using a course porosity gas dispersion tube. To each flask was added tert-butyl N-[2-[5-[(1R)-1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]-N-tert-butoxycarbonyl-carbamate (54 g, 71.36 mmol in each flask) dissolved in DCE (8 L in each flask) and both flasks were strongly purged with nitrogen at room temperature. Both flasks were heated to 62° C. and Grubbs 1$^{st}$ Generation Catalyst (9 g, 10.94 mmol in each flask) was added to each reaction and stirred at 400 rpm while setting an internal temperature control to 75° C. with strong nitrogen purging (both reactions reached 75° C. after approximately 20 min). After 5 h 15 min, the internal temperature control was set to 45° C. After approximately 2 h, 2-sulfanylpyridine-3-carboxylic acid (11 g, 70.89 mmol in each flask) was added to each flask followed by triethylamine (10 mL, 71.75 mmol in each flask). On completion of addition, the nitrogen purge was turned off and both reaction flasks were stirred at 45° C. open to air overnight. The reactions were then removed from heat and 130 g of silica gel was added to each reaction and each was stirred at room temperature. After approximately 2 h, the green mixtures were combined and filtered over Celite then concentrated by rotary evaporation at 43° C. The obtained residue was dissolved in dichloromethane/heptane 1:1 (400 mL) and the formed orange solid was removed by filtration. The greenish mother liquor was evaporated to give 115.5 g of a green foam. Dissolved this material in 500 mL of 1:1 dichloromethane/hexanes then loaded onto a 3 kg silica gel column (column volume=4800 mL, flow rate=900 mL/min). Ran a gradient of 2% to 9% EtOAc in hexanes over 43 minutes (8 column volumes), then ran at 9% EtOAc until the product finished eluting giving 77.8 g of impure product. This material was co-evaporated with methanol (~500 mL) then diluted with methanol (200 mL) to give 234.5 g of a methanolic solution, which was halved and each half was purified by reverse phase chromatography (3.8 kg $C_{18}$ column, column volume=3300 mL, flow rate=375 mL/min, loaded as solution in methanol). Ran the column at 55% acetonitrile for 5 minutes (0.5 column volumes), then at a gradient of 55% to 100% acetonitrile in water over 170 minutes (19-20 column volumes), then held at 100% acetonitrile until the product and impurities finished eluting. Clean product fractions from both columns were combined and concentrated by rotary evaporation then transferred with ethanol into 5 L flask, evaporated and carefully dried (becomes a foam) to give as a mixture of olefin isomers, tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (55.5 g, 53%). ESI-MS m/z calc. 728.26447, found 729.0 (M+1)$^+$; Retention time: 3.82 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 3: tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate

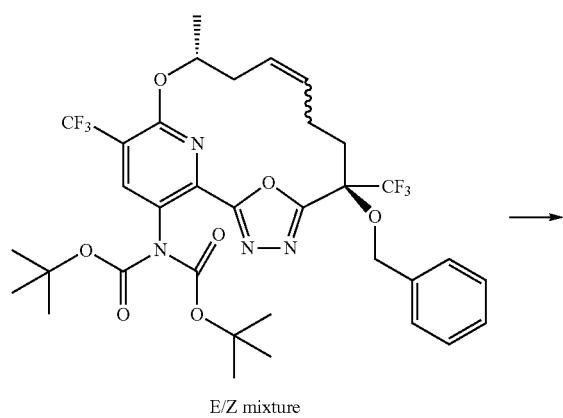

E/Z mixture

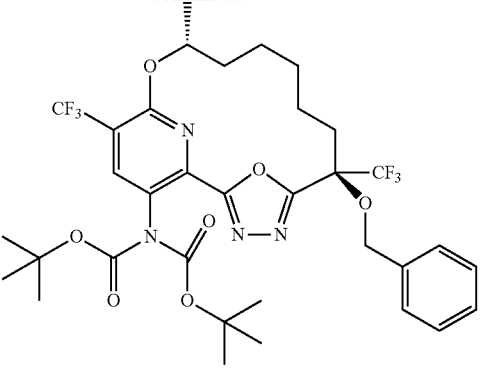

tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (11.7 g, 16.06 mmol) was dissolved in stirring ethanol (230 mL) and cycled the flask 3 times vacuum/nitrogen and treated with 10% Pd/C (50% water wet, 2.2 g of 5% w/w, 1.034 mmol). The mixture was cycled 3 times between vacuum/nitrogen and 3 times between vacuum/hydrogen. The mixture was then stirred strongly under hydrogen (balloon) for 7.5 h. The catalyst was removed by filtration, replaced with fresh 10% Pd/C (50% water wet, 2.2 g of 5% w/w, 1.034 mmol) and stirred vigorously under hydrogen (balloon) overnight. Then, the catalyst was removed again by filtration, the filtrate evaporated and the residue (11.3 g, 1 g set aside) was dissolved in ethanol (230 mL) charged with fresh 10% Pd/C (50% water wet, 2.2 g of 5% w/w, 1.034 mmol) and stirred vigorously under hydrogen (balloon) for 6 h, recharged again with fresh 10% Pd/C (50% water wet, 2.2 g of 5% w/w, 1.034 mmol) and stirred vigorously under hydrogen (balloon) overnight. The catalyst was removed by filtration and the filtrate was evaporated (10 g of residue obtained). This crude material (10 g+1 g set aside above) was purified by silica gel chromatography (330 g column, liquid load in dichloromethane) with a linear gradient of 0% to 15% ethyl acetate in hexane until the product eluted followed by 15% to 100% ethyl acetate in hexane to giving, as a colorless foam, tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (9.1 g, 78%). ESI-MS m/z calc. 730.2801, found 731.0 (M+1)$^+$; Retention time: 3.89 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 4: (6R,12R)-17-Amino-12-methyl-6,15-bis(trifluoromethyl)-13,19-dioxa-3,4,18-triazatricyclo[12.3.1.1²,⁵]nonadeca-1(18),2,4,14,16-pentaen-6-ol, Compound 11

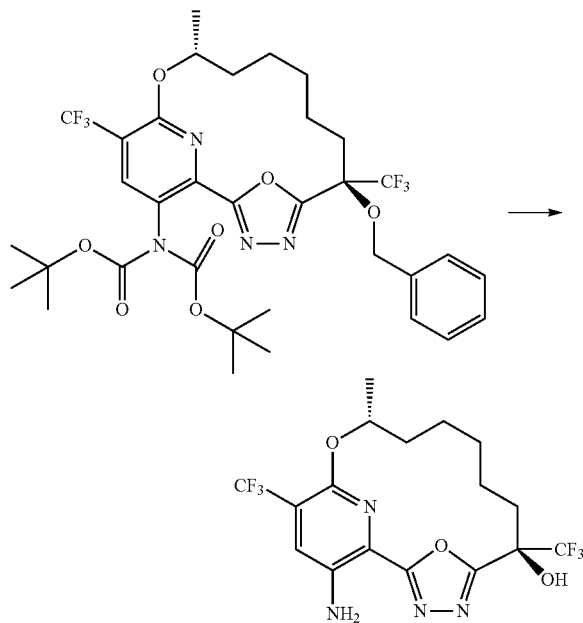

tert-Butyl N-[(6R,12R)-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]-N-tert-butoxycarbonyl-carbamate (8.6 g, 11.77 mmol) was dissolved in ethanol (172 mL) then the flask was cycled 3 times between vacuum/nitrogen. Treated the mixture with 10% Pd/C (50% water wet, 1.8 g of 5% w/w, 0.8457 mmol) then cycled 3 times between vacuum/nitrogen and 3 times between vacuum/hydrogen and then stirred vigorously under hydrogen (balloon) at room temperature for 18 h. The mixture was cycled 3 times between vacuum/nitrogen, filtered over Celite washing with ethanol and then the filtrate was evaporated to give 7.3 g of tert-butyl N-tert-butoxycarbonyl-N-[(6R,12R)-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate an off-white solid. This material was dissolved in dichloromethane (69 mL), cooled in an ice bath under nitrogen and slowly treated with TFA (23 mL, 298.5 mmol). The solution was stirred in the ice bath for 5 min and then at room temperature for 1 h. The pale-yellow solution was diluted with heptane (~100 mL) and evaporated to give a yellow solid mass. The residue was diluted again with heptane (~100-200 mL) and dichloromethane was added under warming until a yellow solution was obtained. Most of the dichloromethane was removed by rotary evaporation (35° C. water bath, 100 mbar pressure) to give a fine yellow suspension. The suspension was swirled for ~1 h at room temperature, filtered washing the solid with dry ice chilled heptane and then dried over 3 days under vacuum with a nitrogen leak at 50° C. to give as a pale yellow solid, (6R,12R)-17-amino-12-methyl-6,15-bis(trifluoromethyl)-13,19-dioxa-3,4,18-triazatricyclo[12.3.1.1²,⁵]nonadeca-1(18),2,4,14,16-pentaen-6-ol (4.68 g, 90%). $^1$H NMR (400 MHz, DMSO-d$_6$) δ 7.77 (s, 1H), 7.55 (s, 1H), 6.34 (s, 2H), 4.90-4.70 (m, 1H), 2.47 (dd, J=7.8, 5.5 Hz, 1H), 2.29 (t, J=11.2 Hz, 1H), 2.11 (ddd, J=14.4, 8.7, 6.1 Hz, 1H), 1.73 (dt, J=12.7, 7.6 Hz, 2H), 1.59-1.38 (m, 4H), 1.35 (d, J=6.3 Hz, 3H), 1.18 (ddt, J=12.4, 9.6, 6.2 Hz, 1H) ppm. $^1$H NMR (400 MHz, Chloroform-d) δ 7.42 (d, J=0.8 Hz, 1H), 5.20 (s, 2H), 4.75 (dtt, J=12.6, 6.3, 3.2 Hz, 1H), 3.98 (s, 1H), 2.68 (dtd, J=12.9, 7.6, 2.3 Hz, 1H), 2.38-2.18 (m, 2H), 2.03 (d, J=7.9 Hz, 1H), 1.75-1.46 (m, 5H), 1.41 (d, J=6.3 Hz, 3H), 1.35-1.27 (m, 1H) ppm. $^{19}$F NMR (376 MHz, Chloroform-d) δ −63.95, −77.34 ppm. ESI-MS m/z calc. 440.1283, found 441.0 (M+1)$^+$; Retention time: 2.87 minutes. Final purity was determined by reversed phase UPLC using an Acquity UPLC BEH C$_{18}$ column (50×2.1 mm, 1.7 μm particle) made by Waters (pn: 186002350), and a dual gradient run from 1-99% mobile phase B over 4.5 minutes. Mobile phase A=water (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Step 5: Solid form chracterization of Compound 11 heptane solvate

A. X-Ray Powder Diffraction

The X-ray powder diffraction (XRPD) diffractogram of the product of Step 4, Compound 11 heptane solvate, was acquired at room temperature in transmission mode using a PANalytical Empyrean system equipped with a sealed tube source and a PIXcel 1D Medipix-3 detector (Malvern PANalytical Inc, Westborough, Massachusetts). The X-ray generator operated at a voltage of 45 kV and a current of 40 mA with copper radiation (1.54060 Å). The powder sample was placed on a 96 well sample holder with mylar film and loaded into the instrument. The sample was scanned over the range of about 3° to about 40°2θ with a step size of 0.0131303° and 49 s per step.

The XRPD diffractogram for Compound 11 heptane solvate is provided in FIG. 1, and the XRPD data are summarized below in Table 4.

TABLE 4

| | XRPD signals for Compound 11 heptane solvate | |
|---|---|---|
| XRPD Peak No. | Angle (degrees 2-Theta ± 0.2) | Intensity % |
| 1 | 5.8265 | 100 |
| 2 | 10.1389 | 30.54 |
| 3 | 5.5705 | 22.28 |
| 4 | 18.1061 | 21 |
| 5 | 20.5379 | 15.76 |
| 6 | 11.7247 | 12.43 |
| 7 | 20.9306 | 11.25 |

Figure 2:
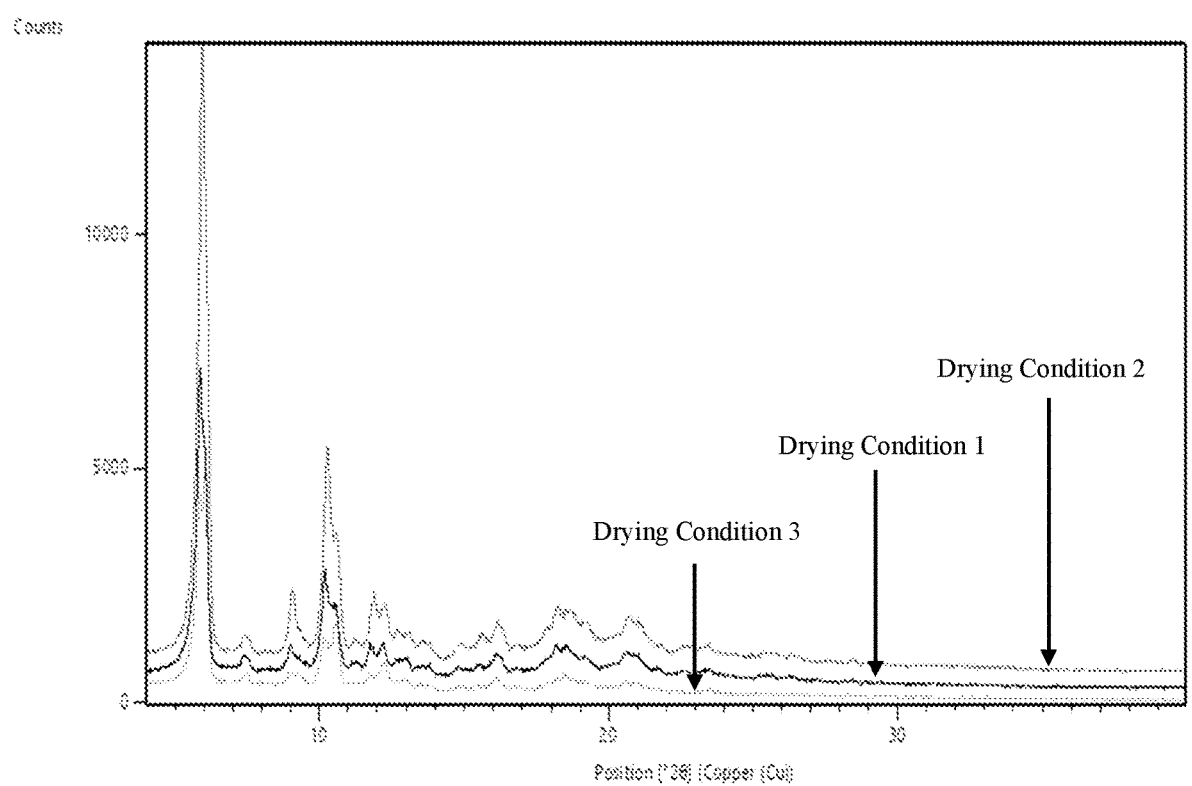
FIG. 2 provides an overlay of X-ray power diffraction (XRPD) patterns of Compound 11 heptane solvate prepared under three different drying conditions.

XRPD diffractograms for Compound 11 heptane solvate samples prepared under three different drying conditions are provided in FIG. 2. The XRPD diffractograms were recorded at room temperature in continuous mode using a PANalytical Empyrean X-ray Diffract meter (Almelo, The Netherlands). The X-Ray was generated using Cu tube operated at 45 kV and 40 mA. Pixel 1d detector was used with anti-scatter slit P8. The Divergence optics is Bragg Brentano High Definition (BBHD) with a 10 mm mask, ⅛ divergence slit, and ½ anti-scatter slit. The continuous scan mode utilized a 0.0131 degree step size and count time of 13.77 seconds per step, integrated over the range from 4 to 40 degrees two-theta. The powder sample was placed on an indented area within a zero background holder and flattened with a glass slide.

Under Drying Condition 1, Compound 11 heptane solvate was dried over the weekend under house vacuum with a nitrogen leak at 50° C. Under Drying Condition 2, Compound 11 heptane solvate was dried over the weekend at 40-45° C. Under Drying Condition 3, Compound 11 heptane solvate was dried for 4 days under house vacuum with a nitrogen bleed at 40-45° C.

The XRPD diffractograms for Compound 11 heptane solvate samples prepared under Drying Condition 1, Drying Condition 2, and Drying Condition 3 are provided in FIG. 2, and the XRPD data are summarized below in Tables 5, 6, and 7. In FIG. 2, the top curve corresponds to Drying Condition 2, the middle curve corresponds to Drying Condition 1, and the bottom curve corresponds to Drying Condition 3. Each curve is substantially similar to each other and to the XRPD of FIG. 1.

TABLE 5

XRPD signals for Compound 11 heptane solvate, Drying Condition 1

| XRPD Peak No. | Angle (degrees 2-Theta ± 0.2) | Intensity % |
|---|---|---|
| 1 | 5.8572 | 100 |
| 2 | 6.0844 | 62.33 |
| 3 | 10.189 | 34.55 |
| 4 | 10.5918 | 21.42 |
| 5 | 18.5355 | 10.59 |
| 6 | 18.1599 | 10.55 |
| 7 | 12.2176 | 10.14 |

TABLE 6

XRPD signals for Compound 11 heptane solvate, Drying Condition 2

| XRPD Peak No. | Angle (degrees 2-Theta ± 0.2) | Intensity % |
|---|---|---|
| 1 | 5.9314 | 100 |
| 2 | 6.1405 | 52.48 |
| 3 | 10.2746 | 33.73 |
| 4 | 10.6383 | 18.32 |
| 5 | 11.9036 | 10 |

TABLE 7

XRPD signals for Compound 11 heptane solvate, Drying Condition 3

| XRPD Peak No. | Angle (degrees 2-Theta ± 0.2) | Intensity % |
|---|---|---|
| 1 | 6.0778 | 100 |
| 2 | 5.812 | 81.49 |
| 3 | 10.6059 | 29.34 |
| 4 | 10.1304 | 21.77 |
| 5 | 12.27 | 12.64 |

B. Differential Scanning Calorimetry Analysis

The melting point of the product of Step 4, Compound 11 heptane solvate, was measured using the TA Instruments Q2000 DSC.

The DSC thermogram for Compound 11 heptane solvate is provided in FIG. 2. The thermogram for Compound 11 heptane solvate shows an endotherm at ~93.45° C. and recrystallization at ~103° C.

C. Solid-State $^{13}$C NMR

The $^{13}$C SSNMR of the product of Step 4, Compound 11 heptane solvate, was acquired using the procedure described in the General Methods. The $^{13}$C SSNMR spectrum for Compound 11 heptane solvate Form is provided in FIG. 3, and the data are summarized below in Table 8.

TABLE 8

$^{13}$C SSNMR signals for Compound 11 heptane solvate

| Peak # | Chem Shift [ppm] | Intensity [rel] |
|---|---|---|
| 1 | 166.3 | 26.5 |
| 2 | 165.8 | 19.3 |
| 3 | 164.6 | 48.8 |
| 4 | 163.4 | 18.2 |
| 5 | 154.8 | 12.9 |
| 6 | 154.0 | 21.1 |
| 7 | 152.1 | 24.5 |
| 8 | 151.6 | 50.5 |
| 9 | 140.2 | 12.3 |
| 10 | 139.4 | 17.5 |
| 11 | 138.5 | 23.1 |
| 12 | 138.0 | 18.9 |
| 13 | 135.1 | 17.6 |
| 14 | 134.6 | 20.4 |
| 15 | 131.3 | 26.2 |
| 16 | 130.2 | 24.2 |
| 17 | 129.6 | 24.3 |
| 18 | 128.5 | 18.0 |
| 19 | 125.7 | 31.6 |
| 20 | 123.7 | 15.1 |
| 21 | 123.2 | 14.6 |
| 22 | 122.9 | 16.7 |
| 23 | 121.1 | 21.9 |
| 24 | 120.2 | 40.6 |
| 25 | 119.2 | 15.1 |
| 26 | 117.8 | 48.6 |
| 27 | 76.2 | 31.3 |
| 28 | 74.4 | 84.8 |
| 29 | 73.7 | 84.5 |
| 30 | 73.3 | 73.1 |
| 31 | 40.0 | 22.3 |
| 32 | 38.6 | 12.0 |
| 33 | 37.6 | 27.9 |
| 34 | 36.9 | 32.7 |
| 35 | 35.7 | 12.6 |
| 36 | 33.6 | 13.5 |
| 37 | 32.5 | 57.6 |
| 38 | 32.0 | 69.7 |
| 39 | 30.4 | 56.4 |
| 40 | 30.1 | 50.3 |
| 41 | 29.5 | 44.7 |
| 42 | 28.8 | 36.63 |
| 43 | 28.1 | 21.1 |
| 44 | 27.1 | 29.6 |
| 45 | 25.3 | 27.1 |
| 46 | 23.1 | 90.9 |
| 47 | 22.7 | 88.1 |
| 48 | 22.0 | 46.4 |
| 49 | 21.6 | 48.1 |
| 50 | 20.3 | 100.0 |
| 51 | 19.6 | 83.0 |
| 52 | 18.3 | 24.6 |
| 53 | 17.6 | 47.9 |
| 54 | 13.8 | 51.6 |
| 55 | 13.1 | 39.3 |
| 56 | 12.5 | 82.3 |

D. Solid-State $^{19}$F NMR

The $^{19}$F SSNMR of the product of Step 4, Compound 11 heptane solvate, was acquired using the procedure described in the General Methods. The $^{19}$F SSNMR spectrum for Compound 11 heptane solvate is provided in FIG. 4, and the data are summarized below in Table 9.

TABLE 9

| | 19F SSNMR signals for Compound 11 heptane solvate | |
|---|---|---|
| Peak # | Chem Shift [ppm] | Intensity [rel] |
| 1 | −63.5 | 4.4 |
| 2 | −63.8 | 3.4 |
| 3 | −65.1 | 12.2 |
| 4 | −65.8 | 7.6 |
| 5 | −66.3 | 7.8 |
| 6 | −67.0 | 12.5 |
| 7 | −74.0 | 2.1 |
| 8 | −74.9 | 4.2 |
| 9 | −76.6 | 10.0 |
| 10 | −77.6 | 5.9 |

E. Thermogravimetric Analysis (TGA)

TGA was used to investigate the presence of residual solvents in the lots characterized and identify the temperature at which decomposition of the sample occurs. TGA data were collected on a Mettler Toledo TGA/DSC 3+ STARe System.

Figure 6B:
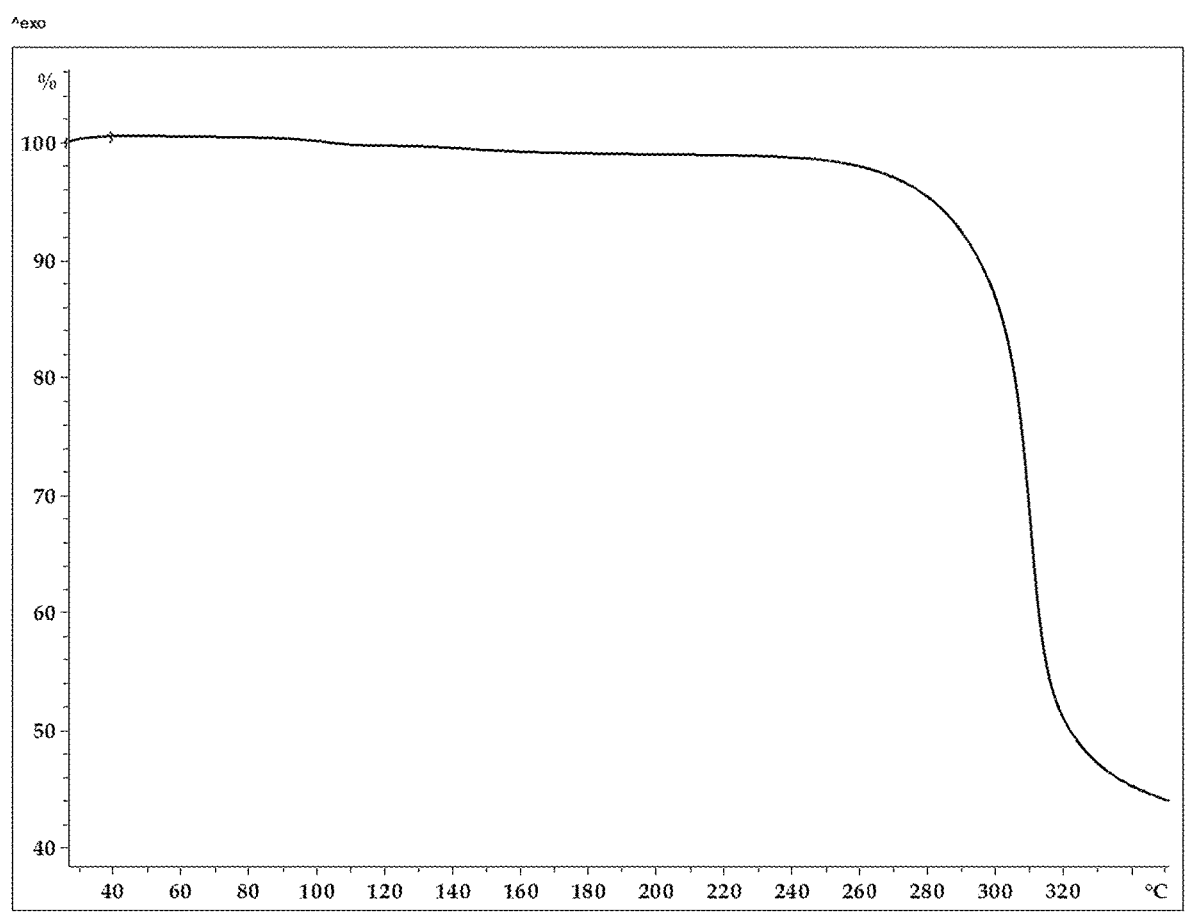
FIG. 6B provides a thermogravimetric analysis (TGA) curve for Compound 11 heptane solvate (Drying Condition 2).
Figure 6C:
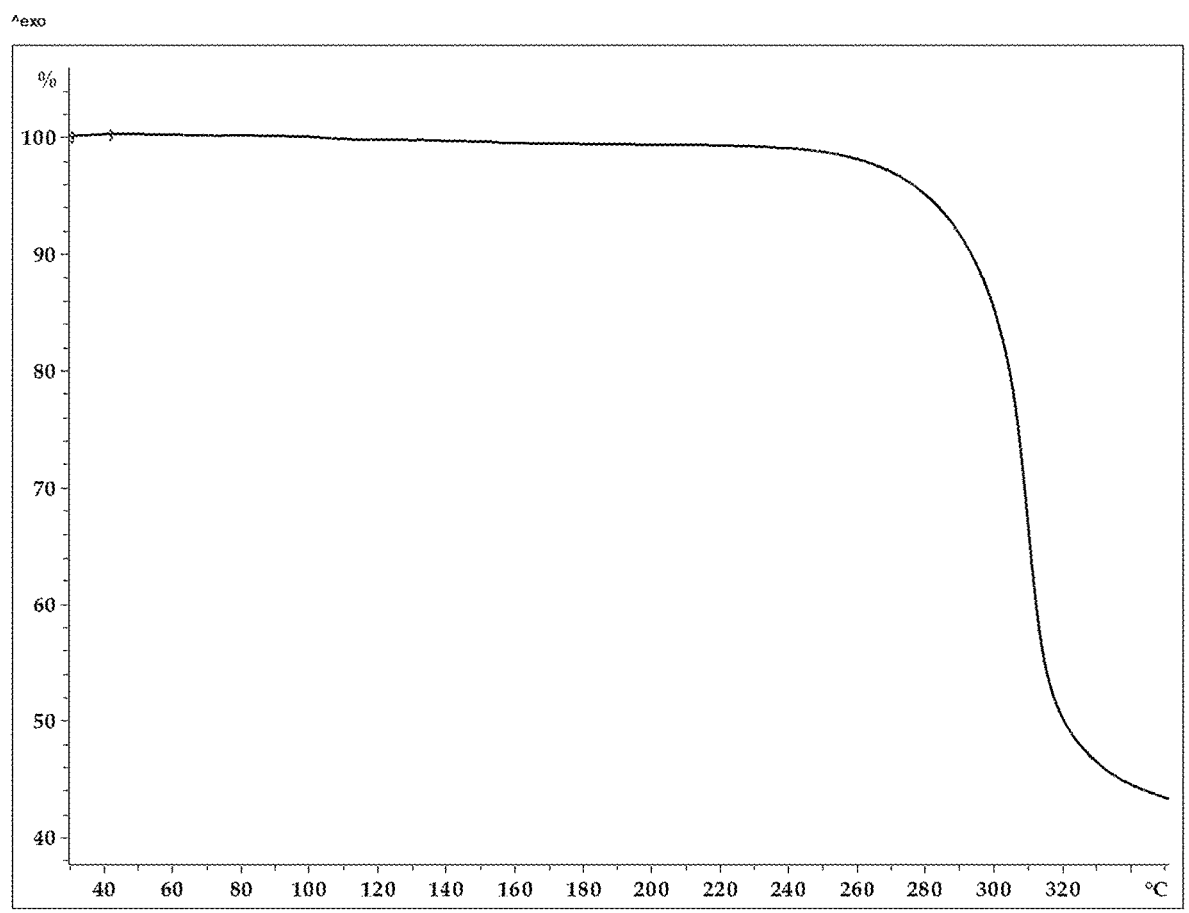
FIG. 6C provides a thermogravimetric analysis (TGA) curve for Compound 11 heptane solvate (Drying Condition 3).

The TGA curve for Compound 11 heptane solvate prepared under Drying Condition 1 is provided in FIG. 6A. The TGA curve for Compound 11 heptane solvate prepared under Drying Condition 2 is provided in FIG. 6B. The TGA curve for Compound 11 heptane solvate prepared under Drying Condition 3 is provided in FIG. 6C. Each of the curves in FIGS. 6A, 6B, and 6C are substantially similar to each other.

Example 9: Preparation of (6S,12R)-17-amino-12-methyl-6,15-b is (trifluo romethyl)-13,19-dioxa-3,4,18-triazatricyclo[12.3.1.12,5]nonadeca-1(18),2,4,14,16-pentaen-6-ol (hydrochloride salt), Compound 12

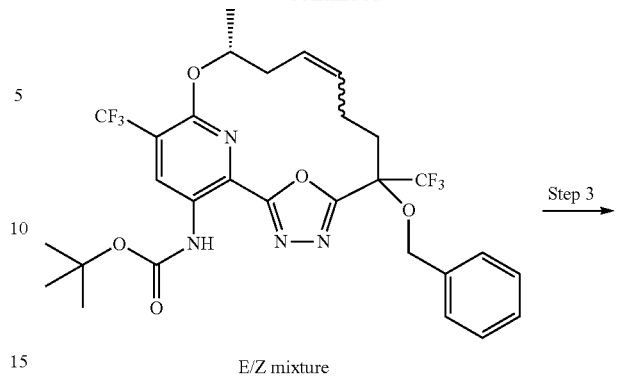

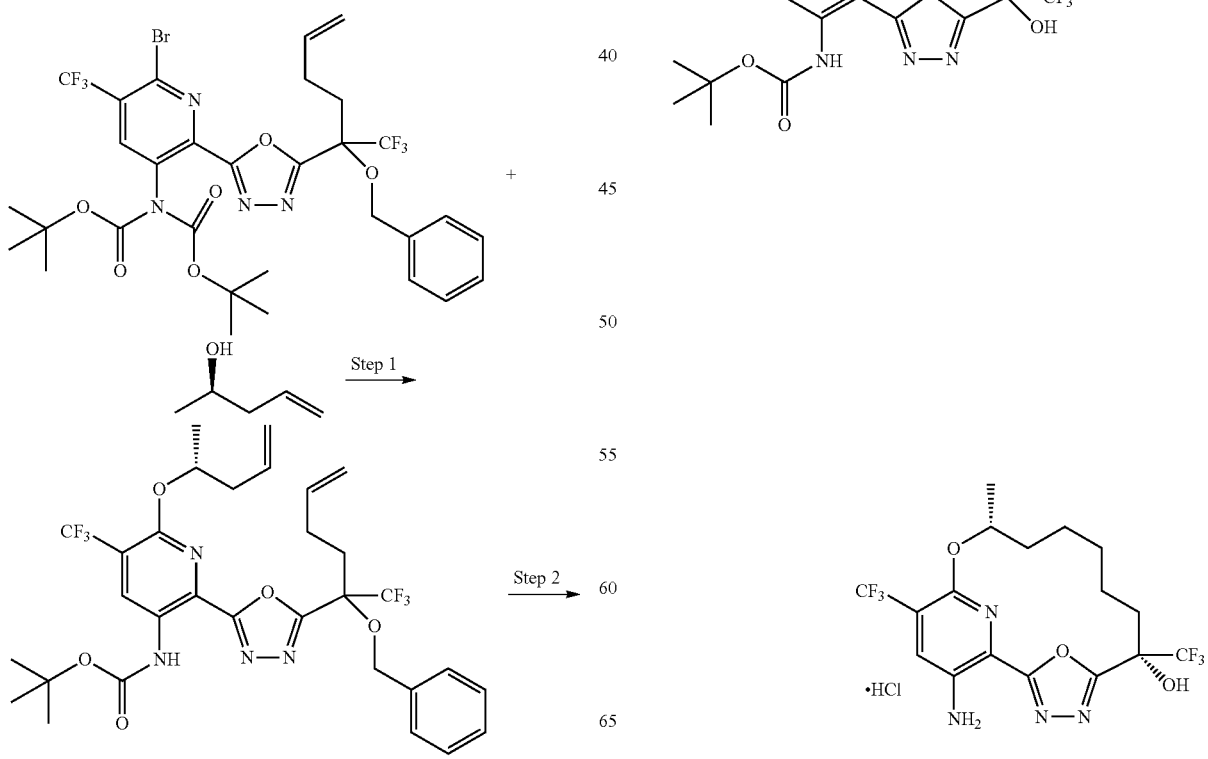

Step 1: tert-Butyl N-[2-[5-[1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]carbamate

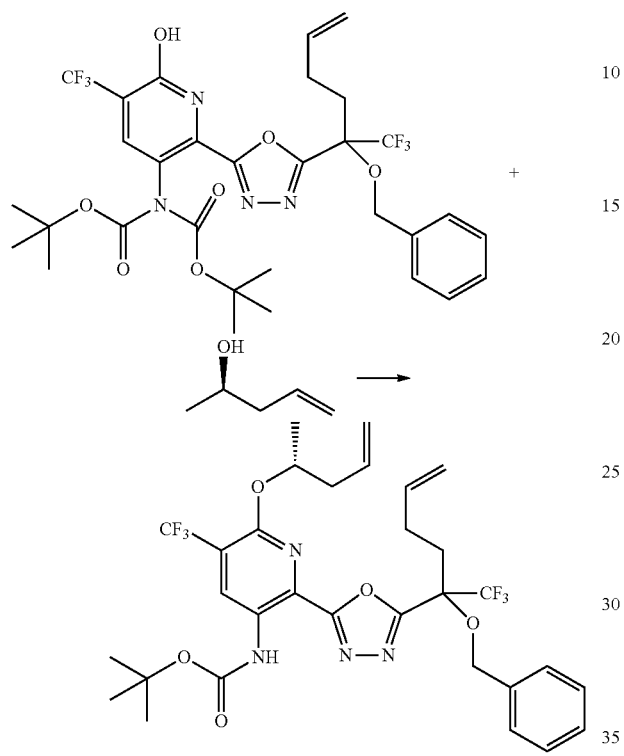

To a solution of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (500 mg, 0.6653 mmol) in DMSO (5 mL) was added (2R)-pent-4-en-2-ol (350 μL, 3.401 mmol), cesium carbonate (751 mg, 2.305 mmol) and iodocopper (31 mg, 0.1628 mmol) and the reaction mixture was heated at 100° C. for 6 h in an oil bath. The reaction mixture was poured onto crushed ice and extracted with ethyl acetate and washed with brine. The organics were separated, dried over sodium sulfate, filtered and evaporated. The resultant brown residue was purified by silica gel chromatography using a shallow gradient 100% hexanes to 50% EtOAc in hexanes to afford as light brown viscous oil, tert-butyl N-[2-[5-[1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]carbamate (120 mg, 27%). $^1$H NMR (400 MHz, DMSO-$d_6$) δ 9.71 (s, 1H), 8.86 (s, 1H), 7.46-7.28 (m, 5H), 5.91-5.72 (m, 2H), 5.24 (qt, J=6.1, 3.1 Hz, 1H), 5.16-4.97 (m, 4H), 4.75 (d, J=11.0 Hz, 1H), 4.66 (d, J=11.0 Hz, 1H), 2.50-2.40 (m, 4H), 2.32 (d, J=8.1 Hz, 2H), 1.49 (s, 9H), 1.32 (d, J=6.2 Hz, 3H) ppm. ESI-MS m/z calc. 656.24335, found 657.3 (M+1)$^+$; Retention time: 0.84 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=water (0.05% $CF_3CO_2H$). Mobile phase B=acetonitrile (0.035% $CF_3CO_2H$). Flow rate=1.5 mL/min, injection volume=1.5 μL, and column temperature=60° C.

Step 2: tert-Butyl N-[(12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]carbamate (E/Z Mixture)

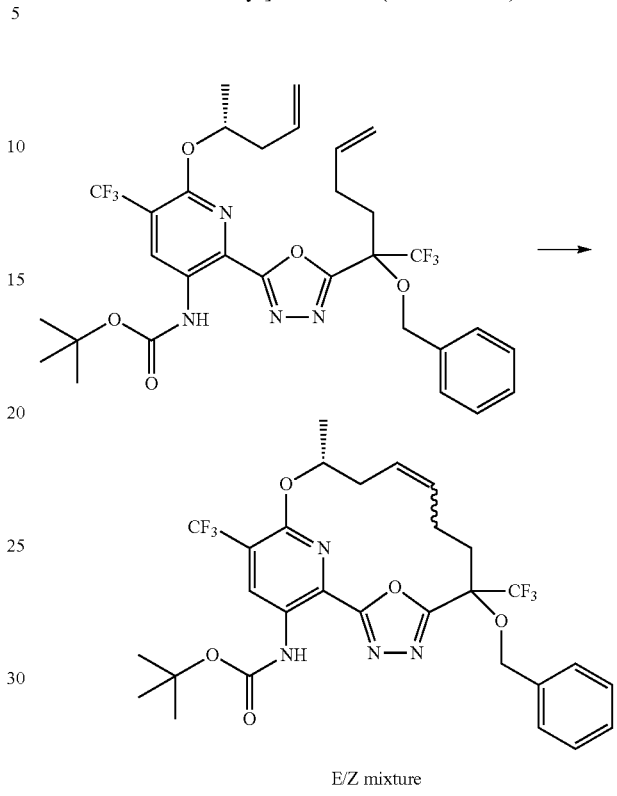

E/Z mixture

To a degassed solution of [1,3-bis(2,4,6-trimethylphenyl)imidazolidin-2-ylidene]-dichloro-[(2-isopropoxyphenyl)methylene]ruthenium (32 mg, 0.05107 mmol) (Grubbs 2nd generation catalyst) in DCE (50 mL) was added a degassed solution of tert-butyl N-[2-[5-[1-benzyloxy-1-(trifluoromethyl)pent-4-enyl]-1,3,4-oxadiazol-2-yl]-6-[(1R)-1-methylbut-3-enoxy]-5-(trifluoromethyl)-3-pyridyl]carbamate (150 mg, 0.2284 mmol) in DCE (50 mL) slowly dropwise under a stream of nitrogen flow bubbling through the solution over 30 min and the reaction mixture was then heated at 50° C. for 5 h. The reaction was stopped, and the solvents were removed by rotary evaporation. The resultant brown residue was purified by silica gel chromatography using a shallow gradient from 100% hexanes to 30% EtOAc in hexanes to afford as a mixture of olefin isomers, tert-butyl N-[(12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]carbamate (E/Z mixture) (102 mg, 36%) which co-eluted with some unreacted starting material. ESI-MS m/z calc. 628.21204, found 629.2 (M+1)$^+$; Retention time: 0.36 minutes. This material was used directly in the ensuing step. ESI-MS m/z calc. 628.21204, found 629.2 (M+1)$^+$; Retention time: 0.36 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=water (0.05% $CF_3CO_2H$). Mobile phase B=acetonitrile (0.035% $CF_3CO_2H$). Flow rate=1.5 mL/min, injection volume=1.5 μL, and column temperature=60° C.

Step 3: tert-Butyl N-[(12R)-6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate

Step 4: (6S,12R)-17-Amino-12-methyl-6,15-bis(trifluoromethyl)-13,19-dioxa-3,4,18-triazatricyclo[12.3.1.12,5]nonadeca-1(18),2,4,14,16-pentaen-6-ol (hydrochloride salt), Compound 12

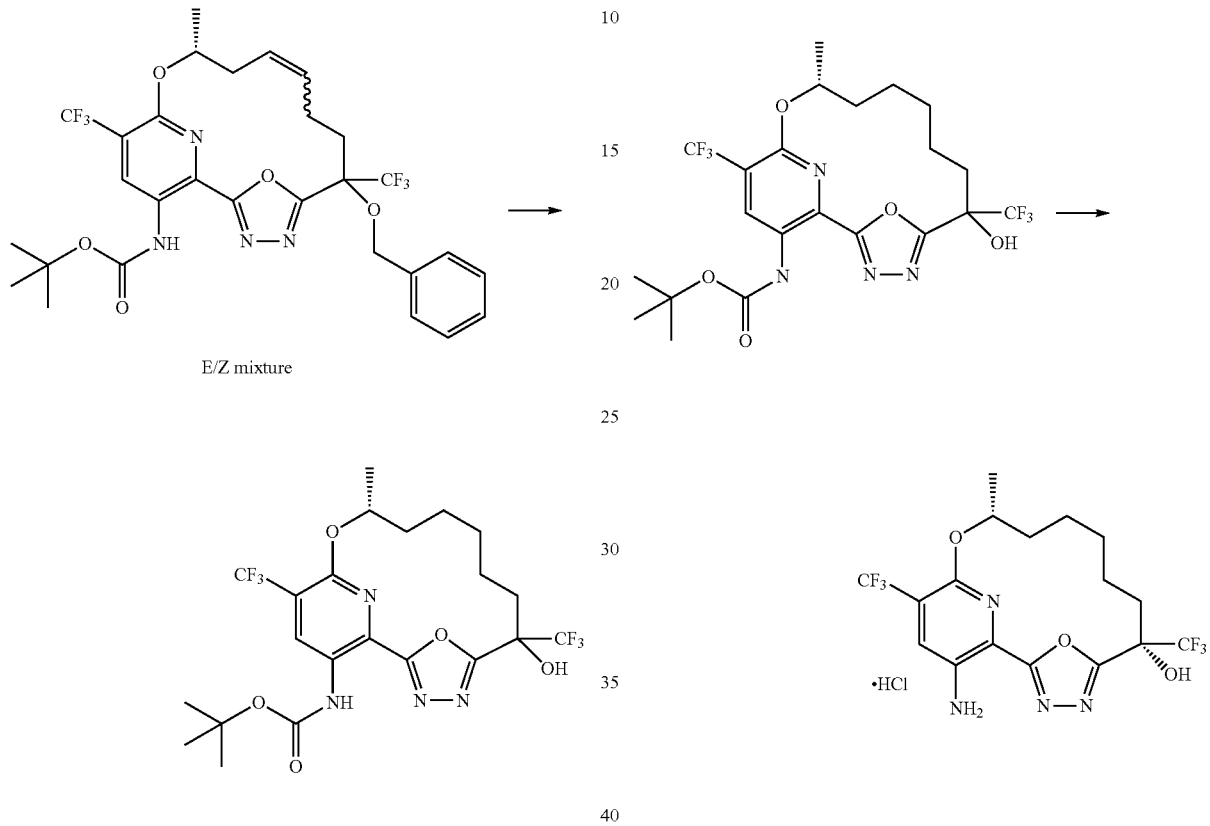

To a solution of tert-butyl N-[(12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]carbamate (E/Z mixture) (102 mg, 0.08114 mmol) in AcOH (5 mL) was added 10% w/w Pd/C (54 mg, 0.05074 mmol) in a 250 mL flask equipped with a hydrogen balloon using a 3-way adaptor. Subjected the flask to vacuum and backfilled with nitrogen gas three times then subjected to vacuum. Filled the vessel with hydrogen gas and the mixture was stirred at room temperature for 15 h. Subjected the vessel to vacuum and backfilled with nitrogen gas three times then diluted with ethyl acetate and filtered over Celite. The filtrate was concentrated to afford tert-butyl N-[(12R)-6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (120 mg, 96%) which was used directly in the ensuing step. ESI-MS m/z calc. 540.1807, found 541.2 (M+1)$^+$; Retention time: 0.57 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=water (0.05% $CF_3CO_2H$). Mobile phase B=acetonitrile (0.035% $CF_3CO_2H$). Flow rate=1.5 mL/min, injection volume=1.5 μL, and column temperature=60° C.

To a solution of tert-butyl N-[(12R)-6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (120 mg, 0.2220 mmol) was added TFA (500 mL, 6.490 mol) and dichloromethane (1.5 mL) (pre made solution of 1:4 TFA/dichloromethane) and the reaction was stirred at room temperature for about 1 h. The solvents were removed by evaporation and the residue was dissolved in DMSO (1 mL) and purified by reverse phase HPLC using a gradient run from 40% to 85% acetonitrile in water (+5 mM HCl) over 30.0 minutes to afford as a light brown solid and the second diastereomer to elute, (6S,12R)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol (hydrochloride salt) (14.7 mg, 28%). $^1$H NMR (400 MHz, DMSO-$d_6$) δ 7.78 (s, 1H), 4.72 (ddt, J=11.5, 7.7, 3.8 Hz, 1H), 2.61-2.52 (m, 1H), 2.24-2.03 (m, 2H), 1.68 (s, 1H), 1.59 (h, J=7.5, 6.4 Hz, 2H), 1.54-1.38 (m, 3H), 1.34 (d, J=6.3 Hz, 3H), 1.21-1.10 (m, 1H) ppm. ESI-MS m/z calc. 440.1283, found 441.1 (M+1)$^+$; Retention time: 2.87 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Example 10: Preparation of (6S,12S)-17-amino-12-methyl-6,15-bis(trifluoromethyl)-13,19-dioxa-3,4,18-triazatricyclo[12.3.1.1²,⁵]nonadeca-1(18),2,4,14,16-pentaen-6-ol (hydrochloride salt), Compound 13

Step 1: tert-Butyl N-[2-[5-[1-benzyloxy-1-(trifluoromethyl)pent-4-enyl]-1,3,4-oxadiazol-2-yl]-6-[(1S)-1-methylbut-3-enoxy]-5-(trifluoromethyl)-3-pyridyl]-N-tert-butoxycarbonyl-carbamate

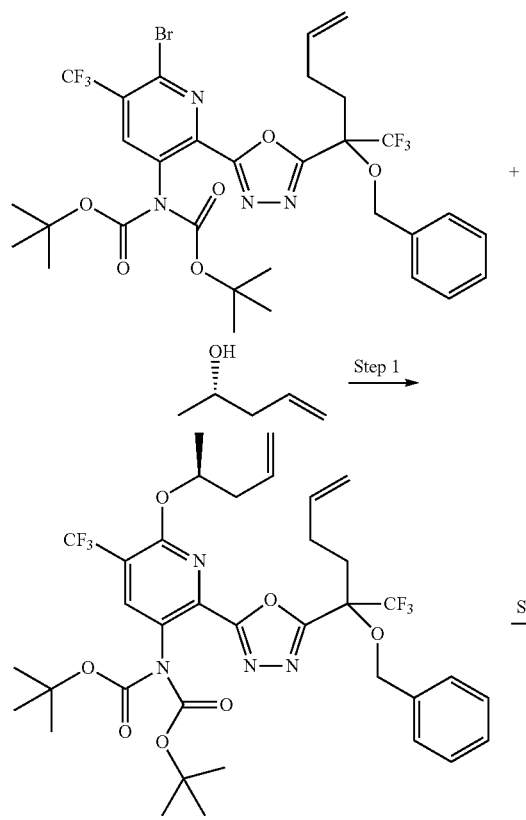

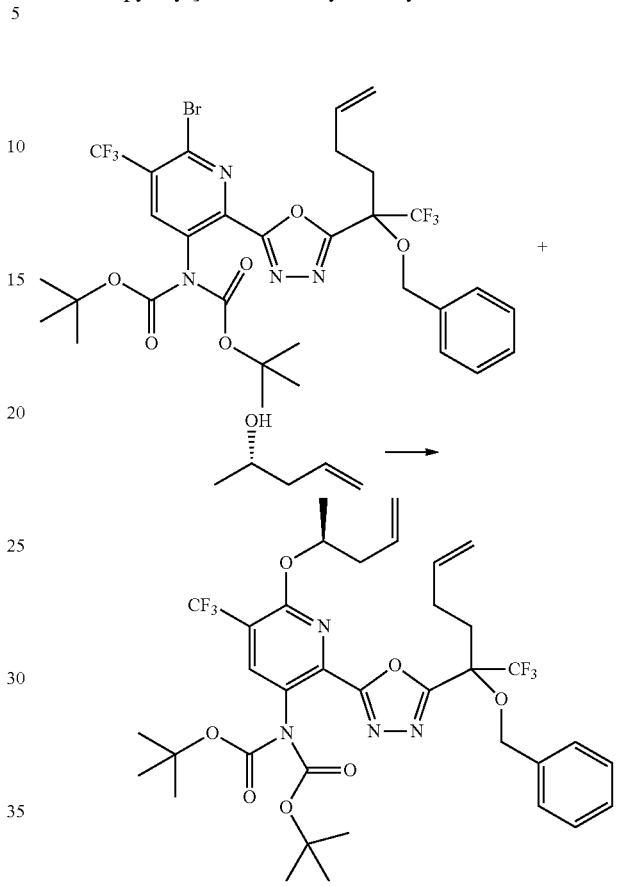

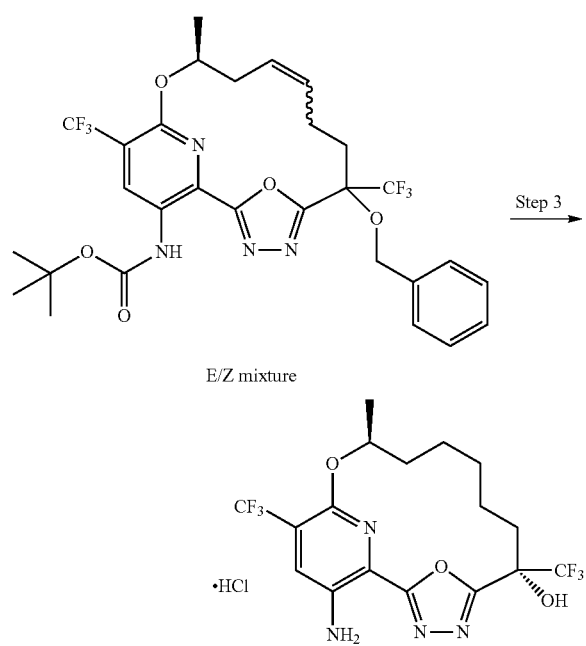

To a solution of tert-butyl N-[2-[5-[1-benzyloxy-1-(trifluoromethyl)pent-4-enyl]-1,3,4-oxadiazol-2-yl]-6-bromo-5-(trifluoromethyl)-3-pyridyl]-N-tert-butoxycarbonyl-carbamate (800 mg, 1.065 mmol) in DMSO (10 mL) was added (2S)-pent-4-en-2-ol (550 μL, 5.345 mmol), cesium carbonate (1.1 g, 3.376 mmol) and iodocopper (47 mg, 0.2468 mmol) and the reaction mixture was heated at 80° C. for 3 h. The reaction mixture was poured onto crushed ice and extracted with ethyl acetate and the organic phase was washed with brine. The organic layer was dried over sodium sulfate, filtered and evaporated. The resultant brown residue was purified by silica gel chromatography using a shallow gradient from 100% hexanes to 30% EtOAc in hexanes to afford tert-butyl N-[2-[5-[1-benzyloxy-1-(trifluoromethyl)pent-4-enyl]-1,3,4-oxadiazol-2-yl]-6-1(1S)-1-methylbut-3-enoxyl-5-(trifluoromethyl)-3-pyridyl]-N-tert-butoxycarbonyl-carbamate (303 mg, 38%). $^1$H NMR (400 MHz, DMSO-$d_6$) δ 8.21 (s, 1H), 7.41-7.30 (m, 5H), 5.90-5.75 (m, 2H), 5.43 (qt, J=7.7, 3.9 Hz, 1H), 5.12-4.98 (m, 4H), 4.81 (d, J=11.1 Hz, 1H), 4.68 (d, J=11.0 Hz, 1H), 2.60-2.47 (m, 4H), 2.39-2.26 (m, 2H), 1.38-1.26 (m, 21H) ppm. ESI-MS m/z calc. 756.2958, found 757.47 (M+1)$^+$; Retention time: 0.78 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=water (0.05% $CF_3CO_2H$). Mobile phase B=acetonitrile (0.035% CF₃CO₂H). Flow rate=1.5 mL/min, injection volume=1.5 μL, and column temperature=60° C.

Step 2: tert-Butyl N-[(12S)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]carbamate (E/Z Mixture)

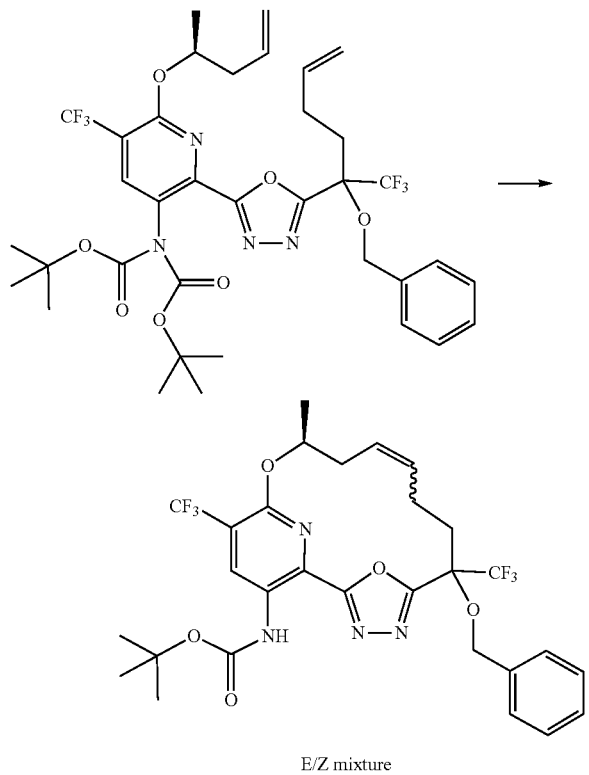

E/Z mixture

To a degassed solution of [1,3-bis(2,4,6-trimethylphenypimidazolidin-2-ylidene]-dichloro-[(2-isopropoxyphenyl)methylene]ruthenium (43 mg, 0.06862 mmol) (Grubbs 2nd generation catalyst) in DCE (50 mL) was added a degassed solution of tert-butyl N-[2-[5-[1-benzyloxy-1-(trifluoromethyl)pent-4-enyl]-1,3,4-oxadiazol-2-yl]-6-[(1S)-1-methylbut-3-enoxy]-5-(trifluoromethyl)-3-pyridyl]-N-tert-butoxycarbonyl-carbamate (200 mg, 0.2643 mmol) in DCE (50 mL) slowly dropwise under a stream of nitrogen flow bubbling through the solution over 30 min and on completion of addition the reaction mixture was heated at 50° C. for 5 h. The reaction was stopped, and the solvents removed by rotary evaporation. The resultant brown residue was purified by silica gel chromatography using a shallow gradient from 100% hexanes to 30% EtOAc in hexanes to afford as a mixture of olefin isomers, tert-butyl N-[(12S)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]carbamate (E/Z mixture) (150 mg, 45%) along with some unreacted starting material which co-eluted with the product. This material was used directly in the ensuing step without further purification. ESI-MS m/z calc. 628.21204, found 629.3 (M+1)⁺; Retention time: 0.7 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=water (0.05% CF₃CO₂H). Mobile phase B=acetonitrile (0.035% CF₃CO₂H). Flow rate=1.5 mL/min, injection volume=1.5 μL, and column temperature=60° C.

Step 3: (6S,12S)-17-Amino-12-methyl-6,15-bis(trifluoromethyl)-13,19-dioxa-3,4,18-triazatricyclo[12.3.1.12,5]nonadeca-1(18),2,4,14,16-pentaen-6-ol (hydrochloride salt), Compound 13

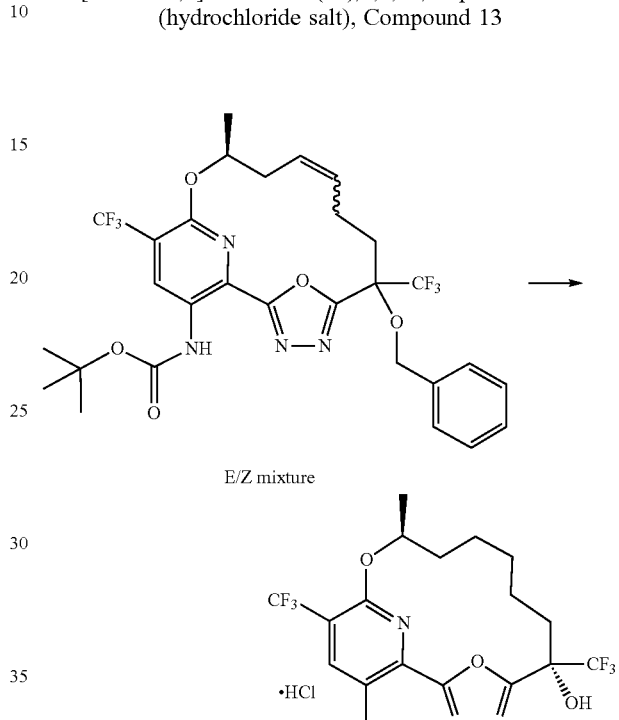

E/Z mixture

To a solution of tert-butyl N-[(12S)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]carbamate (E/Z mixture) (150 mg, 0.2386 mmol) in AcOH (5 mL) was added 10% w/w Pd/C (78 mg, 0.07329 mmol) in a 250 mL flask equipped with a hydrogen balloon using a 3-way adaptor. Subjected to vacuum and backfilled with nitrogen gas three times then subjected to vacuum. Filled the vessel with hydrogen gas and the mixture was stirred at room temperature for 15 h. Subjected to vacuum and backfilled with nitrogen gas three times then diluted with ethyl acetate and filtered over Celite. The filtrate was concentrated to afford 125 mg of tert-butyl N-[(12S)-6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate as a mixture of diastereomers. This material was dissolved in a 1:3 mixture of a premixed solution of TFA (500 μL, 6.490 mmol) and dichloromethane (1.5 mL) and the mixture was stirred for 30 min at room temperature. The solvent was removed by rotary evaporation and the resulting residue was purified by reverse phase HPLC using a gradient from 40% to 85% acetonitrile in water (+5 mM HCl) over 30.0 minutes to afford as a light brown solid and the first enantiomer to elute, (6S,12S)-17-amino-12-methyl-6,15-bis(trifluoromethyl)-13,19-dioxa-3,4,18-triazatricyclo[12.3.1.12,5]nonadeca-1(18),2,4,14,16-pentaen-6-ol (hydrochloride salt) (20.6 mg, 36%). ¹H NMR (400 MHz, Chloroform-d) δ 7.42 (s, 1H), 4.75 (ddt, J=10.6, 6.7, 3.4 Hz, 1H), 4.06-3.76 (m, 1H), 2.76-2.63 (m, 1H), 2.28 (t, J=7.6 Hz, 2H), 2.01 (d, J=5.7 Hz, 1H), 1.61 (m, 4H), 1.50 (dd, J=12.0, 6.5 Hz, 1H), 1.41 (d, J=6.3 Hz, 3H), 1.33-1.26 (m, 1H), 0.89 (m, 1H) ppm. ESI-MS m/z calc. 440.1283, found 441.1 (M+1)+; Retention time: 2.82 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Example 11: Preparation of (6R,12S)-17-amino-12-methyl-6,15-bis(trifluoromethyl)-13,19-dioxa-3,4,18-triazatricyclo[12.3.1.1²,⁵]nonadeca-1(18),2,4,14,16-pentaen-6-ol, Compound 14

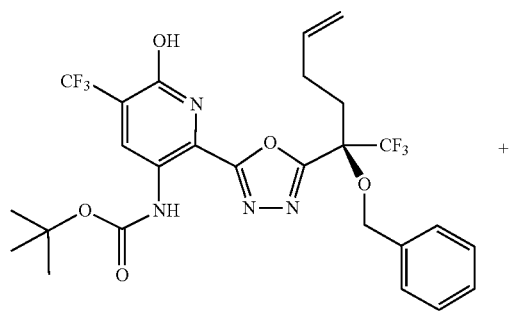

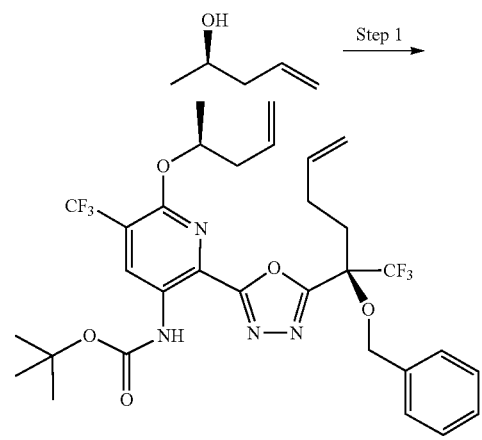

E/Z mixture

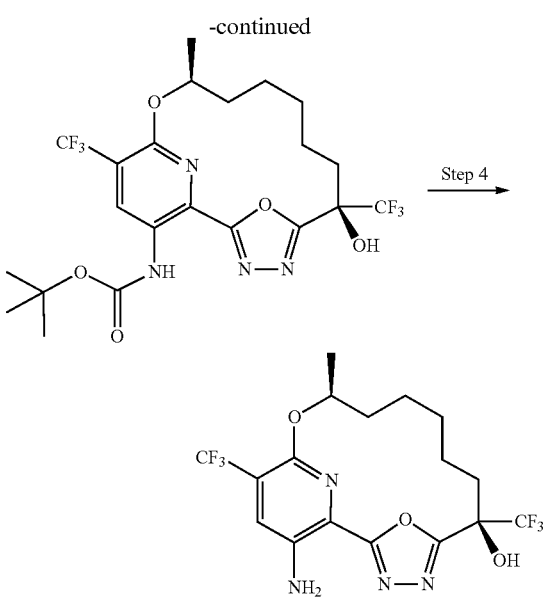

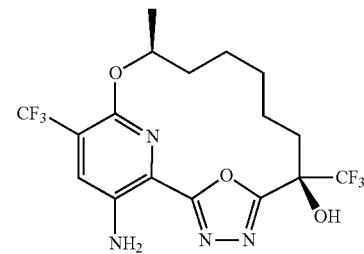 [SMILES: C[C@H]1CCCCC[C@](O)(C(F)(F)F)c2nnc(o2)-c2nc(c(C(F)(F)F)cc2N)O1]

Step 1: tert-Butyl N-[2-[5-[(1R)-1-benzyloxy-1-(trifluoromethyl)pent-4-enyl]-1,3,4-oxadiazol-2-yl]-6-[(1S)-1-methylbut-3-enoxy]-5-(trifluoromethyl)-3-pyridyl]carbamate

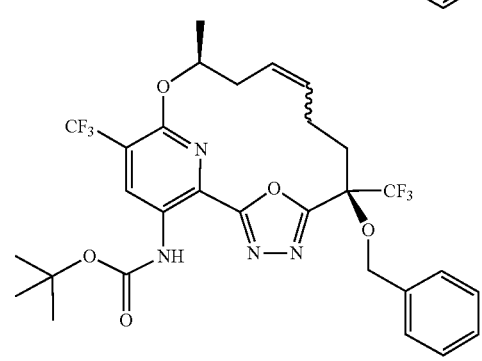

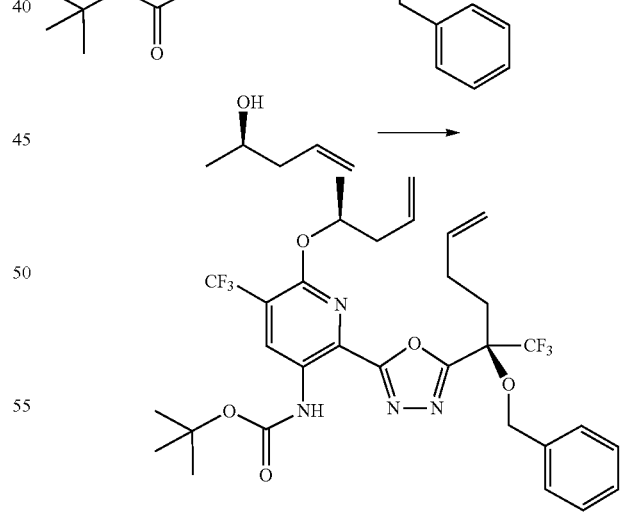

To a solution of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]carbamate (417.3 mg, 0.7091 mmol) and (2R)-pent-4-en-2-ol (109.5 μL, 1.064 mmol) in toluene (8.784 mL) was added triphenylphosphine (246.6 μL, 1.064 mmol). After stirring at room temperature for 1 min, DIAD (223.5 μL, 1.135 mmol) was added and the mixture was stirred at room temperature for 5 min. Diluted the reaction mixture with EtOAc then washed with saturated aqueous sodium bicarbonate (1×), saturated aqueous NH₄Cl (1×) and brine (1×) then dried over magnesium sulfate, filtered and concentrated to a yellow oil which was purified by silica gel chromatography using a gradient from 100% hexanes to 100% EtOAc giving as a clear, slightly yellow syrup, tert-butyl N-[2-[5-[(1R)-1-benzyloxy-1-(trifluoromethyl)pent-4-enyl]-1,3,4-oxadiazol-2-yl]-6-[(1S)-1-methylbut-3-enoxy]-5-(trifluoromethyl)-3-pyridyl]carbamate (433.8 mg, 93%). ¹H NMR (400 MHz, Chloroform-d) δ 9.81 (s, 1H), 9.16 (s, 1H), 7.42-7.37 (m, 2H), 7.36-7.28 (m, 3H), 5.90-5.72 (m, 2H), 5.26 (q, J=6.1 Hz, 1H), 5.13-4.97 (m, 4H), 4.83 (d, J=10.8 Hz, 1H), 4.68 (d, J=10.9 Hz, 1H), 2.51 (m, 2H), 2.46-2.36 (m, 3H), 2.27 (d, J=11.2 Hz, 1H), 1.55 (s, 9H), 1.36 (d, J=6.2 Hz, 3H) ppm. ESI-MS m/z calc. 656.24335, found 657.3 (M+1)⁺; Retention time: 0.86 minutes. Final purity was determined by reversed phase UPLC using an Acquity UPLC BEH C₁₈ column (30×2.1 mm, 1.7 µm particle) made by Waters (pn: 186002349), and a dual gradient run from 50-99% mobile phase B over 1.0 minutes. Mobile phase A=water (0.05% CF₃CO₂H). Mobile phase B=acetonitrile (0.035% CF₃CO₂H). Flow rate=1.5 mL/min, injection volume=1.5 µL, and column temperature=60° C.

Step 2: tert-Butyl N-[(6R,12S)-6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaen-17-yl]carbamate (E/Z Mixture)

tert-butyl N-[2-[5-[(1R)-1-benzyloxy-1-(trifluoromethyl)pent-4-enyl]-1,3,4-oxadiazol-2-yl]-6-[(1S)-1-methylbut-3-enoxy]-5-(trifluoromethyl)-3-pyridyl]carbamate (1.5269 g, 2.325 mmol) in toluene (229 mL) slowly dropwise under a stream of nitrogen flow bubbling through the solution over 10 min and the reaction mixture was heated at 100° C. for 60 min. The mixture was removed from the heating bath and 2-sulfanylpyridine-3-carboxylic acid (180.5 mg, 1.163 mmol) was added. The resulting mixture was stirred for 10 min then concentrated by rotary evaporation to a residue which was chromatographed on a 275 g reverse phase C₁₈ column eluting with a gradient from 50% to 100% acetonitrile in water giving as an off-white/yellow foam, tert-butyl N-[(6R,12S)-6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaen-17-yl]carbamate (E/Z mixture) (324.3 mg, 22%). ESI-MS m/z calc. 628.21204, found 629.2 (M+1)⁺; Retention time: 0.82 minutes. Final purity was determined by reversed phase UPLC using an Acquity UPLC BEH C₁₈ column (30×2.1 mm, 1.7 µm particle) made by Waters (pn: 186002349), and a dual gradient run from 50-99% mobile phase B over 1.0 minutes. Mobile phase A=water (0.05% CF₃CO₂H). Mobile phase B=acetonitrile (0.035% CF₃CO₂H). Flow rate=1.5 mL/min, injection volume=1.5 µL, and column temperature=60° C.

Step 3: tert-Butyl N-[(6R,12S)-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate

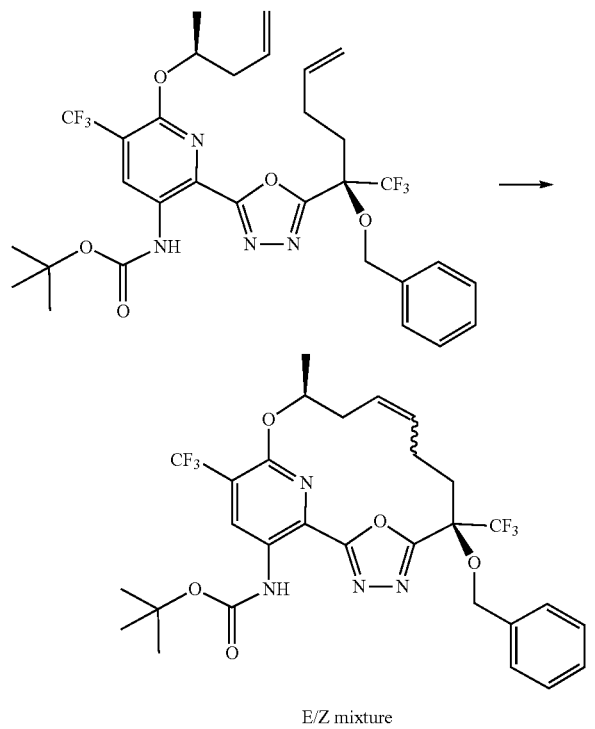

E/Z mixture

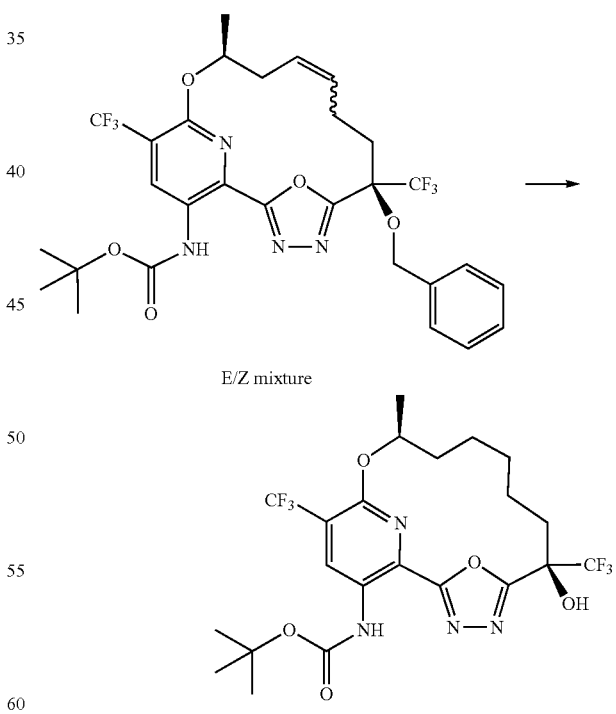

E/Z mixture

To a degassed solution of [1,3-bis(2,4,6-trimethylphenyl)imidazolidin-2-ylidene]-dichloro-[(2-isopropoxyphenyl)methylene]ruthenium (378.2 mg, 0.6036 mmol) (Hoveyda Grubbs 2nd Gen catalyst) in toluene (229 mL) stirring at 100° C. with a reflux condenser and nitrogen bubbling through the solution was added a degassed solution of To a solution of tert-butyl N-[(6R,12S)-6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaen-17-yl]carbamate (E/Z mixture) (324.3 mg, 0.5159 mmol) in AcOH (10.81 mL) was added 10% w/w Pd/C (168.7 mg, 0.1585 mmol, 50% water wet) and hydrogen gas was bubbled through the stirring mixture for 15 minutes then the reaction was sealed and capped with a hydrogen balloon and stirred for 16 h. Added 10% w/w Pd/C (54.9 mg, 0.05159 mmol, 50% water wet), stirred for 1 h then purged the flask with nitrogen and filtered over Celite eluting with EtOAc. The filtrate was concentrated then purified by silica gel chromatography using a gradient from 100% hexanes to 100% EtOAc giving as a white foam, tert-butyl N-[(6R,12S)-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (216 mg, 77%). ESI-MS m/z calc. 540.1807, found 541.2 (M+1)⁺; Retention time: 0.61 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=water (0.05% $CF_3CO_2H$). Mobile phase B=acetonitrile (0.035% $CF_3CO_2H$). Flow rate=1.5 mL/min, injection volume=1.5 μL, and column temperature=60° C.

Step 4: (6R,12S)-17-Amino-12-methyl-6,15-bis(trifluoromethyl)-13,19-dioxa-3,4,18-triazatricyclo[12.3.1.1²,⁵]nonadeca-1(18),2,4,14,16-pentaen-6-ol, Compound 14 solid, (6R,12S)-17-amino-12-methyl-6,15-bis(trifluoromethyl)-13,19-dioxa-3,4,18-triazatricyclo[12.3.1.1²,⁵]nonadeca-1(18),2,4,14,16-pentaen-6-ol (177.1 mg, 100%). ¹H NMR (400 MHz, DMSO-$d_6$) δ 7.76 (s, 1H), 7.59 (s, 1H), 6.36 (s, 2H), 4.73 (dq, J=6.4, 3.1, 2.4 Hz, 1H), 2.56 (d, J=5.5 Hz, 1H), 2.22-2.04 (m, 2H), 1.74-1.64 (m, 1H), 1.59 (d, J=7.9 Hz, 2H), 1.54-1.43 (m, 3H), 1.34 (d, J=6.3 Hz, 3H), 1.22-1.10 (m, 1H) ppm. ESI-MS m/z calc. 440.1283, found 441.1 (M+1)⁺; Retention time: 2.02 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Example 12: Preparation of 16-amino-12,12-dioxo-6,14-bis(trifluoromethyl)-18-oxa-12λ⁶-thia-3,4,17-triazatricyclo[11.3.1.1²,⁵]octadeca-1(17),2,4,13,15-pentaen-6-ol (enantiomer 1), Compound 15 and 16-amino-12,12-dioxo-6,14-bis(trifluoromethyl)-18-oxa-12λ⁶-thia-3,4,17-triazatricyclo[11.3.1.1²,⁵]octadeca-1(17),2,4,13,15-pentaen-6-ol (enantiomer 2), Compound 16

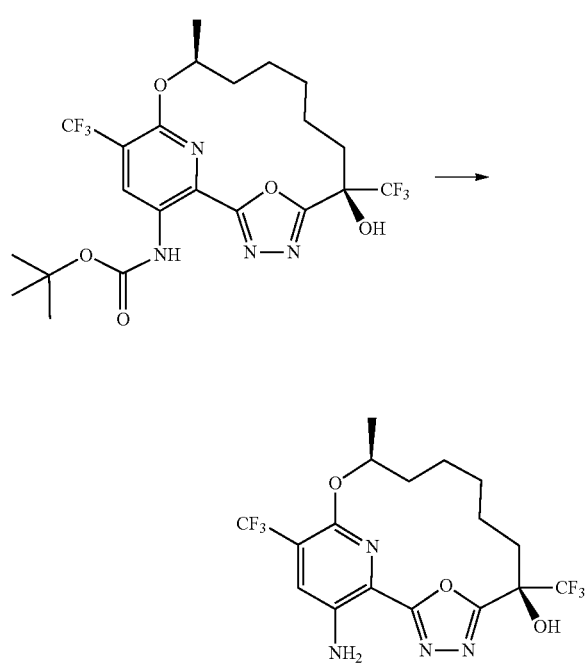 [SMILES: C[C@H]1CCCCC[C@](O)(C(F)(F)F)c2nnc(o2)-c2nc(c(C(F)(F)F)cc2NC(=O)OC(C)(C)C)O1 ; C[C@H]1CCCCC[C@](O)(C(F)(F)F)c2nnc(o2)-c2nc(c(C(F)(F)F)cc2N)O1]

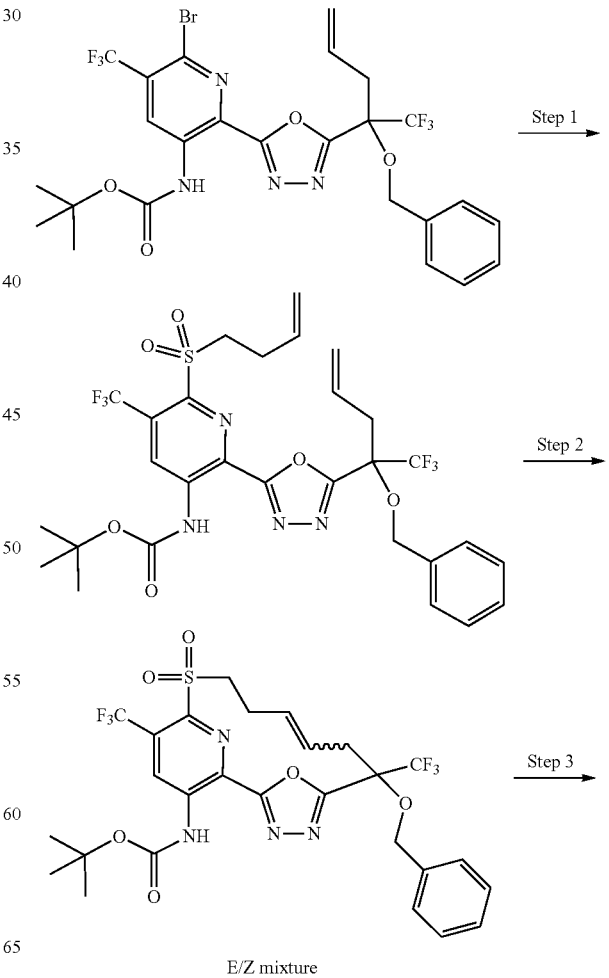

To a stirring solution of tert-butyl N-[(6R,12S)-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (216 mg, 0.3997 mmol) in dichloromethane (2.16 mL) was added TFA (769.6 μL, 9.989 mmol) and the resulting mixture was stirred at room temperature for 1 h then concentrated by rotary evaporation to a yellow residue. The residue was chromatographed on a 100 g reverse phase $C_{18}$ column eluting with a gradient from 50% to 100% acetonitrile in water giving as a pale yellow 289
-continued

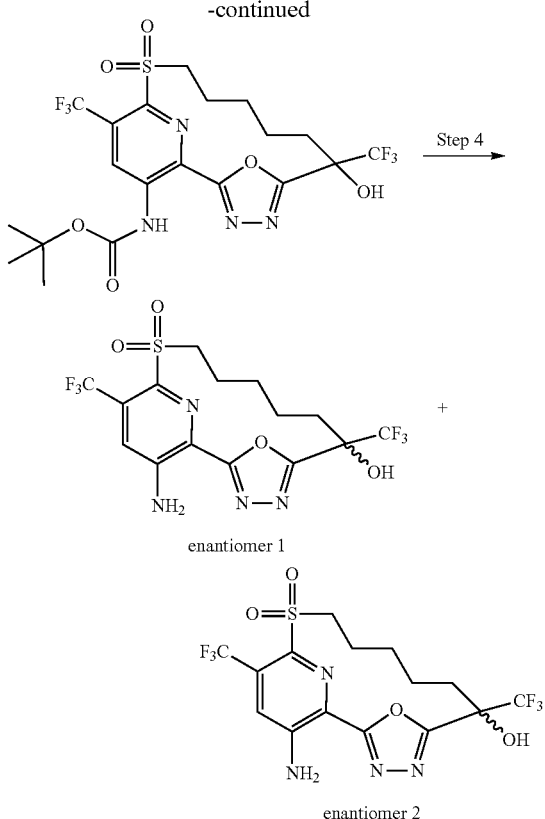

enantiomer 1 enantiomer 2

Step 1: tert-Butyl N-[2-[5-[1-benzyloxy-t-(trifluoromethyl)but-3-enyl]-1,3,4-oxadiazol-2-yl]-6-but-3-enylsulfonyl-5-(trifluoromethyl)-3-pyridyl]carbamate

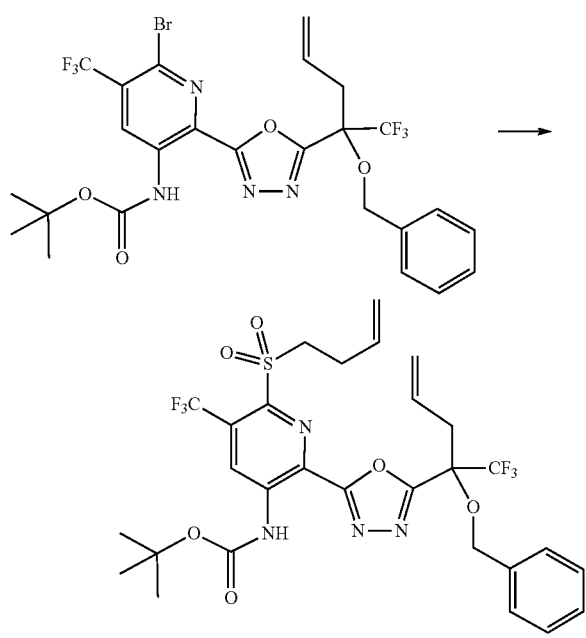

A mixture of tert-butyl N-[2-[5-[1-benzyloxy-1-(trifluoromethyl)but-3-enyl]-1,3,4-oxadiazol-2-yl]-6-bromo-5-(trifluoromethyl)-3-pyridyl]carbamate (225 mg, 0.3530 mmol), but-3-ene-1-sulfinate (sodium salt) (150 mg, 1.055 mmol), and iodocopper (202 mg, 1.061 mmol) in DMSO (2.2 mL) was heated at 100° C. for 3 h, then diluted with ether and water, filtered through Celite, the layers partitioned and the organic layer washed with water, brine, dried ($MgSO_4$) and evaporated. Purification by silica gel chromatography (0-20% EtOAc in hexanes) provided tert-butyl N-[2-[5-[1-benzyloxy-1-(trifluoromethyl)but-3-enyl]-1,3,4-oxadiazol-2-yl]-6-but-3-enylsulfonyl-5-(trifluoromethyl)-3-pyridyl]carbamate (99 mg, 41%). $^1$H NMR (400 MHz, Chloroform-d) δ 10.36 (s, 1H), 9.56 (s, 1H), 7.41-7.28 (m, 5H), 5.91 (dt, J=17.0, 8.5 Hz, 1H), 5.74 (ddt, J=16.8, 10.2, 6.5 Hz, 1H), 5.32-5.17 (m, 2H), 5.10-5.04 (m, 1H), 5.02 (dq, J=10.2, 1.3 Hz, 1H), 4.83 (d, J=10.9 Hz, 1H), 4.67 (d, J=10.9 Hz, 1H), 3.80-3.60 (m, 2H), 3.29-3.14 (m, 2H), 2.65-2.56 (m, 2H), 1.54 (s, 9H) ppm; $^{19}$F NMR (376 MHz, Chloroform-d) δ −58.49, −73.15 ppm. ESI-MS m/z calc. 676.179, found 677.2 (M+1)$^+$; Retention time: 0.87 minutes. Final purity was determined by reversed phase UPLC using an Acquity UPLC BEH $C_{18}$ column (30×2.1 mm, 1.7 μm particle) made by Waters (pn: 186002349), and a dual gradient run from 1-99% mobile phase B over 1.0 minutes. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

Step 2: tert-Butyl N-[6-benzyloxy-12,12-dioxo-6,14-bis(trifluoromethyl)-18-oxa-12λ$^6$-thia-3,4,17-triazatricyclo[11.3.1.12,5]octadeca-1(16),2,4,8,13(17),14-hexaen-16-yl]carbamate (E/Z Mixture)

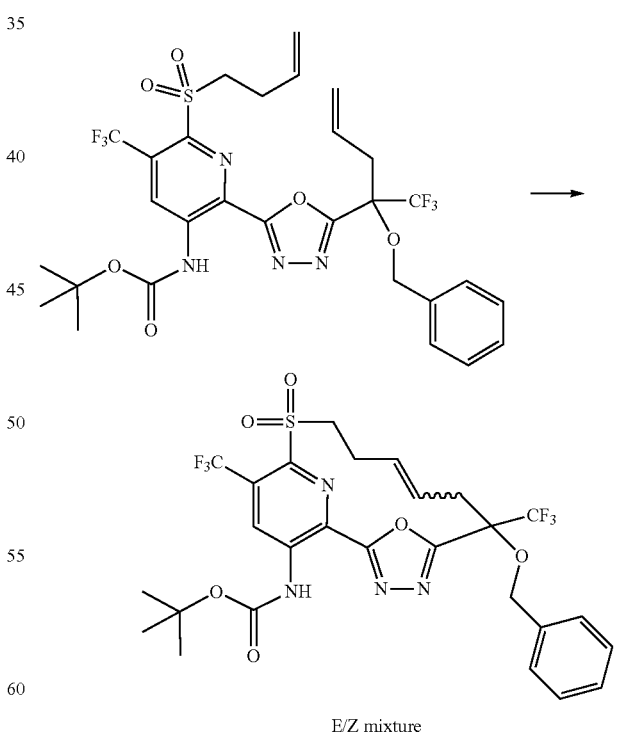

E/Z mixture

In a 3-neck round bottom flask, a solution of tert-butyl N-[2-[5-[1-benzyloxy-1-(trifluoromethyl)but-3-enyl]-1,3,4-oxadiazol-2-yl]-6-but-3-enylsulfonyl-5-(trifluoromethyl)-3-pyridyl]carbamate (206 mg, 0.3045 mmol) in DCE (10 mL)

was slowly added dropwise from an addition funnel over 45 min to a solution of dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II) (34 mg, 0.04634 mmol) in DCE (25 mL) heated at 70° C. with $N_2$ bubbling through the solution. The mixture was stirred at 70° C. with $N_2$ bubbling a further 90 min and then the solvent was evaporated. Purification by silica gel chromatography (0-20% EtOAc in hexanes) provided tert-butyl N-[6-benzyloxy-12,12-dioxo-6,14-bis (trifluoromethyl)-18-oxa-12$\lambda^6$-thia-3,4,17-triazatricyclo[11.3.1.12,5]octadeca-1(16),2,4,8,13(17),14-hexaen-16-yl]carbamate (E/Z mixture) (92 mg, 44%). $^1$H NMR (400 MHz, Chloroform-d) δ 9.46 (s, 1H), 9.42 (s, 1H), 7.37-7.27 (m, 2H), 7.25-7.16 (m, 3H), 5.88-5.64 (m, 2H), 4.92 (d, J=11.6 Hz, 1H), 4.54 (d, J=11.6 Hz, 1H), 4.13-3.98 (m, 1H), 3.59 (dt, J=15.6, 5.9 Hz, 1H), 3.12 (dd, J=14.6, 4.8 Hz, 1H), 2.87-2.76 (m, 2H), 2.69-2.62 (m, 1H), 1.58 (s, 9H) ppm; $^{19}$F NMR (376 MHz, Chloroform-d) δ −58.84, −74.24 ppm; UV/vis $\lambda_{max}$ 233, 268, 322 nm. ESI-MS m/z calc. 648.1477, found 649.1 (M+1)$^+$; Retention time: 0.83 minutes. Final purity was determined by reversed phase UPLC using an Acquity UPLC BEH $C_{18}$ column (30×2.1 mm, 1.7 μm particle) made by Waters (pn: 186002349), and a dual gradient run from 1-99% mobile phase B over 1.0 minutes. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

Step 3: tert-Butyl N-[6-hydroxy-12,12-dioxo-6,14-bis(trifluoromethyl)-18-oxa-12$\lambda^6$-thia-3,4,17-triazatricyclo[11.3.1.12,5]octadeca-1(16),2,4,13(17),14-pentaen-16-yl]carbamate

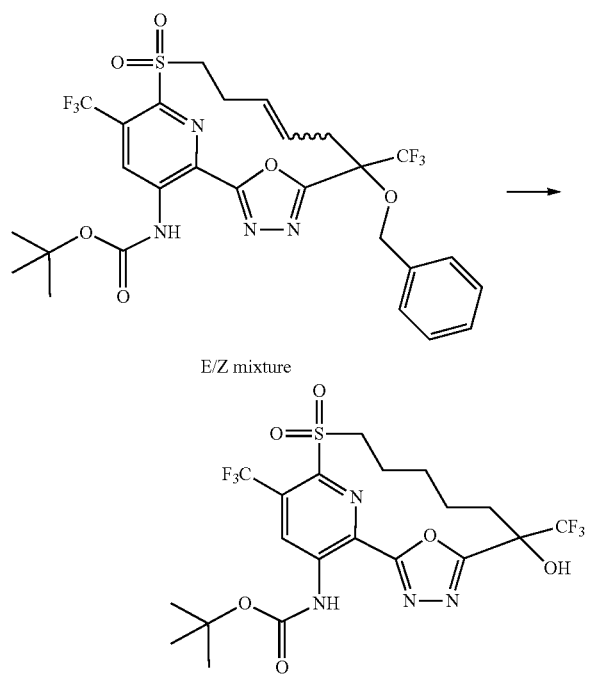

E/Z mixture

A mixture of tert-butyl N-[6-benzyloxy-12,12-dioxo-6,14-bis(trifluoromethyl)-18-oxa-12$\lambda^6$-thia-3,4,17-triazatricyclo[11.3.1.12,5]octadeca-1(16),2,4,8,13(17),14-hexaen-16-yl]carbamate (E/Z mixture) (90 mg, 0.1304 mmol) and Pd/C (42 mg of 10% w/w, 0.03947 mmol) in AcOH (850 μL) was stirred at room temperature under 180 psi $H_2$ in a stainless steel pressure vessel for 36 h. Then the mixture was filtered and the filtrate was evaporated to provide ter t-butyl N-[6-hydroxy-12,12-dioxo-6,14-bis(trifluoromethyl)-18-oxa-12$\lambda^6$-thia-3,4,17-triazatricyclo[11.3.1.12,5]octadeca-1(16),2,4,13(17),14-pentaen-16-yl]carbamate (81 mg, 102%). ESI-MS m/z calc. 560.1164, found 561.2 (M+1)$^+$; Retention time: 0.69 minutes. Final purity was determined by reversed phase UPLC using an Acquity UPLC BEH $C_{18}$ column (30×2.1 mm, 1.7 μm particle) made by Waters (pn: 186002349), and a dual gradient run from 1-99% mobile phase B over 1.0 minutes. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.; UV/vis $\lambda_{max}$ 233, 268, 323 nm.

Step 4: 16-Amino-12,12-dioxo-6,14-bis(trifluoromethyl)-18-oxa-12$\lambda^6$-thia-3,4,17-triazatricyclo[11.3.1.12,5]octadeca-1(17),2,4,13,15-pentaen-6-ol (enantiomer 1) and 16-amino-12,12-dioxo-6,14-bis(trifluoromethyl)-18-oxa-12$\lambda^6$-thia-3,4,17-triazatricyclo[11.3.1.12,5]octadeca-1(17),2,4,13,15-pentaen-6-ol (enantiomer 2)

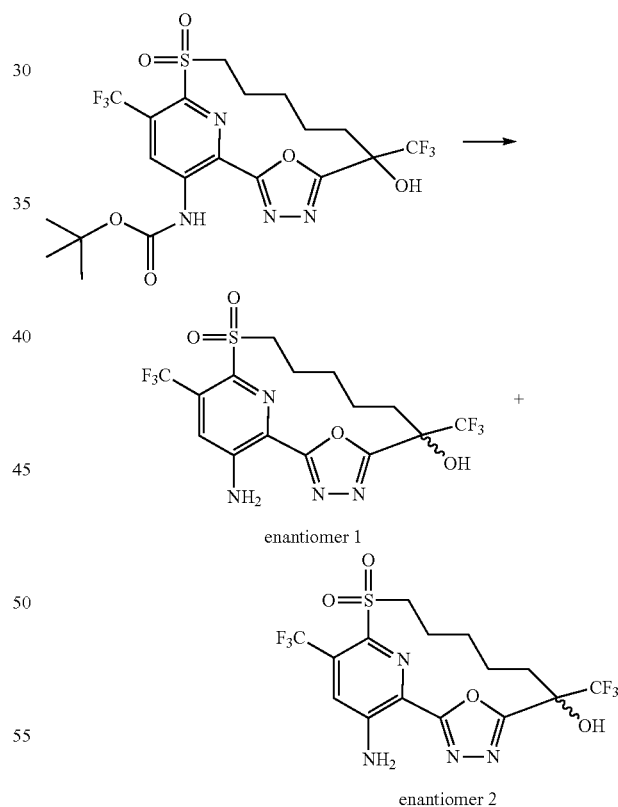

enantiomer 1 enantiomer 2 tert-Butyl N-[6-hydroxy-12,12-dioxo-6,14-bis(trifluoromethyl)-18-oxa-12$\lambda^6$-thia-3,4,17-triazatricyclo[11.3.1.12,5]octadeca-1(16),2,4,13(17),14-pentaen-16-yl]carbamate (81 mg, 0.13 mmol) was dissolved into TFA (1.27 mL), water (68 μL) and triisopropylsilane (40 μL, 0.1953 mmol), and stirred at room temperature for 15 min, then solvents evaporated. The residue was subjected to chiral separation by SFC chromatography using a ChiralPak AD (250×21.2 mm column, 5 µm particle size) with 5% to 30% methanol (5 mM NH$_3$)/and carbon dioxide mobile phase at 10 mL/min over 10.0 min (injection volume=330 µL of 25 mg/mL solution in methanol) giving as the first enantiomer to elute 16-amino-12,12-dioxo-6,14-bis(trifluoromethyl)-18-oxa-12λ$^6$-thia-3,4,17-triazatricyclo[11.3.1.12,5]octadeca-1(17),2,4,13,15-pentaen-6-ol (16 mg, 27%) as a white crystalline solid. $^1$H NMR (400 MHz, DMSO-d$_6$) δ 7.84 (s, 1H), 7.66 (s, 1H, D$_2$O exchanged), 7.39 (s, 2H, D$_2$O exchanged), 3.87-3.69 (m, 1H), 3.57-3.41 (m, 1H), 2.30-2.02 (m, 4H), 1.70 (m, 2H), 1.58-1.45 (m, 2H) ppm; $^{19}$F NMR (376 MHz, DMSO-d$_6$) δ −58.27, −77.73; UV/vis λ$_{max}$ 230, 275, 353 nm. ESI-MS m/z calc. 460.064, found 461.0 (M+1)$^+$; Retention time: 1.04 minutes. Final purity was determined by reversed phase HPLC-MS using an Onyx Monolithic C$_{18}$ column (50×4.6 mm) sold by Phenomenex (pn: CH0-7644), and a dual gradient run from 1-99% mobile phase B over 2.9 minutes. Mobile phase A=H$_2$O (0.05% CF$_3$CO$_2$H). Mobile phase B=CH$_3$CN (0.035% CF$_3$CO$_2$H). Flow rate=12 mL/min, injection volume=50 µL, and column temperature=25° C.

The second enantiomer to elute was 16-amino-12,12-dioxo-6,14-bis(trifluoromethyl)-18-oxa-12λ$^6$-thia-3,4,17-triazatricyclo[11.3.1.12,5]octadeca-1(17),2,4,13,15-pentaen-6-ol (14.4 mg, 24%) as a white crystalline solid. $^1$H NMR (400 MHz, DMSO-d$_6$) δ 7.84 (s, 1H), 7.66 (s, 1H, D$_2$O exchanged), 7.39 (s, 2H, D$_2$O exchanged), 3.84-3.70 (m, 1H), 3.55-3.43 (m, 1H), 2.31-2.00 (m, 4H), 1.70 (s, 2H), 1.56-1.45 (m, 2H) ppm; $^{19}$F NMR (376 MHz, DMSO-d$_6$) δ −58.27, −77.73 ppm; UV/vis λ$_{max}$ 230, 275, 353 nm. ESI-MS m/z calc. 460.064, found 460.9 (M+1)$^+$; Retention time: 1.04 minutes. Final purity was determined by reversed phase HPLC-MS using an Onyx Monolithic C$_{18}$ column (50×4.6 mm) sold by Phenomenex (pn: CH0-7644), and a dual gradient run from 1-99% mobile phase B over 2.9 minutes. Mobile phase A=H$_2$O (0.05% CF$_3$CO$_2$H). Mobile phase B=CH$_3$CN (0.035% CF$_3$CO$_2$H). Flow rate=12 mL/min, injection volume=50 µL, and column temperature=25° C.

Example 13: Preparation of 21-amino-6,19-bis(trifluoromethyl)-17,23-dioxa-3,4,22-triazatetracyclo[16.3.1.12,5.011,16]tricosa-1(22),2,4,11(16),12,14,18,20-octaen-6-ol (hydrochloride salt), Compound 17

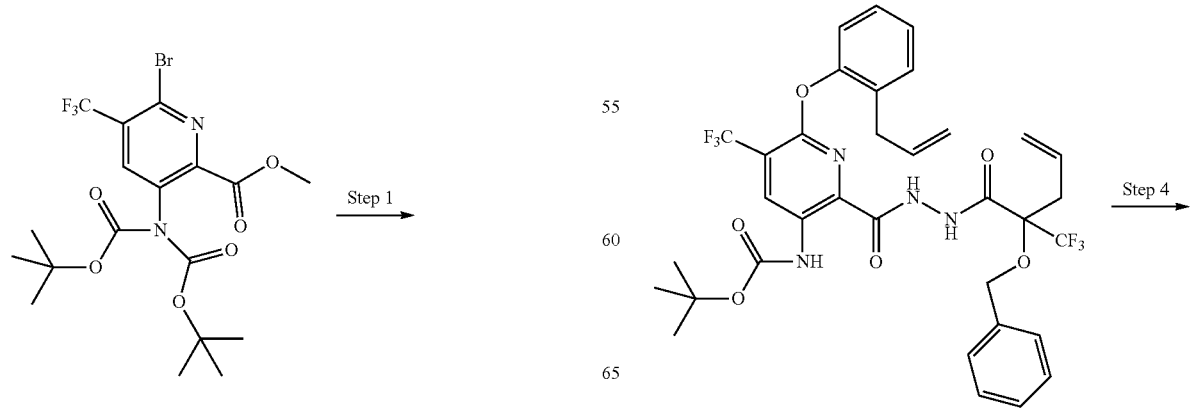

-continued

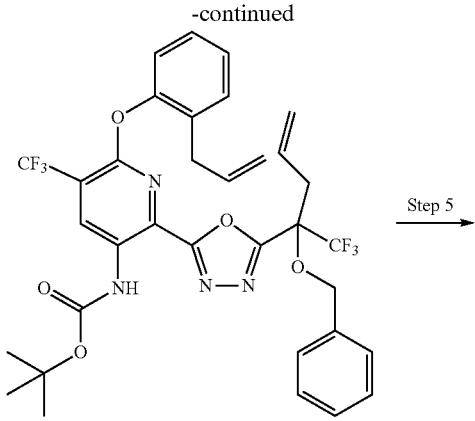

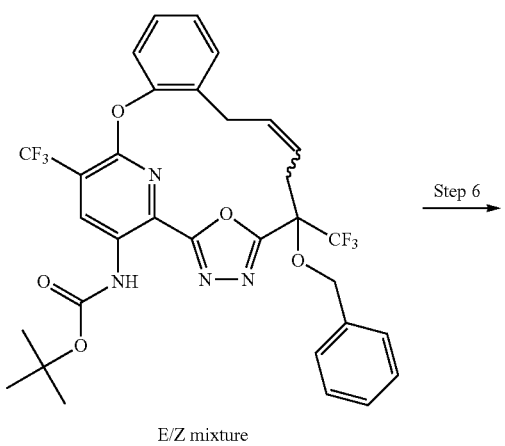

E/Z mixture

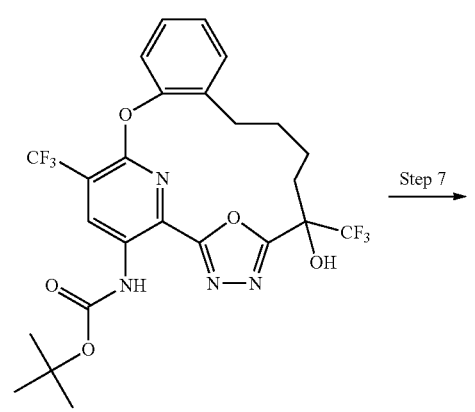

·HCl

Step 1: Methyl 6-(2-allylphenoxy)-3-[bis(tert-butoxycarbonyl)amino]-5-(trifluoromethyl)pyridine-2-carboxylate

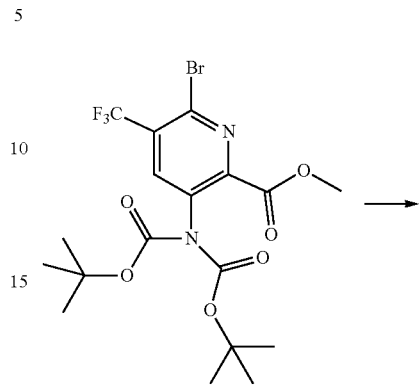

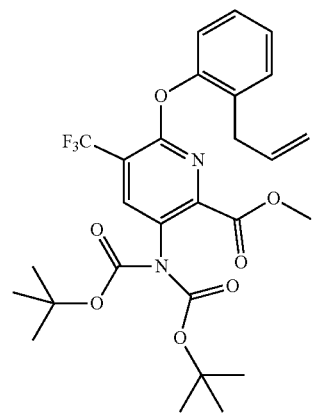

To a solution of methyl 3-[bis(tert-butoxycarbonyl)amino]-6-bromo-5-(trifluoromethyl)pyridine-2-carboxylate (1.2 g, 2.403 mmol) in DMSO (12 mL) was added 2-allylphenol (380 μL, 2.911 mmol), cesium carbonate (2.43 g, 7.458 mmol) and iodocopper (100 mg, 0.5251 mmol) and the reaction mixture was heated at 100° C. for 30 min in an oil bath. LCMS shows completion of the reaction. The reaction mixture was poured on crushed ice and extracted with ethyl acetate and washed with brine. The organics were separated, dried over sodium sulfate, and evaporated. The resultant brown residue was purified by silica gel column chromatography using a gradient of 100% hexanes to 100% EtOAc to afford methyl 6-(2-allylphenoxy)-3-[bis(tert-butoxycarbonyl)amino]-5-(trifluoromethyppyridine-2-carboxylate (612 mg, 46%). $^1$H NMR (400 MHz, Chloroform-d) δ 7.85 (s, 1H), 7.30-7.25 (m, 2H), 7.20 (t, J=7.6 Hz, 2H), 5.88 (ddt, J=16.8, 10.1, 6.6 Hz, 1H), 5.02-4.94 (m, 2H), 3.79 (s, 3H), 3.32 (d, J=6.7 Hz, 2H), 1.42 (s, 18H) ppm; ESI-MS m/z calc. 552.2083, found 453.1 (M+1)$^+$; Retention time: 0.75 minutes. Final purity was determined by reversed phase UPLC using an Acquity UPLC BEH $C_{18}$ column (30×2.1 mm, 1.7 μm particle) made by Waters (pn: 186002349), and a dual gradient run from 30-99% mobile phase B over 1.0 minutes. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

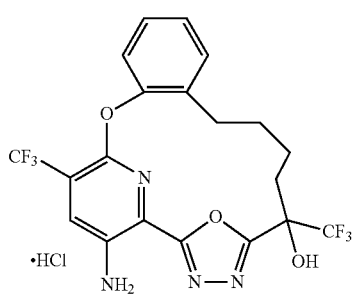

Step 2: 6-(2-Allylphenoxy)-3-(tert-butoxycarbonylamino)-5-(trifluoromethyl)pyridine-2-carboxylic acid

Step 3: tert-Butyl N-[6-(2-allylphenoxy)-2-[[[2-benzyloxy-2-(trifluoromethyl)pent-4-enoyl]amino]carbamoyl]-5-(trifluoromethyl)-3-pyridyl]carbamate

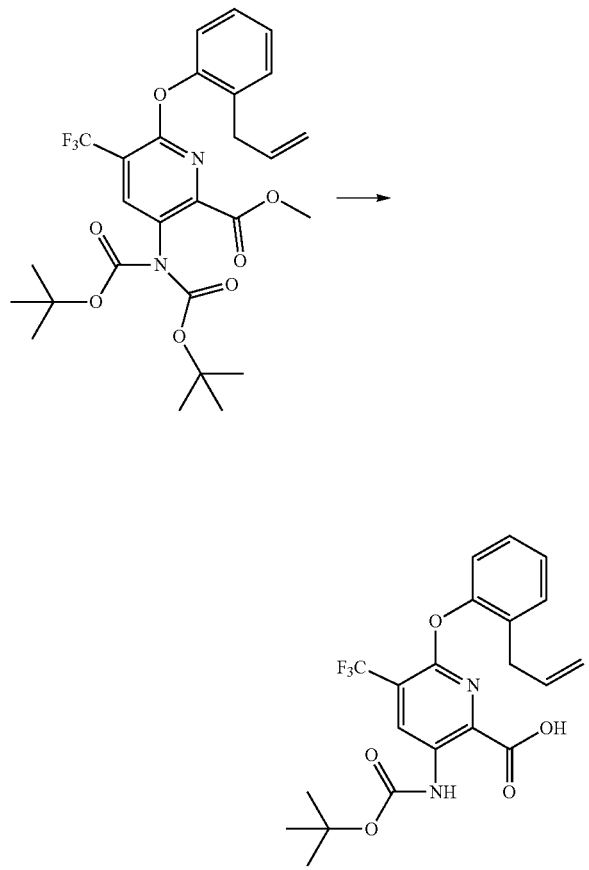 [SMILES: C=CCc1ccccc1Oc1nc(C(=O)OC)c(N(C(=O)OC(C)(C)C)C(=O)OC(C)(C)C)cc1C(F)(F)F ; C=CCc1ccccc1Oc1nc(C(=O)O)c(NC(=O)OC(C)(C)C)cc1C(F)(F)F]

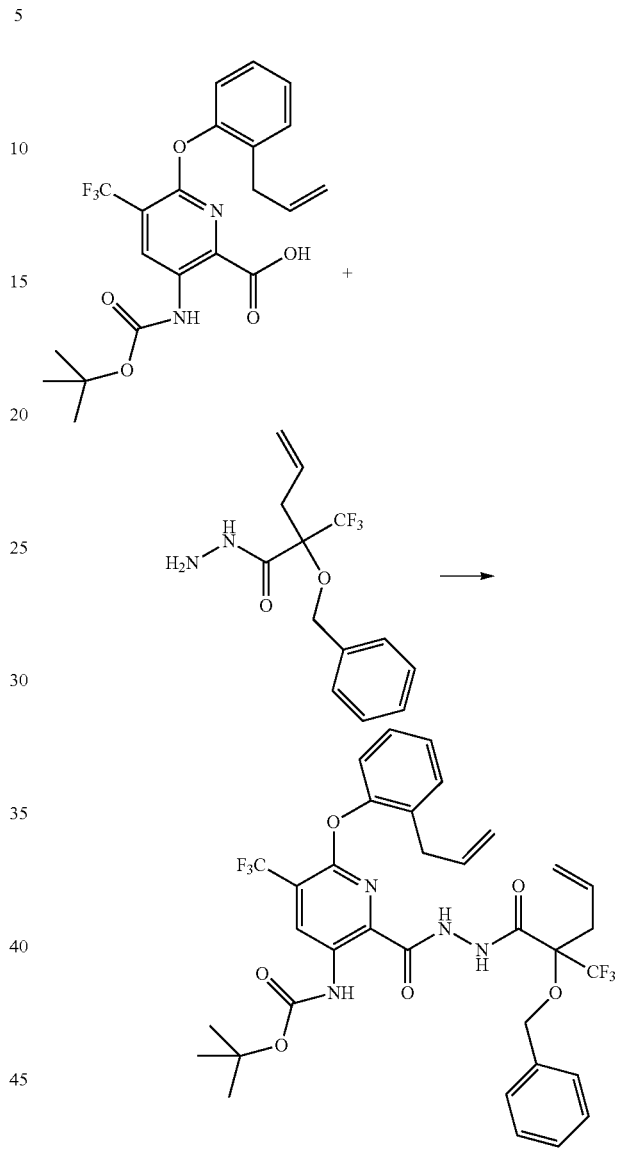

To a solution of methyl 6-(2-allylphenoxy)-34bis(tert-butoxycarbonyl)aminol-5-(trifluoromethyl)pyridine-2-carboxylate (612 mg, 1.108 mmol) in THF (8 mL), MeOH (8 mL), and water (8 mL) was added LiOH (86 mg, 3.591 mmol). The mixture was stirred at room temperature for 30 min.
THF and methanol were removed under reduced pressure and then 10 mL HCl (10%) was carefully added to pH ~6 and the product was extracted by EtOAc (2×50 mL). The organic phases were combined, washed with brine (5 mL), dried over anhydrous sodium sulfate, filtered and concentrated in vacuo and placed under high vacuum for 12 hours to afford as a yellow solid 6-(2-allylphenoxy)-3-(tert-butoxycarbonylamino)-5-(trifluoromethyl)pyridine-2-carboxylic acid (482 mg, 99%). ESI-MS m/z calc. 438.14026, found 439.13 (M+1)$^+$; Retention time: 0.69 minutes. Final purity was determined by reversed phase UPLC using an Acquity UPLC BEH C$_{18}$ column (30×2.1 mm, 1.7 μm particle) made by Waters (pn: 186002349), and a dual gradient run from 30-99% mobile phase B over 1.0 minutes. Mobile phase A=H$_2$O (0.05% CF$_3$CO$_2$H). Mobile phase B=CH$_3$CN (0.035% CF$_3$CO$_2$H). Flow rate=1.5 mL/min, injection volume=1.5 μL, and column temperature=60° C.

To a solution of 6-(2-allylphenoxy)-3-(tert-butoxycarbonylamino)-5-(trifluoromethyl)pyridine-2-carboxylic acid (394.8 mg, 0.9006 mmol) and 2-benzyloxy-2-(trifluoromethyl)pent-4-enehydrazide (312.5 mg, 1.084 mmol) in DMF (5 mL) was added DIEA (527.0 μL, 3.026 mmol), followed by HATU (526.6 mg, 1.385 mmol). The reaction mixture was stirred at room temperature for 4 h. The mixture was diluted with water and extracted with ethyl acetate. The organic phases combined and dried over MgSO$_4$, filtered, and concentrated in vacuo. The resultant brown residue was purified by silica gel column chromatography using a gradient of 100% hexanes to 30% EtOAc-hexanes to afford tert-butyl N-[6-(2-allylphenoxy)-2-[[[2-benzyloxy-2-(trifluoromethyl)pent-4-enoyl]amino]carbamoyl]-5-(trifluoromethyl)-3-pyridyl]carbamate (543 mg, 85%). ESI-MS m/z calc. 708.2383, found 808.0 (M+1)$^+$; Retention time: 0.7 minutes. Final purity was determined by reversed phase UPLC using an Acquity UPLC BEH C$_{18}$ column (30×2.1 mm, 1.7 µm particle) made by Waters (pn: 186002349), and a dual gradient run from 50-99% mobile phase B over 1.0 minutes. Mobile phase A=H₂O (0.05% CF₃CO₂H). Mobile phase B=CH₃CN (0.035% CF₃CO₂H). Flow rate=1.5 mL/min, injection volume=1.5 µL, and column temperature=60° C.

Step 4: tert-Butyl N-[6-(2-allylphenoxy)-2-[5-[1-benzyloxy-1-(trifluoromethyl)but-3-enyl]-1,3,4-oxadiazol-2-yl]-5-(trifluoromethyl)-3-pyridyl]carbamate

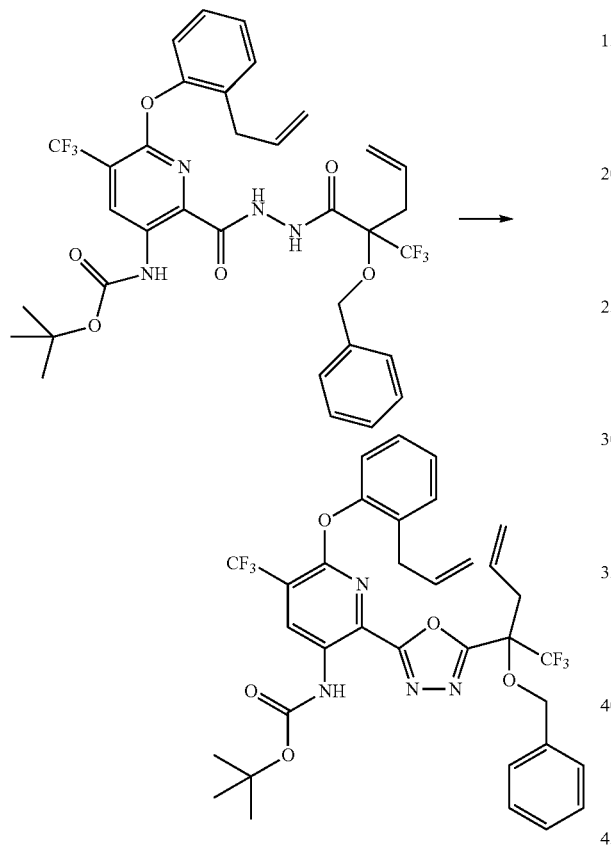

To a solution of tert-butyl N-[6-(2-allylphenoxy)-2-[[[2-benzyloxy-2-(trifluoromethyl)pent-4-enoyl]amino]carbamoyl]-5-(trifluoromethyl)-3-pyridyl]carbamate (630 mg, 0.8890 mmol) in acetonitrile (75 mL) was added DIEA (500 µL, 2.871 mmol) and was heated to 70° C., then 4-methylbenzenesulfonyl chloride (255 mg, 1.338 mmol) was added in 3 portions (85 mg each portion in 10 min intervals). The resulted mixture was heated at 70° C. for 16 hours. The reaction mixture was cooled and quenched with saturated solution of sodium bicarbonate and extracted with ethyl acetate. The combined organic layers were washed with brine, dried over sodium sulfate, filtered, and evaporated in vacuo. The resultant brown residue was purified by silica gel column chromatography using a gradient from 100% hexanes to 30% EtOAc to afford tert-butyl N-[6-(2-allylphenoxy)-2-[5-[1-benzyloxy-1-(trifluoromethyl)but-3-enyl]-1,3,4-oxadiazol-2-yl]-5-(trifluoromethyl)-3-pyridyl]carbamate (336 mg, 55%). ¹H NMR (400 MHz, DMSO-d₆) δ 9.72 (s, 1H), 8.99 (s, 1H), 7.35-7.29 (m, 4H), 7.25 (m, 5H), 5.90-5.72 (m, 2H), 5.23-5.10 (m, 2H), 4.96-4.87 (m, 2H), 4.66 (d, J=10.9 Hz, 1H), 4.52 (d, J=10.9 Hz, 1H), 3.29 (dd, J=11.3, 6.8 Hz, 2H), 3.10 (d, J=7.1 Hz, 2H), 1.49 (s, 9H) ppm. ESI-MS m/z calc. 690.22766, found 691.3 (M+1)⁺; Retention time: 0.81 minutes. Final purity was determined by reversed phase UPLC using an Acquity UPLC BEH C₁₈ column (30×2.1 mm, 1.7 µm particle) made by Waters (pn: 186002349), and a dual gradient run from 50-99% mobile phase B over 1.0 minutes. Mobile phase A=H₂O (0.05% CF₃CO₂H). Mobile phase B=CH₃CN (0.035% CF₃CO₂H). Flow rate=1.5 mL/min, injection volume=1.5 µL, and column temperature=60° C.

Step 5: tert-Butyl N-[6-(benzyloxy)-6,19-bis(trifluoromethyl)-17,23-dioxa-3,4,22-triazatetracyclo[16.3.1.1²,⁵.0¹¹,¹⁶]tricosa-1(22),2,4,8,11(16),12,14,18,20-nonaen-21-yl]carbamate (E/Z Mixture)

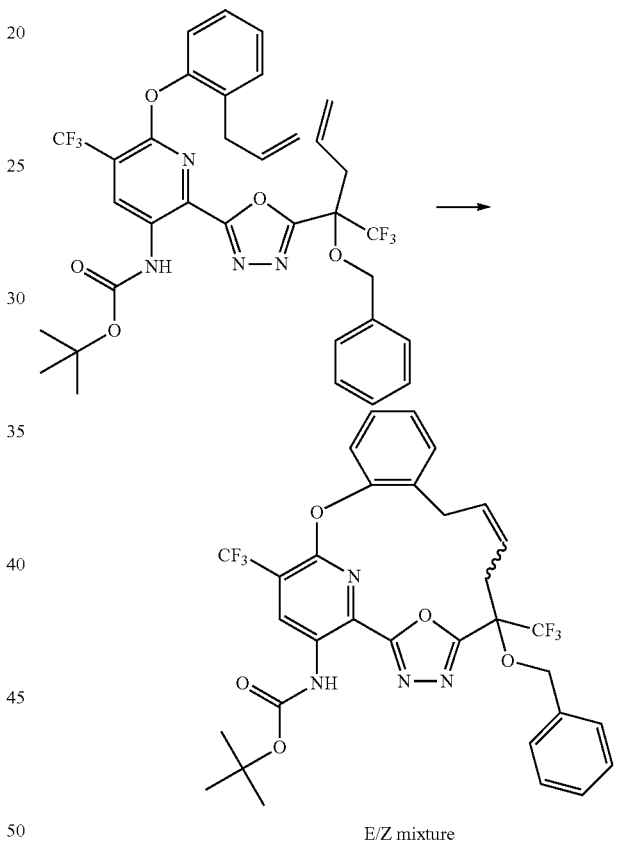

E/Z mixture

To a degassed solution of benzylidene-[1,3-bis(2,4,6-trimethylphenyl)imidazolidin-2-ylidene]-dichloro-ruthenium;tricyclohexylphosphane (6 mg, 0.007067 mmol) (Grubbs-2nd Gen catalyst) in DCE (30 mL) was added degassed solution of tert-butyl N-[6-(2-allylphenoxy)-2-[5-[1-benzyloxy-1-(trifluoromethyl)but-3-enyl]-1,3,4-oxadiazol-2-yl]-5-(trifluoromethyl)-3-pyridyl]carbamate (212 mg, 0.3070 mmol) in DCE (30 mL) slowly dropwise under a stream of N₂ flow bubbling through the solution over 30 min and the reaction mixture was heated at 50° C. for 5 h. The temperature was increased to 70° C. and the reaction mixture was heated overnight. The reaction was stopped, and the solvents removed in vacuo. The resultant brown residue was purified by silica gel column chromatography using a shallow gradient of 100% hexanes to 30% EtOAc-hexanes to afford tert-butyl N-[6-(benzyloxy)-6,19-bis(trifluoromethyl)-17,23-dioxa-3,4,22-triazatetracyclo[16.3.1.1²,⁵.0¹¹,¹⁶]tricosa-1(22),2,4,8,11(16),12,14,18,20-nonaen-21-yl]carbamate (E/Z mixture) (126 mg, 62%). ESI-MS m/z calc. 662.1964, found 663.19 (M+1)⁺; Retention time: 0.74 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=$CH_3CN$ (0.035% $CF_3CO_2H$). Flow rate=1.5 mL/min, injection volume=1.5 μL, and column temperature=60° C.

Step 6: tert-Butyl N-[6-hydroxy-6,19-bis(trifluoromethyl)-17,23-dioxa-3,4,22-triazatetracyclo[16.3.1.1²,⁵.0¹¹,¹⁶]tricosa-1(22),2,4,11(16),12,14,18,20-octaen-21-yl]carbamate

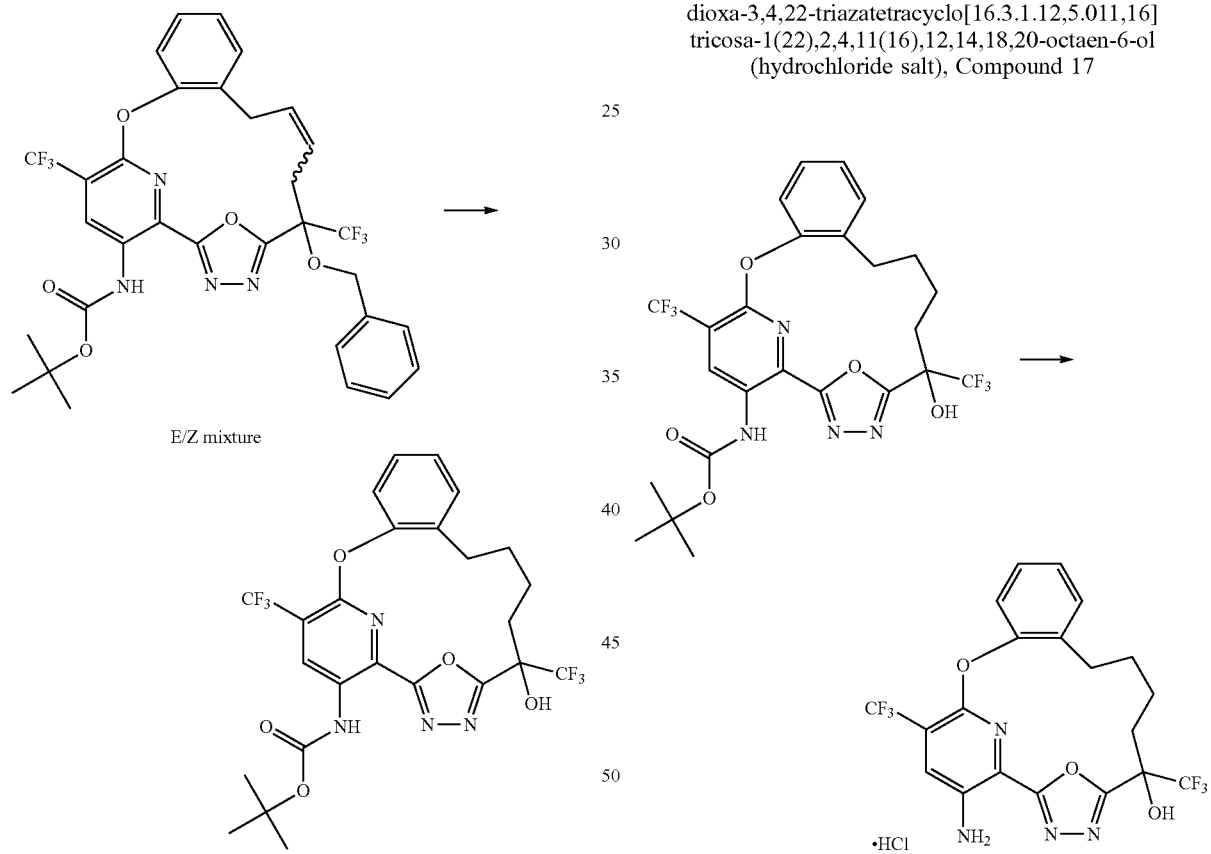

E/Z mixture

To a solution of a 1:1 isomeric mixture of tert-butyl N-[6-(benzyloxy)-6,19-bis(trifluoromethyl)-17,23-dioxa-3,4,22-triazatetracyclo[16.3.1.1²,⁵.0¹¹,¹⁶]tricosa-1(22),2,4,8,11(16),12,14,18,20-nonaen-21-yl]carbamate (E/Z mixture) (120 mg, 0.1811 mmol) and tert-butyl N-[6-(2-allylphenoxy)-2-[5-[1-hydroxy-1-(trifluoromethyl)but-3-enyl]-1,3,4-oxadiazol-2-yl]-5-(trifluoromethyl)-3-pyridyl]carbamate (120 mg, 0.1998 mmol) in AcOH (5 mL) was added Pd/C (42 mg of 10% w/w, 0.03947 mmol) in a round-bottomed flask equipped with a $H_2$ balloon using a 3-way adaptor. Subjected to vacuum and backfilled with nitrogen gas three times then subjected to vacuum. Filled the flask with hydrogen gas then stirred the mixture for 15 hours. Subjected to vacuum and backfilled with nitrogen gas three times then diluted with ethyl acetate and filtered over Celite. Filtrate was concentrated and dried under high vacuum. The resultant brown residue was purified by silica gel column chromatography using a shallow gradient of 100% hexanes to 30% EtOAc-hexanes to afford tert-butyl N-[6-hydroxy-6,19-bis(trifluoromethyl)-17,23-dioxa-3,4,22-triazatetracyclo[16.3.1.1²,⁵.0¹¹,¹⁶]tricosa-1(22),2,4,11(16),12,14,18,20-octaen-21-yl]carbamate (14.2 mg, 27%); ESI-MS m/z calc. 574.1651, found 575.2 (M+1)⁺; Retention time: 1.31 minutes. Final purity was determined by reversed phase UPLC using an Acquity UPLC BEH $C_{18}$ column (50×2.1 mm, 1.7 μm particle) made by Waters (pn: 186002350), and a dual gradient run from 50-99% mobile phase B over 2.9 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Step 7: 21-Amino-6,19-bis(trifluoromethyl)-17,23-dioxa-3,4,22-triazatetracyclo[16.3.1.1²,⁵.0¹¹,¹⁶]tricosa-1(22),2,4,11(16),12,14,18,20-octaen-6-ol (hydrochloride salt), Compound 17

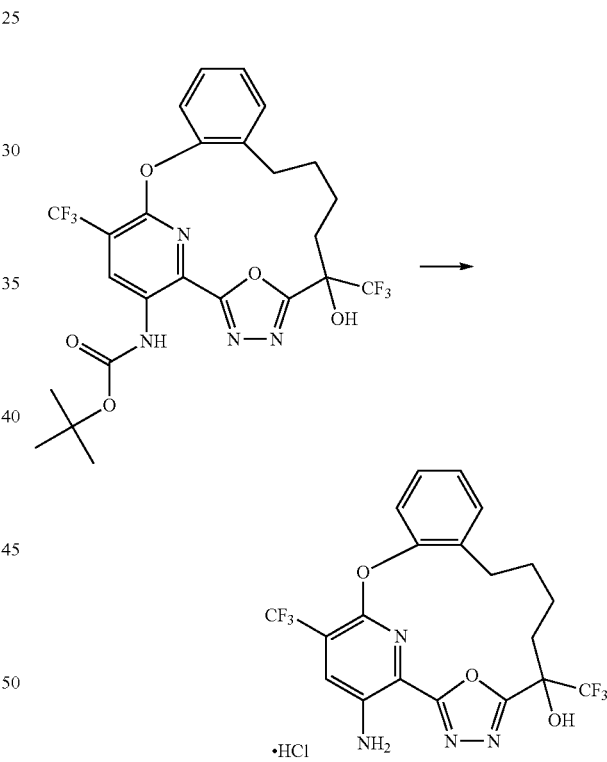

To a solution of tert-butyl N-[6-hydroxy-6,19-bis(trifluoromethyl)-17,23-dioxa-3,4,22-triazatetracyclo[16.3.1.1²,⁵.0¹¹,¹⁶]tricosa-1(22),2,4,11(16),12,14,18,20-octaen-21-yl]carbamate (13 mg, 0.02263 mmol) was added TFA (100 μL, 1.298 mmol) and DCM (400 μL) (pre made solution of 1:4 TFA-DCM) and the reaction was stirred at room temperature for about 1 h. LCMS shows the completion of reaction. Solvents were removed and dissolved in DMSO (1 mL) and the residue was purified by a reverse phase HPLC-MS method using a dual gradient run from 50-99% mobile phase B over 15.0 minutes (mobile phase A=$H_2O$ (5 mM HCl); mobile phase B=$CH_3CN$) to afford 21-amino-6,19-bis(trifluoromethyl)-17,23-dioxa-3,4,22-triazatetracyclo

[16.3.1.1²,⁵.0¹¹,¹⁶]tricosa-1(22),2,4,11(16),12,14,18,20-octaen-6-ol (Hydrochloride salt) (2.6 mg, 22%) as an off-white amorphous solid. $^1$H NMR (400 MHz, Chloroform-d) δ 7.49 (s, 1H), 7.35-7.33 (m, 1H), 7.21-7.14 (m, 3H), 5.36 (s, 2H), 3.63 (s, 1H), 3.06-2.89 (m, 2H), 2.29 (m, 1H), 2.22-2.14 (m, 1H), 2.13-2.05 (m, 2H), 1.92 (d, J=5.2 Hz, 2H) ppm. ESI-MS m/z calc. 474.11267, found 475.13 (M+1)$^+$; Retention time: 2.76 minutes. Final purity was determined by reversed phase UPLC using an Acquity UPLC BEH C$_{18}$ column (50×2.1 mm, 1.7 µm particle) made by Waters (pn: 186002350), and a dual gradient run from 1-99% mobile phase B over 4.5 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 µL, and column temperature=60° C.

Example 14: Preparation of (15R)-20-amino-8-fluoro-15-methyl-6,18-bis(trifluoromethyl)-16,23-dioxa-3,4,21-triazatetracyclo[15.3.1.1²,⁵.1⁷,¹¹]tri-cosa-1(21),2,4,7(22),8,10,17,19-octaen-6-ol (diastereomer pair), Compound 18

Step 1: 3-[bis(tert-Butoxycarbonyl)amino]-6-[(1R)-1-methylbut-3-enoxy]-5-(trifluoromethyl)pyridine-2-carboxylic acid

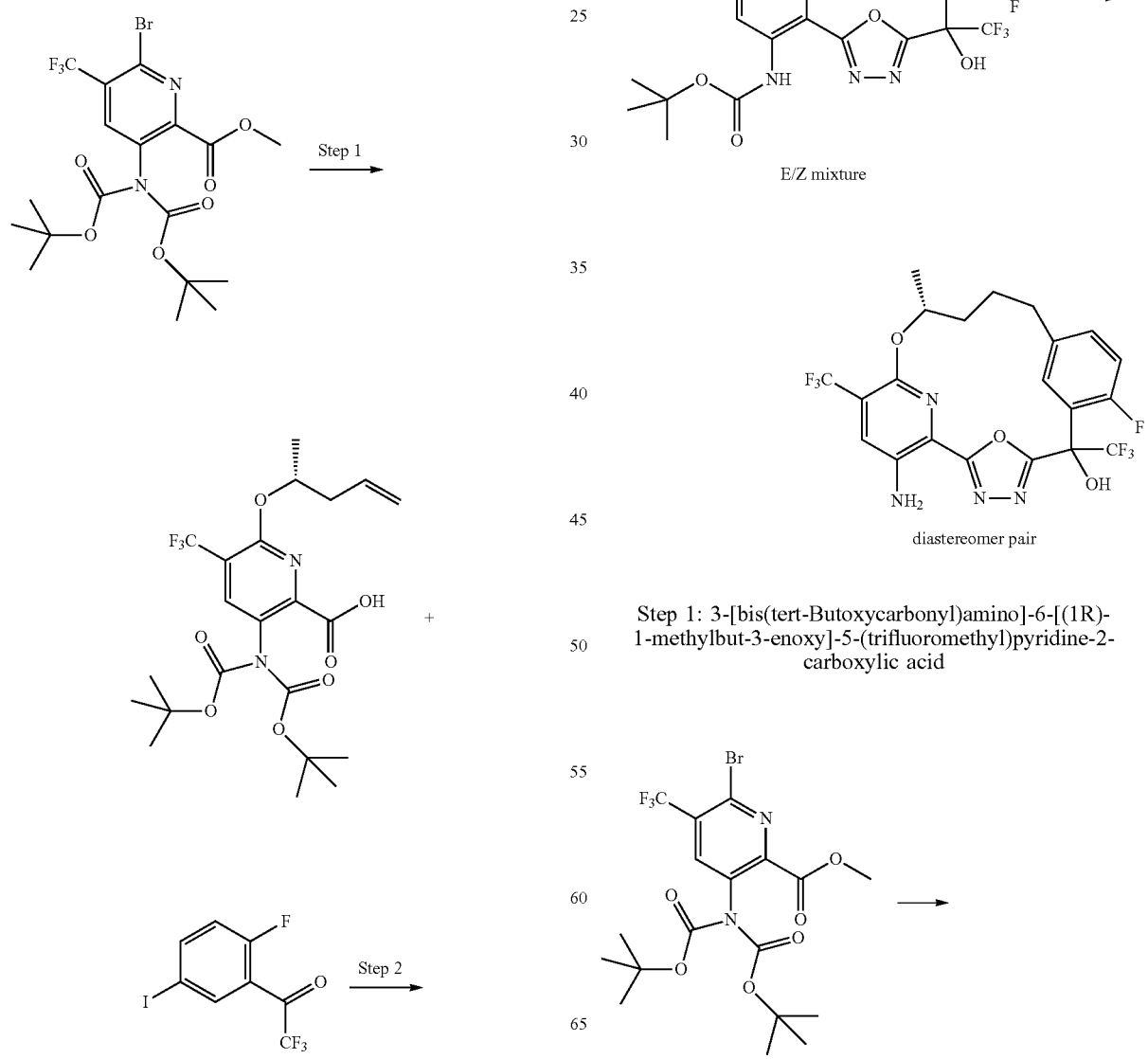

305

-continued

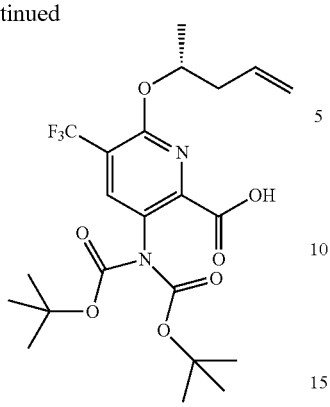

To a solution of methyl 3-[bis(tert-butoxycarbonyl)amino]-6-bromo-5-(trifluoromethyl)pyridine-2-carboxylate (500 mg, 1.001 mmol) in DMSO (2 mL) was added (2R)-pent-4-en-2-ol (160 µL, 1.555 mmol), cesium carbonate (504 mg, 1.547 mmol) and iodocopper (47 mg, 0.2468 mmol) and the reaction mixture was heated at 100° C. for 3 h. The reaction mixture was cooled to RT and poured on crushed ice and extracted with ethyl acetate and washed with brine. The organics were separated, dried over sodium sulfate, and evaporated. The resultant brown residue was purified by silica gel column chromatography using 100% hexanes to 30% EtOAc-hexanes to afford 3-[bis(tert-butoxycarbonyl)amino]-6-[(1R)-1-methylbut-3-enoxy]-5-(trifluoromethyl)pyridine-2-carboxylic acid (64 mg, 26%). $^1$H NMR (400 MHz, Chloroform-d) δ 10.17 (s, 1H), 7.63 (s, 1H), 5.73 (ddt, J=17.2, 10.2, 7.1 Hz, 1H), 5.20 (p, J=6.4 Hz, 1H), 5.17-5.07 (m, 2H), 2.48 (dt, J=13.5, 6.6 Hz, 1H), 2.37 (dt, J=14.1, 6.9 Hz, 1H), 1.45 (d, J=3.0 Hz, 18H), 1.34 (d, J=6.3 Hz, 3H) ppm. ESI-MS m/z calc. 490.1927, found 391.2 (M-Boc)$^+$. Retention time: 0.5 minutes. Final purity was determined by reversed phase UPLC using an Acquity UPLC BEH C$_{18}$ column (30×2.1 mm, 1.7 µm particle) made by Waters (pn: 186002349), and a dual gradient run from 30-99% mobile phase B over 1.0 minutes. Mobile phase A=H$_2$O (0.05% CF$_3$CO$_2$H). Mobile phase B=acetonitrile (0.035% CF$_3$CO$_2$H). Flow rate=1.5 mL/min, injection volume=1.5 µL, and column temperature=60° C.

Step 2: tert-Butyl N-tert-butoxycarbonyl-N-[6-[(1R)-1-methylbut-3-enoxy]-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate

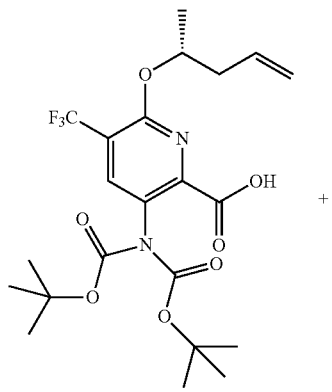

+

306

-continued

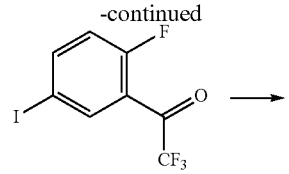

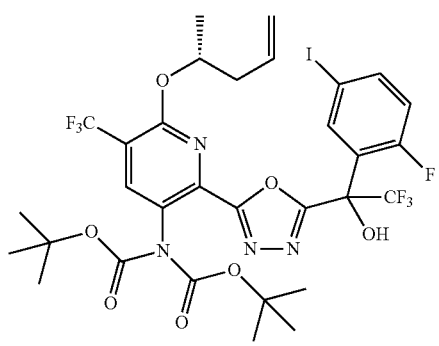

To a pre-heated at 50° C. stirred solution of 3-[bis(tert-butoxycarbonyl)amino]-6-[(1R)-1-methylbut-3-enoxy]-5-(trifluoromethyl)pyridine-2-carboxylic acid (120 mg, 0.2447 mmol) and 2,2,2-trifluoro-1-(2-fluoro-5-iodo-phenyl)ethanone (121 mg, 0.3805 mmol) in DMF (2 mL) was added (isocyanoimino)triphenylphosphorane (113 mg, 0.3738 mmol) at once. The mixture was stirred at room temperature overnight then it was diluted with EtOAc (50 mL), washed with water and brine consecutively, then dried over sodium sulfate and filtered. The filtrate was concentrated to dryness. The resultant brown residue was purified by silica gel column chromatography using 100% hexanes to 50% EtOAc-hexanes to provide a light brown viscous oil, tert-butyl N-tert-butoxycarbonyl-N-[6-[(1R)-1-methylbut-3-enoxy]-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (103 mg, 51%). $^1$H NMR (400 MHz, Chloroform-d) δ 8.17 (d, J=2.2 Hz, 1H), 7.81 (s, 1H), 7.76 (ddd, J=8.6, 4.6, 2.2 Hz, 1H), 6.83 (ddd, J=10.4, 8.7, 1.2 Hz, 1H), 5.79 (ddtd, J=17.4, 10.9, 7.1, 4.0 Hz, 1H), 5.38 (hept, J=6.2 Hz, 1H), 5.14-5.01 (m, 2H), 4.84 (d, J=3.9 Hz, 1H), 2.53 (dtd, J=13.7, 6.7, 2.9 Hz, 1H), 2.42 (dt, J=13.7, 6.7 Hz, 1H), 1.66 (s, 3H), 1.38 (dd, J=4.1, 2.1 Hz, 18H) ppm. ESI-MS m/z calc. 832.12036, found 733.1 (M-Boc)$^+$. Retention time: 0.79 minutes. Final purity was determined by reversed phase UPLC using an Acquity UPLC BEH C$_{18}$ column (30×2.1 mm, 1.7 µm particle) made by Waters (pn: 186002349), and a dual gradient run from 30-99% mobile phase B over 1.0 minutes. Mobile phase A=H$_2$O (0.05% CF$_3$CO$_2$H). Mobile phase B=acetonitrile (0.035% CF$_3$CO$_2$H). Flow rate=1.5 mL/min, injection volume=1.5 µL, and column temperature=60° C.

Step 3: tert-Butyl N-[(15R)-8-fluoro-6-hydroxy-15-methyl-6,18-bis(trifluoromethyl)-16,23-dioxa-3,4,21-triazatetracyclo[15.3.1.12,5.17,11]tricosa-1(21),2,4,7(22),8,10,12,17,19-nonaen-20-yl]carbamate (E/Z mixture)

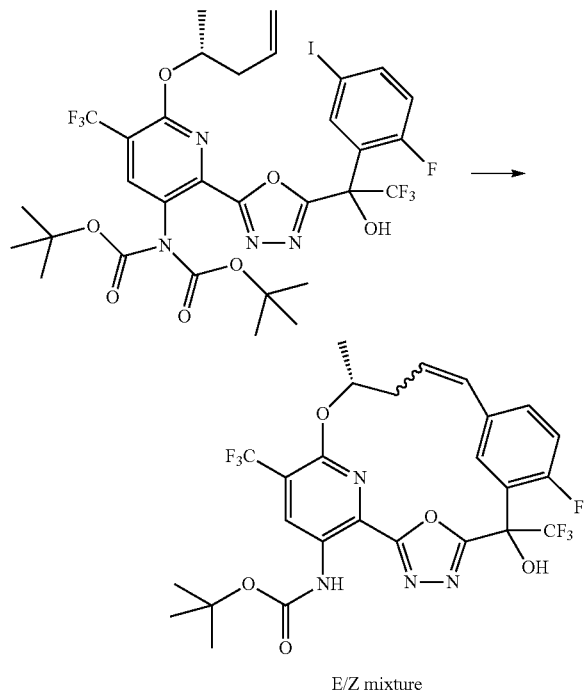

Step 4: (15R)-20-Amino-8-fluoro-15-methyl-6,18-bis(trifluoromethyl)-16,23-dioxa-3,4,21-triazatetracyclo[15.3.1.12,5.17,11]tricosa-1(21),2,4,7(22),8,10,17,19-octaen-6-ol (diastereomer pair), Compound 18

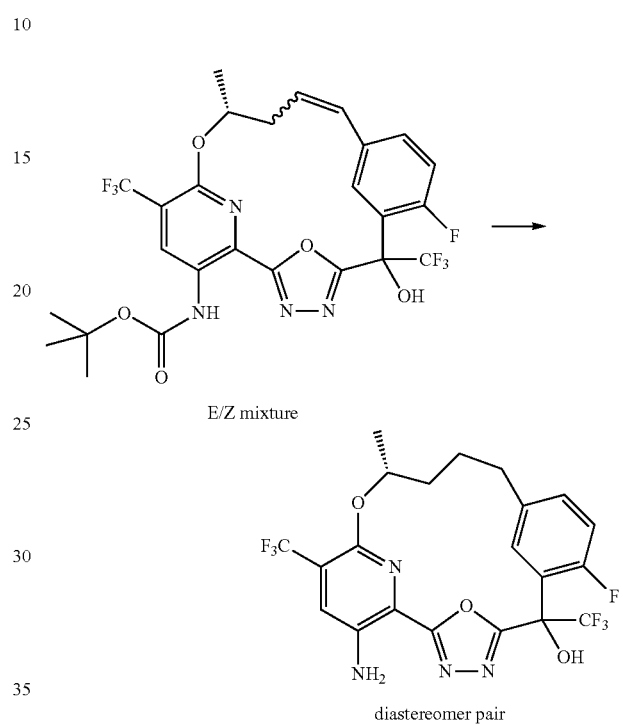

To a stirred solution of tert-butyl N-tert-butoxycarbonyl-N-[6-[(1R)-1-methylbut-3-enoxy]-2-[5-[2,2,2-trifluoro-1-(2-fluoro-5-iodo-phenyl)-1-hydroxy-ethyl]-1,3,4-oxadiazol-2-yl]-5-(trifluoromethyl)-3-pyridyl]carbamate (100 mg, 0.1201 mmol) in acetonitrile (10 mL) was added Palladium (II) acetate (8 mg, 0.03563 mmol) followed by tris-o-tolylphosphane (21 mg, 0.06900 mmol) and triethylamine (60 μL, 0.4305 mmol) and the solution was bubbled with $N_2$ for 1 min then heated by microwave irradiation at 120° C. for 0.5 h. The mixture was cooled to room temperature then diluted with EtOAc and washed with saturated aqueous $NH_4Cl$ (1×) and brine (1×) then dried over sodium sulfate, filtered and concentrated to a yellow oil. The resulting material was dissolved in DMSO, filtered and purified using a reverse phase HPLC-MS method using a Luna $C_{18}$ column (75×30 mm, 5 μm particle size) sold by Phenomenex (pn: 00C-4252-U0-AX), and a dual gradient run from 50-99% mobile phase B over 15.0 minutes (mobile phase A=$H_2O$ (5 mM HCl), mobile phase B=acetonitrile, flow rate=50 mL/min, injection volume=950 μL and column temperature=25° C. giving a yellow solid, tert-butyl N-[(15R)-8-fluoro-6-hydroxy-15-methyl-6,18-bis(trifluoromethyl)-16,23-dioxa-3,4,21-triazatetracyclo[15.3.1.12,5.17,1 1]tricosa-1(21),2,4,7(22),8,10,12,17,19-nonaen-20-yl]carbamate (E/Z mixture) (21 mg, 29%). ESI-MS m/z calc. 604.15564, found 605.03 (M+1)⁺; Retention time: 0.55 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

Part 1: To a solution of tert-butyl N-[(15R)-8-fluoro-6-hydroxy-15-methyl-6,18-bis(trifluoromethyl)-16,23-dioxa-3,4,21-triazatetracyclo[15.3.1.12,5.17,11]tricosa-1(21),2,4,7(22),8,10,12,17,19-nonaen-20-yl]carbamate (E/Z mixture) (20 mg, 0.03309 mmol) in ethanol (2 mL) was added Pd/C (18 mg of 10% w/w, 0.01691 mmol) in a round bottom flask equipped with a $H_2$ balloon using a 3-way adaptor. The mixture was subjected to vacuum and backfilled with nitrogen gas three times then subjected to vacuum. The flask was filled with hydrogen gas then stirred the mixture for 15 hours. The mixture was subjected to vacuum and backfilled with nitrogen gas three times then diluted with ethyl acetate and filtered over Celite. The filtrate was concentrated and dried under high vacuum.

Part 2: The material from Step 1 was dissolved in TFA (100 μL, 1.298 mmol) and DCM (400 μL) (pre-made solution of 1: 4 TFA-DCM) and the reaction was stirred at room temperature for about 1 h. Solvents were removed and dissolved in DMSO (1 mL) and the residue was purified by a reverse phase HPLC-MS method using a dual gradient run from 30-99% mobile phase B over 15.0 minutes using a mobile phase A=$H_2O$ (5 mM HCl) and a mobile phase B=acetonitrile to afford (15R)-20-amino-8-fluoro-15-methyl-6,18-bis(trifluoromethyl)-16,23-dioxa-3,4,21-triazatetracyclo[15.3.1.12,5.17,11]tricosa-1(21),2,4,7(22),8,10,17,19-octaen-6-ol (2 mg, 12%) as diastereomeric mixture. ESI-MS m/z calc. 506.1189, found 507.1 (M+1)⁺; Retention time: 2.93 minutes; Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Example 15: Preparation of (6R,13S)-17-Amino-13-oxido-6,15-bis(trifluoromethyl)-19-oxa-13-thionia-3,4,18-triazatricyclo[12.3.1.12,5]nonadeca-1(18),2,4,14,16-pentaen-6-ol, Compound 19, and (6R,13R)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol, Compound 20

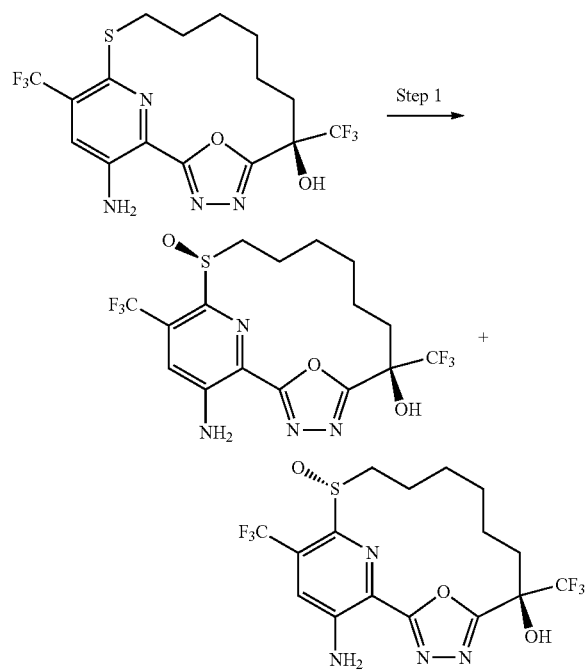

Step 1: (6R,13S)-17-Amino-13-oxido-6,15-bis(trifluoromethyl)-19-oxa-13-thionia-3,4,18-triazatricyclo[12.3.1.12,5]nonadeca-1(18),2,4,14,16-pentaen-6-ol, Compound 19, and (6R,13R)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol, Compound 20

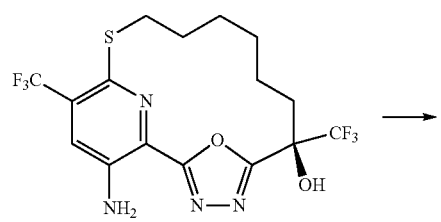

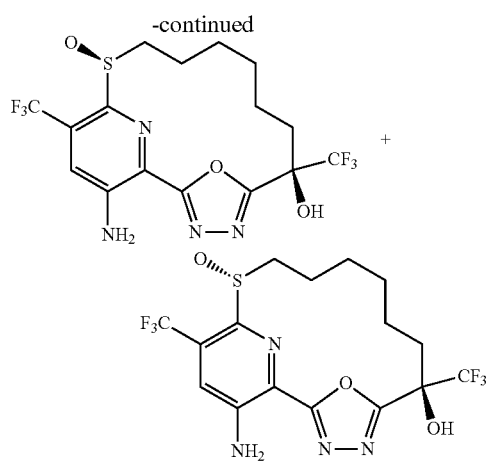

To a solution of (6R)-17-amino-6,15-bis(trifluoromethyl)-19-oxa-13-thia-3,4,18-triazatricyclo[12.3.1.12,5]nonadeca-1(18),2,4,14,16-pentaen-6-ol (56 mg, 0.127 mmol) in EtOAc (1.5 mL) cooled by ice bath was added 3-chlorobenzenecarboperoxoic acid (802 μL of 0.11 M, 0.088 mmol) as a solution in EtOAc and the mixture stirred at 0° C. for 15 min. Then 3-chlorobenzenecarboperoxoic acid (227 μL of 0.11 M, 0.025 mmol) as a solution in EtOAc was added and the mixture was stirred at 0° C. for 15 additional minutes. Then more 3-chlorobenzenecarboperoxoic acid (85 μL of 0.11 M, 0.0094 mmol) as a solution in EtOAc was added and the mixture stirred at 0° C. for 15 min. Then the mixture was diluted with EtOAc (30 mL) and MeOH (1 mL) and washed with 5% Na$_2$S$_2$O$_3$, 1 M NaHCO$_3$, dried (MgSO$_4$) and evaporated. The residue was purified by silica gel chromatography (12 g SiO$_2$, 10-50% of a solution (10% MeOH in EtOAc) to hexanes over 20 min) eluted first 2.3 mgs (4%) of recovered starting material (6R)-17-amino-6,15-bis(trifluoromethyl)-19-oxa-13-thia-3,4,18-triazatricyclo[12.3.1.12,5]nonadeca-1(18),2,4,14,16-pentaen-6-ol. Continued elution provided (6R,13R)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol (2.6 mg, 4%). Continued elution provided (6R,13S)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol and then a mixture of (6R,13S)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol and (6R,13R)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol.

The mixture of (6R,13S)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol and (6R,13R)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol was dissolved in 1:1 MeOH/acetonitrile and subjected to preparative HPLC eluting with 30-70% acetonitrile vs 5 mM HCl in water at 50 mL/min over 14 min through a Luna 5 μM C$_{18}$ 100μ 75×30 mm column to provide the first eluent as a white solid (6R,13R)-17-amino-13-oxido-6,15-bis(trifluoromethyl)-19-oxa-13-thionia-3,4,18-triazatricyclo[12.3.1.12,5]nonadeca-1(18),2,4,14,16-pentaen-6-ol (18 mg, 31%): $^1$H NMR (400 MHz, Methanol-d$_4$) δ 7.82 (s, 1H), 3.80 (td, J=12.5, 5.1 Hz, 1H), 3.15 (td, J=12.4, 3.8 Hz, 1H), 2.37 (td, J=13.0, 11.5, 3.3 Hz, 1H), 2.29-2.17 (m, 1H), 2.09-1.97 (m, 1H), 1.95-1.84 (m, 1H), 1.83-1.65 (m, 4H), 1.59 (t, J=8.6 Hz, 2H) ppm; $^{19}$F NMR (376 MHz, Methanol-$d_4$) δ -60.52, -80.84 ppm; ESI-MS m/z calc. 458.08472, found 459.1 (M+1)$^+$; Retention time: 0.94 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=12 mL/min, injection volume=50 μL, and column temperature=25° C. Continued elution provided second eluent (6R, 13S)-17-amino-13-oxido-6,15-bis(trifluoromethyl)-19-oxa-13-thionia-3,4,18-triazatricyclo[12.3.1.1$^{2,5}$]nonadeca-1(18),2,4,14,16-pentaen-6-ol (19 mg, 33%): $^1$H NMR (400 MHz, Methanol-$d_4$) δ 7.81 (s, 1H), 3.75 (td, J=12.7, 4.0 Hz, 1H), 3.28-3.17 (m, 1H), 2.48-2.27 (m, 3H), 2.25-2.11 (m, 1H), 1.72 (dddd, J=32.5, 20.0, 13.7, 8.0 Hz, 6H) ppm; $^{19}$F NMR (376 MHz, Methanol-$d_4$) δ -60.41, -80.81; ESI-MS m/z calc. 458.08472, found 459.0 (M+1)$^+$; Retention time: 1.09 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=12 mL/min, injection volume=50 μL, and column temperature=25° C.

Step 2: Solid Form Chracterization of Crystalline Compound 19 (Neat Form)

Compound 19 (15 mg) was dissolved in 0.45 mL of methanol. The solution was allowed to sit at room temperature for 2 hours. Cubes with slightly opaque faces formed.

Single crystals of crystalline Compound 19 (neat form) were grown by slow cooling a methanol solution from 80° C. to 25° C. X-ray diffraction data were acquired at 100 K on a Bruker diffractometer equipped with Mo $K_α$ radiation (λ=0.71073 Å) and a CCD detector. The structure was solved and refined using SHELX programs (Sheldrick, G. M., Acta Cryst., (2008) A64, 112-122). The results are summarized in Table 10 below.

TABLE 10

| Single crystal elucidation of crystalline Compound 19 (neat form) | |
|---|---|
| Crystal System | Tetragonal |
| Space Group | P4$_1$2$_1$2 |
| a (Å) | 9.8237(4) |
| b (Å) | 9.8237(4) |
| c (Å) | 37.0548(18) |
| α (°) | 90 |
| β (°) | 90 |
| γ (°) | 90 |
| V (Å$^3$) | 3576.0(3) |
| Z/Z' | 8/1 |
| Temperature | 100K |

Step 3: Solid Form Chracterization of Crystalline Compound 20 (Neat Form)

Compound 20 (10 mg) was dissolved in 0.3 mL of methanol. The solution was heated, then cooled to room temperature over 2 hours. Clear rectangular prisms were obtained.

Single crystals crystalline Compound 20 (neat form) were grown by slow cooling of a methanol solution. X-ray diffraction data were acquired at 100 K on a Bruker diffractometer equipped with Mo $K_α$ radiation (λ=0.71073 Å) and a CCD detector. The structure was solved and refined using SHELX programs (Sheldrick, G. M., Acta Cryst., (2008) A64, 112-122) and results are summarized in Table 11 below.

TABLE 11

| Single crystal elucidation of crystalline Compound 20 (neat form) | |
|---|---|
| Crystal System | Orthorhombic |
| Space Group | P2$_1$2$_1$2$_1$ |
| a (Å) | 10.6547(4) |
| b (Å) | 13.7046(5) |
| c (Å) | 25.5376(11) |
| α (°) | 90 |
| β (°) | 90 |
| γ (°) | 90 |
| V (Å$^3$) | 3729.0(3) |
| Z/Z' | 8/1 |
| Temperature | 100K |

Example 16: (6R)-17-Amino-6,15-bis(trifluoromethyl)-19-oxa-13-thia-3,4,18-triazatricyclo[12.3.1.1$^{2,5}$]nonadeca-1(18),2,4,14,16-pentaen-6-ol, Compound 21

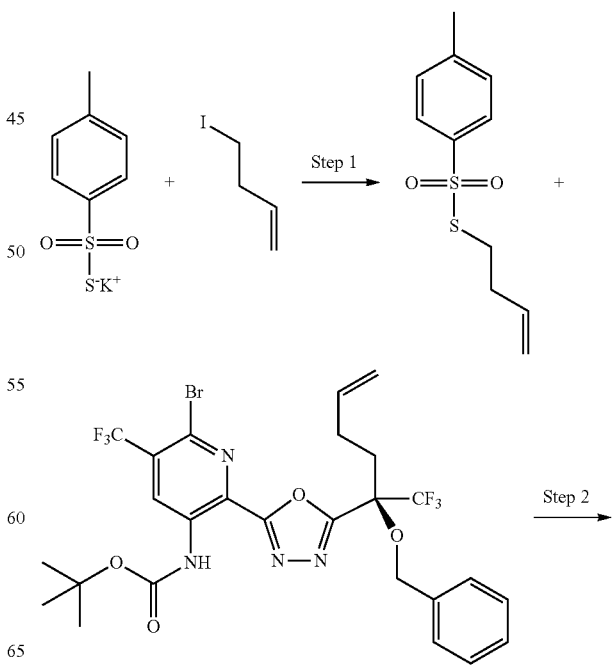

314

Step 1:
1-But-3-enylsulfanylsulfonyl-4-methyl-benzene

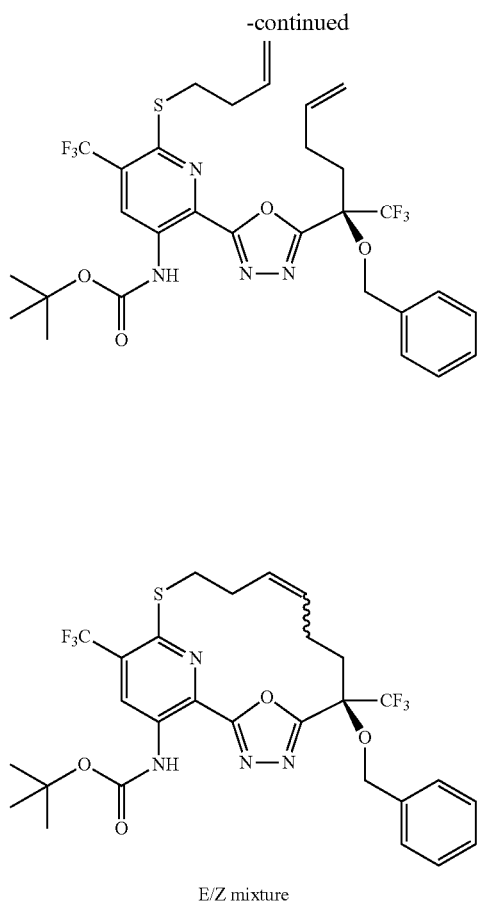

313
-continued

E/Z mixture

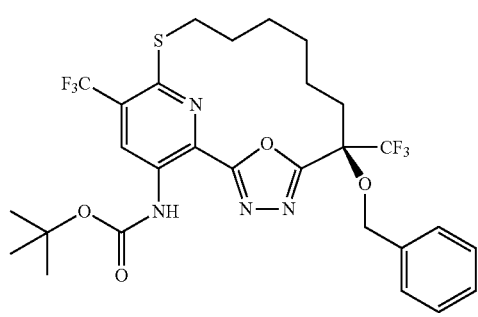

Step 3

Step 4

Step 5

A mixture of 1-methyl-4-sulfidosulfonyl-benzene (potassium salt) (2000 mg, 8.836 mmol), and 4-iodobut-1-ene (913 µL, 8.026 mmol) in DMF (20 mL) was stirred at 60° C. for 30 min, then diluted with ether and washed with water (2×) and brine, dried (MgSO$_4$) and evaporated. The residue was purified by silica gel chromatography (0-15% EtOAc in hexanes over 15 min) to provide 1-but-3-enylsulfanylsulfonyl-4-methyl-benzene (1.516 g, 78%). $^1$H NMR (400 MHz, Chloroform-d) δ 7.87-7.78 (m, 2H), 7.35 (d, J=8.0 Hz, 2H), 5.68 (ddt, J=17.0, 10.4, 6.7 Hz, 1H), 5.06-4.98 (m, 2H), 3.05 (t, J=7.3 Hz, 2H), 2.46 (s, 3H), 2.40-2.29 (m, 2H) ppm. ESI-MS m/z calc. 242.04352, Retention time: 0.6 minutes. Final purity was determined by reversed phase UPLC using an Acquity UPLC BEH C$_{18}$ column (30×2.1 mm, 1.7 µm particle) made by Waters (pn: 186002349), and a dual gradient run from 1-99% mobile phase B over 1.0 minutes. Mobile phase A=H$_2$O (0.05% CF$_3$CO$_2$H). Mobile phase B=acetonitrile (0.035% CF$_3$CO$_2$H). Flow rate=1.5 mL/min, injection volume=1.5 µL, and column temperature=60° C.

Step 2: tert-Butyl N-[2-[5-[(1R)-1-benzyloxy-1-(trifluoromethyl)pent-4-enyl]-1,3,4-oxadiazol-2-yl]-6-but-3-enylsulfanyl-5-(trifluoromethyl)-3-pyridyl] carbamate

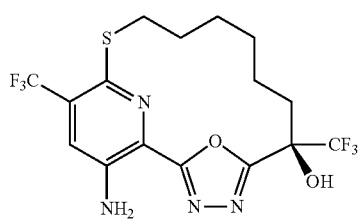

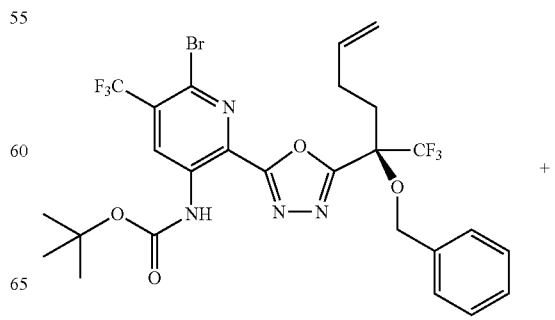

+

-continued

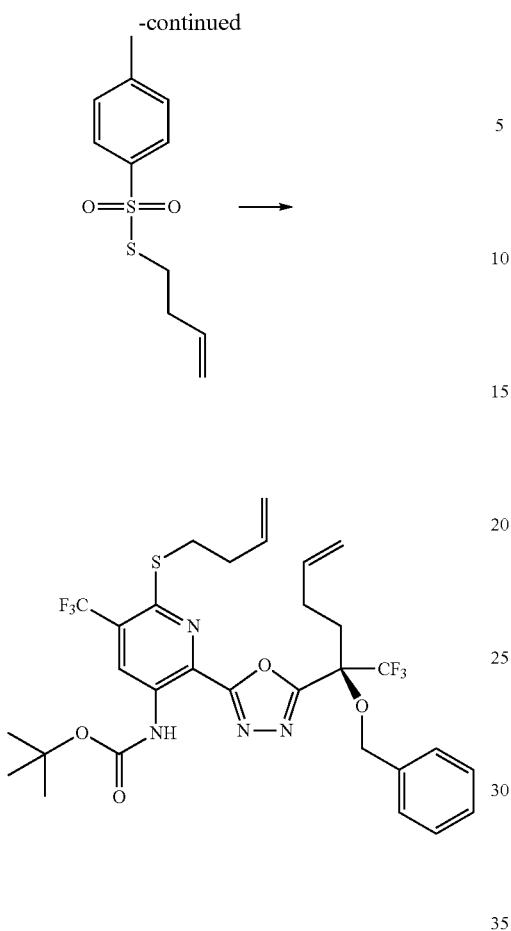

To tert-butyl N-[2-[5-[1-benzyloxy-1-(trifluoromethyl) pent-4-enyl]-1,3,4-oxadiazol-2-yl]-6-bromo-5-(trifluoromethyl)-3-pyridyl]carbamate (57 mg, 0.08750 mmol) in ether (1.15 mL) at −78° C. was added n-BuLi (76 µL of 2.5 M, 0.1900 mmol) as a solution in hexanes and the mixture stirred at −78° C. for 15 min, then a solution of 1-but-3-enylsulfanylsulfonyl-4-methyl-benzene (28 mg, 0.1155 mmol) in ether (285 µL) was added dropwise. The mixture was stirred at −78° C. for 15 min and at 0° C. for 15 min. The mixture was diluted with 1 M NH₄Cl in water and ether then partitioned. The organic layer was separated and washed with 1 M NaHCO₃, dried (MgSO₄) and evaporated. The residue was purified by silica gel chromatography (0-10% EtOAc in hexanes over 15 min) provided tert-butyl N-[2-[5-[(1R)-1-benzyloxy-1-(trifluoromethyl)pent-4-enyl]-1,3,4-oxadiazol-2-yl]-6-but-3-enylsulfanyl-5-(trifluoromethyl)-3-pyridyl]carbamate (33 mg, 57%). $^1$H NMR (400 MHz, Chloroform-d) δ 9.95 (s, 1H), 9.18 (s, 1H), 7.45-7.28 (m, 5H), 5.94-5.65 (m, 2H), 5.13-4.97 (m, 4H), 4.84 (d, J=10.8 Hz, 1H), 4.68 (d, J=10.9 Hz, 1H), 3.36-3.27 (m, 2H), 2.62-2.16 (m, 6H), 1.56 (s, 9H) ppm; $^{19}$F NMR (376 MHz, Chloroform-d) δ −63.55, −72.90 ppm. ESI-MS m/z calc. 658.20483, found 659.3 (M+1)$^+$; Retention time: 2.09 minutes. Final purity was determined by reversed phase UPLC using an Acquity UPLC BEH C$_{18}$ column (50×2.1 mm, 1.7 µm particle) made by Waters (pn: 186002350), and a dual gradient run from 50-99% mobile phase B over 2.9 minutes. Mobile phase A=H₂O (0.05% CF₃CO₂H). Mobile phase B=acetonitrile (0.035% CF₃CO₂H). Flow rate=1.2 mL/min, injection volume=1.5 µL, and column temperature=60° C.

Step 3: tert-Butyl N-[(6R)-6-benzyloxy-6,15-bis(trifluoromethyl)-19-oxa-13-thia-3,4,18-triazatricyclo[12.3.1.1²,⁵]nonadeca-1(18),2,4,9,14,16-hexaen-17-yl]carbamate (E/Z Mixture)

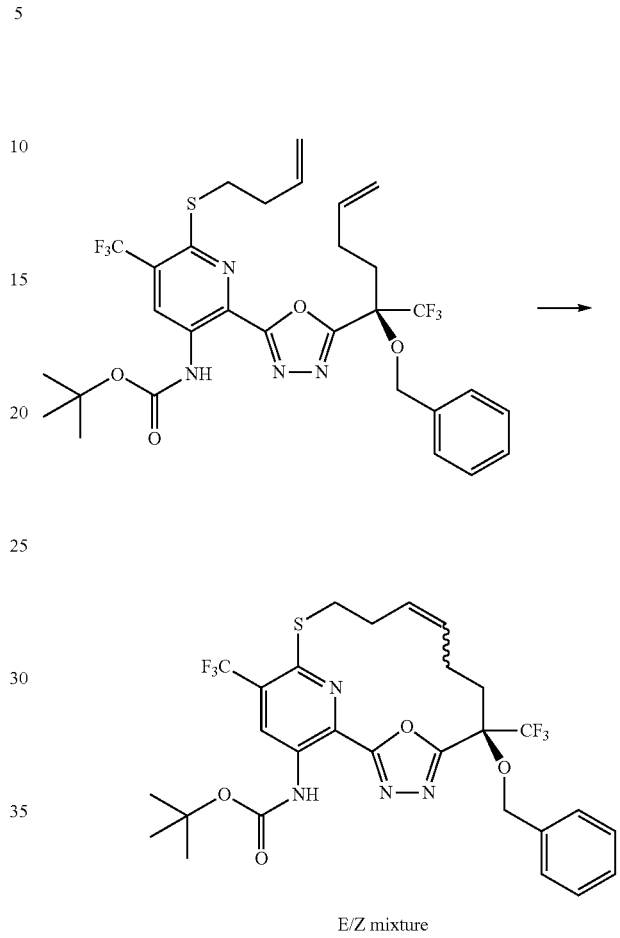

E/Z mixture

A solution of tert-butyl N-[2-[5-[(1R)-1-benzyloxy-1-(trifluoromethyl)pent-4-enyl]-1,3,4-oxadiazol-2-yl]-6-but-3-enylsulfanyl-5-(trifluoromethyl)-3-pyridyl]carbamate (209 mg, 0.3173 mmol) in DCE (15 mL) was dropwise added to a 80° C. preheated solution of benzylidene-[1,3-bis(2,4,6-trimethylphenyl)imidazolidin-2-ylidene]-dichloro-ruthenium;tricyclohexylphosphane (40 mg, 0.04712 mmol) in DCE (15 mL) and the resulting mixture heated at 80° C. for 45 min. Then the solvent was evaporated. The residue was purified by silica gel chromatography (0-5% EtOAc in hexanes over 15 min) to provide tert-butyl N-[(6R)-6-benzyloxy-6,15-bis(trifluoromethyl)-19-oxa-13-thia-3,4,18-triazatricyclo[12.3.1.1²,⁵]nonadeca-1(17),2,4,9,14(18),15-hexaen-17-yl]carbamate (E/Z mixture) (158 mg, 79%). ESI-MS m/z calc. 630.1735, found 631.2 (M+1)$^+$; Retention time: 0.67 minutes. Final purity was determined by reversed phase UPLC using an Acquity UPLC BEH C$_{18}$ column (30×2.1 mm, 1.7 µm particle) made by Waters (pn: 186002349), and a dual gradient run from 50-99% mobile phase B over 1.0 minutes. Mobile phase A=H₂O (0.05% CF₃CO₂H). Mobile phase B=acetonitrile (0.035% CF₃CO₂H). Flow rate=1.5 mL/min, injection volume=1.5 µL, and column temperature=60° C.

317

Step 4: tert-Butyl N-[(6R)-6-benzyloxy-6,15-bis(trifluoromethyl)-19-oxa-13-thia-3,4,18-triazatricyclo[12.3.1.1²,⁵]nonadeca-1(18),2,4,14,16-pentaen-17-yl]carbamate

318

Step 5: (6R)-17-Amino-6,15-bis(trifluoromethyl)-19-oxa-13-thia-3,4,18-triazatricyclo[12.3.1.1²,⁵]nonadeca-1(18),2,4,14,16-pentaen-6-ol, Compound 21

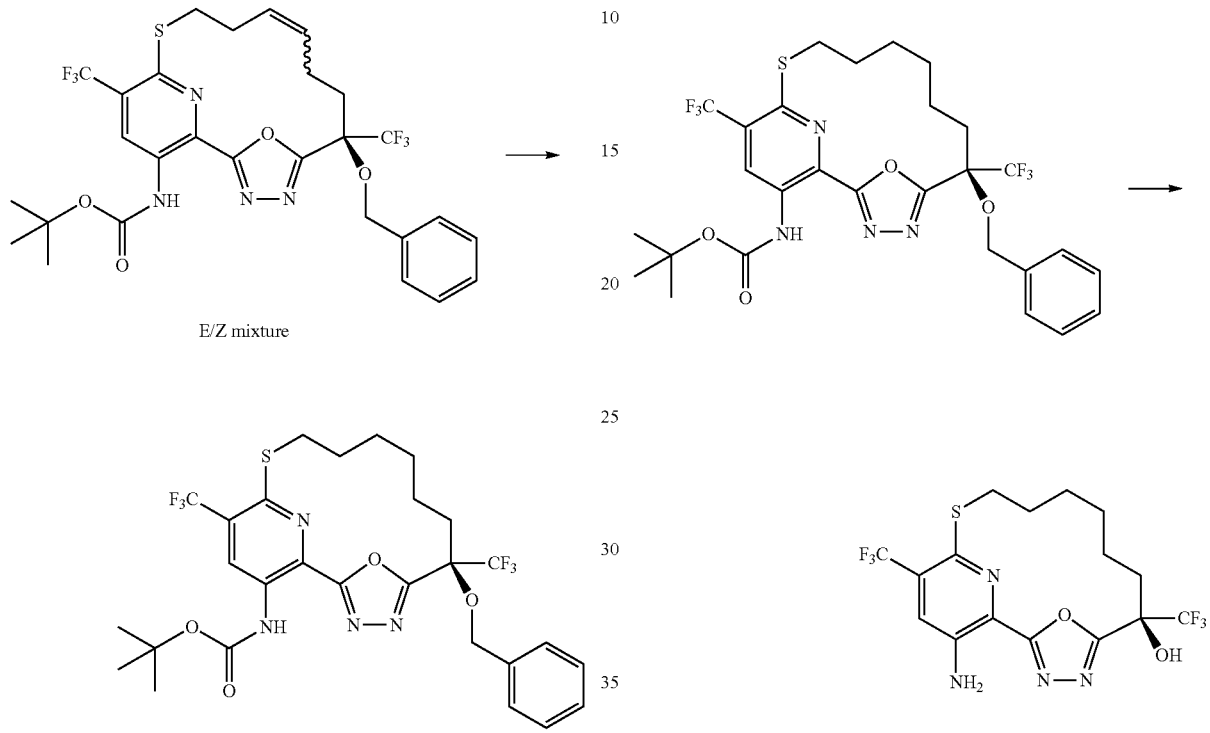

A mixture of tert-butyl N-[(6R)-6-benzyloxy-6,15-bis(trifluoromethyl)-19-oxa-13-thia-3,4,18-triazatricyclo[12.3.1.1²,⁵]nonadeca-1(17),2,4,9,14(18),15-hexaen-17-yl]carbamate (E/Z mixture) (158 mg, 0.2506 mmol) and Pd/C (50 mg of 10% w/w, 0.04698 mmol) in EtOAc (800 μL) and MeOH (800 μL) was stirred at room temperature under 200 psi $H_2$ in a stainless steel pressure vessel for 23 h. Then the mixture was filtered and the filtrate evaporated to provide tert-butyl N-[(6R)-6-benzyloxy-6,15-bis(trifluoromethyl)-19-oxa-13-thia-3,4,18-triazatricyclo[12.3.1.1²,⁵]nonadeca-1(17),2,4,14(18),15-pentaen-17-yl]carbamate (160 mg, 100%). $^1$H NMR (400 MHz, Chloroform-d) δ 9.70 (s, 1H), 9.14 (s, 1H), 7.33-7.22 (m, 5H), 4.86 (d, J=11.2 Hz, 1H), 4.79 (d, J=11.2 Hz, 1H), 3.06 (ddt, J=13.8, 9.5, 4.8 Hz, 2H), 2.44 (dt, J=15.8, 8.5 Hz, 1H), 2.27 (dt, J=14.5, 7.0 Hz, 1H), 2.04 (s, 1H), 1.97-1.84 (m, 1H), 1.78 (dq, J=13.7, 6.7 Hz, 2H), 1.64 (dt, J=12.8, 6.7 Hz, 1H), 1.59-1.51 (m, 13H) ppm; $^{19}$F NMR (376 MHz, Chloroform-d) δ −63.64, −74.38 ppm. ESI-MS m/z calc. 632.1892, found 633.3 (M+1)⁺; Retention time: 0.7 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

To a solution of tert-butyl N-[(6R)-6-benzyloxy-6,15-bis(trifluoromethyl)-19-oxa-13-thia-3,4,18-triazatricyclo[12.3.1.1²,⁵]nonadeca-1(17),2,4,14(18),15-pentaen-17-yl]carbamate (57 mg, 0.090 mmol) in DCM (2 mL) at 0° C. was added $BCl_3$ (2 mL of 1 M, 2.00 mmol) as a solution in DCM and the mixture stirred at room temperature for 22 h. Then the mixture was evaporated, and the residue dissolved in EtOAc (70 mL) and methanol (0.5 mL) and washed with 1 M $NaHCO_3$, brine, dried ($MgSO_4$) and evaporated. The residue was purified by silica gel chromatography (0-25% EtOAc in hexanes over 15 min) to provide (6R)-17-amino-6,15-bis(trifluoromethyl)-19-oxa-13-thia-3,4,18-triazatricyclo[12.3.1.1²,⁵]nonadeca-1(18),2,4,14,16-pentaen-6-ol (61 mg, 62%). $^1$H NMR (400 MHz, Methanol-$d_4$) δ 7.62 (s, 1H), 3.16 (ddd, J=13.7, 12.1, 4.2 Hz, 1H), 2.97 (td, J=13.2, 4.1 Hz, 1H), 2.35 (ddd, J=14.4, 11.2, 3.3 Hz, 1H), 2.20 (dddt, J=19.8, 14.3, 10.6, 5.1 Hz, 2H), 1.83-1.50 (m, 7H) ppm; $^{19}$F NMR (376 MHz, Methanol-$d_4$) δ −64.96, −80.84 ppm. ESI-MS m/z calc. 442.0898, found 443.0 (M+1)⁺; Retention time: 1.61 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=12 mL/min, injection volume=50 μL, and column temperature=25° C.

Example 17: (6R)-16-amino-6,14-bis(trifluoromethyl)-18-oxa-12-thia-3,4,17-triazatricyclo[11.3.1.1²,⁵]octadeca-1(17),2,4,13,15-pentaen-6-ol, Compound 22
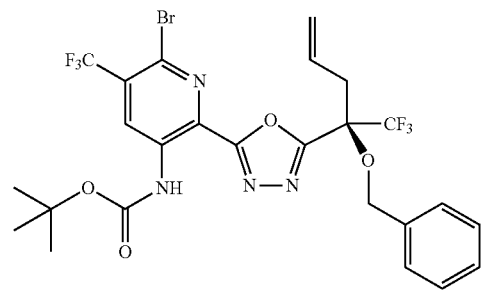
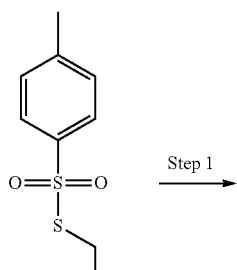
Step 1
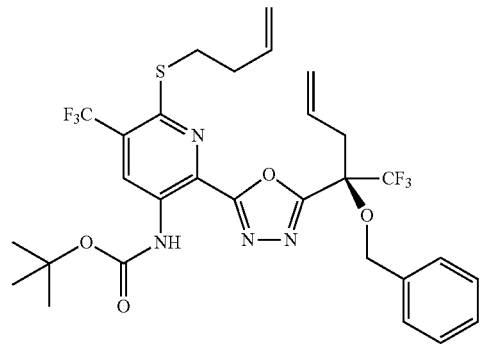
E/Z mixture
-continued
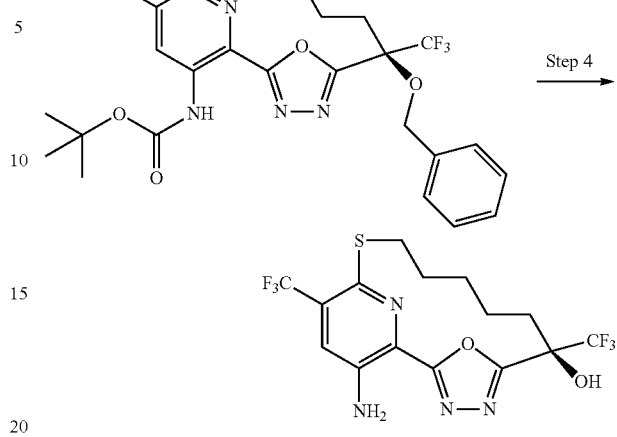
Step 4
Step 1: tert-Butyl N-[2-[5-[(1R)-1-benzyloxy-1-(trifluoromethyl)but-3-enyl]-1,3,4-oxadiazol-2-yl]-6-but-3-enylsulfanyl-5-(trifluoromethyl)-3-pyridyl]carbamate
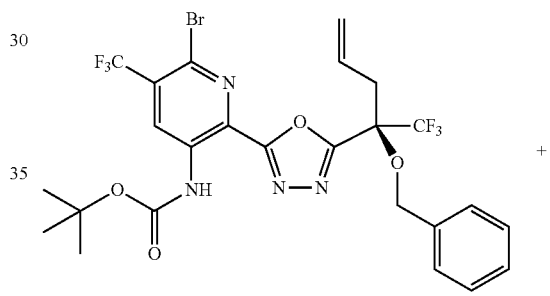
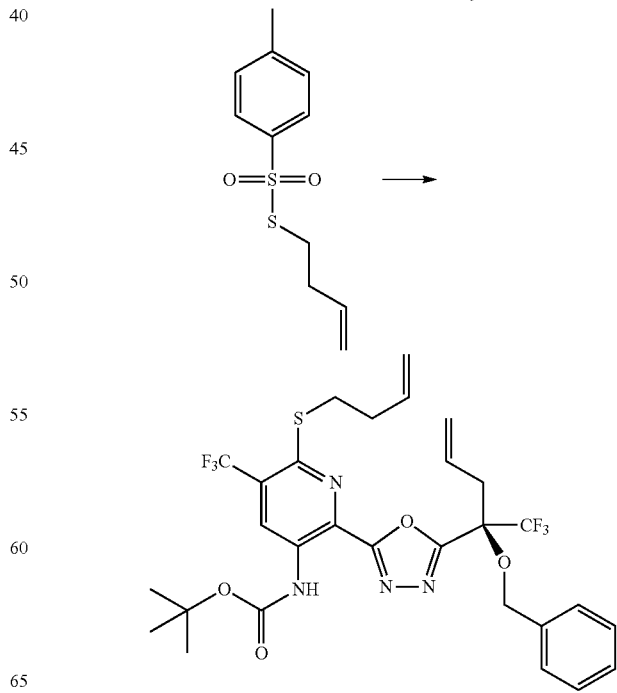
Step 3
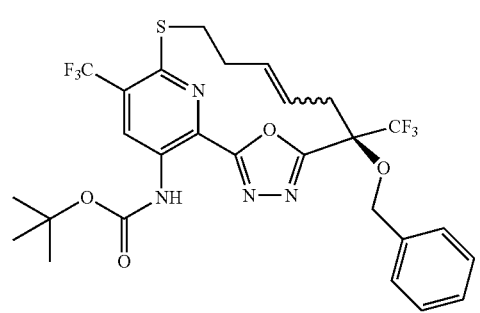

To tert-butyl N-[2-[5-[(1R)-1-benzyloxy-1-(trifluoromethyl)but-3-enyl]-1,3,4-oxadiazol-2-yl]-6-bromo-5-(trifluoromethyl)-3-pyridyl]carbamate (96 mg, 0.1506 mmol) in ether (1.8 mL) at −78° C. was added n-BuLi (130 µL, of 2.5 M, 0.3250 mmol) as a solution in hexanes, then a solution of 1-but-3-enylsulfanylsulfonyl-4-methyl-benzene (48 mg, 0.1981 mmol) in ether (500 µL) was added dropwise. The mixture was stirred at −78° C. for 15 min and at 0° C. for 15 min. The mixture was diluted with 1 M NH$_4$Cl in water and ether then partitioned. The organic layer was separated and washed with 1 M NaHCO$_3$, dried (MgSO$_4$) and evaporated. The residue was purified by silica gel chromatography (0-5% EtOAc in hexanes over 15 min) to provide tert-butyl N-[2-[5-[(1R)-1-benzyloxy-1-(trifluoromethyl)but-3-enyl]-1,3,4-oxadiazol-2-yl]-6-but-3-enylsulfanyl-5-(trifluoromethyl)-3-pyridyl]carbamate (42 mg, 43%). $^1$H NMR (400 MHz, Chloroform-d) δ 9.94 (s, 1H), 9.17 (s, 1H), 7.40-7.28 (m, 5H), 6.09-5.76 (m, 2H), 5.25 (dd, J=17.0, 1.5 Hz, 1H), 5.22-5.18 (m, 1H), 5.07 (dd, J=17.2, 1.7 Hz, 1H), 5.01 (dd, J=10.2, 1.6 Hz, 1H), 4.83 (d, J=10.9 Hz, 1H), 4.68 (d, J=10.8 Hz, 1H), 3.31 (td, J=7.1, 2.8 Hz, 2H), 3.21 (t, J=6.4 Hz, 2H), 2.48 (q, J=7.0 Hz, 2H), 1.56 (s, 9H) ppm; $^{19}$F NMR (376 MHz, Chloroform-d) δ −63.56, −73.16 ppm. ESI-MS m/z calc. 644.1892, found 645.2 (M+1)$^+$; Retention time: 0.7 minutes. Final purity was determined by reversed phase UPLC using an Acquity UPLC BEH C$_{18}$ column (30×2.1 mm, 1.7 µm particle) made by Waters (pn: 186002349), and a dual gradient run from 50-99% mobile phase B over 1.0 minutes. Mobile phase A=H$_2$O (0.05% CF$_3$CO$_2$H). Mobile phase B=acetonitrile (0.035% CF$_3$CO$_2$H). Flow rate=1.5 mL/min, injection volume=1.5 µL, and column temperature=60° C.

Step 2: tert-Butyl N-[(6R)-6-benzyloxy-6,14-bis(trifluoromethyl)-18-oxa-12-thia-3,4,17-triazatricyclo[11.3.1.1$^{2,5}$]octadeca-1(17),2,4,8,13,15-hexaen-16-yl]carbamate (E/Z Mixture)

A solution of tert-butyl N-[2-[5-[(1R)-1-benzyloxy-1-(trifluoromethyl)but-3-enyl]-1,3,4-oxadiazol-2-yl]-6-but-3-enylsulfanyl-5-(trifluoromethyl)-3-pyridyl]carbamate (140 mg, 0.2172 mmol) in toluene (10 mL) was added dropwise to a 120° C. preheated solution of 1,3-bis(o-tolyl)-4,5-dihydroimidazole;dichloro-[(2-isopropoxyphenyl)methylene]ruthenium (19 mg, 0.03330 mmol) in toluene (10 mL) and the mixture heated at 120° C. for 45 min. Then more 1,3-bis(o-tolyl)-4,5-dihydroimidazole;dichloro-[(2-isopropoxyphenyl)methylene]ruthenium (12 mg, 0.02103 mmol) was added and heating continued at 120° C. for 55 min and this process was carried out one more time precisely. Then more 1,3-bis(o-tolyl)-4,5-dihydroimidazole;dichloro-[(2-isopropoxyphenyl)methylene]ruthenium (2.7 mg, 0.004733 mmol) was added and heating at 120° C. continued for 60 min and this process was carried out two more times precisely. The solvent was evaporated and the residue purified by silica gel chromatography (12 g SiO$_2$, 0-30% of a solution of 10% EtOAc in hexanes from 100% hexanes over 20 min) to provide tert-butyl N-[(6R)-6-benzyloxy-6,14-bis(trifluoromethyl)-18-oxa-12-thia-3,4,17-triazatricyclo[11.3.1.1$^{2,5}$]octadeca-1(16),2,4,8,13(17),14-hexaen-16-yl]carbamate (E/Z mixture) (20 mg, 13%). ESI-MS m/z calc. 616.1579, found 617.1 (M+1)$^+$; Retention time: 0.62 minutes. Final purity was determined by reversed phase UPLC using an Acquity UPLC BEH C$_{18}$ column (30×2.1 mm, 1.7 µm particle) made by Waters (pn: 186002349), and a dual gradient run from 50-99% mobile phase B over 1.0 minutes. Mobile phase A=H$_2$O (0.05% CF$_3$CO$_2$H). Mobile phase B=acetonitrile (0.035% CF$_3$CO$_2$H). Flow rate=1.5 mL/min, injection volume=1.5 µL, and column temperature=60° C.

Step 3: tert-Butyl N-[(6R)-6-benzyloxy-6,14-bis(trifluoromethyl)-18-oxa-12-thia-3,4,17-triazatricyclo[11.3.1.1$^{2,5}$]octadeca-1(17),2,4,13,15-pentaen-16-yl]carbamate

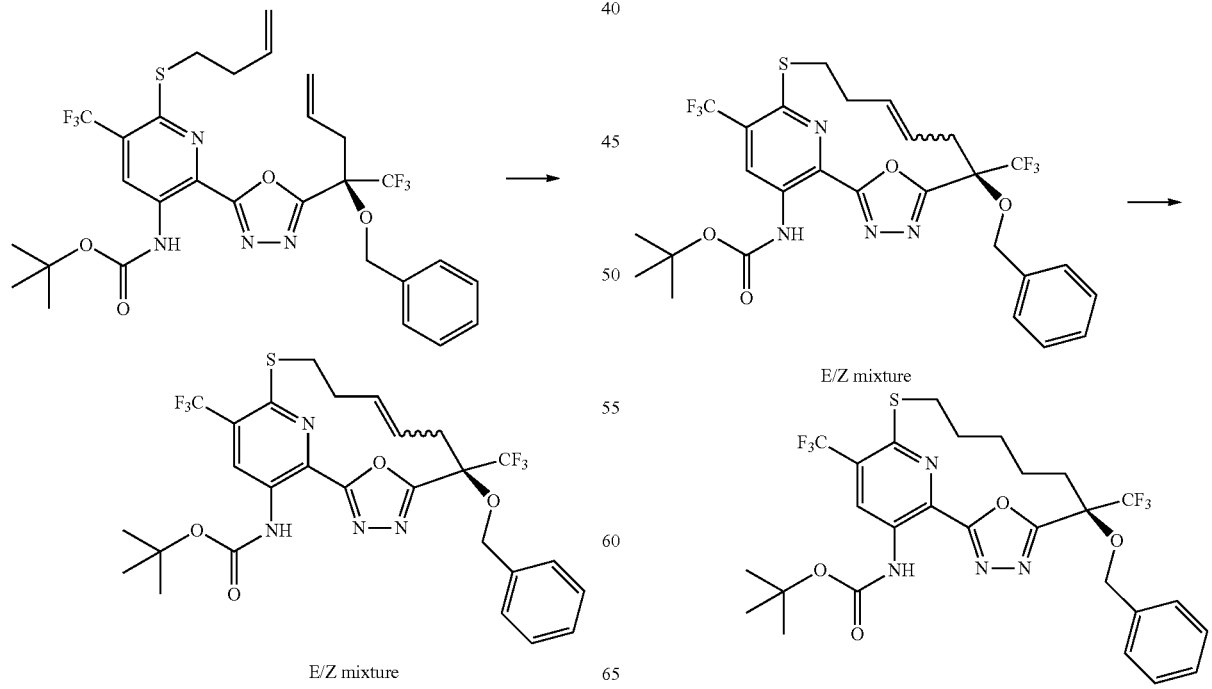

E/Z mixture

E/Z mixture

A mixture of tert-butyl N-[(6R)-6-benzyloxy-6,14-bis(trifluoromethyl)-18-oxa-12-thia-3,4,17-triazatricyclo[11.3.1.1²,⁵]octadeca-1(16),2,4,8,13(17),14-hexaen-16-yl]carbamate (E/Z mixture) (24 mg, 0.03309 mmol), and palladium on carbon (11 mg of 10% w/w, 0.01034 mmol) in EtOAc (300 µL) and MeOH (300 µL) was stirred at room temperature under 200 psi H₂ for 40 h, filtered and solvent evaporated. The residue was purified by silica gel chromatography (0-30% of a solution of 10% EtOAc in hexanes from 100% hexanes over 18 min) to provide tert-butyl N-[(6R)-6-benzyloxy-6,14-bis(trifluoromethyl)-18-oxa-12-thia-3,4,17-triazatricyclo[11.3.1.1²,⁵]octadeca-1(16),2,4,13(17),14-pentaen-16-yl]carbamate (16 mg, 78%). ESI-MS m/z calc. 618.1735, found 619.2 (M+1)⁺; Retention time: 0.64 minutes. Final purity was determined by reversed phase UPLC using an Acquity UPLC BEH $C_{18}$ column (30×2.1 mm, 1.7 µm particle) made by Waters (pn: 186002349), and a dual gradient run from 50-99% mobile phase B over 1.0 minutes. Mobile phase A=H₂O (0.05% $CF_3CO_2H$). Mobile phase B=acetonitrile (0.035% $CF_3CO_2H$). Flow rate=1.5 mL/min, injection volume=1.5 µL, and column temperature=60° C.

Step 4: (6R)-16-Amino-6,14-bis(trifluoromethyl)-18-oxa-12-thia-3,4,17-triazatricyclo[11.3.1.1²,⁵]octadeca-1(17),2,4,13,15-pentaen-6-ol, Compound 22

To a solution of tert-butyl N-[(6R)-6-benzyloxy-6,14-bis(trifluoromethyl)-18-oxa-12-thia-3,4,17-triazatricyclo[11.3.1.1²,⁵]octadeca-1(16),2,4,13(17),14-pentaen-16-yl]carbamate (16 mg, 0.02587 mmol) in DCM (160 µL) at 0° C. was added BCl₃ (520 µL of 1 M, 0.5200 mmol) as a solution in DCM and the mixture stirred at room temperature for 24 h. Then the mixture was evaporated and the residue dissolved in EtOAc (20 mL) and methanol (2 mL) and washed with 1 M NaHCO₃, brine, dried (MgSO₄) and evaporated. The residue was purified by silica gel chromatography (5-25% EtOAc in hexanes over 15 min) to provide (6R)-16-amino-6,14-bis(trifluoromethyl)-18-oxa-12-thia-3,4,17-triazatricyclo[11.3.1.1²,⁵]octadeca-1(17),2,4,13,15-pentaen-6-ol (4.5 mg, 41%). ¹H NMR (400 MHz, Methanol-d₄) δ 7.47 (s, 1H), 3.05 (td, J=13.1, 4.3 Hz, 1H), 2.87 (td, J=13.6, 13.1, 4.5 Hz, 1H), 2.25-2.00 (m, 3H), 1.91-1.84 (m, 1H), 1.79 (dq, J=10.9, 6.3, 5.9 Hz, 2H), 1.50 (p, J=5.5 Hz, 2H) ppm; ¹⁹F NMR (376 MHz, Methanol-d₄) δ -64.87, -80.28 ppm. ESI-MS m/z calc. 428.07416, found 429.0 (M+1)⁺; Retention time: 1.49 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=H₂O (0.05% $CF_3CO_2H$). Mobile phase B=acetonitrile (0.035% $CF_3CO_2H$). Flow rate=12 mL/min, injection volume=50 µL, and column temperature=25° C.

Example 18: Preparation of (6R)-16-amino-12-oxido-6,14-bis(trifluoromethyl)-18-oxa-12-thionia-3,4,17-triazatricyclo[11.3.1.1²,⁵]octadeca-1(17),2,4,13,15-pentaen-6-ol (enantiomer 1), Compound 23, and (6R)-16-amino-12-oxido-6,14-bis(trifluoromethyl)-18-oxa-12-thionia-3,4,17-triazatricyclo[11.3.1.1²,⁵]octadeca-1(17),2,4,13,15-pentaen-6-ol (enantiomer 2), Compound 24

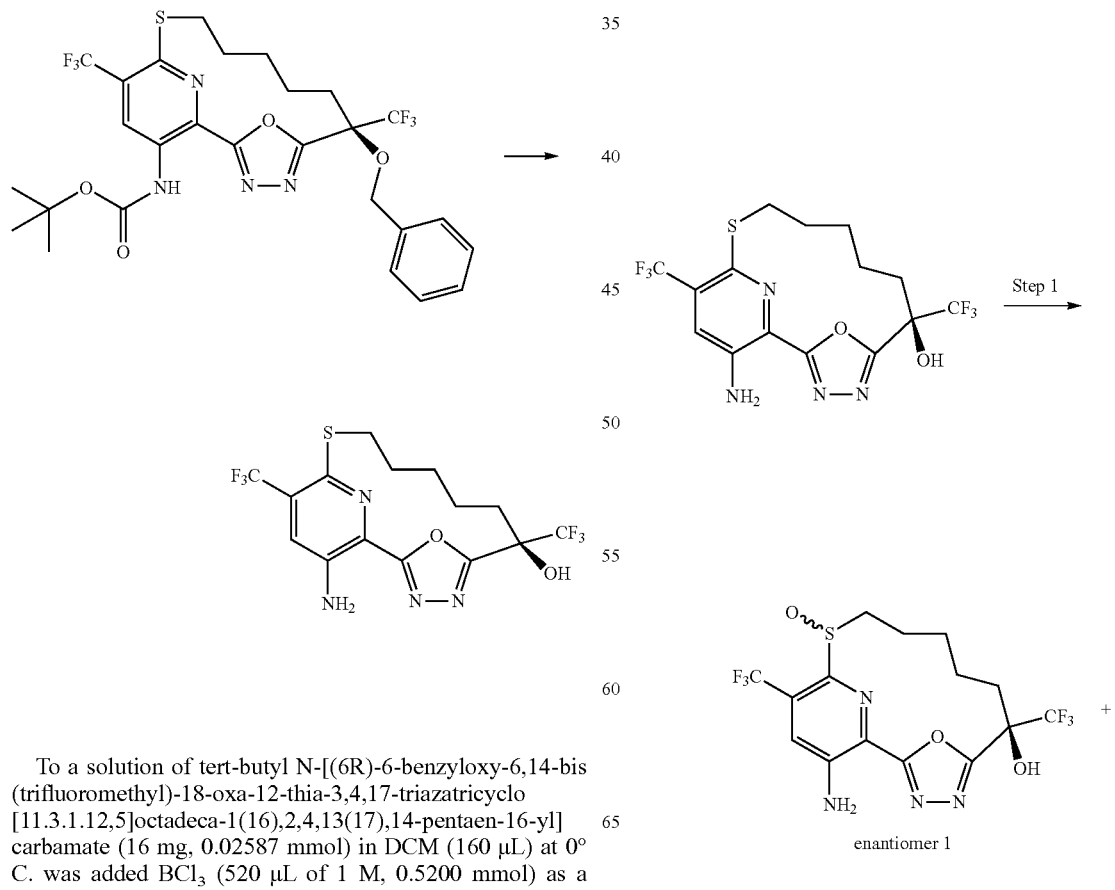

enantiomer 1

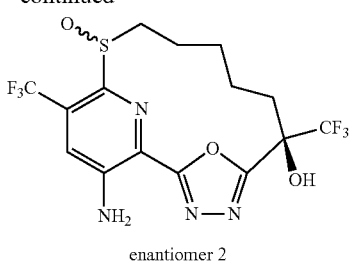

enantiomer 2

Step 1: (6R)-16-Amino-12-oxido-6,14-bis(trifluoromethyl)-18-oxa-12-thionia-3,4,17-triazatricyclo[11.3.1.12,5]octadeca-1(17),2,4,13,15-pentaen-6-ol (enantiomer 1), Compound 23, and (6R)-16-amino-12-oxido-6,14-bis(trifluoromethyl)-18-oxa-12-thionia-3,4,17-triazatricyclo[11.3.1.12,5]octadeca-1(17),2,4,13,15-pentaen-6-ol (enantiomer 2), Compound 24

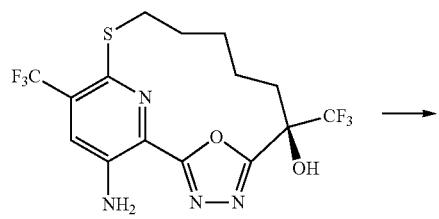

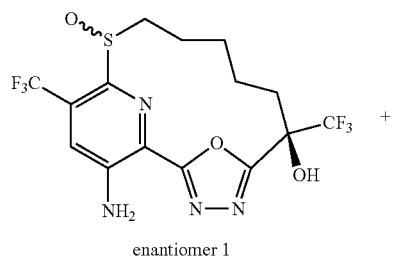

enantiomer 1

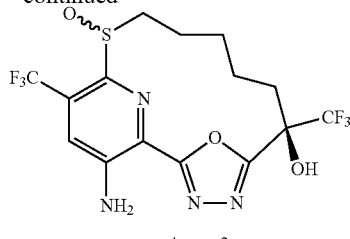

enantiomer 2

To a solution of (6R)-16-amino-6,14-bis(trifluoromethyl)-18-oxa-12-thia-3,4,17-triazatricyclo[11.3.1.12,5]octadeca-1(17),2,4,13,15-pentaen-6-ol (3.7 mg, 0.0086 mmol) in EtOAc (222.0 µL) cooled by ice bath was added 3-chlorobenzenecarboperoxoic acid (44 µL of 0.11 M, 0.0048 mmol) as a solution in EtOAc and the mixture stirred at 0° C. for 15 min. Then 3-chlorobenzenecarboperoxoic acid (20 µL of 0.11 M, 0.0022 mmol) as a solution in EtOAc was added and the mixture stirred at 0° C. for 15 additional minutes. Then more 3-chlorobenzenecarboperoxoic acid (8 µL of 0.11 M, 0.00088 mmol) as a solution in EtOAc was added with the mixture stirred at 0° C. for 15 min. Then the mixture was diluted with EtOAc (30 mL) and MeOH (1 mL) and washed with 5% $Na_2S_2O_3$, 1 M $NaHCO_3$, dried ($MgSO_4$) and evaporated. The mixture residue was dissolved into 1:1 MeOH/acetonitrile and subjected to preparative HPLC eluting with 30-99% acetonitrile vs 5 mM HCl in water at 50 mL/min over 14 min through a Luna 5 µM $C_{18}$ 100 Å 75×30 mm column to provide first eluting isomer as a white solid (6R)-16-amino-12-oxido-6,14-bis(trifluoromethyl)-18-oxa-12-thionia-3,4,17-triazatricyclo[11.3.1.12,5]octadeca-1(17),2,4,13,15-pentaen-6-ol (enantiomer 1) (2 mg, 52%). $^1$H NMR (400 MHz, Methanol-$d_4$) δ 7.77 (s, 1H), 3.83 (ddd, J=13.1, 11.3, 5.5 Hz, 1H), 3.06 (ddd, J=13.2, 11.1, 3.8 Hz, 1H), 2.38 (dt, J=15.3, 7.8 Hz, 2H), 2.14-2.04 (m, 1H), 2.01-1.87 (m, 3H), 1.85-1.67 (m, 2H) ppm; $^{19}$F NMR (376 MHz, Methanol-$d_4$) δ −60.67, −80.30 ppm. ESI-MS m/z calc. 444.0691, found 445.0 (M+1)$^+$; Retention time: 1.0 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=12 mL/min, injection volume=50 µL, and column temperature=25° C.

Continued elution provided as a white solid (6R)-16-amino-12-oxido-6,14-bis(trifluoromethyl)-18-oxa-12-thionia-3,4,17-triazatricyclo[11.3.1.12,5]octadeca-1(17),2,4,13,15-pentaen-6-ol (enantiomer 2) (1.6 mg, 42%). $^1$H NMR (400 MHz, Methanol-$d_4$) δ 7.76 (s, 1H), 3.64 (td, J=12.5, 5.0 Hz, 1H), 3.22 (dd, J=13.1, 3.8 Hz, 1H), 2.43 (dp, J=9.1, 6.4, 4.3 Hz, 1H), 2.28 (t, J=7.2 Hz, 2H), 2.09-1.87 (m, 2H), 1.75 (ddt, J=34.2, 7.8, 3.7 Hz, 3H) ppm; $^{19}$F NMR (376 MHz, Methanol-$d_4$) δ −60.71, −80.20 ppm. ESI-MS m/z calc. 444.0691, found 445.0 (M+1)$^+$; Retention time: 0.81 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=12 mL/min, injection volume=50 µL, and column temperature=25° C.

Example 19: Preparation of (6R,12R)-17-amino-6-hydroxy-12-methyl-6,15-bis(trifluoromethyl)-13,19-dioxa-3,4,18-triazatricyclo[12.3.1.12,5]nonadeca-1(18),2,4,14,16-pentaen-10-one (hydrochloride salt), Compound 25, and (6R,12R)-17-amino-6-hydroxy-12-methyl-6,15-bis(trifluoromethyl)-13,19-dioxa-3,4,18-triazatricyclo[12.3.1.12,5]nonadeca-1(18),2,4,14,16-pentaen-9-one (hydrochloride salt), Compound 26
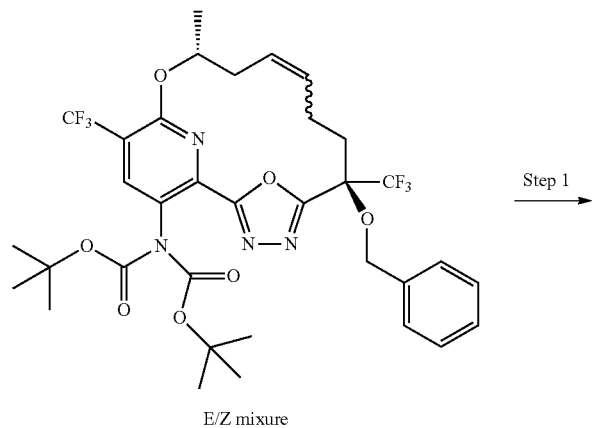
E/Z mixture
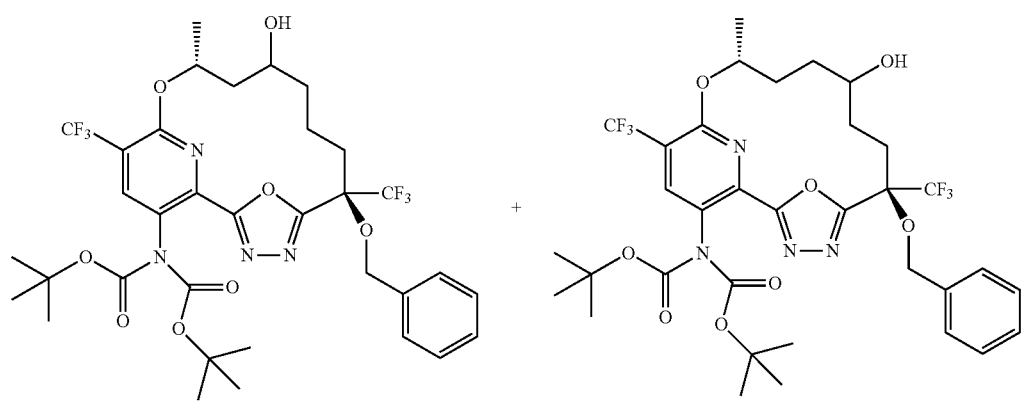
mixture of regioisomeric diastereomers
Step 2

329 330

-continued

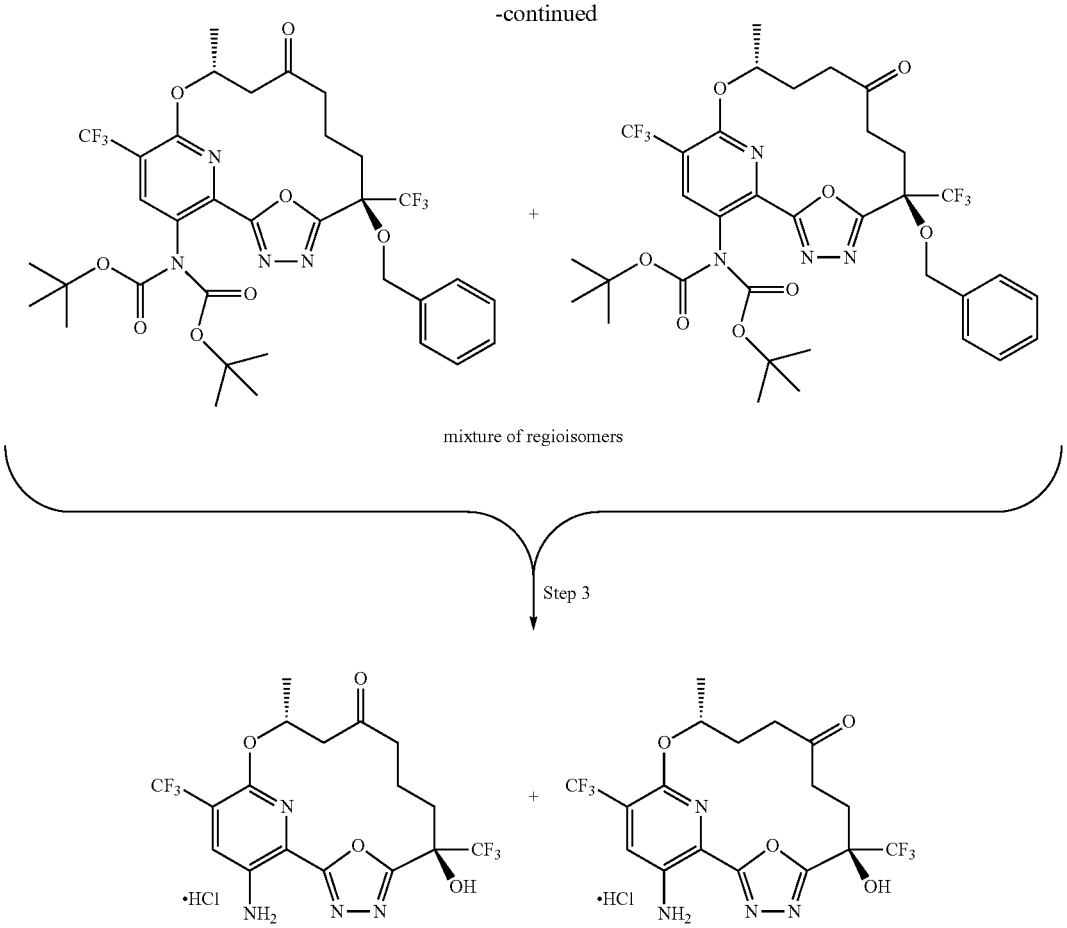

mixture of regioisomers

Step 3

Step 1: tert-Butyl N-[(6R,12R)-6-benzyloxy-9-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]-N-tert-butoxycarbonyl-carbamate and tert-butyl N-[(6R,12R)-6-benzyloxy-10-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]-N-tert-butoxycarbonyl-carbamate (mixture of regioisomeric diastereomers)

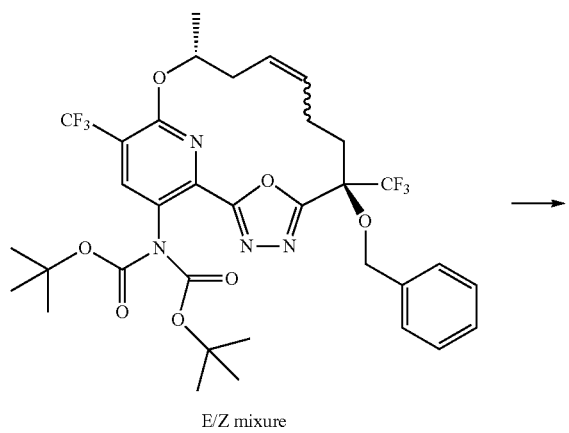

E/Z mixure

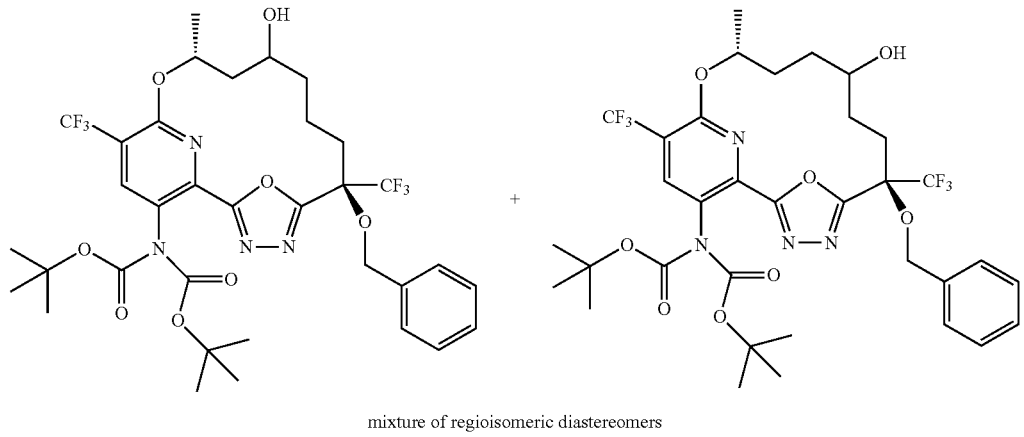

mixture of regioisomeric diastereomers

To a solution of tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (190 mg, 0.2607 mmol) in THF (3 mL) at 0° C. was added dropwise borane dimethylsulfide complex (200 µL of 2 M, 0.4000 mmol) and let the resulting mixture stir for 15 min at 0° C. Allowed the reaction warm to room temperature and stirred for 1 h. Added additional borane dimethylsulfide complex (200 µL of 2 M, 0.4000 mmol) and stirred at room temperature for an additional 30 minutes. Cooled the reaction to 0° C. before quenching with aqueous NaOH (1.5 mL of 1 M, 1.500 mmol) followed by the addition of hydrogen peroxide (600 µL of 30% w/v, 5.292 mmol). Allowed the resulting mixture stir for 30 min at room temperature then the mixture was extracted with ethyl acetate (2×80 mL). The organic layers were combined, washed with brine (80 mL), dried over sodium sulfate, filtered and concentrated. The crude residue was then purified by silica gel chromatography (80 gram column) using a gradient from 100% hexanes to 100% ethyl acetate to collect as a 1:1 inseparable mixture of regioisomeric diastereomers, tert-butyl N-[(6R,12R)-6-benzyloxy-9-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate and tert-butyl N-[(6R,12R)-6-benzyloxy-10-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (mixture of regioisomeric diastereomers) (128 mg, 66%). ESI-MS m/z calc. 746.275, found 747.4 (M+1)$^+$; Retention time: 1.89 minutes. Final purity was determined by reversed phase UPLC using an Acquity UPLC BEH $C_{18}$ column (50×2.1 mm, 1.7 µm particle) made by Waters (pn: 186002350), and a dual gradient run from 30-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 and column temperature=60° C.

Step 2: tert-Butyl N-[(6R,12R)-6-benzyloxy-12-methyl-9-oxo-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate and tert-butyl N-[(6R,12R)-6-benzyloxy-12-methyl-10-oxo-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate

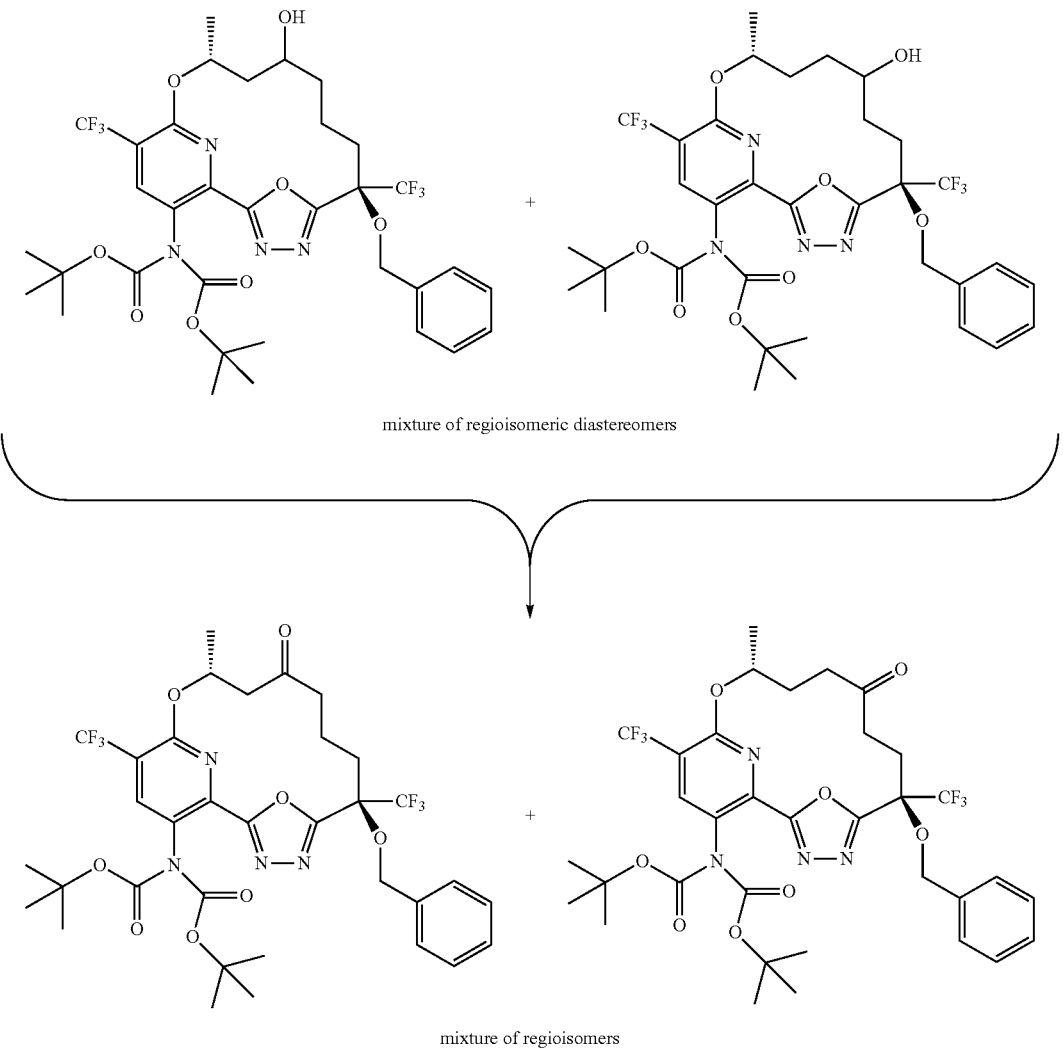

To a solution of a 1:1 mixture of regioisomeric diastereomers, tert-butyl N-[(6R,12R)-6-benzyloxy-9-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate and tert-butyl N-[(6R,12R)-6-benzyloxy-10-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (mixture of regioisomeric diastereomers) (106 mg, 0.142 mmol) in dichloromethane (2 mL) was added Dess-Martin Periodinane (92 mg, 0.2169 mmol) at 0° C. and the mixture was stirred for 1 h allowing the reaction to warm up to room temperature. The reaction was diluted with ether (10 mL) and filtered through Celite. The filtrate was washed with saturated aqueous sodium bicarbonate and with brine, dried over sodium sulfate, filtered and concentrated. The resulting material was dissolved in 2 mL of DMSO, filtered and the filtrate was purified by reverse phase HPLC using a gradient from 50% to 99% acetonitrile in water (+5 mM HCl) giving as an inseparable ~1:1 mixture of regioisomers, tert-butyl N-[(6R,12R)-6-benzyloxy-12-methyl-9-oxo-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate and tert-butyl N-[(6R,12R)-6-benzyloxy-12-methyl-10-oxo-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (44 mg, 42%). ESI-MS m/z calc. 744.2594, found 645.2 (M-Boc+1)⁺; Retention time: 2.05 minutes. Final purity was determined by reversed phase UPLC using an Acquity UPLC BEH $C_{18}$ column (50×2.1 mm, 1.7 μm particle) made by Waters (pn: 186002350), and a dual gradient run from 30-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 3: (6R,12R)-17-Amino-6-hydroxy-12-methyl-6,15-bis(trifluoromethyl)-13,19-dioxa-3,4,18-triazatricyclo[12.3.1.1².⁵]nonadeca-1(18),2,4,14,16-pentaen-10-one, Compound 25, and (6R,12R)-17-amino-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-9-one, Compound 26 subjected to vacuum and backfilled with nitrogen gas three times then subjected to vacuum. The flask was filled with hydrogen gas then stirred the mixture for 15 h. The vessel was subjected to vacuum and backfilled with nitrogen gas three times then diluted with ethyl acetate and filtered over Celite. The filtrate was concentrated and dried under reduced pressure. The resulting residue was dissolved in TFA (1.5 mL, 19.47 mmol) and dichloromethane (4.5 mL) (pre-made solution of 1:3 TFA/dichloromethane) and the reaction was stirred at room temperature for about 1 h. The solvents were removed by rotary evaporation and the residue was dissolved in DMSO (1 mL) then purified by reverse phase HPLC using a gradient from 30% to 99% acetonitrile in water (+5 mM HCl) to afford the first eluting regioisomer (based on H NMR AB pattern of —O CH (CH3)—CH2—CO) as (6R,12R)-17-amino-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-10-one (Hydrochloride salt) (2.3 mg, 41%). ¹H NMR (400 MHz,

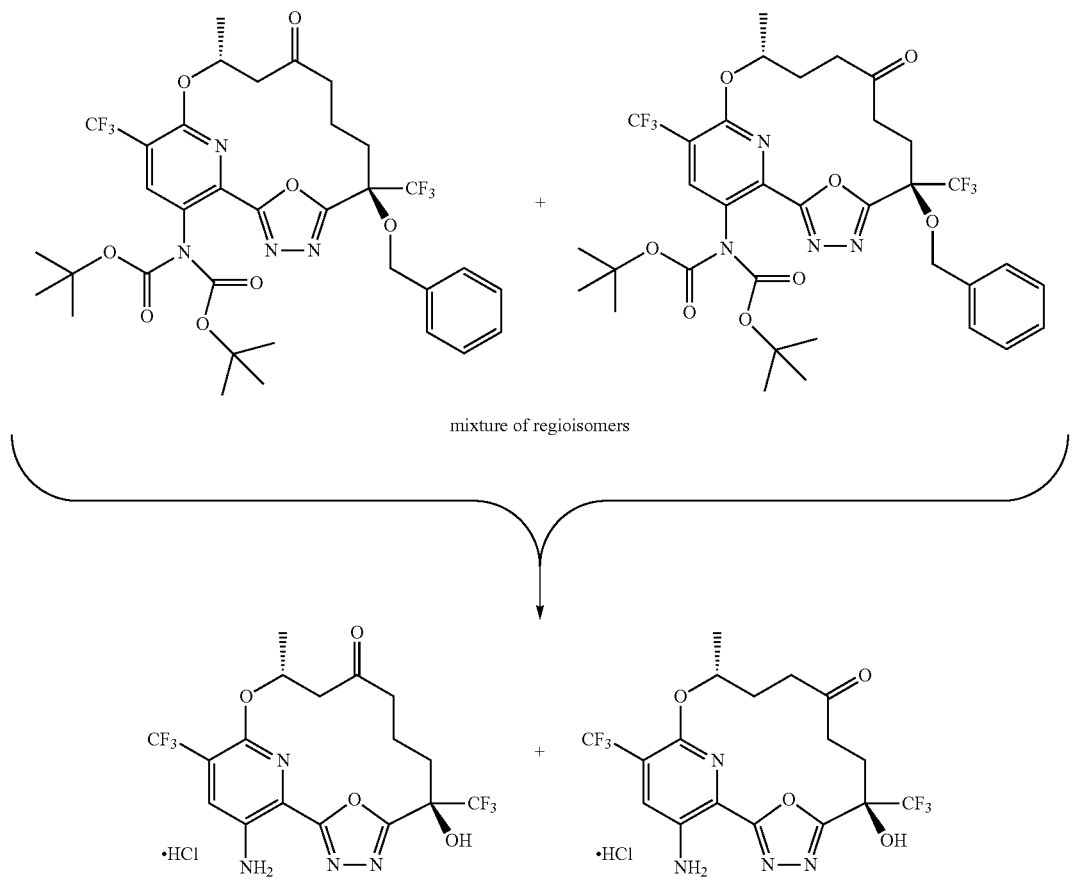

mixture of regioisomers

To a solution of a 1:1 mixture of regioisomers, tert-butyl N-[(6R,12R)-6-benzyloxy-12-methyl-9-oxo-6,15-bis(trifluoromethyl)-13,19-dioxa-3,4,18-triazatricyclo[12.3.1.1²,⁵]nonadeca-1(18),2,4,14,16-pentaen-17-yl]-N-tert-butoxycarbonyl-carbamate and tert-butyl N-[(6R,12R)-6-benzyloxy-12-methyl-10-oxo-6,15-bis(trifluoromethyl)-13,19-dioxa-3,4,18-triazatricyclo[12.3.1.1²,⁵]nonadeca-1(18),2,4,14,16-pentaen-17-yl]-N-tert-butoxycarbonyl-carbamate (34 mg, 0.0457 mmol) in ethanol (5 mL) was added Pd/C (116 mg of 10% w/w, 0.1090 mmol) in a flask equipped with a hydrogen balloon using a 3-way adaptor. The material was Chloroform-d) δ 7.61 (s, 1H), 6.92 (dq, J=16.0, 6.9 Hz, 1H), 6.13 (dq, J=15.8, 1.7 Hz, 1H), 2.67 (t, J=6.7 Hz, 2H), 2.46 (ddd, J=15.1, 10.2, 5.7 Hz, 1H), 2.13 (ddd, J=14.7, 10.3, 5.0 Hz, 1H), 1.90 (dd, J=6.9, 1.6 Hz, 3H), 1.83 (dd, J=10.4, 4.8 Hz, 2H), 1.71-1.42 (m, 2H) ppm. ESI-MS m/z calc. 454.10757, found 455.1 (M+1)⁺; Retention time: 1.34 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=1.2 mL/min, injection volume=1.5 μL, and column temperature=60° C. and the later eluting regioisomer as (6R,12R)-17-amino-6-hydroxy-12-methyl-6,15-bis(trifluoromethyl)-13,19-dioxa-3,4,18-triazatricyclo[12.3.1.12,5]nonadeca-1(18),2,4,14,16-pentaen-9-one (Hydrochloride salt) (3.0 mg, 54%). $^1$H NMR (400 MHz, Chloroform-d) δ 7.41 (s, 1H), 6.27 (s, 1H), 5.42-5.35 (m, 1H), 2.99 (ddd, J=18.3, 11.2, 2.1 Hz, 1H), 2.89-2.80 (m, 1H), 2.79-2.63 (m, 2H), 2.52 (ddd, J=18.1, 7.2, 2.2 Hz, 1H), 2.35-2.26 (m, 1H), 2.13-2.01 (m, 1H), 1.99-1.89 (m, 1H), 1.42 (d, J=6.4 Hz, 3H) ppm. ESI-MS m/z calc. 454.10757, found 455.0 (M+1)$^+$; Retention time: 1.7 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Example 20: Preparation of 20-amino-6,18-bis(trifluoromethyl)-16,23-dioxa-3,4,21-triazatetracyclo[15.3.1.12,5.111,15]tricosa-1(21),2,4,11(22),12,14,17,19-octaen-6-ol (enantiomer 1), Compound 27, 20-amino-6,18-bis(trifluoromethyl)-16,23-dioxa-3,4,21-triazatetracyclo[15.3.1.12,5.111,15]tricosa-1(21),2,4,11(22),12,14,17,19-octaen-6-ol (enantiomer 2), Compound 28, 19-amino-9-methyl-6,17-bis(trifluoromethyl)-15,22-dioxa-3,4,20-triazatetracyclo[14.3.1.12,5.110,14]docosa-1(20),2,4,10(21),11,13,16,18-octaen-6-ol (diastereomer pair 1), Compound 29, and 19-amino-9-methyl-6,17-bis(trifluoromethyl)-15,22-dioxa-3,4,20-triazatetracyclo[14.3.1.12,5.110,14]docosa-1(20),2,4,10(21),11,13,16,18-octaen-6-ol (diastereomer pair 2), Compound 30

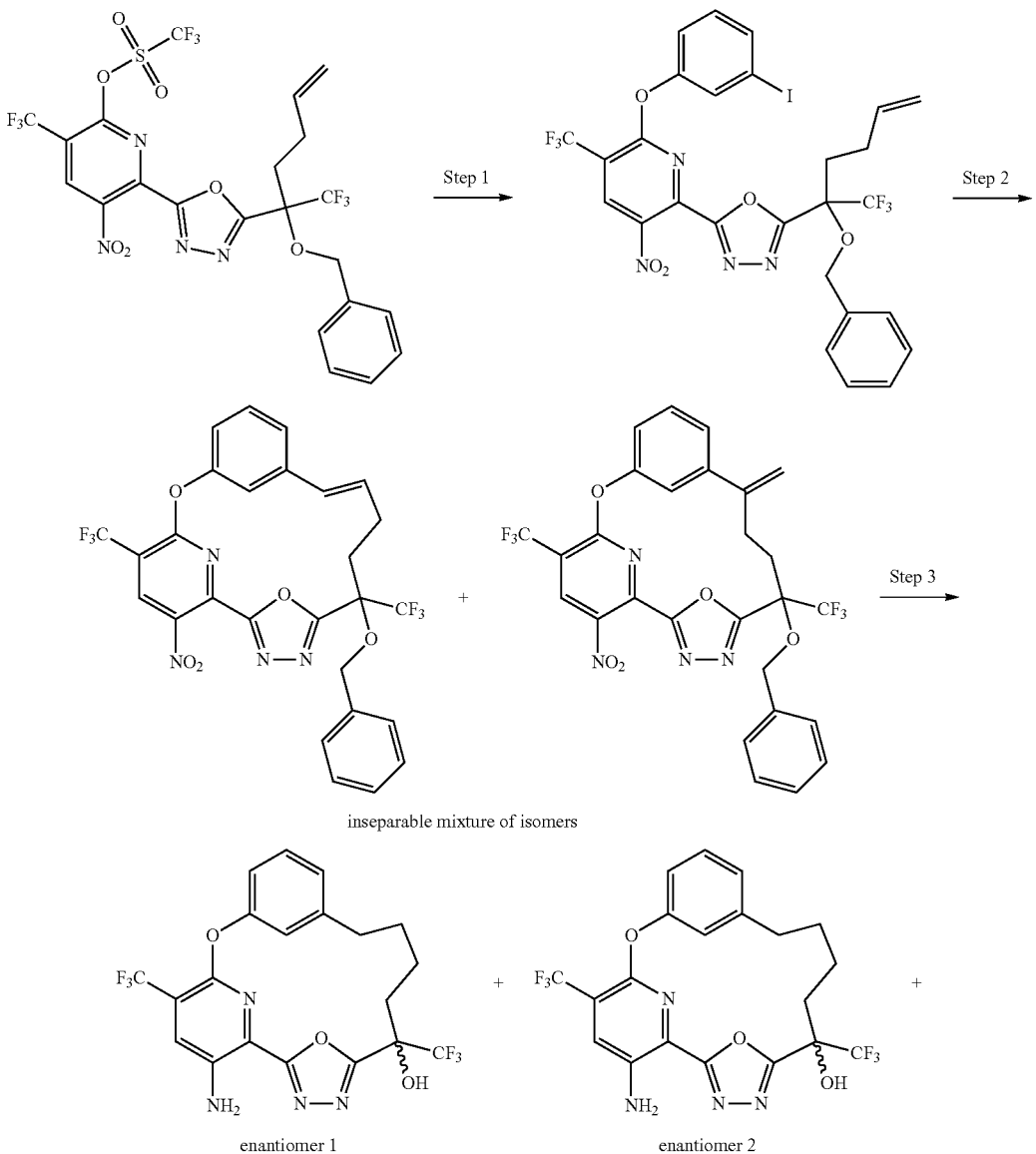

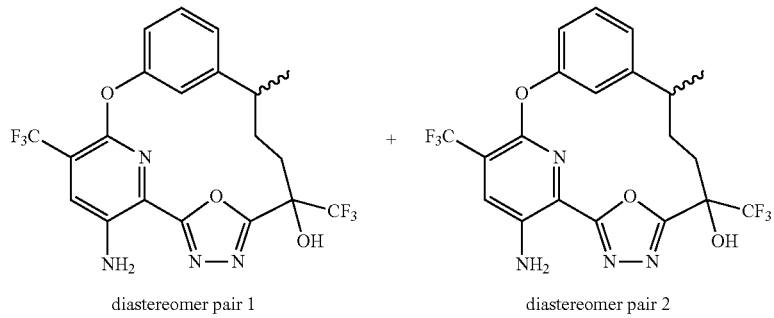

diastereomer pair 1 + diastereomer pair 2

Step 1: 2-[1-Benzyloxy-1-(trifluoromethyl)pent-4-enyl]-5-[6-(3-iodophenoxy)-3-nitro-5-(trifluoromethyl)-2-pyridyl]-1,3,4-oxadiazole

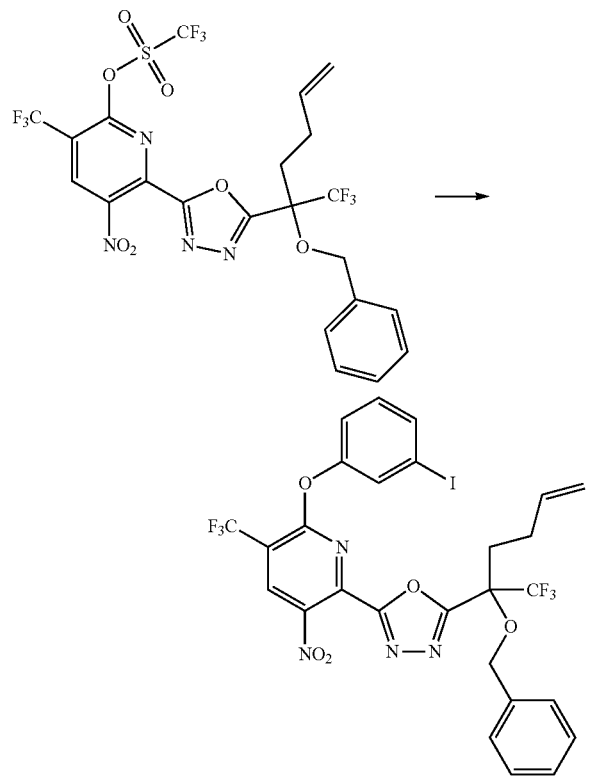

The reagent 3-iodophenol (30 mg, 0.1364 mmol) was added to a mixture of [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (69 mg, 0.1061 mmol) and $Cs_2CO_3$ (35 mg, 0.1074 mmol) in DMF (1.4 mL) and was stirred at 0° C. for 1 h and then at room temperature for 2 h. The mixture was diluted with ether, washed with water (2×), brine, dried ($MgSO_4$) and evaporated. The residue was purified by silica gel chromatography (12 g $SiO_2$, 0-10% EtOAc in hexanes over 20 min) to provide 2-[1-benzyloxy-1-(trifluoromethyl)pent-4-enyl]-5-[6-(3-iodophenoxy)-3-nitro-5-(trifluoromethyl)-2-pyridyl]-1,3,4-oxadiazole (51 mg, 67%). $^1$H NMR (400 MHz, Chloroform-d) δ 8.76 (s, 1H), 7.67-7.56 (m, 2H), 7.40-7.28 (m, 5H), 7.23 (ddd, J=8.3, 2.3, 1.0 Hz, 1H), 7.12 (t, J=8.0 Hz, 1H), 5.71 (ddt, J=16.7, 10.1, 6.3 Hz, 1H), 5.00 (dd, J=17.1, 1.6 Hz, 1H), 4.94 (dd, J=10.3, 1.6 Hz, 1H), 4.77 (d, J=10.6 Hz, 1H), 4.61 (d, J=10.6 Hz, 1H), 2.55-2.25 (m, 3H), 2.24-2.11 (m, 1H) ppm; $^{19}$F NMR (376 MHz, Chloroform-d) δ-64.07, −73.02 ppm. ESI-MS m/z calc. 720.03046, found 721.0 (M+1)$^+$; Retention time: 0.56 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

Step 2: (9E)-6-(Benzyloxy)-20-nitro-6,18-bis(trifluoromethyl)-16,23-dioxa-3,4,21-triazatetracyclo[15.3.1.12,5.111,15]tricosa-1(21),2,4,9,11(22),12,14,17,19-nonaene and 6-(benzyloxy)-9-methylidene-19-nitro-6,17-bis(trifluoromethyl)-15,22-dioxa-3,4,20-triazatetracyclo[14.3.1.12,5.110,14]docosa-1(20),2,4,10(21),11,13,16,18-octaene (Inseparable Mixture of Isomers)

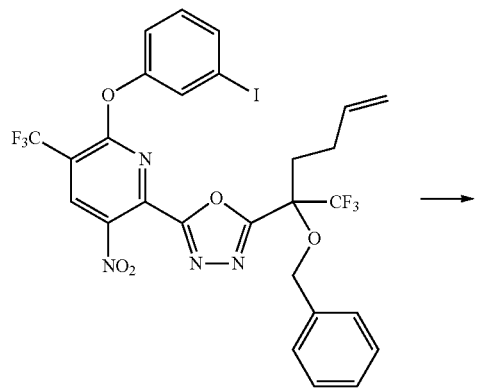

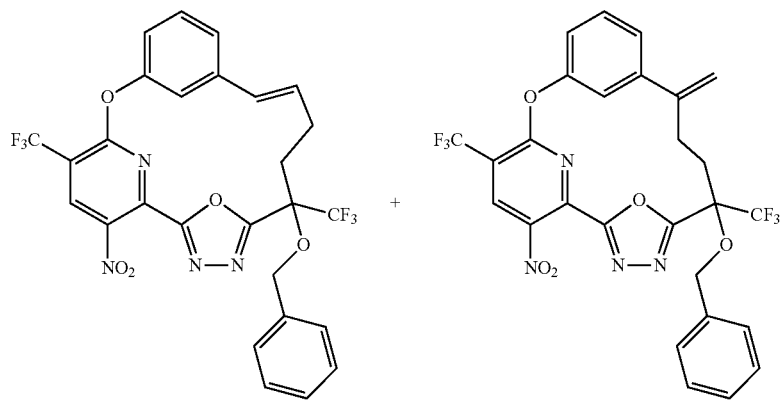

inseparable mixture of isomers

A mixture of 2-[1-benzyloxy-1-(trifluoromethyl)pent-4-enyl]-5-[6-(3-iodophenoxy)-3-nitro-5-(trifluoromethyl)-2-pyridyl]-1,3,4-oxadiazole (126 mg, 0.1749 mmol), palladium (II) acetate (10 mg, 0.04454 mmol), tris-o-tolylphosphane (27 mg, 0.08871 mmol) and triethylamine (51 µL, 0.3659 mmol) in acetonitrile (6.3 mL) was bubbled with $N_2$ for 1 min then heated at 100° C. for 1 h. The mixture was diluted with ether and washed with 1 M $NH_4Cl$, 1 M $NaHCO_3$, brine then dried ($MgSO_4$) and evaporated. The residue was purified by silica gel chromatography (24 g $SiO_2$, 0-50% of a solution (20% EtOAc in hexanes) to hexanes over 20 min) to provide as a 2:1 inseparable mixture of isomers, (9E)-6-(benzyloxy)-20-nitro-6,18-bis(trifluoromethyl)-16,23-dioxa-3,4,21-triazatetracyclo[15.3.1.12, 5.111,15]tricosa-1(21),2,4,9,11(22),12,14,17,19-nonaene (69 mg, 66% purity, 44%). ESI-MS m/z calc. 592.11816, found 593.1 $(M+1)^+$; Retention time: 0.55 minutes and 6-(benzyloxy)-9-methylidene-19-nitro-6,17-bis(trifluoromethyl)-15,22-dioxa-3,4,20-triazatetracyclo[14.3.1.12,5.110, 14]docosa-1(20),2,4,10(21),11,13,16,18-octaene (69 mg, 33% purity, 22%). ESI-MS m/z calc. 592.11816, found 593.1 $(M+1)^+$; Retention time: 0.54 minutes. Final purities were determined by reversed phase UPLC using an Acquity UPLC BEH $C_{18}$ column (30×2.1 mm, 1.7 µm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 µL, and column temperature=60° C.

Step 3: 20-Amino-6,18-bis(trifluoromethyl)-16,23-dioxa-3,4,21-triazatetracyclo[15.3.1.1²,⁵.1¹¹,¹⁵]tricosa-1(21),2,4,11(22),12,14,17,19-octaen-6-ol (enantiomer 1), Compound 27, 20-amino-6,18-bis(trifluoromethyl)-16,23-dioxa-3,4,21-triazatetracyclo[15.3.1.1²,⁵.1¹¹,¹⁵]tricosa-1(21),2,4,11(22),12,14,17,19-octaen-6-ol (enantiomer 2), Compound 28, 19-amino-9-methyl-6,17-bis(trifluoromethyl)-15,22-dioxa-3,4,20-triazatetracyclo[14.3.1.1²,⁵.1¹⁰,¹⁴]docosa-1(20),2,4,10(21),11,13,16,18-octaen-6-ol (diastereomer pair 1), Compound 29, and 19-amino-9-methyl-6,17-bis(trifluoromethyl)-15,22-dioxa-3,4,20-triazatetracyclo[14.3.1.1²,⁵.1¹⁰,¹⁴]docosa-1(20),2,4,10(21),11,13,16,18-octaen-6-ol (diastereomer pair 2), Compound 30

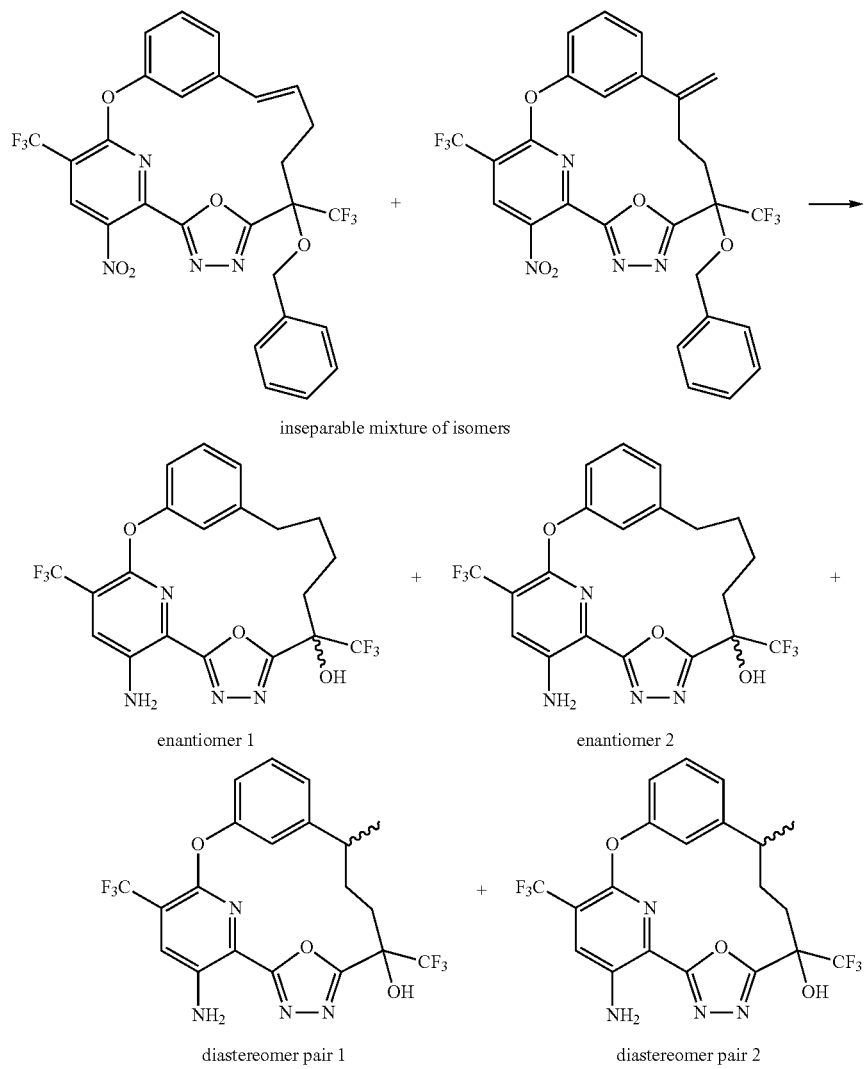

A 2:1 inseparable mixture of isomers, (9E)-6-(benzyloxy)-20-nitro-6,18-bis(trifluoromethyl)-16,23-dioxa-3,4,21-triazatetracyclo[15.3.1.1²,⁵.1¹¹,¹⁵]tricosa-1(21),2,4,9,11(22),12,14,17,19-nonaene (47 mg, 66% purity, 0.052 mmol) and 6-(benzyloxy)-9-methylidene-19-nitro-6,17-bis(trifluoromethyl)-15,22-dioxa-3,4,20-triazatetracyclo[14.3.1.1²,⁵.1¹⁰,¹⁴]docosa-1(20),2,4,10(21),11,13,16,18-octaene (23 mg, 33% purity, 0.013 mmol) and Pd/C (38 mg of 10% w/w, 0.03571 mmol) in EtOAc (1.3 mL) was stirred at room temperature under 200 psi H₂ in a stainless steel pressure vessel for 16 h. Then the mixture was filtered and the filtrate evaporated. The residue was mixed with iron (50 mg, 0.8953 mmol), THF (0.5 mL), EtOH (0.25 mL) and HCl (125 μL of 4 M, 0.5000 mmol) as a solution in water at 60°

C. for 30 min then diluted with EtOAc, filtered and the filtrate washed with 1 M NaHCO$_3$, dried (MgSO$_4$) and evaporated. The residue was purified by silica gel chromatography (24 g SiO$_2$, 5-40% of a solution (20% EtOAc in hexanes) to hexanes over 20 min) to provide, eluting first, an inseparable mixture of 6-(benzyloxy)-6,18-bis(trifluoromethyl)-16,23-dioxa-3,4,21-triazatetracyclo[15.3.1.1$^{2,5}$.1$^{11,15}$]tricosa-1(21),2,4,11(22),12,14,17,19-octaen-20-amine (30 mg, 92%) and the first diastereomeric pair of isomers as 6-(benzyloxy)-9-methyl-6,17-bis(trifluoromethyl)-15,22-dioxa-3,4,20-triazatetracyclo[14.3.1.1$^{2,5}$.1$^{10,14}$]docosa-1(20),2,4,10(21),11,13,16,18-octaen-19-amine (diastereomer pair 1) in an undetermined ratio. Continued elution provided the second diastereomeric pair isomers as 6-(benzyloxy)-9-methyl-6,17-bis(trifluoromethyl)-15,22-dioxa-3,4,20-triazatetracyclo[14.3.1.1$^{2,5}$.1$^{10,14}$]docosa-1(20),2,4,10(21),11,13,16,18-octaen-19-amine (diastereomer pair 2) (10 mg, 34%).

The inseparable mixture of 6-(benzyloxy)-6,18-bis(trifluoromethyl)-16,23-dioxa-3,4,21-triazatetracyclo [15.3.1.1$^{2,5}$.1$^{11,15}$]tricosa-1(21),2,4,11(22),12,14,17,19-octaen-20-amine and the first diastereomeric pair isomers of 6-(benzyloxy)-9-methyl-6,17-bis(trifluoromethyl)-15,22-dioxa-3,4,20-triazatetracyclo[14.3.1.1$^{2,5}$.1$^{10,14}$]docosa-1(20),2,4,10(21),11,13,16,18-octaen-19-amine (diastereomer pair 1) was dissolved into TFA (0.3 mL) and water (0.015 mL) and heated at 60° C. for 1 h, then diluted with EtOAc and washed with 1 M NaHCO$_3$, dried and evaporated. The residue was purified by silica gel chromatography (12 g SiO$_2$, 5-40% EtOAc in hexanes over 20 min) to provide first, racemic 20-amino-6,18-bis(trifluoromethyl)-16,23-dioxa-3,4,21-triazatetracyclo[15.3.1.1$^{2,5}$.1$^{11,15}$]tricosa-1(21),2,4,11(22),12,14,17,19-octaen-6-ol, the separation of which into single enantiomers is described below. ESI-MS m/z calc. 474.11267, found 475.2 (M+1)$^+$; Retention time: 0.71 minutes. Continued elution provided the first diastereomeric pair isomers of 19-amino-9-methyl-6,17-bis(trifluoromethyl)-15,22-dioxa-3,4,20-triazatetracyclo[14.3.1.1$^{2,5}$.1$^{10,14}$]docosa-1(20),2,4,10(21),11,13,16,18-octaen-6-ol (diastereomer pair 1) (1.4 mg, 6%). $^1$H NMR (400 MHz, Chloroform-d) δ 7.50 (s, 1H), 7.32 (t, J=7.8 Hz, 1H), 7.23 (d, J=2.0 Hz, 1H), 7.09-7.00 (m, 2H), 5.17 (s, 2H), 3.74-3.59 (m, 1H), 2.88-2.69 (m, 1H), 2.26-1.94 (m, 3H), 1.49-1.35 (m, 1H), 1.25 (d, J=7.0 Hz, 3H) ppm; $^{19}$F NMR (376 MHz, Chloroform-d) δ −63.36, −80.78 ppm. ESI-MS m/z calc. 474.11267, found 475.1 (M+1)$^+$; Retention time: 1.54 minutes. Final purity was determined by reversed phase HPLC-MS using an Onyx Monolithic C$_{18}$ column (50×4.6 mm) sold by Phenomenex (pn: CH0-7644), and a dual gradient run from 1-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=12 mL/min, injection volume=50 μL, and column temperature=25° C.

The racemic mixture of 20-amino-6,18-bis(trifluoromethyl)-16,23-dioxa-3,4,21-triazatetracyclo[15.3.1.1$^{2,5}$.1$^{11,15}$]tricosa-1(21),2,4,11(22),12,14,17,19-octaen-6-ol obtained above was dissolved into 1:1 acetonitrile/MeOH and purified by preparative SFC eluting a gradient of 5 mM NH$_3$ in methanol to CO$_2$ (5-15% over 10 min at 60 mL/min) though a 21.2×250 mm AS3 column, 5 μm particle, providing as the first enantiomer to elute, 20-amino-6,18-bis(trifluoromethyl)-16,23-dioxa-3,4,21-triazatetracyclo [15.3.1.1$^{2,5}$.1$^{11,15}$]tricosa-1(21),2,4,11(22),12,14,17,19-octaen-6-ol (enantiomer 1) (3.5 mg, 14%). $^1$H NMR (400 MHz, Chloroform-d) δ 7.51 (s, 1H), 7.48 (d, J=2.0 Hz, 1H), 7.31 (t, J=7.8 Hz, 1H), 7.06 (d, J=7.6 Hz, 1H), 6.98 (dd, J=8.1, 2.3 Hz, 1H), 5.45 (s, 2H), 3.71 (s, 1H), 2.82 (ddd, J=14.1, 6.7, 3.8 Hz, 1H), 2.70 (ddd, J=13.7, 8.7, 4.0 Hz, 1H), 2.29 (ddd, J=14.3, 12.6, 5.1 Hz, 1H), 2.07-2.03 (m, 1H), 2.00-1.92 (m, 1H), 1.86-1.66 (m, 3H) ppm; $^{19}$F NMR (376 MHz, Chloroform-d) δ −63.64, −78.87 ppm. ESI-MS m/z calc. 474.11267, found 475.2 (M+1)$^+$; Retention time: 1.57 minutes. Final purity was determined by reversed phase HPLC-MS using an Onyx Monolithic C$_{18}$ column (50×4.6 mm) sold by Phenomenex (pn: CH0-7644), and a dual gradient run from 1-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=12 mL/min, injection volume=50 μL, and column temperature=25° C. and as the second enantiomer to elute, 20-amino-6,18-bis(trifluoromethyl)-16,23-dioxa-3,4,21-triazatetracyclo [15.3.1.1$^{2,5}$.1$^{11,15}$]tricosa-1(21),2,4,11(22),12,14,17,19-octaen-6-ol (enantiomer 2) (2.9 mg, 12%). $^1$H NMR (400 MHz, Chloroform-d) δ 7.52 (s, 1H), 7.48 (d, J=2.0 Hz, 1H), 7.31 (t, J=7.8 Hz, 1H), 7.06 (d, J=7.6 Hz, 1H), 7.02-6.95 (m, 1H), 5.45 (s, 2H), 3.69 (d, J=6.2 Hz, 1H), 2.82 (ddd, J=14.0, 6.7, 3.8 Hz, 1H), 2.70 (ddd, J=13.7, 8.7, 4.0 Hz, 1H), 2.29 (td, J=13.4, 12.9, 5.1 Hz, 1H), 2.08-1.91 (m, 3H), 1.87-1.64 (m, 2H) ppm; $^{19}$F NMR (376 MHz, Chloroform-d) δ −63.64, −78.87 ppm. ESI-MS m/z calc. 474.11267, found 475.2 (M+1)$^+$; Retention time: 1.58 minutes. Final purity was determined by reversed phase HPLC-MS using an Onyx Monolithic C$_{18}$ column (50×4.6 mm) sold by Phenomenex (pn: CH0-7644), and a dual gradient run from 1-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=12 mL/min, injection volume=50 μL, and column temperature=25° C.

The second diastereomeric pair of isomers described above, 6-(benzyloxy)-9-methyl-6,17-bis(trifluoromethyl)-15,22-dioxa-3,4,20-triazatetracyclo[14.3.1.1$^{2,5}$.1$^{10,14}$]docosa-1(20),2,4,10(21),11,13,16,18-octaen-19-amine (diastereomer pair 2) was dissolved into TFA (0.3 mL) and water (0.015 mL) and heated at 60 C for 1 h, then diluted with EtOAc and washed with 1 M NaHCO$_3$, dried and evaporated. The residue was purified by silica gel chromatography (12 g SiO$_2$, 5-40% EtOAc in hexanes over 20 min) to provide 19-amino-9-methyl-6,17-bis(trifluoromethyl)-15,22-dioxa-3,4,20-triazatetracyclo[14.3.1.1$^{2,5}$.1$^{10,14}$]docosa-1(20),2,4,10(21),11,13,16,18-octaen-6-ol (diastereomer pair 2) (2.6 mg, 10%). $^1$H NMR (400 MHz, Chloroform-d) δ 7.49 (s, 1H), 7.34 (t, J=2.2 Hz, 1H), 7.32 (d, J=7.8 Hz, 1H), 7.07 (d, J=7.6 Hz, 1H), 7.01 (dd, J=8.1, 2.2 Hz, 1H), 5.16 (s, 2H), 3.54 (s, 1H), 2.93 (t, J=7.4 Hz, 1H), 2.25 (t, J=13.4 Hz, 1H), 2.08 (td, J=13.3, 4.6 Hz, 1H), 1.98 (dt, J=13.0, 10.7 Hz, 1H), 1.81 (t, J=13.2 Hz, 1H), 1.33 (d, J=7.1 Hz, 3H) ppm; $^{19}$F NMR (376 MHz, Chloroform-d) δ −63.34, −77.95 ppm. ESI-MS m/z calc. 474.11267, found 475.1 (M+1)$^+$; Retention time: 1.54 minutes. Final purity was determined by reversed phase HPLC-MS using an Onyx Monolithic C$_{18}$ column (50×4.6 mm) sold by Phenomenex (pn: CH0-7644), and a dual gradient run from 1-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=12 mL/min, injection volume=50 μL, and column temperature=25° C.

Example 21: Preparation of 20-amino-13-fluoro-6,18-bis(trifluoromethyl)-16,23-dioxa-3,4,21-triazatetracyclo[15.3.1.1²,⁵.1¹¹,¹⁵]tricosa-1(21),2,4,11(22),12,14,17,19-octaen-6-ol (enantiomer 1), Compound 31, and 20-amino-13-fluoro-6,18-bis(trifluoromethyl)-16,23-dioxa-3,4,21-triazatetracyclo[15.3.1.1²,⁵.1¹¹,¹⁵]tricosa-1(21),2,4,11(22),12,14,17,19-octaen-6-ol (enantiomer 2), Compound 32

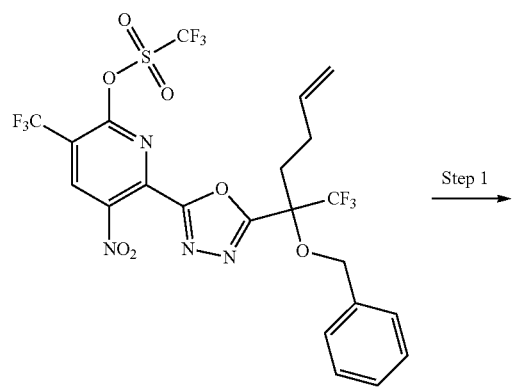

Step 1 →

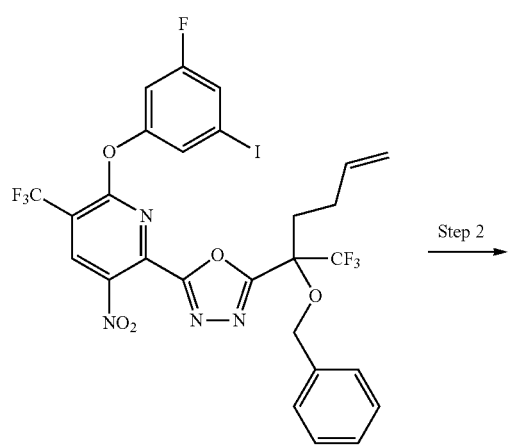

Step 2 →

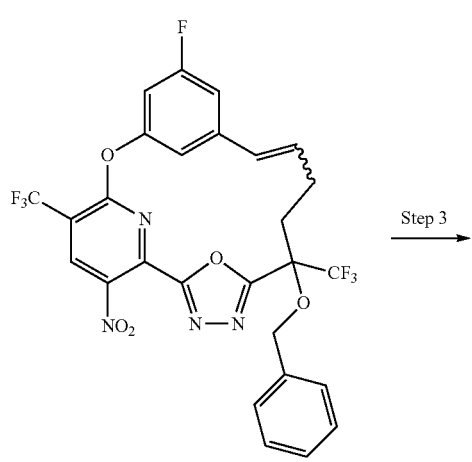

E/Z mixture

Step 3 →

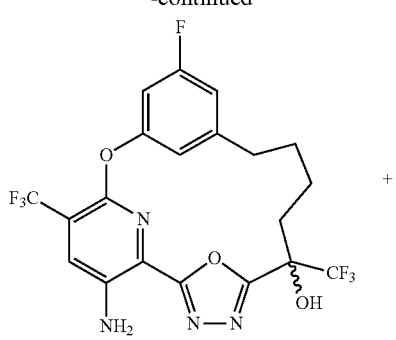

enantiomer 1

+

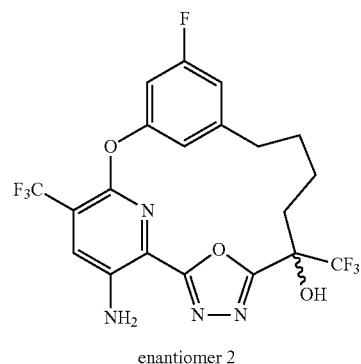

enantiomer 2

Step 1: 2-[1-Benzyloxy-1-(trifluoromethyl)pent-4-enyl]-5-[6-(3-fluoro-5-iodo-phenoxy)-3-nitro-5-(trifluoromethyl)-2-pyridyl]-1,3,4-oxadiazole

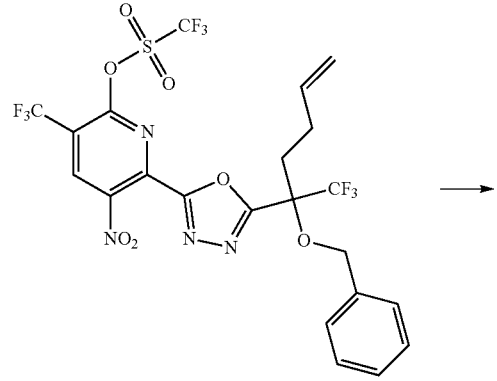

→

Step 2: 6-(Benzyloxy)-13-fluoro-20-nitro-6,18-bis(trifluoromethyl)-16,23-dioxa-3,4,21-triazatetracyclo[15.3.1.12,5.111,15]tricosa-1(21),2,4,9,11(22),12,14,17,19-nonaene (E/Z Mixture)

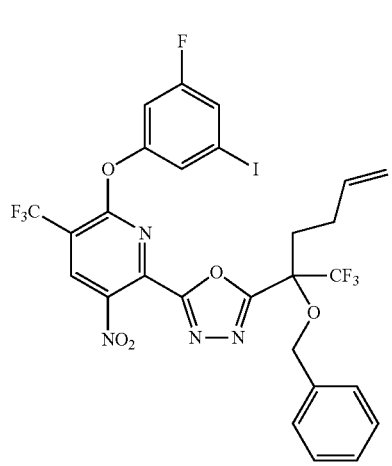

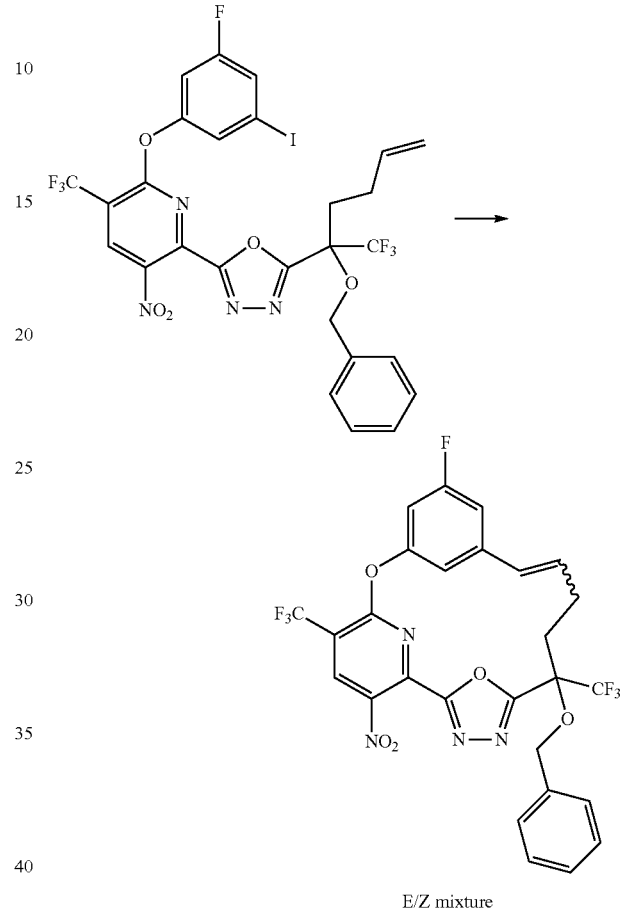

E/Z mixture

The reagent $Cs_2CO_3$ (127 mg, 0.3898 mmol) was added to a mixture of [6-[5-[1-benzyloxy-1-(trifluoromethyl)pent-4-enyl]-1,3,4-oxadiazol-2-yl]-5-nitro-3-(trifluoromethyl)-2-pyridyl] trifluoromethanesulfonate (230 mg, 0.3536 mmol) and 3-fluoro-5-iodo-phenol (134 mg, 0.565 mmol) in DMF (4 mL) and was stirred at 0° C. for 1 h. The mixture was diluted with ether, washed with water (2×), brine, dried ($MgSO_4$) and evaporated. The residue was purified by silica gel chromatography (12 g $SiO_2$, 0-30% of a solution (20% EtOAc in hexanes) to hexanes over 15 min) to provide 2-[1-benzyloxy-1-(trifluoromethyl)pent-4-enyl]-5-[6-(3-fluoro-5-iodo-phenoxy)-3-nitro-5-(trifluoromethyl)-2-pyridyl]-1,3,4-oxadiazole (180 mg, 55%). $^1$H NMR (400 MHz, Chloroform-d) δ 8.76 (s, 1H), 7.43-7.41 (m, 1H), 7.39 (dd, J=7.7, 1.6 Hz, 1H), 7.36-7.29 (m, 5H), 7.01 (dt, J=8.7, 2.3 Hz, 1H), 5.73 (ddd, J=17.0, 10.4, 6.4 Hz, 1H), 5.01 (d, J=17.4 Hz, 1H), 4.95 (d, J=10.2 Hz, 1H), 4.80 (d, J=10.6 Hz, 1H), 4.62 (d, J=10.6 Hz, 1H), 2.54-2.28 (m, 3H), 2.20 (dt, J=17.3, 7.9 Hz, 1H) ppm; $^{19}$F NMR (376 MHz, Chloroform-d) δ −63.97, −73.02, −108.26 ppm. ESI-MS m/z calc. 738.021, found 739.0 (M+1)$^+$; Retention time: 0.6 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

A mixture of 2-[1-benzyloxy-1-(trifluoromethyl)pent-4-enyl]-5-[6-(3-fluoro-5-iodo-phenoxy)-3-nitro-5-(trifluoromethyl)-2-pyridyl]-1,3,4-oxadiazole (180 mg, 0.2438 mmol), palladium (II) acetate (10 mg, 0.04454 mmol), tris-o-tolylphosphane (27 mg, 0.08871 mmol) and triethylamine (51 μL, 0.3659 mmol) in acetonitrile (6.3 mL) was bubbled with $N_2$ for 1 min then heated to 100° C. for 1 h. The mixture was diluted with ether and washed with 1 M $NH_4Cl$, 1 M $NaHCO_3$, brine then dried ($MgSO_4$) and evaporated. The residue was purified by silica gel chromatography (24 g $SiO_2$, 0-50% of a solution (20% EtOAc in hexanes) to hexanes over 20 min) to provide 6-(benzyloxy)-13-fluoro-20-nitro-6,18-bis(trifluoromethyl)-16,23-dioxa-3,4,21-triazatetracyclo[15.3.1.12,5.111,15]tricosa-1(21),2,4,9,11(22),12,14,17,19-nonaene (E/Z mixture) (35 mg, 18%). $^1$H NMR (400 MHz, Chloroform-d) δ 8.79 (s, 1H), 7.35-7.27 (m, 6H), 6.89-6.77 (m, 2H), 6.50 (d, J=11.5 Hz, 1H), 5.79-5.65 (m, 1H), 4.90 (d, J=10.8 Hz, 1H), 4.67 (d, J=11.0 Hz, 1H), 2.88-2.71 (m, 1H), 2.66-2.52 (m, 1H), 2.39 (td, J=13.5, 3.2 Hz, 1H), 2.34-2.14 (m, 1H) ppm; $^{19}$F NMR (376 MHz, Chloroform-d) δ −63.53, −63.87, −73.43, −73.64, −110.37, −110.61 ppm. ESI-MS m/z calc. 610.1087, found 611.2 (M+1)$^+$; Retention time: 0.55 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

Step 3: 20-Amino-13-fluoro-6,18-bis(trifluoromethyl)-16,23-dioxa-3,4,21-triazatetracyclo[15.3.1.1 2,5.1 11,15]tricosa-1(21),2,4,11(22),12,14,17,19-octaen-6-ol (enantiomer 1), Compound 31, and 20-amino-13-fluoro-6,18-bis(trifluoromethyl)-16,23-dioxa-3,4,21-triazatetracyclo[15.3.1.1 2,5.1 11,15]tricosa-1(21),2,4,11(22),12,14,17,19-octaen-6-ol (enantiomer 2), Compound 32

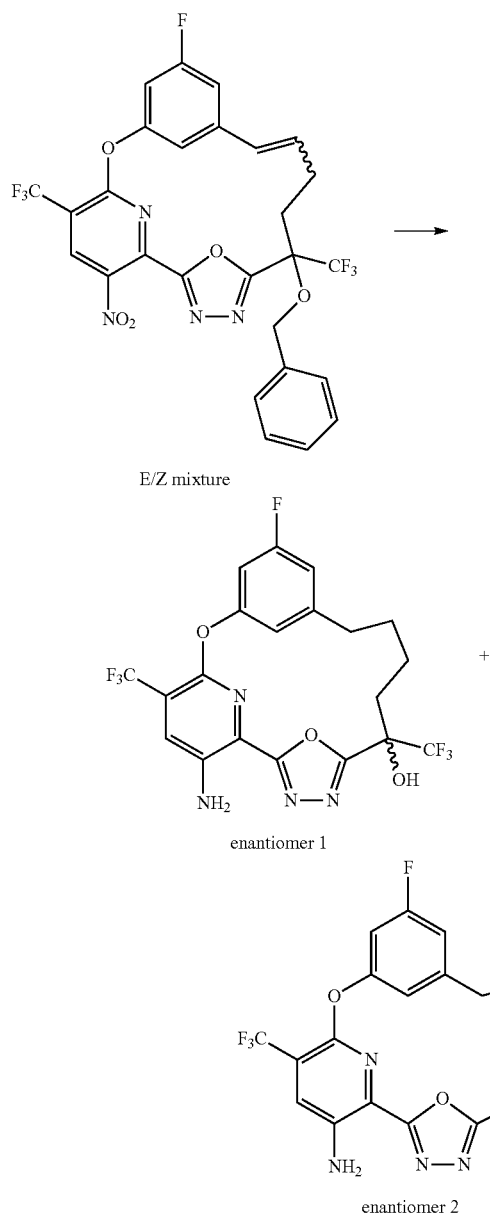

Part 1: A mixture of 6-(benzyloxy)-13-fluoro-20-nitro-6,18-bis(trifluoromethyl)-16,23-dioxa-3,4,21-triazatetracyclo[15.3.1.1 2,5.1 11,15]tricosa-1(21),2,4,9,11(22),12,14,17,19-nonaene (E/Z mixture) (35 mg, 0.05734 mmol) and Pd/C (15 mg of 10% w/w, 0.01410 mmol) in AcOH (400 μL), MeOH (400 μL) and EtOAc (800 μL) was stirred at room temperature under 200 psi $H_2$ in a stainless steel pressure vessel for 20 h. Then the mixture was filtered and the filtrate evaporated to provide 6-(benzyloxy)-13-fluoro-6,18-bis(trifluoromethyl)-16,23-dioxa-3,4,21-triazatetracyclo[15.3.1.1 2,5.1 11,15]tricosa-1(21),2,4,11(22),12,14,17,19-octaen-20-amine which was taken directly to the next reaction. ESI-MS m/z calc. 582.1502, found 583.2 (M+1)$^+$; Retention time: 0.58 minutes. Final purity was determined by reversed phase UPLC using an Acquity UPLC BEH $C_{18}$ column (30×2.1 mm, 1.7 μm particle) made by Waters (pn: 186002349), and a dual gradient run from 50-99% mobile phase B over 1.0 minutes. Mobile phase A=$H_2O$ (0.05% $CF_3CO_2H$). Mobile phase B=acetonitrile (0.035% $CF_3CO_2H$). Flow rate=1.5 mL/min, injection volume=1.5 μL, and column temperature=60° C.

Part 2: 6-(Benzyloxy)-13-fluoro-6,18-bis(trifluoromethyl)-16,23-dioxa-3,4,21-triazatetracyclo[15.3.1.1 2,5.1 11,15]tricosa-1(21),2,4,11(22),12,14,17,19-octaen-20-amine was dissolved in TFA (300 μL) and water (15 μL) and heated at 60° C. for 1 h, then diluted with EtOAc and washed with 1 M $NaHCO_3$, dried and evaporated. The residue was purified by silica gel chromatography (12 g $SiO_2$, 5-40% EtOAc in hexanes over 20 min) to provide 20-amino-13-fluoro-6,18-bis(trifluoromethyl)-16,23-dioxa-3,4,21-triazatetracyclo[15.3.1.1 2,5.1 11,15]tricosa-1(21),2,4,11(22),12,14,17,19-octaen-6-ol (2.4 mg, 9%). $^1$H NMR (400 MHz, Chloroform-d) δ 7.53 (s, 1H), 7.28 (s, 1H), 6.79 (dd, J=9.2, 2.2 Hz, 1H), 6.73 (dd, J=9.2, 2.3 Hz, 1H), 5.51 (s, 2H), 3.68 (s, 1H), 2.80 (ddd, J=14.0, 6.9, 3.7 Hz, 1H), 2.69 (ddd, J=13.8, 8.8, 3.8 Hz, 1H), 2.29 (td, J=13.3, 5.1 Hz, 1H), 2.05 (d, J=13.1 Hz, 1H), 2.01-1.91 (m, 1H), 1.85-1.67 (m, 3H) ppm; $^{19}$F NMR (376 MHz, Chloroform-d) δ −63.62, −78.86, −112.30 ppm. ESI-MS m/z calc. 492.10324, found 493.1 (M+1)$^+$; Retention time: 1.62 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=12 mL/min, injection volume=50 μL, and column temperature=25° C.

Part 3: Racemic 20-amino-13-fluoro-6,18-bis(trifluoromethyl)-16,23-dioxa-3,4,21-triazatetracyclo[15.3.1.1 2,5.1 11,15]tricosa-1(21),2,4,11(22),12,14,17,19-octaen-6-ol was dissolved into 1:1 acetonitrile/MeOH and purified by preparative SFC eluting a gradient of 5 mM $NH_3$ in methanol to $CO_2$ (5-15% over 10 min at 60 mL/min) though a 21.2×250 mm AS3 column, 5 μm particle, providing first eluent 20-amino-13-fluoro-6,18-bis(trifluoromethyl)-16,23-dioxa-3,4,21-triazatetracyclo[15.3.1.1 2,5.1 11,15]tricosa-1(21),2,4,11(22),12,14,17,19-octaen-6-ol, (enantiomer 1) (1.7 mg, 5%). $^1$H NMR (400 MHz, Chloroform-d) δ 7.53 (s, 1H), 7.28 (d, J=1.7 Hz, 1H), 6.79 (dt, J=9.3, 2.0 Hz, 1H), 6.73 (dt, J=9.1, 2.3 Hz, 1H), 5.51 (s, 2H), 3.67 (s, 1H), 2.80 (ddd, J=14.1, 6.8, 3.7 Hz, 1H), 2.68 (ddd, J=20.2, 9.7, 5.0 Hz, 1H), 2.29 (ddd, J=14.1, 12.5, 5.1 Hz, 1H), 2.10-2.02 (m, 2H), 2.01-1.89 (m, 1H), 1.85-1.67 (m, 2H) ppm; $^{19}$F NMR (376 MHz, Chloroform-d) δ −63.62, −78.86, −112.30 ppm; ESI-MS m/z calc. 492.10324, found 493.1 (M+1)$^+$; Retention time: 1.61 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=H₂O (0.05% CF₃CO₂H). Mobile phase B=acetonitrile (0.035% CF₃CO₂H). Flow rate=12 mL/min, injection volume=50 μL, and column temperature=25° C.

Continued elution provided as the second eluent 20-amino-13-fluoro-6,18-bis(trifluoromethyl)-16,23-dioxa-3,4,21-triazatetracyclo[15.3.1.1²,⁵.1¹¹,¹⁵]tricosa-1(21),2,4,11(22),12,14,17,19-octaen-6-ol (enantiomer 2) (1.4 mg, 7%). ¹H NMR (400 MHz, Chloroform-d) δ 7.53 (s, 1H), 7.28 (d, J=1.8 Hz, 1H), 6.79 (dt, J=9.1, 2.0 Hz, 1H), 6.73 (dt, J=9.2, 2.3 Hz, 1H), 5.51 (s, 2H), 3.63 (s, 1H), 2.80 (ddd, J=14.0, 6.8, 3.7 Hz, 1H), 2.69 (ddd, J=13.8, 8.7, 3.8 Hz, 1H), 2.29 (ddd, J=14.1, 12.4, 5.1 Hz, 1H), 2.11-2.02 (m, 2H), 2.01-1.89 (m, 1H), 1.85-1.66 (m, 2H) ppm; ¹⁹F NMR (376 MHz, Chloroform-d) δ −63.62, −78.87, −112.30 ppm; ESI-MS m/z calc. 492.10324, found 493.1 (M+1)⁺; Retention time: 1.62 minutes. Final purity was determined by reversed phase HPLC-MS using an Onyx Monolithic C₁₈ column (50×4.6 mm) sold by Phenomenex (pn: CH0-7644), and a dual gradient run from 1-99% mobile phase B over 2.9 minutes. Mobile phase A=H₂O (0.05% CF₃CO₂H). Mobile phase B=acetonitrile (0.035% CF₃CO₂H). Flow rate=12 mL/min, injection volume=50 μL, and column temperature=25° C.

Example 22: Preparation of 19-amino-12-fluoro-9-methyl-6,17-bis(trifluoromethyl)-15,22-dioxa-3,4,20-triazatetracyclo[14.3.1.1²,⁵.1¹⁰,¹⁴]docosa-1(20),2,4,10(21),11,13,16,18-octaen-6-ol (diastereomer pair 1), Compound 33

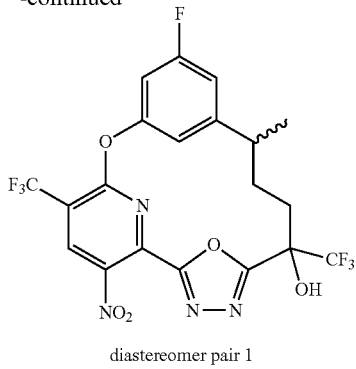

diastereomer pair 1

Step 1: 6-(Benzyloxy)-12-fluoro-9-methylidene-19-nitro-6,17-bis(trifluoromethyl)-15,22-dioxa-3,4,20-triazatetracyclo[14.3.1.1²,⁵.1¹⁰,¹⁴]docosa-1(20),2,4,10(21),11,13,16,18-octaene

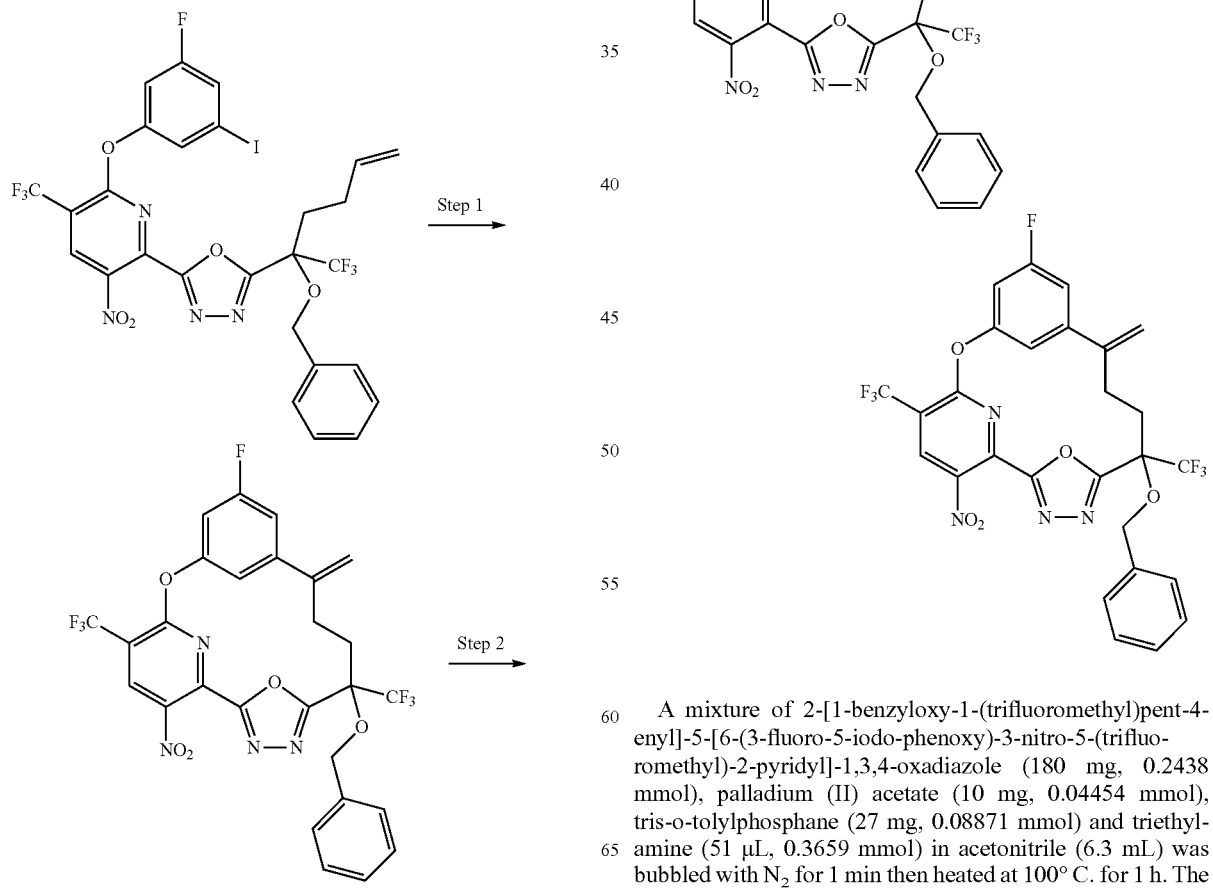

A mixture of 2-[1-benzyloxy-1-(trifluoromethyl)pent-4-enyl]-5-[6-(3-fluoro-5-iodo-phenoxy)-3-nitro-5-(trifluoromethyl)-2-pyridyl]-1,3,4-oxadiazole (180 mg, 0.2438 mmol), palladium (II) acetate (10 mg, 0.04454 mmol), tris-o-tolylphosphane (27 mg, 0.08871 mmol) and triethylamine (51 μL, 0.3659 mmol) in acetonitrile (6.3 mL) was bubbled with N₂ for 1 min then heated at 100° C. for 1 h. The mixture was diluted with ether and washed with 1 M NH₄Cl, 1 M NaHCO$_3$, brine then dried (MgSO$_4$) and evaporated. The residue was purified by silica gel chromatography (24 g SiO$_2$, 0-50% of a solution (20% EtOAc in hexanes) to hexanes over 20 min) to provide 6-(benzyloxy)-12-fluoro-9-methylidene-19-nitro-6,17-bis(trifluoromethyl)-15,22-dioxa-3,4,20-triazatetracyclo[14.3.1.1 2,5.1 10,14]docosa-1(20),2,4,10(21),11,13,16,18-octaene (9.4 mg, 6%). $^1$H NMR (400 MHz, Chloroform-d) δ 8.65 (s, 1H), 7.32-7.27 (m, 2H), 7.23 (d, J=15.5 Hz, 4H), 6.84 (dt, J=8.9, 2.4 Hz, 2H), 5.94-5.76 (m, 1H), 5.53 (dt, J=14.9, 6.7 Hz, 1H), 4.83 (d, J=11.3 Hz, 1H), 4.41 (d, J=11.3 Hz, 1H), 3.37 (d, J=5.9 Hz, 2H), 3.11 (dd, J=14.9, 5.6 Hz, 1H), 2.78 (dd, J=15.2, 7.9 Hz, 1H) ppm; $^{19}$F NMR (376 MHz, Chloroform-d) δ −63.81, −73.39, −110.54 ppm. ESI-MS m/z calc. 610.1087, found 611.2 (M+1)$^+$; Retention time: 0.52 minutes. Final purity was determined by reversed phase UPLC using an Acquity UPLC BEH C$_{18}$ column (30×2.1 mm, 1.7 μm particle) made by Waters (pn: 186002349), and a dual gradient run from 50-99% mobile phase B over 1.0 minutes. Mobile phase A=H$_2$O (0.05% CF$_3$CO$_2$H). Mobile phase B=CH$_3$CN (0.035% CF$_3$CO$_2$H). Flow rate=1.5 mL/min, injection volume=1.5 μL, and column temperature=60° C.

Step 2: 19-Amino-12-fluoro-9-methyl-6,17-bis (trifluoromethyl)-15,22-dioxa-3,4,20-triazatetracyclo [14.3.1.12,5.110,14]docosa-1(20),2,4,10(21),11,13,16,18-octaen-6-ol (diastereomer pair 1), Compound 33

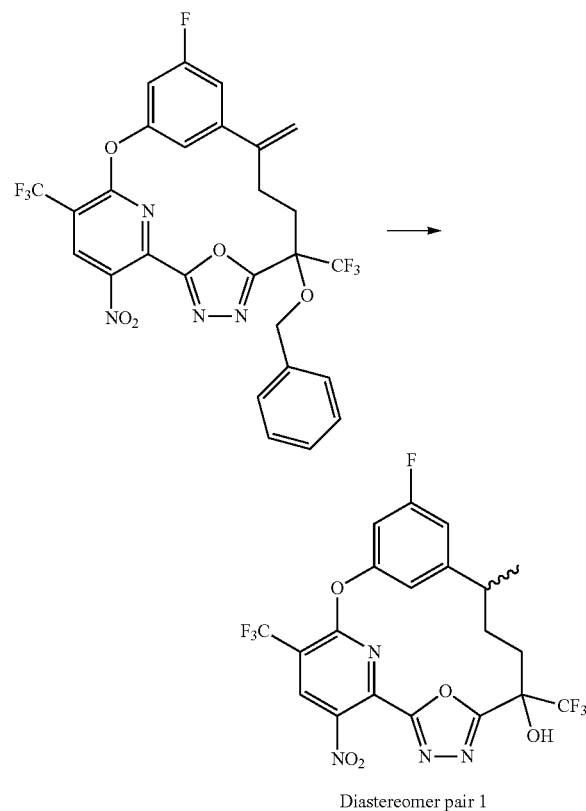

Diastereomer pair 1

Part 1: A mixture of 6-(benzyloxy)-12-fluoro-9-methylidene-19-nitro-6,17-bis(trifluoromethyl)-15,22-dioxa-3,4,20-triazatetracyclo[14.3.1.12,5.110,14]docosa-1(20),2,4,10(21),11,13,16,18-octaene (9.4 mg, 0.01540 mmol) and Pd/C (15 mg of 10% w/w, 0.01410 mmol) in AcOH (400 μL), MeOH (400 μL) and EtOAc (800 μL) was stirred at room temperature under 200 psi H$_2$ in a stainless steel pressure vessel for 20 h. Then the mixture was filtered and the filtrate evaporated to provide 6-(benzyloxy)-12-fluoro-9-methyl-6,17-bis(trifluoromethyl)-15,22-dioxa-3,4,20-triazatetracyclo [14.3.1.12,5.110,14]docosa-1(20),2,4,10(21),11,13,16,18-octaen-19-amine. ESI-MS m/z calc. 582.1502, found 583.2 (M+1)$^+$; Retention time: 0.59 minutes (yield missing). Final purity was determined by reversed phase UPLC using an Acquity UPLC BEH C$_{18}$ column (30×2.1 mm, 1.7 μm particle) made by Waters (pn: 186002349), and a dual gradient run from 50-99% mobile phase B over 1.0 minutes. Mobile phase A=H$_2$O (0.05% CF$_3$CO$_2$H). Mobile phase B=acetonitrile (0.035% CF$_3$CO$_2$H). Flow rate=1.5 mL/min, injection volume=1.5 μL, and column temperature=60° C.

Part 2: 6-(Benzyloxy)-12-fluoro-9-methyl-6,17-bis(trifluoromethyl)-15,22-dioxa-3,4,20-triazatetracyclo [14.3.1.12,5.110,14]docosa-1(20),2,4,10(21),11,13,16,18-octaen-19-amine was dissolved in TFA (300 μL) and water (15 μL) and heated at 60° C. for 1 h, then diluted with EtOAc and washed with 1 M NaHCO$_3$, dried and evaporated. The residue was purified by silica gel chromatography (12 g SiO$_2$, 5-40% EtOAc in hexanes over 20 min) to provide diastereomer pair 1, 19-amino-12-fluoro-9-methyl-6,17-bis (trifluoromethyl)-15,22-dioxa-3,4,20-triazatetracyclo [14.3.1.12,5.110,14]docosa-1(20),2,4,10(21),11,13,16,18-octaen-6-ol (1.3 mg, 4%). $^1$H NMR (400 MHz, Chloroform-d) δ 7.50 (s, 1H), 7.13 (d, J=2.1 Hz, 1H), 6.82 (dt, J=9.6, 1.9 Hz, 1H), 6.77 (dt, J=9.1, 2.2 Hz, 1H), 5.20 (s, 2H), 3.44 (s, 1H), 2.95 (d, J=8.8 Hz, 1H), 2.25 (t, J=13.3 Hz, 1H), 2.13-1.90 (m, 2H), 1.79 (t, J=13.3 Hz, 1H), 1.32 (d, J=7.1 Hz, 3H) ppm; $^{19}$F NMR (376 MHz, Chloroform-d) δ-63.31, −78.21, −112.26 ppm. ESI-MS m/z calc. 492.10324, found 493.1 (M+1)$^+$; Retention time: 1.83 minutes. Final purity was determined by reversed phase HPLC-MS using an Onyx Monolithic C$_{18}$ column (50×4.6 mm) sold by Phenomenex (pn: CH0-7644), and a dual gradient run from 1-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=12 mL/min, injection volume=50 μL, and column temperature=25° C.

Example 23: Preparation of (6R)-17-amino-12-isopropyl-6,15-bis(trifluoromethyl)-13,19-dioxa-3,4,18-triazatricyclo[12.3.1.12,5]nonadeca-1(18),2,4,14,16-pentaen-6-ol (enantiomer 1) (hydrochloride salt), Compound 34, and (6R)-17-amino-12-isopropyl-6,15-bis(trifluoromethyl)-13,19-dioxa-3,4,18-triazatricyclo[12.3.1.12,5]nonadeca-1(18),2,4,14,16-pentaen-6-ol (enantiomer 2) (hydrochloride salt), Compound 35

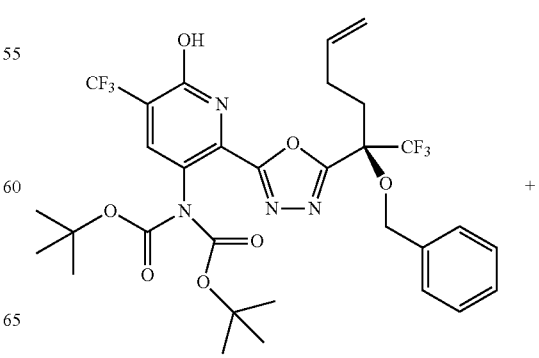

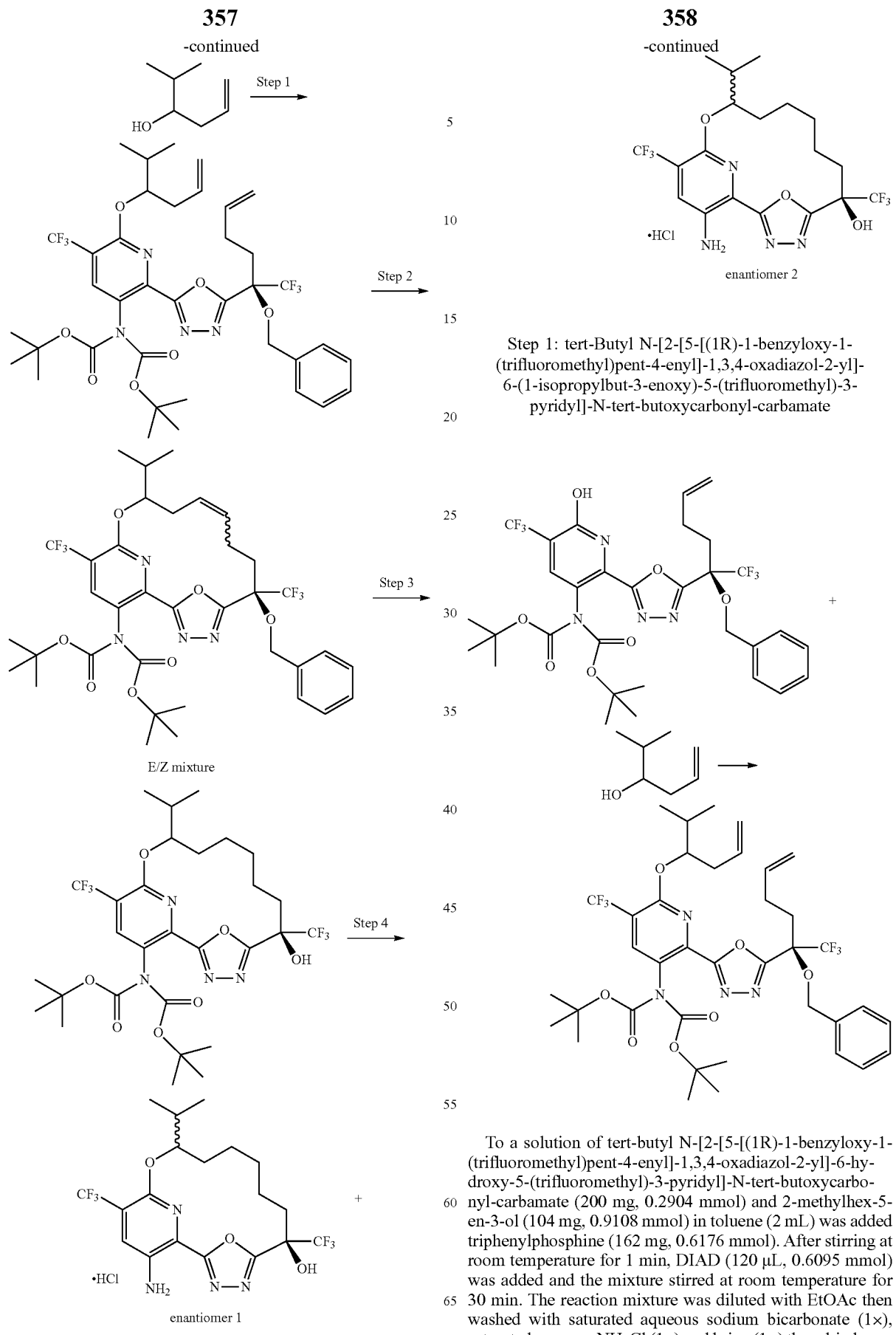

Step 1: tert-Butyl N-[2-[5-[(1R)-1-benzyloxy-1-(trifluoromethyl)pent-4-enyl]-1,3,4-oxadiazol-2-yl]-6-(1-isopropylbut-3-enoxy)-5-(trifluoromethyl)-3-pyridyl]-N-tert-butoxycarbonyl-carbamate To a solution of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (200 mg, 0.2904 mmol) and 2-methylhex-5-en-3-ol (104 mg, 0.9108 mmol) in toluene (2 mL) was added triphenylphosphine (162 mg, 0.6176 mmol). After stirring at room temperature for 1 min, DIAD (120 μL, 0.6095 mmol) was added and the mixture stirred at room temperature for 30 min. The reaction mixture was diluted with EtOAc then washed with saturated aqueous sodium bicarbonate (1×), saturated aqueous NH₄Cl (1×) and brine (1×) then dried over magnesium sulfate, filtered and concentrated to a yellow oil which was purified by silica gel chromatography using a gradient of 0% to 50% EtOAc in hexanes giving as a diastereomeric mixture and clear, slightly yellow syrup, tert-butyl N-[2-[5-[(1R)-1-benzyloxy-1-(trifluoromethyl) pent-4-enyl]-1,3,4-oxadiazol-2-yl]-6-(1-isopropylbut-3-enoxy)-5-(trifluoromethyl)-3-pyridyl]-N-tert-butoxycarbonyl-carbamate (168 mg, 74%). ESI-MS m/z calc. 784.3271, found 785.3 (M+I)$^+$; Retention time: 2.23 minutes. Final purity was determined by reversed phase UPLC using an Acquity UPLC BEH $C_{18}$ column (50×2.1 mm, 1.7 μm particle) made by Waters (pn: 186002350), and a dual gradient run from 50-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 2: tert-Butyl N-[(6R)-6-benzyloxy-12-isopropyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z Mixture)

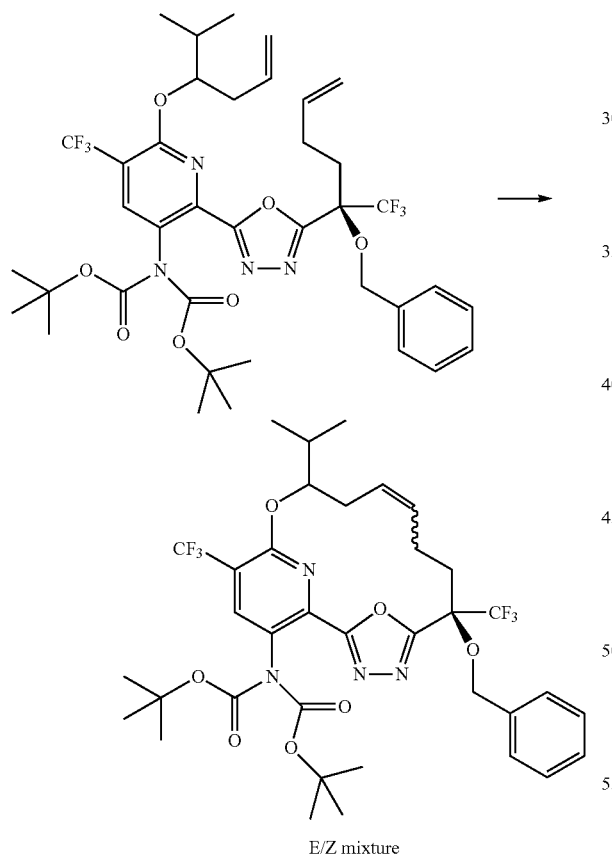

E/Z mixture

To a degassed solution of tert-butyl N-[2-[5-[(1R)-1-benzyloxy-1-(trifluoromethyl)pent-4-enyl]-1,3,4-oxadiazol-2-yl]-6-(1-isopropylbut-3-enoxy)-5-(trifluoromethyl)-3-pyridyl]-N-tert-butoxycarbonyl-carbamate (164 mg, 0.2090 mmol) in DCE (100 mL) was added dichloro[1,3-bis(2,4,6-trimethylphenyl)-2-imidazolidinylidene][[5-[(dimethylamino)sulfonyl]-2-(1-methylethoxy-O)phenyl]methylene-C]ruthenium(II) (Zhan catalyst-1B, 18 mg, 0.02453 mmol) all at once and the reaction mixture was heated at 60° C. for ~6 h. The reaction was quenched with few drops of DMSO and the solvents were removed by rotary evaporation. The resulting brown residue was purified by silica gel chromatography using a gradient of 0 to 50% EtOAc in hexanes giving as a mixture of diastereomers and as a colorless viscous oil, tert-butyl N-[(6R)-6-benzyloxy-12-isopropyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (97 mg, 61%). ESI-MS m/z calc. 756.2958, found 757.3 (M+1)$^+$; Retention time: 2.08 minutes and 2.17 (major fragment 657.3 (M-Boc)$^+$. Final purity was determined by reversed phase UPLC using an Acquity UPLC BEH $C_{18}$ column (50×2.1 mm, 1.7 μm particle) made by Waters (pn: 186002350), and a dual gradient run from 50-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 μL, and column temperature=60° C.

Step 3: tert-Butyl N-tert-butoxycarbonyl-N-[(6R)-6-hydroxy-12-isopropyl-6,15-bis(trifluoromethyl)-13,19-dioxa-3,4,18-triazatricyclo[12.3.1.12,5]nonadeca-1(18),2,4,14,16-pentaen-17-yl]carbamate

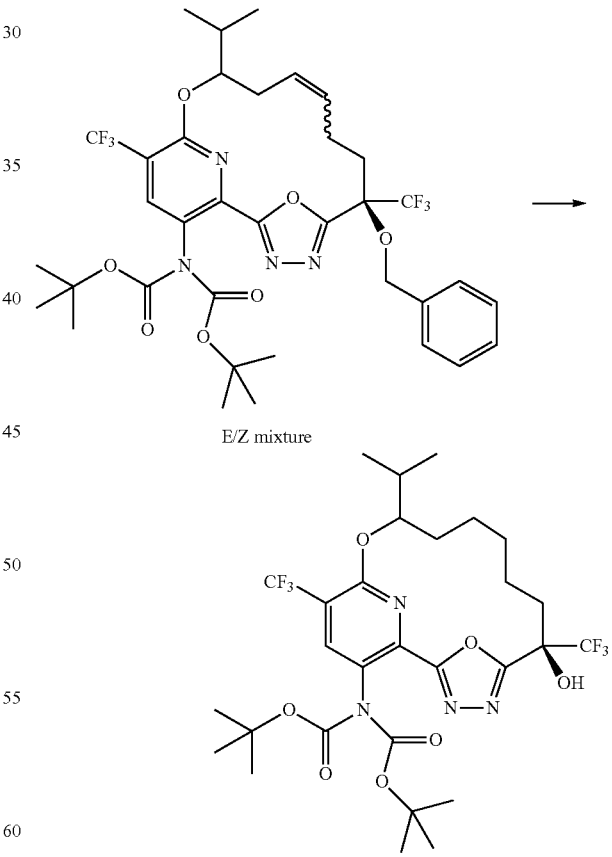

E/Z mixture

To a solution of tert-butyl N-[(6R)-6-benzyloxy-12-isopropyl-6,15-bis(trifluoromethyl)-13,19-dioxa-3,4,18-triazatricyclo[12.3.1.12,5]nonadeca-1(18),2,4,9,14,16-hexaen-17-yl]-N-tert-butoxycarbonyl-carbamate (E/Z mixture) (97 mg, 0.1282 mmol) in EtOH (5 mL) was added Pd/C (46 mg of 10% w/w, 0.04322 mmol, 50% water by weight) in a 250 mL flask equipped with a hydrogen balloon using a 3-way adaptor. The flask was subjected to vacuum and backfilled with nitrogen gas three times then subjected to vacuum again. The vessel was filled with hydrogen gas and the mixture was stirred at room temperature overnight. The flask was subjected to vacuum and backfilled with nitrogen gas three times then diluted with ethyl acetate and filtered over Celite. The filtrate was concentrated to give, as a colorless viscous oil and a mixture of diastereomers, tert-butyl N-tert-butoxycarbonyl-N-[(6R)-6-hydroxy-12-isopropyl-6,15-bis(trifluoromethyl)-13,19-dioxa-3,4,18-triazatricyclo[12.3.1.1²,⁵]nonadeca-1(18),2,4,14,16-pentaen-17-yl]carbamate (85 mg, 99%); ESI-MS m/z calc. 668.26447, found 569.2 (M-Boc+1)⁺; Retention time: 1.62 minutes and Retention time: 1.65 minutes (inseparable diastereomers). Final purity was determined by reversed phase UPLC using an Acquity UPLC BEH $C_{18}$ column (50×2.1 mm, 1.7 µm particle) made by Waters (pn: 186002350), and a dual gradient run from 50-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 µL, and column temperature=60° C.

Step 4: (6R)-17-Amino-12-isopropyl-6,15-bis(trifluoromethyl)-13,19-dioxa-3,4,18-triazatricyclo[12.3.1.1²,⁵]nonadeca-1(18),2,4,14,16-pentaen-6-ol (enantiomer 1) (hydrochloride salt), Compound 34, and (6R)-17-amino-12-isopropyl-6,15-bis(trifluoromethyl)-13,19-dioxa-3,4,18-triazatricyclo[12.3.1.1²,⁵]nonadeca-1(18),2,4,14,16-pentaen-6-ol (enantiomer 2) (hydrochloride salt), Compound 35

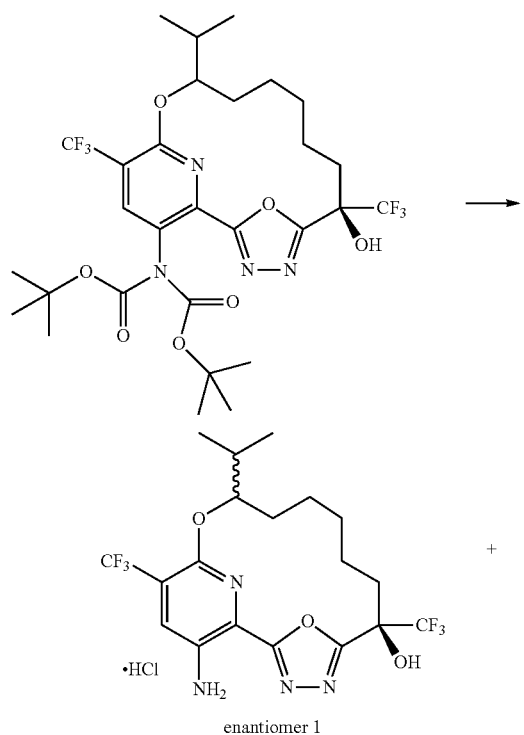

enantiomer 1

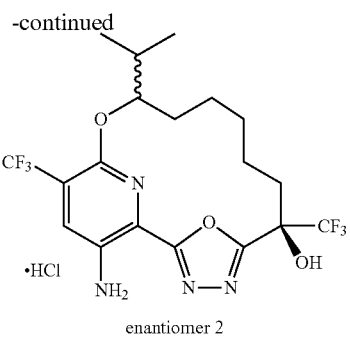

enantiomer 2 tert-Butyl N-tert-butoxycarbonyl-N-[(6R)-6-hydroxy-12-isopropyl-6,15-bis(trifluoromethyl)-13,19-dioxa-3,4,18-triazatricyclo[12.3.1.1²,⁵]nonadeca-1(18),2,4,14,16-pentaen-17-yl]carbamate (80 mg, 0.1196 mmol) was dissolved in a pre-made solution (1:3 TFA/dichloromethane) of TFA (250 µL, 3.245 mmol) and dichloromethane (750 µL). The reaction was stirred for ~1 h and the solvents were evaporated. The resultant residue was dissolved in 2 mL of MeOH and purified by reverse phase HPLC using a gradient from 40% to 80% acetonitrile in water (+5 mM HCl) over 30.0 minutes giving as an off-white solid and the first enantiomer to elute, (6R)-17-amino-12-isopropyl-6,15-bis(trifluoromethyl)-13,19-dioxa-3,4,18-triazatricyclo[12.3.1.1²,⁵]nonadeca-1(18),2,4,14,16-pentaen-6-ol (hydrochloride salt, enantiomer 1) (18.3 mg, 61%). $^1$H NMR (400 MHz, DMSO-$d_6$) δ 7.77 (s, 1H), 7.57 (s, 1H), 6.35 (s, 2H), 4.59 (dt, J=5.9, 2.7 Hz, 1H), 2.34-2.22 (m, 2H), 2.18-2.07 (m, 1H), 2.01-1.88 (m, 1H), 1.69 (m, 2H), 1.58-1.35 (m, 5H), 0.99 (d, J=2.7 Hz, 3H), 0.98 (d, J=2.7 Hz, 3H) ppm; ESI-MS m/z calc. 468.1596, found 469.1 (M+1)⁺; Retention time: 1.74 minutes. Final purity was determined by reversed phase UPLC using an Acquity UPLC BEH $C_{18}$ column (50×2.1 mm, 1.7 µm particle) made by Waters (pn: 186002350), and a dual gradient run from 30-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 µL, and column temperature=60° C. The second enantiomer to elute, as an off-white solid, was (6R)-17-amino-12-isopropyl-6,15-bis(trifluoromethyl)-13,19-dioxa-3,4,18-triazatricyclo[12.3.1.1²,⁵]nonadeca-1(18),2,4,14,16-pentaen-6-ol (hydrochloride salt, enantiomer 2) (19.0 mg, 63%). $^1$H NMR (400 MHz, DMSO-$d_6$) δ 7.77 (s, 1H), 7.57 (s, 1H), 6.35 (s, 2H), 4.60-4.39 (m, 1H), 2.34-2.24 (m, 1H), 2.18 (d, J=8.6 Hz, 1H), 2.14-2.04 (m, 1H), 1.99-1.89 (m, 1H), 1.63 (s, 3H), 1.42 (d, J=23.7 Hz, 4H), 1.00 (d, J=2.5 Hz, 3H), 0.98 (d, J=2.4 Hz, 3H) ppm; ESI-MS m/z calc. 468.1596, found 469.2 (M+1)⁺; Retention time: 1.79 minutes. Final purity was determined by reversed phase UPLC using an Acquity UPLC BEH $C_{18}$ column (50×2.1 mm, 1.7 µm particle) made by Waters (pn: 186002350), and a dual gradient run from 30-99% mobile phase B over 2.9 minutes. Mobile phase A=water (0.05% $CF_3CO_2H$). Mobile phase B=acetonitrile (0.035% $CF_3CO_2H$). Flow rate=1.2 mL/min, injection volume=1.5 µL, and column temperature=60° C.

Example 24: Preparation of (6R,12R)-17-amino-12-(hydroxymethyl)-6,15-bis(trifluoromethyl)-13,19-dioxa-3,4,18-triazatricyclo[12.3.1.1²,⁵]nonadeca-1(18),2,4,14,16-pentaen-6-ol, Compound 36
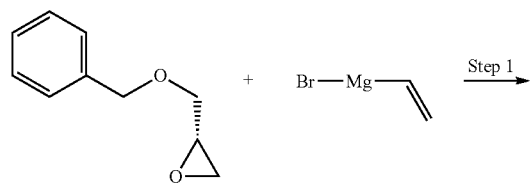
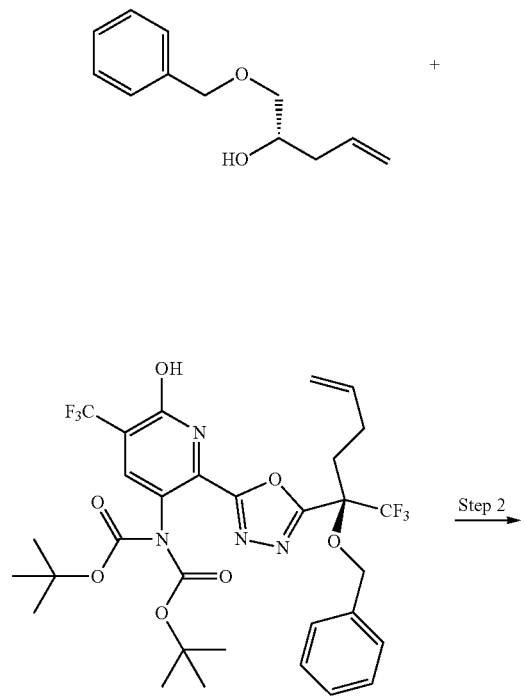
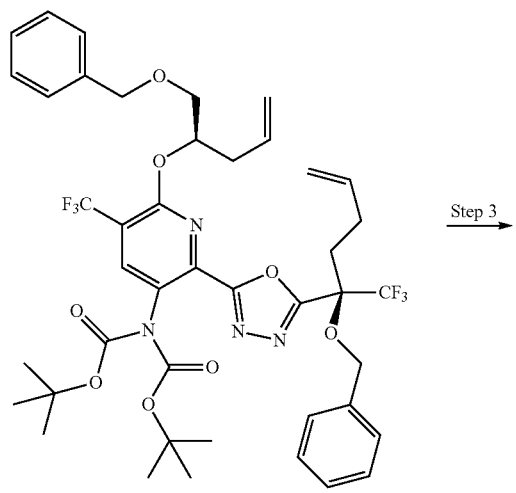
-continued
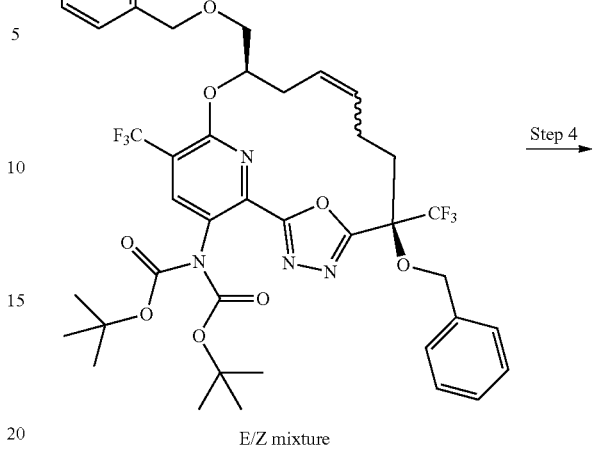
E/Z mixture
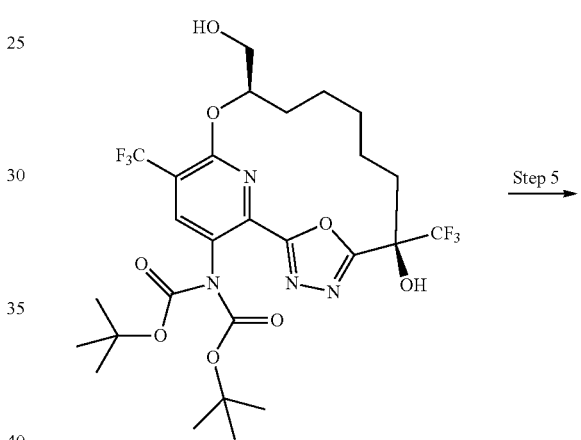
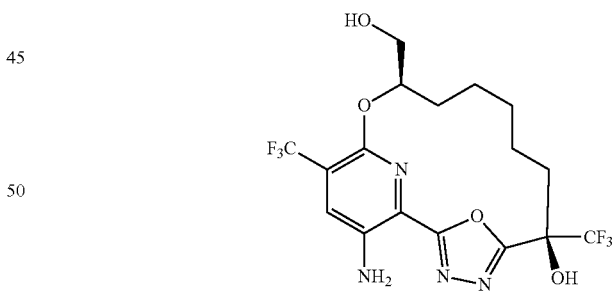
Step 1: (2S)-1-Benzyloxypent-4-en-2-ol
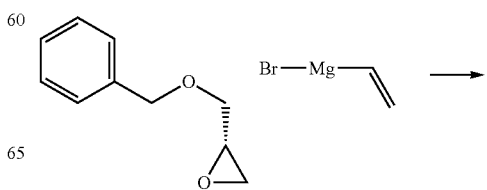

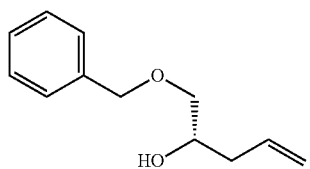

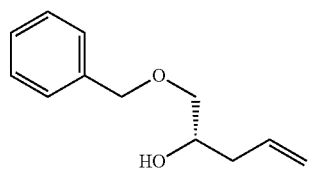

To a solution of bromo(vinyl)magnesium (37 mL of 1 M, 37.000 mmol) was added copper bromide (350 mg, 2.4399 mmol) at 0° C., then the black mixture was stirred at −78° C. After 5 min, a solution of (2S)-2-(benzyloxymethyl)oxirane (2 g, 12.180 mmol) in THF (20 mL) was added dropwise over 30 min at −78° C. Then the black mixture was stirred at −78° C. for 30 min. Then methanol (5 mL) was added at −78° C., followed by aqueous hydrogen chloride (2M, 24 mL) and then the mixture was stirred at room temperature for 5 min. MTBE (40 mL) was then added, the aqueous layer was separated and extracted with MTBE (2×20 mL). The organic layers were washed with aqueous hydrogen chloride (1M, 40 mL), water (40 mL), aqueous sodium thiosulfate (10%, 40 mL) and again with water (40 mL). The organic layers were dried over sodium sulfate and concentrated under vacuum to give crude (2S)-1-benzyloxypent-4-en-2-ol (2.46 g, 102%) as a yellow oil. ESI-MS m/z calc. 192.11504, found 193.0 (M+1)$^+$; Retention time: 1.92 minutes; LCMS Method: Kinetex Polar C$_{18}$, 3.0×50 mm 2.6 μm, 3 min, 5-95% acetonitrile in H$_2$O (0.1% Formic Acid) 1.2 ml/min.

Step 2: tert-Butyl N-[6-[(1R)-1-(benzyloxymethyl)but-3-enoxy]-2-[5-[(1R)-1-benzyloxy-1-(trifluoromethyl)pent-4-enyl]-1,3,4-oxadiazol-2-yl]-5-(trifluoromethyl)-3-pyridyl]-N-tert-butoxycarbonyl-carbamate

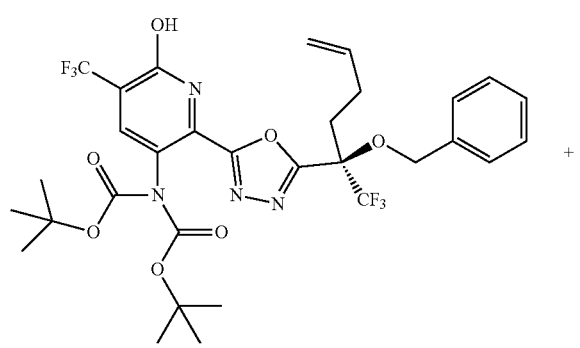

+

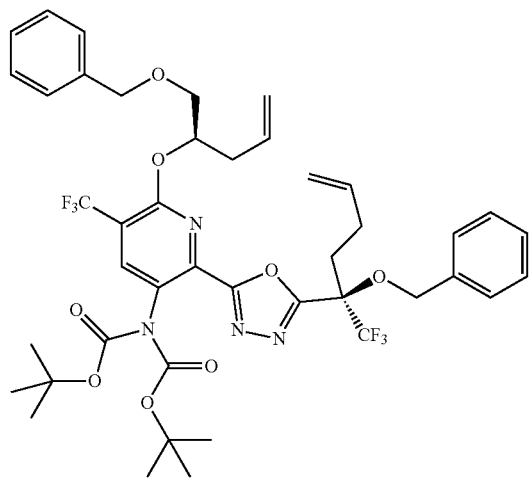

A solution of tert-butyl N-[2-[5-[1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (1.2 g, 1.7426 mmol) and (2S)-1-benzyloxypent-4-en-2-ol (1.42 g, 7.3861 mmol) in toluene (12 mL) was treated with triphenylphosphine (1.35 g, 5.1471 mmol) followed by DIAD (1.0815 g, 1.03 mL, 5.3485 mmol) at rt. The yellow solution was stirred at room temperature overnight. The yellow suspension was concentrated under vacuum, then dry-packed on silica with DCM. Purification by chromatography over a 120 g silica column (1-30% EtOAc/heptanes) gave tert-butyl N46-[(1R)-1-(benzyloxymethyl)but-3-enoxyl-2-[5-[1-benzyloxy-1-(trifluoromethyl)pent-4-enyl]-1,3,4-oxadiazol-2-yl]-5-(trifluoromethyl)-3-pyridyl]-N-tert-butoxycarbonyl-carbamate (1.5 g, 99%) as a yellow oil. $^1$H NMR (400 MHz, CDCl$_3$) δ 7.85 (s, 1H), 7.41-7.24 (m, 10H), 5.78 (m, 2H), 5.61-5.52 (m, 1H), 5.14-4.95 (m, 4H), 4.80 (d, J=10.6 Hz, 1H), 4.66-4.51 (m, 3H), 3.80-3.64 (m, 2H), 2.64-2.16 (m, 6H), 1.43 (d, J=2.3 Hz, 18H) ppm. $^{19}$F NMR (377 MHz, CDCl$_3$) δ −64.05 (s, 3F), −73.04 (s, 3F) ppm.

367

Step 3: tert-Butyl N-[(6R,12R)-6-benzyloxy-12-(benzyloxymethyl)-6,15-bis(trifluoromethyl)-13,19-dioxa-3,4,18-triazatricyclo[12.3.1.12,5]nonadeca-1(17),2,4,9,14(18),15-hexaen-17-yl]-N-tert-butoxycarbonyl-carbamate (E/Z Mixture)

368

Step 4: tert-Butyl N-tert-butoxycarbonyl-N-[(6R,12R)-6-hydroxy-12-(hydroxymethyl)-6,15-bis(trifluoromethyl)-13,19-dioxa-3,4,18-triazatricyclo[12.3.1.12,5]nonadeca-1(17),2,4,14(18),15-pentaen-17-yl]carbamate

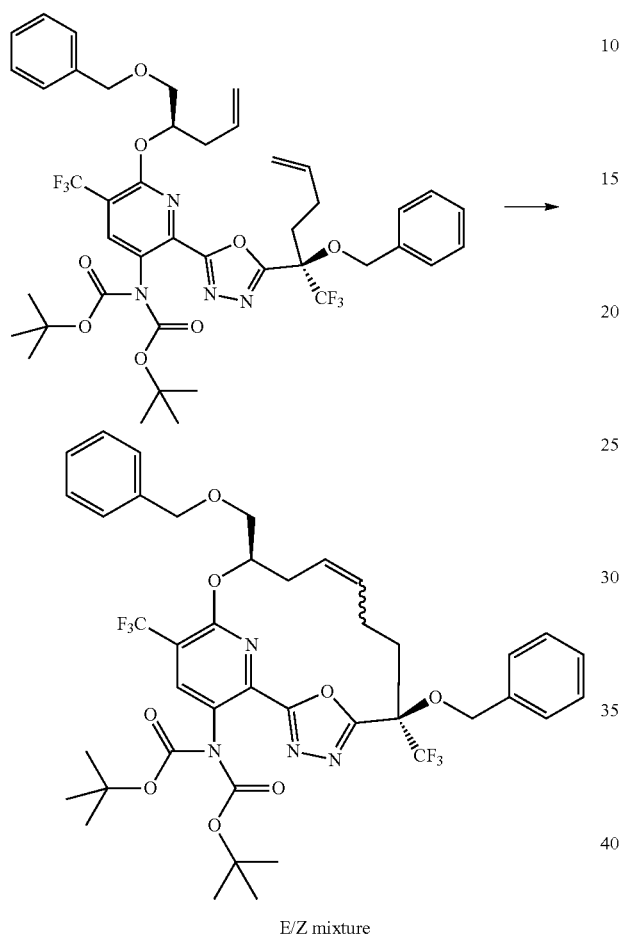

E/Z mixture

Nitrogen was bubbled throughout a solution of tert-butyl N-[6-[(1R)-1-(benzyloxymethyl)but-3-enoxy]-2-[5-[(1R)-1-benzyloxy-1-(trifluoromethyl)pent-4-enyl]-1,3,4-oxadiazol-2-yl]-5-(trifluoromethyl)-3-pyridyl]-N-tert-butoxycarbonyl-carbamate (200 mg, 0.2304 mmol) in DCE (62 mL) for 30 min. Zhan catalyst-1B (18 mg, 0.0245 mmol) was then added at rt, and nitrogen was bubbled again for 5 min. The light yellow solution was stirred at 60° C. (pre-heated oil bath) for 2.5 h. The brown solution was cooled to rt, then DMSO (~5 drops) was added to quench the catalyst. The solvent was removed under vacuum and the residue was dry-packed on silica with DCM. The product was purified by chromatography on a 40 g silica column (1-30% EtOAc/heptanes) to give tert-butyl N-[(6R,12R)-6-benzyloxy-12-(benzyloxymethyl)-6,15-bis(trifluoromethyl)-13,19-dioxa-3,4,18-triazatricyclo[12.3.1.12,5]nonadeca-1(17),2,4,9,14(18),15-hexaen-17-yl]-N-tert-butoxycarbonyl-carbamate (E/Z mixture) (134 mg, 46%) as a light yellow oil. ESI-MS m/z calc. 834.30634, Retention time: 4.54 minutes; LCMS Method: Kinetex Polar $C_{18}$ 3.0×50 mm 2.6 μm, 6 min, 5-95% acetonitrile in $H_2O$ (0.1% formic acid) 1.2 mL/min.

Palladium over charcoal (280 mg, 10% w/w, 0.2631 mmol) was added to a degassed solution of tert-butyl N-[(6R,12R)-6-benzyloxy-12-(benzyloxymethyl)-6,15-bis(trifluoromethyl)-13,19-dioxa-3,4,18-triazatricyclo[12.3.1.12,5]nonadeca-1(17),2,4,9,14(18),15-hexaen-17-yl]-N-tert-butoxy carbonyl-carbamate (E/Z mixture) (880 mg, 0.8296 mmol) in methanol (40 mL) at rt. The black suspension was degassed with nitrogen for 5 min, then hydrogen was bubbled throughout the suspension for 5 min. Then the mixture was stirred at room temperature for three days under a hydrogen atmosphere. The black suspension was filtered through Celite with DCM, and concentrated under vacuum to give crude tert-butyl N-tert-butoxy carbonyl-N-[(6R,12R)-6-hy droxy-12-(hydroxymethyl)-6,15-bis(trifluoromethyl)-13,19-dioxa-3,4,18-triazatricyclo[12.3.1.12,5]nonadeca-1(17),2,4,14(18),15-pentaen-17-yl]carbamate (630 mg, 87%) as a white solid. $^{19}F$ NMR (377 MHz, $CDCl_3$) δ −63.73 (s, 3F), −80.72 (s, 3F) ppm. ESI-MS m/z calc. 656.2281, found 501.0 $(M-155)^+$; Retention time: 3.47 minutes; LCMS Method: Kinetex Polar $C_{18}$ 3.0×50 mm 2.6 μm, 6 min, 5-95% acetonitrile in $H_2O$ (0.1% formic acid) 1.2 mL/min.

369

Step 5: (6R,12R)-17-Amino-12-(hydroxymethyl)-6,15-bis(trifluoromethyl)-13,19-dioxa-3,4,18-triazatricyclo[12.3.1.12,5]nonadeca-1(18),2,4,14,16-pentaen-6-ol, Compound 36

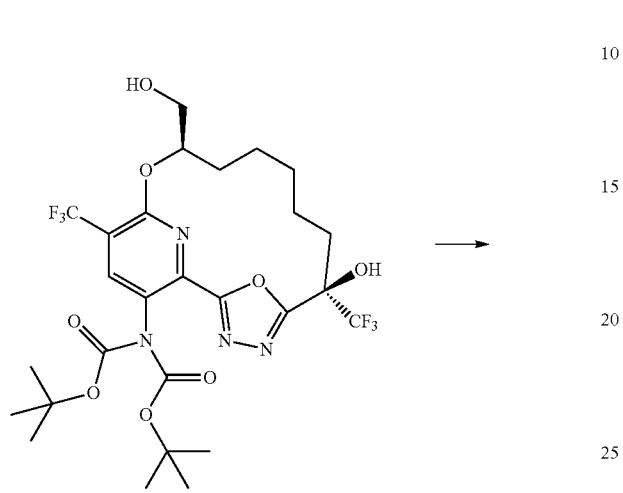

tert-Butyl N-tert-butoxycarbonyl-N-[(6R,12R)-6-hydroxy-12-(hydroxymethyl)-6,15-bis(trifluoromethyl)-13,19-dioxa-3,4,18-triazatricyclo[12.3.1.12,5]nonadeca-1(17),2,4,14(18),15-pentaen-17-yl]carbamate (630 mg, 0.7196 mmol) was dissolved in a solution of hydrogen chloride in 1,4-dioxane (4 mL of 4 M, 16.000 mmol) at rt. The solution was stirred at room temperature overnight. The solvent was evaporated under vacuum and the residual orange oil was purified by reverse phase chromatography over a 50 g $C_{18}$ column (5-80% acetonitrile/0.1% formic acid in water) to give (6R,12R)-17-amino-12-(hydroxymethyl)-6,15-bis(trifluoromethyl)-13,19-dioxa-3,4,18-triazatricyclo[12.3.1.12,5]nonadeca-1(18),2,4,14,16-pentaen-6-ol (199 mg, 59%) as a light yellow solid. $^1$H NMR (400 MHz, DMSO-$d_6$) δ 7.77 (s, 1H), 7.59 (s, 1H), 6.38 (br s, 2H), 4.68 (t, J=5.3 Hz, 1H), 4.65-4.57 (m, 1H), 3.68-3.56 (m, 2H), 2.28-2.05 (m, 3H), 1.69-1.30 (m, 7H) ppm. $^{19}$F NMR (377 MHz, DMSO-$d_6$) δ −62.23 (s, 3F), −79.01 (s, 3F) ppm. ESI-MS m/z calc. 456.12323, found 457.1 (M+1)$^+$; Retention time: 2.91 minutes; LCMS Method: Kinetex Polar $C_{18}$ 3.0×50 mm 2.6 μm, 6 min, 5-95% acetonitrile in $H_2O$ (0.1% formic acid) 1.2 mL/min.

370

Example 25: Preparation of (6R,12S)-17-amino-12-(hydroxymethyl)-6,15-bis(trifluoromethyl)-13,19-dioxa-3,4,18-triazatricyclo[12.3.1.12,5]nonadeca-1(18),2,4,14,16-pentaen-6-ol, Compound 37

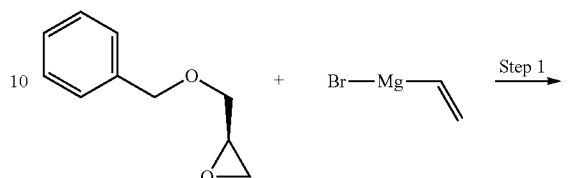

Step 1

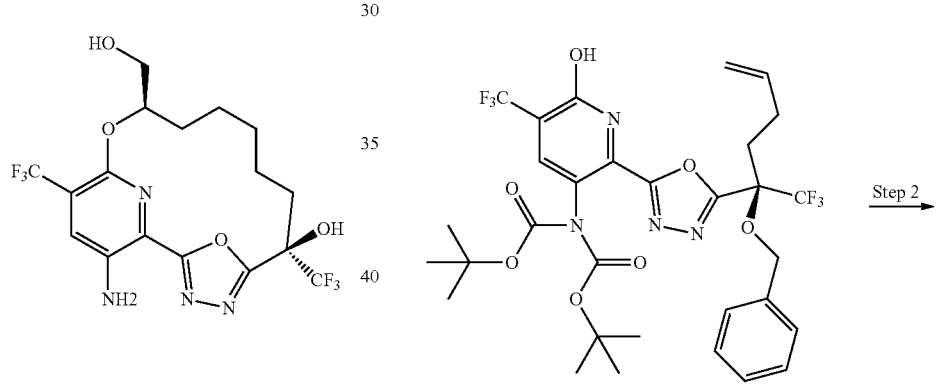

Step 2

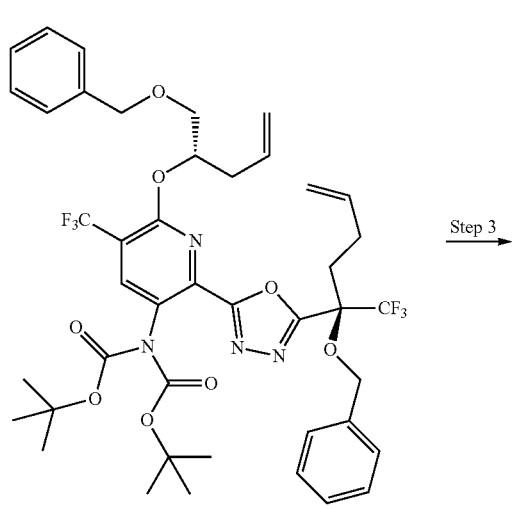

Step 3

371
-continued

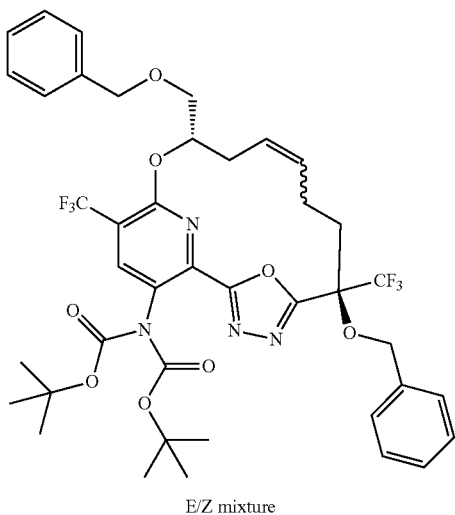

E/Z mixture

Step 4 →

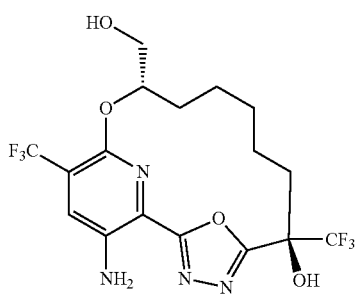

Step 5 →

372

Step 1: (2R)-1-Benzyloxypent-4-en-2-ol

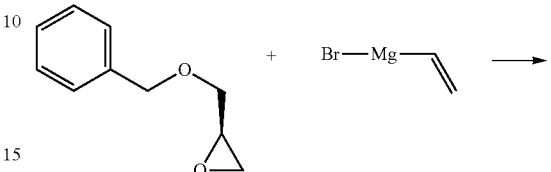

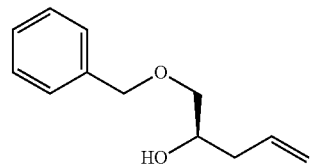

To a solution of bromo(vinyl)magnesium in THF (92 mL of 1 M, 92.000 mmol) was added copper bromide (870 mg, 6.0648 mmol) at 0° C., then the black mixture was stirred at −78° C. After 5 min, a solution of (2R)-2-(benzyloxymethyl) oxirane (5 g, 30.450 mmol) in THF (50 mL) was added dropwise with a dropping funnel over 15 min at −78° C. Then the black mixture was stirred at −78° C. for 40 min. Then methanol (13 mL) was added at −78° C., followed by aqueous hydrogen chloride (2M, 80 mL) and then stirred at room temperature for 5 min. MTBE (80 mL) was then added, the aqueous layer was separated and extracted with MTBE (2×40 mL). The organic layer was washed with aqueous hydrogen chloride (1M, 50 mL), water (50 mL), aqueous sodium thiosulfate (10%, 50 mL) and again with water (50 mL). The organic layer was dried over sodium sulfate, filtered and concentrated under vacuum to give a yellow oil (6.01 g). The crude oil was purified by chromatography over a 120 g silica column (1-50% MTBE/heptanes) to give (2R)-1-benzyloxypent-4-en-2-ol (5.89 g, 97%) as a light yellow oil. $^1$H NMR (400 MHz, CDCl$_3$) δ 7.42-7.28 (m, 5H), 5.84 (ddt, J=17.2, 10.1, 7.1 Hz, 1H), 5.20-5.05 (m, 2H), 4.57 (s, 2H), 3.90 (qd, J=6.7, 3.5 Hz, 1H), 3.53 (dd, J=9.5, 3.4 Hz, 1H), 3.39 (dd, J=9.5, 7.4 Hz, 1H), 2.35 (br s, 1H), 2.28 (t, J=6.7 Hz, 2H) ppm. ESI-MS m/z calc. 192.11504, found 193.2 (M+1)$^+$; Retention time: 2.51 minutes; LCMS Method: Kinetex Polar C$_{18}$ 3.0×50 mm 2.6 µm, 6 min, 5-95% acetonitrile in H$_2$O (0.1% formic acid) 1.2 mL/min.

373

Step 2: tert-Butyl N-[6-[(1S)-1-(benzyloxymethyl)but-3-enoxy]-2-[5-[(1R)-1-benzyloxy-1-(trifluoromethyl)pent-4-enyl]-1,3,4-oxadiazol-2-yl]-5-(trifluoromethyl)-3-pyridyl]-N-tert-butoxycarbonyl-carbamate

374

Step 3: tert-Butyl N-[(6R,12S)-6-benzyloxy-12-(benzyloxymethyl)-6,15-bis(trifluoromethyl)-13,19-dioxa-3,4,18-triazatricyclo[12.3.1.12,5]nonadeca-1(17),2,4,9,14(18),15-hexaen-17-yl]-N-tert-butoxycarbonyl-carbamate (E/Z Mixture)

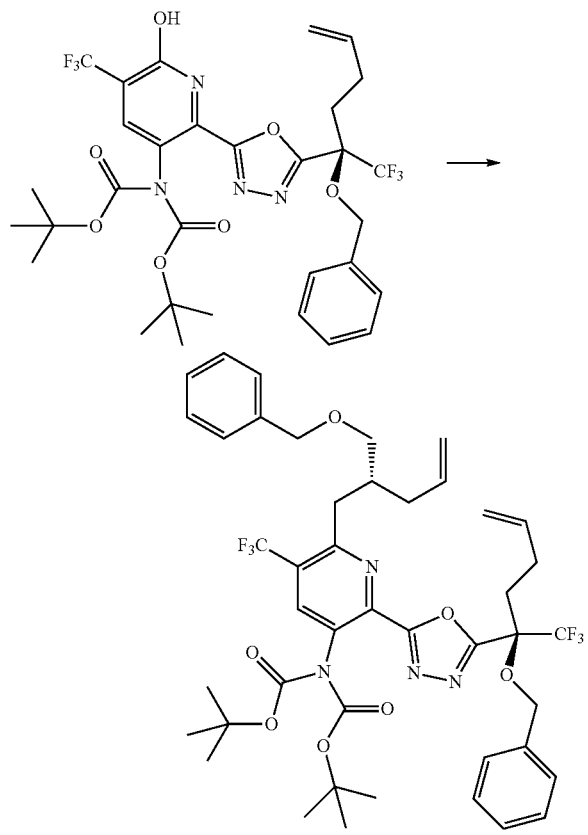

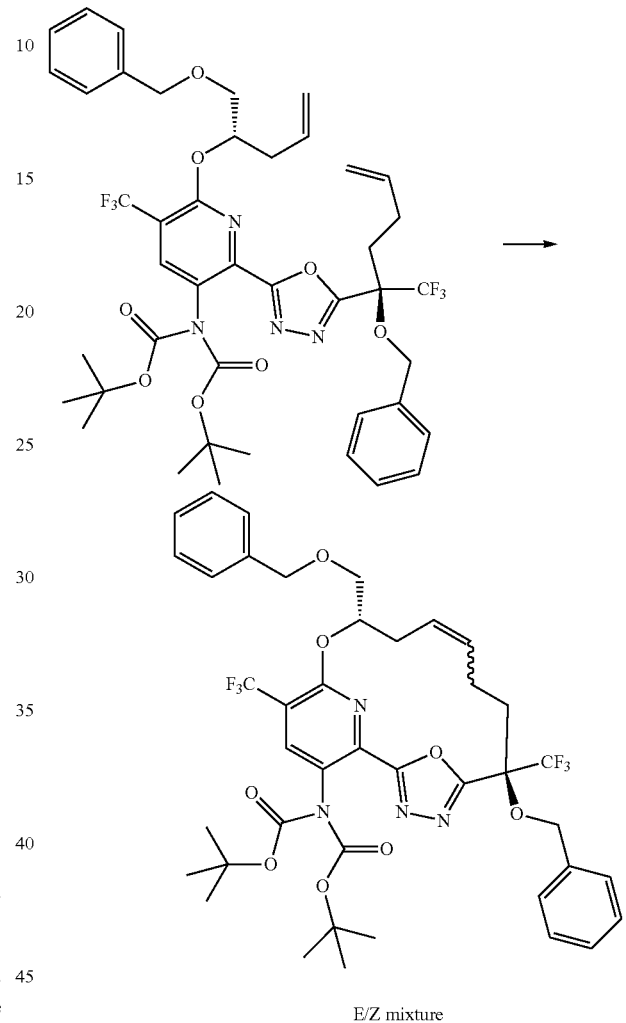

E/Z mixture

A solution of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (1 g, 1.4522 mmol) and (2R)-1-benzyloxypent-4-en-2-ol (837 mg, 4.3536 mmol) in toluene (10 mL) was treated with triphenylphosphine (796 mg, 3.0349 mmol) followed by DIAD (616.20 mg, 0.6 mL, 3.0474 mmol) at room temperature. The yellow solution was stirred at room temperature overnight. The yellow suspension was concentrated under vacuum, then dry-packed on silica with DCM. Purification by chromatography over a 120 g silica column (0-30% ethyl acetate in heptanes) gave tert-butyl N-[6-[(1S)-1-(benzyloxymethyl)but-3-enoxy]-2-[5-[(1R)-1-benzyloxy-1-(trifluoromethyl)pent-4-enyl]-1,3,4-oxadiazol-2-yl]-5-(trifluoromethyl)-3-pyridyl]-N-tert-butoxycarbonyl-carbamate (1.21 g, 96%) as a yellow oil. $^1$H NMR (400 MHz, CDCl$_3$) δ 7.85 (s, 1H), 7.41-7.27 (m, 10H), 5.85-5.69 (m, 2H), 5.59-5.52 (m, 1H), 5.14-4.94 (m, 4H), 4.80 (d, J=10.5 Hz, 1H), 4.62 (d, J=10.8 Hz, 1H), 4.60-4.51 (m, 2H), 3.78-3.64 (m, 2H), 2.65-2.14 (m, 6H), 1.43 (s, 18H) ppm. $^{19}$F NMR (377 MHz, CDCl$_3$) δ −64.05 (s, 3F), −73.00 (s, 3F) ppm. ESI-MS m/z calc. 862.33765, found 864.1 (M+1)$^+$; Retention time: 4.65 minutes; LCMS Method: Kinetex Polar C$_{18}$ 3.0×50 mm 2.6 μm, 6 min, 5-95% acetonitrile in H$_2$O (0.1% formic acid) 1.2 mL/min.

A stirring solution of tert-butyl N-[6-[(1S)-1-(benzyloxymethyl)but-3-enoxy]-2-[5-[(1R)-1-benzyloxy-1-(trifluoromethyl)pent-4-enyl]-1,3,4-oxadiazol-2-yl]-5-(trifluoromethyl)-3-pyridyl]-N-tert-butoxycarbonyl-carbamate (1.21 g, 1.3911 mmol) in 1,2-dichloroethane (500 mL) was degassed with bubbling with nitrogen gas for 20 hours. To the solution was added Zhan catalyst-1B (118 mg, 0.1608 mmol) then the reaction was heated in an oil bath set at 60° C. for 5.5 hours. Once cooled at room temperature, the catalyst was quenched with a few drops of DMSO (about 5-6 drops) and the reaction was concentrated under reduced pressure. The residue was dry loaded on silica gel and purified by silica gel liquid chromatography eluting from 0% to 30% ethyl acetate in heptane, to afford tert-butyl N-[(6R,12S)-6-benzyloxy-12-(benzyloxymethyl)-6,15-bis(trifluoromethyl)-13,19-dioxa-3,4,18-triazatricyclo[12.3.1.12,5]nonadeca-1(17),2,4,9,14(18),15-hexaen-17-yl]-N-tert-butoxycarbonyl-carbamate (E/Z mixture)(543 mg, 45%) as colorless oil. $^1$H NMR (400 MHz, CDCl$_3$) δ 7.93-7.84 (m, 1H), 7.42-7.23 (m, 10H), 5.65-5.40 (m, 2H), 5.16-4.93 (m, 1H), 4.76-4.67 (m, 3H), 4.67-4.44 (m, 1H), 3.91-3.71 (m, 2H), 3.54-3.43 and 2.83-2.70 (m, 1H), 2.65-2.08 (m, 5H), 1.53-1.38 (m, 18H) ppm. $^{19}$F NMR (377 MHz, CDCl$_3$) δ −63.45 to −63.84 (m, 3F), −73.75 to −74.24 (m, 3F) ppm. Retention time: 4.51 minutes; LCMS Method: Kinetex Polar C$_{18}$ 3.0×50 mm 2.6 μm, 6 min, 5-95% acetonitrile in H$_2$O (0.1% formic acid), flow=1.2 mL/min.

Step 4: tert-Butyl N-tert-butoxycarbonyl-N-[(6R, 12S)-6-hydroxy-12-(hydroxymethyl)-6,15-bis(trifluoromethyl)-13,19-dioxa-3,4,18-triazatricyclo[12.3.1.1$^{2,5}$]nonadeca-1(17),2,4,14(18),15-pentaen-17-yl]carbamate

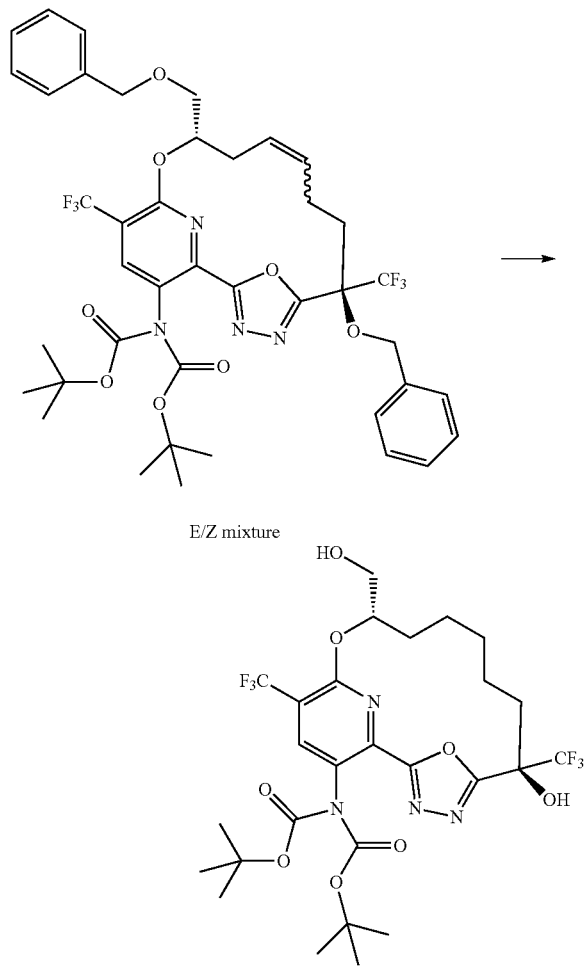

E/Z mixture

Palladium over charcoal (214 mg, 10% w/w, 0.2011 mmol) was added to a degassed solution of tert-butyl N-[(6R,12S)-6-benzyloxy-12-(benzyloxymethyl)-6,15-bis(trifluoromethyl)-13,19-dioxa-3,4,18-triazatricyclo [12.3.1.1$^{2,5}$]nonadeca-1(17),2,4,9,14(18),15-hexaen-17-yl]-N-tert-butoxy carbonyl-carbamate (E/Z mixture) (543 mg, 0.6264 mmol) in methanol (25 mL) at room temperature. The black suspension was degassed with nitrogen for 5 min, then hydrogen was bubbled through the suspension for 5 min. Then the mixture was stirred at room temperature overnight under hydrogen atmosphere. The black suspension was filtered through Celite with DCM, and concentrated under vacuum to give crude tert-butyl N-tert-butoxycarbonyl-N-[(6R,12S)-6-hydroxy-12-(hydroxymethyl)-6,15-bis(trifluoromethyl)-13,19-dioxa-3,4,18-triazatricyclo [12.3.1.1$^{2,5}$]nonadeca-1(17),2,4,14(18),15-pentaen-17-yl] carbamate (446 mg, 96%) as a light yellow oil. $^{1}$H NMR (400 MHz, CDCl$_3$) δ 7.88 (s, 1H), 4.92-4.83 (m, 1H), 3.96-3.82 (m, 2H), 3.60 (br. s, 1H), 2.59-2.47 (m, 1H), 2.38-2.12 (m, 3H), 2.08-1.93 (m, 2H), 1.73-1.33 (m, 23H) ppm. $^{19}$F NMR (377 MHz, CDCl$_3$) δ −63.78 (s, 3F), −77.56 (s, 3F) ppm. ESI-MS m/z calc. 656.2281, found (M+)+; 501.1 (M−155)+; Retention time: 3.54 minutes; LCMS Method: Kinetex Polar C$_{18}$, 3.0×50 mm 2.6 μm, 6 min, 5-95% acetonitrile in H$_2$O (0.1% formic acid), flow=1.2 mL/min.

Step 5: (6R,12S)-17-Amino-12-(hydroxymethyl)-6,15-bis(trifluoromethyl)-13,19-dioxa-3,4,18-triazatricyclo[12.3.1.1$^{2,5}$]nonadeca-1(18),2,4,14,16-pentaen-6-ol, Compound 37

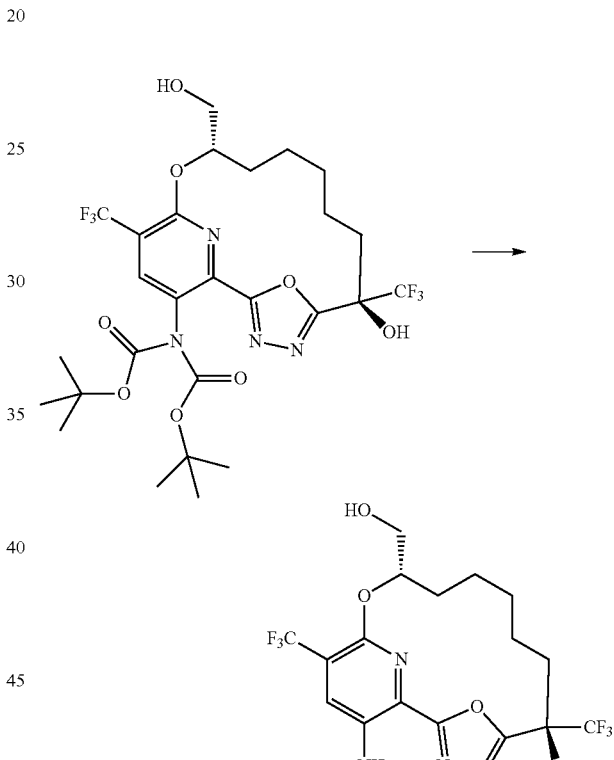

To a 0° C. stirring solution of tert-butyl N-tert-butoxycarbonyl-N-[(6R,12S)-6-hydroxy-12-(hydroxymethyl)-6,15-bis(trifluoromethyl)-13,19-dioxa-3,4,18-triazatricyclo [12.3.1.1$^{2,5}$]nonadeca-1(17),2,4,14(18),15-pentaen-17-yl] carbamate (65 mg, 0.0483 mmol) in 1,4-dioxane (2 mL) was added dropwise a solution of HCl in 1,4-dioxane (0.5 mL of 4 M, 2.0000 mmol). The ice-water cooling bath was removed 2 minutes after the addition and the mixture was stirred at room temperature overnight. Then, more HCl solution in 1,4-dioxane (1.5 mL of 4 M, 6.0000 mmol) was added at room temperature and stirring continued for 4 hours. The volatiles were removed by evaporation under reduced pressure and HCl (2 mL of 4 M, 8.0000 mmol) was added at room temperature. The mixture was stirred overnight with gentle heating at 30° C. The volatiles were removed by evaporation under reduced pressure. The crude was solubilized in dichloromethane (3 mL) and was further-more concentrated by evaporation under reduced pressure. Combined lots of crude (6R,12S)-17-amino-12-(hydroxymethyl)-6,15-bis(trifluoromethyl)-13,19-dioxa-3,4,18-triazatricyclo[12.3.1.1²,⁵]nonadeca-1(18),2,4,14,16-pentaen-6-ol were purified by reverse phase $C_{18}$ chromatography on a 50 g column, eluting with a gradient of acetonitrile (0-50%) in water containing 0.1 w/w % of formic acid. Pure fractions were combined and concentrated by evaporation under reduced pressure, then transferred in a 25 mL flask and submitted for freeze-drying (acetonitrile/water) overnight to finally isolate (6R,12S)-17-amino-12-(hydroxymethyl)-6,15-bis(trifluoromethyl)-13,19-dioxa-3,4,18-triazatricyclo[12.3.1.1²,⁵]nonadeca-1(18),2,4,14,16-pentaen-6-ol (127 mg, 49%) as light yellow solid. $^1$H NMR (400 MHz, DMSO-$d_6$) δ 7.77 (s, 1H), 7.58 (s, 1H), 6.44-6.27 (m, 2H), 4.78-4.60 (m, 2H), 3.74-3.52 (m, 2H), 2.35-2.24 (m, 1H), 2.21-2.08 (m, 2H), 1.82-1.33 (m, 7H). $^{19}$F NMR (377 MHz, DMSO-$d_6$) δ −62.24 (s, 3F), −76.43 (s, 3F) ppm. ESI-MS m/z calc. 456.12323, found 457.1 (M+1)$^+$; Retention time: 3.02 minutes; LCMS Method: Kinetex Polar $C_{18}$ 3.0×50 mm 2.6 μm, 6 min, 5-95% acetonitrile in $H_2O$ (0.1% formic acid), flow=1.2 mL/min.

Example 26: Preparation of (6R,12R)-17-amino-9,10-dideuterio-12-methyl-6,15-bis(trifluoromethyl)-13,19-dioxa-3,4,18-triazatricyclo[12.3.1.1²,⁵]nonadeca-1(18),2,4,14,16-pentaen-6-ol, Compound 38

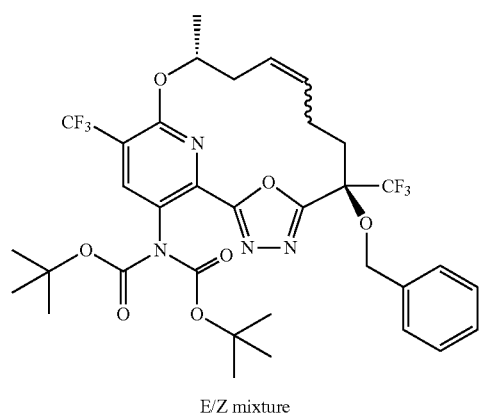

E/Z mixture

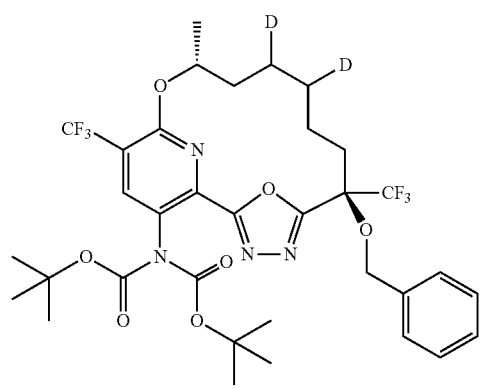

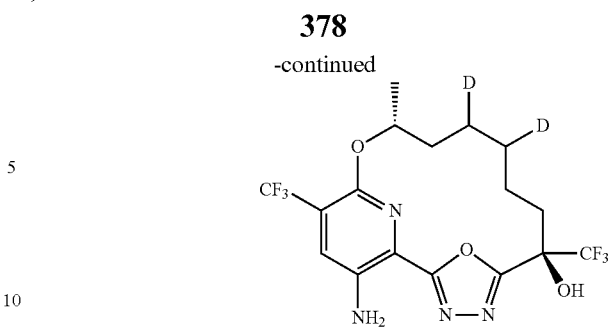

Step 1: tert-Butyl N-tert-butoxycarbonyl-N-[(6R,12R)-9,10-dideuterio-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate

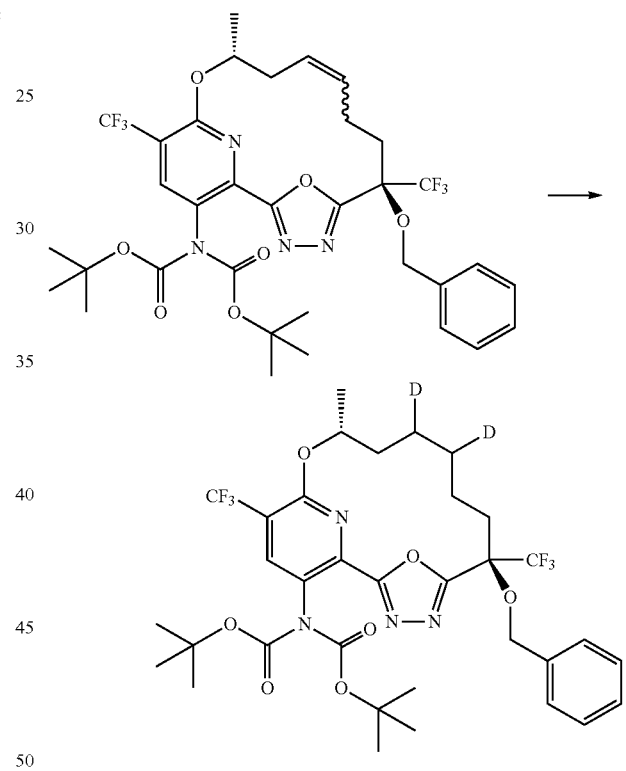

To a solution of tert-butyl N-[(6R,12R)-6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaen-17-yl]-N-tert-butoxycarbonyl-carbamate (E/Z mixture) (200 mg, 0.2745 mmol) in $CD_3OD$ (8 mL) under nitrogen was added 10% palladium on carbon (50 mg, 0.0470 mmol). Nitrogen was replaced with deuterium gas through vacuum for 3 times. The mixture was stirred at room temperature under deuterium atmosphere (balloon) overnight. The mixture was filtered through diatomaceous earth and washed EtOAc and concentrated to give tert-butyl N-tert-butoxycarbonyl-N-[(6R,12R)-9,10-dideuterio-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (184 mg, 100%) as a colorless oil. $^1$H NMR (400 MHz, $CDCl_3$) δ 7.82 (s, 1H), 4.97-4.86 (m, 1H), 3.72-3.54

(m, 1H), 2.71-2.59 (m, 1H), 2.34-2.24 (m, 1H), 2.21-2.11 (m, 1H), 2.08-1.96 (m, 1H), 1.67-1.19 (m, 25H) ppm. $^{19}$F NMR (377 MHz, CDCl$_3$) δ −63.99 (s, 3F), −77.58 (s, 3F) ppm.

Step 2: (6R,12R)-17-Amino-9,10-dideuterio-12-methyl-6,15-bis(trifluoromethyl)-13,19-dioxa-3,4,18-triazatricyclo[12.3.1.12,5]nonadeca-1(18),2,4,14,16-pentaen-6-ol, Compound 38

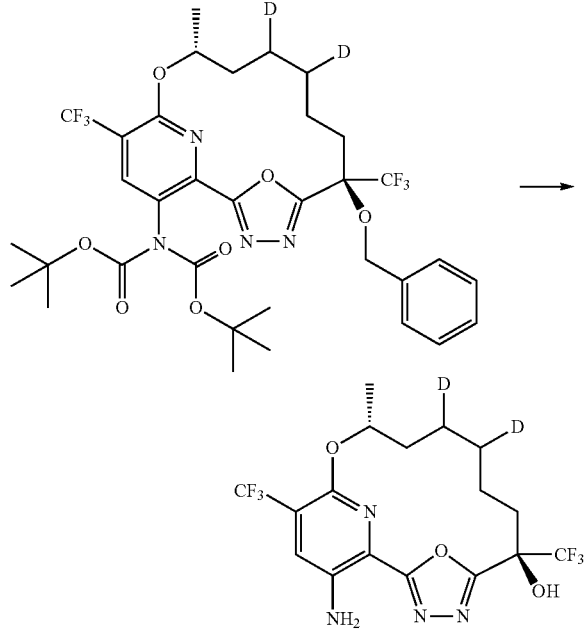

To a solution of tert-butyl N-tert-butoxycarbonyl-N-[(6R,12R)-9,10-dideuterio-6-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (184 mg, 0.2749 mmol) in CH$_2$Cl$_2$ (2 mL) was added TFA (2.9600 g, 2 mL, 25.960 mmol). The mixture was stirred at room temperature for 1.5 h. The mixture was concentrated and co-evaporated with EtOAc (3×5 mL). The residue was dissolved in EtOAc (20 mL), washed with saturated NaHCO$_3$ (5 mL) and dried with Na$_2$SO$_4$, filtered and concentrated. The residue was purified by silica gel chromatography (24 g SiO$_2$, eluting 0 to 30% EtOAc/heptanes) and the product was dissolved in minimum of acetonitrile and water and freeze-dried overnight to afford (6R,12R)-17-amino-9,10-dideuterio-12-methyl-6,15-bis(trifluoromethyl)-13,19-dioxa-3,4,18-triazatricyclo[12.3.1.12,5]nonadeca-1(18),2,4,14,16-pentaen-6-ol (103 mg, 83%) as a yellow solid. ESI-MS m/z calc. 442.1409, found 443.1 (M+1)$^+$; Retention time: 3.63 minutes. $^1$H NMR (400 MHz, DMSO-d$_6$) δ 7.76 (s, 1H), 7.57 (s, 1H), 6.35 (s, 2H), 4.84-4.74 (m, 1H), 2.49-2.42 (m, 1H), 2.33-2.21 (m, 1H), 2.15-2.04 (m, 1H), 1.77-1.65 (m, 1H), 1.56-1.36 (m, 3H), 1.34 (d, J=6.4 Hz, 3H), 1.25-1.12 (m, 1H) ppm. $^{19}$F NMR (377 MHz, DMSO-d$_6$) δ −62.50 (s, 3F), −76.38 (br s, 3F) ppm. ESI-MS m/z calc. 442.14087, found 443.1 (M+1)$^+$; Retention time: 3.63 minutes; LCMS Method: Kinetex Polar C$_{18}$ 3.0×50 mm 2.6 μm, 6 min, 5-95% acetonitrile in H$_2$O (0.1% formic acid) 1.2 mL/min.

Example 27: Preparation of (6R,12R)-17-amino-11,11,12-trideuterio-12-(trideuteriomethyl)-6,15-bis(trifluoromethyl)-13,19-dioxa-3,4,18-triazatricyclo[12.3.1.12,5]nonadeca-1(18),2,4,14,16-pentaen-6-ol, Compound 39

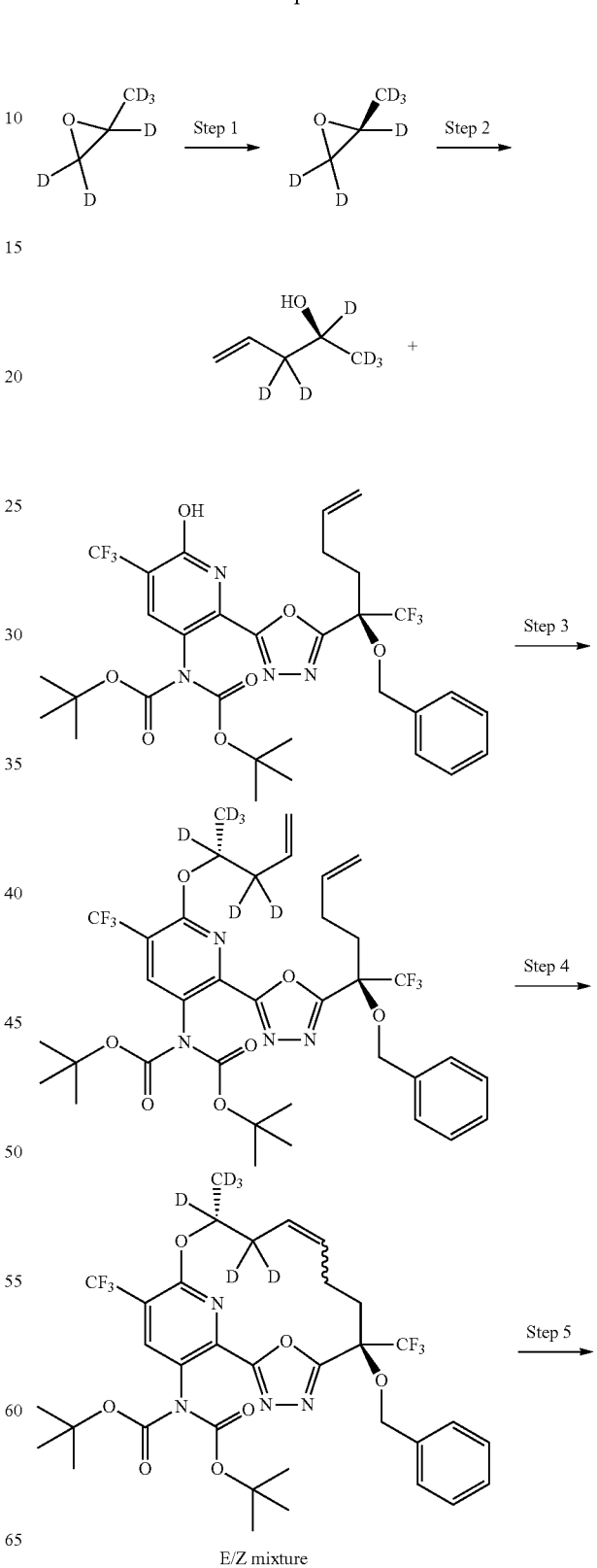

-continued

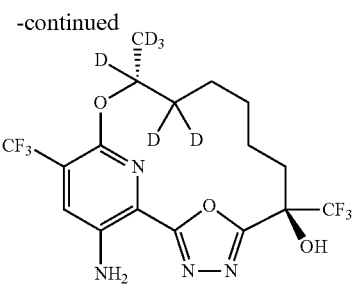

Step 1: (S)-2-(Methyl-d3)oxirane-2,3,3-d₃

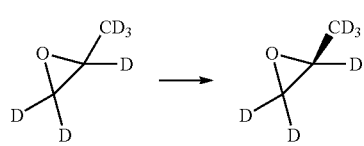 [SMILES: [2H]C([2H])([2H])C1([2H])OC1([2H])[2H] ; [2H]C([2H])([2H])[C@]1([2H])OC1([2H])[2H]]

Acetic acid (0.94 mL, 16.41 mmol, 0.021 eq.) was added to a solution of (1S,2S)-(+)-[1,2-cyclohexanediamino-N,N'-bis-(3,5-di-tert-butylsalicylidene)]cobalt(II) ((S,S)-Co (salen) Jacobsen catalyst) (0.943 g, 1.56 mmol) in toluene (25 mL). The resulting solution was stirred at room temperature open to air for 30 minutes over which time the color changed from orange-red to dark-brown. The solution was concentrated under reduced pressure to give a crude brown solid. Racemic 2-(methyl-d₃)oxirane-2,3,3-d₃ (50 g, 781.25 mmol, 1 equiv) was added to dissolve the crude catalyst at room temperature and then cooled in an ice bath to 0° C. Deuterium oxide (8.6 mL, 429.69 mmol, 0.55 equiv) was added dropwise over 10 minutes. The reaction mixture was allowed to warm to room temperature and stirred overnight. Distillation of the mixture under atmosphere pressure gave (S)-2-(methyl-d₃)oxirane-2,3,3-d₃ (17.23 g, boiling point=31.5-34.5° C., 34.5% yield) as a colorless oil which was stored in a freezer.

Step 2: (S)-Pent-4-en-1,1,1,2,3,3-d₆-2-ol

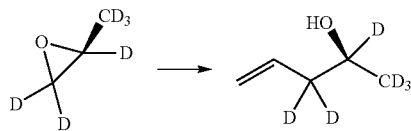

A solution of 1M vinyl magnesium bromide in THF (100 mL, 100 mmol) was added dropwise while maintaining the temperature below −10° C. to a mixture of copper(I) chloride (0.20 g, 2 mmol) and lithium chloride (0.17 g, 4 mmol) in anhydrous THF (40 mL). The mixture was stirred at −5 to −10° C. for 15 minutes, and then cooled to −15° C. A solution of (S)-2-(methyl-d₃)oxirane-2,3,3-d₃ (6.4 g, 100 mmol) in anhydrous THF (100 mL) was added dropwise while maintaining the temperature below −5° C. The resulting mixture was stirred at −10° C. to 0° C. for 4 hours. Saturated ammonium chloride in deuterium oxide (50 mL) was added slowly to quench the reaction while maintaining the temperature below 10° C. Deuterium oxide (50 mL) was added and the mixture was stirred in an ice bath for 30 minutes. The layers were separated, and the organic layer was washed with a saturated ammonium chloride in deuterium oxide (30 mL). The combined aqueous layers were extracted with diethyl ether (3×50 mL). The combined organic layers were washed with saturated brine (50 mL), dried over sodium sulfate, filtered and concentrated by distillation under atmosphere pressure to give the desired (S)-pent-4-en-1,1,1,2,3,3-d6-2-ol as a colorless oil (Fraction A: 1.29 g, boiling point=80-100° C.; Fraction B: 2.27 g, boiling point=100-80° C.; Fraction C: 0.40 g, boiling point=80-65° C., 40% combined yield). ¹H NMR indicated that fraction A contained 0.25 molar ratio of THF, both fraction B and C were solvent free. Additional compound (S)-2-(methyl-d₃)oxirane-2,3,3-d₃ (2×5 g) was processed as described above to give compound (S)-pent-4-en-1,1,1,2,3,3-d6-2-ol as a colorless oil (Fraction A: 1.46 g, boiling point=75-95° C.; Fraction B: 4.30 g, boiling point=95-100-75° C.; Fraction C: 0.83 g, boiling point=80-65° C., 40% combined yield). ¹H NMR indicated that fraction A contained 0.50 molar ratio of THF, both fraction B and C were solvent free.

Step 3: tert-Butyl N-[2-[5-[(1R)-1-benzyloxy-1-(trifluoromethyl)pent-4-enyl]-1,3,4-oxadiazol-2-yl]-6-[(1R)-1,2,2-trideuterio-1-(trideuteriomethyl)but-3-enoxy]-5-(trifluoromethyl)-3-pyridyf]-N-tert-butoxycarbonyl-carbamate

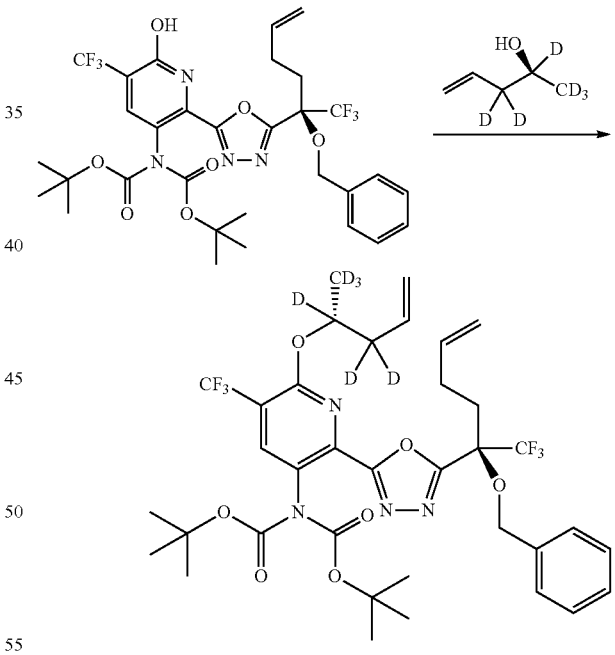

A solution of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (6.2 g, 9.04 mmol), triphenylphosphine (2.9 g, 10.9 mmol) and (S)-pent-4-en-1,1,1,2,3,3-d₆-2-ol (1.0 g, 10.9 mmol) in toluene (45.0 mL) was stirred under a nitrogen atmosphere was heated to 45° C. Diisopropyl azodicarboxylate (2.3 mL, 11.8 mmol) was added slowly over 20 minutes, maintaining an internal temperature of less than 55° C. The reaction mixture was cooled to room temperature and diluted with ethyl acetate (50 mL) and water (50 mL). The organic layer was separated, washed with water (50 mL), saturated brine (50 mL), dried over sodium sulfate, filtered and concentrated under reduced pressure. The crude product was purified by silica gel chromatography (120 g SiO$_2$), eluting with a gradient of 0 to 10% ethyl acetate in hexanes to give tert-butyl N-[2-[5-[(1R)-1-benzyloxy-1-(trifluoromethyl)pent-4-enyl]-1,3,4-oxadiazol-2-yl]-6-[(1R)-1,2,2-trideuterio-1-(trideuteriomethyl)but-3-enoxy]-5-(trifluoromethyl)-3-pyridyl]-N-tert-butoxycarbonyl-carbamate as a clear, colorless oil (5.7 g, 83% yield). $^1$H NMR (400 MHz, DMSO-d$_6$) δ 8.56 (d, J=0.7 Hz, 1H), 7.44-7.29 (m, 5H), 5.92-5.70 (m, 2H), 5.10 (dd, J=4.5, 1.9 Hz, 1H), 5.06 (dd, J=4.5, 1.9 Hz, 1H), 5.01 (ddd, J=9.7, 7.7, 1.9 Hz, 2H), 4.77 (d, J=11.1 Hz, 1H), 4.67 (d, J=11.1 Hz, 1H), 2.63-2.52 (m, 1H), 2.47 (d, J=15.0 Hz, 1H), 2.27 (ddt, J=16.0, 10.4, 6.0 Hz, 2H), 1.28 (d, J=12.6 Hz, 18H) ppm. $^2$H NMR (400 MHz, DMSO) δ 5.33 (bs, 1D), 1.28 (s, 6D) ppm. $^{19}$F NMR (400 MHz, DMSO-d$_6$) δ −62.70, −73.26 ppm. ESI-MS m/z calc. 762.33, found 785.3 (M+Na)$^+$; Retention time: 14.5 minutes. Final purity was determined by reversed phase HPLC using an Atlantis T3, 3 μm, 2.1×50 mm made by Waters (pn: 186003717), and a dual gradient run from 5-95% mobile phase B over 14 minutes with a 4 min hold at 95% B. Mobile phase A=H$_2$O (0.1% CF$_3$CO$_2$H). Mobile phase B=acetonitrile (0.1% CF$_3$CO$_2$H). Flow rate=0.7 mL/min, injection volume=2 μL and column temperature=40° C.

Step 4: tert-Butyl N-[(6R,12R)-6-benzyloxy-11,11,12-trideuterio-12-(trideuteriomethyl)-6,15-bis(trifluoromethyl)-13,19-dioxa-3,4,18-triazatricyclo[12.3.1.1 2,5]nonadeca-1(18),2,4,9,14,16-hexaen-17-yl]-N-tert-butoxycarbonyl-carbamate (E/Z Mixture)

In a 3-necked flask charged with stirring bar, a gas dispersion needle, a condenser and a bubbler, tert-butyl N-[2-[5-[(1R)-1-benzyloxy-1-(trifluoromethyl)pent-4-enyl]-1,3,4-oxadiazol-2-yl]-6-[(1R)-1,2,2-trideuterio-1-(trideuteriomethyl)but-3-enoxy]-5-(trifluoromethyl)-3-pyridyl]-N-tert-butoxycarbonyl-carbamate (5.4 g, 7.079 mmol) in DCE (810 mL, 0.009 M) was purged with N$_2$ for 1 hour. The mixture was heated to 75° C., then benzylidene-bis(tricyclohexylphosphine)dichlororuthenium (1.201 g, 1.416 mmol) was added as a solid. The reaction was stirred at 75° C. with N$_2$ purging. After 5 hours additional benzylidene-bis(tricyclohexylphosphine)dichlororuthenium (0.45 g, 0.531 mmol) was added and the mixture was heated at 75° C. for 2 additional hours. The internal temperature was decreased to 50° C., and 2-sulfanylpyridine-3-carboxylic acid (1.091 g, 7.033 mmol, 0.993 equiv.) was added followed by triethylamine (0.72 g, 7.115 mmol) and the reaction temperature was set to 45° C. The material was allowed to stir overnight. The mixture was removed from heating and 13 g of silica gel was added and stirred for 0.5 h at ambient temperature. The mixture was filtered over Celite, rinsed with DCE, and concentrated under reduced pressure. To the residue was added DCM/heptane (1:3, 50 mL), followed by filtration and the insoluble precipitate was washed with heptane. The filtrate was concentrated to give the crude material. The crude compound was dissolved in DCM/heptane (1:1, 4 vols), and chromatographed on a 120 g normal phase silica column using a gradient of 0% to 5% EtOAc/hexanes over 13 min, followed by a gradient of 5% EtOAc for 23 min affording the crude product as colorless oil. The collected oil was then dissolved in MeOH (3 vols) and loaded onto a 50 g C$_{18}$ reverse phase column which was eluted using a gradient of 40% to 100% acetonitrile/water over 20 min. The resulting pure fractions were concentrated and dried under house vacuum overnight to give tert-butyl N-[(6R,12R)-6-benzyloxy-11,11,12-trideuterio-12-(trideuteriomethyl)-6,15-bis(trifluoromethyl)-13,19-dioxa-3,4,18-triazatricyclo[12.3.1.1 2,5]nonadeca-1(18),2,4,9,14,16-hexaen-17-yl]-N-tert-butoxycarbonyl-carbamate (E/Z mixture) as a white foam (2.21 g, 42.5%) which was used directly in the next step.

Step 5: (6R,12R)-17-Amino-11,11,12-trideuterio-12-(trideuteriomethyl)-6,15-bis(trifluoromethyl)-13,19-dioxa-3,4,18-triazatricyclo[12.3.1.1 2,5]nonadeca-1(18),2,4,14,16-pentaen-6-ol, Compound 39

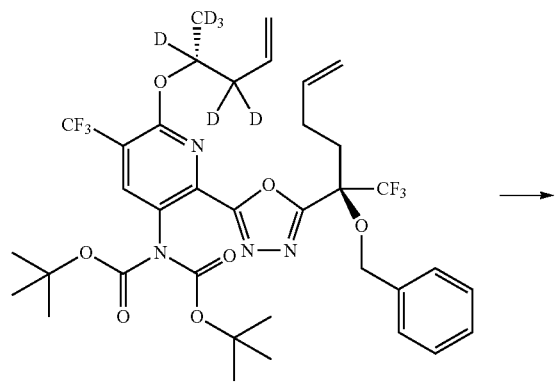

E/Z mixture

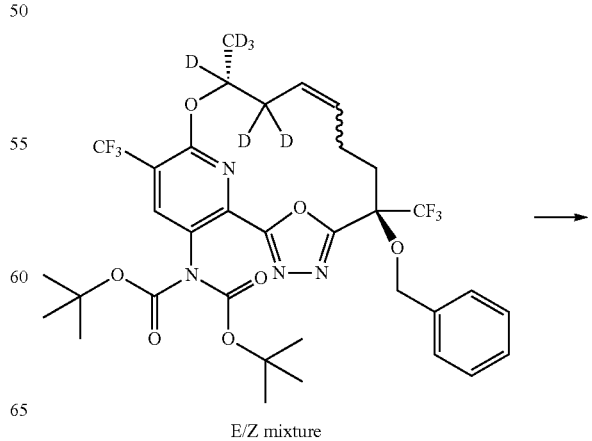

E/Z mixture

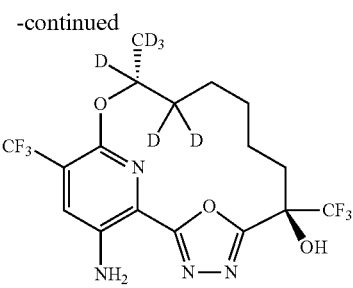

tert-Butyl N-[(6R,12R)-6-benzyloxy-11,11,12-trideuterio-12-(trideuteriomethyl)-6,15-bis(trifluoromethyl)-13,19-dioxa-3,4,18-triazatricyclo[12.3.1.1 2,5]nonadeca-1(18),2,4,9,14,16-hexaen-17-yl]-N-tert-butoxycarbonyl-carbamate (E/Z mixture) (2.21 g, 3.008 mmol) was dissolved in EtOH (44.2 mL, 0.068 M), and the vacuum and nitrogen was cycled 3X then treated with 10% Pd/C (50% wet palladium) (0.445 g, 4.181 mmol). The mixture was stirred at ambient temperature under a hydrogen balloon for 23 h. The vacuum and hydrogen was cycled 3×, then filtered over Celite, washed with ethanol and evaporated under reduced pressure to give the crude tert-butyl N-tert-butoxycarbonyl-N-[(6R,12R)-11,11,12-trideuterio-6-hydroxy-12-(trideuteriomethyl)-6,15-bis(trifluoromethyl)-13,19-dioxa-3,4,18-triazatricyclo[12.3.1.1 2,5]nonadeca-1(18),2,4,14,16-pentaen-17-yl]carbamate. The white foam was dissolved in DCM (17.68 mL, 0.17 M), cooled in an ice bath and treated with trifluoroacetic acid (5.294 mL, 69.182 mmol) under $N_2$. Then the ice bath was removed and the pale yellow solution was stirred for 2 h. The yellow solution was diluted with heptane (10 mL), filtered, and the filtrate was evaporated under reduced pressure. The crude material was treated with DCM (2.4 mL) in 50° C. water bath, then the yellow clear solution was diluted with hot (60° C.) heptane (12 mL), stirred in the warm water bath and allowed to slowly cool to ambient. The formed suspension was stirred at ambient temperature overnight, and the white solid was collected and rinsed with heptane to give the first crop of product. The compound was dried in the vacuum oven at 40° C. purging with nitrogen overnight. The mother liquor was concentrated and loaded on a $C_{18}$ reverse phase chromatography (50 g) eluting with acetonitrile/water (30-80%) over 25 min. The obtained pale yellow solid was treated with hot DCM/heptane (1 mL/5 mL) then allowed to cool to ambient temperature overnight. The formed solid was collected and rinsed with heptane to give 0.5 g of product as the second crop. The combined crops were dried in the vacuum oven at 45° C. under nitrogen $N_2$ giving the off-white solid (6R,12R)-17-amino-11,11,12-trideuterio-12-(trideuteriomethyl)-6,15-bis(trifluoromethyl)-13,19-dioxa-3,4,18-triazatricyclo[12.3.1.1 2,5]nonadeca-1(18),2,4,14,16-pentaen-6-ol (1.14 g, 84.9%). $^1$H NMR (400 MHz, DMSO-$d_6$) δ 7.76 (s, 1H), 7.58 (s, 1H), 6.35 (s, 2H), 2.29 (t, J=11.7 Hz, 1H), 2.16 2.04 (m, 1H), 1.73 (s, 2H), 1.56 1.44 (m, 1H), 1.44 (s, 3H) ppm. ESI-MS m/z calc. 446.166, found 447.225 (M+1)$^+$; Retention time: 2.895 minutes. Final purity was determined by reversed phase UPLC using an Acquity UPLC BEH $C_{18}$ column (50×2.1 mm, 1.7 μm particle) made by Waters (pn: 186002350), and a dual gradient run from 1-99% mobile phase B over 4.5 minutes. Mobile phase A=$H_2O$ (0.05% $CF_3CO_2H$). Mobile phase B=acetonitrile (0.035% $CF_3CO_2H$). Flow rate=1.2 mL/min, injection volume=1.5 μL, and column temperature=60° C.

Example 28: Preparation of (6R,12R)-17-amino-12-methyl-6,15-bis(trifluoromethyl)-13,19-dioxa-3,4,18-triazatricyclo[12.3.1.1 2,5]nonadeca-1(18),2,4,14,16-pentaene-6,11-diol (diastereomer 1), Compound 40, and (6R,12R)-17-amino-12-methyl-6,15-bis(trifluoromethyl)-13,19-dioxa-3,4,18-triazatricyclo[12.3.1.1 2,5]nonadeca-1(18),2,4,14,16-pentaene-6,11-diol (diastereomer 2), Compound 41

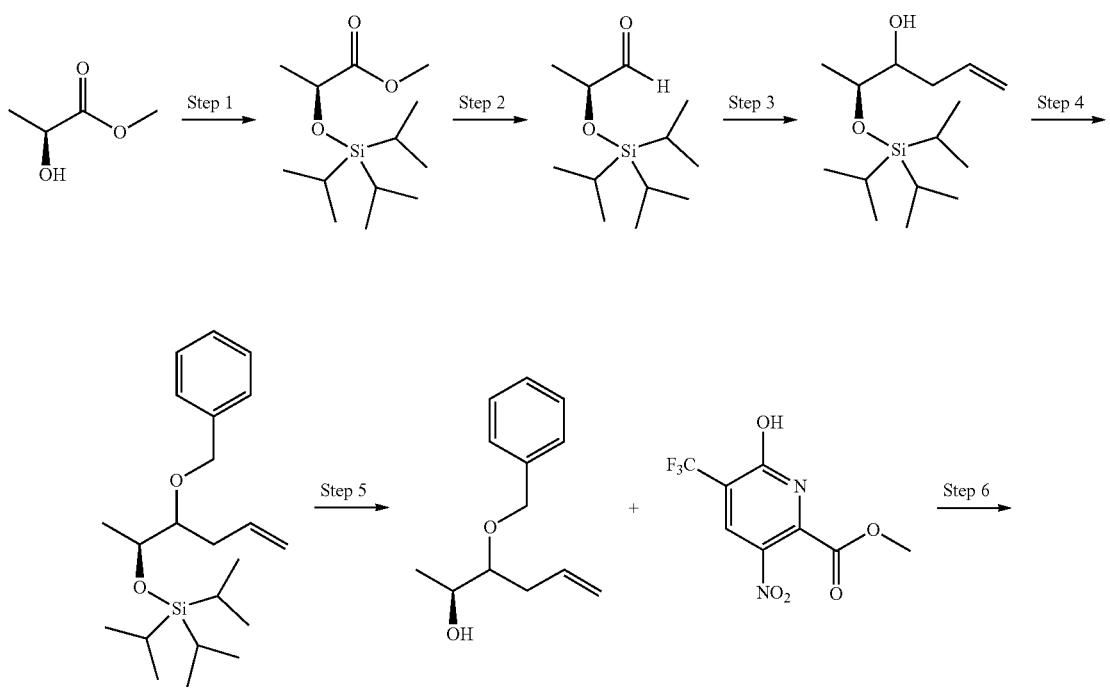

387
388
-continued
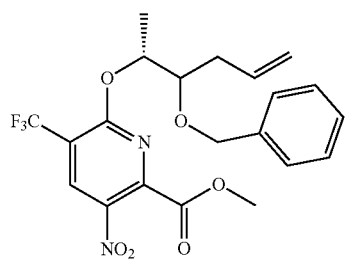 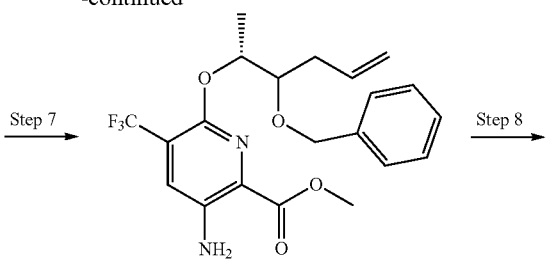
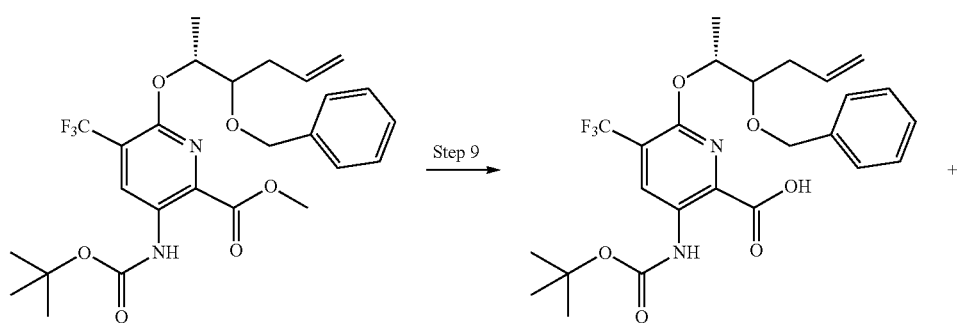
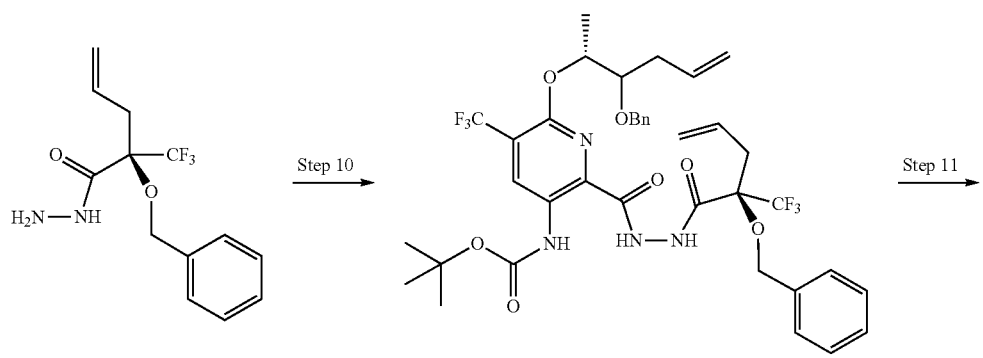
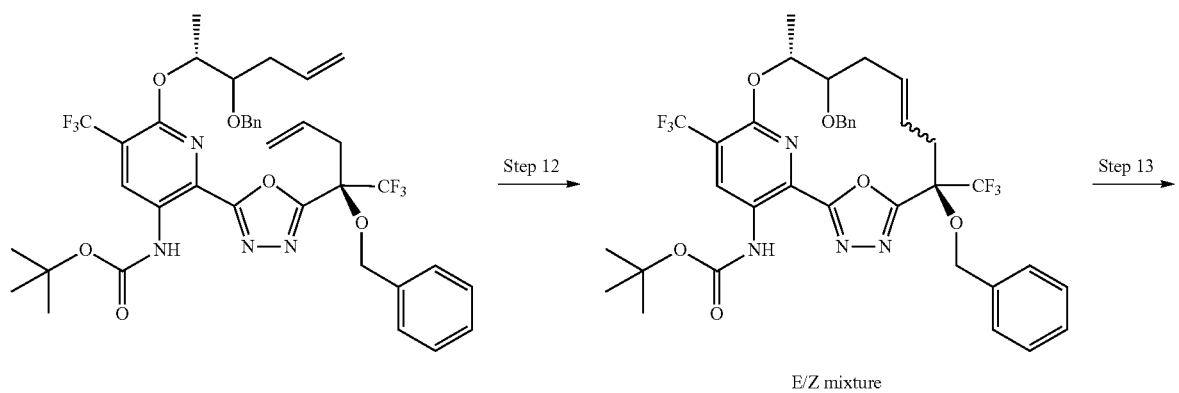
E/Z mixture

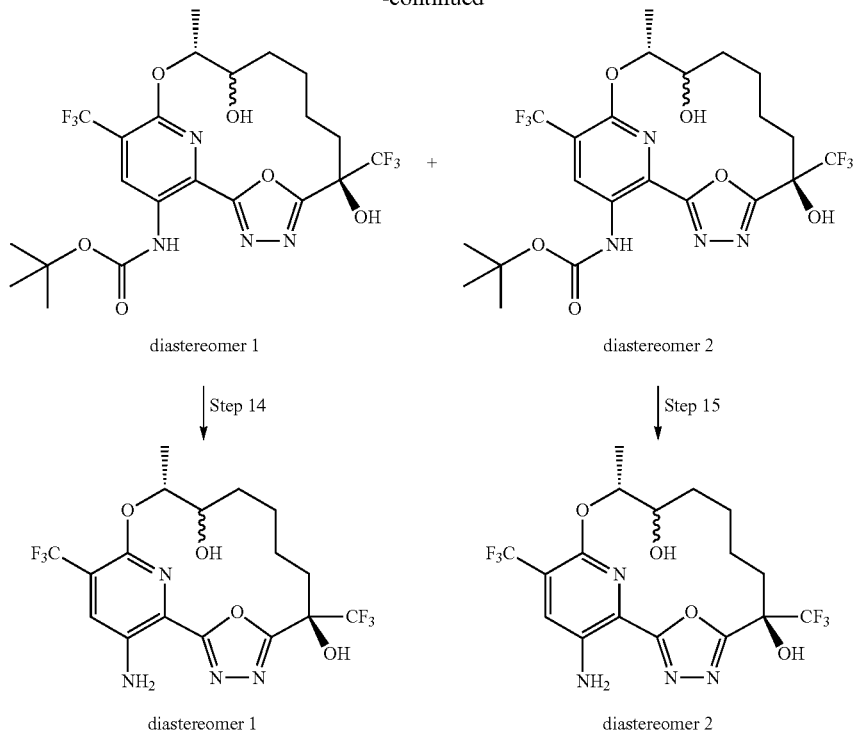

diastereomer 1       diastereomer 2

↓ Step 14       ↓ Step 15 diastereomer 1       diastereomer 2

Step 1: Methyl (2S)-2-triisopropylsilyloxypropanoate

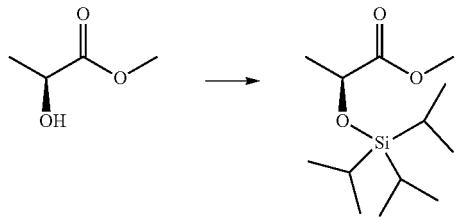

Step 2: (2S)-2-Triisopropylsilyloxypropanal

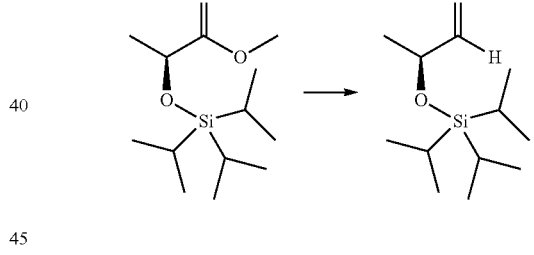

Into a 500 mL round bottom flask was added a solution of methyl (2,S)-2-hydroxypropanoate (10.702 g, 10 mL, 100.74 mmol) and imidazole (16.5 g, 242.37 mmol) in DCM (220 mL). The solution was cooled to 0° C., and chloro(triisopropyl)silane (22.957 g, 26 mL, 116.69 mmol) was added to the reaction mixture dropwise over 30 minutes. The reaction mixture was warmed to room temperature as the ice melted and stirred overnight. The reaction mixture was poured into a separatory funnel and washed with water (100 mL), saturated sodium bicarbonate (100 mL), brine (100 mL), 1 N HCl (100 mL) and brine (100 mL). The organic layer was dried over anhydrous sodium sulfate and concentrated under vacuum. The residue was purified by silica gel chromatography using 0 to 5% ether in hexane to furnish methyl (2S)-2-triisopropylsilyloxypropanoate (25.4 g, 97%) as a clear liquid. $^1$H NMR (500 MHz, Chloroform-d) δ 4.44 (q, J=6.7, 6.7, 6.7 Hz, 1H), 3.72 (s, 3H), 1.43 (d, J=6.7 Hz, 3H), 1.19 0.99 (m, 21H) ppm.

Into a solution of methyl (2S)-2-triisopropylsilyloxypropanoate (1.008 g, 3.8703 mmol) in anhydrous DCM (18 mL) was added 1.0 M DIBAL-H in toluene (7.8 mL of 1 M, 7.8000 mmol) dropwise at −78° C. After the addition, the reaction was stirred at the same temperature for 0.5 hour. It was quenched with ethyl acetate (4 mL) at the same temperature, and the reaction was warmed to 0° C. in an ice bath. Saturated sodium potassium tartrate aqueous solution (10 mL) was added. The reaction was stirred overnight. Two layers were separated. The aqueous layer was extracted with DCM (3×15 mL). The combined organic layers were dried over anhydrous sodium sulfate and concentrated under vacuum. The residue was loaded onto a column directly and purified by silica gel chromatography using 0 to 10% diethyl ether in hexane to furnish (2S)-2-triisopropylsilyloxypropanal (838 mg, 94%) as a clear liquid. $^1$H NMR (500 MHz, Chloroform-d) δ 9.66 (d, J=1.8 Hz, 1H), 4.18 (qd, J=6.8, 6.8, 6.8, 1.7 Hz, 1H), 1.30 (d, J=6.8 Hz, 3H), 1.17-0.97 (m, 21H) ppm.

Step 3: (2S)-2-Triisopropylsilyloxyhex-5-en-3-ol

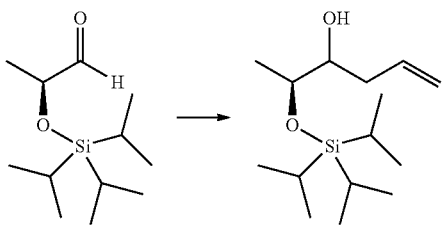 [SMILES: CC(C)[Si](O[C@@H](C)C=O)(C(C)C)C(C)C ; C=CCC(O)[C@H](C)O[Si](C(C)C)(C(C)C)C(C)C]

Into a solution of (2S)-2-triisopropylsilyloxypropanal (18.24 g, 79.160 mmol) in anhydrous DCM (350 mL) was added allyl(bromo)magnesium in diethyl ether (90 mL of 1 M, 90.000 mmol) dropwise at −30° C. The reaction was stirred at the same temperature for 45 minutes, then raised to 0° C. and stirred for another 15 minutes. The reaction was quenched with 10% ammonium chloride (300 mL). Two layers were separated, and the aqueous layer was extracted with DCM (2×250 mL). The combined organic layers were washed with brine (150 mL), dried over anhydrous magnesium sulfate and concentrated under vacuum. The residue was purified by silica gel chromatography using 0 to 20% ether in hexane to furnish a 1:1 mixture of diastereomers, (2S)-2-triisopropylsilyloxyhex-5-en-3-ol (18 g, 83%) as a clear liquid. $^1$H NMR (500 MHz, Chloroform-d) δ 6.01 5.75 (m, 1H), 5.21 4.99 (m, 2H), 4.00-3.82 (m, 1H), 3.75-3.37 (m, 1H), 2.53-2.03 (m, 3H), 1.28-0.90 (m, 24H) ppm.

Step 4: [(1S)-2-Benzyloxy-1-methyl-pent-4-enoxy]-triisopropyl-silane

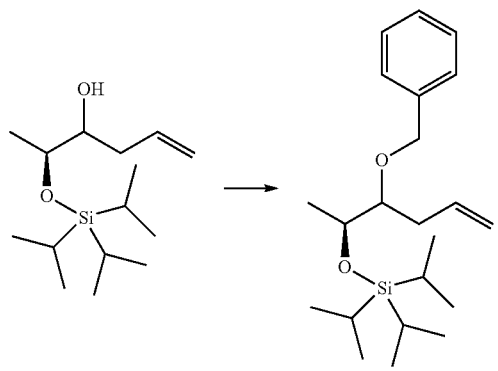 [SMILES: C=CCC(O)[C@H](C)O[Si](C(C)C)(C(C)C)C(C)C ; C=CCC(OCc1ccccc1)[C@H](C)O[Si](C(C)C)(C(C)C)C(C)C]

A slurry of NaH (110 mg, 60% w/w, 2.7503 mmol) in anhydrous DMF (10 mL) was cooled to 0° C. A solution of (2S)-2-triisopropylsilyloxyhex-5-en-3-ol (672 mg, 2.4661 mmol) in anhydrous DMF (10 mL) was added to the reaction mixture dropwise. The reaction mixture was stirred at room temperature for 4 hours. Bromomethylbenzene (504.00 mg, 0.35 mL, 2.9468 mmol) was added to the reaction mixture at 0° C. dropwise. The reaction was then stirred at room temperature for 2 hours. The reaction was poured over 10% ammonium chloride aqueous solution (30 mL) and extracted with diethyl ether (3×30 mL). The combined organic layers were washed with brine (3×30 mL), dried over anhydrous magnesium sulfate and concentrated under vacuum. The residue was purified by silica gel chromatography using 0 to 50% DCM in hexane to furnish a 1:1 mixture of diastereomers, [(1S)-2-benzyloxy-1-methyl-pent-4-enoxy]-triisopropyl-silane (957 mg, 100%) as a clear liquid. $^1$H NMR (500 MHz, Chloroform-d) δ 7.42-7.22 (m, 5H), 6.01-5.78 (m, 1H), 5.15-4.88 (m, 2H), 4.85-4.53 (m, 2H), 4.20-3.90 (m, 1H), 3.63-3.35 (m, 1H), 2.58-2.08 (m, 2H), 1.31-1.10 (m, 3H), 1.11-0.78 (m, 21H) ppm.

Step 5: (2S)-3-Benzyloxyhex-5-en-2-ol

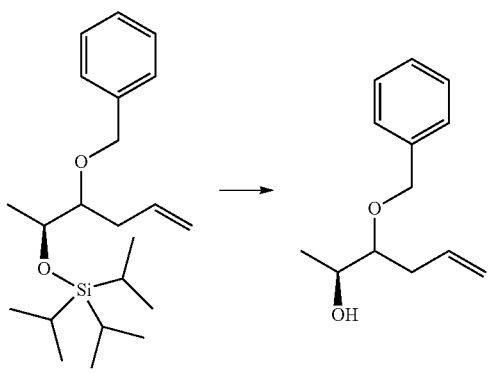 [SMILES: C=CCC(OCc1ccccc1)[C@H](C)O[Si](C(C)C)(C(C)C)C(C)C ; C=CCC(OCc1ccccc1)[C@H](C)O]

Into a solution of [(1S)-2-benzyloxy-1-methyl-pent-4-enoxy]-triisopropyl-silane (14.76 g, 40.704 mmol) in anhydrous THF (140 mL) was added 1M TBAF in THF (41 mL of 1 M, 41.000 mmol) dropwise at 0° C. The reaction was slowly raised to room temperature and stirred overnight. The reaction was concentrated under vacuum to remove THF. The residue was diluted with ethyl acetate (400 mL) and washed with water (100 mL). The organic layer was dried over anhydrous sodium sulfate and concentrated under vacuum. The residue was purified by silica gel chromatography using 0 to 20% ethyl acetate in hexane to furnish a mixture of diastereomers, (2S)-3-benzyloxyhex-5-en-2-ol (7.363 g, 88%) as a clear liquid. $^1$H NMR (500 MHz, Chloroform-d) δ 7.45-7.20 (m, 5H), 5.96-5.77 (m, 1H), 5.20-4.99 (m, 2H), 4.78-4.44 (m, 2H), 3.98-3.67 (m, 1H), 3.47-3.20 (m, 1H), 2.56-1.94 (m, 3H), 1.24-1.12 (m, 3H) ppm.

Step 6: Methyl 6-[(1R)-2-benzyloxy-1-methyl-pent-4-enoxy]-3-nitro-5-(trifluoromethyl)pyridine-2-carboxylate

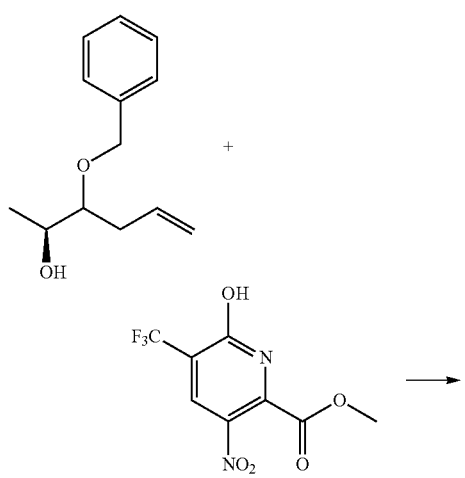

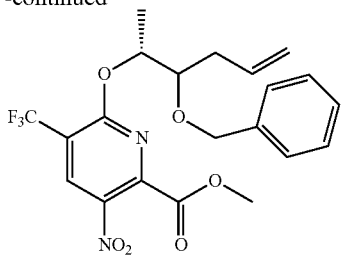

Into a reaction vial was charged with methyl 6-hydroxy-3-nitro-5-(trifluoromethyl)pyridine-2-carboxylate (67 mg, 0.2518 mmol), (2S)-3-benzyloxyhex-5-en-2-ol (71 mg, 0.3442 mmol) and triphenylphosphine (99 mg, 0.0875 mL, 0.3775 mmol) in anhydrous THF (1 mL). DIAD (69.948 mg, 0.067 mL, 0.3459 mmol) was added to the reaction mixture dropwise at 0° C. The reaction was stirred at room temperature for 24 hours. The solvent was removed under vacuum. The residue was purified by silica gel chromatography directly using 0 to 10% ethyl acetate in hexane to furnish methyl 6-[(1R)-2-benzyloxy-1-methyl-pent-4-enoxy]-3-nitro-5-(trifluoromethyl)pyridine-2-carboxylate (71 mg, 60%) as a clear gel. $^1$H NMR (500 MHz, Chloroform-d) δ 8.73-8.46 (m, 1H), 7.43-7.16 (m, 5H), 5.98-5.72 (m, 1H), 5.72-5.50 (m, 1H), 5.19-4.93 (m, 2H), 4.73-4.61 (m, 1H), 4.61-4.54 (m, 1H), 4.12-3.91 (m, 3H), 3.84-3.61 (m, 1H), 2.54-2.26 (m, 2H), 1.47-1.35 (m, 3H) ppm. ESI-MS m/z calc. 454.13516, found 455.1 (M+1)$^+$; Retention time: 3.96 minutes; LCMS Method: Merck Millipore Chromolith SpeedROD $C_{18}$ column (50×4.6 mm) and a dual gradient run from 5-100% mobile phase B over 6 minutes. Mobile phase A=water (0.1% $CF_3CO_2H$). Mobile phase B=acetonitrile (0.1% $CF_3CO_2H$).

Step 7: Methyl 3-amino-6-[(1R)-2-benzyloxy-1-methyl-pent-4-enoxy]-5-(trifluoromethyl)pyridine-2-carboxylate

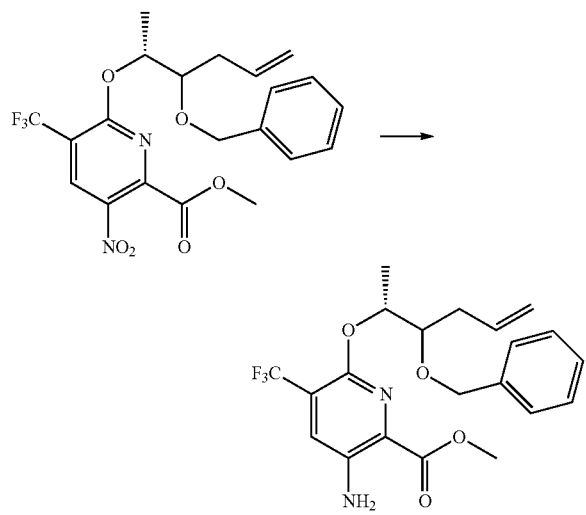

Into a solution of methyl 6-[(1R)-2-benzyloxy-1-methyl-pent-4-enoxy]-3-nitro-5-(trifluoromethyl)pyridine-2-carboxylate (1.255 g, 2.6514 mmol) in acetic acid (15 mL) was added iron (740.34 mg, 13.257 mmol) at rt. The reaction was stirred at room temperature for 3 hours. The reaction mixture was diluted with methanol (15 mL) and filtered through a pad of Celite. The filtrate was concentrated under vacuum. The residue was diluted with ethyl acetate (50 mL) and saturated sodium bicarbonate (100 mL). The solution was filtered through a pad of Celite. Two layers were separated and the aqueous layer was extracted with ethyl acetate (2×50 mL). The combined organic layers were washed with brine (50 mL), dried over anhydrous sodium sulfate and concentrated under vacuum. The residue was purified by silica gel chromatography using 0 to 15% ethyl acetate in hexane to furnish methyl 3-amino-6-[(1R)-2-benzyloxy-1-methyl-pent-4-enoxy]-5-(trifluoromethyl)pyridine-2-carboxylate (1.073 g, 93%) as a yellow gel. ESI-MS m/z calc. 424.161, found 425.0 (M+1)$^+$; Retention time: 3.89 minutes; LCMS Method: Merck Millipore Chromolith SpeedROD $C_{18}$ column (50×4.6 mm) and a dual gradient run from 5-100% mobile phase B over 6 minutes. Mobile phase A=water (0.1% $CF_3CO_2H$). Mobile phase B=acetonitrile (0.1% $CF_3CO_2H$).

Step 8: Methyl 6-[(1R)-2-benzyloxy-1-methyl-pent-4-enoxy]-3-(tert-butoxycarbonylamino)-5-(trifluoromethyppyridine-2-carboxylate

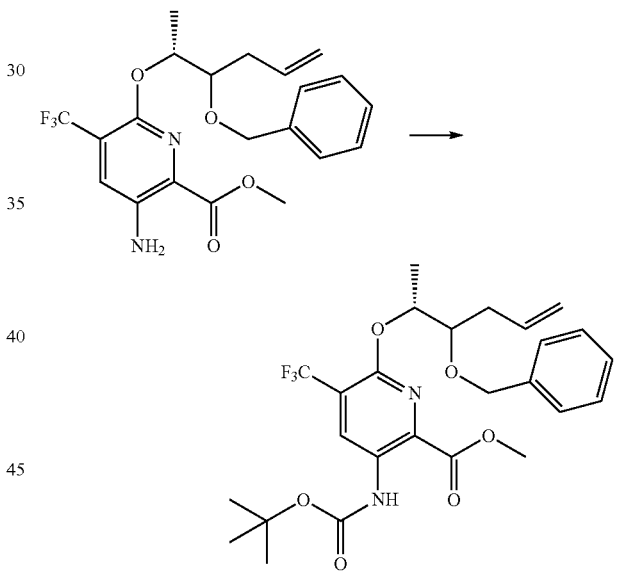

Into a solution of methyl 3-amino-6-[(1R)-2-benzyloxy-1-methyl-pent-4-enoxy]-5-(trifluoromethyl)pyridine-2-carboxylate (1.073 g, 2.4776 mmol) and Boc$_2$O (1.34 g, 6.1398 mmol) in anhydrous THF (20 mL) was added 1.0 M NaHMDS in THF (5 mL of 1 M, 5.000 mmol) dropwise at −78° C. The reaction was stirred at the same temperature for 1 hour. The reaction was quenched cold with 10% ammonium chloride (20 mL). The reaction was warmed up to room temperature and extracted with ethyl acetate (3×30 mL). The combined organic layers were washed with brine (20 mL), dried over anhydrous sodium sulfate and concentrated under vacuum. The residue was purified by silica gel chromatography using 0 to 15% ethyl acetate in hexane to furnish methyl 6-[(1R)-2-benzyloxy-1-methyl-pent-4-enoxy]-3-(tert-butoxycarbonylamino)-5-(trifluoromethyp-pyridine-2-carboxylate (1.328 g, 100%) as a clear gel. ESI-MS m/z calc. 524.21344, found 525.3 (M+1)$^+$; Reten- Step 9: 6-[(1R)-2-Benzyloxy-1-methyl-pent-4-enoxy]-3-(tert-butoxycarbonylamino)-5-(trifluoromethyl)pyridine-2-carboxylic acid

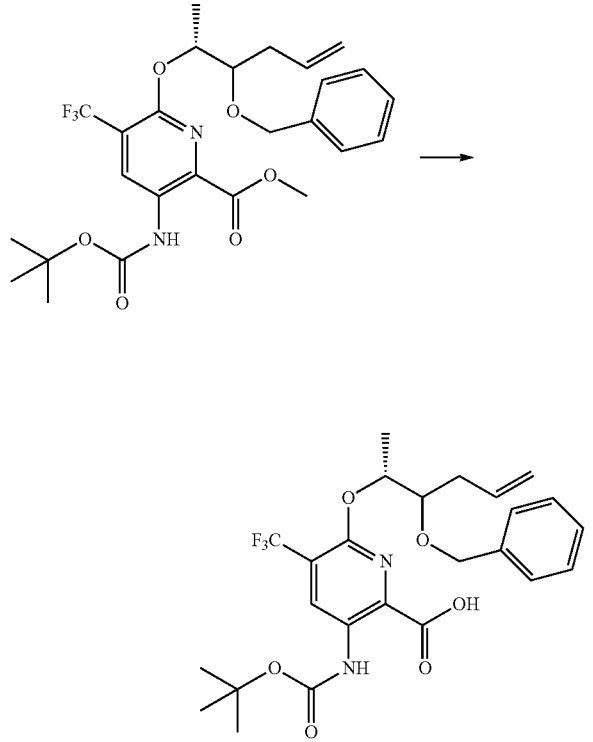 [SMILES: C=CCC(OCc1ccccc1)[C@@H](C)Oc1nc(C(=O)OC)c(NC(=O)OC(C)(C)C)cc1C(F)(F)F ; C=CCC(OCc1ccccc1)[C@@H](C)Oc1nc(C(=O)O)c(NC(=O)OC(C)(C)C)cc1C(F)(F)F]

Step 10: tert-Butyl N-[6-[(1R)-2-benzyloxy-1-methyl-pent-4-enoxy]-2-[[[(2R)-2-benzyloxy-2-(trifluoromethyl)pent-4-enoyl]amino]carbamoyl]-5-(trifluoromethyl)-3-pyridyl]carbamate

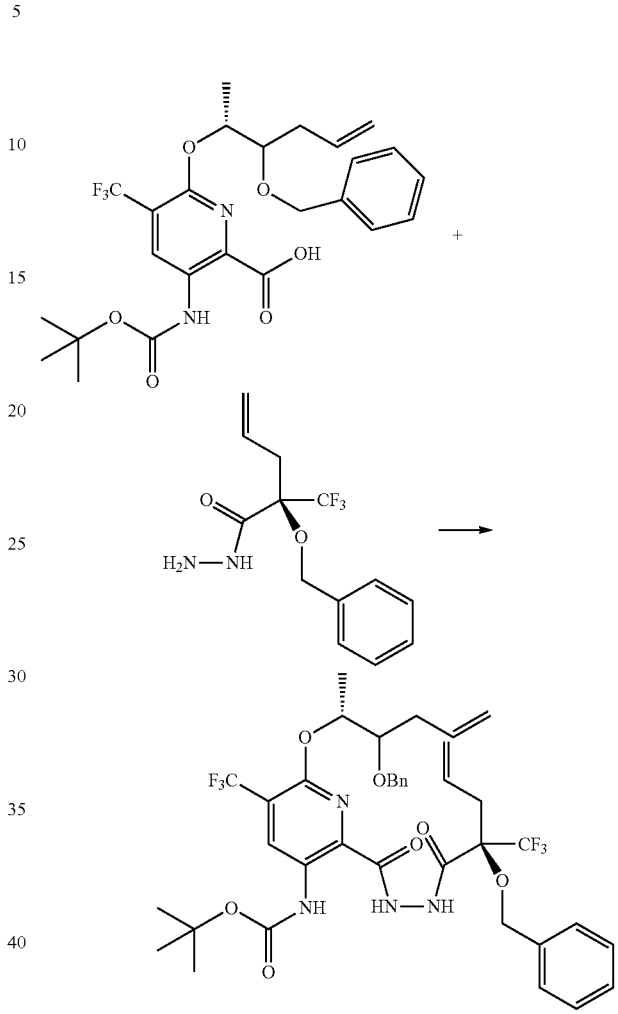

Into a solution of methyl 6-[(1R)-2-benzyloxy-1-methyl-pent-4-enoxy]-3-(tert-butoxycarbonylamino)-5-(trifluoromethyppyridine-2-carboxylate (1.328 g, 2.4812 mmol) in THF (15 mL) was added a solution of LiOH (299 mg, 12.485 mmol) in water (5 mL). The reaction was stirred at room temperature for 1 hour. The reaction was acidified with 1 N HCl to pH 1. The reaction was diluted with ethyl acetate (30 mL) and water (10 mL). Two layers were separated, and the aqueous layer was extracted with ethyl acetate (2×30 mL). The combined organic layers were washed with brine (30 mL), dried over anhydrous sodium sulfate and concentrated under vacuum to furnish 6-[(1R)-2-benzyloxy-1-methyl-pent-4-enoxy]-3-(tert-butoxycarbonylamino)-5-(trifluoromethyppyridine-2-carboxylic acid (1.067 g, 83%) as a light yellow gel. ESI-MS m/z calc. 510.19778, found 511.2 (M+1)$^+$; Retention time: 4.21 minutes; LCMS Method: Merck Millipore Chromolith SpeedROD $C_{18}$ column (50×4.6 mm) and a dual gradient run from 5-100% mobile phase B over 6 minutes. Mobile phase A=water (0.1% $CF_3CO_2H$). Mobile phase B=acetonitrile (0.1% $CF_3CO_2H$).

Into a solution of 6-[(1R)-2-benzyloxy-1-methyl-pent-4-enoxy]-3-(tert-butoxycarbonylamino)-5-(trifluoromethyp-pyridine-2-carboxylic acid (1.067 g, 2.0483 mmol), (2R)-2-benzyloxy-2-(trifluoromethyl)pent-4-enehydrazide (600 mg, 2.0814 mmol) and pyridine (733.50 mg, 0.75 mL, 9.2731 mmol) in ethyl acetate (10 mL) was added 1-propanephosphonic anhydride ($T_3P$) (913.99 mg, 1.71 mL of 50 w/w, 1.4363 mmol) in ethyl acetate. The reaction was then heated to 50° C. and stirred for 1 hour. The reaction was diluted with ethyl acetate (100 mL) and washed with 10% ammonium chloride (30 mL) and brine (30 mL). The organic solution was dried over anhydrous sodium sulfate and concentrated under vacuum. The residue was purified by silica gel chromatography using 0 to 30% ethyl acetate in hexane to furnish tert-butyl N-[6-[(1R)-2-benzyloxy-1-methyl-pent-4-enoxy]-2-[[[(2R)-2-benzyloxy-2-(trifluoromethyl)pent-4-enoyl]amino]carbamoyl]-5-(trifluoromethyl)-3-pyridyl]carbamate (1.506 g, 92%) as a white solid. ESI-MS m/z calc. 780.2958, found 781.7 (M+1)$^+$; Retention time: 4.54 minutes; LCMS Method: Merck Millipore Chromolith SpeedROD $C_{18}$ column (50×4.6 mm) and a dual gradient run from 5-100% mobile phase B over 6 minutes.

Mobile phase A=water (0.1% CF₃CO₂H). Mobile phase B=acetonitrile (0.1% CF₃CO₂H).

Step 11: tert-Butyl N-[6-[(1R)-2-benzyloxy-1-methyl-pent-4-enoxy]-2-[5-[(1R)-1-benzyloxy-1-(trifluoromethyl)but-3-enyl]-1,3,4-oxadiazol-2-yl]-5-(trifluoromethyl)-3-pyridyl]carbamate Step 12: tert-Butyl N-[(6R,12R)-6,11-dibenzyloxy-12-methyl-6,15-bis(trifluoromethyl)-13,19-dioxa-3,4,18-triazatricyclo[12.3.1.1²,⁵]nonadeca-1(18),2,4,8,14,16-hexaen-17-yl]carbamate (E/Z Mixture)

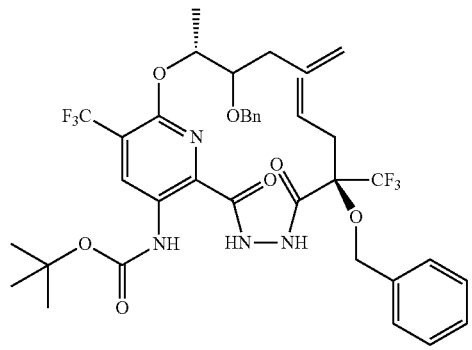

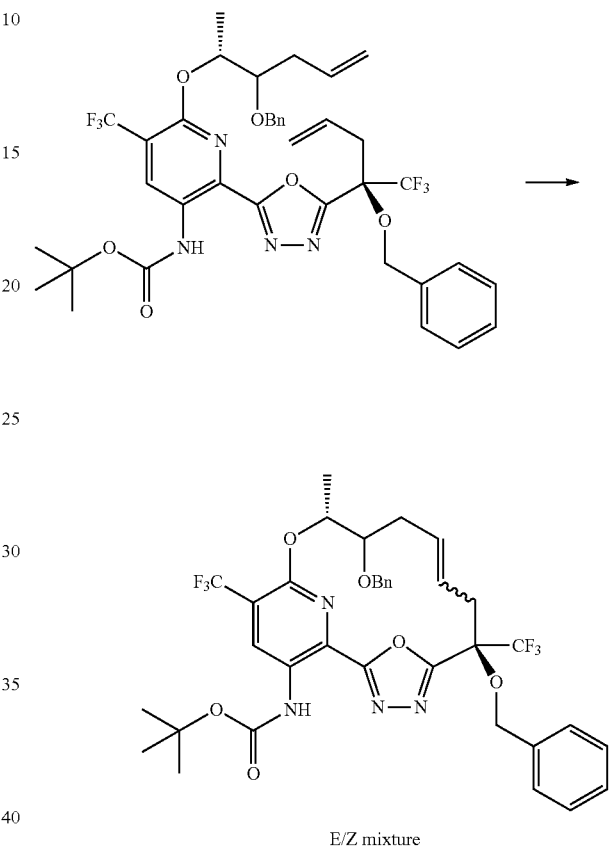

E/Z mixture

To a solution of tert-butyl N-[6-[(1R)-2-benzyloxy-1-methyl-pent-4-enoxy]-2-[[[(2R)-2-benzyloxy-2-(trifluoromethyl)pent-4-enoyl]amino]carbamoyl]-5-(trifluoromethyl)-3-pyridyl]carbamate (1.506 g, 1.8903 mmol) and DIEA (742.00 mg, 1 mL, 5.7411 mmol) in acetonitrile (25 mL) was added p-toluenesulfonyl chloride (440 mg, 2.3079 mmol) at 50° C. The reaction was heated to 70° C. and stirred for 3 hours. The reaction was cooled to room temperature and diluted with ethyl acetate (100 mL). The organic solution was washed with 10% ammonium chloride (30 mL) and brine (30 mL), dried over anhydrous sodium sulfate and concentrated under vacuum. The residue was purified by silica gel chromatography using 0 to 5% ethyl acetate in hexane to provide tert-butyl N-[6-[(1R)-2-benzyloxy-1-methyl-pent-4-enoxy]-2-[5-[(1R)-1-benzyloxy-1-(trifluoromethyl)but-3-enyl]-1,3,4-oxadiazol-2-yl]-5-(trifluoromethyl)-3-pyridyl]carbamate (1.278 g, 87%) as a yellow gel. ESI-MS m/z calc. 762.2852, found 763.6 (M+1)⁺; Retention time: 4.79 minutes; Merck Millipore Chromolith, SpeedROD $C_{18}$ column (50×4.6 mm) and a dual gradient run from 5-100% mobile phase B over 6 minutes. Mobile phase A=water (0.1% CF₃CO₂H). Mobile phase B=acetonitrile.

A reaction vial was charged with tert-butyl N-[6-[(1R)-2-benzyloxy-1-methyl-pent-4-enoxy]-2-[5-[(1R)-1-benzyloxy-1-(trifluoromethyl)but-3-enyl]-1,3,4-oxadiazol-2-yl]-5-(trifluoromethyl)-3-pyridyl]carbamate (108 mg, 0.1388 mmol) and anhydrous DCE (20 mL). The reaction mixture was purged with argon for 2 minutes. The vial was sealed and heated to 50° C. Zhan catalyst-1B (10 mg, 0.0131 mmol) was added to the reaction mixture. The reaction was stirred at 70° C. for 2 days. The reaction was concentrated under reduced pressure. The residue was purified by silica gel chromatography using 0 to 10% ethyl acetate in hexane to furnish tert-butyl N-[(6R,12R)-6,11-dibenzyloxy-12-methyl-6,15-bis(trifluoromethyl)-13,19-dioxa-3,4,18-triazatricyclo[12.3.1.1²,⁵]nonadeca-1(18),2,4,8,14,16-hexaen-17-yl]carbamate (E/Z mixture) (88 mg, 56%) as a clear gel. ESI-MS m/z calc. 734.2539, found 735.0 (M+1)⁺; Retention time: 4.77 minutes; LCMS Method: Merck Millipore Chromolith SpeedROD $C_{18}$ column (50×4.6 mm) and a dual gradient run from 5-100% mobile phase B over 6 minutes. Mobile phase A=water (0.1% CF₃CO₂H). Mobile phase B=acetonitrile (0.1% CF₃CO₂H).

Step 13: tert-Butyl N-[(6R,12R)-6,11-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate

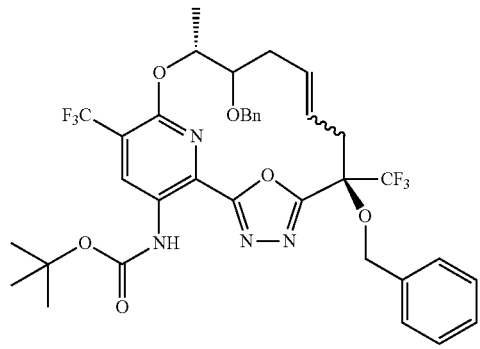

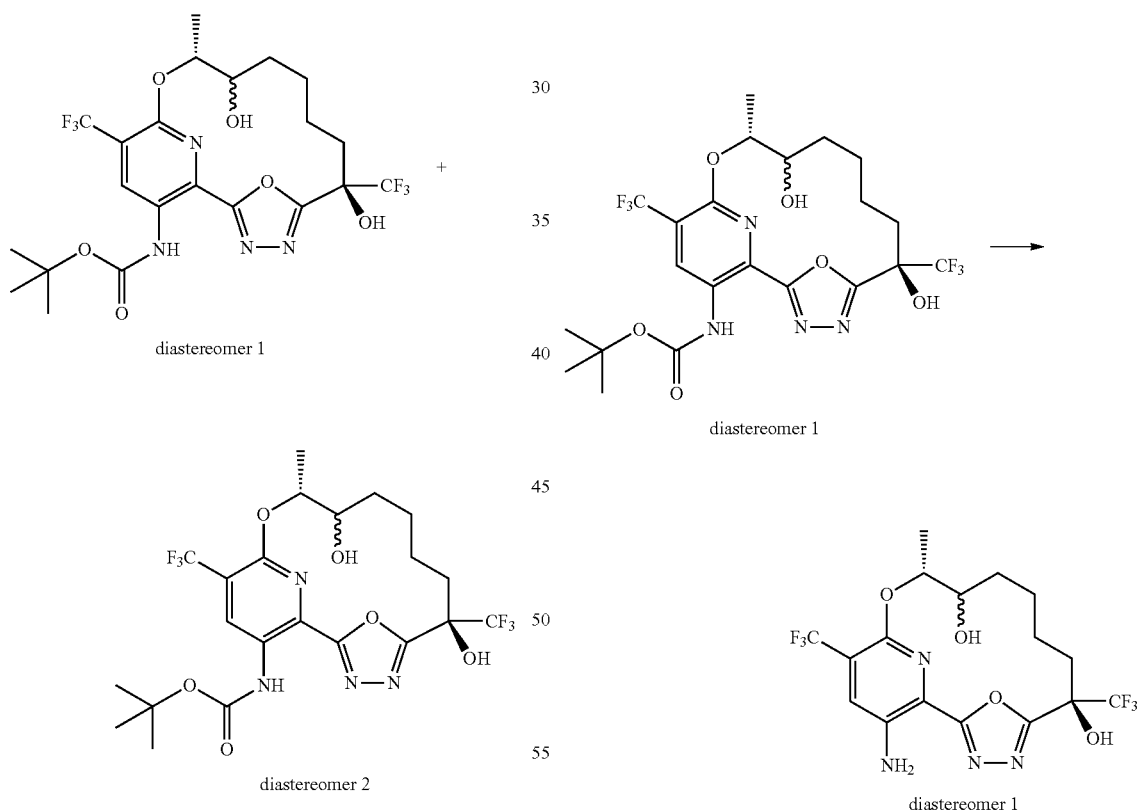

overnight. The catalyst was filtered off through a pad of Celite. The solvent was evaporated under vacuum. The residue was purified by silica gel chromatography (0 to 20% ethyl acetate in hexane) to furnish as the first isomer to elute, tert-butyl N-[(6R,12R)-6,11-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 1) (20 mg, 46%). ESI-MS m/z calc. 556.1757, found 557.2 (M+1)$^+$; Retention time: 3.61 minutes and as the second isomer to elute, tert-butyl N-[(6R,12R)-6,11-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 2) (12 mg, 28%). ESI-MS m/z calc. 556.1757, found 557.3 (M+1)$^+$; Retention time: 3.65 minutes. LCMS Method: Merck Millipore Chromolith SpeedROD C$_{18}$ column (50× 4.6 mm) and a dual gradient run from 5-100% mobile phase B over 6 minutes. Mobile phase A=water (0.1% CF$_3$CO$_2$H). Mobile phase B=acetonitrile (0.1% CF$_3$CO$_2$H.

Step 14: (6R,12R)-17-Amino-12-methyl-6,15-bis(trifluoromethyl)-13,19-dioxa-3,4,18-triazatricyclo[12.3.1.12,5]nonadeca-1(18),2,4,14,16-pentaene-6,11-diol (diastereomer 1), Compound 40

A reaction flask was charged with tert-butyl N-[(6R,12R)-6,11-dibenzyloxy-12-methyl-6,15-bis(trifluoromethyl)-13,19-dioxa-3,4,18-triazatricyclo[12.3.1.12,5]nonadeca-1(18),2,4,8,14,16-hexaen-17-yl]carbamate (E/Z mixture) (88 mg, 0.0779 mmol) in ethanol (5 mL). Then 10% Pd/C (50 mg, 10% w/w, 0.0470 mmol) was added to the reaction mixture. The reaction was hydrogenated under 1 atm of hydrogen gas A microwave vial was charged with tert-butyl N-[(6R,12R)-6,11-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 1) (133 mg, 0.2295 mmol) and hexafluoroisopropanol (5 mL). The vial was sealed and heated at 100° C. for 2.5 hours in a microwave reactor. The solvent was removed under vacuum. Purification by silica gel chromatography (0 to 30% ethyl acetate in hexane) provided (6R,12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,11-diol (diastereomer 1) (75.8 mg, 71%) as a yellow oil. $^1$H NMR (500 MHz, DMSO-d$_6$) δ 7.77 (s, 1H), 7.59 (s, 1H), 6.35 (s, 2H), 4.88-4.69 (m, 1H), 4.59-4.52 (m, 1H), 4.50 (d, J=6.1 Hz, 1H), 2.36 (t, J=12.5 Hz, 1H), 2.12-1.99 (m, 1H), 1.76-1.60 (m, 3H), 1.54-1.40 (m, 2H), 1.35-1.27 (m, 1H), 1.24 (d, J=6.6 Hz, 3H) ppm. ESI-MS m/z calc. 456.12323, found 457.3 (M+1)$^+$; Retention time: 2.17 minutes; LCMS Method: Waters Cortex 2.7 u C$_{18}$ (3.0 mm×50 mm), 55° C.; flow: 1.2 mL/min; mobile phase: 100% water with 0.1% trifluoroacetic acid then 100% acetonitrile with 0.1% trifluoroacetic acid, gradient of 5% to 100% B over 4 min, with equilibration at 100% B for 0.5 min, then 5% B over 1.5 min.

Step 15: (6R,12R)-17-Amino-12-methyl-6,15-bis(trifluoromethyl)-13,19-dioxa-3,4,18-triazatricyclo[12.3.1.1²,⁵]nonadeca-1(18),2,4,14,16-pentaene-6,11-diol (diastereomer 2), Compound 41

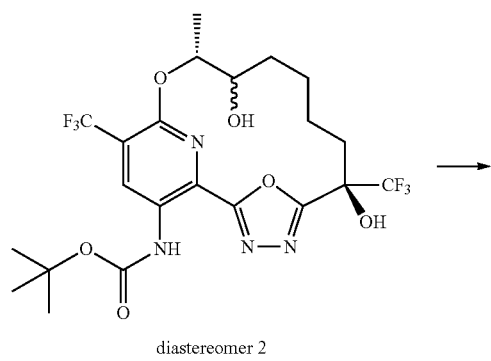

diastereomer 2

-continued

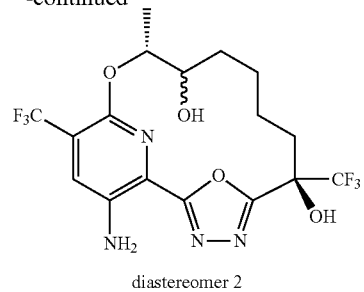

diastereomer 2

A microwavable vial was charged with tert-butyl N-[(6R,12R)-6,11-dihydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (diastereomer 2) (75 mg, 0.1321 mmol) and hexafluoroisopropanol (5 mL). The reaction was heated at 100° C. in a microwave reactor for 2.5 hours. The solvent was removed under vacuum. Purification by silica gel chromatography (0 to 30% ethyl acetate in hexane) provided (6R,12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,11-diol (diastereomer 2) (39.2 mg, 63%) as a yellow oil. $^1$H NMR (500 MHz, DMSO-d$_6$) δ 7.75 (s, 1H), 7.57 (s, 1H), 6.37 (s, 2H), 5.09-4.92 (m, 1H), 4.50 (d, J=6.4 Hz, 1H), 3.75-3.58 (m, 1H), 2.36-2.26 (m, 1H), 2.24-2.13 (m, 1H), 2.08-1.95 (m, 1H), 1.75-1.62 (m, 1H), 1.62-1.50 (m, 1H), 1.44-1.35 (m, 2H), 1.34 (d, J=6.7 Hz, 3H), 1.22-1.07 (m, 1H) ppm. ESI-MS m/z calc. 456.12323, found 457.3 (M+1)$^+$; Retention time: 2.23 minutes; LCMS Method: Waters Cortex 2.7 u C$_{18}$ (3.0 mm×50 mm), 55° C.; flow: 1.2 mL/min; mobile phase: 100% water with 0.1% trifluoroacetic acid then 100% acetonitrile with 0.1% trifluoroacetic acid, gradient of 5% to 100% B over 4 min, with equilibration at 100% B for 0.5 min, then 5% B over 1.5 min.

Example 29: Preparation of (6R,12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,9-diol (diastereomer 1), Compound 42

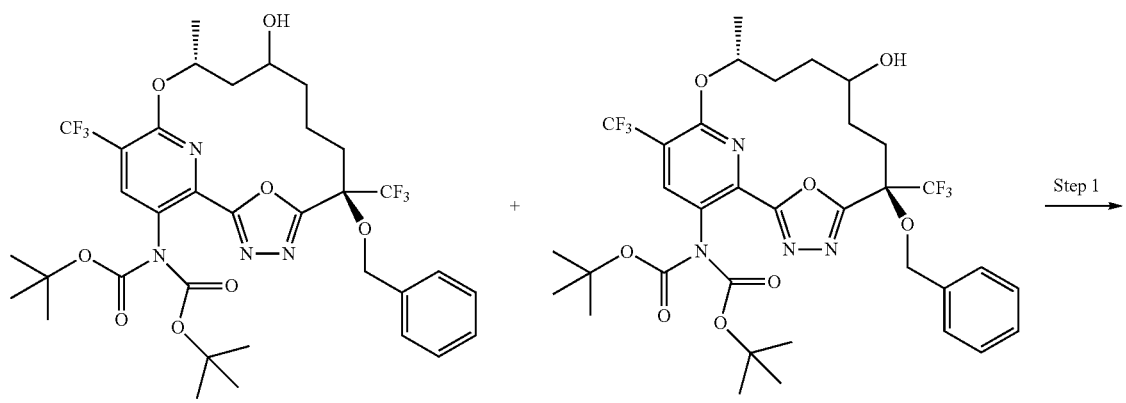

mixture of regioisomeric diastereomers

-continued
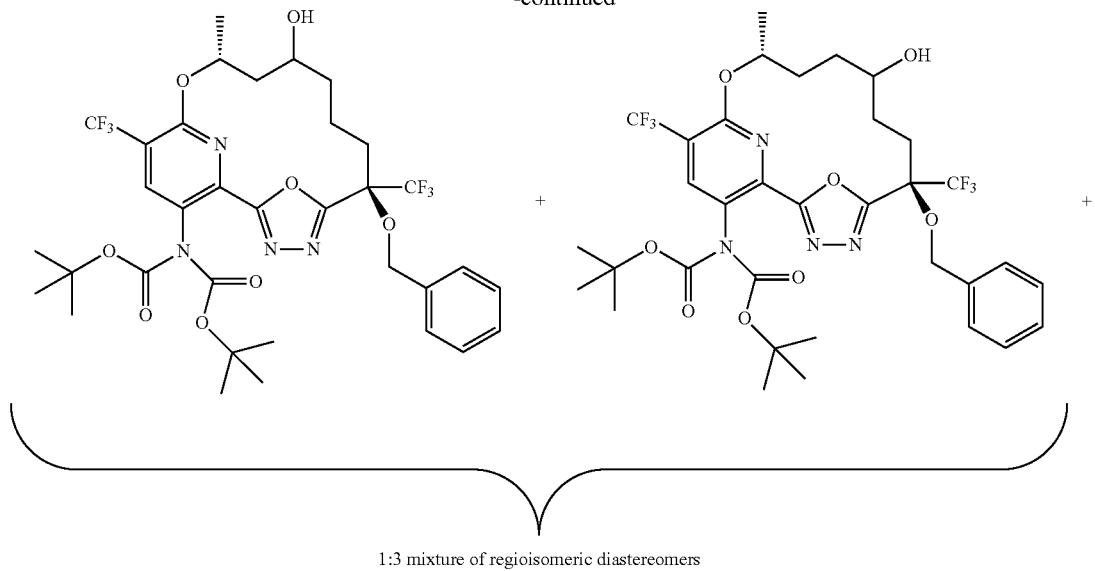
1:3 mixture of regioisomeric diastereomers
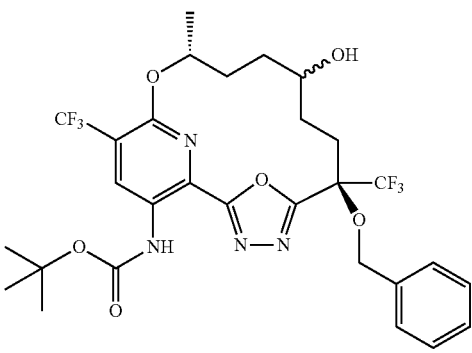
diastereomer 1
Step 2 ↓
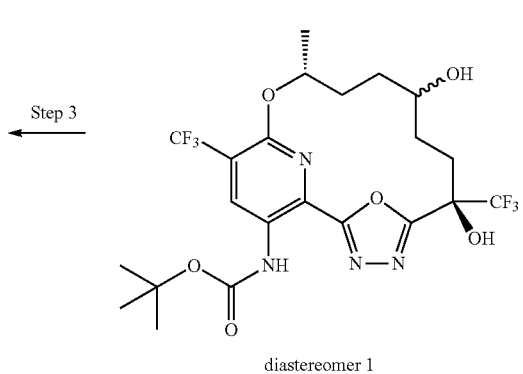
diastereomer 1 ← Step 3 — diastereomer 1

Step 1: tert-Butyl N-[(6R,12R)-6-benzyloxy-9-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 1)

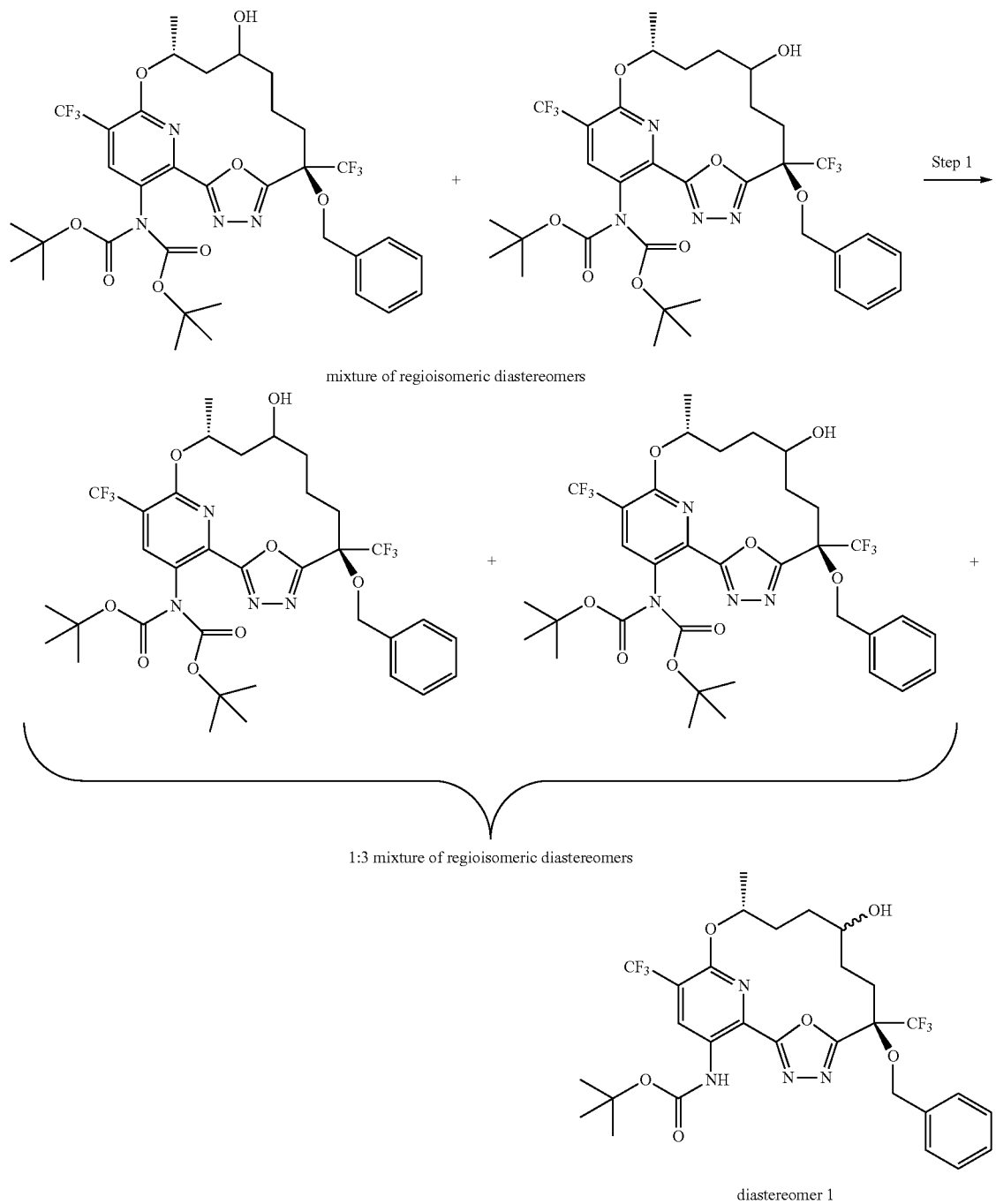

mixture of regioisomeric diastereomers

1:3 mixture of regioisomeric diastereomers diastereomer 1

To a solution of tert-butyl N-[(6R,12R)-6-benzyloxy-9-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate and tert-butyl N-[(6R,12R)-6-benzyloxy-10-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]-N-tert-butoxycarbonyl-carbamate (mixture of regioisomeric diastereomers) (0.45 g, 0.6027 mmol) in DCM (30 mL) was added silica gel (4.5 g, 74.895 mmol). The mixture was stirred at room temperature for 2 days. The mixture was concentrated and purified by silica gel chromatography (80 g SiO₂, eluting 0 to 10% EtOAc/DCM) twice and silica gel chromatography (80 g SiO₂, eluting 10% to 30% EtOAc/heptanes) to provide a 1:3 mixture of two regional isomers, tert-butyl N-[(6R,12R)-6-benzyloxy-9-hydroxy-12-methyl-6,15-bis(trifluoromethyl)-13,19-dioxa-3,4,18-triazatricyclo[12.3.1.1².⁵]nonadeca-1(18),2,4,14,16-pentaen-17-yl]carbamate (minor diastereomer) and tert-butyl N-[(6R,12R)-6-benzyloxy-10-hydroxy-12-methyl-6,15-bis(trifluoromethyl)-13,19-dioxa-3,4,18-triazatricyclo[12.3.1.1².⁵]nonadeca-1(18),2,4,14,16-pentaen-17-yl]carbamate (major diastereomer) (215 mg, 55%) as a semi solid. $^1$H NMR (400 MHz, CDCl₃) δ 9.29-9.17 (m, 1H), 9.16-9.11 (m, 1H), 7.38-7.28 (m, 5H), 4.92-4.79 (m, 1H), 4.79-4.67 (m, 2H), 4.16-3.92 (m, 1H), 2.77 (br dd, J=13.1, 3.8 Hz, 1H), 2.67-2.55 (m, 1H), 2.48-2.25 (m, 1H), 1.98-1.80 (m, 2H), 1.78-1.63 (m, 3H), 1.59 (d, J=6.4 Hz, 3H), 1.56 (s, 9H), 1.50-1.46 (m, 1H) ppm. $^{19}$F NMR for the major product (377 MHz, CDCl₃) δ −63.88 (s, 3F), −74.11 (s, 3F). $^{19}$F NMR for the minor product (377 MHz, CDCl₃) δ −63.86 (s, 3F), −74.07 (s, 3F) ppm; as well as pure tert-butyl N-[(6R,12R)-6-benzyloxy-9-hydroxy-12-methyl-6,15-bis(trifluoromethyl)-13,19-dioxa-3,4,18-triazatricyclo[12.3.1.1².⁵]nonadeca-1(18),2,4,14,16-pentaen-17-yl]carbamate (diastereomer 1) (175 mg, 45%) as a colorless oil. $^1$H NMR (400 MHz, CDCl₃) δ 9.17-9.08 (m, 2H), 7.37-7.28 (m, 5H), 5.07-4.96 (m, 1H), 4.79 (d, J=10.8 Hz, 1H), 4.47 (d, J=10.8 Hz, 1H), 4.40-4.29 (m, 1H), 2.69-2.56 (m, 1H), 2.30 (dt, J=14.8, 5.8 Hz, 1H), 2.24-2.14 (m, 1H), 2.06-1.89 (m, 2H), 1.77-1.60 (m, 3H), 1.57 (s, 9H), 1.53-1.50 (m, 1H), 1.48 (d, J=6.1 Hz, 3H) ppm. $^{19}$F NMR (377 MHz, CDCl₃) δ −63.84 (s, 3F), −73.91 (s, 3F) ppm.

Step 2: tert-Butyl N-[(6R,12R)-6,9-dihydroxy-12-methyl-6,15-bis(trifluoromethyl)-13,19-dioxa-3,4,18-triazatricyclo[12.3.1.1².⁵]nonadeca-1(18),2,4,14,16-pentaen-17-yl]carbamate (diastereomer 1)

To a solution of tert-butyl N-[(6R,12R)-6-benzyloxy-9-hydroxy-12-methyl-6,15-bis(trifluoromethyl)-13,19-dioxa-3,4,18-triazatricyclo[12.3.1.1².⁵]nonadeca-1(18),2,4,14,16-pentaen-17-yl]carbamate (diastereomer 1) (60 mg, 0.0928 mmol) in MeOH (5 mL) was added 10% palladium on carbon 50% wet (30 mg, 0.0141 mmol). The mixture was stirred under hydrogen (balloon) at room temperature overnight. The mixture was filtered through diatomaceous earth and washed with EtOAc. The filtrate was concentrated and the residue was purified by silica gel chromatography (24 g SiO₂, eluting 10 to 30% EtOAc/CH₂Cl₂) to afford tert-butyl N-[(6R,12R)-6,9-dihydroxy-12-methyl-6,15-bis(trifluoromethyl)-13,19-dioxa-3,4,18-triazatricyclo[12.3.1.1².⁵]nonadeca-1(18),2,4,14,16-pentaen-17-yl]carbamate (diastereomer 1) (48 mg, 93%) as a white solid. $^1$H NMR (400 MHz, CDCl₃) δ 9.15 (s, 1H), 9.07 (s, 1H), 6.65 (br s, 1H), 5.07-4.94 (m, 1H), 4.15-4.06 (m, 1H), 3.29 (br d, J=10.0 Hz, 1H), 2.58 (br t, J=11.9 Hz, 1H), 2.52-2.37 (m, 2H), 2.21-2.08 (m, 1H), 2.05-1.96 (m, 1H), 1.82-1.66 (m, 2H), 1.56 (s, 9H), 1.54-1.47 (m, 4H) ppm. $^{19}$F NMR (377 MHz, CDCl₃) δ −63.96 (s, 3F), −78.47 (s, 3F) ppm. ESI-MS m/z calc. 556.17566, found 557.1 (M+1)⁺; Retention time: 3.62 minutes; LCMS Method: Kinetex Polar C₁₈ 3.0×50 mm 2.6 μm, 6 min, 5-95% acetonitrile in H₂O (0.1% formic acid) 1.2 mL/min.

Step 3: (6R,12R)-17-Amino-12-methyl-6,15-bis(trifluoromethyl)-13,19-dioxa-3,4,18-triazatricyclo[12.3.1.1².⁵]nonadeca-1(18),2,4,14,16-pentaene-6,9-diol (diastereomer 1), Compound 42

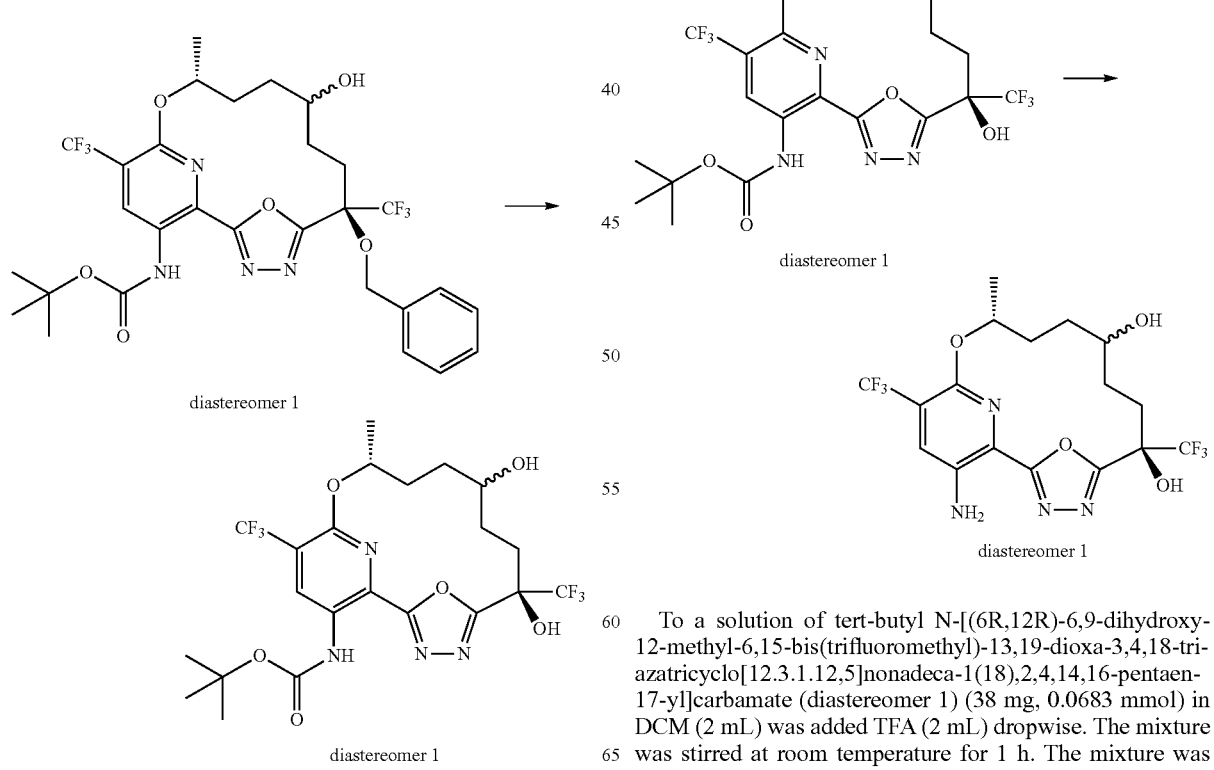

diastereomer 1 diastereomer 1

To a solution of tert-butyl N-[(6R,12R)-6,9-dihydroxy-12-methyl-6,15-bis(trifluoromethyl)-13,19-dioxa-3,4,18-triazatricyclo[12.3.1.1².⁵]nonadeca-1(18),2,4,14,16-pentaen-17-yl]carbamate (diastereomer 1) (38 mg, 0.0683 mmol) in DCM (2 mL) was added TFA (2 mL) dropwise. The mixture was stirred at room temperature for 1 h. The mixture was concentrated under reduced pressure at room temperature and co-evaporated with MeOH (2×3 mL). The residue was dissolved in EtOAc (20 mL) and washed with saturated NaHCO₃ (5 mL), dried with Na₂SO₄, filtered and concentrated. The residue was purified by flash chromatography (12 g SiO₂, eluting 10 to 50% EtOAc/CH₂Cl₂) to afford (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaene-6,9-diol (diastereomer 1) (23 mg, 74%) as a pale-yellow solid. ¹H NMR (400 MHz, DMSO-d₆) δ 7.76 (s, 1H), 7.59 (s, 1H), 6.35 (s, 2H), 5.00-4.89 (m, 1H), 4.57 (d, J=5.1 Hz, 1H), 3.98-3.87 (m, 1H), 2.37-2.23 (m, 3H), 2.07-1.98 (m, 1H), 1.62-1.48 (m, 2H), 1.42-1.28 (m, 5H) ppm. ¹⁹F NMR (377 MHz, DMSO-d₆) δ −62.51 (s, 3F), −76.36 (s, 3F) ppm. ESI-MS m/z calc. 456.12323, found 457.1 (M+1)⁺; Retention time: 2.94 minutes; LCMS Method: Kinetex Polar C₁₈ 3.0×50 mm 2.6 μm, 6 min, 5-95% acetonitrile in H₂O (0.1% formic acid) 1.2 mL/min.

Example 30: Preparation of (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaene-6,10-diol (diastereomer 1), Compound 43

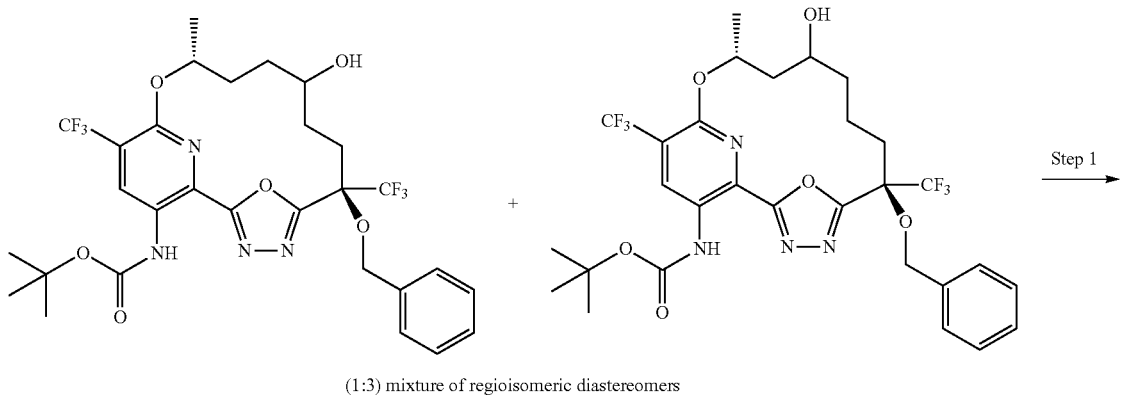

(1:3) mixture of regioisomeric diastereomers

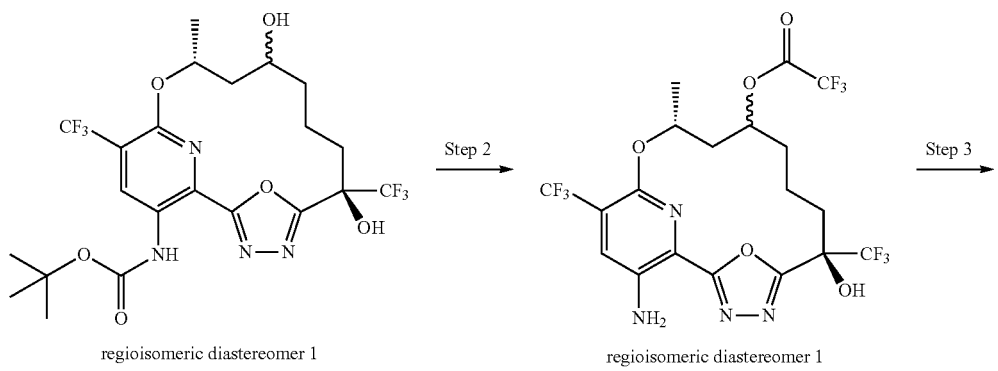

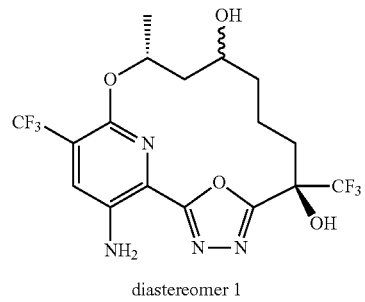

diastereomer 1

Step 1: tert-Butyl N-[(6R,12R)-6,10-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (regioisomeric diastereomer 1)

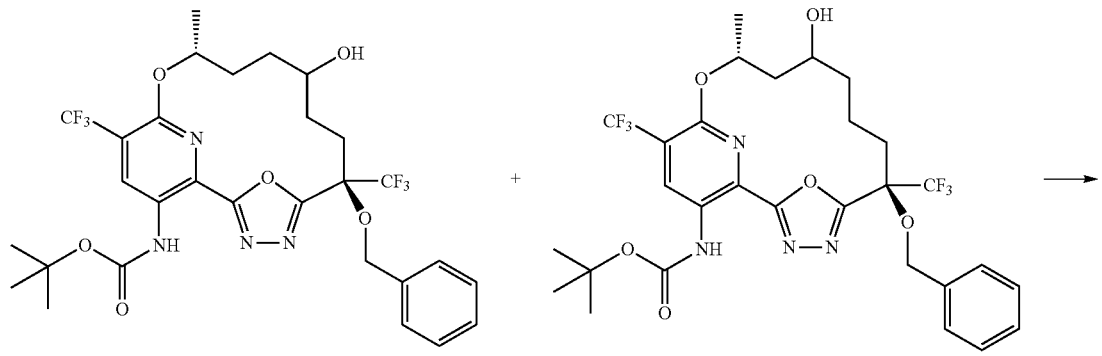

(1:3) mixture of regioisomeric diastereomers

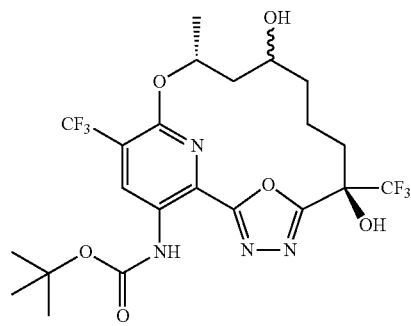

regioisomeric diastereomer 1

To a solution of a 1:3 mixture of tert-butyl N-[(6R,12R)-6-benzyloxy-9-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate and tert-butyl N-[(6R,12R)-6-benzyloxy-10-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (1:3 mixture of regioisomeric diastereomers) (80 mg, 0.1237 mmol) in MeOH (3 mL) was added 10% palladium on carbon 50% wet (30 mg, 0.0141 mmol). Air was replaced by nitrogen through vacuum for 3 times. The mixture was stirred under hydrogen (balloon) at room temperature overnight. The mixture was filtered through diatomaceous earth and washed with EtOAc. The filtrate was concentrated and purified by silica gel chromatography (40 g SiO$_2$, eluting 0 to 30% EtOAc/heptanes) twice to afford tert-butyl N-[(6R,12R)-6,10-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (regioisomeric diastereomer 1) (30 mg, 44%) as a colorless oil. $^1$H NMR (400 MHz, CDCl$_3$) δ 9.11 (s, 1H), 9.06 (s, 1H), 4.87-4.74 (m, 1H), 4.25-4.09 (m, 1H), 3.94 (br s, 1H), 2.85 (br dd, J=13.3, 3.8 Hz, 1H), 2.47-2.25 (m, 2H), 2.01-1.79 (m, 3H), 1.73-1.65 (m, 1H), 1.62-1.47 (m, 14H) ppm. $^{19}$F NMR (377 MHz, CDCl$_3$) δ −63.88 (s, 3F), −77.40 (s, 3F) ppm. ESI-MS m/z calc. 556.17566, found 557.1 (M+1)$^+$; Retention time: 3.62 minutes; LCMS Method: Kinetex Polar C$_{18}$ 3.0×50 mm 2.6 μm, 6 min, 5-95% acetonitrile in H$_2$O (0.1% formic acid) 1.2 mL/min.

Step 2: [(6R,12R)-17-Amino-6-hydroxy-12-methyl-6,15-bis(trifluoromethyl)-13,19-dioxa-3,4,18-triazatricyclo[12.3.1.12,5]nonadeca-1(18),2,4,14,16-pentaen-10-yl]2,2,2-trifluoroacetate (regioisomeric diastereomer 1)

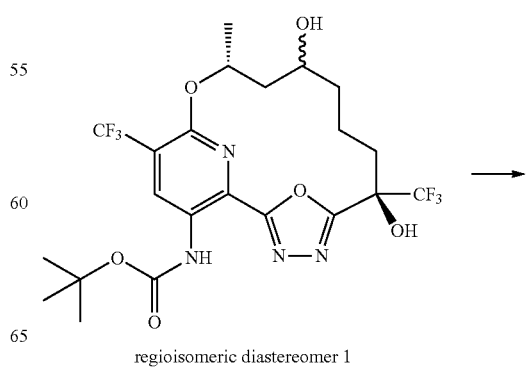

regioisomeric diastereomer 1

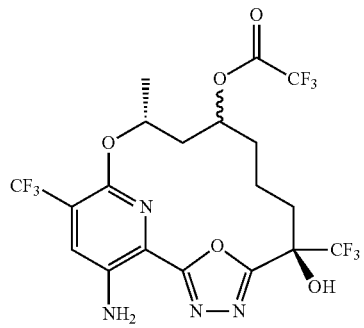

regioisomeric diastereomer 1

To a solution of tert-butyl N-[(6R,12R)-6,10-dihydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (regioisomeric diastereomer 1) (30 mg, 0.0539 mmol) in DCM (2 mL) was added TFA (2.9600 g, 2 mL, 25.960 mmol). The mixture was stirred at room temperature for 1 h. The mixture was concentrated under reduced pressure at 40° C. The residue was purified by silica gel chromatography (24 g SiO$_2$, eluting 0 to 30% EtOAc/heptanes) to afford [(6R,12R)-17-amino-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-10-yl]2,2,2-trifluoroacetate (regioisomeric diastereomer 1) (27 mg, 91%) as a pale-yellow oil. $^1$H NMR (400 MHz, CDCl$_3$) δ 7.46 (s, 1H), 5.59 (tdd, J=8.5, 3.9, 2.3 Hz, 1H), 5.37 (s, 2H), 4.58 (quin, J=6.7 Hz, 1H), 3.82 (s, 1H), 3.01 (dd, J=14.3, 3.8 Hz, 1H), 2.64 (br t, J=12.2 Hz, 1H), 2.39-2.28 (m, 1H), 2.11-2.01 (m, 1H), 2.00-1.71 (m, 4H), 1.51 (d, J=6.4 Hz, 3H) ppm. $^{19}$F NMR (377 MHz, CDCl$_3$) δ −64.00 (s, 3F), −75.28 (s, 3F), −77.43 (s, 3F) ppm.

Step 3: (6R,12R)-17-Amino-12-methyl-6,15-bis(trifluoromethyl)-13,19-dioxa-3,4,18-triazatricyclo[12.3.1.1²,⁵]nonadeca-1(18),2,4,14,16-pentaene-6,10-diol (diastereomer 1), Compound 43

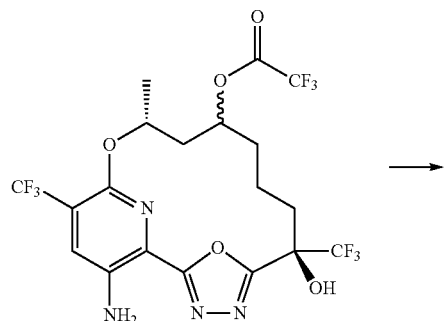

regioisomeric diastereomer 1

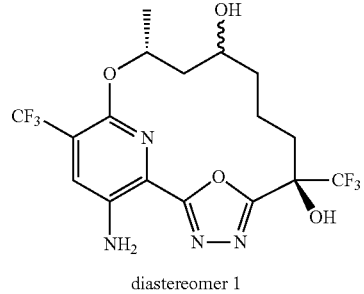

diastereomer 1

To a solution of [(6R,12R)-17-amino-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-10-yl]2,2,2-trifluoroacetate (regioisomeric diastereomer 1) (27 mg, 0.0489 mmol) in THF (2 mL) at 0° C. was added a solution of NaOH (8.6 mg, 0.2150 mmol) in H$_2$O (0.5 mL). The mixture was stirred at 0° C. for 1 h, treated with saturated NaHCO$_3$ (5 mL) and brine (3 mL). The mixture was extracted with EtOAc (3×10 mL). The combined organic layers were dried with Na$_2$SO$_4$, filtered and concentrated. The residue was purified by silica gel chromatography (12 g SiO$_2$, eluting 20 to 50% EtOAc/CH$_2$Cl$_2$) to afford (6R,12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,10-diol (diastereomer 1) (17 mg, 76%) as a pale-yellow solid. $^1$H NMR (400 MHz, DMSO-d$_6$) δ 7.77 (s, 1H), 7.61 (s, 1H), 6.37 (s, 2H), 4.76-4.65 (m, 1H), 4.52 (d, J=5.1 Hz, 1H), 3.97-3.84 (m, 1H), 2.60 (br dd, J=12.3, 4.5 Hz, 1H), 2.43-2.32 (m, 1H), 2.16-2.02 (m, 1H), 1.75-1.50 (m, 4H), 1.44 (d, J=6.4 Hz, 3H), 1.31-1.22 (m, 1H) ppm. $^{19}$F NMR (377 MHz, DMSO-d$_6$) δ −62.55 (s, 3F), −76.26 (s, 3F) ppm. ESI-MS m/z calc. 456.12323, found 457.1 (M+1)$^+$; Retention time: 2.87 minutes; LCMS Method: Kinetex Polar C$_{18}$ 3.0×50 mm 2.6 μm, 6 min, 5-95% acetonitrile in H$_2$O (0.1% formic acid) 1.2 mL/min.

Example 31: Preparation of (6R,12R)-17-amino-8,9-dideuterio-12-methyl-6,15-bis(trifluoromethyl)-13,19-dioxa-3,4,18-triazatricyclo[12.3.1.1²,⁵]nonadeca-1(17),2,4,14(18),15-pentaen-6-ol, Compound 44

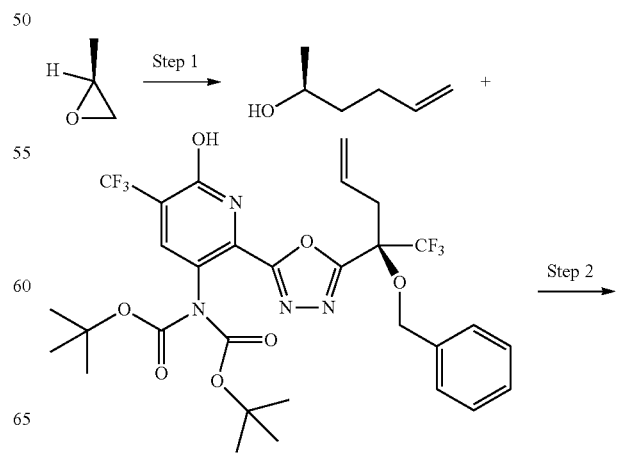

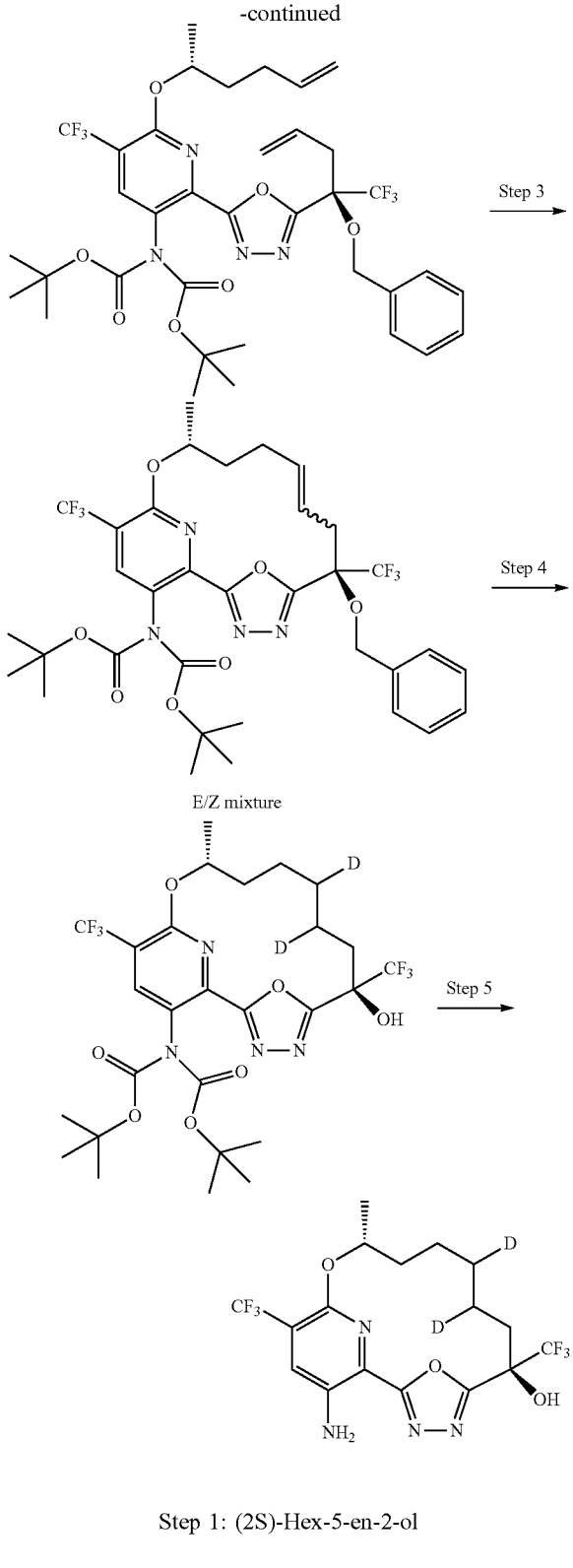

E/Z mixture

Step 1: (2S)-Hex-5-en-2-ol

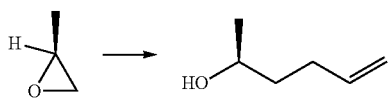

To a yellow solution of allyl(bromo)magnesium (103 mL of 1 M, 103.00 mmol) in diethyl ether was added copper bromide (975 mg, 6.7968 mmol) at 0° C., then the black mixture was stirred at −78° C. After 5 min, a solution of (2S)-2-methyloxirane (1.9896 g, 2.4 mL, 34.257 mmol) in THF (30 mL) was added dropwise with a dropping funnel over 20 min at −78° C. Then the black mixture was stirred at −78° C. for 30 min. Then methanol (16 mL) was added at −78° C., followed by aqueous hydrogen chloride (2M, 80 mL) and then stirred at room temperature for 5 min. MTBE (120 mL) was then added, the aqueous layer was separated and extracted with MTBE (2×120 mL). The organic layers were washed with aqueous hydrogen chloride (1M, 50 mL), water (50 mL), aqueous sodium thiosulphate (10%, 50 mL) and again with water (50 mL). The organic layers were dried over sodium sulphate and concentrated under vacuum. The oil residue was dry loaded with silica gel and purified by liquid chromatography on silica gel eluting with portions of ethyl acetate (0-30%) in heptanes to afford (2S)-hex-5-en-2-ol (1.66 g, 44%) as a light yellow oil. $^1$H NMR (400 MHz, CDCl$_3$) δ 5.93-5.75 (m, 1H), 5.14-4.89 (m, 2H), 3.92-3.72 (m, 1H), 2.28-2.01 (m, 2H), 1.66-1.45 (m, 2H), 1.24-1.18 (m, 3H) ppm.

Step 2: tert-Butyl N-[2-[5-[(1R)-1-benzyloxy-1-(trifluoromethyl)but-3-enyl]-1,3,4-oxadiazol-2-yl]-6-[(1R)-1-methylpent-4-enoxy]-5-(trifluoromethyl)-3-pyridyl]-N-tert-butoxycarbonyl-carbamate

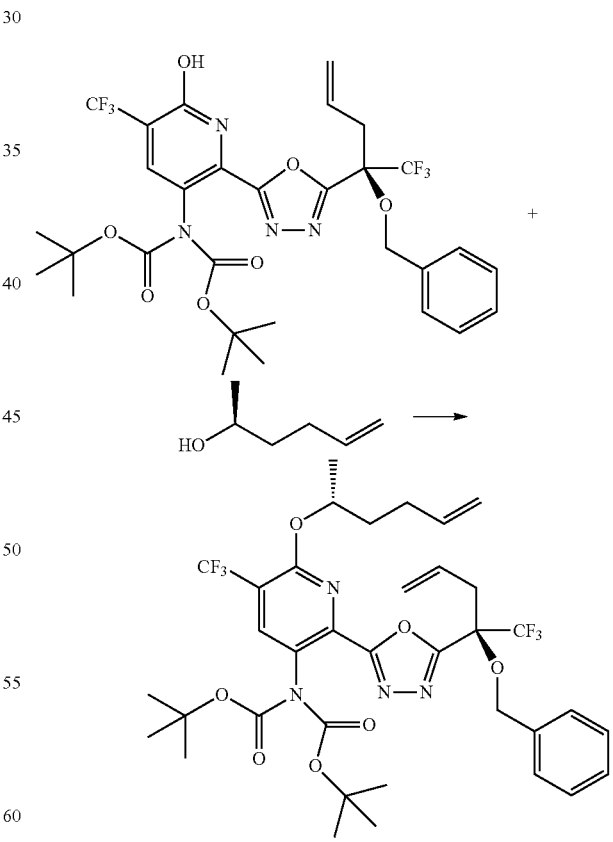

To a solution of tert-butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate (325 mg, 0.4818 mmol) and (2S)-hex-5-en-2-ol (160 mg, 1.4377 mmol) in toluene (4 mL) was treated with triphenylphosphine (264 mg, 1.0065 mmol) followed by DIAD (205.40 mg, 0.2 mL, 1.0158 mmol) at room temperature. The yellow solution was stirred at room temperature for overnight. The yellow suspension was concentrated under vacuum, then dry-packed on silica with DCM. Purification by silica gel chromatography (0-30% EtOAc/heptanes) gave tert-butyl N-[2-[5-[(1R)-1-benzyloxy-1-(trifluoromethyl)but-3-enyl]-1,3,4-oxadiazol-2-yl]-6-[(1R)-1-methylpent-4-enoxy]-5-(trifluoromethyl)-3-pyridyl]-N-tert-butoxycarbonyl-carbamate (320 mg, 74%) as a yellow oil. $^1$H NMR (400 MHz, CDCl$_3$) δ 7.83 (s, 1H), 7.35 (d, J=8.3 Hz, 5H), 5.93 (td, J=17.0, 7.1 Hz, 1H), 5.86-5.74 (m, 1H), 5.37-5.28 (m, 1H), 5.28-5.15 (m, 2H), 5.03-4.88 (m, 2H), 4.82 (d, J=10.8 Hz, 1H), 4.63 (d, J=10.8 Hz, 1H), 3.28-3.11 (m, 2H), 2.27-2.02 (m, 2H), 1.97-1.84 (m, 1H), 1.79-1.66 (m, 1H), 1.43 (s, 18H), 1.38 (d, J=6.1 Hz, 3H) ppm. $^{19}$F NMR (377 MHz, CDCl$_3$) δ −64.13 to −64.28 (m, 3F), −73.32 to −73.43 (m, 3F) ppm.

Step 3: tert-Butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-17-yl]-N-tert-butoxycarbonyl-carbamate (E/Z Mixture)

To a stirring solution of tert-butyl N-[2-[5-[(1R)-1-benzyloxy-1-(trifluoromethyl)but-3-enyl]-1,3,4-oxadiazol-2-yl]-6-[(1R)-1-methylpent-4-enoxy]-5-(trifluoromethyl)-3-pyridyl]-N-tert-butoxycarbonyl-carbamate (320 mg, 0.3582 mmol) in 1,2-dichloroethane (175 mL) was degassed with bubbling with nitrogen gas for 24 hours. To the solution at 60° C. was added Zhan catalyst-1B (18 mg, 0.0245 mmol) then the reaction was stirred at this temperature for 40 minutes. Then, an equal amount of Zhan catalyst-1B (18 mg, 0.0245 mmol) was added and stirring continued at 60° C. for 2.5 hours. Once cooled to room temperature, the catalyst was quenched with a few drops of DMSO (about 5-6) and the reaction was concentrated under reduced pressure. The residue was purified by silica gel chromatography using a gradient from 0% to 90% ethyl acetate in heptanes to afford tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-17-yl]-N-tert-butoxycarbonyl-carbamate (E/Z mixture) (290 mg, 73%) as white solid which still contained a small amount of an unknown impurity. $^1$H NMR (400 MHz, CDCl$_3$) δ 7.82 (s, 1H), 7.34-7.24 (m, 5H), 5.84 (dt, J=14.9, 7.2 Hz, 1H), 5.76-5.64 (m, 1H), 5.28-5.15 (m, 1H), 4.79 (d, J=11.0 Hz, 1H), 4.50 (d, J=11.2 Hz, 1H), 3.13 (dd, J=14.4, 7.3 Hz, 1H), 2.77 (dd, J=14.4, 6.8 Hz, 1H), 2.33 (dt, J=13.7, 6.8 Hz, 1H), 2.13-2.03 (m, 1H), 1.98 (dd, J=13.0, 7.1 Hz, 1H), 1.72-1.60 (m, 1H), 1.50 (d, J=6.4 Hz, 3H), 1.46 (s, 18H) ppm. $^{19}$F NMR (377 MHz, CDCl$_3$) δ −63.96 (s, 3F), −74.55 (s, 3F) ppm. ESI-MS m/z calc. 728.26447, found 573.2 (M-155, -Boc, -$^t$Bu)$^+$; Retention time: 4.48 minutes; LCMS Method: XBridge C$_{18}$ 4.6×75 mm 5 μm, initial gradient at 95% NH$_4$HCO$_3$/5% acetonitrile 6 min run with 1 min equilibration, gradient 0 to 3 min at 95% acetonitrile and held for 3 minutes, with a flow rate of 1.5 mL/min.

Step 4: tert-Butyl N-tert-butoxycarbonyl-N-[(6R,12R)-8,9-dideuterio-6-hydroxy-12-methyl-6,15-bis(trifluoromethyl)-13,19-dioxa-3,4,18-triazatricyclo[12.3.1.12,5]nonadeca-1(17),2,4,14(18),15-pentaen-17-yl]carbamate

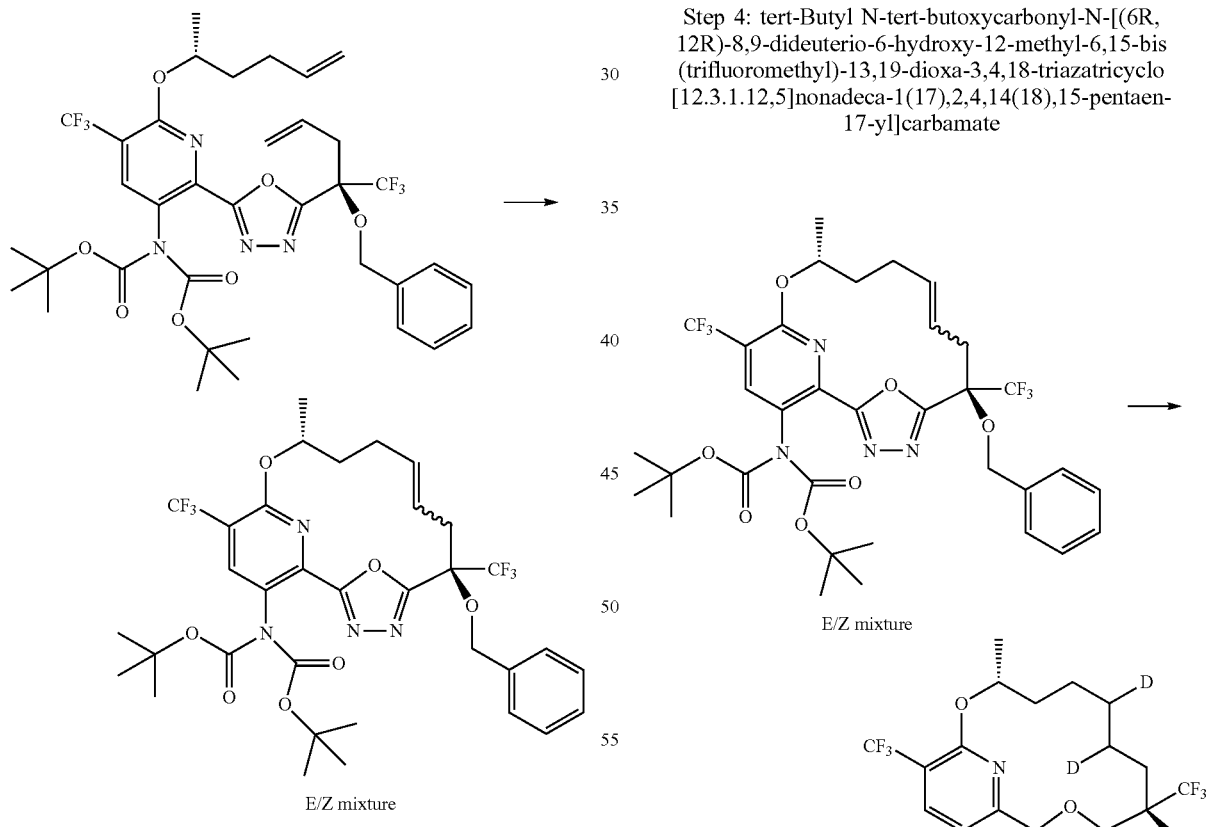

E/Z mixture

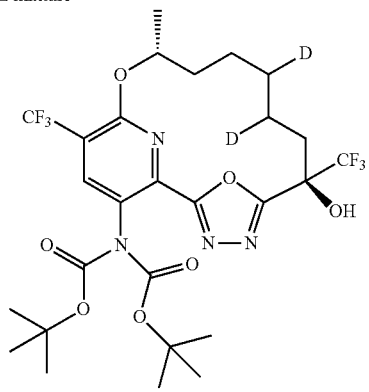

To a solution of tert-butyl N-[(6R,12R)-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-17-yl]-N-tert-butoxycarbonyl-carbamate (E/Z mixture) (140 mg, 0.1921 mmol) in CD₃OD (5.6 mL) under nitrogen was added 10% palladium on carbon (36 mg, 0.0338 mmol). Nitrogen was replaced with deuterium gas through vacuum for 3 cycles. The mixture was stirred at room temperature under deuterium atmosphere (balloon) overnight. The mixture was filtered through a pad of Celite and washed with EtOAc (30 mL) and then concentrated by evaporation under reduced pressure to give tert-butyl N-tert-butoxycarbonyl-N-[(6R,12R)-8,9-dideuterio-6-hydroxy-12-methyl-6,15-bis(trifluoromethyl)-13,19-dioxa-3,4,18-triazatricyclo[12.3.1.12,5]nonadeca-1(17),2,4,14(18),15-pentaen-17-yl]carbamate (127 mg, 88%) as a colorless oil. $^1$H NMR (400 MHz, CDCl₃) δ 7.83 (s, 1H), 5.00-4.85 (m, 1H), 3.95-3.65 (m, 1H), 2.73-2.55 (m, 1H), 2.34-2.22 (m, 1H), 2.21-2.10 (m, 1H), 2.08-1.96 (m, 1H), 1.67-1.19 (m, 25H) ppm. $^{19}$F NMR (377 MHz, CDCl₃) δ -63.99 (s, 3F), -77.58 (s, 3F) ppm. ESI-MS m/z calc. 642.2457, found 487.1 (M−155)⁺; Retention time: 4.01 minutes. LCMS Method: Kinetex Polar C₁₈ 3.0×50 mm 2.6 μm, 6 min, 5-95% acetonitrile in H₂O (0.1% formic acid) at 1.2 mL/min.

Step 5: (6R,12R)-17-Amino-8,9-dideuterio-12-methyl-6,15-bis(trifluoromethyl)-13,19-dioxa-3,4,18-triazatricyclo[12.3.1.12,5]nonadeca-1(17),2,4,14(18),15-pentaen-6-ol, Compound 44

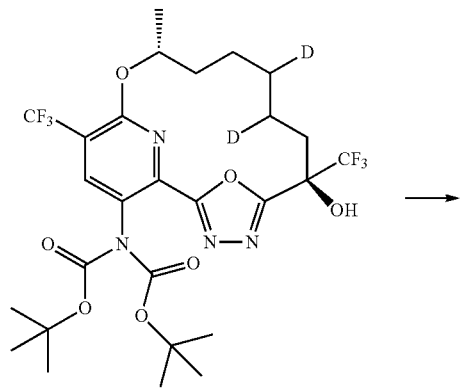

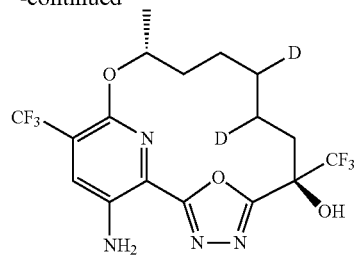

To a solution of tert-butyl N-tert-butoxycarbonyl-N-[(6R,12R)-8,9-dideuterio-6-hydroxy-12-methyl-6,15-bis(trifluoromethyl)-13,19-dioxa-3,4,18-triazatricyclo[12.3.1.12,5]nonadeca-1(17),2,4,14(18),15-pentaen-17-yl]carbamate (127 mg, 0.1682 mmol) in dichloromethane (1.4 mL) was added 2,2,2-trifluoroacetic acid (2.0720 g, 1.4 mL, 18.172 mmol). The mixture was stirred at room temperature for 2.5 hours. The mixture was then diluted with dichloromethane (5 mL), then concentrated by evaporation under reduced pressure. The residue was dissolved in ethyl acetate (100 mL), washed with aqueous saturated solution of sodium bicarbonate (3×15 mL) and brine (1×15 mL) then dried with anhydrous sodium sulphate, filtered and concentrated by evaporation under reduced pressure. The residue was purified by silica gel chromatography (12 g SiO₂, 0 to 25% portions of ethyl acetate in heptanes). The product was dissolved in a minimum amount of acetonitrile and water, and freeze-dried overnight to afford (6R,12R)-17-amino-8,9-dideuterio-12-methyl-6,15-bis(trifluoromethyl)-13,19-dioxa-3,4,18-triazatricyclo[12.3.1.12,5]nonadeca-1(17),2,4,14(18),15-pentaen-6-ol (70 mg, 94%) as a yellow solid. $^1$H NMR (400 MHz, DMSO-d₆) δ 7.77 (s, 1H), 7.56 (s, 1H), 6.35 (s, 2H), 4.85-4.73 (m, 1H), 2.49-2.43 (m, 1H), 2.32-2.20 (m, 1H), 2.14-2.04 (m, 1H), 1.73-1.66 (m, 1H), 1.58-1.37 (m, 3H), 1.34 (d, J=6.1 Hz, 3H), 1.22-1.12 (m, 1H) ppm. $^{19}$F NMR (377 MHz, DMSO-d₆) δ -62.50 (s, 3F), -76.40 (s, 3F) ppm. ESI-MS m/z calc. 442.1409, found 443.1 (M+1)⁺; Retention time: 3.53 minutes. LCMS Method: Kinetex Polar C₁₈ 3.0×50 mm 2.6 μm, 6 min, 5-95% acetonitrile in H₂O (0.1% formic acid) 1.2 mL/min.

Example 32: Preparation of (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaene-6,9-diol (diastereomer 2), Compound 45

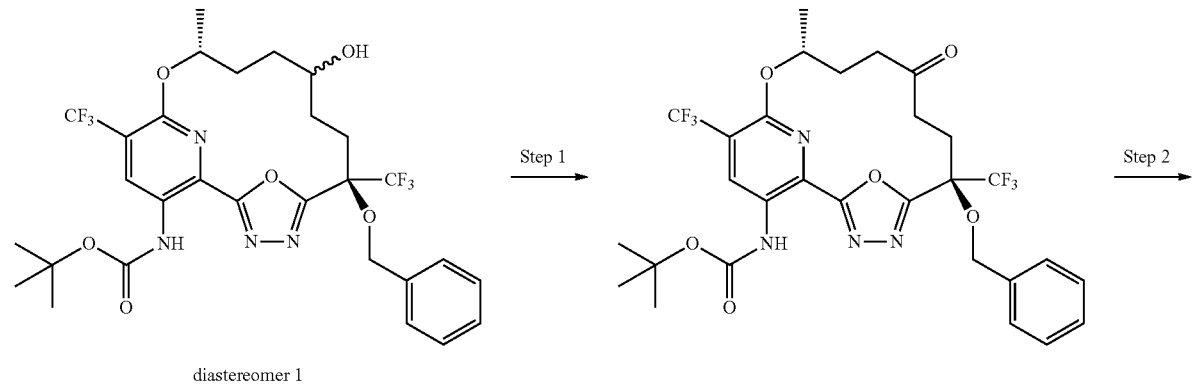

421

422

-continued

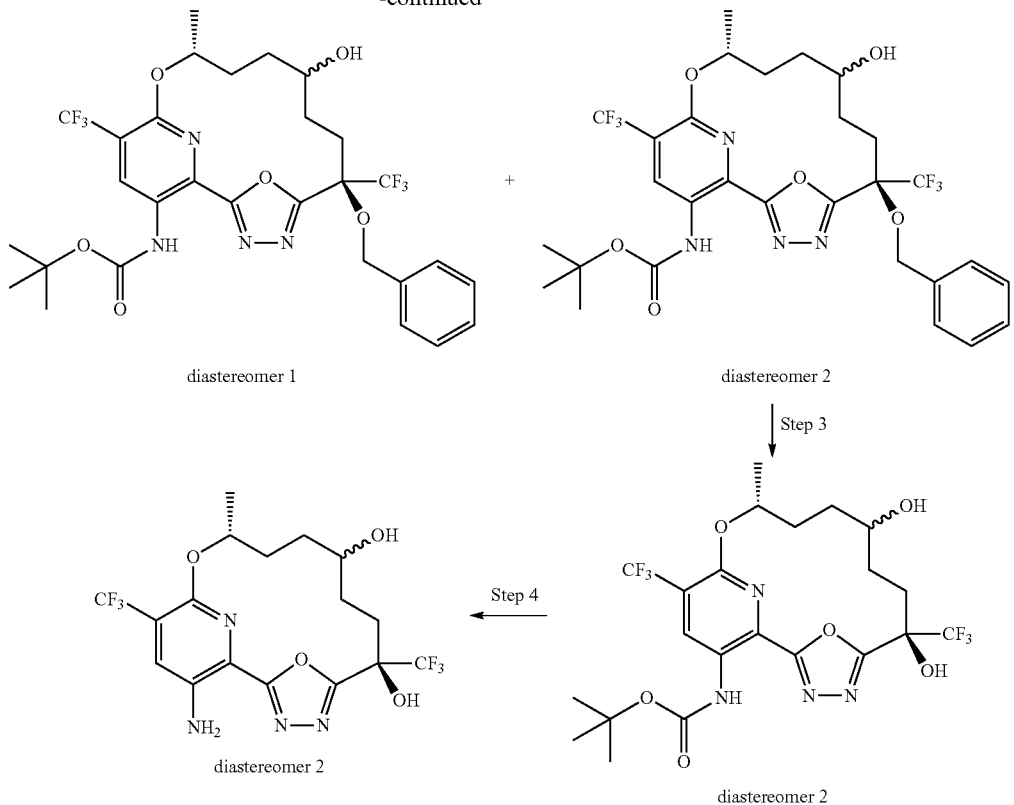

diastereomer 1 + diastereomer 2

Step 3 ↓

Step 4 ← diastereomer 2 diastereomer 2

Step 1: tert-Butyl N-[(6R,12R)-6-benzyloxy-12-methyl-9-oxo-6,15-bis(trifluoromethyl)-13,19-dioxa-3,4,18-triazatricyclo[12.3.1.1²,⁵]nonadeca-1(18),2,4,14,16-pentaen-17-yl]carbamate -continued

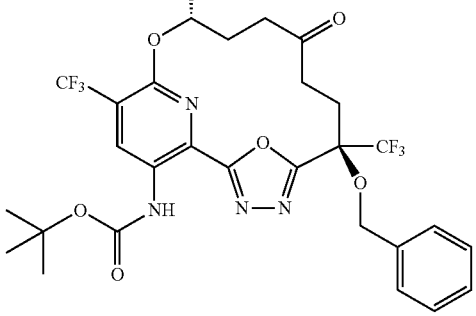

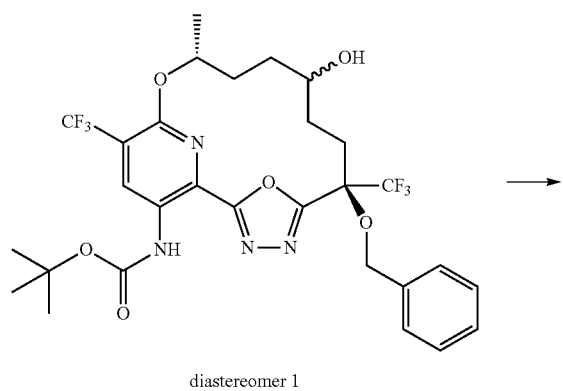

diastereomer 1

→

To a solution of tert-butyl N-[(6R,12R)-6-benzyloxy-9-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (147 mg, 0.2274 mmol) in DCM (12 mL) was added $NaHCO_3$ (320 mg, 3.8092 mmol). The mixture was cooled to 0° C. and Dess-Martin Periodinane (108 mg, 0.2546 mmol) was added. The mixture was slowly warmed to room temperature and stirred at room temperature overnight. The mixture was treated with saturated $NaHCO_3$ (8 mL) and extracted with $CH_2Cl_2$ (3×10 mL). The combined organic layers were dried with $Na_2SO_4$, filtered and concentrated. The residue was purified by flash chromatography (24 g $SiO_2$, eluting 10 to 30% EtOAc/heptanes) to afford tert-butyl N-[(6R,12R)-6-benzyloxy-12-methyl-9-oxo-6,15-bis(trifluoromethyl)-13,19-dioxa-3,4,18-triazatricyclo[12.3.1.1²,⁵]nonadeca-1(18),2,4,14,16-pentaen-17-yl]carbamate (120 mg, 82%) as a colorless oil. ¹H NMR (400

MHz, CDCl₃) δ 9.48 (s, 1H), 9.14 (s, 1H), 7.36-7.27 (m, 5H), 5.10-5.00 (m, 1H), 4.73 (d, J=11.2 Hz, 1H), 4.57 (d, J=11.0 Hz, 1H), 3.06-2.91 (m, 3H), 2.71 (ddd, J=16.9, 10.1, 2.3 Hz, 1H), 2.60-2.47 (m, 2H), 2.29-2.18 (m, 1H), 1.88-1.76 (m, 1H), 1.55 (s, 9H), 1.48 (d, J=6.4 Hz, 3H) ppm. ¹⁹F NMR (377 MHz, CDCl₃) δ −63.85 (s, 3F), −74.57 (s, 3F) ppm.

Step 2: tert-Butyl N-[(6R,12R)-6-benzyloxy-9-hydroxy-12-methyl-6,15-bis(trifluoromethyl)-13,19-dioxa-3,4,18-triazatricyclo[12.3.1.1.2,5]nonadeca-1(18),2,4,14,16-pentaen-17-yl]carbamate (diastereomer 2)

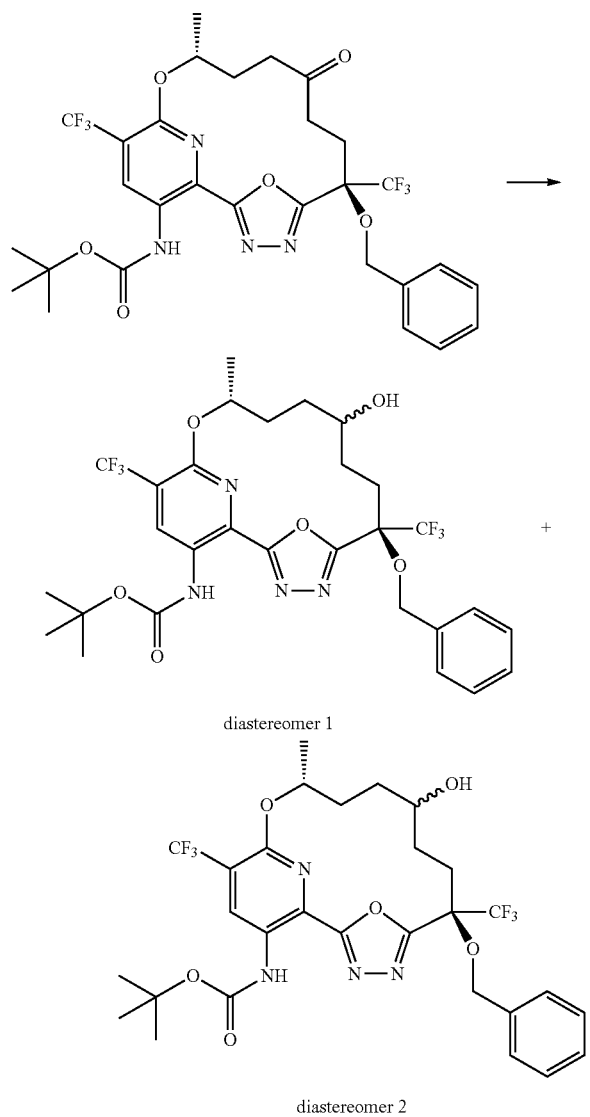

diastereomer 1 diastereomer 2

To a solution of tert-butyl N-[(6R,12R)-6-benzyloxy-12-methyl-9-oxo-6,15-bis(trifluoromethyl)-13,19-dioxa-3,4,18-triazatricyclo[12.3.1.1.2,5]nonadeca-1(18),2,4,14,16-pentaen-17-yl]carbamate (120 mg, 0.1862 mmol) in EtOH (10 mL) at 0° C. was added a solution of NaBH₄ (4.8 mg, 0.1269 mmol) in EtOH (1 mL) dropwise. The mixture was stirred at room temperature for 1 h. More NaBH₄ (4 mg, 0.1057 mmol) was added. The mixture was stirred at room temperature for 20 min. Acetone (1 mL) was added. The mixture was stirred at room temperature for 5 min. Sat. NaHCO₃ (1 mL) was added. The mixture was concentrated to remove EtOH. The residue was treated with water (2 mL) and extracted with CH₂Cl₂ (3×10 mL). The combined organic layers were dried with Na₂SO₄, filtered and concentrated. The residue was purified by silica gel chromatography (80 g SiO₂, eluting 10 to 30% EtOAc/heptanes) to afford two diastereomers. The desired diastereomer 2, tert-butyl N-[(6R,12R)-6-benzyloxy-9-hydroxy-12-methyl-6,15-bis(trifluoromethyl)-13,19-dioxa-3,4,18-triazatricyclo[12.3.1.1.2,5]nonadeca-1(18),2,4,14,16-pentaen-17-yl]carbamate (diastereomer 2) (60 mg, 50%) as a colorless oil. ¹H NMR (400 MHz, CDCl₃) δ 9.18 (s, 1H), 9.12 (s, 1H), 7.36-7.27 (m, 5H), 4.85-4.67 (m, 3H), 4.01-3.90 (m, 1H), 2.79 (t, J=12.3 Hz, 1H), 2.51-2.31 (m, 2H), 2.25-2.12 (m, 1H), 1.97-1.78 (m, 2H), 1.73-1.63 (m, 2H), 1.56 (s, 9H), 1.54-1.51 (m, 1H), 1.49 (d, J=6.4 Hz, 3H) ppm. ¹⁹F NMR (377 MHz, CDCl₃) δ −63.87 (s, 3F), −74.08 (s, 3F) ppm. ESI-MS m/z calc. 646.2226, found 647.2 (M+1)⁺; Retention time: 4.14 minutes; LCMS Method: Kinetex Polar C₁₈ 3.0×50 mm 2.6 μm, 6 min, 5-95% acetonitrile in H₂O (0.1% formic acid) 1.2 mL/min.

The other enantiomer, diastereomer 1, was the first to elute tert-butyl N-[(6R,12R)-6-benzyloxy-9-hydroxy-12-methyl-6,15-bis(trifluoromethyl)-13,19-dioxa-3,4,18-triazatricyclo[12.3.1.1.2,5]nonadeca-1(18),2,4,14,16-pentaen-17-yl]carbamate (60 mg, 50%) as a colorless oil. ¹H NMR (400 MHz, CDCl₃) δ 9.16-9.07 (m, 2H), 7.36-7.28 (m, 5H), 5.01 (ddd, J=9.5, 6.4, 3.2 Hz, 1H), 4.79 (d, J=10.8 Hz, 1H), 4.47 (d, J=10.5 Hz, 1H), 4.40-4.27 (m, 1H), 2.63 (dt, J=14.7, 7.7 Hz, 1H), 2.30 (dt, J=14.8, 5.7 Hz, 1H), 2.24-2.14 (m, 1H), 2.05-1.92 (m, 2H), 1.77-1.68 (m, 3H), 1.57 (s, 9H), 1.54-1.51 (m, 1H), 1.48 (d, J=6.4 Hz, 3H) ppm. ¹⁹F NMR (377 MHz, CDCl₃) δ −63.85 (s, 3F), −73.92 (s, 3F) ppm. ESI-MS m/z calc. 646.2226, found 647.2 (M+1)⁺; Retention time: 4.16 minutes; LCMS Method: Kinetex Polar C₁₈ 3.0×50 mm 2.6 μm, 6 min, 5-95% acetonitrile in H₂O (0.1% formic acid) 1.2 mL/min.

Step 3: tert-Butyl N-[(6R,12R)-6,9-dihydroxy-12-methyl-6,15-bis(trifluoromethyl)-13,19-dioxa-3,4,18-triazatricyclo[12.3.1.1.2,5]nonadeca-1(18),2,4,14,16-pentaen-17-yl]carbamate (diastereomer 2)

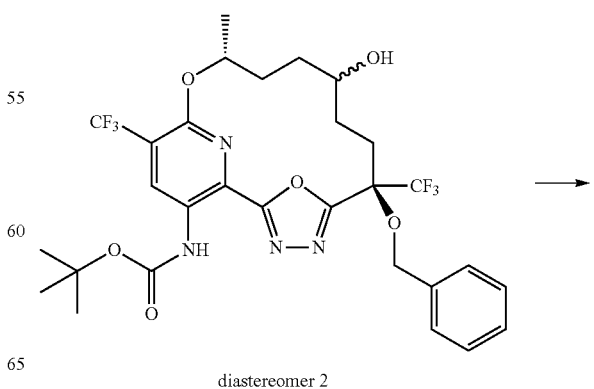

diastereomer 2

-continued

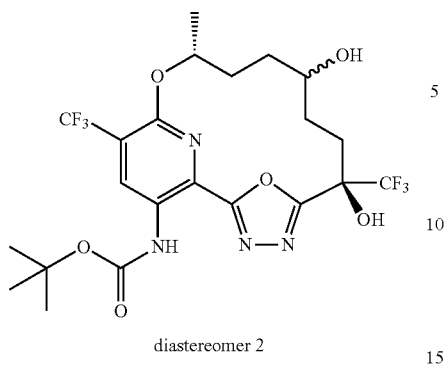

diastereomer 2

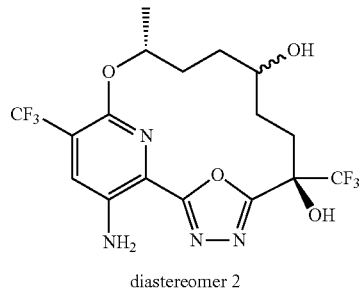

diastereomer 2

To a solution of tert-butyl N-[(6R,12R)-6-benzyloxy-9-hydroxy-12-methyl-6,15-bis(trifluoromethyl)-13,19-dioxa-3,4,18-triazatricyclo[12.3.1.1`2,5`]nonadeca-1(18),2,4,14,16-pentaen-17-yl]carbamate (diastereomer 2) (60 mg, 0.0928 mmol) in MeOH (5 mL) was added 10% palladium on carbon 50% wet (30 mg, 0.0141 mmol). The mixture was stirred under hydrogen (balloon) at room temperature overnight. The mixture was filtered through diatomaceous earth and washed with EtOAc. The filtrate was concentrated and purification by silica gel chromatography (24 g SiO$_2$, eluting 10 to 30% EtOAc/CH$_2$Cl$_2$) provided tert-butyl N-[(6R,12R)-6,9-dihydroxy-12-methyl-6,15-bis(trifluoromethyl)-13,19-dioxa-3,4,18-triazatricyclo[12.3.1.1`2,5`]nonadeca-1(18),2,4,14,16-pentaen-17-yl]carbamate (diastereomer 2) (48 mg, 93%) as a white solid. $^1$H NMR (400 MHz, CDCl$_3$) δ 9.15 (s, 1H), 9.07 (s, 1H), 6.65 (br s, 1H), 5.07-4.94 (m, 1H), 4.15-4.06 (m, 1H), 3.29 (br d, J=10.0 Hz, 1H), 2.58 (br t, J=11.9 Hz, 1H), 2.52-2.37 (m, 2H), 2.21-2.08 (m, 1H), 2.05-1.96 (m, 1H), 1.82-1.66 (m, 2H), 1.56 (s, 9H), 1.54-1.47 (m, 4H) ppm. $^{19}$F NMR (377 MHz, CDCl$_3$) δ −63.96 (s, 3F), −78.47 (s, 3F) ppm. ESI-MS m/z calc. 556.17566, found 557.1 (M+1)$^+$; Retention time: 3.62 minutes; LCMS Method: Kinetex Polar C$_{18}$ 3.0×50 mm 2.6 μm, 6 min, 5-95% acetonitrile in H$_2$O (0.1% formic acid) 1.2 mL/min.

Step 4: (6R,12R)-17-Amino-12-methyl-6,15-bis(trifluoromethyl)-13,19-dioxa-3,4,18-triazatricyclo[12.3.1.1`2,5`]nonadeca-1(18),2,4,14,16-pentaene-6,9-diol (diastereomer 2), Compound 45

To a solution of tert-butyl N-[(6R,12R)-6,9-dihydroxy-12-methyl-6,15-bis(trifluoromethyl)-13,19-dioxa-3,4,18-triazatricyclo[12.3.1.1`2,5`]nonadeca-1(18),2,4,14,16-pentaen-17-yl]carbamate (diastereomer 2) (38 mg, 0.0683 mmol) in CH$_2$Cl$_2$ (2 mL) at 0° C. was added TFA (1.4800 g, 1 mL, 12.980 mmol). The mixture was stirred at 13-15° C. for 1 h. MeOH (2 mL) was added. The mixture was concentrated and co-evaporated with MeOH (2×3 mL). The residue was dissolved in EtOAc (20 mL) and washed with saturated NaHCO$_3$ (4 mL), dried with Na$_2$SO$_4$, filtered and concentrated. The residue was purified by silica gel chromatography (12 g SiO$_2$, 10 to 30% EtOAc/CH$_2$Cl$_2$) and the product was freeze dried to afford (6R,12R)-17-amino-12-methyl-6,15-bis(trifluoromethyl)-13,19-dioxa-3,4,18-triazatricyclo[12.3.1.1`2,5`]nonadeca-1(18),2,4,14,16-pentaene-6,9-diol (diastereomer 2) (19 mg, 57%) as a pale-yellow solid. $^1$H NMR (400 MHz, DMSO-d$_6$) δ 7.75 (s, 1H), 7.61 (s, 1H), 6.33 (s, 2H), 4.70-4.55 (m, 2H), 3.73-3.62 (m, 1H), 2.46-2.29 (m, 2H), 2.19-2.08 (m, 1H), 2.02-1.90 (m, 1H), 1.71-1.45 (m, 3H), 1.35 (d, J=6.1 Hz, 3H), 1.30-1.21 (m, 1H) ppm. $^{19}$F NMR (377 MHz, DMSO-d$_6$) δ −62.47 (s, 3F), −76.20 (br. s., 3F) ppm. ESI-MS m/z calc. 456.1232, found 457.1 (M+1)$^+$; Retention time: 2.89 minutes; Kinetex Polar C$_{18}$ 3.0×50 mm 2.6 μm, 6 min, 5-95% acetonitrile in H$_2$O (0.1% formic acid) 1.2 mL/min.

Example 33: Preparation of (6R,12R)-17-amino-12-methyl-6,15-bis(trifluoromethyl)-13,19-dioxa-3,4,18-triazatricyclo[12.3.1.1`2,5`]nonadeca-1(18),2,4,14,16-pentaene-6,10-diol (diastereomer 2), Compound 46

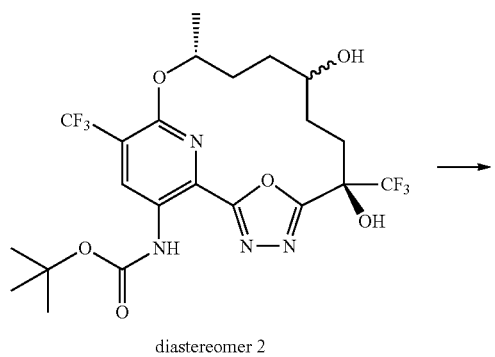

diastereomer 2

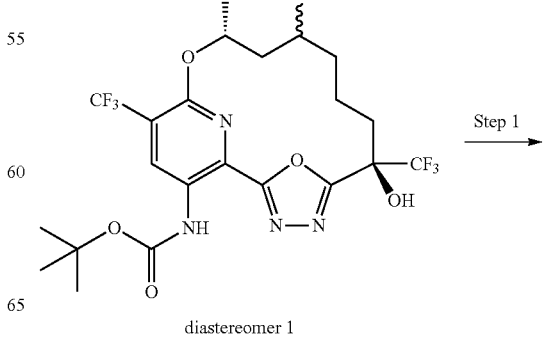

diastereomer 1

Step 1

427

-continued

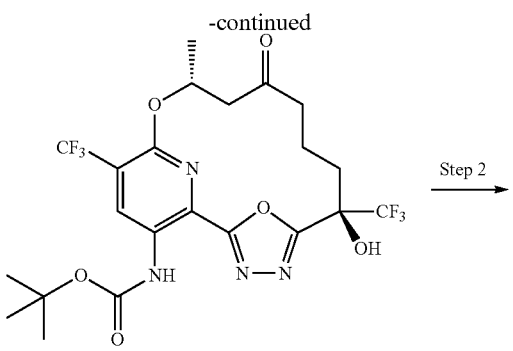

Step 2 →

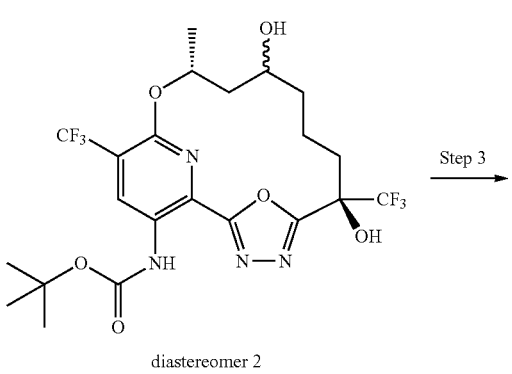

diastereomer 2

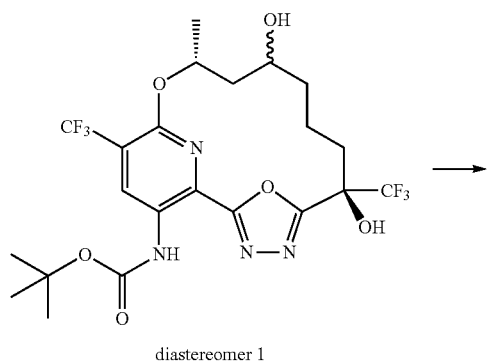

diastereomer 2

Step 1: tert-Butyl N-[(6R,12R)-6-hydroxy-12-methyl-10-oxo-6,15-bis(trifluoromethyl)-13,19-dioxa-3,4,18-triazatricyclo[12.3.1.12,5]nonadeca-1(18),2,4,14,16-pentaen-17-yl]carbamate

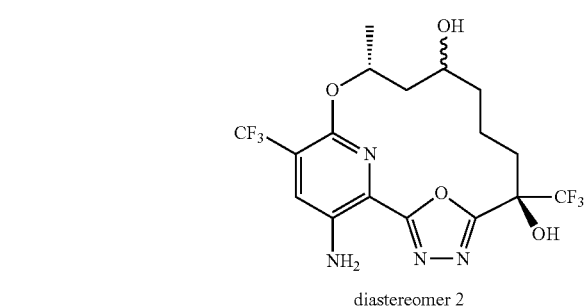

diastereomer 1

428

-continued

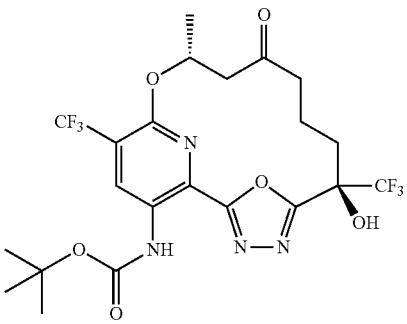

To a solution of tert-butyl N-[(6R,12R)-6,10-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (65 mg, 0.1168 mmol) in $CH_2Cl_2$ (8 mL) was added $NaHCO_3$ (168 mg, 1.9998 mmol). The mixture was cooled to 0° C. and Dess-Martin periodinane (51 mg, 0.1202 mmol) was added. The mixture was allowed to slowly warm to room temperature and stirred at room temperature overnight. The mixture was treated with saturated $NaHCO_3$ (10 mL) and extracted with $CH_2Cl_2$ (3×10 mL). The combined organic layers were dried with $Na_2SO_4$, filtered and concentrated. The residue was purified by silica gel chromatography (12 g $SiO_2$, eluting 10 to 60% EtOAc/heptanes) to afford tert-butyl N-[(6R,12R)-6-hydroxy-12-methyl-10-oxo-6,15-bis(trifluoromethyl)-13,19-dioxa-3,4,18-triazatricyclo[12.3.1.12,5]nonadeca-1(18),2,4,14,16-pentaen-17-yl]carbamate (38 mg, 59%) as a white solid. $^1H$ NMR (400 MHz, $CDCl_3$) δ 9.24 (s, 1H), 9.14 (s, 1H), 5.24 (quind, J=6.4, 2.0 Hz, 1H), 4.75 (s, 1H), 3.56 (dd, J=18.3, 1.7 Hz, 1H), 2.75-2.59 (m, 3H), 2.47 (dd, J=18.3, 6.1 Hz, 1H), 2.25-2.07 (m, 2H), 2.00-1.87 (m, 1H), 1.55 (s, 9H), 1.53 (d, J=6.6 Hz, 3H) ppm. $^{19}F$ NMR (377 MHz, $CDCl_3$) δ −63.83 (s, 3F), −78.16 (s, 3F) ppm. ESI-MS m/z calc. 554.16003, found 499.1 (M−55)$^+$; Retention time: 2.36 minutes; LCMS Method: Kinetex Polar $C_{18}$ 3.0×50 mm 2.6 μm, 3 min, 5-95% acetonitrile in $H_2O$ (0.1% formic acid) 1.2 mL/min.

Step 2: tert-Butyl N-[(6R,12R)-6,10-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 2)

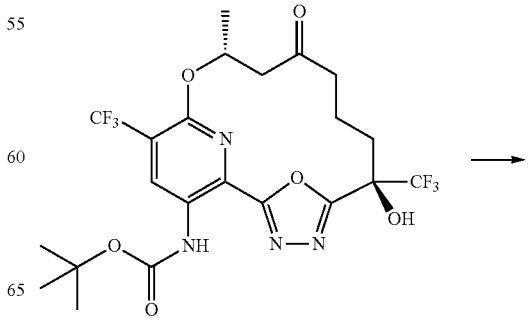

-continued

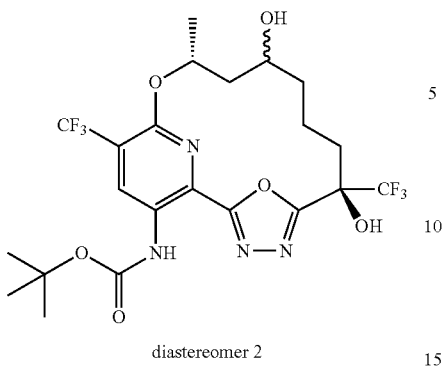

diastereomer 2

To a solution of tert-butyl N-[(6R,12R)-6-hydroxy-12-methyl-10-oxo-6,15-bis(trifluoromethyl)-13,19-dioxa-3,4,18-triazatricyclo[12.3.1.12,5]nonadeca-1(18),2,4,14,16-pentaen-17-yl]carbamate (33 mg, 0.0595 mmol) in EtOH (4 mL) at 0° C. was added a solution of NaBH$_4$ (2.1 mg, 0.0555 mmol) in EtOH (0.5 mL). The mixture was at 0° C. for 4 h. Acetone (1 mL) was added. The mixture was stirred at 0° C. for 5 min. Sat. NaHCO$_3$ (5 mL) was added. The mixture was extracted with EtOAc (3×10 mL). The combined organic layers were dried with Na$_2$SO$_4$, filtered and concentrated. The residue was purified by silica gel chromatography (12 g SiO$_2$, eluting 0 to 50% EtOAc/heptanes) to afford tert-butyl N-[(6R,12R)-6,10-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 2) (10 mg, 30%) as a pale-yellow solid. $^1$H NMR (400 MHz, CDCl$_3$) δ 9.13 (s, 2H), 5.27-5.16 (m, 1H), 4.06-3.95 (m, 1H), 3.85 (s, 1H), 2.58-2.38 (m, 3H), 2.34-2.23 (m, 1H), 2.04-1.90 (m, 1H), 1.78-1.63 (m, 4H), 1.56 (s, 9H), 1.49 (d, J=6.4 Hz, 3H) ppm. $^{19}$F NMR (377 MHz, CDCl$_3$) δ −63.85 (s, 3F), −77.65 (s, 3F) ppm. ESI-MS m/z calc. 556.17566, found 557.2 (M+1)$^+$; Retention time: 3.5 minutes; LCMS Method: Kinetex Polar C$_{18}$ 3.0×50 mm 2.6 µm, 6 min, 5-95% acetonitrile in H$_2$O (0.1% formic acid) 1.2 mL/min.

Step 3: (6R,12R)-17-Amino-12-methyl-6,15-bis(trifluoromethyl)-13,19-dioxa-3,4,18-triazatricyclo[12.3.1.12,5]nonadeca-1(18),2,4,14,16-pentaene-6,10-diol (diastereomer 2), Compound 46

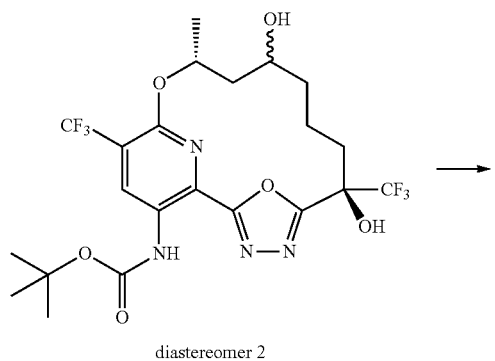

diastereomer 2

-continued

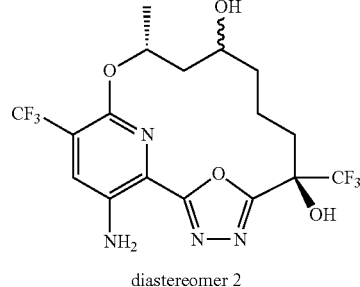

diastereomer 2

To a solution of tert-butyl N-[(6R,12R)-6,10-dihydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 2) (20 mg, 0.0359 mmol) in CH$_2$Cl$_2$ (2 mL) at 0° C. was added TFA (740.00 mg, 0.5 mL, 6.4899 mmol) dropwise. The mixture was stirred at 0° C. for 1 h and at 9-13° C. for 1 h. The mixture was treated with MeOH (1 mL) and concentrated at rt, co-evaporated with MeOH (2×2 mL). The residue was treated with saturated NaHCO$_3$ (5 mL) and extracted with CH$_2$Cl$_2$ (3×10 mL). The combined organic layers were dried with Na$_2$SO$_4$, filtered and concentrated. Purification by silica gel chromatography (24 g SiO$_2$, eluting 10 to 30% EtOAc/CH$_2$Cl$_2$) provided trifluoroacetate formed with the secondary alcohol (about 3 mg) and the first crop of the desired product. Trifluoroacetate was dissolved in THF (1 mL) and treated with 1 N aqueous NaOH (0.1 mL) at room temperature for 20 min. The mixture was treated with saturated NaHCO$_3$ (1 mL) and extracted with CH$_2$Cl$_2$ (2×5 mL). The combined organic layers were dried with Na$_2$SO$_4$, filtered and concentrated. Purification by silica gel chromatography (24 g SiO$_2$, eluting 10 to 30% EtOAc/CH$_2$Cl$_2$) provided the second crop. The two crops were combined and freeze dried to give (6R,12R)-17-amino-12-methyl-6,15-bis(trifluoromethyl)-13,19-dioxa-3,4,18-triazatricyclo[12.3.1.12,5]nonadeca-1(18),2,4,14,16-pentaene-6,10-diol (diastereomer 2) (10 mg, 59%) as a pale-yellow solid. $^1$H NMR (400 MHz, DMSO-d$_6$) δ 7.76 (s, 1H), 7.58 (s, 1H), 6.37 (s, 2H), 5.23-5.14 (m, 1H), 4.38 (d, J=4.9 Hz, 1H), 3.63-3.52 (m, 1H), 2.47-2.42 (m, 1H), 2.34-2.25 (m, 1H), 2.14-2.00 (m, 2H), 1.84-1.70 (m, 1H), 1.55-1.65 (m, 1H), 1.45-1.37 (m, 1H), 1.35 (d, J=6.6 Hz, 3H), 1.32-1.25 (m, 1H) ppm. $^{19}$F NMR (377 MHz, DMSO-d$_6$) δ −62.50 (s, 3F), −77.01 (s, 3F) ppm. ESI-MS m/z calc. 456.12323, found 457.1 (M+1)$^+$; Retention time: 2.76 minutes; LCMS Method: Kinetex Polar C$_{18}$ 3.0×50 mm 2.6 µm, 6 min, 5-95% acetonitrile in H$_2$O (0.1% formic acid) 1.2 mL/min.

Example 34: Preparation of (6R)-17-amino-12-(cyclopropylmethyl)-6,15-bis(trifluoromethyl)-13,19-dioxa-3,4,18-triazatricyclo[12.3.1.12,5]nonadeca-1(18),2,4,14,16-pentaen-6-ol (enantiomer 1), Compound 47, and (6R)-17-amino-12-(cyclopropylmethyl)-6,15-bis(trifluoromethyl)-13,19-dioxa-3,4,18-triazatricyclo[12.3.1.12,5]nonadeca-1(18),2,4,14,16-pentaen-6-ol (enantiomer 2), Compound 48

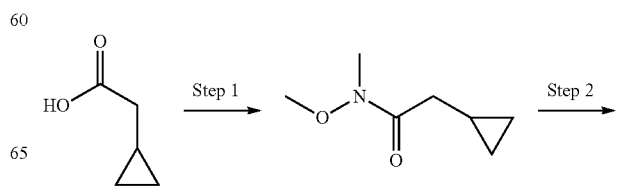

431
-continued
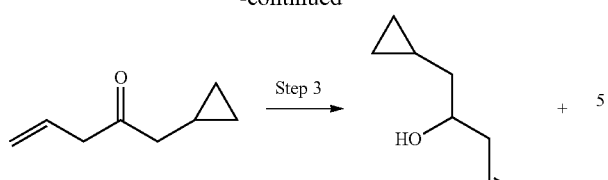
Step 3
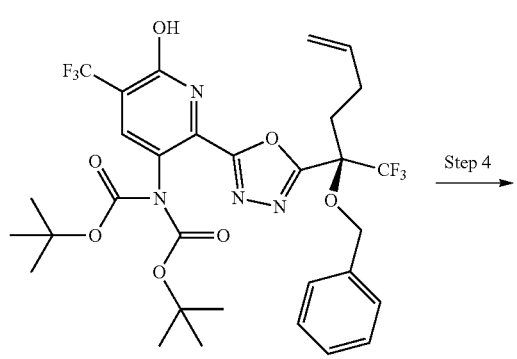
Step 4
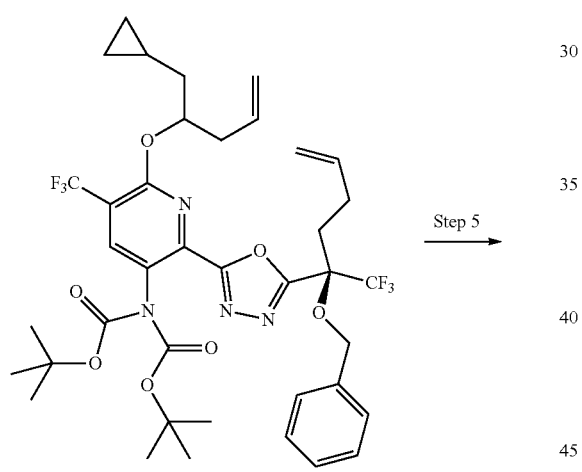
Step 5
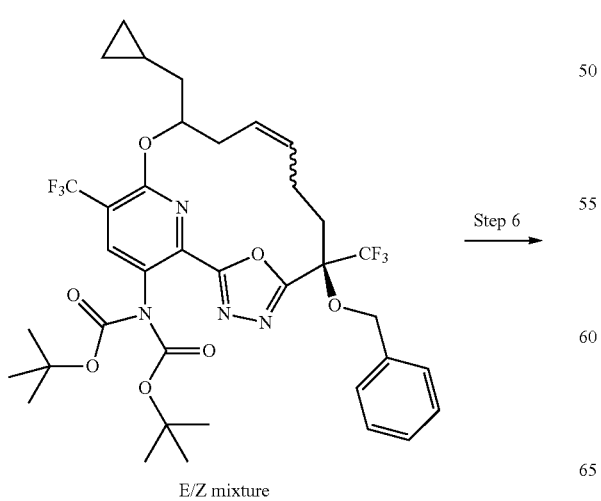
E/Z mixture
432
-continued
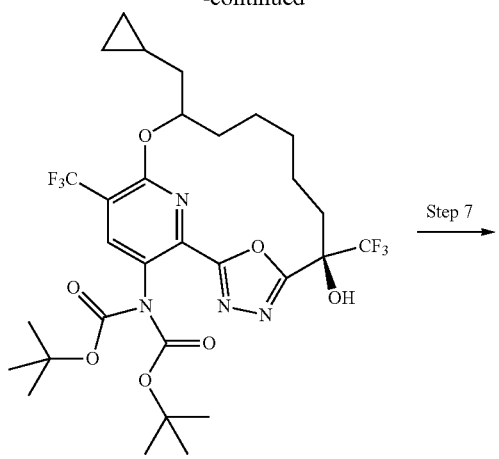
Step 7
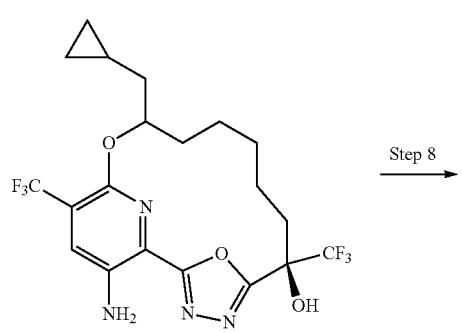
Step 8
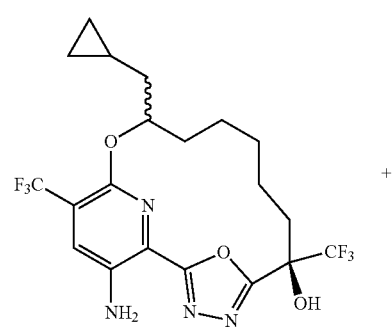
enantiomer 1
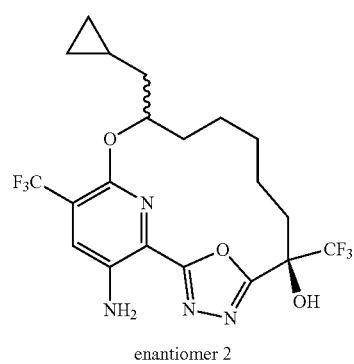
enantiomer 2

Step 1: 2-Cyclopropyl-N-methoxy-N-methyl-acetamide

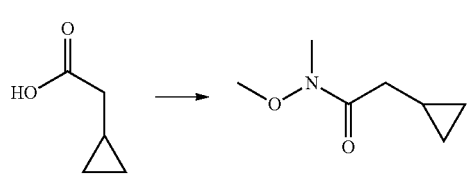

To a stirred solution of 2-cyclopropylacetic acid (10 g, 99.884 mmol) in DCM (100 mL) was added CDI (18.5 g, 114.09 mmol) portion wise and the reaction mixture was stirred for 2 h at 25° C. Then, N,O-dimethyl hydroxylamine (hydrochloride salt) (10.000 g, 102.52 mmol) was added in one portion. The reaction mixture was stirred for 12 h at 25° C., poured into ice-cold water (100 mL) and extracted with ethyl acetate (300×2). The combined organic layer was washed with brine (100 mL), dried over anhydrous $Na_2SO_4$ and concentrated under reduced pressure. The crude product was purified by column chromatography over silica gel (230-400 mesh) using 12% (ethyl acetate-hexane) as eluent to afford 2-cyclopropyl-N-methoxy-N-methyl-acetamide (12 g, 84%). $^1$H NMR (400 MHz, DMSO-$d_6$) δ 3.63 (s, 3H), 3.08 (s, 3H), 2.29 (d, J=6.8 Hz, 2H), 0.991-0.92 (m, 1H), 0.46-0.42 (m, 2H), 0.12-0.09 (m, 2H) ppm. ESI-MS m/z calc. 143.09464, found 144.0 (M+1)$^+$; Retention time: 2.29 minutes; LCMS Method: TCG method 10: Zorbax Ext $C_{18}$, 50×4.6 mm 5 μm, 5 min run, 10-90% acetonitrile in water (10 μM $NH_4OAc$ modifier), 1.2 mL/min.

Step 2: 1-Cyclopropylpent-4-en-2-one

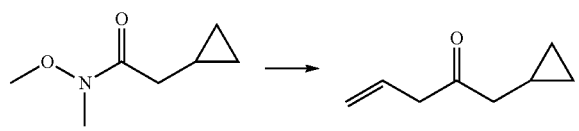

A solution of 2-cyclopropyl-N-methoxy-N-methyl-acetamide (0.5 g, 3.4920 mmol) in THF (10.5 mL) was cooled to −78° C. and treated with a solution of allylmagnesium bromide (5 mL of 1 M, 5.0000 mmol) in $Et_2O$ at −78° C. over 22 minutes. The reaction was held at this temperature for 2 h and 10 min. and then treated with saturated aqueous $NH_4Cl$ (50 mL) at −78° C. The organic layer was decanted, and the aqueous phase was extracted with DCM (4×40 mL). The combined organics were washed with $NH_4Cl$ (30 mL), dried over $Na_2SO_4$ and concentrated in vacuo carefully at 25° C., to give a crude residue (0.564 g). The residue contained the product 1-cyclopropylpent-4-en-2-one (564 mg, 77%) as a clear oil. $^1$H NMR (500 MHz, Chloroform-d) δ 6.00-5.86 (m, 1H), 5.22-5.08 (m, 2H), 3.22 (d, J=7.0 Hz, 2H), 2.32 (d, J=6.9 Hz, 2H), 1.07-0.93 (m, 1H), 0.61-0.53 (m, 2H), 0.11 (q, J=5.2 Hz, 2H) ppm.

Step 3: 1-Cyclopropylpent-4-en-2-ol

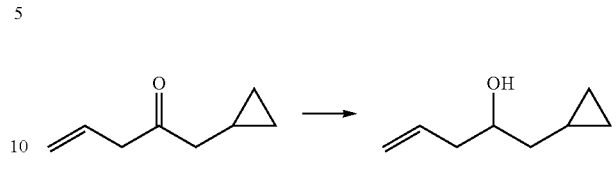

A slurry of lithium aluminum hydride (1.24 g, 32.671 mmol) in THF (36 mL) was cooled to −78° C. under nitrogen. The slurry was treated dropwise with a solution of 1-cyclopropylpent-4-en-2-one (3 g, 21.743 mmol) in THF (7 mL) over 40 minutes and held at this temperature an additional 2 h. The slurry was treated carefully dropwise with $H_2O$ (20 mL) at −78° C. and then diluted with DCM (150 mL) and warmed to room temperature by removing the bath, and stirred for 30 minutes at rt. A white gel was generated as the second component of the biphasic mixture. The mixture was filtered through Celite and rinsed with $CH_2Cl_2$ (2×200 mL). The filtrate was concentrated in vacuo (28° C., 140 mmHg) to obtain a light yellow crude oil (2.99 g). The crude residue was purified by silica gel chromatography (120 g $SiO_2$, loaded in hexanes, eluted with 0-10% $Et_2O$ in hexanes over a 40 minute gradient). The pure fractions were combined and the solvents were carefully removed under reduced pressure (28° C., 140 mm Hg) to obtain the target 1-cyclopropylpent-4-en-2-ol (1.41 g, 51%) as a transparent colorless oil. $^1$H NMR (500 MHz, Chloroform-d) δ 5.85 (dddd, J=17.0, 10.4, 7.8, 6.5 Hz, 1H), 5.18-5.10 (m, 2H), 3.77 (tt, J=7.6, 4.7 Hz, 1H), 2.40-2.31 (m, 1H), 2.19 (dtt, J=14.0, 7.8, 1.2 Hz, 1H), 1.47-1.31 (m, 2H), 0.82-0.70 (m, 1H), 0.55-0.41 (m, 2H), 0.12 (dtd, J=9.2, 4.8, 3.3 Hz, 1H), 0.08-0.03 (m, 1H) ppm.

Step 4: tert-Butyl N-[2-[5-[(1R)-1-benzyloxy-1-(trifluoromethyl)pent-4-enyl]-1,3,4-oxadiazol-2-yl]-6-[1-(cyclopropylmethyl)but-3-enoxy]-5-(trifluoromethyl)-3-pyridyl]-N-tert-butoxycarbonyl-carbamate

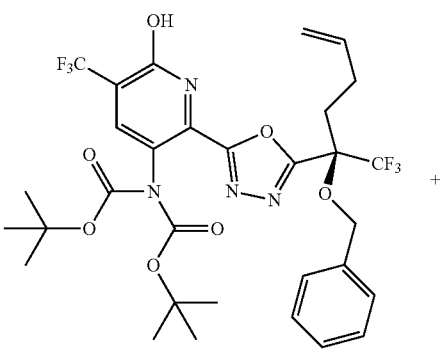

+

435

-continued

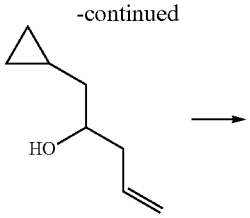

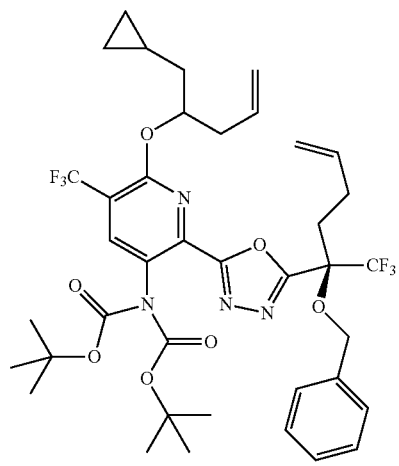

A solution of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (500 mg, 0.7116 mmol) and 1-cyclopropylpent-4-en-2-ol (200 mg, 1.7830 mmol) in toluene (5 mL) was treated with DIAD (261.00 mg, 0.25 mL, 1.2908 mmol) dropwise over one minute followed by triphenylphosphine (289 mg, 1.1019 mmol) in one portion at room temperature under argon. The reaction stirred for a total of 24 h at rt. The reaction was treated with NaHCO$_3$ (20 mL) and diluted with EtOAc (100 mL). Then organic layer was washed with saturated aqueous NaHCO$_3$ (1×20 mL), saturated aqueous NH$_4$Cl (1×20 mL) and brine (1×20 mL) then dried over Na$_2$SO$_4$, filtered and concentrated in vacuo to obtain a yellow crude oil (1.13 g). The crude residue was purified by silica gel chromatography (80 g SiO$_2$, dry loaded, eluted with 0-50% EtOAc in hexanes over a 20 min. gradient). The pure fractions were combined and the solvent was evaporated in vacuo to obtain the product tert-butyl N-[2-[5-[(1R)-1-benzyloxy-1-(trifluoromethyl)pent-4-enyl]-1,3,4-oxadiazol-2-yl]-6-[1-(cyclopropylmethyl)but-3-enoxy]-5-(trifluoromethyl)-3-pyridyl]-N-tert-butoxycarbonyl-carbamate (465 mg, 76%) as a colorless oil. ESI-MS m/z calc. 796.3271, found 797.8 (M+1)$^+$; Retention time: 9.44 minutes; LCMS Method: Merck Millipore Chromolith SpeedROD C$_{18}$ column (50×4.6 mm) and a dual gradient run from 5-100% mobile phase B over 12 minutes. Mobile phase A=water (0.1% CF$_3$CO$_2$H). Mobile phase B=acetonitrile (0.1% CF$_3$CO$_2$H).

436

Step 5: tert-Butyl N-[(6R)-6-benzyloxy-12-(cyclopropylmethyl)-6,15-bis(trifluoromethyl)-13,19-dioxa-3,4,18-triazatricyclo[12.3.1.12,5]nonadeca-1(17),2,4,9,14(18),15-hexaen-17-yl]-N-tert-butoxycarbonyl-carbamate (E/Z Mixture)

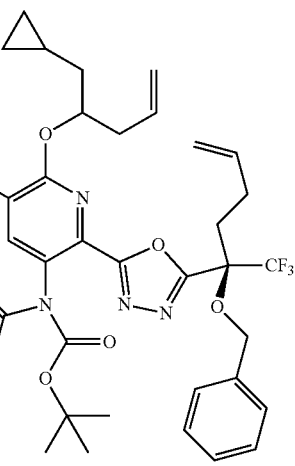

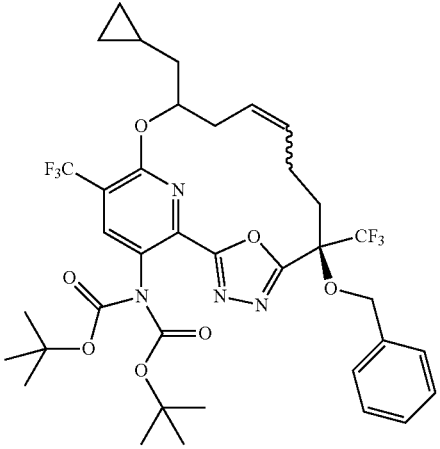

A flask was charged with tert-butyl N-[2-[5-[(1R)-1-benzyloxy-1-(trifluoromethyl)pent-4-enyl]-1,3,4-oxadiazol-2-yl]-6-[1-(cyclopropylmethyl)but-3-enoxy]-5-(trifluoromethyl)-3-pyridyl]-N-tert-butoxycarbonyl-carbamate (465 mg, 0.5836 mmol) followed by 1,2-dichloroethane (280 mL) under argon. The reaction solution was treated with Zhan catalyst-1B (52 mg, 0.0708 mmol) at rt. The reaction was heated at 70° C. for 16 hours. LCMS indicated greater than 95% conversion of the starting material to products. LCMS indicated no additional conversion of tentative starting material peak. The reaction was treated with a drop of DMSO and the contents of the reaction vessel were concentrated onto SiO$_2$. The material was purified by silica gel chromatography (40 g SiO$_2$, dry loaded, eluted with 0-15% EtOAc in hexanes over a 20 min. gradient). The material was recovered impure and the fractions containing the target were combined and the solvent was evaporated in vacuo to obtain the product tert-butyl N-[(6R)-6-benzyloxy-12-(cyclopropylmethyl)-6,15-bis(trifluoromethyl)-13,19-dioxa-3,4,18-triazatricyclo[12.3.1.12,5]nonadeca-1(17),2,4,9,14(18),15-hexaen-17-yl]-N-tert-butoxy carbonyl-carbamate (E/Z mixture) (272 mg, 52%) as a mixture of diastereomers; the material appeared as a transparent oil. Both peaks at 9.10 and 9.25 min. respectively: ESI-MS m/z calc. 768.2958, found 769.8 (M+1)⁺; Retention time: 9.1 minutes; LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 6: tert-Butyl N-tert-butoxycarbonyl-N-[(6R)-12-(cyclopropylmethyl)-6-hydroxy-6,15-bis(trifluoromethyl)-13,19-dioxa-3,4,18-triazatricyclo[12.3.1.12,5]nonadeca-1(17),2,4,14(18),15-pentaen-17-yl]carbamate

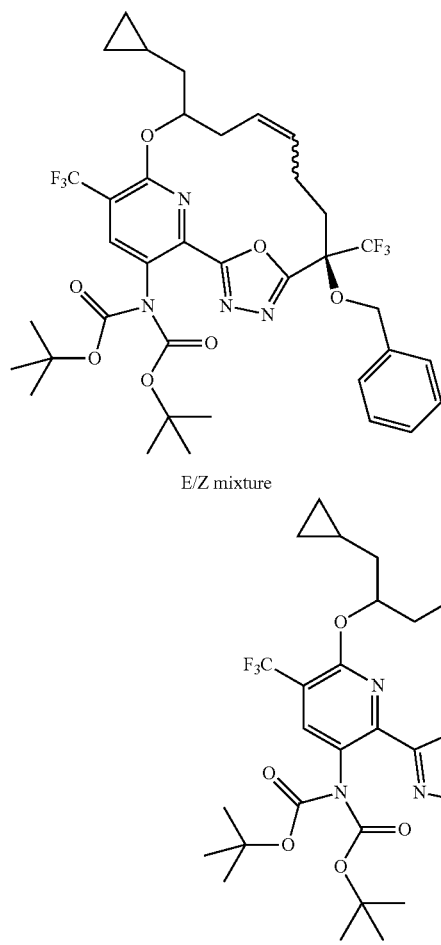

A flask was charged with tert-butyl N-[(6R)-6-benzyloxy-12-(cyclopropylmethyl)-6,15-bis(trifluoromethyl)-13,19-dioxa-3,4,18-triazatricyclo[12.3.1.12,5]nonadeca-1(17),2,4,9,14(18),15-hexaen-17-yl]-N-tert-butoxy carbonyl-carbamate (E/Z mixture) (88 mg, 0.1145 mmol) in EtOH (4.8 mL). Then $N_2$ was bubbled through the solution for 5 minutes. Then the solution was treated with Pd/C (24 mg, 10% w/w, 0.0226 mmol) at room temperature and $N_2$ was bubbled through the solution for 5 minutes. Then $H_2$ gas was bubbled through the mixture for 20 min. and held under an atmosphere of $H_2$ with a balloon. The reaction was complete in 11 h. The mixture was diluted with EtOAc and filtered through Celite. The filtrate was concentrated in vacuo to obtain the product tert-butyl N-tert-butoxycarbonyl-N-[(6R)-12-(cyclopropylmethyl)-6-hydroxy-6,15-bis(trifluoromethyl)-13,19-dioxa-3,4,18-triazatricyclo[12.3.1.12,5]nonadeca-1(17),2,4,14(18),15-pentaen-17-yl]carbamate (74 mg, 94%) as a mixture of diastereomers; the material appeared as a light yellow oil which became a resin-like foam when thoroughly dried. ESI-MS m/z calc. 680.26447, found 581.3 (M−99)⁺; Retention time: 8.01 minutes; LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 7: (6R)-17-Amino-12-(cyclopropylmethyl)-6,15-bis(trifluoromethyl)-13,19-dioxa-3,4,18-triazatricyclo[12.3.1.12,5]nonadeca-1(18),2,4,14,16-pentaen-6-ol (trifluoroacetate salt)

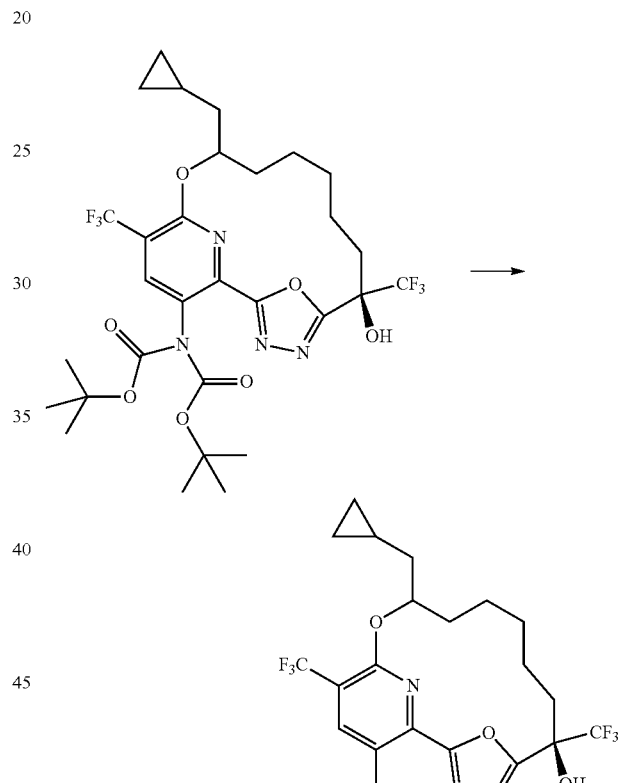

A vial was charged with tert-butyl N-tert-butoxycarbonyl-N-[(6R)-12-(cyclopropylmethyl)-6-hydroxy-6,15-bis(trifluoromethyl)-13,19-dioxa-3,4,18-triazatricyclo[12.3.1.12,5]nonadeca-1(17),2,4,14(18),15-pentaen-17-yl]carbamate (155 mg, 0.2277 mmol) and treated with a solution of TFA (518.00 mg, 0.35 mL, 4.5429 mmol) in DCM (1.4 mL) at 0° C. The reaction was warmed to room temperature over 3 hours. LCMS indicated the transformation was complete. The reaction was concentrated in vacuo to obtain a crude residue of the target product (128 mg). The material was further purified by reverse phase HPLC (Higgins Analytical $C_{18}$ 250×20 mm (50-95% B over a 70 min. gradient), 25 mL/min, 254 nm, Buffer A: 0.1% $CF_3CO_2H$ in $H_2O$, Buffer B: 0.1% $CF_3CO_2H$ in acetonitrile). The pure fractions were combined and the solvent was evaporated in vacuo to obtain the product (6R)-17-amino-12-(cyclopropylmethyl)-6,15- bis(trifluoromethyl)-13,19-dioxa-3,4,18-triazatricyclo[12.3.1.1²,⁵]nonadeca-1(18),2,4,14,16-pentaen-6-ol (trifluoroacetate salt) (71 mg, 51%) as a dark yellow resin. ESI-MS m/z calc. 480.1596, found 481.3 (M+1)$^+$; Retention time: 3.27 minutes; LCMS Method: Water Cortex 2.7 u C$_{18}$ (3.0 mm×50 mm), temp: 55° C.; Flow: 1.2 mL/min; mobile phase: 100% water with 0.1% CF$_3$CO$_2$H then 100% acetonitrile with 0.1% CF$_3$CO$_2$H, grad: 5% to 100% B over 4 min, held at 100% B for 0.5 min, then equilibrated to 5% B over 1.5 min.

Step 8: (6R)-17-Amino-12-(cyclopropylmethyl)-6,15-bis(trifluoromethyl)-13,19-dioxa-3,4,18-triazatricyclo[12.3.1.1²,⁵]nonadeca-1(18),2,4,14,16-pentaen-6-ol (enantiomer 1), Compound 47, and (6R)-17-amino-12-(cyclopropylmethyl)-6,15-bis(trifluoromethyl)-13,19-dioxa-3,4,18-triazatricyclo[12.3.1.1²,⁵]nonadeca-1(18),2,4,14,16-pentaen-6-ol (enantiomer 2), Compound 48

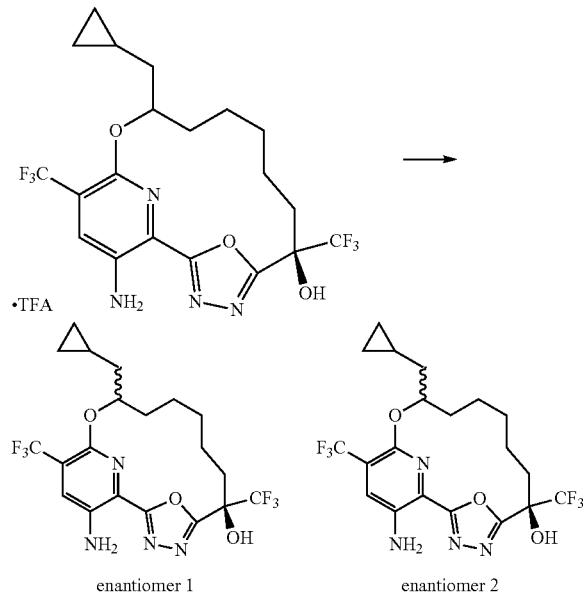

The two diastereomers of (6R)-17-amino-12-(cyclopropylmethyl)-6,15-bis(trifluoromethyl)-13,19-dioxa-3,4,18-triazatricyclo[12.3.1.1²,⁵]nonadeca-1(18),2,4,14,16-pentaen-6-ol (trifluoroacetate salt) (83 mg, 0.1728 mmol) were separated by supercritical fluid chromatography (SFC) using 0.1% diethylamine in EtOH as co-solvents. Fractions containing each diastereomer were then concentrated under reduced pressure and freeze-dried (acetonitrile/water mixture) to afford (6R)-17-amino-12-(cyclopropylmethyl)-6,15-bis(trifluoromethyl)-13,19-dioxa-3,4,18-triazatricyclo[12.3.1.1²,⁵]nonadeca-1(18),2,4,14,16-pentaen-6-ol (enantiomer 1) (45 mg) and (6R)-17-amino-12-(cyclopropylmethyl)-6,15-bis(trifluoromethyl)-13,19-dioxa-3,4,18-triazatricyclo[12.3.1.1²,⁵]nonadeca-1(18),2,4,14,16-pentaen-6-ol (enantiomer 2) (31 mg). Co-evaporation of the enantiomer 1 (2 mg) with acetonitrile (2×3 mL) could not remove isopropanol. Enantiomer 1 (2 mg) was dissolved in EtOAc and washing with 1 N HCl could remove isopropanol but a byproduct was observed by $^1$H NMR. Enantiomer 1 (about 39 mg) was purified by silica gel chromatography (24 g SiO$_2$, eluting 10 to 30% EtOAc/CH$_2$Cl$_2$) and freeze dried to afford (6R)-17-amino-12-(cyclopropylmethyl)-6,15-bis(trifluoromethyl)-13,19-dioxa-3,4,18-triazatricyclo[12.3.1.1²,⁵]nonadeca-1(18),2,4,14,16-pentaen-6-ol (enantiomer 1) (34 mg, 40%) as a pale-yellow solid. $^1$H NMR (400 MHz, DMSO-d$_6$) δ 7.77 (s, 1H), 7.58 (s, 1H), 6.36 (s, 2H), 4.69-4.58 (m, 1H), 2.48-2.43 (m, 1H), 2.26-2.15 (m, 1H), 2.12-2.00 (m, 1H), 1.79 (ddd, J=14.5, 9.0, 5.3 Hz, 1H), 1.72-1.54 (m, 3H), 1.54-1.40 (m, 3H), 1.35 (ddd, J=14.5, 8.2, 2.4 Hz, 1H), 1.30-1.21 (m, 1H), 0.94-0.83 (m, 1H), 0.50-0.41 (m, 1H), 0.35 (tt, J=8.7, 4.4 Hz, 1H), 0.16 (dq, J=9.0, 4.6 Hz, 1H), 0.08 to −0.01 (m, 1H) ppm. $^{19}$F NMR (377 MHz, DMSO-d$_6$) δ −62.38 (s, 3F), −79.03 (s, 3F) ppm. ESI-MS m/z calc. 480.1596, found 481.2 (M+1)$^+$; Retention time: 3.83 minutes; LCMS Method: Kinetex Polar C$_{18}$ 3.0×50 mm 2.6 μm, 6 min, 5-95% acetonitrile in H$_2$O (0.1% formic acid) 1.2 mL/min.

Product enantiomer 2 (about 29 mg) was purified by flash chromatography (24 g SiO$_2$, eluting 10 to 30% EtOAc/CH$_2$Cl$_2$) and freeze dried to afford (6R)-17-amino-12-(cyclopropylmethyl)-6,15-bis(trifluoromethyl)-13,19-dioxa-3,4,18-triazatricyclo[12.3.1.1²,⁵]nonadeca-1(18),2,4,14,16-pentaen-6-ol (enantiomer 2) (27 mg, 32%) as a pale-yellow solid. ESI-MS m/z calc. 480.1596, found 481.1 (M+1)$^+$; Retention time: 3.81 minutes. $^1$H NMR (400 MHz, DMSO-d$_6$) δ 7.77 (s, 1H), 7.57 (s, 1H), 6.36 (s, 2H), 4.70 (t, J=9.3 Hz, 1H), 2.44-2.35 (m, 1H), 2.35-2.24 (m, 1H), 2.15-2.03 (m, 1H), 1.84-1.64 (m, 3H), 1.58-1.33 (m, 5H), 1.32-1.21 (m, 1H), 0.94-0.82 (m, 1H), 0.51-0.42 (m, 1H), 0.35 (tt, J=8.5, 4.5 Hz, 1H), 0.16 (dq, J=9.0, 4.6 Hz, 1H), 0.08 to −0.01 (m, 1H) ppm. $^{19}$F NMR (377 MHz, DMSO-d$_6$) δ −62.39 (s, 3F), −76.37 (s, 3F) ppm. ESI-MS m/z calc. 480.1596, found 481.1 (M+1)$^+$; Retention time: 3.81 minutes; LCMS Method: Kinetex Polar C$_{18}$ 3.0×50 mm 2.6 μm, 6 min, 5-95% acetonitrile in H$_2$O (0.1% formic acid) 1.2 mL/min.

Example 35: Preparation of (6R)-17-amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 1), Compound 49, and (6R)-17-amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 2), Compound 50

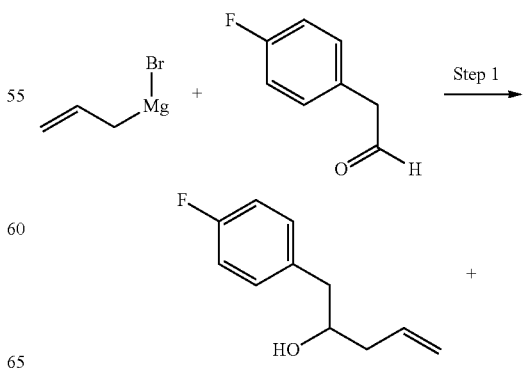

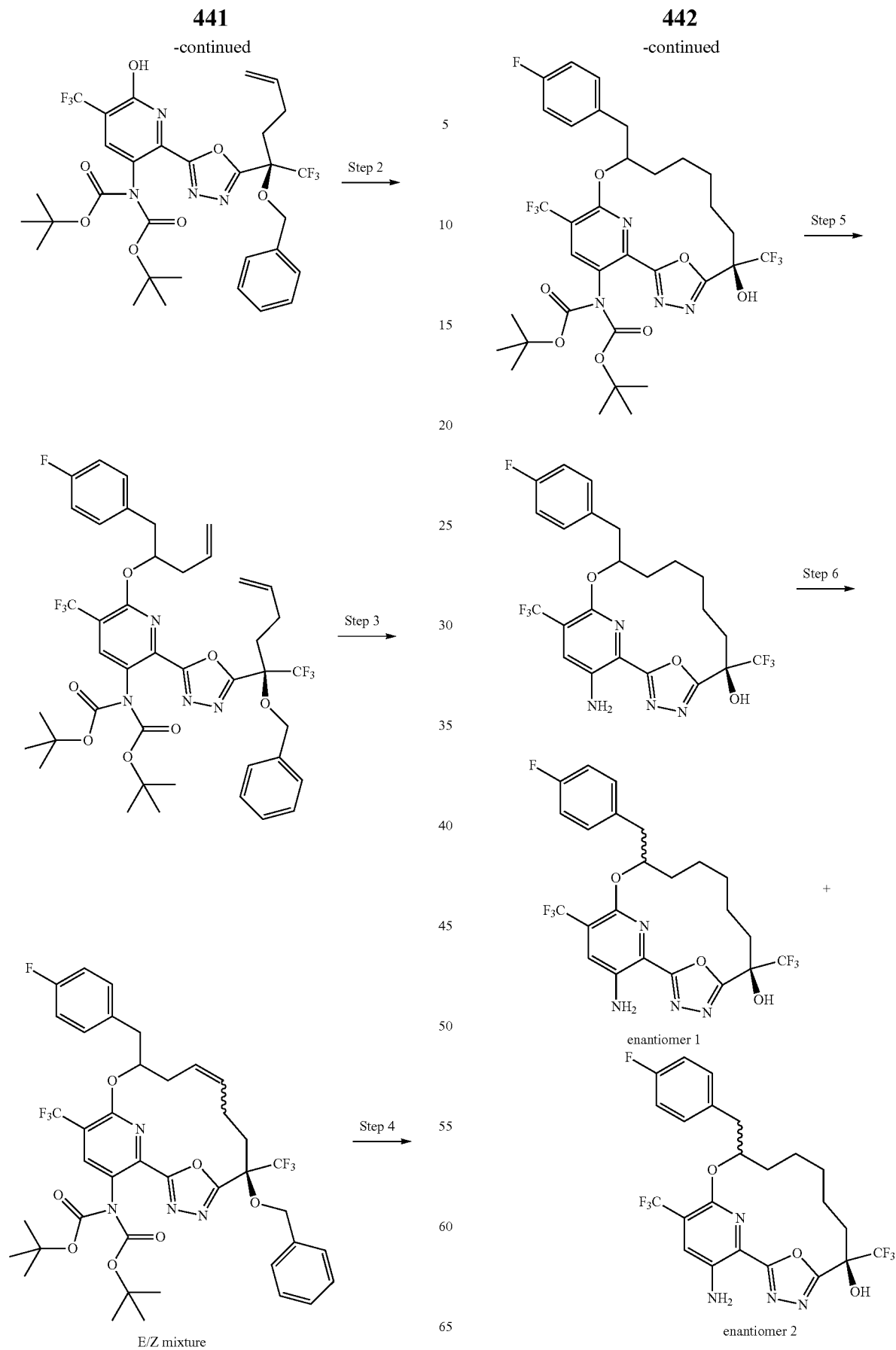

Step 1: 1-(4-Fluorophenyl)pent-4-en-2-ol

Step 2: tert-Butyl N-[2-[5-[(1R)-1-benzyloxy-1-(trifluoromethyl)pent-4-enyl]-1,3,4-oxadiazol-2-yl]-6-[1-[(4-fluorophenyl)methyl]but-3-enoxy]-5-(trifluoromethyl)-3-pyridyl]-N-tert-butoxycarbonyl-carbamate

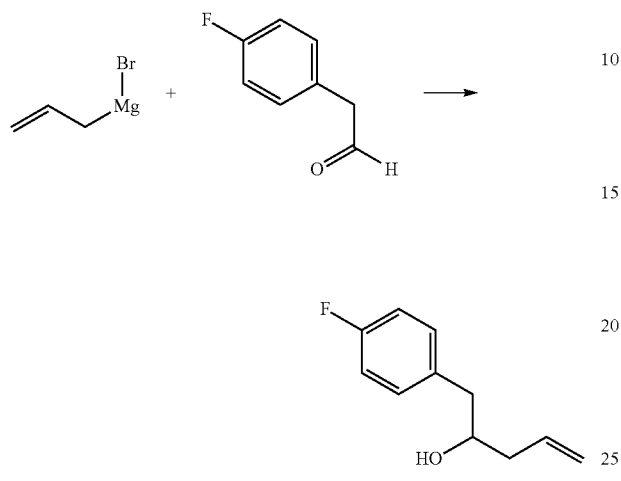

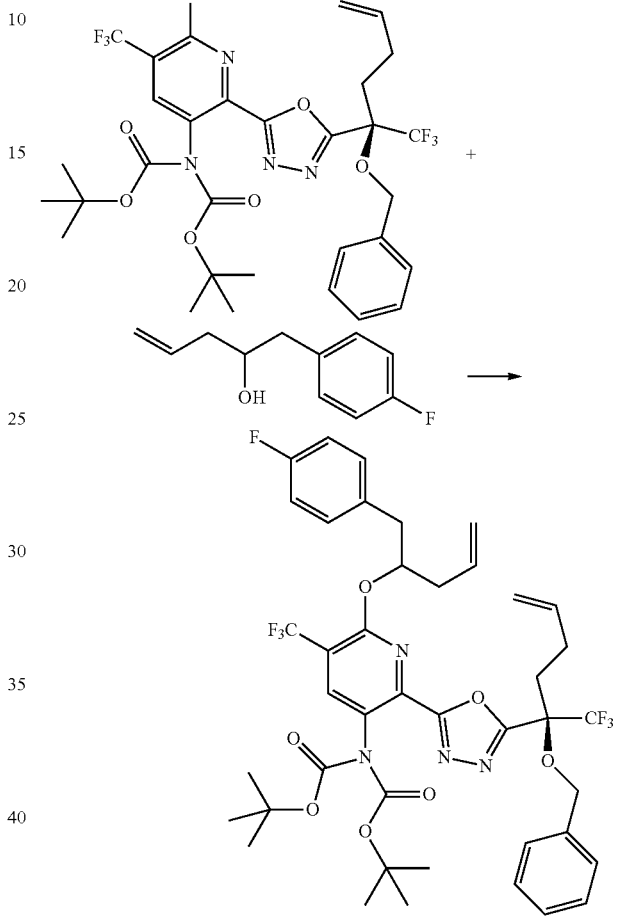

A flame dried round bottom flask was charged with 2-(4-fluorophenyl)acetaldehyde (7.0224 g, 6.6 mL, 48.294 mmol) and diethyl ether (57 mL) and cooled to 0° C. Then allyl(bromo)magnesium (60.4 mL of 1 M, 60.400 mmol) was added dropwise over 30 minutes. The cooling bath was removed and the reaction mixture was allowed to warm to room temperature and stir for one hour. A saturated aqueous solution of ammonium chloride was added to the flask until the white precipitate disappears. The layers were separated and the aqueous layer was washed with ethyl acetate (3×200 mL). The organic layers were combined and washed with a brine solution (2×50 mL). The organic layer was dried over anhydrous sodium sulfate, filtered, and concentrated in vacuo. The crude reaction mixture was dry-loaded on silica gel and purified by liquid chromatography on silica gel, eluting with portions of ethyl acetate (0-30%) in heptanes. Isolated 1-(4-fluorophenyl)pent-4-en-2-ol (4.034 g, 44%) as light yellow oil. $^1$H NMR (400 MHz, CDCl$_3$) δ 7.24-7.15 (m, 2H), 7.06-6.95 (m, 2H), 5.94-5.78 (m, 1H), 5.23-5.10 (m, 2H), 3.86 (qd, J=7.9, 4.6 Hz, 1H), 2.85-2.66 (m, 2H), 2.40-2.28 (m, 1H), 2.27-2.15 (m, 1H), 1.66 (d, J=3.4 Hz, 1H) ppm. $^{19}$F NMR (377 MHz, CDCl$_3$) δ −116.73 to −116.86 (m, 1F) ppm. ESI-MS m/z calc. 180.095, found 163.1 (M−17)$^+$; Retention time: 2.65 minutes. LCMS Method: Kinetex Polar C$_{18}$, 3.0×50 mm 2.6 μm, 6 min, 5-95% acetonitrile in H$_2$O (0.1% formic acid) 1.2 mL/min. A second fraction was isolated also, slightly less pure, 1-(4-fluorophenyl)pent-4-en-2-ol (0.575 g, 6%) as light yellow oil. ESI-MS m/z calc. 180.095, found 163.1 (M−17)$^+$; Retention time: 2.65 minutes. LCMS Method: Kinetex Polar C$_{18}$, 3.0×50 mm 2.6 μm, 6 min, 5-95% acetonitrile in H$_2$O (0.1% formic acid) 1.2 mL/min.

To a solution of tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (250 mg, 0.3630 mmol) and 1-(4-fluorophenyl)pent-4-en-2-ol (102 mg, 0.5660 mmol) in toluene (3 mL) was added triphenylphosphine (204 mg, 0.7778 mmol). After stirring at room temperature for 1 min, DIAD (150 μL, 0.7618 mmol) was added and the mixture stirred at room temperature for 30 minutes. Diluted the reaction mixture with EtOAc then washed with saturated aqueous NaHCO$_3$ (1×), saturated aqueous NH$_4$Cl (1×) and brine (1×) then dried over MgSO$_4$, filtered and concentrated to a yellow oil which was purified by silica gel chromatography using a shallow gradient from 100% hexanes to 50% EtOAc-hexanes giving as diastereomeric mixture, a clear, slightly yellow syrup, tert-butyl N-[2-[5-[(1R)-1-benzyloxy-1-(trifluoromethyl)pent-4-enyl]-1,3,4-oxadiazol-2-yl]-6-[1-[(4-fluorophenyl)methyl]but-3-enoxy]-5-(trifluoromethy 0-3-pyridyl]-N-tert-butoxycarbonyl-carbamate (160 mg, 52%). $^1$H NMR (400 MHz, Chloroform-d) δ 7.80 (s, 1H), 7.35 (ddd, J=6.9, 5.2, 1.9 Hz, 2H), 7.33-7.25 (m, 3H), 7.16 (ddd, J=8.8, 5.4, 2.1 Hz, 2H), 6.90-6.84 (m, 2H), 5.88-5.69

(m, 2H), 5.61-5.48 (m, 1H), 5.11-4.97 (m, 4H), 4.79 (dd, J=10.8, 1.9 Hz, 1H), 4.60 (dd, J=10.7, 7.1 Hz, 1H), 3.05 (ddd, J=13.8, 6.9, 5.3 Hz, 1H), 2.91 (dd, J=13.9, 6.0 Hz, 1H), 2.64-2.08 (m, 5H), 1.40 (d, J=6.8 Hz, 19H) ppm. ESI-MS m/z calc. 850.3176, found 851.5 (M+1)+; Retention time: 2.16 minutes. Final purity was determined by reversed phase UPLC using an Acquity UPLC BEH C$_{18}$ column (50×2.1 mm, 1.7 µm particle) made by Waters (pn: 186002350), and a dual gradient run from 50-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 µL, and column temperature=60° C.

Step 3: tert-Butyl N-[(6R)-6-benzyloxy-12-[(4-fluorophenyl)methyl]-6,15-bis(trifluoromethyl)-13,19-dioxa-3,4,18-triazatricyclo[12.3.1.1 2,5]nonadeca-1(17),2,4,9,14(18),15-hexaen-17-yl]-N-tert-butoxycarbonyl-carbamate (E/Z Mixture)

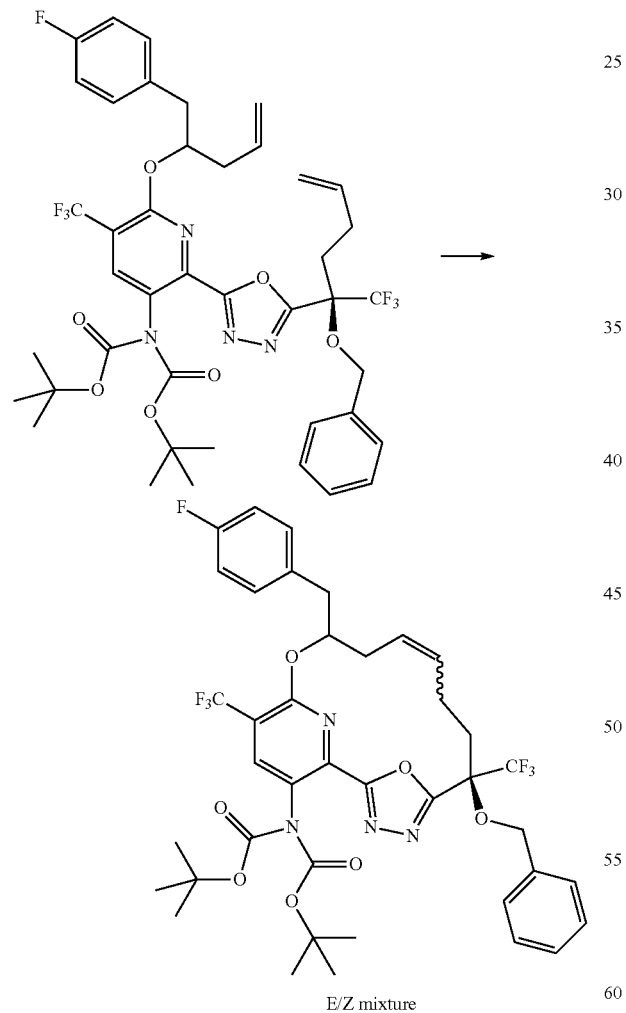

E/Z mixture

To a degassed solution of tert-butyl N-[2-[5-[(1R)-1-benzyloxy-1-(trifluoromethyl)pent-4-enyl]-1,3,4-oxadiazol-2-yl]-6-[1-[(4-fluorophenyl)methyl]but-3-enoxy]-5-(trifluoromethyl)-3-pyridyl]-N-tert-butoxycarbonyl-carbamate (150 mg, 0.1763 mmol) in DCE (75 mL) was added Zhan catalyst-1B (24 mg, 0.03271 mmol) at once and the reaction mixture was heated at 60° C. for about 1 h. Cooled the reaction mixture to room temperature and quenched the reaction with few drops of DMSO and solvents were removed. The resultant brown residue was purified by silica gel column chromatography using a shallow gradient 100% hexanes to 50% EtOAc giving a diastereomeric mixture of tert-butyl N-[(6R)-6-benzyloxy-12-[(4-fluorophenyl)methyl]-6,15-bis(trifluoromethyl)-13,19-dioxa-3,4,18-triazatricyclo[12.3.1.1 2,5]nonadeca-1(17),2,4,9,14(18),15-hexaen-17-yl]-N-tert-butoxycarbonyl-carbamate (E/Z mixture) (92 mg, 63%). ESI-MS m/z calc. 822.2864, found 823.5 (M+1)+; Retention time: 2.03 minutes. Final purity was determined by reversed phase UPLC using an Acquity UPLC BEH C$_{18}$ column (50×2.1 mm, 1.7 µm particle) made by Waters (pn: 186002350), and a dual gradient run from 50-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 µL, and column temperature=60° C.

Step 4: tert-Butyl N-tert-butoxycarbonyl-N-[(6R)-12-[(4-fluorophenyl)methyl]-6-hydroxy-6,15-bis(trifluoromethyl)-13,19-dioxa-3,4,18-triazatricyclo[12.3.1.1 2,5]nonadeca-1(17),2,4,14(18),15-pentaen-17-yl]carbamate

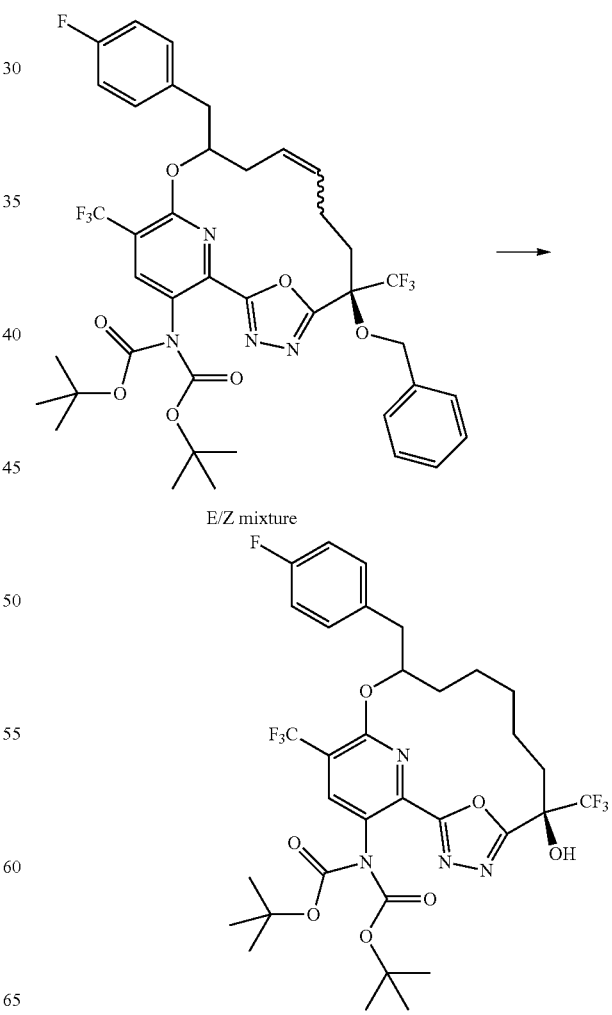

E/Z mixture

447

To a solution of tert-butyl N-[(6R)-6-benzyloxy-12-[(4-fluorophenyl)methyl]-6,15-bis(trifluoromethyl)-13,19-dioxa-3,4,18-triazatricyclo[12.3.1.1²,⁵]nonadeca-1(17),2,4,9,14(18),15-hexaen-17-yl]-N-tert-butoxy carbonyl-carbamate (E/Z mixture) (92 mg, 0.1118 mmol) in EtOH (3 mL) was added, Pd/C (38 mg of 10% w/w, 0.03571 mmol) (50% water) in a 250 mL vessel equipped with a H$_2$-balloon using 3-way adaptor. Subjected to vacuum and backfilled with nitrogen gas three times then subjected to vacuum. Filled the vessel with hydrogen gas and the mixture was stirred at room temperature overnight. Subjected to vacuum and filled with nitrogen gas three times then diluted with ethyl acetate and filtered over Celite. The filtrate was concentrated to give a colorless viscous oil as a diastereomeric mixture tert-butyl N-tert-butoxycarbonyl-N-[(6R)-12-[(4-fluorophenyl)methyl]-6-hydroxy-6,15-bis(trifluoromethyl)-13,19-dioxa-3,4,18-triazatricyclo[12.3.1.1²,⁵]nonadeca-1(17),2,4,14(18),15-pentaen-17-yl]carbamate (72 mg, 88%). ESI-MS m/z calc. 734.25507, found 735.4 (M+1)$^+$; Retention time: 2.07 minutes. Final purity was determined by reversed phase UPLC using an Acquity UPLC BEH C$_{18}$ column (50×2.1 mm, 1.7 μm particle) made by Waters (pn: 186002350), and a dual gradient run from 30-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Step 5: (6R)-17-Amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol tert-butyl N-tert-butoxycarbonyl-N-[(6R)-12-[(4-fluorophenyl)methyl]-6-hydroxy-6,15-bis(trifluoromethyl)-13,19-dioxa-3,4,18-triazatricyclo[12.3.1.1²,⁵]nonadeca-1(17),2,4,14(18),15-pentaen-17-yl]carbamate (72 mg, 0.09800 mmol) was dissolved in a pre-made solution of TFA (250 μL, 3.245 mmol) and DCM (750 μL). Stirred the reaction for about 0.5 h and solvents removed. The resultant residue was dissolved in 2 mL of MeOH and was purified by a reverse phase HPLC-MS method using a dual gradient run from 30-99% mobile phase B over 15.0 minutes. Mobile phase A=H$_2$O (5 mM formic acid) afforded (6R)-17-amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (42 mg, 80%); ESI-MS m/z calc. 534.1502, found 535.2 (M+1)$^+$; Retention time: 1.71 minutes as light yellow amorphous solid. ESI-MS m/z calc. 534.1502, found 535.2 (M+1)$^+$; Retention time: 1.71 minutes. Final purity was determined by reversed phase UPLC using an Acquity UPLC BEH C$_{18}$ column (50×2.1 mm, 1.7 μm particle) made by Waters (pn: 186002350), and a dual gradient run from 30-99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Step 6: (6R)-17-Amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 1), Compound 49, and (6R)-17-amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 2), Compound 50

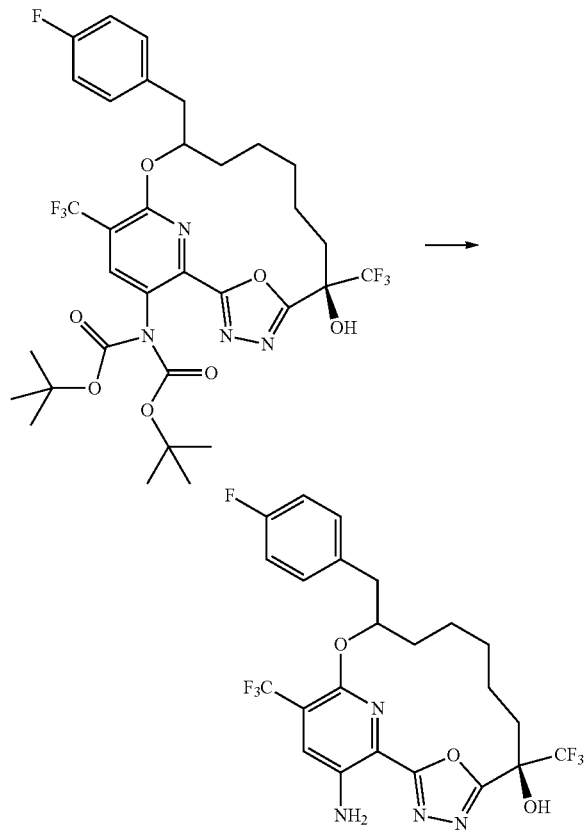

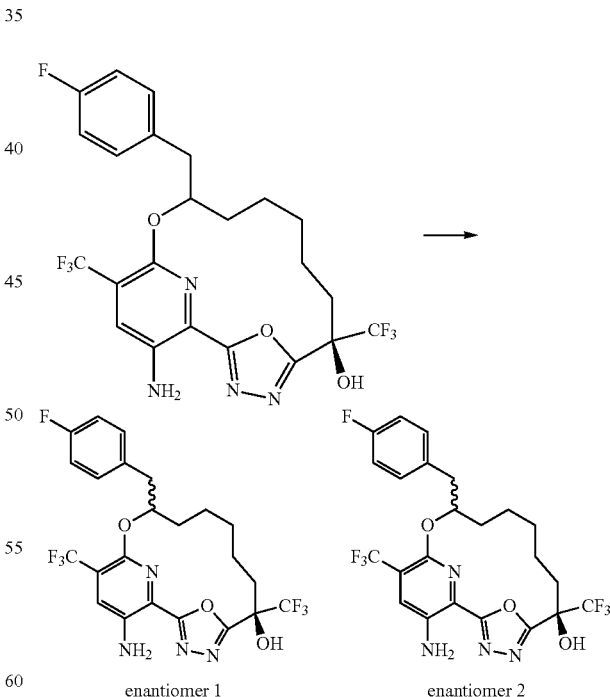

enantiomer 1    enantiomer 2

The diastereomeric mixture of (6R)-17-amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (60 mg, 0.1123 mmol) was purified by preparative SFC eluting with 15% methanol to CO$_2$ though a 2×25 cm OJ-H column, providing the 1st eluent (6R)-17-amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 1) (3.6 mg, 6%). $^1$H NMR (400 MHz, Methanol-$d_4$) δ 7.62 (s, 1H), 7.36-7.29 (m, 2H), 7.03-6.93 (m, 2H), 4.86-4.78 (m, 1H), 3.13 (dd, J=14.3, 2.9 Hz, 1H), 2.95 (dd, J=14.5, 8.6 Hz, 1H), 2.66-2.52 (m, 1H), 2.40 (dd, J=14.4, 9.0 Hz, 1H), 2.15 (dt, J=14.5, 8.0 Hz, 1H), 1.77-1.57 (m, 6H), 1.41-1.29 (m, 1H) ppm. $^{19}$F NMR (376 MHz, Methanol-$d_4$) δ −64.79, −81.78, −119.61 ppm. ESI-MS m/z calc. 534.1502, found 535.4 (M+1)⁺; Retention time: 2.21 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=12 mL/min, injection volume=50 μL, and column temperature=25° C.

Continued elution provided the 2nd eluent, (6R)-17-amino-12-[(4-fluorophenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 2) (2.8 mg, 5%). $^1$H NMR (400 MHz, Methanol-$d_4$) δ 7.63 (s, 1H), 7.32 (dd, J=8.6, 5.6 Hz, 2H), 7.06-6.91 (m, 2H), 5.02-4.91 (m, 1H), 3.14 (dd, J=14.4, 2.9 Hz, 1H), 2.95 (dd, J=14.5, 8.7 Hz, 1H), 2.54 (ddd, J=13.9, 8.5, 6.2 Hz, 1H), 2.40 (t, J=12.0 Hz, 1H), 2.21 (dt, J=14.5, 7.7 Hz, 1H), 1.94-1.72 (m, 3H), 1.68-1.52 (m, 3H), 1.41 (ddd, J=13.0, 9.7, 6.5 Hz, 1H) ppm. $^{19}$F NMR (376 MHz, Methanol-$d_4$) δ −64.76, −78.82, −119.60 ppm. ESI-MS m/z calc. 534.1502, found 535.2 (M+1)⁺; Retention time: 2.23 minutes. Final purity was determined by reversed phase HPLC-MS using an Onyx Monolithic $C_{18}$ column (50×4.6 mm) sold by Phenomenex (pn: CH0-7644), and a dual gradient run from 1-99% mobile phase B over 2.9 minutes. Mobile phase A=$H_2O$ (0.05% $CF_3CO_2H$). Mobile phase B=acetonitrile (0.035% $CF_3CO_2H$). Flow rate=12 mL/min, injection volume=50 μL, and column temperature=25° C.

Example 36: Preparation of (6R)-17-amino-12-[(3-tert-butylphenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 1), Compound 51, and (6R)-17-amino-12-[(3-tert-butylphenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 2), Compound 52

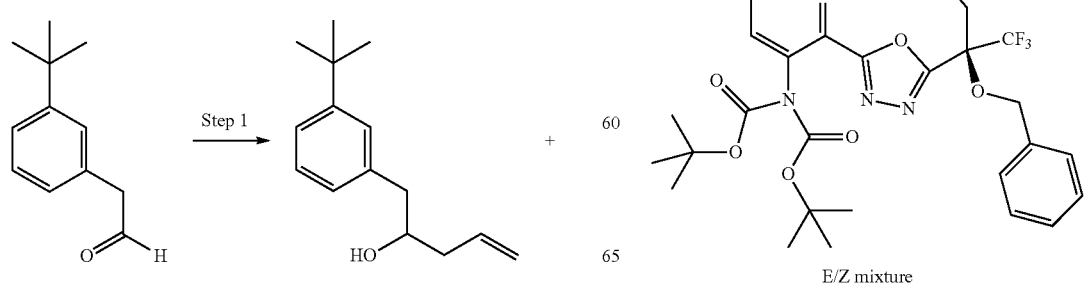

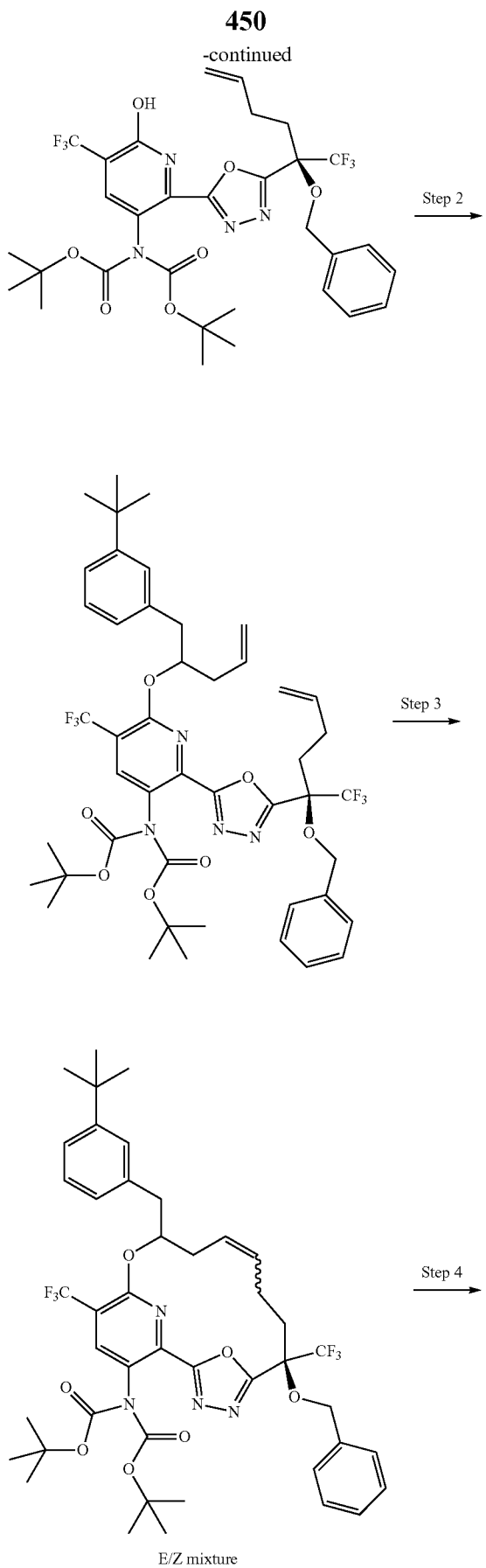

451
-continued

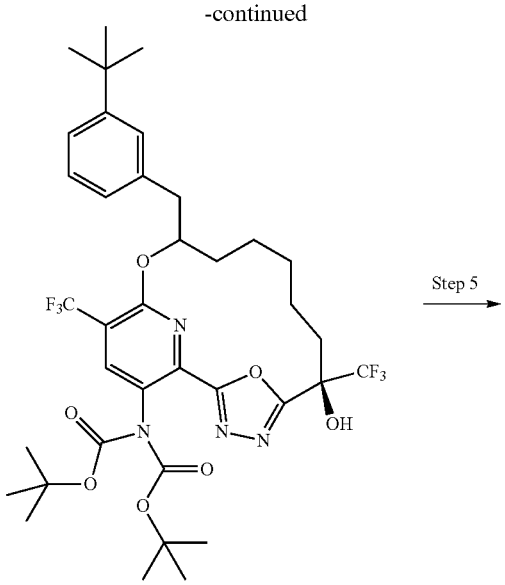

Step 5 →

Step 6 →

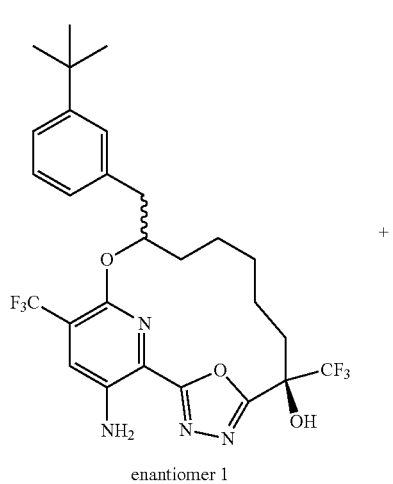

enantiomer 1

452
-continued

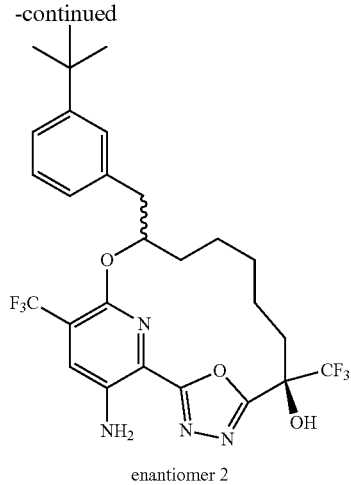

enantiomer 2

+

Step 1: 1-(3-tert-Butylphenyl)pent-4-en-2-ol

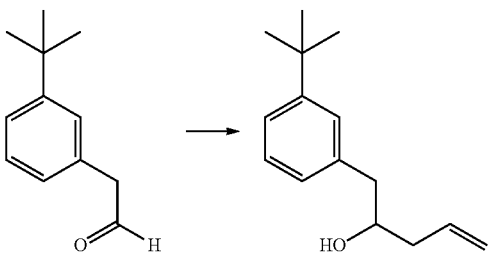

To a dry vial charged with 2-(3-tert-butylphenyl)acetaldehyde (140 mg, 0.7546 mmol) was added anhydrous diethyl ether (4 mL). The solution was cooled to 0° C. before adding allyl(bromo)magnesium (1 mL of 1 M, 1.0000 mmol) dropwise. After the addition, the solution was allowed to warm up to room temperature and stirred for 1 h. A saturated aqueous solution of NH$_4$Cl was added until the white precipitates disappeared. The aqueous layer was then extracted with EtOAc (3×10 mL). The organic layers were then combined, washed with brine, dried with anhydrous sodium sulfate, filtered, and concentrated under reduced pressure. The crude was purified via silica gel column chromatography (eluting 0-20% EtOAc in hexanes) to yield 1-(3-tert-butylphenyl)pent-4-en-2-ol (100 mg, 58%) as a clear oil. $^1$H NMR (500 MHz, DMSO-d$_6$) δ 7.25-7.15 (m, 3H), 7.02-6.98 (m, 1H), 5.95-5.79 (m, 1H), 5.03 (d, J=1.4 Hz, 1H), 5.02-4.99 (m, 1H), 4.58 (d, J=5.4 Hz, 1H), 3.74-3.68 (m, 1H), 2.63 (dd, J=13.1, 6.3 Hz, 2H), 2.19-2.04 (m, 2H), 1.27 (d, J=1.2 Hz, 9H) ppm.

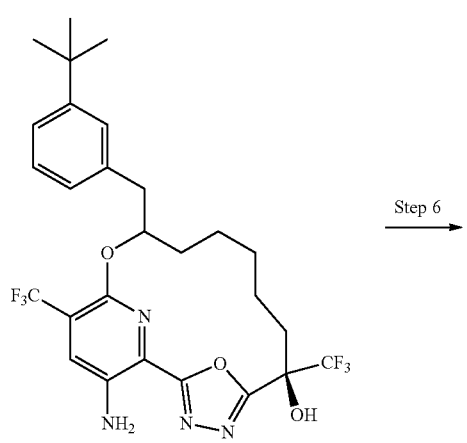

Step 2: tert-Butyl N-[2-[5-[(1R)-1-benzyloxy-1-(trifluoromethyl)pent-4-enyl]-1,3,4-oxadiazol-2-yl]-6-[1-[(3-tert-butylphenyl)methyl]but-3-enoxy]-5-(trifluoromethyl)-3-pyridyl]-N-tert-butoxycarbonyl-carbamate

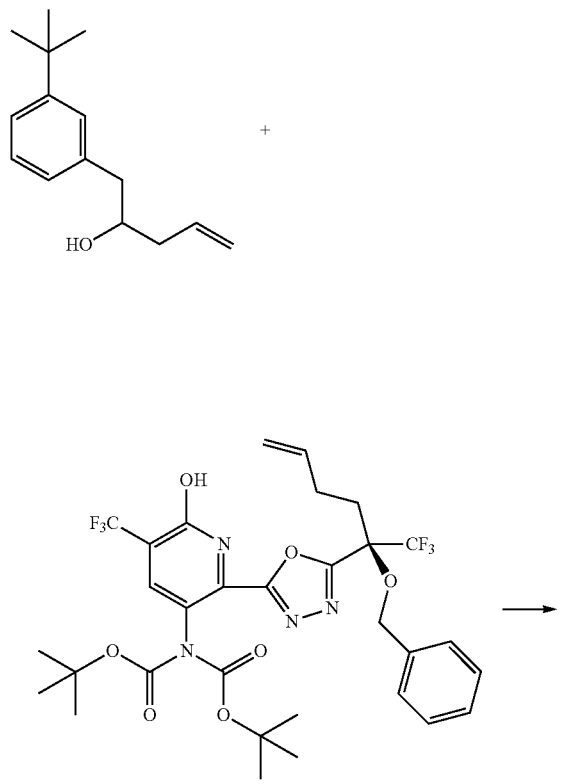

A flask was charged with tert-butyl N-[2-[5-[(1R)-1-benzyloxy-1-(trifluoromethyl)pent-4-enyl]-1,3,4-oxadiazol-2-yl]-6-hydroxy-5-(trifluoromethyl)-3-pyridyl]-N-tert-butoxycarbonyl-carbamate (100 mg, 0.1452 mmol), 1-(3-tert-butylphenyl)pent-4-en-2-ol (30 mg, 0.1374 mmol), triphenylphosphine (76 mg, 0.2898 mmol) and flushed with $N_2$ gas. Then the mixture was treated with toluene (0.3 mL). The solution was treated with DIAD (62.640 mg, 0.06 mL, 0.3098 mmol) in toluene (0.2 mL) over 2 h at rt. The reaction stirred an additional 1 h at rt; LCMS indicated almost no alcohol present. The reaction stirred an additional 72 h; LCMS indicated no alcohol present. The reaction was diluted with EtOAc (15 mL) and washed with saturated $NaHCO_3$ (4 mL), then washed with saturated $NH_4Cl$ (4 mL), then washed with brine (4 mL). The organics were dried over $Na_2SO_4$, filtered, concentrated in vacuo to obtain a crude residue. The crude residue was purified by silica gel chromatography (12 g $SiO_2$, loaded with minimal DCM, eluted with 0-10% EtOAc in hexanes over a 10 column volume gradient). The pure fractions were combined and the solvent was evaporated in vacuo to obtain the product tert-butyl N-[2-[5-[(1R)-1-benzyloxy-1-(trifluoromethyl)pent-4-enyl]-1,3,4-oxadiazol-2-yl]-6-[1-[(3-tert-butylphenyl)methyl]but-3-enoxy]-5-(trifluoromethyl)-3-pyridyl]-N-tert-butoxycarbonyl-carbamate (59 mg, 43%) as a transparent colorless residue. ESI-MS m/z calc. 888.3897, found 789.7 (M−99)+; Retention time: 9.77 minutes. LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 3: tert-Butyl N-[(6R)-6-benzyloxy-12-[(3-tert-butylphenyl)methyl]-6,15-bis(trifluoromethyl)-13,19-dioxa-3,4,18-triazatricyclo[12.3.1.1²,⁵]nonadeca-1(18),2,4,9,14,16-hexaen-17-yl]-N-tert-butoxycarbonyl-carbamate (E/Z Mixture)

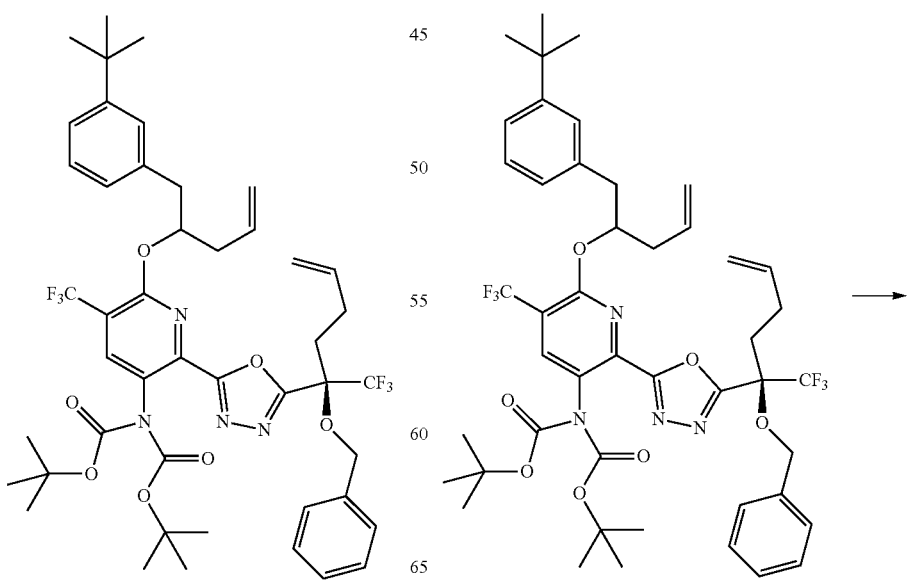

-continued

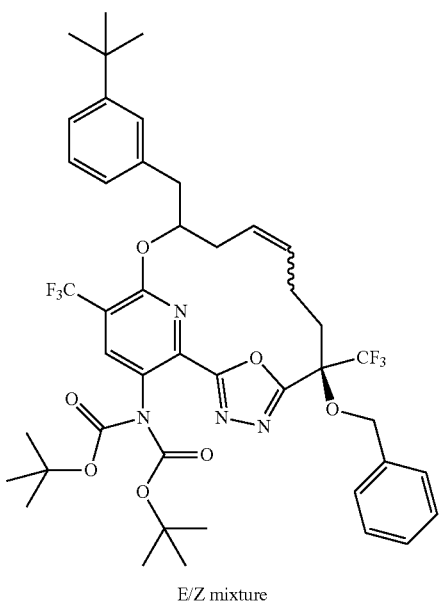

E/Z mixture

A flask was charged with tert-butyl N-[2-[5-[(1R)-1-benzyloxy-1-(trifluoromethyl)pent-4-enyl]-1,3,4-oxadiazol-2-yl]-6-[1-[(3-tert-butylphenyl)methyl]but-3-enoxy]-5-(trifluoromethyl)-3-pyridyl]-N-tert-butoxycarbonyl-carbamate (25 mg, 0.0281 mmol) followed by 1,2-dichloroethane (15 mL) under argon. The reaction solution was treated with Zhan catalyst-1B (2.5 mg, 0.0034 mmol) at room temperature. The reaction was heated at 70° C. for 15 h. The vessel was removed from heat. LCMS indicated SM remained 15%. The reaction was heated at 70° C. for a total of 24 h. LCMS indicated no additional conversion of the starting material to products. The contents of the reaction vessel were concentrated onto $SiO_2$. The material was purified by silica gel chromatography (4 g $SiO_2$, dry loaded, eluted with 0-15% EtOAc in hexanes over a 20 min. gradient). The material was recovered impure and the fractions were combined and the solvent was evaporated in vacuo to obtain the product, tert-butyl N-[(6R)-6-benzyloxy-12-[(3-tert-butylphenyl)methyl]-6,15-bis(trifluoromethyl)-13,19-dioxa-3,4,18-triazatricyclo[12.3.1.1²,⁵]nonadeca-1(18),2,4,9,14,16-hexaen-17-yl]-N-tert-butoxycarbonyl-carbamate (E/Z mixture) (10.7 mg, 38%) as a mixture of diastereomers as a transparent oil. The material was used without further purification in the next step. ESI-MS m/z calc. 860.3584, found 789.7 (M-O$^t$Bu)$^+$; Retention time: 9.58 minutes; LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 4: tert-Butyl N-tert-butoxycarbonyl-N-[(6R)-12-[(3-tert-butylphenyl)methyl]-6-hydroxy-6,15-bis(trifluoromethyl)-13,19-dioxa-3,4,18-triazatricyclo[12.3.1.1²,⁵]nonadeca-1(18),2,4,14,16-pentaen-17-yl]carbamate

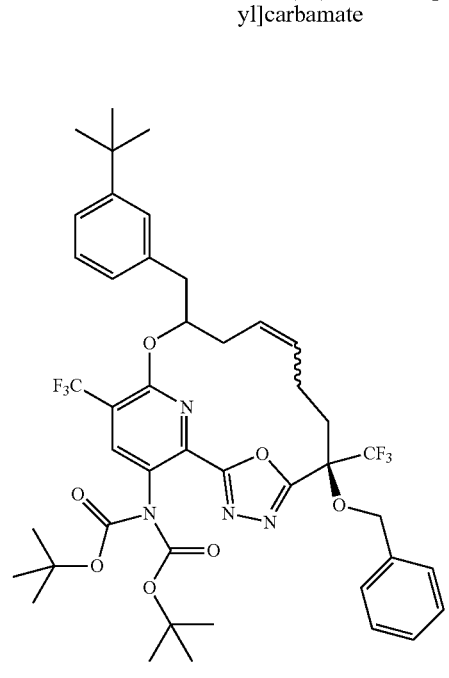

E/Z mixture

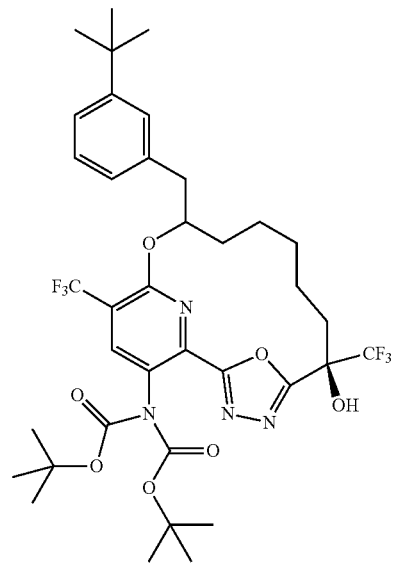

A vial was charged with tert-butyl N-[(6R)-6-benzyloxy-12-[(3-tert-butylphenyl)methyl]-6,15-bis(trifluoromethyl)-13,19-dioxa-3,4,18-triazatricyclo[12.3.1.1²,⁵]nonadeca-1(18),2,4,9,14,16-hexaen-17-yl]-N-tert-butoxycarbonyl-carbamate (E/Z mixture) (11 mg, 0.0109 mmol) in EtOH (0.61 mL). Then $N_2$ was bubbled through the solution for 5 minutes. Then the solution was treated with Pd/C (2.4 mg, 10% w/w, 0.0023 mmol) at room temperature and $N_2$ was bubbled through the solution for 5 minutes. Then $H_2$ gas was bubbled through the mixture for 20 min. and held under an atmosphere of $H_2$ with a balloon. The reaction was complete in 13 h. The mixture was diluted with EtOAc and filtered through Celite. The filtrate was concentrated in vacuo to obtain the product tert-butyl N-tert-butoxycarbonyl-N-

[(6R)-12-[(3-tert-butylphenyl)methyl]-6-hydroxy-6,15-bis(trifluoromethyl)-13,19-dioxa-3,4,18-triazatricyclo[12.3.1.1²,⁵]nonadeca-1(18),2,4,14,16-pentaen-17-yl]carbamate (10 mg, 100%) as a light yellow oil which became a resin-like foam when thoroughly dried. ESI-MS m/z calc. 772.3271, found 673.5 (M−99)+; Retention time: 8.89 minutes. LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 5: (6R)-17-Amino-12-[(3-tert-butylphenyl)methyl]-6,15-bis(trifluoromethyl)-13,19-dioxa-3,4,18-triazatricyclo[12.3.1.1²,⁵]nonadeca-1(18),2,4,14,16-pentaen-6-ol

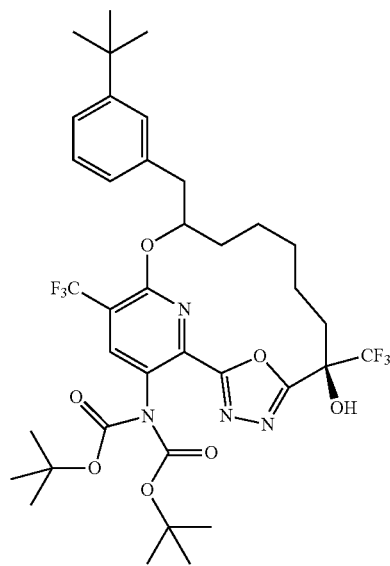

A thick walled glass microwave vial was charged with tert-butyl N-tert-butoxycarbonyl-N-[(6R)-12-[(3-tert-butylphenyl)methyl]-6-hydroxy-6,15-bis(trifluoromethyl)-13,19-dioxa-3,4,18-triazatricyclo[12.3.1.1²,⁵]nonadeca-1(18),2,4,14,16-pentaen-17-yl]carbamate (10 mg, 0.0129 mmol) in a solution of hexafluoro-2-propanol (0.25 mL). The reaction was heated at 100° C. in a microwave vessel for 3 hours. LCMS indicated the transformation was complete. The reaction was concentrated in vacuo to obtain a crude residue of the target (6R)-17-amino-12-[(3-tert-butylphenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (7.4 mg, 98%) as a dark yellow resin. ESI-MS m/z calc. 572.2222, found 573.1 (M+1)+; Retention time: 3.68 minutes. LCMS Method: Merck Millipore Chromolith SpeedROD $C_{18}$ column (50×4.6 mm) and a dual gradient run from 5-100% mobile phase B over 6 minutes. Mobile phase A=water (0.1% $CF_3CO_2H$). Mobile phase B=acetonitrile (0.1% $CF_3CO_2H$).

Step 6: (6R)-17-Amino-12-[(3-tert-butylphenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 1), Compound 51, and (6R)-17-amino-12-[(3-tert-butylphenyl)methyl]-6,15-bis(trifluoromethyl)-13,19-dioxa-3,4,18-triazatricyclo[12.3.1.1²,⁵]nonadeca-1(18),2,4,14,16-pentaen-6-ol (enantiomer 2), Compound 52

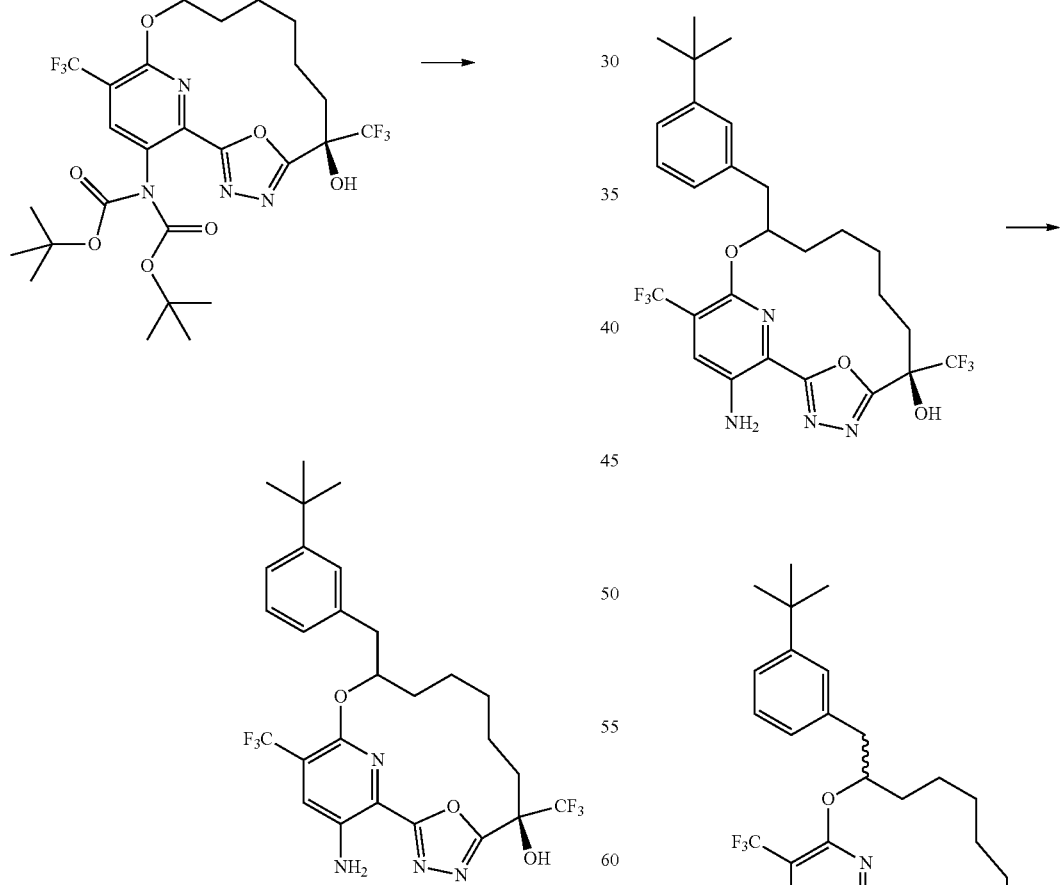

enantiomer 1

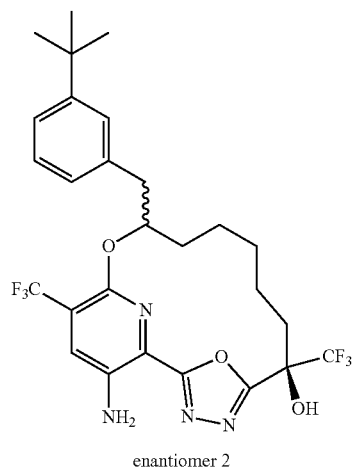 [SMILES: CC(C)(C)c1cccc(CC2CCCCC[C@](O)(C(F)(F)F)C3=NN=C(O3)c3nc(c(C(F)(F)F)cc3N)O2)c1]

enantiomer 2

(6R)-17-Amino-12-[(3-tert-butylphenyl)methyl]-6,15-bis(trifluoromethyl)-13,19-dioxa-3,4,18-triazatricyclo[12.3.1.1 2,5]nonadeca-1(18),2,4,14,16-pentaen-6-ol (79.3 mg, 0.1338 mmol) was purified by preparative SFC eluting with 15% methanol to $CO_2$ though a Cellulose-4 column (40° C.; 100 Bar; Flow rate: 4 mL/min; 10% MeOH; 8.5 min run), providing the two diastereoisomers. First elution afforded (6R)-17-amino-12-[(3-tert-butylphenyl)methyl]-6,15-bis(trifluoromethyl)-13,19-dioxa-3,4,18-triazatricyclo[12.3.1.1 2,5]nonadeca-1(18),2,4,14,16-pentaen-6-ol (enantiomer 1) (30.0 mg, 39%) as an off-white solid with a purity of 99.3%. $^1$H NMR (400 MHz, DMSO-$d_6$) δ 7.72 (s, 1H), 7.59 (s, 1H), 7.28 (s, 1H), 7.24-7.12 (m, 2H), 7.11-7.02 (m, 1H), 6.41-6.32 (m, 2H), 4.93-4.70 (m, 1H), 3.07 (d, J=14.1 Hz, 1H), 2.96-2.81 (m, 1H), 2.55-2.39 (m, 1H), 2.29-2.15 (m, 1H), 2.14-1.98 (m, 1H), 1.73-1.43 (m, 6H), 1.36-1.14 (m, 10H) ppm. $^{19}$F NMR (377 MHz, DMSO-$d_6$) δ −62.12 (s, 3F), −79.06 (s, 3F) ppm. ESI-MS m/z calc. 572.2222, found 573.0 (M+1)$^+$; Retention time: 3.95 minutes. LCMS Method: Kinetex Polar $C_{18}$ 3.0×50 mm 2.6 μm, 6 min, 5-95% acetonitrile in $H_2O$ (0.1% formic acid) 1.2 mL/min.

Continued elution afforded (6R)-17-amino-12-[(3-tert-butylphenyl)methyl]-6,15-bis(trifluoromethyl)-13,19-dioxa-3,4,18-triazatricyclo[12.3.1.1 2,5]nonadeca-1(18),2,4,14,16-pentaen-6-ol (enantiomer 2) (28.6 mg, 37%) as an off-white solid with a purity of 99.9%. $^1$H NMR (400 MHz, DMSO-$d_6$) δ 7.72 (s, 1H), 7.59 (br. s, 1H), 7.28 (s, 1H), 7.24-7.15 (m, 2H), 7.13-7.00 (m, 1H), 6.42-6.28 (m, 2H), 4.87 (t, J=9.0 Hz, 1H), 3.09 (d, J=12.8 Hz, 1H), 2.89 (dd, J=14.4, 8.4 Hz, 1H), 2.42-2.26 (m, 2H), 2.15-1.99 (m, 1H), 1.83-1.59 (m, 3H), 1.57-1.39 (m, 3H), 1.37-1.28 (m, 1H), 1.25 (s, 9H) ppm. $^{19}$F NMR (377 MHz, DMSO-$d_6$) δ −62.12 (s, 3F), −76.37 (s, 3F) ppm. ESI-MS m/z calc. 572.2222, found 573.0 (M+1)$^+$; Retention time: 3.94 minutes; LCMS Method: Kinetex Polar $C_{18}$ 3.0×50 mm 2.6 μm, 6 min, 5-95% acetonitrile in $H_2O$ (0.1% formic acid) 1.2 mL/min.

Example 37: Preparation of (6R,12R)-17-amino-12-methyl-6,15-bis(trifluoromethyl)-13,19-dioxa-3,4,18-triazatricyclo[12.3.1.1 2,5]nonadeca-1(18),2,4,14,16-pentaene-6,8-diol (diastereomer 1), Compound 53

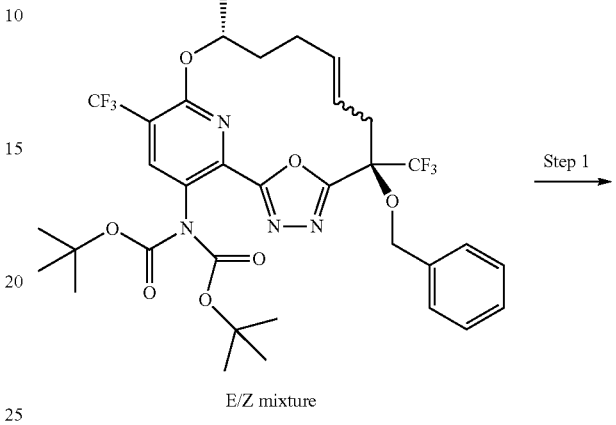

E/Z mixture

Step 1

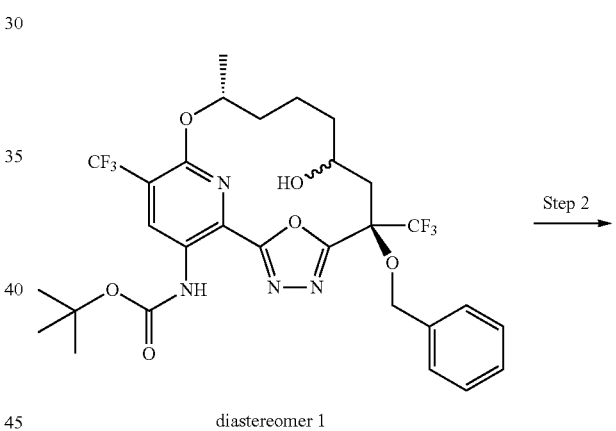

diastereomer 1

Step 2

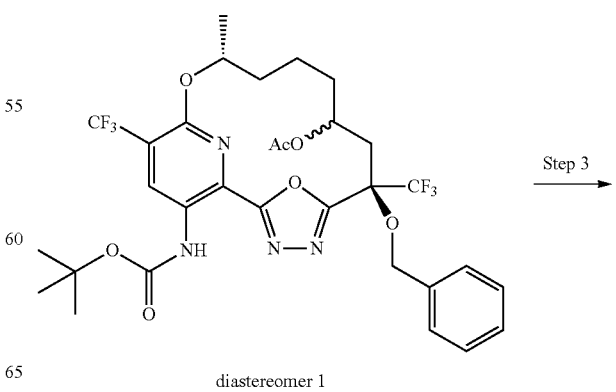

diastereomer 1

Step 3

461
-continued

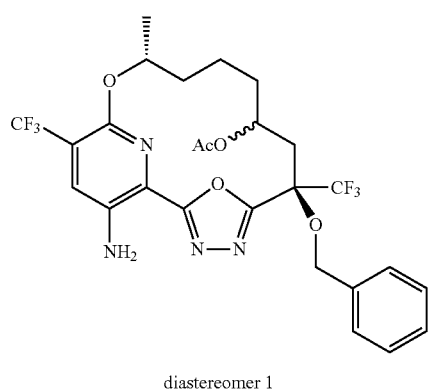

diastereomer 1

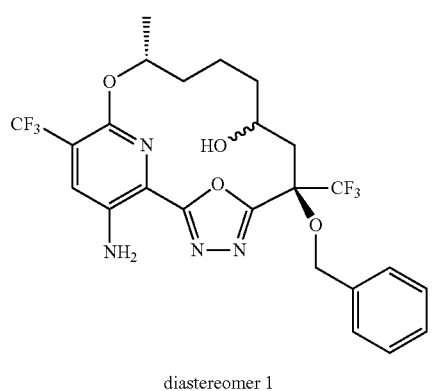

diastereomer 1

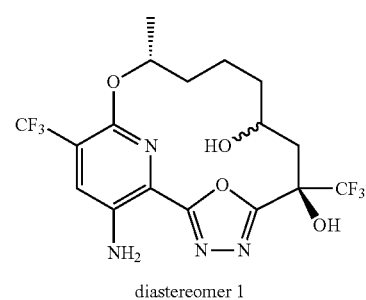

diastereomer 1

Step 4 →

Step 5 →

462

Step 1: tert-Butyl N-[(6R,12R)-6-benzyloxy-8-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (diastereomer 1)

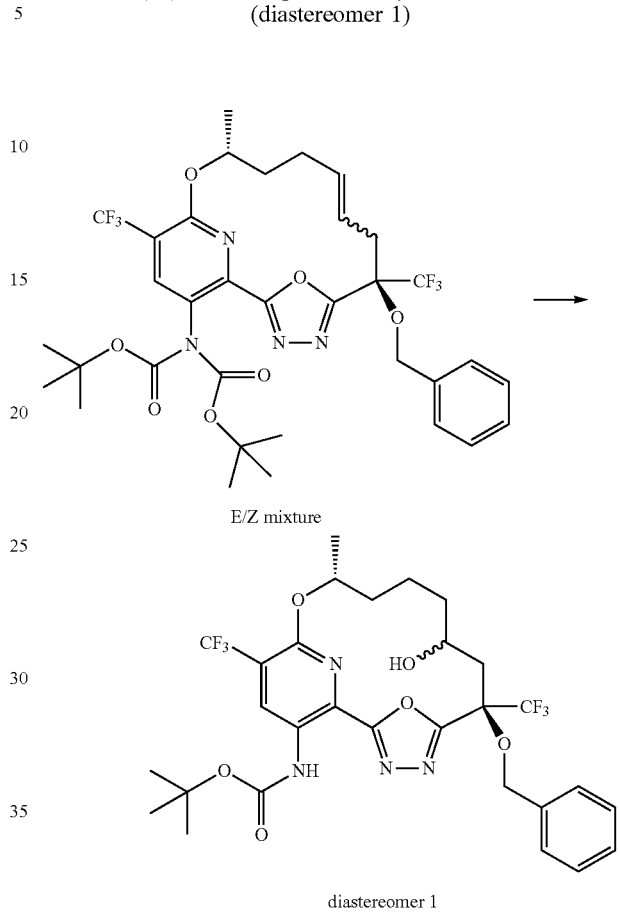

E/Z mixture diastereomer 1

To a solution of tert-butyl N-[(6R,12R)-6-benzyloxy-12-methyl-6,15-bis(trifluoromethyl)-13,19-dioxa-3,4,18-triazatricyclo[12.3.1.1²,⁵]nonadeca-1(18),2,4,8,14,16-hexaen-17-yl]-N-tert-butoxycarbonyl-carbamate (E/Z mixture) (230 mg, 0.2964 mmol) in THF (3.7 mL) at 0° C. under nitrogen was added dropwise borane dimethyl sulfide complex (80.100 mg, 0.1 mL, 1.0544 mmol). The mixture was stirred at 0° C. for 10 min and at room temperature for 1 h and re-cooled to 0° C. NaOH in water (1.8 mL of 1 M, 1.8000 mmol) was added, followed by $H_2O_2$ in water (688.93 mg, 0.6207 mL of 30% w/w, 6.0762 mmol). The mixture was stirred at room temperature for 50 min. A 10% aqueous solution of sodium thiosulfate (9 mL) and brine (7 mL) were added. The mixture was stirred at 0° C. for 10 min and extracted with ethyl acetate (3×20 mL). The combined organic layers were dried with anhydrous sodium sulfate, filtered and concentrated. The residue was purified by silica gel chromatography (24 g $SiO_2$, eluting 0% to 10% ethyl acetate/dichloromethane) to provide a mixture containing the mono-boc diastereomers, tert-butyl N-[(6R,12R)-6-benzyloxy-8-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (59 mg, 16%) as clear oil with some impurities still present, ESI-MS m/z calc. 646.2226, found 647.2 (M+1)⁺; Retention time: 4.16 minutes (Kinetex polar $C_{18}$ (3.0×50 mm) 2.6 μm, 6 min, 5%-95% acetonitrile in $H_2O$ (0.1% formic acid), flow=1.2 mL/min). This material was dry-loaded on silica gel and purified by liquid chromatography on a 12 g silica gel column eluting with 0% to 30% portions of ethyl acetate in heptanes. At 16% ethyl acetate in heptanes, the target product eluted, tert-butyl N-[(6R,12R)-6-benzyloxy-8-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 1) (17 mg, 26%) and was isolated as a sticky white foam which still contained some minor impurities. $^1$H NMR (400 MHz, CDCl$_3$) δ 9.28 (s, 1H), 9.13 (s, 1H), 7.40-7.28 (m, 5H), 5.10-4.99 (m, 1H), 4.73 (d, J=11.0 Hz, 1H), 4.65 (d, J=10.3 Hz, 1H), 4.24-4.15 (m, 1H), 2.72-2.61 (m, 1H), 2.57-2.48 (m, 1H), 2.47-2.36 (m, 1H), 2.25-2.13 (m, 1H), 1.85-1.61 (m, 5H), 1.56 (s, 9H), 1.46 (d, J=6.1 Hz, 3H) ppm. $^{19}$F NMR (377 MHz, CDCl$_3$) δ -63.93 (s, 3F), -74.31 (s, 3F) ppm. ESI-MS m/z calc. 646.2226, found 647.2 (M+1)+; Retention time: 4.15 minutes; LCMS Method: Kinetex Polar C$_{18}$ (3.0×50 mm) 2.6 μm, 6 min, 5-95% MeCN in H$_2$O (0.1% formic acid), flow=1.2 mL/min.

Step 2: [(6R,12R)-6-Benzyloxy-17-(tert-butoxycarbonylamino)-12-methyl-6,15-bis(trifluoromethyl)-13,19-dioxa-3,4,18-triazatricyclo[12.3.1.12,5]nonadeca-1(18),2,4,14,16-pentaen-8-yl]acetate (diastereomer 1)

and concentrated. The residue was purified by silica gel chromatography (12 g SiO$_2$, eluting 0 to 25% EtOAc/heptanes) to afford [(6R,12R)-6-benzyloxy-17-(tert-butoxycarbonylamino)-12-methyl-6,15-bis(trifluoromethyl)-13,19-dioxa-3,4,18-triazatricyclo[12.3.1.12,5]nonadeca-1(18),2,4,14,16-pentaen-8-yl]acetate (diastereomer 1) (14 mg, 88%) as a pale-yellow oil. $^1$H NMR (400 MHz, CDCl$_3$) δ 9.23 (s, 1H), 9.13 (s, 1H), 7.36-7.27 (m, 5H), 5.44-5.33 (m, 1H), 4.95-4.84 (m, 1H), 4.78 (d, J=11.0 Hz, 1H), 4.60 (d, J=11.0 Hz, 1H), 2.68-2.56 (m, 2H), 2.55-2.45 (m, 1H), 2.20-2.10 (m, 1H), 2.01 (s, 3H), 1.74-1.64 (m, 1H), 1.56 (s, 9H), 1.53-1.46 (m, 1H), 1.44 (d, J=6.4 Hz, 3H), 1.41-1.30 (m, 2H) ppm. $^{19}$F NMR (377 MHz, CDCl$_3$) δ -63.94 (s, 3F), -74.58 (s, 3F) ppm.

Step 3: [(6R,12R)-17-Amino-6-benzyloxy-12-methyl-6,15-bis(trifluoromethyl)-13,19-dioxa-3,4,18-triazatricyclo[12.3.1.12,5]nonadeca-1(18),2,4,14,16-pentaen-8-yl]acetate (diastereomer 1)

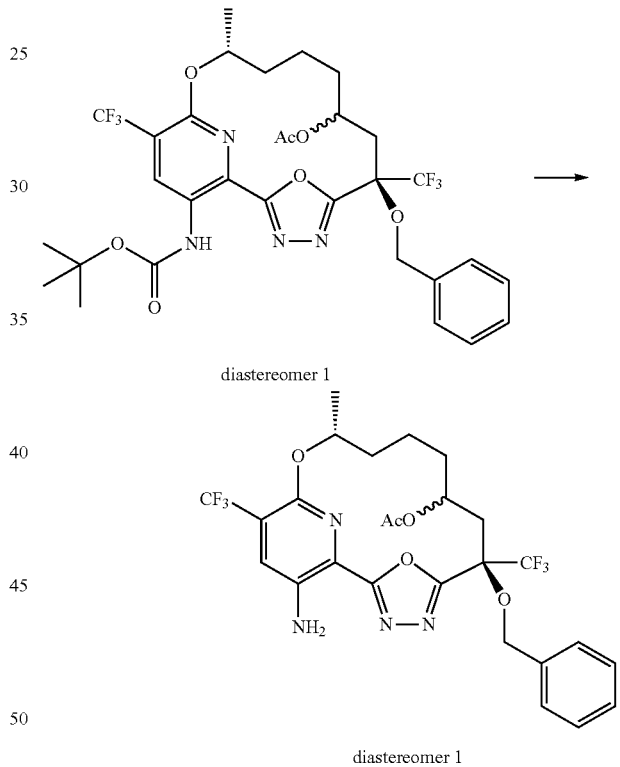

diastereomer 1

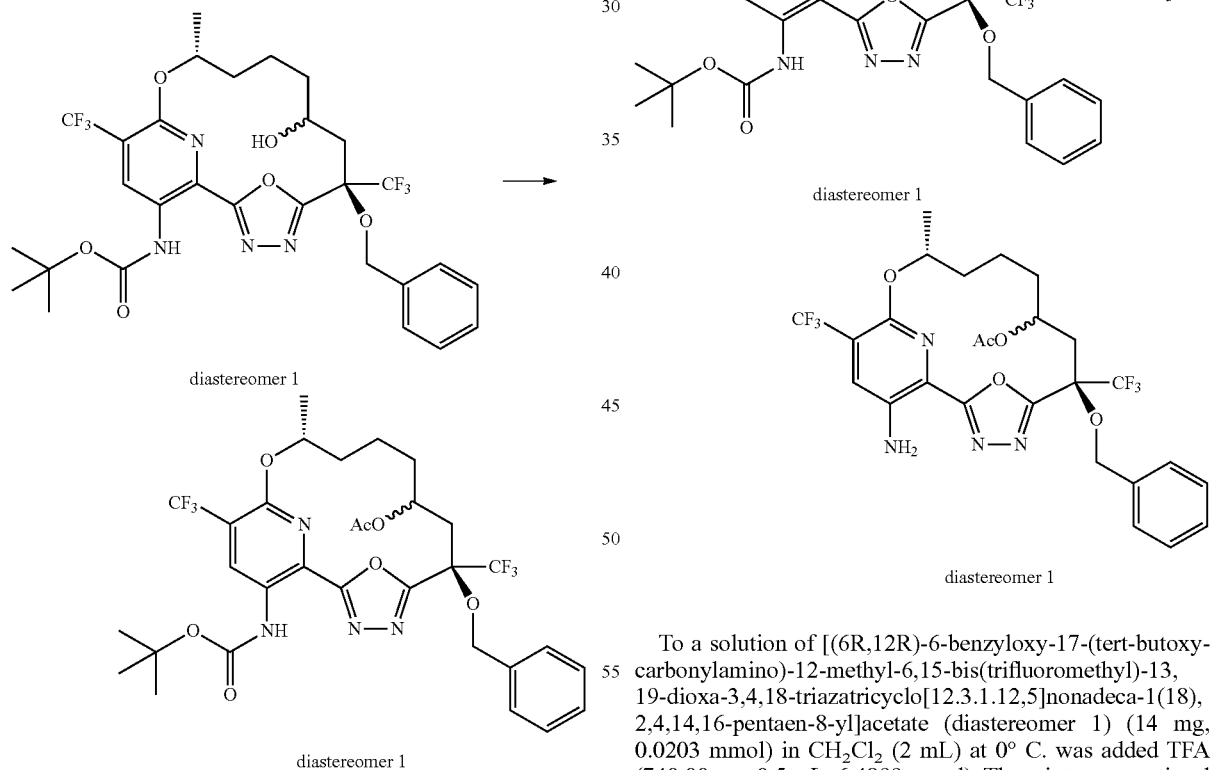

diastereomer 1

To a solution of tert-butyl N-[(6R,12R)-6-benzyloxy-8-hydroxy-12-methyl-6,15-bis(trifluoromethyl)-13,19-dioxa-3,4,18-triazatricyclo[12.3.1.12,5]nonadeca-1(18),2,4,14,16-pentaen-17-yl]carbamate (diastereomer 1) (15 mg, 0.0232 mmol) in CH$_2$Cl$_2$ (1 mL) at 0° C. was added DMAP (8 mg, 0.0655 mmol), followed by acetic anhydride (6 mg, 0.0055 mL, 0.0588 mmol). The mixture was stirred at rt for 2.5 h To a solution of [(6R,12R)-6-benzyloxy-17-(tert-butoxycarbonylamino)-12-methyl-6,15-bis(trifluoromethyl)-13,19-dioxa-3,4,18-triazatricyclo[12.3.1.12,5]nonadeca-1(18),2,4,14,16-pentaen-8-yl]acetate (diastereomer 1) (14 mg, 0.0203 mmol) in CH$_2$Cl$_2$ (2 mL) at 0° C. was added TFA (740.00 mg, 0.5 mL, 6.4899 mmol). The mixture was stirred at 10-13° C. for 1.5 h. The solvents were removed by a gentle flow of nitrogen. The residue was treated with 2 drops of 28% aqueous ammonia and purified by silica gel chromatography (4 g SiO$_2$, eluting 10% to 40% EtOAc/heptanes) to afford [(6R,12R)-17-amino-6-benzyloxy-12-methyl-6,15-bis(trifluoromethyl)-13,19-dioxa-3,4,18-triazatricyclo[12.3.1.12,5]nonadeca-1(18),2,4,14,16-pentaen-8-yl]acetate (diastereomer 1) (9 mg, 75%) as a pale-yellow oil. ¹H NMR (400 MHz, CDCl₃) δ 7.45 (s, 1H), 7.37-7.28 (m, 5H), 5.45-5.37 (m, 1H), 5.34 (s, 2H), 4.90-4.80 (m, 1H), 4.77 (d, J=10.8 Hz, 1H), 4.61 (d, J=11.0 Hz, 1H), 2.70-2.46 (m, 3H), 2.23-2.12 (m, 1H), 2.01 (s, 3H), 1.73-1.62 (m, 1H), 1.55-1.43 (m, 2H), 1.41 (d, J=6.4 Hz, 3H), 1.37-1.29 (m, 1H) ppm. ¹⁹F NMR (377 MHz, CDCl₃) δ −64.02 (s, 3F), −74.67 (s, 3F) ppm.

Step 4: (6R,12R)-17-Amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-ol (diastereomer 1)

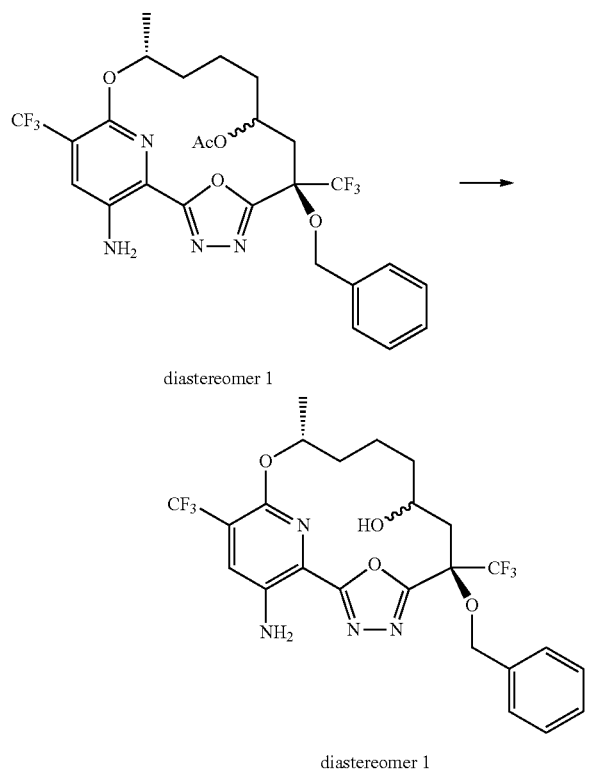

diastereomer 1 diastereomer 1

To a solution of [(6R,12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-yl] acetate (diastereomer 1) (9 mg, 0.0153 mmol) in THF (2 mL) was added aqueous NaOH (0.4 mL of 1 M, 0.4000 mmol). The mixture was stirred at rt for 1 h. MeOH (395.50 mg, 0.5 mL, 12.343 mmol) was added. The mixture was stirred at room temperature overnight. The mixture was concentrated and the residue was treated with saturated aqueous NaHCO₃ (3 mL). The mixture was extracted with EtOAc (3×8 mL). The combined organic layers were dried with Na₂SO₄, filtered and concentrated. The residue was purified by silica gel chromatography (4 g SiO₂, eluting 20% to 50% EtOAc/heptanes) to afford (6R,12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-ol (diastereomer 1) (8 mg, 96%) as a pale-yellow oil. ¹H NMR (400 MHz, CDCl₃) δ 7.45 (s, 1H), 7.38-7.28 (m, 5H), 5.36 (s, 2H), 5.04-4.92 (m, 1H), 4.76-4.69 (m, 1H), 4.68-4.61 (m, 1H), 4.27-4.17 (m, 1H), 2.71-2.62 (m, 1H), 2.56-2.38 (m, 2H), 2.29-2.18 (m, 1H), 1.85-1.69 (m, 2H), 1.67-1.61 (m, 1H), 1.54-1.47 (m, 1H), 1.43 (d, J=6.4 Hz, 3H), 1.39-1.33 (m, 1H) ppm. ¹⁹F NMR (377 MHz, CDCl₃) δ −63.99 (s, 3F), −74.38 (s, 3F) ppm. ESI-MS m/z calc. 546.17017, found 546.9 (M+1)⁺; Retention time: 2.22 minutes; LCMS Method: Kinetex Polar C₁₈ (3.0×50 mm), 2.6 μm, 3 min, 5-95% MeCN in H₂O (0.1% formic acid), flow=1.2 mL/min.

Step 5: (6R,12R)-17-Amino-12-methyl-6,15-bis(trifluoromethyl)-13,19-dioxa-3,4,18-triazatricyclo[12.3.1.1²,⁵]nonadeca-1(18),2,4,14,16-pentaene-6,8-diol (diastereomer 1), Compound 53

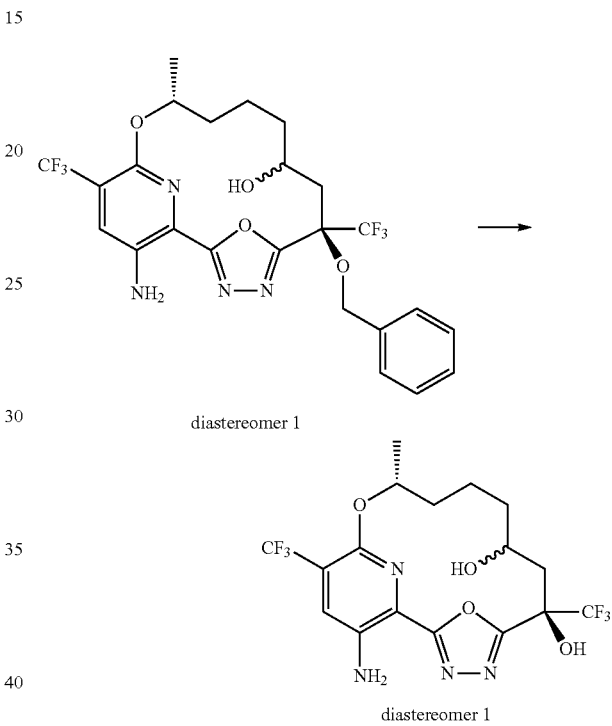

diastereomer 1 diastereomer 1

A mixture of (6R,12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-ol (diastereomer 1) (8 mg, 0.0146 mmol) and palladium on carbon 5% wet (7 mg, 0.0033 mmol) in MeOH (2 mL) was stirred under hydrogen (balloon) at room temperature overnight. The mixture was filtered through diatomaceous earth and washed with EtOAc. The filtrate was concentrated and the residue was purified by silica gel chromatography (12 g SiO₂, eluting 30% to 50% EtOAc/pentane) and freeze dried to afford (6R,12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,8-diol (diastereomer 1) (4.6 mg, 68%) as a pale-yellow solid. ¹H NMR (400 MHz, DMSO-d₆) δ 7.76 (s, 1H), 7.52 (s, 1H), 6.37 (s, 2H), 5.01-4.89 (m, 1H), 4.55 (d, J=6.8 Hz, 1H), 3.94-3.79 (m, 1H), 2.39-2.09 (m, 4H), 1.83-1.69 (m, 1H), 1.45-1.37 (m, 1H), 1.34 (d, J=6.4 Hz, 3H), 1.27-1.13 (m, 2H) ppm. ¹⁹F NMR (377 MHz, DMSO-d₆) δ −62.51 (s, 3F), −76.79 (s, 3F) ppm. ESI-MS m/z calc. 456.12323, found 456.9 (M+1)⁺; Retention time: 2.78 minutes; LCMS Method: Kinetex Polar C₁₈ (3.0×50 mm), 2.6 μm, 6 min, 5-95% MeCN in H₂O (0.1% formic acid), flow=1.2 mL/min.

Example 38: Preparation of (6R)-17-amino-12-ethyl-6,15-bis(trifluoromethyl)-13,19-dioxa-3,4,18-triazatricyclo[12.3.1.1²,⁵]nonadeca-1(18),2,4,14,16-pentaen-6-ol (enantiomer 1), Compound 54, and (6R)-17-amino-12-ethyl-6,15-bis(trifluoromethyl)-13,19-dioxa-3,4,18-triazatricyclo[12.3.1.1²,⁵]nonadeca-1(18),2,4,14,16-pentaen-6-ol (enantiomer 2), Compound 55
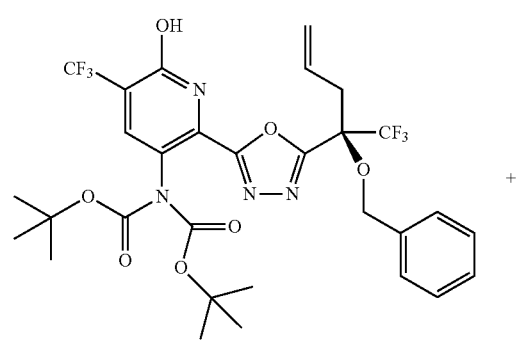
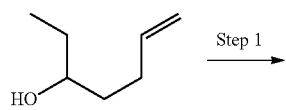
Step 1
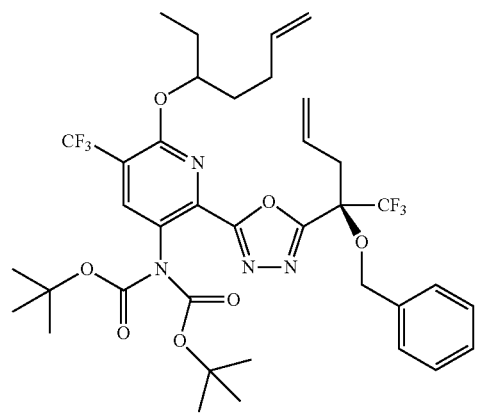
Step 2
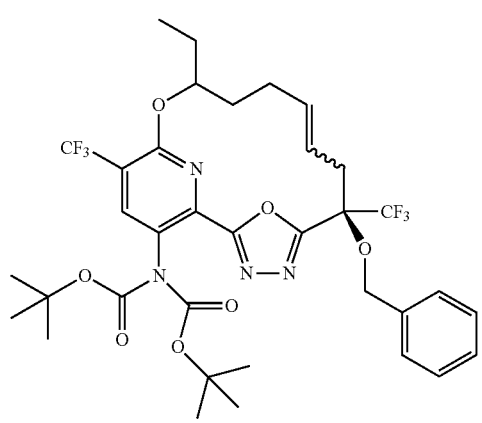
E/Z mixture
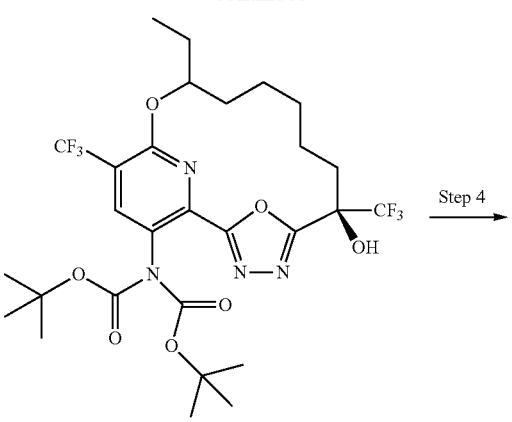
Step 4
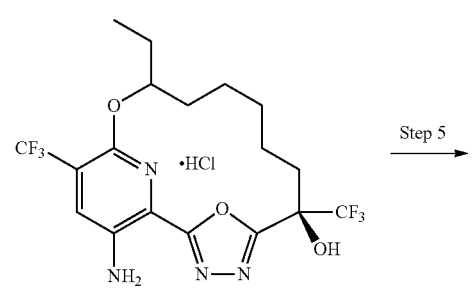
Step 5
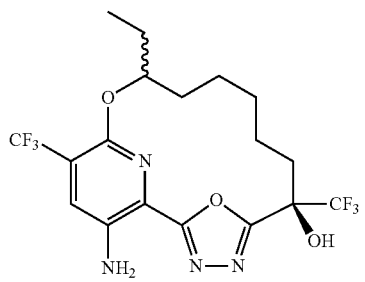
enantiomer 1
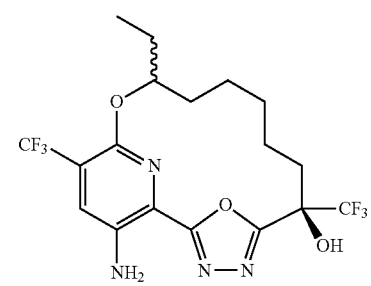
enantiomer 2

Step 1: tert-Butyl N-[2-[5-[(1R)-1-benzyloxy-1-(trifluoromethyl)but-3-enyl]-1,3,4-oxadiazol-2-yl]-6-(1-ethylpent-4-enoxy)-5-(trifluoromethyl)-3-pyridyl]-N-tert-butoxycarbonyl-carbamate

Step 2: tert-Butyl N-[(6R)-6-benzyloxy-12-ethyl-6,15-bis(trifluoromethyl)-13,19-dioxa-3,4,18-triazatricyclo[12.3.1.12,5]nonadeca-1(18),2,4,8,14,16-hexaen-17-yl]-N-tert-butoxycarbonyl-carbamate (E/Z Mixture)

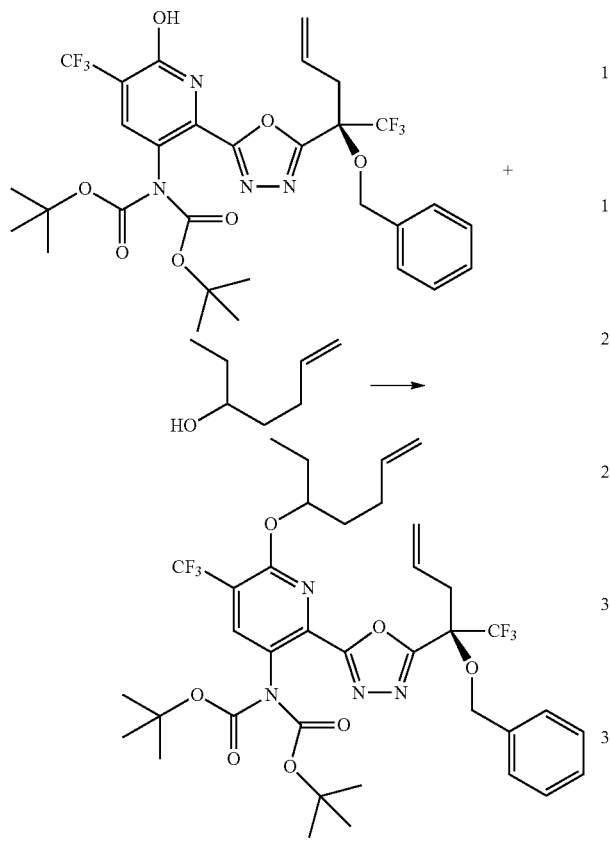

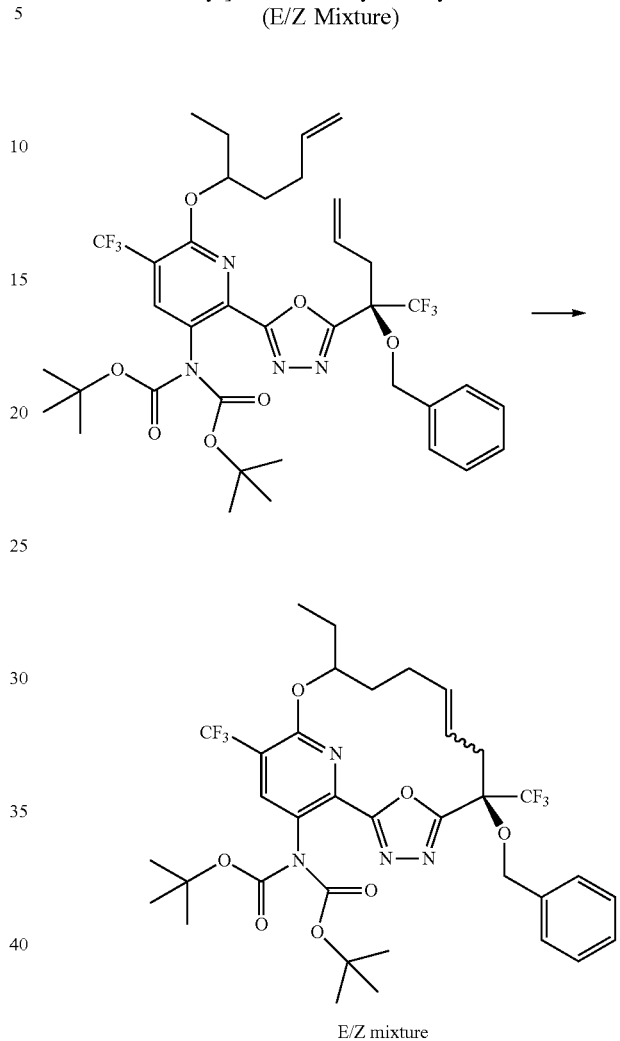

E/Z mixture

A solution of tert-butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate (1 g, 1.4824 mmol), hept-6-en-3-ol (260 mg, 2.2770 mmol), and triphenylphosphine (800 mg, 0.7067 mL, 3.0501 mmol) in THF (40 mL) at 0° C. was stirred for 30 min and DIAD (626.40 mg, 0.6 mL, 3.0978 mmol) was added dropwise. The reaction mixture was warmed to rt and stirred for 2 h. The reaction mixture was concentrated and the residue was purified by silica gel chromatography (40 g column, 0 to 15% EtOAc in hexanes for 30 min) provided as a clear oil, tert-butyl N-[2-[5-[(1R)-1-benzyloxy-1-(trifluoromethyl)but-3-enyl]-1,3,4-oxadiazol-2-yl]-6-(1-ethylpent-4-enoxy)-5-(trifluoromethyl)-3-pyridyl]-N-tert-butoxycarbonyl-carbamate (1.07 g, 94%). $^1$H NMR (500 MHz, CDCl$_3$) δ 7.82 (s, 1H), 7.41-7.18 (m, 5H), 5.98-5.86 (m, 1H), 5.85-5.72 (m, 1H), 5.32-5.21 (m, 2H), 5.18 (d, J=10.2 Hz, 1H), 4.99-4.93 (m, 1H), 4.91 (dd, J=10.2, 2.4 Hz, 1H), 4.80 (dd, J=10.7, 2.7 Hz, 1H), 4.62 (dd, J=10.6, 5.7 Hz, 1H), 3.28-3.08 (m, 2H), 2.22-2.03 (m, 2H), 1.93-1.83 (m, 1H), 1.81-1.70 (m, 3H), 1.42 (s, 18H), 0.96-0.88 (m, 3H). ESI-MS m/z calc. 770.3114, found 671.5 (M+H-Boc)$^+$; Retention time: 4.74 minutes. LCMS Method: Merck Millipore Chromolith SpeedROD C$_{18}$ column (50×4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

A solution of tert-butyl N-[2-[5-[(1R)-1-benzyloxy-1-(trifluoromethyl)but-3-enyl]-1,3,4-oxadiazol-2-yl]-6-(1-ethylpent-4-enoxy)-5-(trifluoromethyl)-3-pyridyl]-N-tert-butoxycarbonyl-carbamate (0.88 g, 1.0846 mmol) in DCE (200 mL) was degassed for 15 min and heated at 50° C. under nitrogen atmosphere for 15 min. Zhan catalyst-1B (200 mg, 0.2722 mmol) was then added and the mixture was heated at 70° C. overnight. The reaction mixture was cooled and concentrated under reduced pressure. The residue was purified by silica gel chromatography (40 g column, 0-10% EtOAc in hexanes) to provide as a white solid, tert-butyl N-[(6R)-6-benzyloxy-12-ethyl-6,15-bis(trifluoromethyl)-13,19-dioxa-3,4,18-triazatricyclo[12.3.1.12,5]nonadeca-1(18),2,4,8,14,16-hexaen-17-yl]-N-tert-butoxycarbonyl-carbamate (E/Z mixture) (0.85 g, 91%). ESI-MS m/z calc. 742.2801, found 643.3 (M+H-Boc)$^+$; Retention time: 4.68 minutes. LCMS Method: Merck Millipore Chromolith SpeedROD C$_{18}$ column (50×4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

Step 3: tert-Butyl N-tert-butoxycarbonyl-N-[(6R)-12-ethyl-6-hydroxy-6,15-bis(trifluoromethyl)-13,19-dioxa-3,4,18-triazatricyclo[12.3.1.1².⁵]nonadeca-1(18),2,4,14,16-pentaen-17-yl]carbamate

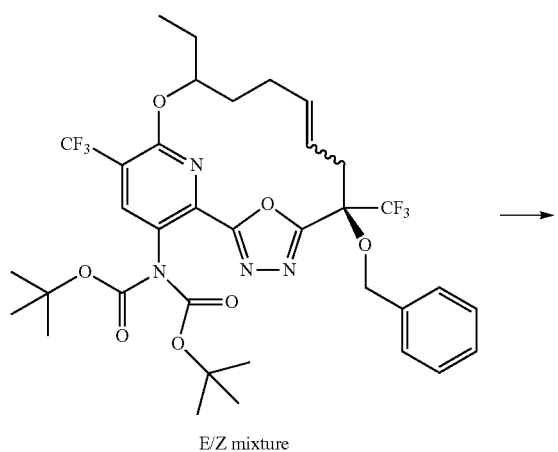

E/Z mixture

A solution of tert-butyl N-[(6R)-6-benzyloxy-12-ethyl-6,15-bis(trifluoromethyl)-13,19-dioxa-3,4,18-triazatricyclo[12.3.1.1²,⁵]nonadeca-1(18),2,4,8,14,16-hexaen-17-yl]-N-tert-butoxycarbonyl-carbamate (E/Z mixture) (0.746 g, 1.0044 mmol) in MeOH (40 mL) was purged with nitrogen three times. It was then backfilled with hydrogen two times before subjecting it to hydrogenation at 60 psi for 22 h using a Parr shaker. After the reaction was done, the reaction mixture was filtered over a pad of Celite and the filter cake was rinsed with MeOH (3×20 mL). The combined filtrate was concentrated and the residue was dried in vacuo overnight provided as a clear oil, tert-butyl N-tert-butoxycarbonyl-N-[(6R)-12-ethyl-6-hydroxy-6,15-bis(trifluoromethyl)-13,19-dioxa-3,4,18-triazatricyclo[12.3.1.1²,⁵]nonadeca-1(18),2,4,14,16-pentaen-17-yl]carbamate (660 mg, 98%). ESI-MS m/z calc. 654.24884, found 555.3 (M+H-Boc)⁺.

Step 4: (6R)-17-Amino-12-ethyl-6,15-bis(trifluoromethyl)-13,19-dioxa-3,4,18-triazatricyclo[12.3.1.1²,⁵]nonadeca-1(18),2,4,14,16-pentaen-6-ol

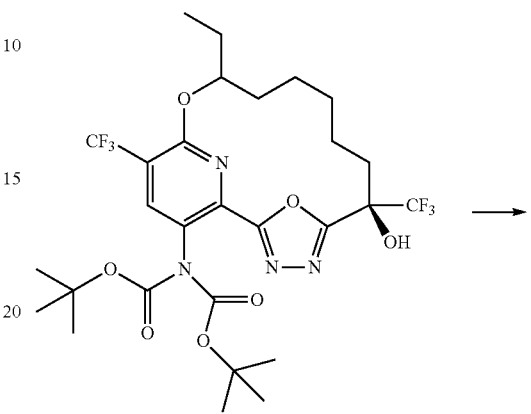

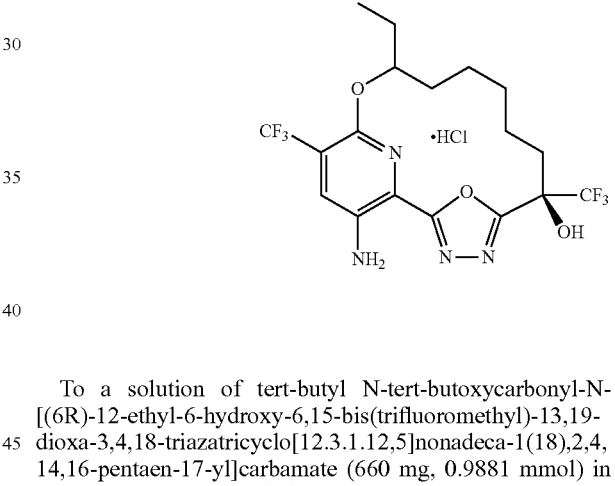

To a solution of tert-butyl N-tert-butoxycarbonyl-N-[(6R)-12-ethyl-6-hydroxy-6,15-bis(trifluoromethyl)-13,19-dioxa-3,4,18-triazatricyclo[12.3.1.1²,⁵]nonadeca-1(18),2,4,14,16-pentaen-17-yl]carbamate (660 mg, 0.9881 mmol) in DCM (50 mL) was added TFA (14.800 g, 10 mL, 129.80 mmol). The resulting yellow solution was stirred at room temperature for 2 h. The reaction mixture was concentrated and purified by reverse phase chromatography (buffer A: water buffered with 5 mM HCl; buffer B: 100% ACN, 55% to 100% over 40 min) provided after lyophilization as a yellow powder, (6R)-17-amino-12-ethyl-6,15-bis(trifluoromethyl)-13,19-dioxa-3,4,18-triazatricyclo[12.3.1.1²,⁵] nonadeca-1(18),2,4,14,16-pentaen-6-ol (hydrochloride salt) (255.7 mg, 51%). $^1$H NMR (500 MHz, DMSO-$d_6$) δ 7.76 (s, 1H), 7.57 (s, 1H), 6.36 (s, 2H), 4.52 (dt, J=26.9, 9.2 Hz, 1H), 2.48-2.39 (m, 1H), 2.18 (t, J=11.4 Hz, 1H), 2.12-2.01 (m, 1H), 1.83-1.72 (m, 1H), 1.70-1.54 (m, 4H), 1.55-1.37 (m, 3H), 1.29-1.15 (m, 1H), 0.96 (t, J=7.3 Hz, 3H). ESI-MS m/z calc. 454.14395, found 97.27 (M+1)⁺; Retention time: 3.16 minutes. LCMS Method: Waters Cortex 2.7 μm particle size $C_{18}$ (3.0 mm×50 mm), 55° C.; flow: 1.2 mL/min; mobile phase: 100% water with 0.1% trifluoroacetic acid then 100% acetonitrile with 0.1% trifluoroacetic acid, gradient of 5% to 100% B over 4 min, with equilibration at 100% B for 0.5 min, then 5% B over 1.5 min.

Step 5: (6R)-17-Amino-12-ethyl-6,15-bis(trifluoromethyl)-13,19-dioxa-3,4,18-triazatricyclo[12.3.1.1².⁵]nonadeca-1(18),2,4,14,16-pentaen-6-ol (enantiomer 1), Compound 54, and (6R)-17-amino-12-ethyl-6,15-bis(trifluoromethyl)-13,19-dioxa-3,4,18-triazatricyclo[12.3.1.1².⁵]nonadeca-1(18),2,4,14,16-pentaen-6-ol (enantiomer 2), Compound 55

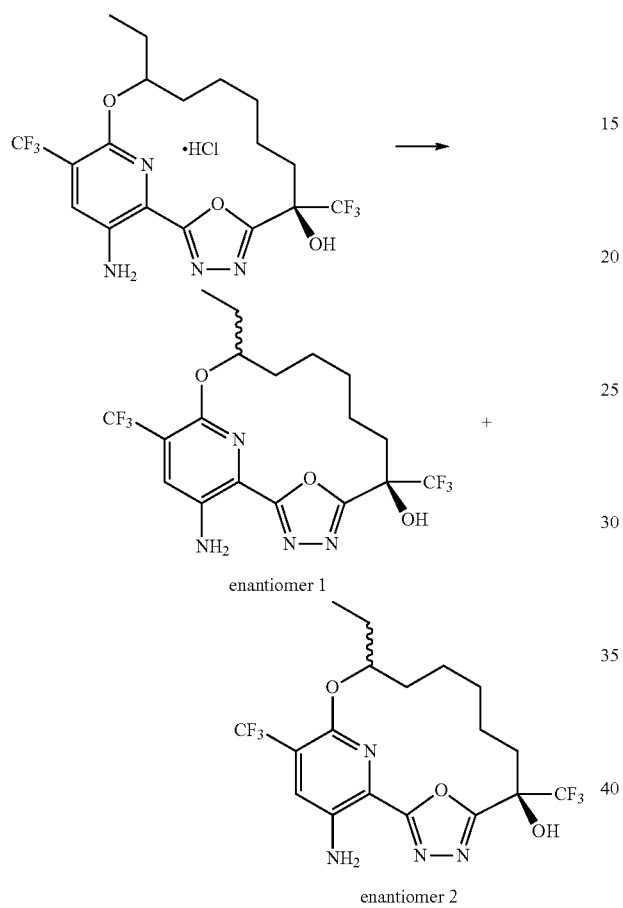

enantiomer 1 enantiomer 2

The diastereomeric mixture, (6R)-17-amino-12-ethyl-6,15-bis(trifluoromethyl)-13,19-dioxa-3,4,18-triazatricyclo[12.3.1.1².⁵]nonadeca-1(18),2,4,14,16-pentaen-6-ol (255.7 mg, 0.5622 mmol) was purified by SFC using Cellulose 4 column (250×30 mm, 5 μm particle size) using a dual gradient run from 10% EtOH (0.1% diethylamine) and 90% $CO_2$. Both isomers were redissolved in EtOAc (5 mL) then washed with 1 M HCl (1×10 mL), saturated sodium bicarbonate (1×10 mL) and brine (1×10 mL). The organic layer was dried over anhydrous sodium sulfate, concentrated under vacuum and lyophilized. SFC peak 1 provided as a light yellow solid, (6R)-17-amino-12-ethyl-6,15-bis(trifluoromethyl)-13,19-dioxa-3,4,18-triazatricyclo[12.3.1.1².⁵]nonadeca-1(18),2,4,14,16-pentaen-6-ol (enantiomer 1) (134 mg, 52%). $^1$H NMR (400 MHz, DMSO-$d_6$) δ 7.77 (s, 1H), 7.60 (s, 1H), 6.36 (s, 2H), 4.51 (t, J=9.0 Hz, 1H), 2.54-2.41 (m, 1H), 2.24-2.14 (m, 1H), 2.12-2.00 (m, 1H), 1.85-1.73 (m, 1H), 1.71-1.38 (m, 7H), 1.31-1.16 (m, 1H), 0.97 (t, J=7.2 Hz, 3H). $^{19}$F NMR (377 MHz, DMSO-$d_6$) δ -62.45 (s, 3F), -79.05 (s, 3F). ESI-MS m/z calc. 454.144, found 455.2 (M+1)⁺; Retention time: 3.54 minutes. SFC peak 2 provided as a light yellow solid (6R)-17-amino-12-ethyl-6,15-bis(trifluoromethyl)-13,19-dioxa-3,4,18-triazatricyclo[12.3.1.1².⁵]nonadeca-1(18),2,4,14,16-pentaen-6-ol (enantiomer 2) (126 mg, 49%). $^1$H NMR (400 MHz, DMSO-$d_6$) δ 7.78 (s, 1H), 7.59 (s, 1H), 6.36 (s, 2H), 4.56 (t, J=9.4 Hz, 1H), 2.46-2.36 (m, 1H), 2.35-2.24 (m, 1H), 2.14-2.05 (m, 1H), 1.87-1.66 (m, 3H), 1.64-1.35 (m, 5H), 1.33-1.20 (m, 1H), 0.97 (t, J=7.2 Hz, 3H). $^{19}$F NMR (377 MHz, DMSO-$d_6$) δ -62.46 (s, 3F), -76.36 (s, 3F). ESI-MS m/z calc. 454.144, found 455.2 (M+1)⁺; Retention time: 3.5 minutes. LCMS Method: Kinetex Polar $C_{18}$ column (3.0×50 mm, 2.6 μm particle size, 6 minute run, 5% to 95% acetonitrile in water (0.1% formic acid modifier), flow rate=1.2 mL/min).

Example 39: Preparation of (12R)-17-amino-12-methyl-6,15-bis(trifluoromethyl)-13,19-dioxa-3,4,18-triazatricyclo[12.3.1.1².⁵]nonadeca-1(18),2,4,14,16-pentaene-6,7-diol (enantiomer 1), Compound 56, and (12R)-17-amino-12-methyl-6,15-bis(trifluoromethyl)-13,19-dioxa-3,4,18-triazatricyclo[12.3.1.1².⁵]nonadeca-1(18),2,4,14,16-pentaene-6,7-diol (enantiomer 2), Compound 57

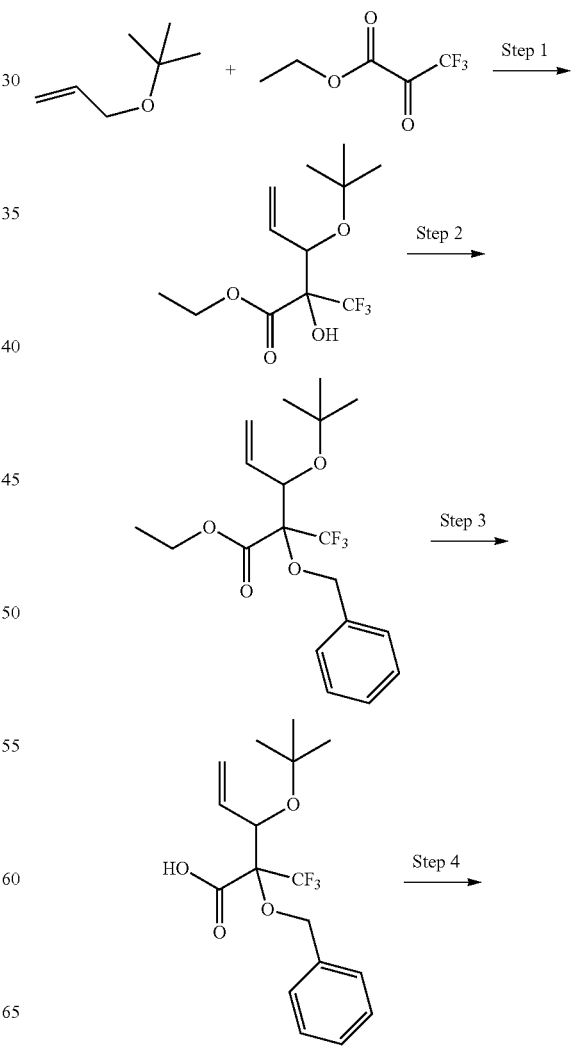

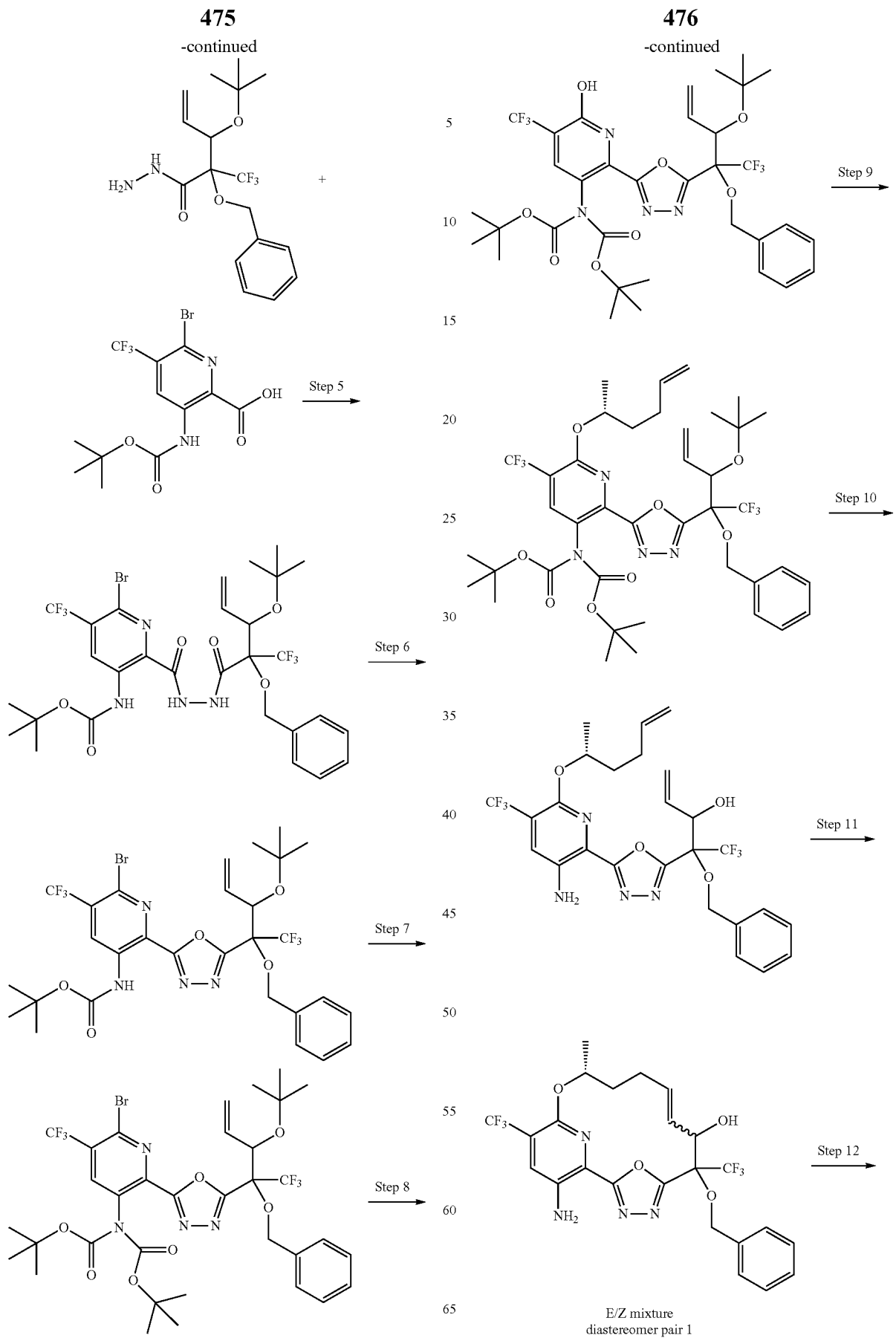

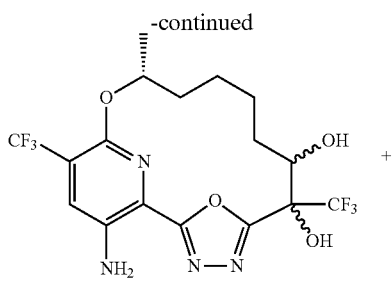

enantiomer 1

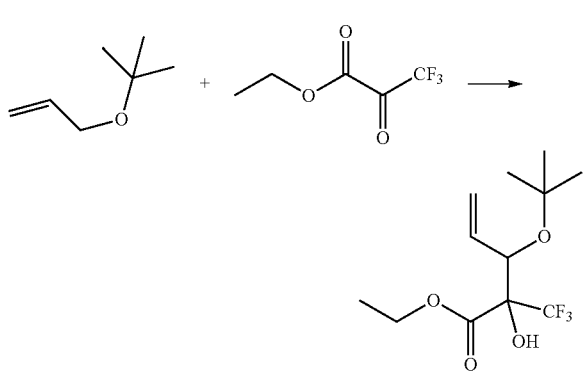

enantiomer 2

Step 1: Ethyl 3-tert-butoxy-2-hydroxy-2-(trifluoromethyl)pent-4-enoate

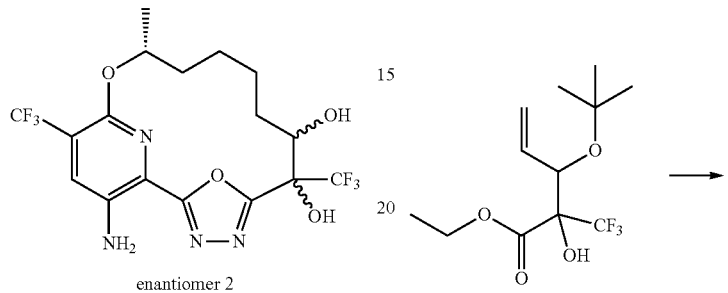

A flame-dried flask was charged with 2-allyloxy-2-methylpropane (5.55 g, 43.259 mmol), THF (100 mL) and TMEDA (4.4175 g, 5.7 mL, 38.015 mmol). The flask was cooled in a dry-ice acetone bath and treated dropwise with a cyclohexane solution of sec-butyllithium (27 mL of 1.4 M, 37.800 mmol). After 45 minutes, heptane solution of trimethylaluminum (19 mL of 2 M, 38.000 mmol) was added and the reaction mixture was stirred for another 45 minutes. Ethyl 3,3,3-trifluoro-2-oxo-propanoate (5.1320 g, 4 mL, 30.173 mmol) was added and the reaction was stirred for about 4.0 hours in the cold bath. The reaction was quenched slowly with 1 N aqueous HCl (150 mL) and stirred vigorously at room temperature for few minutes. Transferred to a 1.0 L separatory funnel with 1 N HCl (200 mL) and extracted with diethyl ether (1×300 mL, 2×150 mL). The combined organic layers were washed with saturated aqueous sodium bicarbonate (200 mL), brine (200 mL), dried over sodium sulfate, filtered, and concentrated under reduced pressure. The residue was purified by silica gel chromatography (330-g column, eluting from 0% to 20% ethyl acetate in heptanes) to afford as a colorless oil and single diastereomer pair, ethyl 3-tert-butoxy-2-hydroxy-2-(trifluoromethyl)pent-4-enoate (3.24 g, 38%). $^1$H NMR (400 MHz, CDCl$_3$) δ 5.87 (ddd, J=17.7, 10.1, 7.9 Hz, 1H), 5.32-5.21 (m, 2H), 4.55 (d, J=8.1 Hz, 1H), 4.39-4.23 (m, 2H), 3.85 (s, 1H), 1.33 (t, J=7.2 Hz, 3H), 1.23 (s, 9H). $^{19}$F NMR (377 MHz, CDCl$_3$) δ −73.35 (s, 3F).

Step 2: Ethyl 2-benzyloxy-3-tert-butoxy-2-(trifluoromethyl)pent-4-enoate

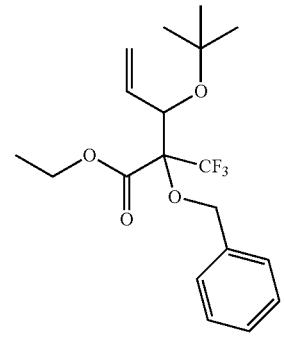

A solution of ethyl 3-tert-butoxy-2-hydroxy-2-(trifluoromethyl)pent-4-enoate (3.24 g, 11.398 mmol) in DMF (50 mL) was cooled in an ice bath and treated with a mineral oil suspension of sodium hydride (563 mg, 60% w/w, 14.076 mmol). After 40 minutes, bromomethyl benzene (2.6459 g, 1.84 mL, 15.470 mmol) was added and the reaction was gradually warm to room temperature and stirred overnight. Transferred to a 1.0 L separatory funnel with water (450 mL) and the aqueous layer was extracted with MTBE (4×150 mL). The combined organic layers washed with water (2×150 mL), brine (150 mL), dried over sodium sulfate, filtered, and concentrated under reduced pressure. The residue was purified by silica gel chromatography (220 g column, eluting from 0% to 20% ethyl acetate in heptanes) to afford as a colorless oil, ethyl 2-benzyloxy-3-tert-butoxy-2-(trifluoromethyl)pent-4-enoate (3.86 g, 83%). $^1$H NMR (400 MHz, CDCl$_3$) δ 7.46-7.41 (m, 2H), 7.39-7.32 (m, 2H), 7.32-7.28 (m, 1H), 5.98 (ddd, J=17.9, 9.3, 8.6 Hz, 1H), 5.27-5.22 (m, 1H), 5.21 (s, 1H), 4.92-4.85 (m, 1H), 4.79-4.73 (m, 1H), 4.59 (d, J=8.1 Hz, 1H), 4.28 (q, J=7.1 Hz, 2H), 1.32 (t, J=7.1 Hz, 3H), 1.20 (s, 9H). $^{19}$F NMR (377 MHz, CDCl$_3$) δ −65.50 (s, 3F). ESI-MS m/z calc. 374.1705, found 397.2 (M+23)$^+$; Retention time: 2.45 minutes. LCMS Method: Kinetex Polar C$_{18}$ column (3.0×50 mm, 2.6 lam particle size, 3 minute run, 5% to 95% acetonitrile in water (0.1% formic acid modifier), flow rate=1.2 mL/min).

Step 3: 2-Benzyloxy-3-tert-butoxy-2-(trifluoromethyl)pent-4-enoic acid

Step 4: 2-Benzyloxy-3-tert-butoxy-2-(trifluoromethyl)pent-4-enehydrazide

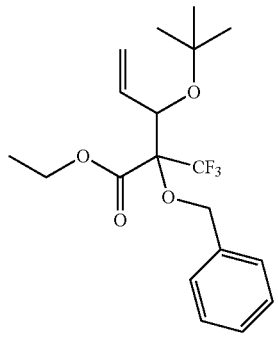

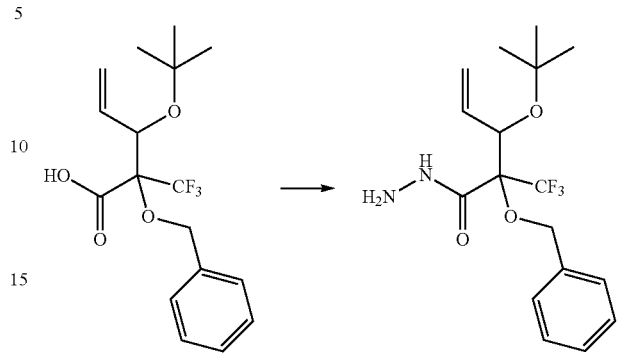

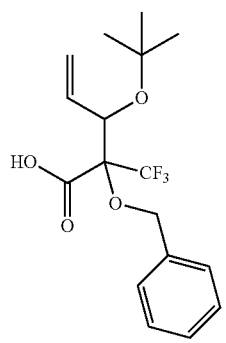

A solution of sodium hydroxide (1.13 g, 28.252 mmol) in water (10 mL) was added to a solution of ethyl 2-benzyloxy-3-tert-butoxy-2-(trifluoromethyl)pent-4-enoate (3.4 g, 8.6908 mmol) in methanol (30 mL). The reaction mixture was stirred in an oil bath at 70° C. for 4 days. The reaction was cooled to room temperature and concentrated under reduced pressure to remove methanol. Added water (100 mL) and acidified to pH of 1-2 with 1 N aqueous HCl. Transferred to a 500 mL separatory funnel and the aqueous layer was extracted with ethyl acetate (3×100 mL). The combined organic layers washed with water (100 mL), brine (100 mL), dried over sodium sulfate, filtered and concentrated under reduced pressure to afford as a yellow oil, 2-benzyloxy-3-tert-butoxy-2-(trifluoromethyl)pent-4-enoic acid (3.29 g, 97%). $^1$H NMR (400 MHz, DMSO-$d_6$) δ 14.11 (br. s., 1H), 7.45-7.26 (m, 5H), 5.86 (ddd, J=17.6, 10.0, 8.1 Hz, 1H), 5.34-5.20 (m, 2H), 4.88 (d, J=11.2 Hz, 1H), 4.67-4.56 (m, 2H), 1.15 (s, 9H). $^{19}$F NMR (377 MHz, DMSO-$d_6$) δ −64.77 (s, 3F). ESI-MS m/z calc. 346.1392, found no ionization; Retention time: 2.15 minutes. LCMS Method: Kinetex Polar $C_{18}$ column (3.0×50 mm, 2.6 μm particle size, 3 minute run, 5% to 95% acetonitrile in water (0.1% formic acid modifier), flow rate=1.2 mL/min).

A solution of 2-benzyloxy-3-tert-butoxy-2-(trifluoromethyl)pent-4-enoic acid (3.29 g, 8.4354 mmol) and triethylamine (2.5410 g, 3.5 mL, 25.111 mmol) in DMF (50 mL) was treated with HATU (6.46 g, 16.990 mmol) and stirred at room temperature for 20 minutes. Cooled in an ice bath and added hydrazine.H$_2$O (6.7080 g, 10 mL, 87.099 mmol). After about 10 minutes, removed the ice bath and the reaction was stirred at room temperature for about 18 hours. Transferred to a 1.0 L separatory funnel with water (450 mL) and the aqueous layer was extracted with ethyl acetate (4×150 mL). The combined organic layers washed with water (2×250 mL), brine (200 mL), dried over sodium sulfate, filtered, and concentrated under reduced pressure. The residue was purified by silica gel chromatography (220 g column, eluting from 0% to 50% ethyl acetate in heptanes) to afford as a colorless oil, 2-benzyloxy-3-tert-butoxy-2-(trifluoromethyl)pent-4-enehydrazide (2.836 g, 91%) that solidified on standing. $^1$H NMR (400 MHz, DMSO-$d_6$) δ 9.08 (br. s., 1H), 7.45-7.25 (m, 5H), 5.81 (ddd, J=17.4, 10.5, 7.1 Hz, 1H), 5.27 (d, J=17.1 Hz, 1H), 5.21 (d, J=10.5 Hz, 1H), 5.11-4.99 (m, 2H), 4.90 (d, J=7.3 Hz, 1H), 4.36 (d, J=4.4 Hz, 2H), 1.18 (s, 9H). $^{19}$F NMR (377 MHz, DMSO-$d_6$) δ −67.28 (s, 3F). ESI-MS m/z calc. 360.1661, found 305.1 (M−55)$^+$; Retention time: 2.13 minutes. LCMS Method: Kinetex Polar $C_{18}$ column (3.0×50 mm, 2.6 μm particle size, 3 minute run, 5% to 95% acetonitrile in water (0.1% formic acid modifier), flow rate=1.2 mL/min).

Step 5: tert-Butyl N-[2-[[[2-benzyloxy-3-tert-butoxy-2-(trifluoromethyl)pent-4-enoyl]amino]carbamoyl]-6-bromo-5-(trifluoromethyl)-3-pyridyl]carbamate

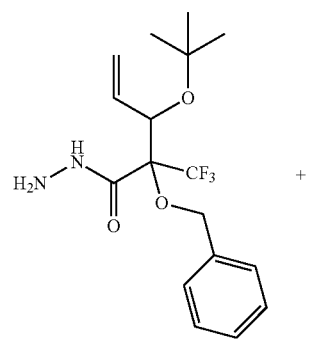 +

-continued

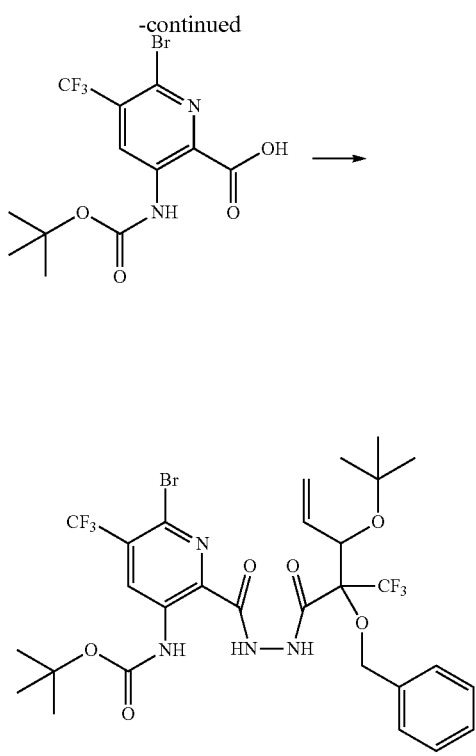

A mixture of 6-bromo-3-(ter t-butoxycarbonylamino)-5-(trifluoromethyl)pyridine-2-carboxylic acid (661 mg, 1.7163 mmol) and 2-benzyloxy-3-tert-butoxy-2-(trifluoromethyl)pent-4-enehydrazide (601 mg, 1.6260 mmol) in ethyl acetate (10 mL) was treated successively with pyridine (508.56 mg, 0.52 mL, 6.4293 mmol) and an ethyl acetate solution of T$_3$P (1.86 g, 50% w/w, 2.9229 mmol) at room temperature., The reaction mixture was stirred for 23 hours, transferred to a 250 mL separatory funnel with saturated aqueous ammonium chloride (100 mL) and extracted with ethyl acetate (2×75 mL). The combined organic layers were washed with saturated aqueous sodium bicarbonate (100 mL), brine (100 mL), dried over sodium sulfate, filtered, and concentrated under reduced pressure. The residue was purified by silica gel chromatography (80-g column, eluting from 0% to 50% ethyl acetate in heptanes) to afford as a thick pale amber oil, tert-butyfl N-[2-[[[2-benzyloxy-3-tert-butoxy-2-(trifluoromethyl)pent-4-enoyl]amino]carbamoyl]-6-bromo-5-(trifluoromethyl)-3-pyridyl]carbamate (1.1 g, 92%). $^1$H NMR (400 MHz, DMSO-d$_6$) δ 11.04 (s, 1H), 10.84 (s, 1H), 10.10 (s, 1H), 9.13 (s, 1H), 7.47-7.41 (m, 2H), 7.40-7.33 (m, 2H), 7.33-7.28 (m, 1H), 6.02 (ddd, J=17.1, 10.6, 6.4 Hz, 1H), 5.46 (d, J=17.1 Hz, 1H), 5.35 (d, J=10.5 Hz, 1H), 5.19 (d, J=11.7 Hz, 1H), 5.10 (d, J=12.5 Hz, 1H), 4.95 (d, J=6.4 Hz, 1H), 1.49 (s, 9H), 1.22 (s, 9H). $^{19}$F NMR (377 MHz, DMSO-d$_6$) δ -62.86 (s, 3F), -67.31 (s, 3F). ESI-MS m/z calc. 726.1488, found 571.0 (M-155)$^+$; Retention time: 2.85 minutes. LCMS Method: Kinetex Polar C$_{18}$ column (3.0×50 mm, 2.6 µm particle size, 3 minute run, 5% to 95% acetonitrile in water (0.1% formic acid modifier), flow rate=1.2 mL/min).

Step 6: tert-Butyl N-[2-[5-[1-benzyloxy-2-tert-butoxy-1-(trifluoromethyl)but-3-enyl]-1,3,4-oxadiazol-2-yl]-6-bromo-5-(trifluoromethyl)-3-pyridyl]carbamate

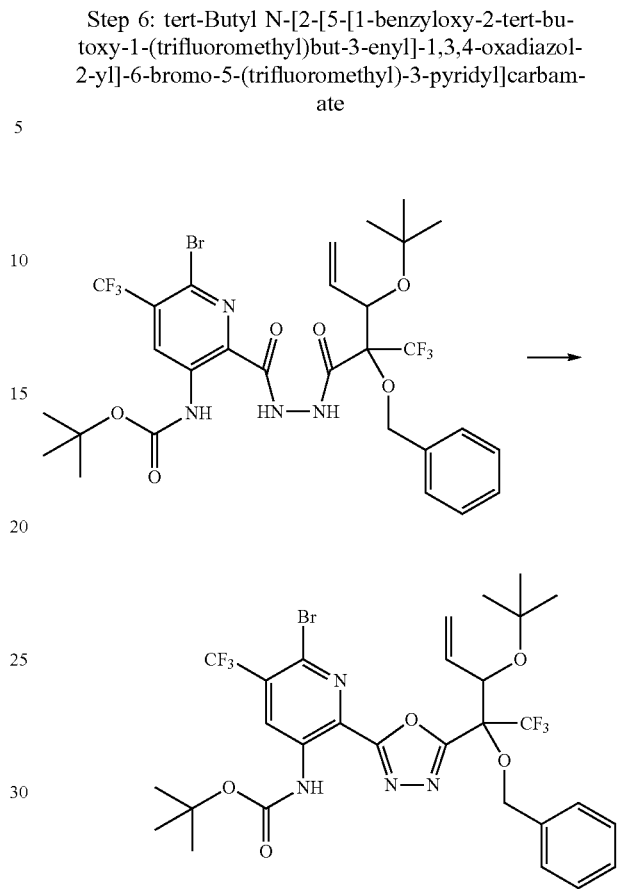

A solution of tert-butyl N-[2-[[[2-benzyloxy-3-tert-butoxy-2-(trifluoromethyl)pent-4-enoyl]amino]carbamoyl]-6-bromo-5-(trifluoromethyl)-3-pyridyl]carbamate (1.1 g, 1.4969 mmol) and DIPEA (682.64 mg, 0.92 mL, 5.2818 mmol) in acetonitrile (24 mL) was heated in an oil bath at 60° C. Addedp-TsCl (322 mg, 1.6890 mmol) and the reaction was heated in the oil bath for 90 minutes. Once cooled to room temperature, the reaction was concentrated under reduced pressure to remove the acetonitrile. Transferred to a 250 mL separatory funnel with saturated aqueous sodium bicarbonate (100 mL) and the aqueous layer was extracted with ethyl acetate (2×75 mL). The combined organic layers were washed with brine (100 mL), dried over sodium sulfate, filtered, and concentrated under reduced pressure. The residue was purified by silica gel chromatography (80 g column, eluting from 0% to 30% ethyl acetate in heptanes) to afford as a pale amber oil, tert-butyl N-[2-[5-[1-benzyloxy-2-tert-butoxy-1-(trifluoromethyl)but-3-enyl]-1,3,4-oxadiazol-2-yl]-6-bromo-5-(trifluoromethyl)-3-pyridyl]carbamate (0.96 g, 88%). $^1$H NMR (400 MHz, CDCl$_3$) δ 10.26 (s, 1H), 9.37 (s, 1H), 7.57-7.51 (m, 2H), 7.46-7.38 (m, 2H), 7.36-7.30 (m, 1H), 6.01 (ddd, J=17.5, 9.4, 8.3 Hz, 1H), 5.32-5.20 (m, 2H), 4.90-4.83 (m, 1H), 4.83-4.75 (m, 2H), 1.58 (s, 9H), 1.12 (s, 9H). $^{19}$F NMR (377 MHz, CDCl$_3$) δ -63.73 (s, 3F), -66.73 (s, 3F). ESI-MS m/z calc. 708.1382, found 597.0 (M-111)$^+$; Retention time: 4.85 minutes. LCMS Method:) (Bridge C$_{18}$ column (4.6×75 mm, 5 mm particle size, 6 minute run with 1 minute equilibration, initial mobile phase at 95% aqueous NH$_4$HCO$_3$/5% acetonitrile, gradient from 0 to 3 minutes to 95% MeCN and held for 3 minutes, flow=1.5 mL/min).

Step 7: tert-Butyl N-[2-[5-[1-benzyloxy-2-tert-butoxy-1-(trifluoromethyl)but-3-enyl]-1,3,4-oxadiazol-2-yl]-6-bromo-5-(trifluoromethyl)-3-pyridyl]-N-tert-butoxycarbonyl-carbamate

Step 8: tert-Butyl N-[2-[5-[1-benzyloxy-2-tert-butoxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate

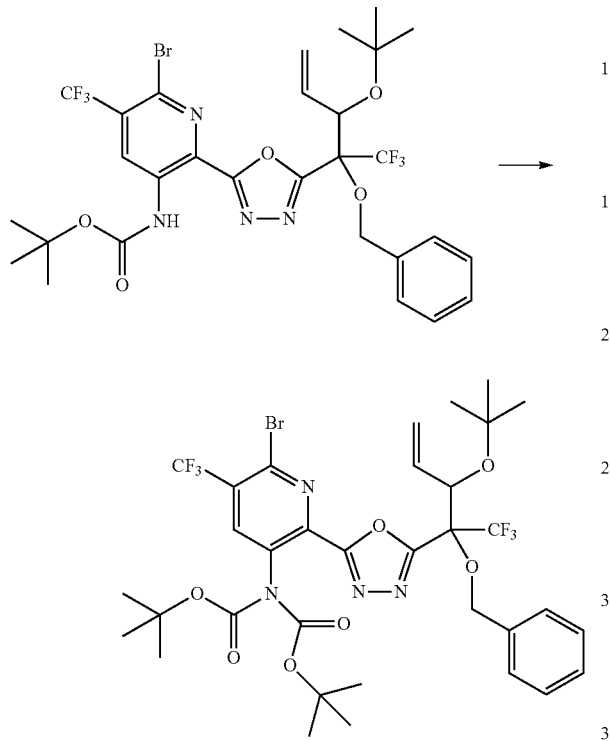

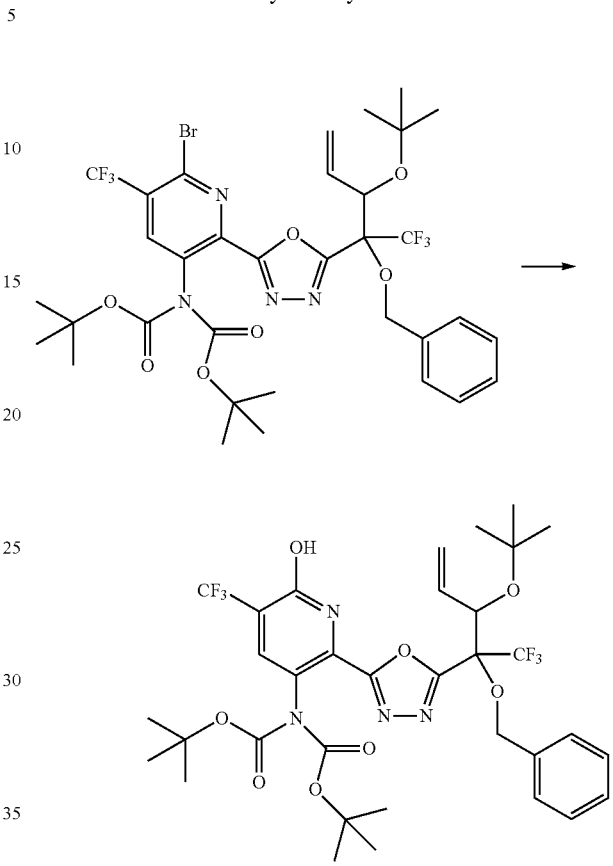

A solution of tert-butyl N-[2-[5-[1-benzyloxy-2-tert-butoxy-1-(trifluoromethyl)but-3-enyl]-1,3,4-oxadiazol-2-yl]-6-bromo-5-(trifluoromethyl)-3-pyridyl]carbamate (1.21 g, 1.6697 mmol), DIPEA (237.44 mg, 0.32 mL, 1.8372 mmol) and DMAP (10 mg, 0.0819 mmol) in MTBE (25 mL) was treated with di-tert-butyl dicarbonate (479 mg, 0.5042 mL, 2.1948 mmol) and stirred at room temperature for about 5 hours. The reaction mixture was transferred to a 125 mL separatory funnel with water (75 mL) and MTBE (100 mL). After extraction, the layers were separated, and the organic layer was washed with brine (75 mL). The organic layer was dried over sodium sulfate, filtered, and concentrated under reduced pressure. The residue was purified by silica gel chromatography (80 m g column, eluting from 0% to 25% ethyl acetate in heptanes) to afford as a colorless oil, tert-butyl N-[2-[5-[1-benzyloxy-2-tert-butoxy-1-(trifluoromethyl)but-3-enyl]-1,3,4-oxadiazol-2-yl]-6-bromo-5-(trifluoromethyl)-3-pyridyl]-N-tert-butoxycarbonyl-carbamate (1.26 g, 91%) that solidified on standing to a white solid. $^1$H NMR (400 MHz, CDCl$_3$) δ 7.95 (s, 1H), 7.57-7.48 (m, 2H), 7.45-7.37 (m, 2H), 7.36-7.30 (m, 1H), 5.98 (ddd, J=17.4, 9.7, 7.9 Hz, 1H), 5.28-5.15 (m, 2H), 4.86-4.72 (m, 3H), 1.44 (s, 18H), 1.08 (s, 9H). $^{19}$F NMR (377 MHz, CDCl$_3$) δ −63.74 (s, 3F), −66.63 (s, 3F). ESI-MS m/z calc. 808.1906, found 597.0 (M−211)$^+$; Retention time: 4.57 minutes. LCMS Method: XBridge C$_{18}$ column (4.6×75 mm, 5 mm particle size, 6 minute run with 1 minute equilibration, initial mobile phase at 95% aqueous NH$_4$HCO$_3$/5% acetonitrile, gradient from 0 to 3 minutes to 95% MeCN and held for 3 minutes, flow=1.5 mL/min).

To a mixture of tert-butyl N-[2-[5-[1-benzyloxy-2-tert-butoxy-1-(trifluoromethyl)but-3-enyl]-1,3,4-oxadiazol-2-yl]-6-bromo-5-(trifluoromethyl)-3-pyridyl]-N-tert-butoxycarbonyl-carbamate (1.18 g, 1.4575 mmol) in DMSO (12 mL) was added cesium acetate (899 mg, 4.6835 mmol). The mixture was stirred at 85° C. for 5 h and cooled to rt. The mixture was transferred to a 250 mL separatory funnel with saturated aqueous ammonium chloride (25 mL) and water (125 mL) and extracted with 1:1 mixture of MTBE and heptanes (3×50 mL). The combined organic layers were washed with water (2×50 mL), brine (50 mL), dried over sodium sulfate, filtered and concentrated under reduced pressure to afford as an off-white foamy solid, tert-butyl N-[2-[5-[1-benzyloxy-2-tert-butoxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate (1.2 g, 105%, contaminated with residual MTBE). $^1$H NMR (400 MHz, CDCl$_3$) δ 7.75 (s, 1H), 7.45-7.30 (m, 5H), 7.16-7.08 (m, 1H), 6.03-5.91 (m, 1H), 5.31-5.21 (m, 2H), 4.91-4.75 (m, 3H), 1.47 (s, 9H), 1.42 (s, 9H), 1.07 (s, 9H). $^{19}$F NMR (377 MHz, CDCl$_3$) δ −65.88 (br. s., 3F), −66.39 (s, 3F). ESI-MS m/z calc. 746.275, found 535.2 (M−211)$^+$; Retention time: 3.35 minutes. LCMS Method: SunFire C$_{18}$ column (75×4.6 mm, 3.5 mm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Step 9: tert-Butyl N-[2-[5-[1-benzyloxy-2-tert-butoxy-1-(trifluoromethyl)but-3-enyl]-1,3,4-oxadiazol-2-yl]-6-[(1R)-1-methylpent-4-enoxy]-5-(trifluoromethyl)-3-pyridyl]-N-tert-butoxycarbonyl-carbamate

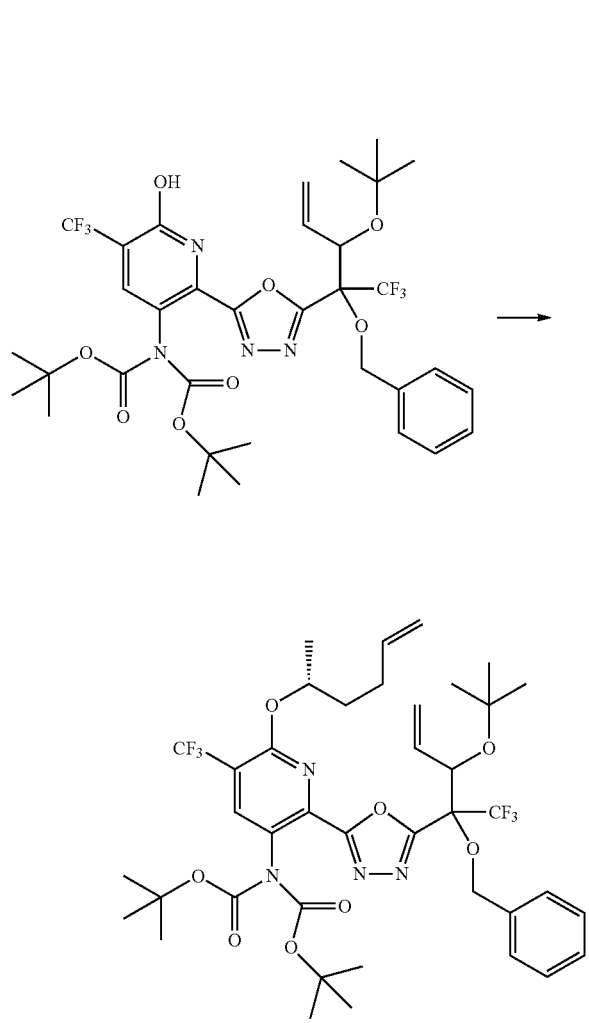

A solution of tert-butyl N-[2-[5-[1-benzyloxy-2-tert-butoxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate (1.0883 g, 1.4575 mmol) and (2S)-hex-5-en-2-ol (494 mg, 4.4389 mmol) in toluene (24 mL) was treated successively with triphenylphosphine (883 mg, 3.3666 mmol) and DIAD (677.82 mg, 0.66 mL, 3.3521 mmol) and the reaction was stirred at room temperature for 19 hours. Concentrated under reduced pressure and purified by silica gel chromatography (80 g column, eluting from 0% to 20% ethyl acetate in heptanes) to afford as a colorless oil, tert-butyl N-[2-[5-[1-benzyloxy-2-tert-butoxy-1-(trifluoromethyl)but-3-enyl]-1,3,4-oxadiazol-2-yl]-6-[(1R)-1-methylpent-4-enoxy]-5-(trifluoromethyl)-3-pyridyl]-N-tert-butoxycarbonyl-carbamate (1.07 g, 68%). ESI-MS m/z calc. 828.3533, found 617.2 (M−211)+; Retention time: 5.09 minutes. LCMS Method:) XBridge $C_{18}$ column (4.6×75 mm, 5 mm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

Step 10: 4-[5-[3-Amino-6-[(1R)-1-methylpent-4-enoxy]-5-(trifluoromethyl)-2-pyridyl]-1,3,4-oxadiazol-2-yl]-4-benzyloxy-5,5,5-trifluoro-pent-1-en-3-ol

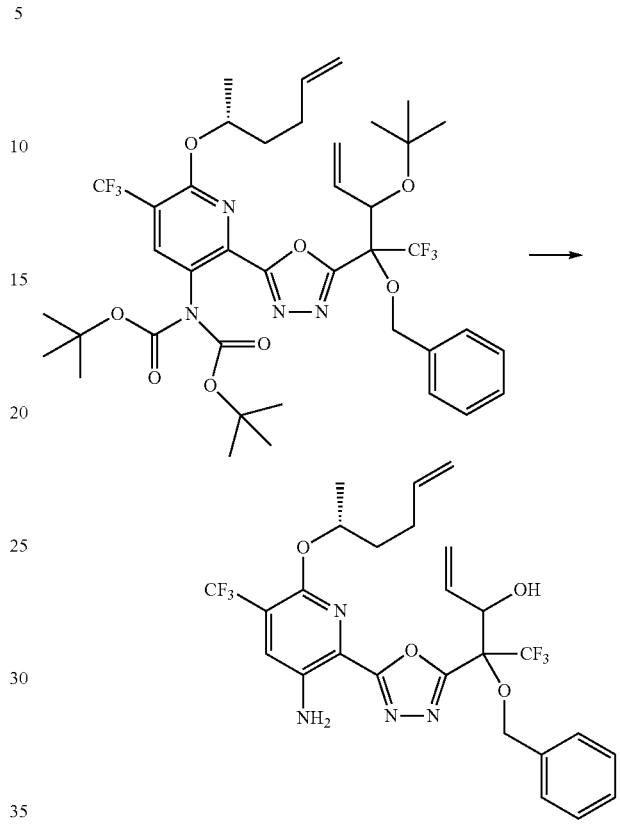

A solution of tert-butyl N-[2-[5-[1-benzyloxy-2-tert-butoxy-1-(trifluoromethyl)but-3-enyl]-1,3,4-oxadiazol-2-yl]-6-[(1R)-1-methylpent-4-enoxy]-5-(trifluoromethyl)-3-pyridyl]-N-tert-butoxycarbonyl-carbamate (1.07 g, 1.2910 mmol) in dichloromethane (15 mL) and TFA (22.200 g, 15 mL, 194.70 mmol) was stirred at room temperature for 4.5 hours. The reaction was concentrated under reduced pressure and the residue was transferred to a 250 mL separatory funnel with dichloromethane (50 mL) and saturated aqueous sodium bicarbonate (75 mL). After extraction, the layers were separated, and the aqueous layer was extracted again with dichloromethane (2×50 mL). The combined organic layers were washed with brine (50 mL), dried over sodium sulfate, filtered, and concentrated under reduced pressure. The residue was purified by silica gel chromatography (40 g column, eluting from 0% to 30% ethyl acetate in heptanes) to afford as a yellow oil and about 1:1 diastereomers mixture of 4-[5-[3-amino-6-[(1R)-1-methylpent-4-enoxy]-5-(trifluoromethyl)-2-pyridyl]-1,3,4-oxadiazol-2-yl]-4-benzyloxy-5,5,5-trifluoro-pent-1-en-3-ol (585 mg, 72%). $^1$H NMR (400 MHz, $CDCl_3$) δ 7.51-7.43 (m, 3H), 7.41-7.31 (m, 3H), 6.06-5.92 (m, 1H), 5.91-5.76 (m, 1H), 5.63 (br. s., 2H), 5.36 (d, J=17.1 Hz, 1H), 5.25 (d, J=10.3 Hz, 1H), 5.22-5.14 (m, 1H), 5.13-5.04 (m, 1H), 5.04-4.85 (m, 3H), 4.84-4.76 (m, 1H), 3.01-2.75 (m, 1H), 2.29-2.07 (m, 2H), 1.93-1.82 (m, 1H), 1.76-1.64 (m, 1H), 1.37 (d, J=6.1 Hz, 3H, diastereomer A), 1.32 (d, J=6.1 Hz, 3H, diastereomer B). $^{19}$F NMR (377 MHz, $CDCl_3$) δ −64.19 (s, 3F), −68.24 (s, 3F, diastereomer A), −68.30 (s, 3F, diastereomer ESI-MS m/z calc. 572.1858, found 573.2 (M+1)+; Retention time: 4.12 minutes. LCMS

487

Method: XBridge $C_{18}$ column (4.6×75 mm, 5 mm particle size, 6 minute run with 1 minute equilibration, initial mobile phase at 95% aqueous $NH_4HCO_3$/5% acetonitrile, gradient from 0 to 3 minutes to 95 MeCN and held for 3 minutes, flow=1.5 mL/min).

Step 11: (12R)-17-Amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-ol (E/Z Mixture, diastereomer pair 1)

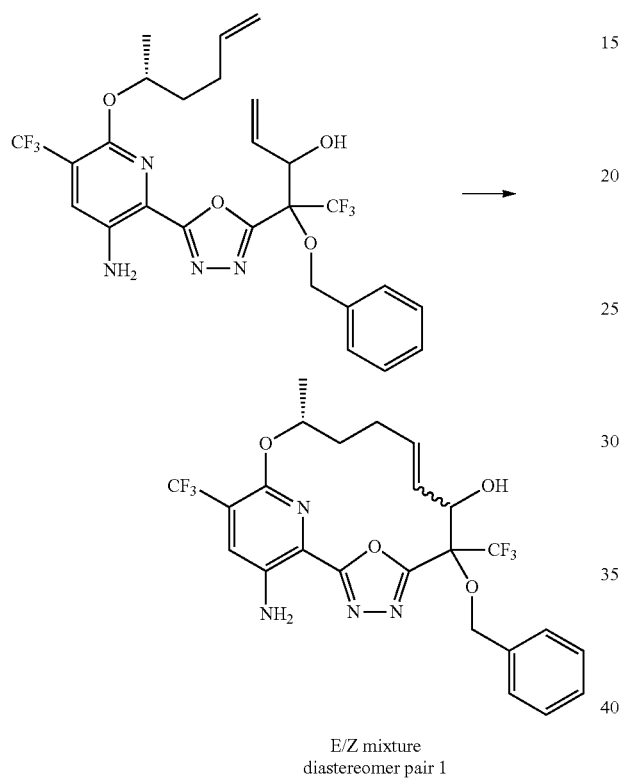

A solution of 4-[5-[3-amino-6-[(1R)-1-methylpent-4-enoxy]-5-(trifluoromethyl)-2-pyridyl]-1,3,4-oxadiazol-2-yl]-4-benzyloxy-5,5,5-trifluoro-pent-1-en-3-ol (98.7 mg, 0.1572 mmol) in dichloroethane (50 mL) was bubbled with nitrogen gas for 21 hours. The solution was heated in an oil bath at 70° C. and treated with Zhan-1B catalyst (8 mg, 0.0109 mmol). After 30 minutes, a second portion of Zhan-1B catalyst (8 mg, 0.0109 mmol) was added and heated for 3 hours. The reaction mixture was cooled to room temperature, DMSO (4 drops) was added and concentrated under reduced pressure. The residue was purified by silica gel chromatography (24 g column, eluting from 0% to 40% ethyl acetate in heptanes) to afford as a dark amber oil, (12R)-17-amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-ol (E/Z mixture, diastereomer pair 1) (79.6 mg, 76%). ESI-MS m/z calc. 544.1545, found 545.2 (M+1)+; Retention time: 3.85 minutes. LCMS Method: XBridge $C_{18}$ column (4.6×75 mm, 5 mm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

488

Step 12: (12R)-17-Amino-12-methyl-6,15-bis(trifluoromethyl)-13,19-dioxa-3,4,18-triazatricyclo[12.3.1.12,5]nonadeca-1(18),2,4,14,16-pentaene-6,7-diol (enantiomer 1), Compound 56, and (12R)-17-amino-12-methyl-6,15-bis(trifluoromethyl)-13,19-dioxa-3,4,18-triazatricyclo[12.3.1.12,5]nonadeca-1(18),2,4,14,16-pentaene-6,7-diol (enantiomer 2), Compound 57

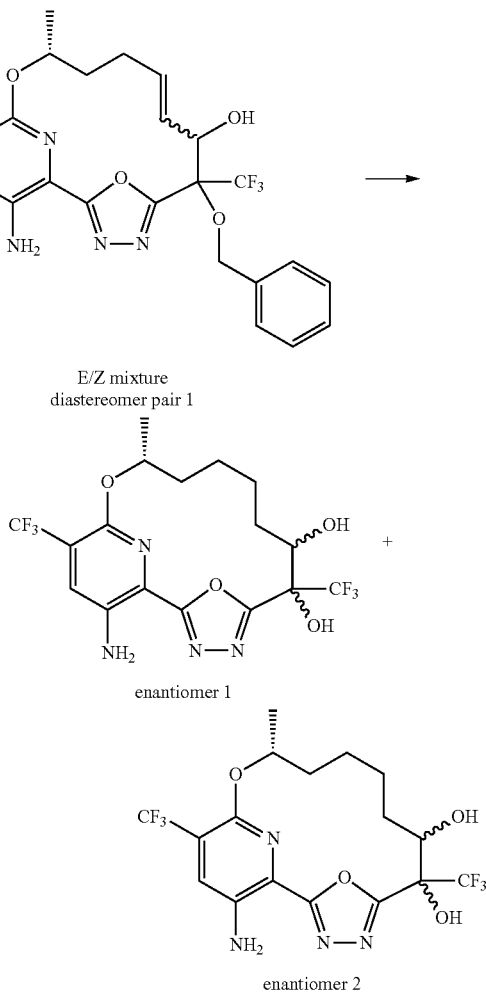

A solution of (12R)-17-amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-ol (E/Z mixture, diastereomer pair 1) (25 mg, 0.0459 mmol) in methanol (2 mL) was purged three times with nitrogen gas. Added palladium on carbon (30 mg, 5% w/w, 0.0141 mmol), purged the reaction three times with hydrogen gas and the reaction was stirred at room temperature for 5 hours. The reaction was purged twice with nitrogen, filtered over a pad of celite and washed with methanol. The solvent was removed under reduced pressure and the residue was purified by silica gel chromatography (4 g column, eluting from 0% to 40% ethyl acetate in heptanes). The resultant solid was purified by SFC using Cellulose 4 column (150×12.2 mm, 5 μm particle size) using a dual gradient run from 10% MeOH (no modifier) and 90% $CO_2$ with flow rate of 75 mL/min giving as a pale-yellow solid, (12R)-17-amino-12- methyl-6,15-bis(trifluoromethyl)-13,19-dioxa-3,4,18-triazatricyclo[12.3.1.1²,⁵]nonadeca-1(18),2,4,14,16-pentaene-6,7-diol (enantiomer 1) (10.5 mg, 48%). $^1$H NMR (400 MHz, DMSO-d$_6$) δ 7.75 (s, 1H), 7.50 (s, 1H), 6.32 (s, 2H), 5.38 (d, J=8.8 Hz, 1H), 4.83-4.66 (m, 1H), 4.42-4.25 (m, 1H), 2.48-2.40 (m, 1H), 1.84-1.71 (m, 1H), 1.66-1.56 (m, 2H), 1.55-1.46 (m, 1H), 1.45-1.37 (m, 2H), 1.34 (d, J=6.4 Hz, 3H), 1.21-1.10 (m, 1H). $^{19}$F NMR (377 MHz, DMSO-d$_6$) δ −62.50 (s, 3F), −73.40 (s, 3F). ESI-MS m/z calc. 456.1232, found 457.1 (M+1)$^+$; Retention time: 3.38 minutes. Also, isolated as an off white solid, (12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,7-diol (enantiomer 2) (9 mg, 42%). $^1$H NMR (400 MHz, DMSO-d$_6$) δ 7.74 (s, 1H), 7.52 (s, 1H), 6.24 (s, 2H), 5.62 (d, J=6.6 Hz, 1H), 5.04-4.86 (m, 1H), 4.19-3.99 (m, 1H), 2.43-2.29 (m, 1H), 2.20-2.08 (m, 1H), 2.07-1.95 (m, 1H), 1.64-1.43 (m, 3H), 1.32 (d, J=6.4 Hz, 3H), 1.30-1.20 (m, 2H). $^{19}$F NMR (377 MHz, DMSO-d$_6$) δ −62.46 (s, 3F), −73.70 (s, 3F). ESI-MS m/z calc. 456.1232, found 457.1 (M+1)$^+$; Retention time: 3.47 minutes. LCMS Method: XBridge C$_{18}$ column (4.6×75 mm, 5 mm particle size, 6 minute run with 1 minute equilibration, initial mobile phase at 95% aqueous NH$_4$HCO$_3$/5% acetonitrile, gradient from 0 to 3 minutes to 95 MeCN and held for 3 minutes, flow=1.5 mL/min).

Example 40: Preparation of (6R,12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,8-diol (diastereomer 2), Compound 58

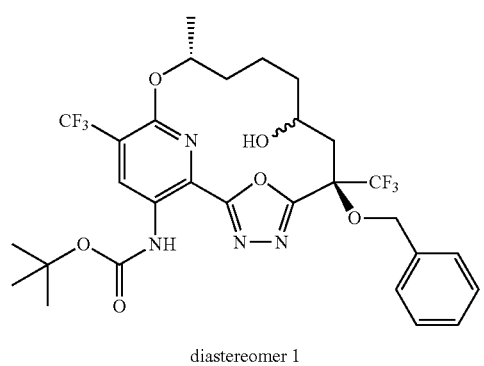

diastereomer 1

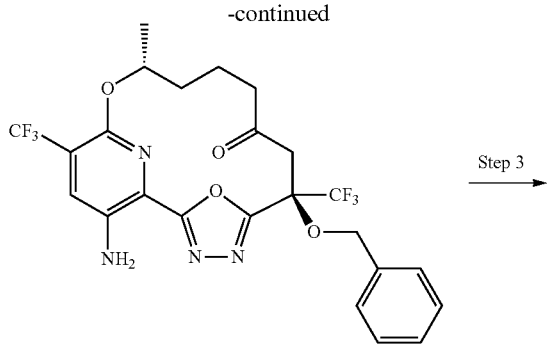

Step 3

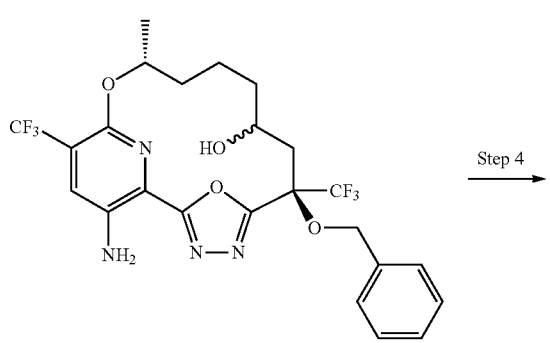

diastereomer 2

Step 4

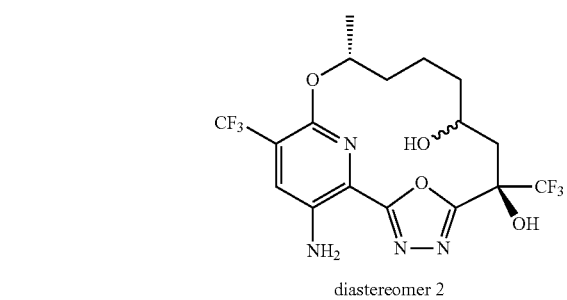

diastereomer 2

Step 1: tert-Butyl N-[(6R,12R)-6-benzyloxy-12-methyl-8-oxo-6,15-bis(trifluoromethyl)-13,19-dioxa-3,4,18-triazatricyclo[12.3.1.1²,⁵]nonadeca-1(18),2,4,14,16-pentaen-17-yl]carbamate

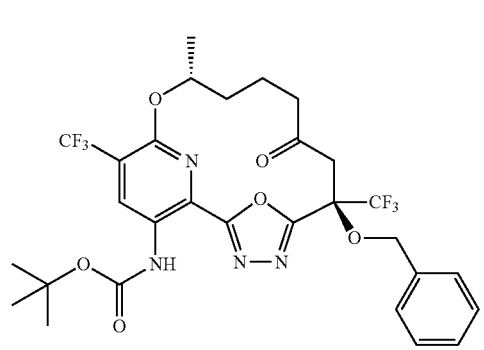

Step 2

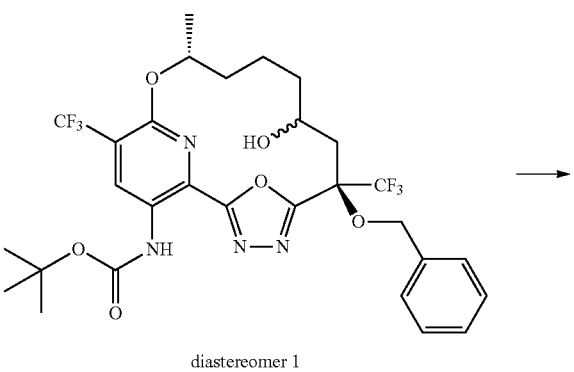

diastereomer 1

491

-continued

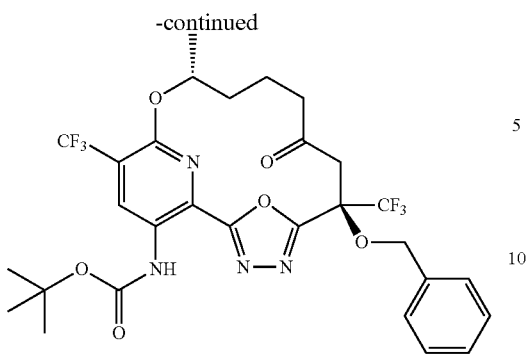

To a solution of tert-butyl N-[(6R,12R)-6-benzyloxy-8-hydroxy-12-methyl-6,15-bis(trifluoromethyl)-13,19-dioxa-3,4,18-triazatricyclo[12.3.1.1²,⁵]nonadeca-1(18),2,4,14,16-pentaen-17-yl]carbamate (diastereomer 1) (120 mg, 0.1856 mmol) in $CH_2Cl_2$ (20 mL) at 0° C. was added $NaHCO_3$ (294 mg, 3.4997 mmol), followed by Dess-Martin periodinane (102 mg, 0.2405 mmol) and the mixture was stirred at rt overnight. The mixture was treated with 10% aq. $Na_2S_2O_3$ (5 mL) and stirred at rt for 5 min. The resulting mixture was extracted with $CH_2Cl_2$ (3×15 mL). The combined organic layers were dried over $Na_2SO_4$, filtered and concentrated. The residue was purified by silica gel chromatography (24 g column, eluting from 0% to 30% EtOAc/heptanes) to afford as a colorless oil, tert-butyl N-[(6R,12R)-6-benzyloxy-12-methyl-8-oxo-6,15-bis(trifluoromethyl)-13,19-dioxa-3,4,18-triazatricyclo[12.3.1.1²,⁵]nonadeca-1(18),2,4,14,16-pentaen-17-yl]carbamate (110 mg, 92%). $^1H$ NMR (400 MHz, $CDCl_3$) δ 9.10 (br. s, 1H), 9.09 (s, 1H), 7.34-7.23 (m, 5H), 4.91 (d, J=11.0 Hz, 1H), 4.89-4.81 (m, 1H), 4.49 (d, J=11.0 Hz, 1H), 3.41 (d, J=15.2 Hz, 1H), 3.16 (ddd, J=19.1, 10.2, 2.7 Hz, 1H), 3.08 (d, J=15.2 Hz, 1H), 2.64-2.54 (m, 1H), 2.43-2.32 (m, 1H), 1.98-1.86 (m, 1H), 1.56 (s, 9H), 1.50-1.35 (m, 5H). $^{19}F$ NMR (377 MHz, $CDCl_3$) δ −63.89 (s, 3F), −74.36 (s, 3F). ESI-MS m/z calc. 644.207, found 589.1 (M−55)⁺; Retention time: 5.46 minutes. LCMS Method: SunFire $C_{18}$ column (75×4.6 mm, 3.5 mm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Step 2: (6R,12R)-17-Amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-one

492

-continued

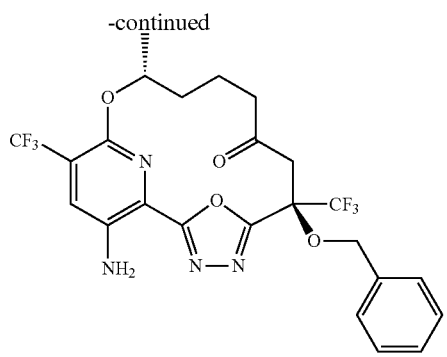

To a solution of tert-butyl N-[(6R,12R)-6-benzyloxy-12-methyl-8-oxo-6,15-bis(trifluoromethyl)-13,19-dioxa-3,4,18-triazatricyclo[12.3.1.1²,⁵]nonadeca-1(18),2,4,14,16-pentaen-17-yl]carbamate (26 mg, 0.0403 mmol) in $CH_2Cl_2$ (2 mL) at 0° C. was added TFA (740.00 mg, 0.5 mL, 6.4899 mmol) dropwise. The mixture was stirred at 8 to 13° C. for 1 h. The solvents were removed by a gentle nitrogen flow at 10° C. with stirring. The residue was treated with sat. $NaHCO_3$ (5 mL) and extracted with $CH_2Cl_2$ (3×8 mL). The combined organic layers were dried over $Na_2SO_4$, filtered and concentrated. The residue was purified by silica gel chromatography (12 g column, eluting from 0% to 35% EtOAc/heptanes) to afford as a pale-yellow solid, (6R,12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-one (21 mg, 96%). $^1H$ NMR (400 MHz, $CDCl_3$) δ 7.43 (s, 1H), 7.35-7.27 (m, 5H), 5.27 (br. s, 2H), 4.89 (d, J=11.2 Hz, 1H), 4.87-4.80 (m, 1H), 4.47 (d, J=11.0 Hz, 1H), 3.39 (d, J=15.2 Hz, 1H), 3.30-3.20 (m, 1H), 3.06 (d, J=14.9 Hz, 1H), 2.62-2.53 (m, 1H), 2.43-2.32 (m, 1H), 1.98-1.87 (m, 1H), 1.47-1.41 (m, 1H), 1.39 (d, J=6.4 Hz, 3H), 1.37-1.32 (m, 1H). $^{19}F$ NMR (377 MHz, $CDCl_3$) δ −63.99 (s, 3F), −74.33 (s, 3F).

Step 3: (6R,12R)-17-Amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-ol (diastereomer 2)

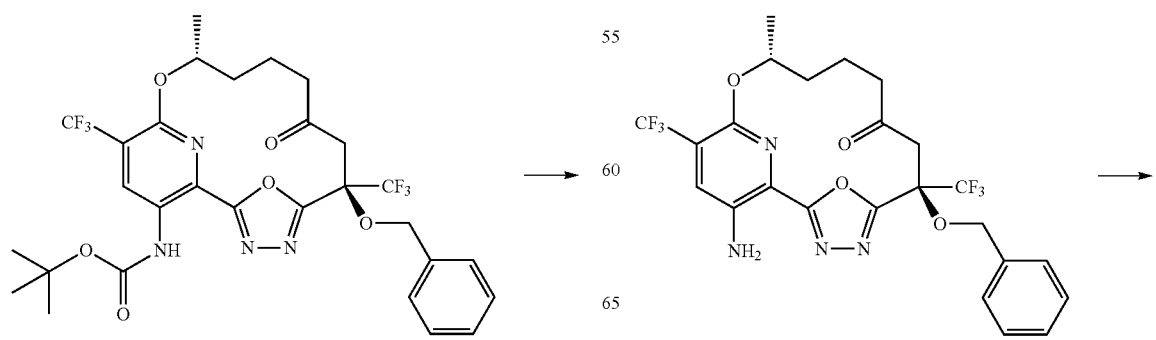

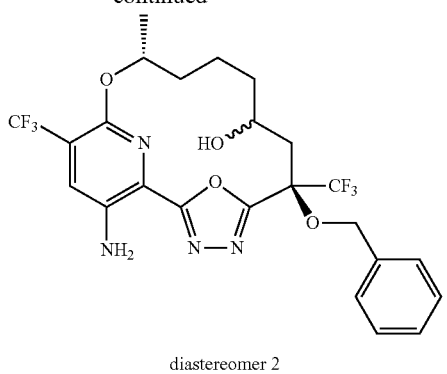

diastereomer 2

To a solution of (6R,12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-one (21 mg, 0.0386 mmol) in MeOH (3 mL) at 0° C. was added tetramethylammonium borohydride (9.6 mg, 0.1079 mmol). The mixture was stirred at 0° C. for 1.5 h. Acetone (0.5 mL) was added and the reaction mixture was stirred at 0° C. for 5 min. The mixture was treated with sat. NaHCO₃ (5 mL) and extracted with EtOAc (3×10 mL). The combined organic layers were dried with Na₂SO₄, filtered and concentrated. The residue was purified by silica gel chromatography (24 g column, eluting from 0% to 35% EtOAc/heptanes) to afford as a pale-yellow oil, (6R,12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-ol (diastereomer 2) (20 mg, 95%). ¹H NMR (400 MHz, CDCl₃) δ 7.45 (s, 1H), 7.33-7.27 (m, 2H), 7.27-7.20 (m, 3H), 5.25 (br. s, 2H), 5.04-4.94 (m, 2H), 4.93-4.82 (m, 1H), 4.57 (d, J=11.2 Hz, 1H), 2.79 (br. s, 1H), 2.57 (dd, J=15.2, 8.3 Hz, 1H), 2.35-2.24 (m, 1H), 2.12 (d, J=15.2 Hz, 1H), 1.90-1.74 (m, 2H), 1.71-1.58 (m, 3H), 1.40 (d, J=6.4 Hz, 3H). ¹⁹F NMR (377 MHz, CDCl₃) δ −64.03 (s, 3F), −74.22 (s, 3F).

Step 4: (6R,12R)-17-Amino-12-methyl-6,15-bis(trifluoromethyl)-13,19-dioxa-3,4,18-triazatricyclo[12.3.1.1²,⁵]nonadeca-1(18),2,4,14,16-pentaene-6,8-diol (diastereomer 2), Compound 58

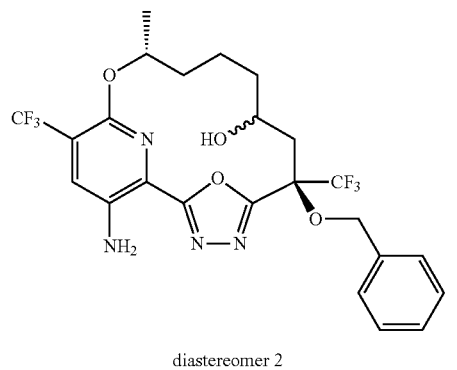

diastereomer 2

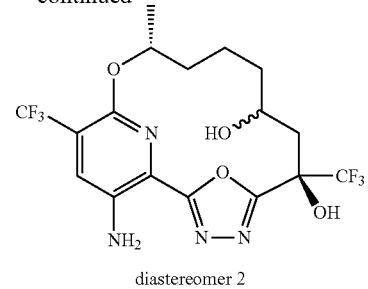

diastereomer 2

A mixture of (6R,12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-ol (diastereomer 2) (23 mg, 0.0421 mmol) and palladium on carbon (9 mg, 10% 50% wet, 0.0042 mmol) in MeOH (4 mL) was stirred under hydrogen balloon at rt overnight. The mixture was filtered through Celite and washed with EtOAc. The filtrate was concentrated and the residue was purified by silica gel chromatography (24 g column, eluting from 20% to 50% EtOAc/pentane) and freeze dried to afford as a pale-yellow solid (6R,12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,8-diol (diastereomer 2) (15 mg, 78%). ¹H NMR (400 MHz, DMSO-d₆) δ 7.76 (s, 1H), 7.69 (s, 1H), 6.29 (s, 2H), 5.06-4.97 (m, 1H), 4.82 (d, J=5.1 Hz, 1H), 4.47-4.37 (m, 1H), 2.29-2.20 (m, 1H), 2.13-1.92 (m, 3H), 1.72-1.52 (m, 2H), 1.49-1.37 (m, 1H), 1.33 (d, J=6.4 Hz, 3H), 1.30-1.23 (m, 1H). ¹⁹F NMR (377 MHz, DMSO-d₆) δ −62.48 (s, 3F), −78.47 (s, 3F). ESI-MS m/z calc. 456.1232, found 457.2 (M+1)⁺; Retention time: 3.04 minutes. LCMS Method: Kinetex Polar C₁₈ column (3.0×50 mm, 2.6 µm particle size, 6 minute run, 5% to 95% acetonitrile in water (0.1% formic acid modifier), flow rate=1.2 mL/min).

Example 41: Preparation of (6R,12R)-17-amino-12-methyl-6,15-bis(trifluoromethyl)-10,13,19-trioxa-3,4,18-triazatricyclo[12.3.1.1²,⁵]nonadeca-1(18),2,4,14,16-pentaen-6-ol, Compound 59

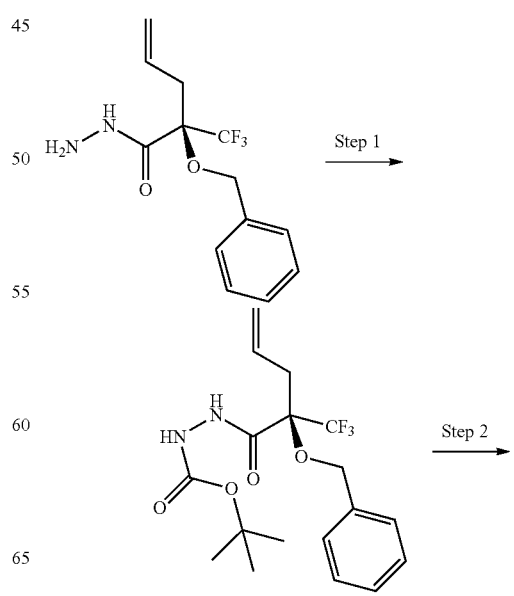

495
-continued
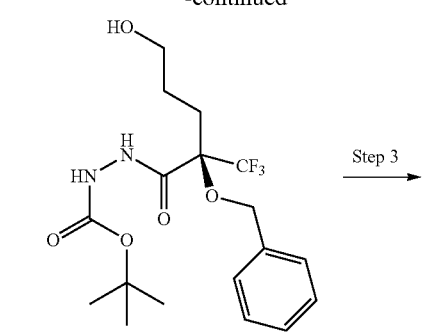
Step 3
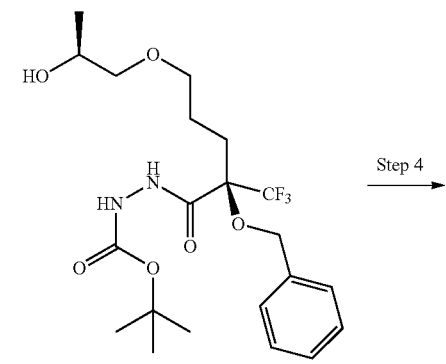
Step 4
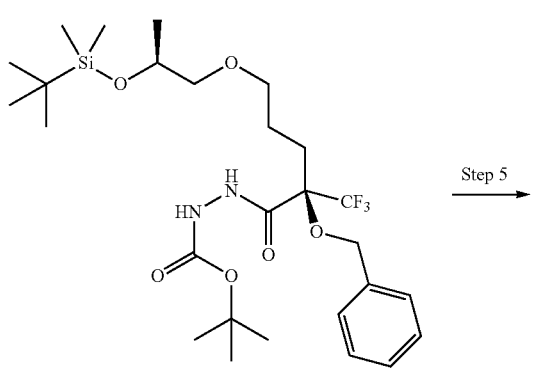
Step 5
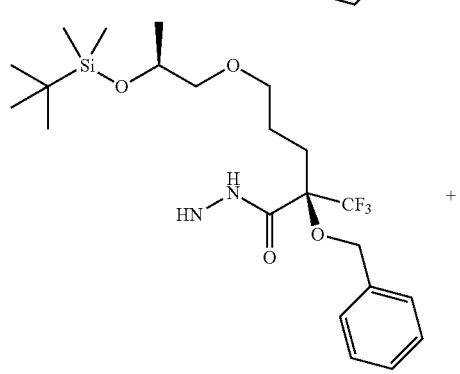
+
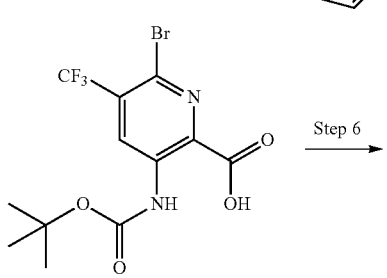
Step 6
496
-continued
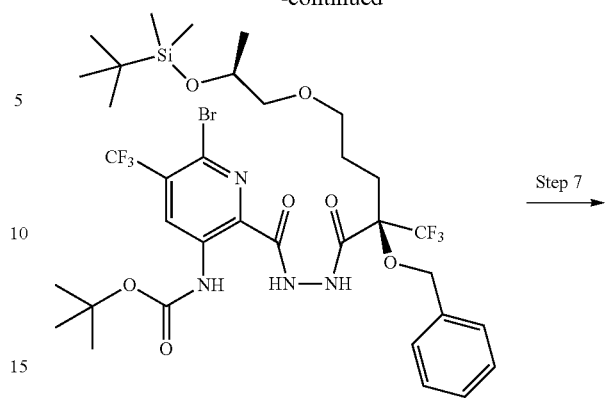
Step 7
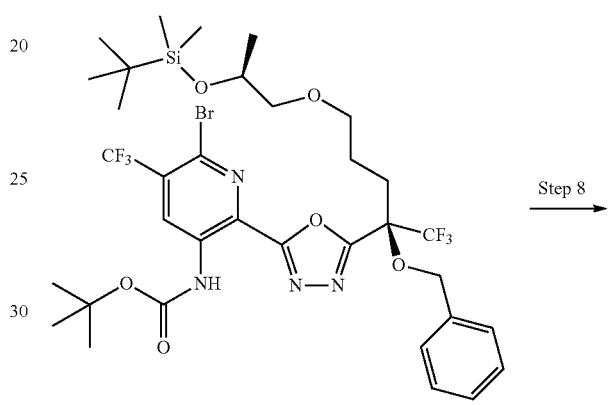
Step 8
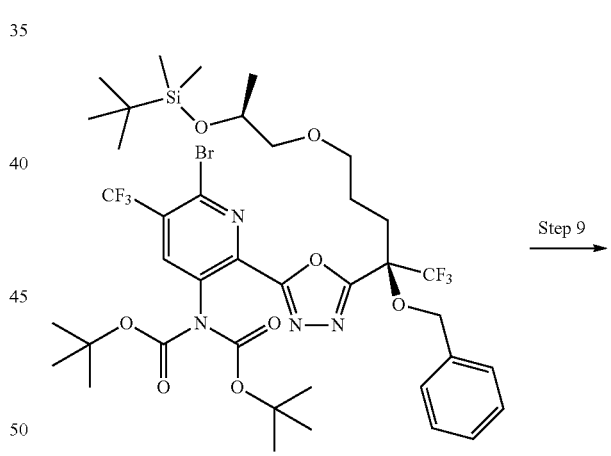
Step 9
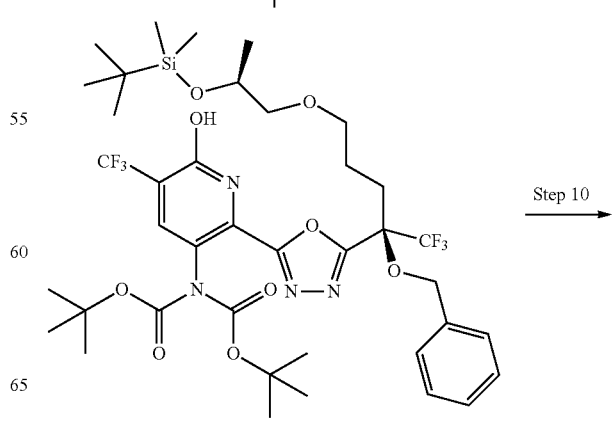
Step 10

497
-continued

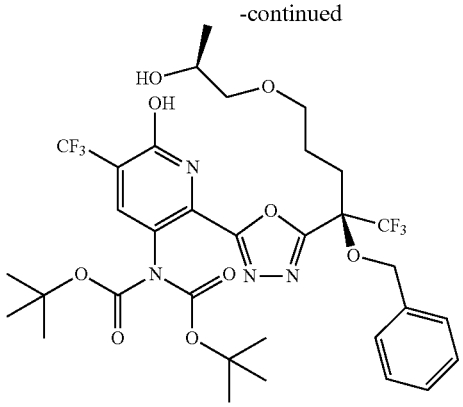

Step 11 →

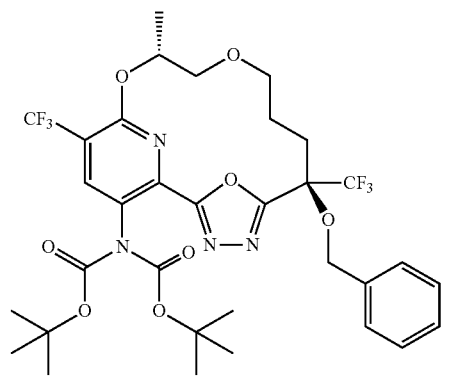

Step 12 →

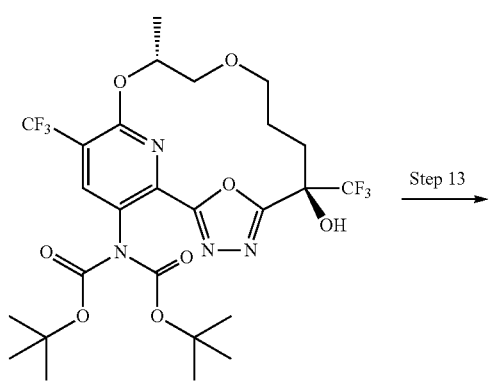

Step 13 →

498

Step 1: tert-Butyl N-[[(2R)-2-benzyloxy-2-(trifluoromethyl)pent-4-enoyl]amino]carbamate

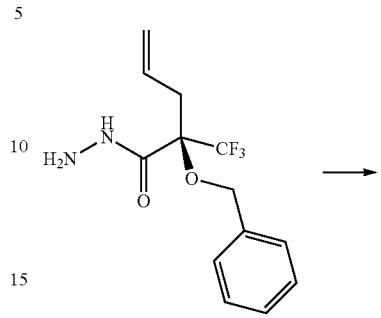

→

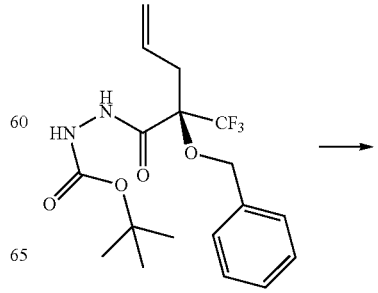

A reaction vial was charged with (2R)-2-benzyloxy-2-(trifluoromethyl)pent-4-enehydrazide (3.479 g, 12.069 mmol) and TEA (3.7026 g, 5.1 mL, 36.591 mmol) in DCM (30 mL). Boc$_2$O (3.26 g, 14.937 mmol) was added and the reaction mixture was stirred at rt overnight. The reaction was diluted with DCM (100 mL) and washed with 1 N HCl (30 mL), saturated sodium bicarbonate (30 mL) and brine (30 mL). The organic layer was dried over anhydrous sodium sulfate and concentrated under vacuum. The residue was purified by silica gel chromatography using 0% to 30% ethyl acetate in hexane to furnish as a white solid, tert-butyl N-[[(2R)-2-benzyloxy-2-(trifluoromethyl)pent-4-enoyl]amino]carbamate (3.914 g, 84%). ESI-MS m/z calc. 388.161, found 333.2 (M−55)$^+$; Retention time: 3.46 minutes. LCMS Method: Merck Millipore Chromolith SpeedROD C$_{18}$ column (50×4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

Step 2: tert-Butyl N-[[(2R)-2-benzyloxy-5-hydroxy-2-(trifluoromethyl)pentanoyl]amino]carbamate

→

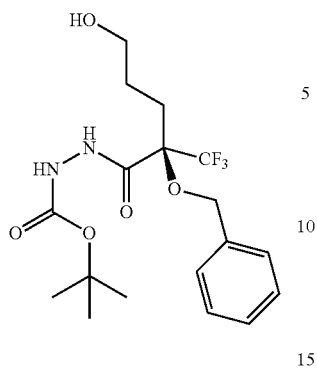

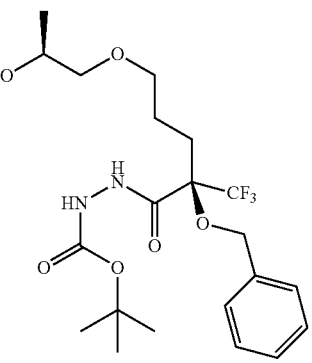

Into a solution of tert-butyl N-[[(2R)-2-benzyloxy-2-(trifluoromethyl)pent-4-enoyl]amino]carbamate (3.75 g, 9.6555 mmol) in anhydrous THF (53 mL) was added 9-Borabicyclo[3.3.1]nonane (105 mL of 0.5 M in THF, 52.500 mmol) dropwise at rt and the reaction was stirred at rt for 80 minutes. The reaction was quenched with methanol (16 mL) at 0° C. slowly and NaOH (105 mL of 1 M, 105.00 mmol), $H_2O_2$ (17.649 g, 53 mL of 30% w/w, 155.66 mmol) was added. The reaction was stirred at rt for 1 hour and diluted with ethyl acetate (320 mL). Two layers were separated, and the aqueous layer was extracted with ethyl acetate (2×95 mL). The combined organic layers were washed with saturated sodium thiosulfate (130 mL) and brine (130 mL), dried over anhydrous magnesium sulfate and concentrated. The residue was purified by silica gel chromatography using 10% to 50% acetone in hexane to provide as a white solid, tert-butyl N-[[(2R)-2-benzyloxy-5-hydroxy-2-(trifluoromethyl)pentanoyl]amino]carbamate (3.76 g, 96%). ESI-MS m/z calc. 406.1716, found 407.5 (M+1)+; Retention time: 3.02 minutes. LCMS Method: Merck Millipore Chromolith SpeedROD $C_{18}$ column (50×4.6 mm) and a dual gradient run from 5% to 100% mobile phase B over 6 minutes. Mobile phase A=water (0.1% $CF_3CO_2H$). Mobile phase B=acetonitrile (0.1% $CF_3CO_2H$).

To a solution of tert-butyl N-[[(2R)-2-benzyloxy-5-hydroxy-2-(trifluoromethyl)pentanoyl]amino]carbamate (3.34 g, 8.2186 mmol) in THF (35 mL) was added t-BuOK in THF (33 mL of 1 M, 33.000 mmol) at 0° C. and stirred for 10 minutes. (2S)-2-methyloxirane (994.80 mg, 1.2 mL, 17.128 mmol) was added slowly at 0° C. and stirred for 10 minutes. The reaction mixture was stirred at 45° C. for 1.5 hours. The reaction mixture was cooled to room temperature and quenched with saturated aqueous $NH_4Cl$ (70 mL). The mixture was extracted with EtOAc (3×50 mL), washed with brine (70 mL), dried over $Na_2SO_4$, filtered, and concentrated. The residue was purified by silica gel chromatography using 0% to 50% EtOAc in hexane to provide as pale yellow oil, tert-butyl N-[[(2R)-2-benzyloxy-5-[(2S)-2-hydroxypropoxy]-2-(trifluoromethyl)pentanoyl]amino]carbamate (1.65 g, 42%) ESI-MS m/z calc. 464.2134, found 465.4 (M+1)+; Retention time: 3.06 minutes. LCMS Method: Merck Millipore Chromolith SpeedROD $C_{18}$ column (50×4.6 mm) and a dual gradient run from 5% to 100% mobile phase B over 6 minutes. Mobile phase A=water (0.1% $CF_3CO_2H$). Mobile phase B=acetonitrile (0.1% $CF_3CO_2H$).

Step 3: tert-Butyl N-[[(2R)-2-benzyloxy-5-[(2S)-2-hydroxypropoxy]-2-(trifluoromethyl)pentanoyl]amino]carbamate Step 4: tert-Butyl N-[[(2R)-2-benzyloxy-5-[(2S)-2-[tert-butyl(dimethyl)silyl]oxypropoxy]-2-(trifluoromethyl)pentanoyl]amino]carbamate

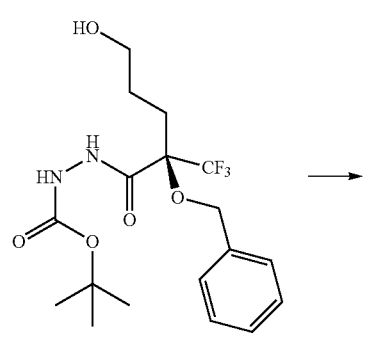

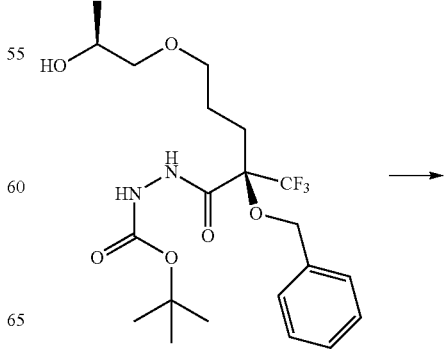

-continued

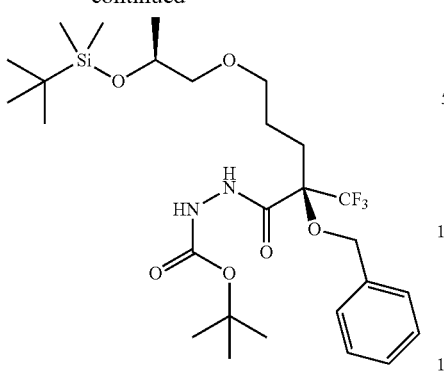

To a solution of tert-butyl N-[[(2R)-2-benzyloxy-5-[(2S)-2-hydroxypropoxy]-2-(trifluoromethyl)pentanoyl]amino]carbamate (1.65 g, 3.4458 mmol) in DMF (35 mL) was added TBSCl (1.08 g, 7.1655 mmol) followed by Imidazole (972.5 mg, 14.285 mmol). The reaction mixture was stirred at room temperature for 3 hours. The reaction mixture was quenched with saturated aqueous $NH_4Cl$ (70 mL), extracted with EtOAc (3×50 mL), washed with brine (70 mL), dried over $Na_2SO_4$, filtered, and concentrated. The residue was purified by silica gel chromatography using 0% to 15% EtOAc in hexane to provide as light yellow gel, tert-butyl N-[[(2R)-2-benzyloxy-5-[(2S)-2-[tert-butyl(dimethyl)silyl]oxypropoxy]-2-(trifluoromethyl)pentanoyl]amino]carbamate (1.683 g, 84%). ESI-MS m/z calc. 578.2999, found 579.7 (M+1)$^+$; Retention time: 4.47 minutes. LCMS Method: Merck Millipore Chromolith SpeedROD $C_{18}$ column (50× 4.6 mm) and a dual gradient run from 5% to 100% mobile phase B over 6 minutes. Mobile phase A=water (0.1% $CF_3CO_2H$). Mobile phase B=acetonitrile (0.1% $CF_3CO_2H$).

Step 5: (2R)-2-Benzyloxy-5-[(2S)-2-[tert-butybdimethyl)silyl]oxypropoxy]-2-(trifluoromethyl)pentanehydrazide

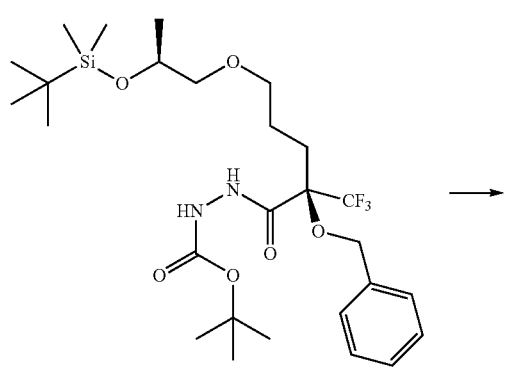

-continued

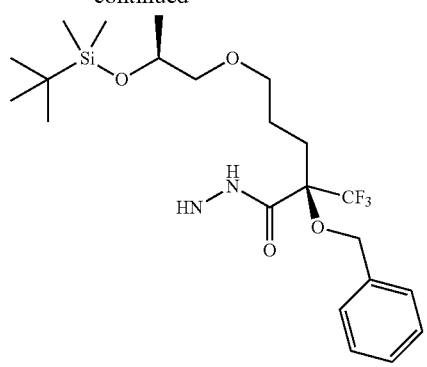

A solution of tert-butyl N-[[(2R)-2-benzyloxy-5-[(2S)-2-[tert-butyl(dimethyl)silyl]oxypropoxy]-2-(trifluoromethyl)pentanoyl]amino]carbamate (1.772 g, 3.0618 mmol) in HFIP (32 mL) was heated in a microwave reactor at 100° C. for 1.5 h. The reaction was concentrated and the residue was purified by silica gel chromatography by using 0% to 80% EtOAc in hexanes to afford as clear gel (2R)-2-benzyloxy-5-[(2S)-2-[tert-butyl)dimethyl)silyl]oxypropoxy]-2-(trifluoromethyl)pentanehydrazide (1.442 g, 98%). ESI-MS m/z calc. 478.2475, found 479.2 (M+1)$^+$; Retention time: 3.96 minutes. LCMS Method: Merck Millipore Chromolith SpeedROD $C_{18}$ column (50×4.6 mm) and a dual gradient run from 5% to 100% mobile phase B over 6 minutes. Mobile phase A=water (0.1% $CF_3CO_2H$). Mobile phase B=acetonitrile (0.1% $CF_3CO_2H$).

Step 6: tert-Butyl N-[2-[[[(2R)-2-benzyloxy-5-[(2S)-2-[tert-butyl(dimethyl)silyl]oxypropoxy]-2-(trifluoromethyl)pentanoyl]amino]carbamoyl]-6-bromo-5-(trifluoromethyl)-3-pyridyl]carbamate

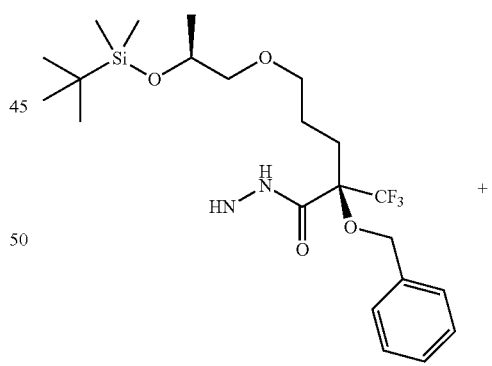

+

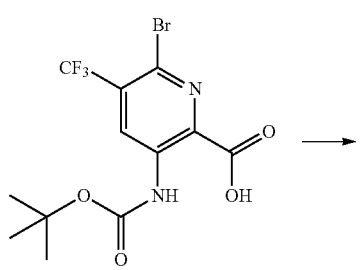

-continued

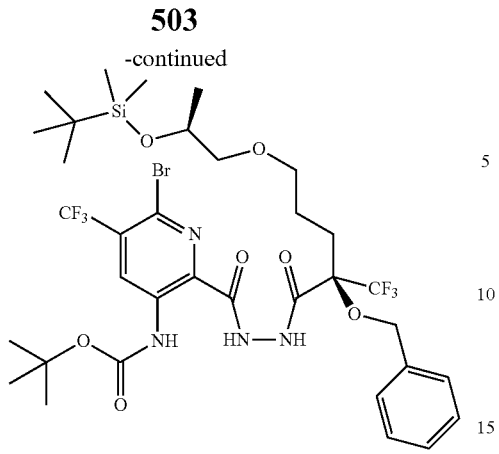

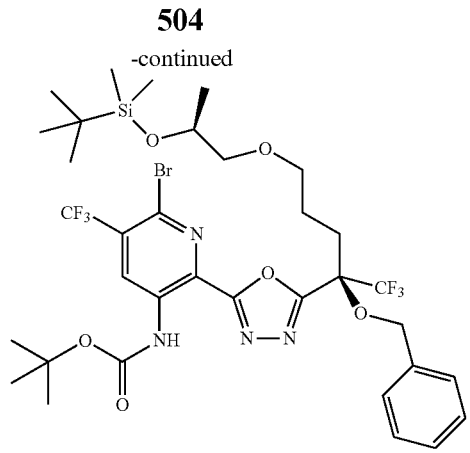

Into a solution of (2R)-2-benzyloxy-5-[(2S)-2-[tert-butyl(dimethyl)silyl]oxypropoxy]-2-(trifluoromethyl)pentanehydrazide (1.44 g, 3.0086 mmol) and 6-bromo-3-(tert-butoxycarbonylamino)-5-(trifluoromethyl)pyridine-2-carboxylic acid (1.38 g, 3.5832 mmol) in anhydrous DMF (50 mL) was added TEA (3.6518 g, 5.03 mL, 36.089 mmol), followed by T$_3$P (2.213 g, 2.07 mL of 50% w/w, 3.4776 mmol) in ethyl acetate. The reaction was stirred at rt for overnight. Again, to the reaction mixture was added TEA (3.6518 g, 5.03 mL, 36.089 mmol), followed by T$_3$P (2.213 g, 2.07 mL of 50% w/w, 3.4776 mmol) in ethyl acetate. The reaction mixture was stirred at room temperature for 2 hours. The reaction was quenched with saturated ammonium chloride (100 mL) and ethyl acetate (150 mL). The aqueous layer was extracted with ethyl acetate (2×100 mL). The combined organic layers were washed with brine (2×100 mL), dried over anhydrous sodium sulfate and concentrated. The residue was purified by silica gel chromatography using 0% to 20% acetone in hexane to provide as off white foam, tert-butyl N-[2-[[[(2R)-2-benzyloxy-5-[(2S)-2-[tert-butyl(dimethyl)silyl]oxypropoxy]-2-(trifluoromethyl)pentanoyl]amino]carbamoyl]-6-bromo-5-(trifluoromethyl)-3-pyridyl]carbamate (1.4724 g, 56%). ESI-MS m/z calc. 844.2302, found 845.5 (M+1)$^+$; Retention time: 4.88 minutes. LCMS Method: Merck Millipore Chromolith SpeedROD C$_{18}$ column (50×4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

Step 7: tert-Butyl N-[2-[5-[(1R)-1-benzyloxy-4-[(2S)-2-[tert-butyl(dimethyl)silyl]oxypropoxy]-1-(trifluoromethyl)butyl]-1,3,4-oxadiazol-2-yl]-6-bromo-5-(trifluoromethyl)-3-pyridyl]carbamate

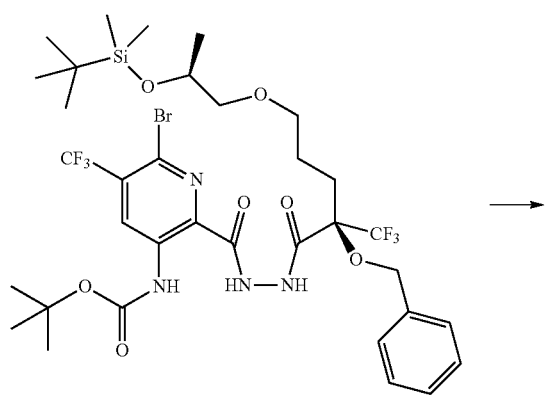

Into a solution of tert-butyl N-[2-[[[(2R)-2-benzyloxy-5-[(2S)-2-[tert-butyl(dimethyl)silyl]oxypropoxy]-2-(trifluoromethyl)pentanoyl]amino]carbamoyl]-6-bromo-5-(trifluoromethyl)-3-pyridyl]carbamate (1.457 g, 1.6711 mmol) and DIEA (934.92 mg, 1.26 mL, 7.2338 mmol) in acetonitrile (25 mL) was added p-TsCl (359.8 mg, 1.8873 mmol). The reaction was stirred at 70° C. for 1.5 hours. Solvent was removed and the residue was purified by silica gel chromatography using 0% to 20% ethyl acetate in hexane to provide as yellow gel, tert-butyl N-[2-[5-[(1R)-1-benzyloxy-4-[(2S)-2-[tert-butyl(dimethyl)silyl]oxypropoxy]-1-(trifluoromethyl)butyl]-1,3,4-oxadiazol-2-yl]-6-bromo-5-(trifluoromethyl)-3-pyridyl]carbamate (1.2036 g, 87%). ESI-MS m/z calc. 826.2196, found 827.5 (M+1)$^+$; Retention time: 5.25 minutes. LCMS Method: Merck Millipore Chromolith SpeedROD C$_{18}$ column (50×4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

Step 8: tert-Butyl N-[2-[5-[(1R)-1-benzyloxy-4-[(2S)-2-[tert-butyl(dimethyl)silyl]oxypropoxy]-1-(trifluoromethyl)butyl]-1,3,4-oxadiazol-2-yl]-6-bromo-5-(trifluoromethyl)-3-pyridyl]-N-tert-butoxycarbonyl-carbamate

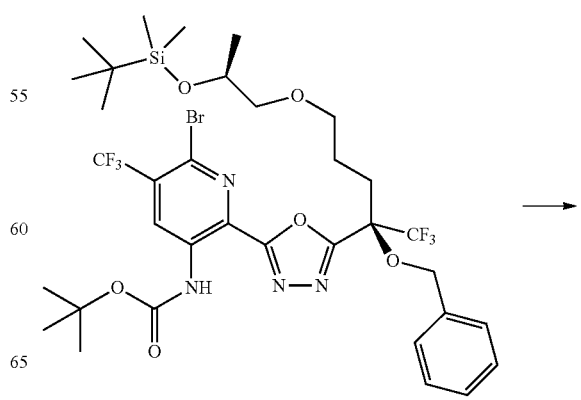

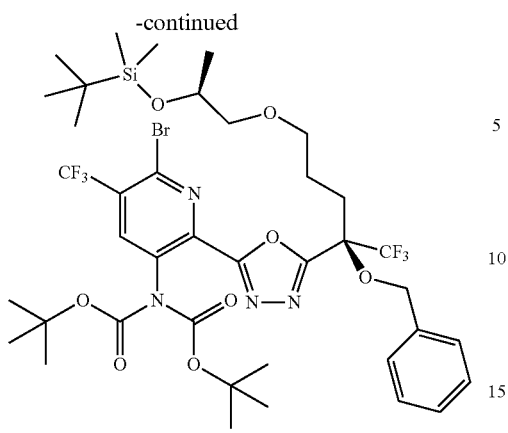

To a mixture of tert-butyl N-[2-[5-[(1R)-1-benzyloxy-4-[(2S)-2-[tert-butyl (dimethyl)silyl]oxypropoxy]-1-(trifluoromethyl)butyl]-1,3,4-oxadiazol-2-yl]-6-bromo-5-(trifluoromethyl)-3-pyridyl]carbamate (1.2036 g, 1.4541 mmol) and DIEA (296.80 mg, 0.4 mL, 2.2964 mmol) in MTBE (14 mL) at room temperature was added DMAP (17.8 mg, 0.1457 mmol) followed by (Boc)$_2$O (539.8 mg, 2.4733 mmol). The reaction mixture was stirred at room temperature for 17 hours. The mixture was diluted with EtOAc (60 ml), washed with water (30 mL), brine (30 mL), dried over Na$_2$SO$_4$, filtered and concentrated. The residue was purified by silica gel chromatography (40 g column, from 0 to10% EtOAc in Hexanes,) to afford as light yellow gel, tert-butyl N-[2-[5-[(1R)-1-benzyloxy-4-[(2S)-2-[tert-butyl(dimethyl)silyl]oxypropoxy]-1-(trifluoromethyl)butyl]-1,3,4-oxadiazol-2-yl]-6-bromo-5-(trifluoromethyl)-3-pyridyl]-N-tert-butoxycarbonyl-carbamate (1.34 g, 99%). ESI-MS m/z calc. 926.272, found 827.3 (M+H-Boc)$^+$; Retention time: 5.01 minutes. LCMS Method: Merck Millipore Chromolith SpeedROD C$_{18}$ column (50×4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

Step 9: tert-Butyl N-[2-[5-[(1R)-1-benzyloxy-4-[(2S)-2-[tert-butyl(dimethyl)silyl]oxypropoxy]-1-(trifluoromethyl)butyl]-1,3,4-oxadiazol-2-yl]-6-hydroxy-5-(trifluoromethyl)-3-pyridyl]-N-tert-butoxycarbonyl-carbamate

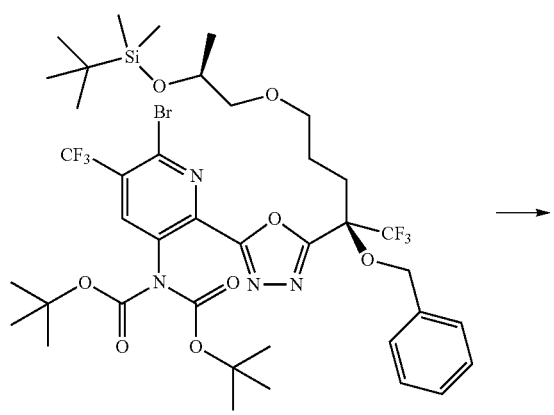

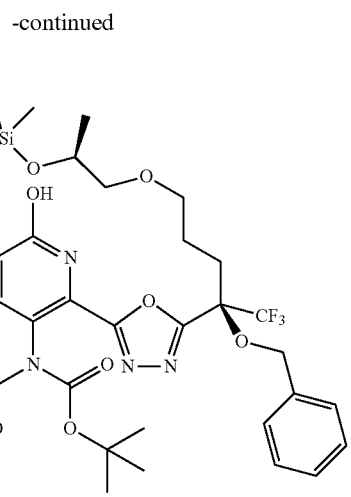

To a solution of tert-butyl N-[2-[5-[(1R)-1-benzyloxy-4-[(2S)-2-[tert-butyl(dimethyl)silyl]oxypropoxy]-1-(trifluoromethyl)butyl]-1,3,4-oxadiazol-2-yl]-6-bromo-5-(trifluoromethyl)-3-pyridyl]-N-tert-butoxycarbonyl-carbamate (1.3 g, 1.4011 mmol) in DMSO (14 mL) was added cesium acetate (808.8 mg, 4.2136 mmol). The reaction mixture was stirred at 80° C. for 7 hours. The reaction mixture was cooled to room temperature and diluted with EtOAc (120 mL) and water (40 mL). Layers were separated, and the organic layer was washed with water (3×30 mL), brine (30 mL), dried over Na$_2$SO$_4$, filtered, and concentrated. The residue was purified by silica gel chromatography using 0% to 50% EtOAc in hexanes to provide as white foam, tert-butyl N-[2-[5-[(1R)-1-benzyloxy-4-[(2S)-2-[tert-butyl(dimethyl)silyl]oxypropoxy]-1-(trifluoromethyl)butyl]-1,3,4-oxadiazol-2-yl]-6-hydroxy-5-(trifluoromethyl)-3-pyridyl]-N-tert-butoxycarbonyl-carbamate (1.0947 g, 90%). $^1$H NMR (500 MHz, CDCl$_3$) δ 7.75 (s, 1H), 7.35-7.28 (m, 5H), 4.84 (d, J=10.9 Hz, 1H), 4.62 (d, J=10.8 Hz, 1H), 4.00-3.91 (m, 1H), 3.51-3.42 (m, 2H), 3.37 (dd, J=9.5, 6.1 Hz, 1H), 3.24 (dd, J=9.5, 5.1 Hz, 1H), 2.51 (t, J=8.2 Hz, 2H), 1.86-1.77 (m, 1H), 1.76-1.67 (m, 1H), 1.40 (d, J=4.5 Hz,18H), 1.15 (d, J=6.2 Hz, 3H), 0.88 (s, 9H), 0.07 (d, J=7.2 Hz, 6H). ESI-MS m/z calc. 864.3564, found 765.8 (M+H-Boc)$^+$; Retention time: 4.75 minutes. LCMS Method: Merck Millipore Chromolith SpeedROD C$_{18}$ column (50×4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

507

Step 10: tert-Butyl N-[2-[5-[(1R)-1-benzyloxy-4-[(2S)-2-hydroxypropoxy]-1-(trifluoromethyl)butyl]-1,3,4-oxadiazol-2-yl]-6-hydroxy-5-(trifluoromethyl)-3-pyridyl]-N-tert-butoxycarbonyl-carbamate

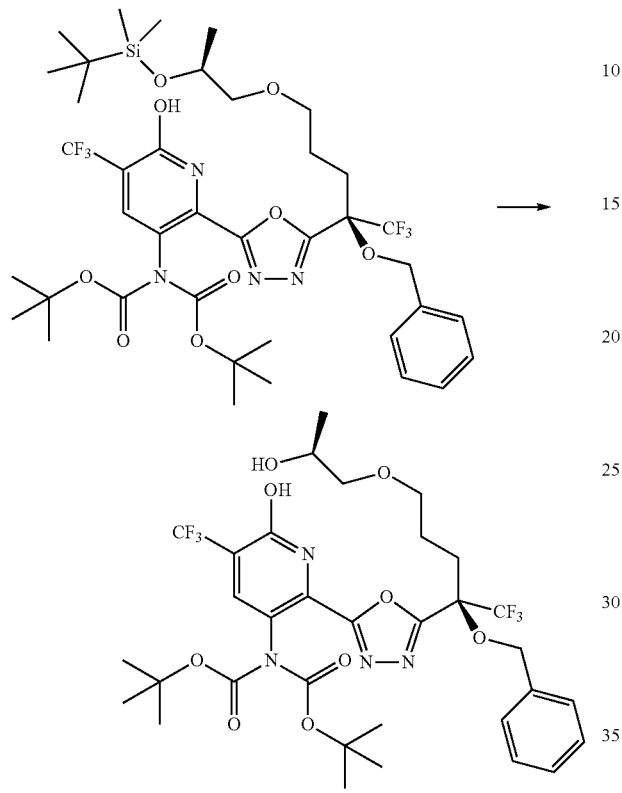

To a solution of tert-butyl N-[2-[5-[(1R)-1-benzyloxy-4-[(2S)-2-[tert-butyl(dimethyl)silyl]oxypropoxy]-1-(trifluoromethyl)butyl]-1,3,4-oxadiazol-2-yl]-6-hydroxy-5-(trifluoromethyl)-3-pyridyl]-N-tert-butoxycarbonyl-carbamate (1.079 g, 1.2475 mmol) in THF (10 mL) was added TBAF in THF (12.5 mL of 1 M, 12.500 mmol), and stirred at 35° C. for 3 hours. To the reaction mixture was added aqueous saturated NH$_4$Cl (80 mL) and extracted with EtOAc (3×50 mL). The combined organic layers were washed with water (50 mL), brine (50 mL), dried over Na$_2$SO$_4$, filtered, and concentrated. The residue was purified by silica gel chromatography using 0% to 80% ethyl acetate in hexane to provide as white foam, tert-butyl N-[2-[5-[(1R)-1-benzyloxy-4-[(2S)-2-hydroxypropoxy]-1-(trifluoromethyl)butyl]-1,3,4-oxadiazol-2-yl]-6-hydroxy-5-(trifluoromethyl)-3-pyridyl]-N-tert-butoxycarbonyl-carbamate (916.6 mg, 98%). $^1$H NMR (500 MHz, CDCl$_3$) δ 7.81 (s, 1H), 7.36-7.27 (m, 5H), 4.90 (d, J=10.8 Hz, 1H), 4.78 (d, J=10.8 Hz, 1H), 4.17-4.10 (m, 1H), 3.57-3.51 (m, 1H), 3.47 (dd, J=9.0, 3.0 Hz, 1H), 3.45-3.39 (m, 1H), 3.24 (t, J=8.9 Hz, 1H), 2.64-2.44 (m, 2H), 1.70-1.59 (m, 2H), 1.40 (d, J=7.0 Hz, 18H), 1.23 (d, J=6.4 Hz, 3H). ESI-MS m/z calc. 750.2699, found 651.4 (M+H-Boc)$^+$; Retention time: 3.75 minutes. LCMS Method: Merck Millipore Chromolith SpeedROD C$_{18}$ column (50×4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

508

Step 11: tert-Butyl N-[(6R,12R)-6-benzyloxy-12-methyl-6,15-bis(trifluoromethyl)-10,13,19-trioxa-3,4,18-triazatricyclo[12.3.1.12,5]nonadeca-1(18),2,4,14,16-pentaen-17-yl]-N-tert-butoxycarbonyl-carbamate

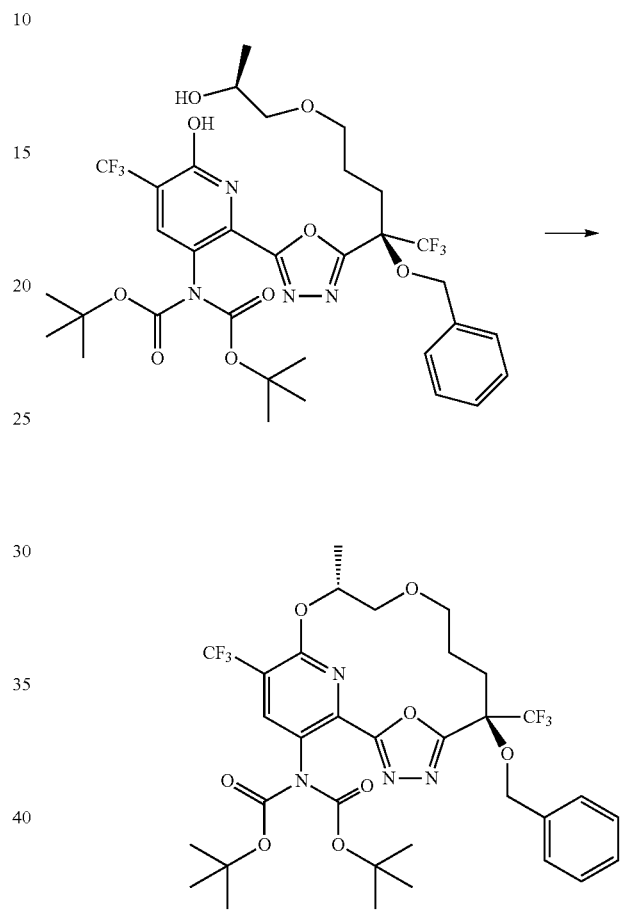

A solution of tert-butyl N-[2-[5-[(1R)-1-benzyloxy-4-[(2S)-2-hydroxypropoxy]-1-(trifluoromethyl)butyl]-1,3,4-oxadiazol-2-yl]-6-hydroxy-5-(trifluoromethyl)-3-pyridyl]-N-tert-butoxycarbonyl-carbamate (845.7 mg, 1.1266 mmol) and PPh$_3$ (778.2 mg, 2.9670 mmol) in THF (75 mL) at room temperature was added DIAD (605.52 mg, 0.58 mL, 2.9945 mmol) drop-wise. The reaction mixture was stirred at room temperature for 5 hours. The reaction mixture was concentrated and the residue was purified directly by silica gel chromatography using 0% to 15% ethyl acetate in hexane to provide as white foam, tert-butyl N-[(6R,12R)-6-benzyloxy-12-methyl-6,15-bis(trifluoromethyl)-10,13,19-trioxa-3,4,18-triazatricyclo[12.3.1.12,5]nonadeca-1(18),2,4,14,16-pentaen-17-yl]-N-tert-butoxycarbonyl-carbamate (416.8 mg, 50%). ESI-MS m/z calc. 732.2594, found 733.5 (M+1)$^+$; Retention time: 4.36 minutes. LCMS Method: Merck Millipore Chromolith SpeedROD C$_{18}$ column (50× 4.6 mm) and a dual gradient run from 5% to 100% mobile phase B over 6 minutes. Mobile phase A=water (0.1% CF$_3$CO$_2$H). Mobile phase B=acetonitrile (0.1% CF$_3$CO$_2$H).

Step 12: tert-Butyl N-tert-butoxycarbonyl-N-[(6R,12R)-6-hydroxy-12-methyl-6,15-bis(trifluoromethyl)-10,13,19-trioxa-3,4,18-triazatricyclo[12.3.1.12,5]nonadeca-1(18),2,4,14,16-pentaen-17-yl]carbamate Step 13: (6R,12R)-17-Amino-12-methyl-6,15-bis(trifluoromethyl)-10,13,19-trioxa-3,4,18-triazatricyclo[12.3.1.12,5]nonadeca-1(18),2,4,14,16-pentaen-6-ol, Compound 59

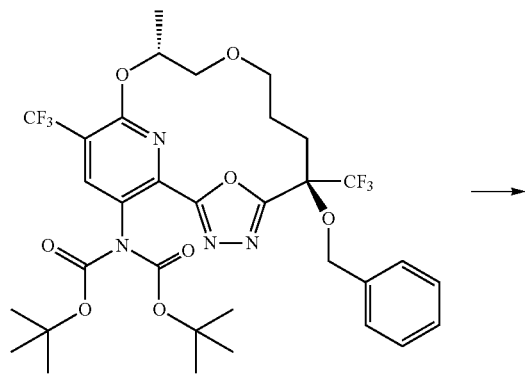

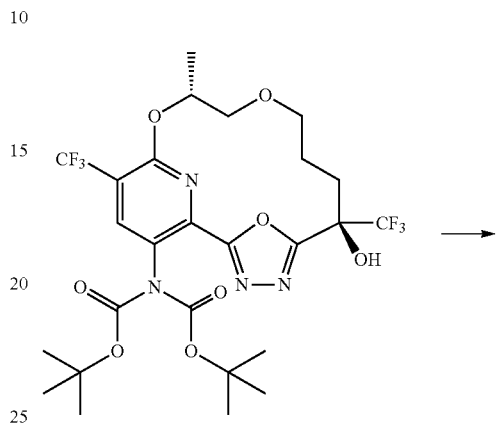

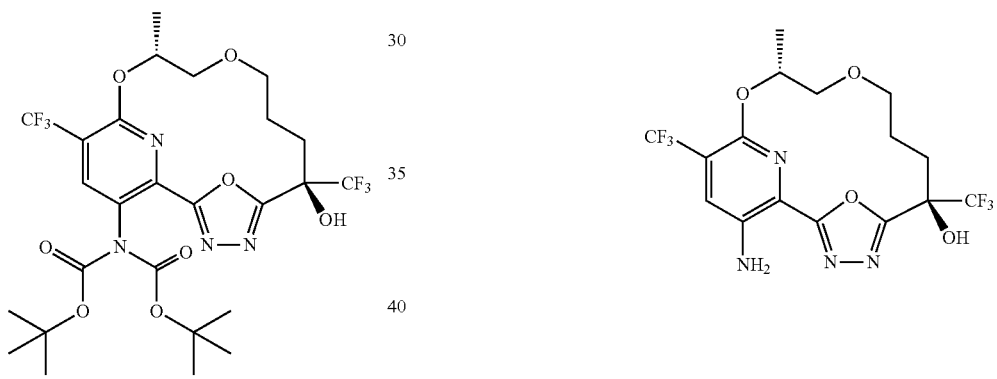

To a solution of tert-butyl N-[(6R,12R)-6-benzyloxy-12-methyl-6,15-bis(trifluoromethyl)-10,13,19-trioxa-3,4,18-triazatricyclo[12.3.1.12,5]nonadeca-1(18),2,4,14,16-pentaen-17-yl]-N-tert-butoxycarbonyl-carbamate (391.2 mg, 0.5339 mmol) in ethanol (45 mL) was added 10% Pd/C (200.3 mg, 1.8822 mmol). The reaction mixture was degassed and refilled hydrogen gas (X 2), and the reaction mixture was stirred under hydrogen atmosphere at room temperature for 16 hours. The reaction mixture was filtered through Celite, rinsed with EtOAc (30 mL), and concentrated to provide as a white foam, tert-butyl N-tert-butoxycarbonyl-N-[(6R,12R)-6-hydroxy-12-methyl-6,15-bis(trifluoromethyl)-10,13,19-trioxa-3,4,18-triazatricyclo[12.3.1.12,5]nonadeca-1(18),2,4,14,16-pentaen-17-yl]carbamate (352.4 mg, 100%). ESI-MS m/z calc. 642.2124, found 643.2 (M+1)$^+$; Retention time: 3.85 minutes. LCMS Method: Merck Millipore Chromolith SpeedROD $C_{18}$ column (50×4.6 mm) and a dual gradient run from 5% to 100% mobile phase B over 6 minutes. Mobile phase A=water (0.1% $CF_3CO_2H$). Mobile phase B=acetonitrile (0.1% $CF_3CO_2H$).

A solution of ter t-butyl N-tert-butoxycarbonyl-N-[(6R,12R)-6-hydroxy-12-methyl-6,15-bis(trifluoromethyl)-10,13,19-trioxa-3,4,18-triazatricyclo[12.3.1.12,5]nonadeca-1(18),2,4,14,16-pentaen-17-yl]carbamate (352.4 mg, 0.5320 mmol) in HFIP (15 mL) was placed in a microwave vial and sealed. It was heated at 100° C. in microwave synthesizer for 2 hours. The reaction was concentrated and the residue was purified by silica gel chromatography by using 0% to 35% EtOAc in hexanes to provide as off white solid, (6R,12R)-17-amino-12-methyl-6,15-bis(trifluoromethyl)-10,13,19-trioxa-3,4,18-triazatricyclo[12.3.1.12,5]nonadeca-1(18),2,4,14,16-pentaen-6-ol (212.6 mg, 88%). $^1$H NMR (500 MHz, CDCl$_3$) δ 7.43 (s, 1H), 5.20 (s, 2H), 4.90 (q, J=6.9 Hz, 1H), 4.49 (d, J=8.9 Hz, 1H), 3.97-3.88 (m, 1H), 3.62-3.53 (m, 2H), 3.19 (t, J=8.5 Hz, 1H), 2.45 (t, J=12.1 Hz, 1H), 2.30-2.14 (m, 2H), 1.77-1.68 (m, 1H), 1.52 (d, J=6.4 Hz, 3H). ESI-MS m/z calc. 442.10757, found 443.2 (M+1)$^+$; Retention time: 2.59 minutes. LCMS Method: Cortess $C_{18}$ 2.7 μm particle size column (3.0×50 mm) sold by Waters (pn: 186007370), and a dual gradient run from 5% to 100% mobile phase B over 6.0 minutes. Mobile phase A=water (+0.1% $CF_3CO_2H$), mobile phase B=acetonitrile (0.1% $CF_3CO_2H$), flow rate=1.2 mL/min, injection volume=2 μL and column temperature=55° C.

Example 42: Preparation of (6R,12R)-17-amino-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-8-one, Compound 60

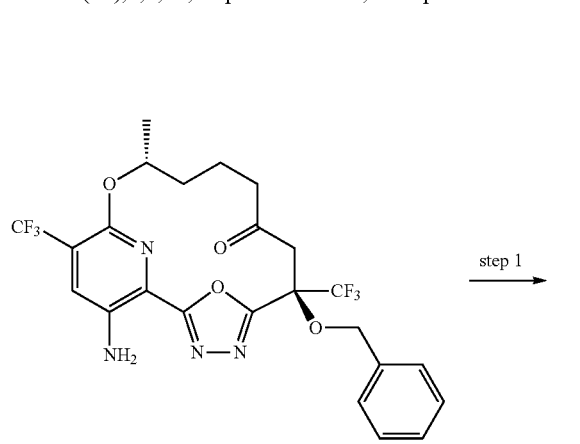

Step 1: (6R,12R)-17-Amino-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-8-one, Compound 60

To a solution of (6R,12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,14,16-pentaen-8-one (32 mg, 0.0588 mmol) in MeOH (4 mL) was added palladium on carbon (9.5 mg, 10%, 50% wet 0.0045 mmol). The mixture was stirred under hydrogen atmosphere at rt overnight. The mixture was filtered through diatomaceous earth and washed with EtOAc. The filtrate was concentrated and the residue was purified by silica gel chromatography (24 g column, eluting 20% to 40% EtOAc/pentane) to afford as a pale-yellow solid, (6R,12R)-17-amino-6-hydroxy-12-methyl-6,15-bis(trifluoromethyl)-13,19-dioxa-3,4,18-triazatricyclo[12.3.1.1²,⁵]nonadeca-1(18),2,4,14,16-pentaen-8-one (21 mg, 76%). $^1$H NMR (400 MHz, DMSO-$d_6$) δ 8.03 (s, 1H), 7.76 (s, 1H), 6.38 (s, 2H), 4.94-4.81 (m, 1H), 3.50 (d, J=15.4 Hz, 1H), 3.30-3.23 (m, 1H), 3.01 (d, J=15.4 Hz, 1H), 2.70 (ddd, J=19.0, 6.4, 2.9 Hz, 1H), 2.35-2.20 (m, 1H), 1.89-1.74 (m, 1H), 1.44-1.27 (m, 5H). $^{19}$F NMR (377 MHz, DMSO-$d_6$) δ −62.58 (s, 3F), −76.69 (s, 3F). ESI-MS m/z calc. 454.1076, found 455.1 (M+1)$^+$; Retention time: 3.02 minutes. LCMS Method: Kinetex Polar $C_{18}$ column (3.0×50 mm, 2.6 μm particle size, 6 minute run, 5% to 95% acetonitrile in water (0.1% formic acid modifier), flow rate=1.2 mL/min).

Example 43: Preparation of (6R)-17-amino-11,11-dimethyl-6,15-bis(trifluoromethyl)-13,19-dioxa-3,4,18-triazatricyclo[12.3.1.1²,⁵]nonadeca-1(18),2,4,14,16-pentaen-6-ol, Compound 61

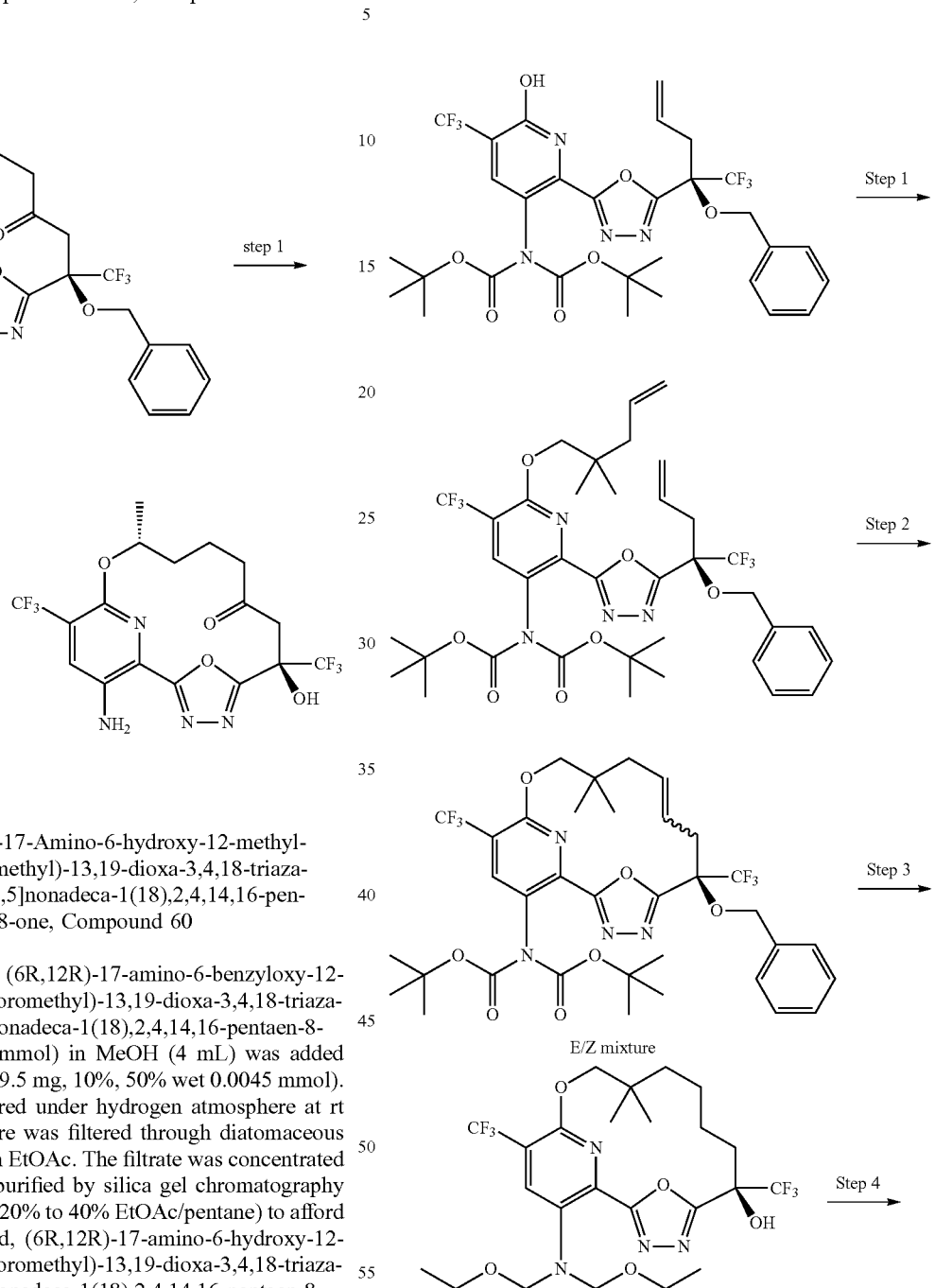

Step 1: tert-Butyl N-[2-[5-[(1R)-1-benzyloxy-1-(trifluoromethyl)but-3-enyl]-1,3,4-oxadiazol-2-yl]-6-(2,2-dimethylpent-4-enoxy)-5-(trifluoromethyl)-3-pyridyl]-N-tert-butoxycarbonyl-carbamate

Step 2: tert-Butyl N-[(6R)-6-benzyloxy-11,11-dimethyl-6,15-bis(trifluoromethyl)-13,19-dioxa-3,4,18-triazatricyclo[12.3.1.12,5]nonadeca-1(18),2,4,8,14,16-hexaen-17-yl]-N-tert-butoxycarbonyl-carbamate (E/Z Mixture)

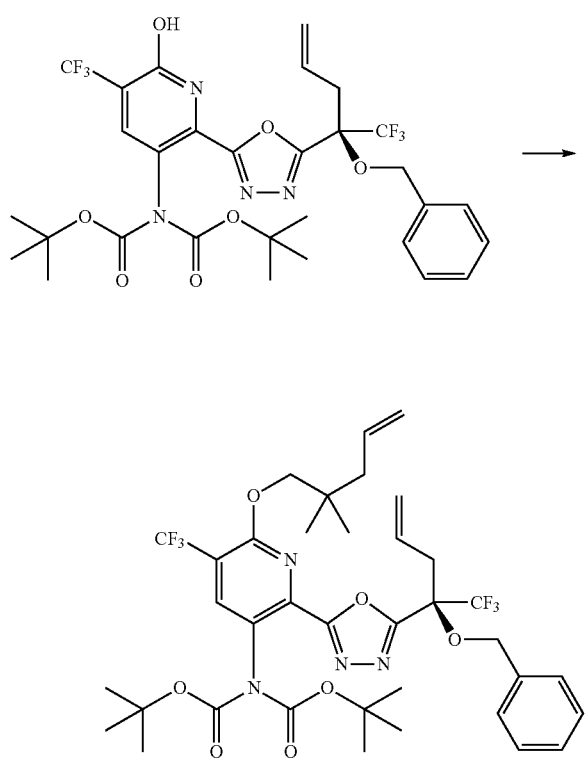

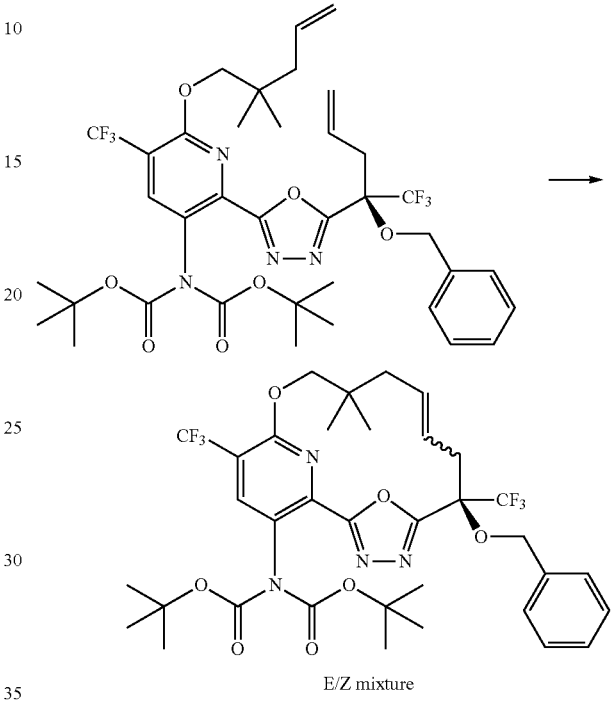

E/Z mixture

A solution of tert-butyl N-[2-[5-[(1R)-1-benzyloxy-1-(trifluoromethyl)but-3-enyl]-1,3,4-oxadiazol-2-yl]-6-hydroxy-5-(trifluoromethyl)-3-pyridyl]-N-tert-butoxycarbonyl-carbamate (1.38 g, 1.8473 mmol) and 2,2-dimethylpent-4-en-1-ol (630 mg, 5.5174 mmol) in toluene (17 mL) was treated with triphenylphosphine (998 mg, 3.8050 mmol) followed by DIAD (770.25 mg, 0.75 mL, 3.8092 mmol) at room temperature. The yellow solution was stirred at room temperature for 24 hours. The yellow suspension was concentrated and the residue was purified by reverse phase chromatography (100 g $C_{18}$ column, eluting with 0% to 90% acetonitrile in water with 0.1 w/w % of formic acid for 5 column volumes followed by isocratic elution with 90% acetonitrile in water with 0.1 w/w % of formic acid for 10 column volumes) to provide as a light yellow oil, tert-butyl N-[2-[5-[(1R)-1-benzyloxy-1-(trifluoromethyl)but-3-enyl]-1,3,4-oxadiazol-2-yl]-6-(2,2-dimethylpent-4-enoxy)-5-(trifluoromethyl)-3-pyridyl]-N-tert-butoxycarbonyl-carbamate (730 mg, 51%). ESI-MS m/z calc. 770.3114, found 615.2 (M−155)+; Retention time: 4.87 minutes. LCMS Method:) XBridge $C_{18}$ column (4.6×75 mm, 5 mm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

A dried 250 mL flask was charged with toluene (100 mL) and the solvent was bubbled with nitrogen for 30 min. Zhan 1B catalyst (40 mg, 0.0545 mmol) was added under gentle flow of nitrogen. The mixture was bubbled with nitrogen for more 10 min and heated to 110° C. A nitrogen-bubbled solution of tert-butyl N-[2-[5-[(1R)-1-benzyloxy-1-(trifluoromethyl)but-3-enyl]-1,3,4-oxadiazol-2-yl]-6-(2,2-dimethylpent-4-enoxy)-5-(trifluoromethyl)-3-pyridyl]-N-tert-butoxycarbonyl-carbamate (200 mg, 0.2595 mmol) in toluene (20 mL) was added dropwise over 0.5 h. After addition was completed, the mixture was bubbled with nitrogen for 5 min. The mixture was continued to stir at 110° C. for 1.5 hours. Again, Zhan 1B catalyst (40 mg, 0.0545 mmol) was added in two portions while heating the reaction mixture at 111° C. for 2 hours. The mixture was then cooled to room temperature and the catalyst was quenched by the addition of DMSO (4-5 drops). The mixture was concentrated and the residue was purified by reverse phase chromatography (50 g C18 column, eluting with 5% to 90% acetonitrile in water containing 0.1 w/w % formic acid for 10 CV then with 90% acetonitrile in water with 0.1 w/w % of formic acid for 10 CV) to provide as brown oil, tert-butyl N-[(6R)-6-benzyloxy-11,11-dimethyl-6,15-bis(trifluoromethyl)-13,19-dioxa-3,4,18-triazatricyclo[12.3.1.12,5]nonadeca-1(18),2,4,8,14,16-hexaen-17-yl]-N-tert-butoxycarbonyl-carbamate (E/Z mixture) (23 mg, 10%). ESI-MS m/z calc. 742.2801, found 587.2 (M−155)+; Retention time: 4.61 minutes. LCMS Method: XBridge $C_{18}$ column (4.6×75 mm, 5 mm particle size, 6 minute run with 1 minute equilibration, initial mobile phase at 95% aqueous NH₄HCO₃/5% acetonitrile, gradient from 0 to 3 minutes to 95% MeCN and held for 3 minutes, flow=1.5 mL/min).

Step 3: tert-Butyl N-tert-butoxycarbonyl-N-[(6R)-6-hydroxy-11,11-dimethyl-6,15-bis(trifluoromethyl)-13,19-dioxa-3,4,18-triazatricyclo[12.3.1.12,5]nonadeca-1(18),2,4,14,16-pentaen-17-yl]carbamate Step 4: (6R)-17-Amino-11,11-dimethyl-6,15-bis(trifluoromethyl)-13,19-dioxa-3,4,18-triazatricyclo[12.3.1.12,5]nonadeca-1(18),2,4,14,16-pentaen-6-ol, Compound 61

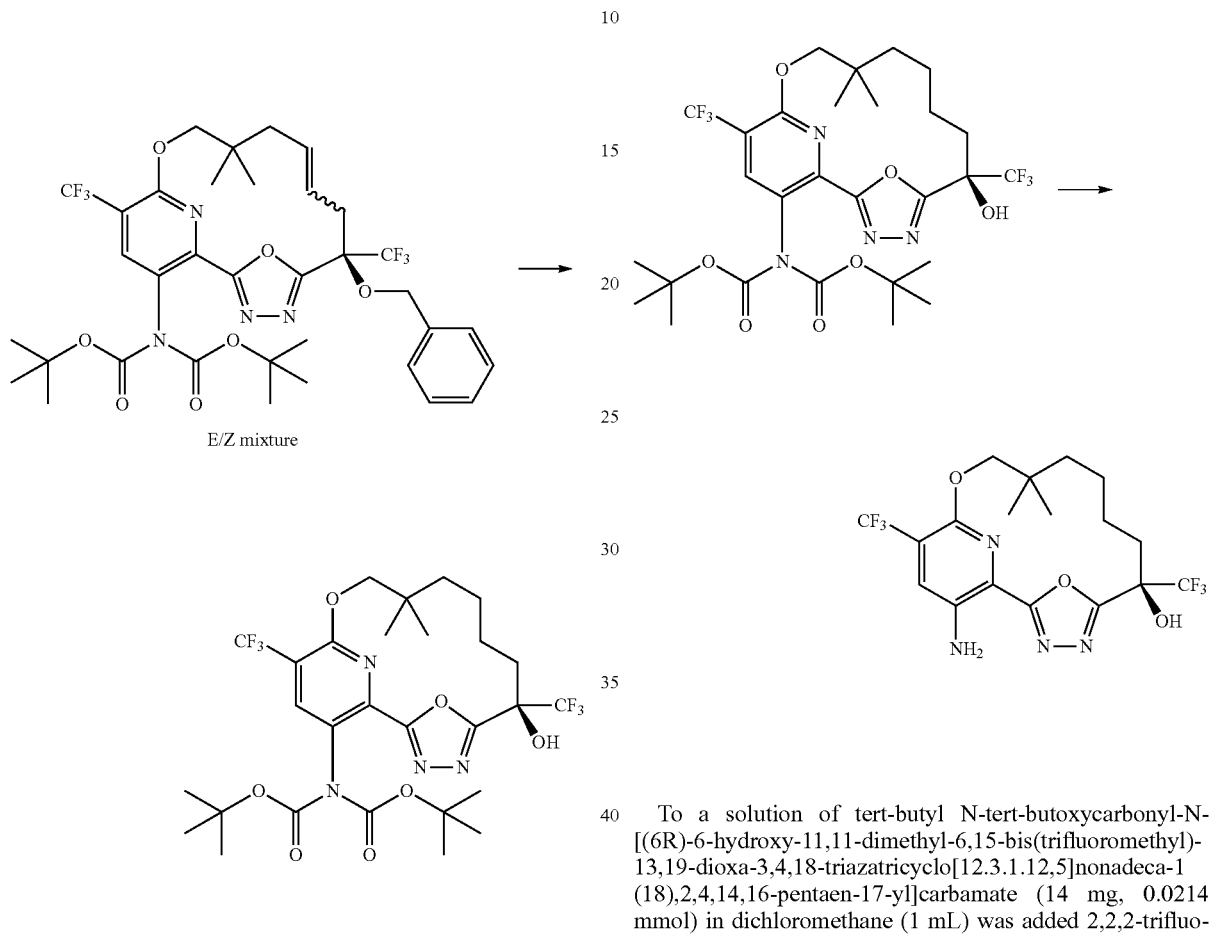

A solution of tert-butyl N-[(6R)-6-benzyloxy-11,11-dimethyl-6,15-bis(trifluoromethyl)-13,19-dioxa-3,4,18-triazatricyclo[12.3.1.12,5]nonadeca-1(18),2,4,8,14,16-hexaen-17-yl]-N-tert-butoxycarbonyl-carbamate (E/Z mixture) (21 mg, 0.0283 mmol) in methanol (5 mL) was purged three times (vacuum then nitrogen gas). Added palladium on carbon (5 mg, 10% w/w, 50% wet 0.0023 mmol), purged twice with hydrogen gas and stirred under hydrogen atmosphere for overnight. The reaction mixture was purged with nitrogen gas, filtered with a nylon 0.45 micron filter and concentrated to provide as a colorless oil, tert-butyl N-tert-butoxycarbonyl-N-[(6R)-6-hydroxy-11,11-dimethyl-6,15-bis(trifluoromethyl)-13,19-dioxa-3,4,18-triazatricyclo[12.3.1.12,5]nonadeca-1(18),2,4,14,16-pentaen-17-yl]carbamate (14 mg, 76%). ESI-MS m/z calc. 654.2488, found 499.2 (M−155)⁺; Retention time: 4.23 minutes. LCMS Method: XBridge C₁₈ column (4.6×75 mm, 5 mm particle size, 6 minute run with 1 minute equilibration, initial mobile phase at 95% aqueous NH₄HCO₃/5% acetonitrile, gradient from 0 to 3 minutes to 95% MeCN and held for 3 minutes, flow=1.5 mL/min).

To a solution of tert-butyl N-tert-butoxycarbonyl-N-[(6R)-6-hydroxy-11,11-dimethyl-6,15-bis(trifluoromethyl)-13,19-dioxa-3,4,18-triazatricyclo[12.3.1.12,5]nonadeca-1(18),2,4,14,16-pentaen-17-yl]carbamate (14 mg, 0.0214 mmol) in dichloromethane (1 mL) was added 2,2,2-trifluoroacetic acid (1.4800 g, 1 mL, 12.980 mmol). The mixture was stirred at room temperature for 2 hours. The mixture was diluted with dichloromethane (5 mL) and concentrated. The residue was dissolved in ethyl acetate (40 mL), washed with aqueous saturated solution of sodium bicarbonate (3×10 mL), brine (1×20 mL), dried over anhydrous sodium sulphate, filtered and concentrated. The material was purified by reverse phase chromatography (15.5 g C18 column, using a gradient from 0% to 95% water (+0.1 v % FA) and MeCN) to provide as an off-white solid, (6R)-17-amino-11,11-dimethyl-6,15-bis(trifluoromethyl)-13,19-dioxa-3,4,18-triazatricyclo[12.3.1.12,5]nonadeca-1(18),2,4,14,16-pentaen-6-ol (2.6 mg, 26%). ¹H NMR (400 MHz, CD₃OD) δ 7.65 (s, 1H), 4.47 (br. s., 1H), 4.17 (br. s., 1H), 2.44-2.30 (m, 2H), 2.14-2.09 (m, 1H), 2.05-1.92 (m, 2H), 1.46-1.40 (m, 2H), 1.26-1.21 (m, 1H), 0.98 (s, 3H), 0.96 (s, 3H). ¹⁹F NMR (377 MHz, CD₃OD) δ −65.62 (s, 3F), −80.82 (br. s., 3F). ESI-MS m/z calc. 454.144, found 455.1 (M+1)⁺; Retention time: 3.95 minutes. LCMS Method: XBridge C₁₈ column (4.6×75 mm, 5 mm particle size, 6 minute run with 1 minute equilibration, initial mobile phase at 95% aqueous NH₄HCO₃/5% acetonitrile, gradient from 0 to 3 minutes to 95% MeCN and held for 3 minutes, flow=1.5 mL/min).

517

Example 44: Preparation of (12R)-17-amino-12-methyl-6,15-bis(trifluoromethyl)-13,19-dioxa-3,4,18-triazatricyclo[12.3.1.1²,⁵]nonadeca-1(18),2,4,14,16-pentaene-6,7-diol (enantiomer 3), Compound 62

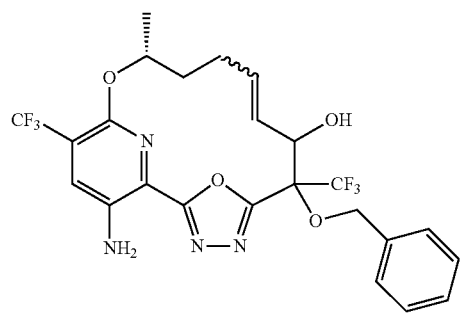

E/Z mixture
diastereomer pair 1

Step 1 →

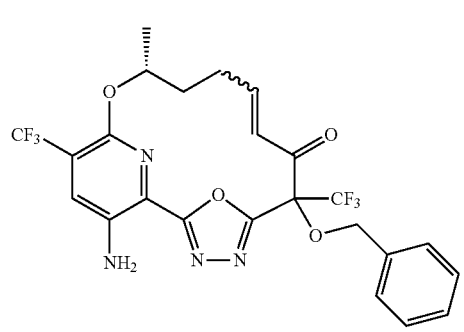

E/Z mixture

Step 2 →

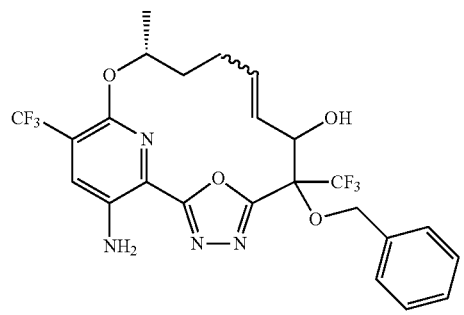

E/Z mixture
diastereomer pair 2

Step 3 →

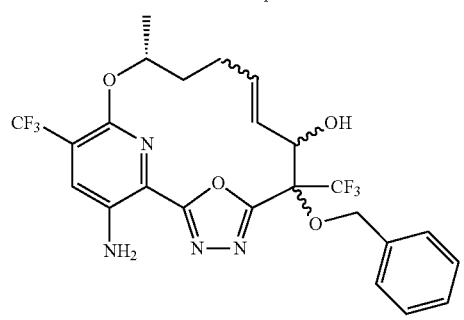

E/Z mixture, enantiomer 3

Step 4 →

518

-continued

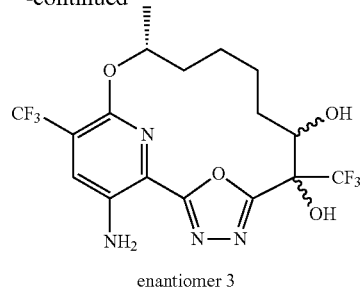

enantiomer 3

Step 1: (12R)-17-Amino-6-benzyloxy-12-methyl-6,15-bis(trifluoromethyl)-13,19-dioxa-3,4,18-triazatricyclo[12.3.1.1²,⁵]nonadeca-1(18),2,4,8,14,16-hexaen-7-one (E/Z Mixture)

[Structure]

E/Z mixture
diastereomer pair 1

→

[Structure]

E/Z mixture

To a solution of (12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,8,14,16-hexaen-7-ol (E/Z mixture, diastereomer pair 1) (30 mg, 0.0551 mmol) in $CH_2Cl_2$ (3 mL) was added $NaHCO_3$ (90 mg, 1.0713 mmol), followed by Dess-Martin periodinane (30 mg, 0.0707 mmol). The mixture was stirred at room temperature for 3 h. Saturated $NaHCO_3$ (3 mL) and 10% aq. $Na_2S_2O_3$ (3 mL) were added. The mixture was stirred at room temperature for 5 min and extracted with $CH_2Cl_2$ (3×10 mL). The combined organic layers were dried with $Na_2SO_4$, filtered and concentrated. The residue was purified by silica gel chromatography (eluting from 0% to 30% EtOAc/heptanes) to afford as a pale-yellow oil, (12R)-17-amino-6-benzyloxy-12-methyl-6,15-bis(trifluoromethyl)-13,19-dioxa-3,4,18-triazatricyclo[12.3.1.1²,⁵]nonadeca-1(18),2,4,8,14,16-hexaen-7-one (E/Z mixture) (24 mg, 80%). $^1$H NMR (400 MHz, $CDCl_3$) δ

7.45-7.26 (m, 4H), 7.27-7.13 (m, 3H), 7.06-6.76 (m, 1H), 5.35-5.19 (m, 2H), 5.07-4.88 (m, 2H), 4.76-4.69 (m, 1H). 2.51-2.08 (m, 3H), 1.76-1.66 (m, 1H), 1.47-1.42 (m, 3H). NMR (377 MHz, CDCl$_3$) δ −63.98 to −64.01 (m, 3F), −70.18 to −70.70 (m, 3F).

Step 2: (12R)-17-Amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-ol (E/Z Mixture, diastereomer pair 2)

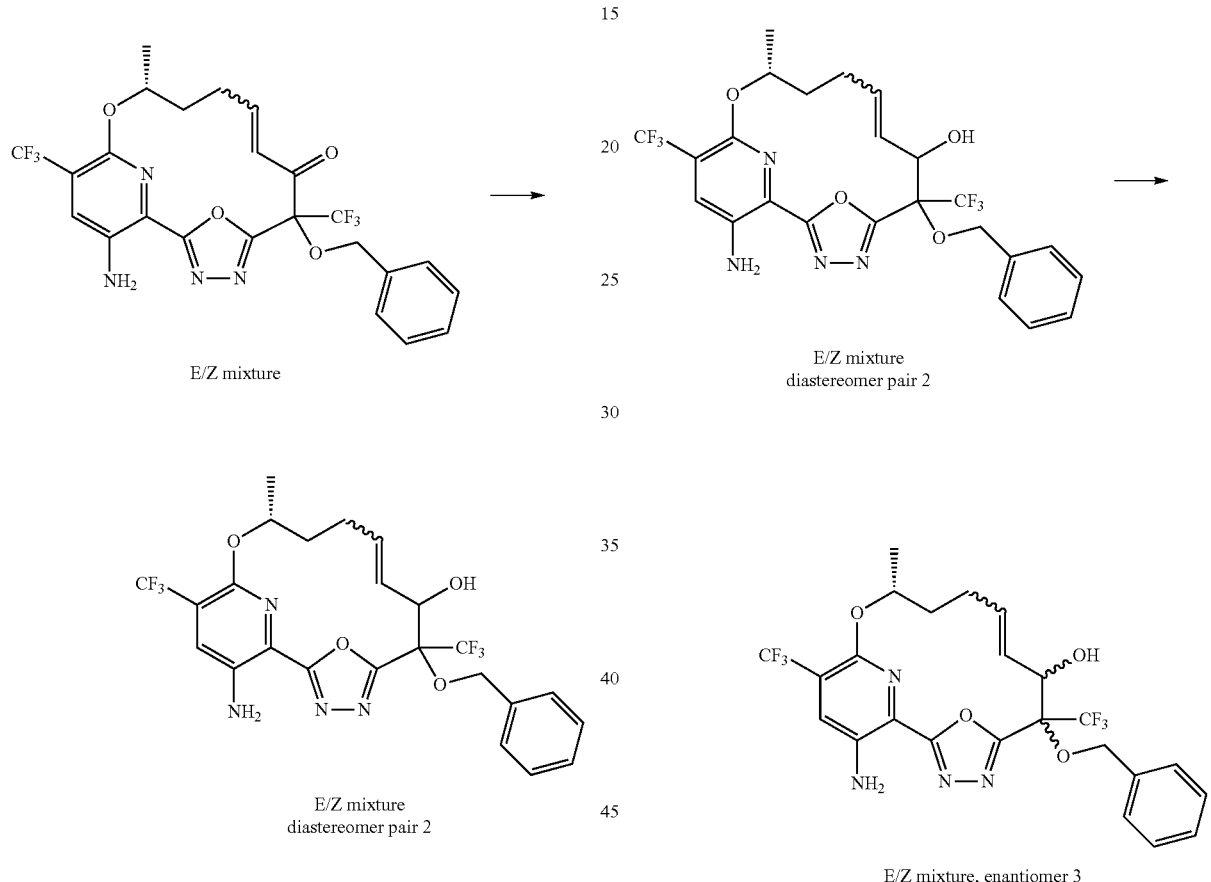

E/Z mixture

E/Z mixture
diastereomer pair 2

E/Z mixture
diastereomer pair 2

E/Z mixture, enantiomer 3

To a solution of (12R)-17-amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-one (E/Z mixture) (28 mg, 0.0516 mmol) in MeOH (2.5 mL) at −5° C. was added tetramethylammonium borohydride (10 mg, 0.1124 mmol). The mixture was stirred at −5° C. for 10 min. Acetone (0.5 mL) was added. The mixture was stirred at −5° C. for 5 min and then treated with saturated aqueous NaHCO$_3$ (5 mL). The mixture was extracted with EtOAc (3×10 mL). The combined organic layers were dried with Na$_2$SO$_4$, filtered and concentrated. The residue was purified by silica gel chromatography (eluting 5% EtOAc/CH$_2$Cl$_2$) to afford as a pale-yellow oil, (12R)-17-amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-ol (E/Z mixture, diastereomer pair 2) (22 mg, 78%). ESI-MS m/z calc. 544.15454, found 545.2 (M+1)$^+$; Retention time: 3.49 minutes. LCMS Method: Kinetex Polar C$_{18}$ column (3.0×50 mm, 2.6 μm particle size, 6 minute run, 5% to 95% acetonitrile in water (0.1% formic acid modifier), flow rate=1.2 mL/min).

Step 3: (12R)-17-Amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-ol (E/Z Mixture, enantiomer 3)

(12R)-17-amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-ol (E/Z mixture, diastereomer pair 2) (40 mg, 0.0735 mmol) was purified by silica gel chromatography (eluting 10 to 30% EtOAc/heptanes) to afford two products. The less polar diastereomer was isolated as a pale-yellow oil, (12R)-17-amino-6-benzyloxy-12-methyl-6,15-bis(trifluoromethyl)-13,19-dioxa-3,4,18-triazatricyclo[12.3.1.12,5]nonadeca-1(18),2,4,8,14,16-hexaen-7-ol (E/Z mixture, enantiomer 3) (16 mg, 37%). ESI-MS m/z calc. 544.15454, found 545.2 (M+1)$^+$; Retention time: 3.5 minutes. LCMS Method: Kinetex Polar C$_{18}$ column (3.0×50 mm, 2.6 μm particle size, 6 minute run, 5% to 95% acetonitrile in water (0.1% formic acid modifier), flow rate=1.2 mL/min).

521

Step 4: (12R)-17-Amino-12-methyl-6,15-bis(trifluoromethyl)-13,19-dioxa-3,4,18-triazatricyclo[12.3.1.1<sup>2,5</sup>]nonadeca-1(18),2,4,14,16-pentaene-6,7-diol (enantiomer 3), Compound 62

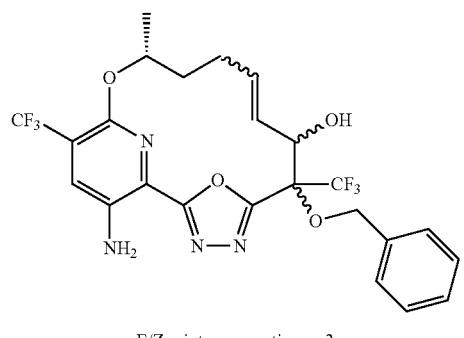

(12R)-17-Amino-6-benzyloxy-12-methyl-6,15-bis(trifluoromethyl)-13,19-dioxa-3,4,18-triazatricyclo[12.3.1.1<sup>2,5</sup>]nonadeca-1(18),2,4,8,14,16-hexaen-7-ol (E/Z mixture, enantiomer 3) (16 mg, 0.0272 mmol) and 10% palladium on carbon (50% wet, 6 mg, 0.0028 mmol) in EtOAc (3 mL) was stirred under hydrogen (balloon) at room temperature overnight. The mixture was filtered through diatomaceous earth and the cake was washed with EtOAc (about 10 mL). The filtrate was concentrated and the residue was purified by silica gel chromatography (eluting 20% to 50% EtOAc/pentane) and freeze dried to afford (12R)-17-amino-12-methyl-6,15-bis(trifluoromethyl)-13,19-dioxa-3,4,18-triazatricyclo[12.3.1.1<sup>2,5</sup>]nonadeca-1(18),2,4,14,16-pentaene-6,7-diol (enantiomer 3) (7 mg, 52%) as a pale-yellow solid. $^1$H NMR (400 MHz, DMSO-$d_6$) δ 7.75 (s, 1H), 7.57 (s, 1H), 6.27 (s, 2H), 5.51 (d, J=6.8 Hz, 1H), 4.88-4.78 (m, 1H), 4.35-4.26 (m, 1H), 2.63-2.51 (m, 2H), 1.96-1.83 (m, 1H), 1.75-1.64 (m, 1H), 1.63-1.53 (m, 1H), 1.52-1.43 (m, 1H), 1.37-1.28 (m, 5H). $^{19}$F NMR (377 MHz, DMSO-$d_6$) δ −62.43 (s, 3F), −73.86 (s, 3F). ESI-MS m/z calc. 456.12323, found 457.2 (M+1)$^+$; Retention time: 2.99 minutes. LCMS Method: Kinetex Polar $C_{18}$ column (3.0×50 mm, 2.6 μm particle size, 6 minute run, 5% to 95% acetonitrile in water (0.1% formic acid modifier), flow rate=1.2 mL/min).

522

Example 45: Preparation of (6R,13R)-18-amino-13-methyl-6,16-bis(trifluoromethyl)-14,20-dioxa-3,4,19-triazatetracyclo[13.3.1.1<sup>2,5</sup>.0<sup>9,11</sup>]icosa-1(19),2,4,15,17-pentaen-6-ol (enantiomer 1), Compound 63, and (6R,13R)-18-amino-13-methyl-6,16-bis(trifluoromethyl)-14,20-dioxa-3,4,19-triazatetracyclo[13.3.1.1<sup>2,5</sup>.0<sup>9,11</sup>]icosa-1(19),2,4,15,17-pentaen-6-ol (enantiomer 2), Compound 64

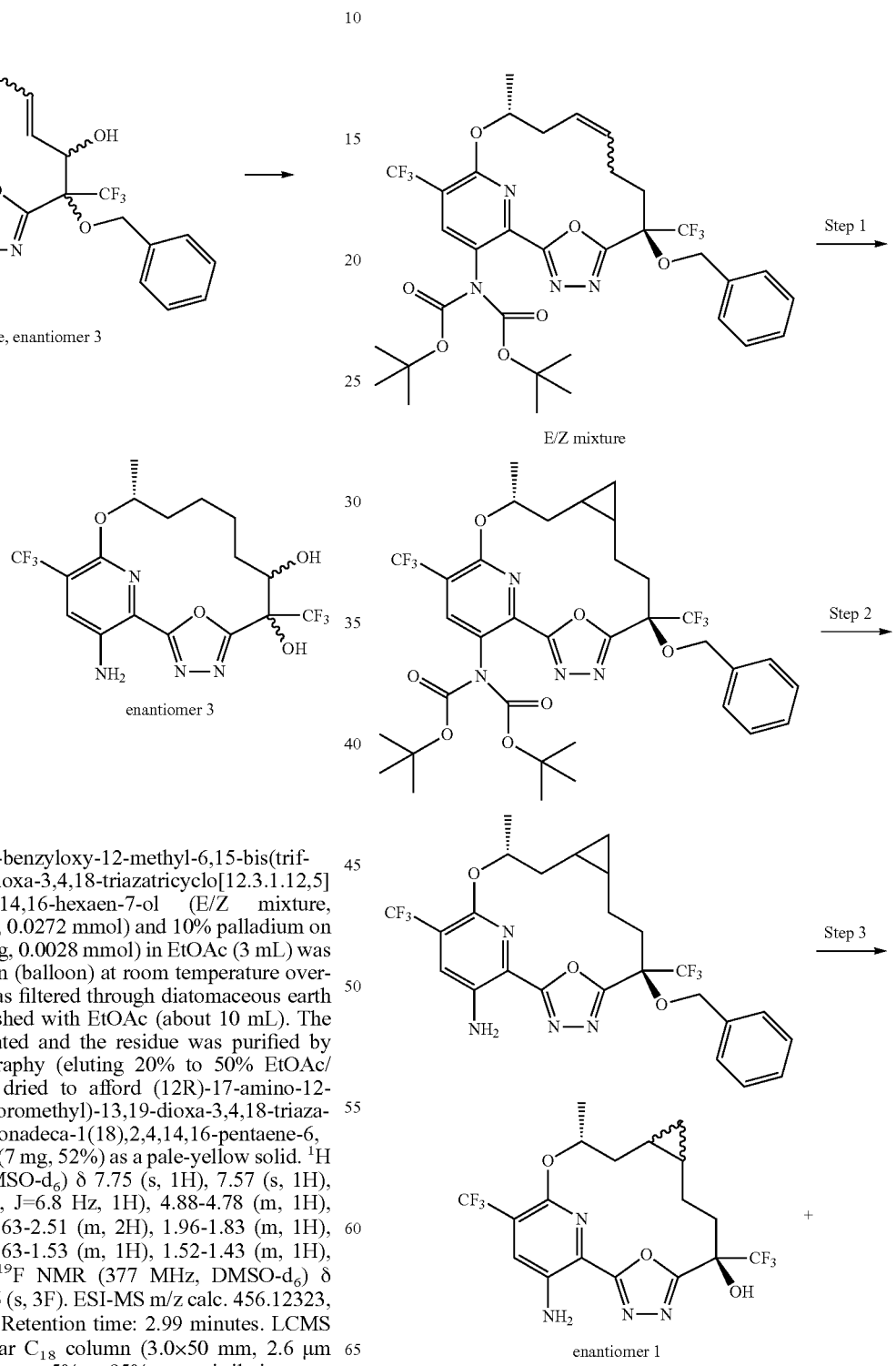

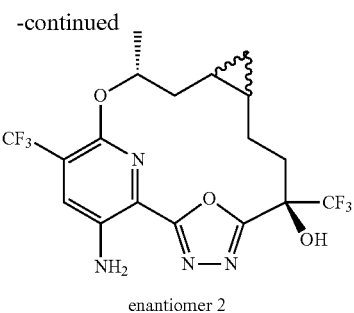

enantiomer 2

Step 1: tert-Butyl N-[(6R,13R)-6-benzyloxy-13-methyl-6,16-bis(trifluoromethyl)-14,20-dioxa-3,4,19-triazatetracyclo[13.3.1.12,5.09,11]icosa-1(19),2,4,15,17-pentaen-18-yl]-N-tert-butoxycarbonyl-carbamate

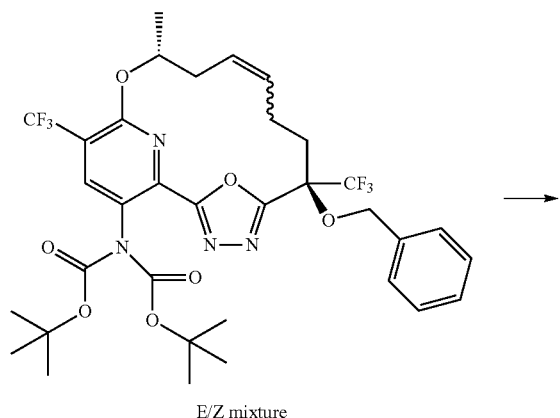

E/Z mixture

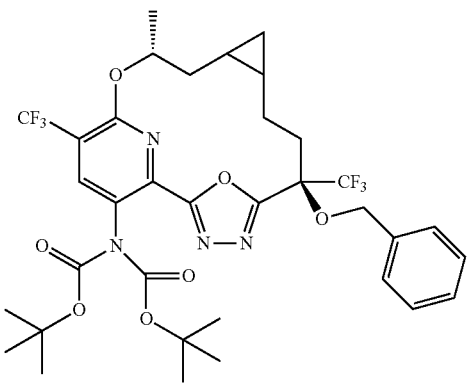

A flask was charged with potassium hydroxide (800 mg, 14.259 mmol) and water (3.4 mL) was added. The mixture was stirred for 2 min until KOH was dissolved. Diethyl ether (14 mL) was added. The mixture was cooled to 0° C. and 1-methyl-1-nitroso-urea (700 mg, 6.1118 mmol) was added. The mixture was stirred at 0° C. for 30 min. Stirring was stopped and the mixture was cooled to −78° C. Once the aqueous phase was frozen, the yellow ethereal layer was transferred by a plastic pipette to another flask with two pellets (about 220 mg) of potassium hydroxide. The flask stayed at 0° C. for 5 min. Half of the formed diazomethane solution in ether (~7 mL) was added by a plastic pipette to a solution of tert-butyl N-[(6R,12R)-6-benzyloxy-12-methyl-6,15-bis(trifluoromethyl)-13,19-dioxa-3,4,18-triaza-tricyclo[12.3.1.12,5]nonadeca-1(18),2,4,9,14,16-hexaen-17-yl]-N-tert-butoxycarbonyl-carbamate (E/Z mixture) (200 mg, 0.2536 mmol) in THF (10 mL) at 0° C. A solution of palladium diacetate (12 mg, 0.0535 mmol) in THF (3.4 mL) was added dropwise. The resulting mixture was stirred at 0° C. for 15 min and then the remainder of the ethereal diazomethane solution (~7 mL) was added. The brown solution was allowed to warm to room temperature and stirred for 1 h. For a second time, a flask was charged with potassium hydroxide (800 mg, 14.259 mmol) and water (4 mL) was added. The mixture was stirred for 2 min until KOH was dissolved. Diethyl ether (14 mL) was added. The mixture was cooled to 0° C. and 1-methyl-1-nitroso-urea (700 mg, 6.7908 mmol) was added. The mixture was stirred at 0° C. for 30 min. Stirring was stopped and the mixture was cooled to −78° C. Once the aqueous phase was frozen, the yellow ethereal layer was transferred to another flask with 220 mgs of potassium hydroxide. The flask stayed at 0° C. for 5 min. Half of this diazomethane solution in ether (~7 mL) was added to the previous reaction solution. A solution of palladium diacetate (12 mg, 0.0535 mmol) in THF (3 mL) was added dropwise to the reaction mixture. The resulting mixture was stirred at 0° C. for 15 min and then the remainder of the ethereal diazomethane solution (~7 mL) was added. The brown solution was allowed to warm to room temperature and stirred for 1 h. For a third time, a flask was charged with potassium hydroxide (800 mg, 14.259 mmol) and water (3.5 mL) was added. The mixture was stirred for 2 min until KOH was dissolved. Diethyl ether (14 mL) was added. The mixture was cooled to 0° C. and 1-methyl-1-nitroso-urea (700 mg, 6.7908 mmol) was added. The mixture was stirred at 0° C. for 30 min. Stirring was stopped and the mixture was cooled to −78° C. Once the aqueous phase was frozen, the yellow ethereal layer was transferred to another flask with 220 mgs of potassium hydroxide. The flask stayed at 0° C. for 5 min. Half of this diazomethane solution in ether (~7 mL) was added by a plastic pipette to the previous reaction solution. A solution of palladium diacetate (12 mg, 0.0535 mmol) in THF (3 mL) was added dropwise. The resulting mixture was stirred at 0° C. for 15 min and then the remainder of the ethereal diazomethane solution (~7 mL) was added. The brown solution was allowed to warm to room temperature and stirred for 1 h. Nitrogen was bubbled through the black mixture for 10 min, then the solvents were removed under vacuum (at 25° C.). The residue was purified by reverse phase chromatography over a 50 g silica column (5% to 90% CH$_3$CN/0.01% formic acid in water) to give a diastereomeric mixture of tert-butyl N-[(6R,13R)-6-benzyloxy-13-methyl-6,16-bis(trifluoromethyl)-14,20-dioxa-3,4,19-triaza-tetracyclo[13.3.1.12,5.09,11]icosa-1(19),2,4,15,17-pentaen-18-yl]-N-tert-butoxycarbonyl-carbamate (123 mg, 64%) as a white solid. ESI-MS m/z calc. 742.2801, found 587.2 (M−155)$^+$; Retention time: 4.6 minutes. LCMS Method: XBridge C$_{18}$ column (4.6×75 mm, 5 μm particle size, 6 minute run with 1 minute equilibration, initial mobile phase at 95% aqueous NH$_4$HCO$_3$/5% acetonitrile, gradient from 0 to 3 minutes to 95% MeCN and held for 3 minutes, flow=1.5 mL/min).

525

Step 2: (6R,13R)-6-Benzyloxy-13-methyl-6,16-bis(trifluoromethyl)-14,20-dioxa-3,4,19-triazatetracyclo[13.3.1.1²,⁵.0⁹,¹¹]icosa-1(19),2,4,15,17-pentaen-18-amine

526

Step 3: (6R,13R)-18-Amino-13-methyl-6,16-bis(trifluoromethyl)-14,20-dioxa-3,4,19-triazatetracyclo[13.3.1.1²,⁵.0⁹,¹¹]icosa-1(19),2,4,15,17-pentaen-6-ol (enantiomer 1), Compound 63, and (6R,13R)-18-amino-13-methyl-6,16-bis(trifluoromethyl)-14,20-dioxa-3,4,19-triazatetracyclo[13.3.1.1²,⁵.0⁹,¹¹]icosa-1(19),2,4,15,17-pentaen-6-ol (enantiomer 2), Compound 64

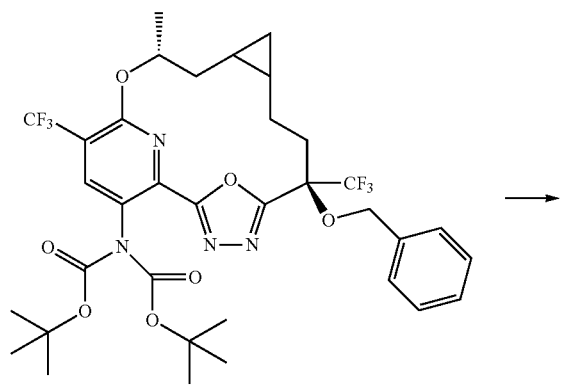

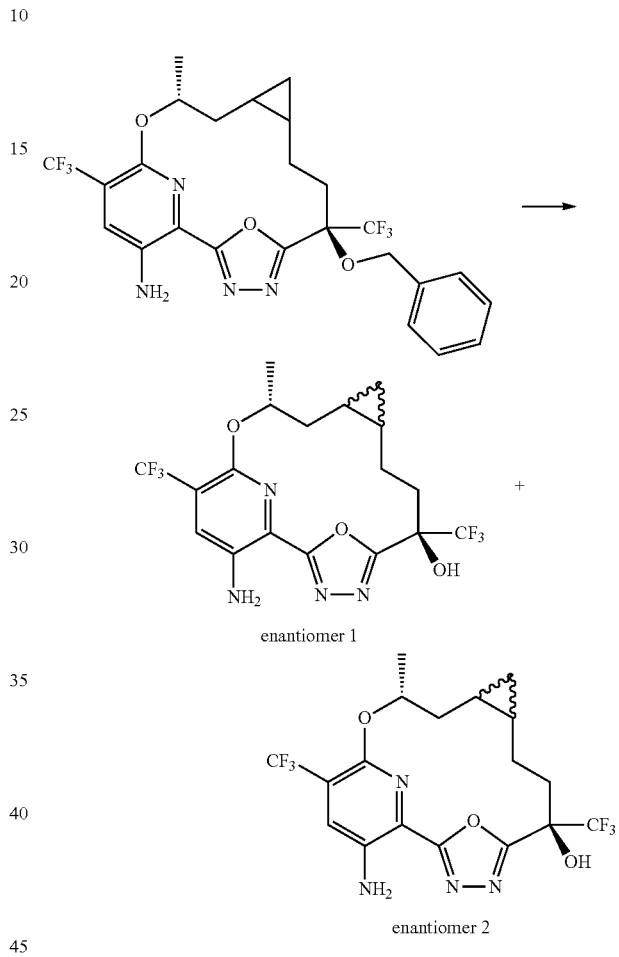

enantiomer 1 enantiomer 2

Trifluoroacetic acid (740.00 mg, 0.5 mL, 6.4899 mmol) was added to a yellow solution of tert-butyl N-[(6R,13R)-6-benzyloxy-13-methyl-6,16-bis(trifluoromethyl)-14,20-dioxa-3,4,19-triazatetracyclo[13.3.1.1²,⁵.0⁹,¹¹]icosa-1(19),2,4,15,17-pentaen-18-yl]-N-tert-butoxycarbonyl-carbamate (120 mg, 0.1582 mmol) in DCM (2.4 mL) at room temperature and the mixture was stirred for 1 h. The orange solution was concentrated under vacuum. The residual TFA was co-evaporated with $CH_3CN$ (3×4 mL), $CH_3CN$/toluene (1×4 mL) and toluene (3×4 mL) then dried under high vacuum to give crude (6R,13R)-6-benzyloxy-13-methyl-6,16-bis(trifluoromethyl)-14,20-dioxa-3,4,19-triazatetracyclo[13.3.1.1²,⁵.0⁹,¹¹]icosa-1(19),2,4,15,17-pentaen-18-amine (103 mg, quant.) as a light orange oil. ESI-MS m/z calc. 542.17523, found 543.2 (M+1)⁺; Retention time: 4.35 minutes. LCMS Method: XBridge $C_{18}$ column (4.6×75 mm, 5 μm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

Palladium on carbon (10% w/w, 18 mg, 0.0169 mmol) was added to a degassed solution of (6R,13R)-6-benzyloxy-13-methyl-6,16-bis(trifluoromethyl)-14,20-dioxa-3,4,19-triazatetracyclo[13.3.1.1²,⁵.0⁹,¹¹]icosa-1(19),2,4,15,17-pentaen-18-amine (90 mg, 0.1659 mmol) in methanol (2 mL) at room temperature. The black suspension was purged with nitrogen for 5 min, then hydrogen was bubbled through the suspension for 5 min. Then, the mixture was stirred at room temperature overnight under hydrogen atmosphere. The black suspension was filtered over Celite and the cake was washed with DCM (3×5 mL) then concentrated the filtrate under vacuum to give a fluorescent yellow oil. Purified by reverse phase chromatography over a 50 g $C_{18}$ column (5% to 90% $CH_3CN$/0.02% HCl in water) to give a yellow solid (57 mg, 98.6% of purity). This solid was subjected to SFC separation using the following conditions: Lux Cellulose 3 column, (250×21.2 mm), 5 μm column at 40° C., eluant: 10% ethanol (0.1% diethylamine), 90% $CO_2$, flow rate: 75 mL/min, concentration: 5.7 mg/mL in ethanol (0.1.% diethylamine), injection volume: 200 μL, pressure: 100 bar, wavelength: 250 nm. Evaporation of the solvents provided two isomers. Both were redissolved in EtOAc (5 mL) then washed with 0.5 M hydrogen chloride aqueous solution (1×10 mL), saturated sodium bicarbonate aqueous solution (1×10 mL) and brine (1×10 mL). The organic layer of each was dried over anhydrous sodium sulfate and then concentrated under vacuum. Both isomers were then lyophilized to afford as the first compound to elute under the SFC conditions and a light yellow solid, (6R,13R)-18-amino-13-methyl-6,16-bis(trifluoromethyl)-14,20-dioxa-3,4,19-triazatetracyclo[13.3.1.12,5.09,11]icosa-1(19),2,4,15,17-pentaen-6-ol (enantiomer 1) (15.6 mg, 20%). $^1$H NMR (400 MHz, MeOD) δ 7.66 (s, 1H), 5.34-5.19 (m, 1H), 2.96-2.79 (m, 1H), 2.52 (dd, J=15.2, 8.1 Hz, 1H), 1.96-1.81 (m, 2H), 1.45 (d, J=6.4 Hz, 3H), 1.04-0.96 (m, 2H), 0.91 (t, J=12.5 Hz, 1H), 0.59-0.44 (m, 1H), 0.36-0.27 (m, 1H), 0.26-0.17 (m, 1H). $^{19}$F NMR (377 MHz, MeOD) δ -65.42 (s, 3F), -80.26 (s, 3F). ESI-MS m/z calc. 452.1283, found 453.1 (M+1)$^+$; Retention time: 3.8 minutes. LCMS Method: XBridge C$_{18}$ column (4.6×75 mm, 5 µm particle size, 6 minute run with 1 minute equilibration, initial mobile phase at 95% aqueous NH$_4$HCO$_3$/5% acetonitrile, gradient from 0 to 3 minutes to 95% MeCN and held for 3 minutes, flow=1.5 mL/min).

The second peak to elute under the above SFC conditions was repurified by SFC using the following conditions: Lux Cellulose 3 column, (250×21.2 mm), 5 µm column at 40° C., eluant: 10% ethanol (0.1% diethylamine), 90% CO$_2$, flow rate: 75 mL/min, concentration: 21 mg/mL in ethanol (0.1.% diethylamine), injection volume: 200 µL, pressure: 100 bar, wavelength: 250 nm. Evaporation of the solvent and lyophilization provided as a light yellow solid, (6R,13R)-18-amino-13-methyl-6,16-bis(trifluoromethyl)-14,20-dioxa-3,4,19-triazatetracyclo[13.3.1.12,5.09,11]icosa-1(19),2,4,15,17-pentaen-6-ol (enantiomer 2) (9.61 mg, 13%). $^1$H NMR (400 MHz, MeOD) δ 7.64 (s, 1H), 5.56-5.38 (m, 1H), 2.63-2.48 (m, 1H), 2.41-2.17 (m, 2H), 2.09-1.87 (m, 1H), 1.32 (d, J=6.6 Hz, 3H), 1.24-1.14 (m, 1H), 1.13-1.04 (m, 1H), 0.94-0.68 (m, 2H), 0.27-0.10 (m, 2H). $^{19}$F NMR (377 MHz, MeOD) δ -65.27 (s, 3F), -78.81 (s, 3F). ESI-MS m/z calc. 452.1283, found 453.1 (M+1)$^+$; Retention time: 3.79 minutes. LCMS Method: XBridge C$_{18}$ column (4.6×75 mm, 5 µm particle size, 6 minute run with 1 minute equilibration, initial mobile phase at 95% aqueous NH$_4$HCO$_3$/5% acetonitrile, gradient from 0 to 3 minutes to 95% MeCN and held for 3 minutes, flow=1.5 mL/min).

Example 46: Preparation of (6R)-12-cyclopropyl-17-(ethylamino)-6,15-bis(trifluoromethyl)-13,19-dioxa-3,4,18-triazatricyclo[12.3.1.12,5]nonadeca-1(17),2,4,14(18),15-pentaen-6-ol (enantiomer 1), Compound 65, and (6R)-12-cyclopropyl-17-(ethylamino)-6,15-bis(trifluoromethyl)-13,19-dioxa-3,4,18-triazatricyclo[12.3.1.12,5]nonadeca-1(17),2,4,14(18),15-pentaen-6-ol (enantiomer 2), Compound 66

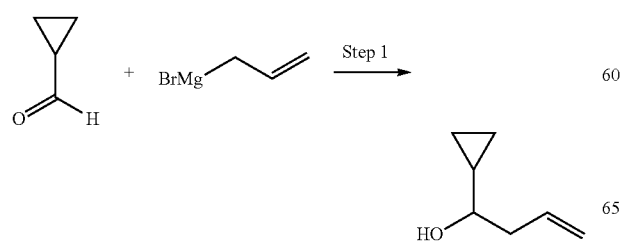

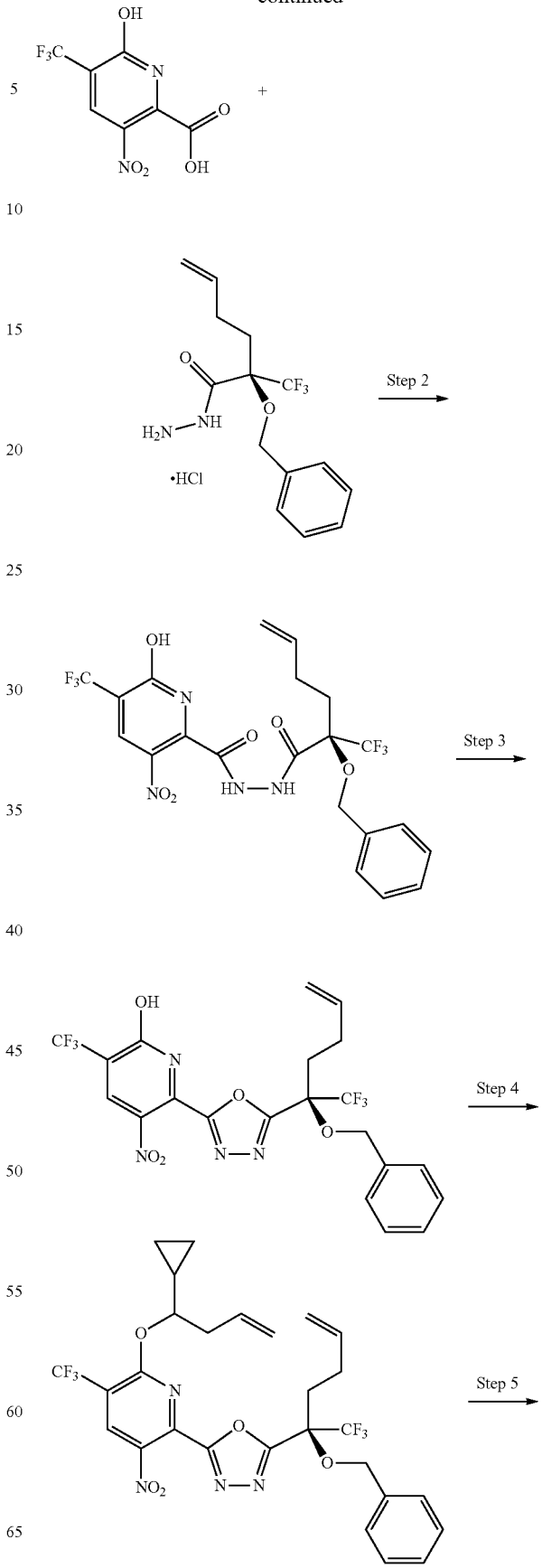

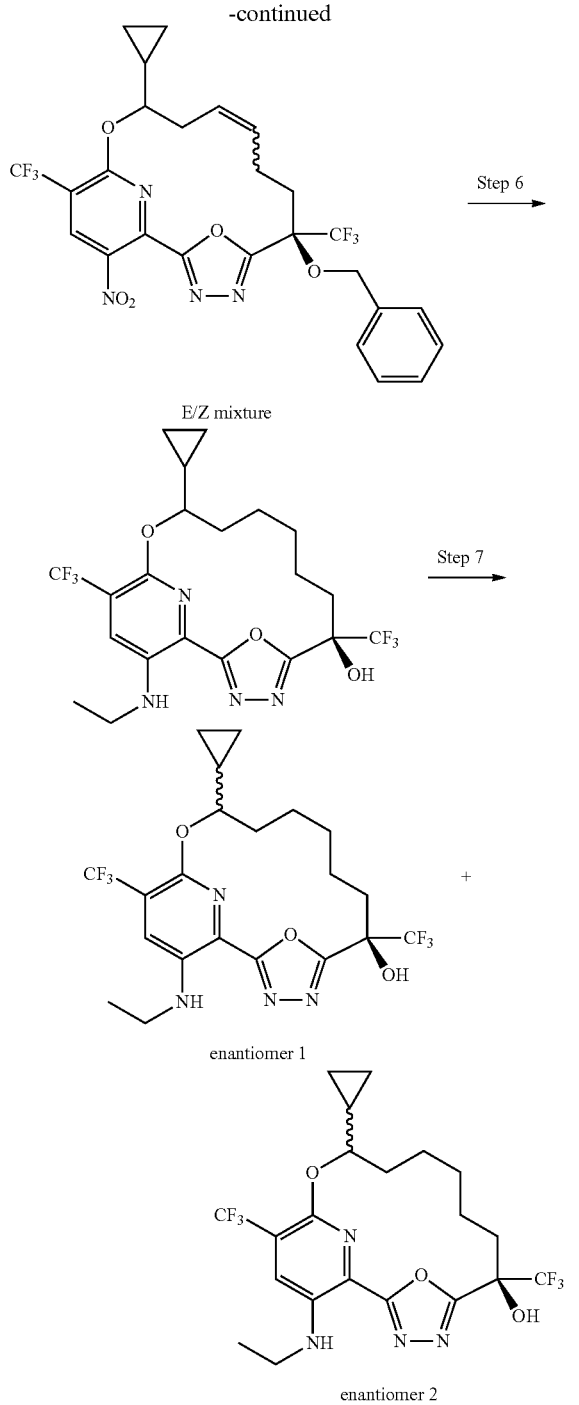

E/Z mixture

Step 7 → enantiomer 1

+ enantiomer 2

Step 1: 1-Cyclopropylbut-3-en-1-ol

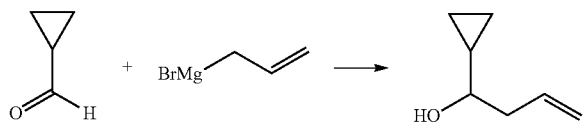

To a stirred solution of cyclopropanecarbaldehyde (5.0427 g, 5.6 mL, 69.068 mmol) in diethyl ether (50 mL) in a three neck 250 mL flask was added a solution of allyl(bromo)magnesium (69.5 mL of 1 M, 69.5 mmol) in diethyl ether at −20° C. The resulting solution was stirred for 1 h from −20° C. to 0° C. The reaction was then quenched with the addition of 25 mL aqueous saturated solution of ammonium chloride and extracted with 2×50 mL of diethyl ether. The combined organic extracts were washed with 1×50 mL of brine, dried over anhydrous sodium sulfate and concentrated under vacuum to afford as a light yellow oil, 1-cyclopropylbut-3-en-1-ol (6.008 g, 74%). $^1$H NMR (400 MHz, DMSO-$d_6$) δ 5.88 (ddt, J=17.2, 10.2, 7.1 Hz, 1H), 5.08-4.94 (m, 2H), 4.54-4.35 (m, 1H), 2.91 (q, J=6.5 Hz, 1H), 2.28-2.14 (m, 2H), 0.84-0.73 (m, 1H), 0.40-0.28 (m, 2H), 0.27-0.19 (m, 1H), 0.18-0.09 (m, 1H).

Step 2: N-[(2R)-2-Benzyloxy-2-(trifluoromethyl) hex-5-enoyl]-6-hydroxy-3-nitro-5-(trifluoromethyl) pyridine-2-carbohydrazide

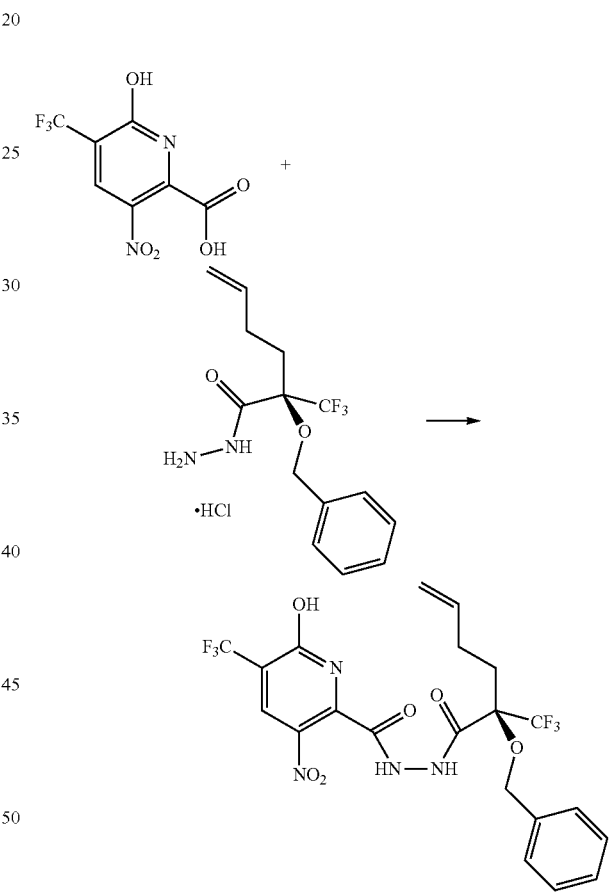

6-Hydroxy-3-nitro-5-(trifluoromethyl)pyridine-2-carboxylic acid (203 mg, 0.8052 mmol) and (2R)-2-benzyloxy-2-(trifluoromethyl)hex-5-enehydrazide (hydrochloride salt) (260 mg, 0.7675 mmol) were dissolved in a mixture of ethyl acetate (5 mL) and triethylamine (326.7 mg, 0.45 mL, 3.2286 mmol). Propylphosphonic anhydride (0.7 mL of 1.68 M, 1.176 mmol) solution in ethyl acetate was then added at room temperature (20 to 25° C.) and the reaction stirred for 3.5 hours at room temperature. It was then quenched with an aqueous saturated solution of ammonium chloride (5 mL). The phases were separated and the organic phase was washed with an aqueous saturated solution of ammonium chloride (5 mL) and then with an aqueous (5% w/v) solution of sodium bicarbonate (2×5 mL), dried over anhydrous sodium sulfate, filtered and concentrated by evaporation under reduced pressure. Drying on a vacuum pump overnight gave as a yellow solid, N'-[(2R)-2-benzyloxy-2-(trifluoromethyphex-5-enoyl]-6-hydroxy-3-nitro-5-(trifluoromethyl)pyridine-2-carbohydrazide (430 mg, 96%). ESI-MS m/z calc. 536.1131, found 537.2 (M+1)+; Retention time: 3.04 minutes. LCMS Method: Kinetex Polar $C_{18}$ column (3.0×50 mm, 2.6 µm particle size, 6 minute run, 5% to 95% acetonitrile in water (0.1% formic acid modifier), flow rate=1.2 mL/min).

Step 3: 6-[5-[(1R)-1-Benzyloxy-1-(trifluoromethyl)pent-4-enyl]-1,3,4-oxadiazol-2-yl]-5-nitro-3-(trifluoromethyl)pyridin-2-ol

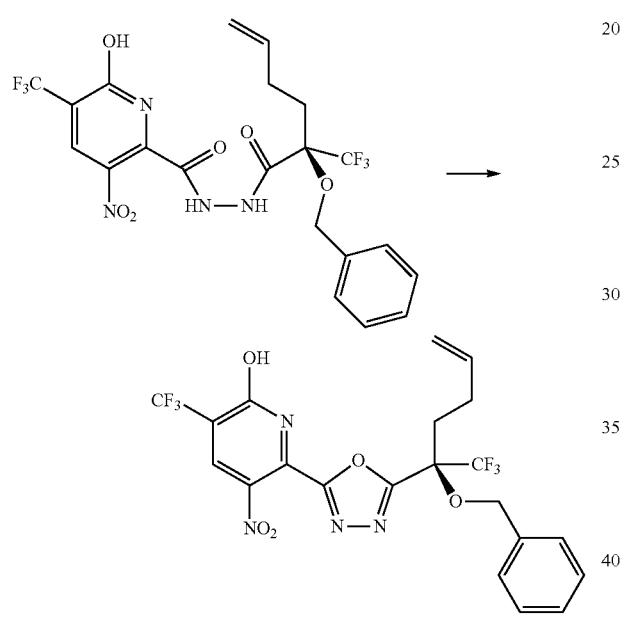

Step 4: 2-[(1R)-1-Benzyloxy-1-(trifluoromethyl)pent-4-enyl]-5-[6-(1-cyclopropylbut-3-enoxy)-3-nitro-5-(trifluoromethyl)-2-pyridyl]-1,3,4-oxadiazole

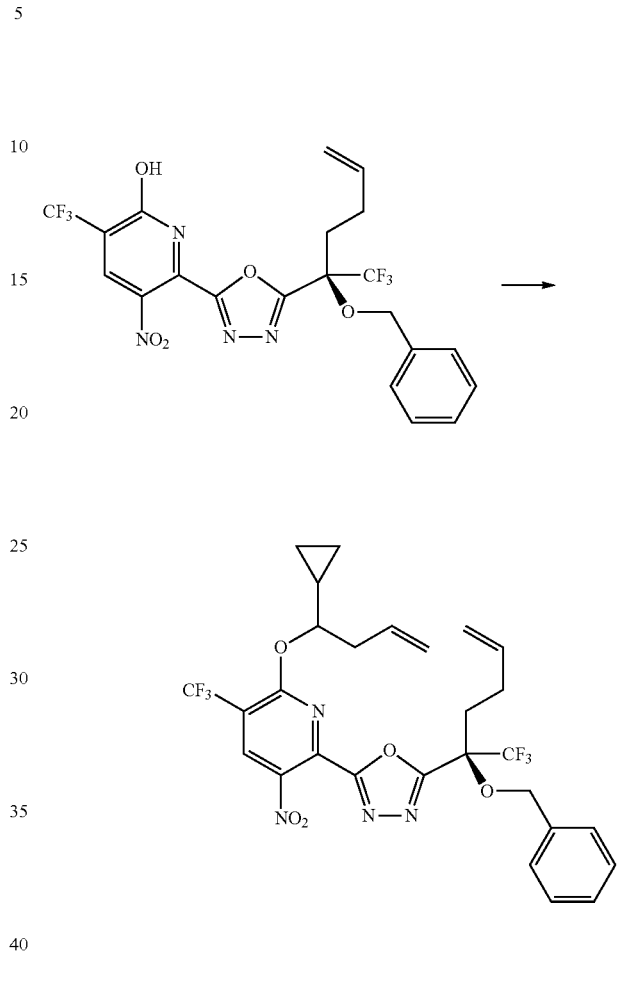

To a solution of N'-[(2R)-2-benzyloxy-2-(trifluoromethyphex-5-enoyl]-6-hydroxy-3-nitro-5-(trifluoromethyl)pyridine-2-carbohydrazide (6.47 g, 8.4557 mmol) and N,N-diisopropylethylamine (5.8618 g, 7.9 mL, 45.355 mmol) in acetonitrile (200 mL) at 0° C. was added 4-methylbenzenesulfonyl chloride (3.71 g, 19.460 mmol) in portions. After the addition, the cooling bath was removed and the reaction was stirred at 26° C. for 44 hours. The volatiles were removed by evaporation under reduced pressure. The residue was dissolved in ethyl acetate (180 mL) and washed with 0.5 N aqueous solution of hydrochloric acid (3×25 mL) and brine (2×15 mL). The organic layer was dried over anhydrous sodium sulfate, filtered and concentrated by evaporation under reduced pressure which gave 6-[5-[(1R)-1-benzyloxy-1-(trifluoromethyl)pent-4-enyl]-1,3,4-oxadiazol-2-yl]-5-nitro-3-(trifluoromethyl)pyridin-2-ol (6.67 g, 70%) as brown sticky residue. ESI-MS m/z calc. 518.1025, found 519.1 (M+1)+; Retention time: 3.1 minutes. LCMS Method: XBridge $C_{18}$ column (4.6×75 mm, 5 mm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

To a 25 mL round bottom flask containing 6-[5-[(1R)-1-benzyloxy-1-(trifluoromethyl)pent-4-enyl]-1,3,4-oxadiazol-2-yl]-5-nitro-3-(trifluoromethyl)pyridin-2-ol (418 mg, 0.7395 mmol) was added triphenylphosphine (395 mg, 1.506 mmol) and 1-cyclopropylbut-3-en-1-ol (245.1 mg, 0.2 mL, 2.0758 mmol), then toluene (8.5 mL). To the mixture stirring at room temperature was added dropwise DIAD (308.1 mg, 0.3 mL, 1.5237 mmol) then continued stirring for 4 hours. After standing at room temperature for 72 hours, the mixture was concentrated by evaporation under reduced pressure. The residue was purified by reverse phase chromatography on a $C_{18}$ 50 g aqueous column, eluting with a 5% to 80% gradient of acetonitrile in basic water (pH=10, ammonium bicarbonate) for 8 column volumes, then with 80% acetonitrile in basic water (pH=10, ammonium bicarbonate) over 10 column volumes. Selected fractions were concentrated by evaporation under reduced pressure to afford 2-[(1R)-1-benzyloxy-1-(trifluoromethyl)pent-4-enyl]-5-[6-(1-cyclopropylbut-3-enoxy)-3-nitro-5-(trifluoromethyl)-2-pyridyl]-1,3,4-oxadiazole (250 mg, 54%) as a light yellow solid. ESI-MS m/z calc. 612.1807, found 613.2 (M+1)+; Retention time: 4.08 minutes. LCMS Method: Kinetex Polar $C_{18}$ column (3.0×50 mm, 2.6 µm particle size, 6 minute run, 5% to 95% acetonitrile in water (0.1% formic acid modifier), flow rate=1.2 mL/min).

Step 5: (6R)-6-Benzyloxy-12-cyclopropyl-17-nitro-6,15-bis(trifluoromethyl)-13,19-dioxa-3,4,18-triazatricyclo[12.3.1.12,5]nonadeca-1(17),2,4,9,14(18),15-hexaene (E/Z Mixture)

Step 6: (6R)-12-Cyclopropyl-17-(ethylamino)-6,15-bis(trifluoromethyl)-13,19-dioxa-3,4,18-triazatricyclo[12.3.1.12,5]nonadeca-1(17),2,4,14(18),15-pentaen-6-ol

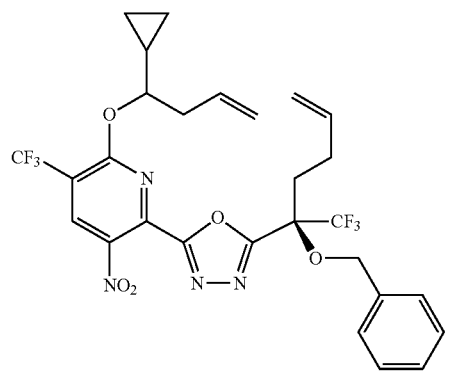

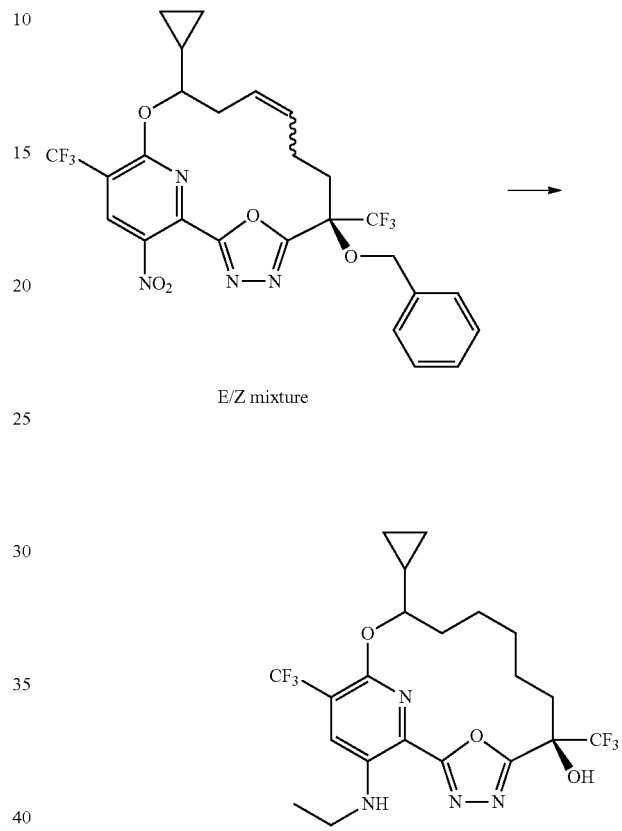

A dried 250-mL flask was charged with 1,2-dichloroethane (98 mL). The solvent was bubbled with nitrogen for 30 min. Zhan catalyst-1B (29 mg, 0.0395 mmol) was added under a gentle flow of nitrogen. The mixture was bubbled with nitrogen for 10 min and heated to 60° C. A nitrogen-bubbled solution of 2-[(1R)-1-benzyloxy-1-(trifluoromethyl)pent-4-enyl]-5-[6-(1-cyclopropylbut-3-enoxy)-3-nitro-5-(trifluoromethyl)-2-pyridyl]-1,3,4-oxadiazole (98 mg, 0.1578 mmol) was added dropwise over 1 h. The mixture was stirred at 70° C. for 1.25 h and then cooled to room temperature. Then, 5 drops of DMSO were added to quench the catalyst. The mixture was concentrated on silica gel (3 g) and purified by silica gel chromatography (eluting with a gradient of 5% to 25% ethyl acetate in heptanes) to afford (6R)-6-benzyloxy-12-cyclopropyl-17-nitro-6,15-bis(trifluoromethyl)-13,19-dioxa-3,4,18-triazatricyclo[12.3.1.12,5]nonadeca-1(17),2,4,9,14(18),15-hexaene (E/Z mixture) (60 mg, 59%) as a light yellow solid. ESI-MS m/z calc. 584.1494, found 585.2 (M+1)$^+$; Retention time: 4.22 minutes. LCMS Method: XBridge $C_{18}$ column (4.6×75 mm, 5 mm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

A solution of (6R)-6-benzyloxy-12-cyclopropyl-17-nitro-6,15-bis(trifluoromethyl)-13,19-dioxa-3,4,18-triazatricyclo[12.3.1.12,5]nonadeca-1(17),2,4,9,14(18),15-hexaene (E/Z mixture) (60 mg, 0.1027 mmol) in ethanol (4 mL) was bubbled with nitrogen gas for 5 minutes. After adding palladium on carbon (63 mg, 5 w/w, 0.0296 mmol), hydrogen gas was bubbled in the reaction mixture for 5 minutes and then the reaction was left to stir under one atmosphere of hydrogen for about 22 hours. The reaction was purged twice with nitrogen gas then filtered over a pad of celite and the cake was washed with ethanol (30 mL). The volatiles were removed under reduced pressure to afford a 54 mg residue as an intense yellow oil. The residue was dry loaded on silica gel and purified by silica gel chromatography eluting with gradient of ethyl acetate (0% to 30%) in heptanes which afforded (6R)-12-cyclopropyl-17-(ethylamino)-6,15-bis(trifluoromethyl)-13,19-dioxa-3,4,18-triazatricyclo[12.3.1.12,5]nonadeca-1(17),2,4,14(18),15-pentaen-6-ol (22 mg, 43%) as a light yellow solid. ESI-MS m/z calc. 494.1753, found 495.2 (M+1)$^+$; Retention time: 3.8 minutes. LCMS Method: Kinetex Polar $C_{18}$ column (3.0×50 mm, 2.6 μm particle size, 6 minute run, 5% to 95% acetonitrile in water (0.1% formic acid modifier), flow rate=1.2 mL/min).

Step 7: (6R)-12-Cyclopropyl-17-(ethylamino)-6,15-bis(trifluoromethyl)-13,19-dioxa-3,4,18-triazatricyclo[12.3.1.1²,⁵]nonadeca-1(17),2,4,14(18),15-pentaen-6-ol (enantiomer 1), Compound 65, and (6R)-12-cyclopropyl-17-(ethylamino)-6,15-bis(trifluoromethyl)-13,19-dioxa-3,4,18-triazatricyclo[12.3.1.1²,⁵]nonadeca-1(17),2,4,14(18),15-pentaen-6-ol (enantiomer 2), Compound 66

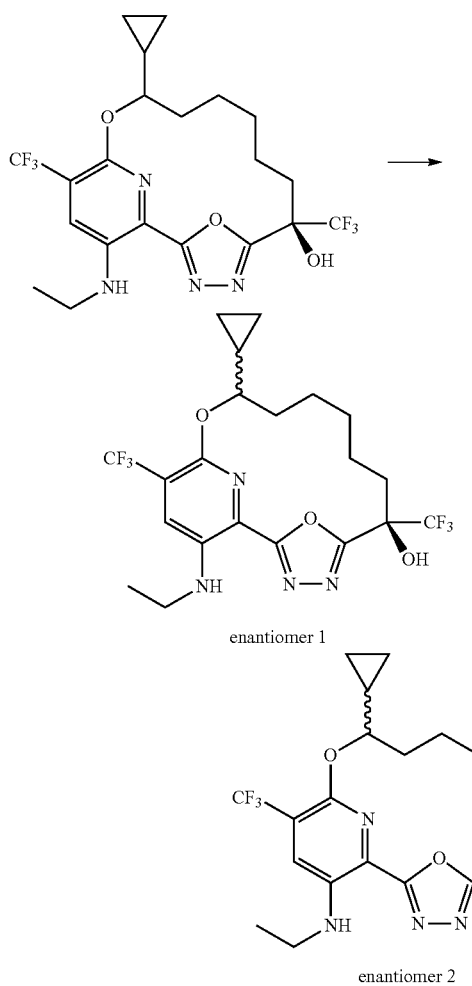

enantiomer 1 enantiomer 2

A diastereomeric mixture of (6R)-12-cyclopropyl-17-(ethylamino)-6,15-bis(trifluoromethyl)-13,19-dioxa-3,4,18-triazatricyclo[12.3.1.1²,⁵]nonadeca-1(17),2,4,14(18),15-pentaen-6-ol (22 mg, 0.0438 mmol) was subjected to SFC separation using the following conditions: Lux 5 μm Cellulose 4 column, (250×21.2 mm, 6.67 mg/injection) at 40° C., eluant: 7% EtOH (0.1% diethylamine), 93% $CO_2$, flow rate: 55 mL/min, injection volume: 400 μL, pressure: 100 bar, wavelength: 250 nm. Evaporation of the solvents and lyophilization provided two isomers:

The first isomer to elute was isolated as a yellow solid, (6R)-12-cyclopropyl-17-(ethylamino)-6,15-bis(trifluoromethyl)-13,19-dioxa-3,4,18-triazatricyclo[12.3.1.1²,⁵]nonadeca-1(17),2,4,14(18),15-pentaen-6-ol (enantiomer 1) (3.8 mg, 17%, 98.4% de). $^1$H NMR (400 MHz, DMSO-$d_6$) δ 7.63 (s, 1H), 7.59 (s, 1H), 6.37 (t, J=5.5 Hz, 1H), 4.17-4.06 (m, 1H), 3.46-3.35 (m, 2H), 2.62-2.53 (m, 1H), 2.21-2.04 (m, 2H), 1.77-1.41 (m, 7H), 1.23 (t, J 7.1 Hz, 3H), 1.17-1.11 (m, 1H), 0.64-0.55 (m, 1H), 0.52-0.39 (m, 2H), 0.31-0.23 (m, 1H). $^{19}$F NMR (377 MHz, DMSO-$d_6$) δ −62.11 (s, 3F), −79.02 (s, 3F). ESI-MS m/z calc. 494.17526, found 495.2 $(M+1)^+$; Retention time: 3.81 minutes. LCMS Method: Kinetex Polar $C_{18}$ column (3.0×50 mm, 2.6 μm particle size, 6 minute run, 5% to 95% acetonitrile in water (0.1% formic acid modifier), flow rate=1.2 mL/min).

The second peak to elute was isolated as a yellow solid, (6R)-12-cyclopropyl-17-(ethylamino)-6,15-bis(trifluoromethyl)-13,19-dioxa-3,4,18-triazatricyclo[12.3.1.1²,⁵]nonadeca-1(17),2,4,14(18),15-pentaen-6-ol (enantiomer 2) (4.6 mg, 21%, 99.9% de). $^1$H NMR (400 MHz, DMSO-$d_6$) δ 7.63 (s, 1H), 7.58 (s, 1H), 6.36 (t, J=5.6 Hz, 1H), 4.26-4.15 (m, 1H), 3.48-3.33 (m, 2H), 2.48-2.44 (m, 1H), 2.31-2.22 (m, 1H), 2.17-2.06 (m, 1H), 1.83-1.61 (m, 3H), 1.57-1.36 (m, 4H), 1.24 (t, J 7.1 Hz, 3H), 1.18-1.14 (m, 1H), 0.66-0.58 (m, 1H), 0.52-0.37 (m, 2H), 0.32-0.23 (m, 1H). $^{19}$F NMR (377 MHz, DMSO-$d_6$) δ −62.13 (s, 3F), −76.35 (s, 3F). ESI-MS m/z calc. 494.17526, found 495.2 $(M+1)^+$; Retention time: 3.8 minutes. LCMS Method: Kinetex Polar $C_{18}$ column (3.0×50 mm, 2.6 μm particle size, 6 minute run, 5% to 95% acetonitrile in water (0.1% formic acid modifier), flow rate=1.2 mL/min).

Example 47: Preparation of (6R,12R)-17-amino-15-(difluoromethyl)-12-methyl-6-(trifluoromethyl)-13,19-dioxa-3,4,18-triazatricyclo[12.3.1.1²,⁵]nonadeca-1(18),2,4,14,16-pentaen-6-ol, Compound 67

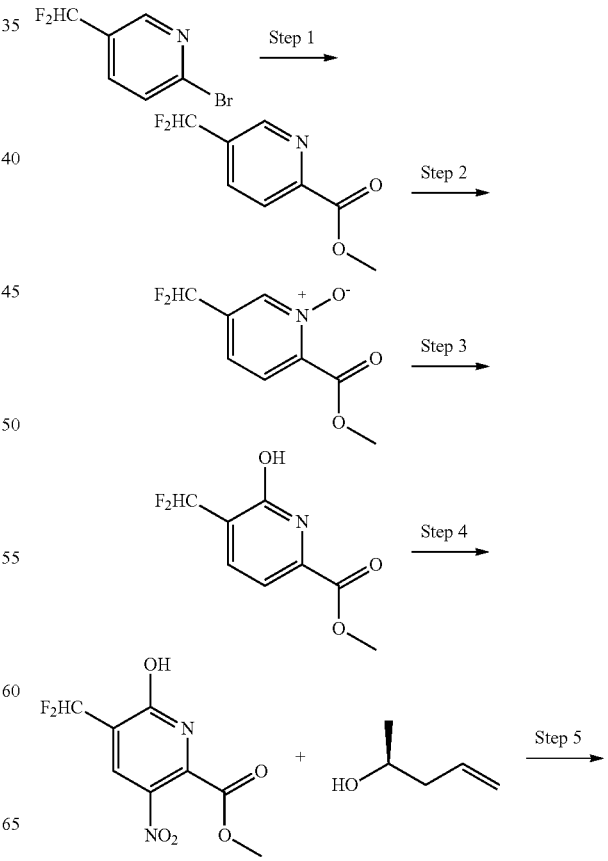

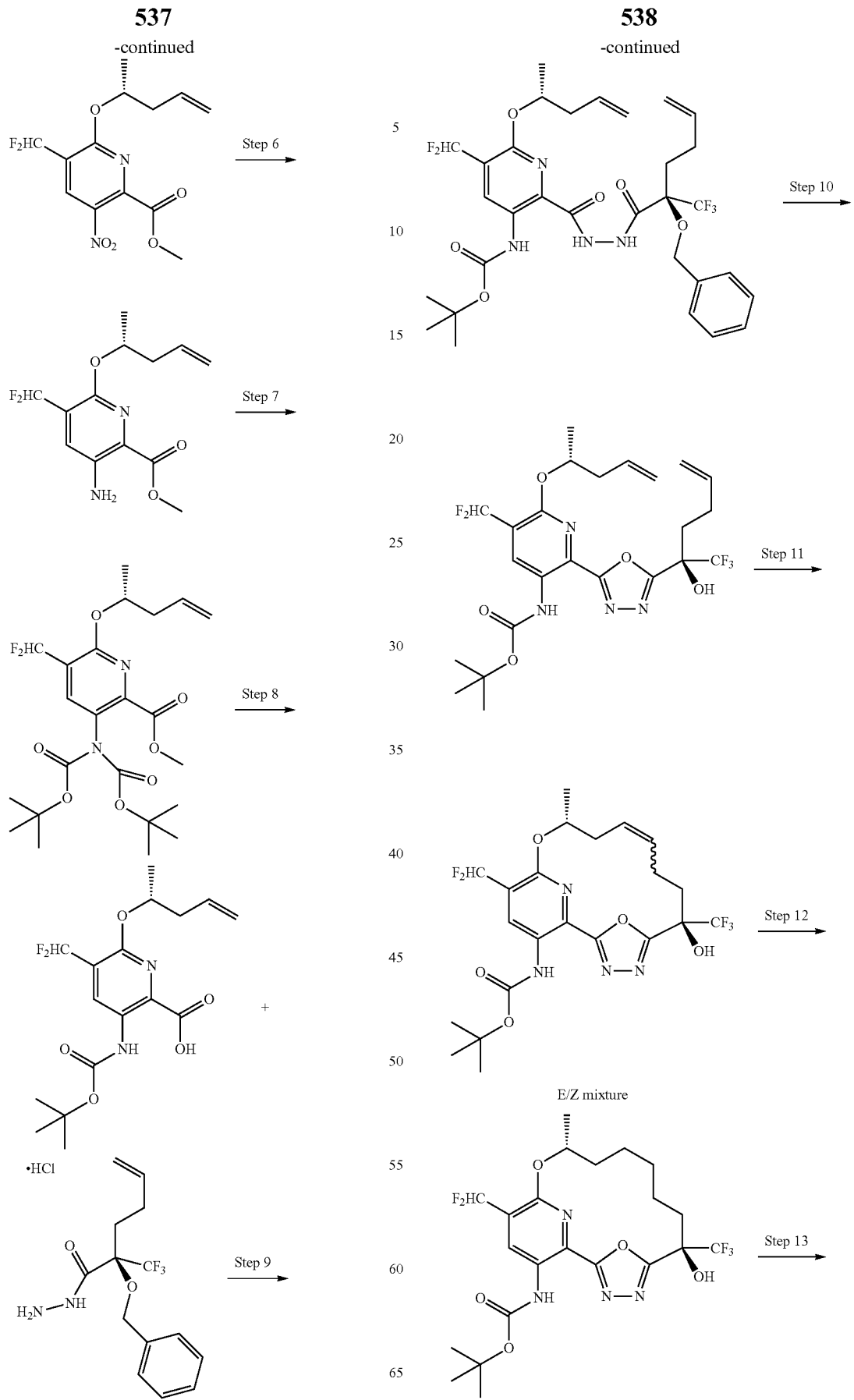

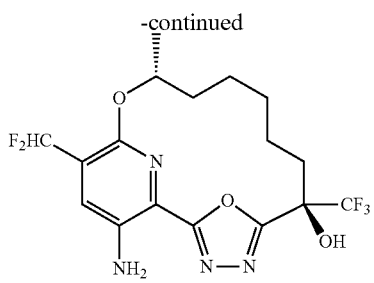

Step 1: Methyl 5-(difluoromethyl)pyridine-2-carboxylate

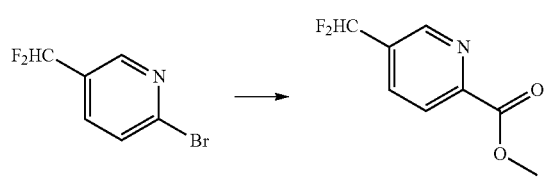

In an autoclave was added 2-bromo-5-(difluoromethyl)pyridine (24 g, 115.38 mmol), methanol (240 mL), triethylamine (27.588 g, 38 mL, 272.64 mmol) and [1,1'-bis(diphenylphosphino)ferrocene]dichloropalladium(II) (2.4 g, 3.28 mmol). The autoclave was purged with nitrogen, then with carbon monoxide. The mixture was heated to 130° C. and the carbon monoxide pressure was adjusted to 120 psi. The mixture was stirred 3 h at 130° C., then cooled down to 25° C. overnight. The mixture was purged with nitrogen and concentrated under vacuum. The resulting solid was diluted with ethyl acetate (500 mL). Water (200 mL) and sodium carbonate (20 g) were added and the mixture was vigorously stirred for 10 minutes. The layers were separated and the organic layer was washed with water (200 mL) and brine (200 mL), dried over sodium sulfate, then filtered and evaporated under reduced pressure. The residue was purified by silica gel column chromatography (eluting from 20% to 50% of ethyl acetate in heptanes) to afford methyl 5-(difluoromethyl)pyridine-2-carboxylate (8.1 g, 38%) as a white solid. $^1$H NMR (400 MHz, CDCl$_3$) δ 8.89 (s, 1H), 8.25 (d, J=8.1 Hz, 1H), 8.02 (d, J=8.1 Hz, 1H), 6.97-6.61 (m, 1H), 4.05 (s, 3H). $^{19}$F NMR (377 MHz, CDCl$_3$) δ −113.58 (d, J=54.5 Hz, 2F). ESI-MS m/z calc. 187.04448, found 188.2 (M+1)$^+$; Retention time: 1.48 minutes. LCMS Method: Kinetex Polar C$_{18}$ column (3.0×50 mm, 2.6 μm particle size, 3 minute run, 5% to 95% acetonitrile in water (0.1% formic acid modifier), flow rate=1.2 mL/min).

Step 2: Methyl 5-(difluoromethyl)-1-oxido-pyridin-1-ium-2-carboxylate

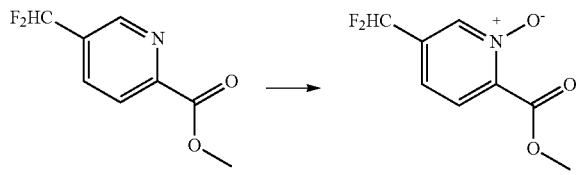

Urea hydrogen peroxide (13.7 g, 145.64 mmol) was stirred into a solution of methyl 5-(difluoromethyl)pyridine-2-carboxylate (8.1 g, 43.282 mmol) in DCE (70 mL). Trifluoroacetic anhydride (24.025 g, 15.9 mL, 114.39 mmol) was then added over 20 minutes at a temperature of −10° C., using a cooling bath (CO$_2$/acetone bath). The reaction mixture was then stirred for a further 30 minutes at a temperature of 0° C. and then for 1 hour at ambient temperature. The reaction mixture was poured into ice-water (150 mL) and adjusted to pH=2-3 with around 150 mL of aqueous 1N sodium hydroxide solution. The mixture was diluted with dichloromethane (200 mL) and then layers were separated. The aqueous phase was extracted with dichloromethane (2×150 mL). The combined organic phase was washed with brine (150 mL), dried over anhydrous sodium sulfate, filtered and concentrated under reduced pressure to give methyl 5-(difluoromethyl)-1-oxido-pyridin-1-ium-2-carboxylate (8.39 g, 87%) as a yellow solid. $^1$H NMR (400 MHz, CDCl$_3$) δ 8.41 (s, 1H), 7.72 (d, J=8.1 Hz, 1H), 7.43-7.36 (m, 1H), 6.84-6.47 (m, 1H), 4.03 (s, 3H). $^{19}$F NMR (377 MHz, CDCl$_3$) δ −115.27 (d, J=55.9 Hz, 2F). ESI-MS m/z calc. 203.0394, found 204.1 (M+1)$^+$; Retention time: 0.73 minutes. LCMS Method: Kinetex Polar C$_{18}$ column (3.0×50 mm, 2.6 μm particle size, 3 minute run, 5% to 95% acetonitrile in water (0.1% formic acid modifier), flow rate=1.2 mL/min).

Step 3: Methyl 5-(difluoromethyl)-6-hydroxy-pyridine-2-carboxylate

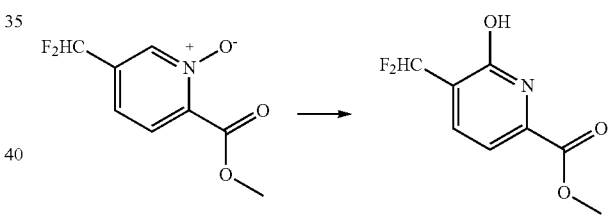

Trifluoroacetic anhydride (84.616 g, 56 mL, 402.87 mmol) was added dropwise to a mixture of methyl 5-(difluoromethyl)-1-oxido-pyridin-1-ium-2-carboxylate (11.63 g, 47.06 mmol) in DMF (130 mL) at a temperature of 0° C. for 30 minutes. The mixture was then heated at 48° C. and was stirred for a further 4 hours then the reaction was stirred at room temperature overnight. The reaction mixture was concentrated under reduced pressure to remove trifluoroacetic anhydride. The residual DMF solution was poured into water (1 L) at 0° C. The precipitated solid was collected by filtration and washed with water (200 mL). The solid was dried under high vacuum which gave as an off-white solid, methyl 5-(difluoromethyl)-6-hydroxy-pyridine-2-carboxylate (5.74 g, 60%). $^1$H NMR (400 MHz, DMSO-d$_6$) δ 12.29 (br. s., 1H), 7.88 (d, J=7.3 Hz, 1H), 7.13 (s, 1H), 7.07-6.76 (m, 1H), 3.87 (s, 3H). $^{19}$F NMR (377 MHz, DMSO-d$_6$) δ −118.60 (br. s., 2F). ESI-MS m/z calc. 203.0394, found 204.1 (M+1)$^+$; Retention time: 1.34 minutes. LCMS Method: Kinetex Polar C$_{18}$ column (3.0×50 mm, 2.6 μm particle size, 3 minute run, 5% to 95% acetonitrile in water (0.1% formic acid modifier), flow rate=1.2 mL/min).

Step 4: Methyl 5-(difluoromethyl)-6-hydroxy-3-nitro-pyridine-2-carboxylate

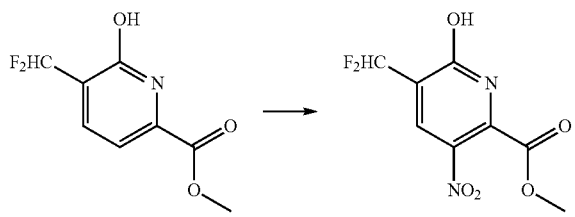 [SMILES: COC(=O)c1ccc(C(F)F)c(O)n1 ; COC(=O)c1nc(O)c(C(F)F)cc1[N+](=O)[O-]]

To an ice-cooled solution of methyl 5-(difluoromethyl)-6-hydroxy-pyridine-2-carboxylate (7.43 g, 36.575 mmol) in sulfuric acid (48 mL of 18.4 M, 883.2 mmol) was added nitric acid (2.5 mL of 15.8 M, 39.5 mmol) dropwise. After 5 min, the ice bath was removed and the reaction mixture was stirred at 45° C. overnight. The reaction was precipitated on ice-water (300 mL). The solution was cooled at 0° C. for 15 minutes then the solid was isolated by filtration and washed with water (200 mL). The solid was dried overnight under high vacuum to give methyl 5-(difluoromethyl)-6-hydroxy-3-nitro-pyridine-2-carboxylate (5.47 g, 56%) as an off-white solid. $^1$H NMR (400 MHz, DMSO-$d_6$) δ 8.41 (s, 1H), 7.19-6.75 (m, 1H), 3.94 (s, 3H). $^{19}$F NMR (377 MHz, DMSO-$d_6$) δ −118.87 (d, J=54.5 Hz, 2F). ESI-MS m/z calc. 248.02448, found 249.1 (M+1)$^+$; Retention time: 1.6 minutes. LCMS Method: Kinetex Polar $C_{18}$ column (3.0×50 mm, 2.6 μm particle size, 3 minute run, 5% to 95% acetonitrile in water (0.1% formic acid modifier), flow rate=1.2 mL/min).

Step 5: Methyl 5-(difluoromethyl)-6-[(1R)-1-methylbut-3-enoxy]-3-nitro-pyridine-2-carboxylate

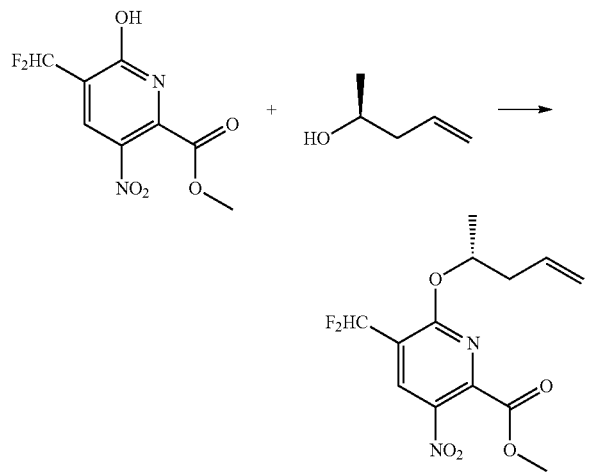

To a solution of methyl 5-(difluoromethyl)-6-hydroxy-3-nitro-pyridine-2-carboxylate (1.6 g, 6.448 mmol) and (2S)-pent-4-en-2-ol (837 mg, 1 mL, 9.7176 mmol) in toluene (31 mL) was added triphenyl phosphine (2.5 g, 9.5316 mmol). After stirring at room temperature for 10 minutes, DIAD (1.9513 g, 1.9 mL, 9.65 mmol) was added and the mixture was stirred at room temperature for 16 h. About half of the toluene was evaporated under reduced pressure and the crude was directly loaded onto a 120 g silica cartridge. Silica gel chromatography purification was performed using a gradient of 0% to 5% EtOAc in heptanes. Evaporation of the volatiles from the fractions containing the product afforded methyl 5-(difluoromethyl)-6-[(1R)-1-methylbut-3-enoxy]-3-nitro-pyridine-2-carboxylate (1.7 g, 82%) as a light yellow oil. $^1$H NMR (400 MHz, CDCl$_3$) δ 8.61 (s, 1H), 6.80 (t, J=54.5 Hz, 1H), 5.86-5.72 (m, 1H), 5.51 (m, J=6.2 Hz, 1H), 5.20-5.07 (m, 2H), 4.03 (s, 3H), 2.58-2.42 (m, 2H), 1.41 (d, J=6.4 Hz, 3H). $^{19}$F NMR (377 MHz, CDCl$_3$) δ −118.39 (s, 2F). Retention time: 2.1 minutes. LCMS Method: Kinetex Polar $C_{18}$ column (3.0×50 mm, 2.6 μm particle size, 3 minute run, 5% to 95% acetonitrile in water (0.1% formic acid modifier), flow rate=1.2 mL/min).

Step 6: Methyl 3-amino-5-(difluoromethyl)-6-[(1R)-1-methylbut-3-enoxy]pyridine-2-carboxylate

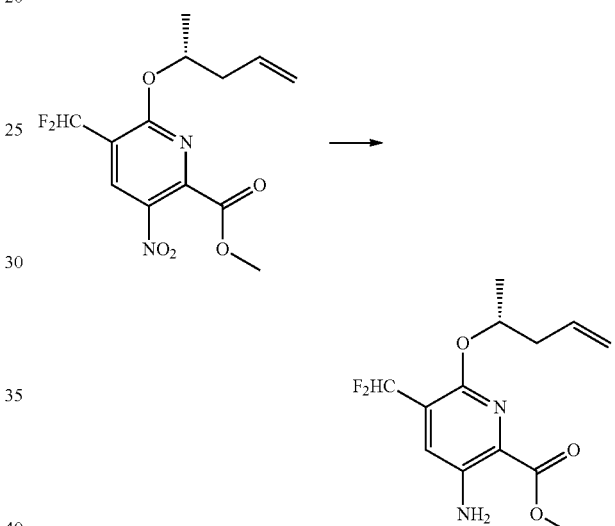

Iron (2.4 g, 42.976 mmol) and ammonium chloride (300 mg, 5.6084 mmol) were added to a solution of methyl 5-(difluoromethyl)-6-[(1R)-1-methylbut-3-enoxy]-3-nitro-pyridine-2-carboxylate (1.4 g, 4.3471 mmol) in ethanol (40 mL) and water (12 mL) at room temperature. The mixture was heated to 80° C. for 16 hours, then cooled to room temperature. The reaction was filtered over Celite, washing the cake with EtOH (100 mL). The volatiles were removed under reduced pressure. The crude residue was purified by reverse phase chromatography on a 120 g $C_{18}$ cartridge using a 40% to 100% gradient of $CH_3CN$ in acidic water (0.1% v/v of formic acid in water). The fractions containing the product were concentrated under reduced pressure until only water was left as solvent. The remaining aqueous phase was extracted with EtOAc (4×30 mL). The combined organic layers were washed with brine, dried over sodium sulfate, filtered and concentrated under reduced pressure which afforded methyl 3-amino-5-(difluoromethyl)-6-1 (1R)-1-methylbut-3-enoxylpyridine-2-carboxylate (727 mg, 58%) as a brown oil. ESI-MS m/z calc. 286.11288, found 287.2 (M+1)$^+$; Retention time: 2.05 minutes. LCMS Method: Kinetex Polar $C_{18}$ column (3.0×50 mm, 2.6 μm particle size, 3 minute run, 5% to 95% acetonitrile in water (0.1% formic acid modifier), flow rate=1.2 mL/min).

Step 7: Methyl 3-[bis(tert-butoxycarbonyl)amino]-5-(difluoromethyl)-6-[(1R)-1-methylbut-3-enoxy]pyridine-2-carboxylate

Step 8: 3-(tert-Butoxycarbonylamino)-5-(difluoromethyl)-6-[(1R)-1-methylbut-3-enoxy]pyridine-2-carboxylic acid

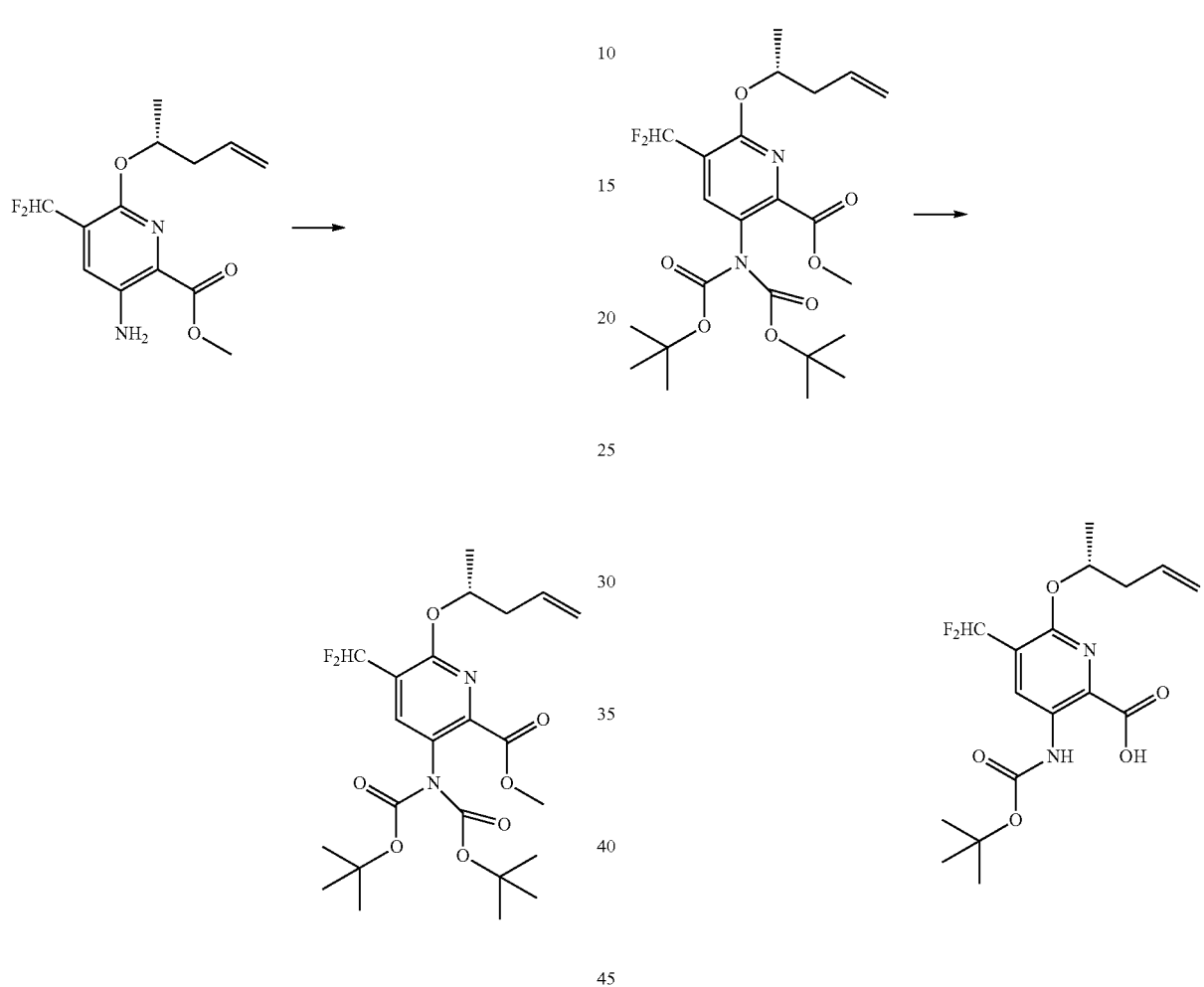

To a solution of methyl 3-amino-5-(difluoromethyl)-6-[(1R)-1-methylbut-3-enoxy]pyridine-2-carboxylate (100 mg, 0.3409 mmol) in DCM (3 mL) was added (Boc)$_2$O (298 mg, 1.3654 mmol) followed by DMAP (4 mg, 0.0327 mmol). The reaction mixture was stirred at room temperature for 20 h and the volatiles were removed under reduced pressure. The crude residue was purified by flash-chromatography on a 24 g silica gel cartridge, using a gradient of 0% to 10% ethyl acetate in heptanes which afforded methyl 3-[bis(tert-butoxy carbonyl)amino]-5-(difluoromethyl)-6-[(1R)-1-methylbut-3-enoxy]pyridine-2-carboxylate (64 mg, 25%) as a light yellow oil. ESI-MS m/z calc. 486.21774, found 387.2 (M−99)$^+$; Retention time: 2.29 minutes. LCMS Method: Kinetex Polar C$_{18}$ column (3.0×50 mm, 2.6 µm particle size, 3 minute run, 5% to 95% acetonitrile in water (0.1% formic acid modifier), flow rate=1.2 mL/min).

To a solution of methyl 3-[bis(tert-butoxycarbonyl)amino]-5-(difluoromethyl)-6-[(1R)-1-methylbut-3-enoxy]pyridine-2-carboxylate (800 mg, 1.6444 mmol) in MeOH (6 mL) and THF (6 mL) was added a solution of lithium hydroxide monohydrate (300 mg, 7.1491 mmol) in water (3 mL). The mixture was stirred at 50° C. for 16 h. The reaction mixture was then cooled down to room temperature and 5 mL of aqueous 1 N HCl was added. The volatiles were removed under reduced pressure and water (5 mL) was added. The pH was adjusted to 2 using aqueous 1 N HCl and the product was extracted with EtOAc (3×15 mL). The combined organic phases were washed with brine (15 mL), dried over sodium sulfate, filtered and concentrated under reduced pressure which afforded 3-(tert-butoxycarbonylamino)-5-(difluoromethyl)-6-[(1R)-1-methylbut-3-enoxy]pyridine-2-carboxylic acid (650 mg, 98%) as a yellow oil. Retention time: 2.23 minutes. LCMS Method: Kinetex Polar C$_{18}$ column (3.0×50 mm, 2.6 µm particle size, 3 minute run, 5% to 95% acetonitrile in water (0.1% formic acid modifier), flow rate=1.2 mL/min).

Step 9: tert-Butyl N-[2-[[[(2R)-2-benzyloxy-2-(trifluoromethyphex-5-enoyl]amino]carbamoyl]-5-(difluoromethyl)-6-[(1R)-1-methylbut-3-enoxy]-3-pyridyl]carbamate

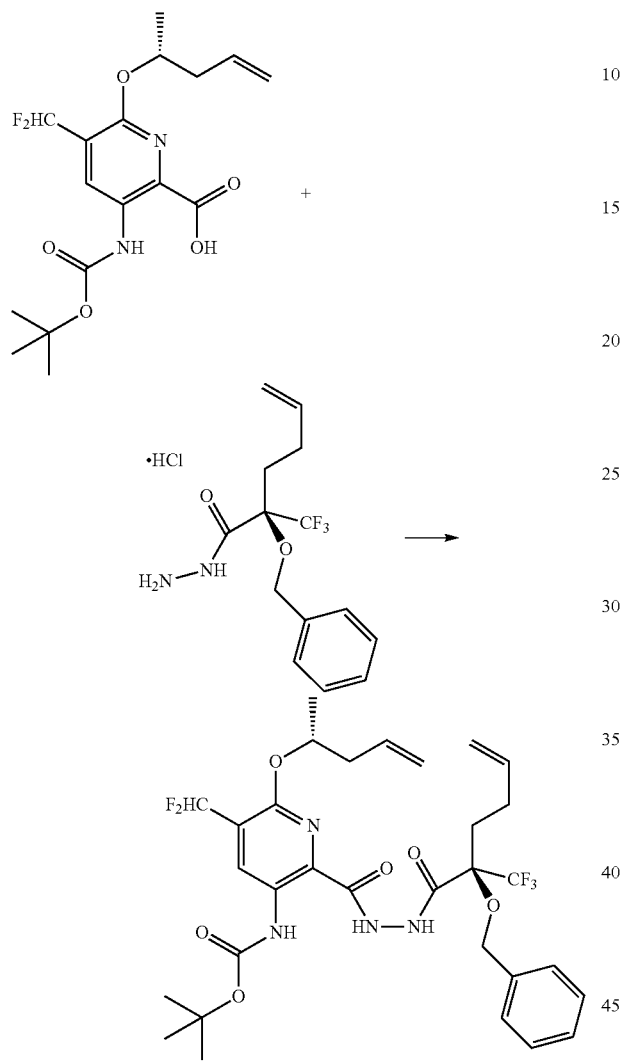

HATU (790 mg, 2.0777 mmol) was added to an orange solution of 3-(tert-butoxycarbonylamino)-5-(difluoromethyl)-6-[(1R)-1-methylbut-3-enoxy]pyridine-2-carboxylic acid (650 mg, 1.7334 mmol), (2R)-2-benzyloxy-2-(trifluoromethyl)hex-5-enehydrazide (hydrochloride salt) (705 mg, 2.0812 mmol) and DIPEA (1.1872 g, 1.6 mL, 9.1858 mmol) in DMF (11 mL) at room temperature. The solution was stirred at room temperature for 2 h. The reaction was directly loaded on a 275 g $C_{18}$ cartridge and the purification was run eluting with a gradient of 50% to 100% $CH_3CN$ in acidic water (0.1% v/v of formic acid in water). The fractions containing the product were concentrated under reduced pressure, co-evaporated with a 1:1 mixture of $CH_3CN$/water and lyophilized which afforded tert-butyl N-[2-[[[(2R)-2-benzyloxy-2-(trifluoromethyphex-5-enoyl]amino]carbamoyl]-5-(difluoromethyl)-6-[(1R)-1-methylbut-3-enoxy]-3-pyridyl]carbamate (690 mg, 61%) as a white solid. $^1$H NMR (400 MHz, DMSO-$d_6$) δ 10.74 (s, 1H), 10.66 (s, 1H), 10.30 (s, 1H), 8.91 (s, 1H), 7.55-7.48 (m, 2H), 7.42-7.35 (m, 2H), 7.35-7.30 (m, 1H), 7.07 (t, J=54.5 Hz, 1H), 6.03-5.79 (m, 2H), 5.79-5.67 (m, 1H), 5.15-5.06 (m, 2H), 5.05-4.99 (m, 2H), 4.91-4.77 (m, 2H), 2.39 (t, J=6.5 Hz, 2H), 2.36-2.27 (m, 2H), 2.26-2.14 (m, 2H), 1.47 (s, 9H), 1.26 (d, J=6.4 Hz, 3H). $^{19}$F NMR (377 MHz, DMSO-$d_6$) δ -71.86 (s, 3F), -117.49 (d, J=54.5 Hz, 2F). ESI-MS m/z calc. 656.2633, found 557.3 (M+1)$^+$; Retention time: 5.36 minutes. LCMS Method: SunFire $C_{18}$ column (75×4.6 mm, 3.5 µm particle size, 6 minute run, mobile phase conditions: initial 95% water +0.1% formic acid/5% acetonitrile +0.1% formic acid, linear gradient to 95% acetonitrile for 4 min, held for 2 min at 95% acetonitrile, temperature=45° C., flow=1.5 mL/min).

Step 10: tert-Butyl N-[2-[5-[(1R)-1-benzyloxy-1-(trifluoromethyl)pent-4-enyl]-1,3,4-oxadiazol-2-yl]-5-(difluoromethyl)-6-[(1R)-1-methylbut-3-enoxy]-3-pyridyl]carbamate

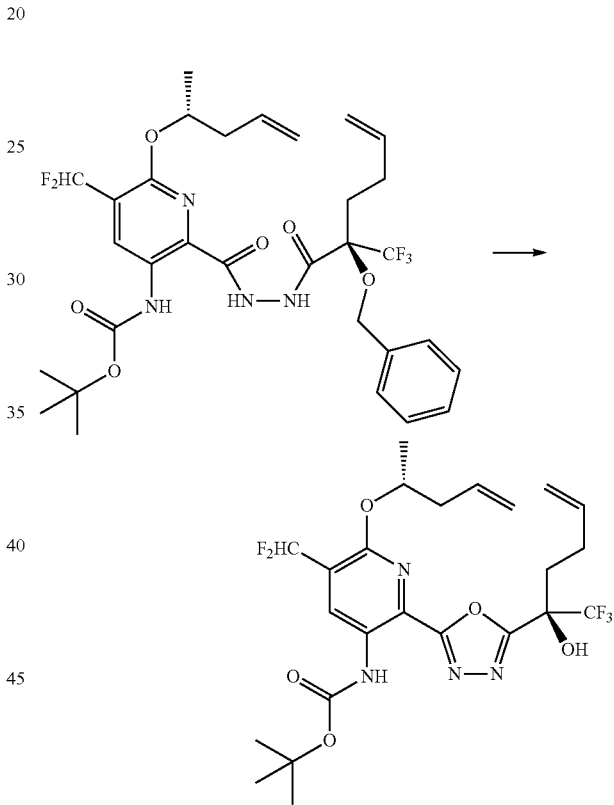

To a solution of tert-butyl N-[2-[[[(2R)-2-benzyloxy-2-(trifluoromethyphex-5-enoyl]amino]carbamoyl]-5-(difluoromethyl)-6-[(1R)-1-methylbut-3-enoxy]-3-pyridyl]carbamate (490 mg, 0.7455 mmol) in 1,2-dichloroethane (15 mL) and N,N-diisopropylethylamine (742 mg, 1 mL, 5.7411 mmol) was added toluenesulfonyl chloride (430 mg, 2.2555 mmol). The reaction was stirred at 50° C. for 20 h then cooled down to room temperature. The volatiles were removed under reduced pressure and the crude residue was purified by reverse phase chromatography on a 50 g $C_{18}$ cartridge using a gradient of 50% to 100% $CH_3CN$ in acidic water (0.1% v/v of formic acid in water). The fractions containing the product were concentrated under reduced pressure which afforded tert-butyl N-[2-[5-[(1R)-1-benzyloxy-1-(trifluoromethyl)pent-4-enyl]-1,3,4-oxadiazol-2-yl]-5-(difluoromethyl)-6-[(1R)-1-methylbut-3-enoxy]-3- pyridyl]carbamate (351 mg, 73%) as a tan oil. ESI-MS m/z calc. 638.25275, found 639.3 (M+1)+; Retention time: 4.82 minutes. LCMS Method:) XBridge C$_{18}$ column (4.6×75 mm, 5 μm particle size, 6 minute run with 1 minute equilibration, initial mobile phase at 95% aqueous NH$_4$HCO$_3$/5% acetonitrile, gradient from 0 to 3 minutes to 95% MeCN and held for 3 minutes, flow=1.5 mL/min).

Step 11: tert-Butyl N-[(6R,12R)-6-benzyloxy-15-(difluoromethyl)-12-methyl-6-(trifluoromethyl)-13,19-dioxa-3,4,18-triazatricyclo[12.3.1.1 2,5]nonadeca-1(18),2,4,9,14,16-hexaen-17-yl]carbamate (E/Z Mixture)

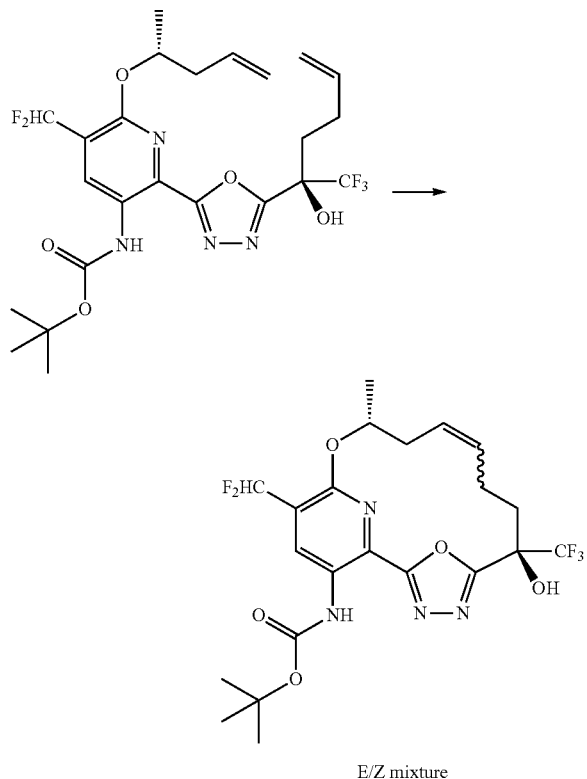

E/Z mixture

A solution of tert-butyl N-[2-[5-[(1R)-1-benzyloxy-1-(trifluoromethyl)pent-4-enyl]-1,3,4-oxadiazol-2-yl]-5-(difluoromethyl)-6-[(1R)-1-methylbut-3-enoxy]-3-pyridyl]carbamate (350 mg, 0.5442 mmol) in dichloroethane (180 mL) was bubbled with nitrogen gas for 1.5 h. The solution was then placed in an oil bath set at 60° C. and a first portion of Zhan catalyst-1B (28 mg, 0.0382 mmol) was added. After 1 h, a second lot of Zhan catalyst-1B (20 mg, 0.0273 mmol) was added and heating was continued for another 1 h. Once cooled to room temperature, the reaction was quenched with DMSO (8 drops), the volatiles were removed under reduced pressure and the residue was directly purified by reverse phase chromatography on a 50 g C$_{18}$ cartridge, eluting with a gradient of 65% to 100% CH$_3$CN in acidic water (0.1% v/v of formic acid in water). The fractions containing the product were concentrated under reduced pressure which afforded tert-butyl N-[(6R,12R)-6-benzyloxy-15-(difluoromethyl)-12-methyl-6-(trifluoromethyl)-13,19-dioxa-3,4,18-triazatricyclo[12.3.1.1 2,5]nonadeca-1(18),2,4,9,14,16-hexaen-17-yl]carbamate (E/Z mixture) (87 mg, 26%) as a brown oil. ESI-MS m/z calc. 610.22144, found 611.3 (M+1)+; Retention time: 4.55 minutes. LCMS Method: XBridge C$_{18}$ column (4.6×75 mm, 5 μm particle size, 6 minute run with 1 minute equilibration, initial mobile phase at 95% aqueous NH$_4$HCO$_3$/5% acetonitrile, gradient from 0 to 3 minutes to 95 MeCN and held for 3 minutes, flow=1.5 mL/min).

Step 12: tert-Butyl N-[(6R,12R)-15-(difluoromethyl)-6-hydroxy-12-methyl-6-(trifluoromethyl)-13,19-dioxa-3,4,18-triazatricyclo[12.3.1.1 2,5]nonadeca-1(18),2,4,14,16-pentaen-17-yl]carbamate

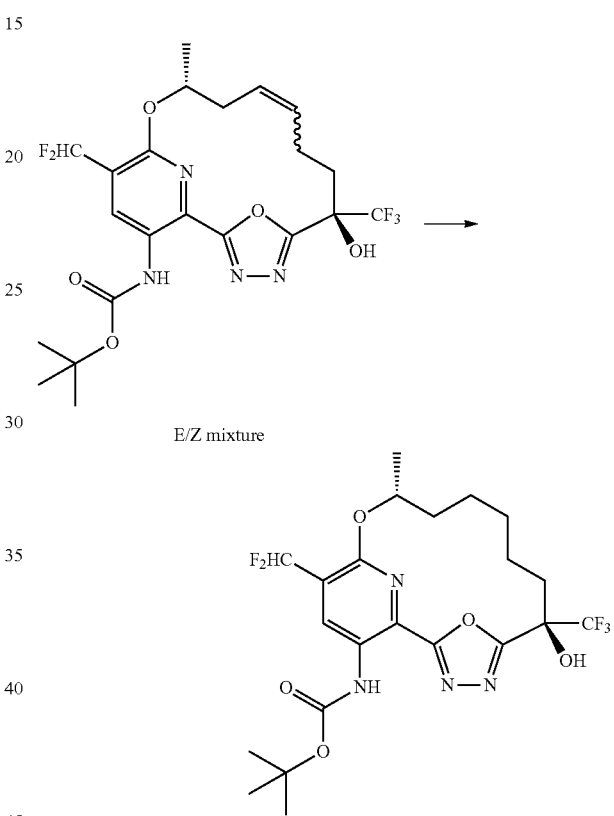

E/Z mixture

To palladium on carbon (85 mg, 5% w/w, 0.0399 mmol) under nitrogen was added a solution of tert-butyl N-[(6R,12R)-6-benzyloxy-15-(difluoromethyl)-12-methyl-6-(trifluoromethyl)-13,19-dioxa-3,4,18-triazatricyclo[12.3.1.1 2,5]nonadeca-1(18),2,4,9,14,16-hexaen-17-yl]carbamate (E/Z mixture) (85 mg, 0.1357 mmol) in THF (10 mL) acidified with a drop of acetic acid (1.056 mg, 1 μL, 0.0176 mmol). Hydrogen was bubbled in for 1 min and the reaction was stirred at room temperature for 16 h. Nitrogen was bubbled in for 5 min and the reaction mixture was filtered over Celite, washing the cake with CH$_3$CN (40 mL). The filtrate was filtered again and the resulting filtrate was concentrated under reduced pressure which afforded tert-butyl N-[(6R,12R)-15-(difluoromethyl)-6-hydroxy-12-methyl-6-(trifluoromethyl)-13,19-dioxa-3,4,18-triazatricyclo[12.3.1.1 2,5]nonadeca-1(18),2,4,14,16-pentaen-17-yl]carbamate (77 mg, 99%) as a tan solid. ESI-MS m/z calc. 522.1902, found 467.2 (M−56)+; Retention time: 2.37 minutes. LCMS Method: Kinetex Polar C$_{18}$ column (3.0×50 mm, 2.6 μm particle size, 3 minute run, 5% to 95% acetonitrile in water (0.1% formic acid modifier), flow rate=1.2 mL/min).

549

Step 13: (6R,12R)-17-Amino-15-(difluoromethyl)-12-methyl-6-(trifluoromethyl)-13,19-dioxa-3,4,18-triazatricyclo[12.3.1.1²,⁵]nonadeca-1(18),2,4,14,16-pentaen-6-ol, Compound 67

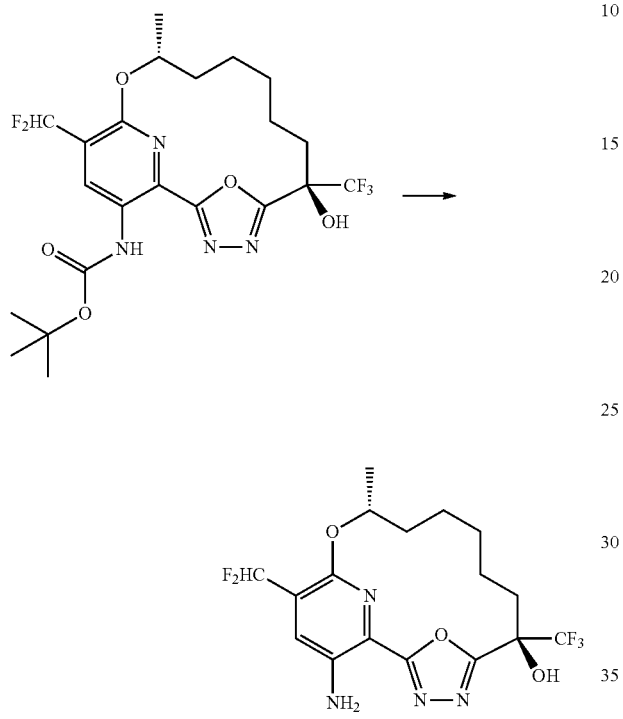

To a solution of tert-butyl N-[(6R,12R)-15-(difluoromethyl)-6-hydroxy-12-methyl-6-(trifluoromethyl)-13,19-dioxa-3,4,18-triazatricyclo[12.3.1.1²,⁵]nonadeca-1(18),2,4,14,16-pentaen-17-yl]carbamate (75 mg, 0.1397 mmol) in DCM (10 mL) was added TFA (2.96 g, 2 mL, 25.96 mmol). The reaction mixture was stirred at room temperature for 1 h. The volatiles were removed under reduced pressure and the crude material was co-evaporated twice with toluene (10 mL each time). The resulting oil was purified by reverse phase chromatography on a 15.5 g $C_{18}$ cartridge, eluting from 5% to 100% acetonitrile in water (pH=7). The fractions containing the product were concentrated under reduced pressure and lyophilized which afforded (6R,12R)-17-amino-15-(difluoromethyl)-12-methyl-6-(trifluoromethyl)-13,19-dioxa-3,4,18-triazatricyclo[12.3.1.1²,⁵]nonadeca-1(18),2,4,14,16-pentaen-6-ol (39 mg, 65%) as a yellow solid. $^1$H NMR (400 MHz, DMSO-$d_6$) δ 7.60 (s, 1H), 7.56 (s, 1H), 7.01 (t, J=54.5 Hz, 1H), 6.29 (s, 2H), 4.81-4.70 (m, 1H), 2.48-2.42 (m, 1H), 2.35-2.23 (m, 1H), 2.16-2.05 (m, 1H), 1.73 (br. s., 2H), 1.60-1.39 (m, 4H), 1.35 (d, J=6.4 Hz, 3H), 1.22-1.11 (m, 1H). $^{19}$F NMR (377 MHz, DMSO-$d_6$) δ −76.38 (s, 3F), −115.10 to −116.53 (m, 1F), −116.69 to −118.00 (m, 1F). ESI-MS m/z calc. 422.13773, found 423.1 (M+1)$^+$; Retention time: 3.22 minutes. LCMS Method: Kinetex Polar $C_{18}$ column (3.0×50 mm, 2.6 μm particle size, 6 minute run, 5% to 95% acetonitrile in water (0.1% formic acid modifier), flow rate=1.2 mL/min).

550

Example 48: Preparation of (6R)-17-amino-12-cyclopropyl-6,15-bis(trifluoromethyl)-13,19-dioxa-3,4,18-triazatricyclo[12.3.1.1²,⁵]nonadeca-1(18),2,4,14,16-pentaen-6-ol (enantiomer 1), Compound 68, and (6R)-17-amino-12-cyclopropyl-6,15-bis(trifluoromethyl)-13,19-dioxa-3,4,18-triazatricyclo[12.3.1.1²,⁵]nonadeca-1(18),2,4,14,16-pentaen-6-ol (enantiomer 2), Compound 69

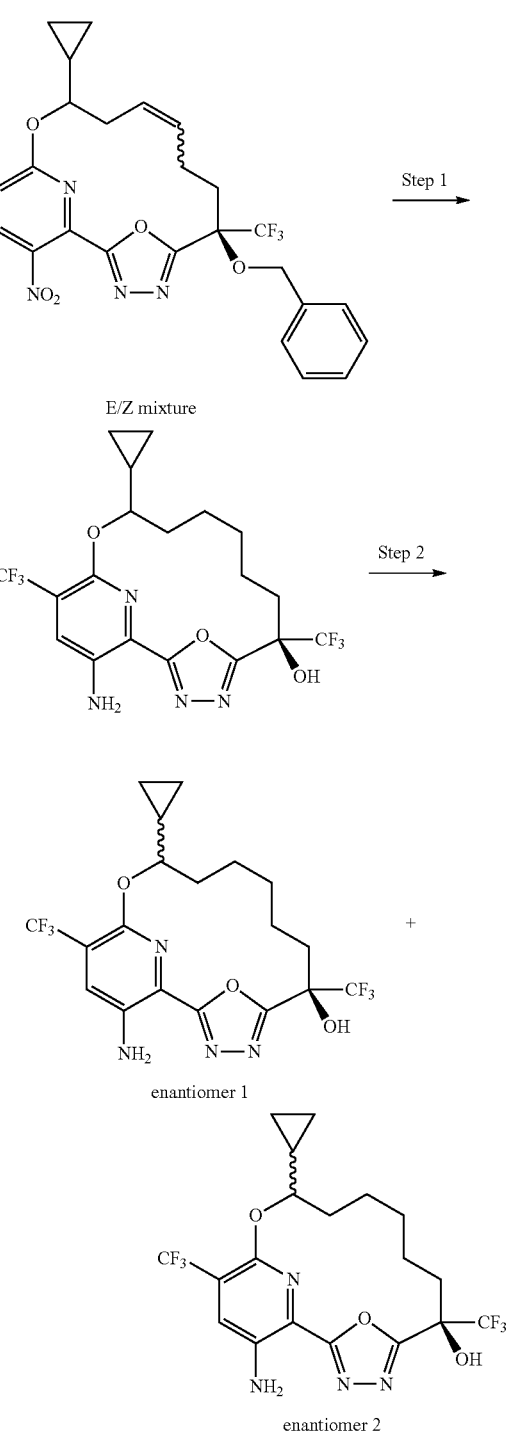

Step 1: (6R)-17-Amino-12-cyclopropyl-6,15-bis(trifluoromethyl)-13,19-dioxa-3,4,18-triazatricyclo[12.3.1.12,5]nonadeca-1(18),2,4,14,16-pentaen-6-ol

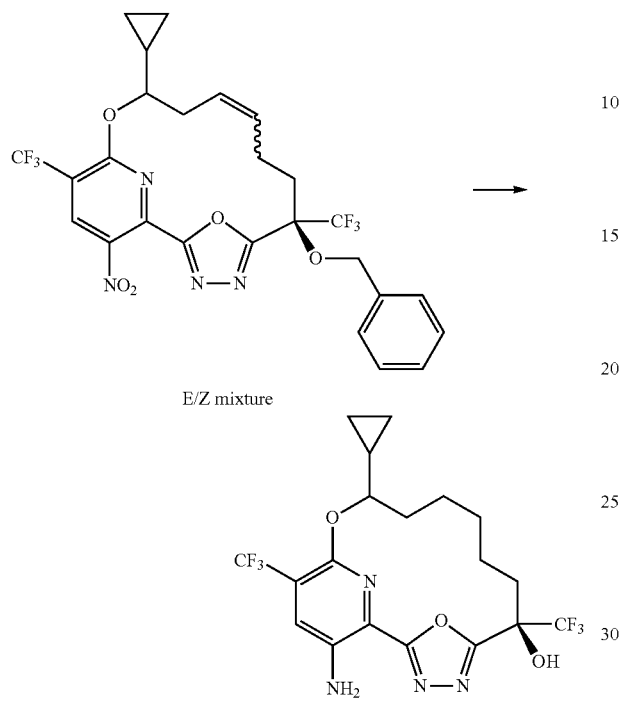

E/Z mixture

A solution of (6R)-6-benzyloxy-12-cyclopropyl-17-nitro-6,15-bis(trifluoromethyl)-13,19-dioxa-3,4,18-triazatricyclo[12.3.1.12,5]nonadeca-1(17),2,4,9,14(18),15-hexaene (E/Z mixture) (48 mg, 0.0812 mmol) in tetrahydrofuran (3 mL) was purged with nitrogen gas for 5 minutes, then added palladium on carbon (53 mg, 5 w/w, 0.0249 mmol) and hydrogen gas was bubbled in for 5 minutes. The reaction was left to stir under one atmosphere of hydrogen for about 22 hours. The reaction was purged with nitrogen gas then filtered over a pad of Celite and the cake was washed with ethyl acetate (30 mL). The volatiles were removed under reduced pressure. The residue was solubilized in tetrahydrofuran (3 mL) and the resulting solution was purged with nitrogen gas for 5 minutes. Added palladium on carbon (53 mg, 5 w/w, 0.0249 mmol) then hydrogen gas was bubbled in for 5 minutes. The reaction was left to stir under one atmosphere of hydrogen for another 22 hours. The reaction was purged again with nitrogen gas, then added more palladium on carbon (25 mg, 5% w/w, 0.0117 mmol) and hydrogen gas was bubbled in for 5 minutes. The reaction was left to stir under one atmosphere of hydrogen for 4 more hours. The reaction was purged with nitrogen gas then filtered over a pad of celite and the cake was washed with ethyl acetate (30 mL). The volatiles were removed under reduced pressure and the resulted yellow oil residue was dry loaded on silica gel and purified by silica gel chromatography eluting with a 0% to 30% gradient of ethyl acetate in heptanes which afforded (6R)-17-amino-12-cyclopropyl-6,15-bis(trifluoromethyl)-13,19-dioxa-3,4,18-triazatricyclo[12.3.1.12,5]nonadeca-1(18),2,4,14,16-pentaen-6-ol (24 mg, 63%) as a light yellow solid. ESI-MS m/z calc. 466.14395, found 467.2 (M+1)+; Retention time: 3.48 minutes. LCMS Method: Kinetex Polar $C_{18}$ column (3.0×50 mm, 2.6 μm particle size, 6 minute run, 5% to 95% acetonitrile in water (0.1% formic acid modifier), flow rate=1.2 mL/min).

Step 2: (6R)-17-Amino-12-cyclopropyl-6,15-bis(trifluoromethyl)-13,19-dioxa-3,4,18-triazatricyclo[12.3.1.12,5]nonadeca-1(18),2,4,14,16-pentaen-6-ol (enantiomer 1), Compound 68, and (6R)-17-amino-12-cyclopropyl-6,15-bis(trifluoromethyl)-13,19-dioxa-3,4,18-triazatricyclo[12.3.1.12,5]nonadeca-1(18),2,4,14,16-pentaen-6-ol (enantiomer 2), Compound 69

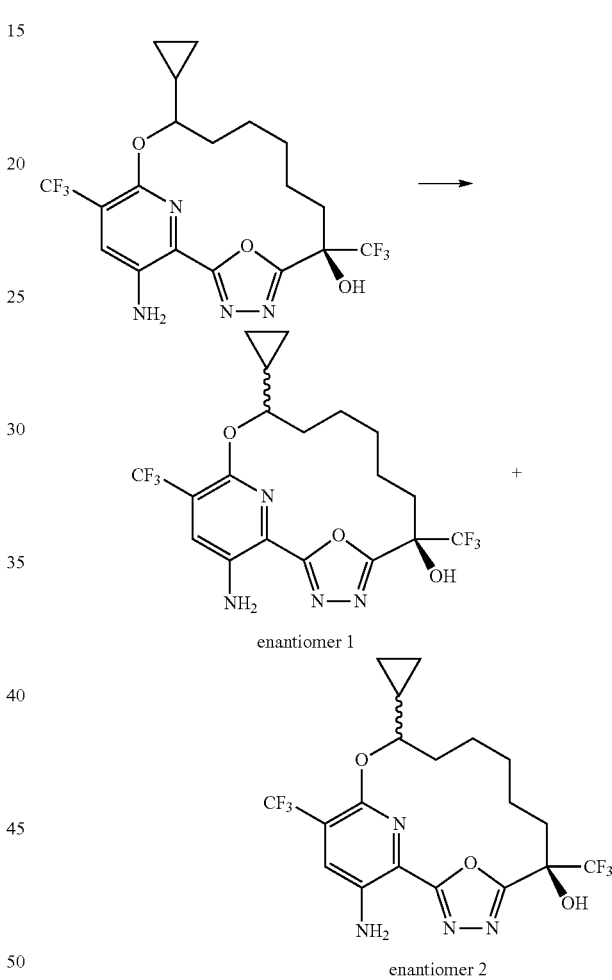

enantiomer 1 enantiomer 2

A diastereomeric mixture of (6R)-17-amino-12-cyclopropyl-6,15-bis(trifluoromethyl)-13,19-dioxa-3,4,18-triazatricyclo[12.3.1.12,5]nonadeca-1(18),2,4,14,16-pentaen-6-ol (24 mg, 0.0514 mmol) was subjected to SFC separation using the following conditions: Lux 5 μm Cellulose 4 column, (250×21.2 mm, 4.8 mg/injection) at 40° C., eluant: 7% reagent alcohol (+0.1% diethylamine)/93% $CO_2$, flow rate: 75 mL/min, injection volume: 400 uL, pressure: 100 bar, wavelength: 250 nm. Evaporation of the solvents and lyophilization provided two isomers.

The first isomer to elute under the above SFC conditions was further purified using reverse phase chromatography eluting with 70% acetonitrile in acidic water (containing 0.1% v/v of formic acid) which gave as a yellow solid, (6R)-17-amino-12-cyclopropyl-6,15-bis(trifluoromethyl)-

13,19-dioxa-3,4,18-triazatricyclo[12.3.1.1²,⁵]nonadeca-1 (18),2,4,14,16-pentaen-6-ol (enantiomer 1) (7.1 mg, 29%, 98.6% de). $^1$H NMR (400 MHz, DMSO-$d_6$) δ 7.75 (s, 1H), 7.58 (s, 1H), 6.34 (s, 2H), 4.15-4.07 (m, 1H), 2.61-2.53 (m, 1H), 2.22-2.03 (m, 2H), 1.80-1.37 (m, 7H), 1.18-1.08 (m, 1H), 0.63-0.55 (m, 1H), 0.52-0.38 (m, 2H), 0.31-0.22 (m, 1H). $^{19}$F NMR (377 MHz, DMSO-$d_6$) δ −62.51 (s, 3F), −79.02 (s, 3F). ESI-MS m/z calc. 466.14395, found 467.1 (M+1)$^+$; Retention time: 4.9 minutes. LCMS Method: SunFire $C_{18}$ column (75×4.6 mm, 3.5 lam particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

The second peak to elute gave SFC peak 2 followed by reverse phase chromatography eluting with 70% acetonitrile in acidic water (containing 0.1% v/v of formic acid) gave as a light yellow solid (6R)-17-amino-12-cyclopropyl-6,15-bis(trifluoromethyl)-13,19-dioxa-3,4,18-triazatricyclo[12.3.1.1²,⁵]nonadeca-1(18),2,4,14,16-pentaen-6-ol (enantiomer 2) (5.36 mg, 22%, 97.7% de). $^1$H NMR (400 MHz, DMSO-$d_6$) δ 7.75 (s, 1H), 7.57 (s, 1H), 6.33 (s, 2H), 4.24-4.14 (m, 1H), 2.48-2.42 (m, 1H), 2.31-2.21 (m, 1H), 2.17-2.07 (m, 1H), 1.82-1.62 (m, 3H), 1.57-1.38 (m, 4H), 1.19-1.08 (m, 1H), 0.67-0.56 (m, 1H), 0.52-0.36 (m, 2H), 0.32-0.22 (m, 1H). $^{19}$F NMR (377 MHz, DMSO-$d_6$) δ −62.53 (s, 3F), −76.34 (s, 3F). ESI-MS m/z calc. 466.14395, found 467.1 (M+1)$^+$; Retention time: 4.85 minutes. LCMS Method: SunFire $C_{18}$ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Example 49: Preparation of (12R)-17-amino-12-methyl-6,15-bis(trifluoromethyl)-8,13,19-trioxa-3,4,18-triazatricyclo[12.3.1.1²,⁵]nonadeca-1(18),2,4,14,16-pentaen-6-ol (diastereomer 1), Compound 70, and (12R)-17-amino-12-methyl-6,15-bis(trifluoromethyl)-8,13,19-trioxa-3,4,18-triazatricyclo[12.3.1.1²,⁵]nonadeca-1(18),2,4,14,16-pentaen-6-ol (diastereomer 2), Compound 71

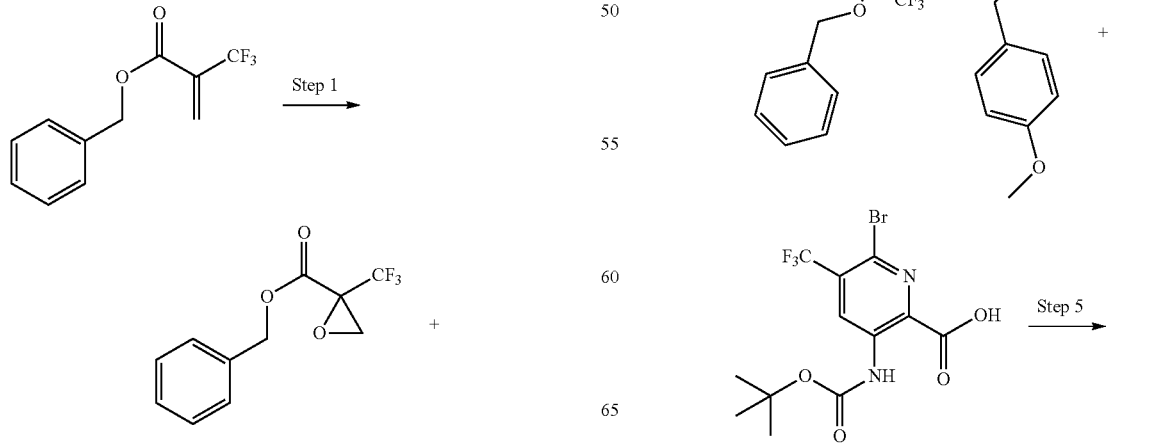

555
-continued
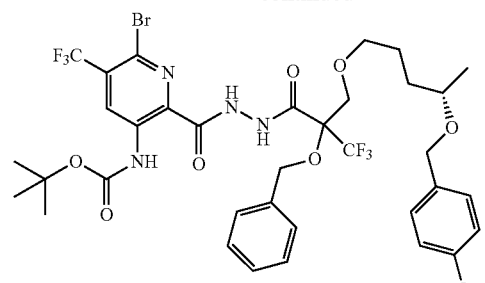
556
-continued
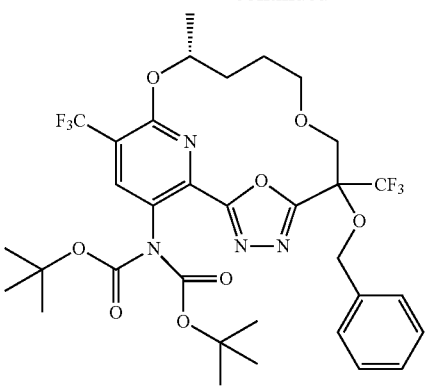
Step 6 →
Step 11 →
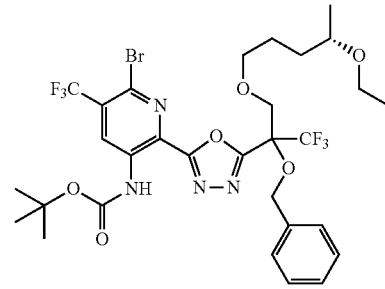
Step 7 →
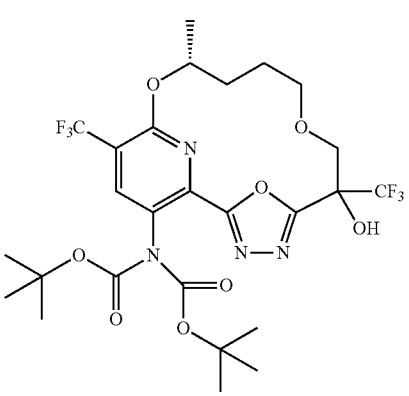
Step 12 →
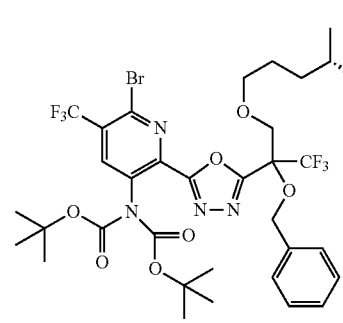
Step 8 →
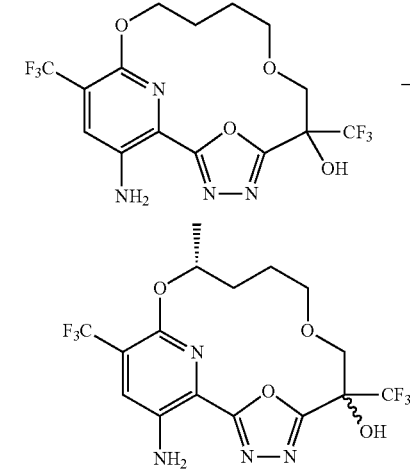
Step 13 →
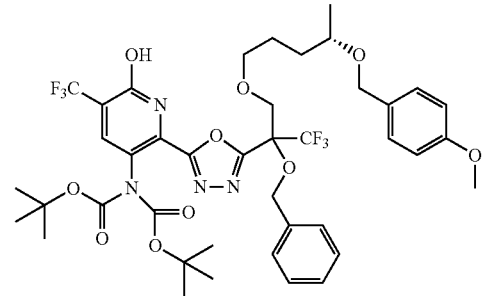
Step 9 →
diastereomer 1
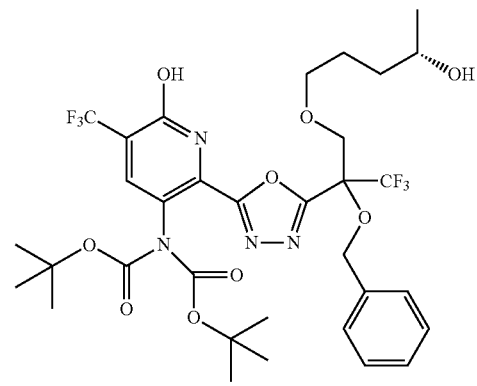
Step 10 →
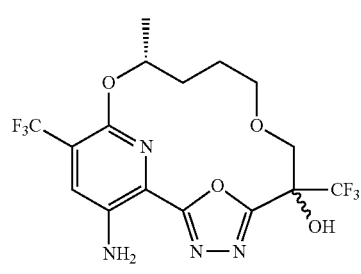
diastereomer 2

Step 1: Benzyl 2-(trifluoromethyl)oxirane-2-carboxylate

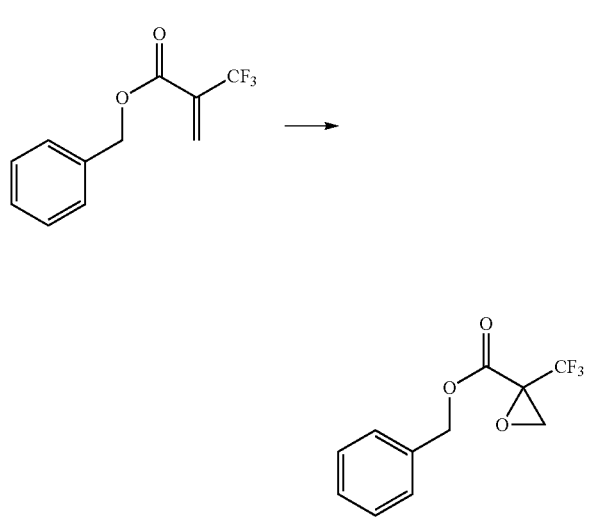

Benzyl 2-(trifluoromethyl)prop-2-enoate (50.45 g, 214.79 mmol) was dissolved in a mixture of dioxane (1000 mL) and water (200 mL). The mixture was cooled in an ice-water bath. With vigorous stirring, NaHCO$_3$ (91.2 g, 1.0856 mol) was added, followed by portion-wise addition of oxone (135.5 g). The addition took 80 minutes then the mixture was stirred at the same temperature for 20 min before 90 minutes of stirring at room temperature. Water (300 mL) and ethyl acetate (300 mL) were added and the layers were separated. The organic layer was washed with brine, dried over anhydrous MgSO$_4$, filtered and concentrated. The residue was purified by silica gel chromatography using a gradient from 5% to 50% ethyl acetate in hexanes to afford the product as colorless oil, benzyl 2-(trifluoromethyl)oxirane-2-carboxylate (57.49 g, 98%). $^1$H NMR (500 MHz, Chloroform-d) δ 7.62-7.28 (m, 5H), 5.33 (d, J=12.3 Hz, 1H), 5.28 (d, J=12.2 Hz, 1H), 3.30 3.18 (m, 2H).

Step 2: Benzyl 3,3,3-trifluoro-2-hydroxy-2-[[(4S)-4-[(4-methoxyphenyl)methoxy]pentoxy]methyl]propanoate

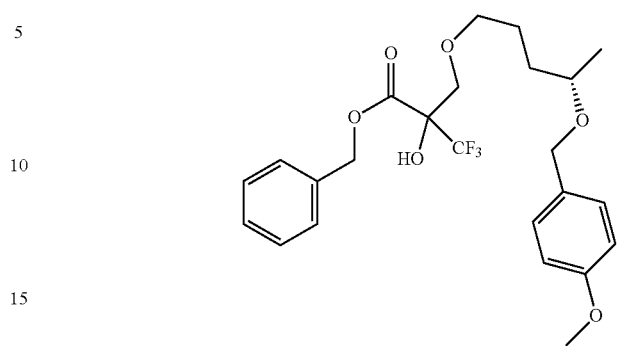

To a solution of (4S)-4-[(4-methoxyphenyl)methoxy]pentan-1-ol (1.48 g, 6.5918 mmol) in EtOAc (6.5 mL) was added benzyl 2-(trifluoromethyl)oxirane-2-carboxylate (2.2 g, 8.9364 mmol) then magnesium triflate (2.13 g, 6.6058 mmol) and the mixture stirred at 85° C. for 24 h. To the reaction was added EtOAc (60 mL) and water (20 mL) and then extracted the mixture with EtOAc (2×50 mL), washed the organic fractions with brine (25 mL), dried over Na$_2$SO$_4$, filtered and concentrated under vacuum. The residue was purified by silica gel flash chromatography (loaded on silica gel with benzene and eluted with 0% to 15% EtOAc in hexanes over a 45 min gradient) to provide as a colorless oil, benzyl 3,3,3-trifluoro-2-hydroxy-2-[[(4S)-4-[(4-methoxyphenyl)methoxy]pentoxy]methyl]propanoate (1.1 g, 35%). ESI-MS m/z calc. 470.1916, found 471.1 (M+1)$^+$; Retention time: 6.5 minutes. LCMS Method: Merck Millipore Chromolith SpeedROD C$_{18}$ column (50×4.6 mm) and a dual gradient run from 5-100% mobile phase B over 12 minutes. Mobile phase A=water (0.1% CF$_3$CO$_2$H). Mobile phase B=acetonitrile (0.1% CF$_3$CO$_2$H).

Step 3: Benzyl 2-benzyloxy-3,3,3-trifluoro-2-[[(4S)-4-[(4-methoxyphenyl)methoxy]pentoxy]methyl]propanoate

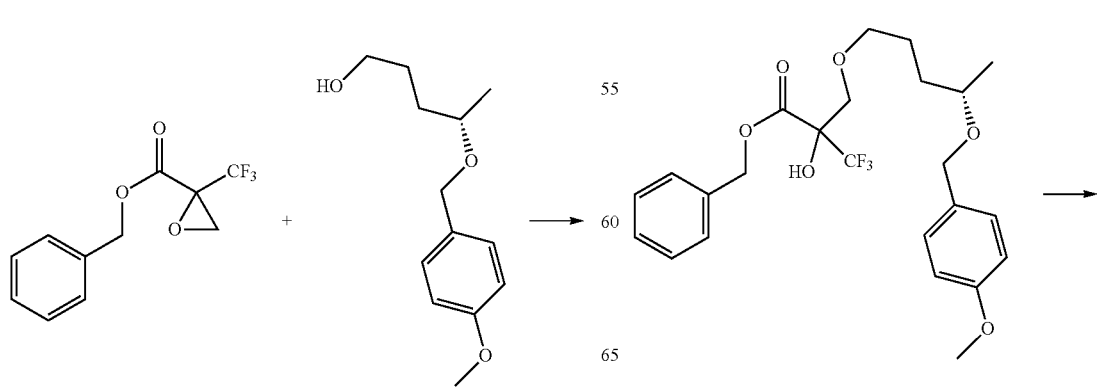

559
-continued

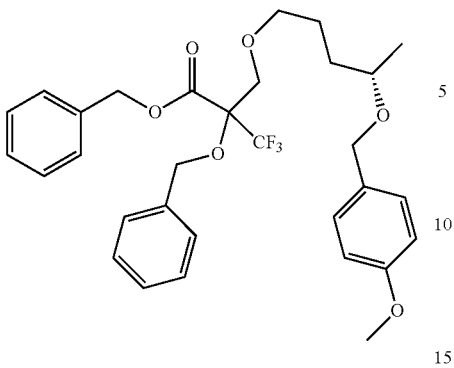

A solution of benzyl 3,3,3-trifluoro-2-hydroxy-2-[[(4S)-4-[(4-methoxyphenyl)methoxy]pentoxy]methyl]propanoate (1.1 g, 2.3380 mmol) in DMF (5.5 mL) was cooled to 0° C. and then added benzyl bromide (720 mg, 0.5 mL, 4.21 mmol) and tetrabutyl ammonium iodide (171 mg, 0.463 mmol) followed by sodium hydride (125 mg, 3.1253 mmol) in one portion and the resulting mixture was stirred for 4 h at 0° C. Warmed the mixture to room temperature and stirred for 12 h. Added more sodium hydride (38 mg, 0.9501 mmol) and benzyl bromide (288 mg, 0.2 mL, 1.6839 mmol) at 0° C. then stirred at room temperature for 30 minutes. The reaction was quenched with $NH_4Cl$ (30 mL) at room temperature and extracted with EtOAc (3×75 mL). The combined organic phases were then washed with brine (1×100 mL), dried over $Na_2SO_4$, filtered and concentrated under vacuum. The residue was purified by silica gel flash chromatography (eluted with a gradient from 0% to 10% EtOAc in hexanes over 50 min) to provide as a colorless oil, benzyl 2-benzyloxy-3,3,3-trifluoro-2-[[(4S)-4-[(4-methoxyphenyl)methoxy]pentoxy]methyl]propanoate (1 g, 76%). ESI-MS m/z calc. 560.2386, found 561.2 (M+1)⁺; Retention time: 7.88 minutes. LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 4: 2-Benzyloxy-3,3,3-trifluoro-2-[[(4S)-4-[(4-methoxyphenyl)methoxy]pentoxy]methyl]propane-hydrazide 560
-continued

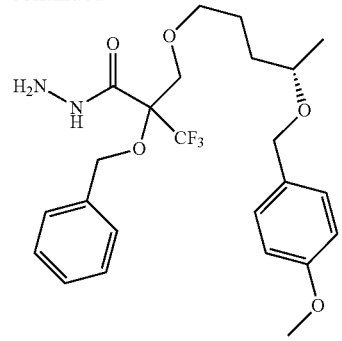

To a solution of benzyl 2-benzyloxy-3,3,3-trifluoro-2-[[(4S)-4-[(4-methoxyphenyl)methoxy]pentoxy]methyl]propanoate (1.64 g, 2.9254 mmol) in methanol (1 mL) was added 3,4,6,7,8,9-hexahydro-2H-pyrimido[1,2-a]pyrimidine (164 mg, 1.1782 mmol), then hydrazine hydrate (193.99 mg, 0.19 mL, 3.8751 mmol) and stirred at room temperature for 10 min. The reaction was stirred for 14 h at room temperature then additional hydrazine hydrate (204.20 mg, 0.2 mL, 4.0791 mmol) was added and the mixture was stirred for 30 minutes. The reaction was then quenched with water (30 mL), extracted with TBME (3×40 mL) and the combined organic layers were washed with saturated aqueous $NaHCO_3$ (50 mL), brine (100 mL) dried over $MgSO_4$, filtered and concentrated under vacuum. The residue was purified by silica gel flash chromatography (loaded with benzene/DCM and eluted with a gradient from 0% to 10% MeOH in DCM over 40 min) to provide clean product and mixed fractions containing product. The mixed fractions were concentrated and repurified by silica gel flash chromatography (loaded with benzene and eluted with a gradient from 0% to 5% methanol in dichloromethane over 40 min) and combined with the clean product from the first column to provide as an amber oil, 2-benzyloxy-3,3,3-trifluoro-2-[[(4S)-4-[(4-methoxyphenyl)methoxy]pentoxy]methyl]propanehydrazide (500 mg, 35%). ESI-MS m/z calc. 484.2185, found 485.5 (M+1)⁺; Retention time: 5.52 minutes. LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 5: tert-Butyl N-[2-[[[2-benzyloxy-3,3,3-trifluoro-2-[[(4S)-4-[(4-methoxyphenyl)methoxy]pentoxy]methyl]propanoyl]amino]carbamoyl]-6-bromo-5-(trifluoromethyl)-3-pyridyl]carbamate

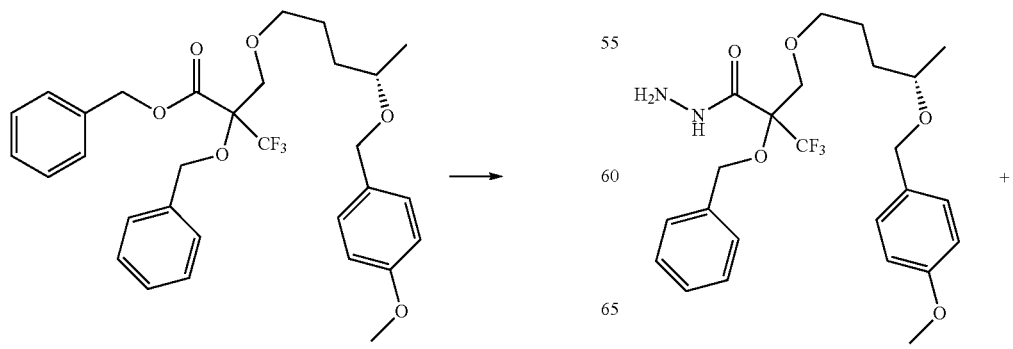

561

-continued

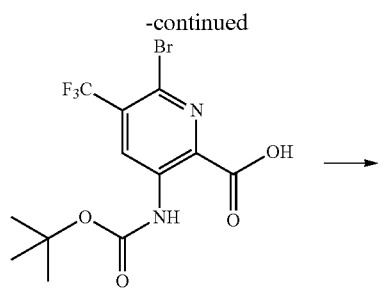

→

562

Step 6: tert-Butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-bromo-5-(trifluoromethyl)-3-pyridyl]carbamate

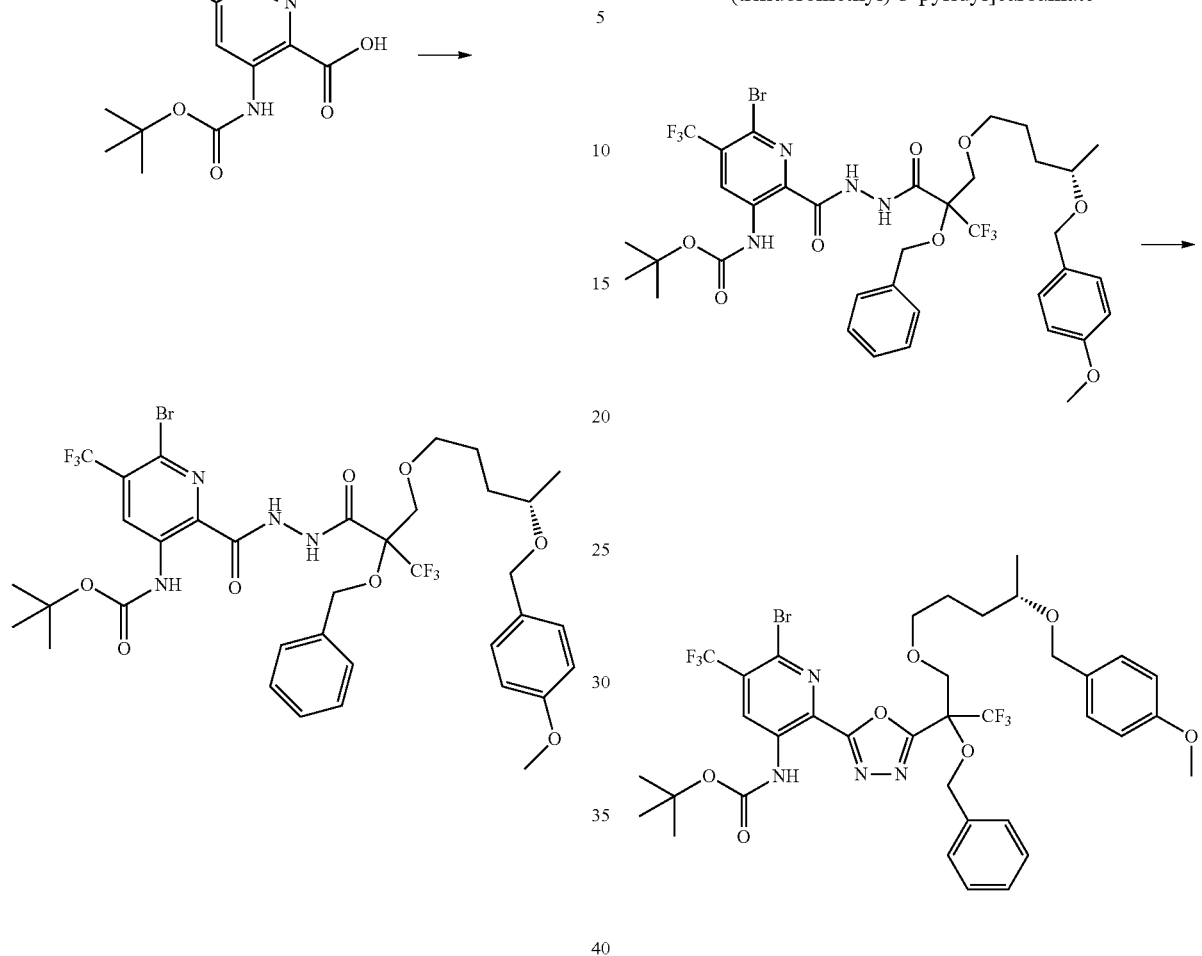

To a solution of 6-bromo-3-(tert-butoxycarbonylamino)-5-(trifluoromethyl)pyridine-2-carboxylic acid (416 mg, 1.0801 mmol) and 2-benzyloxy-3,3,3-trifluoro-2-[[(4S)-4-[(4-methoxyphenyl)methoxy]pentoxy]methyl]propanehydrazide (520 mg, 1.0733 mmol) in EtOAc (5.2 mL) was added T3P (1.13 g, 50% w/w, 1.7757 mmol) then pyridine (391.2 mg, 0.4 mL, 4.9456 mmol) at room temperature and the reaction was stirred for 5 h. The reaction was diluted with EtOAc (20 mL), washed with saturated aqueous $NH_4Cl$ (5 mL), then $NaHCO_3$ (20 mL) and the aqueous layers were back-extracted with EtOAc (2×40 mL). The combined organic layers were washed with brine, dried over $Na_2SO_4$, filtered and concentrated under vacuum. The residue was purified by silica gel flash chromatography (eluted with a gradient from 0% to 20% EtOAc in hexanes over 40 min) to provide, as a pale yellow oil, tert-butyl N-[2-[[[2-benzyloxy-3,3,3-trifluoro-2-[[(4S)-4-[(4-methoxyphenyl)methoxy]pentoxy]methyl]propanoyl]amino]carbamoyl]-6-bromo-5-(trifluoromethyl)-3-pyridyl]carbamate (586.2 mg, 64%). ESI-MS m/z calc. 850.2012, found 851.6 $(M+1)^+$; Retention time: 8.46 minutes. LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

To a solution of tert-butyl N-[2-[[[2-benzyloxy-3,3,3-trifluoro-2-[[(4S)-4-[(4-methoxyphenyl)methoxy]pentoxy]methyl]propanoyl]amino]carbamoyl]-6-bromo-5-(trifluoromethyl)-3-pyridyl]carbamate (586 mg, 0.6881 mmol) in acetonitrile (7.6 mL) was added tosyl chloride (152 mg, 0.7973 mmol) then DIPEA (267.12 mg, 0.36 mL, 2.0668 mmol) and the reaction mixture was stirred for 5 h at room temperature. The reaction was diluted with EtOAc (40 mL), washed with saturated aqueous $NH_4Cl$ (15 mL) and brine (30 mL) then dried over $Na_2SO_4$, filtered and concentrated under vacuum. The residue was purified by silica gel flash chromatography (loaded with benzene and eluted with 0% to 10% EtOAc in hexanes over a 30 min gradient) to provide as a colorless oil, tert-butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-bromo-5-(trifluoromethyl)-3-pyridyl]carbamate (425 mg, 73%). ESI-MS m/z calc. 832.1906, found 833.5 $(M+1)^+$; Retention time: 9.08 minutes. LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 7: tert-Butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-bromo-5-(trifluoromethyl)-3-pyridyl]-N-tert-butoxycarbonyl-carbamate Step 8: tert-Butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-hydroxy-5-(trifluoromethyl)-3-pyridyl]-N-tert-butoxycarbonyl-carbamate

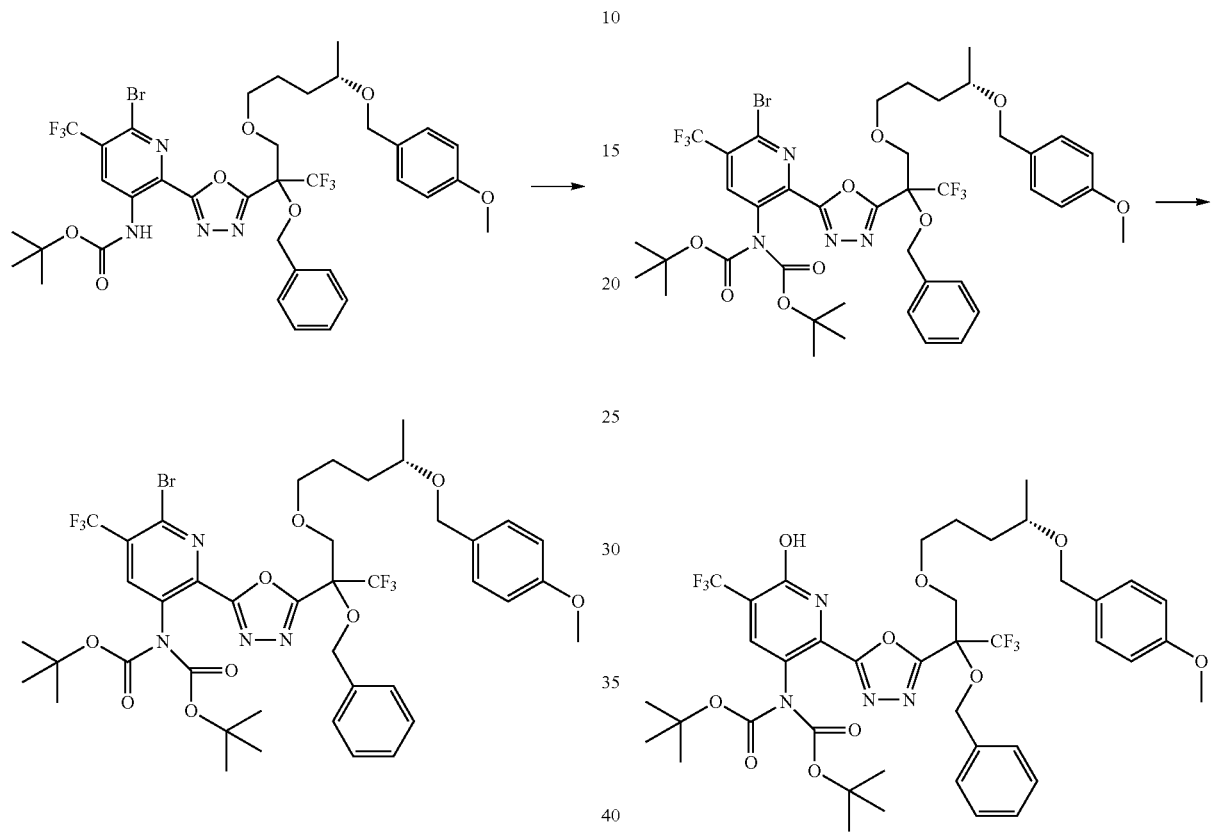

To a solution of tert-butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-bromo-5-(trifluoromethyl)-3-pyridyl]carbamate (425 mg, 0.5098 mmol) in TBME (4.35 mL) was added DIPEA (161.76 mg, 0.218 mL, 1.2516 mmol) and DMAP (22 mg, 0.1801 mmol). Di-tert-butyl dicarbonate (351.5 mg, 0.37 mL, 1.6106 mmol) was then added and the reaction stirred for 12 h at room temperature. The reaction was added to water (10 mL) and then the organics were extracted with TBME (50 mL). The organic solution was washed with water (50 mL), brine (50 mL), dried over $Na_2SO_4$, filtered and concentrated under vacuum. The residue was purified by silica gel flash chromatography (loaded with benzene and eluted with 0% to 10% EtOAc in hexanes over a 30 min gradient) to provide as a colorless oil, tert-butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-bromo-5-(trifluoromethyl)-3-pyridyl]-N-tert-butoxycarbonyl-carbamate (476 mg, 99%). ESI-MS m/z calc. 932.2431, found 933.7 $(M+1)^+$; Retention time: 8.76 minutes. LCMS Method: Merck Millipore Chromolith SpeedROD $C_{18}$ column (50× 4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

To a solution of tert-butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-bromo-5-(trifluoromethyl)-3-pyridyl]-N-tert-butoxycarbonyl-carbamate (476 mg, 0.5098 mmol) in DMSO (4.75 mL) was added cesium acetate (395 mg, 2.0578 mmol) and placed in a 86° C. reaction plate for 6 h. The reaction was cooled to room temperature and diluted with TBME (20 mL) and aqueous $NH_4Cl$ (15 mL) and extracted with TBME (5×20 mL). The combined organic layers were washed with brine (2×15 mL), dried over $Na_2SO_4$, filtered and concentrated under vacuum to provide as a colorless oil, tert-butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-hydroxy-5-(trifluoromethyl)-3-pyridyl]-N-tert-butoxycarbonyl-carbamate (444 mg, 95%). ESI-MS m/z calc. 870.3275, found 871.8 $(M+1)^+$; Retention time: 7.85 minutes. LCMS Method: Merck Millipore Chromolith SpeedROD $C_{18}$ column (50×4.6 mm) and a dual gradient run from 5-100% mobile phase B over 12 minutes. Mobile phase A=water (0.1% $CF_3CO_2H$). Mobile phase B=acetonitrile (0.1% $CF_3CO_2H$).

Step 9: tert-Butyl N-[2-[5-[1-benzyloxy-2,2,2-trifluoro-1-[[(4S)-4-hydroxypentoxy]methyl]ethyl]-1,3,4-oxadiazol-2-yl]-6-hydroxy-5-(trifluoromethyl)-3-pyridyl]-N-tert-butoxycarbonyl-carbamate Step 10: tert-Butyl N-[(12R)-6-benzyloxy-12-methyl-6,15-bis(trifluoromethyl)-8,13,19-trioxa-3,4,18-triazatricyclo[12.3.1.12,5]nonadeca-1(18),2,4,14,16-pentaen-17-yl]-N-tert-butoxycarbonyl-carbamate

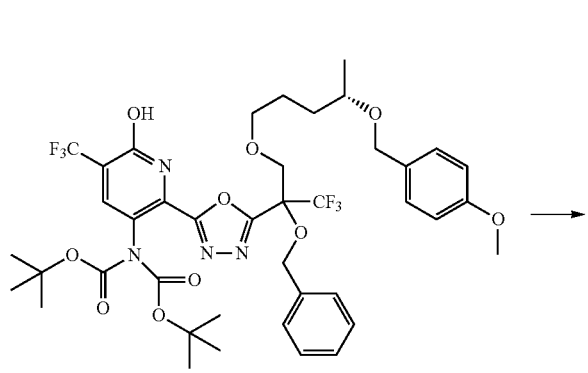

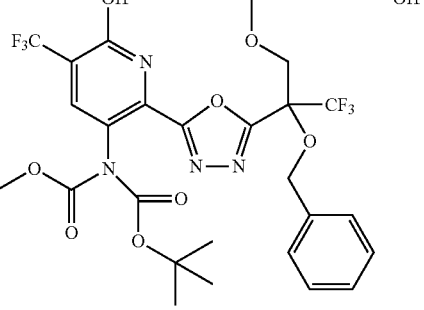

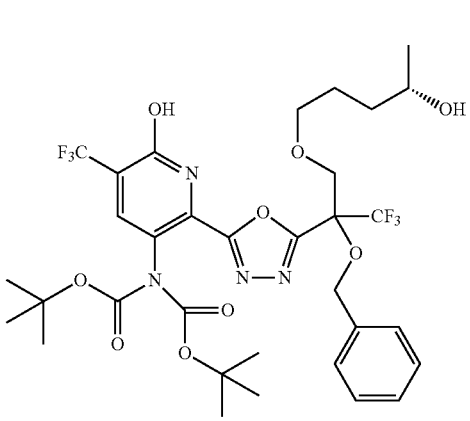

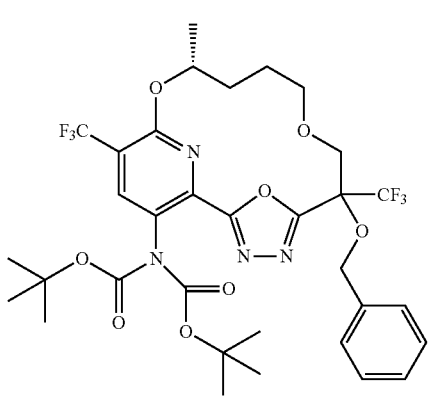

To a solution of tert-butyl N-[2-[5-[1-benzyloxy-2,2,2-trifluoro-1-[[(4S)-4-[(4-methoxyphenyl)methoxy]pentoxy]methyl]ethyl]-1,3,4-oxadiazol-2-yl]-6-hydroxy-5-(trifluoromethyl)-3-pyridyl]-N-tert-butoxycarbonyl-carbamate (440 mg, 0.5053 mmol) in DCM (3.9 mL) was added DDQ (128 mg, 0.5639 mmol) then water (0.22 mL). The colorless reaction solution instantly became a grey suspension upon addition of DDQ. The mixture was stirred 1.5 h at 30° C. then diluted with DCM (20 mL), washed with saturated aqueous NaHCO₃ (15 mL), dried over MgSO₄, filtered and concentrated under vacuum (400 mg crude obtained). The residue was purified by silica gel flash chromatography (loaded with benzene and eluted with 0% to 50% EtOAc in hexanes over a 30 min gradient) to provide tert-butyl N-[2-[5-[1-benzyloxy-2,2,2-trifluoro-1-[[(4S)-4-hydroxypentoxy]methyl]ethyl]-1,3,4-oxadiazol-2-yl]-6-hydroxy-5-(trifluoromethyl)-3-pyridyl]-N-tert-butoxycarbonyl-carbamate (310 mg, 81%). ESI-MS m/z calc. 750.2699, found 651.3 (M−100+H)⁺; Retention time: 6.95 minutes. LCMS Method: Merck Millipore Chromolith SpeedROD C₁₈ column (50×4.6 mm) and a dual gradient run from 5-100% mobile phase B over 12 minutes. Mobile phase A=water (0.1% CF₃CO₂H). Mobile phase B=acetonitrile (0.1% CF₃CO₂H).

To a solution of tert-butyl N-[2-[5-[1-benzyloxy-2,2,2-trifluoro-1-[[(4S)-4-hydroxypentoxy]methyl]ethyl]-1,3,4-oxadiazol-2-yl]-6-hydroxy-5-(trifluoromethyl)-3-pyridyl]-N-tert-butoxycarbonyl-carbamate (274 mg, 0.3650 mmol) in toluene (60 mL) was added triphenylphosphine (196 mg, 0.7473 mmol) followed by DIAD (146.16 mg, 0.14 mL, 0.7228 mmol) at room temperature. After 6 h, the reaction was diluted with EtOAc (30 mL) and washed with saturated aqueous NaHCO₃ (20 mL), saturated aqueous NH₄Cl (20 mL) and brine (2×50 mL) then dried over Na₂SO₄, filtered and concentrated under vacuum (650 mg crude obtained). The residue was purified by silica gel flash chromatography (loaded with minimal benzene and eluted with 0% to 5% EtOAc in hexanes over an 80 minute gradient, then 5% to 10% EtOAc in hexanes over a 10 minute gradient) to provide both diastereomers of tert-butyl N-[(12R)-6-benzyloxy-12-methyl-6,15-bis(trifluoromethyl)-8,13,19-trioxa-3,4,18-triazatricyclo[12.3.1.12,5]nonadeca-1(18),2,4,14,16-pentaen-17-yl]-N-tert-butoxycarbonyl-carbamate (160 mg, 59%). ESI-MS m/z calc. 732.2594, found 733.6 (M+1)⁺; Retention time: 8.57 minutes. LCMS Method: Merck Millipore Chromolith SpeedROD C₁₈ column (50×4.6 mm) and a dual gradient run from 5-100% mobile phase B over 12 minutes. Mobile phase A=water (0.1% CF₃CO₂H). Mobile phase B=acetonitrile (0.1% CF₃CO₂H).

Step 11: tert-Butyl N-tert-butoxycarbonyl-N-[(12R)-6-hydroxy-12-methyl-6,15-bis(trifluoromethyl)-8,13,19-trioxa-3,4,18-triazatricyclo[12.3.1.12,5]nonadeca-1(18),2,4,14,16-pentaen-17-yl]carbamate Step 12: (12R)-17-Amino-12-methyl-6,15-bis(trifluoromethyl)-8,13,19-trioxa-3,4,18-triazatricyclo[12.3.1.12,5]nonadeca-1(18),2,4,14,16-pentaen-6-ol

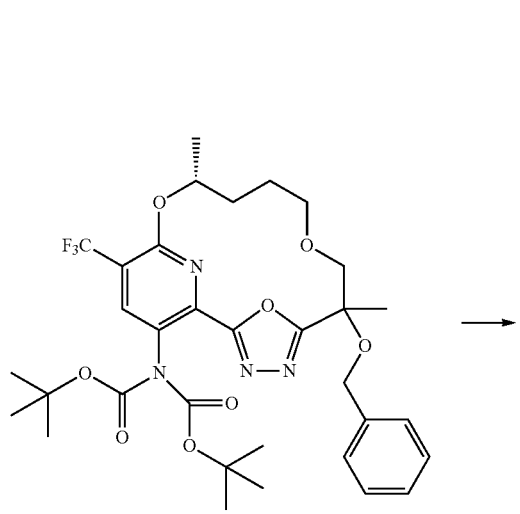

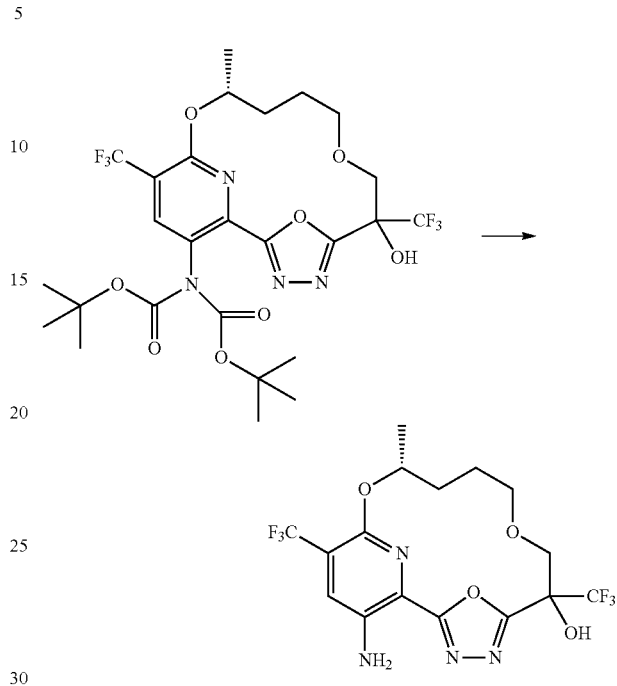

A solution of tert-butyl N-tert-butoxycarbonyl-N-[(12R)-6-hydroxy-12-methyl-6,15-bis(trifluoromethyl)-8,13,19-trioxa-3,4,18-triazatricyclo[12.3.1.12,5]nonadeca-1(18),2,4,14,16-pentaen-17-yl]carbamate (17.5 mg, 0.0272 mmol) was heated at 100° C. in a microwave reactor for 2 h. The reaction was concentrated under vacuum to provide as a yellow foam, (12R)-17-amino-12-methyl-6,15-bis(trifluoromethyl)-8,13,19-trioxa-3,4,18-triazatricyclo[12.3.1.12,5]nonadeca-1(18),2,4,14,16-pentaen-6-ol (12 mg, 95%). ESI-MS m/z calc. 442.1076, found 443.5 (M+1)$^+$; Retention time: 6.08 minutes. LCMS Method: Merck Millipore Chromolith SpeedROD C$_{18}$ column (50×4.6 mm) and a dual gradient run from 5-100% mobile phase B over 12 minutes. Mobile phase A=water (0.1% CF$_3$CO$_2$H). Mobile phase B=acetonitrile (0.1% CF$_3$CO$_2$H).

To a solution of tert-butyl N-[(12R)-6-benzyloxy-12-methyl-6,15-bis(trifluoromethyl)-8,13,19-trioxa-3,4,18-triazatricyclo[12.3.1.12,5]nonadeca-1(18),2,4,14,16-pentaen-17-yl]-N-tert-butoxycarbonyl-carbamate (40 mg, 0.0546 mmol) in ethanol (1.36 mL) was added 10% palladium on carbon (22 mg, 0.0207 mmol) under nitrogen atmosphere, then the reaction atmosphere was exchanged for hydrogen gas. The reaction was stirred at room temperature under a balloon of hydrogen for 45 minutes. The reaction was filtered through packed celite and the filtrate was concentrated under vacuum to provide as a yellow foam, tert-butyl N-tert-butoxycarbonyl-N-[(12R)-6-hydroxy-12-methyl-6,15-bis(trifluoromethyl)-8,13,19-trioxa-3,4,18-triazatricyclo[12.3.1.12,5]nonadeca-1(18),2,4,14,16-pentaen-17-yl]carbamate (17 mg, 48%). ESI-MS m/z calc. 642.2124, found 543.1 (M−100+H)$^+$; Retention time: 7.39 minutes. LCMS Method: Merck Millipore Chromolith SpeedROD C$_{18}$ column (50×4.6 mm) and a dual gradient run from 5-100% mobile phase B over 12 minutes. Mobile phase A=water (0.1% CF$_3$CO$_2$H). Mobile phase B=acetonitrile (0.1% CF$_3$CO$_2$H).

Step 13: (12R)-17-Amino-12-methyl-6,15-bis(trifluoromethyl)-8,13,19-trioxa-3,4,18-triazatricyclo[12.3.1.12,5]nonadeca-1(18),2,4,14,16-pentaen-6-ol (diastereomer 1), Compound 70, and (12R)-17-amino-12-methyl-6,15-bis(trifluoromethyl)-8,13,19-trioxa-3,4,18-triazatricyclo[12.3.1.12,5]nonadeca-1(18),2,4,14,16-pentaen-6-ol (diastereomer 2), Compound 71

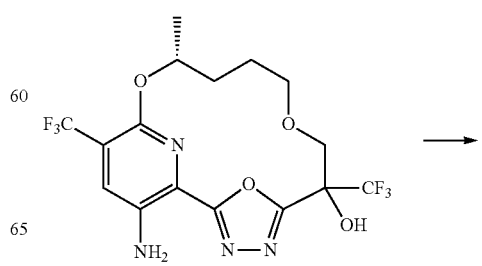

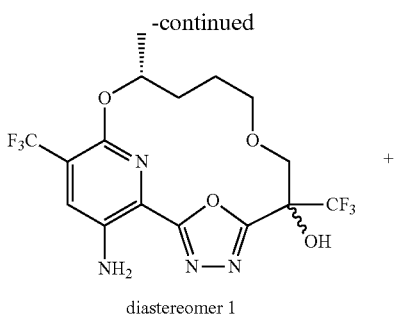

diastereomer 1

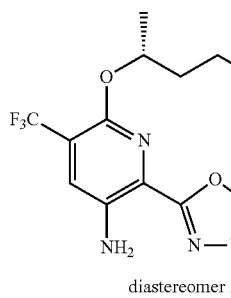

diastereomer 2

(12R)-17-Amino-12-methyl-6,15-bis(trifluoromethyl)-8,13,19-trioxa-3,4,18-triazatricyclo[12.3.1.12,5]nonadeca-1(18),2,4,14,16-pentaen-6-ol (19 mg, 0.04296 mmol) was separated into the individual diastereomers by chiral SFC using a normal phase SFC-MS method with a Phenomenex LUX-4 column (250×10 mm; 5□m) at 50° C. (mobile phase was 8% MeOH (+20 mM NH3)/92% CO2 at a 10 mL/min flow, concentration of the sample was 20.3 mg/mL in methanol, injection volume=70 μL with an outlet pressure of 128 bar and detection wavelength of 224 nm). The first peak to elute afforded as a light yellow solid, (12R)-17-amino-12-methyl-6,15-bis(trifluoromethyl)-8,13,19-trioxa-3,4,18-triazatricyclo[12.3.1.12,5]nonadeca-1(18),2,4,14,16-pentaen-6-ol (diastereomer 1) (2.5 mg, 26%). $^1$H NMR (400 MHz, Chloroform-d) δ 7.41 (d, J=0.8 Hz, 1H), 5.16 (s, 2H), 4.85-4.71 (m, 1H), 4.12 (d, J=10.6 Hz, 1H), 3.99-3.88 (m, 2H), 3.64 (ddd, J=8.9, 6.5, 4.6 Hz, 1H), 2.85-2.77 (m, 1H), 2.07-1.96 (m, 2H), 1.78-1.67 (m, 1H), 1.40 (d, J=6.4 Hz, 3H), 1.35-1.20 (m, 1H). ESI-MS m/z calc. 442.10757, found 443.2 (M+1)$^+$; Retention time: 1.76 minutes. ESI-MS m/z calc. 442.10757, found 443.2 (M+1)+; Retention time: 1.76 minutes. LCMS Method: Acquity UPLC BEH C$_{18}$ column (50×2.1 mm, 1.7 μm particle) made by Waters (pn: 186002350), and a dual gradient run from 1% to 99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

The second peak to elute afforded as a light yellow solid, (12R)-17-amino-12-methyl-6,15-bis(trifluoromethyl)-8,13,19-trioxa-3,4,18-triazatricyclo[12.3.1.12,5]nonadeca-1(18),2,4,14,16-pentaen-6-ol (diastereomer 2) (1.9 mg, 19%). $^1$H NMR (400 MHz, Chloroform-d) δ 7.45-7.38 (m, 1H), 5.21 (s, 2H), 4.86-4.77 (m, 1H), 4.16 (d, J=10.4 Hz, 1H), 4.02 (d, J=10.3 Hz, 1H), 3.97-3.91 (m, 1H), 3.74-3.67 (m, 1H), 2.79-2.67 (m, 1H), 1.96-1.87 (m, 1H), 1.87-1.75 (m, 1H), 1.41 (d, J=6.5 Hz, 3H), 1.39-1.34 (m, 1H), 1.34-1.24 (m, 1H). ESI-MS m/z calc. 442.10757, found 443.2 (M+1)$^+$; Retention time: 1.78 minutes. LCMS Method: Acquity UPLC BEH C$_{18}$ column (50×2.1 mm, 1.7 μm particle) made by Waters (pn: 186002350), and a dual gradient run from 1% to 99% mobile phase B over 2.9 minutes. Mobile phase A=H$_2$O (0.05% CF$_3$CO$_2$H). Mobile phase B=acetonitrile (0.035% CF$_3$CO$_2$H). Flow rate=1.2 mL/min, injection volume=1.5 μL, and column temperature=60° C.

Example 50: Preparation of (12R)-17-amino-12-methyl-6,15-bis(trifluoromethyl)-9,13,19-trioxa-3,4,18-triazatricyclo[12.3.1.12,5]nonadeca-1(18),2,4,14,16-pentaen-6-ol (diastereomer 1), Compound 72, and (12R)-17-amino-12-methyl-6,15-bis(trifluoromethyl)-9,13,19-trioxa-3,4,18-triazatricyclo[12.3.1.12,5]nonadeca-1(18),2,4,14,16-pentaen-6-ol (diastereomer 2), Compound 73

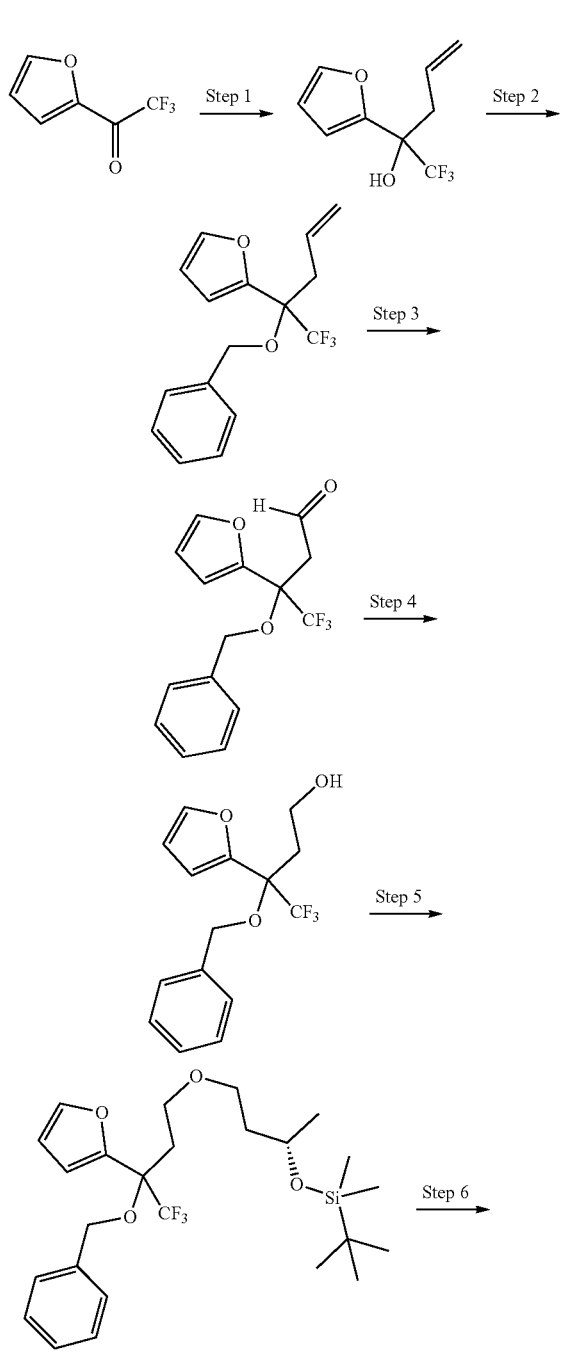

571
-continued
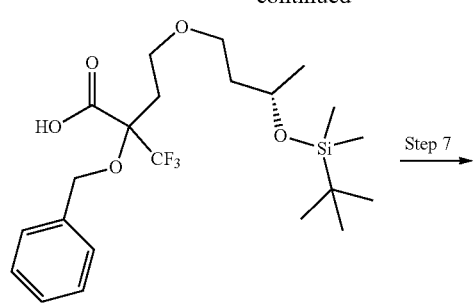
Step 7
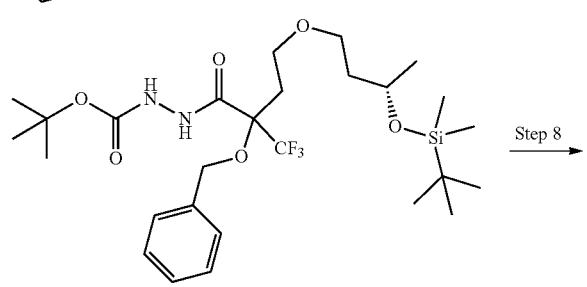
Step 8
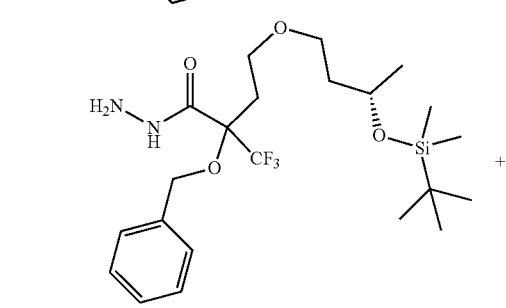
+
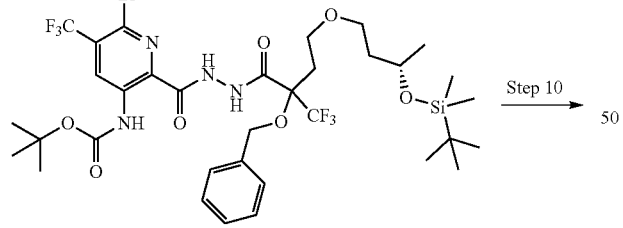
Step 9
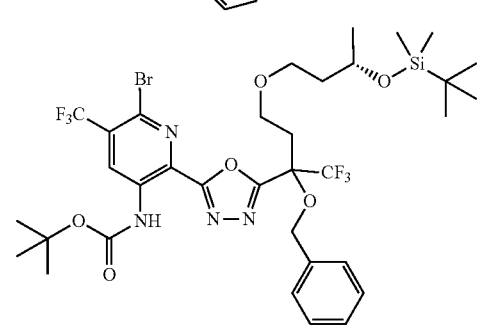
Step 10
572
-continued
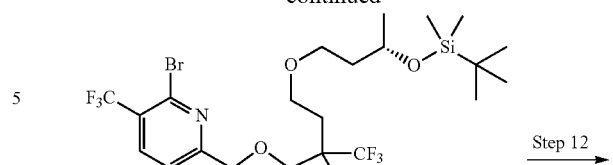
Step 12
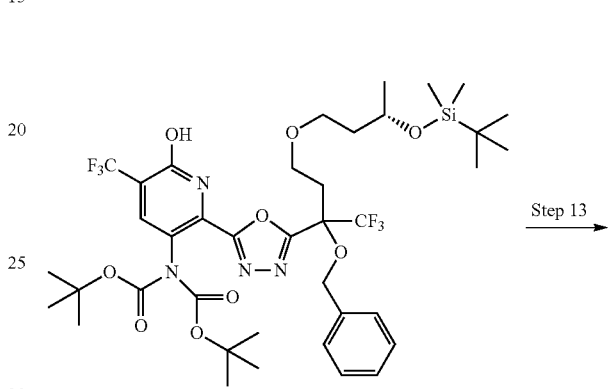
Step 13
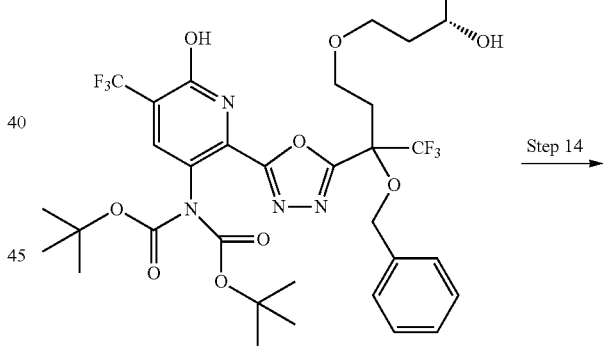
Step 14
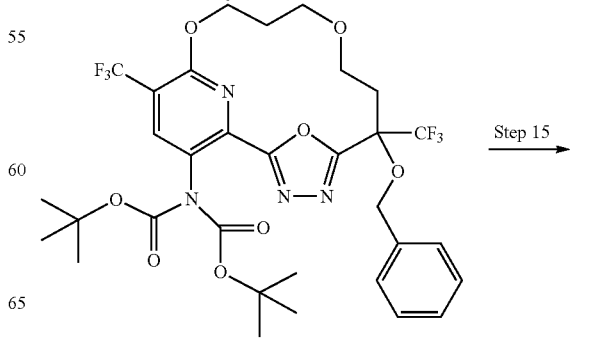
Step 15

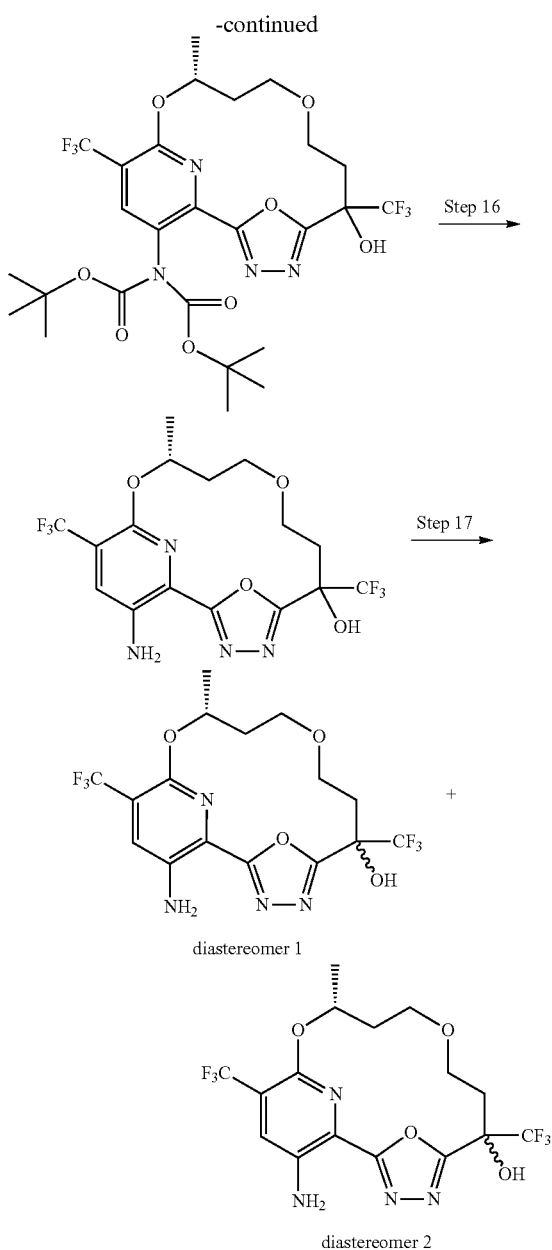

Step 16

Step 17 diastereomer 1 diastereomer 2

Step 1: 1,1,1-Trifluoro-2-(2-furyl)pent-4-en-2-ol

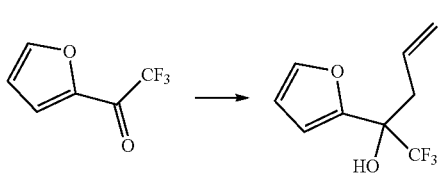

Allylmagnesium chloride in THF (53 mL of 2 M, 106 mmol) was diluted with ether (60 mL) and cooled in an ice-water bath under nitrogen. With rapid stirring, 2,2,2-trifluoro-1-(2-furyl)ethanone (4.2 g, 20.478 mmol) in ether (10 mL) was added quickly. The mixture was stirred at 0° C. for 30 min then cooled to −20° C. Aqueous hydrochloric acid (10 mL, 2 N) was added and the layers were separated. The ether layer was washed with brine, dried over anhydrous MgSO₄, filtered and concentrated to afford as a crude yellow oil, 1,1,1-trifluoro-2-(2-furyl)pent-4-en-2-ol (5 g, quant.). ¹H NMR (500 MHz, Chloroform-d) δ 7.45 (s, 1H), 6.48 (d, J=3.4, 1H), 6.41 (d, J=3.3, 1H), 5.70 5.57 (m, 1H), 5.29 5.15 (m, 2H), 3.05 (s, 1H), 3.00-2.89 (m, 1H), 2.81-2.71 (m, 1H).

Step 2: 2-[1-Benzyloxy-1-(trifluoromethyl)but-3-enyl]furan

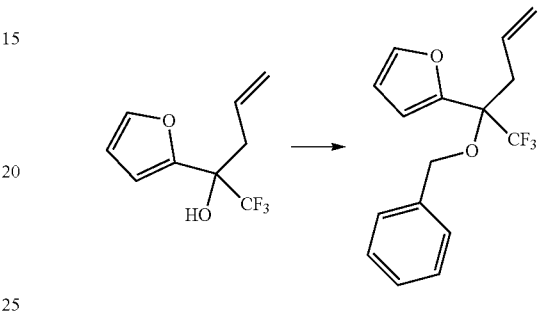

1,1,1-Trifluoro-2-(2-furyl)pent-4-en-2-ol (3 g, 11.641 mmol) was dissolved in DMF (30 mL) and the solution was cooled in an ice-water bath. Sodium hydride in mineral oil (822 mg, 20.552 mmol) was added and the solution became a light brownish mixture. The mixture was stirred 5 minutes then bromomethylbenzene (3.024 g, 2.1 mL, 17.681 mmol) was added followed by tetrabutylammonium iodide (878 mg, 2.377 mmol). The mixture was stirred at 30° C. for 16 h. Saturated aqueous NH₄Cl (15 mL) was added followed by EtOAc (30 mL). The layers were separated and the organic layer was washed with water then brine, dried over anhydrous MgSO₄, filtered and concentrated. The residue was purified by silica gel chromatography (40 g column), using a gradient from 0% to 15% EtOAc in hexanes to afford as a pale yellow oil, 2[1-benzyloxy-1-(trifluoromethyl)but-3-enyl]furan (3.4 g, 89%). ¹H NMR (500 MHz, Chloroform-d) δ 7.59-7.44 (m, 1H), 7.43-7.23 (m, 5H), 6.60 (d, J=3.4 Hz, 1H), 6.51-6.36 (m, 1H), 5.26-5.03 (m, 3H), 4.55-4.35 (m, 2H), 3.17-2.91 (m, 2H).

Step 3:
3-Benzyloxy-4,4,4-trifluoro-3-(2-furyl)butanal

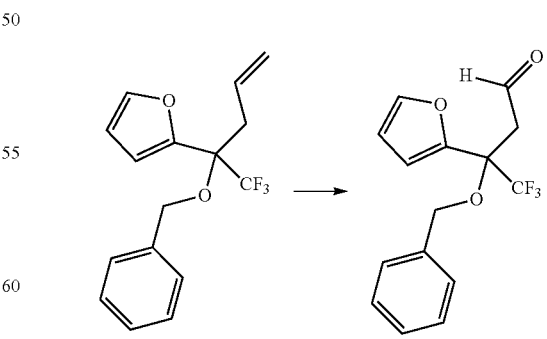

2-[1-Benzyloxy-1-(trifluoromethyl)but-3-enyl]furan (5.3 g, 16.994 mmol) was mixed with THF (40 mL) and water (20 mL) at room temperature. NaIO₄ (10.9 g, 50.960 mmol), 2,6 lutidine (4.4304 g, 4.8 mL, 41.346 mmol) and O₅O₄ in tert-butanol (1.2 g, 2.5% w/w, 0.118 mmol) were added. After 10 minutes of stirring, more water (5 mL) was added. The mixture was stirred at room temperature for 15 h. EtOAc (15 mL) and water (15 mL) were added and the layers were separated. The organic layer was washed with brine, dried over anhydrous MgSO$_4$, filtered and concentrated. The residue was purified by silica gel chromatography (80 g column), using a gradient from 0% to 15% EtOAc in hexanes, to afford as a pale yellow oil, 3-benzyloxy-4,4,4-trifluoro-3-(2-furyl)butanal (3.72 g, 70%). $^1$H NMR (500 MHz, Chloroform-d) δ 9.87 (t, J=2.2 Hz, 1H), 7.54 (s, 1H), 7.44-7.12 (m, 5H), 6.69(d, J=3.1 Hz, 1H), 6.60-6.41 (m, 1H), 4.57 (d, J=11.0 Hz, 1H), 4.39 (d, J=11.0 Hz, 1H), 3.12 (d, J=2.7 Hz, 2H).

Step 4:
3-Benzyloxy-4,4,4-trifluoro-3-(2-furyl)butan-1-ol

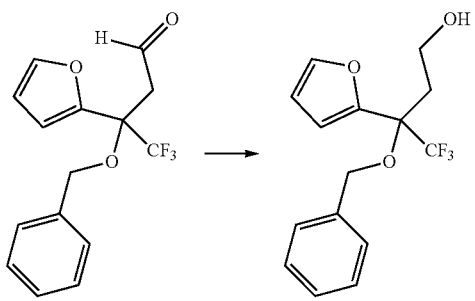 [SMILES: O=CCC(OCc1ccccc1)(c1ccco1)C(F)(F)F ; OCCC(OCc1ccccc1)(c1ccco1)C(F)(F)F]

3-Benzyloxy-4,4,4-trifluoro-3-(2-furyl)butanal (3.72 g, 11.849 mmol) was dissolved in MeOH (40 mL) and cooled in an ice-water bath. NaBH$_4$ (480 mg, 0.5079 mL, 12.688 mmol) was added and the mixture was stirred at the same temperature for 15 minutes. Saturated aqueous NH$_4$Cl (5 mL) was added and the mixture was concentrated to ⅓ of its original volume. EtOAc (40 mL) and water (40 mL) were added and the resulting layers were separated. The organic layer was washed with brine, dried over anhydrous MgSO$_4$, filtered and concentrated to afford as a colorless oil, 3-benzyloxy-4,4,4-trifluoro-3-(2-furyl)butan-1-ol (3.7 g, 94%). $^1$H NMR (500 MHz, Chloroform-d) δ 7.52 (s, 1H), 7.41-7.27 (m, 5H), 6.67-6.54 (m, 1H), 6.51-6.39 (m, 1H), 4.54 (d, J=10.9 Hz, 1H), 4.43 (d, J=10.9 Hz, 1H), 3.95-3.80 (m, 2H), 2.57-2.40 (m, 2H), 2.00 (s, 1H).

Step 5: [(1S)-3-[3-Benzyloxy-4,4,4-trifluoro-3-(2-furyl)butoxy]-1-methyl-propoxy]-tert-butyl-dimethyl-silane

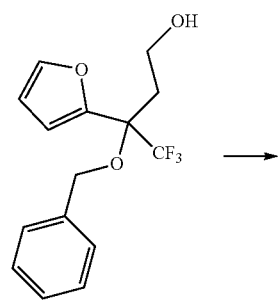

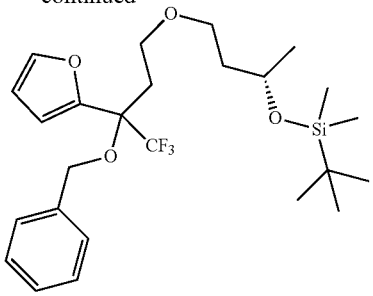

3-Benzyloxy-4,4,4-trifluoro-3-(2-furyl)butan-1-ol (980 mg, 2.9373 mmol) was dissolved in DMF (8 mL) and the mixture was briefly chilled with an ice-water bath. Sodium hydride in mineral oil (202 mg, 5.0505 mmol) was added. The mixture was stirred at room temperature for 15 minutes. tert-Butyl-[(1S)-3-iodo-1-methyl-propoxy]-dimethyl-silane (2.15 g, 6.499 mmol) in DMF (2 mL) was added and the mixture was stirred at room temperature under nitrogen balloon for 72 h. Saturated aqueous NH$_4$Cl (5 mL) was added followed by EtOAc (20 mL) and water (20 mL). The layers were separated and the organic layer was washed with more water (2×20 mL) and brine then dried over anhydrous MgSO$_4$, filtered and concentrated. The residue was purified by silica gel chromatography (40 g column), using a gradient from 0% to 10% EtOAc in hexanes to afford as a colorless oil, [(1S)-3-[3-benzyloxy-4,4,4-trifluoro-3-(2-furyl)butoxy]-1-methyl-propoxy]-tert-butyl-dimethyl-silane (760 mg, 51%). $^1$H NMR (500 MHz, Chloroform-d) δ 7.49 (s, 1H), 7.37 to 7.25 (m, 5H), 6.58 (d, J=3.5 Hz, 1H), 6.47 to 6.36 (m, 1H), 4.55 to 4.36 (m, 2H), 3.98 to 3.85 (m, 1H), 3.61 to 3.51 (m, 2H), 3.51 to 3.37 (m, 2H), 2.69 to 2.35 (m, 2H), 1.60 to 1.50 (m, 2H), 1.15 to 1.09 (m, 3H), 0.94 to 0.84 (m, 9H), 0.06 to −0.02 (m, 6H).

Step 6: 2-Benzyloxy-4-[(3S)-3-[tert-butyl(dimethyl)silyl]oxybutoxy]-2-(trifluoromethyl)butanoic acid

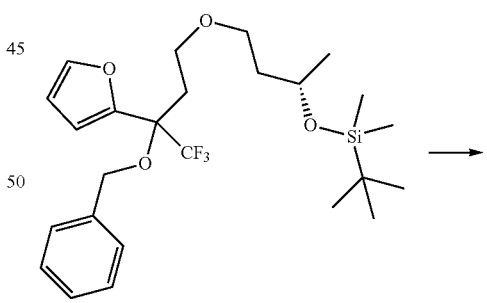

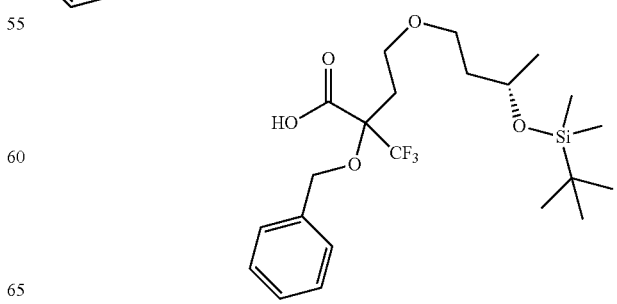

[(1S)-3-[3-benzyloxy-4,4,4-trifluoro-3-(2-furyl)butoxy]-1-methyl-propoxy]-tert-butyl-dimethyl-silane (700 mg, 1.2946 mmol) was mixed in CH₃CN (5.5 mL), CCl₄ (5.5 mL) and water (9 mL) at room temperature. NaIO₄ (1.68 g, 7.8544 mmol) was added, followed by ruthenium(III) chloride (15 mg, 0.0723 mmol). The mixture was stirred at room temperature for 15 h then more NaIO₄ (278 mg, 1.2997 mmol) was added and the mixture was stirred for an additional hour. Ethyl acetate (30 mL) and water (30 mL) were added and the layers were separated. The organic layer was washed with brine, dried over anhydrous MgSO₄, filtered and concentrated to afford crude 2-benzyloxy-4-[(3S)-3-[tert-butyl(dimethyl)silyl]oxybutoxy]-2-(trifluoromethyl)butanoic acid (800 mg, quant.). ESI-MS m/z calc. 464.2206, found 465.6 (M+1)⁺; Retention time: 4.33 minutes. LCMS Method: Merck Millipore Chromolith SpeedROD C₁₈ column (50×4.6 mm) and a dual gradient run from 5% to 100% mobile phase B over 6 minutes. Mobile phase A=water (0.1% CF₃CO₂H). Mobile phase B=acetonitrile (0.1% CF₃CO₂H).

Step 7: tert-Butyl N-[[2-benzyloxy-4-[(3S)-3-[tert-butyl(dimethyl)silyl]oxybutoxy]-2-(trifluoromethyl)butanoyl]amino]carbamate

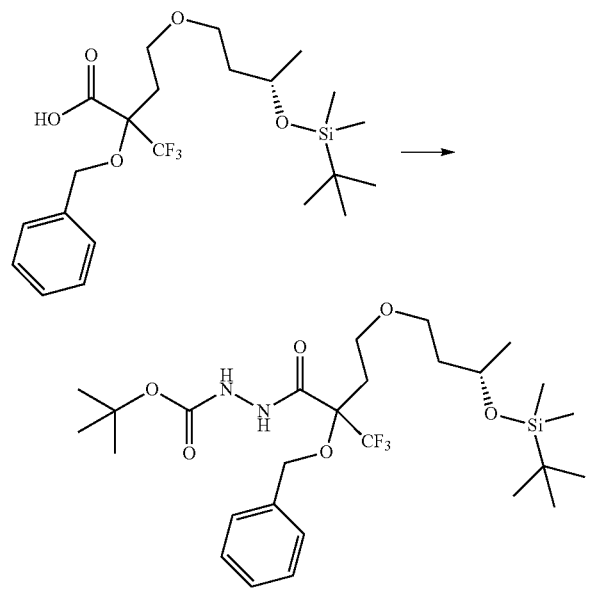

2-Benzyloxy-4-[(3S)-3-[tert-butyl(dimethyl)silyl]oxybutoxy]-2-(trifluoromethyl)butanoic acid (610 mg, 1.116 mmol) was dissolved in DMF (15 mL) at room temperature. tert-Butyl N-aminocarbamate (221 mg, 1.6722 mmol) was added, followed by HATU (638 mg, 1.6779 mmol) and TEA (217.8 mg, 0.3 mL, 2.1524 mmol). After 30 min, water (40 mL) and EtOAc (40 mL) were added and the layers were separated. The organic layer was washed with more water (3×30 mL) and brine then dried over anhydrous MgSO₄, filtered and concentrated to furnish as a crude colorless oil, tert-butyl N-[[2-benzyloxy-4-[(3S)-3-[tert-butyl(dimethyl)silyl]oxybutoxy]-2-(trifluoromethyl)butanoyl]amino]carbamate (260 mg, 38%). ESI-MS m/z calc. 578.2999, found 579.7 (M+1)⁺; Retention time: 5.1 minutes. LCMS Method: Merck Millipore Chromolith SpeedROD C₁₈ column (50× 4.6 mm) and a dual gradient run from 5% to 100% mobile phase B over 6 minutes. Mobile phase A=water (0.1% CF₃CO₂H). Mobile phase B=acetonitrile (0.1% CF₃CO₂H).

Step 8: 2-Benzyloxy-4-[(3S)-3-[tert-butyl(dimethyl)silyl]oxybutoxy]-2-(trifluoromethyl)butanehydrazide

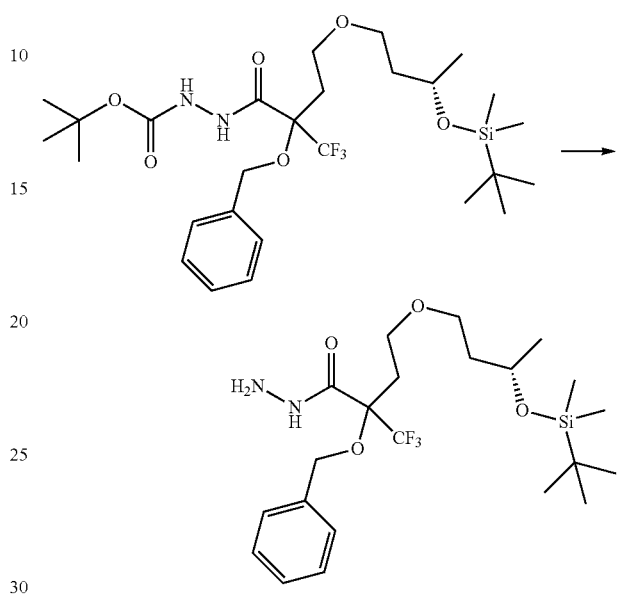

tert-Butyl N-[[2-benzyloxy-4-[(3S)-3-[tert-butyl(dimethyl)silyl]oxybutoxy]-2-(trifluoromethyl)butanoyl]amino]carbamate (268 mg, 0.4399 mmol) and 1,1,1,3,3,3-hexafluoro-2-propanol (32 g, 20 mL, 190.43 mmol) were sealed in a microwave tube and heated at 100° C. for 110 minutes. The mixture was then concentrated and the residue was purified by silica gel chromatography (40 g column) using a gradient from 0% to 15% EtOAc in hexanes to afford as a white foam, 2-benzyloxy-4-[(3S)-3-[tert-butyl(dimethyl)silyl]oxybutoxy]-2-(trifluoromethyl)butanehydrazide (127 mg, 57%). ESI-MS m/z calc. 478.2475, found 479.3 (M+1)⁺; Retention time: 3.89 minutes. LCMS Method: Merck Millipore Chromolith SpeedROD C₁₈ column (50× 4.6 mm) and a dual gradient run from 5% to 100% mobile phase B over 6 minutes. Mobile phase A=water (0.1% CF₃CO₂H). Mobile phase B=acetonitrile (0.1% CF₃CO₂H).

Step 9: tert-Butyl N-[2-[[[2-benzyloxy-4-[(3S)-3-[tert-butyl(dimethyl)silyl]oxybutoxy]-2-(trifluoromethyl)butanoyl]amino]carbamoyl]-6-bromo-5-(trifluoromethyl)-3-pyridyl]carbamate

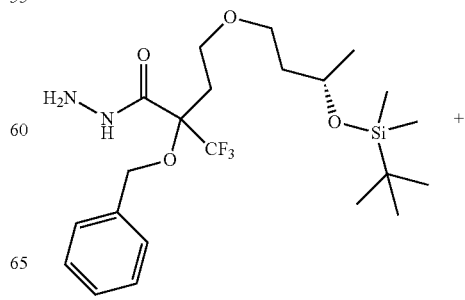

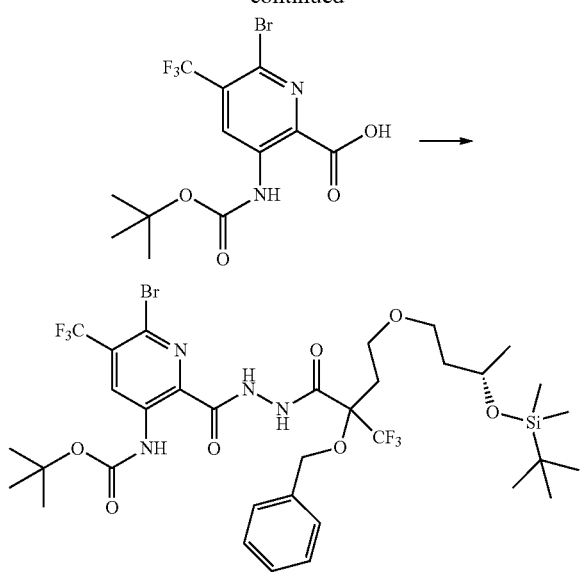

2-Benzyloxy-4-[(3S)-3-[tert-butyl(dimethyl)silyl]oxybutoxy]-2-(trifluoromethyl)butanehydrazide (127 mg, 0.2521 mmol) was dissolved in EtOAc (2 mL) at room temperature. 6-Bromo-3-(tert-butoxycarbonylamino)-5-(trifluoromethyl)pyridine-2-carboxylic acid (118 mg, 0.3064 mmol) was added, followed by pyridine (97.8 mg, 0.1 mL, 1.2364 mmol) and T3P in EtOAc (160.35 mg, 0.3 mL of 50% w/w, 0.2520 mmol). The mixture was stirred at room temperature for 14 h. The mixture was concentrated and the residue was purified by silica gel chromatography (40 g column) using a gradient from 0% to 50% EtOAc in hexanes to afford as a white foam, tert-butyl N-[2-[[[2-benzyloxy-4-[(3S)-3-[tert-butyl(dimethyl)silyl]oxybutoxy]-2-(trifluoromethyl)butanoyl]amino]carbamoyl]-6-bromo-5-(trifluoromethyl)-3-pyridyl]carbamate (200 mg, 84%). ESI-MS m/z calc. 844.2302, found 791.5 (M−53)⁺; Retention time: 5.09 minutes. LCMS Method: Merck Millipore Chromolith SpeedROD C₁₈ column (50×4.6 mm) and a dual gradient run from 5% to 100% mobile phase B over 6 minutes. Mobile phase A=water (0.1% CF₃CO₂H). Mobile phase B=acetonitrile (0.1% CF₃CO₂H).

Step 10: tert-Butyl N-[2-[5-[1-benzyloxy-3-[(3S)-3-[tert-butyl(dimethyl)silyl]oxybutoxy]-1-(trifluoromethyl)propyl]-1,3,4-oxadiazol-2-yl]-6-bromo-5-(trifluoromethyl)-3-pyridyl]carbamate

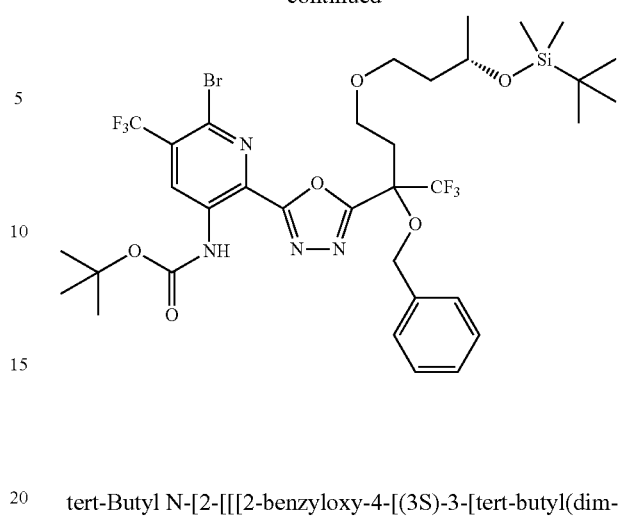

tert-Butyl N-[2-[[[2-benzyloxy-4-[(3S)-3-[tert-butyl(dimethyl)silyl]oxybutoxy]-2-(trifluoromethyl)butanoyl]amino]carbamoyl]-6-bromo-5-(trifluoromethyl)-3-pyridyl]carbamate (200 mg, 0.2128 mmol) was dissolved in CH₃CN (2 mL) at room temperature. DIEA (96.46 mg, 0.13 mL, 0.7463 mmol) was added followed by TsCl (60 mg, 0.3147 mmol). The mixture was stirred at room temperature for 5 h then concentrated to ⅓ of its volume and diluted with EtOAc (20 mL) and saturated aqueous NH₄Cl (20 mL). The resulting layers were separated and the organic layer was washed with brine, dried over anhydrous MgSO₄, filtered and concentrated. The residue was purified by silica gel chromatography (40 g column) using a gradient from 0% to 10% EtOAc in hexanes to afford as a colorless oil, tert-butyl N-[2-[5-[1-benzyloxy-3-[(3S)-3-[tert-butyl(dimethyl)silyl]oxybutoxy]-1-(trifluoromethyl)propyl]-1,3,4-oxadiazol-2-yl]-6-bromo-5-(trifluoromethyl)-3-pyridyl]carbamate (110 mg, 59%). ESI-MS m/z calc. 826.2196, found 771.5 (M−55)⁺; Retention time: 5.25 minutes. LCMS Method: Merck Millipore Chromolith SpeedROD C₁₈ column (50×4.6 mm) and a dual gradient run from 5% to 100% mobile phase B over 6 minutes. Mobile phase A=water (0.1% CF₃CO₂H). Mobile phase B=acetonitrile (0.1% CF₃CO₂H).

Step 11: tert-Butyl N-[2-[5-[1-benzyloxy-3-[(3S)-3-[tert-butyl(dimethyl)silyl]oxybutoxy]-1-(trifluoromethyl)propyl]-1,3,4-oxadiazol-2-yl]-6-bromo-5-(trifluoromethyl)-3-pyridyl]-N-tert-butoxycarbonylcarbamate

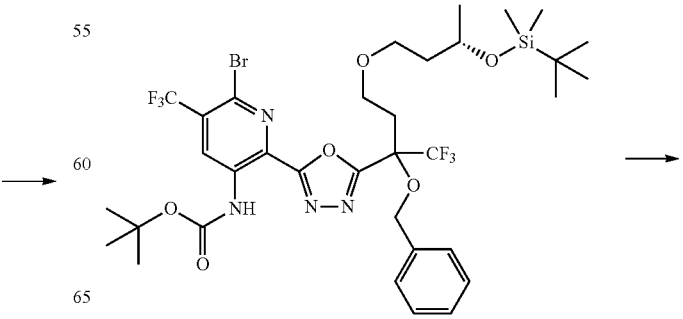

581

-continued

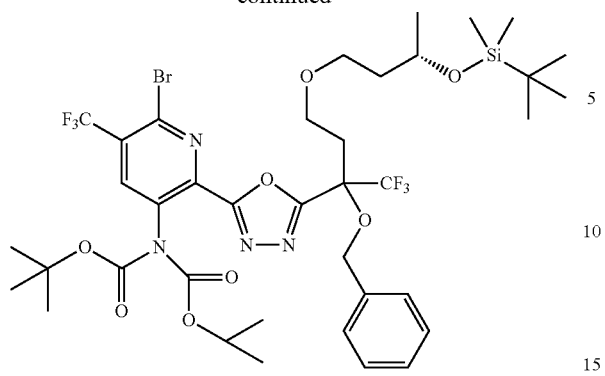

tert-Butyl N-[2-[5-[1-benzyloxy-3-[(3S)-3-[tert-butyhdimethyl)silyl]oxybutoxy]-1-(trifluoromethyl)propyl]-1,3,4-oxadiazol-2-yl]-6-bromo-5-(trifluoromethyl)-3-pyridyl]carbamate (110 mg, 0.1262 mmol) was mixed with MTBE (2 mL) at room temperature. Di-tert-butyl dicarbonate (51 mg, 0.0537 mL, 0.2337 mmol) was added followed by DMAP (1 mg, 0.0082 mmol) and DIEA (22.26 mg, 0.03 mL, 0.1722 mmol). The mixture was stirred at room temperature for 14 h and was then concentrated and purified by silica gel chromatography (24 g column) using a gradient from 0% to 20% EtOAc in hexanes to afford as a white foam, tert-butyl N-[2-[5-[1-benzyloxy-3-[(3S)-3-[tert-butyl(dimethyl)silyl]oxybutoxy]-1-(trifluoromethyl)propyl]-1,3,4-oxadiazol-2-yl]-6-bromo-5-(trifluoromethyl)-3-pyridyl]-N-tert-butoxycarbonyl-carbamate (122 mg, 99%). ESI-MS m/z calc. 926.272, found 773.5 (M−154)⁺; Retention time: 5.17 minutes. LCMS Method: Merck Millipore Chromolith SpeedROD $C_{18}$ column (50×4.6 mm) and a dual gradient run from 5 to 100% mobile phase B over 6 minutes. Mobile phase A=water (0.1% $CF_3CO_2H$). Mobile phase B=acetonitrile (0.1% $CF_3CO_2H$).

Step 12: tert-Butyl N-[2-[5-[1-benzyloxy-3-[(3S)-3-[tert-butyl(dimethyl)silyl]oxybutoxy]-1-(trifluoromethyl)propyl]-1,3,4-oxadiazol-2-yl]-6-hydroxy-5-(trifluoromethyl)-3-pyridyl]-N-tert-butoxycarbonyl-carbamate

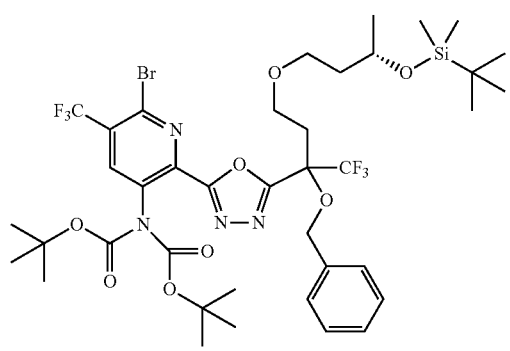

582

-continued

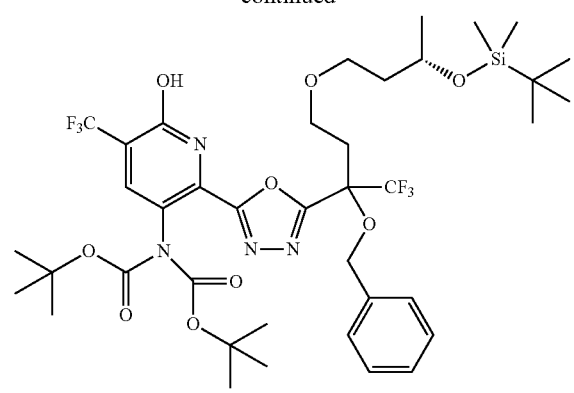

tert-Butyl N-[2-[5-[1-benzyloxy-3-[(3S)-3-[tert-butyl(dimethyl)silyl]oxybutoxy]-1-(trifluoromethyl)propyl]-1,3,4-oxadiazol-2-yl]-6-bromo-5-(trifluoromethyl)-3-pyridyl]-N-tert-butoxycarbonyl-carbamate (122 mg, 0.1249 mmol) was dissolved in DMSO (1 mL). Cesium acetate (72 mg, 0.3751 mmol) was added and the mixture was placed in a 70° C. oil bath and stirred under a balloon of nitrogen for 20 h. The mixture was cooled to room temperature and diluted with EtOAc (20 mL) and saturated aqueous $NaHCO_3$ (20 mL). The layers were separated and the organic layer was washed with more water (2×20 mL) and brine then dried over anhydrous $MgSO_4$, filtered and concentrated to afford as a pale yellow oil, tert-butyl N-[2-[5-[1-benzyloxy-3-[(3S)-3-[tert-butyl(dimethyl)silyl]oxybutoxy]-1-(trifluoromethyl)propyl]-1,3,4-oxadiazol-2-yl]-6-hydroxy-5-(trifluoromethyl)-3-pyridyl]-N-tert-butoxycarbonyl-carbamate (120 mg, 94%). ESI-MS m/z calc. 864.3564, found 765.7 (M−99)⁺; Retention time: 4.86 minutes. LCMS Method: Merck Millipore Chromolith SpeedROD $C_{18}$ column (50×4.6 mm) and a dual gradient run from 5% to 100% mobile phase B over 6 minutes. Mobile phase A=water (0.1% $CF_3CO_2H$). Mobile phase B=acetonitrile (0.1% $CF_3CO_2H$).

Step 13: tert-Butyl N-[2-[5-[1-benzyloxy-3-[(3S)-3-hydroxybutoxy]-1-(trifluoromethyl)propyl]-1,3,4-oxadiazol-2-yl]-6-hydroxy-5-(trifluoromethyl)-3-pyridyl]-N-tert-butoxycarbonyl-carbamate

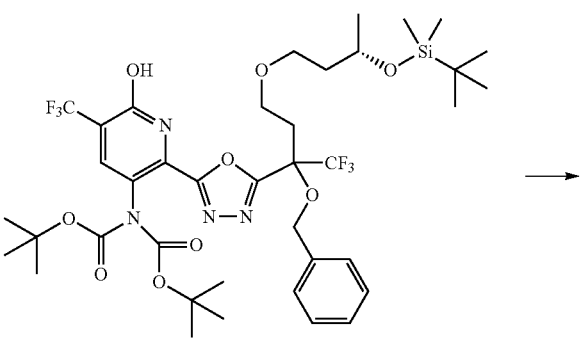

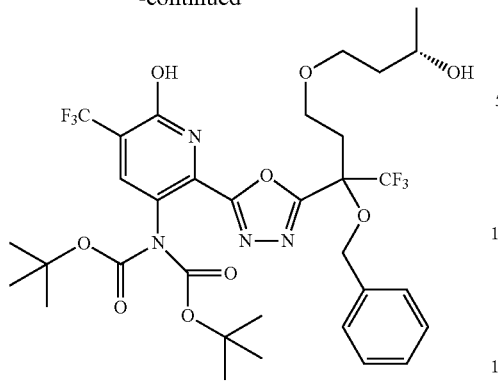

tert-Butyl N-[2-[5-[1-benzyloxy-3-[(3S)-3-[tert-butyl(dimethyl)silyl]oxybutoxy]-1-(trifluoromethyl)propyl]-1,3,4-oxadiazol-2-yl]-6-hydroxy-5-(trifluoromethyl)-3-pyridyl]-N-tert-butoxycarbonyl-carbamate (120 mg, 0.1179 mmol) was dissolved in THF (2 mL) at room temperature. Tetrabutylammonium fluoride in THF (88.7 mg, 0.1 mL, 0.3392 mmol) was added. The mixture was stirred at room temperature for 5 h and then placed in a 40° C. oil bath. Stirring continued for 14 h then more tetrabutylammonium fluoride in THF (354.8 mg, 0.4 mL, 1.357 mmol) was added. After 6 h, DMF (2 mL) was added and stirring was continued for 15 h. More tetrabutylammonium fluoride in THF (354.8 mg, 0.4 mL, 1.357 mmol) was added. After another 16 h, the mixture was diluted with EtOAc (30 mL) and water (40 mL) and the layers were separated. The organic layer was washed with brine, dried over anhydrous $MgSO_4$, filtered and concentrated. The residue was purified by silica gel chromatography (12 g column), using a gradient from 10% to 90% EtOAc in hexanes to afford as a white foam, tert-butyl N-[2-[5-[1-benzyloxy-3-[(3S)-3-hydroxybutoxy]-1-(trifluoromethyl)propyl]-1,3,4-oxadiazol-2-yl]-6-hydroxy-5-(trifluoromethyl)-3-pyridyl]-N-tert-butoxycarbonyl-carbamate (73 mg, 81%). ESI-MS m/z calc. 750.2699, found 651.7 (M-99)$^+$; Retention time: 3.8 minutes. LCMS Method: Merck Millipore Chromolith SpeedROD $C_{18}$ column (50×4.6 mm) and a dual gradient run from 5% to 100% mobile phase B over 6 minutes. Mobile phase A=water (0.1% $CF_3CO_2H$). Mobile phase B=acetonitrile (0.1% $CF_3CO_2H$).

Step 14: tert-Butyl N-[(12R)-6-benzyloxy-12-methyl-6,15-bis(trifluoromethyl)-9,13,19-trioxa-3,4,18-triazatricyclo[12.3.1.1².⁵]nonadeca-1(18),2,4,14,16-pentaen-17-yl]-N-tert-butoxycarbonyl-carbamate tert-Butyl N-[2-[5-[1-benzyloxy-3-[(3S)-3-hydroxybutoxy]-1-(trifluoromethyl)propyl]-1,3,4-oxadiazol-2-yl]-6-hydroxy-5-(trifluoromethyl)-3-pyridyl]-N-tert-butoxycarbonyl-carbamate (70 mg, 0.0914 mmol) was dissolved in toluene (9 mL) at room temperature and PPh$_3$ (77 mg, 0.068 mL, 0.2936 mmol) was added in one portion followed by DIAD (62.64 mg, 0.06 mL, 0.3098 mmol) via syringe. The mixture was stirred at room temperature for 7 h then concentrated. The residue was purified by silica gel chromatography (12 g column), using a gradient from 0% to 15% EtOAc in hexanes to afford as a white solid, ter t-butyl N-[(12R)-6-benzyloxy-12-methyl-6,15-bis(trifluoromethyl)-9,13,19-trioxa-3,4,18-triazatricyclo[12.3.1.1².⁵]nonadeca-1(18),2,4,14,16-pentaen-17-yl]-N-tert-butoxycarbonyl-carbamate (40 mg, 57%). ESI-MS m/z calc. 732.2594, found 733.6 (M+1)$^+$; Retention time: 4.75 minutes. LCMS Method: Merck Millipore Chromolith SpeedROD $C_{18}$ column (50×4.6 mm) and a dual gradient run from 5% to 100% mobile phase B over 6 minutes. Mobile phase A=water (0.1% $CF_3CO_2H$). Mobile phase B=acetonitrile (0.1% $CF_3CO_2H$).

Step 15: tert-Butyl N-tert-butoxycarbonyl-N-[(12R)-6-hydroxy-12-methyl-6,15-bis(trifluoromethyl)-9,13,19-trioxa-3,4,18-triazatricyclo[12.3.1.1².⁵]nonadeca-1(18),2,4,14,16-pentaen-17-yl]carbamate

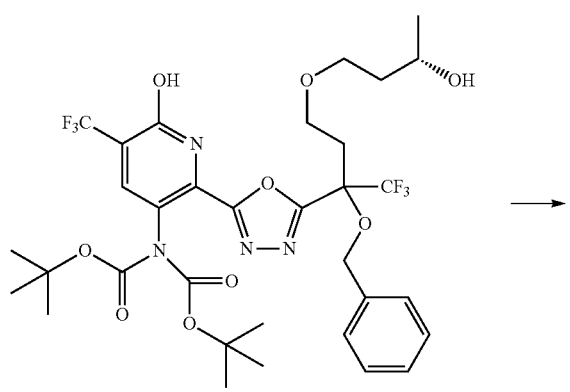

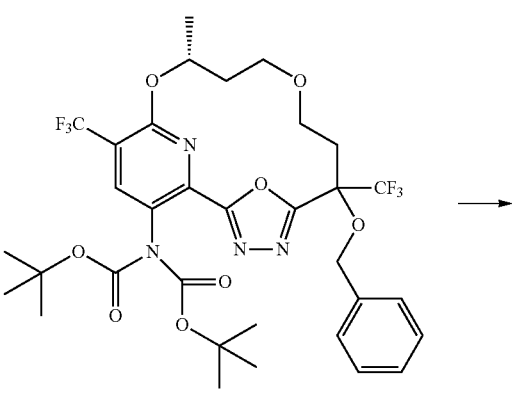

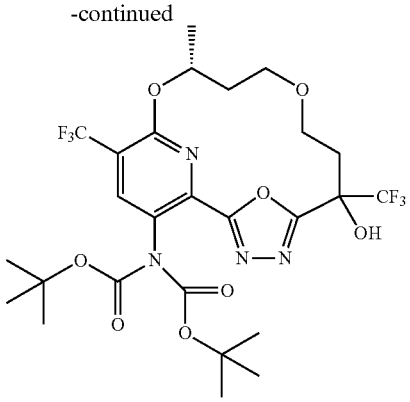

tert-Butyl N-[(12R)-6-benzyloxy-12-methyl-6,15-bis(trifluoromethyl)-9,13,19-trioxa-3,4,18-triazatricyclo[12.3.1.12,5]nonadeca-1(18),2,4,14,16-pentaen-17-yl]-N-tert-butoxycarbonyl-carbamate (40 mg, 0.0519 mmol) was dissolved in EtOH (2 mL) and 10% palladium on carbon (20 mg, 0.1879 mmol) was added. The mixture was purged with hydrogen gas several times and hydrogenated at 50 psi on a Parr shaker for 20 h. The mixture was then filtered through a celite pad, washed with MeOH (~15 mL) and the filtrate was concentrated thoroughly to afford as a crude white solid, tert-butyl N-tert-butoxycarbonyl-N-[(12R)-6-hydroxy-12-methyl-6,15-bis(trifluoromethyl)-9,13,19-trioxa-3,4,18-triazatricyclo[12.3.1.12,5]nonadeca-1(18),2,4,14,16-pentaen-17-yl]carbamate (33 mg, 94%). ESI-MS m/z calc. 642.2124, found 643.4 (M+1)+; Retention time: 4.88 minutes. LCMS Method: Merck Millipore Chromolith SpeedROD C18 column (50×4.6 mm) and a dual gradient run from 5% to 100% mobile phase B over 6 minutes. Mobile phase A=water (0.1% CF3CO2H). Mobile phase B=acetonitrile (0.1% CF3CO2H).

Step 16: (12R)-17-Amino-12-methyl-6,15-bis(trifluoromethyl)-9,13,19-trioxa-3,4,18-triazatricyclo[12.3.1.12,5]nonadeca-1(18),2,4,14,16-pentaen-6-ol

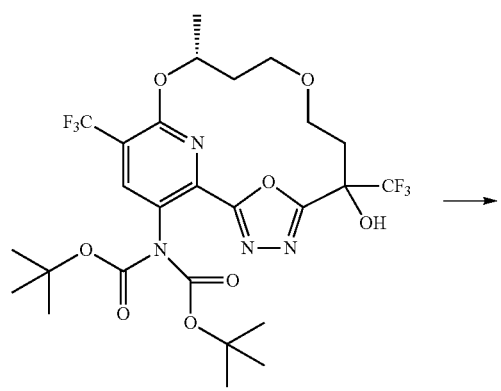

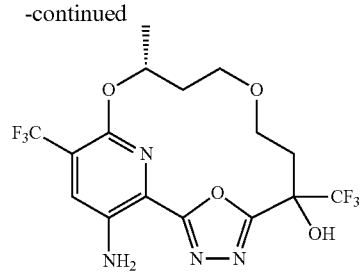

tert-Butyl N-tert-butoxycarbonyl-N-[(12R)-6-hydroxy-12-methyl-6,15-bis(trifluoromethyl)-9,13,19-trioxa-3,4,18-triazatricyclo[12.3.1.12,5]nonadeca-1(18),2,4,14,16-pentaen-17-yl]carbamate (33 mg, 0.0488 mmol) was mixed with 1,1,1,3,3,3-hexafluoro-2-propanol (3.192 g, 2 mL, 18.996 mmol) in a microwave vessel then sealed and heated at 100° C. for 130 minutes. The mixture was then cooled to room temperature and concentrated. The residue was purified by silica gel chromatography (12 g column), using a gradient from 5% to 60% EtOAc in hexanes to afford as a pale yellow solid, (12R)-17-amino-12-methyl-6,15-bis(trifluoromethyl)-9,13,19-trioxa-3,4,18-triazatricyclo[12.3.1.12,5]nonadeca-1(18),2,4,14,16-pentaen-6-ol (21 mg, 89%). ESI-MS m/z calc. 442.1076, found 443.5 (M+1)+; Retention time: 2.71 minutes (average of two diastereomeric peaks). LCMS Method: Waters Cortex 2.7 µm particle size C18 (3.0 mm×50 mm), 55° C.; flow: 1.2 mL/min; mobile phase: 100% water with 0.1% trifluoroacetic acid then 100% acetonitrile with 0.1% trifluoroacetic acid, gradient of 5% to 100% B over 4 min, with equilibration at 100% B for 0.5 min, then 5% B over 1.5 min.

Step 17: (12R)-17-amino-12-methyl-6,15-bis(trifluoromethyl)-9,13,19-trioxa-3,4,18-triazatricyclo[12.3.1.12,5]nonadeca-1(18),2,4,14,16-pentaen-6-ol (diastereomer 1), Compound 72, and (12R)-17-amino-12-methyl-6,15-bis(trifluoromethyl)-9,13,19-trioxa-3,4,18-triazatricyclo[12.3.1.12,5]nonadeca-1(18),2,4,14,16-pentaen-6-ol (diastereomer 2), Compound 73

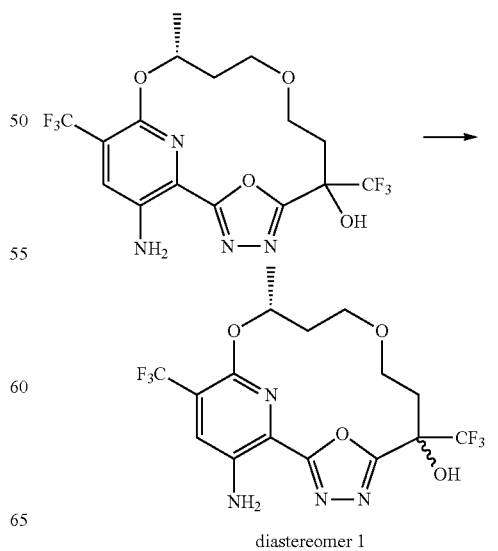

diastereomer 1

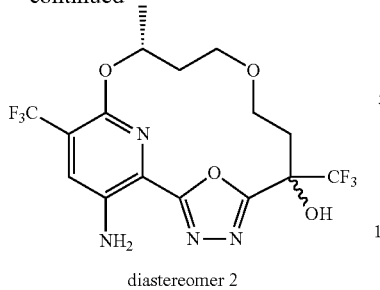

diastereomer 2

(12R)-17-amino-12-methyl-6,15-bis(trifluoromethyl)-9, 13,19-trioxa-3,4,18-triazatricyclo[12.3.1.1²,⁵]nonadeca-1(18),2,4,14,16-pentaen-6-ol (20 mg, 0.04522 mmol) was separated into the individual diastereomers by chiral SFC using a normal phase SFC-MS method utilizing a ChiralCel OJ column (250×10 mm; 5 μm particle size) at 50° C. (mobile phase=7% MeOH (+20 mM $NH_3$)/93% $CO_2$ at a 10 mL/min flow, concentration of the sample was 22.0 mg/mL in methanol, injection volume=70 μL with an outlet pressure of 140 bar, detection wavelength of 224 nm). The first peak to elute afforded as a pale yellow solid, (12R)-17-amino-12-methyl-6,15-bis(trifluoromethyl)-9,13,19-trioxa-3,4,18-triazatricyclo[12.3.1.1²,⁵]nonadeca-1(18),2,4,14,16-pentaen-6-ol (diastereomer 1) (7.2 mg, 69%). ¹H NMR (400 MHz, Chloroform-d) δ 7.40 (s, 1H), 5.39 (pd, J=6.5, 4.3 Hz, 1H), 5.14 (s, 2H), 3.99 (s, 1H), 3.86-3.78 (m, 1H), 3.67-3.61 (m, 1H), 3.60-3.51 (m, 2H), 2.68 (ddd, J=14.9, 8.9, 5.9 Hz, 1H), 2.52 (dt, J=15.2, 4.0 Hz, 1H), 2.40-2.30 (m, 1H), 1.64-1.58 (m, 1H), 1.42 (d, J=6.5 Hz, 3H). ESI-MS m/z calc. 442.10757, found 443.2 (M+1)⁺; Retention time: 1.76 minutes. LCMS Method: Acquity UPLC BEH $C_{18}$ column (50×2.1 mm, 1.7 μm particle) made by Waters (pn: 186002350), and a dual gradient run from 1% to 99% mobile phase B over 2.9 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

The second peak to elute afforded as a pale yellow solid, (12R)-17-amino-12-methyl-6,15-bis(trifluoromethyl)-9,13,19-trioxa-3,4,18-triazatricyclo[12.3.1.1²,⁵]nonadeca-1(18),2,4,14,16-pentaen-6-ol (diastereomer 2) (5.2 mg, 51%). ¹H NMR (400 MHz, Chloroform-d) δ 7.42 (s, 1H), 5.25 (ddt, J=10.2, 6.5, 3.3 Hz, 1H), 5.10 (s, 2H), 4.51 (s, 1H), 3.95 (td, J=9.2, 4.5 Hz, 1H), 3.86 (ddd, J=12.1, 10.3, 1.7 Hz, 1H), 3.62-3.51 (m, 2H), 2.75-2.62 (m, 2H), 2.35 (dt, J=14.9, 4.7 Hz, 1H), 1.49-1.37 (m, 4H). ESI-MS m/z calc. 442.10757, found 443.2 (M+1)⁺; Retention time: 1.76 minutes. LCMS Method: Acquity UPLC BEH $C_{18}$ column (50×2.1 mm, 1.7 μm particle) made by Waters (pn: 186002350), and a dual gradient run from 1% to 99% mobile phase B over 2.9 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 μL, and column temperature=60° C.

Example 51: Preparation of (15R)-15-methyl-18-(trifluoromethyl)-16,22-dioxa-3,4,7,8,21-pentazatetracyclo[15.3.1.1²,⁵.0⁶,¹⁰]docosa-1(21),2,4,6,9,17,19-heptaen-20-amine, Compound 74

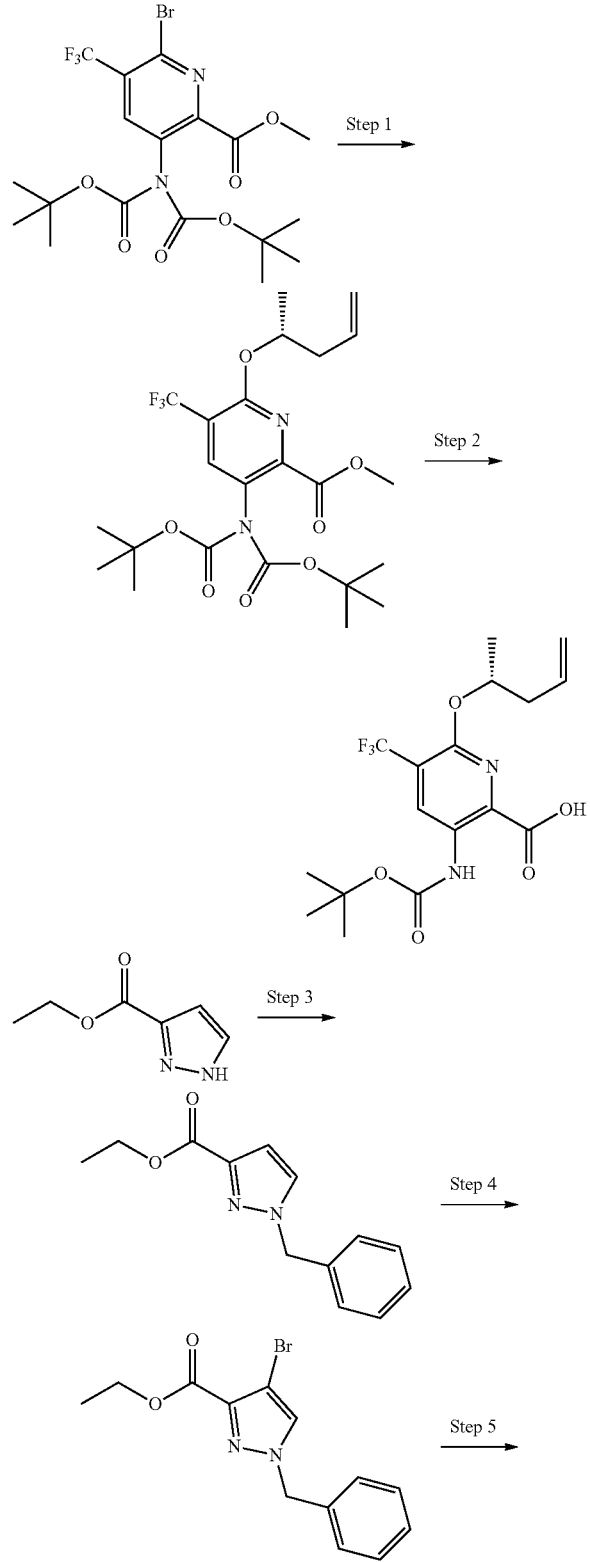

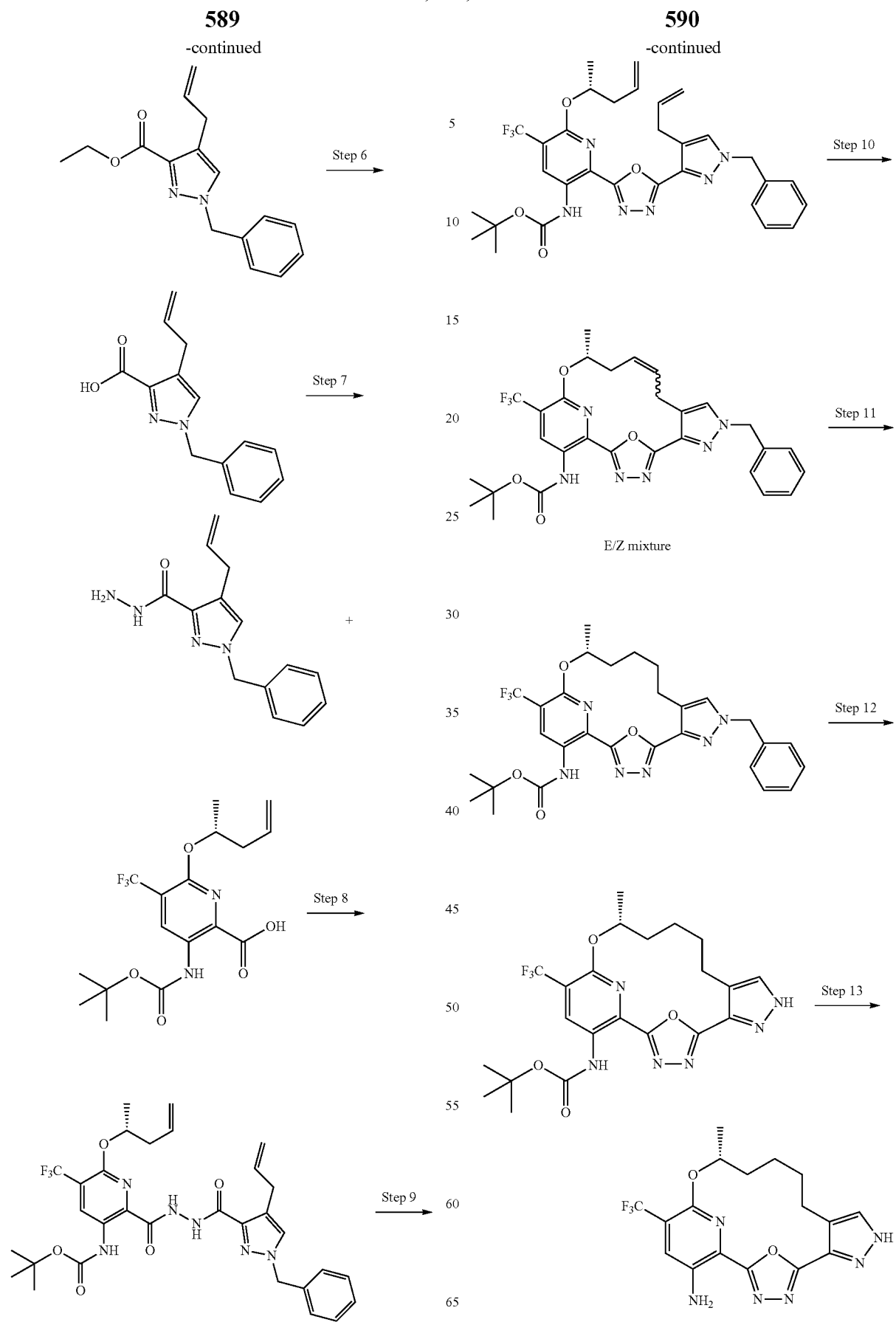

Step 1: Methyl 3-[bis(tert-butoxycarbonyl)amino]-6-[(1R)-1-methylbut-3-enoxy]-5-(trifluoromethyl)pyridine-2-carboxylate

Step 2: 3-(tert-Butoxycarbonylamino)-6-[(1R)-1-methylbut-3-enoxy]-5-(trifluoromethyl)pyridine-2-carboxylic acid

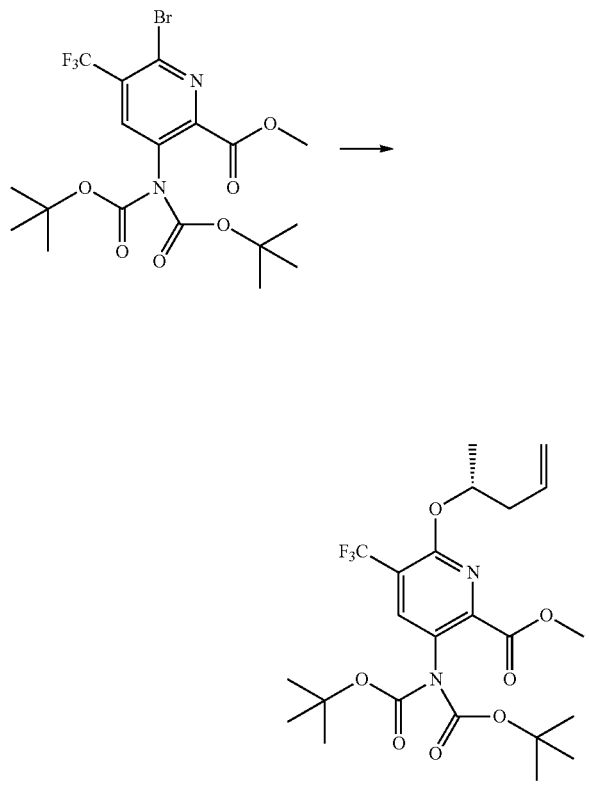

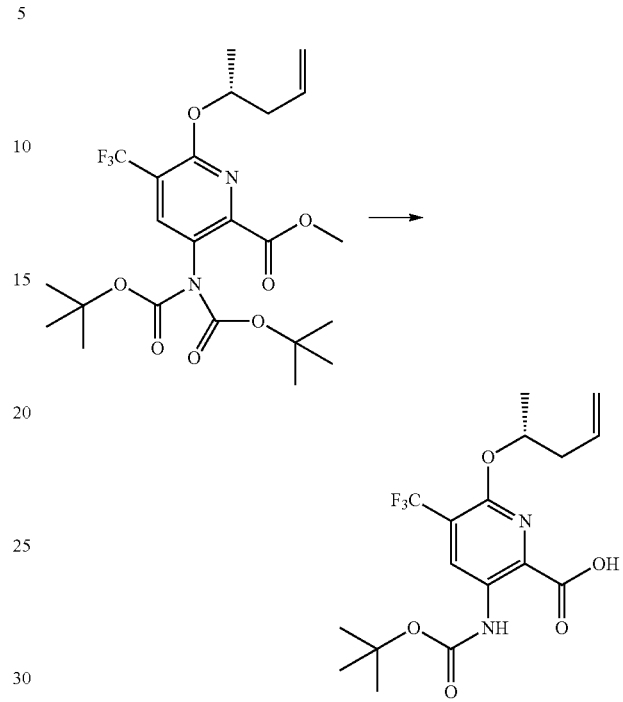

To a solution of methyl 3-[bis(tert-butoxycarbonyl)amino]-6-bromo-5-(trifluoromethyl)pyridine-2-carboxylate (500 mg, 1.001 mmol) in DMSO (5 mL) was added (2R)-pent-4-en-2-ol (160 µL, 1.555 mmol), cesium carbonate (521 mg, 1.599 mmol) and iodocopper (54 mg, 0.2835 mmol) and the reaction mixture was heated at 100° C. for 3 h. The reaction mixture was cooled to room temperature and poured on crushed ice and extracted with ethyl acetate and washed with brine. The organics were separated, dried over sodium sulfate, filtered and evaporated. The resultant brown residue was purified by silica gel column chromatography using a shallow gradient from 100% hexanes to 30% ethyl acetate in hexanes to afford as a colorless oil, methyl 3-[bis(tert-butoxycarbonyl)amino]-6-[(1R)-1-methylbut-3-enoxy]-5-(trifluoromethyl)pyridine-2-carboxylate (216 mg, 43%). ESI-MS m/z calc. 504.20834, found 505.0 (M+1)$^+$; Retention time: 1.73 minutes. LCMS Method: Acquity UPLC BEH $C_{18}$ column (50×2.1 mm, 1.7 µm particle size) made by Waters (pn: 186002350), and a dual gradient run from 30 99% mobile phase B over 2.9 minutes. Mobile phase A=$H_2O$ (0.05% $CF_3CO_2H$). Mobile phase B=$CH_3CN$ (0.035% $CF_3CO_2H$). Flow rate=1.2 mL/min, injection volume=1.5 uL, and column temperature=60° C.

To a solution of methyl 3-[bis(tert-butoxycarbonyl)amino]-6-[(1R)-1-methylbut-3-enoxy]-5-(trifluoromethyl)pyridine-2-carboxylate (3.3 g, 6.5412 mmol) in MeOH (24 mL) and THF (24 mL) was added a solution of lithium hydroxide monohydrate (1.2 g, 28.596 mmol) in water (12 mL). The mixture was stirred at 50° C. for 16 h. The reaction mixture was then cooled down to room temperature and aqueous 1N HCl was added until pH=2 was reached. The volatiles were removed under reduced pressure and the product was extracted with ethyl acetate (3×20 mL). The combined organic phases were washed with brine (20 mL), dried over sodium sulfate, filtered and concentrated under reduced pressure which afforded as a yellow oil, 3-(tert-butoxycarbonylamino)-6-[(1R)-1-methylbut-3-enoxy]-5-(trifluoromethyl)pyridine-2-carboxylic acid (2.66 g, 89%). $^1$H NMR (400 MHz, DMSO-$d_6$) δ 12.12-11.38 (m, 1H), 8.78 (s, 1H), 5.92-5.69 (m, 1H), 5.42-5.33 (m, 1H), 5.14-5.06 (m, 1H), 5.06-5.01 (m, 1H), 2.44-2.37 (m, 2H), 1.46 (s, 9H), 1.25 (d, J=6.4 Hz, 3H). $^{19}$F NMR (377 MHz, DMSO-$d_6$) δ −62.33 (s, 3F). ESI-MS m/z calc. 390.1403, found 389.0 (M−1)$^-$; Retention time: 2.28 minutes. LCMS Method: Kinetex Polar $C_{18}$ column (3.0×50 mm, 2.6 µm particle size, 3 minute run, 5% to 95% acetonitrile in water (0.1% formic acid modifier), flow rate=1.2 mL/min).

Step 3: Ethyl 1-benzylpyrazole-3-carboxylate

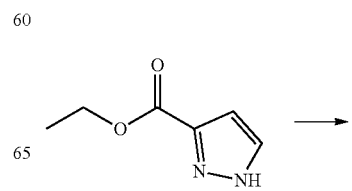

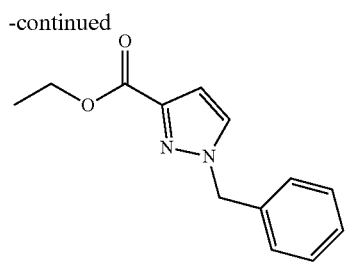

To a suspension of ethyl 1H-pyrazole-5-carboxylate (20 g, 142.71 mmol) and potassium carbonate (60 g, 434.13 mmol) in dimethyl formamide (200 mL) was added benzyl bromide (25.92 g, 18 mL, 151.55 mmol) at room temperature and the mixture was stirred for 3 hours at room temperature. The mixture was diluted with ethyl acetate (500 mL) and washed with water (500 mL). The aqueous layer was extracted with ethyl acetate (250 mL). The combined organic layers were washed with water (500 mL), brine (500 mL), dried over sodium sulfate, filtered, and concentrated under reduced pressure. The residue was purified by silica gel column chromatography (eluted with a gradient of 100% heptane to 30% ethyl acetate in heptane) to give as the second eluting regioisomeric product and a white solid, ethyl 1-benzylpyrazole-3-carboxylate (21.5 g, 65%). $^1$H NMR (400 MHz, CDCl$_3$) δ 7.40-7.30 (m, 4H), 7.26-7.21 (m, 2H), 6.83 (d, J=2.4 Hz, 1H), 5.40 (s, 2H), 4.42 (q, J=7.1 Hz, 2H), 1.41 (t, J=7.1 Hz, 3H). ESI-MS m/z calc. 230.1055, found 231.2 (M+1)$^+$; Retention time: 1.85 minutes; LCMS Method: Kinetex Polar C$_{18}$ 3.0×50 mm, 2.6 μm, 3 min, 5-95% acetonitrile in water (0.1% formic acid), flow=1.2 mL/min.

Step 4: Ethyl 1-benzyl-4-bromo-pyrazole-3-carboxylate

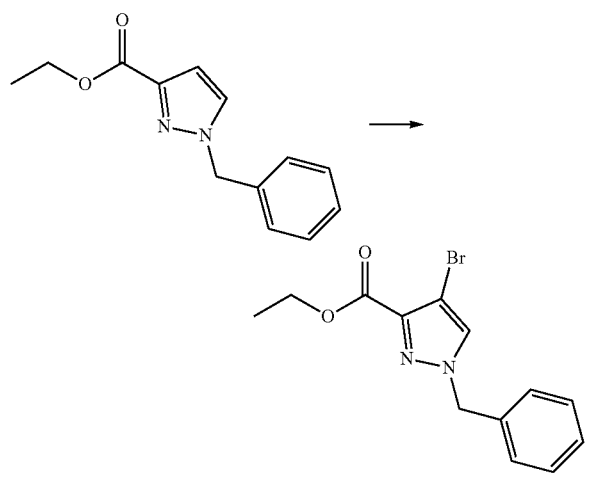

To a solution of ethyl 1-benzylpyrazole-3-carboxylate (7 g, 30.4 mmol) in acetonitrile (140 mL) was added bromine (9.3069 g, 3 mL, 58.238 mmol) at room temperature. After stirring at room temperature overnight, additional bromine (4.9637 g, 1.6 mL, 31.06 mmol) was added and the mixture was stirred at room temperature for 1 day. The mixture was concentrated under reduced pressure, diluted with ethyl acetate (20 mL), and washed with aqueous 10% sodium thiosulfate (200 mL). The aqueous layer was extracted with ethyl acetate/tetrahydrofuran (1/1, 200 mL). The combined organic layer was dried over sodium sulfate, filtered, and concentrated under reduced pressure. The residue was purified by silica gel column chromatography (eluted with a gradient from 0% to 35% ethyl acetate in heptane) to give as a white solid, ethyl 1-benzyl-4-bromo-pyrazole-3-carboxylate (9.1 g, 97%); $^1$H NMR (400 MHz, CDCl3) δ 7.44-7.33 (m, 4H), 7.29-7.24 (m, 2H), 5.36 (s, 2H), 4.45 (q, J=7.2 Hz, 2H), 1.43 (t, J=7.1 Hz, 3H). ESI-MS m/z calc. 308.016, found 309.1 (M+1)$^+$; Retention time: 1.98 minutes. LCMS Method: Kinetex Polar C$_{18}$ column (3.0×50 mm, 2.6 μm particle size, 3 minute run, 5% to 95% acetonitrile in water (0.1% formic acid modifier), flow rate=1.2 mL/min).

Step 5: Ethyl 4-allyl-1-benzyl-pyrazole-3-carboxylate

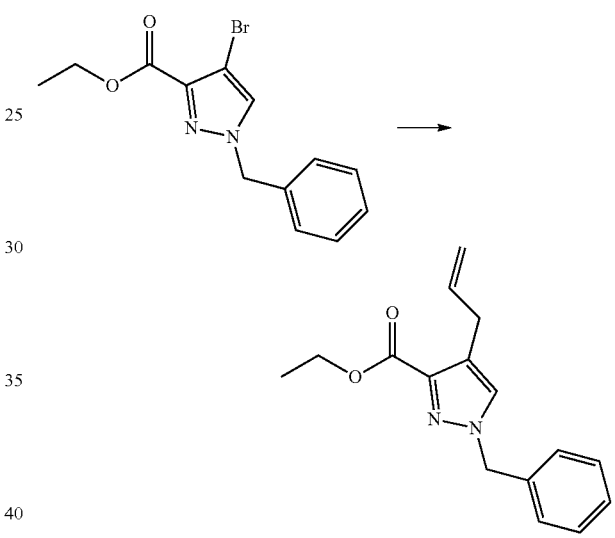

A solution of ethyl 1-benzyl-4-bromo-pyrazole-3-carboxylate (8.7 g, 28.141 mmol) in tetrahydrofuran (130 mL) and water (25 mL) was degassed by bubbling nitrogen for 15 minutes. 1-Allyl-3,3,4,4-tetramethyl-borolane (5.6 g, 6.25 mL, 34.127 mmol) and 1,1'-bis(diphenylphosphino)ferrocene palladium(II) chloride, complex with dichloromethane (3 g, 3.6736 mmol) were added followed by the addition of cesium carbonate (42 mL of 2 M, 84 mmol) under nitrogen. The reaction mixture was heated overnight at 100° C. After cooling down to room temperature, the reaction mixture was diluted with ethyl acetate (150 mL) filtrated through a pad of celite and rinsed with ethyl acetate (2×100 mL). The filtrate was washed with water (2×200 mL) and brine (400 mL). The organic phase was then dried over anhydrous sodium sulfate, filtered and concentrated in vacuo. The resulting mixture was purified by silica gel column chromatography (gradient of 0% to 30% ethyl acetate in heptanes). The desired fractions were collected and the solvent was concentrated under reduced pressure to afford as a white solid, ethyl 4-allyl-1-benzyl-pyrazole-3-carboxylate (5.02 g, 64%). 1H NMR (400 MHz, CDCl3) δ 7.41-7.31 (m, 3H), 7.26-7.21 (m, 2H), 7.15 (s, 1H), 5.94 (ddt, J=17.0, 10.2, 6.6 Hz, 1H), 5.35 (s, 2H), 5.09-4.98 (m, 2H), 4.42 (q, J=7.2 Hz, 2H), 3.50 (d, J=6.6 Hz, 2H), 1.41 (t, J=7.2 Hz, 3H). ESI-MS m/z calc. 270.1368, found 271.2 (M+1)+; Retention time: 2.0 min- Step 6: 4-Allyl-1-benzyl-pyrazole-3-carboxylic acid

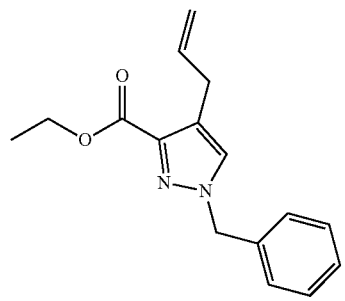

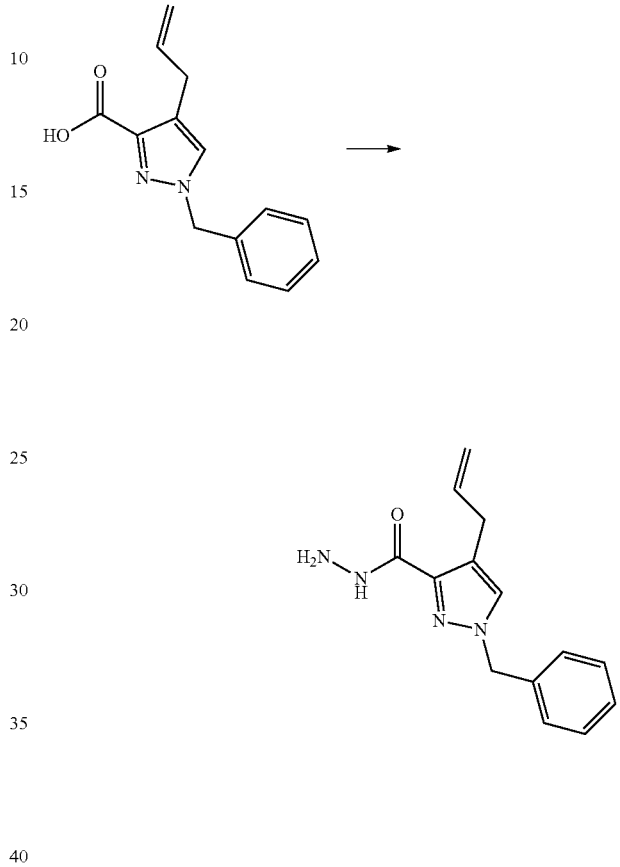

Step 7: 4-Allyl-1-benzyl-pyrazole-3-carbohydrazide

A solution of lithium hydroxide (5 g, 208.78 mmol) in water (10 mL) was added to a solution of ethyl 4-allyl-1-benzyl-pyrazole-3-carboxylate (5 g, 18.015 mmol) in methanol (50 mL) and tetrahydrofuran (25 mL). The reaction was stirred at room temperature for 3 hours. The reaction was then concentrated to remove the methanol. The crude material was diluted in water (100 mL) and the carboxylate sodium salt was washed with heptane (50 mL) and MTBE (50 mL). The aqueous solution was acidified to pH=2 with a 3 N aqueous hydrochloric acid solution. The carboxylic acid was extracted with dichloromethane (4×100 mL) and dried over sodium sulfate. The solution was filtered and concentrated to give as a light-yellow solid, 4-allyl-1-benzyl-pyrazole-3-carboxylic acid (4.45 g, 99%). 1H NMR (400 MHz, CDCl3) δ 12.40-10.19 (m, 1H), 7.48-7.39 (m, 3H), 7.37-7.31 (m, 2H), 7.27 (s, 1H), 6.01 (ddt, J=17.0, 10.2, 6.6 Hz, 1H),5.43 (s, 2H), 5.20-5.04 (m, 2H), 3.59 (d, J=6.6 Hz, 2H). ESI-MS m/z calc. 242.1055, found 243.1 (M+1)+; Retention time: 1.79 minutes; LCMS Method: Kinetex Polar $C_{18}$ column (3.0×50 mm, 2.6 μm particle size, 3 minute run, 5% to 95% acetonitrile in water (0.1% formic acid modifier), flow rate=1.2 mL/min).

A solution of 4-allyl-1-benzyl-pyrazole-3-carboxylic acid (4.15 g, 16.616 mmol) and triethylamine (5.0820 g, 7 mL, 50.222 mmol) in DMF (60 mL) was treated with HATU (13 g, 34.19 mmol) and stirred at room temperature for 20 minutes. The reaction mixture was cooled in an ice bath and hydrazine hydrate (13.416 g, 20 mL, 174.2 mmol) was added. After about 10 minutes, the ice bath was removed and the reaction was stirred at room temperature for about 18 hours. The reaction mixture was transferred to a 1 L separatory funnel with water (450 mL) and the aqueous layer was extracted with ethyl acetate (4×100 mL). The combined organic layers were washed with water (2×200 mL), brine (250 mL), dried over sodium sulfate, filtered and concentrated under reduced pressure. Silica gel chromatography (gradient from 0% to 60% ethyl acetate in heptanes) afforded as a colorless oil, 4-allyl-1-benzyl-pyrazole-3-carbohydrazide (2.45 g, 52%). 1H NMR (400 MHz, DMSO-$d_6$) δ 9.11 (s, 1H), 7.66 (s, 1H), 7.44-7.15 (m, 5H), 5.95 (ddt, J=17.0, 10.2, 6.6 Hz, 1H), 5.30 (s, 2H), 5.10-4.89 (m, 2H), 4.34 (s, 2H), 3.45 (d, J=6.6 Hz, 2H). ESI-MS m/z calc. 256.1324, found 257.2 (M+1)+; Retention time: 3.23 minutes. LCMS Method: SunFire $C_{18}$ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Step 8: tert-Butyl N-[2-[[(4-allyl-1-benzyl-pyrazole-3-carbonyl)amino]carbamoyl]-6-[(1R)-1-methylbut-3-enoxy]-5-(trifluoromethyl)-3-pyridyl]carbamate

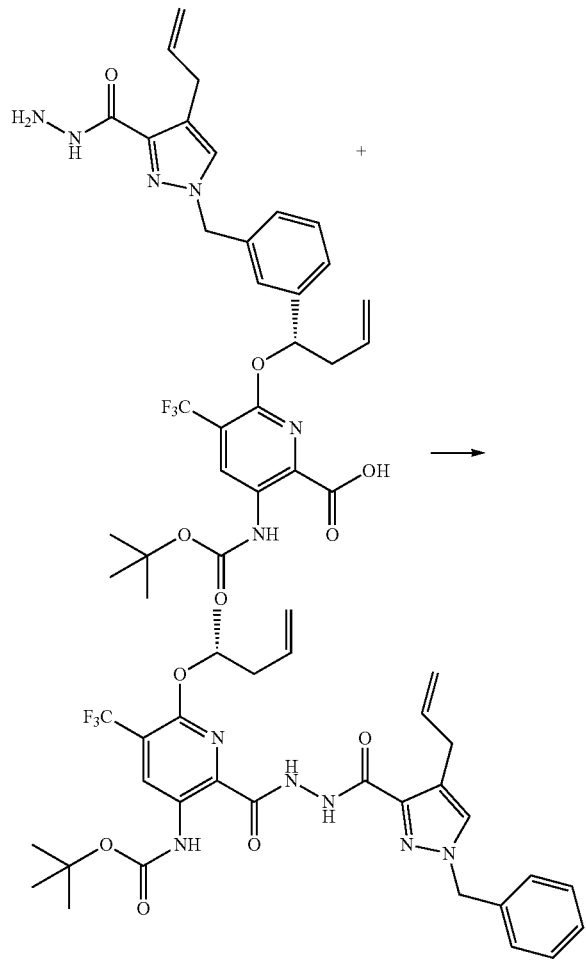

To a solution of 3-(tert-butoxycarbonylamino)-6-[(1R)-1-methylbut-3-enoxy]-5-(trifluoromethyl)pyridine-2-carboxylic acid (200 mg, 0.5088 mmol) in DMF (1.5 mL) was added 4-allyl-1-benzyl-pyrazole-3-carbohydrazide (160 mg, 0.5662 mmol), HATU (235 mg, 0.618 mmol) and DIEA (371 mg, 0.5 mL, 2.8706 mmol) at room temperature. The solution was stirred at room temperature for 2 h and directly loaded on a reversed-phase C$_{18}$ preparatory column. Purification was performed by reversed-phase chromatography (100 gram column. Gradient from 5% to 100% acetonitrile in water with 0.1% formic acid) to afford as a white foam, tert-butyl N-[2-[[(4-allyl-1-benzyl-pyrazole-3-carbonyl)amino]carbamoyl]-6-[(1R)-1-methylbut-3-enoxy]-5-(trifluoromethyl)-3-pyridyl]carbamate (238 mg, 71%). 1H NMR (400 MHz, DMSO-d$_6$) δ 10.83 (s, 1H), 10.65 (s, 1H), 10.15 (s, 1H), 9.01 (s, 1H), 7.77 (s, 1H), 7.50-7.18 (m, 5H), 5.97 (ddt, J=17.0, 10.2, 6.6 Hz, 1H), 5.89-5.74 (m, 2H), 5.39 (s, 2H), 5.18-4.94 (m, 4H), 3.46 (d, J=6.6 Hz, 2H), 2.47-2.32 (m, 2H), 1.47 (s, 9H), 1.25 (d, J=6.1 Hz, 3H). $^{19}$F NMR (377 MHz, DMSO-d$_6$) δ −63.11 (s, 3F). ESI-MS m/z calc. 628.2621, found 529.3 (M−99)+; Retention time: 4.3 minutes. LCMS Method: XBridge C$_{18}$ column (4.6×75 mm, 5 μm particle size, 6 minute run with 1 minute equilibration, initial mobile phase at 95% aqueous NH$_4$HCO$_3$/5% acetonitrile, gradient from 0 to 3 minutes to 95% MeCN and held for 3 minutes, flow=1.5 mL/min).

Step 9: tert-Butyl N-[2-[5-(4-allyl-1-benzyl-pyrazol-3-yl)-1,3,4-oxadiazol-2-yl]-6-[(1R)-1-methylbut-3-enoxy]-5-(trifluoromethyl)-3-pyridyl]carbamate

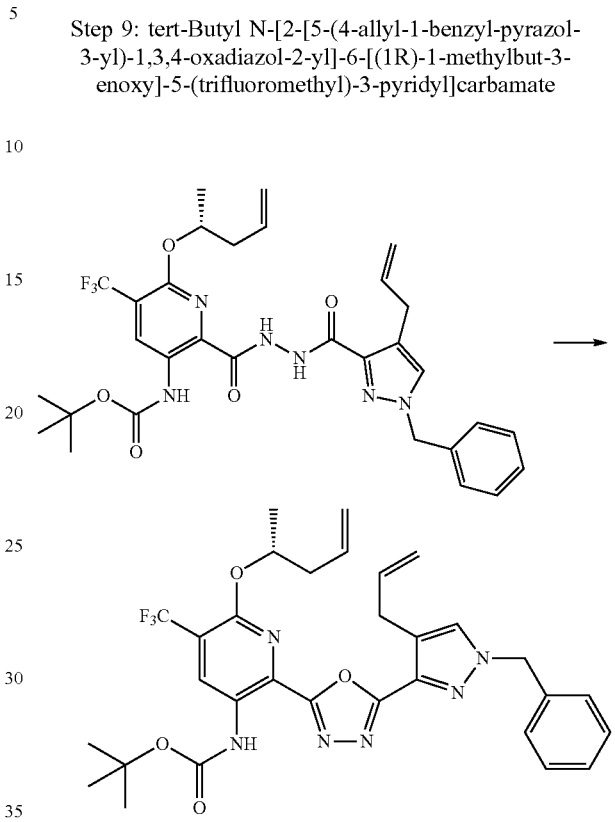

To a solution of tert-butyl N-[2-[[(4-allyl-1-benzyl-pyrazole-3-carbonyl)amino]carbamoyl]-6-[(1R)-1-methylbut-3-enoxy]-5-(trifluoromethyl)-3-pyridyl]carbamate (235 mg, 0.3577 mmol) and toluenesulfonyl chloride (220 mg, 1.154 mmol) in DCE (7 mL) was added N,N-diisopropylethylamine (0.5 mL, 2.8706 mmol) and toluenesulfonyl chloride (220 mg, 1.154 mmol). The reaction was stirred at 50° C. for 20 h then cooled down to room temperature. The volatiles were removed under reduced pressure. Purification was performed by reversed-phase chromatography (50 g column. Gradient from 5% to 95% acetonitrile in water with 0.1% formic acid) to afford as a tan oil, tert-butyl N-[2-[5-(4-allyl-1-benzyl-pyrazol-3-yl)-1,3,4-oxadiazol-2-yl]-6-[(1R)-1-methylbut-3-enoxy]-5-(trifluoromethyl)-3-pyridyl]carbamate (202 mg, 81%). 1H NMR (400 MHz, DMSO-d$_6$) δ 9.93 (s, 1H), 8.92 (s, 1H), 7.96 (s, 1H), 7.42-7.26 (m, 5H), 6.04 (ddt, J=16.8, 10.2, 6.4 Hz, 1H), 5.84 (ddt, J=17.2, 10.1, 7.0 Hz, 1H), 5.46 (s, 2H), 5.34 (m, J=6.1 Hz, 1H), 5.20-5.13 (m, 1H), 5.12-5.00 (m, 3H), 3.59 (d, J=6.6 Hz, 2H), 2.50-2.38 (m, 2H), 1.50 (s, 9H), 1.34 (d, J=6.1 Hz, 3H). 19F NMR (377 MHz, DMSO-d6) δ −62.80 (s, 3F). ESI-MS m/z calc. 610.2515, found 555.2 (M−55)+; Retention time: 2.56 minutes. LCMS Method: Luna C$_{18}$ column (50×3 mm, 3 μm particle size, temperature=45° C., flow=1.5 mL/min, run time=3.5 minutes. Mobile phase conditions: Initial 95% water +0.1% formic acid/5% acetonitrile +0.1% formic acid, linear gradient to 95% acetonitrile +0.1% formic acid over 1.3 minutes then held for 2.2 minute at 95% acetonitrile +0.1% formic acid.

Step 10: tert-Butyl N-[(15R)-8-benzyl-15-methyl-18-(trifluoromethyl)-16,22-dioxa-3,4,7,8,21-pentaza-tetracyclo[15.3.1.1²,⁵.0⁶,¹⁰]docosa-1(21),2,4,6,9,12,17,19-octaen-20-yl]carbamate (E/Z Mixture)

Step 11: tert-Butyl N-[(15R)-8-benzyl-15-methyl-18-(trifluoromethyl)-16,22-dioxa-3,4,7,8,21-pentaza-tetracyclo[15.3.1.1²,⁵.0⁶,¹⁰]docosa-1(21),2,4,6,9,17,19-heptaen-20-yl]carbamate

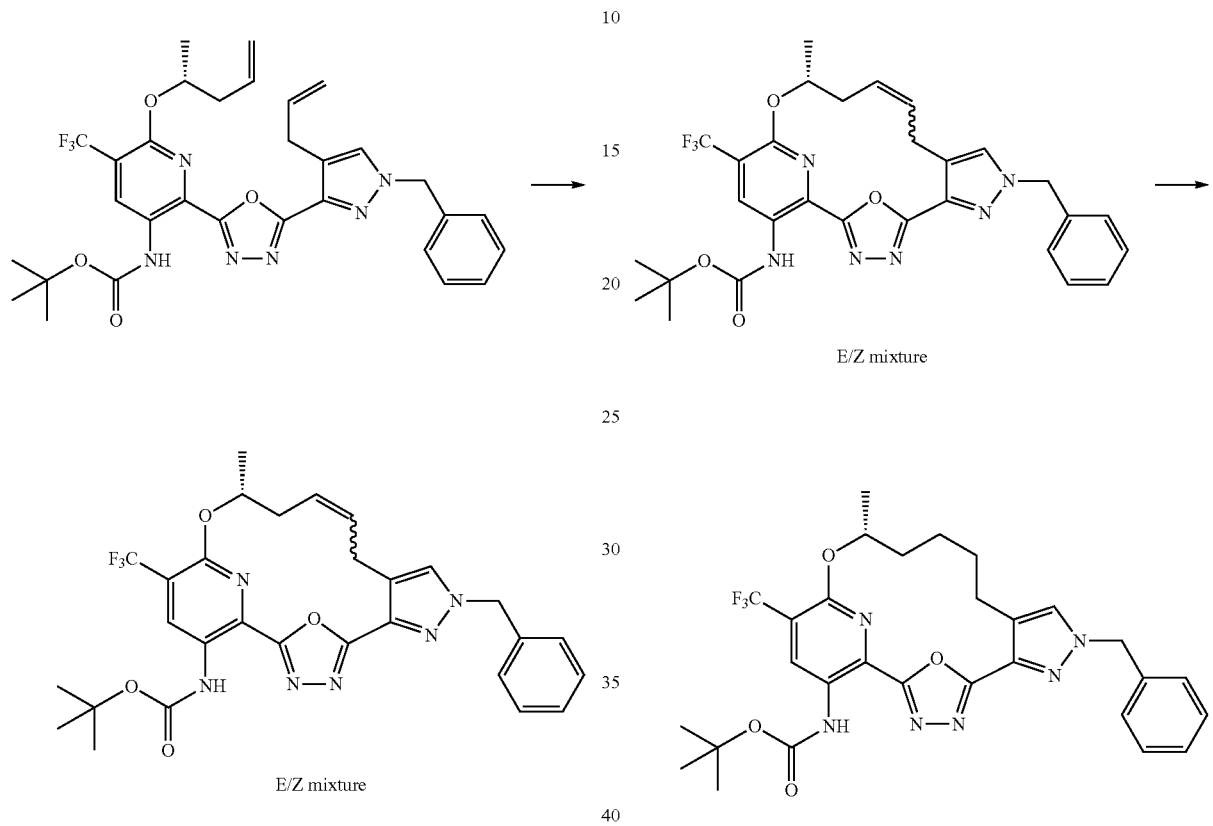

Nitrogen gas was bubbled through a light yellow solution of tert-butyl N-[2-[5-(4-allyl-1-benzyl-pyrazol-3-yl)-1,3,4-oxadiazol-2-yl]-6-[(1R)-1-methylbut-3-enoxy]-5-(trifluoromethyl)-3-pyridyl]carbamate (200 mg, 0.2879 mmol) in dichloroethane (100 mL) for 2 hours. The solution was then placed in an oil bath set at 70° C. and a first portion of Zhan catalyst-1B (20 mg, 0.0273 mmol) was added. The reaction was stirred for 2 hours. DMSO (2 drops) was added and the reaction mixture was cooled down to room temperature. The volatiles were removed under reduced pressure. Purification by silica gel chromatography (gradient from 0% to 30% ethyl acetate in heptanes) afforded as a yellow oil, tert-butyl N-[(15R)-8-benzyl-15-methyl-18-(trifluoromethyl)-16,22-dioxa-3,4,7,8,21-pentazatetracyclo[15.3.1.1²,⁵.0⁶,¹⁰]docosa-1(21),2,4,6,9,12,17,19-octaen-20-yl]carbamate (E/Z mixture) (65 mg, 37%). $^{19}$F NMR (377 MHz, DMSO-$d_6$) δ −62.17−−62.44 (m, 3F). ESI-MS m/z calc. 582.2202, found 583.3 (M+1)+; Retention time: 4.51 minutes. LCMS Method: XBridge $C_{18}$ column (4.6×75 mm, 5 μm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

To palladium hydroxide on carbon (21 mg, 20% w/w, 0.0299 mmol) under nitrogen was added a solution of tert-butyl N-[(15R)-8-benzyl-15-methyl-18-(trifluoromethyl)-16,22-di oxa-3,4,7,8,21-pentazatetracyclo[15.3.1.12,5.06,10]docosa-1(21),2,4,6,9,12,17,19-octaen-20-yl]carbamate (E/Z mixture) (60 mg, 0.0987 mmol) in methanol (5 mL). Hydrogen gas was bubbled into the mixture for 5 min and then the reaction was stirred at room temperature for 4 h under hydrogen atmosphere (balloon). The mixture was filtered through celite, washing with ethyl acetate (50 mL) and the filtrate was concentrated under reduced pressure. Purification of the residue by silica gel chromatography (Gradient from 5% to 60% ethyl acetate in heptanes) afforded as an off-white solid, tert-butyl N-[(15R)-8-benzyl-15-methyl-18-(trifluoromethyl)-16,22-dioxa-3,4,7,8,21-pentazatetracyclo[15.3.1.1²,⁵.0⁶,¹⁰]docosa-1(21),2,4,6,9,17,19-heptaen-20-yl]carbamate (55 mg, 88%). ESI-MS m/z calc. 584.2359, found 585.3 (M+1)+; Retention time: 4.6 minutes. LCMS Method: XBridge $C_{18}$ column (4.6×75 mm, 5 μm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

Step 12: tert-Butyl N-[(15R)-15-methyl-18-(trifluoromethyl)-16,22-dioxa-3,4,7,8,21-pentazatetracyclo[15.3.1.1²,⁵.0⁶,¹⁰]docosa-1(21),2,4,6,9,17,19-heptaen-20-yl]carbamate Step 13: (15R)-15-Methyl-18-(trifluoromethyl)-16,22-dioxa-3,4,7,8,21-pentazatetracyclo[15.3.1.1²,⁵.0⁶,¹⁰]docosa-1(21),2,4,6,9,17,19-heptaen-20-amine, Compound 74

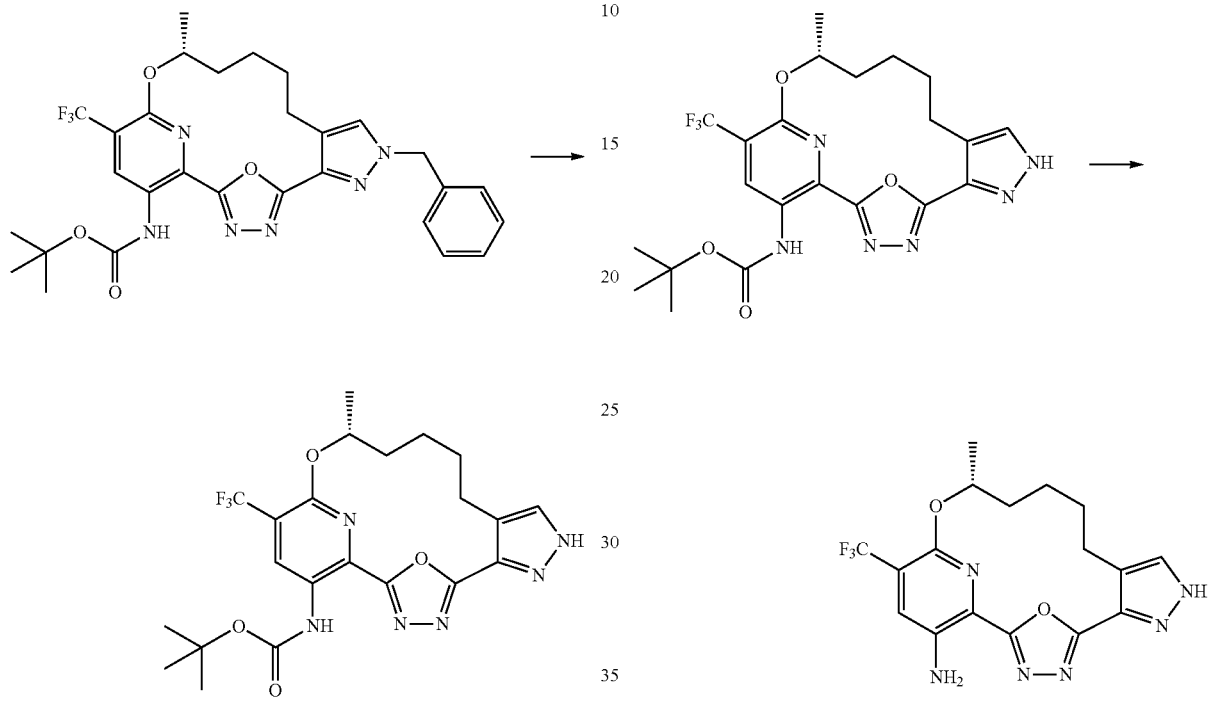

To palladium on carbon (60 mg, 5% w/w, 0.0282 mmol) under nitrogen was added a solution of tert-butyl N-[(15R)-8-benzyl-15-methyl-18-(trifluoromethyl)-16,22-dioxa-3,4,7,8,21-pentazatetracyclo[15.3.1.1²,⁵.0⁶,¹⁰]docosa-1(21),2,4,6,9,17,19-heptaen-20-yl]carbamate (50 mg, 0.0787 mmol) in tetrahydrofuran (10 mL). The tube was sealed and pressurized with hydrogen gas (50 psi). The reaction mixture was stirred at 50° C. for 24 hours. The mixture was then cooled, degassed with nitrogen purge then filtered through celite, washing with ethyl acetate (25 mL). The filtrate was concentrated under reduced pressure. Purification of the residue by silica gel chromatography (Gradient from 0% to 90% ethyl acetate in heptanes) afforded as a yellow solid, tert-butyl N-[(15R)-15-methyl-18-(trifluoromethyl)-16,22-dioxa-3,4,7,8,21-pentazatetracyclo[15.3.1.1²,⁵.0⁶,¹⁰]docosa-1(21),2,4,6,9,17,19-heptaen-20-yl]carbamate (18 mg, 45%). 1H NMR (400 MHz, $CDCl_3$) δ 13.31-12.26 (m, 1H), 9.21 (s, 1H), 9.10 (s, 1H), 7.92 (s, 1H), 5.07-4.91 (m, 1H), 3.12-2.95 (m, 1H), 2.69-2.51 (m, 2H), 2.42-2.25 (m, 1H), 1.72-1.62 (m, 3H), 1.60 (s, 9H), 1.55-1.48 (m, 1H), 1.45 (d, J=6.1 Hz, 3H). 19F NMR (377 MHz, $CDCl_3$) δ −63.70 (s, 3F). ESI-MS m/z calc. 494.1889, found 495.2 (M+1)+; Retention time: 4.21 minutes. LCMS Method:) XBridge $C_{18}$ column (4.6×75 mm, 5 μm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

To a solution of tert-butyl N-[(15R)-15-methyl-18-(trifluoromethyl)-16,22-dioxa-3,4,7,8,21-pentazatetracyclo[15.3.1.1²,⁵.0⁶,¹⁰]docosa-1(21),2,4,6,9,17,19-heptaen-20-yl]carbamate (18 mg, 0.0357 mmol) in dichloromethane (1.8 mL) was added TFA (0.6 mL, 7.7879 mmol) and the mixture was stirred at room temperature for 2 hours. A saturated aqueous $NaHCO_3$ solution was then added dropwise until pH=6-7 was reached. Water (10 mL) and DCM (10 mL) were added and the phases were separated. The aqueous phase was extracted with DCM (3×10 mL). The combined organic layers were concentrated under reduced pressure. Purification of the residue by reversed-phase chromatography (15.5 g column. Gradient from 5% to 90% acetonitrile in water) afforded as a yellow solid after lyophilization, (15R)-15-methyl-18-(trifluoromethyl)-16,22-dioxa-3,4,7,8,21-pentazatetracyclo[15.3.1.1²,⁵.0⁶,¹⁰]docosa-1(21),2,4,6,9,17,19-heptaen-20-amine (11.7 mg, 83%). 1H NMR (400 MHz, DMSO-$d_6$) δ 13.44 (br. s., 1H), 7.86 (br. s., 1H), 7.74 (s, 1H), 6.34 (s, 2H), 4.95-4.80 (m, 1H), 2.99-2.81 (m, 1H), 2.62-2.52 (m, 1H), 2.47-2.37 (m, 1H), 2.34-2.17 (m, 1H), 1.65-1.41 (m, 3H), 1.40-1.28 (m, 4H). 19F NMR (377 MHz, DMSO-d6) δ −62.32 (s, 3F). ESI-MS m/z calc. 394.1365, found 395.1 (M+1)+; Retention time: 3.53 minutes. LCMS Method: XBridge $C_{18}$ column (4.6×75 mm, 5 μm particle size, 6 minute run with 1 minute equilibration, initial mobile phase at 95% aqueous $NH_4HCO_3$/5% acetonitrile, gradient from 0 to 3 minutes to 95% MeCN and held for 3 minutes, flow=1.5 mL/min).

603
Example 52: Preparation of (6R,12R)-6-hydroxy-12-methyl-6,15-bis(trifluoromethyl)-13,19-dioxa-3,4,18-triazatricyclo[12.3.1.1²,⁵]nonadeca-1(18),2,4,14,16-pentaene-17-carboxylic acid, Compound 75
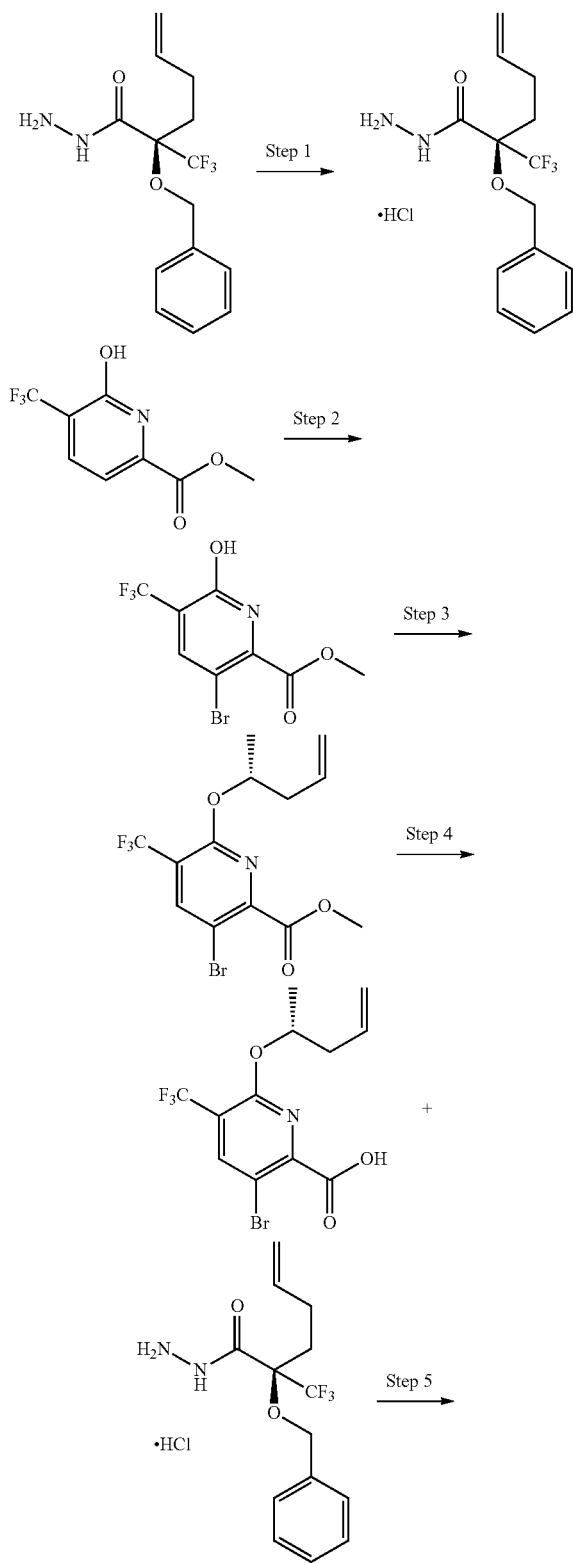
604
-continued
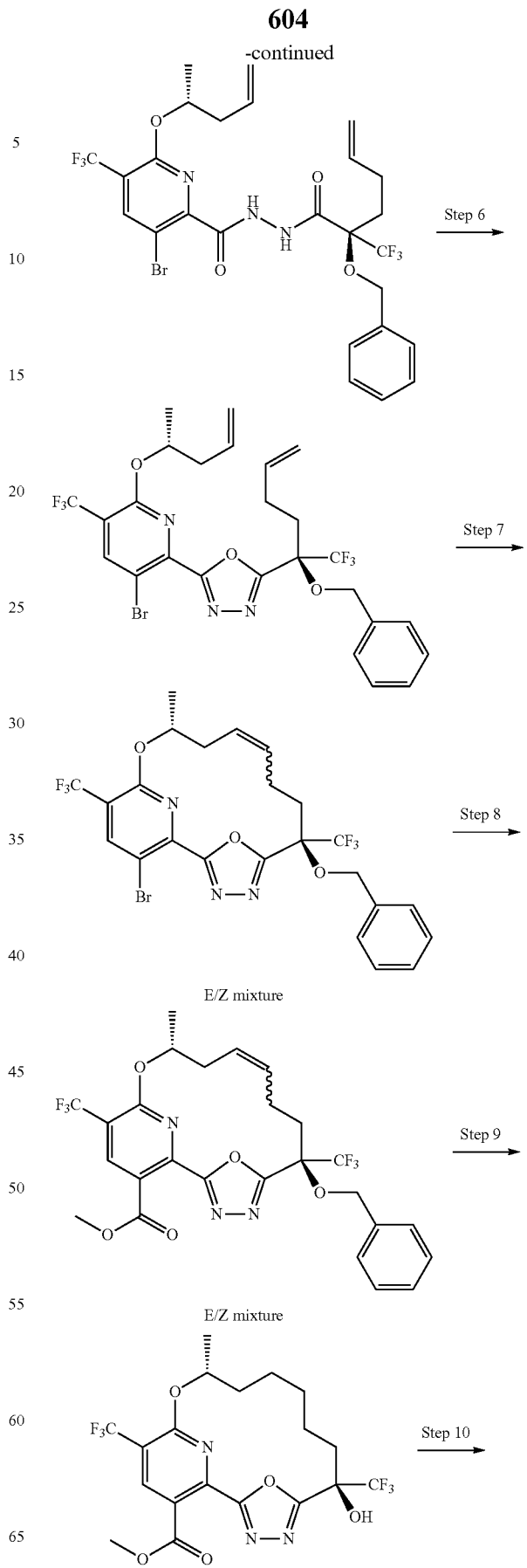

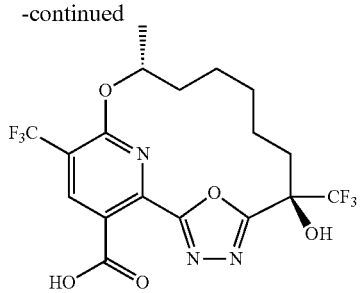

Step 1: (2R)-2-Benzyloxy-2-(trifluoromethyl)hex-5-enehydrazide (hydrochloride salt)

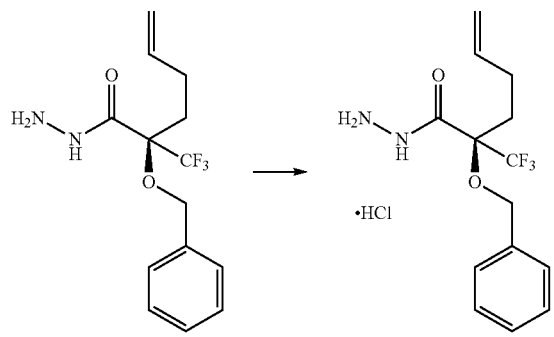 [SMILES: C=CCC[C@@](OCc1ccccc1)(C(=O)NN)C(F)(F)F ; Cl ; C=CCC[C@@](OCc1ccccc1)(C(=O)NN)C(F)(F)F]

To a 0° C. solution of (2R)-2-benzyloxy-2-(trifluoromethyl)hex-5-enehydrazide (3.672 g, 11.722 mmol) in diethyl ether (30 mL) was added dropwise a hydrogen chloride solution (8.8 mL of 2 M, 17.6 mmol) in diethyl ether. More diethyl ether (40 mL) was then added at 0° C. After the addition, the ice-water cooling bath was removed and the mixture was stirred at room temperature over 20 hours. The suspension was filtered on a fritted funnel and the white precipitate was rinsed with diethyl ether (2×15 mL), collected and dried under vacuum to give as a white solid, (2R)-2-benzyloxy-2-(trifluoromethyl)hex-5-enehydrazide (hydrochloride salt) (3.71 g, 90%). $^1$H NMR (400 MHz, DMSO-$d_6$) δ 10.95 (br s, 1H), 10.45-8.71 (m, 3H), 7.51-7.28 (m, 5H), 5.90-5.77 (m, 1H), 5.12-4.97 (m, 2H), 4.79 (s, 2H), 2.40-1.92 (m, 4H). $^{19}$F NMR (377 MHz, DMSO-$d_6$) δ −72.72 (s, 3F). ESI-MS m/z calc. 302.1242, found 303.1 (M+1)$^+$; Retention time: 2.83 minutes. LCMS Method: Kinetex Polar C$_{18}$ column (3.0×50 mm, 2.6 μm particle size, 6 minute run, 5% to 95% acetonitrile in water (0.1% formic acid modifier), flow rate=1.2 mL/min).

Step 2: Methyl 3-bromo-6-hydroxy-5-(trifluoromethyl)pyridine-2-carboxylate

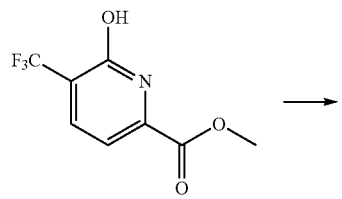

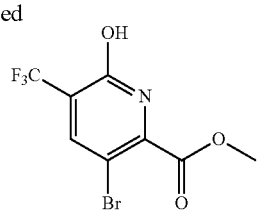

1-Bromopyrrolidine-2,5-dione (18.3 g, 102.82 mmol) was added in three equal portions about 15 minutes apart to methyl 6-hydroxy-5-(trifluoromethyl)pyridine-2-carboxylate (20.6 g, 93.157 mmol) dissolved in DMF (160 mL) and the mixture was left stirring at room temperature 60 minutes after the addition was complete. Deionized water (1 L) was added and the resulting precipitate was filtered and washed with deionized water (3×100 mL) then dried under high vacuum to provide as a white powder, methyl 3-bromo-6-hydroxy-5-(trifluoromethyl)pyridine-2-carboxylate (26.61 g, 95%). $^1$H NMR (300 MHz, CDCl$_3$) ppm 4.03 (s, 3H), 7.98 (s, 1H), 11.53 (br. s., 1H). $^{19}$F NMR (282 MHz, CDCl$_3$) ppm −66.4 (s, 3F). ESI-MS m/z calc. 298.9405, found 300.0 (M+1)$^+$; Retention time: 1.64 minutes. LCMS Method: Kinetex Polar C$_{18}$ column (4.6×50 mm, 2.6 μm particle size, 3 minute run, 5% to 95% acetonitrile in water (0.1% formic acid modifier), flow rate=2.0 mL/min).

Step 3: Methyl 3-bromo-6-[(1R)-1-methylbut-3-enoxy]-5-(trifluoromethyppyridine-2-carboxylate

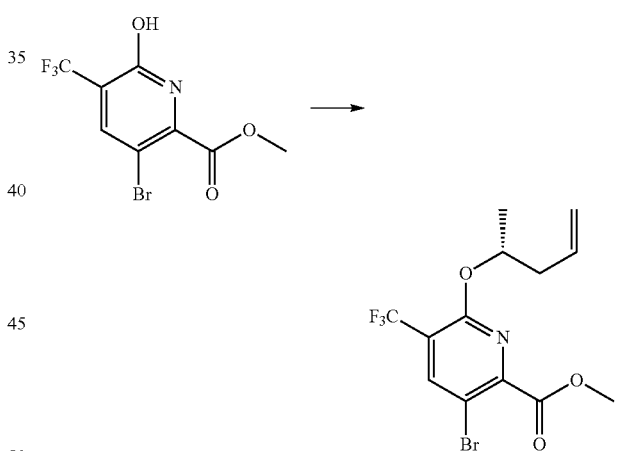

To a solution of methyl 3-bromo-6-hydroxy-5-(trifluoromethyl)pyridine-2-carboxylate (1 g, 3.3297 mmol) and (2S)-pent-4-en-2-ol (420 mg, 4.8762 mmol) in toluene (20 mL) was added triphenyl phosphine (1.3 g, 4.9564 mmol). After stirring at room temperature for 10 minutes, DIAD (1.1297 g, 1.1 mL, 5.5868 mmol) was added and the mixture was stirred at room temperature for 2.5 h. Toluene was evaporated under reduced pressure. Purification by silica gel chromatography (40 g column, Gradient: 0% to 5% ethyl acetate in heptanes) yielded methyl 3-bromo-6-[(1R)-1-methylbut-3-enoxy]-5-(trifluoromethyl)pyridine-2-carboxylate (1.15 g, 94%) as a light yellow oil. $^1$H NMR (400 MHz, CDCl$_3$) δ 8.04 (s, 1H), 5.89-5.76 (m, 1H), 5.37 (m, J=6.1 Hz, 1H), 5.15-5.04 (m, 2H), 4.00 (s, 3H), 2.55-2.38 (m, 2H), 1.36 (d, J=6.1 Hz, 3H). $^{19}$F NMR (377 MHz, CDCl$_3$) δ −64.41 (s, 3F). ESI-MS m/z calc. 367.0031, found 368.0

(M+1)⁺; Retention time: 2.11 minutes. LCMS Method: Luna C$_{18}$ column (50×3 mm, 3 µm particle size, temperature=45° C., flow=1.5 mL/min, run time=2.5 minutes. Mobile phase conditions: Initial 95% water +0.1% formic acid/5% acetonitrile +0.1% formic acid, linear gradient to 95% acetonitrile +0.1% formic acid over 1.3 minutes then held for 1.2 minute at 95% acetonitrile +0.1% formic acid.

Step 4: 3-Bromo-6-[(1R)-1-methylbut-3-enoxy]-5-(trifluoromethyl)pyridine-2-carboxylic acid

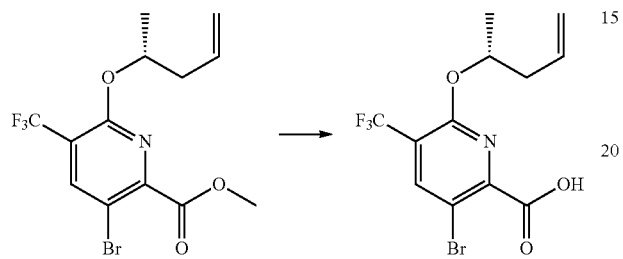

To a solution of methyl 3-bromo-6-[(1R)-1-methylbut-3-enoxy]-5-(trifluoromethyl)pyridine-2-carboxylate (1.11 g, 3.0151 mmol) in MeOH (10 mL) and THF (10 mL) was added a solution of lithium hydroxide hydrate (550 mg, 13.107 mmol) in water (5 mL). The mixture was stirred at room temperature for 2 hours. To the mixture was added aqueous 1 N HCl until pH=2 was reached. The volatiles were removed under reduced pressure and the product was extracted with ethyl acetate (3×40 mL). The combined organic phases were washed with brine (40 mL), dried over sodium sulfate, filtered and concentrated under reduced pressure which gave as a yellow solid, 3-bromo-6-[(1R)-1-methylbut-3-enoxy]-5-(trifluoromethyl)pyridine-2-carboxylic acid (1.1 g, 98%). ¹H NMR (400 MHz, CDCl$_3$) δ 8.21 (s, 1H), 5.89-5.76 (m, 1H), 5.28 (m, J=6.2 Hz, 1H), 5.19-5.09 (m, 2H), 2.61-2.43 (m, 2H), 1.43 (d, J=6.1 Hz, 3H). ¹⁹F NMR (377 MHz, CDCl$_3$) δ −64.44 (s, 3F). ESI-MS m/z calc. 352.9874, found 354.1 (M+1)⁺; Retention time: 2.02 minutes. LCMS Method: Kinetex Polar C$_{18}$ column (3.0×50 mm, 2.6 µm particle size, 3 minute run, 5% to 95% acetonitrile in water (0.1% formic acid modifier), flow rate=1.2 mL/min).

Step 5: N'-[(2R)-2-benzyloxy-2-(trifluoromethyl)hex-5-enoyl]-3-bromo-6-[(1R)-1-methylbut-3-enoxy]-5-(trifluoromethyl)pyridine-2-carbohydrazide

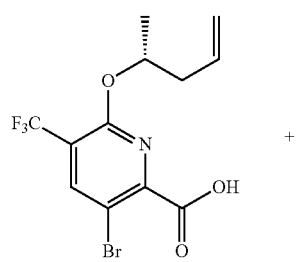 +

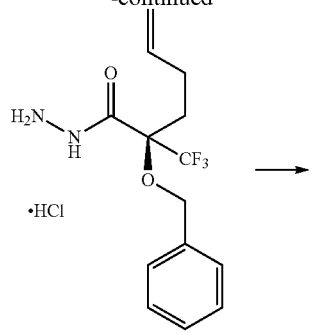

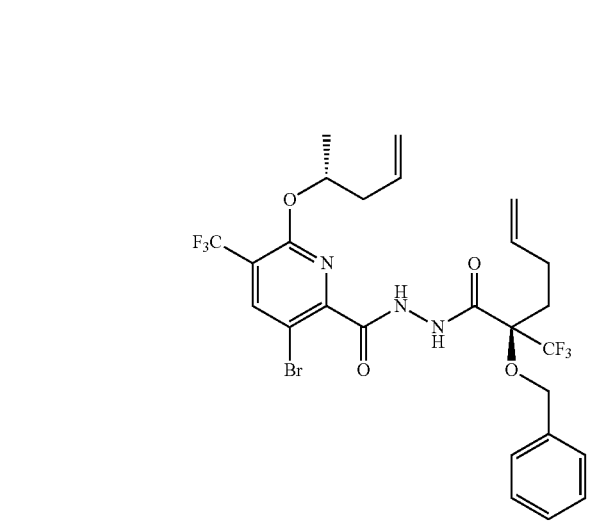

To a solution of 3-bromo-6-[(1R)-1-methylbut-3-enoxy]-5-(trifluoromethyl)pyridine-2-carboxylic acid (1.709 g, 4.7619 mmol) and (2R)-2-benzyloxy-2-(trifluoromethyl)hex-5-enehydrazide (hydrochloride salt) (1.7 g, 5.0184 mmol) in ethyl acetate (30 mL) was added triethylamine (1.8876 g, 2.6 mL, 18.654 mmol) and a solution of T3P (5.2 mL of 50% w/v, 8.1714 mmol) in ethyl acetate. The reaction was stirred at room temperature (20-25° C.) for 72 hours. The mixture was quenched with an aqueous saturated solution of ammonium chloride (20 mL). Ethyl acetate (70 mL) was added to the mixture. The phases were separated and the organic phase was washed with an aqueous saturated solution of ammonium chloride (20 mL) and with an aqueous saturated solution of sodium bicarbonate (2×20 mL), dried over anhydrous sodium sulfate, filtered and concentrated under reduced pressure to afford as a white solid, N'-[(2R)-2-benzyloxy-2-(trifluoromethyl)hex-5-enoyl]-3-bromo-6-[(1R)-1-methylbut-3-enoxy]-5-(trifluoromethyl)pyridine-2-carbohydrazide (2.856 g, 94%). ESI-MS m/z calc. 637.1011, found 638.1 (M+1)⁺; Retention time: 2.14 minutes. LCMS Method: Luna C$_{18}$ column (50×3 mm, 3 µm particle size, temperature=45° C., flow=1.5 mL/min, run time=2.5 minutes. Mobile phase conditions: Initial 95% water +0.1% formic acid/5% acetonitrile +0.1% formic acid, linear gradient to 95% acetonitrile +0.1% formic acid over 1.3 minutes then held for 1.2 minute at 95% acetonitrile +0.1% formic acid.

Step 6: 2-[(1R)-1-Benzyloxy-1-(trifluoromethyl)pent-4-enyl]-5-[3-bromo-6-[(1R)-1-methylbut-3-enoxy]-5-(trifluoromethyl)-2-pyridyl]-1,3,4-oxadiazole

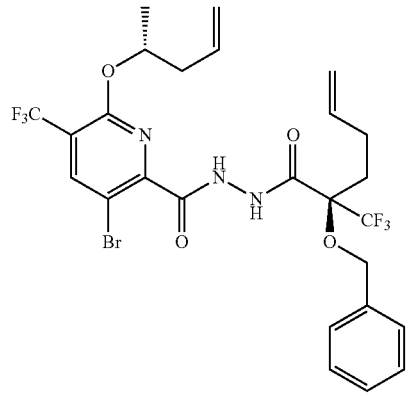

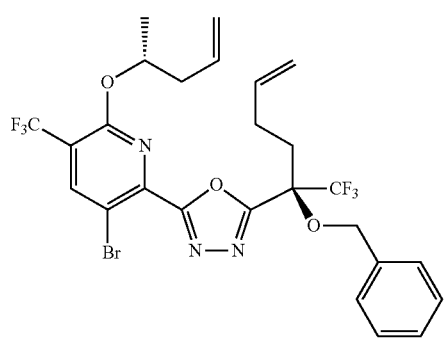

To a solution of N'-[(2R)-2-benzyloxy-2-(trifluoromethyl)hex-5-enoyl]-3-bromo-6-[(1R)-1-methylbut-3-enoxy]-5-(trifluoromethyl)pyridine-2-carbohydrazide (1.49 g, 2.1753 mmol) in 1,2-dichloroethane (25 mL) and N,N-diisopropylethylamine (2.59 g, 3.5 mL, 20.04 mmol) was added toluenesulfonyl chloride (1.3 g, 6.8189 mmol). The reaction was then stirred at 50° C. for 22 h. The reaction was cooled down to room temperature and the volatiles were removed under reduced pressure. The crude residue was purified by reverse phase chromatography (50 gram $C_{18}$ gel cartridge) using a gradient of 5-100% acetonitrile in water (+0.1% v/v of formic acid in water). The fractions containing the product were concentrated under reduced pressure to afford as a yellow oil, 2-[(1R)-1-benzyloxy-1-(trifluoromethyl)pent-4-enyl]-5-[3-bromo-6-[(1R)-1-methylbut-3-enoxy]-5-(trifluoromethyl)-2-pyridyl]-1,3,4-oxadiazole (1.3 g, 86%). ESI-MS m/z calc. 619.0905, found 620.2 (M+1)+; Retention time: 2.596 minutes. LCMS Method: Kinetex Polar $C_{18}$ column (3.0×50 mm, 2.6 µm particle size, 3 minute run, 5% to 95% acetonitrile in water (0.1% formic acid modifier), flow rate=1.2 mL/min).

Step 7: (6R,12R)-6-Benzyloxy-17-bromo-12-methyl-6,15-bis(trifluoromethyl)-13,19-dioxa-3,4,18-triazatricyclo[12.3.1.12,5]nonadeca-1(18),2,4,9,14,16-hexaene (E/Z Mixture)

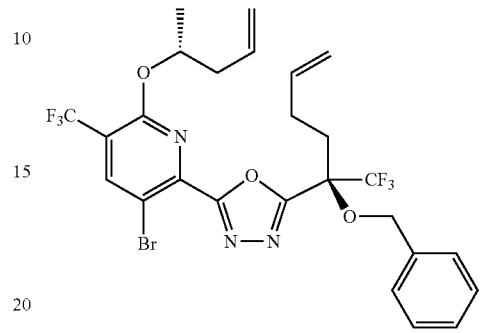

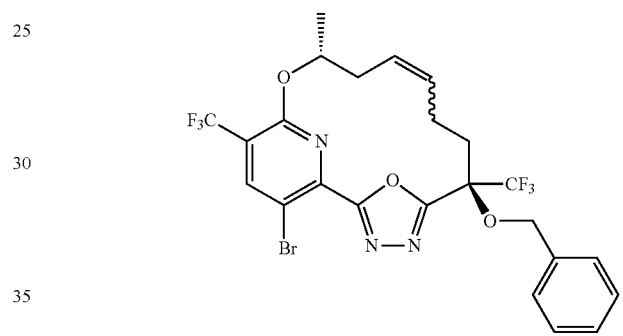

E/Z mixture

To a nitrogen purged solution of 2-[(1R)-1-benzyloxy-1-(trifluoromethyl)pent-4-enyl]-5-[3-bromo-6-[(1R)-1-methylbut-3-enoxy]-5-(trifluoromethyl)-2-pyridyl]-1,3,4-oxadiazole (525 mg, 0.7591 mmol) in dichloroethane (350 mL) at 60° C. was added a first portion of Zhan catalyst-1B (25 mg, 0.0341 mmol). After 1 hour, a second lot of Zhan catalyst-1B (25 mg, 0.0341 mmol) was added and heating was continued for another 1 h. DMSO (2 drops) was added and the reaction mixture was cooled down to room temperature. The volatiles were removed under reduced pressure. The crude material was purified by reversed-phase chromatography ($C_{18}$ column, gradient: 0% to 100% acetonitrile in water containing 0.1% formic acid). The fractions containing the product were concentrated under reduced pressure and lyophilized which gave as a tan solid, (6R,12R)-6-benzyloxy-17-bromo-12-methyl-6,15-bis(trifluoromethyl)-13,19-dioxa-3,4,18-triazatricyclo[12.3.1.12,5]nonadeca-1(18),2,4,9,14,16-hexaene (E/Z mixture) (210 mg, 47%). ESI-MS m/z calc. 591.0592, found 592.0 (M+1)+; Retention time: 2.31 minutes. LCMS Method: Luna $C_{18}$ column (50×3 mm, 3 µm particle size, temperature=45° C., flow=1.5 mL/min, run time=2.5 minutes. Mobile phase conditions: Initial 95% water +0.1% formic acid/5% acetonitrile +0.1% formic acid, linear gradient to 95% acetonitrile +0.1% formic acid over 1.3 minutes then held for 1.2 minute at 95% acetonitrile +0.1% formic acid.

Step 8: Methyl (6R,12R)-6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaene-17-carboxylate (E/Z Mixture)

Step 9: Methyl (6R,12R)-6-hydroxy-12-methyl-6,15-bis(trifluoromethyl)-13,19-dioxa-3,4,18-triazatricyclo[12.3.1.1²,⁵]nonadeca-1(18),2,4,14,16-pentaene-17-carboxylate

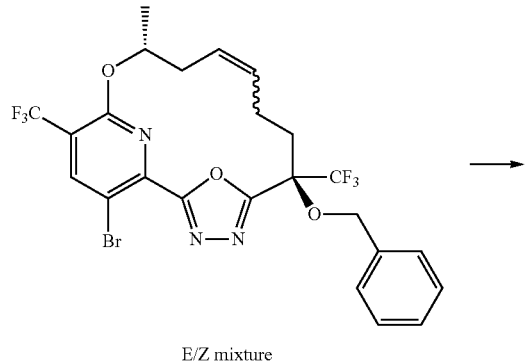

E/Z mixture

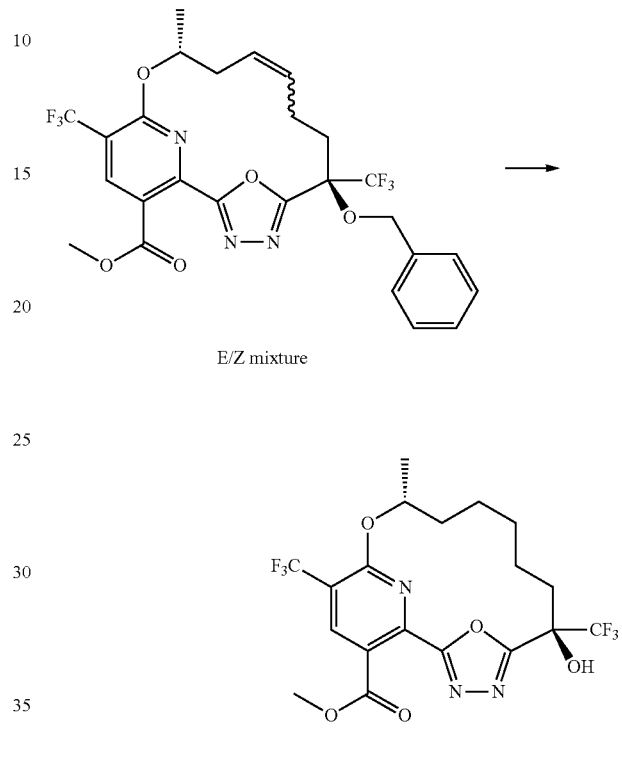

E/Z mixture

To a solution of (6R,12R)-6-benzyloxy-17-bromo-12-methyl-6,15-bis(trifluoromethyl)-13,19-dioxa-3,4,18-triazatricyclo[12.3.1.1²,⁵]nonadeca-1(18),2,4,9,14,16-hexaene (E/Z mixture) (200 mg, 0.3262 mmol) in anhydrous methanol (6 mL) in an autoclave was added Pd(dppf)Cl$_2$ dichloromethane adduct (40 mg, 0.0482 mmol) and triethylamine (108.9 mg, 0.15 mL, 1.0762 mmol). The autoclave was purged with nitrogen, then with carbon monoxide. The mixture was heated to 100° C. and the carbon monoxide pressure was adjusted to 80 psi. The mixture was stirred for 17 h. The solution was cooled down to 25° C., purged with nitrogen and concentrated under reduced pressure. The crude material was purified by silica gel chromatography (40 g column, gradient: 0% to 20% ethyl acetate in heptanes) to afford as a colorless oil, methyl (6R,12R)-6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaene-17-carboxylate (E/Z mixture) (144 mg, 77%). ESI-MS m/z calc. 571.1542, found 572.2 (M+1)⁺; Retention time: 2.2 minutes. LCMS Method: Luna C$_{18}$ column (50×3 mm, 3 μm particle size, temperature=45° C., flow=1.5 mL/min, run time=2.5 minutes. Mobile phase conditions: Initial 95% water +0.1% formic acid/5% acetonitrile +0.1% formic acid, linear gradient to 95% acetonitrile +0.1% formic acid over 1.3 minutes then held for 1.2 minute at 95% acetonitrile +0.1% formic acid.

To a solution of methyl (6R,12R)-6-benzyloxy-12-methyl-6,15-bis(trifluoromethyl)-13,19-dioxa-3,4,18-triazatricyclo[12.3.1.1²,⁵]nonadeca-1(18),2,4,9,14,16-hexaene-17-carboxylate (E/Z mixture) (165 mg, 0.2887 mmol) in MeOH (8 mL) under nitrogen atmosphere was added palladium on carbon (62 mg, 10% w/w, 0.0583 mmol). Hydrogen gas was bubbled in for 5 minutes and the reaction was stirred at room temperature for 24 h. The mixture was purged with nitrogen, filtered over celite, washed with methanol (40 mL) and concentrated under reduced pressure to afford as a light brown oil, methyl (6R,12R)-6-hydroxy-12-methyl-6,15-bis(trifluoromethyl)-13,19-dioxa-3,4,18-triazatricyclo[12.3.1.1²,⁵]nonadeca-1(18),2,4,14,16-pentaene-17-carboxylate (121 mg, 85%). ¹H NMR (400 MHz, DMSO-d$_6$) δ 8.53 (s, 1H), 7.75 (s, 1H), 5.10-5.00 (m, 1H), 3.87 (s, 3H), 2.34-2.27 (m, 1H), 2.20-2.13 (m, 2H), 1.67-1.57 (m, 1H), 1.39 (d, J=6.6 Hz, 9H). ¹⁹F NMR (377 MHz, DMSO-d$_6$) δ −62.63 (s, 3F), −76.86 (s, 3F). ESI-MS m/z calc. 483.1229, found 484.2 (M+1)⁺; Retention time: 1.99 minutes. LCMS Method: Luna C$_{18}$ column (50×3 mm, 3 μm particle size, temperature=45° C., flow=1.5 mL/min, run time=2.5 minutes. Mobile phase conditions: Initial 95% water +0.1% formic acid/5% acetonitrile +0.1% formic acid, linear gradient to 95% acetonitrile +0.1% formic acid over 1.3 minutes then held for 1.2 minute at 95% acetonitrile +0.1% formic acid.% CH3CN 0.1% FA,. T: 45 C, Flow: 1.5 mL/min.

Step 10: (6R,12R)-6-Hydroxy-12-methyl-6,15-bis (trifluoromethyl)-13,19-dioxa-3,4,18-triazatricyclo [12.3.1.1^2,5]nonadeca-1(18),2,4,14,16-pentaene-17-carboxylic acid, Compound 75

Example 53: Preparation of (6R,12R)-17-(hydroxymethyl)-12-methyl-6,15-bis(trifluoromethyl)-13,19-dioxa-3,4,18-triazatricyclo[12.3.1.1^2,5]nonadeca-1(18),2,4,14,16-pentaen-6-ol, Compound 76

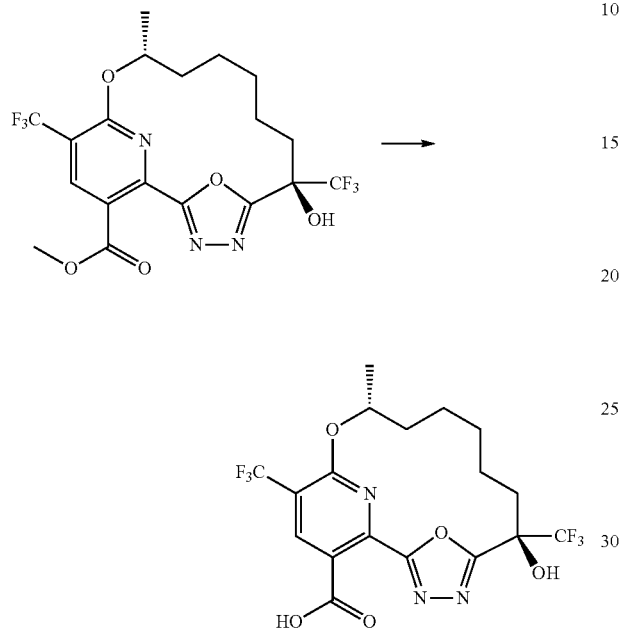

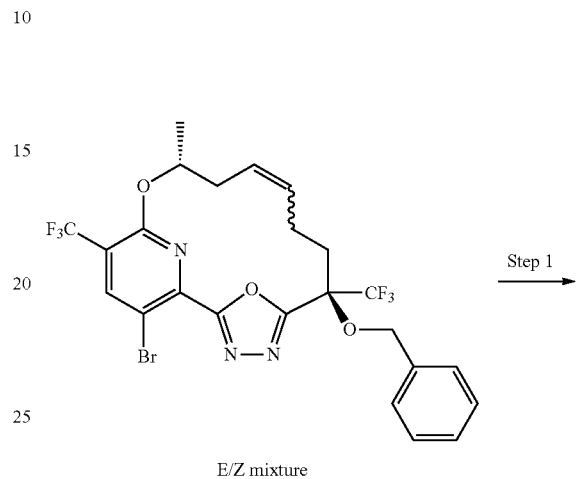

E/Z mixture

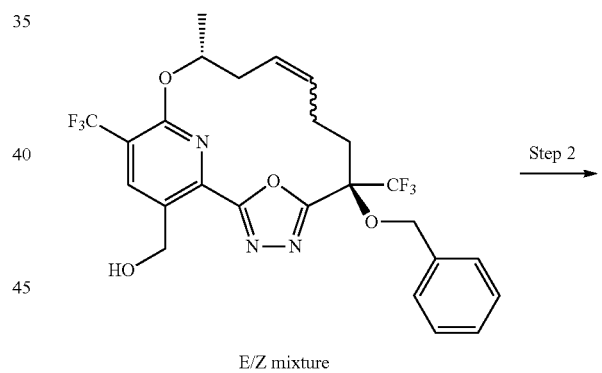

E/Z mixture

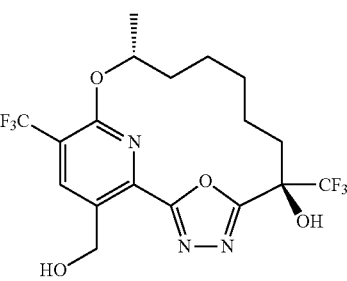

To a solution of methyl (6R,12R)-6-hydroxy-12-methyl-6,15-bis(trifluoromethyl)-13,19-dioxa-3,4,18-triazatricyclo [12.3.1.1^2,5]nonadeca-1(18),2,4,14,16-pentaene-17-carboxylate (21 mg, 0.0434 mmol) in THF (0.75 mL) was added a solution of lithium hydroxide monohydrate (20 mg, 0.4766 mmol) in water (0.25 mL). The mixture was stirred at 0° C. for 15 minutes. To the mixture was added saturated aqueous ammonium chloride solution (2 mL) and aqueous 10% citric acid until pH=4 was reached. The product was extracted with ethyl acetate (3×15 mL). The combined organic phases were washed with brine (20 mL), dried over sodium sulfate, filtered and concentrated under reduced pressure. Purification of the residue by reversed-phase chromatography (15.5 g $C_{18}$ column, gradient: 5% to 100% acetonitrile in water containing 0.1% formic acid) afforded as a white solid after lyophilization, (6R,12R)-6-hydroxy-12-methyl-6,15-bis(trifluoromethyl)-13,19-dioxa-3,4,18-triazatricyclo[12.3.1.1^2,5]nonadeca-1(18),2,4,14,16-pentaene-17-carboxylic acid (7.3 mg, 36%). $^1$H NMR (400 MHz, DMSO-$d_6$) δ 13.96 (br. s., 1H), 8.49 (s, 1H), 7.77 (s, 1H), 5.04-4.96 (m, 1H), 2.31-2.25 (m, 1H), 2.20-2.12 (m, 2H), 1.60-1.53 (m, 1H), 1.49-1.43 (m, 1H), 1.41-1.29 (m, 8H). $^{19}$F NMR (377 MHz, DMSO-$d_6$) δ −62.63 (s, 3F), −77.03 (s, 3F). ESI-MS m/z calc. 469.1072, found 468.1 (M−1)$^-$; Retention time: 4.69 minutes. LCMS Method: SunFire $C_{18}$ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Step 1: [(6R,12R)-6-Benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]methanol (E/Z Mixture)

Step 2: (6R,12R)-17-(Hydroxymethyl)-12-methyl-6,15-bis(trifluoromethyl)-13,19-dioxa-3,4,18-triazatricyclo[12.3.1.12,5]nonadeca-1(18),2,4,14,16-pentaen-6-ol, Compound 76

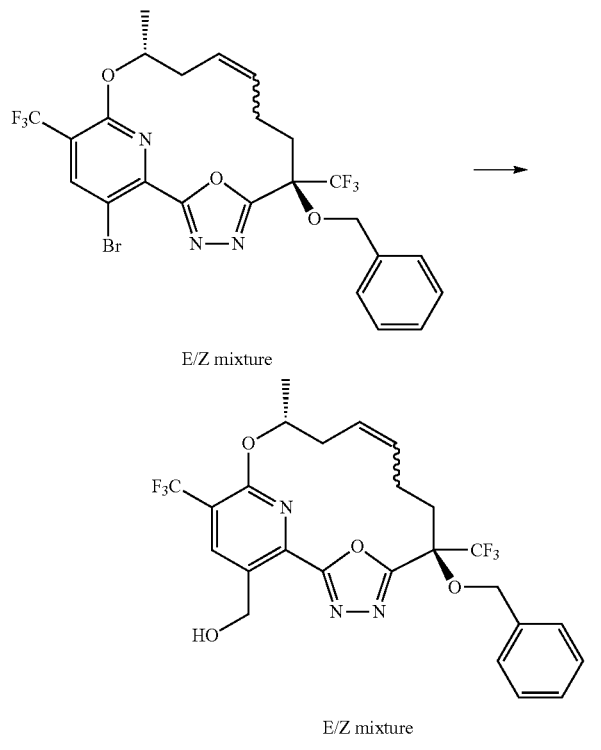

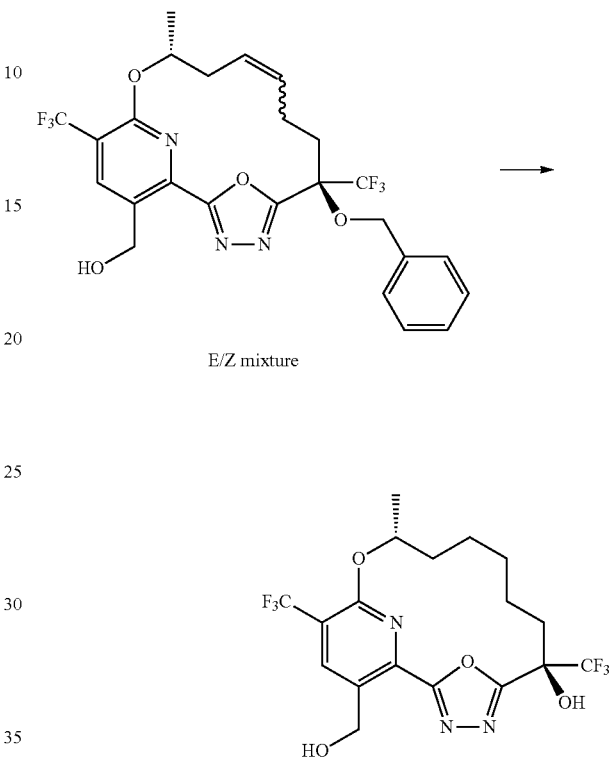

To a solution of (6R,12R)-6-benzyloxy-17-bromo-12-methyl-6,15-bis(trifluoromethyl)-13,19-dioxa-3,4,18-triazatricyclo[12.3.1.12,5]nonadeca-1(18),2,4,9,14,16-hexaene (E/Z mixture) (150 mg, 0.2532 mmol) in 1,4-dioxane (3 mL) was added tributylstannylmethanol (163 mg, 0.5077 mmol) and Pd(dppf)Cl$_2$ dichloromethane adduct (30 mg, 0.0367 mmol). Nitrogen was bubbled in for 5 minutes. The tube was sealed and the reaction mixture was stirred at 95° C. for 16 hours. The volatiles were removed under reduced pressure and the residue was purified by silica gel chromatography (24 g column, gradient: 0% to 20% ethyl acetate in heptanes) which afforded as a white solid, [(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]methanol (E/Z mixture) (58 mg, 42%). $^1$H NMR (400 MHz, CDCl$_3$) δ 8.08 (s, 1H), 7.36-7.28 (m, 5H), 5.67-5.57 (m, 1H), 5.54-5.44 (m, 1H), 5.07-4.93 (m, 2H), 4.92-4.82 (m, 1H), 4.81-4.72 (m, 2H), 4.05 (t, J=7.5 Hz, 1H), 3.67-3.58 (m, 1H), 2.80-2.68 (m, 1H), 2.48-2.40 (m, 2H), 2.36-2.25 (m, 1H), 1.90-1.81 (m, 1H), 1.53 (s, 3H). $^{19}$F NMR (377 MHz, CDCl$_3$) δ −63.81 (s, 3F), −73.92 (s, 3F). ESI-MS m/z calc. 543.1593, found 544.2 (M+1)$^+$; Retention time: 2.13 minutes. LCMS Method: Luna C$_{18}$ column (50×3 mm, 3 μm particle size, temperature=45° C., flow=1.5 mL/min, run time=2.5 minutes. Mobile phase conditions: Initial 95% water +0.1% formic acid/5% acetonitrile +0.1% formic acid, linear gradient to 95% acetonitrile +0.1% formic acid over 1.3 minutes then held for 1.2 minute at 95% acetonitrile +0.1% formic acid.

To a solution of [(6R,12R)-6-benzyloxy-12-methyl-6,15-bis(trifluoromethyl)-13,19-dioxa-3,4,18-triazatricyclo[12.3.1.12,5]nonadeca-1(18),2,4,9,14,16-hexaen-17-yl]methanol (E/Z mixture) (69 mg, 0.1268 mmol) in methanol (5 mL) under nitrogen atmosphere was added palladium on carbon (30 mg, 10% w/w, 0.0282 mmol). Nitrogen was bubbled in for 5 minutes followed by hydrogen gas bubbled in for 5 minutes and the reaction was stirred at room temperature for 16 hours. The mixture was purged with nitrogen gas, filtered over celite, washed with methanol (40 mL) and concentrated under reduced pressure. Purification by reversed-phase chromatography (15.5 g C$_{18}$ column, Gradient: 5% to 100% acetonitrile in water containing 0.1% formic acid) afforded as a white solid, (6R,12R)-17-(hydroxymethyl)-12-methyl-6,15-bis(trifluoromethyl)-13,19-dioxa-3,4,18-triazatricyclo[12.3.1.12,5]nonadeca-1(18),2,4,14,16-pentaen-6-ol (19.7 mg, 33%). $^1$H NMR (400 MHz, DMSO-d$_6$) δ 8.34 (s, 1H), 7.63 (s, 1H), 5.66 (t, J=5.6 Hz, 1H), 5.06-4.94 (m, 3H), 2.48-2.43 (m, 1H), 2.31-2.21 (m, 1H), 2.16-2.08 (m, 1H), 1.77-1.63 (m, 2H), 1.53-1.42 (m, 4H), 1.40 (d, J=6.4 Hz, 3H), 1.32-1.22 (m, 1H). $^{19}$F NMR (377 MHz, DMSO-d$_6$) δ −62.28 (s, 3F), −76.50 (s, 3F). ESI-MS m/z calc. 455.128, found 456.2 (M+1)$^+$; Retention time: 4.5 minutes. LCMS Method: SunFire C$_{18}$ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Example 54: Preparation of (12R)-17-amino-7,7-difluoro-12-methyl-15-(trifluoromethyl)-13,19-dioxa-3,4,18-triazatricyclo[12.3.1.1 2,5]nonadeca-1(18),2,4,14,16-pentaen-6-ol (diastereomer 1), Compound 77
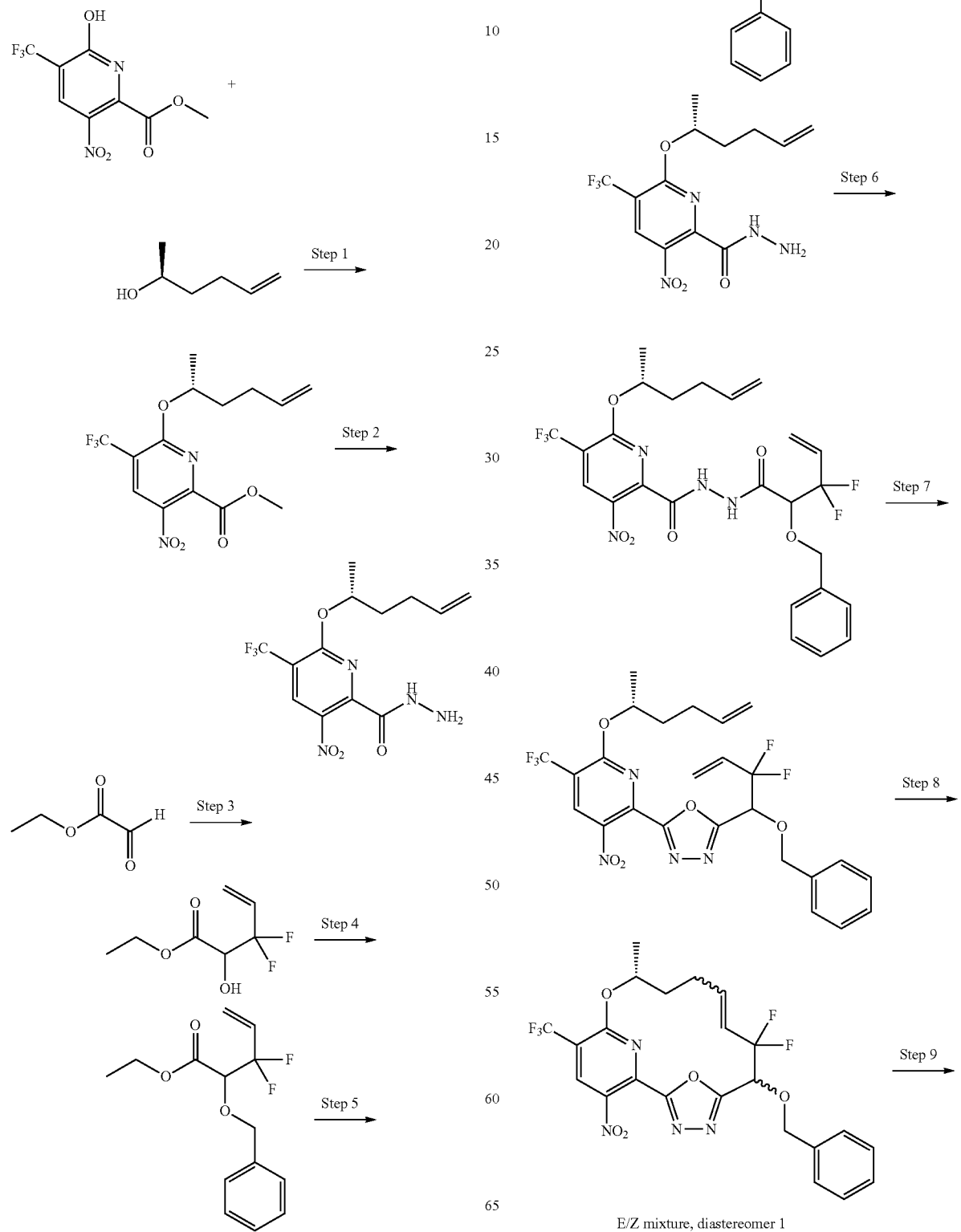
E/Z mixture, diastereomer 1

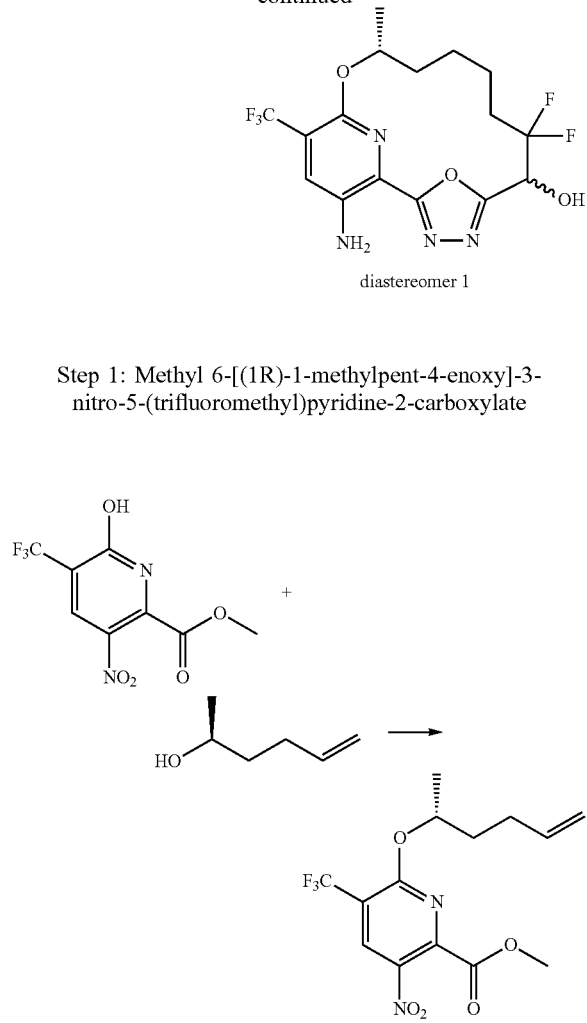

diastereomer 1

Step 1: Methyl 6-[(1R)-1-methylpent-4-enoxy]-3-nitro-5-(trifluoromethyl)pyridine-2-carboxylate To a suspension of methyl 6-hydroxy-3-nitro-5-(trifluoromethyl)pyridine-2-carboxylate (5 g, 18.675 mmol), (2S)-hex-5-en-2-ol (6.45 g, 46.559 mmol) and triphenylphosphine (10.2 g, 38.889 mmol) in toluene (150 mL) was added DIAD (9.5 g, 46.981 mmol) dropwise. The reaction mixture was stirred at 22° C. overnight. Triphenylphosphine (1.95 g) was added to quench the excessive DIAD. The mixture was stirred at 22° C. for 15 min and concentrated on silica gel (50 g). Purification by silica gel chromatography (220 g column; gradient: 0% to 10% ⁱBuOCH₃ in heptanes) afforded as a colorless oil, methyl 6-[(1R)-1-methylpent-4-enoxy]-3-nitro-5-(trifluoromethyl)pyridine-2-carboxylate (6.32 g, 92%, >95% ee). $^1$H NMR (400 MHz, CDCl$_3$) δ 8.64 (s, 1H), 5.87-5.73 (m, 1H), 5.55-5.44 (m, 1H), 5.05-4.93 (m, 2H), 4.03 (s, 3H), 2.26-2.07 (m, 2H), 1.99-1.87 (m, 1H), 1.83-1.71 (m, 1H), 1.41 (d, J=6.4 Hz, 3H). $^{19}$F NMR (377 MHz, CDCl$_3$) δ −64.58 (s, 3F). Retention time: 4.82 minutes. LCMS Method: SunFire C$_{18}$ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min). The measurement of the optical purity was carried out under the following conditions: Isocratic mode, Column: ChiralCel OJ-H, S/No: OJH0CE-MJ029, Flow rate 1 mL/min. Starting condition: 90% hexanes +DEA: 10%: (10% IPA/Hexane), Run time=16 minutes, injection=3 μl, Room temperature=24° C., Wavelength: 215+280 nm.

Step 2: 6-[(1R)-1-Methylpent-4-enoxy]-3-nitro-5-(trifluoromethyl)pyridine-2-carbohydrazide

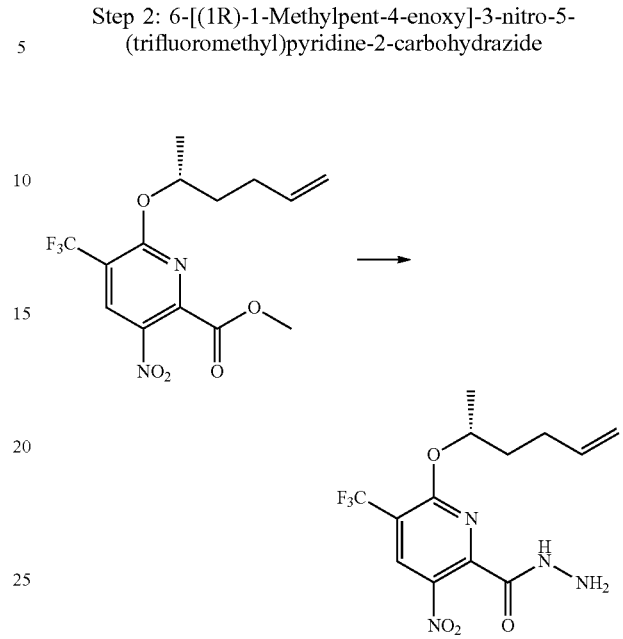

To a solution of methyl 6-[(1R)-1-methylpent-4-enoxy]-3-nitro-5-(trifluoromethyl)pyridine-2-carboxylate (660 mg, 1.8022 mmol) in methanol (14 mL) in a pressure tube was added hydrazine monohydrate (670 mg, 13.384 mmol). The pressure tube was flushed with nitrogen and sealed. The reaction mixture was stirred at 80° C. for 30 min and cooled to room temperature then concentrated under reduced pressure to about 5 g. The residue was purified by reversed-phase chromatography (100 g C$_{18}$ column; gradient: 5% to 80% acetonitrile in water). The desired fractions were concentrated under reduced pressure at 30° C./38 Torr until a white precipitate appeared. The residue was extracted with ⁱBuOCH₃ (3×30 mL). The combined organic layers were washed with brine (5 mL), dried with Na$_2$SO$_4$, filtered and concentrated under reduced pressure to give as a pale-yellow solid, 6-[(1R)-1-methylpent-4-enoxy]-3-nitro-5-(trifluoromethyl)pyridine-2-carbohydrazide (550 mg, 85%). ESI-MS m/z calc. 348.1045, found 267.2 (M−81)$^+$; Retention time: 4.1 minutes. LCMS Method: SunFire C$_{18}$ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Step 3: Ethyl 3,3-difluoro-2-hydroxy-pent-4-enoate

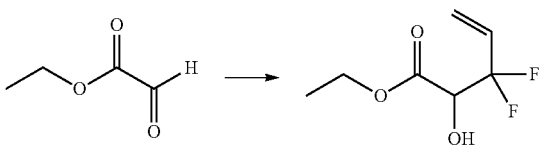

To a solution of 3-bromo-3,3-difluoro-prop-1-ene (4.8 g, 30.582 mmol) and ethyl 2-oxoacetate in toluene (5.9 mL of 50% w/v, 28.896 mmol) in DMF (60 mL) and water (18 mL)

at 10° C. was added indium (7 g, 60.966 mmol, ground before use). The mixture was stirred at room temperature overnight. Ice-water (200 mL) was added. The resulting mixture was stirred for 30 min, diluted with 'BuOCH₃ (100 mL), filtered through diatomaceous earth and the cake was washed with 'BuOCH₃. The aqueous phase was back extracted with 'BuOCH₃ (2×100 mL). The combined organic layers were dried with Na₂SO₄, filtered and concentrated. The residue (5.8 g) was purified by silica gel flash chromatography (gradient from 50% to 100% dichloromethane/ pentane) to afford as a colorless oil, ethyl 3,3-difluoro-2-hydroxy-pent-4-enoate (4.283 g, 82%). ¹H NMR (400 MHz, CDCl₃) δ 6.10-5.93 (m, 1H), 5.82-5.72 (m, 1H), 5.58 (d, J=11.0 Hz, 1H), 4.43-4.27 (m, 3H), 3.22 (d, J=6.4 Hz, 1H), 1.34 (t, J=7.1 Hz, 3H). ¹⁹F NMR (377 MHz, CDCl₃) δ −107.00 to −107.85 (m, 1F), −108.89 to −109.75 (m, 1F). ESI-MS m/z calc. 180.0598, found 181.2 (M+1)⁺; Retention time: 1.47 minutes. LCMS Method: Kinetex Polar C₁₈ column (3.0×50 mm, 2.6 μm particle size, 3 minute run, 5% to 95% acetonitrile in water (0.1% formic acid modifier), flow rate=1.2 mL/min).

Step 4: Ethyl 2-benzyloxy-3,3-difluoro-pent-4-enoate

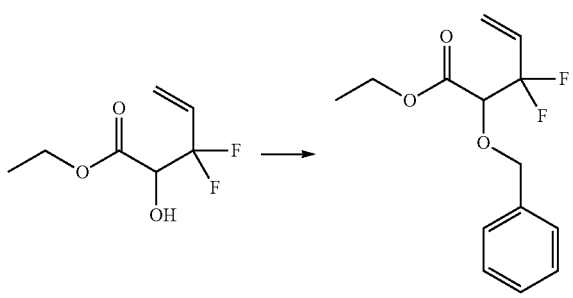 [SMILES: C=CC(F)(F)C(O)C(=O)OCC ; C=CC(F)(F)C(OCc1ccccc1)C(=O)OCC]

To a solution of ethyl 3,3-difluoro-2-hydroxy-pent-4-enoate (2.45 g, 11.832 mmol) in dichloromethane (19 mL) and anhydrous heptane (38 mL) at 0° C. was added benzyl 2,2,2-trichloroacetimidate (7 g, 27.72 mmol). The mixture was stirred at 0° C. for 5 min and triflic acid (400 mg, 2.6653 mmol) was added dropwise, a large amount of white precipitate appeared. The mixture was allowed to slowly warm up to room temperature and stirred at room temperature (5-19° C.) overnight and then cooled to 0° C. Diluted with dichloromethane (50 mL) then saturated NaHCO₃ (20 mL) was added. The two layers were separated and the aqueous layer was extracted with dichloromethane (2×30 mL). The combined organic layers were dried with Na₂SO₄, filtered and concentrated under reduced pressure. Purification by silica gel chromatography (gradient from 0% to 10% ethyl acetate in heptanes) afforded ethyl 2-benzyloxy-3,3-difluoro-pent-4-enoate as a clear oil (1.56 g, 46%). ¹H NMR (400 MHz, CDCl₃) δ 7.45-7.31 (m, 5H), 6.16-6.00 (m, 1H), 5.80-5.71 (m, 1H), 5.56 (d, J=11.2 Hz, 1H), 4.79 (d, J=12.0 Hz, 1H), 4.61 (d, J=12.0 Hz, 1H), 4.33-4.16 (m, 3H), 1.31 (t, J=7.1 Hz, 3H). ¹⁹F NMR (377 MHz, CDCl₃) δ −102.91 to −103.81 (m, 1F), −106.39 to −107.27 (m, 1F). Retention time: 4.4 minutes. LCMS Method: SunFire C₁₈ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Step 5: 2-Benzyloxy-3,3-difluoro-pent-4-enoic acid

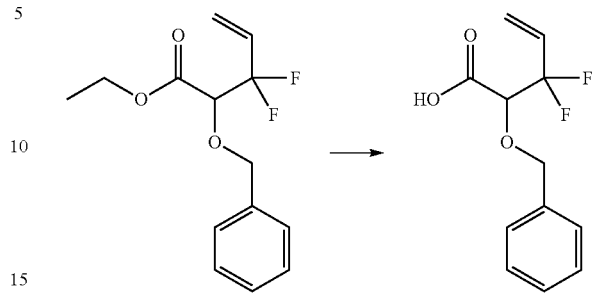

To a solution of ethyl 2-benzyloxy-3,3-difluoro-pent-4-enoate (1.55 g, 5.735 mmol) in DCE (60 mL) was added trimethyltin hydroxide (1.88 g, 10.397 mmol). The mixture was stirred at 82° C. for 30 h and cooled to room temperature. Silica gel (8 g) was added. The mixture was concentrated under reduced pressure then purified by silica gel chromatography (gradient from 0% to 15% methanol in dichloromethane) to give as a colorless oil, 2-benzyloxy-3,3-difluoro-pent-4-enoic acid (1.14 g, 78%). ¹H NMR (400 MHz, CDCl₃) δ 7.42-7.31 (m, 5H), 6.13-5.97 (m, 1H), 5.77 (dt, J=17.4, 2.2 Hz, 1H), 5.58 (d, J=11.0 Hz, 1H), 4.83-4.70 (m, 2H), 4.25 (t, J=9.4 Hz, 1H). ¹⁹F NMR (377 MHz, CDCl₃) δ −103.47 to −104.44 (m, 1F), −106.04 to −106.95 (m, 1F). Retention time: 1.86 minutes. LCMS Method: Kinetex Polar C₁₈ column (3.0×50 mm, 2.6 μm particle size, 3 minute run, 5% to 95% acetonitrile in water (0.1% formic acid modifier), flow rate=1.2 mL/min).

Step 6: n'-(2-Benzyloxy-3,3-difluoro-pent-4-enoyl)-6-[(1R)-1-methylpent-4-enoxy]-3-nitro-5-(trifluoromethyl)pyridine-2-carbohydrazide

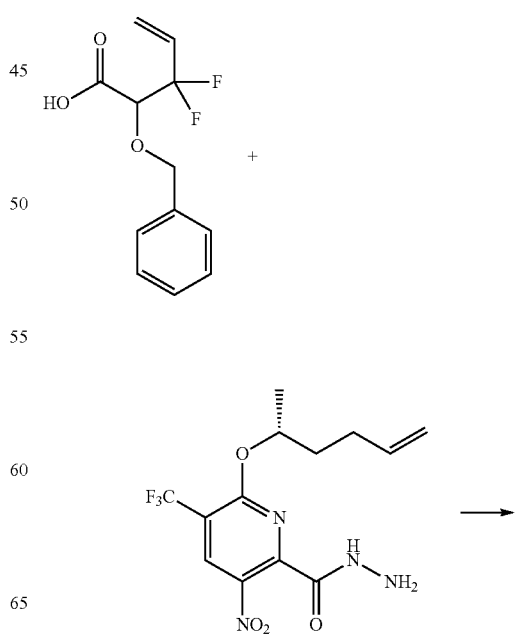

623

-continued

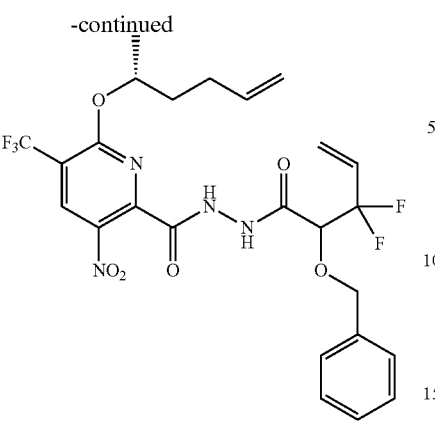

624

Step 7: 2-(1-Benzyloxy-2,2-difluoro-but-3-enyl)-5-[6-[(1R)-1-methylpent-4-enoxy]-3-nitro-5-(trifluoromethyl)-2-pyridyl]-1,3,4-oxadiazole

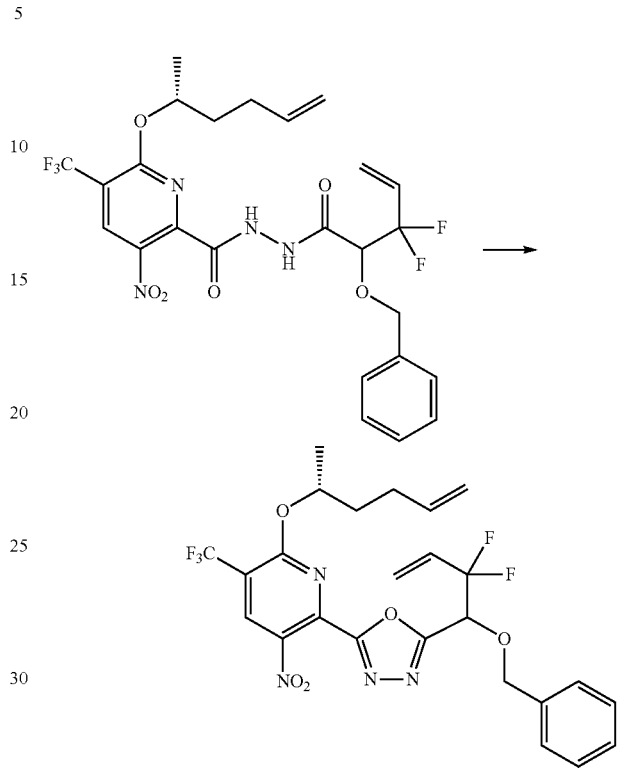

To a solution of 2-benzyloxy-3,3-difluoro-pent-4-enoic acid (850 mg, 3.3338 mmol) in dichloromethane (24 mL) was added oxalyl chloride (549 mg, 0.3773 mL, 4.3254 mmol), followed by DMF (291 mg, 0.3083 mL, 3.9812 mmol) dropwise. The mixture was stirred at room temperature for 2 h and concentrated under reduced pressure to about 14 mL. The residue was added over a period of 15 min to a solution of 6-[(1R)-1-methylpent-4-enoxy]-3-nitro-5-(trifluoromethyl)pyridine-2-carbohydrazide (1.57 g, 4.3817 mmol) and DIPEA (1.75 g, 2.3585 mL, 13.54 mmol) in dichloromethane (24 mL) at 0° C. The reaction mixture was stirred at room temperature for 1 h and cooled to 0° C. Saturated NaHCO$_3$ (25 mL) was added. The mixture was extracted with dichloromethane (3×40 mL). The combined organic layers were dried with Na$_2$SO$_4$, filtered and concentrated under reduced pressure. Purification of the residue by reversed-phase chromatography (150 g C$_{18}$ column; gradient: 5% to 95% acetonitrile in water) afforded as a pale-yellow oil, N'-(2-benzyloxy-3,3-difluoro-pent-4-enoyl)-6-[(1R)-1-methylpent-4-enoxy]-3-nitro-5-(trifluoromethy)pyridine-2-carbohydrazide (1.32 g, 69%). $^1$H NMR (400 MHz, CDCl$_3$) δ 8.35 (s, 1H), 7.43-7.32 (m, 5H), 6.11-5.95 (m, 1H), 5.88-5.71 (m, 2H), 5.57 (d, J=11.0 Hz, 1H), 5.50-5.39 (m, 1H), 5.05-4.94 (m, 2H), 4.86-4.76 (m, 2H), 4.23 (t, J=9.8 Hz, 1H), 2.28-2.08 (m, 2H), 2.00-1.87 (m, 1H), 1.84-1.73 (m, 1H), 1.43 (d, J=6.1 Hz, 3H). Two protons of hydrazide not observed. $^{19}$F NMR (377 MHz, CDCl$_3$) δ −64.54 (s, 3F), −104.49 to −105.35 (m, 1F), −106.38 to −107.26 (m, 1F). ESI-MS m/z calc. 572.1694, found 573.2 (M+1)$^+$; Retention time: 2.02 minutes. LCMS Method: Luna C$_{18}$ column (50×3 mm, 3 μm particle size, temperature=45° C., flow=1.5 mL/min, run time=2.5 minutes. Mobile phase conditions: Initial 95% water +0.1% formic acid/5% acetonitrile +0.1% formic acid, linear gradient to 95% acetonitrile +0.1% formic acid over 1.3 minutes then held for 1.2 minute at 95% acetonitrile +0.1% formic acid.

To a solution of N'-(2-benzyloxy-3,3-difluoro-pent-4-enoyl)-6-[(1R)-1-methylpent-4-enoxy]-3-nitro-5-(trifluoromethyl)pyridine-2-carbohydrazide (573 mg, 0.9739 mmol) in dichloromethane (17 mL) at 0° C. was added DIPEA (761 mg, 1.0256 mL, 5.8881 mmol), followed by trifluoromethanesulfonic anhydride (420 mg, 1.4886 mmol) dropwise. The mixture was stirred at 0° C. for 30 min. Morpholine (520 mg) was added to quench the reaction. The mixture was stirred at 0° C. for 5 min then saturated NaHCO$_3$ (20 mL) was added. The two layers were separated and the aqueous layer was extracted with dichloromethane (2×20 mL). The combined organic layers were dried with Na$_2$SO$_4$, filtered and concentrated under reduced pressure. Purification of the residue by silica gel chromatography (gradient: 0% to 30% ethyl acetate in heptanes) afforded as a pale-yellow oil, 2-(1-benzyloxy-2,2-difluoro-but-3-enyl)-5-[6-[(1R)-1-methylpent-4-enoxy]-3-nitro-5-(trifluoromethyl)-2-pyridyl]-1,3,4-oxadiazole (430 mg, 80%). $^1$H NMR (400 MHz, CDCl$_3$) δ 8.67 (s, 1H), 7.40-7.31 (m, 5H), 6.16-6.01 (m, 1H), 5.86-5.73 (m, 2H), 5.60 (d, J=11.2 Hz, 1H), 5.57-5.48 (m, 1H), 5.07 (dd, J=10.0, 7.6 Hz, 1H), 5.03-4.93 (m, 2H), 4.81 (d, J=11.7 Hz, 1H), 4.60 (d, J=11.7 Hz, 1H), 2.26-2.08 (m, 2H), 2.01-1.89 (m, 1H), 1.85-1.74 (m, 1H), 1.43 (d, J=6.4 Hz, 3H). $^{19}$F NMR (377 MHz, CDCl$_3$) δ −64.62 (s, 3F), −103.56 to −104.43 (m, 1F), −107.41 to −108.26 (m, 1F). ESI-MS m/z calc. 554.1589, found 555.2 (M+1)$^+$; Retention time: 2.17 minutes. LCMS Method: Luna C$_{18}$ column (50×3 mm, 3 μm particle size, temperature=45° C., flow=1.5 mL/min, run time=2.5 minutes. Mobile phase conditions: Initial 95% water +0.1% formic acid/5% acetonitrile +0.1% formic acid, linear gra- Step 8: (12R)-6-benzyloxy-7,7-difluoro-12-methyl-17-nitro-15-(trifluoromethyl)-13,19-dioxa-3,4,18-triazatricyclo[12.3.1.1²,⁵]nonadeca-1(18),2,4,8,14,16-hexaene (E/Z Mixture, diastereomer 1)

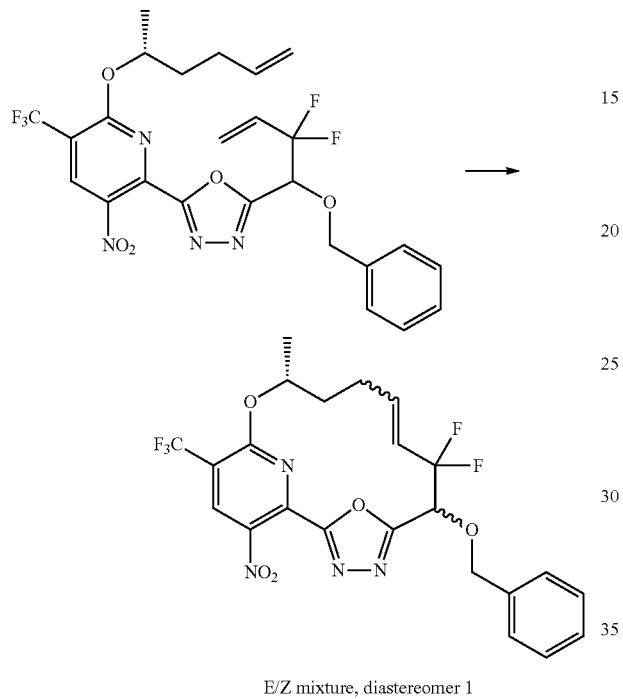

E/Z mixture, diastereomer 1

A 1 liter dried flask was charged with 2-(1-benzyloxy-2,2-difluoro-but-3-enyl)-5-[6-[(1R)-1-methylpent-4-enoxy]-3-nitro-5-(trifluoromethyl)-2-pyridyl]-1,3,4-oxadiazole (400 mg, 0.7185 mmol) and DCE (400 mL). The mixture was bubbled with nitrogen for 1 h and then stirred at 75° C. for 10 min. A solution of Grubbs 2nd generation catalyst (200 mg, 0.2356 mmol) in DCE (4 mL) was added quickly by a syringe. After the mixture was stirred at 75° C. for 15 min, a solution of Grubbs 2nd generation catalyst (80 mg, 0.0942 mmol) in DCE (2 mL) was added quickly by a syringe. The mixture was stirred at 75° C. for 40 min and cooled to room temperature. DMSO (0.3 mL) was added. The mixture was stirred at room temperature for 1 h and then concentrated on silica gel (2 g). Purification by silica gel chromatography (gradient: 0% to 20% ethyl acetate in heptanes) afforded a crude product (225 mg) which was further purified by reversed-phase chromatography (120 g C₁₈ column; gradient: 5% to 95% acetonitrile in water). The desired fractions were collected and concentrated to remove most of the acetonitrile. The residue was extracted with ethyl acetate (3×20 mL). The combined organic layers were dried with Na₂SO₄, filtered and concentrated under reduced pressure to give as a colorless oil, (12R)-6-benzyloxy-7,7-difluoro-12-methyl-17-nitro-15-(trifluoromethyl)-13,19-dioxa-3,4,18-triazatricyclo[12.3.1.1²,⁵]nonadeca-1(18),2,4,8,14,16-hexaene (E/Z mixture, diastereomer 1) (127 mg, 30%). Note: only a single chiral outcome was obtained at the benzyl alcohol carbon, stereochemistry of that center unknown. ESI-MS m/z calc. 526.1276, found 527.2 (M+1)⁺; Retention time: 4.96 minutes. LCMS Method: SunFire C₁₈ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Step 9: (12R)-17-Amino-7,7-difluoro-12-methyl-15-(trifluoromethyl)-13,19-dioxa-3,4,18-triazatricyclo[12.3.1.1²,⁵]nonadeca-1(18),2,4,14,16-pentaen-6-ol (diastereomer 1), Compound 77

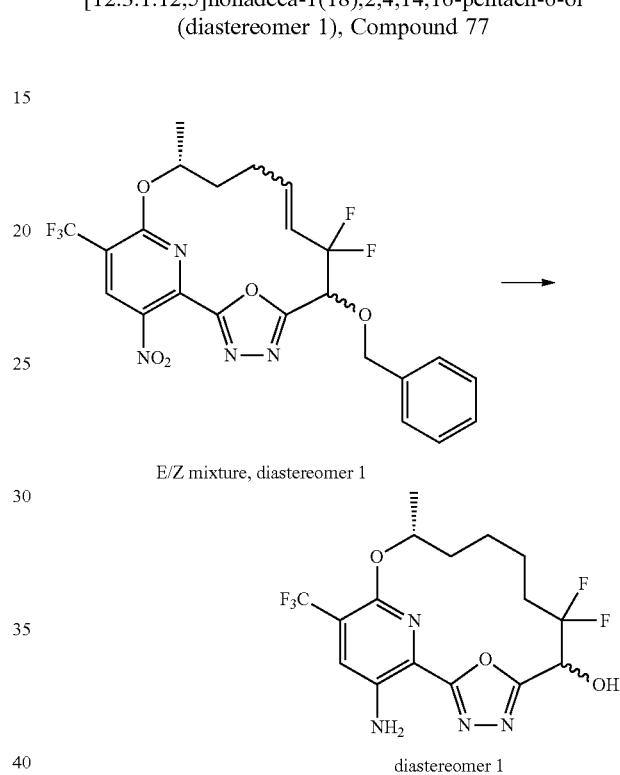

E/Z mixture, diastereomer 1 diastereomer 1

To a solution of (12R)-6-benzyloxy-7,7-difluoro-12-methyl-17-nitro-15-(trifluoromethyl)-13,19-dioxa-3,4,18-triazatricyclo[12.3.1.1²,⁵]nonadeca-1(18),2,4,8,14,16-hexaene (E/Z mixture, diastereomer 1) (250 mg, 0.4165 mmol) in methanol (6 mL) and ethyl acetate (2 mL) in a flask was added 10% palladium on carbon (86 mg, 50% wet, 5% w/w, 0.0404 mmol). The mixture was cooled with ice-water bath. Air in the flask was replaced by nitrogen through vacuum twice. Nitrogen in the flask was replaced by hydrogen through vacuum five times. Ammonia in methanol (0.4 mL of 2 M, 0.8 mmol) was added by a syringe. The reaction mixture was stirred at room temperature for 20 h. The mixture was filtered through Celite, washing with ethyl acetate and the filtrate was concentrated under reduced pressure. Purification of the residue by silica gel chromatography under the same conditions two successive times (gradient: 0% to 40% ethyl acetate in heptanes) afforded as a pale-yellow solid, (12R)-17-amino-7,7-difluoro-12-methyl-15-(trifluoromethyl)-13,19-dioxa-3,4,18-triazatricyclo[12.3.1.1²,⁵]nonadeca-1(18),2,4,14,16-pentaen-6-ol (diastereomer 1) (76 mg, 44%). ¹H NMR (400 MHz, DMSO-d₆) δ 7.75 (s, 1H), 7.21 (d, J=5.6 Hz, 1H), 6.27 (s, 2H), 5.24-5.15 (m, 1H), 5.01-4.90 (m, 1H), 2.32-2.09 (m, 3H), 2.04-1.87 (m, 1H), 1.75-1.62 (m, 1H), 1.59-1.47 (m, 1H), 1.45-1.37 (m, 1H), 1.34 (d, J=6.4 Hz, 3H), 1.32-1.22 (m, 1H). $^{19}$F NMR (377 MHz, DMSO-d$_6$) δ −62.41 (s, 3F), −92.20 to −93.10 (m, 1F), −99.62 to −100.68 (m, 1F). ESI-MS m/z calc. 408.1221, found 409.2 (M+1)$^+$; Retention time: 4.42 minutes. LCMS Method: SunFire C$_{18}$ column (75×4.6 mm, 3.5 μm particle size, 6 minute run, mobile phase conditions: initial 95% water +0.1% formic acid/5% acetonitrile +0.1% formic acid, linear gradient to 95% acetonitrile for 4 min, then held for 2 min at 95% acetonitrile, temperature=45° C., flow=1.5 mL/min).

Example 55: Bioactivity Assay

Ussing Chamber Assay of CFTR-Mediated Short-Circuit Currents

Ussing chamber experiments were performed using human bronchial epithelial (HBE) cells derived from CF subjects heterozygous for F508del and a minimal function CFTR mutation (F508del/MF-HBE) and cultured as previously described (Neuberger T, Burton B, Clark H, Van Goor F Methods Mol Biol 2011:741:39-54). After four days the apical media was removed, and the cells were grown at an air liquid interface for >14 days prior to use. This resulted in a monolayer of fully differentiated columnar cells that were ciliated, features that are characteristic of human bronchial airway epithelia.

To isolate the CFTR-mediated short-circuit (Isc) current, F508del/MF-HBE grown on Costar® Snapwell™ cell culture inserts were mounted in an Ussing chamber and the transepithelial I$_{SC}$ was measured under voltage-clamp recording conditions (V$_{hold}$=0 mV) at 37° C. The basolateral solution contained (in mM) 145 NaCl, 0.83 K$_2$HPO$_4$, 3.3 KH$_2$PO$_4$, 1.2 MgCl$_2$, 1.2 CaCl$_2$, 10 Glucose, 10 HEPES (pH adjusted to 7.4 with NaOH) and the apical solution contained (in mM) 145 NaGluconate, 1.2 MgCl$_2$, 1.2 CaCl$_2$, 10 glucose, 10 HEPES (pH adjusted to 7.4 with NaOH) and 30 μM amiloride to block the epithelial sodium channel. Forskolin (20 μM) was added to the apical surface to activate CFTR, followed by apical addition of a CFTR inhibitor cocktail consisting of BPO, GlyH-101 and CFTR inhibitor 172 (each at 20 μM final assay concentration) to specifically isolate CFTR currents. The CFTR-mediated Isc (μA/cm$^2$) for each condition was determined from the peak forskolin response to the steady-state current following inhibition.

Identification of Potentiator Compounds

The activity of the CFTR potentiator compounds on the CFTR-mediated Isc was determined in Ussing chamber studies as described above. The F508del/MF-HBE cell cultures were incubated with the potentiator compounds at a range of concentrations in combination with 10 μM (14S)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione for 18-24 hours at 37° C. and in the presence of 20% human serum. The concentration of potentiator compounds and (14S)-8-[3-(2-{dispiro[2.0.2.1]heptan-7-yl}ethoxy)-1H-pyrazol-1-yl]-12,12-dimethyl-2λ$^6$-thia-3,9,11,18,23-pentaazatetracyclo[17.3.1.111,14.05,10]tetracosa-1(22),5,7,9,19(23),20-hexaene-2,2,4-trione used during the 18-24 hours incubations was kept constant throughout the Ussing chamber measurement of the CFTR-mediated Isc to ensure compounds were present throughout the entire experiment. The efficacy and potency of the putative F508del potentiators was compared to that of the known Vertex potentiator, ivacaftor (N-[2,4-bis(1,1-dimethylethyl)-5-hydroxyphenyl]-1,4-dihydro-4-oxoquinoline-3-carboxamide).

Table 12 and Table 13 represent CFTR modulating activity for representative compounds of the invention generated using the assay described in this example (EC$_{50}$: +++ is <500 nM; ++ is 500 nM–1 μM; + is >1 μM; and ND is "not determined in this assay").

TABLE 12

Bioactivity

| Comp. No. | Structure | EC$_{50}$ |
|---|---|---|
| 1 | macrocyclic pyridine-oxadiazole with CF$_3$, OH, CF$_3$ substituents | + |
| 2 | macrocyclic pyridine-oxadiazole (enantiomer 1) | ND |
| 3 | macrocyclic pyridine-oxadiazole (enantiomer 2) | + |
| 4 | macrocyclic pyridine-oxadiazole with NH$_2$ substituent | +++ |
| 5 | macrocyclic pyridine-oxadiazole with NH$_2$ substituent | +++ |
| 6 | macrocyclic pyridine-oxadiazole with NH$_2$ substituent | + |

TABLE 12-continued
| Comp. No. | Structure | EC$_{50}$ |
|---|---|---|
| 7 | 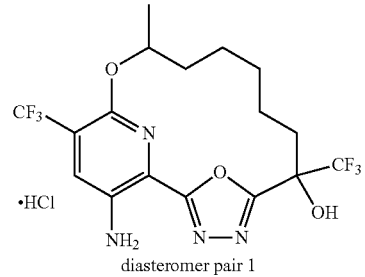 [SMILES: Cl ; CC1CCCCCC(O)(C(F)(F)F)c2nnc(o2)-c2nc(c(C(F)(F)F)cc2N)O1] diasteromer pair 1 | +++ |
| 8 | diasteromer pair 2 | +++ |
| 9 | Enantiomer 1 | +++ |
| 10 | Enantiomer 2 | ND |
| 11 | 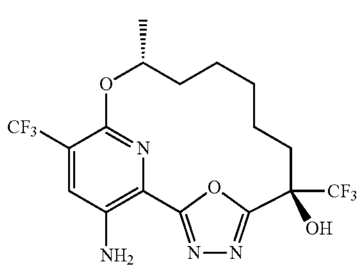 | +++ |
| 12 | 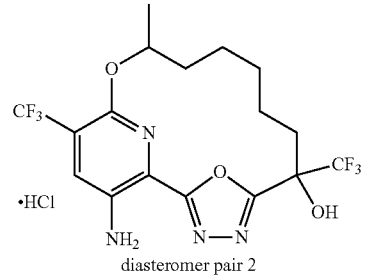 [SMILES: Cl ; CC1CCCCCC(O)(C(F)(F)F)c2nnc(o2)-c2nc(c(C(F)(F)F)cc2N)O1] | +++ |
| 13 | | +++ |
| 14 | | +++ |
| 15 | enantiomer 1 | +++ |
| 16 | enantiomer 2 | ND |

TABLE 12-continued

| Comp. No. | Structure | Bioactivity EC$_{50}$ |
|---|---|---|
| 17 | (structure with phenyl ether macrocycle, CF$_3$, pyridine, NH$_2$, oxadiazole, C(CF$_3$)(OH); ·HCl) | +++ |
| 18 | (structure with methyl-bearing ether macrocycle, fluorophenyl, CF$_3$, pyridine, NH$_2$, oxadiazole, C(CF$_3$)(OH); diastereomer pair) | +++ |
| 19 | (sulfoxide-linked macrocycle, F$_3$C-pyridine, NH$_2$, oxadiazole, C(CF$_3$)(OH)) | +++ |
| 20 | (sulfoxide-linked macrocycle, opposite S=O stereochemistry, F$_3$C-pyridine, NH$_2$, oxadiazole, C(CF$_3$)(OH)) | ++ |
| 21 | (thioether-linked macrocycle, F$_3$C-pyridine, NH$_2$, oxadiazole, C(CF$_3$)(OH)) | +++ |
| 22 | (thioether-linked macrocycle variant, F$_3$C-pyridine, NH$_2$, oxadiazole, C(CF$_3$)(OH)) | +++ |

TABLE 12-continued

| Comp. No. | Structure | Bioactivity EC$_{50}$ |
|---|---|---|
| 23 | (sulfoxide-linked macrocycle; enantiomer 1) | + |
| 24 | (sulfoxide-linked macrocycle; enantiomer 2) | + |
| 25 | (methyl-ether macrocycle with ketone, F$_3$C-pyridine, NH$_2$, oxadiazole, C(CF$_3$)(OH); ·HCl) | + |
| 26 | (methyl-ether macrocycle with ketone, F$_3$C-pyridine, NH$_2$, oxadiazole, C(CF$_3$)(OH); ·HCl) | +++ |
| 27 | (aryl ether macrocycle, F$_3$C-pyridine, NH$_2$, oxadiazole, C(CF$_3$)(OH); enantiomer 1) | +++ |

TABLE 12-continued
| | Bioactivity | |
|---|---|---|
| Comp. No. | Structure | EC$_{50}$ |
| 28 | 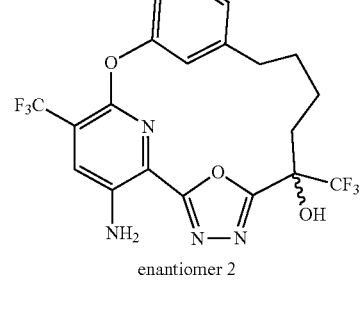<br>enantiomer 2 | + |
| 29 | 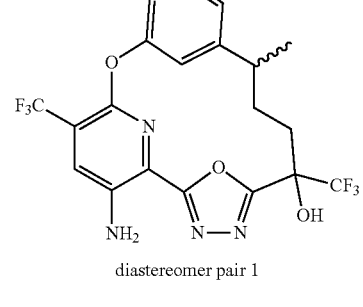<br>diastereomer pair 1 | +++ |
| 30 | 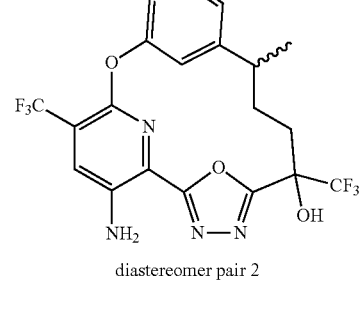<br>diastereomer pair 2 | +++ |
| 31 | 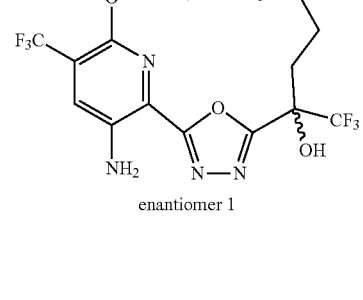<br>enantiomer 1 | +++ |
| 32 | enantiomer 2 | + |
| 33 | Diastereomer pair 1 | +++ |
| 34 | enantiomer 1 | +++ |
| 35 | enantiomer 2 | +++ |

TABLE 12-continued

| Comp. No. | Structure | Bioactivity EC$_{50}$ |
|---|---|---|
| 36 | 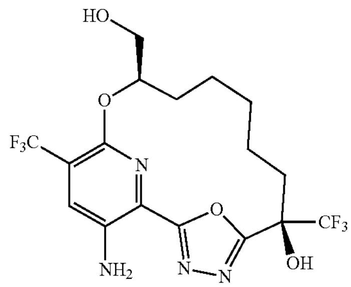 [SMILES: Nc1cc(C(F)(F)F)c2nc1-c1nnc(o1)[C@@](O)(C(F)(F)F)CCCCC[C@H](CO)O2] | +++ |
| 37 | 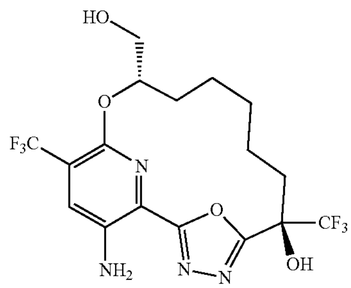 [SMILES: Nc1cc(C(F)(F)F)c2nc1-c1nnc(o1)[C@@](O)(C(F)(F)F)CCCCC[C@@H](CO)O2] | +++ |
| 38 | 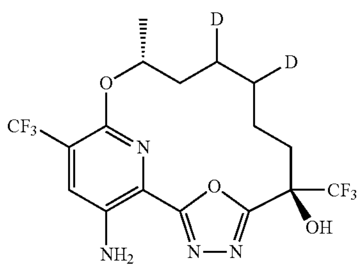 [SMILES: [2H]C1CC[C@](O)(C(F)(F)F)c2nnc(o2)-c2nc(c(C(F)(F)F)cc2N)O[C@H](C)CC1[2H]] | +++ |
| 39 | 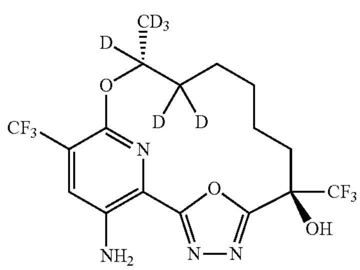 [SMILES: [2H]C([2H])([2H])[C@@]1([2H])Oc2nc(c(N)cc2C(F)(F)F)-c2nnc(o2)[C@@](O)(C(F)(F)F)CCCCC1([2H])[2H]] | +++ |
| 40 | diastereomer 1 | +++ |
| 41 | diastereomer 2 | +++ |
| 42 | diastereomer 1 | +++ |
| 43 | regioisomeric diastereomer 1 | +++ |
| 44 | 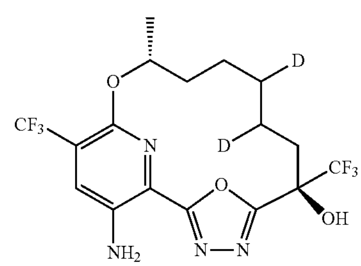 [SMILES: [2H]C1CC[C@@H](C)Oc2nc(c(N)cc2C(F)(F)F)-c2nnc(o2)[C@@](O)(C(F)(F)F)CC1[2H]] | +++ |
| 45 | diastereomer 2 | +++ |

TABLE 12-continued
Bioactivity
| Comp. No. | Structure | EC$_{50}$ |
|---|---|---|
| 46 | 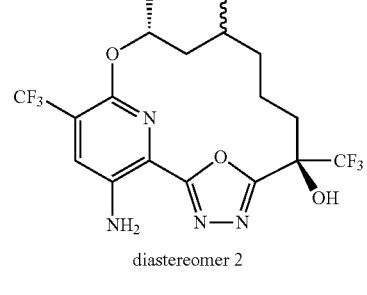 diastereomer 2 | +++ |
| 47 | 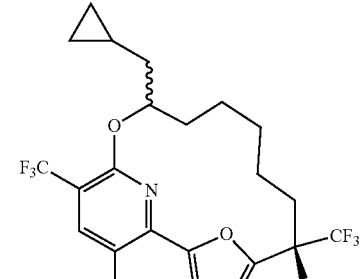 enantiomer 1 | +++ |
| 48 | 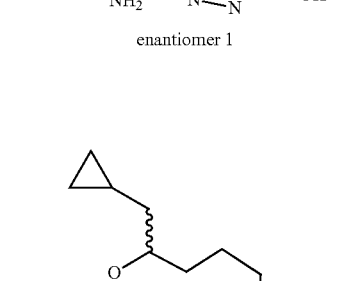 enantiomer 2 | +++ |
| 49 | 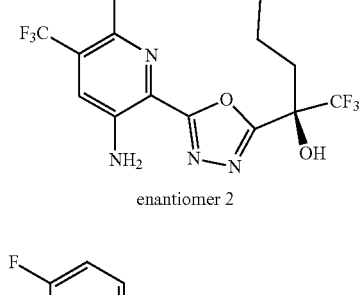 enantiomer 1 | +++ |
| 50 | 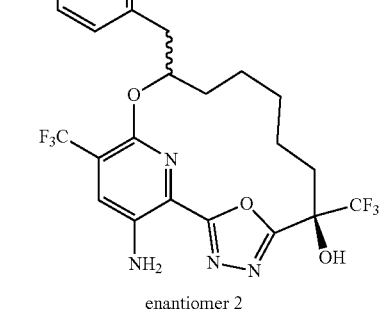 enantiomer 2 | +++ |
| 51 | 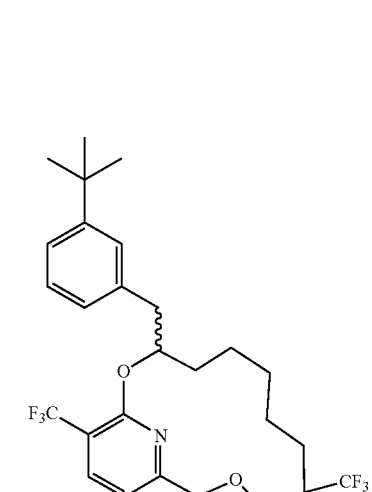 enantiomer 1 | +++ |
| 52 | 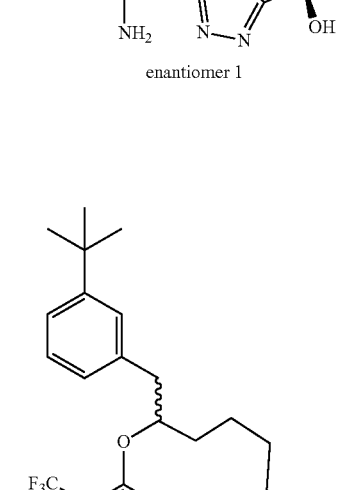 enantiomer 2 | +++ |

TABLE 12-continued
| Comp. No. | Structure | Bioactivity EC$_{50}$ |
|---|---|---|
| 53 | 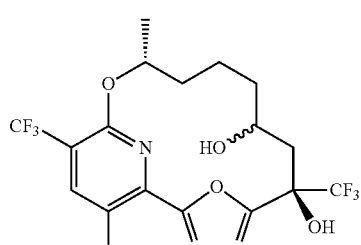 diastereomer 1 | +++ |
TABLE 13
| Comp. No. | Structure | Bioactivity EC$_{50}$ |
|---|---|---|
| 54 | enantiomer 1 | ND |
| 55 | enantiomer 2 | ND |
| 56 | enantiomer 1 | + |
| 57 | enantiomer 2 | +++ |
| 58 | diastereomer 2 | +++ |
| 59 | 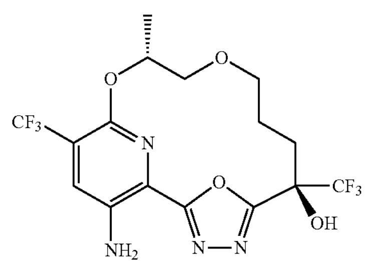 [SMILES: C[C@@H]1COCCC[C@](O)(C(F)(F)F)c2nnc(o2)-c2nc(c(C(F)(F)F)cc2N)O1] | + |
| 60 | 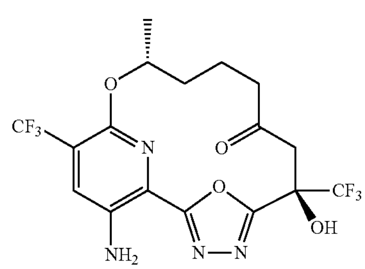 [SMILES: C[C@@H]1CCCC(=O)C[C@](O)(C(F)(F)F)c2nnc(o2)-c2nc(c(C(F)(F)F)cc2N)O1] | ND |
| 61 | 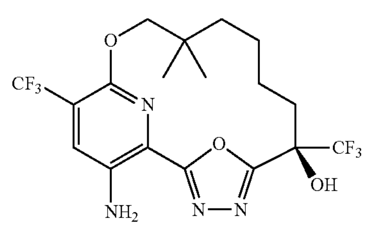 [SMILES: CC1(C)CCCC[C@](O)(C(F)(F)F)c2nnc(o2)-c2nc(c(C(F)(F)F)cc2N)OC1] | +++ |

TABLE 13-continued
| Comp. No. | Structure | EC₅₀ |
|---|---|---|
| 62 | 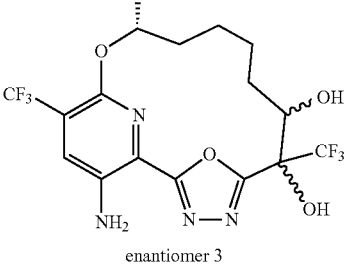 enantiomer 3 | +++ |
| 63 | 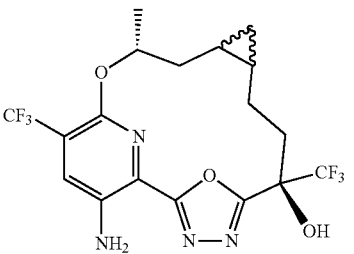 enantiomer 1 | +++ |
| 64 | 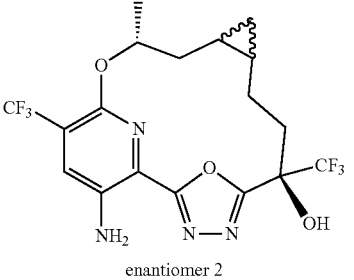 enantiomer 2 | +++ |
| 65 | 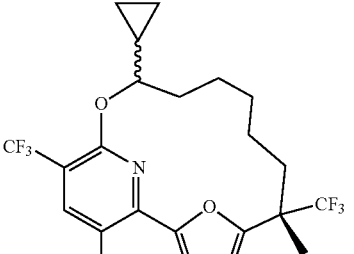 enantiomer 1 | ND |
| 66 | 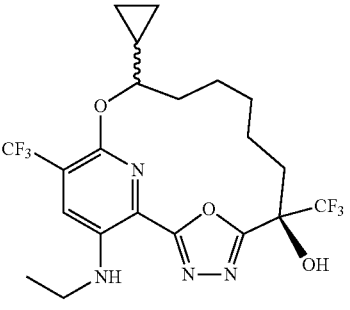 enantiomer 2 | ND |
| 67 | 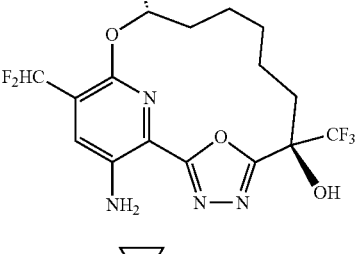 | ND |
| 68 | 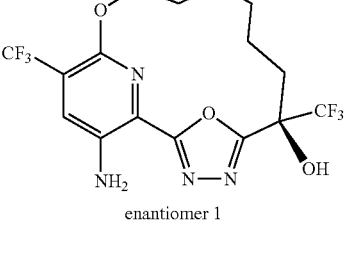 enantiomer 1 | ND |
| 69 | 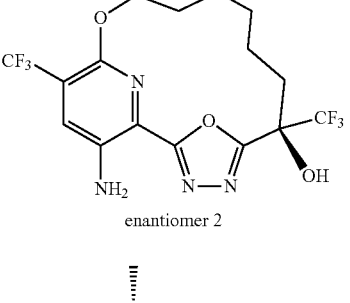 enantiomer 2 | ND |
| 70 | 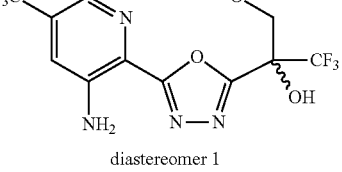 diastereomer 1 | ND |

TABLE 13-continued

Bioactivity

| Comp. No. | Structure | EC$_{50}$ |
|---|---|---|
| 71 | 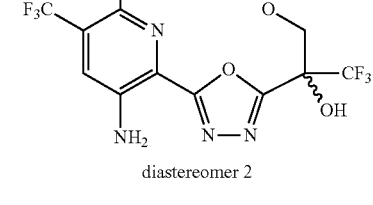 diastereomer 2 | ND |
| 72 | 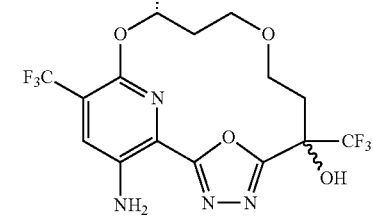 diastereomer 1 | ND |
| 73 | 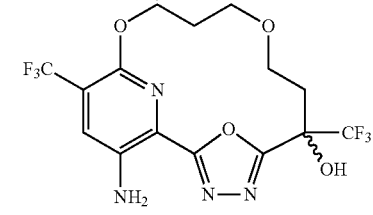 diastereomer 2 | ND |
| 74 | 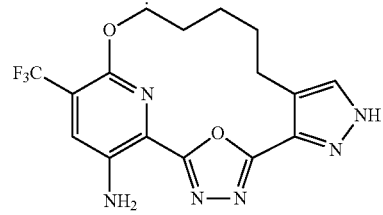 | ND |
| 75 | 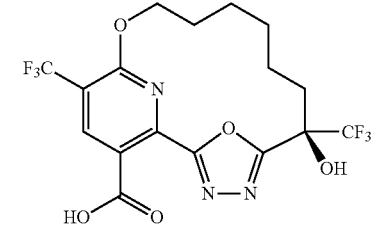 | ND |
| 76 | 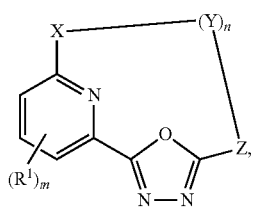 | ND |
| 77 | 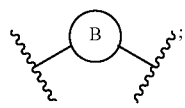 diastereomer 1 | ND |

OTHER EMBODIMENTS

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A compound selected from compounds of Formula I:

$$\underset{(R^1)_m}{\text{[structure I]}}\quad\text{I}$$

and deuterated derivatives and pharmaceutically acceptable salts thereof, wherein:

X is selected from —O—, —S—, —SO—, and —SO$_2$—;
each Y is independently selected from —C(R$^Y$)$_2$—, —O—, —CO—, and

[structure with B]

each R$^Y$ is independently selected from hydrogen, halogen, C$_1$-C$_6$ alkyl (optionally substituted with 1-3 groups independently selected from hydroxy and Q), $C_3$-$C_8$ cycloalkyl, $C_6$-$C_{10}$ aryl, 5- to 10-membered heteroaryl, —$OR^{Y1}$, —$CO_2R^{Y1}$, —$COR^{Y1}$, —$CON(R^{Y1})_2$, and —$N(R^{Y1})_2$; or two instances of $R^Y$ on the same atom may be taken together to form a ring selected from $C_3$-$C_8$ cycloalkyl and 3- to 6-membered heterocyclyl; or two instances of $R^Y$, one of which is on a first atom and the second of which is on an adjacent second atom, may be replaced with a pi bond between the first and second atom;

each $R^{Y1}$ is independently selected from hydrogen and $C_1$-$C_6$ alkyl, or two instances of $R^{Y1}$ bonded to the same nitrogen taken together form a 3- to 6-membered heterocyclyl;

Ring B is selected from:
  $C_6$-$C_{10}$ aryl (optionally substituted with 1-3 groups independently selected from halogen, $C_1$-$C_6$ alkyl, and $C_1$-$C_6$ alkoxy),
  $C_3$-$C_8$ cycloalkyl,
  5- to 10-membered heteroaryl, and
  3- to 6-membered heterocyclyl (optionally substituted with 1-3 groups independently selected from $C_1$-$C_6$ alkyl);

each Q is independently selected from:
  $C_1$-$C_6$ alkyl optionally substituted with 1-3 groups independently selected from:
    halogen,
    oxo,
    $C_6$-$C_{10}$ aryl (optionally substituted with 1-3 groups independently selected from halogen and —$OCF_3$), and
    $C_3$-$C_8$ cycloalkyl,
  $C_3$-$C_8$ cycloalkyl optionally substituted with 1-3 groups independently selected from:
    halogen,
    CN,
    $C_1$-$C_6$ alkyl (optionally substituted with 1-3 groups independently selected from halogen, —$NH_2$, and —NHCOMe),
    $C_1$-$C_6$ alkoxy,
    $C_6$-$C_{10}$ aryl (optionally substituted with 1-3 groups independently selected from $C_1$-$C_6$ alkyl), and
    $C_3$-$C_8$ cycloalkyl,
  $C_6$-$C_{10}$ aryl optionally substituted with 1-3 groups independently selected from:
    halogen,
    CN,
    $C_1$-$C_6$ alkyl (optionally substituted with 1-3 groups independently selected from halogen and hydroxy),
    $C_1$-$C_6$ alkoxy optionally substituted with 1-4 groups independently selected from:
      halogen,
      $C_3$-$C_8$ cycloalkyl (optionally substituted with $CF_3$),
    $C_3$-$C_8$ cycloalkyl (optionally substituted with 1-3 groups independently selected from halogen, $CF_3$, $OCF_3$, and $C_1$-$C_6$ alkyl), and
    $C_6$-$C_{10}$ aryl,
  5- to 10-membered heteroaryl optionally substituted with 1-3 groups independently selected from:
    halogen,
    $C_1$-$C_6$ alkyl (optionally substituted with 1-3 groups independently selected from halogen),
    $C_3$-$C_8$ cycloalkyl (optionally substituted with 1-3 $CF_3$ groups), and
    3- to 10-membered heterocyclyl,
  3- to 10-membered heterocyclyl optionally substituted with 1-3 groups independently selected from:
    $C_1$-$C_6$ alkyl (optionally substituted with 1-3 groups independently selected from oxo and $C_3$-$C_8$ cycloalkyl), and
    oxo;

each $R^1$ is independently selected from halogen, $C_1$-$C_6$ alkyl (optionally substituted with 1-6 groups independently selected from halogen and hydroxy), —$OR^2$, —$N(R^2)_2$, —$CO_2R^2$, —CO—$N(R^2)_2$, —CN, phenyl, benzyl, $C_1$-$C_6$ alkoxy, $C_3$-$C_8$ cycloalkyl, 5- to 6-membered heteroaryl, 3- to 6-membered heterocyclyl, —$SO_2R^2$, —$SR^2$, —$SOR^2$, —$PO(OR^2)_2$, and —$PO(R^2)_2$;

each $R^2$ is independently selected from hydrogen, $C_1$-$C_6$ alkyl (optionally substituted with 1-6 groups independently selected from halogen), and $C_6$-$C_{10}$ aryl (optionally substituted with $C_1$-$C_6$ alkoxy, which is optionally substituted with 1-6 groups independently selected from halogen);

Z is selected from

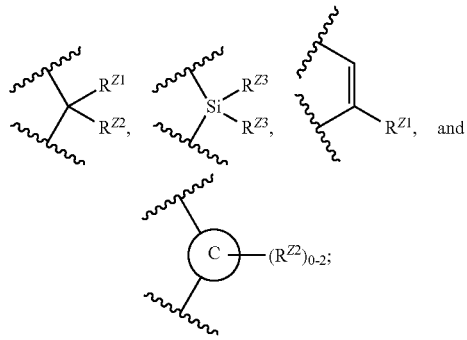

wherein Ring C is selected from $C_6$-$C_{10}$ aryl and 5- to 10-membered heteroaryl;

$R^{Z1}$ is selected from hydrogen, —CN, $C_1$-$C_6$ alkyl (optionally substituted with 1-6 groups independently selected from halogen or 1-3 hydroxy), 3- to 6-membered heterocyclyl, 3- to 6-membered cycloalkyl, 5- to 6-membered aryl, and 5- to 6-membered heteroaryl;

$R^{Z2}$ is selected from hydrogen, halogen, and hydroxy, or $R^{Z1}$ and $R^{Z2}$ taken together form a group selected from oxo and =N—OH;

each $R^{Z3}$ is independently selected from hydroxy, $C_1$-$C_6$ alkoxy, $C_1$-$C_6$ alkyl, $C_1$-$C_6$ haloalkyl, and $C_6$-$C_{10}$ aryl; or two instances of $R^{Z3}$ are taken together to form a 3- to 6-membered heterocyclyl;

n is selected from 4, 5, 6, 7, and 8; and m is selected from 0, 1, 2, and 3.

2. The compound, deuterated derivative, or pharmaceutically acceptable salt according to claim 1, wherein X is —O—.

3. The compound, deuterated derivative, or pharmaceutically acceptable salt according to claim 1, wherein each $R^Y$ is independently selected from hydrogen, halogen, $C_1$-$C_6$ alkyl (optionally substituted with 1-3 groups independently selected from hydroxy and Q), $C_3$-$C_8$ cycloalkyl, and —$OR^{Y1}$.

4. The compound, deuterated derivative, or pharmaceutically acceptable salt according to claim 1, wherein —$OR^{Y1}$ is —OH.

5. The compound, deuterated derivative, or pharmaceutically acceptable salt according to claim 1, wherein each Q is independently selected from:

$C_3$-$C_8$ cycloalkyl, $C_6$-$C_{10}$ aryl optionally substituted with 1-3 groups independently selected from halogen and $C_1$-$C_6$ alkyl.

6. The compound, deuterated derivative, or pharmaceutically acceptable salt according to claim 1, wherein each Q is independently selected from:

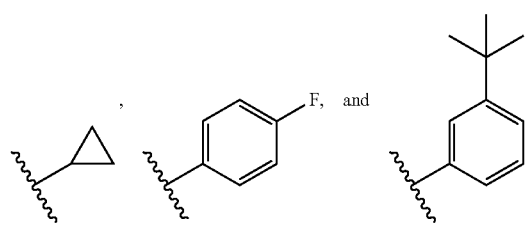

7. The compound, deuterated derivative, or pharmaceutically acceptable salt according to claim 1, wherein each $R^Y$ is independently selected from: hydrogen, fluorine,

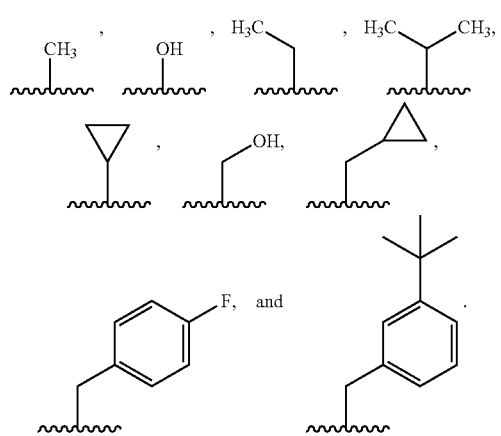

8. The compound, deuterated derivative, or pharmaceutically acceptable salt according to claim 1, wherein Ring B is selected from $C_3$-$C_8$ cycloalkyl and phenyl optionally substituted with 1-3 groups independently selected from halogen.

9. The compound, deuterated derivative, or pharmaceutically acceptable salt according to claim 1, wherein Ring B is selected from:

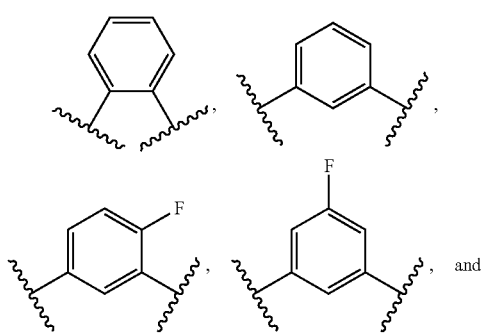

-continued

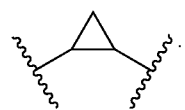

10. The compound, deuterated derivative, or pharmaceutically acceptable salt according to claim 1, wherein n is selected from 4, 5, and 6.

11. The compound, deuterated derivative, or pharmaceutically acceptable salt according to claim 1, wherein —$(Y)_n$— is a group selected from:

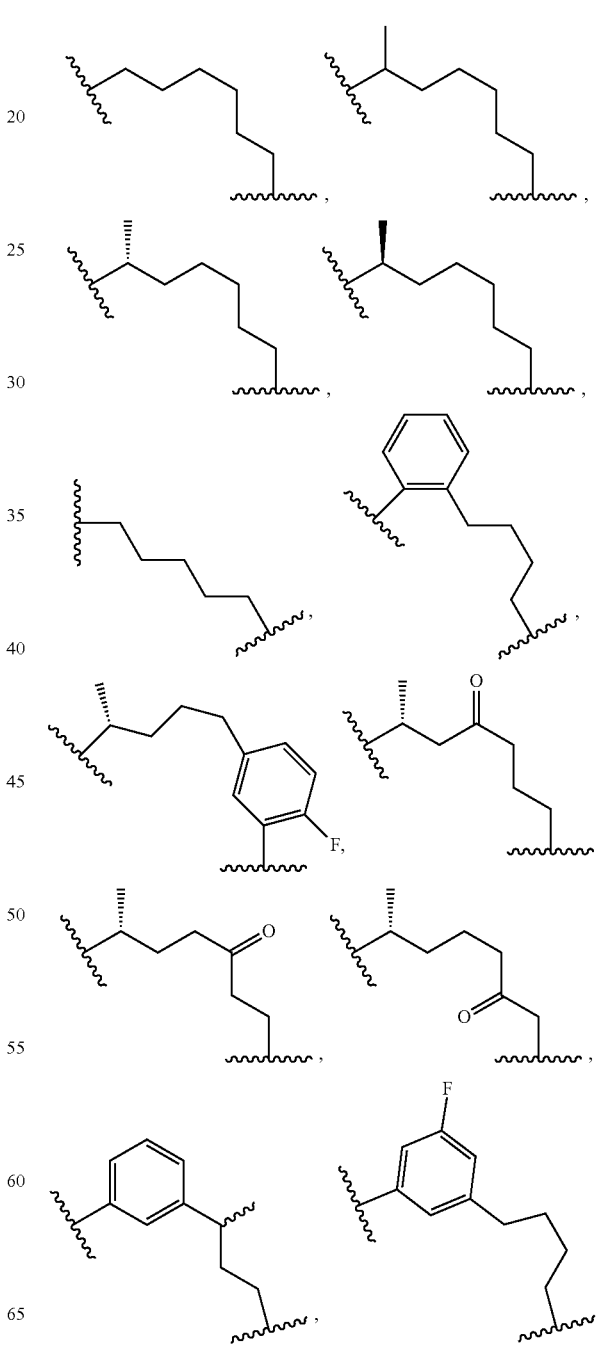

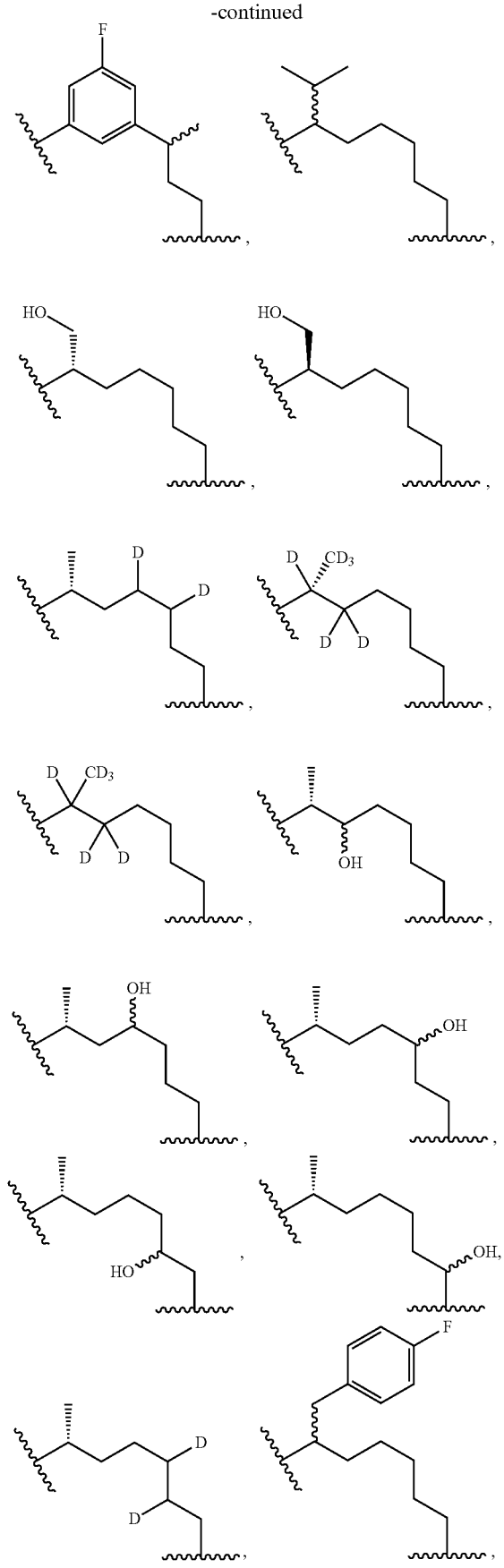
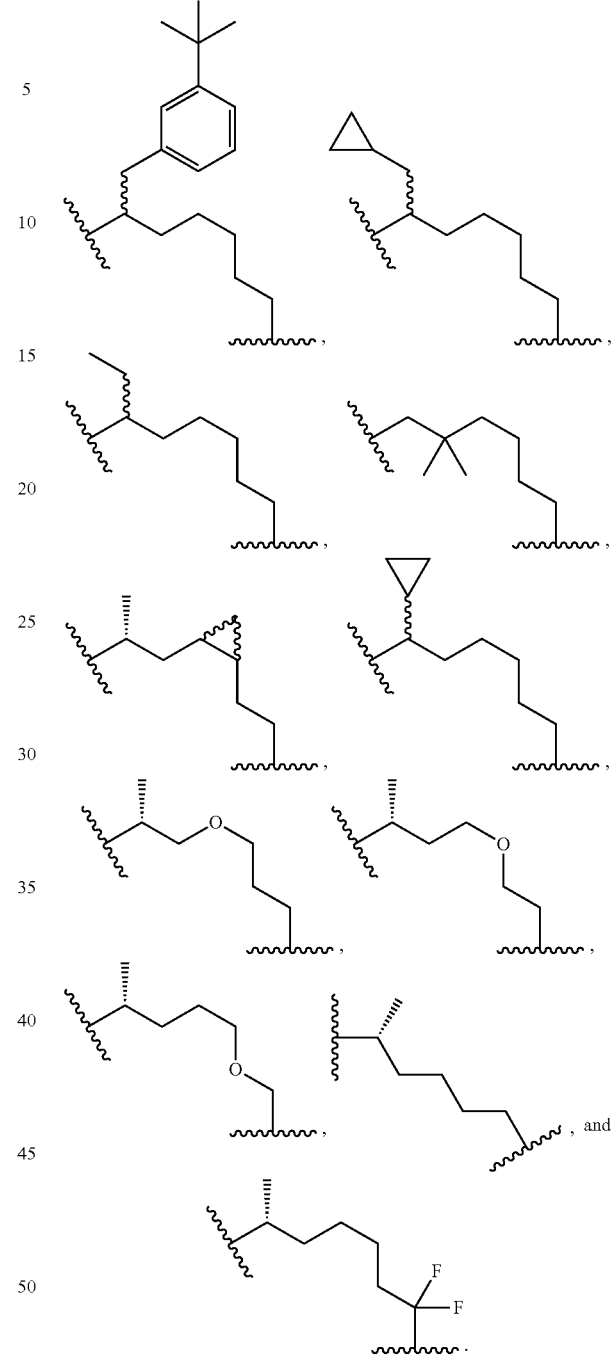

12. The compound, deuterated derivative, or pharmaceutically acceptable salt according to claim 1, wherein each $R^1$ is independently selected from $C_1$-$C_6$ alkyl (optionally substituted with 1-6 groups independently selected from halogen and hydroxy), —N($R^2$)$_2$, and —CO$_2$$R^2$.

13. The compound, deuterated derivative, or pharmaceutically acceptable salt according to claim 1, wherein each $R^2$ is independently selected from hydrogen and $C_1$-$C_6$ alkyl.

14. The compound, deuterated derivative, or pharmaceutically acceptable salt according to claim 1, wherein each $R^1$ is independently selected from —CF$_3$, —NH$_2$, —NH(CH$_2$CH$_3$), CO$_2$H, and CH$_2$OH.

15. The compound, deuterated derivative, or pharmaceutically acceptable salt according to claim 1, wherein Z is selected from

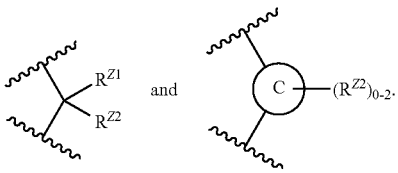

16. The compound, deuterated derivative, or pharmaceutically acceptable salt according to claim 1, wherein the group:

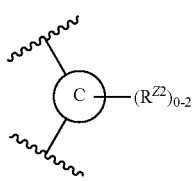

is selected from:

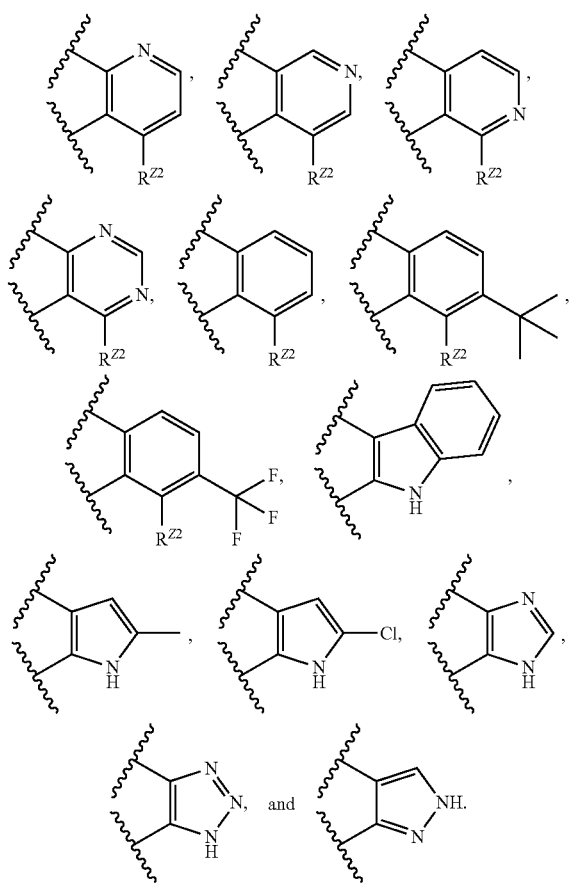

17. The compound, deuterated derivative, or pharmaceutically acceptable salt according to claim 1, wherein the group:

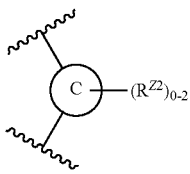

is selected from:

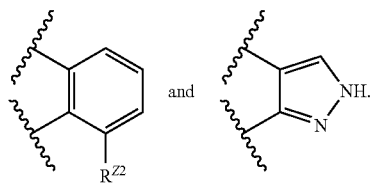

18. The compound, deuterated derivative, or pharmaceutically acceptable salt according to claim 1, wherein $R^{Z1}$ is selected from hydrogen and $C_1$-$C_6$ alkyl (optionally substituted with 1-3 groups selected from halogen).

19. The compound, deuterated derivative, or pharmaceutically acceptable salt according to claim 1, wherein $R^{Z1}$ is selected from hydrogen and —$CF_3$.

20. The compound, deuterated derivative, or pharmaceutically acceptable salt according to claim 1, wherein $R^{Z2}$ is hydroxy.

21. The compound, deuterated derivative, or pharmaceutically acceptable salt according to claim 1, wherein Z is selected from:

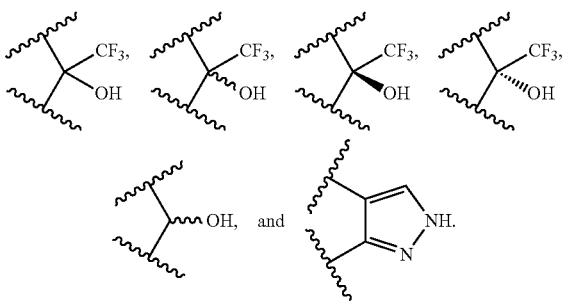

22. The compound, deuterated derivative, or pharmaceutically acceptable salt according to claim 1, wherein m is selected from 1 and 2.

23. The compound, deuterated derivative, or pharmaceutically acceptable salt according to claim 1, wherein:

X is —O—;

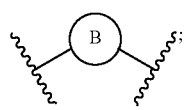

each Y is independently selected from —$C(R^Y)_2$—, —O—, and each $R^Y$ is independently selected from hydrogen and $C_1$-$C_6$ alkyl (optionally substituted with 1-3 groups independently selected from hydroxy and Q);

Ring B is selected from $C_3$-$C_8$ cycloalkyl groups:
each Q is independently selected from: $C_3$-$C_8$ cycloalkyl and $C_6$-$C_{10}$ aryl optionally substituted with 1-3 groups independently selected from halogen and $C_1$-$C_6$ alkyl,
each $R^1$ is independently selected from $C_1$-$C_6$ alkyl (optionally substituted with 1-6 groups independently selected from halogen) and —$NH_2$;
Z is

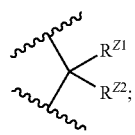

$R^{Z1}$ is selected from $C_1$-$C_6$ alkyl (optionally substituted with 1-6 groups independently selected from halogen);
$R^{Z2}$ is hydroxy;
n is selected from 5 and 6; and
m is 2.

24. The compound, deuterated derivative, or pharmaceutically acceptable salt according to claim 1, wherein each Q is independently selected from:

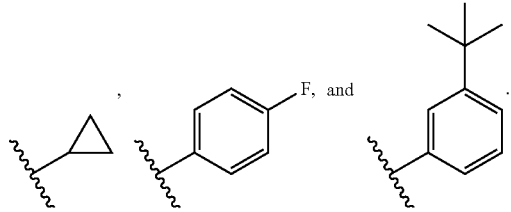

25. The compound, deuterated derivative, or pharmaceutically acceptable salt according to claim 1, wherein each $R^Y$ is independently selected from: hydrogen,

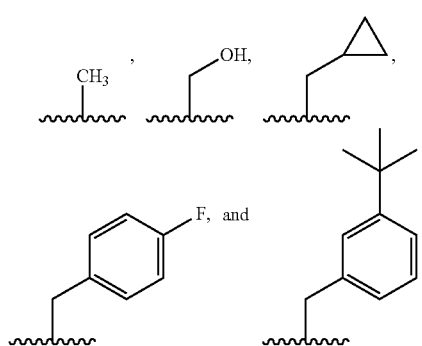

26. The compound, deuterated derivative, or pharmaceutically acceptable salt according to claim 1, wherein Ring B is

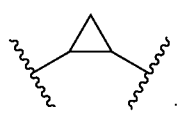

27. The compound, deuterated derivative, or pharmaceutically acceptable salt according to claim 1, wherein —$(Y)_n$— is a group selected from:

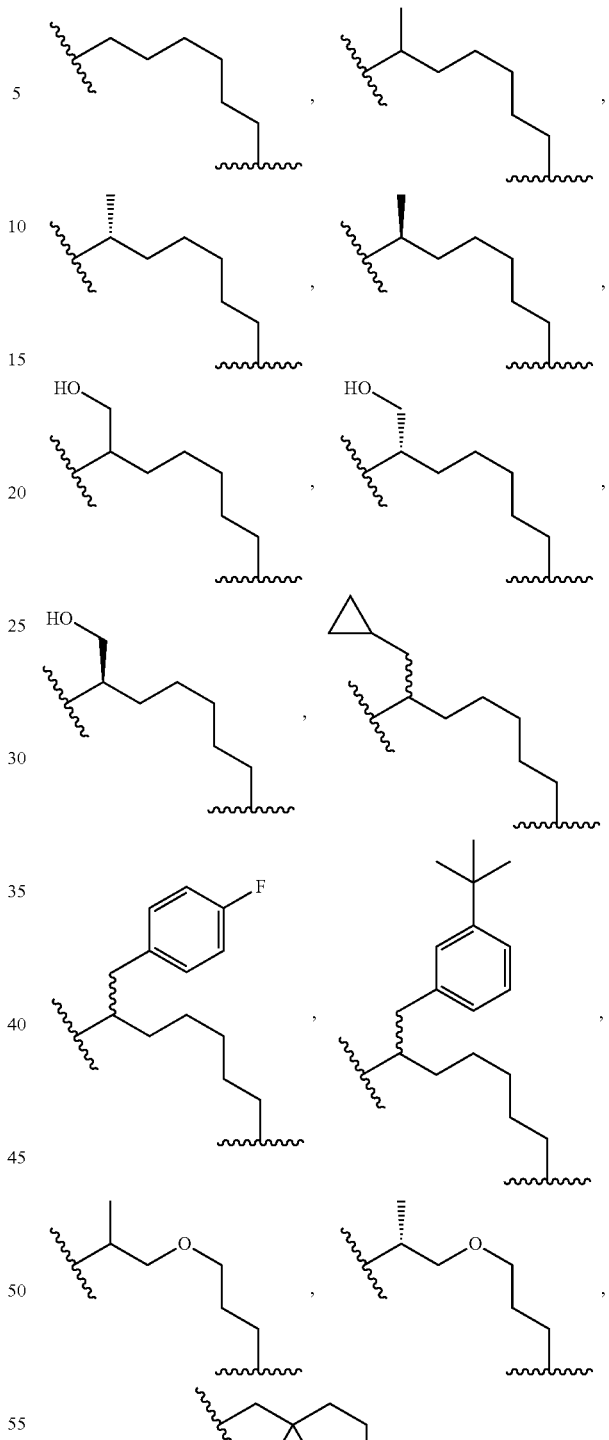

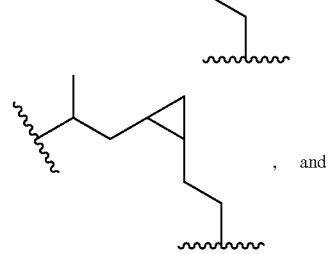

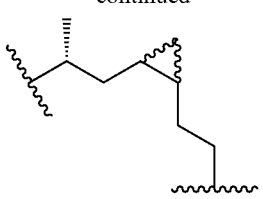

28. The compound, deuterated derivative, or pharmaceutically acceptable salt according to claim 1, wherein $R^{Z1}$ is —$CF_3$.

29. The compound, deuterated derivative, or pharmaceutically acceptable salt according to claim 1, wherein n is 5.

30. The compound, deuterated derivative, or pharmaceutically acceptable salt according to claim 1, wherein n is 6.

31. The compound, deuterated derivative, or pharmaceutically acceptable salt according to claim 1, wherein the compound is selected from:

| Comp. No. | Structure |
|---|---|
| 1 | 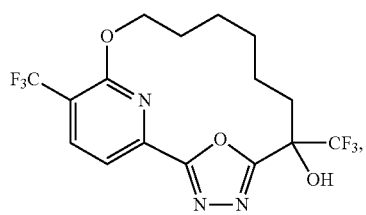 [SMILES: OC1(C(F)(F)F)CCCCCCOc2nc(ccc2C(F)(F)F)C2=NN=C1O2] |
| 2 | 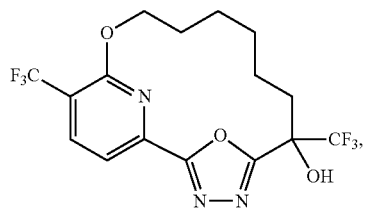 enantiomer 1 |
| 3 | 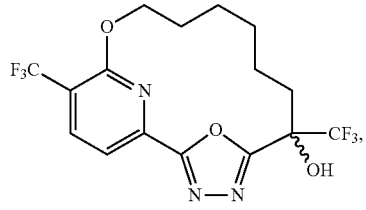 enantiomer 2 |
| 4 | 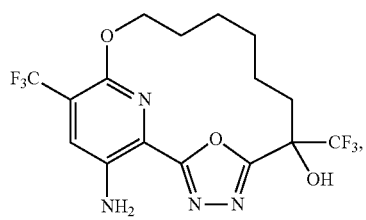 |

| Comp. No. | Structure |
|---|---|
| 5 | 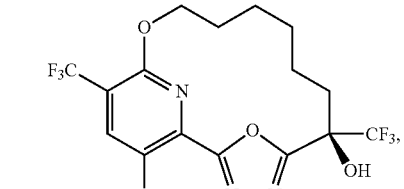 |
| 6 | 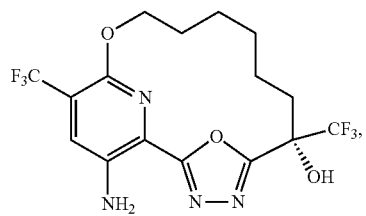 [SMILES: Nc1cc(C(F)(F)F)c2nc1C1=NN=C(O1)[C@](O)(C(F)(F)F)CCCCCCO2] |
| 7 | 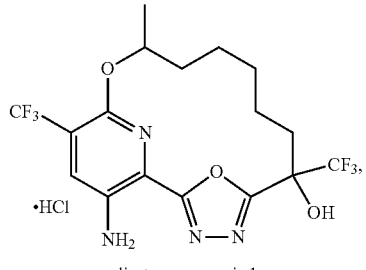 diastereomer pair 1 |
| 8 | 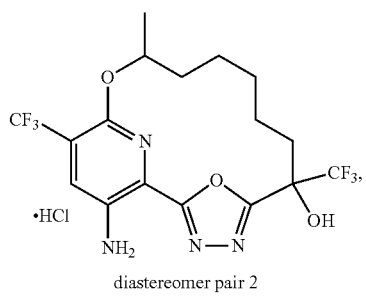 [SMILES: CC1CCCCCC(O)(C(F)(F)F)C2=NN=C(O2)c2nc(c(C(F)(F)F)cc2N)O1 ; Cl] diastereomer pair 2 |
| 9 | 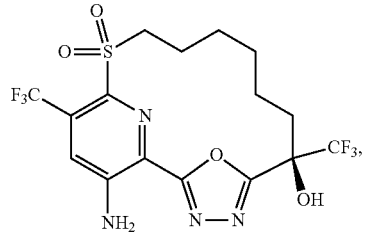 Enantiomer 1 |
| 10 | 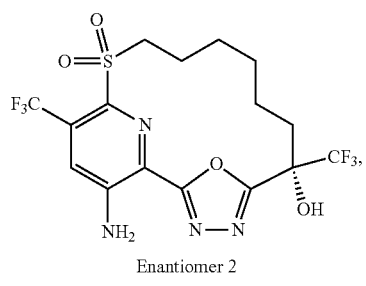 [SMILES: Nc1cc(C(F)(F)F)c2nc1C1=NN=C(O1)[C@](O)(C(F)(F)F)CCCCCCS2(=O)=O] Enantiomer 2 |

-continued

| Comp. No. | Structure |
|---|---|
| 11 | (chemical structure) |
| 12 | (chemical structure) ·HCl |
| 13 | (chemical structure) ·HCl |
| 14 | (chemical structure) |
| 15 | (chemical structure) enantiomer 1 |
| 16 | (chemical structure) enantiomer 2 |
| 17 | (chemical structure) ·HCl |
| 18 | (chemical structure) diastereomer pair |
| 19 | (chemical structure) |
| 20 | (chemical structure) |
| 21 | (chemical structure) |

| Comp. No. | Structure |
|---|---|
| 22 | 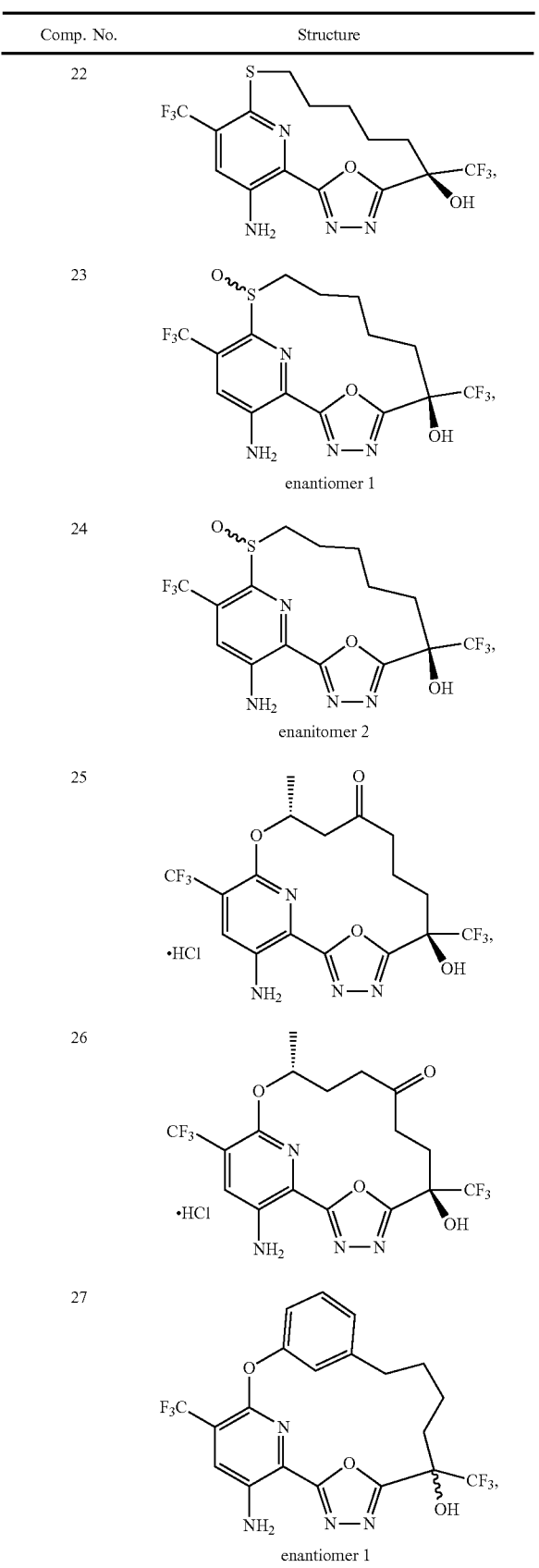 |
| 23 | enantiomer 1 |
| 24 | enanitomer 2 |
| 25 | |
| 26 | |
| 27 | enantiomer 1 |
| Comp. No. | Structure |
|---|---|
| 28 | 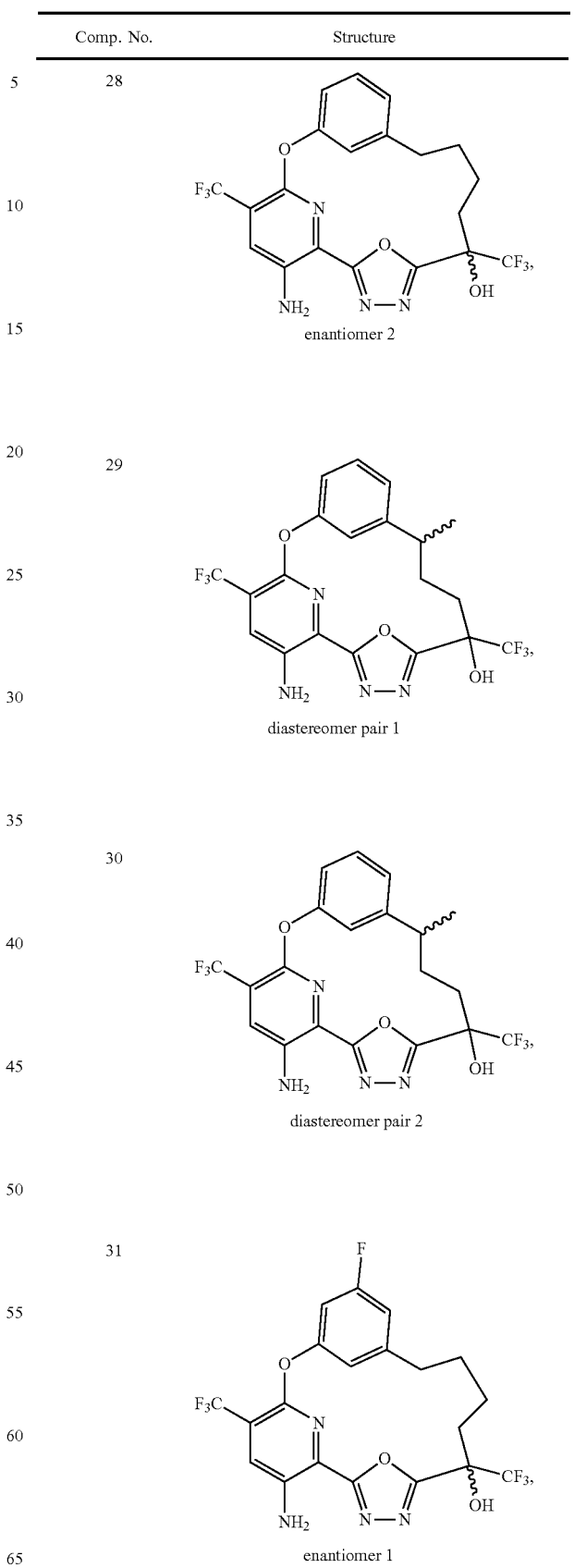 enantiomer 2 |
| 29 | diastereomer pair 1 |
| 30 | diastereomer pair 2 |
| 31 | enantiomer 1 |

| Comp. No. | Structure |
|---|---|
| 32 | 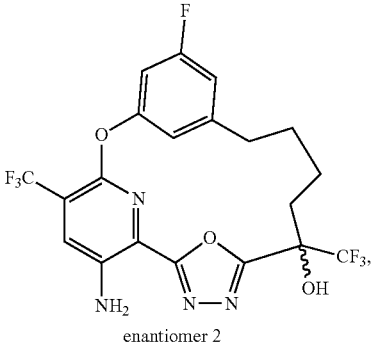 [SMILES: Nc1cc(C(F)(F)F)c2nc1-c1nnc(o1)C(O)(C(F)(F)F)CCCCc1cc(F)cc(c1)O2]<br>enantiomer 2 |
| 33 | 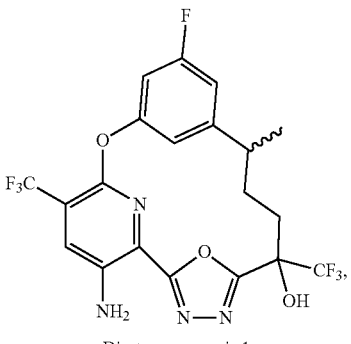<br>Diastereomer pair 1 |
| 34 | 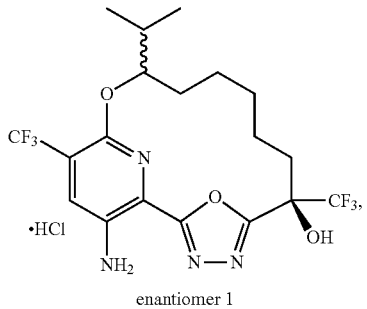 [SMILES: Cl ; CC(C)C1CCCCC[C@](O)(C(F)(F)F)C2=NN=C(O2)c2nc(c(C(F)(F)F)cc2N)O1]<br>enantiomer 1 |
| 35 | 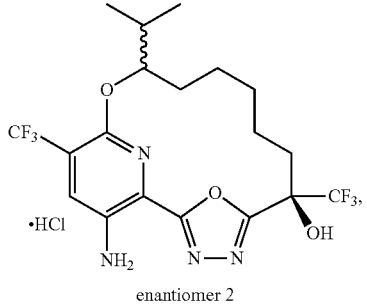 [SMILES: Cl ; CC(C)C1CCCCC[C@](O)(C(F)(F)F)C2=NN=C(O2)c2nc(c(C(F)(F)F)cc2N)O1]<br>enantiomer 2 |
| Comp. No. | Structure |
|---|---|
| 36 | 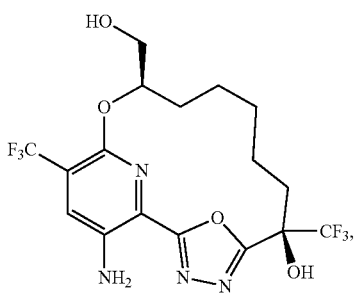 [SMILES: Nc1cc(C(F)(F)F)c2nc1C1=NN=C(O1)[C@@](O)(C(F)(F)F)CCCCC[C@H](CO)O2] |
| 37 | 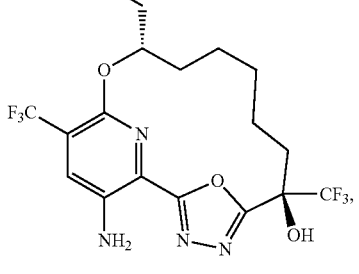 |
| 38 | 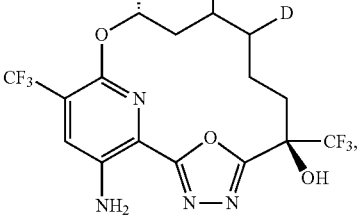 |
| 39 | 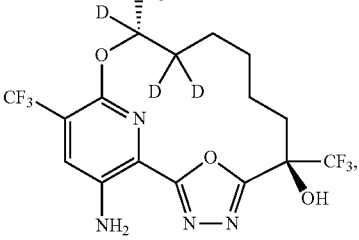 |
| 40 | 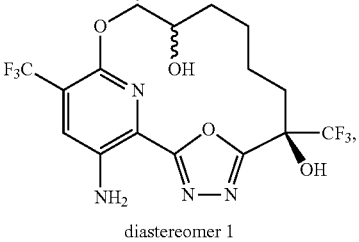<br>diastereomer 1 |

-continued
| Comp. No. | Structure |
|---|---|
| 41 | 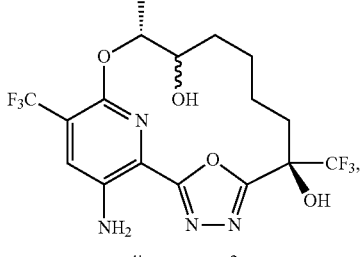 diastereomer 2 |
| 42 | 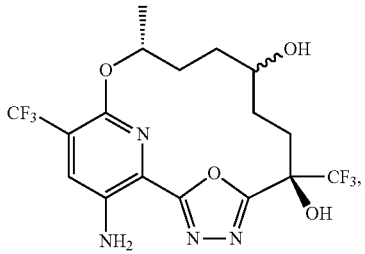 diastereomer 1 |
| 43 | 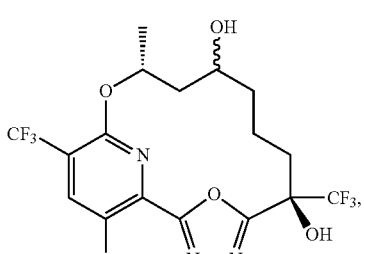 regioisomeric diastereomer 1 |
| 44 | 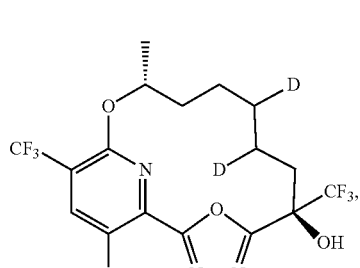 |
| 45 | 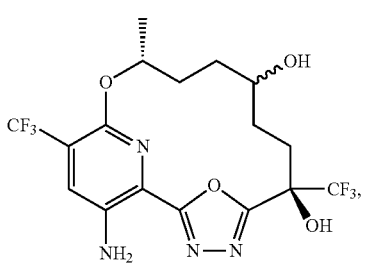 diastereomer 2 |
-continued
| Comp. No. | Structure |
|---|---|
| 46 | 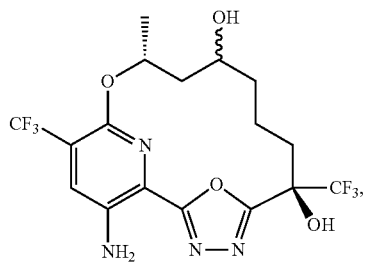 [SMILES: [2H]C1CC[C@](O)(C(F)(F)F)C2=NN=C(O2)c2nc(c(C(F)(F)F)cc2N)O[C@H](C)CC1[2H]] diastereomer 2 |
| 47 | 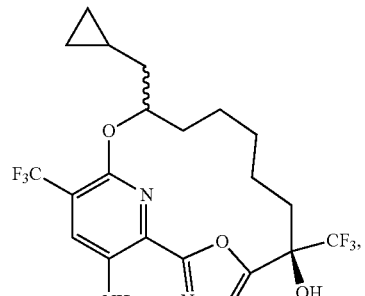 enantiomer 1 |
| 48 | 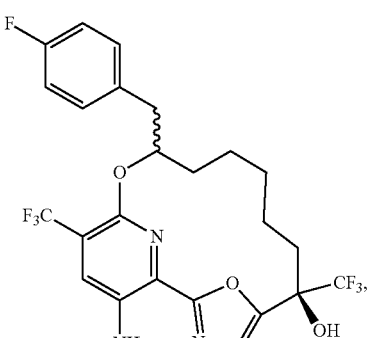 enantiomer 2 |
| 49 | enantiomer 1 |

-continued
| Comp. No. | Structure |
|---|---|
| 50 | 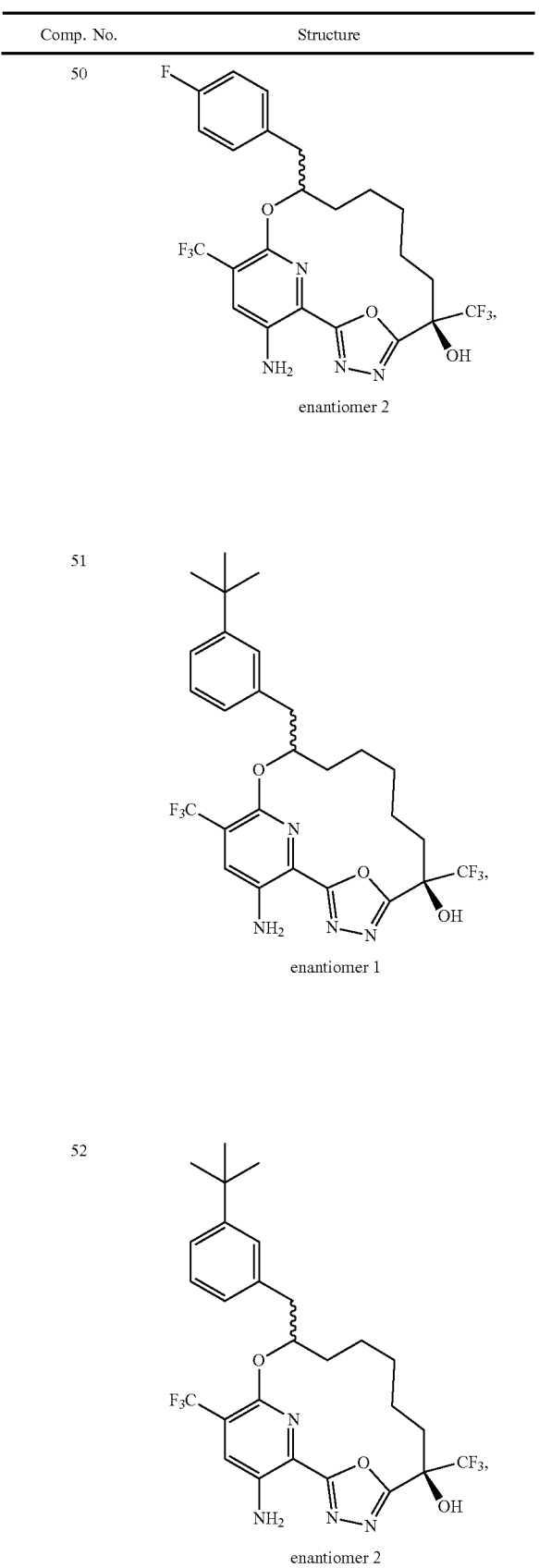 enantiomer 2 |
| 51 | enantiomer 1 |
| 52 | enantiomer 2 |
-continued
| Comp. No. | Structure |
|---|---|
| 53 | 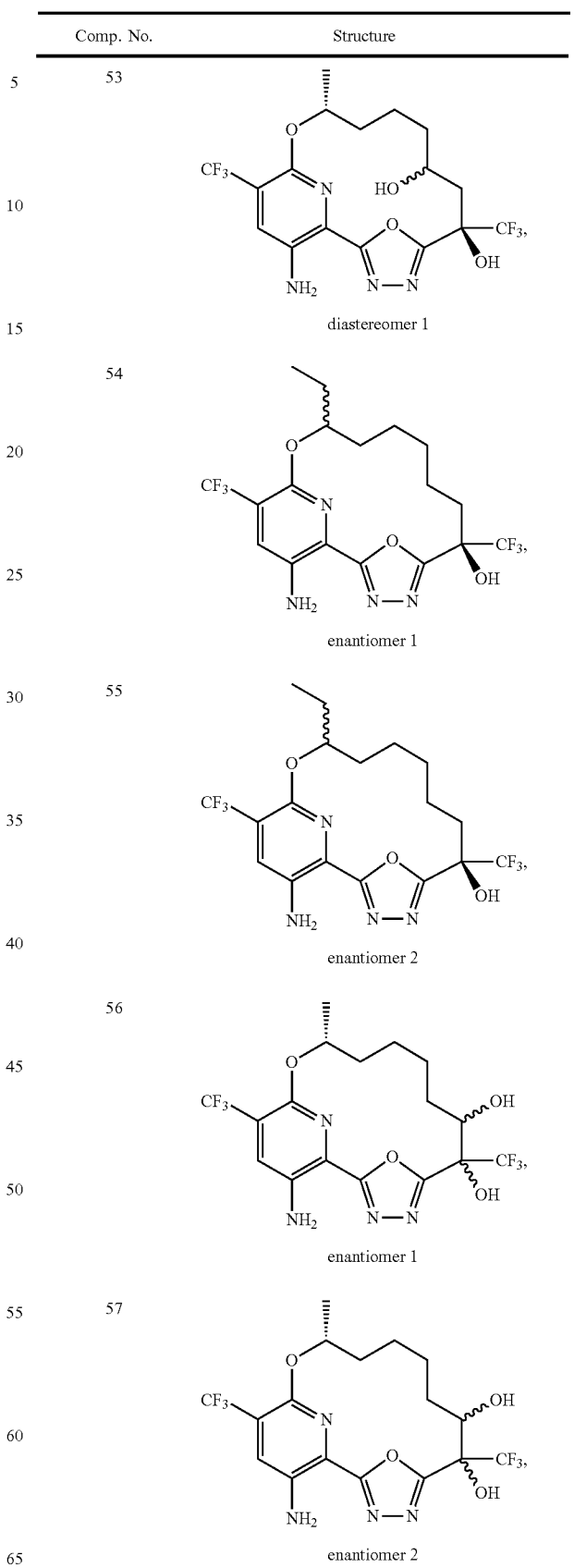 diastereomer 1 |
| 54 | enantiomer 1 |
| 55 | enantiomer 2 |
| 56 | enantiomer 1 |
| 57 | enantiomer 2 |

US 12,269,831 B2
| Comp. No. | Structure |
|---|---|
| 58 | 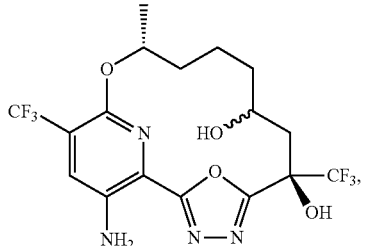 diastereomer 2 |
| 59 | 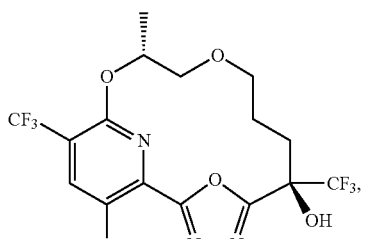 |
| 60 | 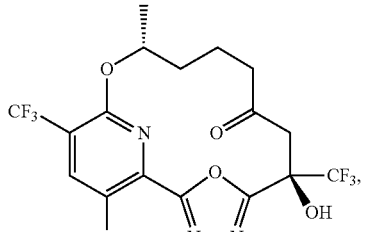 |
| 61 | 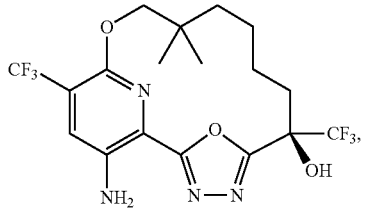 [SMILES: CC1(C)CCCC[C@](O)(C(F)(F)F)C2=NN=C(O2)c2nc(c(C(F)(F)F)cc2N)OC1] |
| 62 | 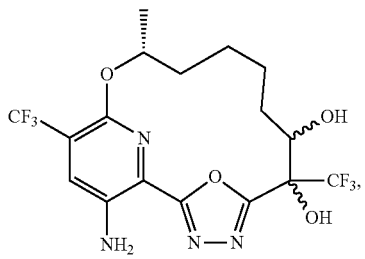 enantiomer 3 |
| Comp. No. | Structure |
|---|---|
| 63 | 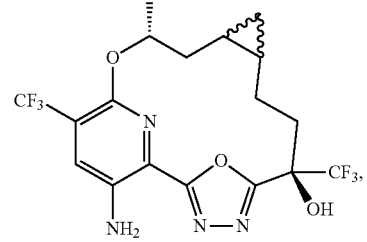 enantiomer 1 |
| 64 | 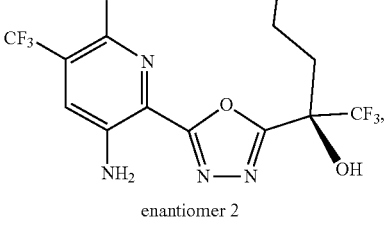 enantiomer 2 |
| 65 | 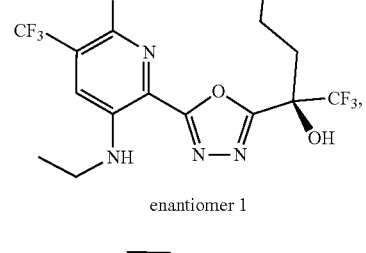 enantiomer 1 |
| 66 | 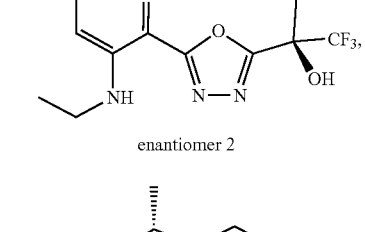 enantiomer 2 |
| 67 | 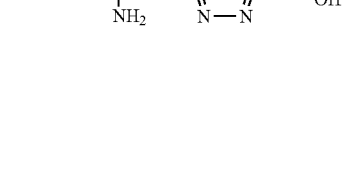 |

US 12,269,831 B2

669
-continued

| Comp. No. | Structure |
|---|---|
| 68 | (enantiomer 1) |
| 69 | (enantiomer 2) |
| 70 | (diastereomer 1) |
| 71 | (diastereomer 2) |
| 72 | (diastereomer 1) |

670
-continued

| Comp. No. | Structure |
|---|---|
| 73 | (diastereomer 2) |
| 74 | |
| 75 | |
| 76 | |
| 77 | (diastereomer 1) | pharmaceutically acceptable salts thereof, and deuterated derivatives of any of the foregoing.

32. The compound, deuterated derivative, or pharmaceutically acceptable salt according to claim 31, wherein the compound is selected from:

| Comp. No. | Structure |
|---|---|
| 5 | 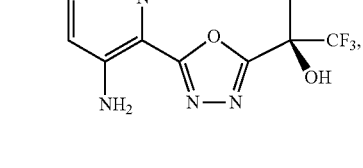 |
| 11 | 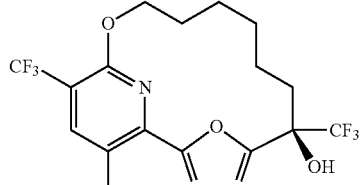 |
| 14 | 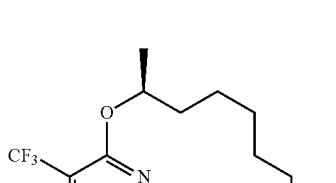 |
| 36 | 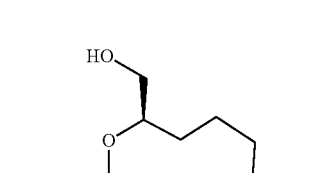 |
| 37 | 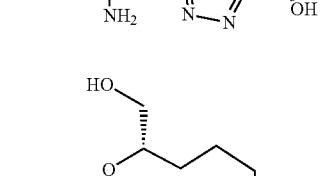 |
-continued
| Comp. No. | Structure |
|---|---|
| 47 | enantiomer 1 |
| 49 | enantiomer 1 |
| 50 | enantiomer 2 |
| 52 | enantiomer 2 |

| Comp. No. | Structure |
|---|---|
| 59 | |
| 61 | |
| 63 | enantiomer 1 |
| 64 | enantiomer 2 | pharmaceutically acceptable salts thereof, and deuterated derivatives of any of the foregoing.

33. A pharmaceutical composition comprising a compound, deuterated derivative, or pharmaceutically acceptable salt according to claim 1 and a pharmaceutically acceptable carrier.

34. The pharmaceutical composition according to claim 33, further comprising one or more additional therapeutic agent(s).

35. A method of treating cystic fibrosis, comprising administering an effective amount of the compound, deuterated derivative, or pharmaceutically acceptable salt according to claim 1.

36. The method according to claim 35, further comprising administering one or more additional therapeutic agent(s).

37. A compound of the formula:

(Compound 11)

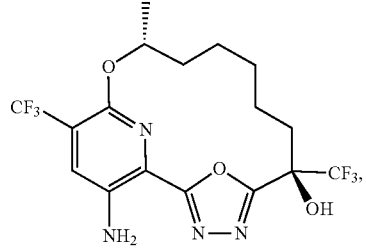

a deuterated derivative thereof, or a pharmaceutically acceptable salt of any of the foregoing.

38. A pharmaceutical composition comprising the compound, deuterated derivative, or pharmaceutically acceptable salt according to claim 37, and a pharmaceutically acceptable carrier.

39. The pharmaceutical composition according to claim 38, further comprising one or more additional therapeutic agent(s).

40. A method of treating cystic fibrosis, comprising administering an effective amount of the compound, deuterated derivative, or pharmaceutically acceptable salt according to claim 37.

41. The method according to claim 40, further comprising administering one or more additional therapeutic agent(s).

* * * * *

UNITED STATES PATENT AND TRADEMARK OFFICE
CERTIFICATE OF CORRECTION

PATENT NO. : 12,269,831 B2
APPLICATION NO. : 17/395838
DATED : April 8, 2025
INVENTOR(S) : Clemens et al.

Page 1 of 1

It is certified that error appears in the above-identified patent and that said Letters Patent is hereby corrected as shown below:

In the Claims

In Claim 23, Column 652, Lines 54-62, after "X is –O–;", delete " 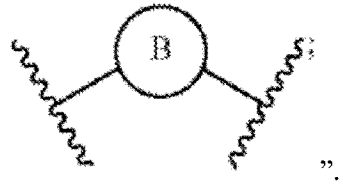 ".

In Claim 23, Column 652, Line 64, after "–O–, and", insert -- 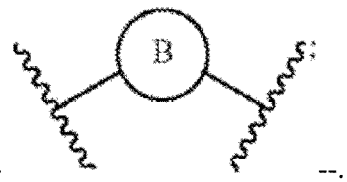 --.

In Claim 31, Column 655, Lines 35-45, in the structure for Comp. No. 2,

" 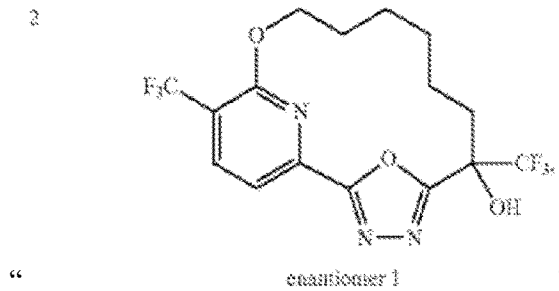 " should read -- 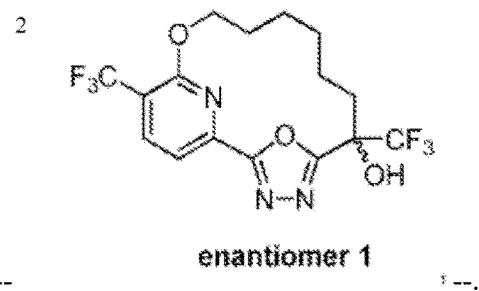 --.

Signed and Sealed this
Fifteenth Day of July, 2025

Coke Morgan Stewart
*Acting Director of the United States Patent and Trademark Office*